US012486450B2

(12) United States Patent
Nakano et al.

(10) Patent No.: US 12,486,450 B2
(45) Date of Patent: Dec. 2, 2025

(54) ORGANIC ELECTROLUMINESCENCE DEVICE AND ELECTRONIC APPARATUS PROVIDED WITH THE SAME

(71) Applicant: IDEMITSU KOSAN CO.,LTD., Tokyo (JP)

(72) Inventors: Yuki Nakano, Sodegaura (JP); Taro Yamaki, Sodegaura (JP); Satomi Tasaki, Sodegaura (JP); Tomoki Kato, Sodegaura (JP); Keita Seda, Sodegaura (JP); Ryota Takahashi, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 955 days.

(21) Appl. No.: 17/282,642

(22) PCT Filed: Oct. 3, 2019

(86) PCT No.: PCT/JP2019/039090

§ 371 (c)(1),
(2) Date: Apr. 2, 2021

(87) PCT Pub. No.: WO2020/071479

PCT Pub. Date: Apr. 9, 2020

(65) Prior Publication Data

US 2021/0384430 A1 Dec. 9, 2021

Related U.S. Application Data

(63) Continuation-in-part of application No. 16/587,468, filed on Sep. 30, 2019, now Pat. No. 10,811,612, and (Continued)

(30) Foreign Application Priority Data

Oct. 3, 2018 (JP) ................................ 2018-188682
Apr. 26, 2019 (JP) ................................ 2019-086182

(51) Int. Cl.
*C09K 11/06* (2006.01)
*C07C 15/28* (2006.01)

(Continued)

(52) U.S. Cl.
CPC .............. *C09K 11/06* (2013.01); *C07C 15/28* (2013.01); *H10K 85/40* (2023.02); *H10K 85/622* (2023.02); *H10K 85/623* (2023.02); *H10K 85/626* (2023.02); *H10K 85/633* (2023.02); *H10K 85/636* (2023.02); *H10K 85/6572* (2023.02); *H10K 85/6574* (2023.02); *H10K 85/6576* (2023.02); *H10K 85/658* (2023.02); *C07B 2200/05* (2013.01); *C07C 2603/24* (2017.05); *C09K 2211/1011* (2013.01);

(Continued)

(58) Field of Classification Search
CPC ........................... H10K 85/626; H10K 85/658
See application file for complete search history.

(56) References Cited

U.S. PATENT DOCUMENTS 8,759,818 B2 * 6/2014 LeCloux ............. H10K 85/626 313/504
2002/0076576 A1 6/2002 Li et al.

(Continued)

FOREIGN PATENT DOCUMENTS

JP 2004-515506 A 5/2004
JP 2010-087496 A 4/2010

(Continued)

OTHER PUBLICATIONS

International Preliminary Report on Patentability from PCT/JP2019/039090 Dtd Apr. 15, 2021(6 pages).

(Continued)

*Primary Examiner* — Liam J Heincer
(74) *Attorney, Agent, or Firm* — Foley & Lardner LLP

(57) ABSTRACT

An organic electroluminescence device induing a cathode, an anode, and an emitting layer disposed between the cathode and the anode, wherein the emitting layer contains a compound represented by the following formula (1) and one or more compounds selected from the group consisting of a compound represented by formula (11), a compound represented by formula (21), a compound represented by formula (31), a compound represented by formula (41), a compound represented by formula (51), a compound represented by formula (61), a compound represented by formula (71) and a compound represented by formula (81). In the formula (1), at east one of $R_1$ to $R_8$ is a deuterium atom.

(1)

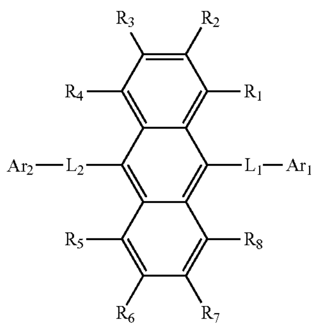

18 Claims, 1 Drawing Sheet

Related U.S. Application Data a continuation-in-part of application No. 16/514,934, filed on Jul. 17, 2019, now abandoned.

(51) Int. Cl.

| | |
|---|---|
| ***H10K 50/11*** | (2023.01) |
| ***H10K 50/15*** | (2023.01) |
| ***H10K 50/16*** | (2023.01) |
| ***H10K 85/40*** | (2023.01) |
| ***H10K 85/60*** | (2023.01) |
| ***H10K 101/10*** | (2023.01) |
| ***H10K 101/40*** | (2023.01) |

(52) U.S. Cl.

CPC .............. *H10K 50/11* (2023.02); *H10K 50/15* (2023.02); *H10K 50/16* (2023.02); *H10K 2101/10* (2023.02); *H10K 2101/40* (2023.02)

(56) References Cited

U.S. PATENT DOCUMENTS

2007/0087222 A1 4/2007 Kim et al.
2010/0051928 A1 3/2010 Fukuzaki
2011/0037057 A1 2/2011 Lecloux et al.
2011/0057173 A1 3/2011 Lecloux et al.
2011/0121269 A1* 5/2011 Lecloux .................. C07C 15/28 564/426
2013/0026422 A1 1/2013 Parham et al.
2014/0001459 A1* 1/2014 Gao ....................... C09K 11/06 257/40
2015/0364693 A1 12/2015 Ito et al.
2016/0211457 A1 7/2016 Ito et al.
2016/0225992 A1* 8/2016 Ito ........................... C09B 57/02
2017/0025608 A1 1/2017 Herron et al.
2018/0301629 A1* 10/2018 Hatakeyama ........ H10K 85/657
2019/0194215 A1 6/2019 Takahashi et al.
2019/0214579 A1* 7/2019 Seda .................. H10K 85/6576
2019/0305227 A1* 10/2019 Yoon .................... C07D 409/10
2019/0312207 A1* 10/2019 Hatakeyama .......... C09K 11/06
2019/0315675 A1* 10/2019 Yang .................. H10K 85/6574
2019/0372023 A1* 12/2019 Hatakeyama ........ H10K 85/111
2019/0393419 A1* 12/2019 Hatakeyama ........ H10K 85/622
2020/0052212 A1* 2/2020 Tasaki ................ H10K 85/6572
2020/0111965 A1* 4/2020 Nakano ................ H10K 85/633
2020/0111974 A1* 4/2020 Nakano ................ H10K 85/615
2020/0176680 A1* 6/2020 Hatakeyama ............. G09F 9/30
2020/0259096 A1* 8/2020 Hatakeyama .......... C09K 11/06
2020/0266350 A1* 8/2020 Hatakeyama .......... C09K 11/06
2020/0335709 A1* 10/2020 Nishimura ........... H10K 85/346
2020/0411771 A1* 12/2020 Kim ................... H10K 85/6572
2021/0005825 A1* 1/2021 Tasaki .................... C09K 11/06
2021/0053998 A1* 2/2021 Kim ................... H10K 85/6572
2021/0062078 A1* 3/2021 Kato .................. H10K 85/6574
2021/0066599 A1* 3/2021 Nakano ................ H10K 85/658
2021/0091313 A1* 3/2021 Maeda ................. H10K 85/626
2021/0336154 A1* 10/2021 Nakano .............. H10K 85/6572
2022/0029099 A1* 1/2022 Yamaki ................... C07C 15/38
2022/0069223 A1* 3/2022 Kim ...................... H10K 85/636
2022/0069232 A1* 3/2022 Haketa ................... H10K 85/40
2022/0376183 A1* 11/2022 Lee ........................ C09K 11/06
2022/0411437 A1* 12/2022 Nakano ................ H10K 85/623
2022/0416171 A1* 12/2022 Tasaki .................... C09K 11/06
2023/0008873 A1* 1/2023 Nakamura .............. C23C 14/24
2023/0009458 A1* 1/2023 Tasaki .................. H10K 85/654
2023/0011996 A1* 1/2023 Nakano ................ C07D 493/04
2023/0019712 A1* 1/2023 Nakano .............. H10K 85/6574
2023/0020436 A1* 1/2023 Nakano ................ C07D 307/77
2023/0042023 A1* 2/2023 Tasaki .................. H10K 85/633
2023/0088213 A1* 3/2023 Tasaki .................... H10K 85/40 257/40
2023/0089512 A1* 3/2023 Nishimura ......... H10K 85/6574 257/40
2023/0171977 A1* 6/2023 Tasaki .................... H05B 33/12 257/40
2023/0209998 A1* 6/2023 Takahashi ............ H10K 85/631 257/40
2023/0242465 A1* 8/2023 Nakano ................ C07D 211/54 257/40
2023/0284529 A1* 9/2023 Park ..................... H10K 85/615
2023/0309380 A1* 9/2023 Mizutani .............. H10K 85/631
2023/0406867 A1* 12/2023 Kim ..................... H10K 85/615
2024/0008363 A1* 1/2024 Itoi ...................... H10K 85/615

FOREIGN PATENT DOCUMENTS

JP 2013-515011 A 5/2013
JP 2017-193618 A 10/2017
KR 10-2010-0131745 A 12/2010
KR 10-2016-0102881 A 8/2016
KR 10-2019-0056338 A 5/2019
WO WO-02/47440 A1 6/2002
WO WO-2010/071362 A2 6/2010
WO WO-2010/099534 A2 9/2010
WO WO-2010/135395 A2 11/2010
WO WO-2011/028216 A1 3/2011
WO WO-2011/087815 A2 7/2011
WO WO-2016152544 A1 * 9/2016 ................ C07F 5/02
WO WO-2020/022751 1/2020

OTHER PUBLICATIONS

International Search Report and Written Opinion from PCT/JP2019/039090 dated Dec. 24, 2019 (13 pages).

International Search Report dated Nov. 26, 2019 for corresponding Application No. PCT/JP2019/039089.

Sugiyama et al—"Synthesis and Evaluation of Deuterated OLED Material", 2013, No. 32, pp. 5-8.

* cited by examiner

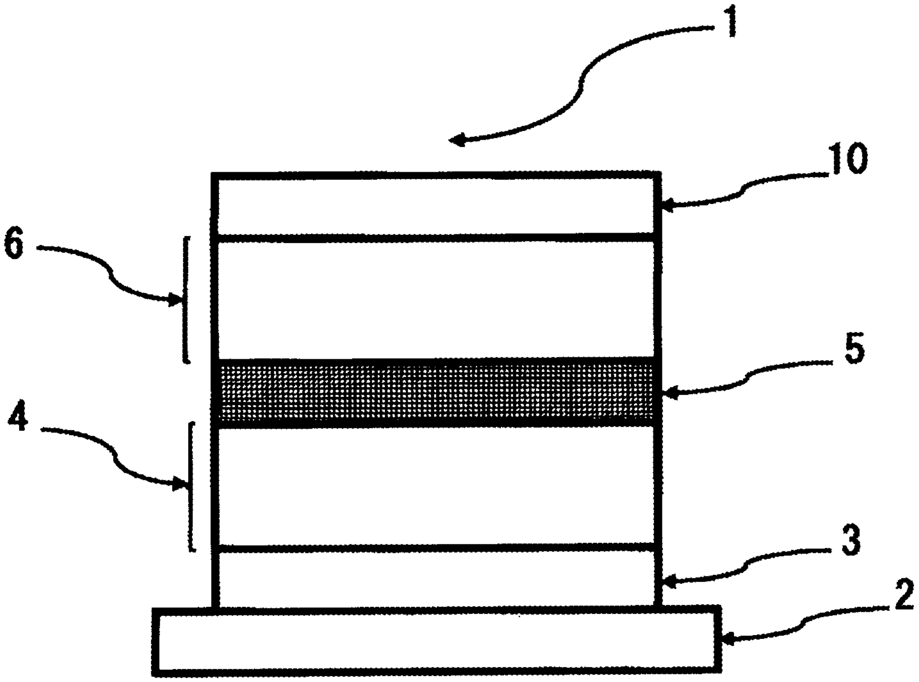
1
10
6
5
4
3
2

ORGANIC ELECTROLUMINESCENCE DEVICE AND ELECTRONIC APPARATUS PROVIDED WITH THE SAME

CROSS-REFERENCE TO RELATED APPLICATIONS

The present application claims priority under 35 U.S.C. § 371 to International Patent Application No. PCT/JP2019/039090, filed Oct. 3, 2019, which claims priority to and the benefit of Japanese Patent Application Nos. 2018-188682, filed on Oct. 3, 2018, 2019-086182, filed on Apr. 26, 2019, and U.S. patent application Ser. No. 16/514,934, filed on Jul. 17, 2019, Ser. No. 16/587,468, filed on Sep. 30, 2019. The contents of these applications are hereby incorporated by reference in their entireties.

TECHNICAL FIELD

The invention relates to an organic electroluminescence device and an electronic apparatus provided with the organic electroluminescence device.

BACKGROUND ART

When a voltage is applied to an organic electroluminescence device (hereinafter may be referred to as an organic EL device), holes are injected to an emitting layer from an anode and electrons are injected to an emitting layer from a cathode. In the emitting layer, injected holes and electrons are re-combined and excitons are formed.

Patent Documents 1 to 4 disclose anthracene compounds having a specific structure used as a host material for an emitting layer in an organic electroluminescence device.

RELATED ART DOCUMENTS

Patent Documents

Patent Document 1: WO2010/099534
Patent Document 2: WO2010/135395
Patent Document 3: WO2011/028216
Patent Document 4: WO2010/071362

SUMMARY OF THE INVENTION

As a material for an organic EL device, various materials are studied to decrease CIEy value in CIE1931 chromaticity diagram. However, a lifetime of an organic EL device becomes shorter when trying to decrease CIEy value, and thus, it is difficult to obtain an organic EL device which satisfies both the properties.

An object of the invention is to provide an organic EL device having a low CIEy value and a long lifetime, and to provide an electronic apparatus provided with the organic EL device.

As a result of extensive studies, the inventors have found that by using a compound represented by formula (1) (host material) and a compound having specific structure (one or more compounds selected from the group consisting of compounds represented by each of formulas (11), (21), (31), (41), (51), (61), (71) and (81): dopant material) in combination, an organic EL device having a low CIEy value and a long lifetime can be obtained, and they have achieved the invention.

According to the invention, the following organic EL device and electric apparatus can be provided.

1. An organic electroluminescence device comprising:
a cathode,
an anode, and
an emitting layer disposed between the cathode and the anode, wherein
the emitting layer comprises a compound represented by the following formula (1) and one or more compounds selected from the group consisting of a compound represented by formula (11), a compound represented by formula (21), a compound represented by formula (31), a compound represented by formula (41), a compound represented by formula (51), a compound represented by formula (61), a compound represented by formula (71) and a compound represented by formula (81):

(1)

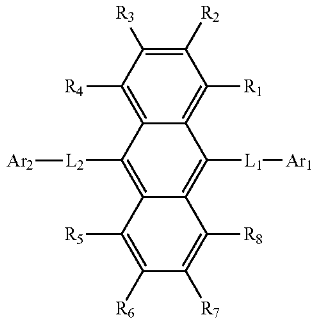

wherein in the formula (1),
$R_1$ to $R_8$ are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
$-Si(R_{901})(R_{902})(R_{903})$,
$-O-(R_{904})$,
$-S-(R_{905})$,
$-N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;
$R_{901}$ to $R_{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
when two or more of $R_{901}$ to $R_{907}$ exist, two or more of $R_{901}$ to $R_{907}$ or may be the same with or different from each other;
at least one of $R_1$ to $R_8$ is a deuterium atom;

two or more adjacent groups of $R_1$ to $R_4$ do not form a ring by bonding with each other, and two or more adjacent groups of $R_5$ to $R_8$ do not form a ring by bonding with each other;

$L_1$ and $L_2$ are independently a single bond, a substituted or unsubstituted phenylene group, a substituted or unsubstituted naphthylene group, a substituted or unsubstituted biphenylene group, a substituted or unsubstituted terphenylene group, a substituted or unsubstituted anthrylene group, or a substituted or unsubstituted phenanthrylene group;

$Ar_1$ and $Ar_2$ are independently a substituted or unsubstituted phenyl group, a substituted or unsubstituted naphthyl group, a substituted or unsubstituted biphenyl group, a substituted or unsubstituted terphenyl group, a substituted or unsubstituted anthryl group, or a substituted or unsubstituted phenanthryl group;

when $L_1$, $L_2$, $Ar_1$ and $Ar_2$ have a substituent, the substituent is an alkyl group having 1 to 50 carbon atoms, an alkenyl group having 2 to 50 carbon atoms, an alkynyl group having 2 to 50 carbon atoms, a cycloalkyl group having 3 to 50 ring carbon atoms, an alkylsilyl group having 1 to 50 carbon atoms, a halogen atom, or a cyano group;

(11)

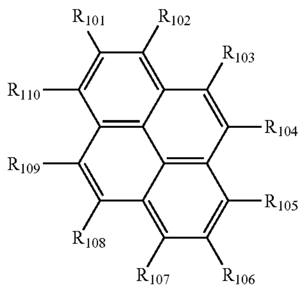

wherein, in the formula (11), one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;

at least one of $R_{10}$ to $R_{110}$ is a monovalent group represented by the formula (12);

$R_{101}$ to $R_{110}$ that do not form the substituted or unsubstituted, saturated or unsaturated ring and that are not a monovalent group represented by the following formula (12) are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $-Si(R_{901})(R_{902})(R_{903})$, $-O-(R_{904})$, $-S-(R_{905})$, $-N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

(12)

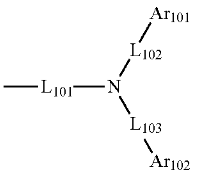

wherein, in the formula (12), $Ar_{101}$ and $Ar_{102}$ are independently a substituted or unsubstituted aryl group having 6 to 50 ring carbon atoms, or a substituted or unsubstituted monovalent heterocyclic group having 5 to 50 ring atoms;

$L_{101}$ to $L_{103}$ are independently a single bonded, a substituted or unsubstituted arylene group having 6 to 30 ring carbon atoms, or a substituted or unsubstituted divalent heterocyclic group having 5 to 30 ring atoms;

(21)

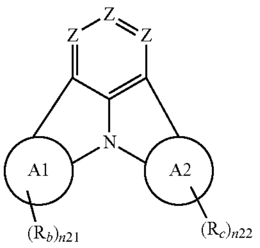

wherein, in the formula (21),

Zs are independently $CR_a$ or N;

A1 ring and A2 ring are independently a substituted or unsubstituted aromatic hydrocarbon ring having 6 to 50 ring carbon atoms, or a substituted or unsubstituted heterocyclic ring having 5 to 50 ring atoms;

when a plurality of $R_a$s exist, two or more adjacent groups of $R_a$ are bonded with each other to form a substituted or unsubstituted, saturated or unsaturated ring, or do not form a substituted or unsubstituted, saturated or unsaturated ring;

when a plurality of $R_b$s exist, one or more pairs of two or more adjacent groups of $R_b$ are bonded with each other to form a substituted or unsubstituted, saturated or unsaturated ring, or do not form a substituted or unsubstituted, saturated or unsaturated ring;

when a plurality of $R_c$s exist, one or more pairs of two or more adjacent groups of $R_c$ are bonded with each other to form a substituted or unsubstituted, saturated or unsaturated ring, or do not form a substituted or unsubstituted, saturated or unsaturated ring;

n21 and n22 are independently an integer of 0 to 4;

$R_a$ to $R_c$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

(31)

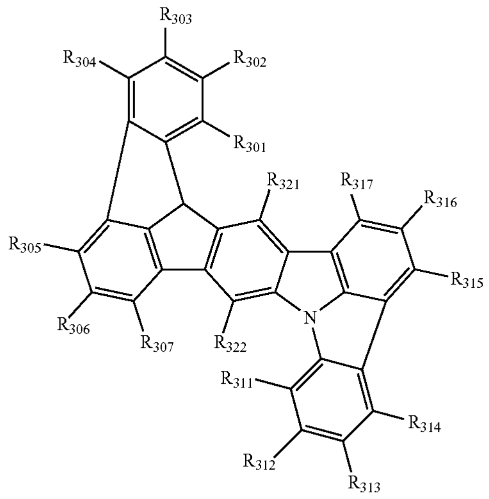

wherein, in the formula (31), one or more pairs of two or more adjacent groups of $R_{301}$ to $R_{307}$ and $R_{311}$ to $R_{317}$ form a substituted or unsubstituted, saturated or unsaturated ring, or do not form a substituted or unsubstituted saturated or unsaturated ring;

$R_{301}$ to $R_{307}$ and $R_{311}$ to $R_{317}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{321}$ and $R_{322}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

(41)

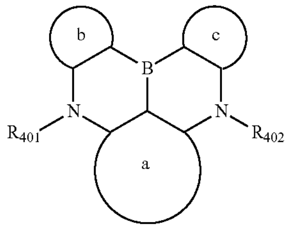

wherein, in the formula (41), a ring, b ring and c ring are independently a substituted or unsubstituted aromatic hydrocarbon ring having 6 to 50 ring carbon atoms, or a substituted or unsubstituted heterocyclic ring having 5 to 50 ring atoms;

$R_{401}$ and $R_{402}$ are independently bonded to the a ring, the b ring or the c ring to form a substituted or unsubstituted heterocyclic ring or do not form a substituted or unsubstituted heterocyclic ring;

$R_{401}$ and $R_{402}$ that do not form the substituted or unsubstituted heterocyclic ring are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

(51)

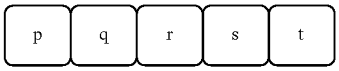

-continued (52)

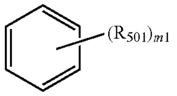

(53)

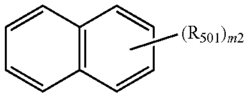

(54)

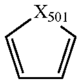

(55)

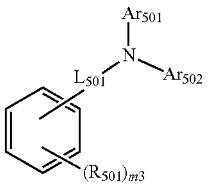

(56)

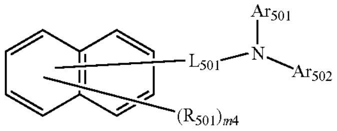

wherein, in the formula (51), r ring is a ring represented by the formula (52) or formula (53) which is fused to an adjacent ring at an arbitrary position;

q ring and s ring are independently a ring represented by the formula (54) which is fused to an adjacent ring at an arbitrary position;

p ring and t ring are independently a ring represented by the formula (55) or the formula (56) which is fused to an adjacent ring at an arbitrary position;

when a plurality of $R_{501}$s exist, adjacent $R_{501}$s are bonded with each other to form a substituted or unsubstituted, saturated or unsaturated ring, or do not form a substituted or unsubstituted, saturated or unsaturated ring;

$X_{501}$ is an oxygen atom, a sulfur atom, or $NR_{502}$;

$R_{501}$ and $R_{502}$ that do not form the substituted or unsubstituted saturated or unsaturated ring are a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

$Ar_{501}$ and $Ar_{502}$ are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

$L_{501}$ is a substituted or unsubstituted alkylene group having 1 to 50 carbon atoms, a substituted or unsubstituted alkenylene group having 2 to 50 carbon atoms, a substituted or unsubstituted alkynylene group having 2 to 50 carbon atoms, a substituted or unsubstituted cycloalkylene group having 3 to 50 ring carbon atoms, a substituted or unsubstituted arylene group having 6 to 50 ring carbon atoms, or a substituted or unsubstituted divalent heterocyclic group having 5 to 50 ring atoms;

m1 is an integer of 0 to 2, m2 is an integer of 0 to 4, m3s are independently an integer of 0 to 3, and m4s are independently an integer of 0 to 5; when a plurality of $R_{501}$s exist, $R_{501}$s may be the same or different;

(61)

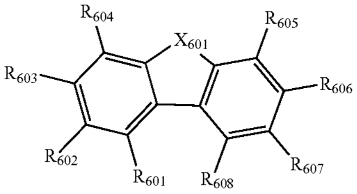

wherein, in the formula (61), at least one pair of $R_{601}$ and $R_{602}$, $R_{602}$ and $R_{603}$, and $R_{603}$ and $R_{604}$ are bonded with each other to form a divalent group represented by the formula (62);

at least one pair of $R_{605}$ and $R_{606}$, $R_{606}$ and $R_{607}$, and $R_{607}$ and $R_{608}$ are bonded with each other to form a divalent group represented by formula (63);

(62)

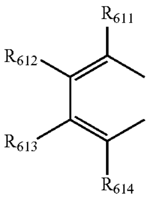

(63)

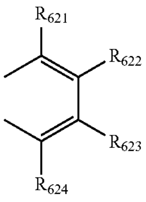

at least one of $R_{601}$ to $R_{604}$ that does not form the divalent group represented by the formula (62), and $R_{611}$ to $R_{614}$ is a monovalent group represented by the following formula (64);

at least one of $R_{605}$ to $R_{608}$ that do not form the divalent group represented by the formula (63), and $R_{621}$ to $R_{624}$ is a monovalent group represented by the following formula (64);

$X_{601}$ is an oxygen atom, a sulfur atom, or $NR_{609}$;

$R_{601}$ to $R_{606}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

(64)

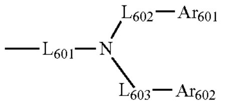

wherein, in the formula (64), $Ar_{601}$ and $Ar_{602}$ are independently a substituted or unsubstituted aryl group having 6 to 50 ring carbon atoms, or a substituted or unsubstituted monovalent heterocyclic group having 5 to 50 ring atoms;

$L_{601}$ to $L_{603}$ are independently a single bonded, a substituted or unsubstituted arylene group having 6 to 30 ring carbon atoms, a substituted or unsubstituted divalent heterocyclic group having 5 to 30 ring atoms, or a divalent linking group formed by bonding 2 to 4 of a substituted or unsubstituted arylene group having 6 to 30 ring carbon atoms, and a substituted or unsubstituted divalent heterocyclic group having 5 to 30 ring atoms;

(71)

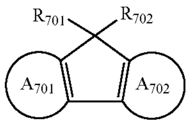

wherein, in the formula (71), $A_{701}$ ring and $A_{702}$ ring are independently a substituted or unsubstituted aromatic hydrocarbon ring having 6 to 50 ring carbon atoms, or a substituted or unsubstituted heterocyclic ring having 5 to 50 ring atoms;

One or more rings selected from the group consisting of $A_{701}$ ring and $A_{702}$ ring are bonded to the bond* of the structure represented by the following formula (72);

(72)

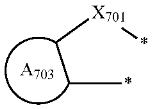

wherein, in the formula (72), $A_{703}$ rings are independently a substituted or unsubstituted aromatic hydrocarbon ring having 6 to 50 ring carbon atoms, or a substituted or unsubstituted heterocyclic ring having 5 to 50 ring atoms;

$X_{701}$ is $NR_{703}$, $C(R_{704})(R_{705})$, $Si(R_{706})(R_{707})$, $Ge(R_{708})(R_{709})$, O, S or Se;

$R_{701}$ and $R_{702}$ are bonded with each other to form a substituted or unsubstituted, saturated or unsaturated ring or do not form a substituted or unsubstituted saturated or unsaturated ring;

$R_{701}$ and $R_{702}$ that do not form the substituted or unsubstituted, saturated or unsaturated ring, and $R_{703}$ to $R_{709}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{905})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

(81)

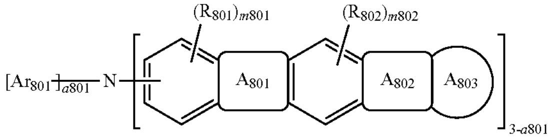

(82)

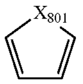

(83)

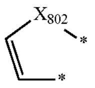

wherein, in the formula (81), $A_{801}$ ring is a ring represented by the formula (82) which is fused to an adjacent ring at an arbitrary position;

$A_{802}$ ring is a ring represented by the formula (83) which is fused to an adjacent ring at an arbitrary position;

two bonds * bond to $A_{803}$ ring at an arbitrary position;

$X_{801}$ and $X_{802}$ are independently $C(R_{803})(R_{804})$, $Si(R_{805})(R_{806})$, an oxygen atom, or a sulfur atom;

$A_{803}$ ring is a substituted or unsubstituted aromatic hydrocarbon ring having 6 to 50 ring carbon atoms, or a substituted or unsubstituted heterocyclic ring having 5 to 50 ring atoms;

$Ar_{801}$ is a substituted or unsubstituted aryl group having 6 to 50 ring carbon atoms, or a substituted or unsubstituted monovalent heterocyclic group having 5 to 50 ring atoms;

$R_{801}$ to $R_{806}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

m801 and m802 are independently an integer of 0 to 2; when m801 is 2, $R_{801}$'s may be the same as or different from each other, and when m802 is 2, $R_{802}$'s may be the same as or different from each other;

a801 is an integer of 0 to 2; when a801 is 0 or 1, the structure in the parentheses indicated by "3-a801" may be the same or different from each other; when a801 is 2, $Ar_{801}s$ may be the same or different from each other.

2. An electronic apparatus provided with the organic electroluminescence device according to the above 1.

According to the invention, an organic EL device having a low CIEy value and a long lifetime, and an electronic apparatus provided with the organic EL device can be provided.

BRIEF DESCRIPTION OF THE DRAWINGS

The FIGURE is a view showing a schematic configuration of one embodiment of the organic EL device of the invention.

MODE FOR CARRYING OUT THE INVENTION

Definition

In this specification, a hydrogen atom means an atom including isotopes different in the number of neutrons, namely, a protium, a deuterium and a tritium.

In the this specification, to a bondable position in which a symbol such as "R", or "D" representing a deuterium atom is not specified in a chemical formula, a hydrogen atom, that is, a light hydrogen atom, a deuterium atom, or a tritium atom is bonded thereto.

In the this specification, a term "ring carbon atoms" represents the number of carbon atoms among atoms forming a subject ring itself of a compound having a structure in which atoms are bonded in a ring form (for example, a monocyclic compound, a fused ring compound, a cross-linked compound, a carbocyclic compound or a heterocyclic compound). When the subject ring is substituted by a substituent, the carbon contained in the substituent is not included in the number of ring carbon atoms. The same shall apply to the "ring carbon atoms" described below, unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. Further, for example, a 9,9-diphenylfluorenyl group has 13 ring carbon atoms, and a 9,9'-spirobifluorenyl group has 25 ring carbon atoms.

Further, when the benzene ring or the naphthalene ring is substituted by an alkyl group as a substituent, for example, the number of carbon atoms of the alkyl group is not included in the ring carbon atoms.

In the this specification, a term "ring atoms" represents the number of atoms forming a subject ring itself of a compound having a structure in which atoms are bonded in a ring form (for example, a monocycle, a fused ring and a ring assembly) (for example, a monocyclic compound, a fused ring compound, a cross-linked compound, a carbocyclic compound or a heterocyclic compound). The term "ring atoms" does not include atoms which do not form the ring (for example, a hydrogen atom which terminates a bond of the atoms forming the ring) or atoms contained in a substituent when the ring is substituted by the substituent. The same shall apply to the "ring atoms" described below, unless otherwise noted. For example, a pyridine ring has 6 ring atoms, a quinazoline ring has 10 ring atoms, and a furan ring has 5 ring atoms. A hydrogen atom bonded with a carbon atom of the pyridine ring or the quinazoline ring or an atom forming the substituent is not included in the number of the ring atoms.

In the this specification, a term "XX to YY carbon atoms" in an expression of "substituted or unsubstituted ZZ group including XX to YY carbon atoms" represents the number of carbon atoms when the ZZ group is unsubstituted. The number of carbon atoms of a substituent when the ZZ group is substituted is not included. Here, "YY" is larger than "XX", and "XX" and "YY" each mean an integer of 1 or more.

In the this specification, a term "XX to YY atoms" in an expression of "substituted or unsubstituted ZZ group including XX to YY atoms" represents the number of atoms when the ZZ group is unsubstituted. The number of atoms of a substituent when the group is substituted is not included. Here, "YY" is larger than "XX", and "XX" and "YY" each mean an integer of 1 or more.

A term "unsubstituted" in the case of "substituted or unsubstituted ZZ group" means that the ZZ group is not substituted by a substituent, and a hydrogen atom is bonded therewith. Alternatively, a term "substituted" in the case of "substituted or unsubstituted ZZ group" means that one or more hydrogen atoms in the ZZ group are substituted by a substituent. Similarly, a term "substituted" in the case of "BB group substituted by an AA group" means that one or more hydrogen atoms in the BB group are substituted by the AA group.

Hereinafter, the substituent described herein will be described.

The number of the ring carbon atoms of the "unsubstituted aryl group" described herein is 6 to 50, preferably 6 to 30, and more preferably 6 to 18, unless otherwise specified.

The number of the ring carbon atoms of the "unsubstituted heterocyclic group" described herein is 5 to 50, preferably 5 to 30, and more preferably 5 to 18, unless otherwise specified.

The number of the carbon atoms of the "unsubstituted alkyl group" described herein is 1 to 50, preferably 1 to 20, and more preferably 1 to 6, unless otherwise specified.

The number of the carbon atoms of the "unsubstituted alkenyl group" described herein is 2 to 50, preferably 2 to 20, and more preferably 2 to 6, unless otherwise specified.

The number of the carbon atoms of the "unsubstituted alkynyl group" described herein is 2 to 50, preferably 2 to 20, and more preferably 2 to 6, unless otherwise specified.

The number of the ring carbon atoms of the "unsubstituted cycloalkyl group" described herein is 3 to 50, preferably 3 to 20, and more preferably 3 to 6, unless otherwise specified.

The number of the ring carbon atoms of the "unsubstituted arylene group" described herein is 6 to 50, preferably 6 to 30, and more preferably 6 to 18, unless otherwise specified.

The number of the ring atoms of the "unsubstituted divalent heterocyclic group" described herein is 5 to 50, preferably 5 to 30, and more preferably 5 to 18, unless otherwise specified.

The number of the carbon atoms of the "unsubstituted alkylene group" described herein is 1 to 50, preferably 1 to 20, and more preferably 1 to 6, unless otherwise specified.

Specific examples (specific example group G1) of the "substituted or unsubstituted aryl group" described herein include an unsubstituted aryl group and a substituted aryl group described below. (Here, a term "unsubstituted aryl group" refers to a case where the "substituted or unsubstituted aryl group" is the "unsubstituted aryl group," and a term "substituted aryl group" refers to a case where the "substituted or unsubstituted aryl group" is the "substituted aryl group". Hereinafter, a case of merely "aryl group" includes both the "unsubstituted aryl group" and the "substituted aryl group".

The "substituted aryl group" refers to a case where the "unsubstituted aryl group" has a substituent, and specific examples thereof include a group in which the "unsubstituted aryl group" has the substituent, and a substituted aryl group described below. It should be noted that examples of the "unsubstituted aryl group" and examples of the "substituted aryl group" listed herein are only one example, and the "substituted aryl group" described herein also includes a group in which a group in which "unsubstituted aryl group" has a substituent further has a substituent, and a group in which "substituted aryl group" further has a substituent, and the like.

An unsubstituted aryl group:
a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group, and
a perylenyl group.

A substituted aryl group:
an o-tolyl group,
a m-tolyl group,
a p-tolyl group,
a p-xylyl group,
a m-xylyl group,
an o-xylyl group,
a p-isopropyl phenyl group,
a m-isopropyl phenyl group,
an o-isopropyl phenyl group,
a p-t-butylphenyl group,
a m-t-butylphenyl group,
an o-t-butylphenyl group,
a 3,4,5-trimethylphenyl group,
a 9,9-dimethylfluorenyl group,
a 9,9-diphenylfluorenyl group
a 9,9-di(4-methylphenyl)fluorenyl group,
a 9,9-di(4-isopropylphenyl)fluorenyl group,
a 9,9-di(4-t-butylphenyl)fluorenyl group,
a cyanophenyl group,
a triphenylsilylphenyl group,
a trimethylsilylphenyl group,
a phenylnaphthyl group, and
a naphthylphenyl group.

The "heterocyclic group" described herein is a ring group including at least one hetero atom in the ring atom. Specific examples of the hetero atom include a nitrogen atom, an oxygen atom, a sulfur atom, a silicon atom, a phosphorus atom and a boron atom.

The "heterocyclic group" described herein may be a monocyclic group, or a fused ring group.

The "heterocyclic group" described herein may be an aromatic heterocyclic group, or an aliphatic heterocyclic group.

Specific examples (specific example group G2) of the "substituted or unsubstituted heterocyclic group" include an unsubstituted heterocyclic group and a substituted heterocyclic group described below. (Here, the unsubstituted heterocyclic group refers to a case where the "substituted or unsubstituted heterocyclic group" is the "unsubstituted heterocyclic group," and the substituted heterocyclic group refers to a case where the "substituted or unsubstituted heterocyclic group" is the "substituted heterocyclic group".

Hereinafter, the case of merely “heterocyclic group” includes both the “unsubstituted heterocyclic group” and the “substituted heterocyclic group”.

The “substituted heterocyclic group” refers to a case where the “unsubstituted heterocyclic group” has a substituent, and specific examples thereof include a group in which the “unsubstituted heterocyclic group” has a substituent, and a substituted heterocyclic group described below. It should be noted that examples of the “unsubstituted heterocyclic group” and examples of the “substituted heterocyclic group” listed herein are merely one example, and the “substituted heterocyclic group” described herein also includes a group in which “unsubstituted heterocyclic group” which has a substituent further has a substituent, and a group in which “substituted heterocyclic group” further has a substituent, and the like.

An unsubstituted heterocyclic group including a nitrogen atom:

a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolyl group,
a phthalazinyl group,
a quinazolinyl group,
a quinoxalinyl group,
a benzimidazolyl group,
an indazolyl group,
a phenanthrolinyl group,
a phenanthridinyl group
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

An unsubstituted heterocyclic group including an oxygen atom:

a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

An unsubstituted heterocyclic group including a sulfur atom:

a thienyl group,
a thiazolyl group,
an isothiazolyl group,
a thiadiazolyl group,
a benzothiophenyl group,
an isobenzothiophenyl group,
a dibenzothiophenyl group,
a naphthobenzothiophenyl group,
a benzothiazolyl group,
a benzisothiazolyl group,
a phenothiazinyl group,
a dinaphthothiophenyl group,
an azadibenzothiophenyl group,
a diazadibenzothiophenyl group,
an azanaphthobenzothiophenyl group, and
a diazanaphthobenzothiophenyl group.

A substituted heterocyclic group including a nitrogen atom:

a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenylyltriazinyl group,
a diphenyltriazinyl group,
a phenylquinazolinyl group, and
a biphenylylquinazolinyl group.

A substituted heterocyclic group including an oxygen atom:

a phenyldibenzofuranyl group,
a methyldibenzofuranyl group,
a t-butyldibenzofuranyl group, and
a monovalent residue of spiro[9H-xanthene-9,9'-[9H]fluorene].

A substituted heterocyclic group including a sulfur atom:

a phenyldibenzothiophenyl group,
a methyldibenzothiophenyl group,
a t-butyldibenzothiophenyl group, and
a monovalent residue of spiro[9H-thioxantene-9,9'-[9H]fluorene].

A monovalent group derived from the following unsubstituted heterocyclic ring containing at least one of a nitrogen atom, an oxygen atom and a sulfur atom by removal of one hydrogen atom bonded to the ring atoms thereof, and a monovalent group in which a monovalent group derived from the following unsubstituted heterocyclic ring has a substituent by removal of one hydrogen atom bonded to the ring atoms thereof:

(XY-1)
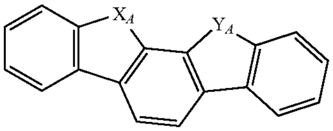
(XY-2)
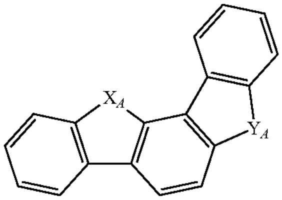
(XY-3)
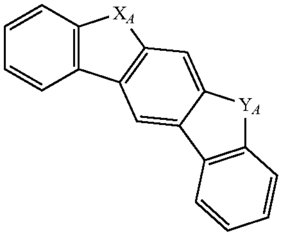
(XY-4)
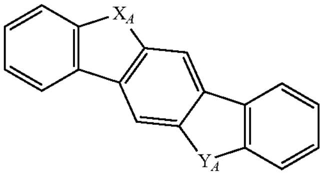
(XY-5)
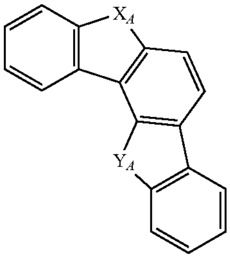
(XY-6)
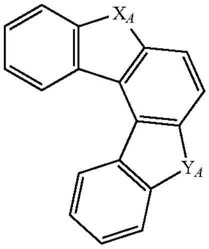
(XY-7)
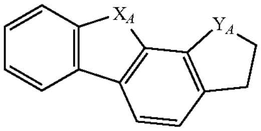
(XY-8)
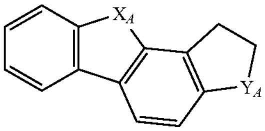
-continued
(XY-9)
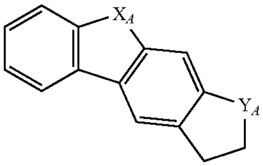
(XY-10)
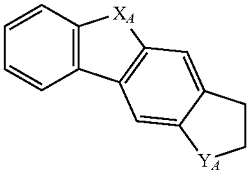
(XY-11)
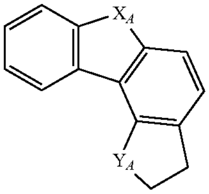
(XY-12)
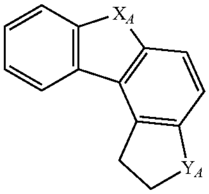
(XY-13)
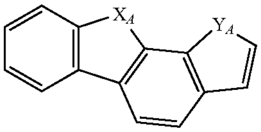
(XY-14)
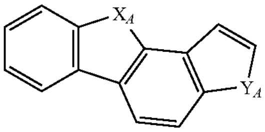
(XY-15)
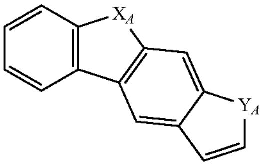
(XY-16)
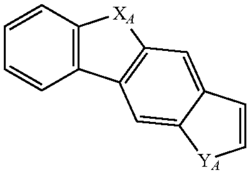
(XY-17)
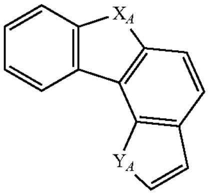

-continued (XY-18)

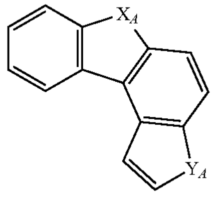

In the formulas (XY-1) to (XY-18), $X_A$ and $Y_A$ are independently an oxygen atom, a sulfur atom, NH or $CH_2$. However, at least one of $X_A$ and $Y_A$ is an oxygen atom, a sulfur atom or NH.

The heterocyclic ring represented by the formulas (XY-1) to (XY-18) becomes a monovalent heterocyclic group including a bond at an arbitrary position.

An expression "the monovalent group derived from the unsubstituted heterocyclic ring represented by the formulas (XY-1) to (XY-18) has a substituent" refers to a case where the hydrogen atom bonded with the carbon atom which constitutes a skeleton of the formulas is substituted by a substituent, or a state in which $X_A$ or $Y_A$ is NH or $CH_2$, and the hydrogen atom in the NH or $CH_2$ is replaced with a substituent.

Specific examples (specific example group G3) of the "substituted or unsubstituted alkyl group" include an unsubstituted alkyl group and a substituted alkyl group described below (Here, the unsubstituted alkyl group refers to a case where the "substituted or unsubstituted alkyl group" is the "unsubstituted alkyl group," and the substituted alkyl group refers to a case where the "substituted or unsubstituted alkyl group" is the "substituted alkyl group"). Hereinafter, the case of merely "alkyl group" includes both the "unsubstituted alkyl group" and the "substituted alkyl group".

The "substituted alkyl group" refers to a case where the "unsubstituted alkyl group" has a substituent, and specific examples thereof include a group in which the "unsubstituted alkyl group" has a substituent, and a substituted alkyl group described below. It should be noted that examples of the "unsubstituted alkyl group" and examples of the "substituted alkyl group" listed herein are merely one example, and the "substituted alkyl group" described herein also includes a group in which "unsubstituted alkyl group" has a substituent further has a substituent, a group in which "substituted alkyl group" further has a substituent, and the like.

An unsubstituted alkyl group:

a methyl group,
an ethyl group,
a n-propyl group,
an isopropyl group,
a n-butyl group,
an isobutyl group,
a s-butyl group, and
a t-butyl group.

A substituted alkyl group:

a heptafluoropropyl group (including an isomer),
a pentafluoroethyl group,
a 2,2,2-trifluoroethyl group, and
a trifluoromethyl group.

Specific examples (specific example group G4) of the "substituted or unsubstituted alkenyl group" include an unsubstituted alkenyl group and a substituted alkenyl group described below. (Here, the unsubstituted alkenyl group refers to a case where the "substituted or unsubstituted alkenyl group" is the "unsubstituted alkenyl group," and the substituted alkenyl group refers to a case where the "substituted or unsubstituted alkenyl group" is the "substituted alkenyl group"). Hereinafter, the case of merely "alkenyl group" includes both the "unsubstituted alkenyl group" and the "substituted alkenyl group".

The "substituted alkenyl group" refers to a case where the "unsubstituted alkenyl group" has a substituent, and specific examples thereof include a group in which the "unsubstituted alkenyl group" has a substituent, and a substituted alkenyl group described below. It should be noted that examples of the "unsubstituted alkenyl group" and examples of the "substituted alkenyl group" listed herein are merely one example, and the "substituted alkenyl group" described herein also includes a group in which "unsubstituted alkenyl group" has a substituent further has a substituent, a group in which "substituted alkenyl group" further has a substituent, and the like.

An unsubstituted alkenyl group and a substituted alkenyl group:

a vinyl group,
an allyl group,
a 1-butenyl group,
a 2-butenyl group,
a 3-butenyl group,
a 1,3-butanedienyl group,
a 1-methylvinyl group,
a 1-methylallyl group,
a 1,1-dimethylallyl group,
a 2-methylallyl group, and
a 1,2-dimethylallyl group.

Specific examples (specific example group G5) of the "substituted or unsubstituted alkynyl group" include an unsubstituted alkynyl group described below. (Here, the unsubstituted alkynyl group refers to a case where the "substituted or unsubstituted alkynyl group" is the "unsubstituted alkynyl group"). Hereinafter, a case of merely "alkynyl group" includes both the "unsubstituted alkynyl group" and the "substituted alkynyl group".

The "substituted alkynyl group" refers to a case where the "unsubstituted alkynyl group" has a substituent, and specific examples thereof include a group in which the "unsubstituted alkynyl group" described below has a substituent.

An unsubstituted alkynyl group:

an ethynyl group.

Specific examples (specific example group G6) of the "substituted or unsubstituted cycloalkyl group" described herein include an unsubstituted cycloalkyl group and a substituted cycloalkyl group described below (Here, the unsubstituted cycloalkyl group refers to a case where the "substituted or unsubstituted cycloalkyl group" is the "unsubstituted cycloalkyl group," and the substituted cycloalkyl group refers to a case where the "substituted or unsubstituted cycloalkyl group" is the "substituted cycloalkyl group"). Hereinafter, a case of merely "cycloalkyl group" includes both the "unsubstituted cycloalkyl group" and the "substituted cycloalkyl group".

The "substituted cycloalkyl group" refers to a case where the "unsubstituted cycloalkyl group" a the substituent, and specific examples thereof include a group in which the "unsubstituted cycloalkyl group" has a substituent, and a substituted cycloalkyl group described below. It should be noted that examples of the "unsubstituted cycloalkyl group" and examples of the "substituted cycloalkyl group" listed herein are merely one example, and the "substituted cycloalkyl group" described herein also includes a group in which "unsubstituted cycloalkyl group" has a substituent further has a substituent, a group in which "substituted cycloalkyl group" further has a substituent, and the like.

An unsubstituted aliphatic ring group:

a cyclopropyl group, a cyclobutyl group, a cyclopentyl group, a cyclohexyl group, a 1-adamantyl group, a 2-adamantyl group, a 1-norbomyl group, and a 2-norbomyl group.

A substituted cycloalkyl group:

a 4-methylcyclohexyl group.

Specific examples (specific example group G7) of the group represented by —Si($R_{901}$)($R_{902}$)($R_{903}$) described herein include —Si(G1)(G1)(G1), —Si(G1)(G2)(G2), —Si(G1)(G1)(G2), —Si(G2)(G2)(G2), —Si(G3)(G3)(G3), —Si(G5)(G5)(G5) and —Si(G6)(G6)(G6).

In which,

G1 is the "aryl group" described in the specific example group G1.

G2 is the "heterocyclic group" described in the specific example group G2.

G3 is the "alkyl group" described in the specific example group G3.

G5 is the "alkynyl group" described in the specific example group G5.

G6 is the "cycloalkyl group" described in the specific example group G6.

Specific examples (specific example group G8) of the group represented by —O—($R_{904}$) described herein include

—O(G1),

—O(G2),

—O(G3) and

—O(G6).

In which,

G1 is the "aryl group" described in the specific example group G1.

G2 is the "heterocyclic group" described in the specific example group G2.

G3 is the "alkyl group" described in the specific example group G3.

G6 is the "cycloalkyl group" described in the specific example group G6.

Specific examples (specific example group G9) of the group represented by —S—($R_{905}$) described herein include

—S(G1),

—S(G2),

—S(G3) and

—S(G6).

In which,

G1 is the "aryl group" described in the specific example group G1.

G2 is the "heterocycle group" described in the specific example group G2.

G3 is the "alkyl group" described in the specific example group G3.

G6 is the "cycloalkyl group" described in the specific example group G6.

Specific examples (specific example group G10) of the group represented by —N($R_{906}$)($R_{907}$) described herein include

—N(G1)(G1),

—N(G2)(G2),

—N(G1)(G2),

—N(G3)(G3) and

—N(G6) (G6).

In which,

G1 is the "aryl group" described in the specific example group G1.

G2 is the "heterocycle group" described in the specific example group G2.

G3 is the "alkyl group" described in the specific example group G3.

G6 is the "cycloalkyl group" described in the specific example group G6.

Specific examples (specific example group G11) of the "halogen atom" described herein include a fluorine atom, a chlorine atom, a bromine atom and an iodine atom.

Specific examples of the "alkoxy group" described herein include a group represented by —O(G3), where G3 is the "alkyl group" described in the specific example group G3. The number of carbon atoms of the "unsubstituted alkoxy group" are 1 to 50, preferably 1 to 30, and more preferably 1 to 18, unless otherwise specified.

Specific examples of the "alkylthio group" described herein include a group represented by —S(G3), where G3 is the "alkyl group" described in the specific example group G3. The number of carbon atoms of the "unsubstituted alkylthio group" are 1 to 50, preferably 1 to 30, and more preferably 1 to 18, unless otherwise specified.

Specific examples of the "aryloxy group" described herein include a group represented by —O(G1), where G1 is the "aryl group" described in the specific example group G1. The number of ring carbon atoms of the "unsubstituted aryloxy group" are 6 to 50, preferably 6 to 30, and more preferably 6 to 18, unless otherwise specified.

Specific examples of the "arylthio group" described herein include a group represented by —S(G1), where G1 is the "aryl group" described in the specific example group G1. The number of ring carbon atoms of the "unsubstituted arylthio group" are 6 to 50, preferably 6 to 30, and more preferably 6 to 18, unless otherwise specified.

Specific examples of the "aralkyl group" described herein include a group represented by -(G3)-(G1), where G3 is the "alkyl group" described in the specific example group G3, and G1 is the "aryl group" described in the specific example group G1. Accordingly, the "aralkyl group" is one embodiment of the "substituted alkyl group" substituted by the "aryl group". The number of carbon atoms of the "unsubstituted aralkyl group," which is the "unsubstituted alkyl group" substituted by the "unsubstituted aryl group," are 7 to 50, preferably 7 to 30, and more preferably 7 to 18, unless otherwise specified.

Specific example of the "aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, and a 2-β-naphthylisopropyl group.

The substituted or unsubstituted aryl group described herein is, unless otherwise specified, preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-diphenylfluorenyl group, or the like.

The substituted or unsubstituted heterocyclic group described herein is, unless otherwise specified, preferably a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (a(9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazole-9-yl group, a phenylcarbazol-9-yl group, a phenyltriazinyl group, a biphenylyltriazinyl group, diphenyltriazinyl group, a phenyldibenzofuranyl group, a phenyldibenzothiophenyl group, an indrocarbazolyl group, a pyrazinyl group, a pyridazinyl group, a quinazolinyl group, a cinnolinyl group, a phthalazinyl group, a quinoxalinyl group, a pyrrolyl group, an indolyl group, a pyrrolo[3,2,1-jk]carbazolyl group, a furanyl group, a benzofuranyl group, a thiophenyl group, a benzothiophenyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, an indro[3,2,1-jk]carbazolyl group, a dibenzothiophenyl group, or the like.

The dibenzofuranyl group and the dibenzothiophenyl group as described above are specifically any group described below, unless otherwise specified.

(XY-76)

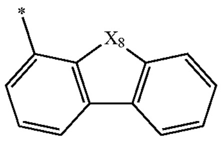

(XY-77)

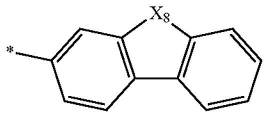

(XY-78)

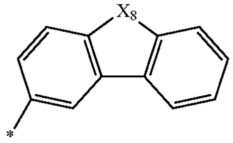

-continued (XY-79)

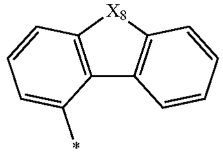

In the formulas (XY-76) to (XY-79), $X_B$ is an oxygen atom or a sulfur atom.

The substituted or unsubstituted alkyl group described herein is, unless otherwise specified, preferably a methyl group, an ethyl group, a propyl group, an isopropyl group, a n-butyl group, an isobutyl group, a t-butyl group, or the like.

The "substituted or unsubstituted arylene group" descried herein refers to a group in which the above-described "aryl group" is converted into divalence, unless otherwise specified. Specific examples (specific example group G12) of the "substituted or unsubstituted arylene group" include a group in which the "aryl group" described in the specific example group G1 is converted into divalence. Namely, specific examples (specific example group G12) of the "substituted or unsubstituted arylene group" refer to a group derived from the "aryl group" described in specific example group G1 by removal of one hydrogen atom bonded to the ring carbon atoms thereof.

Specific examples (specific example group G13) of the "substituted or unsubstituted divalent heterocyclic group" include a group in which the "heterocyclic group" described in the specific example group G2 is converted into divalence. Namely, specific examples (specific example group G13) of the "substituted or unsubstituted divalent heterocyclic group" refer to a group derived from the "heterocyclic group" described in specific example group G2 by removal of one hydrogen atom bonded to the ring atoms thereof.

Specific examples (specific example group G14) of the "substituted or unsubstituted alkylene group" include a group in which the "alkyl group" described in the specific example group G3 is converted into divalence. Namely, specific examples (specific example group G14) of the "substituted or unsubstituted alkylene group" refer to a group derived from the "alkyl group" described in specific example group G3 by removal of one hydrogen atom bonded to the carbon atoms constituting the alkane structure thereof.

The substituted or unsubstituted arylene group described herein is any group described below, unless otherwise specified.

(XY-20)

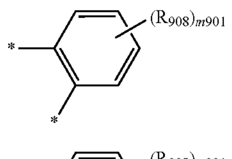

(XY-21)

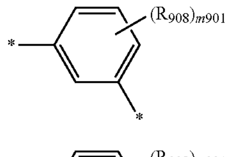

(XY-22)

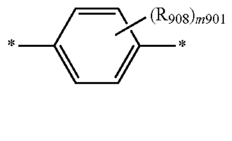

-continued
(XY-23)
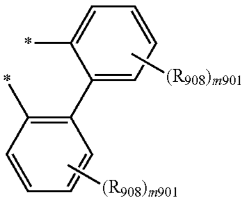
(XY-24)
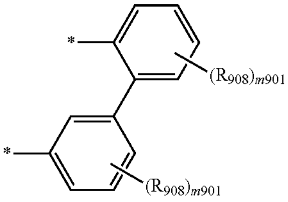
(XY-25)
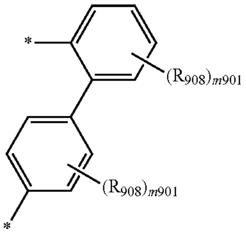
(XY-26)
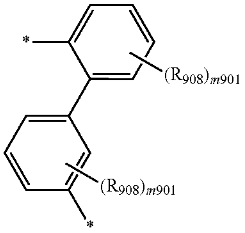
(XY-27)
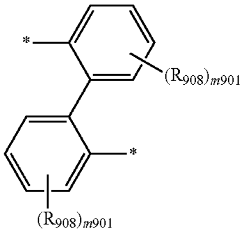
(XY-28)
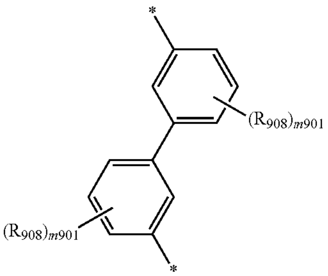
(XY-29)
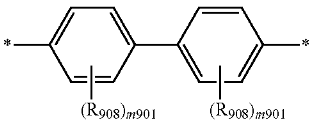
-continued
(XY-83)
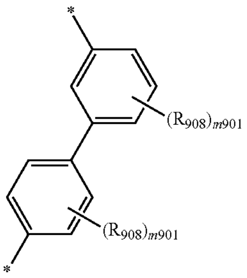
(XY-84)
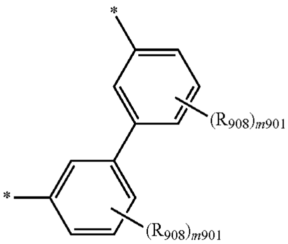
In the formulas (XY-20) to (XY-29), (XY-83) and (XY-84), $R_{908}$ is a substituent.
Then, m901 is an integer of 0 to 4, and when m901 is 2 or more, a plurality of $R_{908}$ may be the same with or different from each other.
(XY-30)
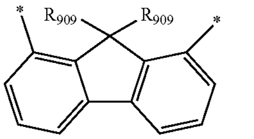
(XY-31)
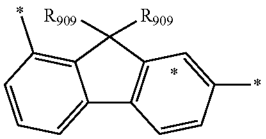
(XY-32)
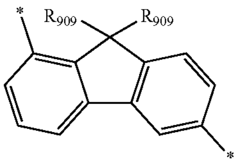
(XY-33)
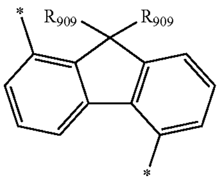
(XY-34)
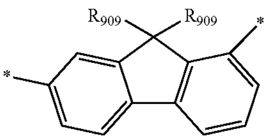

-continued (XY-35)

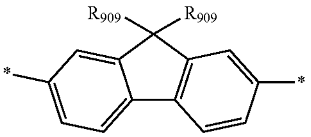

(XY-36)

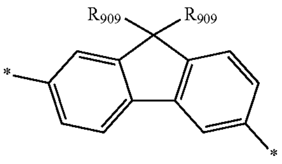

(XY-37)

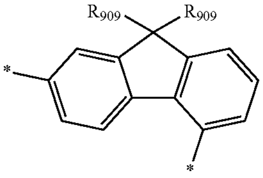

(XY-38)

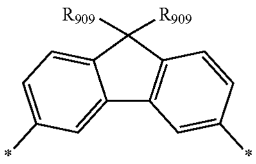

(XY-39)

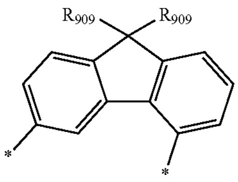

(XY-40)

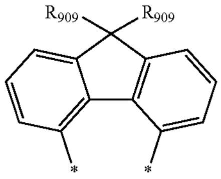

In the formulas (XY-30) to (XY-40), $R_{909}$ is independently a hydrogen atom or a substituent. Two of $R_{909}$ may form a ring by bonding with each other through a single bond.

(XY-41)

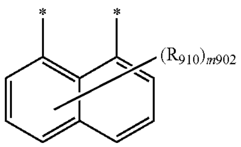

(XY-42)

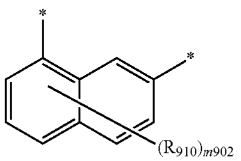

-continued (XY-43)

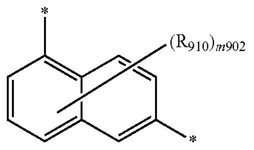

(XY-44)

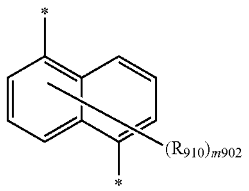

(XY-45)

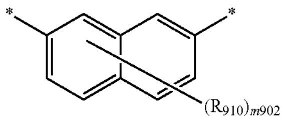

(XY-46)

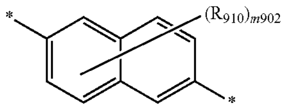

In the formulas (XY-41) to (XY-46), $R_{910}$ is a substituent.

Then, m902 is an integer of 0 to 6. When m902 is 2 or more, a plurality of $R_{910}$ may be the same with or different from each other.

The substituted or unsubstituted divalent heterocyclic group described herein is preferably any group described below, unless otherwise specified.

(XY-50)

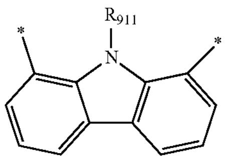

(XY-51)

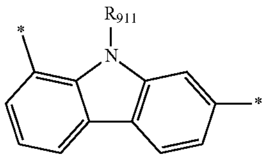

(XY-52)

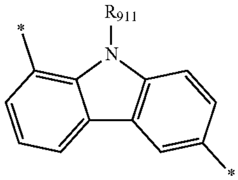

(XY-53)

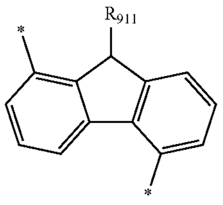

-continued
(XY-54)
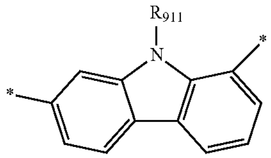
(XY-55)
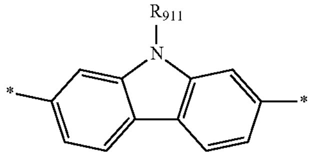
(XY-56)
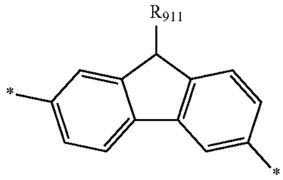
(XY-57)
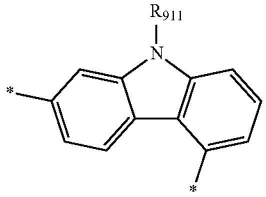
(XY-58)
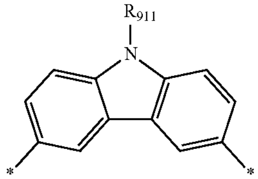
(XY-59)
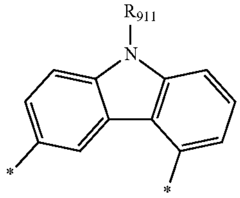
(XY-60)
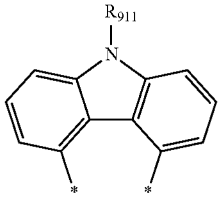
(XY-61)
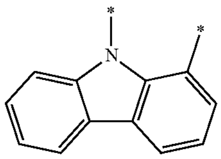
-continued
(XY-62)
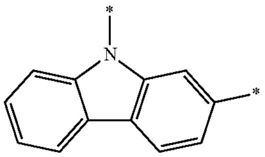
(XY-63)
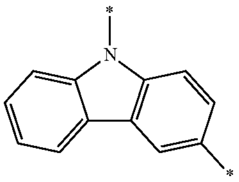
(XY-64)
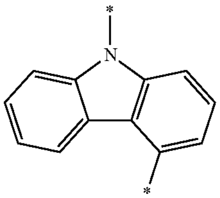
In the formulas (XY-50) to (XY-60), $R_{911}$ is a hydrogen atom or a substituent.
(XY-65)
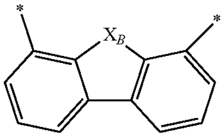
(XY-66)
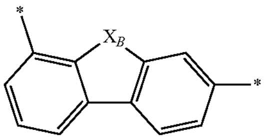
(XY-67)
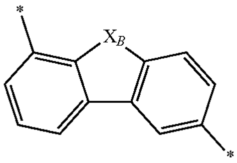
(XY-68)
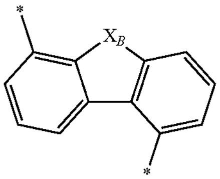
(XY-69)
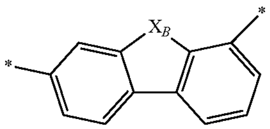
(XY-70)
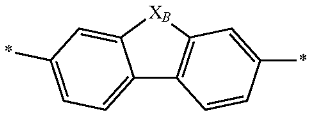

-continued (XY-71)

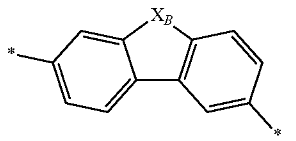

(XY-72)

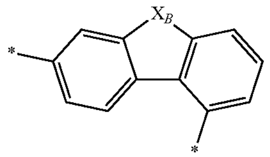

(XY-73)

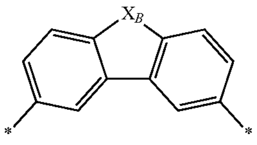

(XY-74)

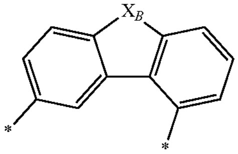

(XY-75)

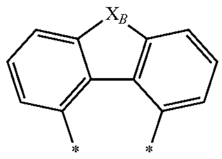

In the formulas (XY-65) to (XY-75), $X_B$ is an oxygen atom or a sulfur atom.

Herein, a case where "one or more sets of two or more groups adjacent to each other form a substituted or unsubstituted and saturated or unsaturated ring by bonding with each other" will be described by taking, as an example, a case of an anthracene compound represented by the following formula (XY-80) in which a mother skeleton is an anthracene ring.

(XY-80)

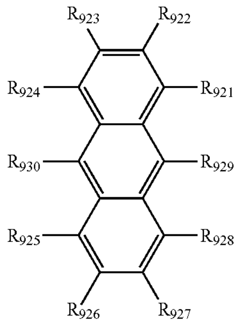

For example, two adjacent to each other into one set when "one or more sets of two or more groups adjacent to each other form the ring by bonding with each other" among $R_{921}$ to $R_{930}$ include $R_{921}$ and $R_{922}$, $R_{922}$ and $R_{923}$, $R_{923}$ and $R_{924}$, $R_{924}$ and $R_{930}$, $R_{930}$ and $R_{925}$, $R_{925}$ and $R_{926}$, $R_{926}$ and $R_{927}$, $R_{927}$ and $R_{928}$, $R_{928}$ and $R_{929}$, and $R_{929}$ and $R_{921}$.

The above-described "one or more sets" means that two or more sets of two groups adjacent to each other may simultaneously form the ring. For example, a case where $R_{921}$ and $R_{922}$ form a ring A by bonding with each other, and simultaneously $R_{925}$ and $R_{926}$ form a ring B by bonding with each other is represented by the following formula (XY-81).

(XY-81)

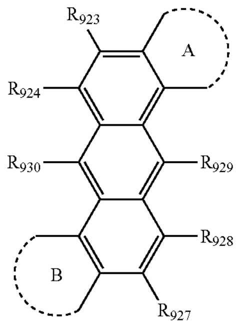

A case where "two or more groups adjacent to each other" form a ring means that, for example, $R_{921}$ and $R_{922}$ form a ring A by bonding with each other, and $R_{922}$ and $R_{923}$ form a ring C by bonding with each other. A case where the ring A and ring C sharing $R_{922}$ are formed, in which the ring A and the ring C are fused to the anthracene mother skeleton by three of $R_{921}$ to $R_{923}$ adjacent to each other, is represented by the following (XY-82).

(XY-82)

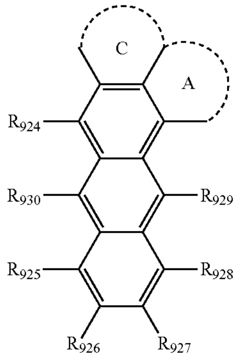

The rings A to C formed in the formulas (XY-81) and (XY-82) are a saturated or unsaturated ring.

A term "unsaturated ring" means an aromatic hydrocarbon ring or an aromatic heterocyclic ring. A term "saturated ring" means an aliphatic hydrocarbon ring or an aliphatic heterocyclic ring.

For example, the ring A formed by $R_{921}$ and $R_{922}$ being bonded with each other, represented by the formula (XY-81), means a ring formed by a carbon atom of the anthracene skeleton bonded with $R_{92}$, a carbon atom of the anthracene skeleton bonded with $R_{922}$, and one or more arbitrary elements. Specific examples include, when the ring A is formed by $R_{921}$ and $R_{922}$, a case where an unsaturated ring is formed of a carbon atom of an anthracene skeleton bonded with $R_{921}$, a carbon atom of the anthracene skeleton bonded with $R_{922}$, and four carbon atoms, in which a ring formed by $R_{921}$ and $R_{922}$ is formed into a benzene ring. Further, when a saturated ring is formed, the ring is formed into a cyclohexane ring.

Here, "arbitrary elements" are preferably a C element, a N element, an O element and a S element. In the arbitrary elements (for example, a case of the C element or the N element), the bond(s) that is(are) not involved in the formation of the ring may be terminated by a hydrogen atom, or may be substituted by an arbitrary substituent. When the ring contains the arbitrary elements other than the C element, the ring to be formed is a heterocyclic ring.

The number of "one or more arbitrary elements" forming the saturated or unsaturated ring is preferably 2 or more and 15 or less, more preferably 3 or more and 12 or less, and further preferably 3 or more and 5 or less.

As specific examples of the aromatic hydrocarbon ring, a structure in which the aryl group described in specific example group G1 is terminated with a hydrogen atom may be mentioned.

As specific examples of the aromatic heterocyclic ring, a structure in which the aromatic heterocyclic group described in specific example group G2 is terminated with a hydrogen atom may be mentioned.

As specific examples of the aliphatic hydrocarbon ring, a structure in which the cycloalkyl group described in specific example group G6 is terminated with a hydrogen atom may be mentioned.

When the above-described "saturated or unsaturated ring" has a substituent, the substituent is an "arbitrary substituent" as described below, for example. When the above-mentioned "saturated or unsaturated ring" has a substituent, specific examples of the substituent refer to the substituents described in above-mentioned "the substituent described herein".

In one embodiment of the this specification, the substituent (hereinafter, referred to as an "arbitrary substituent" in several cases) in the case of the "substituted or unsubstituted" is a group selected from the group consisting of an unsubstituted alkyl group including 1 to 50 carbon atoms, an unsubstituted alkenyl group including 2 to 50 carbon atoms, an unsubstituted alkynyl group including 2 to 50 carbon atoms, an unsubstituted cycloalkyl group including 3 to 50 ring carbon atoms, —Si($R_{901}$)($R_{902}$)($R_{903}$),

—O—($R_{904}$),

—S—($R_{905}$)

N($R_{906}$)($R_{907}$)

wherein, $R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms; and when two or more of $R_{901}$ to $R_{907}$ exist, two or more of $R_{901}$ to $R_{907}$ may be the same with or different from each other, a halogen atom, a cyano group, a nitro group, an unsubstituted aryl group including 6 to 50 ring carbon atoms, and an unsubstituted monovalent heterocyclic group including 5 to 50 ring atoms.

In one embodiment, the substituent in the case of "substituted or unsubstituted" is a group selected from the group consisting of an alkyl group including 1 to 50 carbon atoms, an aryl group including 6 to 50 ring carbon atoms, and a monovalent heterocyclic group including 5 to 50 ring atoms.

In one embodiment, the substituent in the case of "substituted or unsubstituted" is a group selected from the group consisting of an alkyl group including 1 to 18 carbon atoms, an aryl group including 6 to 18 ring carbon atoms, and a monovalent heterocyclic group including 5 to 18 ring atoms.

Specific examples of each group of the arbitrary substituent described above are as described above.

Herein, unless otherwise specified, the saturated or unsaturated ring (preferably substituted or unsubstituted and saturated or unsaturated five-membered or six-membered ring, more preferably a benzene ring) may be formed by the arbitrary substituents adjacent to each other.

Herein, unless otherwise specified, the arbitrary substituent may further have the substituent. Specific examples of the substituent that the arbitrary substituent further has include to the ones same as the arbitrary substituent described above.

[Organic EL Device]

The organic EL device according to one aspect of the invention comprises a cathode, an anode and an emitting layer disposed between the cathode and the anode, and it is characterized in that the emitting layer comprises a compound represented by the following formula (1) and one or more compounds selected from the group consisting of a compound represented by formula (11), a compound represented by formula (21), a compound represented by formula (31), a compound represented by formula (41), a compound represented by formula (51), a compound represented by formula (61), a compound represented by formula (71) and a compound represented by formula (81).

Each compound is described later.

The organic EL device according to one aspect of the invention exhibits high device performance by possessing the above-mentioned constitution. Specifically, it is possible to provide an organic EL device which is able to simultaneously satisfy both characteristics of a low CIEy value and a long life.

According to one aspect of the present invention, a method for improving a performance of an organic EL device can also be provided. The method is characterized in that the compound represented by the formula (1) and one or more compounds selected from the group consisting of the compounds represented by each of formulas (11) to (81) are used in combination in the emitting layer of the organic EL device. Specifically, the method can improve an organic EL device performance as compared with the case where a compound having the same structure as formula (1) except that only protium atoms are contained as hydrogen atoms (hereinafter also referred to as "protium compound") is used as a host material. The case where the protium compound is used means that a host material in an emitting layer consists essentially of the protium compound (the ratio of the protium compound to the sum of the protium compound and the compound represented by formula (1) is 90 mol % or more, 95 mol % or more, or 99 mol % or more).

That is, it is possible to increase a performance of an organic EL device by, instead of a protium compound or in addition to a protium compound, using a compound obtained by replacing at least one protium atoms on an anthracene skeleton of the protium compound with a deuterium atom (a compound represented by formula (1)) as a host material.

A schematic outline of the organic EL device of one aspect of the invention is explained by reference to the FIGURE.

The organic EL device 1 according to one aspect of the invention comprises substrate 2, anode 3, emitting layer 5, cathode 10, organic layer 4 disposed between the anode 3 and the emitting layer 5, and organic layer 6 disposed between the emitting layer 5 and the cathode 10.

The compound represented by the formula (1) and one or more compounds selected from a group consisting of a compound represented by formula (11), a compound represented by formula (21), a compound represented by formula (31), a compound represented by formula (41), a compound represented by formula (51), a compound represented by formula (61), a compound represented by formula (71) and a compound represented by formula (81) are contained in emitting layer 5 disposed between the anode 3 and the cathode 10. These compounds may be used singly or in combination of two or more.

(Compound Represented by Formula (1))

The compound represented by the formula (1) is explained below (1)

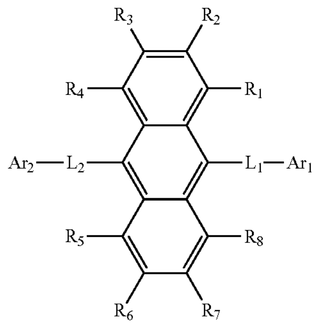

a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

when two or more of $R_{901}$ to $R_{907}$ exist, two or more of $R_{901}$ to $R_{907}$ may be the same with or different from each other;

at least one of $R_1$ to $R_a$ is a deuterium atom;

two or more adjacent groups of $R_1$ to $R_4$ do not form a ring by bonding with each other, and two or more adjacent groups of $R_5$ to $R_8$ do not form a ring by bonding with each other;

$L_1$ and $L_2$ are independently a single bond, a substituted or unsubstituted phenylene group, a substituted or unsubstituted naphthylene group, a substituted or unsubstituted biphenylene group, a substituted or unsubstituted terphenylene group, a substituted or unsubstituted anthrylene group, or a substituted or unsubstituted phenanthrylene group;

$Ar_1$ and $Ar_2$ are independently a substituted or unsubstituted phenyl group, a substituted or unsubstituted naphthyl group, a substituted or unsubstituted biphenyl group, a substituted or unsubstituted terphenyl group, a substituted or unsubstituted anthryl group, or a substituted or unsubstituted phenanthryl group;

when $L_1$, $L_2$, $Ar_1$ and $Ar_2$ have a substituent, the substituent is an alkyl group having 1 to 50 carbon atoms, an alkenyl group having 2 to 50 carbon atoms, an alkynyl group having 2 to 50 carbon atoms, a cycloalkyl group having 3 to 50 ring carbon atoms, an alkylsilyl group having 1 to 50 carbon atoms, a halogen atom, or a cyano group.

All of $R_1$ to $R_8$ may be deuterium atoms or a part of them (e.g., one or two of $R_1$ to $R_a$) may be deuterium atoms.

$R_1$ to $R_8$ that are not deuterium atoms are preferably hydrogen atoms (protium atoms).

In one embodiment, at least one hydrogen atom contained in one or more groups selected from a group consisting of $L_1$ and $L_2$ is a deuterium atom. All hydrogen atoms contained in one or more groups selected from a group consisting of $L_1$ and $L_2$ may be a deuterium atom. In more detail, in one embodiment, one or more groups selected from the group consisting of $L_1$ and $L_2$ are an unsubstituted phenylene group in which at least one hydrogen atom is a deuterium atom, an unsubstituted naphthylene group in which at least one hydrogen atom is a deuterium atom, an unsubstituted biphenylene group in which at least one hydrogen atom is a deuterium atom, an unsubstituted terphenylene group in which at least one hydrogen atom is a deuterium atom, an unsubstituted anthrylene group in which at least one hydrogen atom is a deuterium atom, or an unsubstituted phenanthrylene group in which at least one hydrogen atom is a deuterium atom.

In one embodiment, $L_1$ and $L_2$ are independently a single bond, a substituted or unsubstituted phenylene group, or a naphthylene group. It is preferable that at least one of $L_1$ and L 2 be a single bond.

In one embodiment, at least one hydrogen atom contained in one or more groups selected from a group consisting of $Ar_1$ and $Ar_2$ is a deuterium atom. All hydrogen atoms contained in one or more groups selected from a group consisting of $Ar_1$ and $Ar_2$ may be a deuterium atom. In more detail, in one embodiment, one or more groups selected from the group consisting of $Ar_1$ and $Ar_2$ are an unsubstituted phenyl group in which at least one hydrogen atom is a deuterium atom, an unsubstituted naphthyl group in which at least one hydrogen atom is a deuterium atom, an unsubstituted biphenyl group in which at least one hydrogen atom is a deuterium atom, an unsubstituted terphenyl group in which at least one hydrogen atom is a deuterium atom, an unsubstituted anthryl group in which at least one hydrogen atom is a deuterium atom, or an unsubstituted phenanthryl group in which at least one hydrogen atom is a deuterium atom.

In one embodiment, $Ar_1$ and $Ar_2$ are independently a single bond, a substituted or unsubstituted phenyl group, a substituted or unsubstituted naphthyl group, or a substituted or unsubstituted phenanthryl group.

In one embodiment, the compound represented by the formula (1) is represented by the following formula (1A):

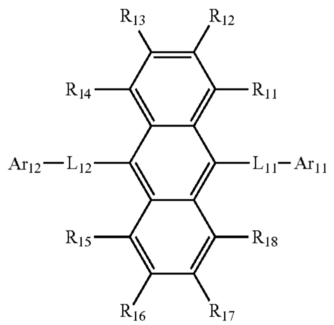

(1A)

wherein in the formula (1A), $R_{11}$ to $R_{18}$ are independently a hydrogen atom, and at least one of $R_{11}$ to $R_{18}$ is a deuterium atom;

adjacent two or more among $R_{11}$ to $R_{14}$ are not bonded with each other to form a ring, and adjacent two or more among $R_{15}$ to $R_{18}$ are not bonded with each other to form a ring;

$L_{11}$ and $L_{12}$ are independently a single bond, an unsubstituted phenylene group, or an unsubstituted naphthylene group; and $Ar_{11}$ and $Ar_{12}$ are independently an unsubstituted phenyl group or an unsubstituted naphthyl group.

In one embodiment, in the formula (1A), at least two of $R_{11}$ to $R_{18}$ are deuterium atoms.

In one embodiment, in the formula (1A), $R_{11}$ to $R_{18}$ are all deuterium atoms.

In one embodiment, in the formula (1A), at least one hydrogen atom contained in one or more selected from the group consisting of $L_{11}$ and $L_{12}$ is a deuterium atom.

In one embodiment, in the formula (1A), at least one hydrogen atom contained in one or more selected from the group consisting of $Ar_{11}$ and $Ar_{12}$ is a deuterium atom.

Existence of a deuterium atom in the compound is confirmed by Mass Spectrometry or $^1H$-NMR Spectrometry. The bonding position of a deuterium atom in the compound is identified by 1H-NMR Spectrometry. In concrete terms, it is confirmed as follows.

If it is identified that, by Mass Spectrometry, a molecular weight of a target compound is greater by "one" than a molecular weight of a corresponding compound in which all hydrogen atoms are protium atoms, it is confirmed that one deuterium atom exists in the target compound. Further, the number of deuterium atoms in a molecule can be confirmed by an integration value obtained by $^1H$-NMR analysis on the target compound, since no signal is observed by performing $^1H$-NMR analysis on a deuterium atom. The bonding position of a deuterium can be identified by performing $^1H$-NMR analysis on the target compound and assigning signals.

It is preferable that, in the compound represented by the formula (1), the content ratio of a compound in which only protium atoms are contained as hydrogen atoms (a compound having the same structure as formula (1) except that only protium atoms are contained as hydrogen atoms (protium compound)) is 99 mol % or less. The content ratio of the protium compound is confirmed by Mass Spectrometry.

In one embodiment, the emitting layer of the organic EL device according to one aspect of the invention contains the compound represented by the formula (1) and a protium compound, and the content ratio of the latter to the total thereof is 99 mol % or less.

In one embodiment, the emitting layer of the organic EL device according to one aspect of the invention contains the compound represented by the formula (1) and a protium compound, and the content ratio of the former to the total thereof is 30 mol % or more, 50 mol % or more, 70 mol % or more, 90 mol % or more, 95 mol % or more, 99 mol % or more, or 100 mol %.

The compound represented by the formula (1) i.e., a compound used in the scope of the present invention can be synthesized in accordance with the synthesis process described in Examples by using publicly known alternative reactions or materials corresponding to a target compound.

Examples of the compound represented by formula (1) include the following compounds. In the following example compounds, D represents a deuterium atom.

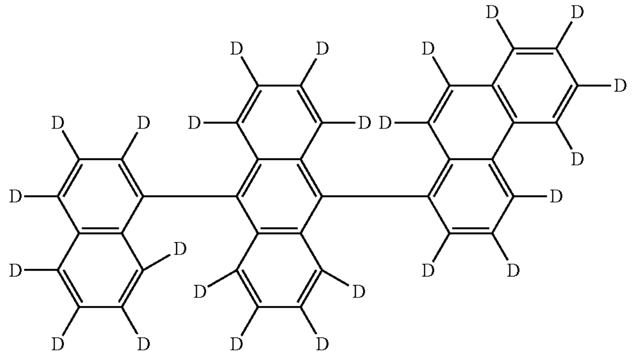

-continued
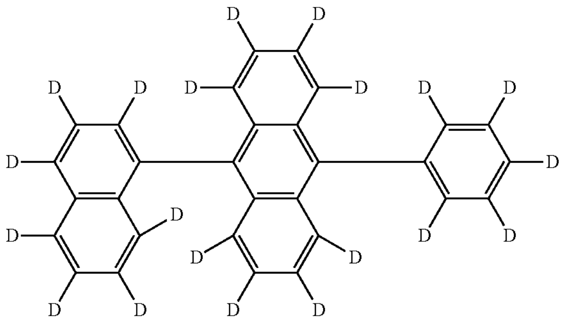
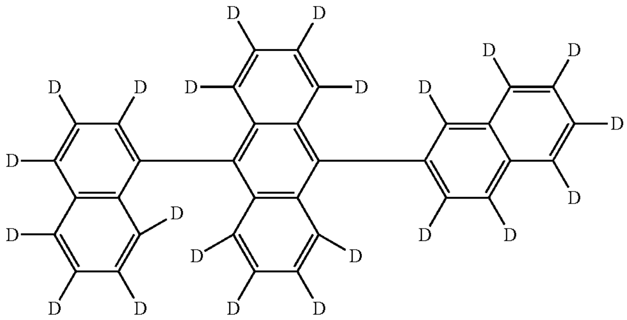
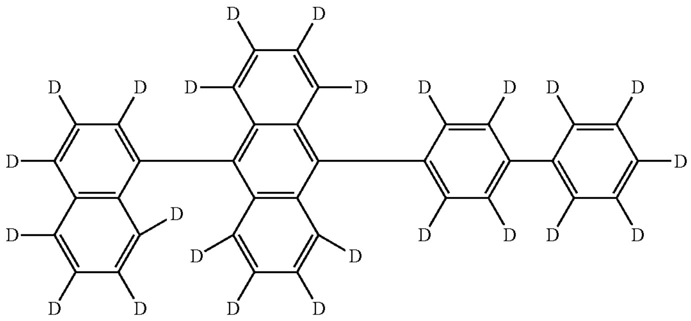
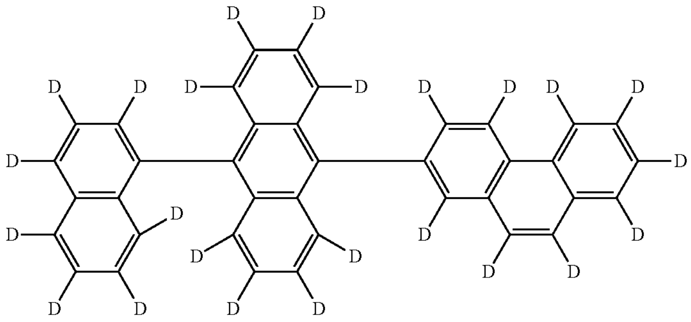
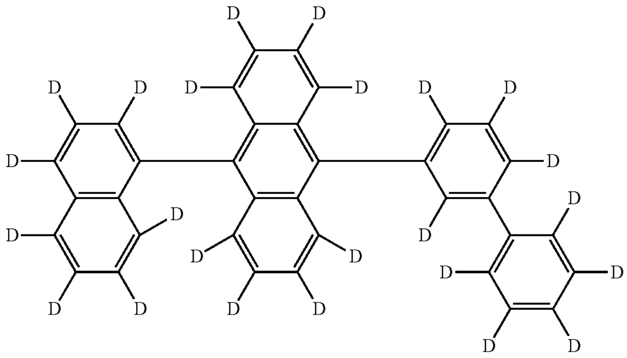

-continued
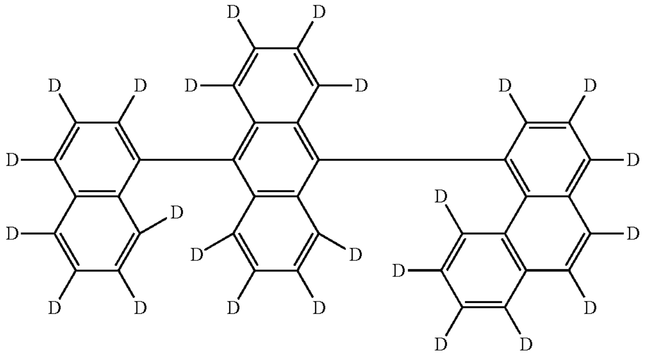
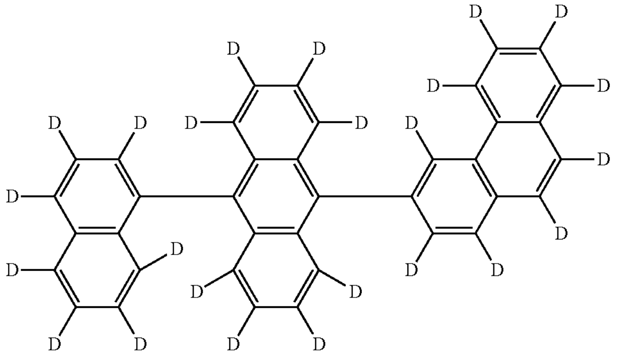
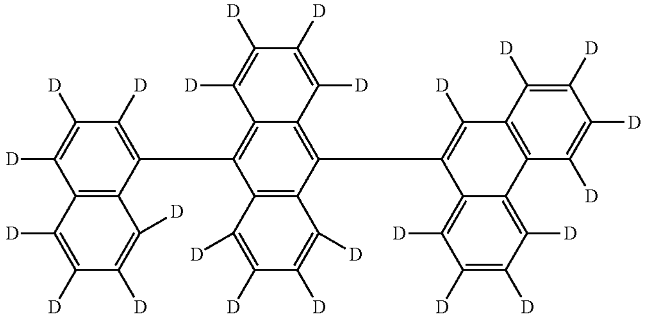
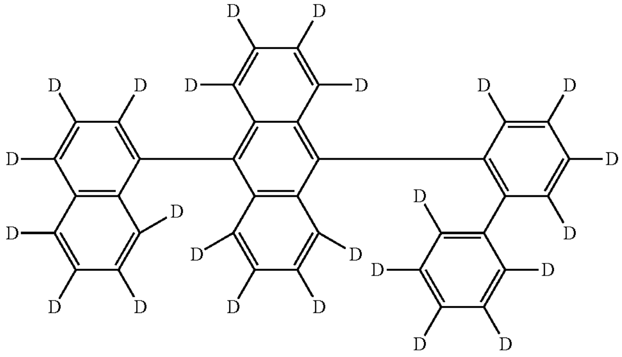
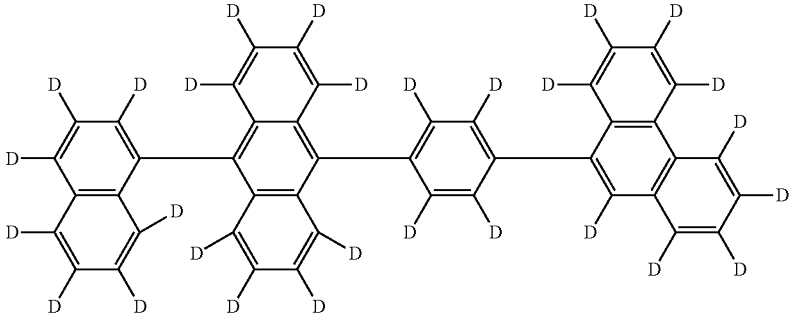

-continued
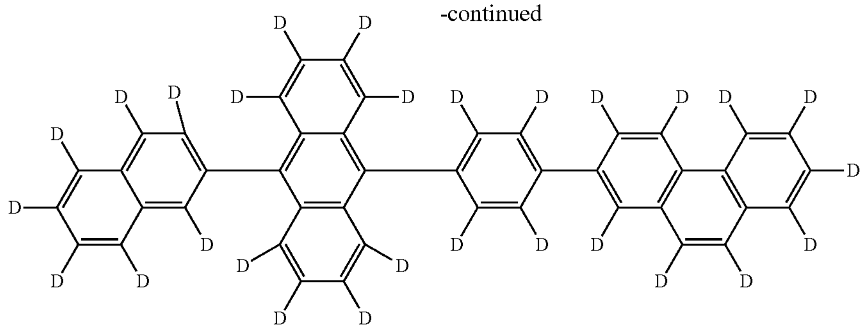
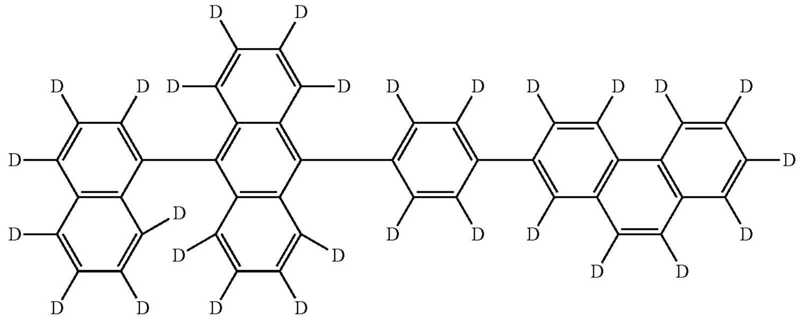
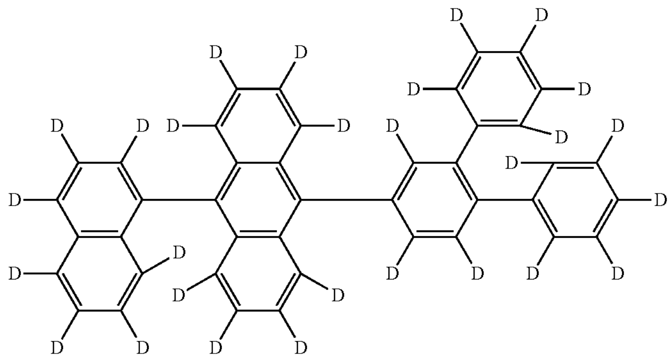
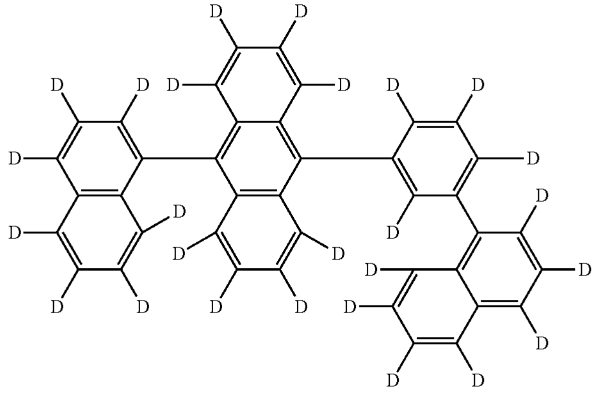
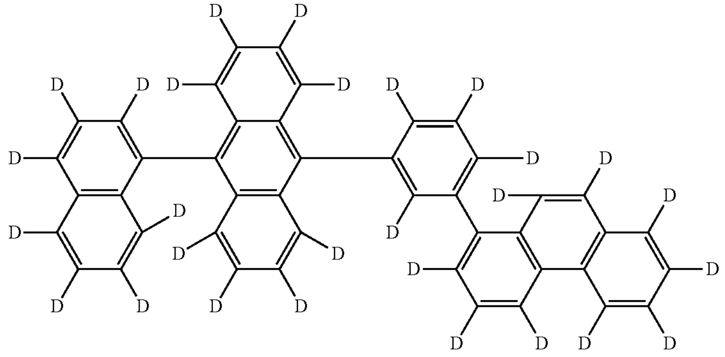

-continued
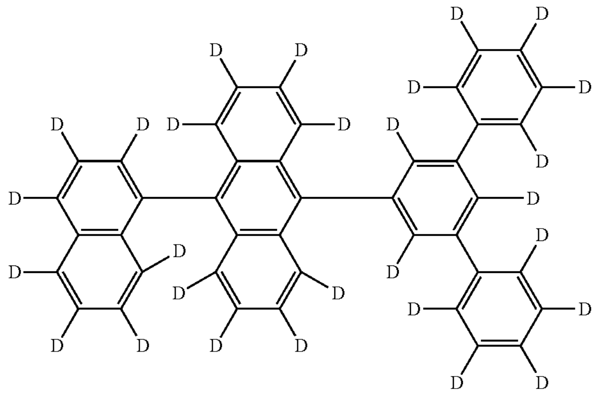
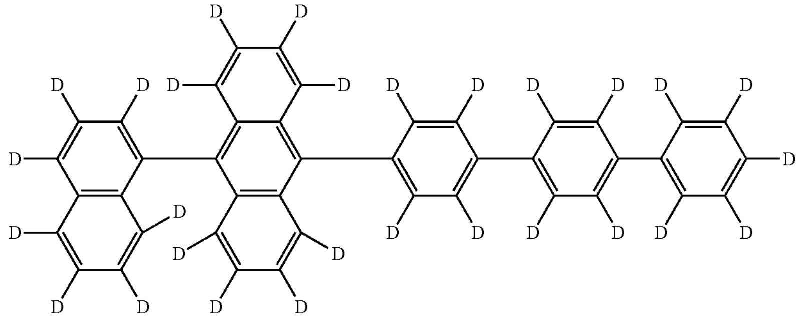
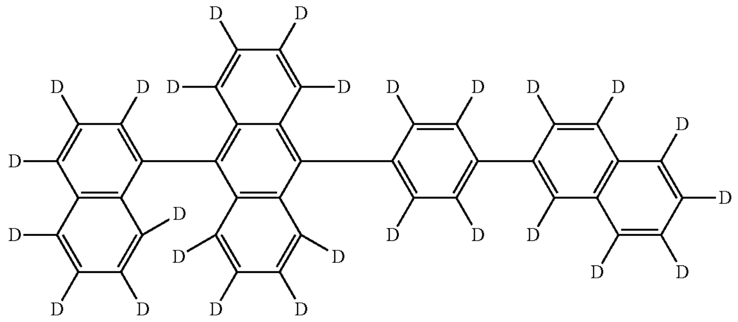
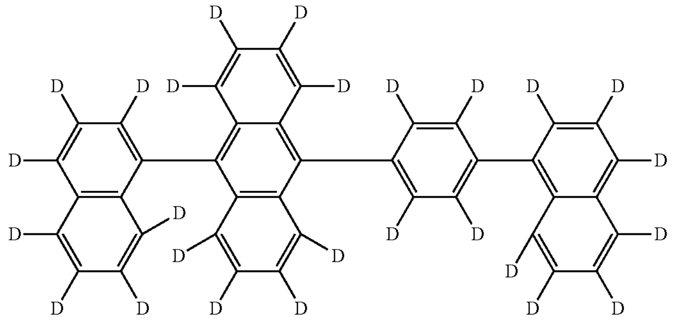

-continued
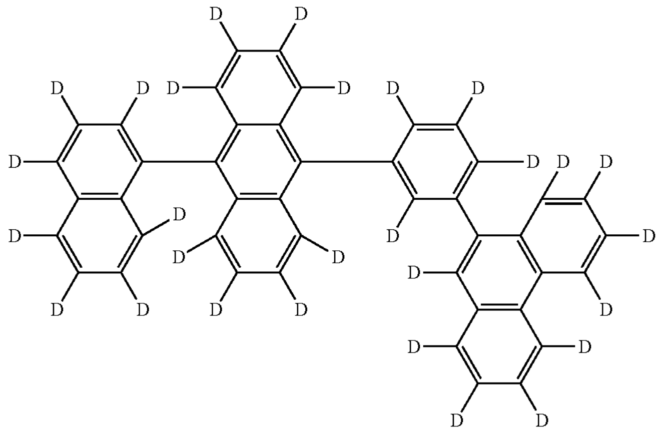
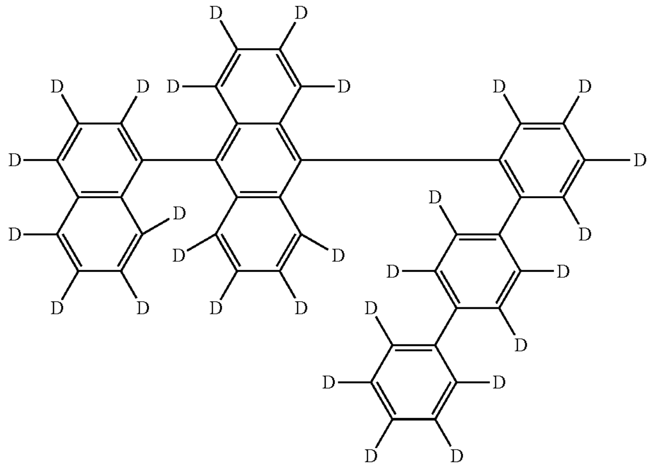
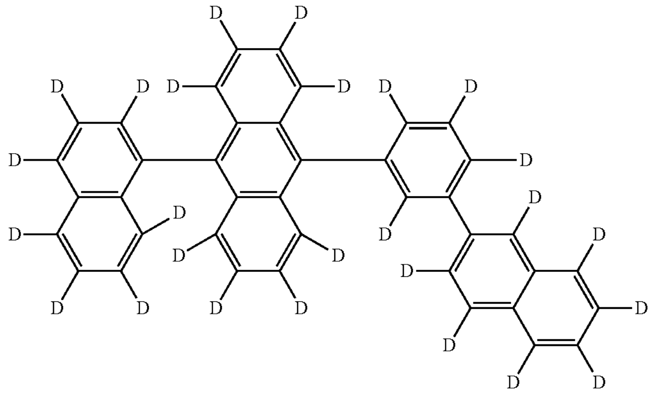

-continued
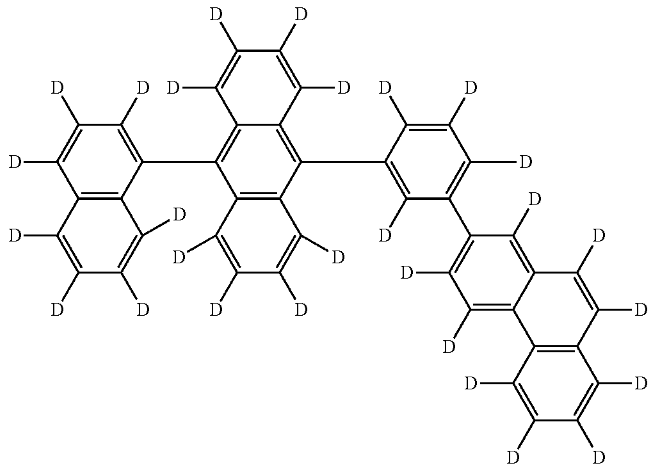
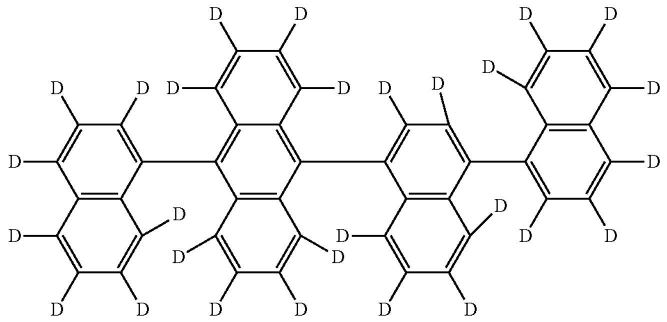
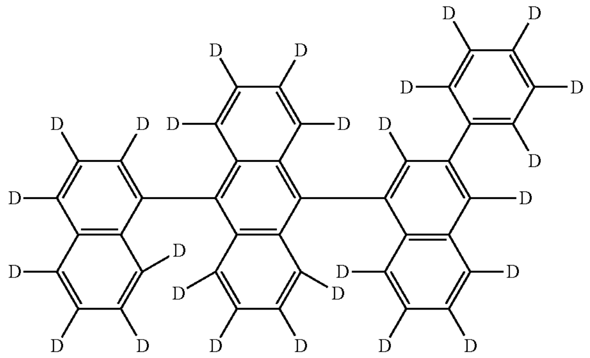
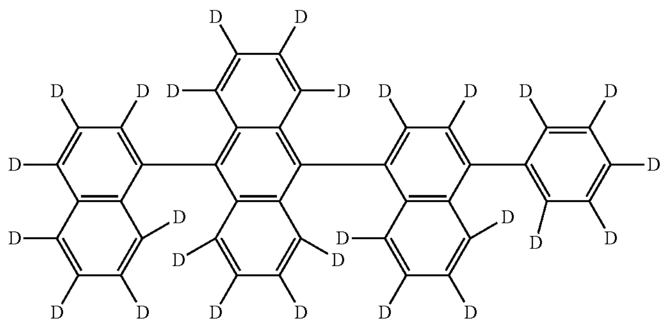

-continued
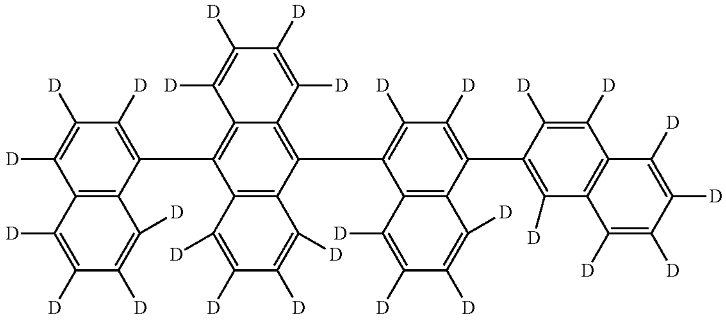
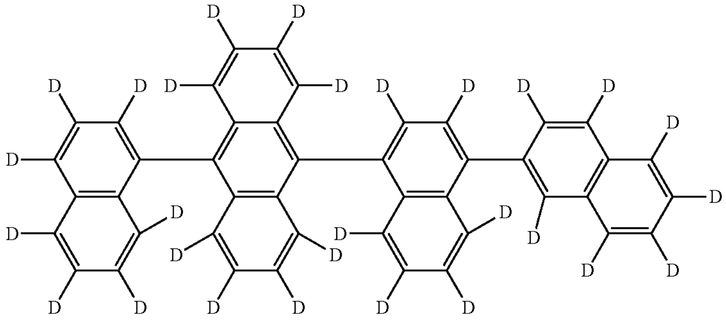
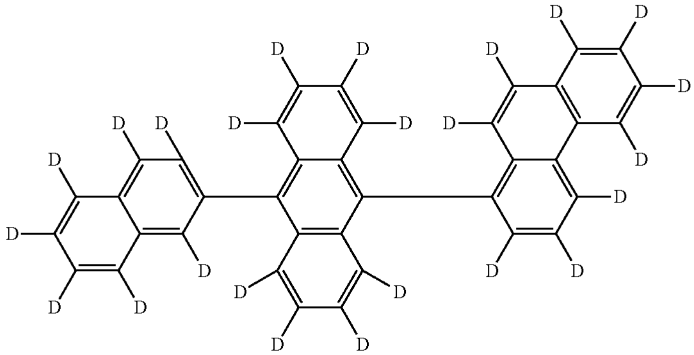
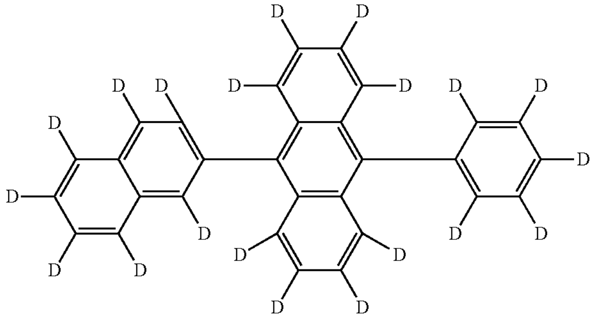
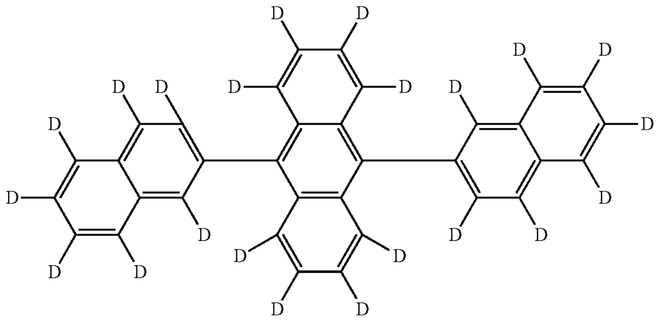

-continued
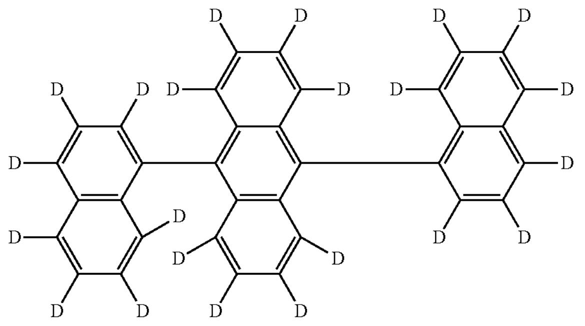
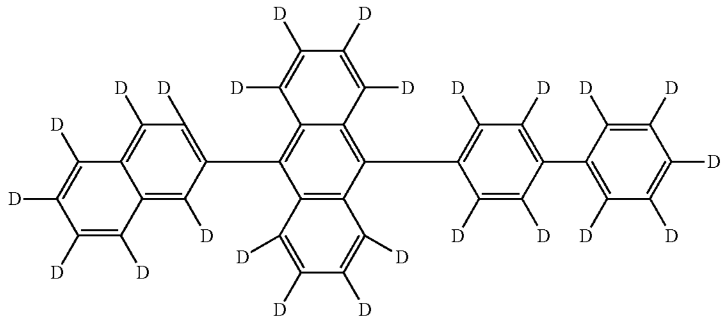
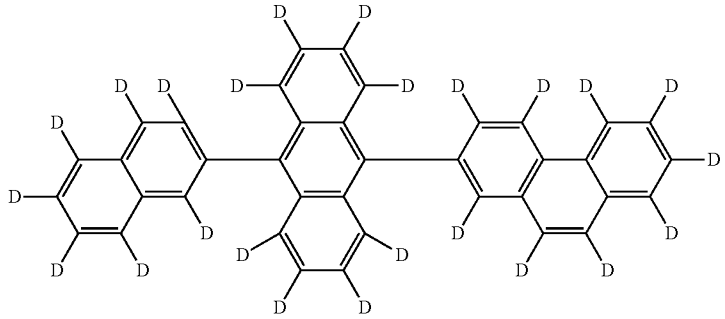
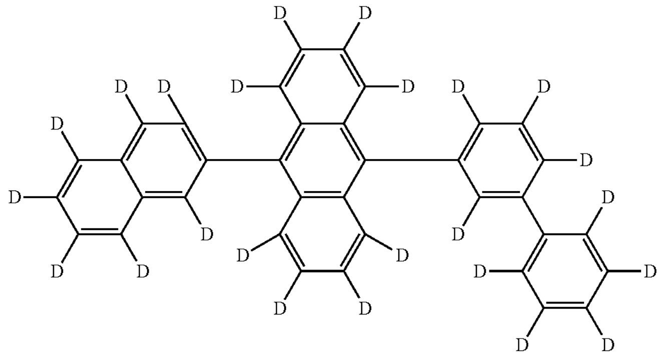
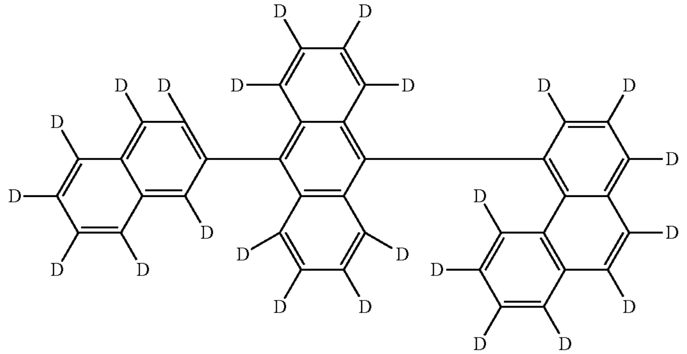

-continued
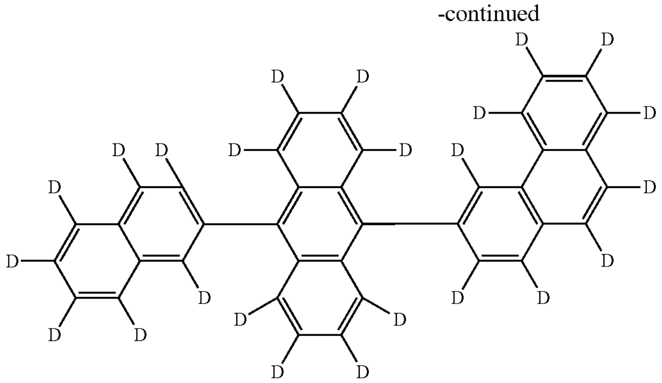
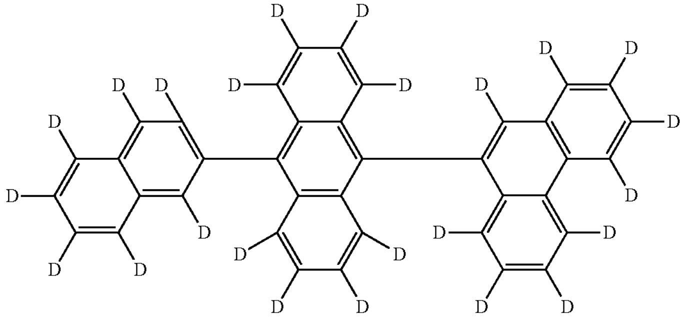
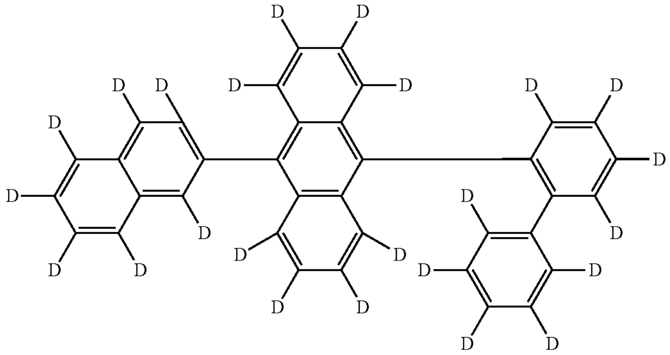
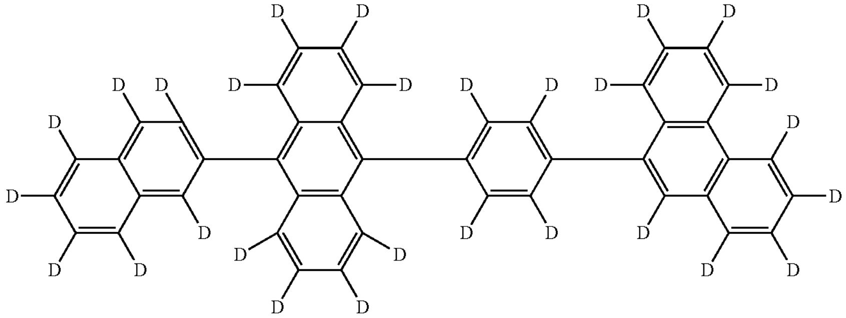
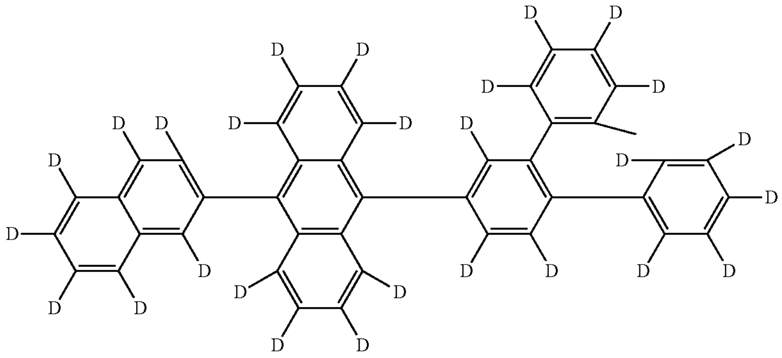

-continued
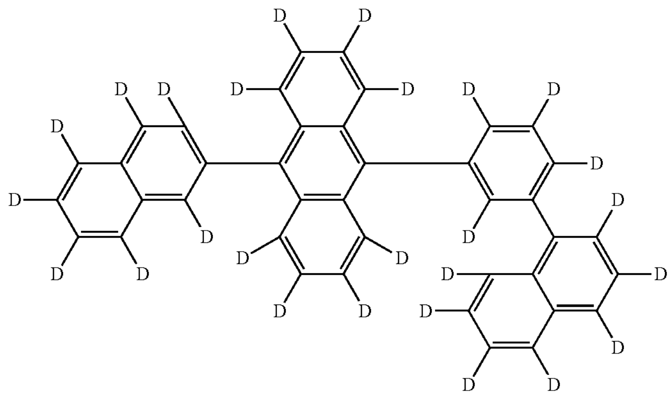
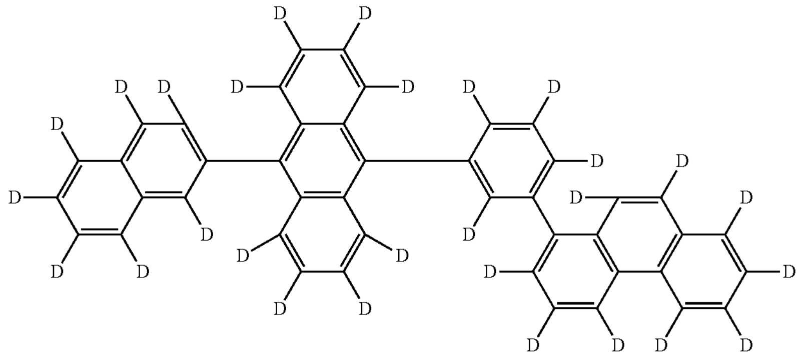
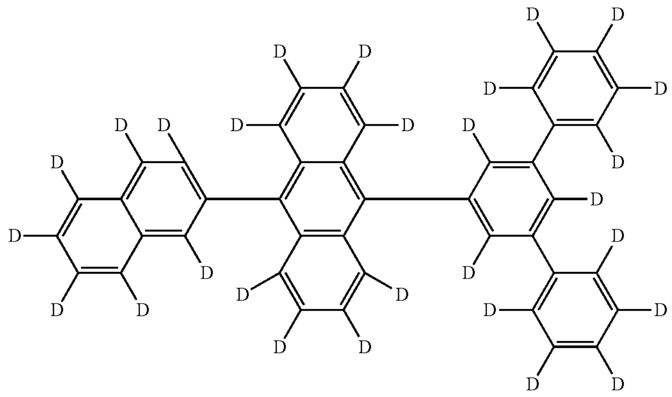
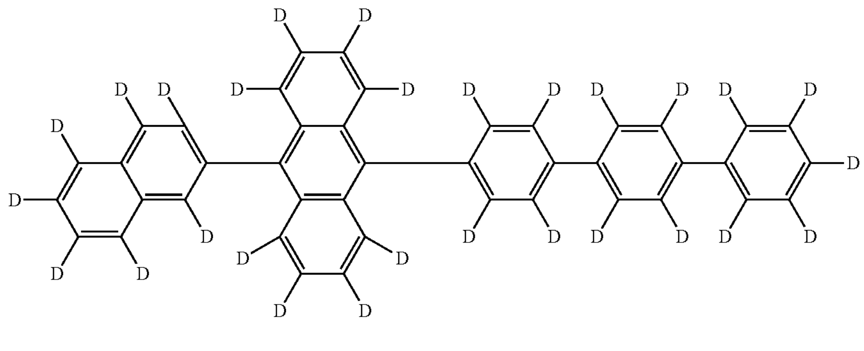

-continued
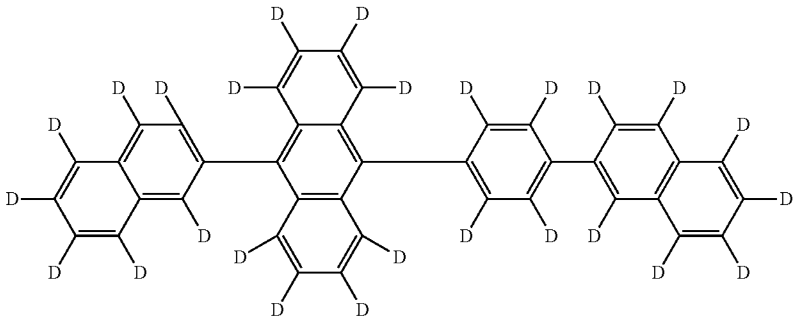
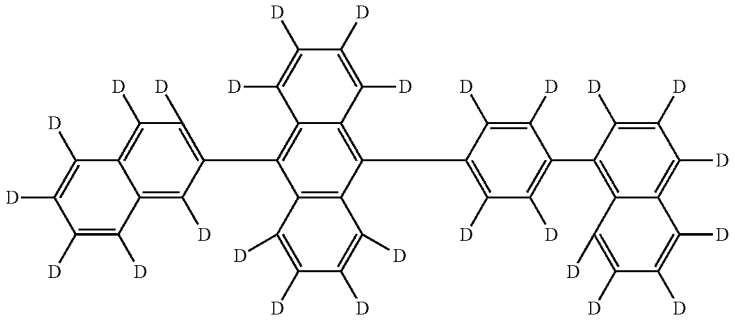
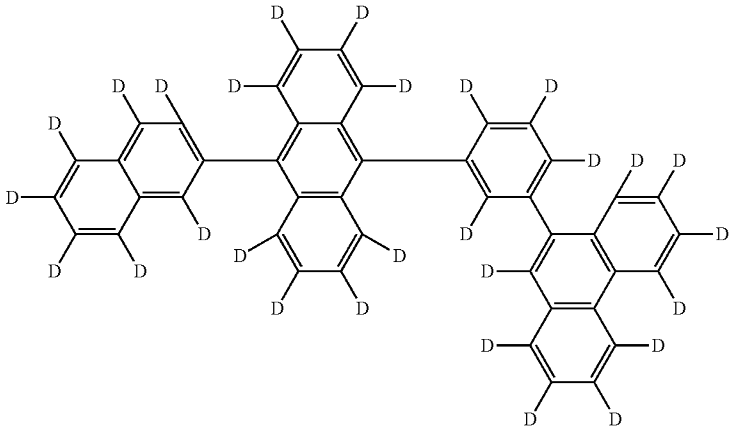
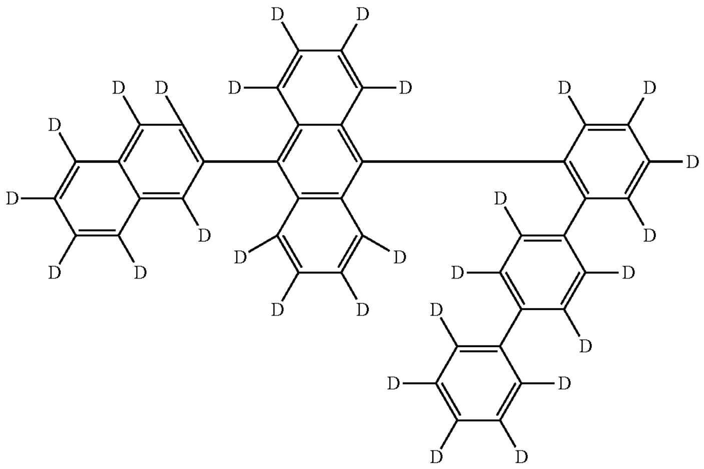

-continued
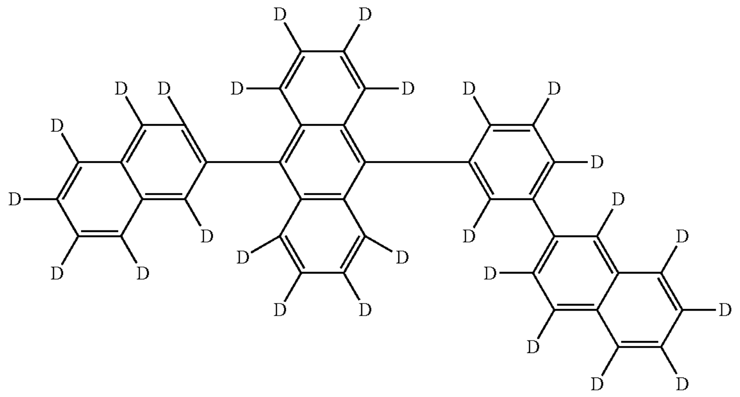
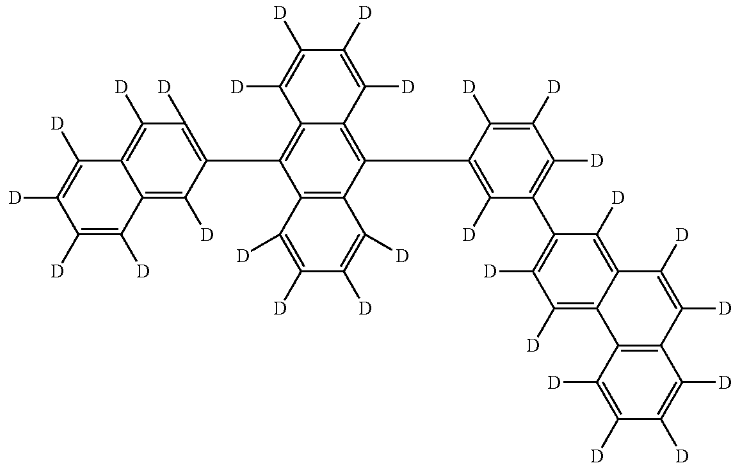
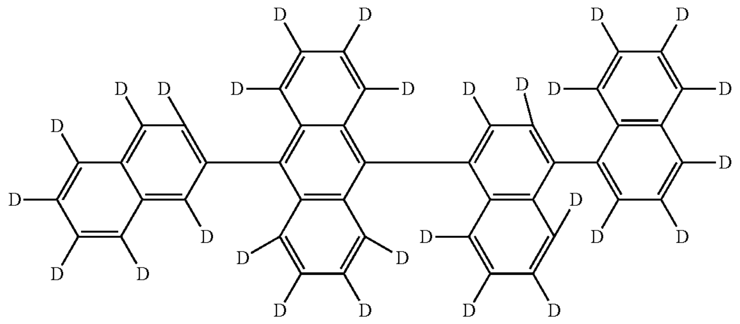
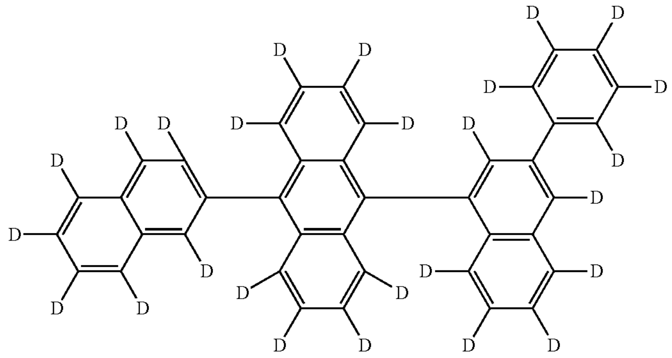

-continued
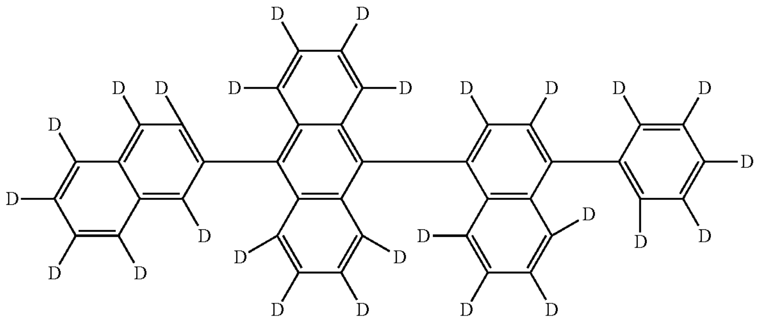
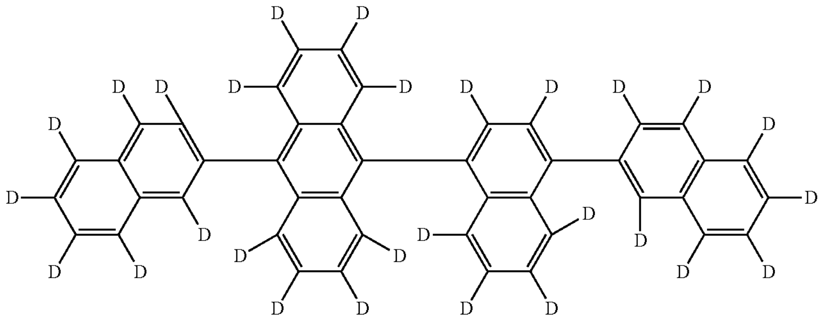
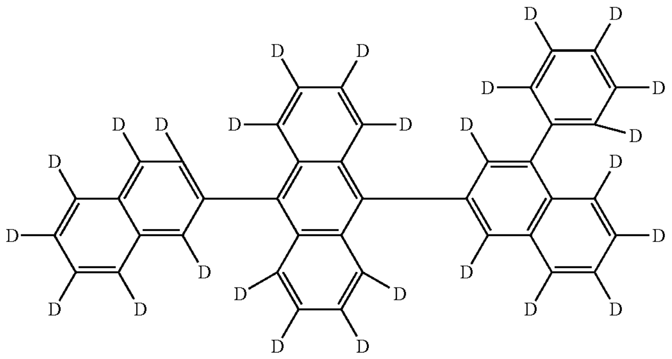
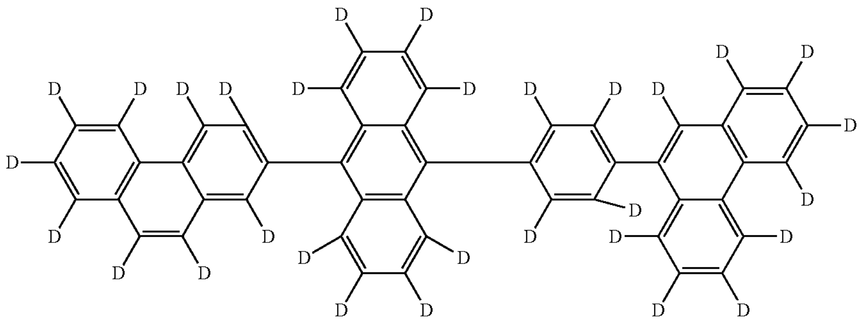
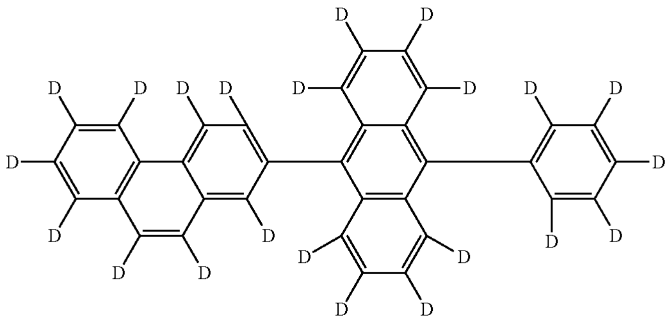

-continued
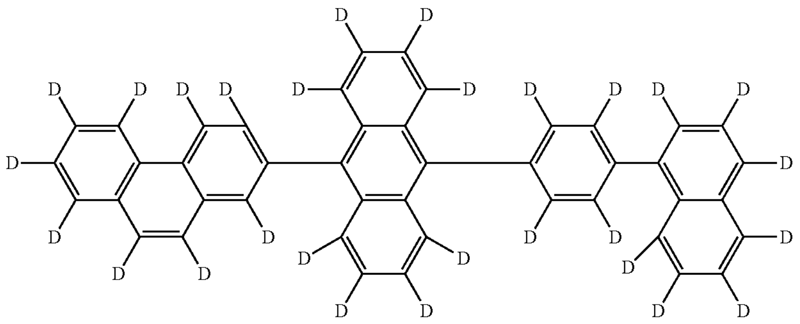
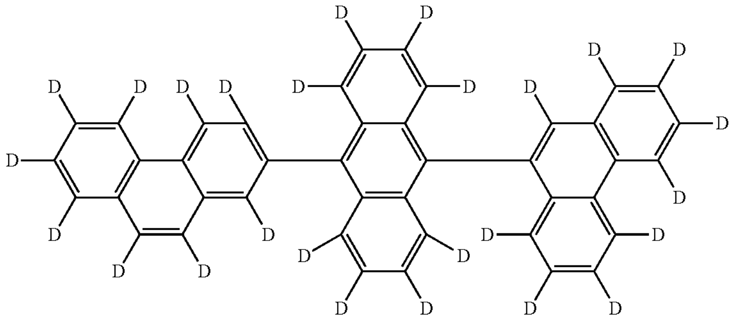
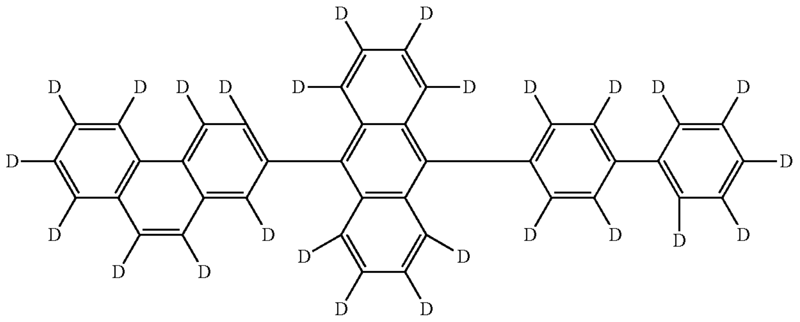
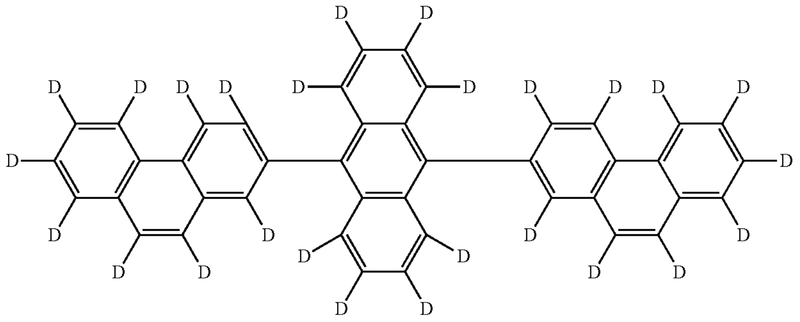
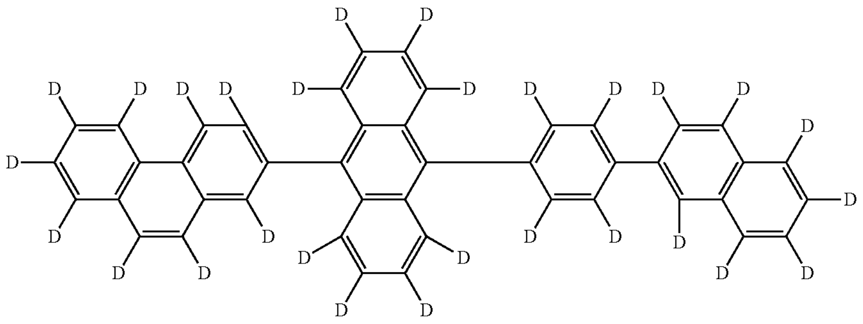

-continued
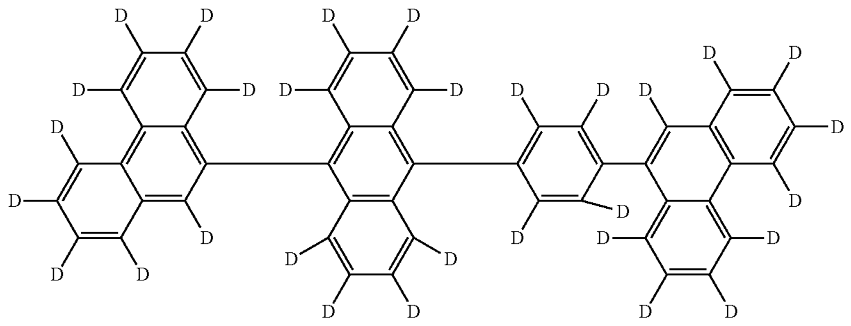
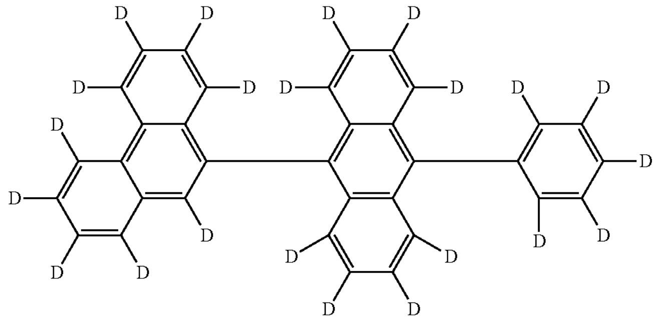
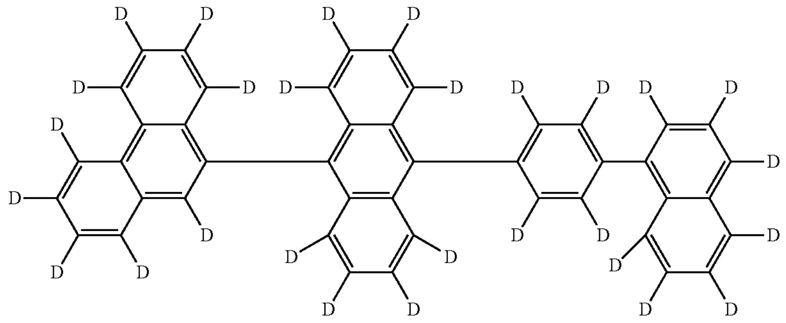
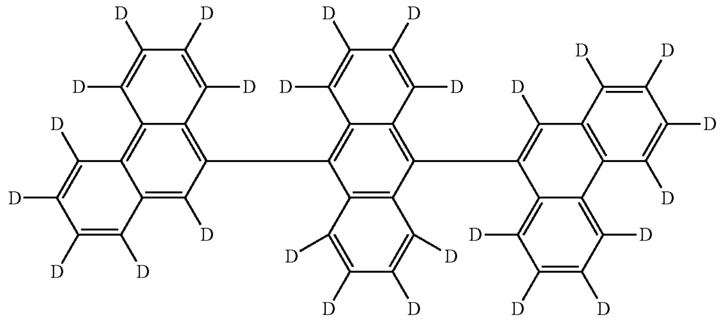
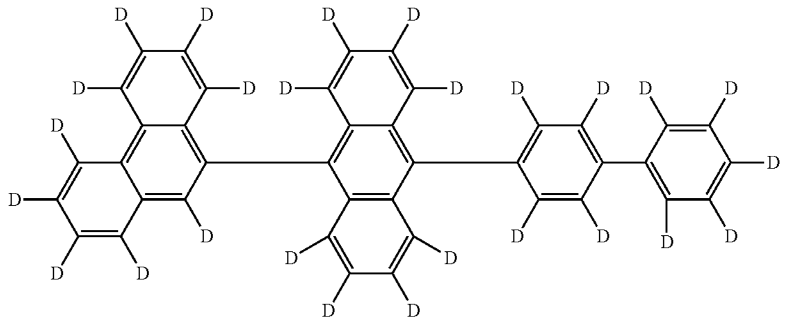

-continued
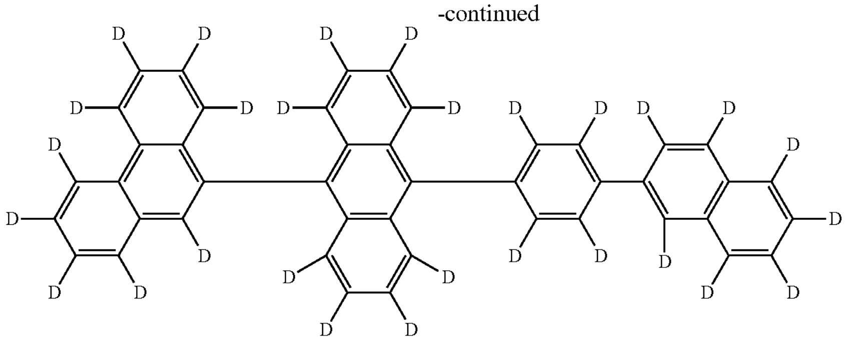
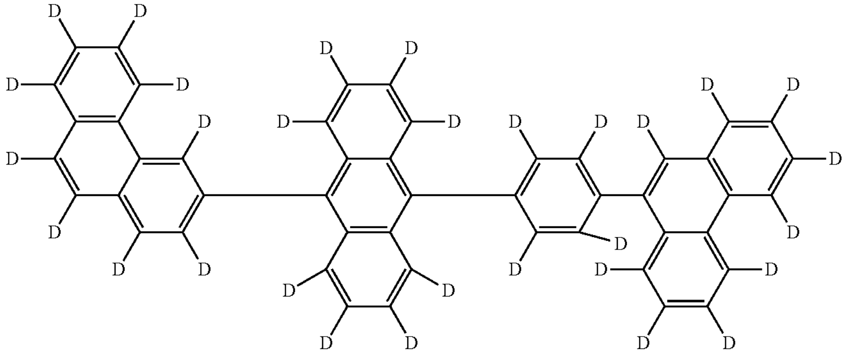
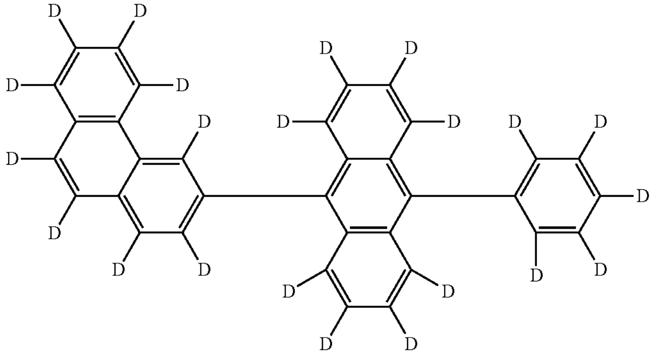
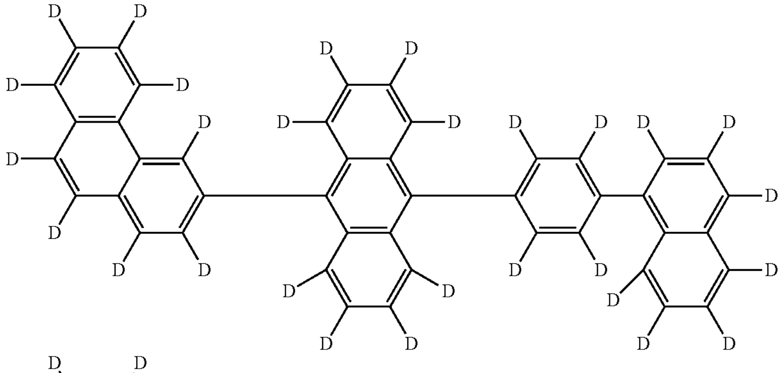
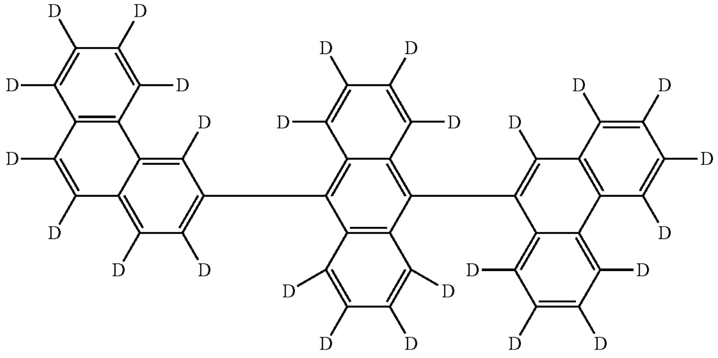

-continued
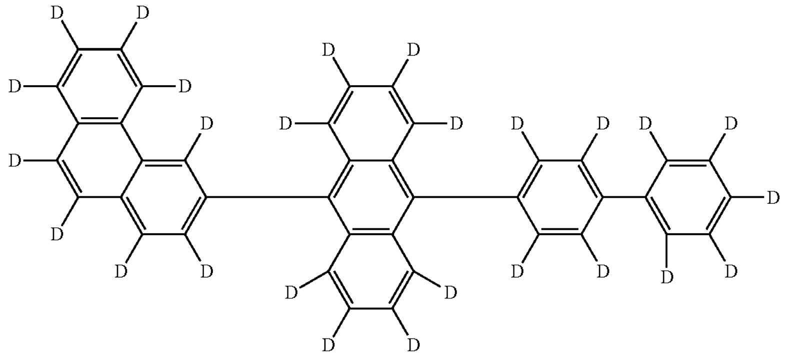
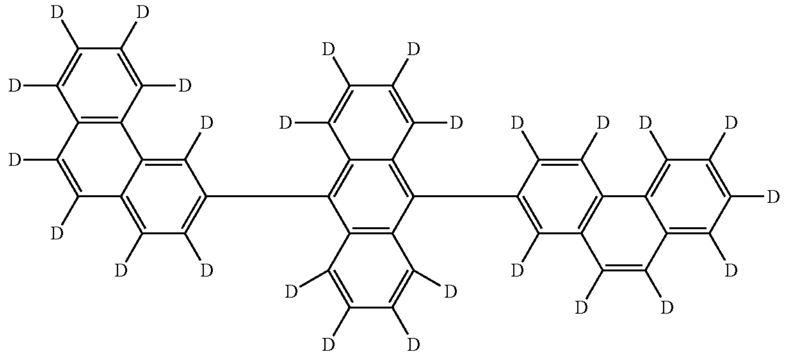
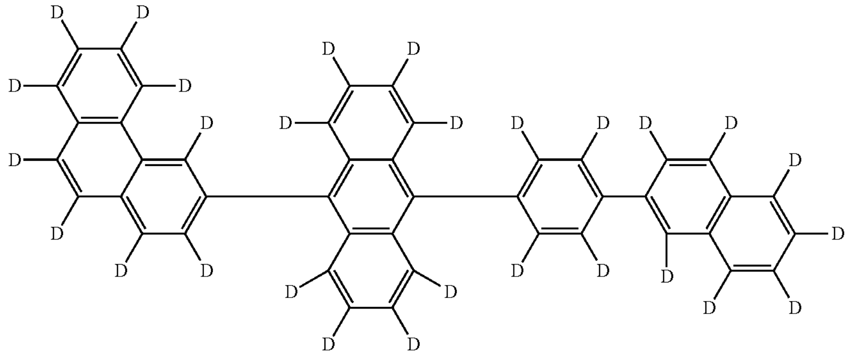
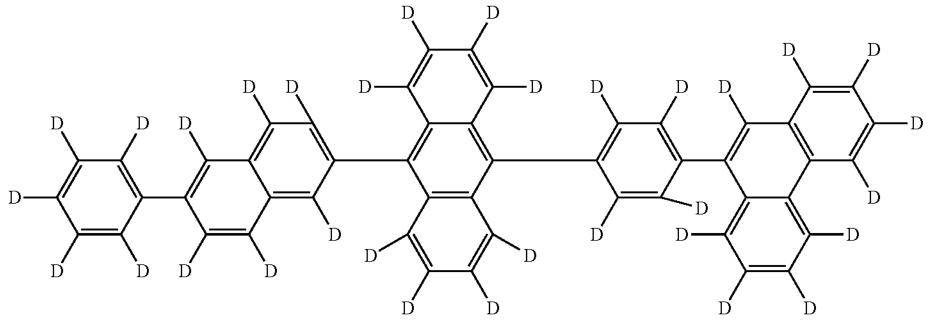
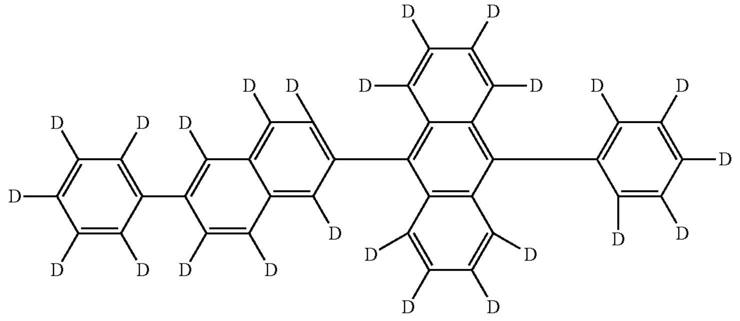

-continued
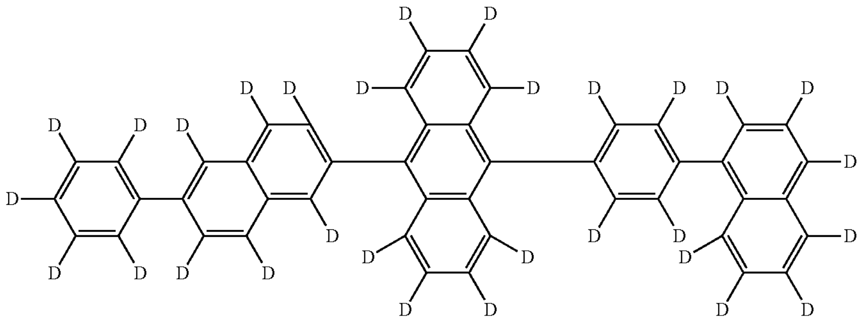
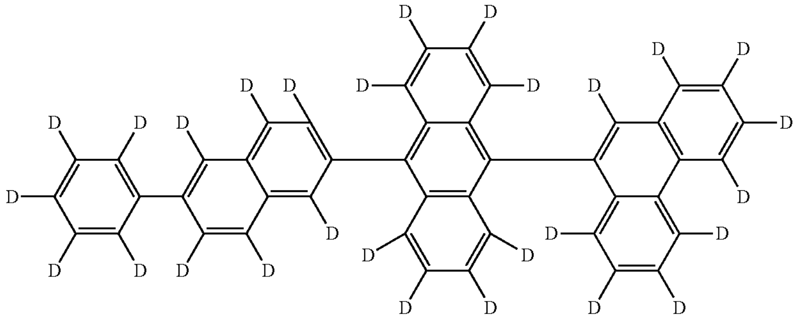
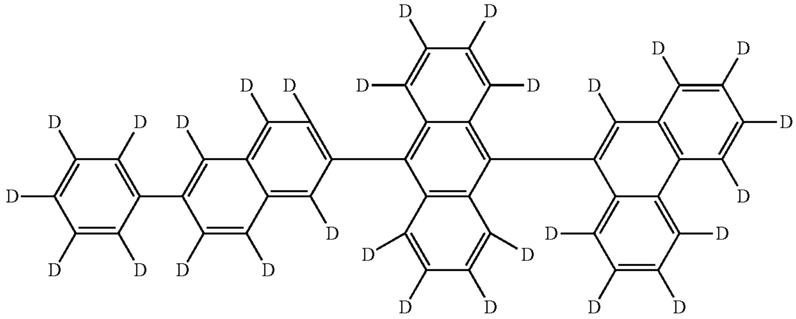
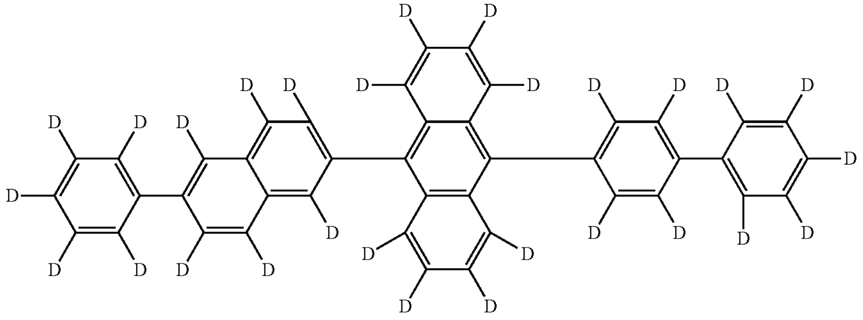
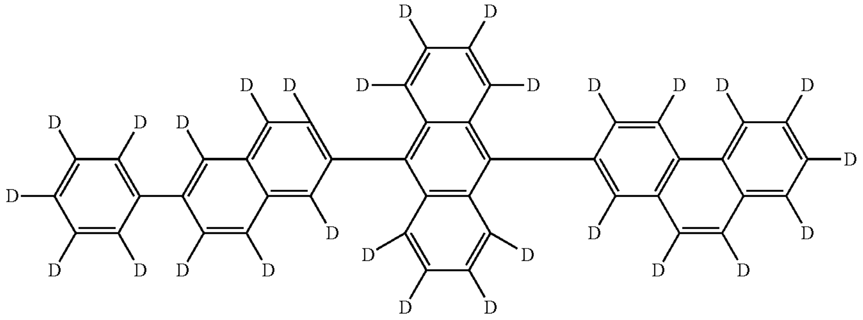

-continued
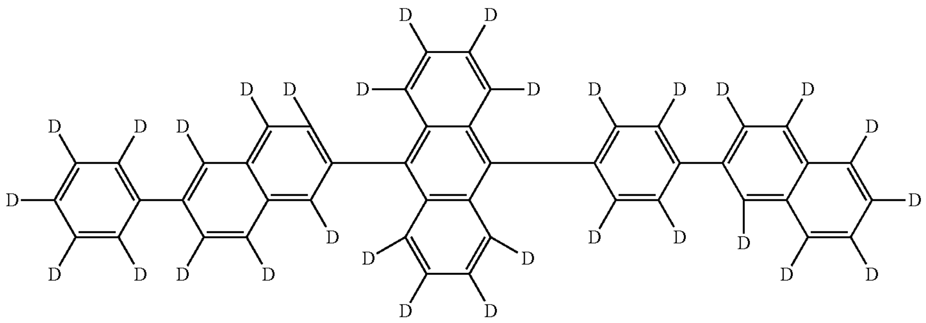
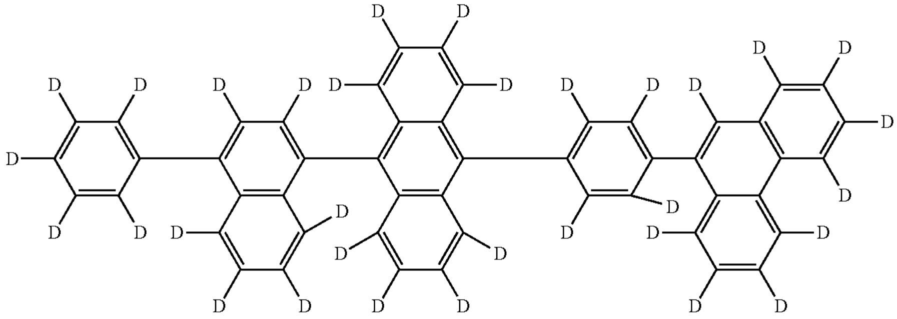
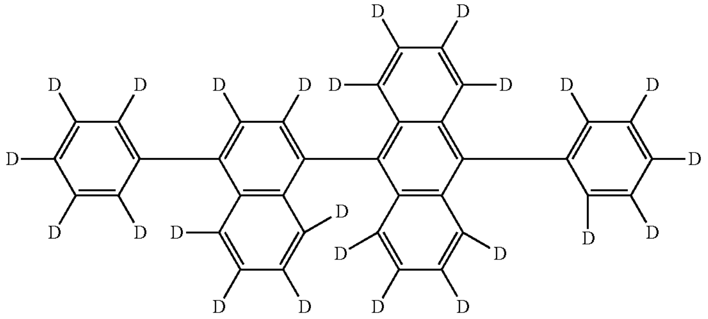
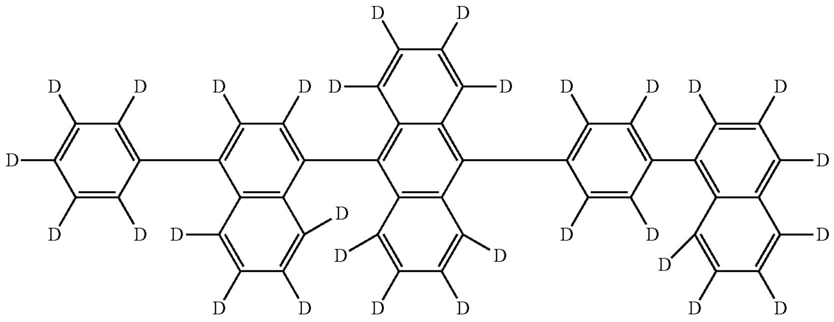
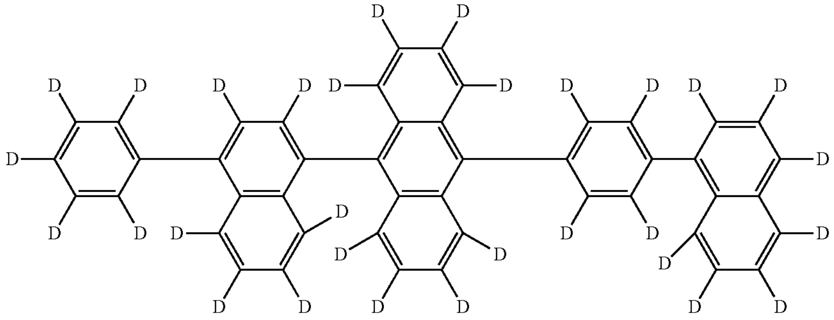

-continued
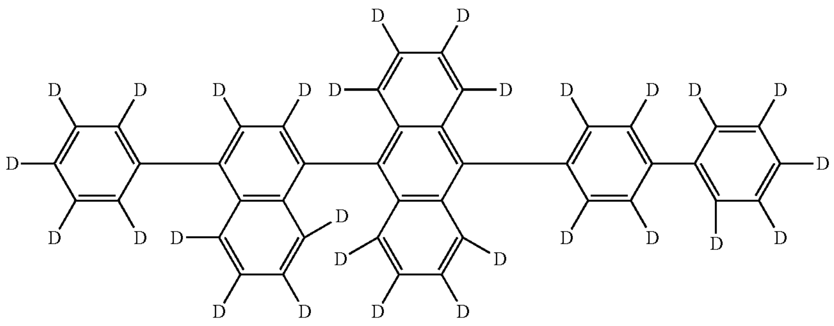
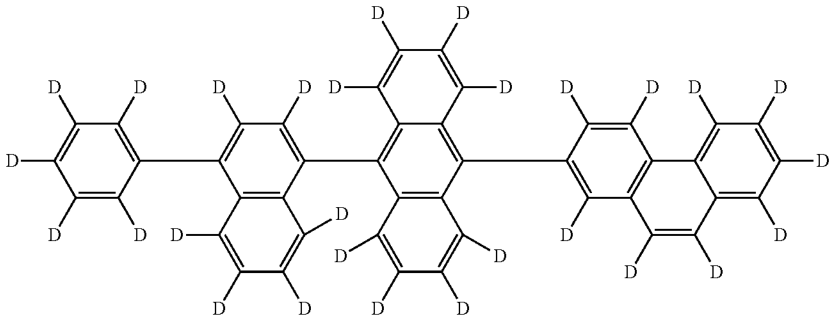
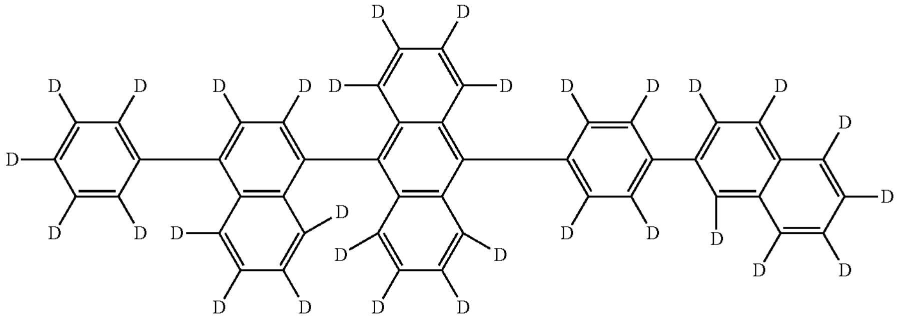
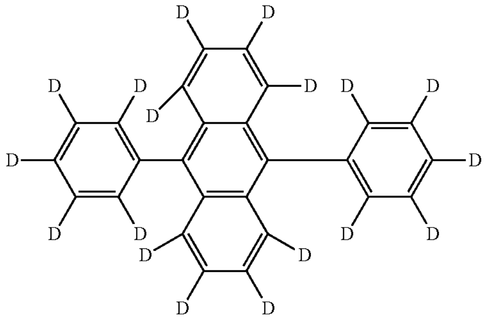
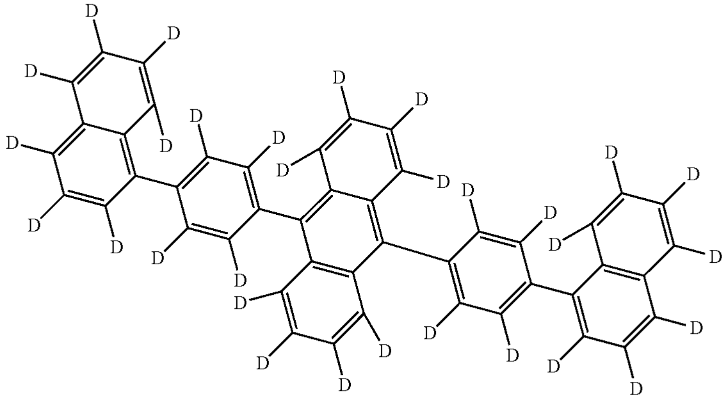

-continued
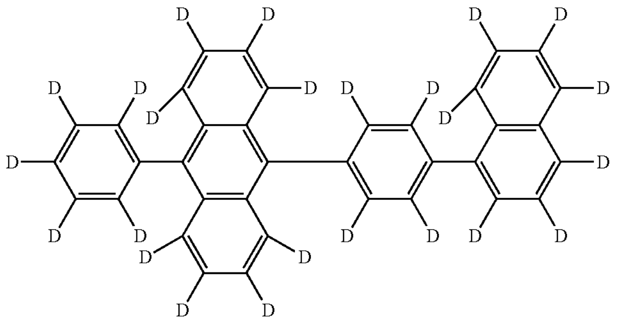
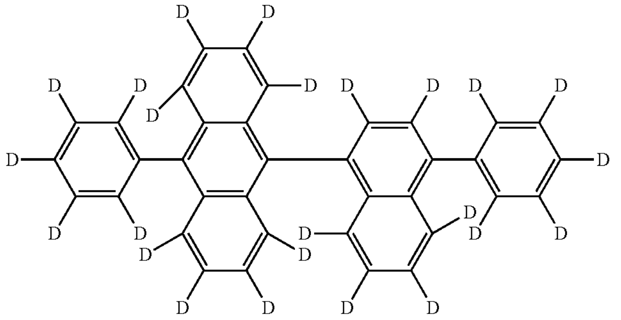
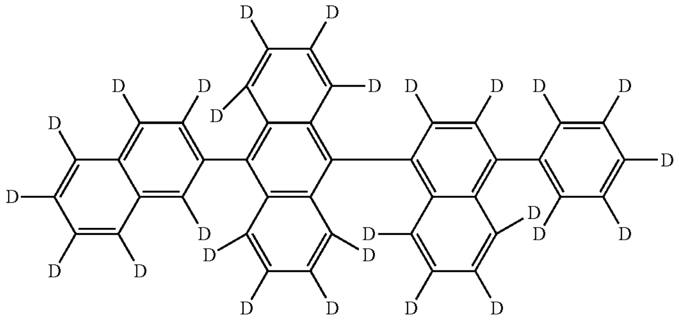
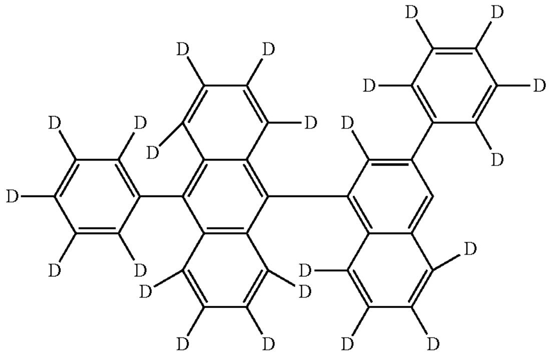
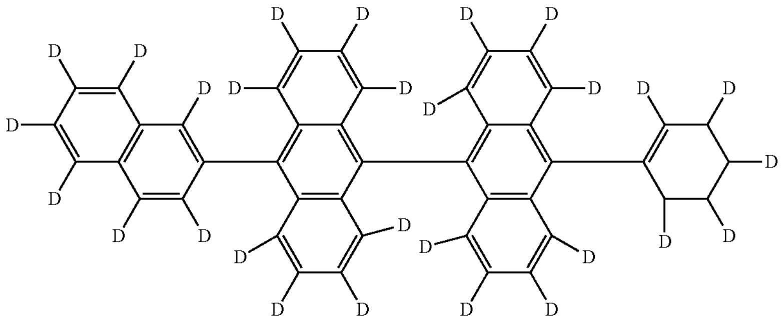

-continued
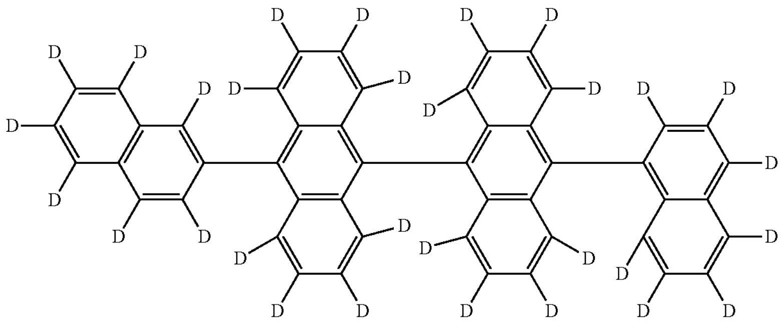
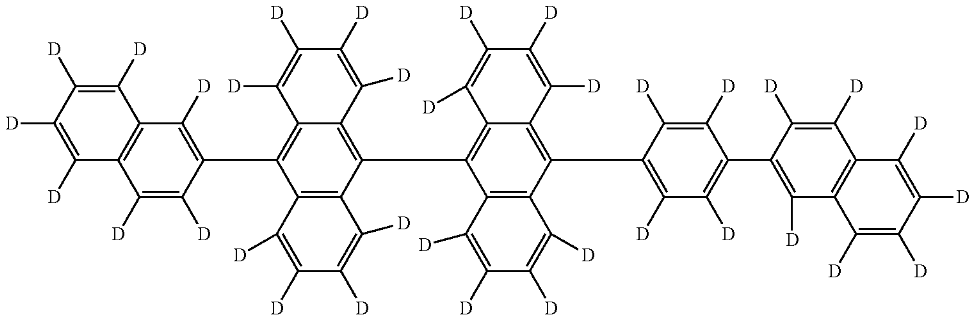
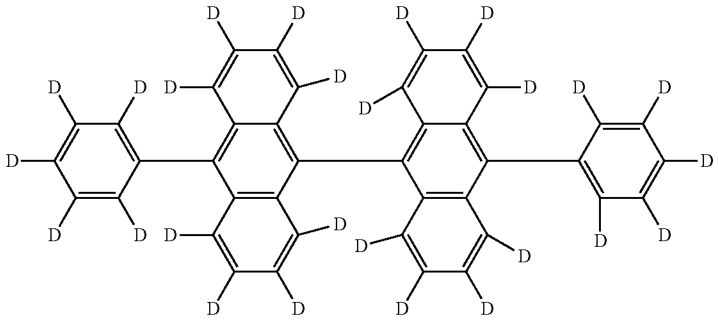
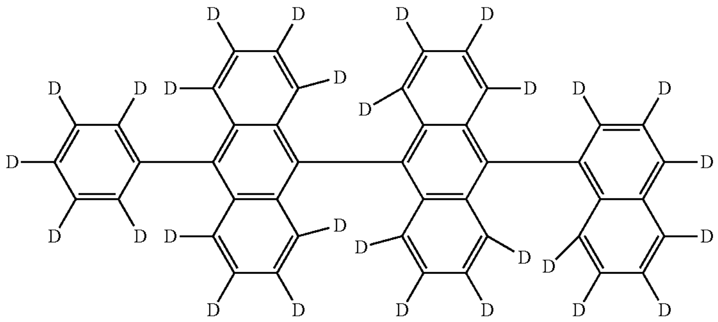
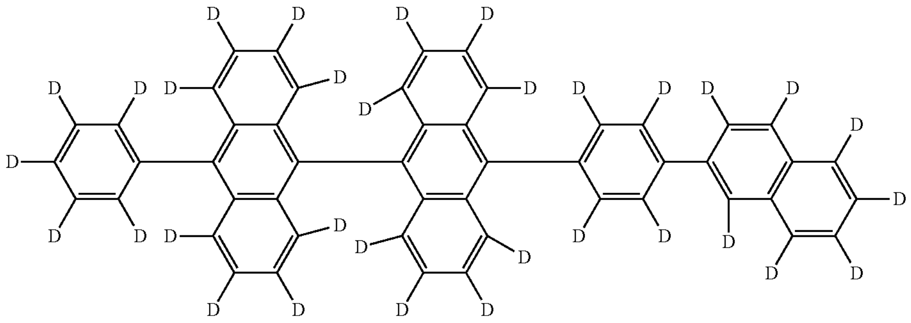

-continued
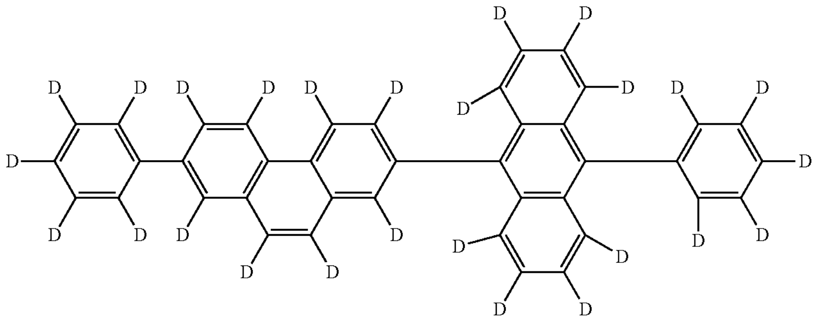
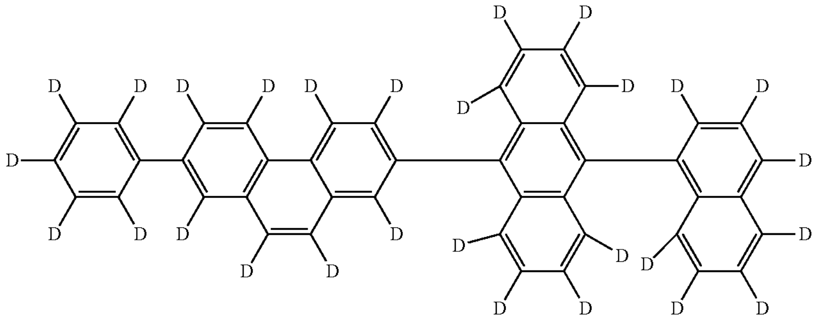
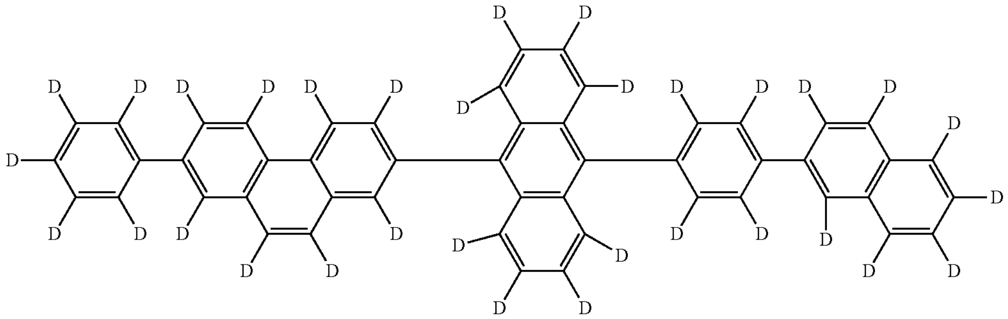
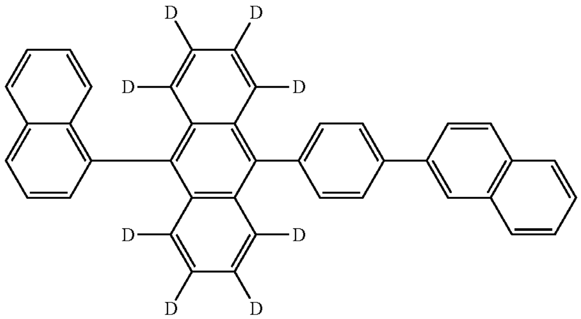
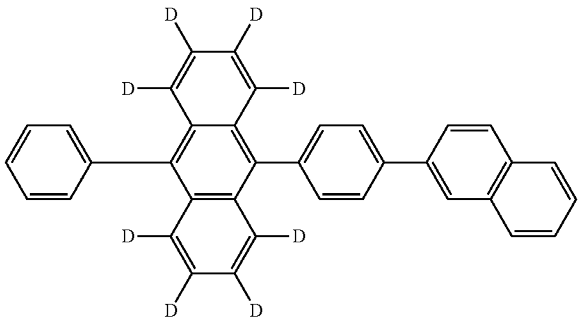

-continued
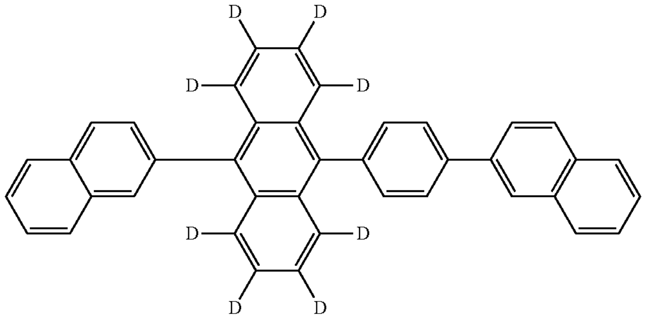
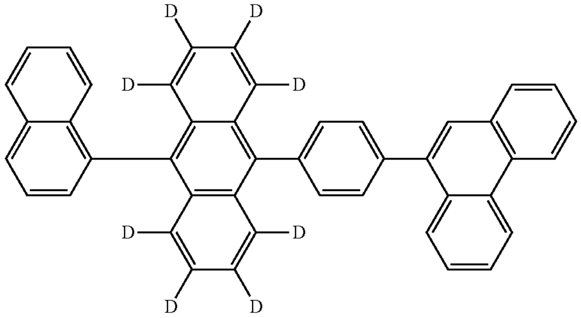
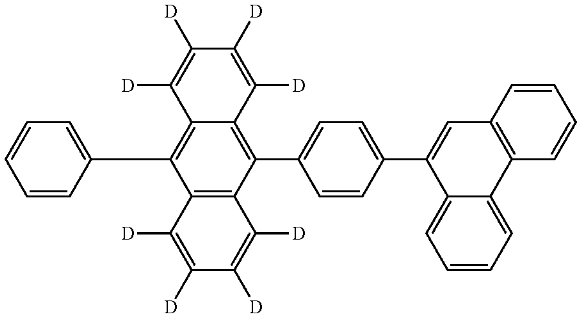
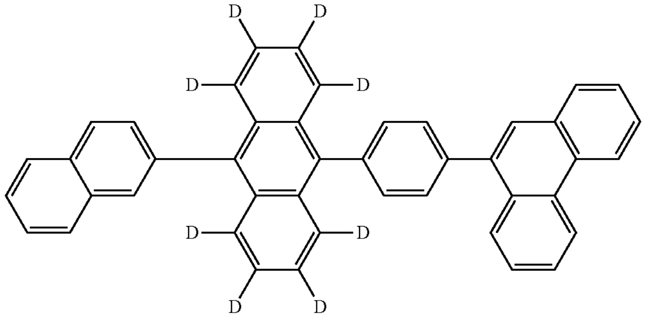
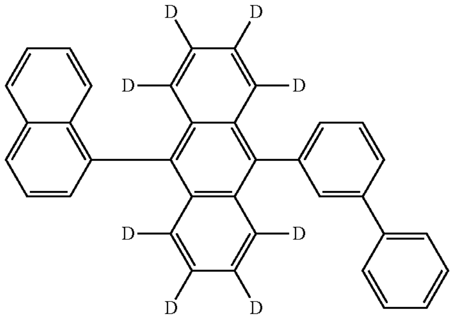

-continued
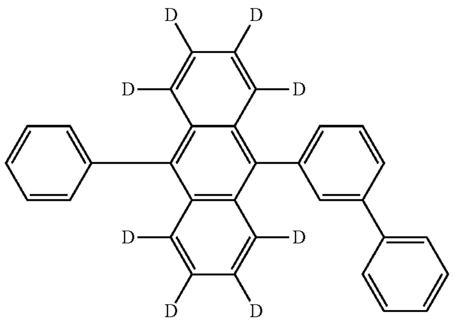
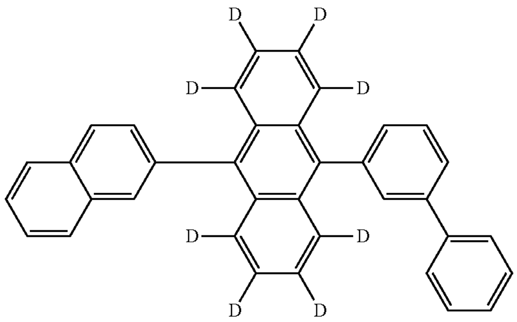
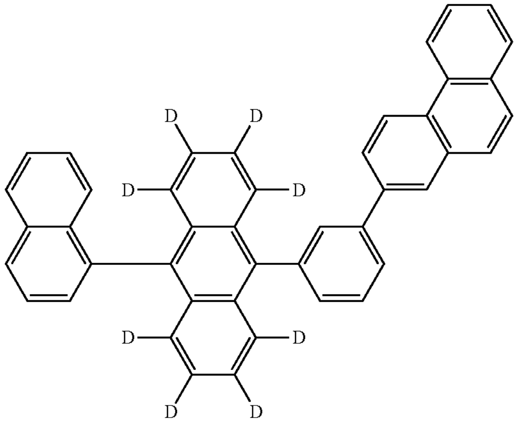
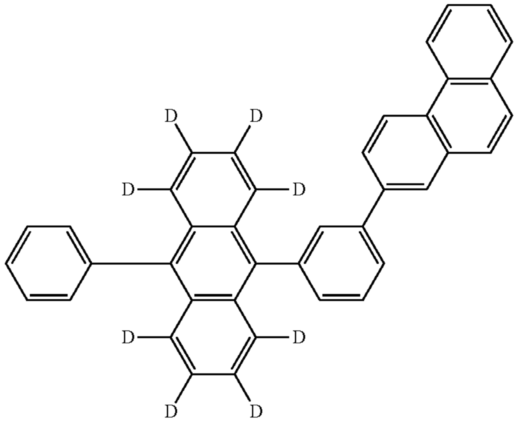

-continued
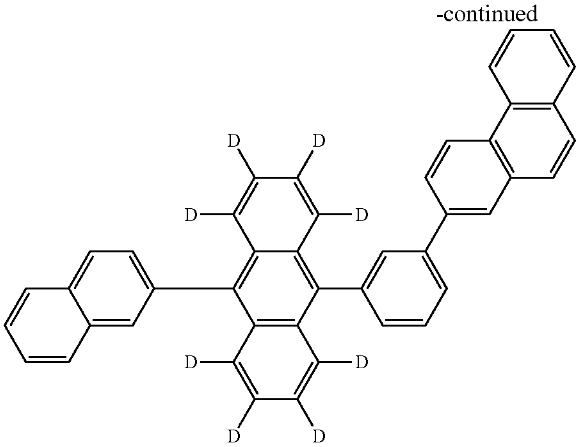
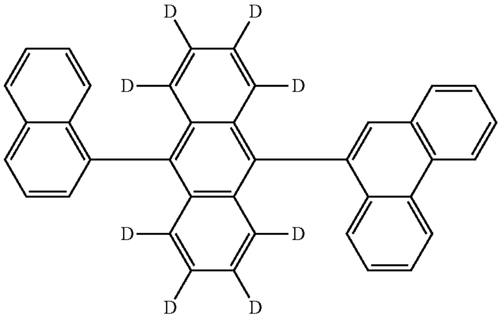
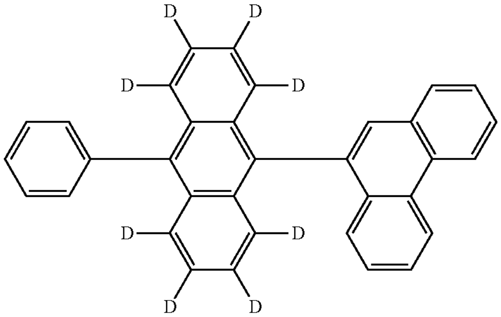
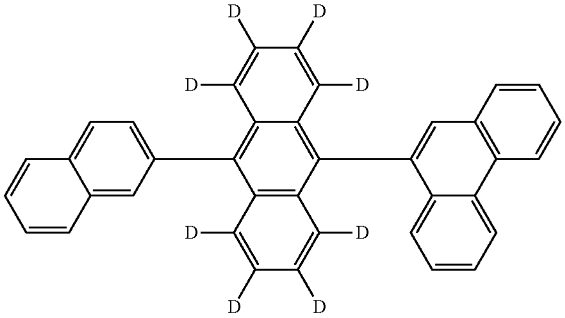
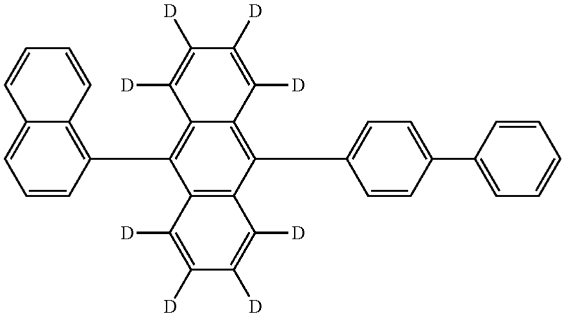

-continued
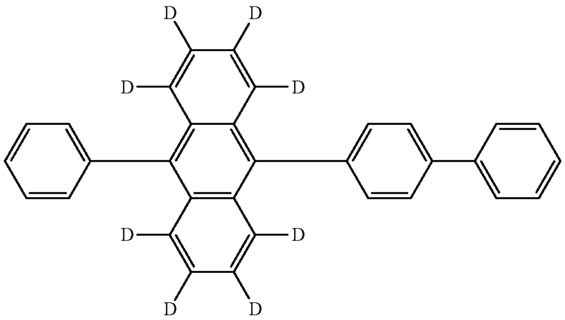
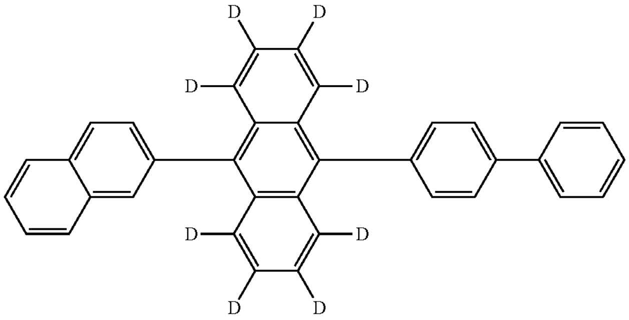
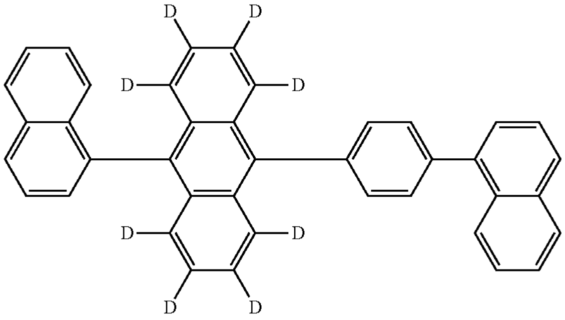
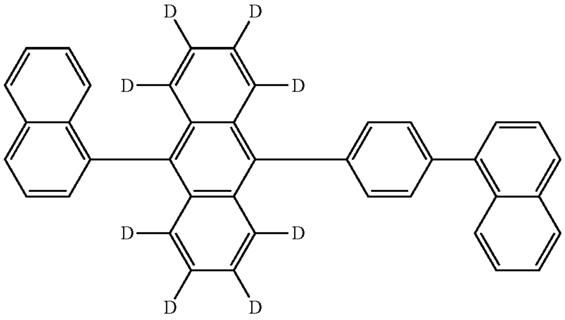
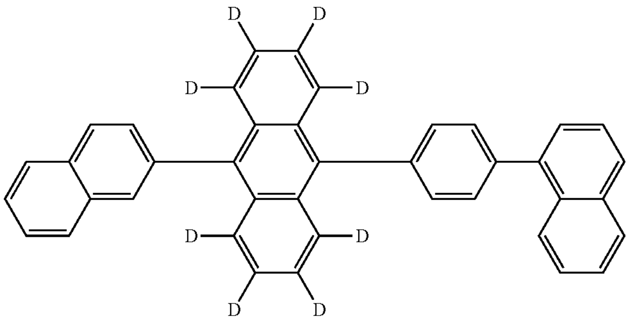

-continued
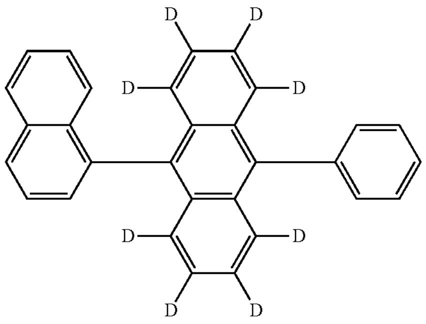
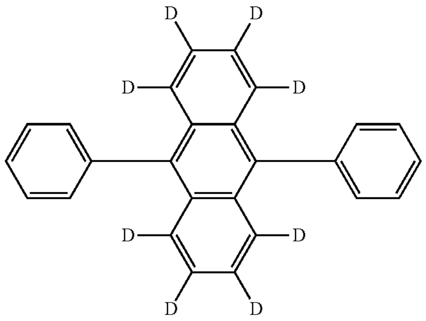
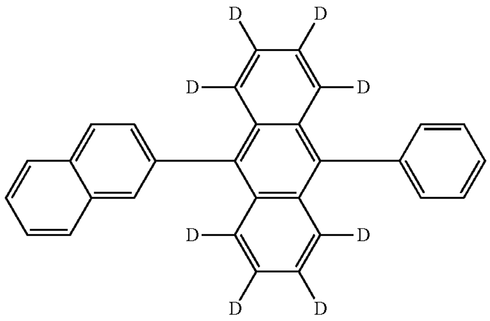
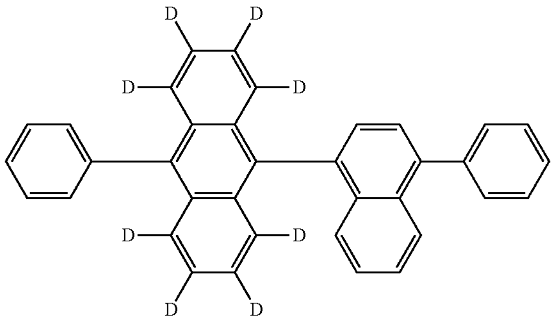
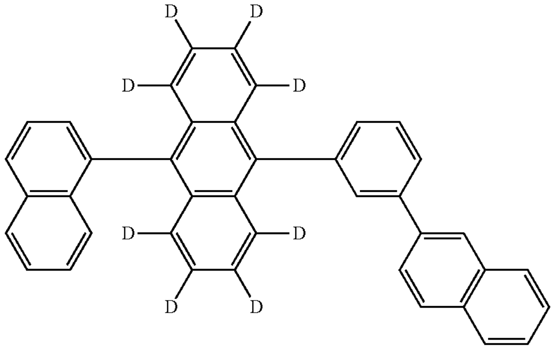

-continued
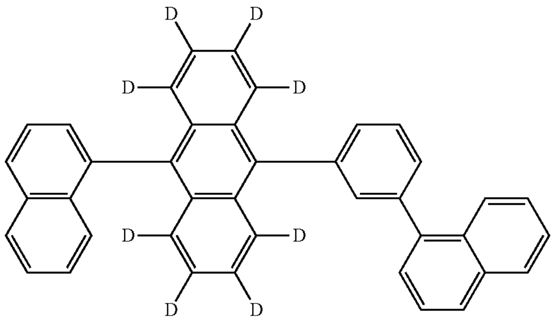
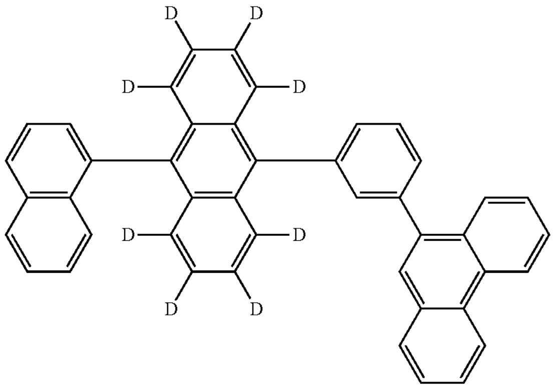
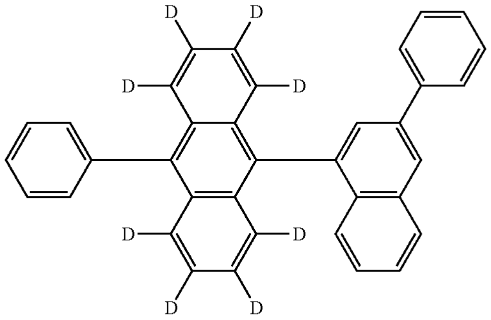
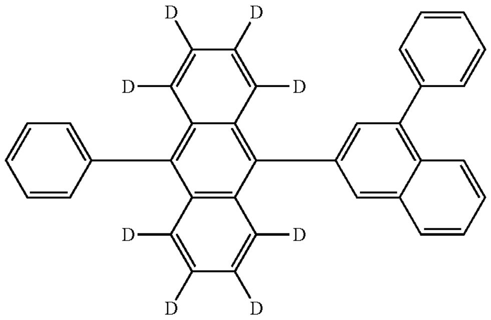
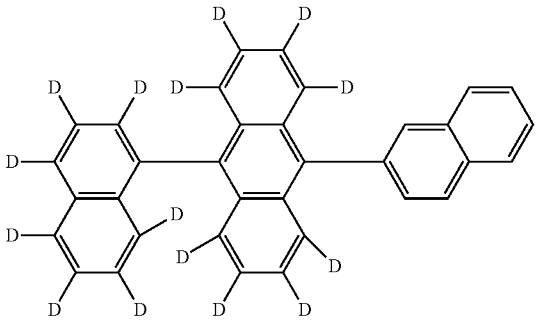

-continued
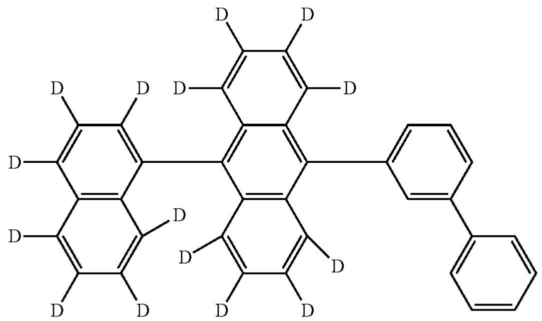
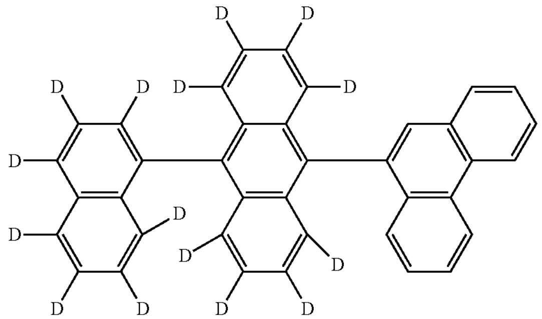
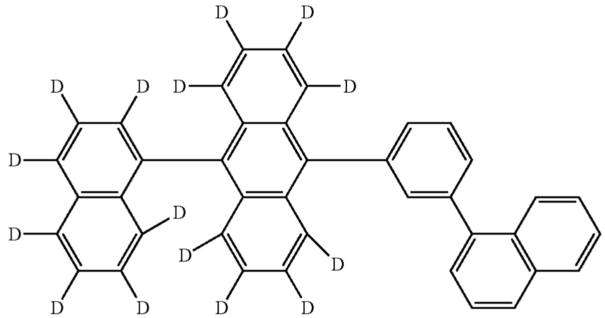
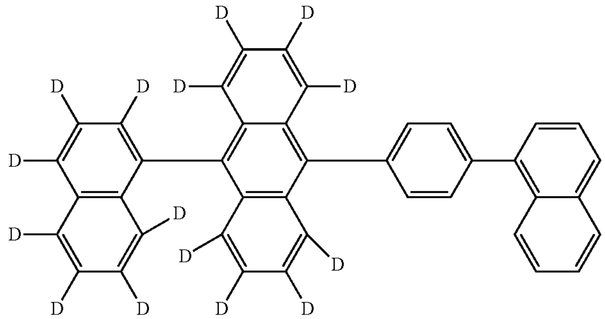
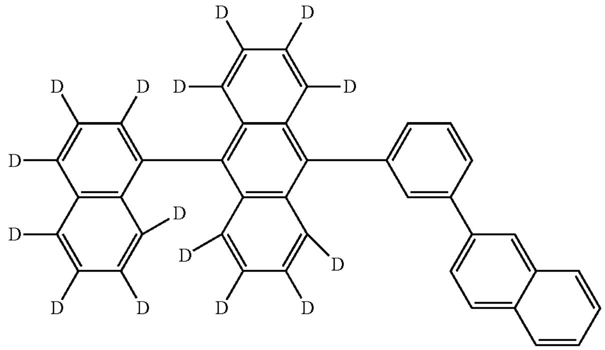

-continued
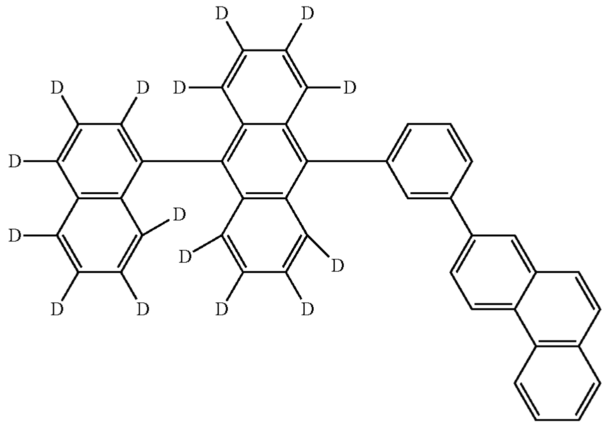
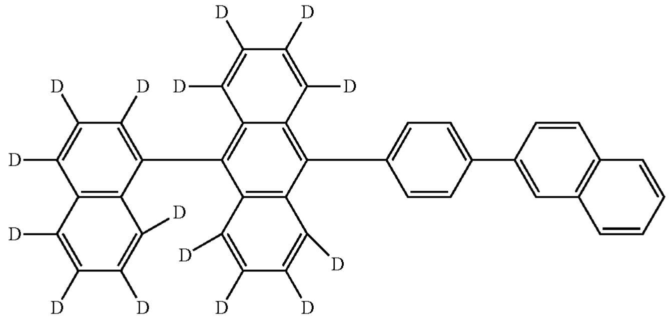
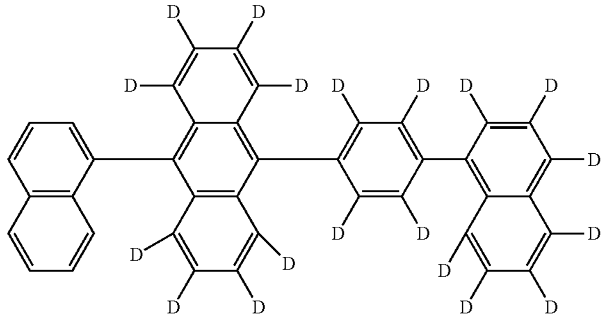
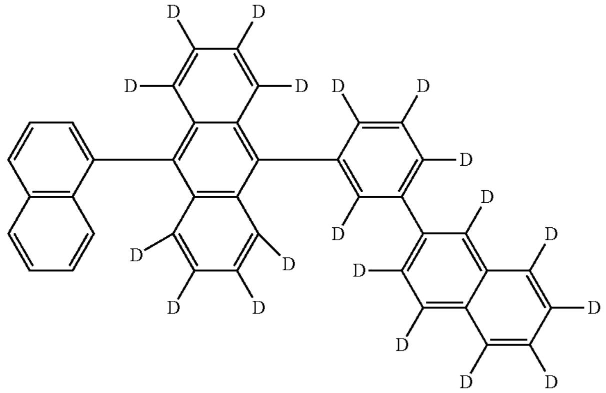

-continued
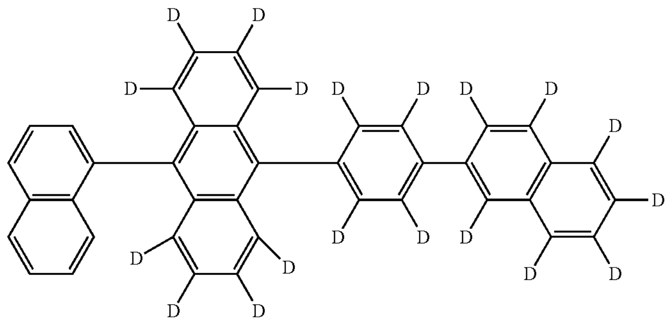
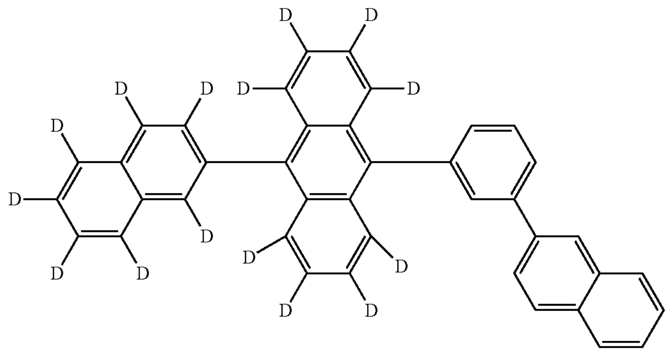
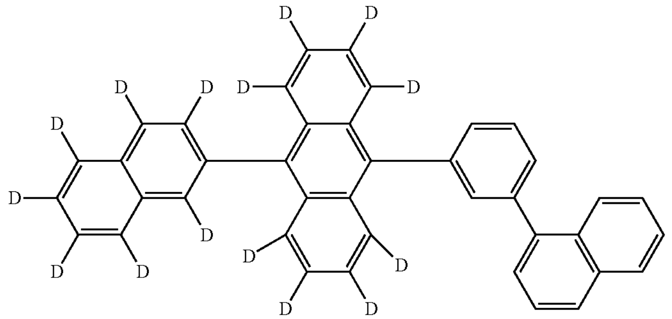
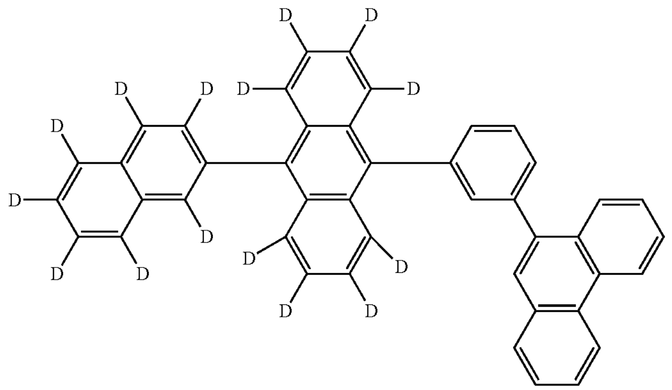
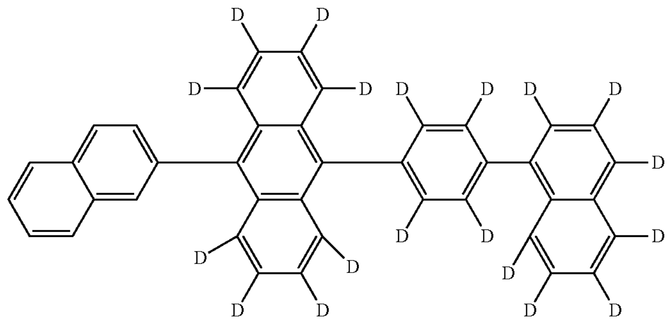

-continued

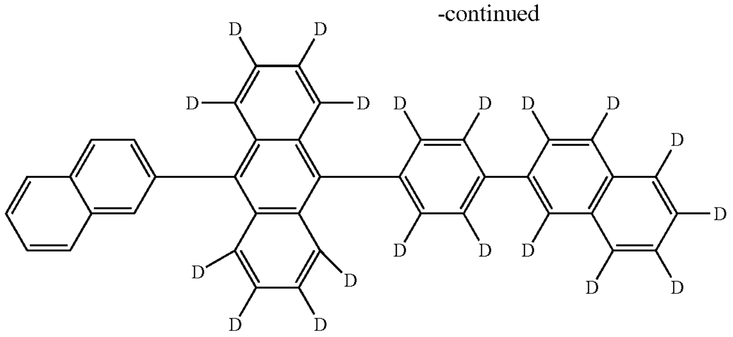

(Compound Represented by Formula (11))

The compound represented by the formula (11) is explained below.

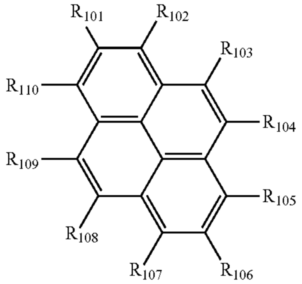

(11)

In the formula (11), one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;

at least one of $R_{101}$ to $R_{110}$ is a monovalent group represented by the formula (12);

$R_{101}$ to $R_{110}$ that do not form the substituted or unsubstituted, saturated or unsaturated ring and that are not a monovalent group represented by the following formula (12) are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

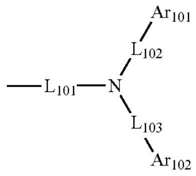

(12)

wherein, in the formula (12), $Ar_{101}$ and $Ar_{102}$ are independently a substituted or unsubstituted aryl group having 6 to 50 ring carbon atoms, or a substituted or unsubstituted monovalent heterocyclic group having 5 to 50 ring atoms;

$L_{101}$ to $L_{103}$ are independently a single bonded, a substituted or unsubstituted arylene group having 6 to 30 ring carbon atoms, or a substituted or unsubstituted divalent heterocyclic group having 5 to 30 ring atoms.

In the formula (11), it is preferable that two of $R_{101}$ to $R_{110}$ be the group represented by the formula (12).

In one embodiment, the compound represented by the formula (11) is represented by the following formula (13):

(13)

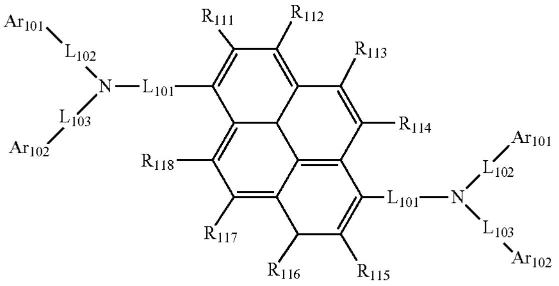

wherein in the formula (13), $R_{111}$ to $R_{118}$ are the same as $R_{101}$ to $R_{110}$ that is not a monovalent group represented by the formula (12) in the formula (11). $Ar_{101}$, $Ar_{102}$, $L_{101}$, $L_{102}$ and $L_{103}$ are as defined in the formula (12).

In the formula (11), $L_{101}$ is preferably a single bond and $L_{102}$ and Lim are preferably a single bond.

In one embodiment, the compound represented by the formula (11) is represented by the formula (14) or (15):

(14)

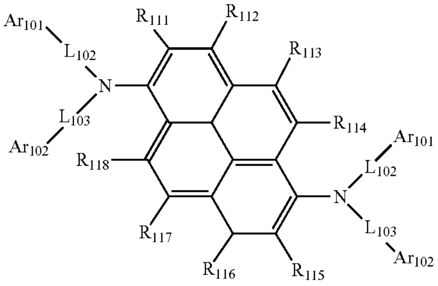

wherein in the formula (14), $R_{111}$ to $R_{118}$ are as defined in the formula (13), $Ar_{101}$, $Ar_{102}$, $L_{102}$ and $L_{103}$ are as defined in the formula (12);

(15)

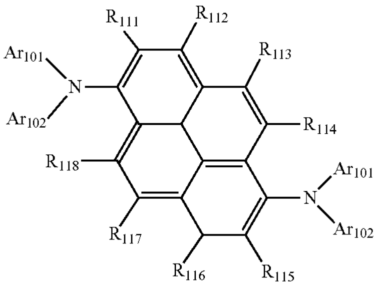

wherein in the formula (15), $R_{111}$ to $R_{118}$ are as defined in the formula (13), $Ar_{101}$ and $Ar_{102}$ are as defined in the formula (12).

In the formula (11) and formula (12), it is preferable that at least one of $Ar_{101}$ and $Ar_{102}$ be the group represented by the following formula (16):

(16)

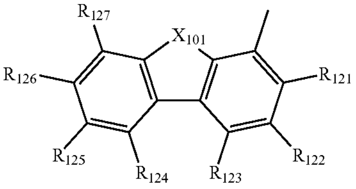

wherein in the formula (16), $X_{101}$ is an oxygen atom or a sulfur atom;

One or more pairs of two or more adjacent groups of $R_{121}$ to $R_{127}$ are bonded with each other to form a substituted or unsubstituted, saturated or unsaturated ring, or do not form a substituted or unsubstituted, saturated or unsaturated ring:

$R_{121}$ to $R_{127}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

It is preferable that $X_{101}$ be an oxygen atom.

It is preferable that at least one of $R_{121}$ to $R_{127}$ be a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

It is preferable that in the formula (11) and formula (12), $Ar_{101}$ be a group represented by the formula (16) and $Ar_{102}$ be a substituted or unsubstituted aryl group having 6 to 50 ring carbon atoms.

In one embodiment, the compound represented by the formula (11) is represented by the following formula (17):

(17)

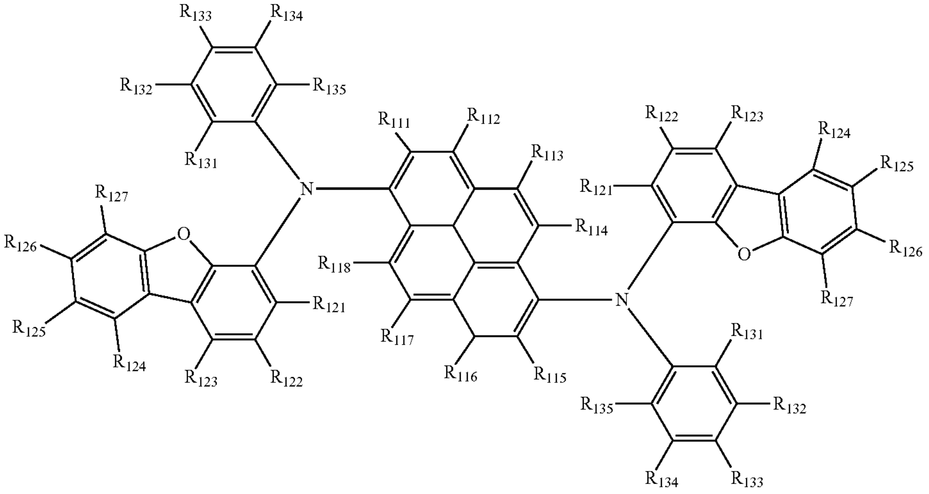

wherein in the formula (17), $R_{111}$ to $R_{118}$ are as defined in the formula (13), and $R_{121}$ to $R_{127}$ are as defined in the formula (16);

$R_{131}$ to $R_{135}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

As the compound represented by the formula (11), the following compounds can be given as specific examples, for example. In the following example compounds, Me represents a methyl group.

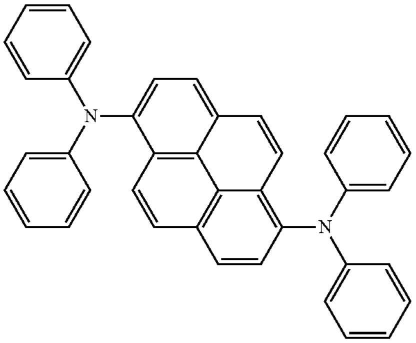

-continued

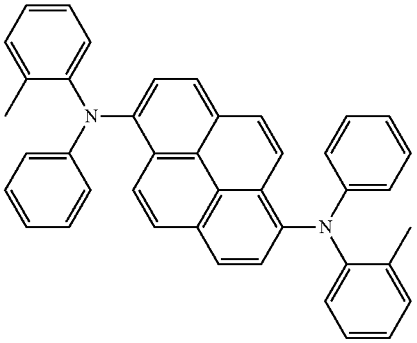

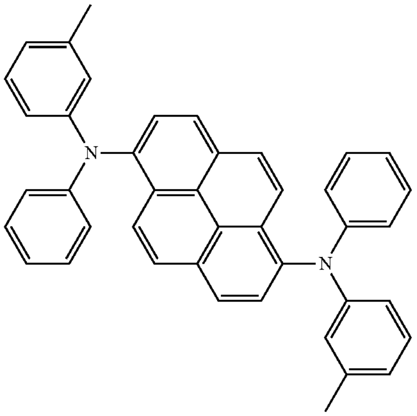

-continued
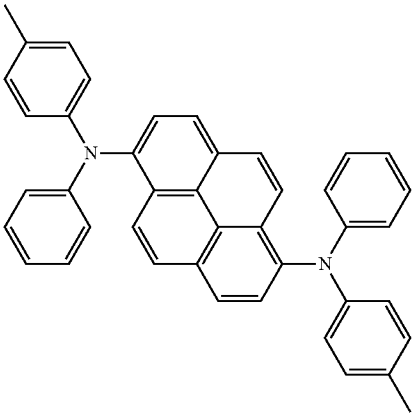
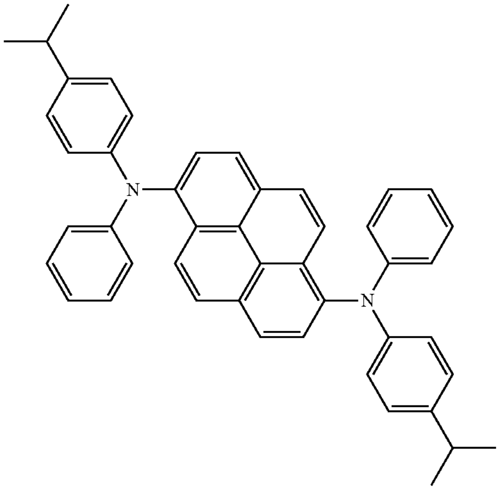
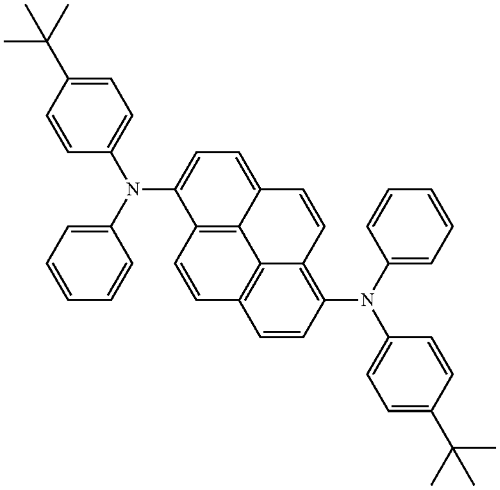
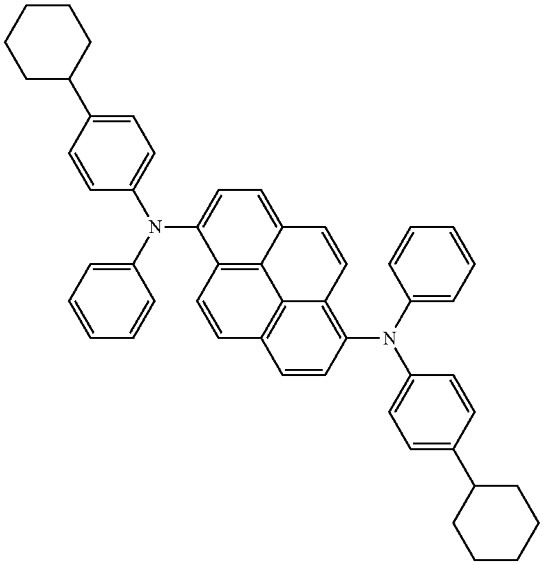
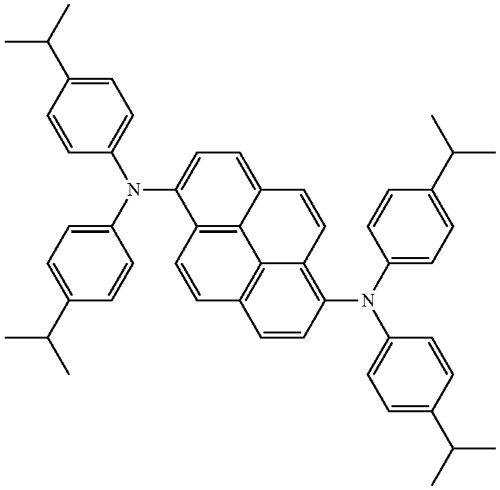
-continued
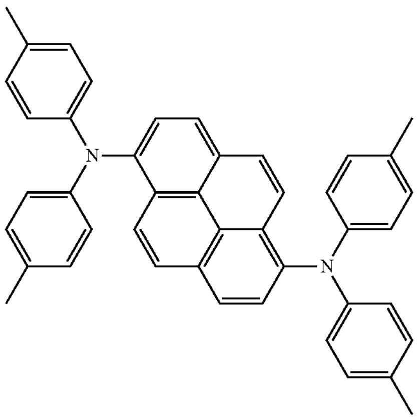

-continued
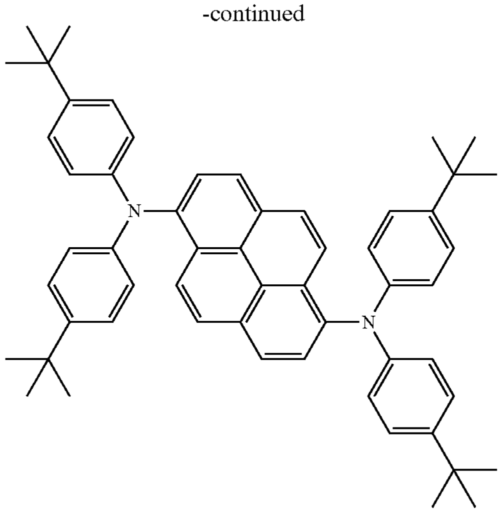
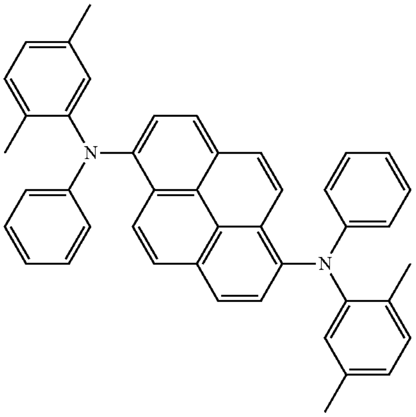
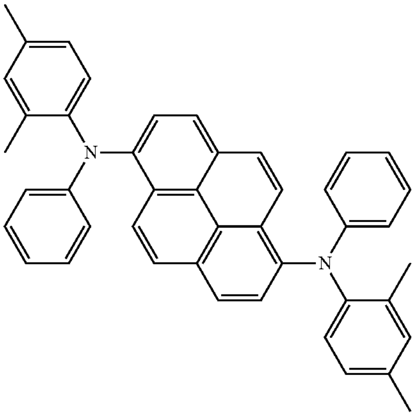
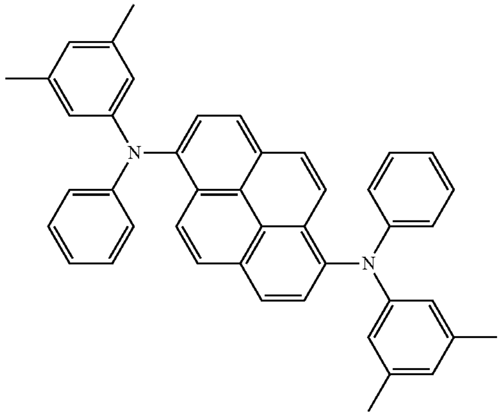
-continued
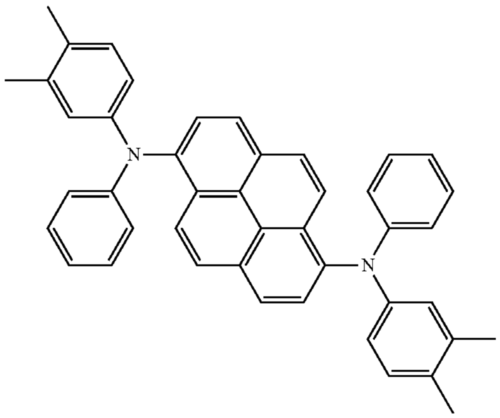
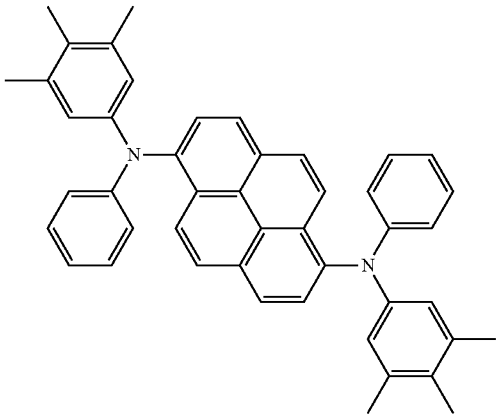
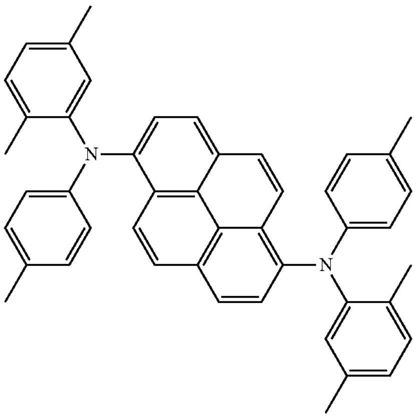
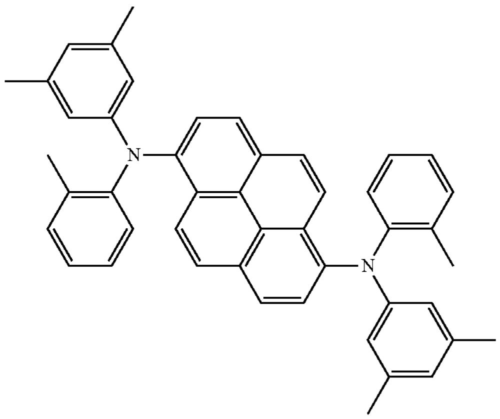

-continued
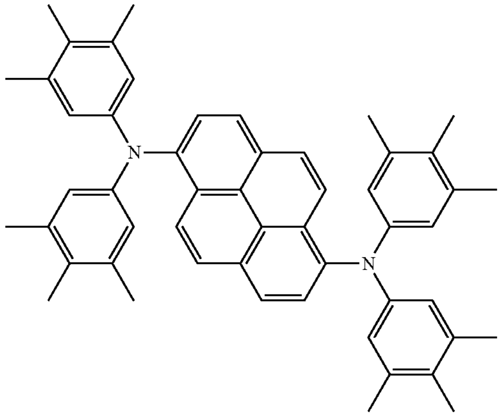
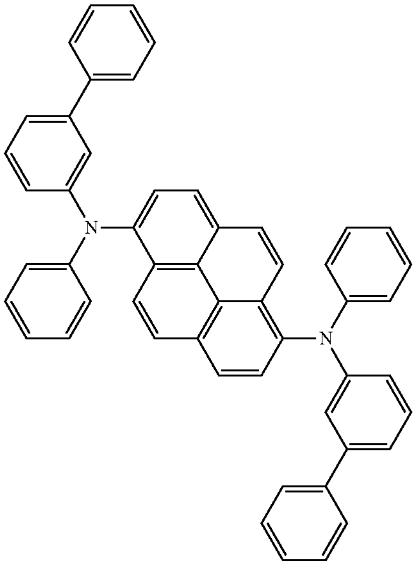
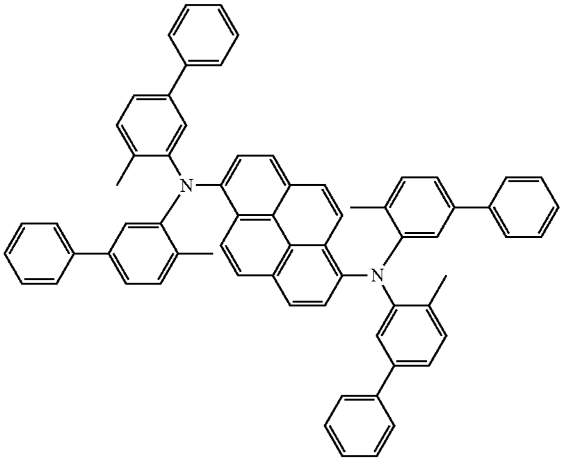
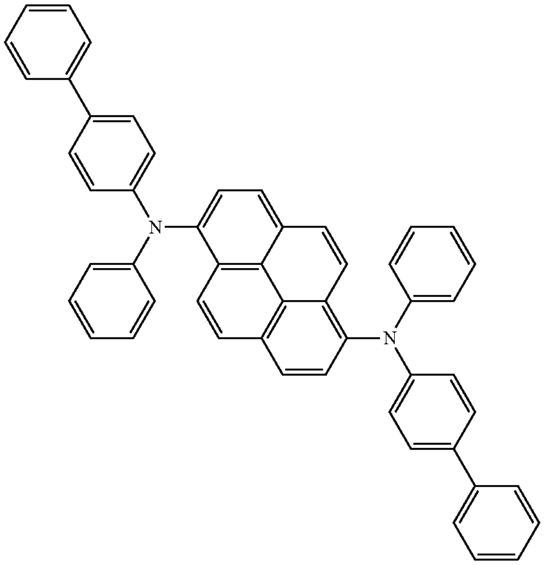
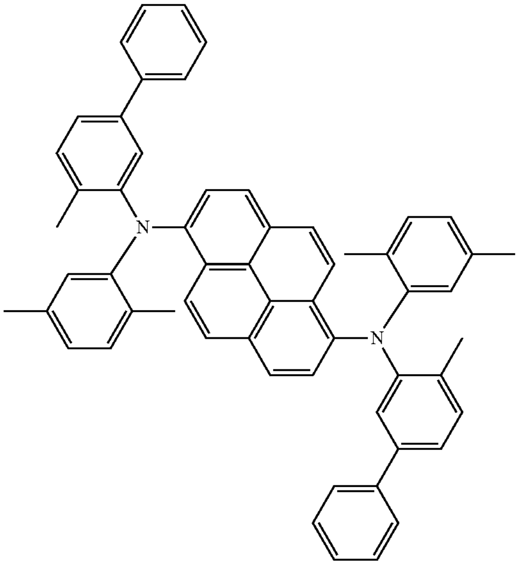
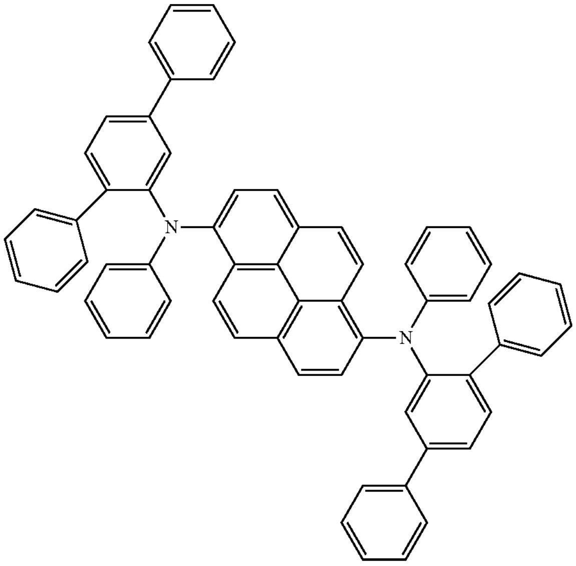
-continued -continued
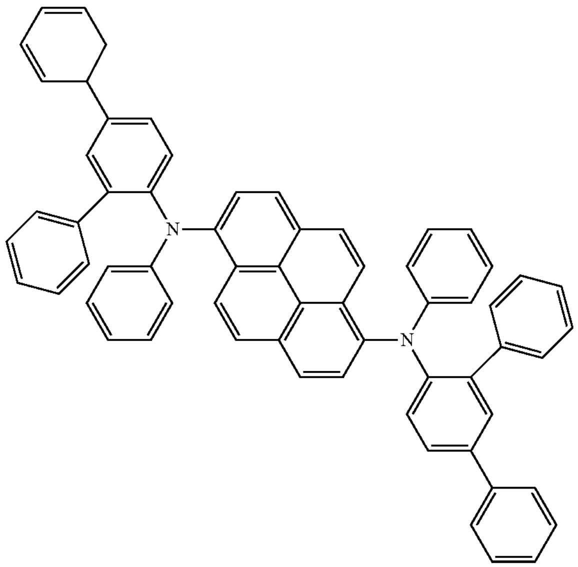
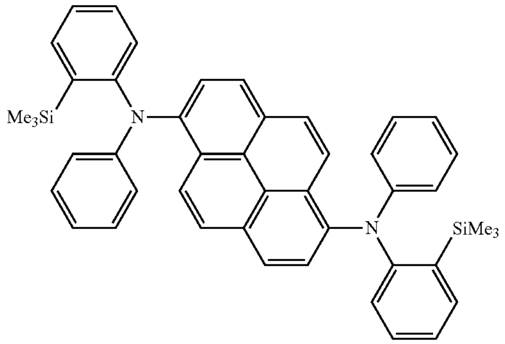
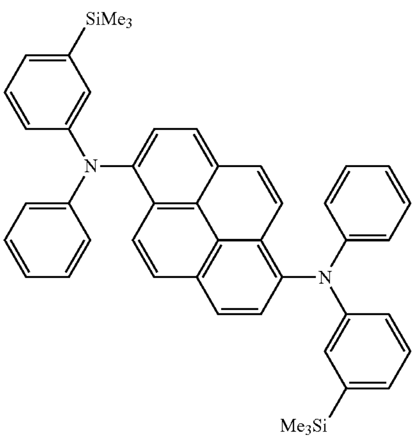
-continued
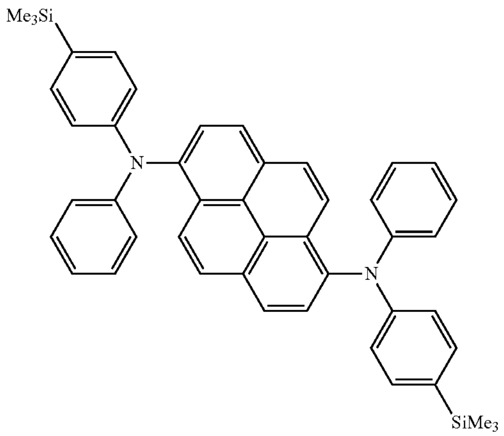
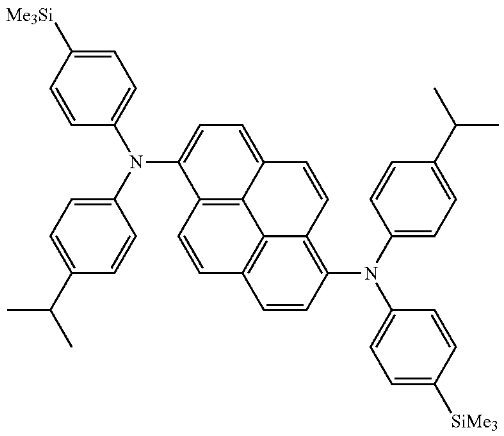
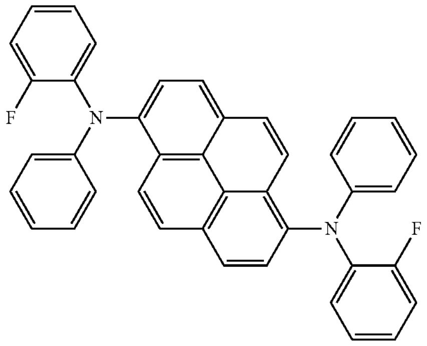
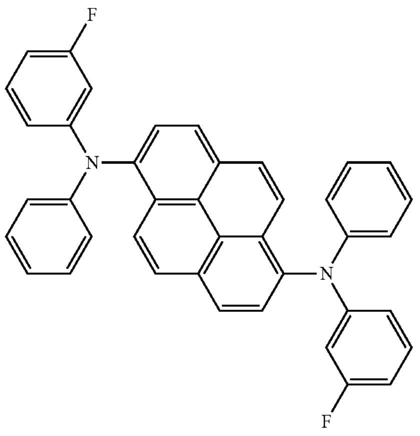

-continued
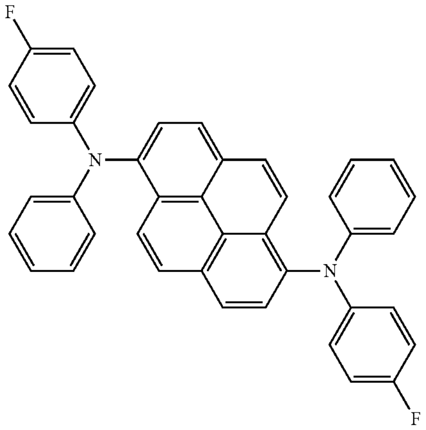
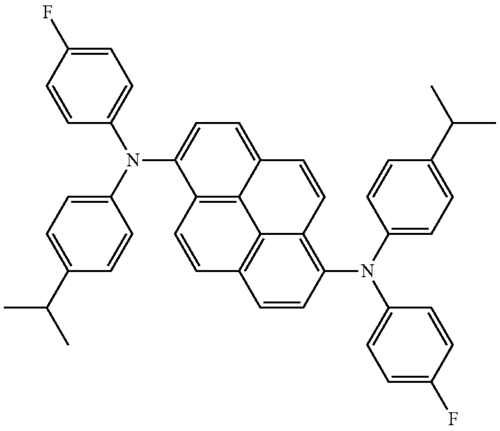
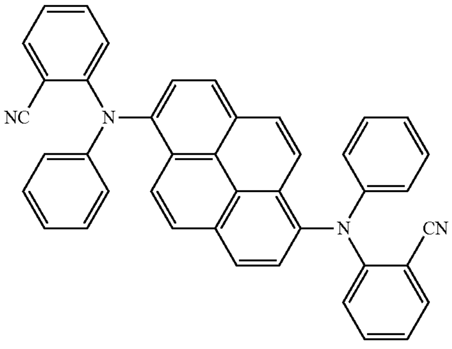
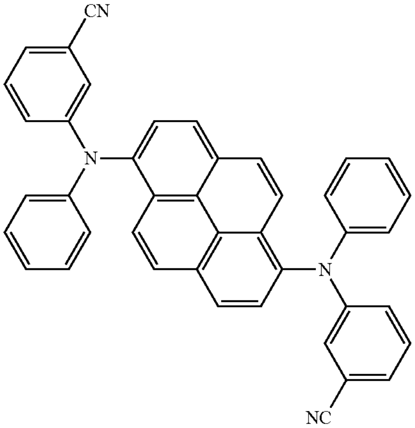
-continued
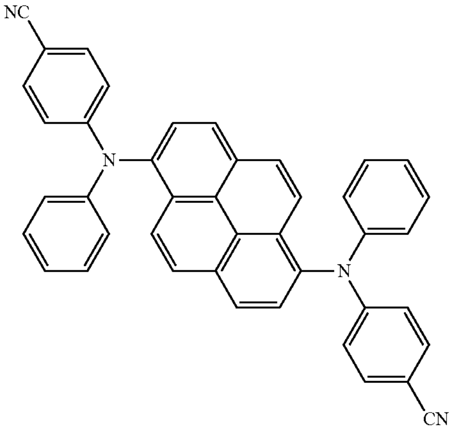
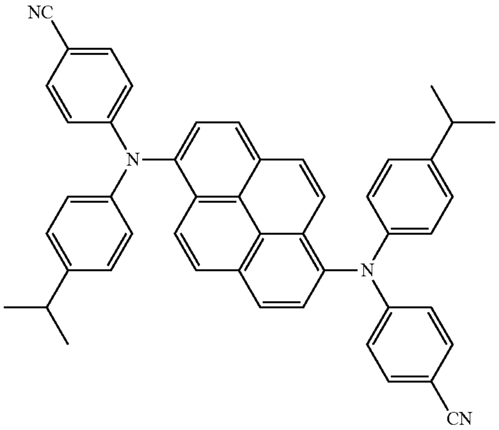
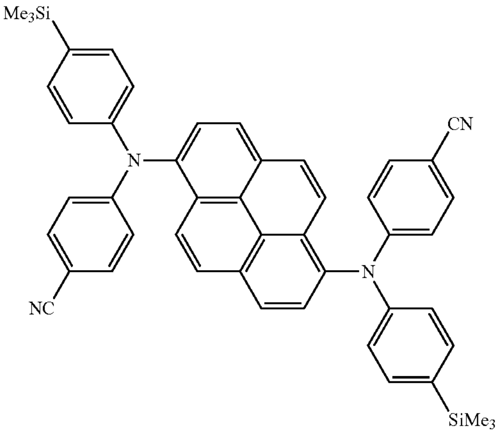
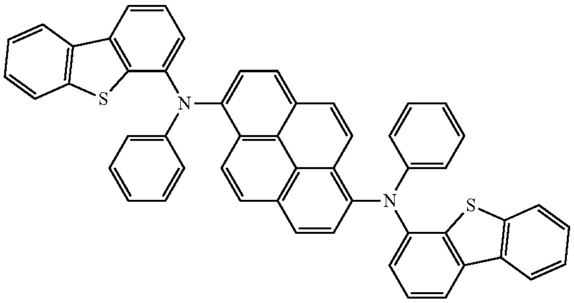

-continued
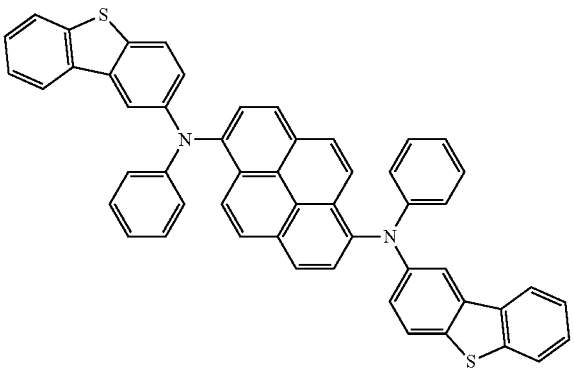
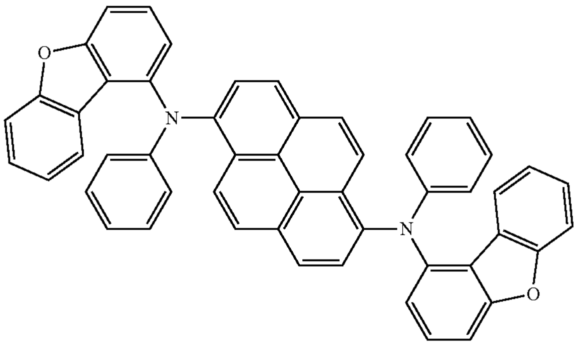
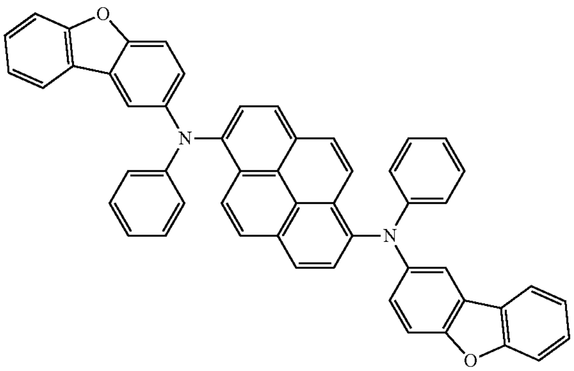
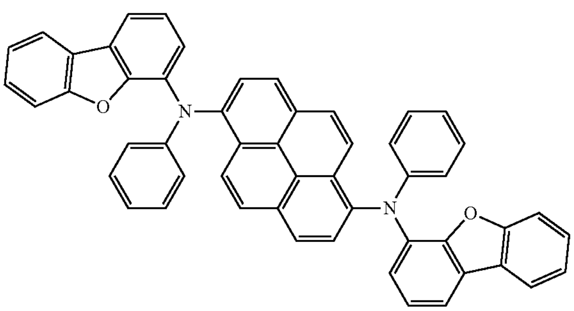
-continued
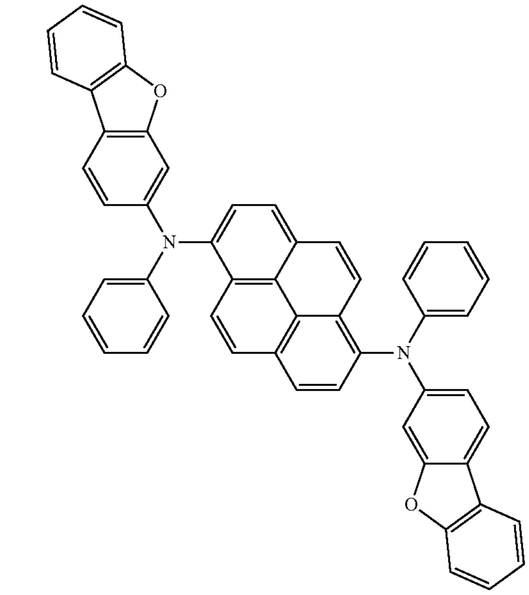
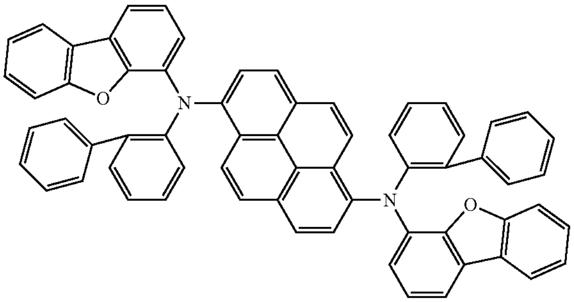
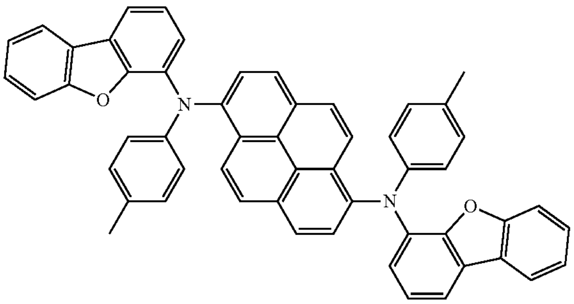
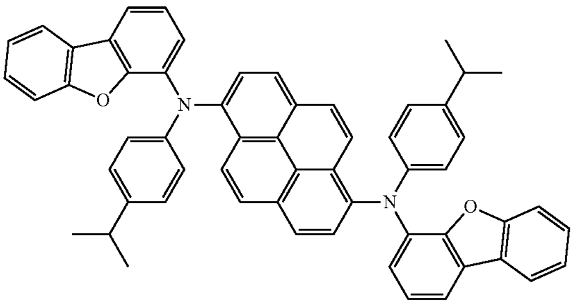

-continued
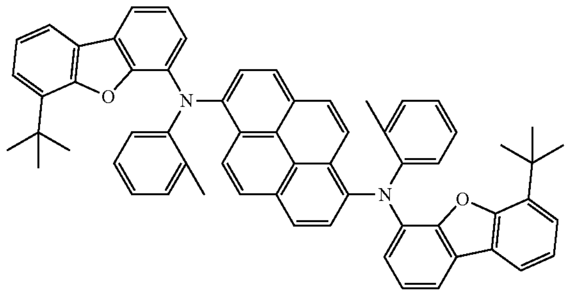
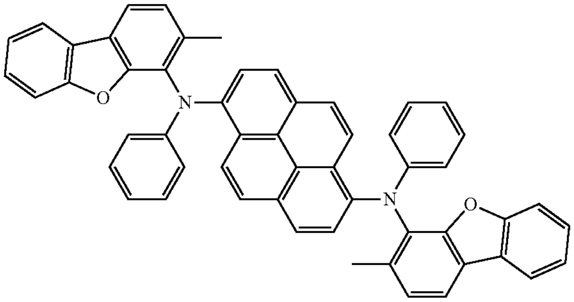
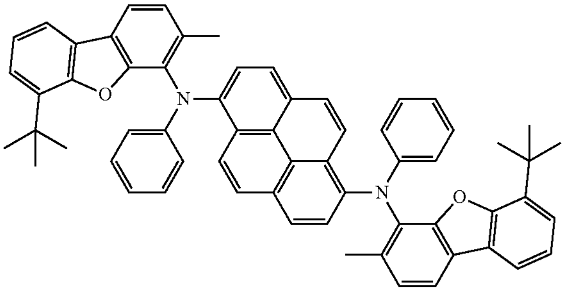
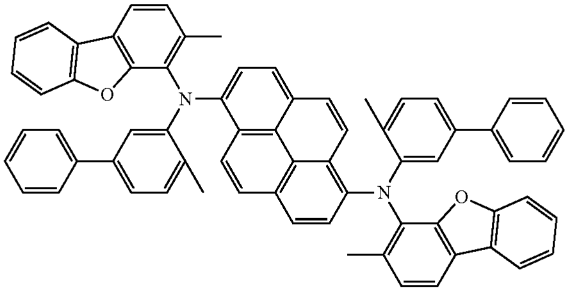
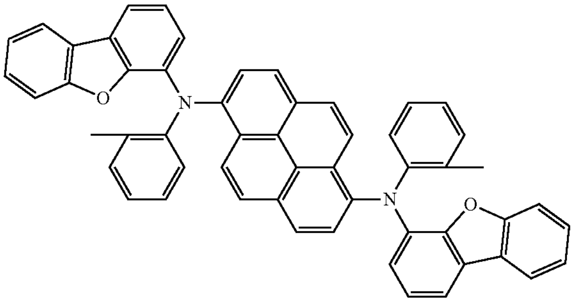
-continued
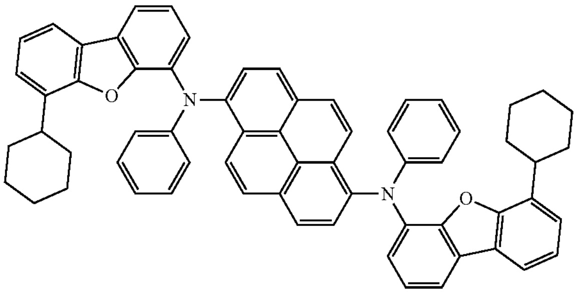
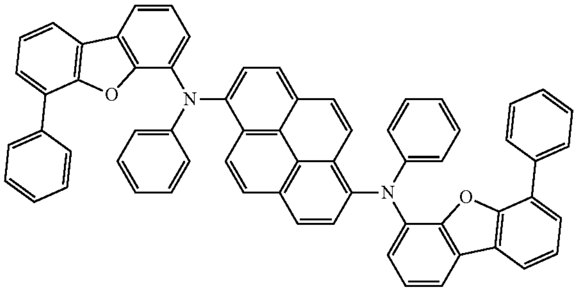
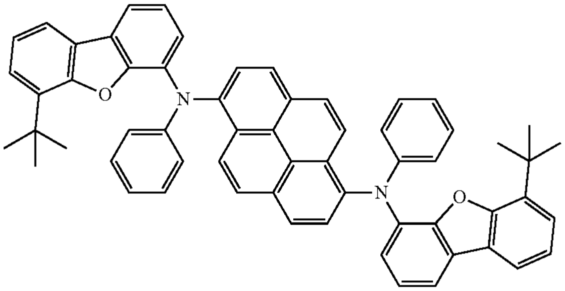
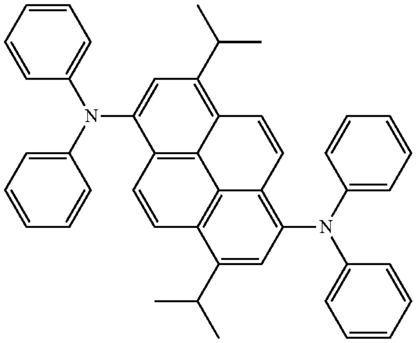
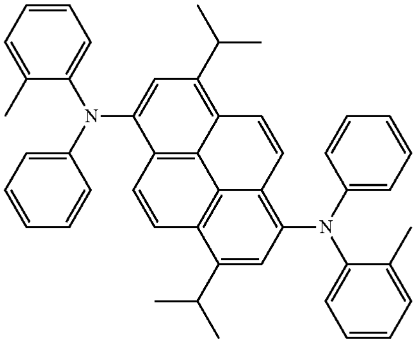

-continued
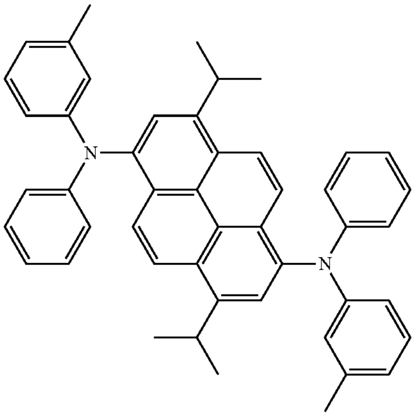
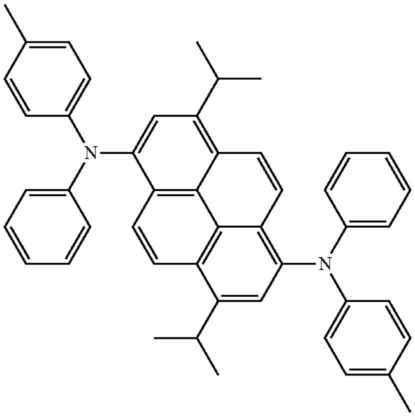
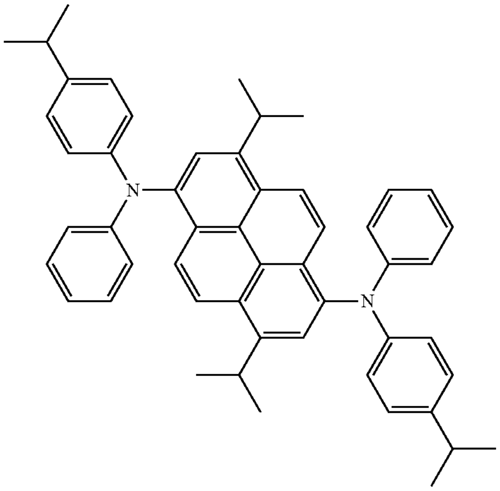
-continued
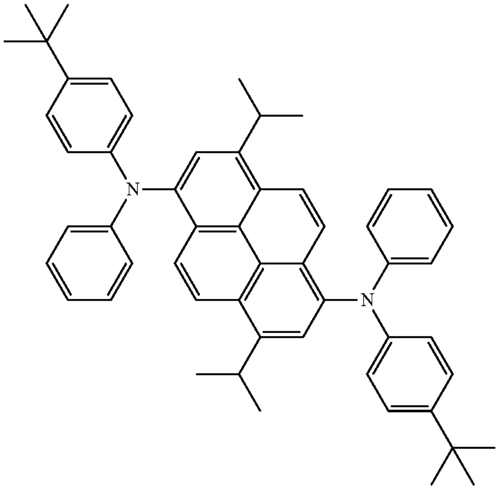
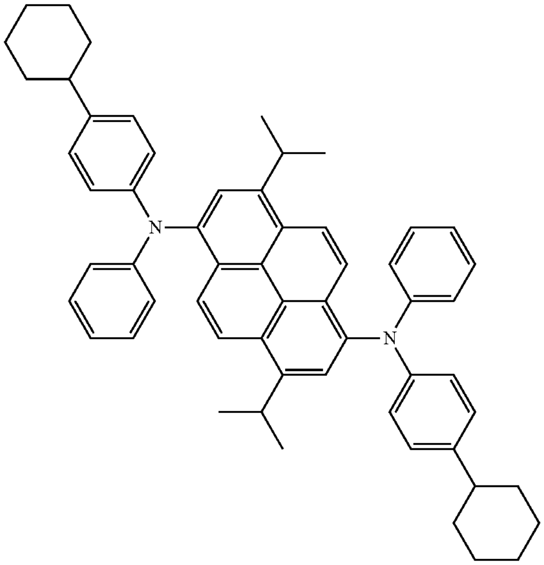
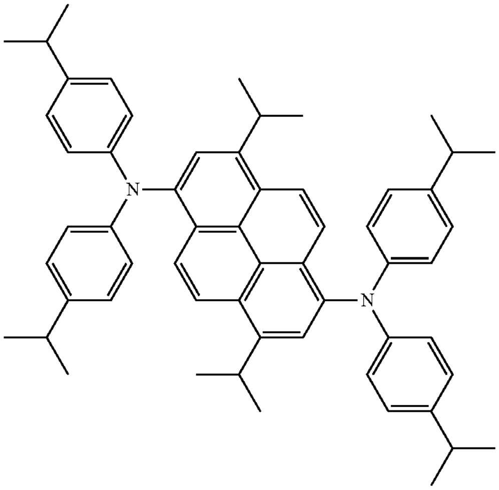

-continued
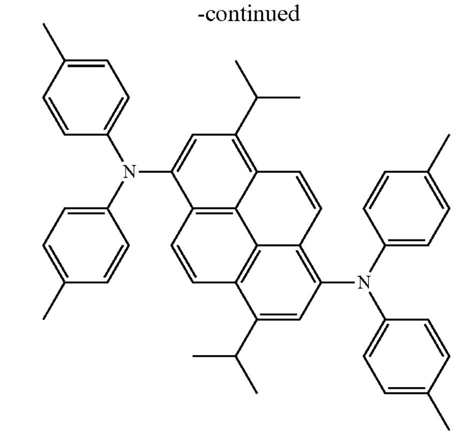
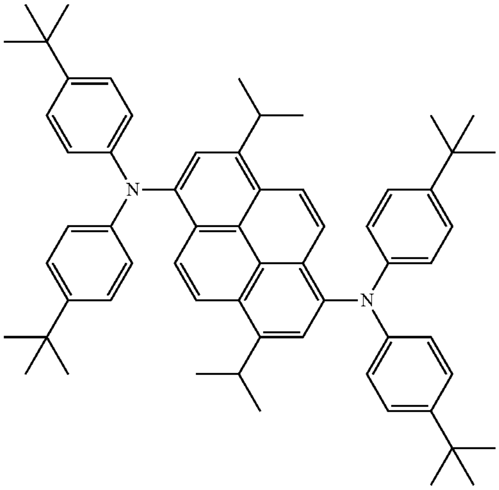
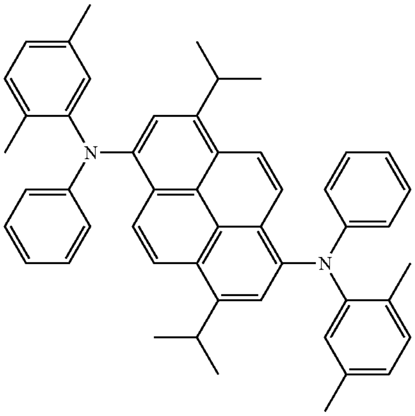
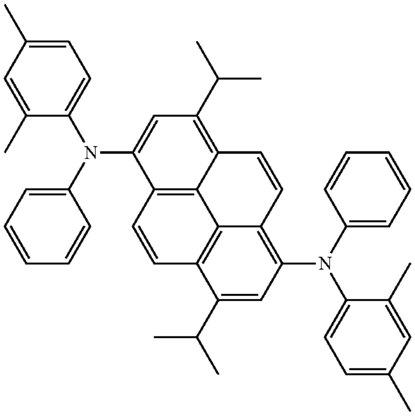
-continued
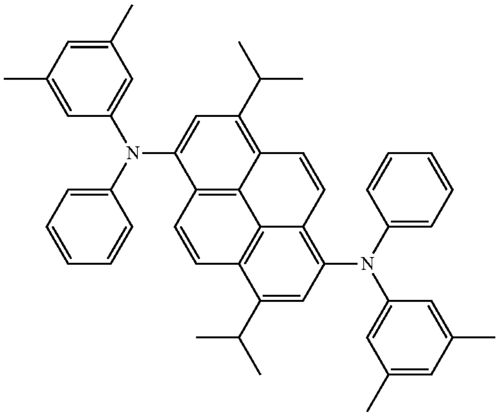
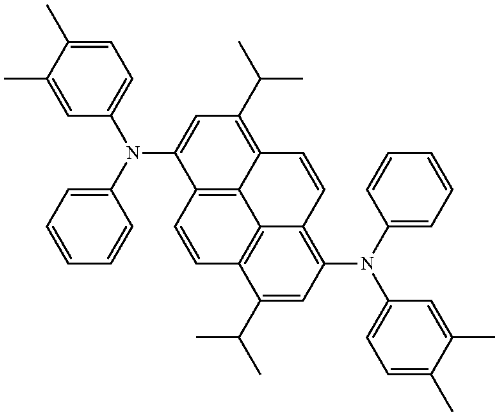
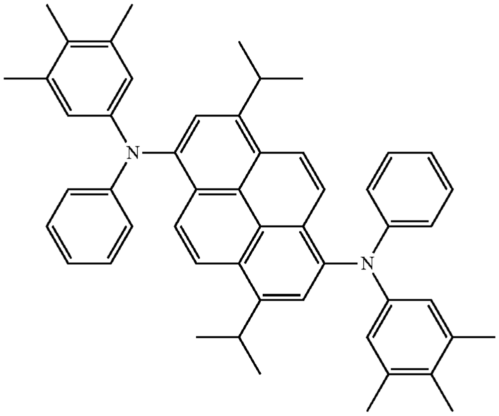
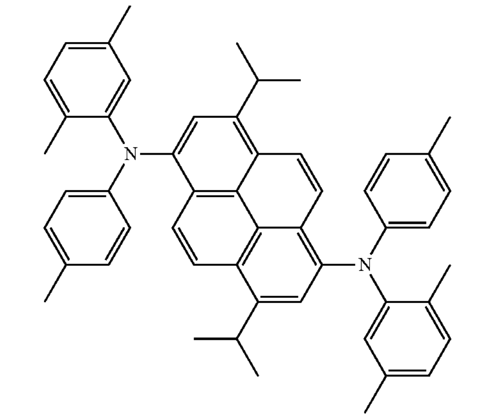

-continued
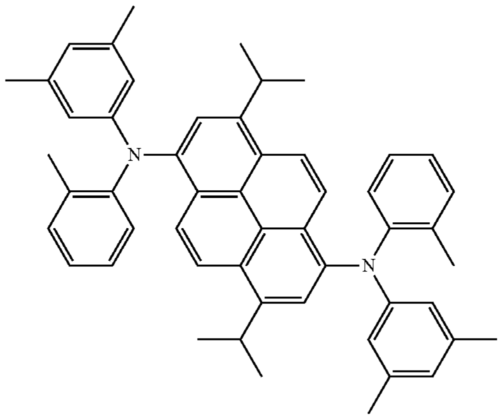
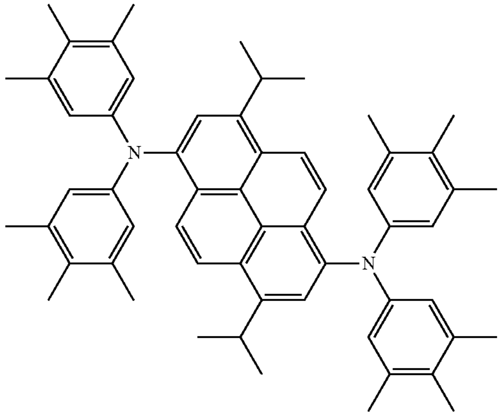
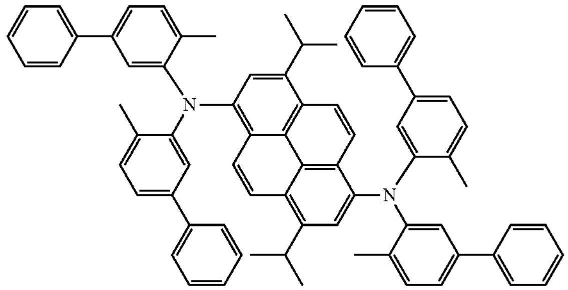
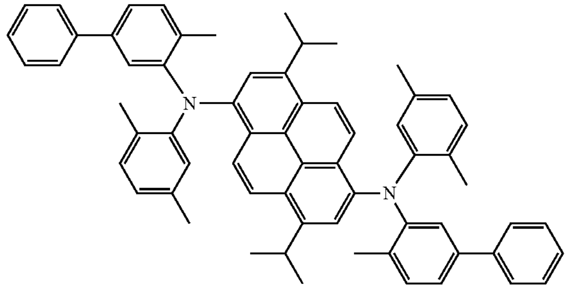
-continued
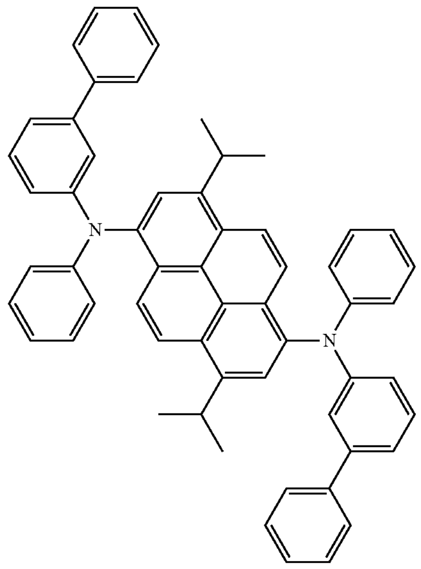
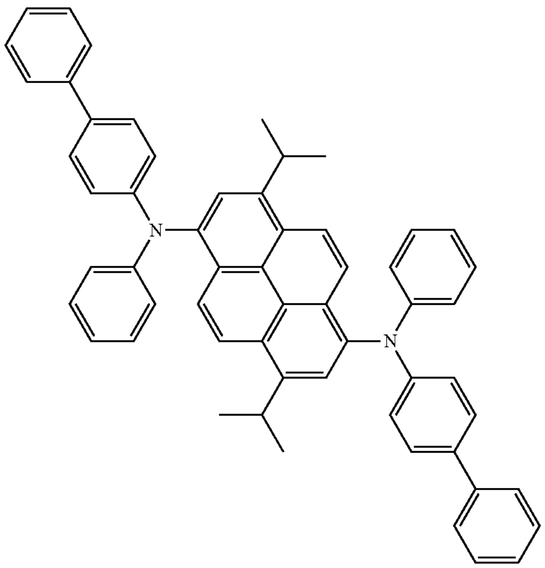
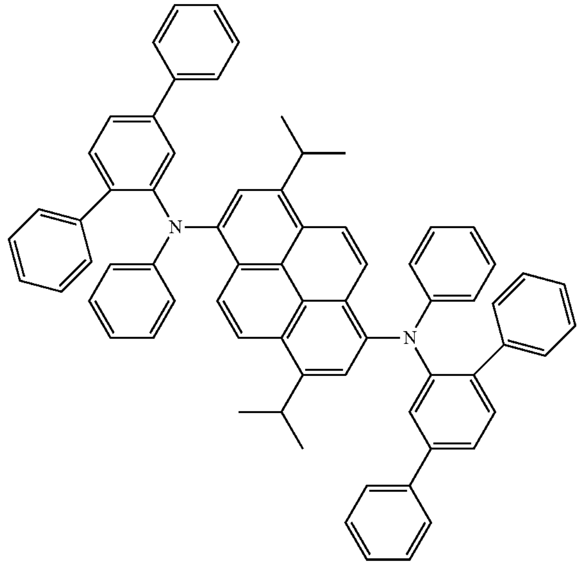

-continued
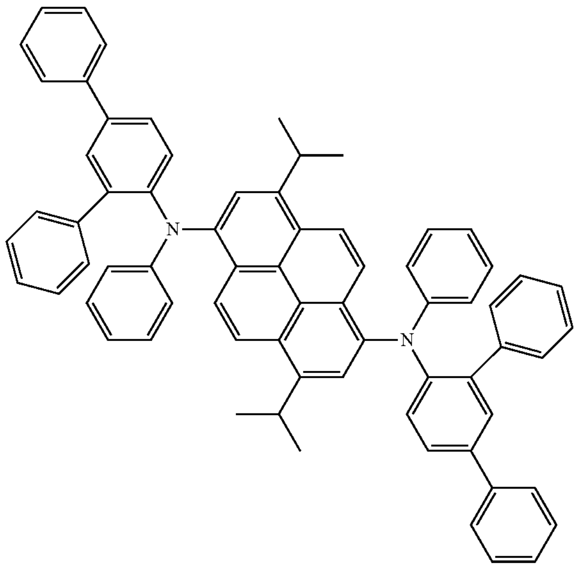
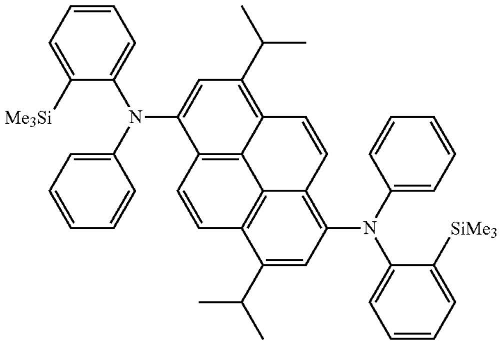
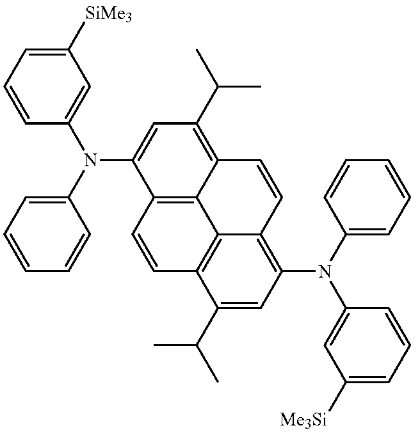
-continued
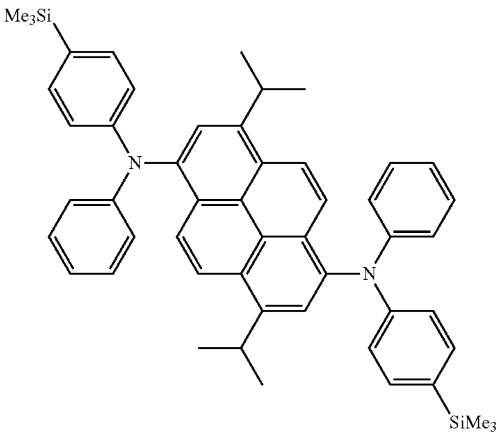
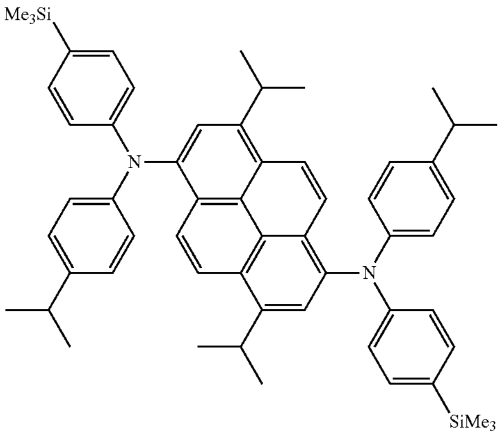
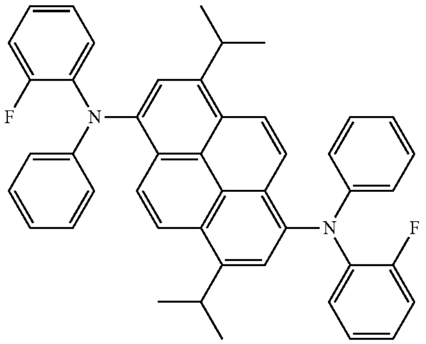
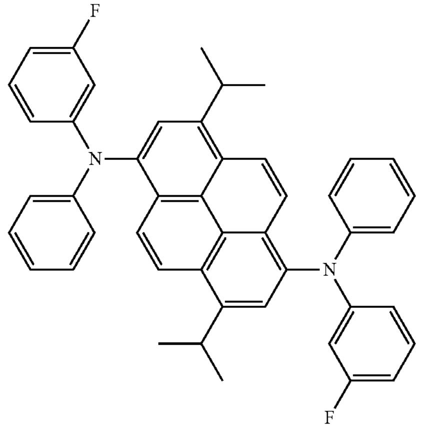

-continued
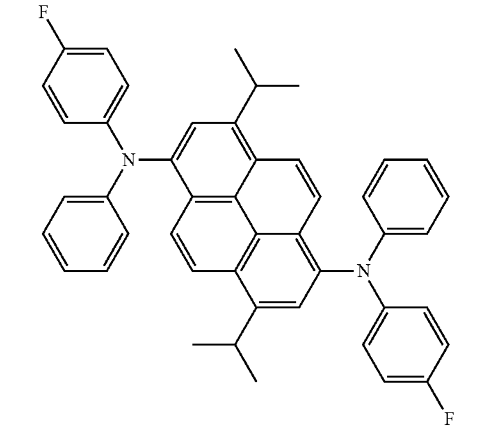
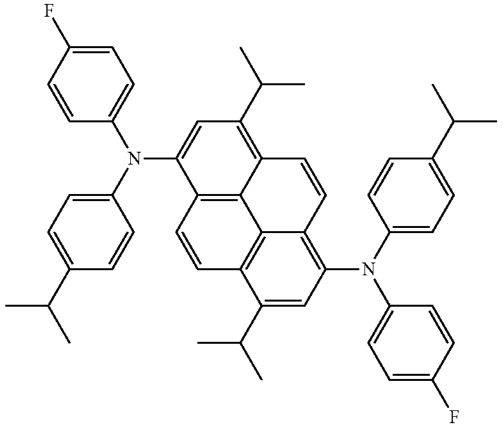
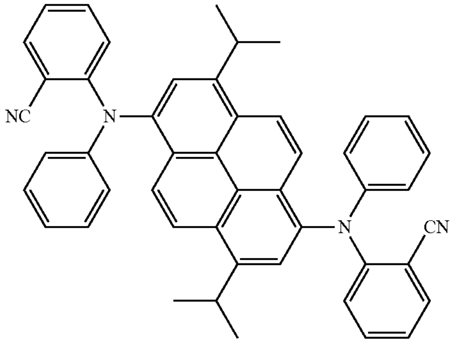
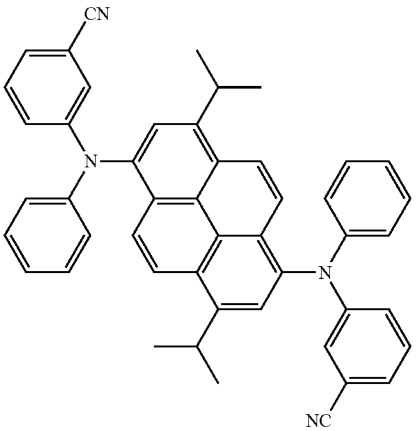
-continued
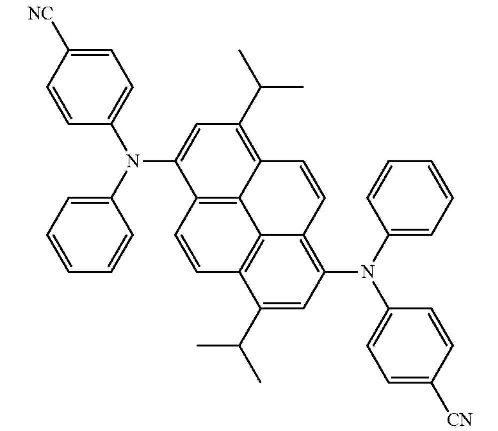
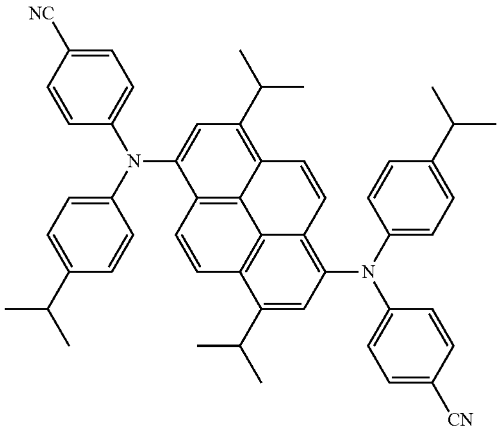
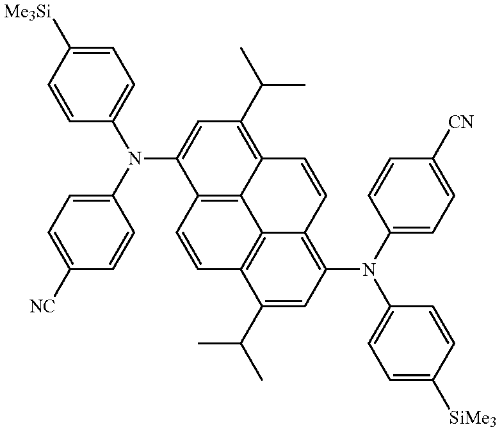
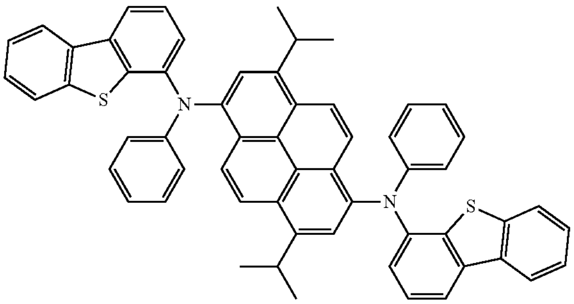

-continued
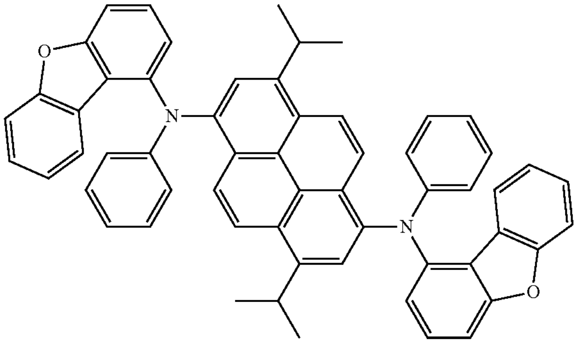
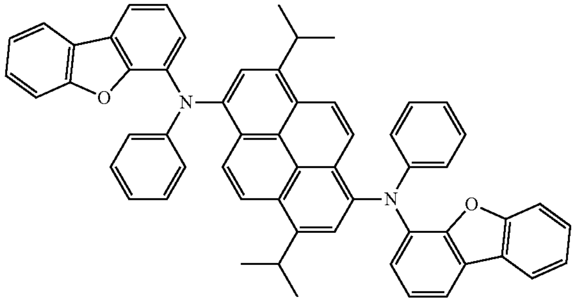
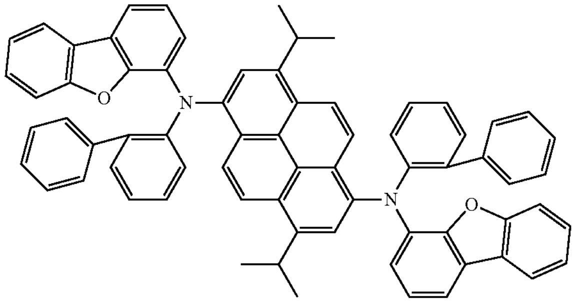
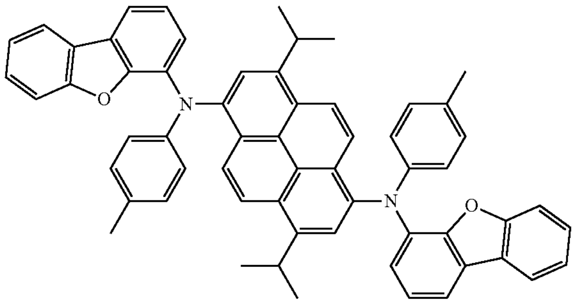
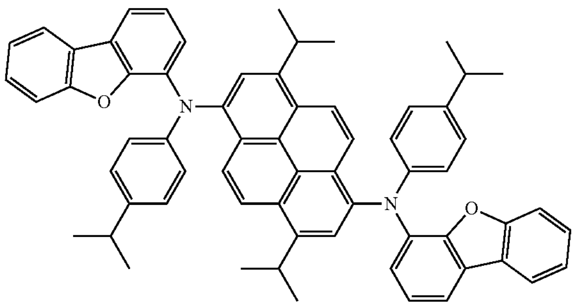
-continued
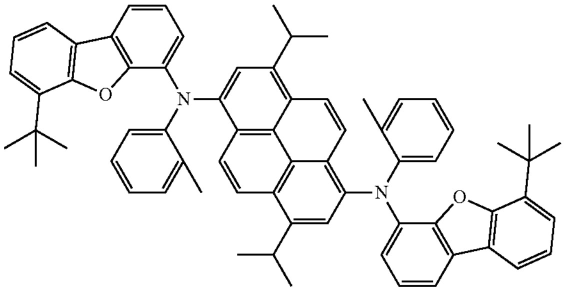
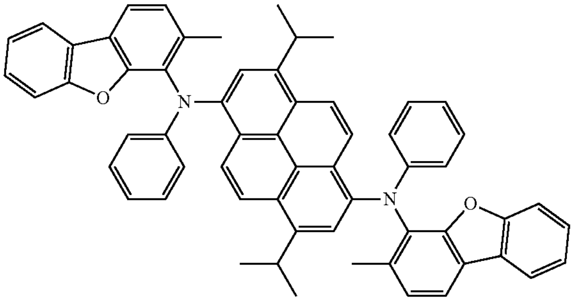
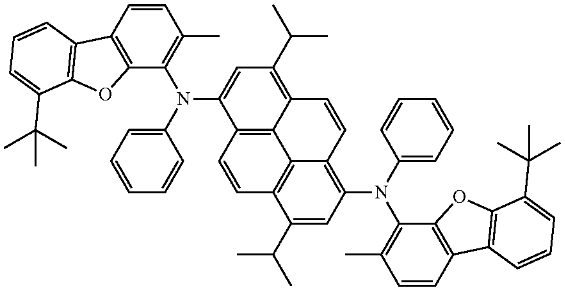
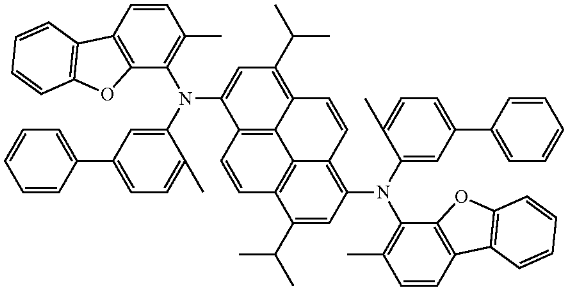
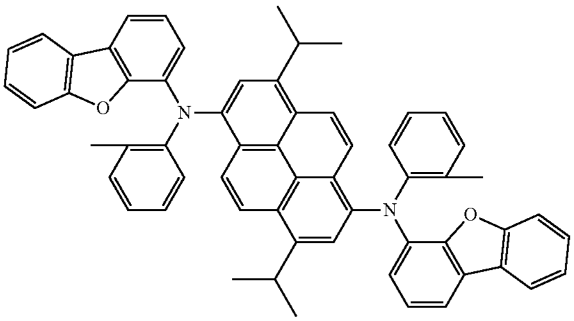

-continued
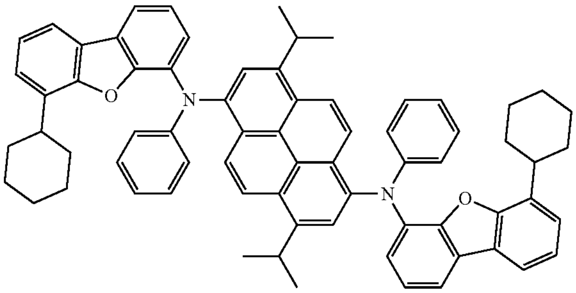
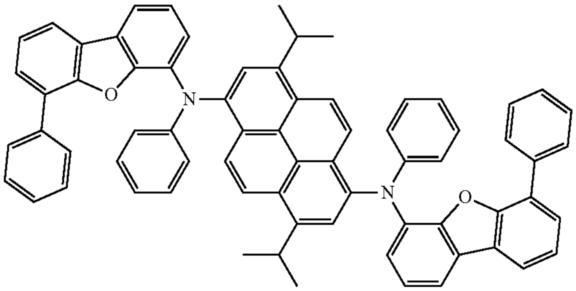
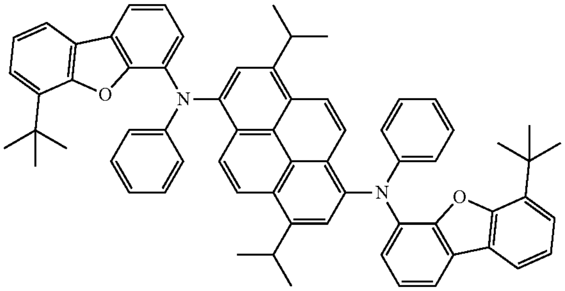
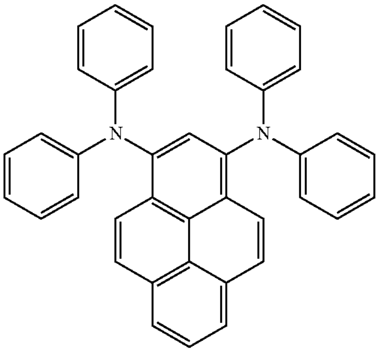
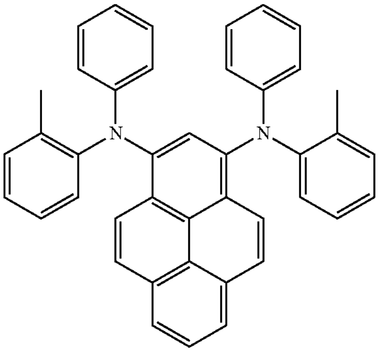
-continued
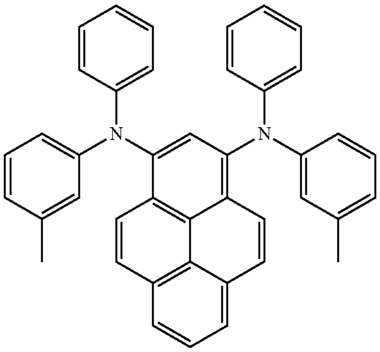
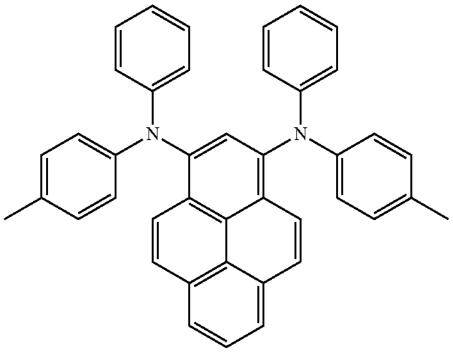
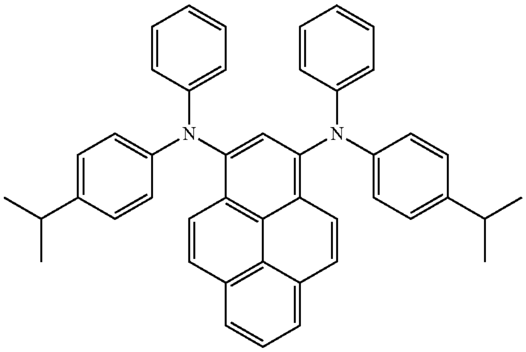
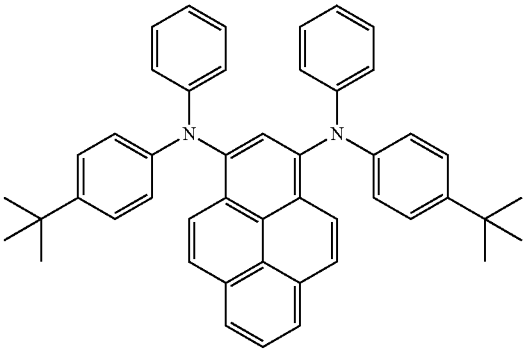

-continued
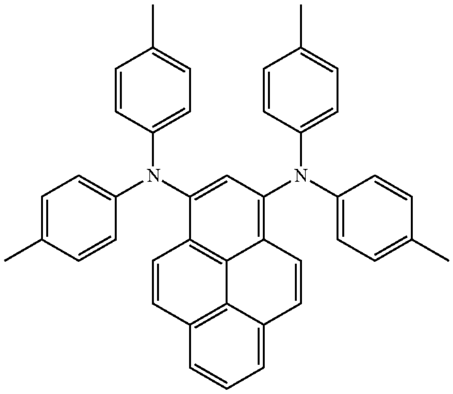
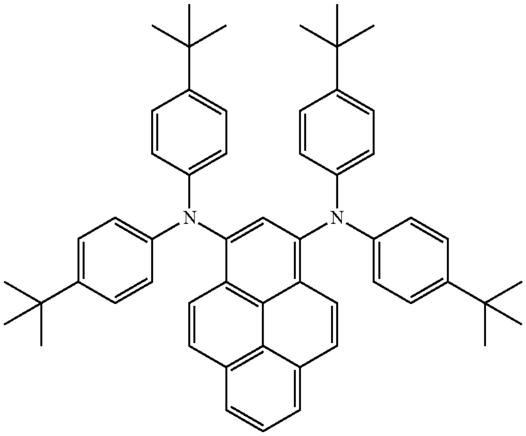
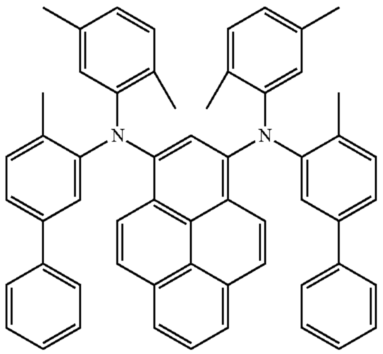
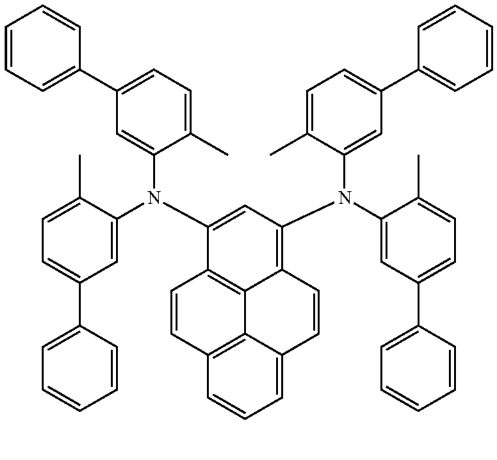
-continued
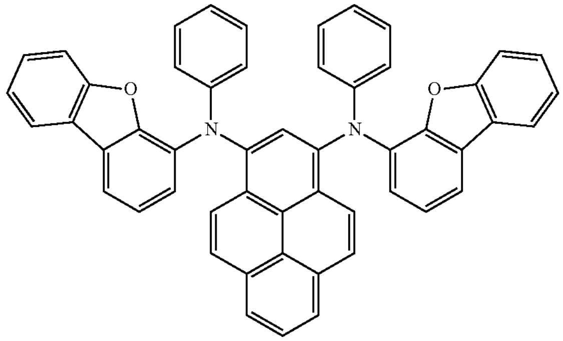
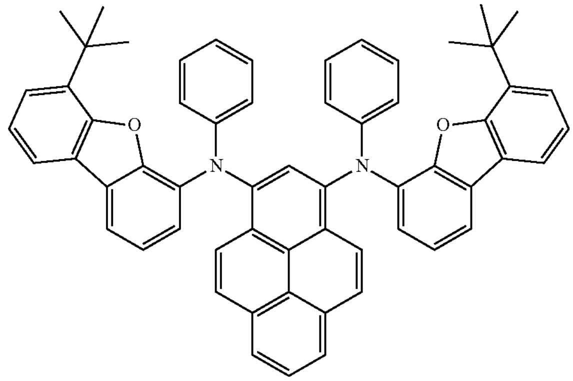
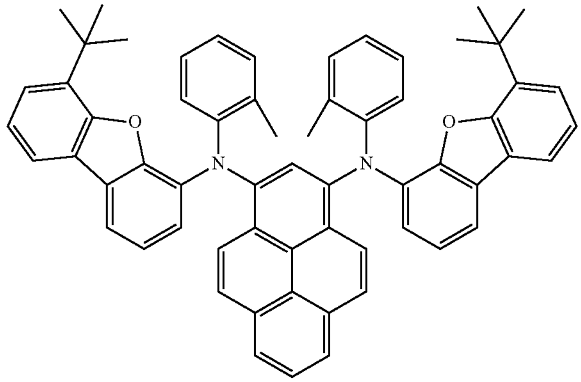
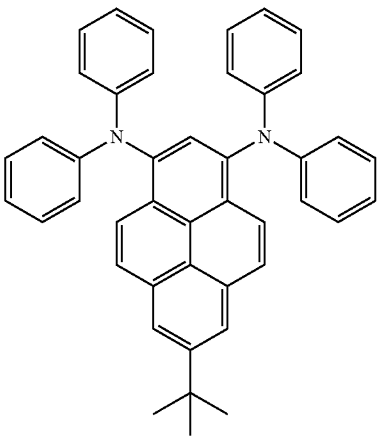

-continued
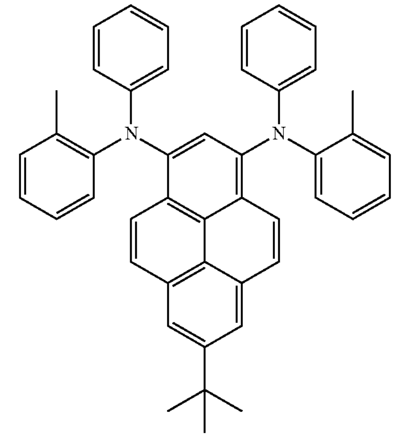
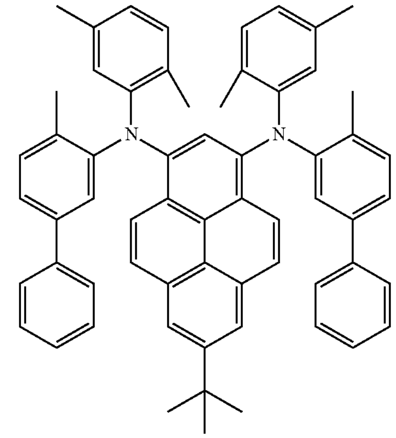
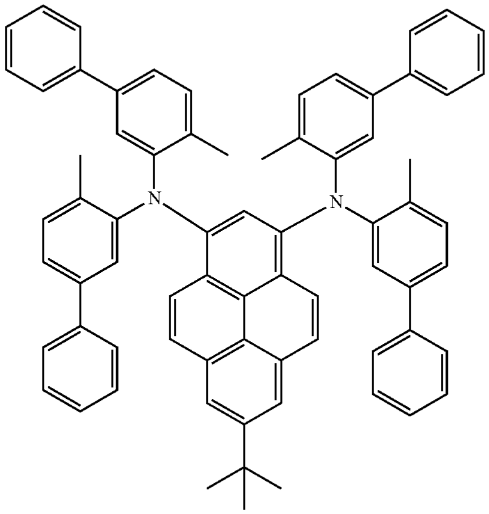
-continued
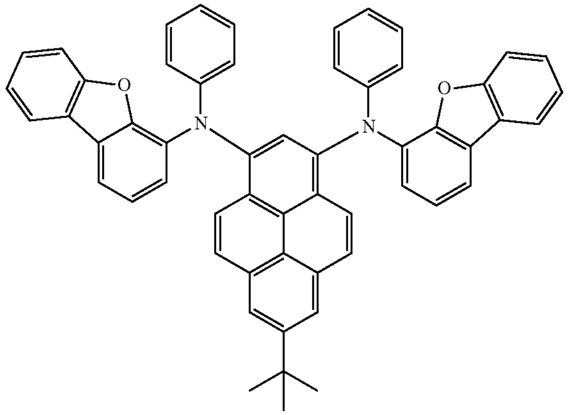
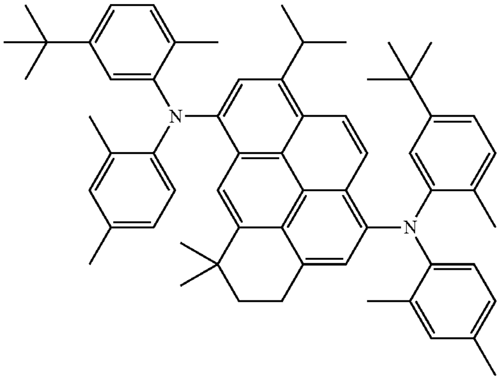
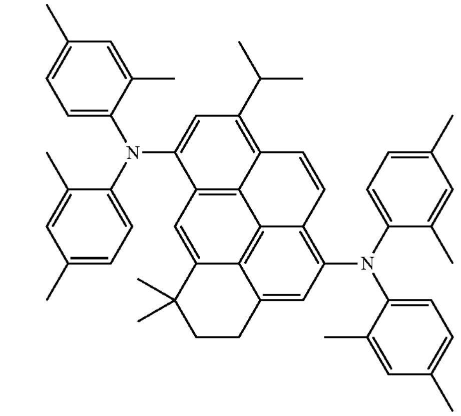
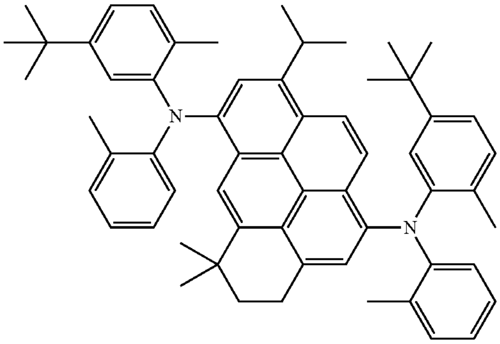

-continued
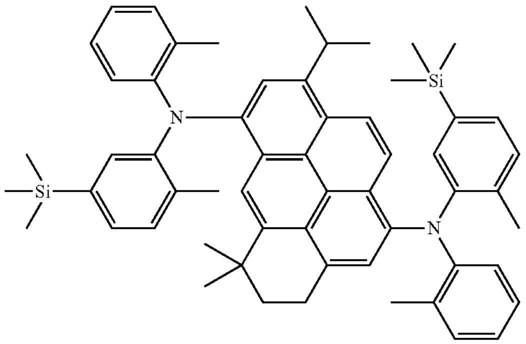
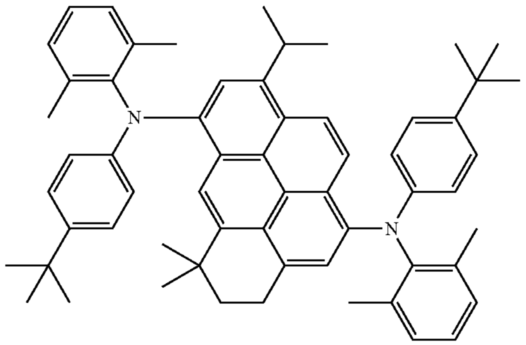
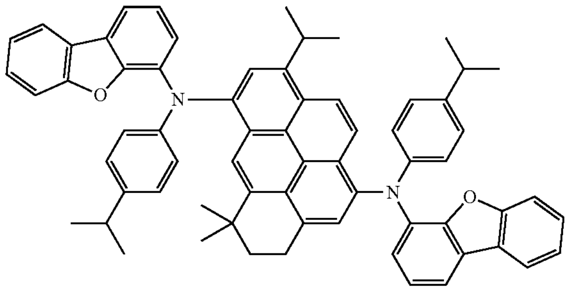
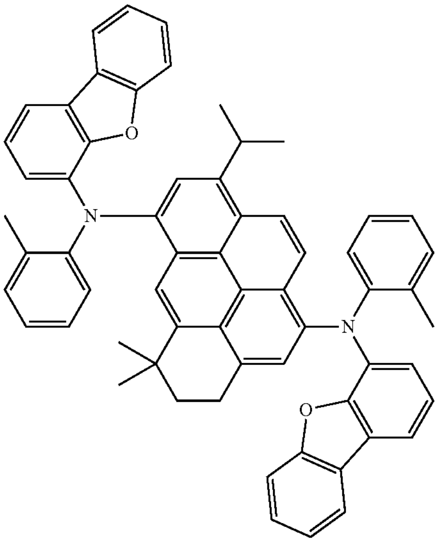
-continued
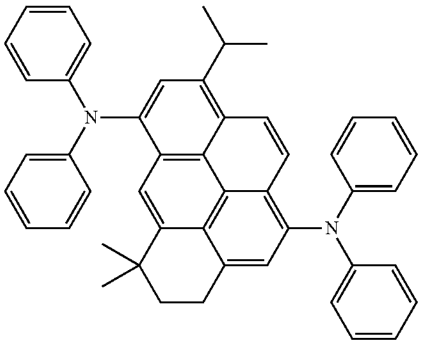
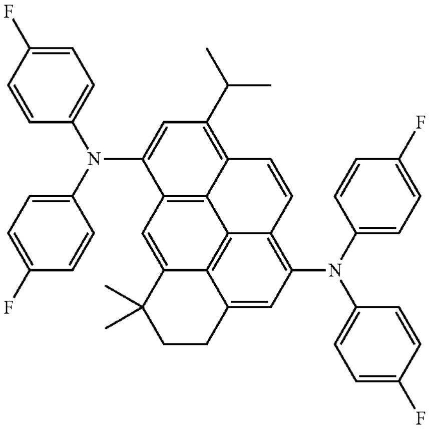
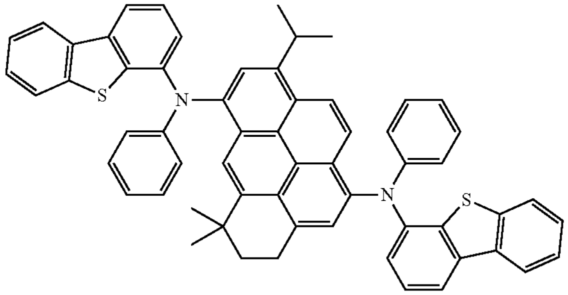
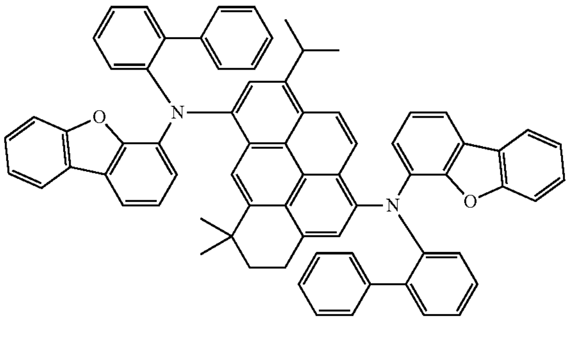

-continued

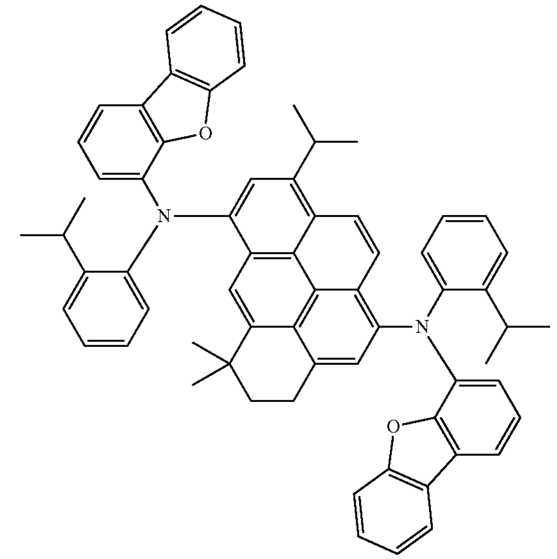

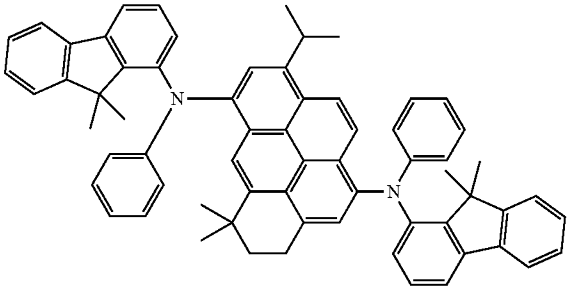

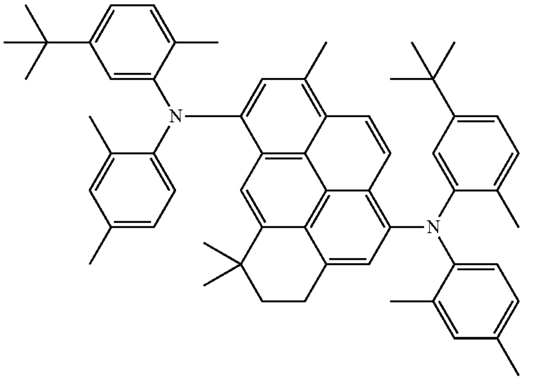

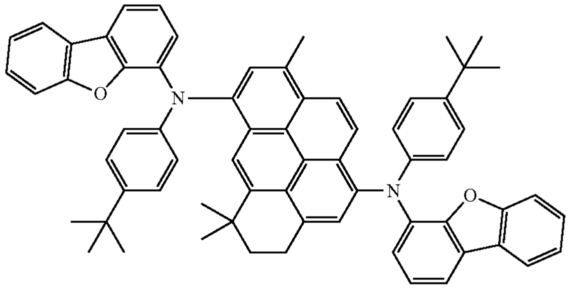

-continued

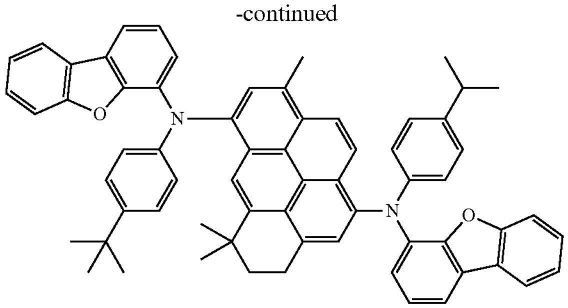

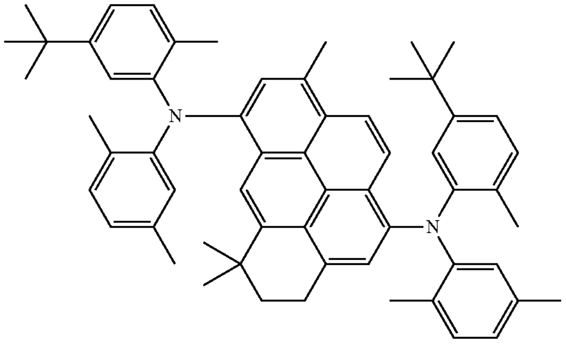

(Compound Represented by Formula (21))

The compound represented by the formula (21) is explained below (21)

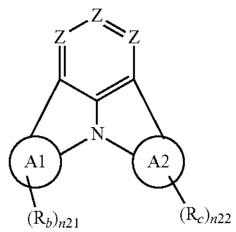

In the formula (21),

Zs are independendly $CR_a$ or N;

A1 ring and A2 ring are independently a substituted or unsubstituted aromatic hydrocarbon ring having 6 to 50 ring carbon atoms, or a substituted or unsubstituted heterocyclic ring having 5 to 50 ring atoms;

when a plurality of $R_a$s exist, two or more adjacent groups of $R_a$ are bonded with each other to form a substituted or unsubstituted, saturated or unsaturated ring, or do not form a substituted or unsubstituted, saturated or unsaturated ring;

when a plurality of $R_b$s exist, one or more pairs of two or more adjacent groups of $R_b$ are bonded with each other to form a substituted or unsubstituted, saturated or unsaturated ring, or do not form a substituted or unsubstituted, saturated or unsaturated ring;

when a plurality of $R_c$s exist, one or more pairs of two or more adjacent groups of $R_c$ are bonded with each other to form a substituted or unsubstituted, saturated or unsaturated ring, or do not form a substituted or unsubstituted, saturated or unsaturated ring;

n21 and n22 are independently an integer of 0 to 4;

$R_a$ to $R_c$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1).

The "aromatic hydrocarbon ring" of A1 ring and A2 ring has the same structure as the compound obtained by introducing a hydrogen atom into the "aryl group" described above. The "aromatic hydrocarbon ring" of the A1 ring and the A2 ring contains two carbon atoms in the fused bicyclic structure at the center of the formula (21) as ring atoms. Examples of "substituted or unsubstituted aromatic hydrocarbon ring having 6 to 50 ring carbon atoms" include compounds in which a hydrogen atom is introduced into the "aryl group" described in the example group G1.

The "heterocyclic ring" of A1 ring and A2 ring has the same structure as the compound obtained by introducing a hydrogen atom into the "heterocyclic group" described above. The "heterocyclic ring" of the A1 ring and the A2 ring contains two carbon atoms in the fused bicyclic structure at the center of the formula (21) as ring atoms. Examples of "substituted or unsubstituted heterocyclic ring having 5 to 50 ring atoms" include compounds in which a hydrogen atom is introduced into the "heterocyclic group" described in the example group G2.

$R_b$ is bonded to one of carbon atoms which form the aromatic hydrocarbon ring of A1 ring, or one of atoms which form the heterocycle of A1 ring.

$R_c$ is bonded to one of carbon atoms which form the aromatic hydrocarbon ring of A2 ring, or one of atoms which form the heterocycle of A2 ring.

It is preferable that at least one (preferably two) of $R_a$ to $R_c$ be a group represented by the following formula (21a):

$$—L_{201}\text{-}Ar_{201} \quad (21a)$$

wherein in the formula (21a), $L_{201}$ is a single bond, a substituted or unsubstituted arylene group having 6 to 30 ring carbon atoms, or a substituted or unsubstituted bivalent heterocyclic group having 5 to 30 ring atoms;

$Ar_{201}$ is a substituted or unsubstituted arylene group having 6 to 50 ring carbon atoms, a substituted or unsubstituted monovalent heterocyclic group having 5 to 50 ring atoms, or a group represented by the following formula (21b):

(21b)

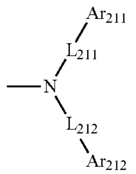

wherein in the formula (21b), $L_{211}$ and $L_{212}$ are independently a single bond, a substituted or unsubstituted arylene group having 6 to 30 ring carbon atoms, or a substituted or unsubstituted divalent heterocyclic group having 5 to 30 ring atoms;

$Ar_{211}$ and $Ar_{212}$ are bonded with each other to form a substituted or unsubstituted, saturated or unsaturated ring, or do not form a substituted or unsubstituted, saturated or unsaturated ring; and $Ar_{211}$ and $Ar_{212}$ that do not form a substituted or unsubstituted, saturated or unsaturated ring are independently a substituted or unsubstituted aryl group having 6 to 50 ring carbon atoms or a substituted or unsubstituted monovalent heterocyclic group having 5 to 50 ring atoms.

In one embodiment, the compound represented by the formula (21) is represented by the following formula (22):

(22)

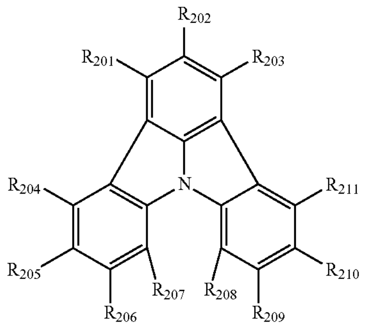

wherein in the formula (22), one or more pairs of two or more adjacent groups of $R_{201}$ to $R_{211}$ are bonded with each other to form a substituted or unsubstituted, saturated or unsaturated ring, or do not form a substituted or unsubstituted saturated or unsaturated ring;

$R_{201}$ to $R_{211}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

It is preferable that at least one (preferably two) of $R_{201}$ to $R_{211}$ be the group represented by the formula (21a). It is preferable that $R_{204}$ and $R_{211}$ be the group represented by the formula (21a).

In one embodiment, the compound represented by the formula (21) is a compound obtained by bonding the structure represented by the following formula (21-1) or (21-2) to A1 ring. In one embodiment, the compound represented by the formula (22) is a compound obtained by bonding the structure represented by the following formula (21-1) or (21-2) to the ring to which $R_{204}$ to $R_{207}$ bonds to.

(21-1)

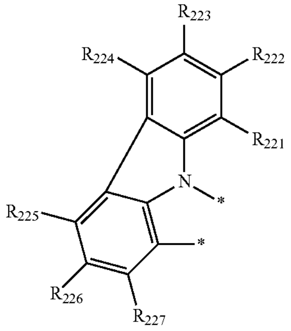

(21-2)

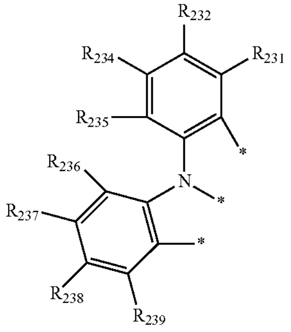

In the formula (21-1), two bonds shown by * independently bond to a ring carbon atom in the aromatic hydrocarbon ring or a ring atom in the heterocyclic group in A1 ring in the formula (21), or bond to one of $R_{204}$ to $R_{207}$ in the formula (22);

wherein in the formula (21-2), three bonds shown by * independently bond to a ring carbon atom in the aromatic hydrocarbon ring or a ring atom in the heterocyclic group in A1 ring in the formula (21), or bond to one of $R_{204}$ to $R_{207}$ in the formula (22);

One or more pairs of two or more adjacent groups of $R_{221}$ to $R_{227}$ and $R_{221}$ to $R_{239}$ are bonded with each other to form a substituted or unsubstituted, saturated or unsaturated ring, or do not form a substituted or unsubstituted, saturated or unsaturated ring;

$R_{221}$ to $R_{227}$ and $R_{231}$ to $R_{239}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1)

In one embodiment, the compound represented by the formula (21) is a compound represented by the following formula (21-3), (21-4), or (21-5):

(21-3)

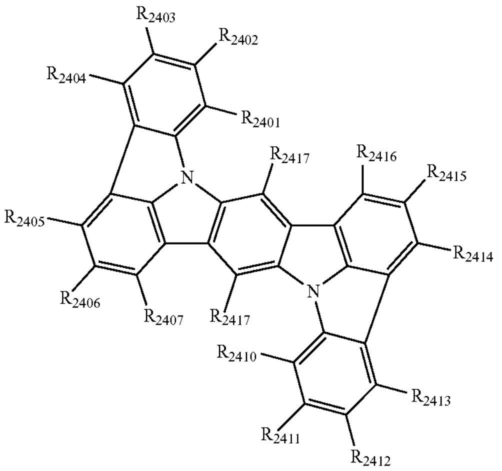

(21-4)

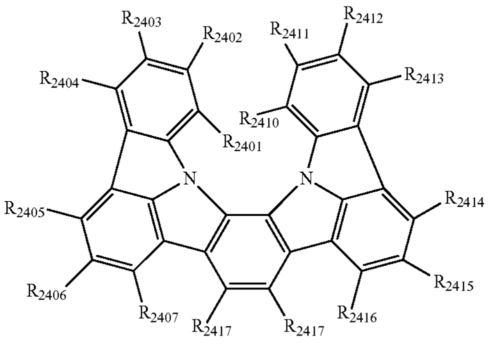

-continued (21-5)

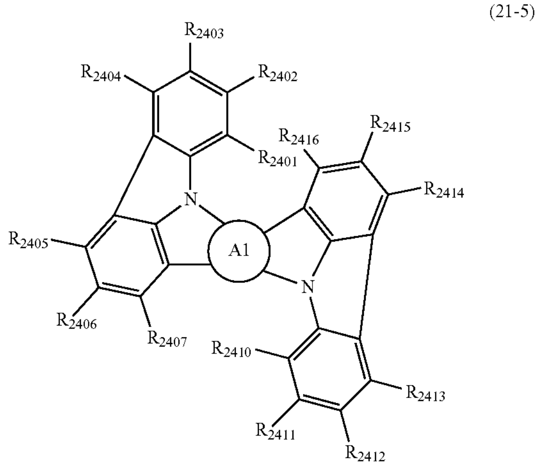

wherein in the formulas (21-3), (21-4) and (21-5),

A1 ring is as defined in the formula (21);

$R_{2401}$ to $R_{2407}$ are the same as $R_{221}$ to $R_{227}$ in the formulas (21-1) and (21-2);

$R_{2410}$ to $R_{2417}$ are the same as $R_{201}$ to $R_{211}$ in the formula (22); and the two $R_{2417}$s may be the same or different.

In one embodiment, the substituted or unsubstituted aromatic hydrocarbon ring having 6 to 50 ring carbon atoms of A1 ring in the formula (21-5) is a substituted or unsubstituted naphthalene ring, or a substituted or unsubstituted fluorene ring.

In one embodiment, the substituted or unsubstituted heterocycle having 5 to 50 ring atoms of A1 ring in the formula (21-5) is a substituted or unsubstituted dibenzofuran ring, a substituted or unsubstituted carbazole ring, or a substituted or unsubstituted dibenzothiophene ring.

In one embodiment, the compound represented by the formula (21) or (22) is selected from the group consisting of the compounds represented by the following formulas (21-6-1) to (21-6-7):

(21-6-1)

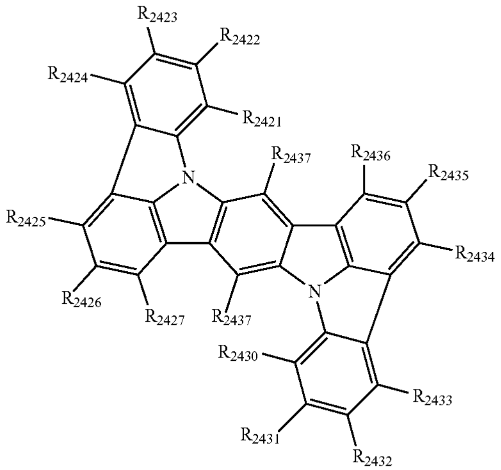

-continued (21-6-2)

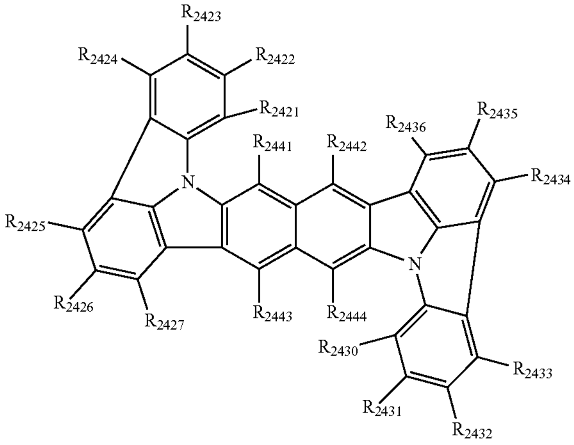

(21-6-3)

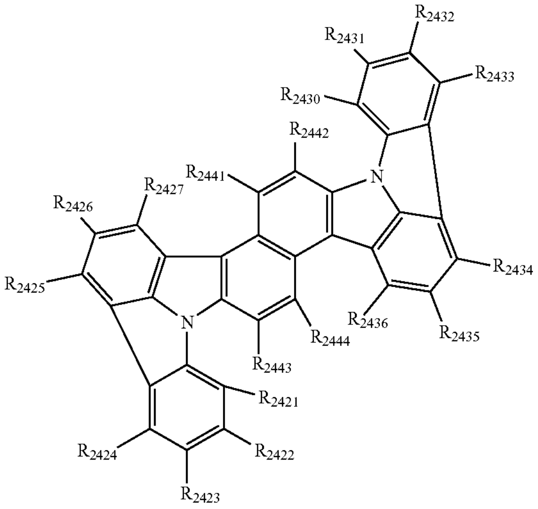

(21-6-4)

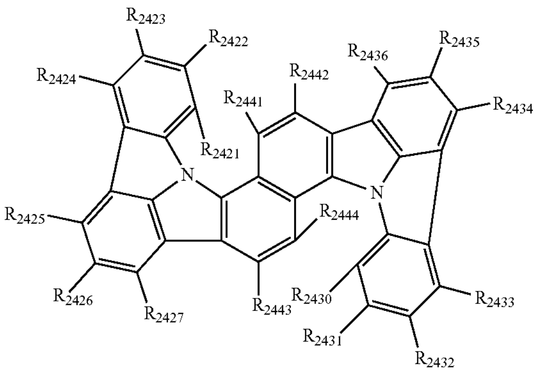

-continued (21-6-5)

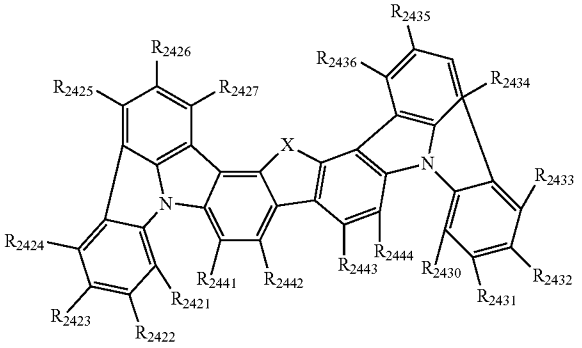

(21-6-6)

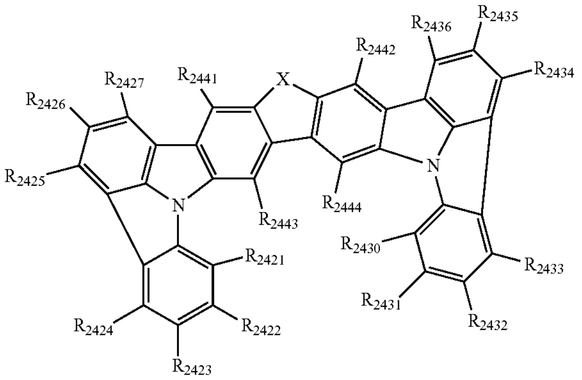

(21-6-7)

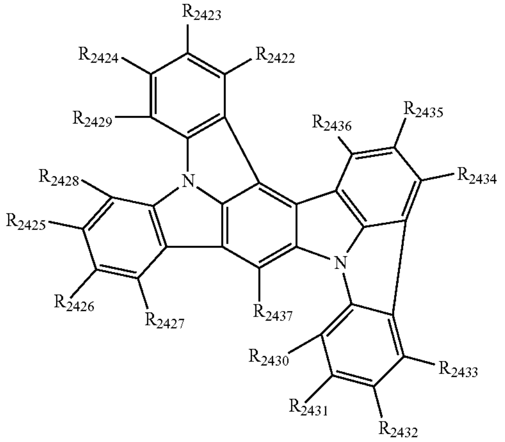

wherein in the formulas (21-6-1) to (21-6-7), $R_{2421}$ to $R_{2427}$ are the same as $R_{221}$ to $R_{227}$ in the formulas (21-1) and (21-2);

$R_{2430}$ to $R_{2437}$ and $R_{2441}$ to $R_{2444}$ are the same as $R_{201}$ to $R_{211}$ in the formula (22);

X is O, $NR_{901}$, or $C(R_{902})$ $(R_{903})$; and $R_{901}$ to $R_{903}$ are as defined in the formula (1).

In one embodiment, in the compound represented by the formula (22), one or more pairs of two or more adjacent groups of $R_{201}$ to $R_{211}$ are bonded with each other to form a substituted or unsubstituted, saturated or unsaturated ring. This embodiment is described in the following formula (25).

(Compound represented by formula (25))

The compound represented by the formula (25) is explained below (25)

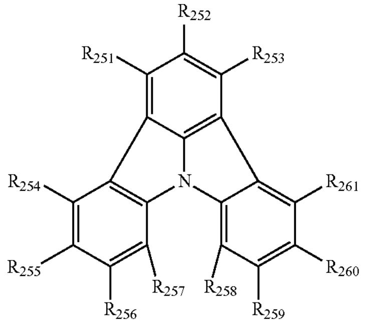

In the formula (25), two or more pairs selected from a group consisting of $R_{251}$ and $R_{252}$, $R_{252}$ and $R_{253}$, $R_{254}$ and $R_{255}$, $R_{255}$ and $R_{256}$, $R_{256}$ and $R_{257}$, $R_{258}$ and $R_{259}$, $R_{259}$ and $R_{260}$, and $R_{260}$ and $R_{261}$ bond with each other to form a substituted or unsubstituted, saturated or unsaturated ring;

Provided that the pair of $R_{251}$ and $R_{252}$ and the pair of $R_{252}$ and $R_{253}$ do not form a ring simultaneously; the pair of $R_{254}$ and $R_{255}$ and the pair of $R_{255}$ and $R_{256}$ do not form a ring simultaneously; the pair of $R_{255}$ and $R_{256}$ and the pair of $R_{256}$ and $R_{257}$ do not form a ring simultaneously; the pair of $R_{258}$ and $R_{259}$ and the pair of $R_{259}$ and $R_{260}$ do not form a ring simultaneously; and the pair of $R_{259}$ and $R_{260}$ and the pair of $R_{260}$ and $R_{261}$ do not form a ring simultaneously;

When two or more rings are formed by $R_{251}$ to $R_{261}$, the rings may be the same or different;

$R_{251}$ to $R_{261}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or $—Si(R_{901})(R_{902})(R_{903})$, $—O—(R_{904})$, $—S—(R_{905}s)$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

In the formula (25), $R_n$ and $R_{n+1}$ (n is an integer selected from 251, 252, 254 to 256 and 258 to 260) bond with each other to form a substituted or unsubstituted, saturated or unsaturated ring together with two ring carbon atoms to which $R_n$ and $R_{n+1}$ bond with. The ring is preferably configured with atoms selected from C atom, O atom, S atom and N atom, and the number of atoms is preferably 3 to 7, more preferably 5 or 6.

The number of the above-described ring structures in the compound represented by the formula (25) is, for example, 2, 3 or 4. Two or more ring structures may exist in the same benzene ring of the main skeleton in the formula (25), or may exist in different benzene rings. For example, the compound has three ring structures, one ring structure may exist in each of the three benzene rings in the formula (25).

As the above-mentioned ring structure in the compound represented by the formula (25), structures represented by the following formulas (251) to (260) can be given, for example.

(251)

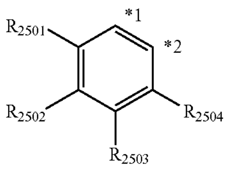

(252)

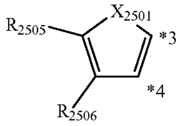

(253)

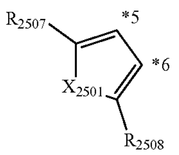

(254)

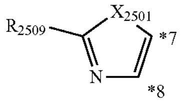

(255)

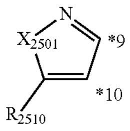

(256)

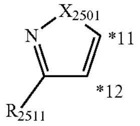

(257)

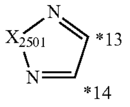

In the formulas (251) to (257), each of *1 and *2, *3 and *4, *5 and *6, *7 and *8, *9 and *10, *11 and * 12, and * 13 and * 14 represents two ring carbon atoms to which $R_n$ and $R_{n+1}$ bond, and $R_n$ may bond to either one of the two ring carbon atoms of *1 and *2, *3 and *4, *5 and *6, *7 and *8, *9 and *10, *11 and *12, and *13 and *14;

$X_{2501}$ is $C(R_{2512})$ $(R_{2513})$, $NR_{2514}$, O or S;

One or more pairs of two or more adjacent groups of $R_{2501}$ to $R_{2506}$ and $R_{2512}$ to $R_{2513}$ are bonded with each other to form a substituted or unsubstituted, saturated or unsaturated ring, or do not form a substituted or unsubstituted saturated or unsaturated ring; and $R_{2501}$ to $R_{2514}$ that do not form a substituted or unsubstituted saturated or unsaturated ring are the same as $R_{251}$ to $R_{261}$.

(258)

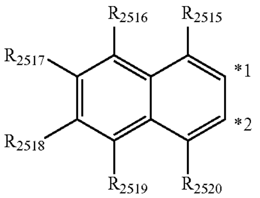

(259)

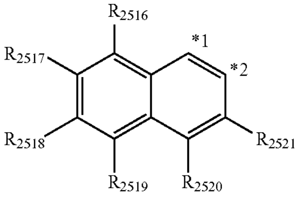

(260)

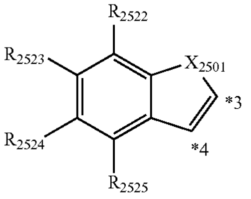

In the formulas (258) to (260), each of * 1 and *2, and *3 and *4 represents two ring carbon atoms to which $R_n$ and $R_{n+1}$ bond, and $R_n$ may bond to either one of the two ring carbon atoms of *1 and *2, or *3 and *4;

$X_{2501}$ is $C(R_{2512})(R_{2513})$, $NR_{2514}$, O or S;

One or more pairs of two or more adjacent groups of $R_{2515}$ to $R_{2525}$ bond to each other to form a substituted or unsubstituted, saturated or unsaturated ring, or do not form a substituted or unsubstituted saturated or unsaturated ring; and $R_{2515}$ to $R_{2521}$ and $R_{2522}$ to $R_{2525}$ that do not form a substituted or unsubstituted saturated or unsaturated ring are the same as $R_{251}$ to $R_{261}$.

In the formula (25), it is preferable that at least one of $R_{252}$, $R_{254}$, $R_{255}$, $R_{260}$ and $R_{261}$ (preferably at least one of $R_{252}$, $R_{255}$, and $R_{260}$, more preferably $R_{252}$) be a group which does not form a ring.

(i) Substituent in the case where the ring structure formed by $R_n$ and $R_{n+1}$ has a substituent in the formula (25), (ii) $R_{251}$ to $R_{261}$ that do not form a ring structure in the formula (25), and (iii) $R_{2501}$ to $R_{2514}$ and $R_{2515}$ to $R_{2525}$ in the formulas (251) to (260) are preferably independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms,

—$N(R_{906})$ $(R_{907})$, a substituted or unsubstituted aryl group having 6 to 50 ring carbon atoms, a substituted or unsubstituted monovalent heterocyclic group having 5 to 50 ring atoms, or a group selected from the following groups.

(261)

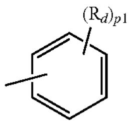

(262)

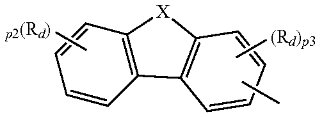

(263)

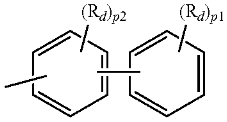

(264)

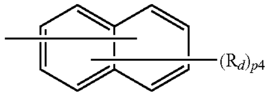

In the formulas (261) to (264), $R_d$ s are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

X is $C(R_{901})(R_{902})$, $NR_{903}$, O, or S;

$R_{901}$ to $R_{907}$ are as defined in the formula (1); and p1 is independently an integer of 0 to 5, p2 is independently an integer of 0 to 4, $p^3$ is an integer of 0 to 3, and p4 is an integer of 0 to 7.

In one embodiment, the compound represented by the formula (25) is represented by the following formulas (25-1) to (25-6):

(25-1)

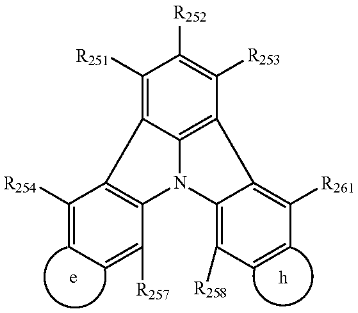

-continued (25-2)

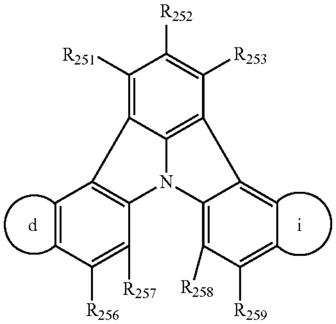

(25-3)

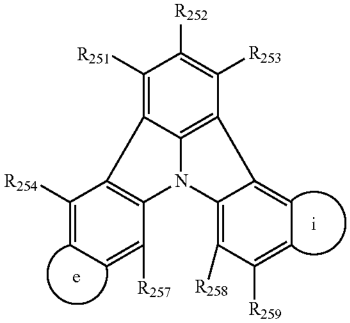

(25-4)

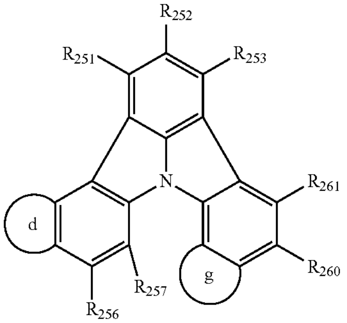

(25-5)

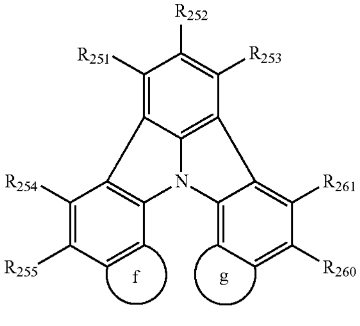

(25-6)

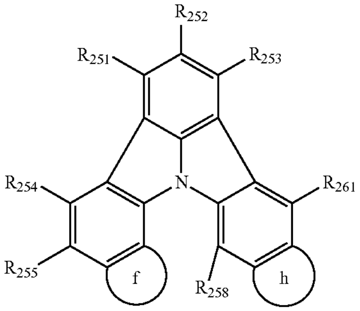

wherein in the formulas (25-1) to (25-6), ring d to ring i are independently a substituted or unsubstituted, saturated or unsaturated ring; and $R_{251}$ to $R_{261}$ are the same as defined in the formula (25).

In one embodiment, the compound represented by the formula (25) is represented by the following formulas (25-7) to (25-12):

(25-7)

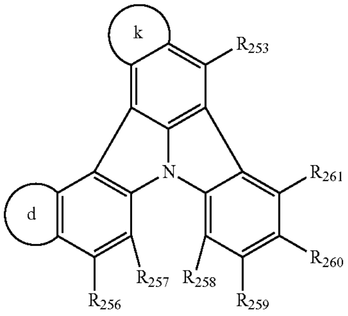

(25-8)

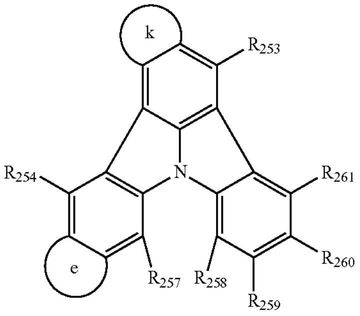

(25-9)

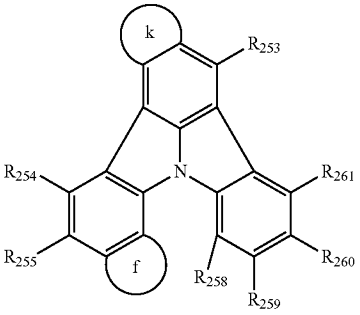

(25-10)

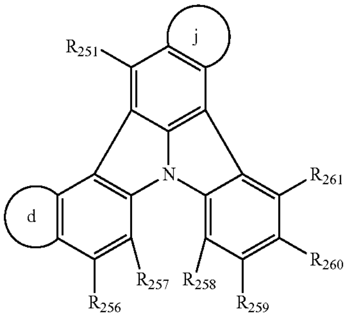

-continued (25-11)

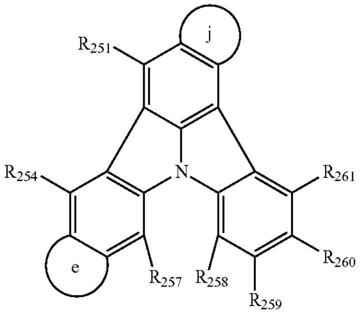

(25-12)

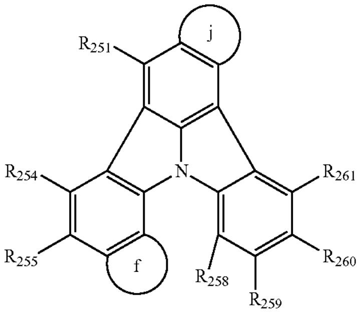

wherein in the formulas (25-7) to (25-12), ring d to ring f, ring k, and ring j are independently a substituted or unsubstituted, saturated or unsaturated ring; and $R_{251}$ to $R_{261}$ are the same as defined in the formula (25).

In one embodiment, the compound represented by the formula (25) is represented by the following formulas (25-13) to (25-21):

(25-13)

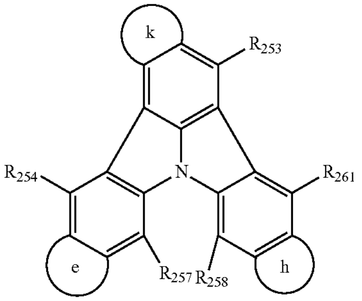

(25-14)

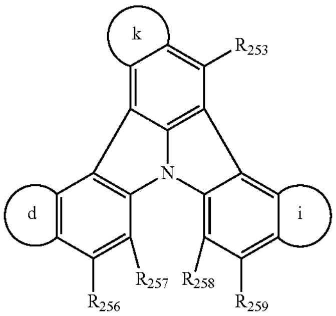

-continued (25-15)

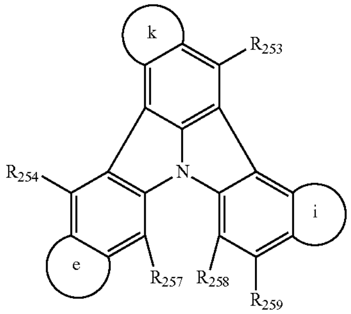

(25-16)

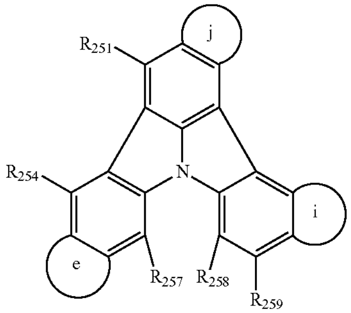

(25-17)

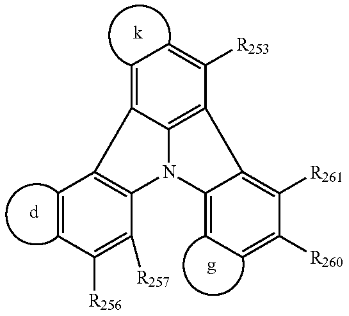

(25-18)

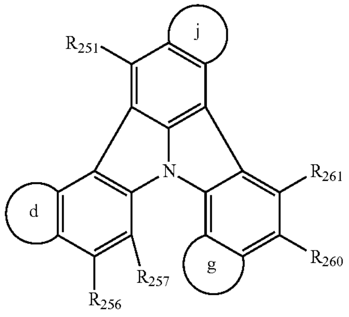

(25-19)

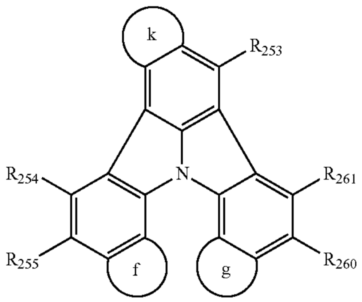

-continued (25-20)

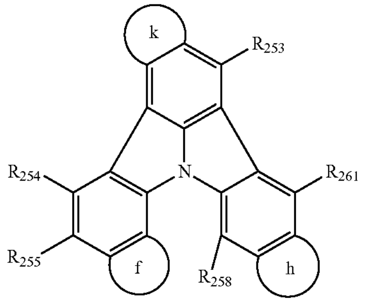

(25-21)

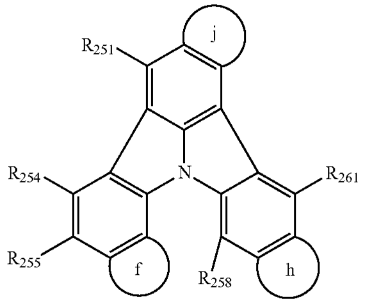

wherein in the formulas (25-13) to (25-21), ring d to ring k are independently a substituted or unsubstituted, saturated or unsaturated ring; and $R_{251}$ to $R_{261}$ are the same as defined in the formula (25).

As a substituent in the case where the ring g or ring h further has a substituent, a substituted or unsubstituted alkyl group having 1 to 50 carbon atoms, a substituted or unsubstituted aryl group having 6 to 50 ring carbon atoms, or a group represented by the formula (261), (263) or (264) can be given for example.

In one embodiment, the compound represented by the formula (25) is represented by one of the following formulas (25-22) to (25-25):

(25-22)

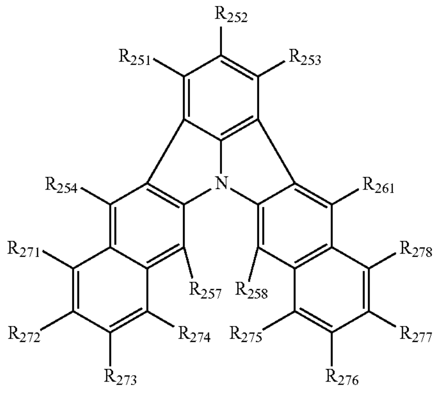

-continued (25-23)

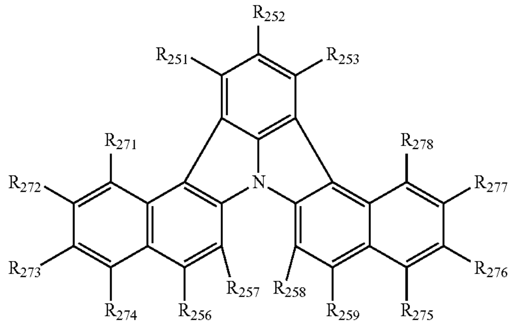

(25-24)

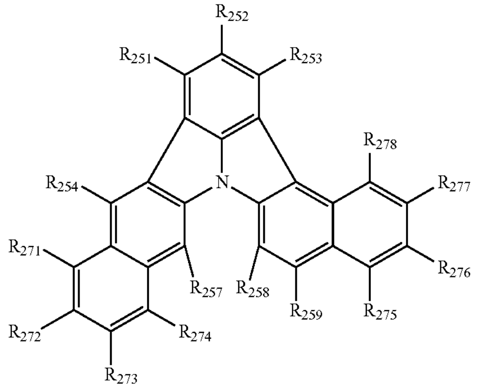

(25-25)

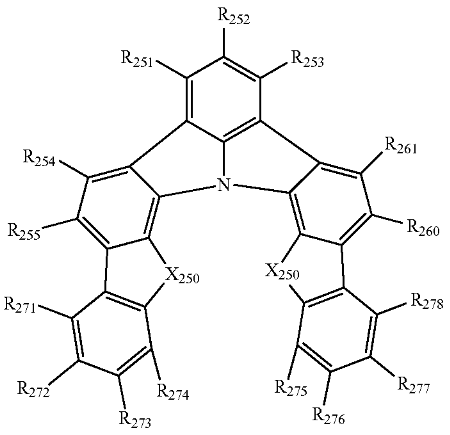

wherein in the formulas (25-22) to (25-25), $X_{250}$ is independently $C(R_{901})(R_{902})$, $NR_{903}$, O or S; are as defined in the formula (1).

In one embodiment, the compound represented by the formula (25) is represented by the following formula (25-26):

(25-26)

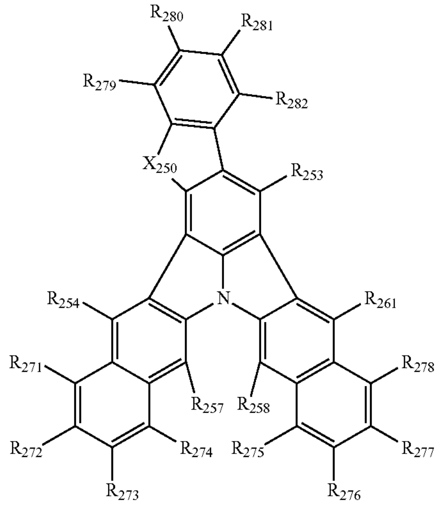

wherein in the formula (25-26), $X_{250}$ is $C(R_{901})(R_{902})$, $NR_{903}$, O or S; $R_{253}$, $R_{254}$, $R_{257}$, $R_{258}$, $R_{261}$, and $R_{271}$ to $R_{282}$ are the same as $R_{251}$ to $R_{261}$ in the formula (25); and $R_{901}$ to $R_{903}$ are as defined in the formula (1).

As the compound represented by the formula (21), the following compounds can be shown for example. In the following example compounds, Me represents methyl group.

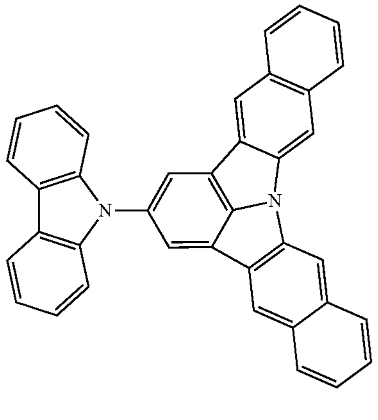

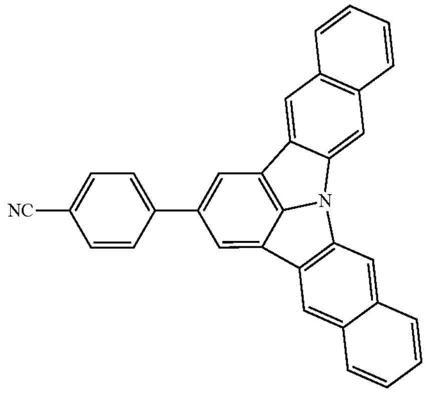

-continued
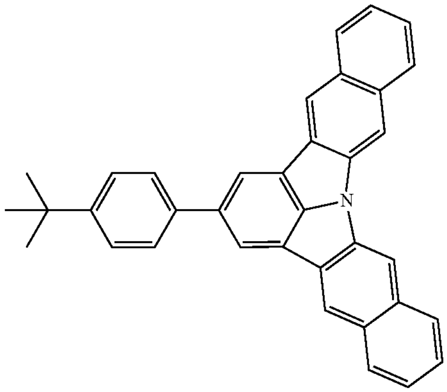
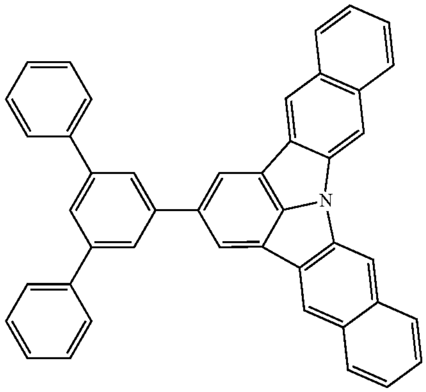
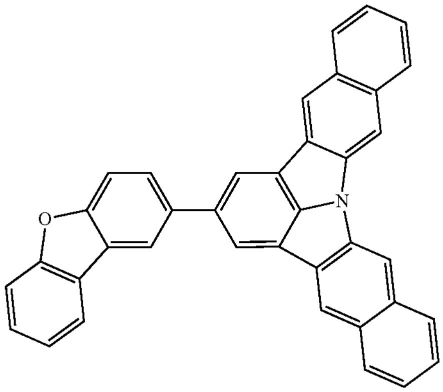
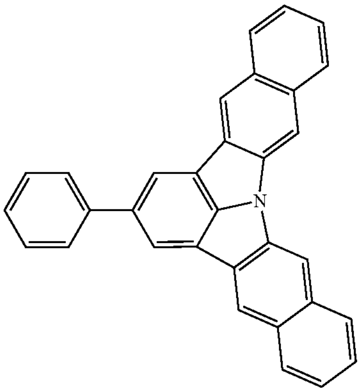
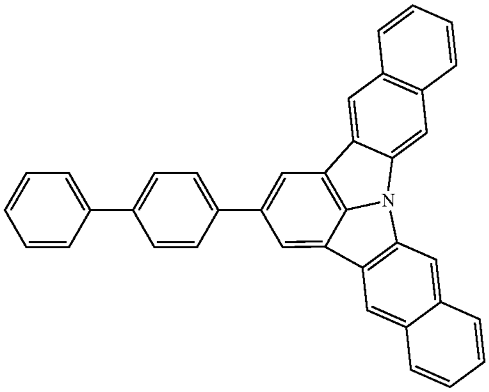
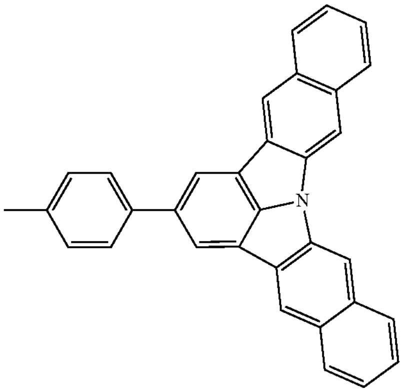
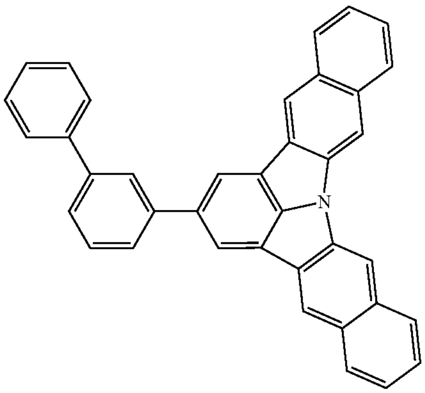
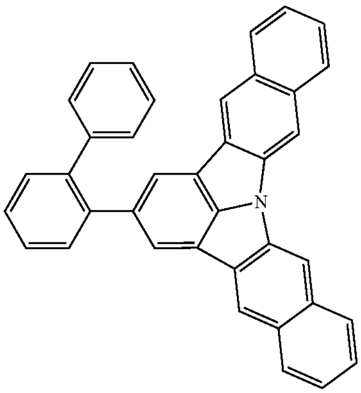

-continued
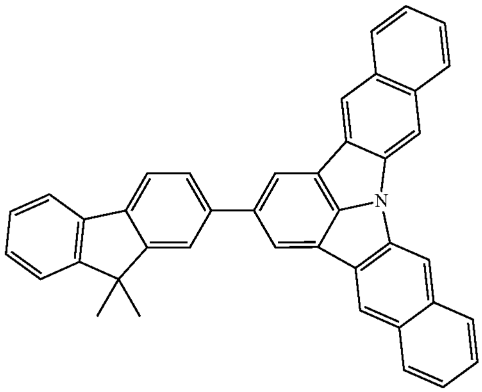
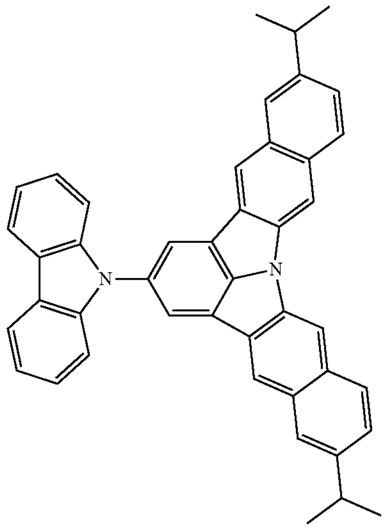
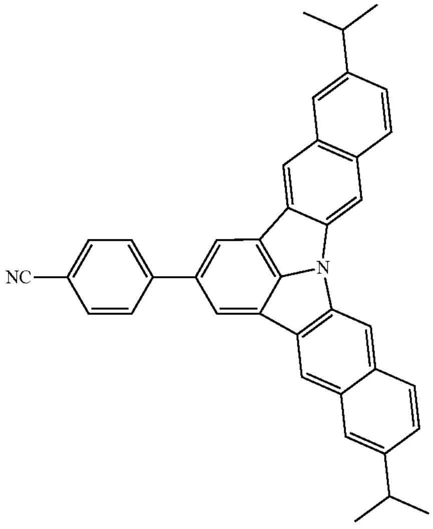
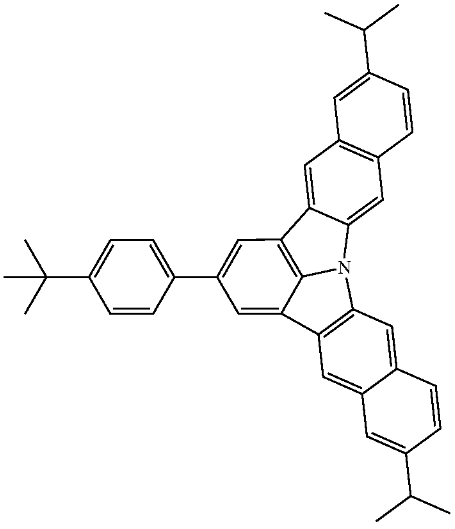
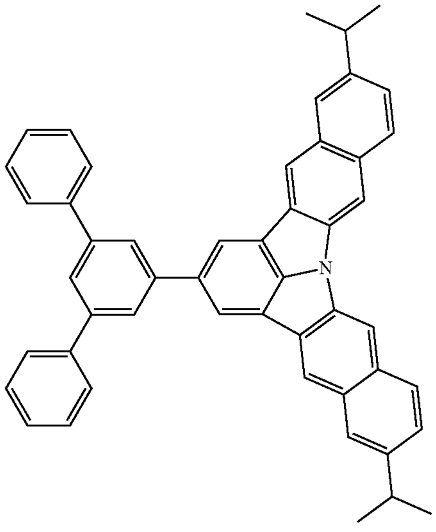
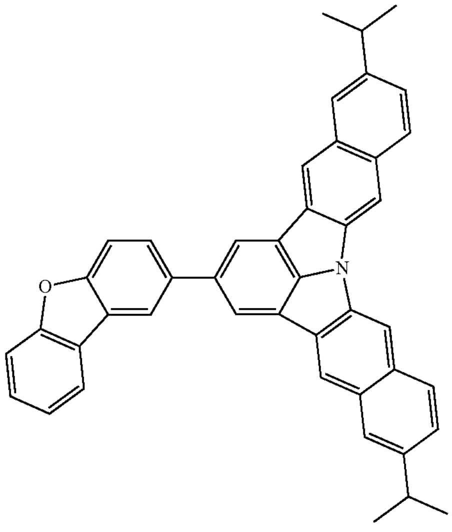

-continued
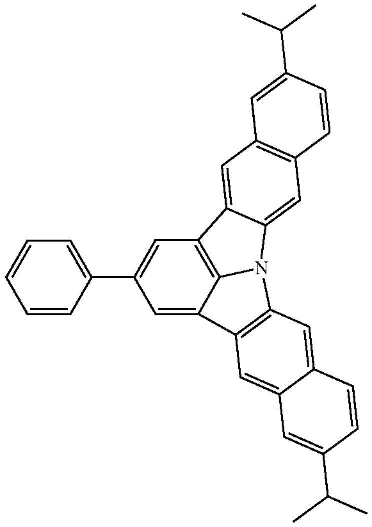
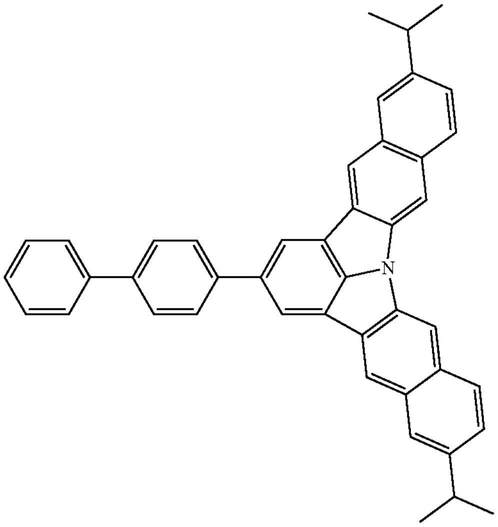
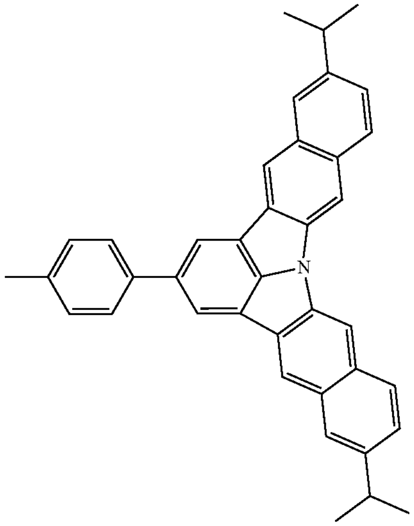
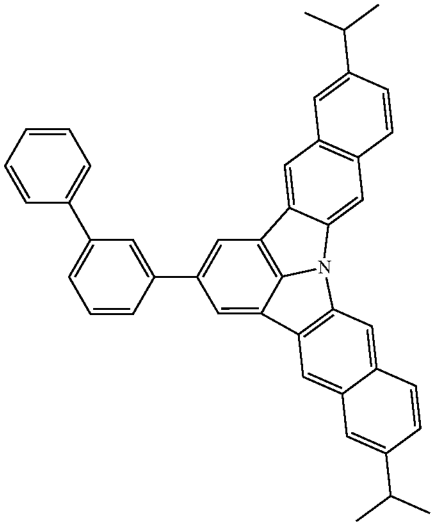
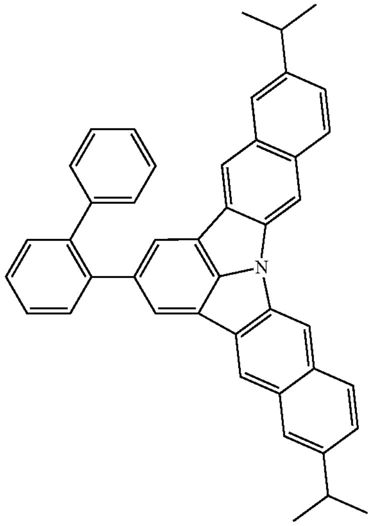
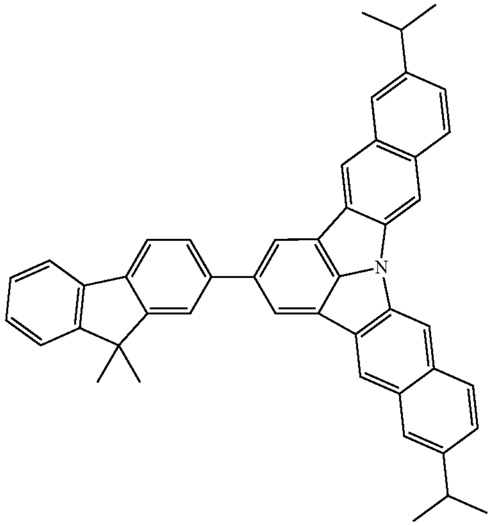

-continued
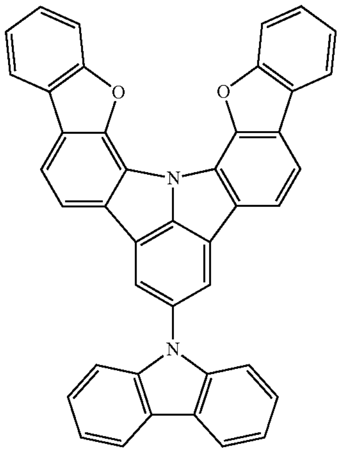
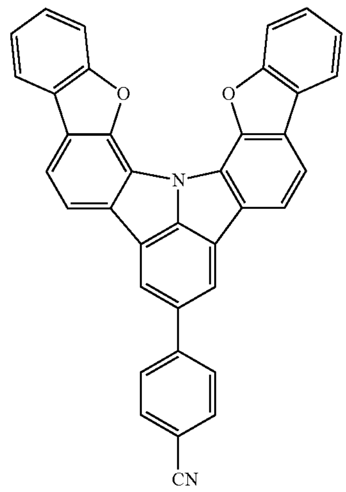
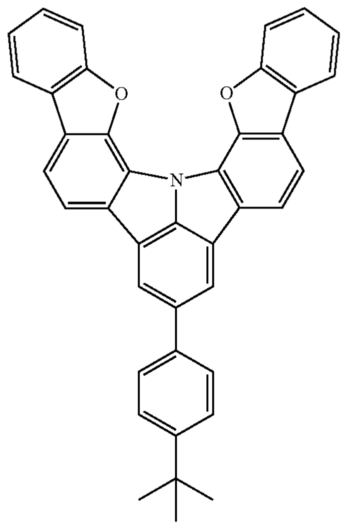
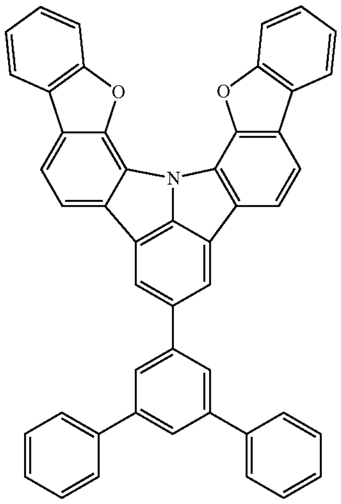
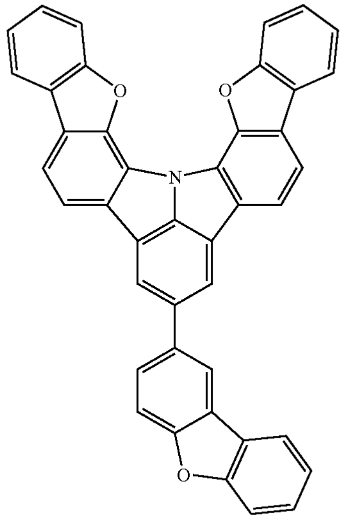
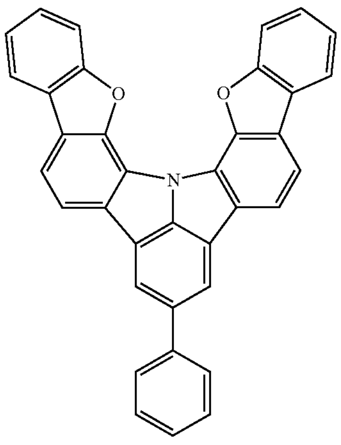
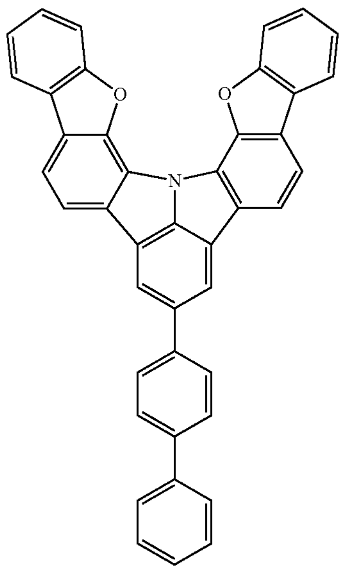
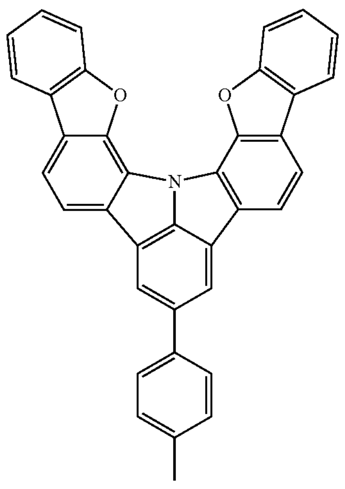

-continued
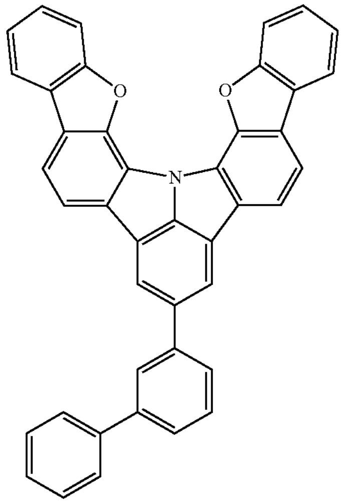
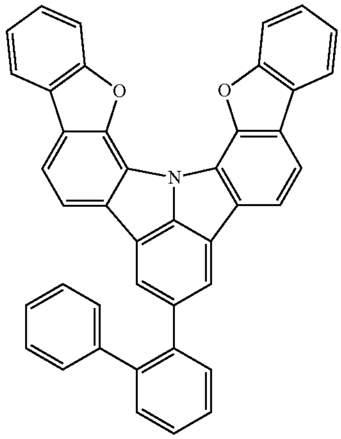
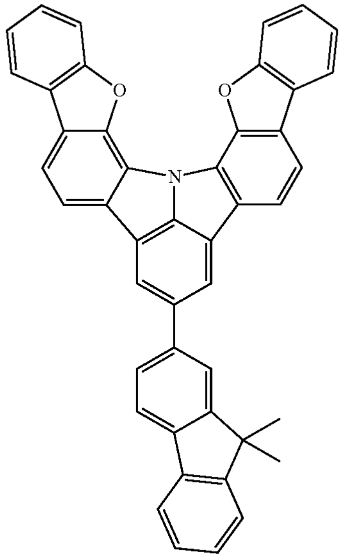
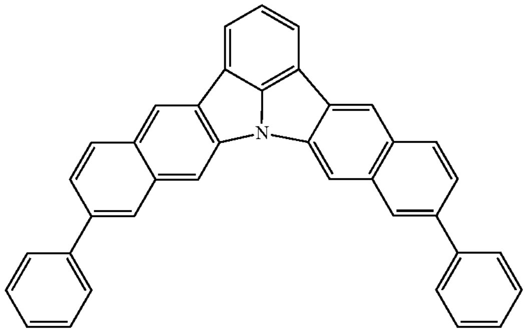
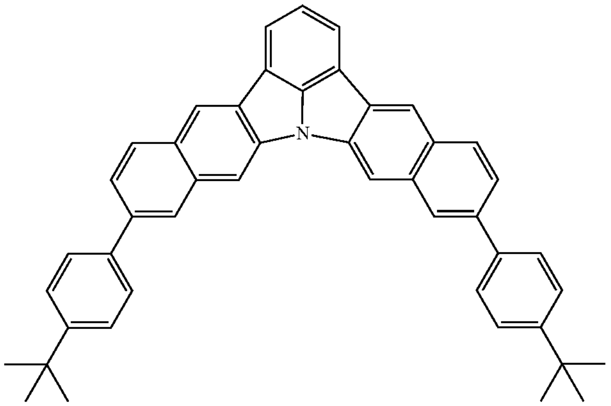
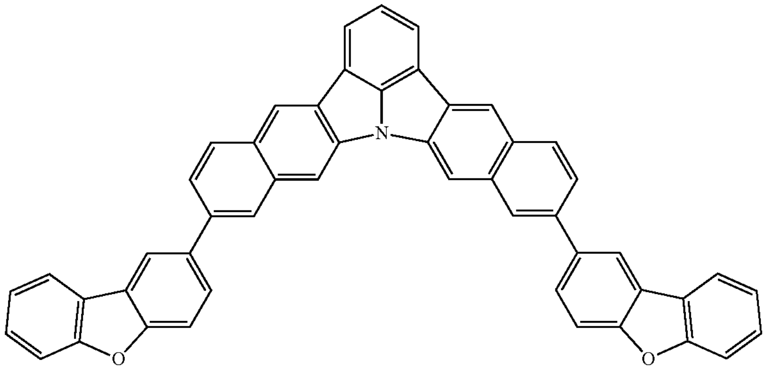
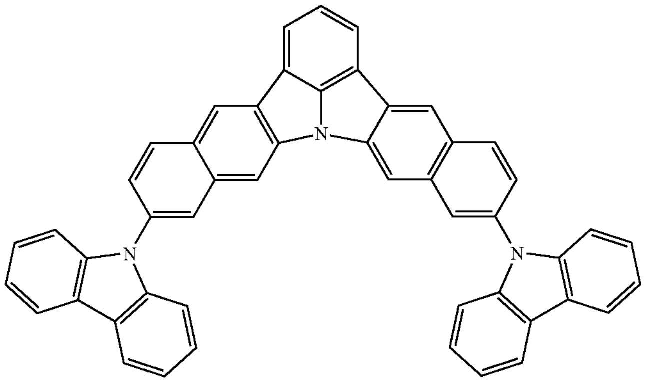

-continued
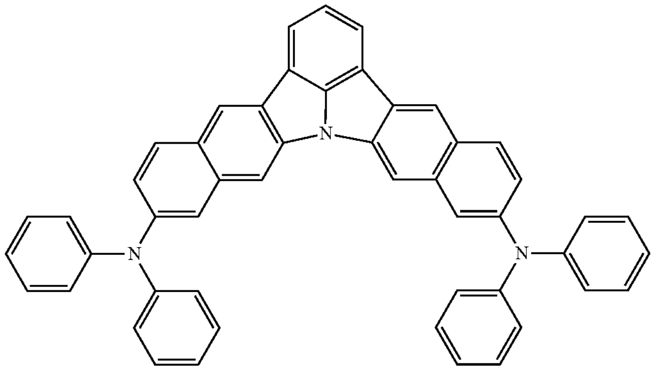
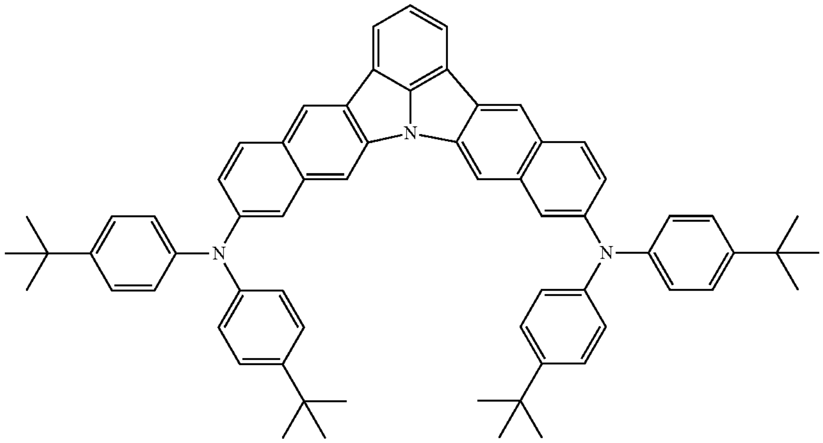
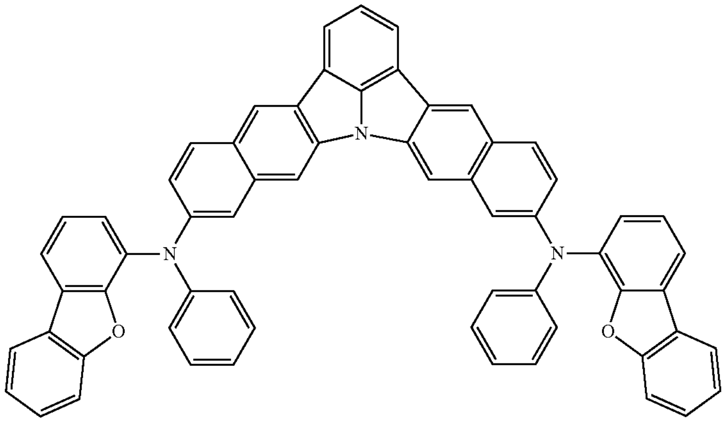
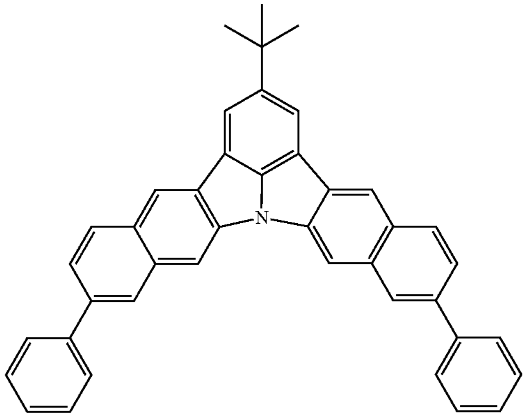
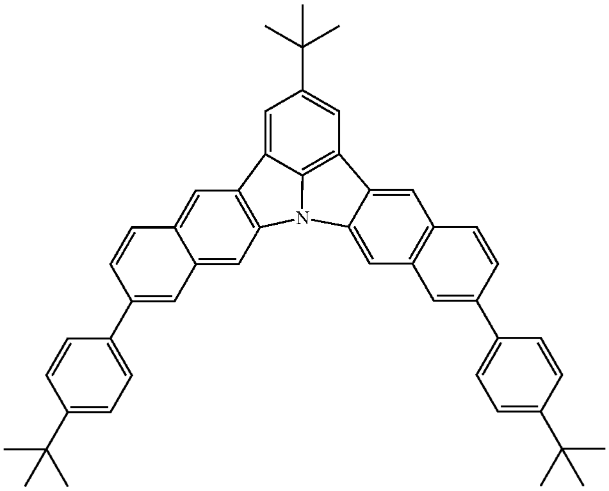

-continued
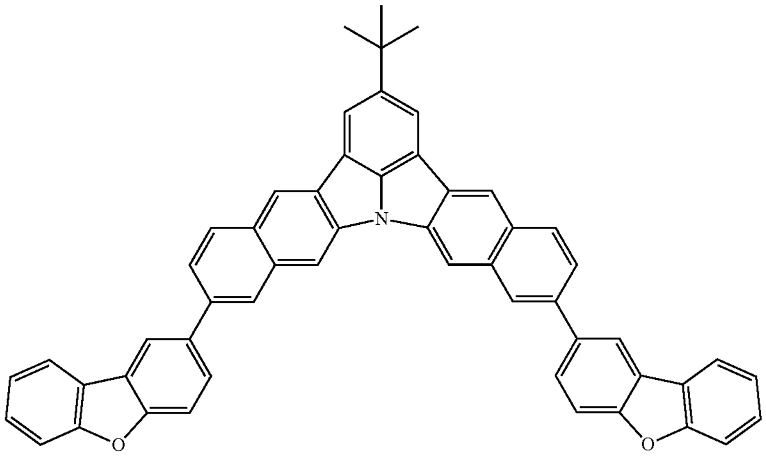
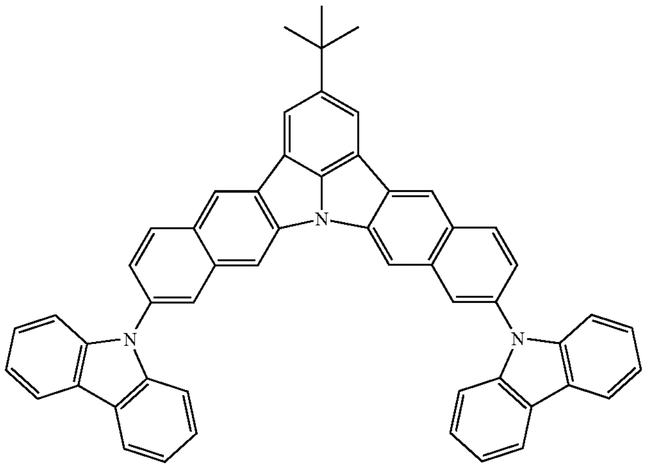
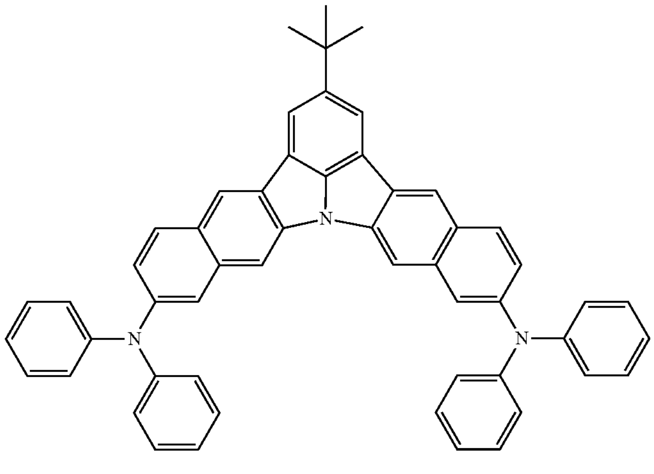

-continued
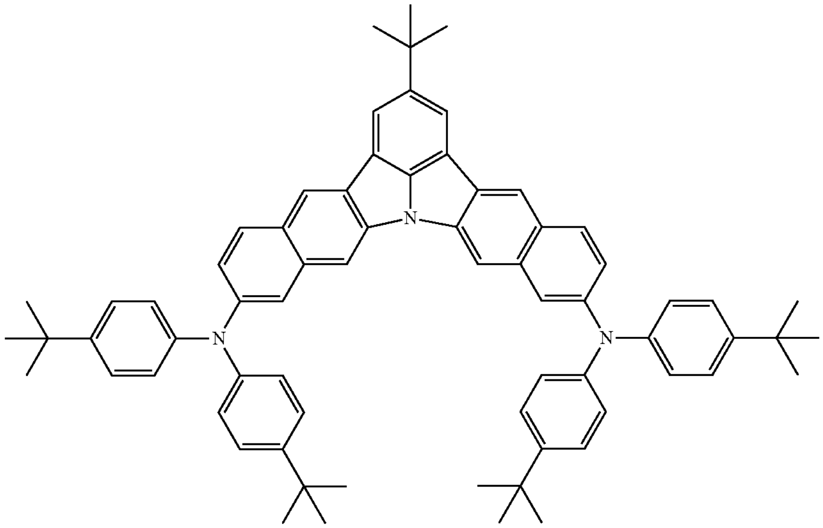
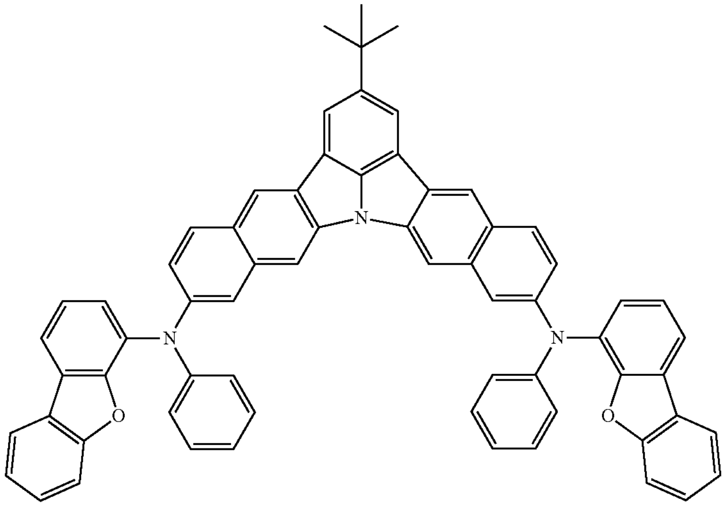
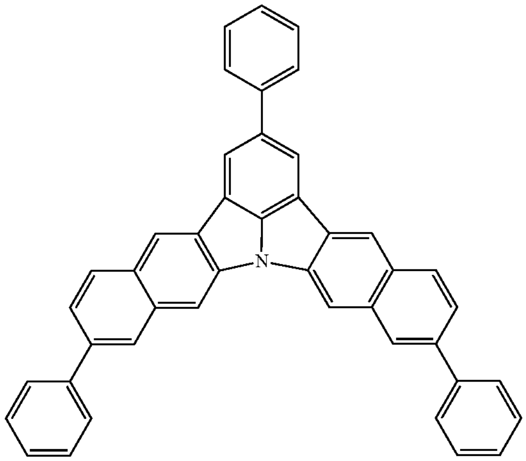
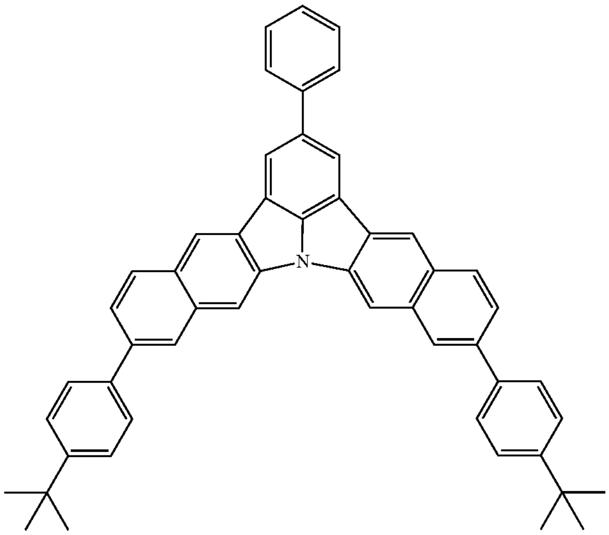

-continued
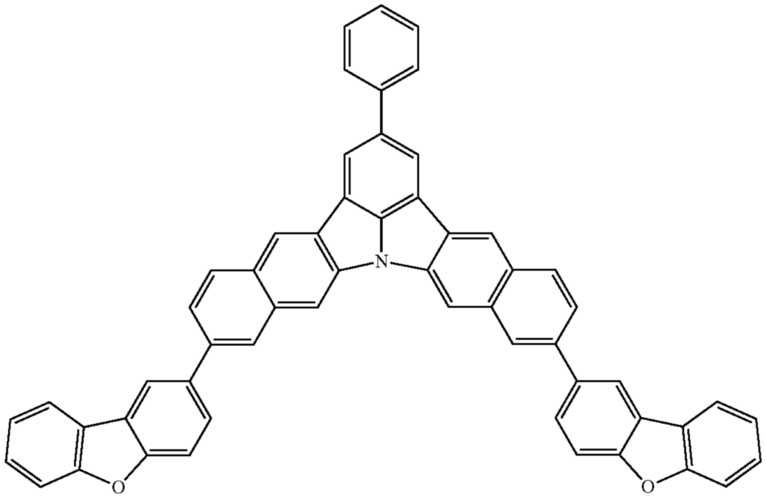
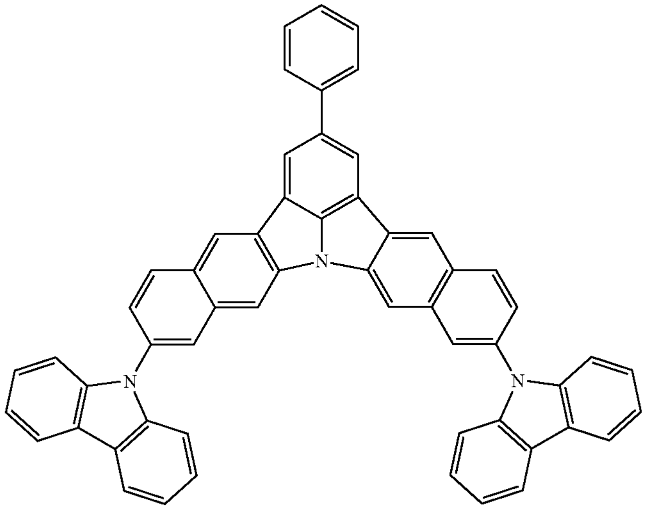
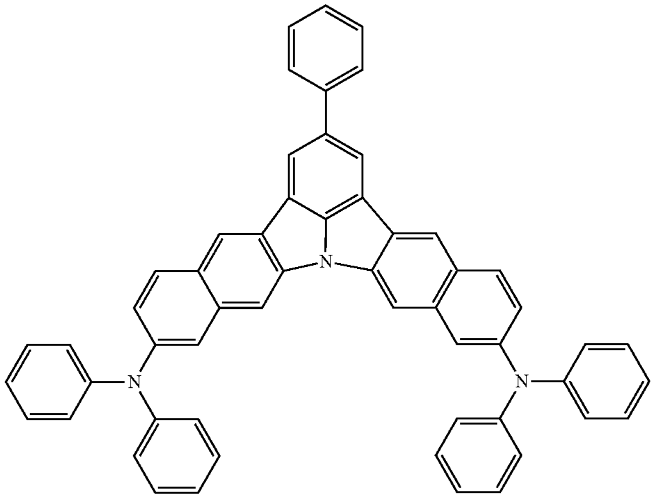

-continued
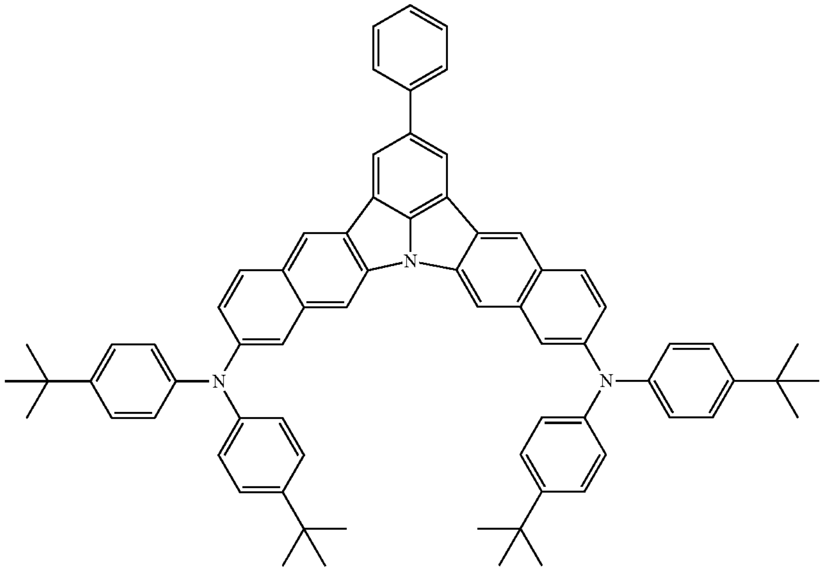
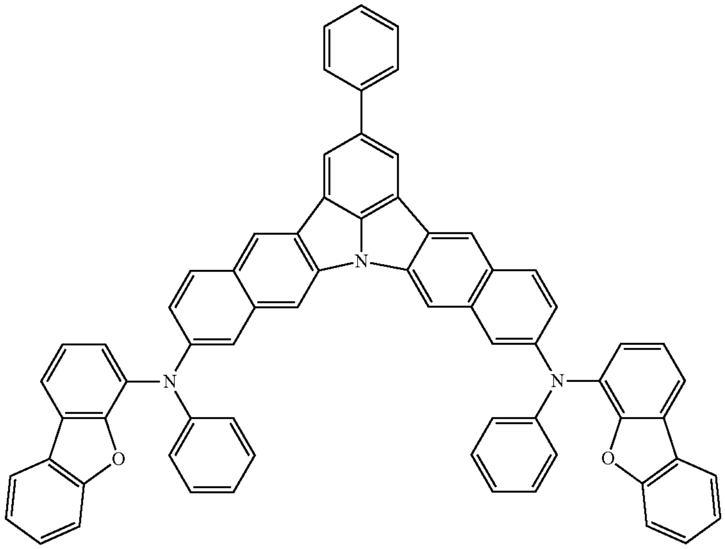

-continued
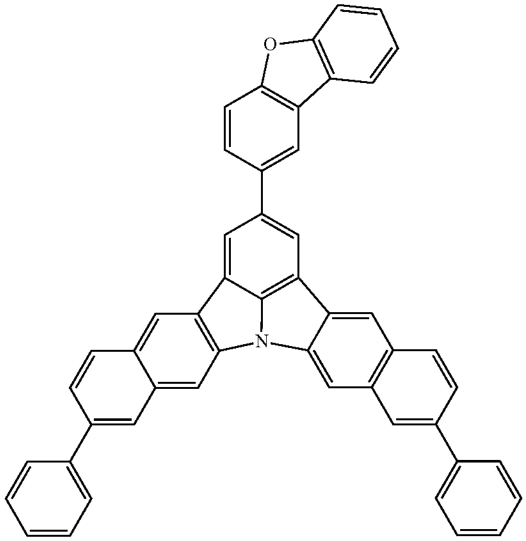
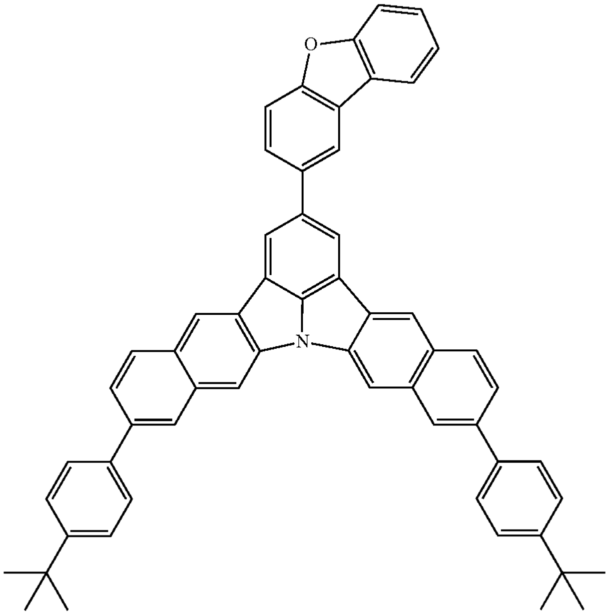
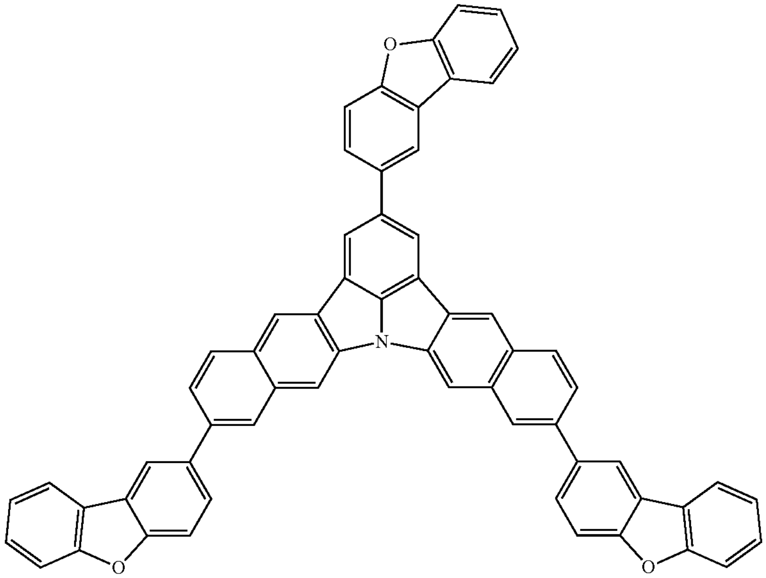

-continued
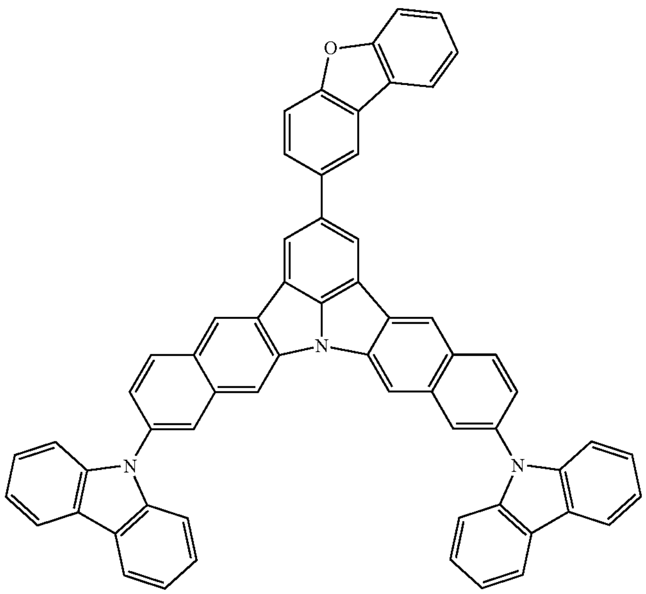
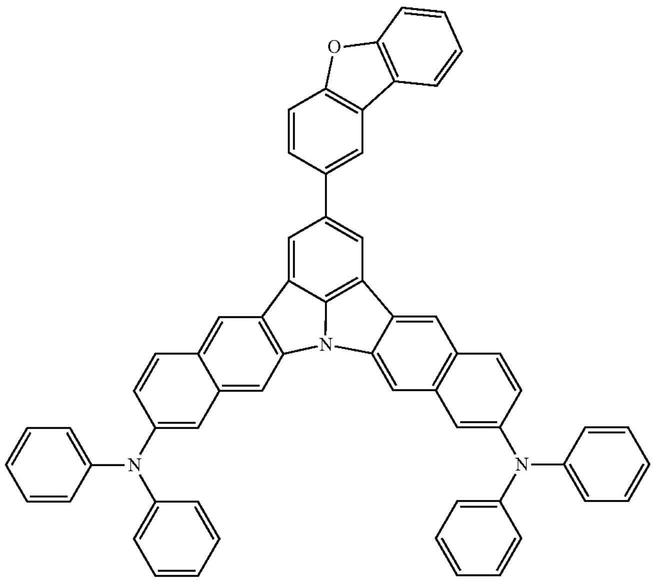

-continued
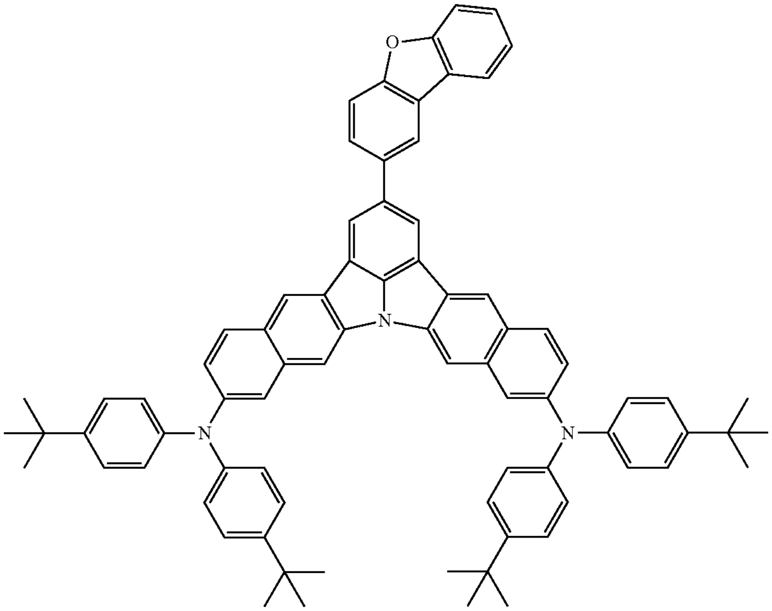
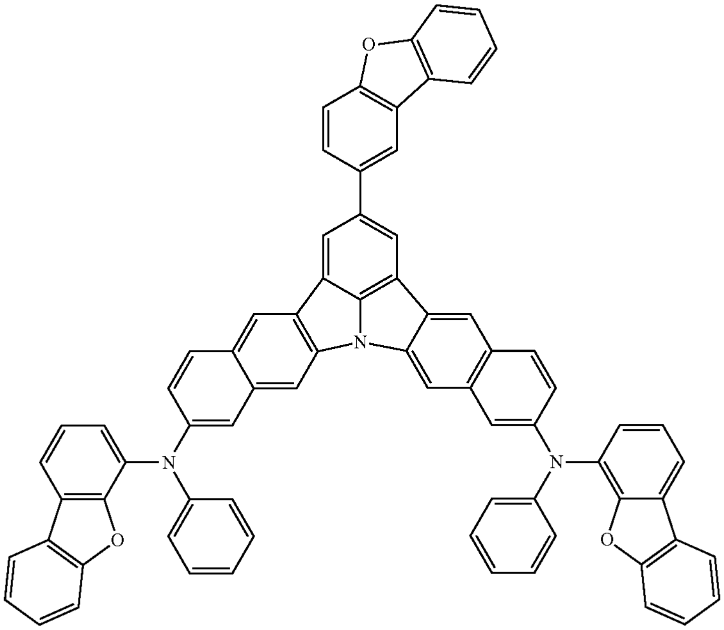 [SMILES: c1ccc(N(c2ccc3cc4c5cc(-c6ccc7oc8ccccc8c7c6)cc6c7cc8ccc(N(c9ccccc9)c9cccc%10c9oc9ccccc9%10)cc8cc7n(c4cc3c2)c56)c2cccc3c2oc2ccccc23)cc1]
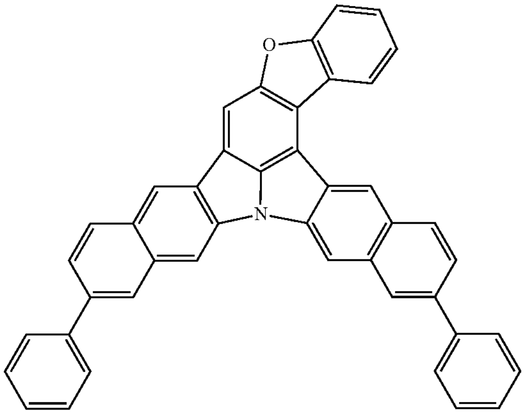
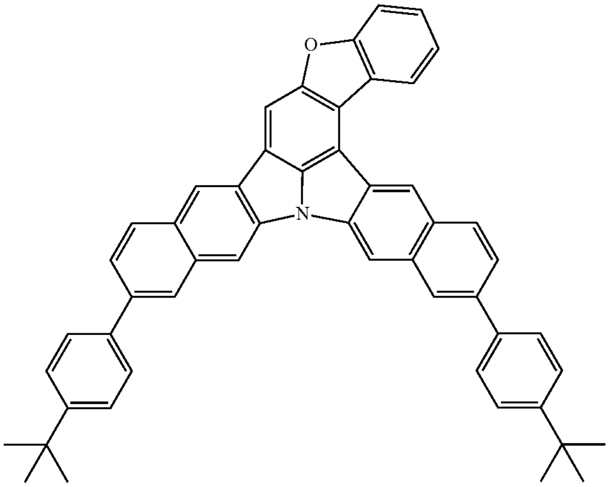

-continued
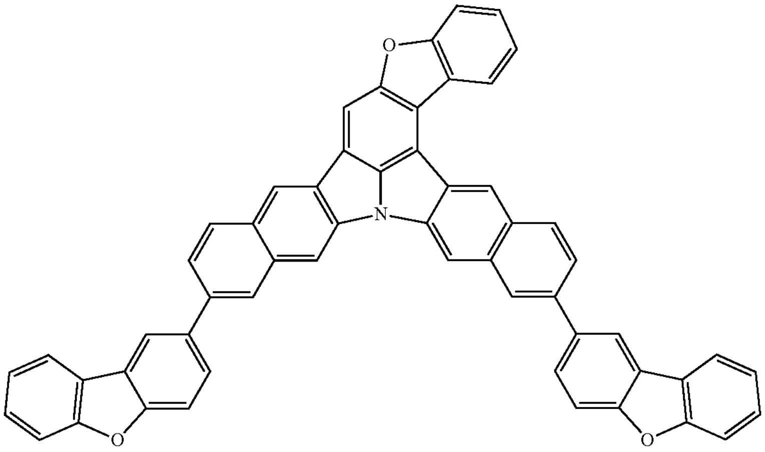
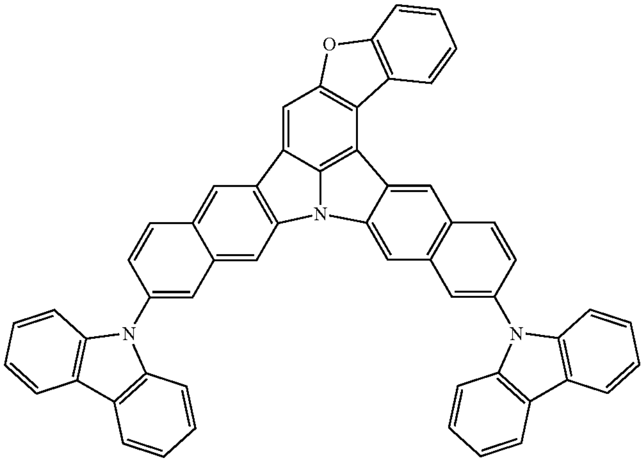
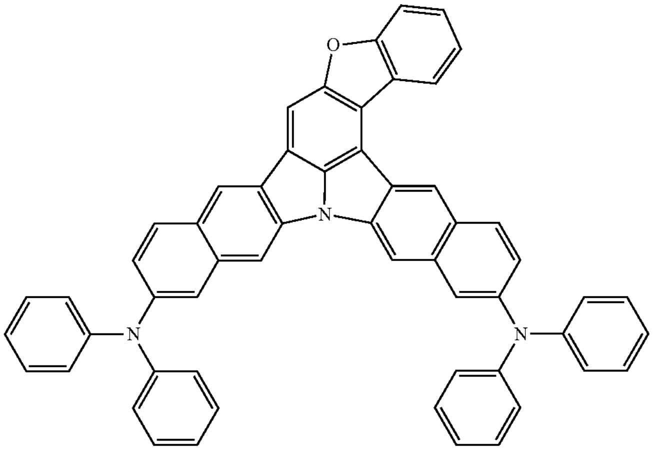

-continued
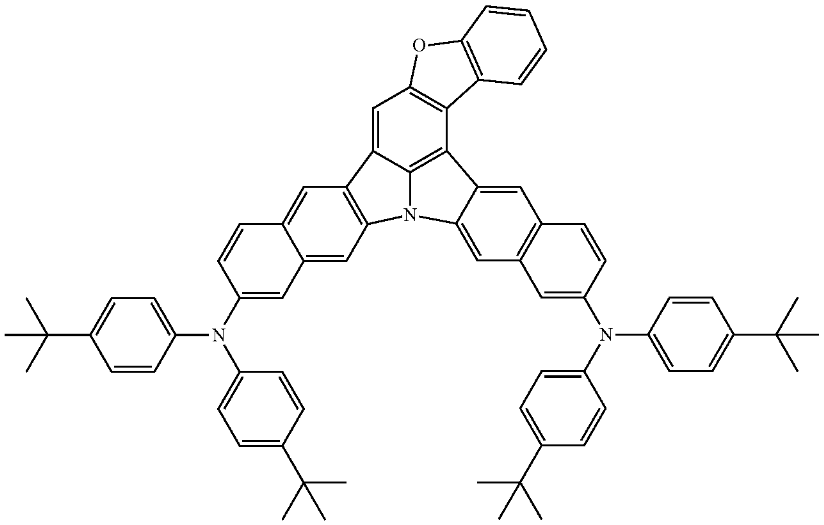
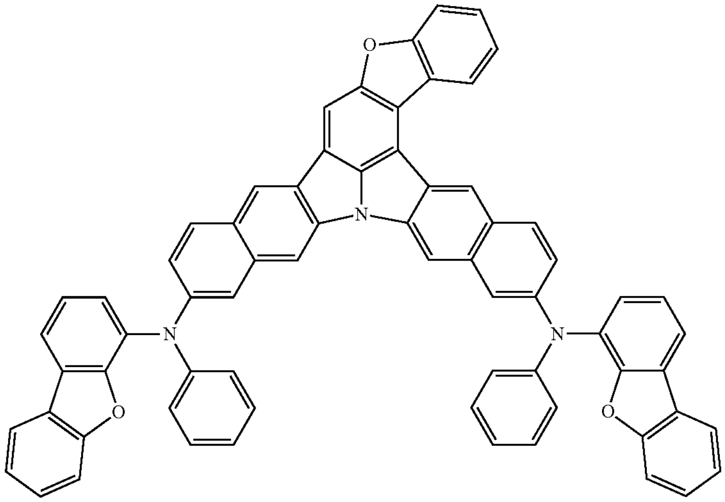
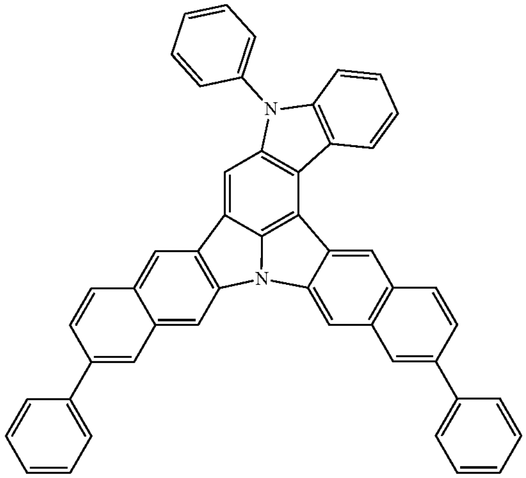
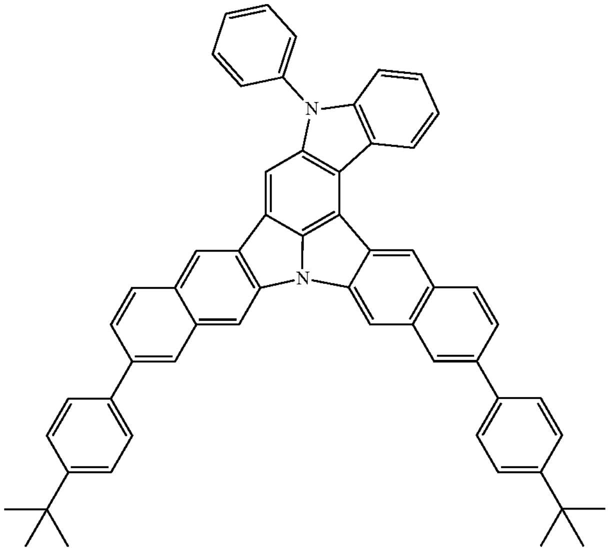

-continued
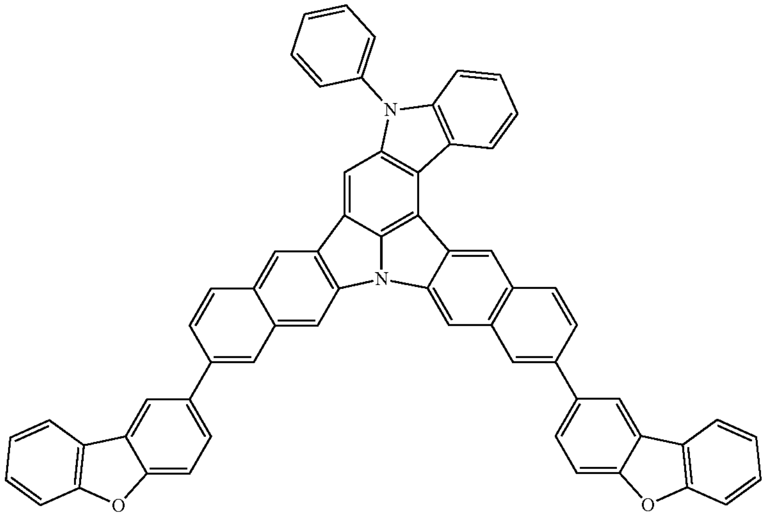
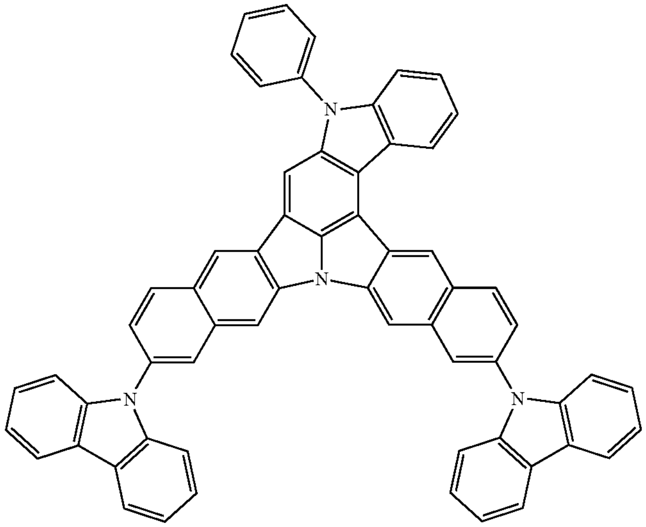
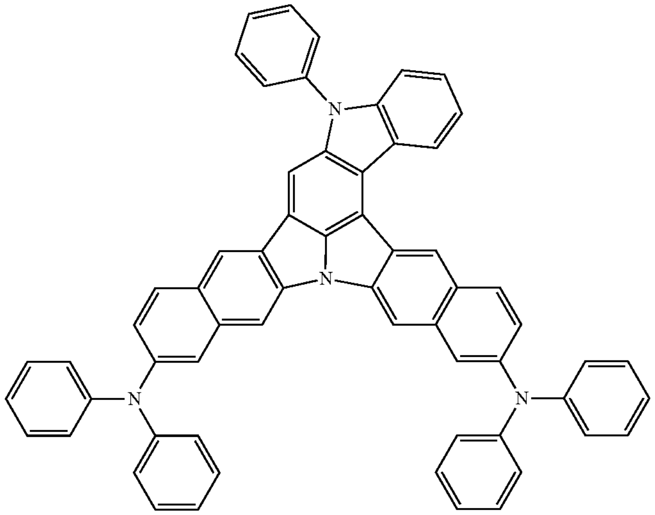

-continued
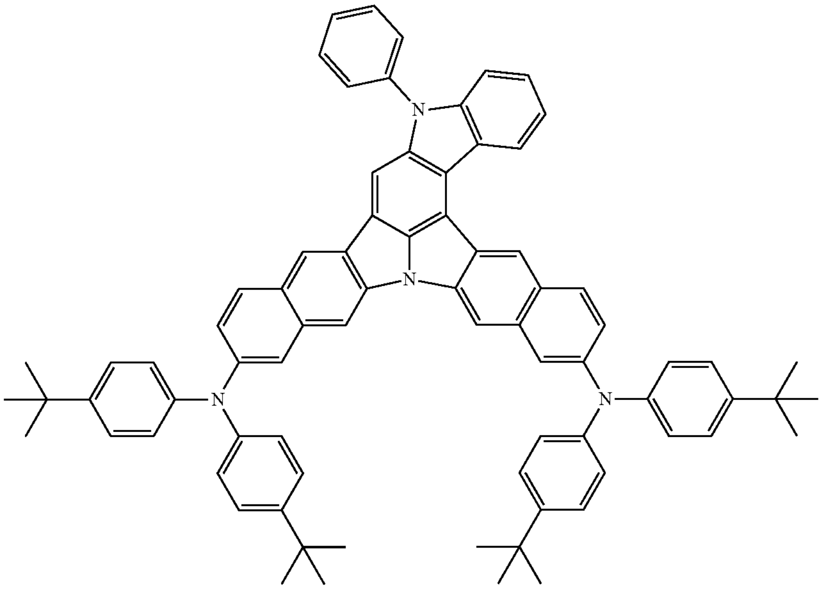
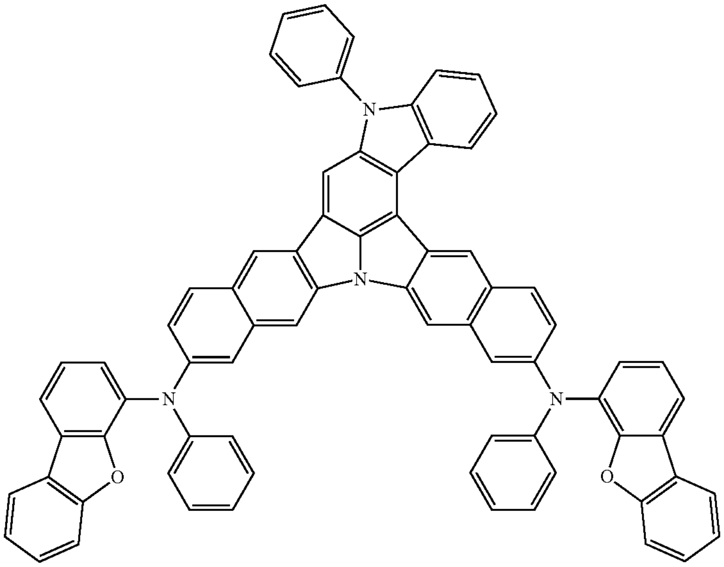
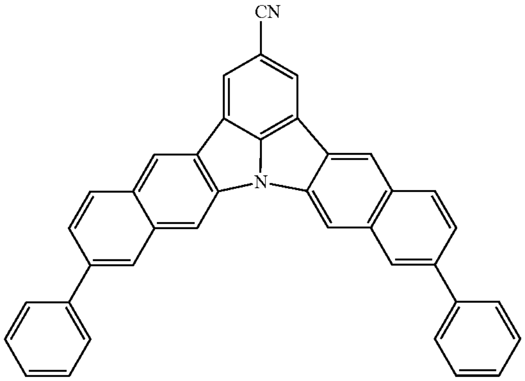
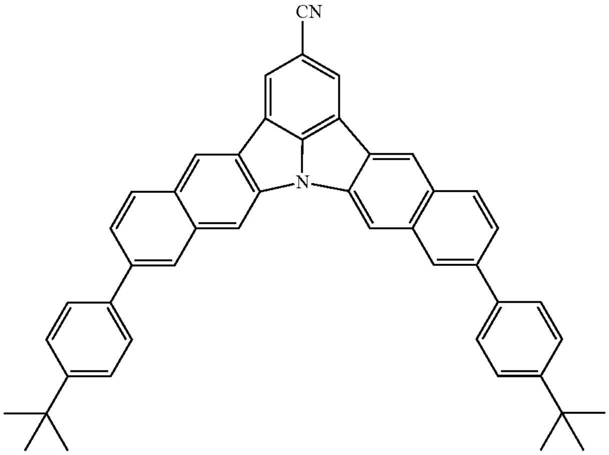

-continued
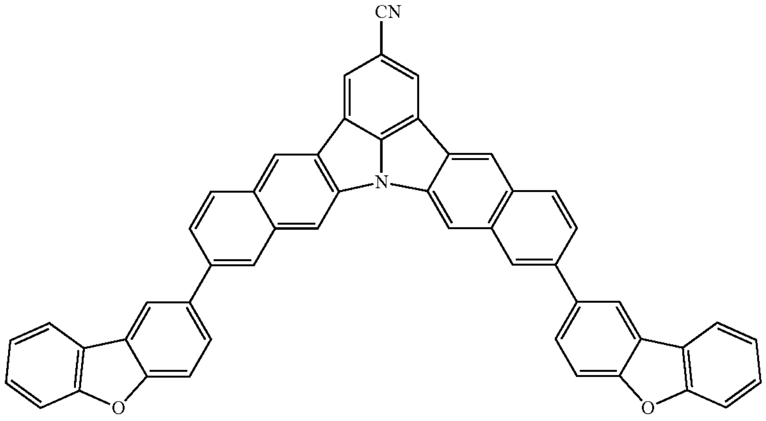
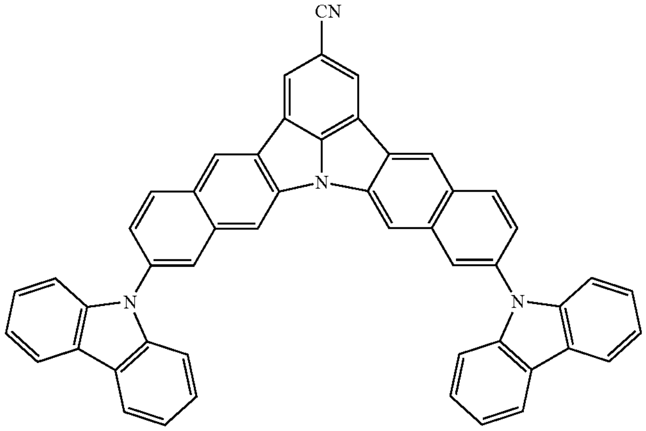
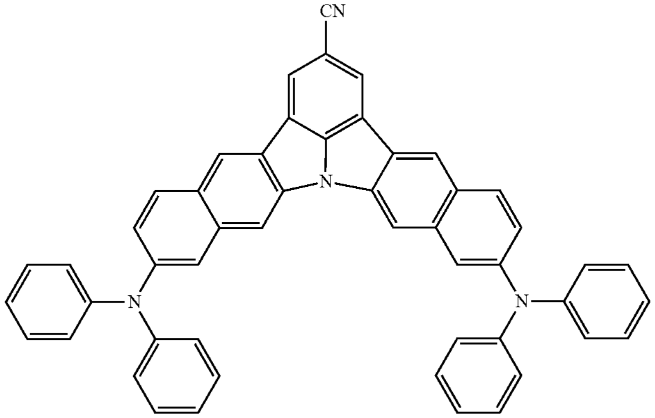

-continued
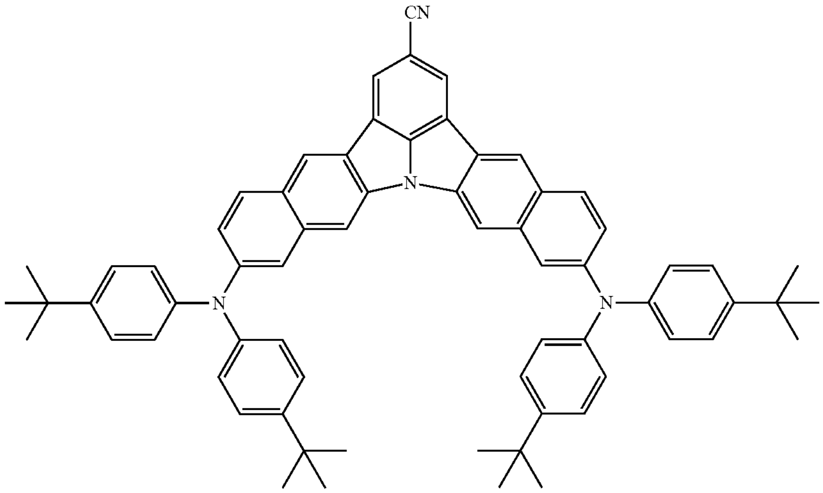
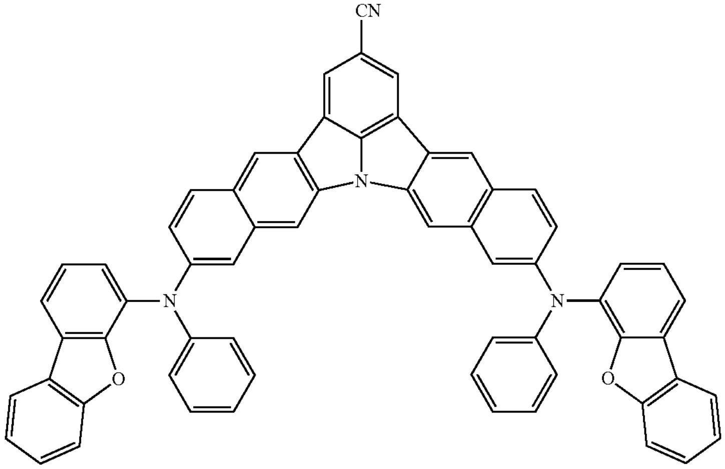
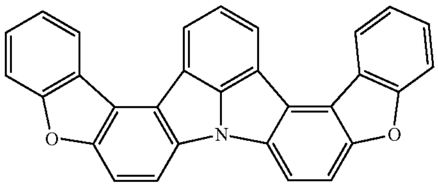
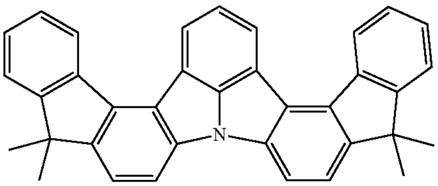
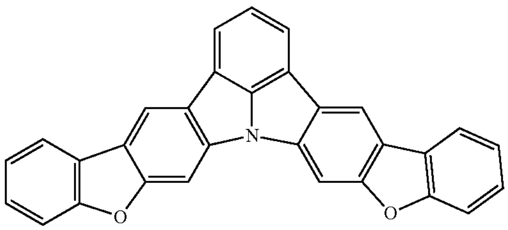
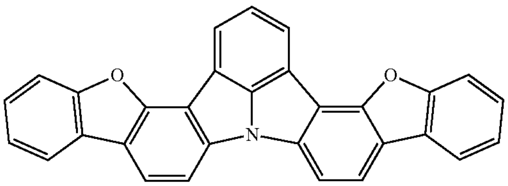
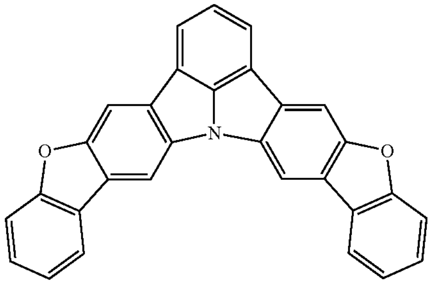
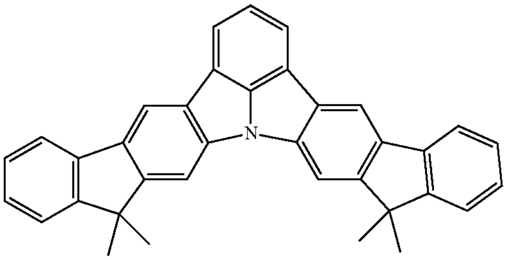

-continued
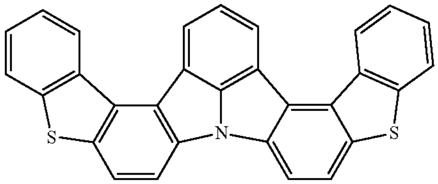
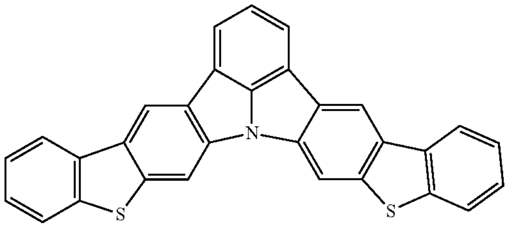
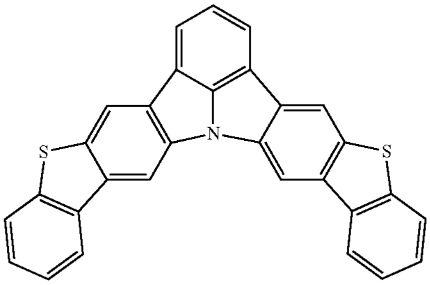
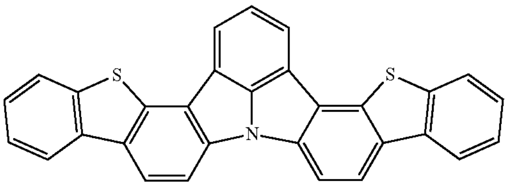
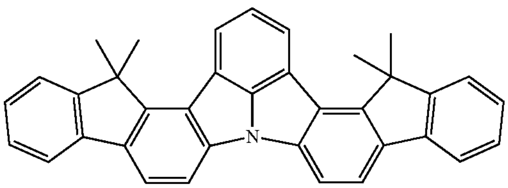
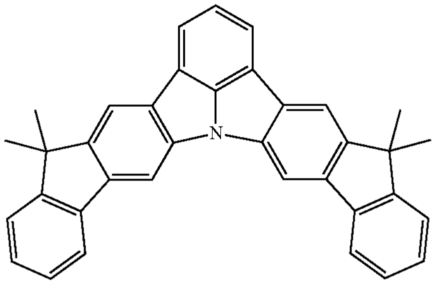
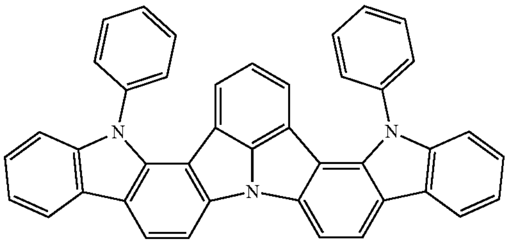
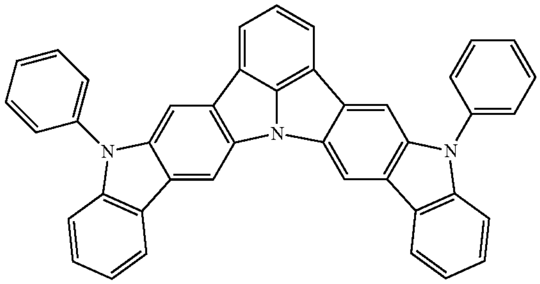
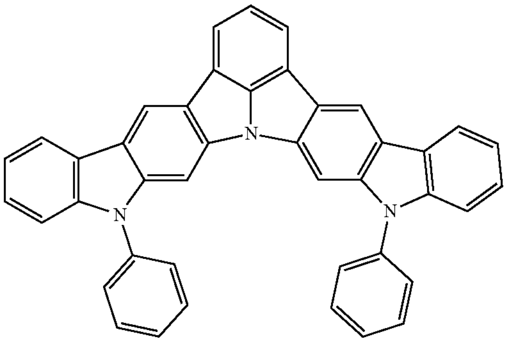
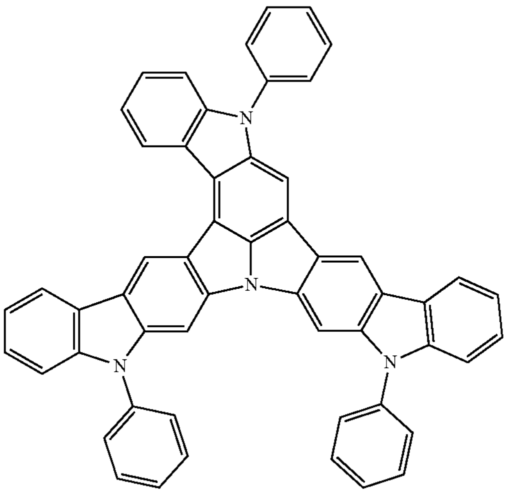

-continued
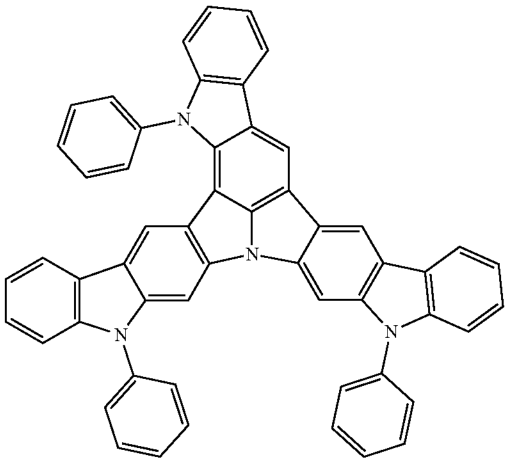
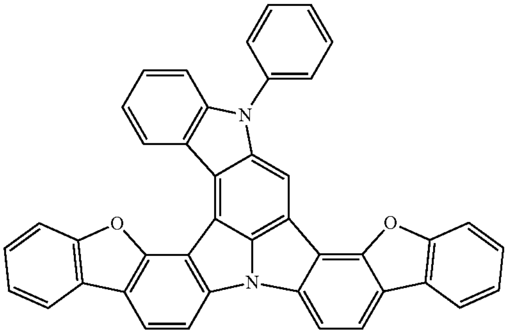
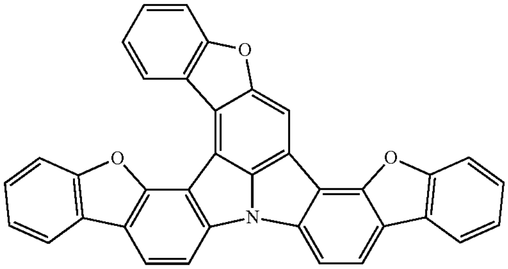
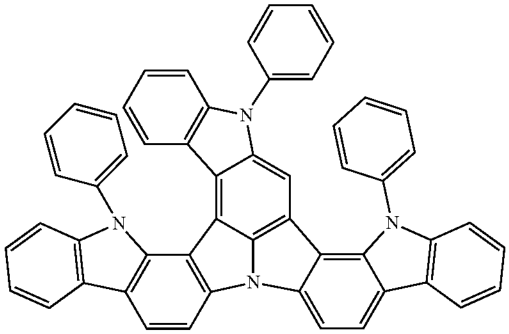
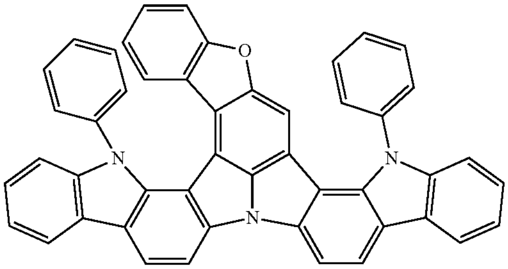
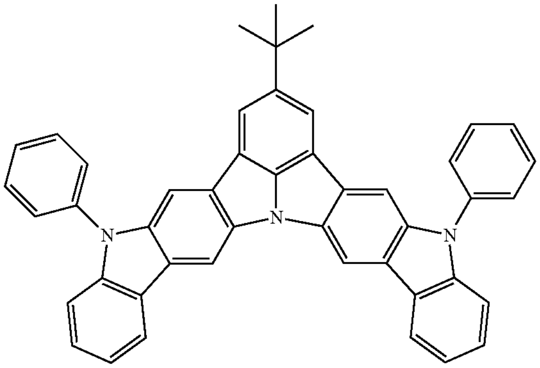
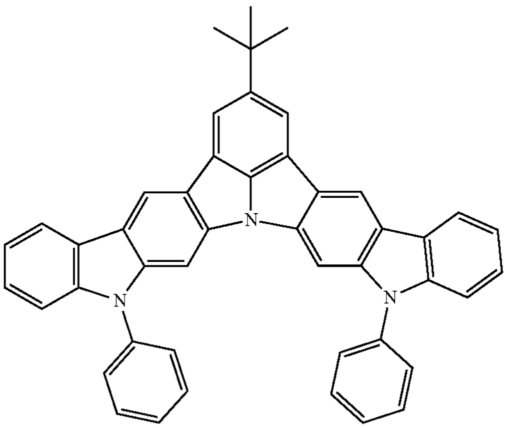
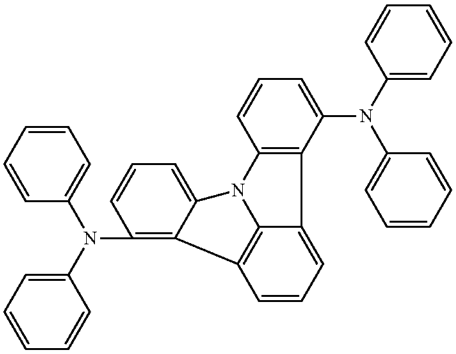

-continued
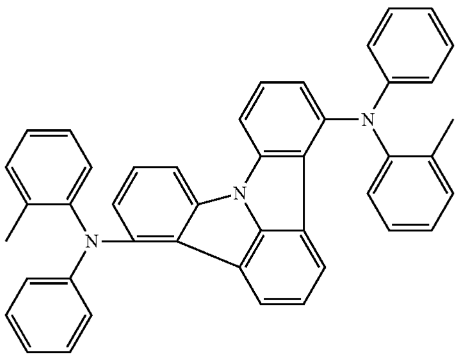
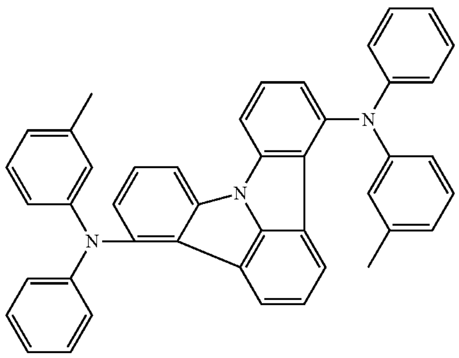
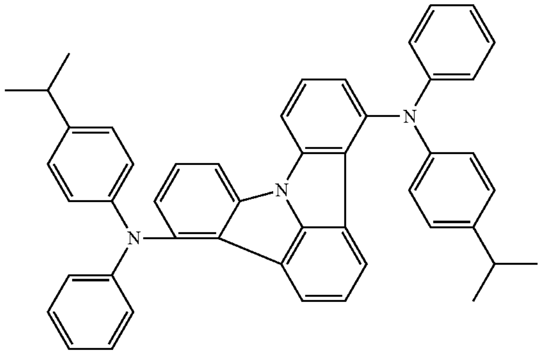
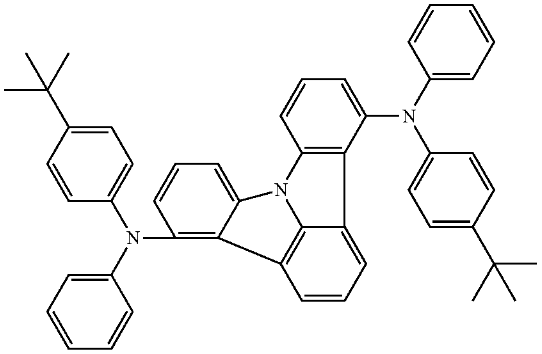
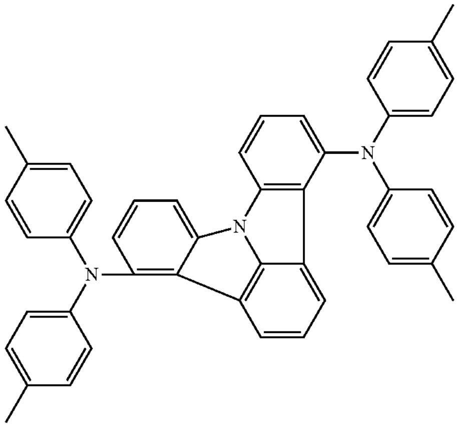
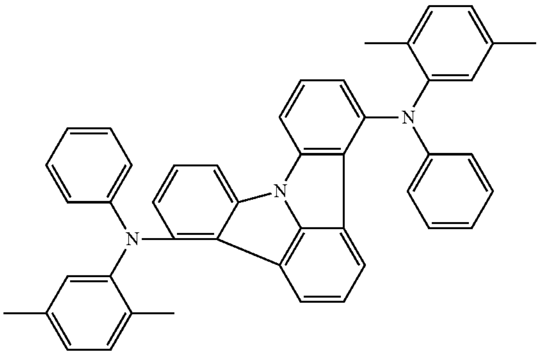
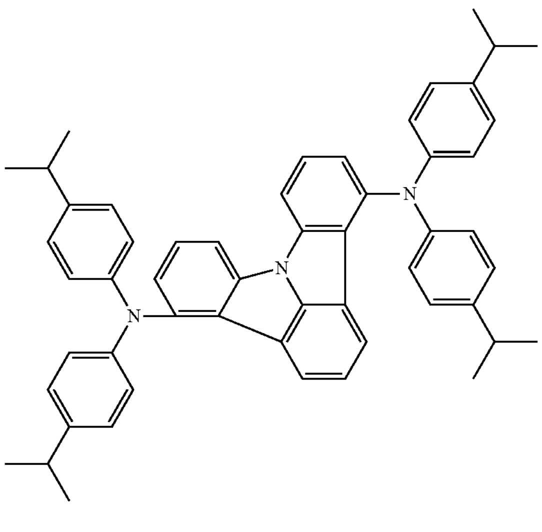
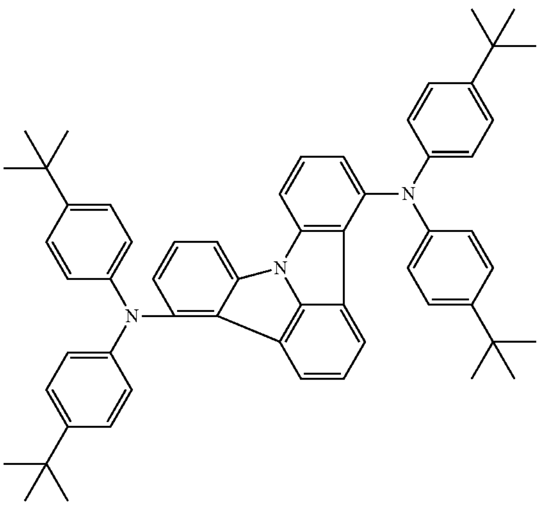

-continued
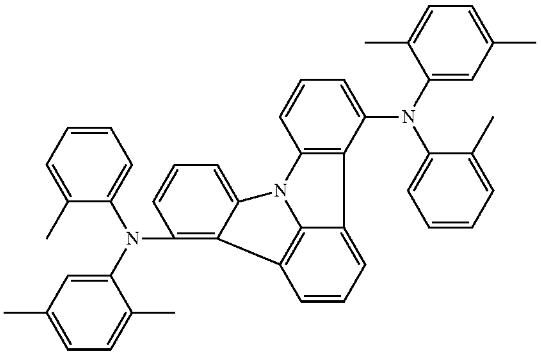
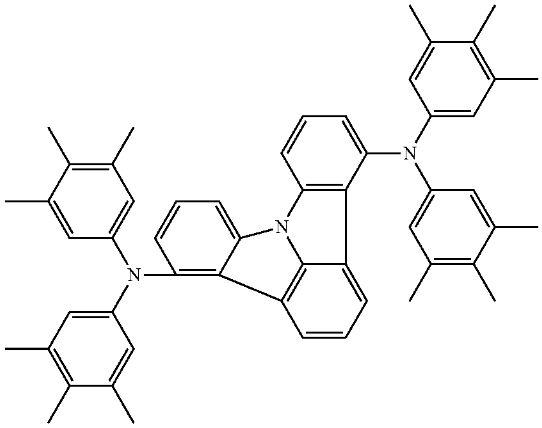
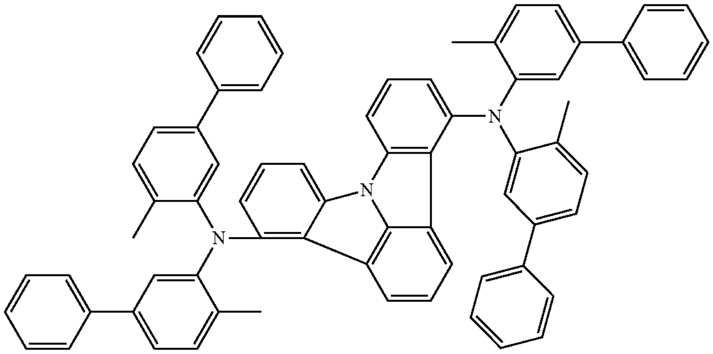
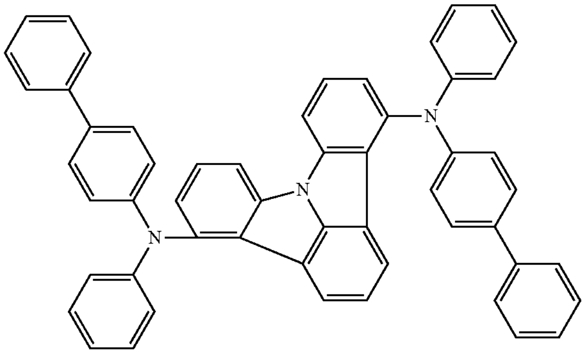
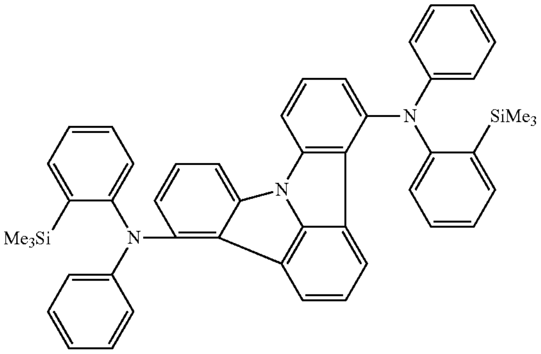
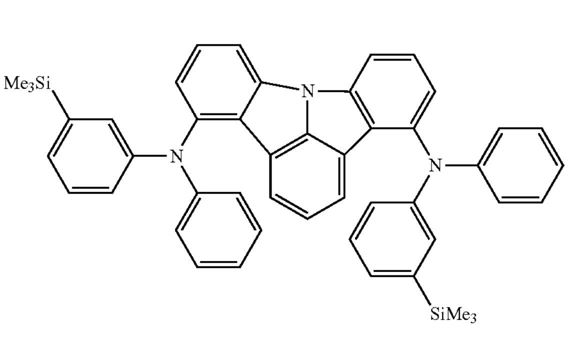
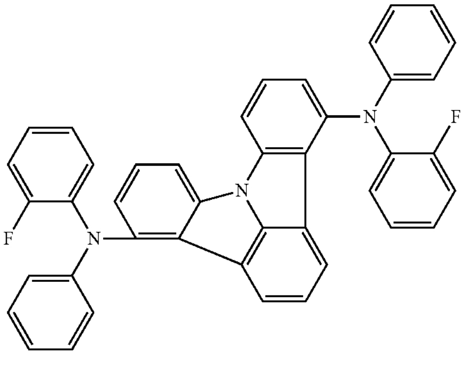

-continued
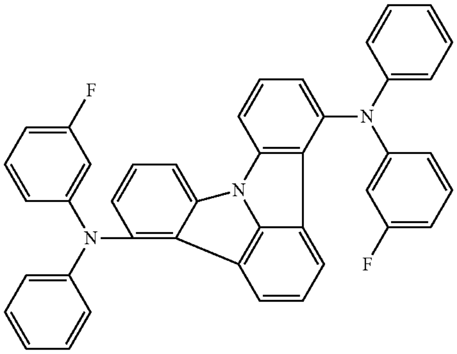
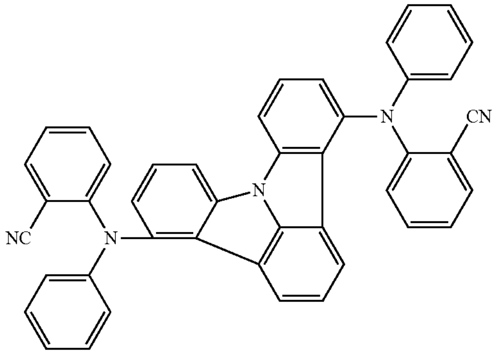
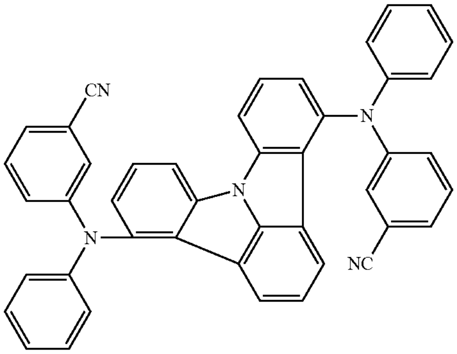
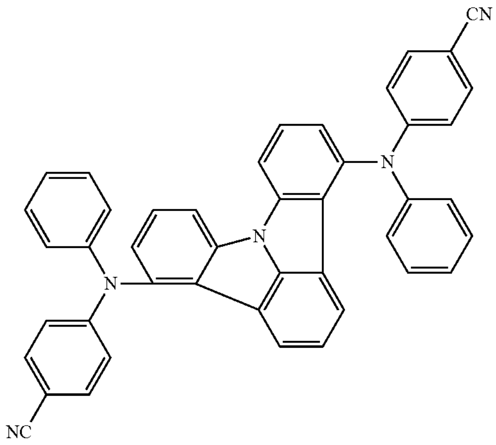
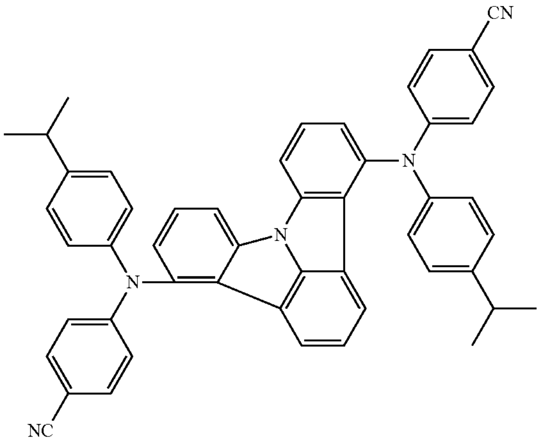
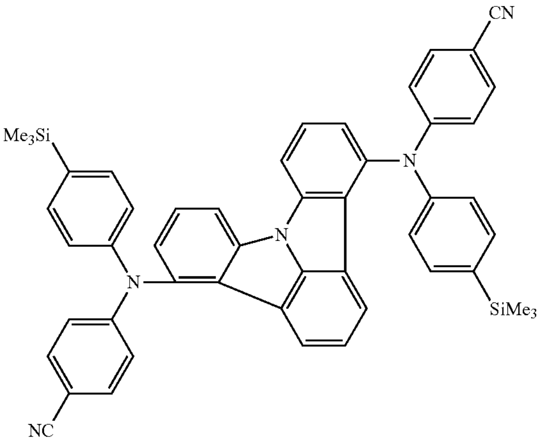
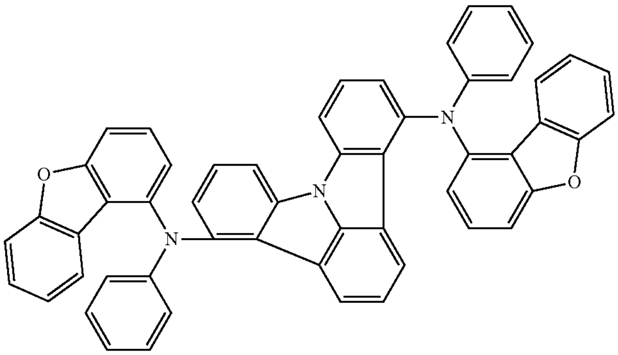

-continued
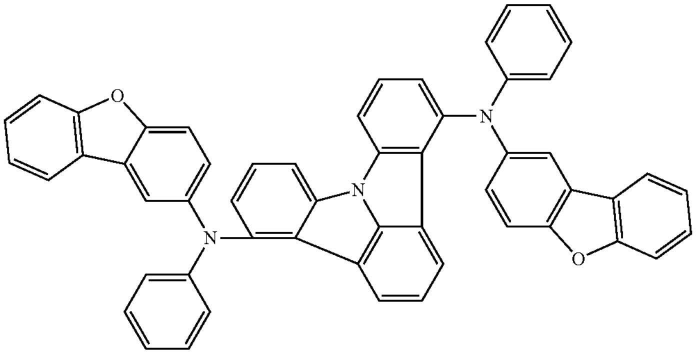
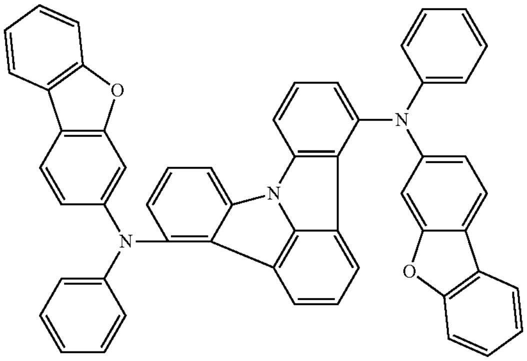
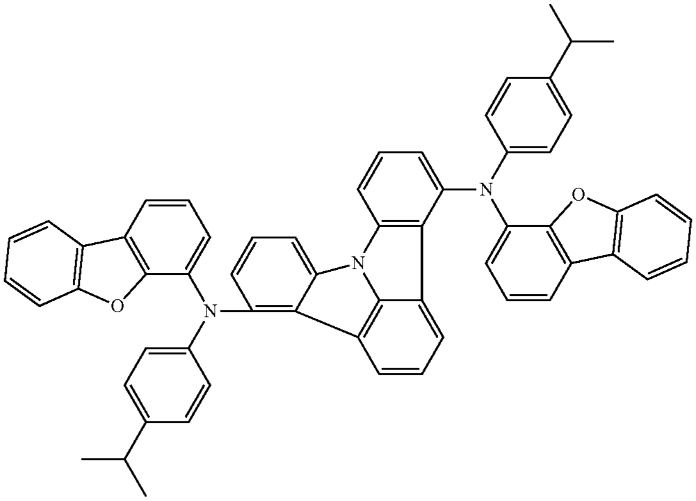
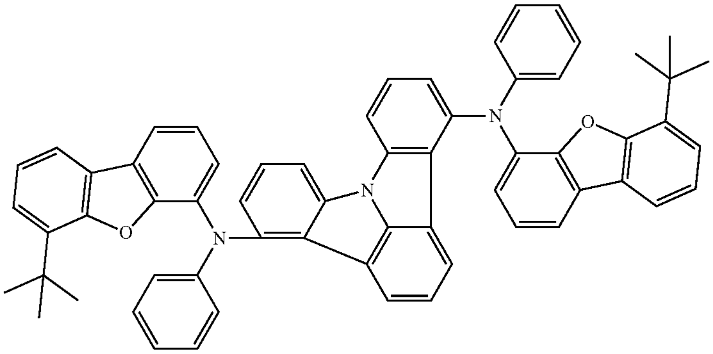

-continued
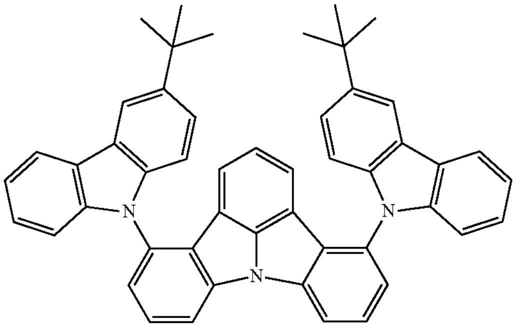
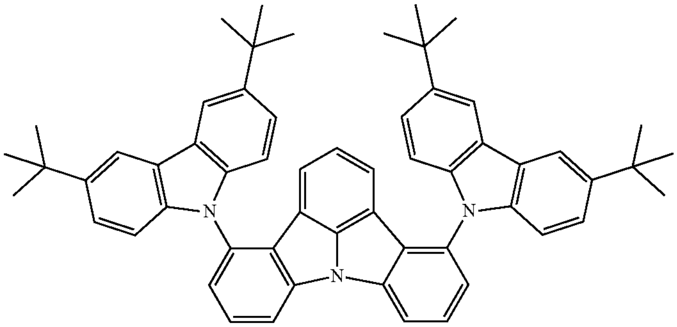
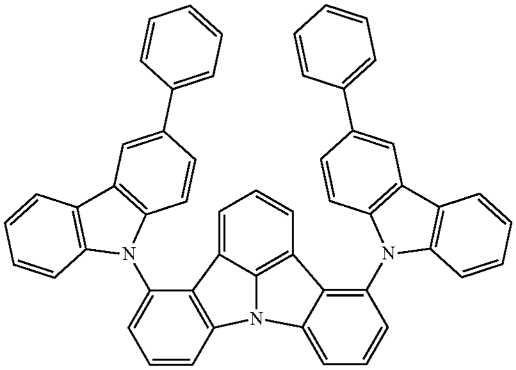
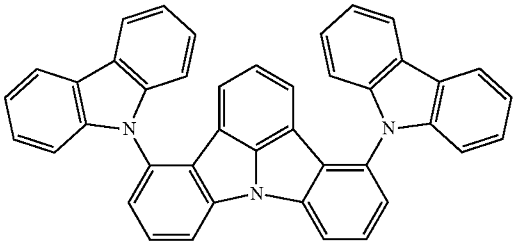
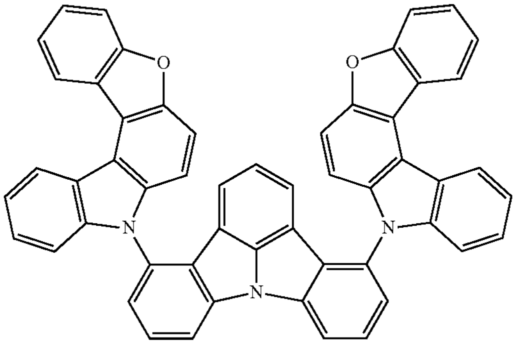
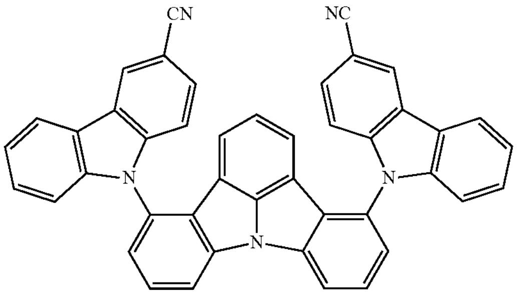
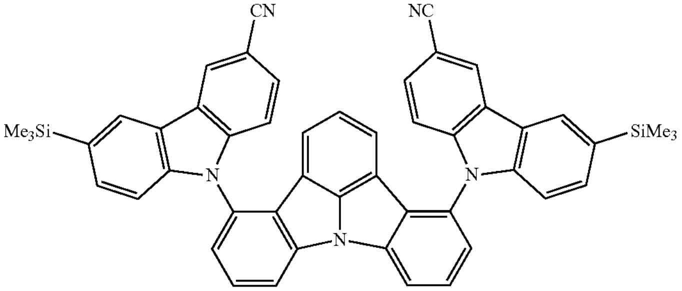

-continued
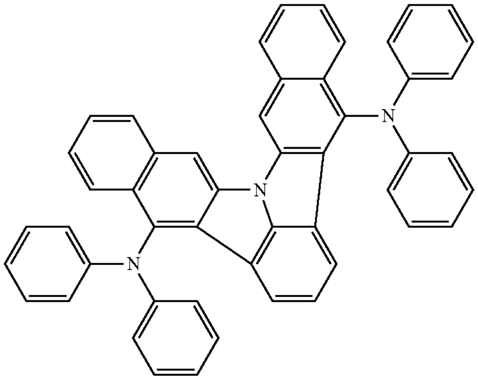
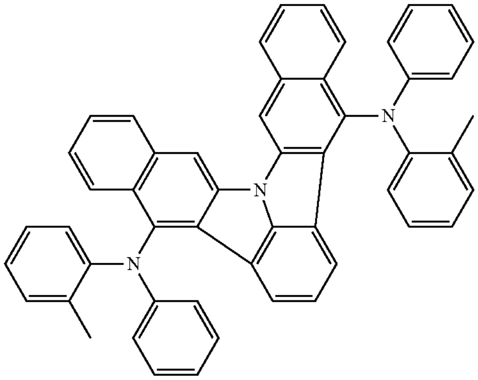
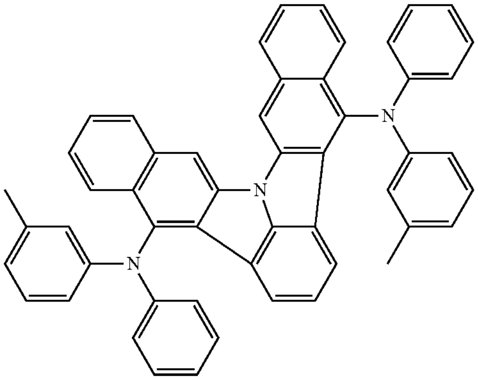
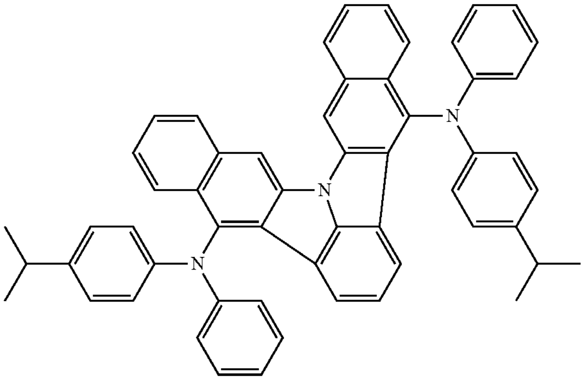
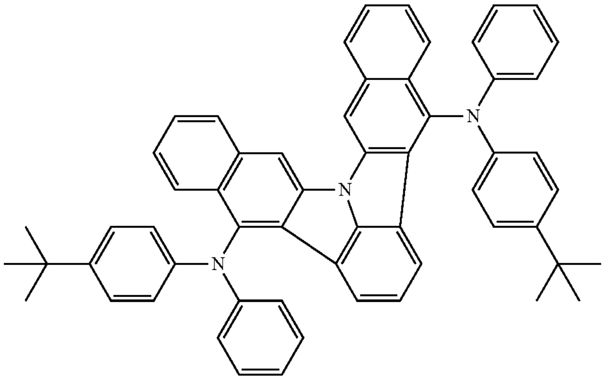
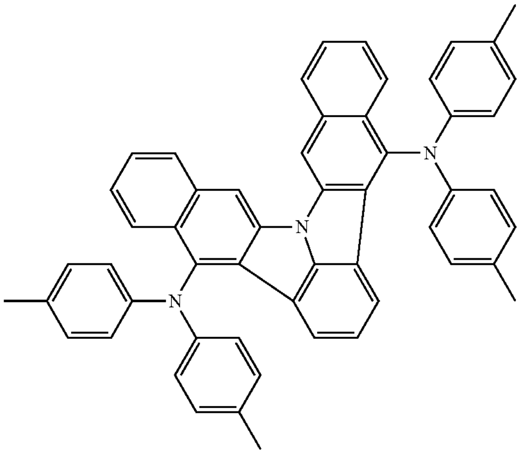

-continued
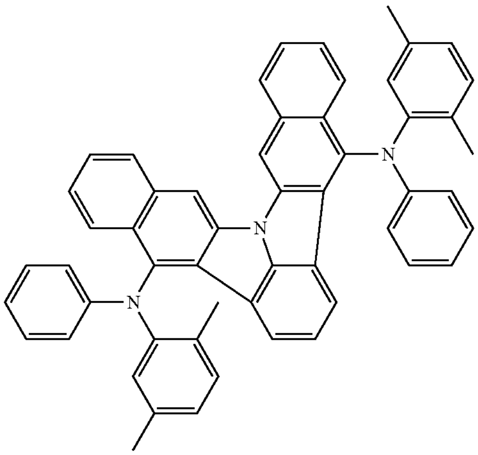
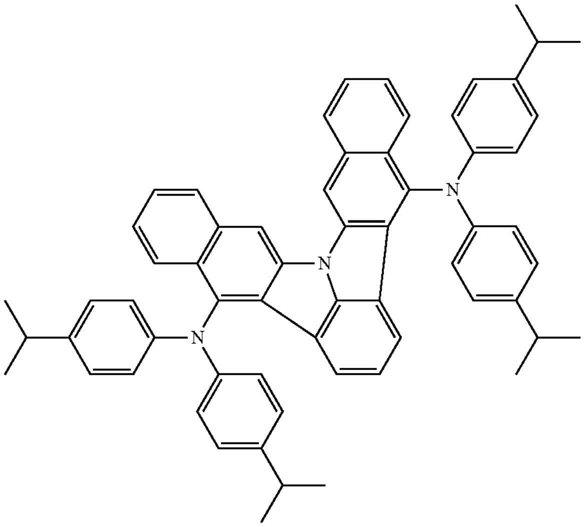
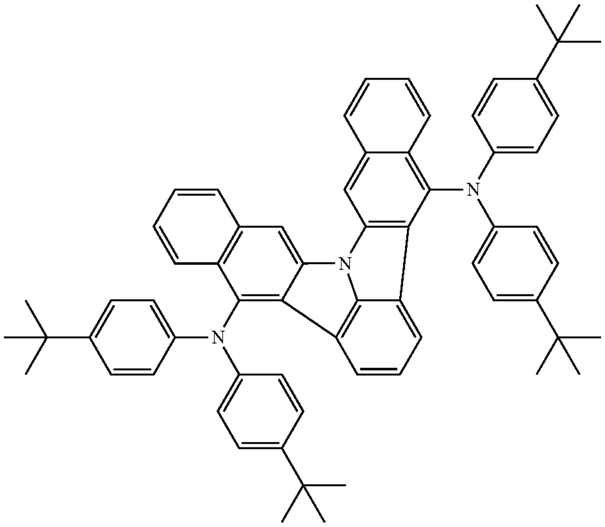
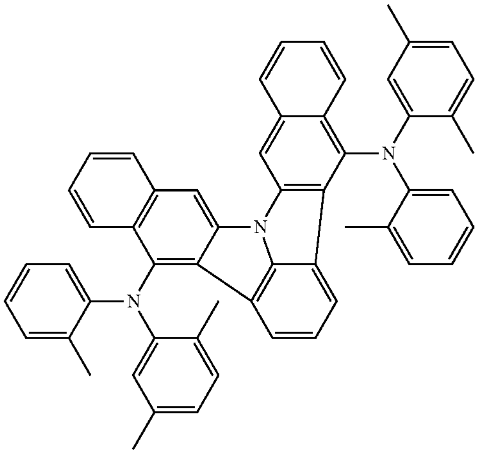
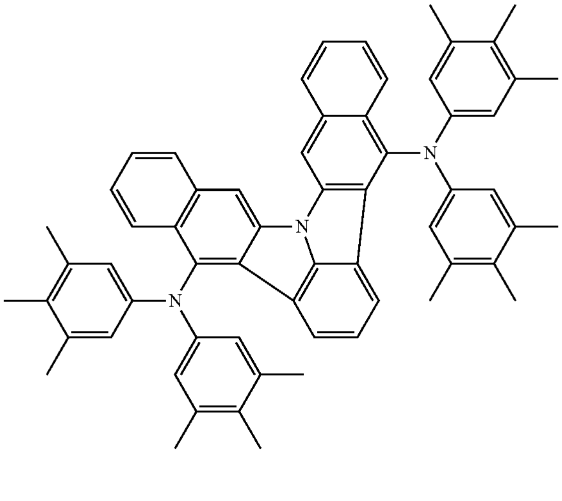

-continued
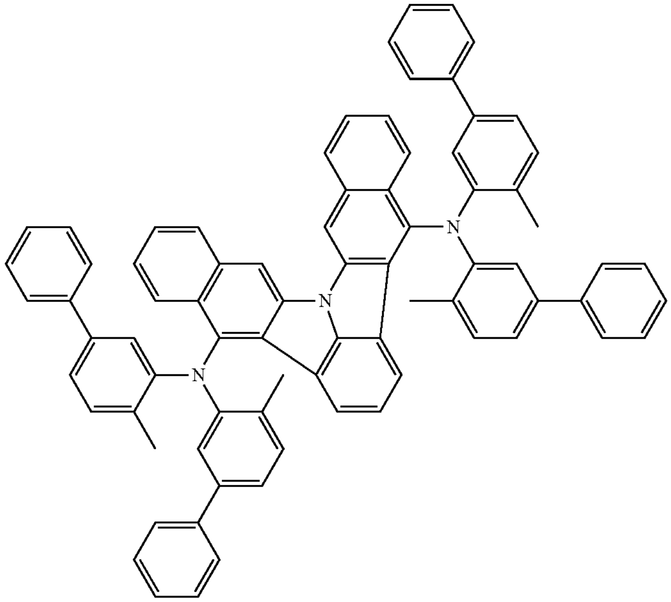
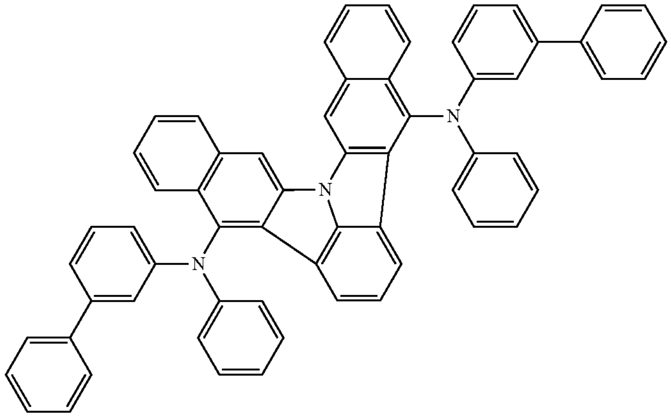
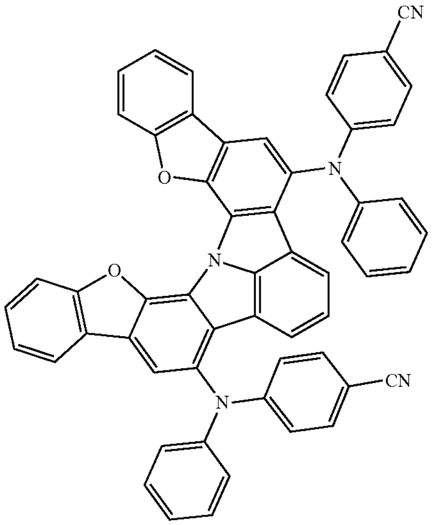
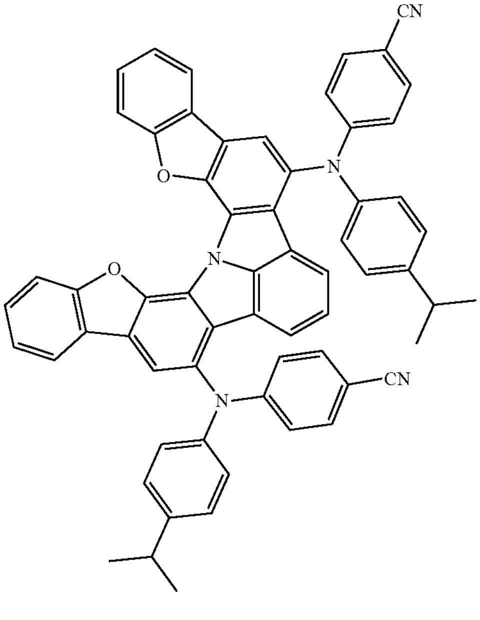
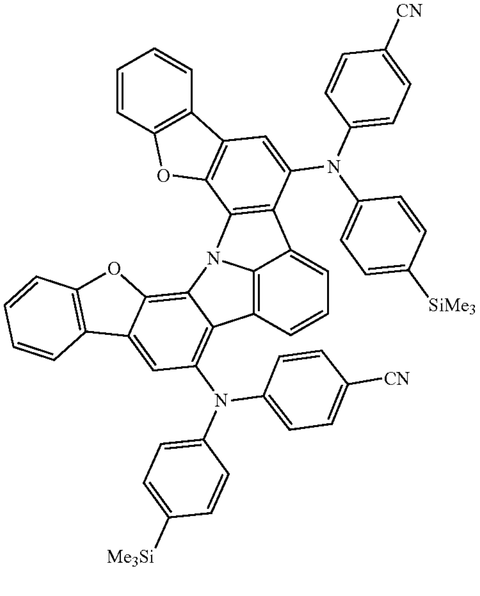

-continued
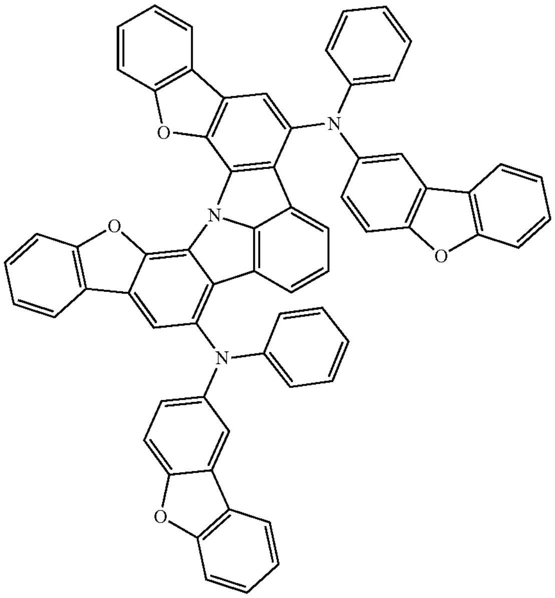
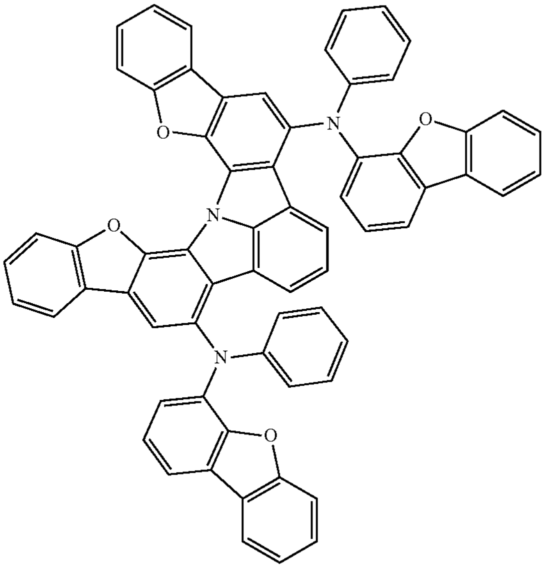
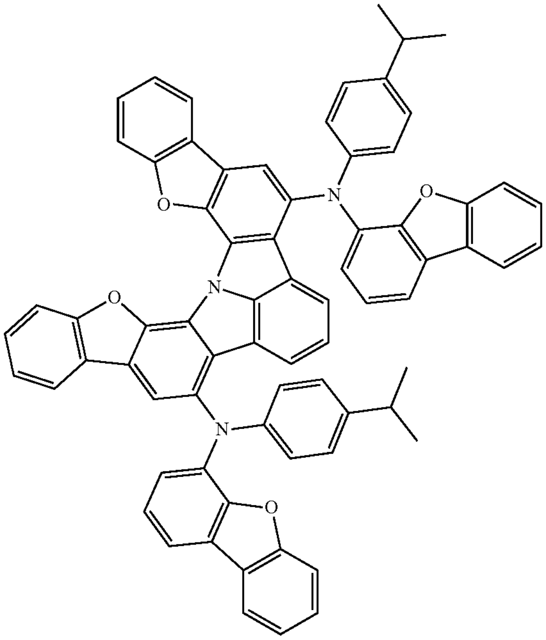
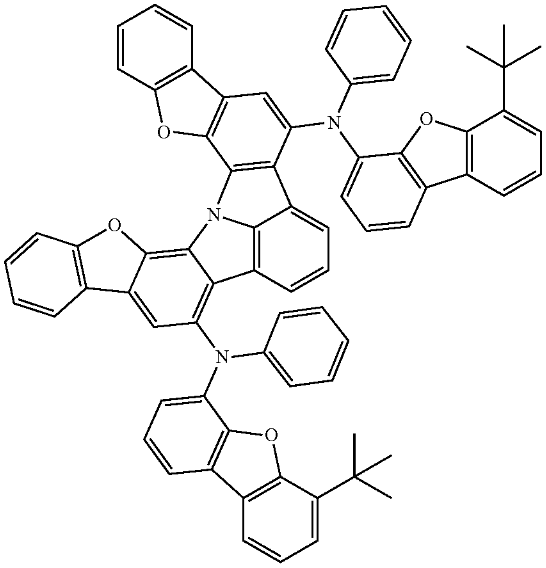

-continued
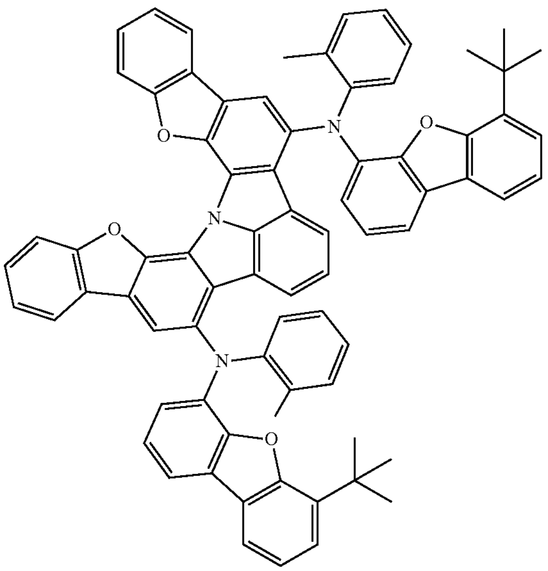
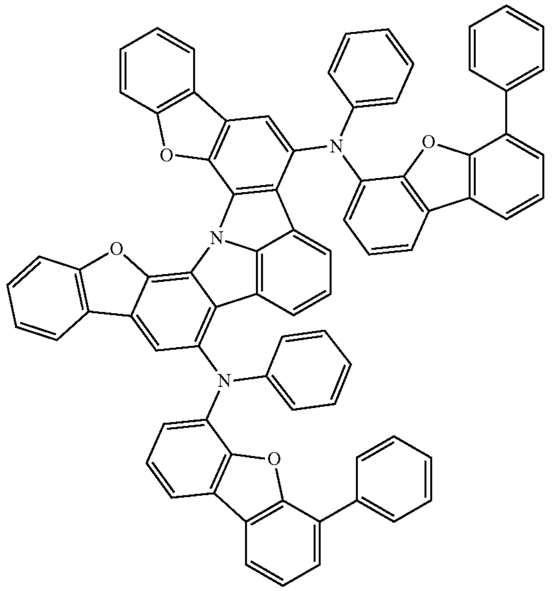
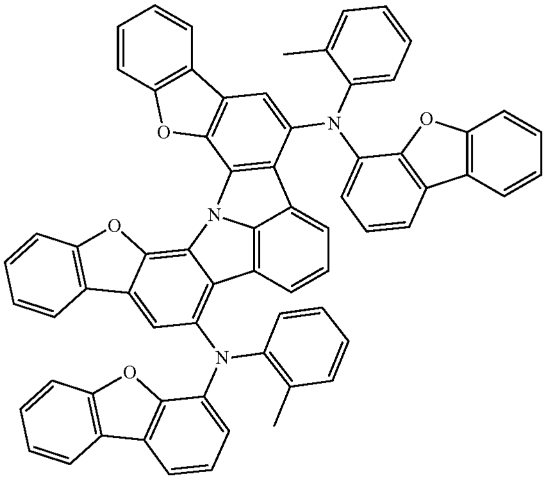
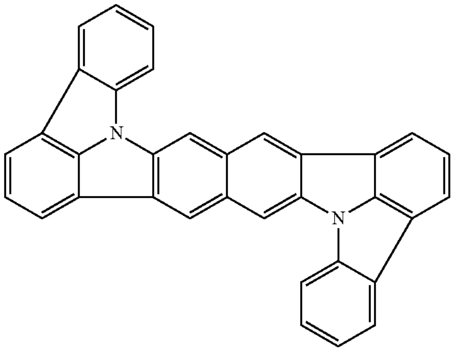
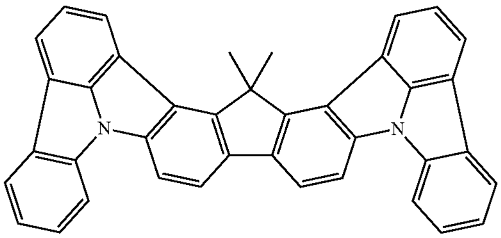
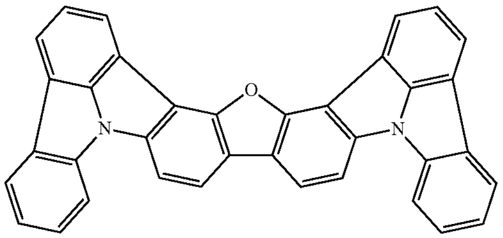
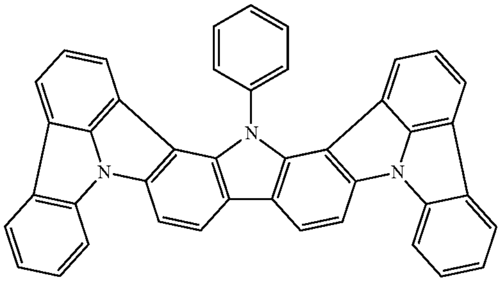
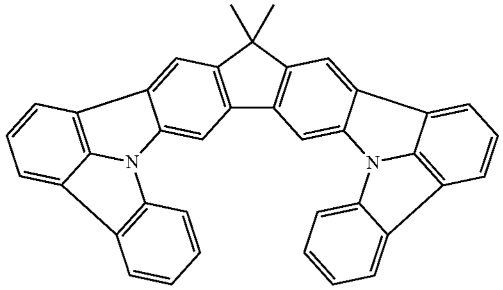

-continued
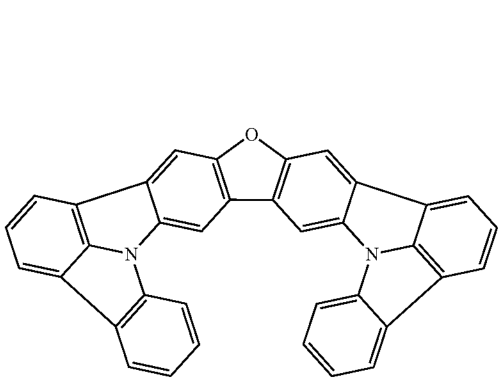
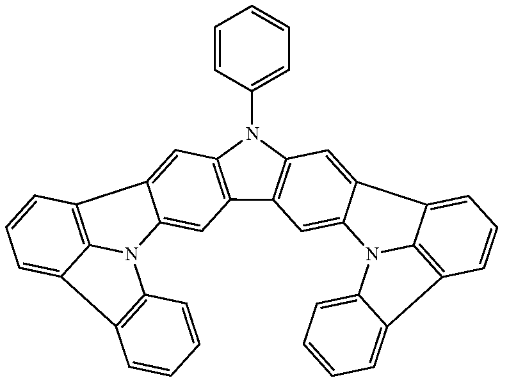
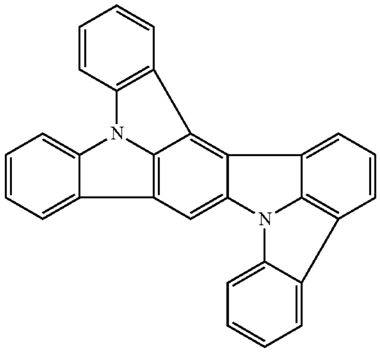
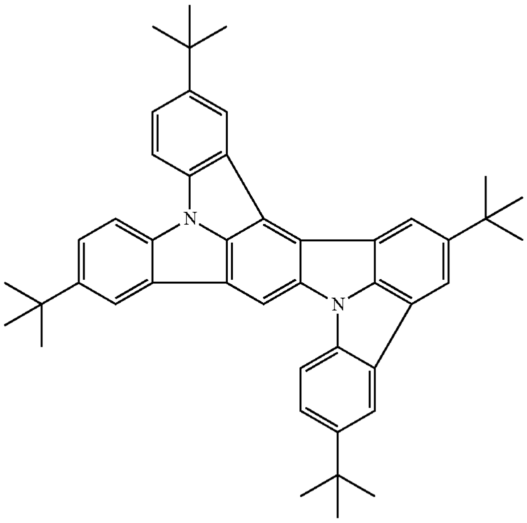
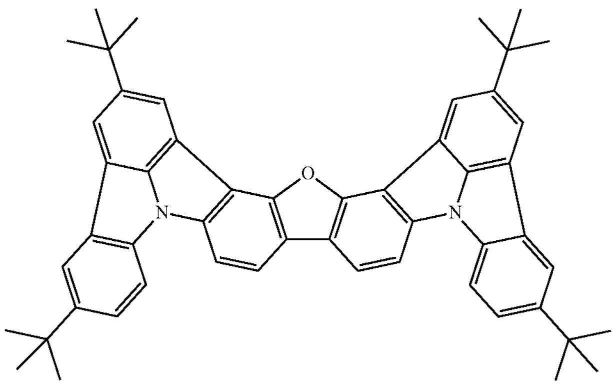 [SMILES: CC(C)(C)c1ccc2c(c1)c1cc(C(C)(C)C)cc3c4c5oc6c(ccc7c6c6cc(C(C)(C)C)cc8c9cc(C(C)(C)C)ccc9n7c86)c5ccc4n2c13]

(Compound Represented by Formula (31))

The compound represented by the formula (31) is explained below. The compound represented by formula (31) is a compound corresponding to the compound represented by the formula (21-3).

(31)

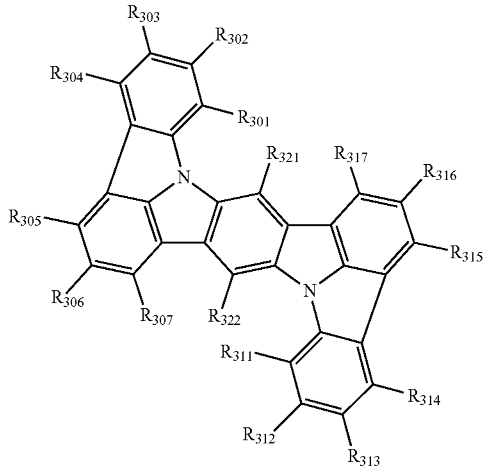

In the formula (31), one or more pairs of two or more adjacent groups of $R_{301}$ to $R_{307}$ and $R_{311}$ to $R_{317}$ form a substituted or unsubstituted, saturated or unsaturated ring, or do not form a substituted or unsubstituted, saturated or unsaturated ring;

$R_{301}$ to $R_{307}$ and $R_{311}$ to $R_{317}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{321}$ and $R_{322}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

Example of "One pair of two or more adjacent groups of $R_{301}$ to $R_{307}$ and $R_{311}$ to $R_{317}$" is pairs of $R_{301}$ and $R_{302}$, $R_{302}$ and $R_{303}$ $R_{303}$ and $R_{304}$, $R_{305}$ and $R_{306}$, $R_{306}$ and $R_{307}$, and $R_{301}$, $R_{302}$ and $R_{303}$, and the like.

In one embodiment, at least one of $R_{301}$ to $R_{307}$ and $R_{311}$ to $R_{317}$, preferably two of $R_{301}$ to $R_{307}$ and $R_{311}$ to $R_{317}$ is a group represented by $—N(R_{906})(R_{907})$.

In one embodiment, $R_{301}$ to $R_{307}$ and $R_{311}$ to $R_{317}$ are independently a hydrogen atom, a substituted or unsubstituted aryl group having 6 to 50 ring carbon atoms, or a substituted or unsubstituted monovalent heterocyclic group having 5 to 50 ring atoms.

In one embodiment, the compound represented by the formula (31) is a compound represented by the following formula (32):

(32)

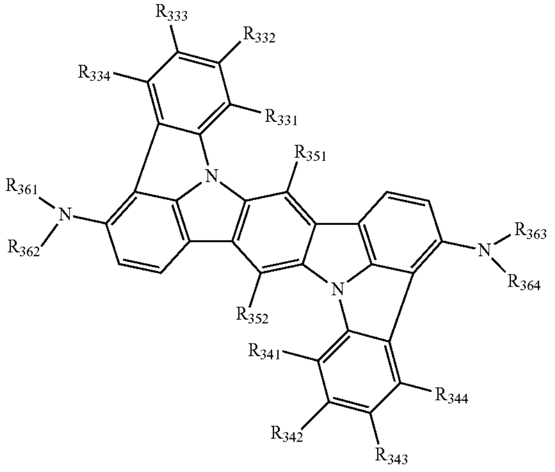

wherein in the formula (32), one or more pairs of two or more adjacent groups of $R_{331}$ to $R_{334}$ and $R_{341}$ to $R_{344}$ form a substituted or unsubstituted, saturated or unsaturated ring, or do not form a substituted or unsubstituted saturated or unsaturated ring;

$R_{331}$ to $R_{334}$ and $R_{341}$ to $R_{344}$ that do not form the substituted or unsubstituted, saturated or unsaturated ring and $R_{351}$ and $R_{352}$ are independently a hydrogen atom, a substituted or unsubstituted aryl group having 6 to 50 ring carbon atoms, or a substituted or unsubstituted monovalent heterocyclic group having 5 to 50 ring atoms; and $R_{361}$ to $R_{364}$ are independently a substituted or unsubstituted aryl group having 6 to 50 ring carbon atoms, or a substituted or unsubstituted monovalent heterocyclic group having 5 to 50 ring atoms.

In one embodiment, the compound represented by the formula (31) is a compound represented by the formula (33):

(33)

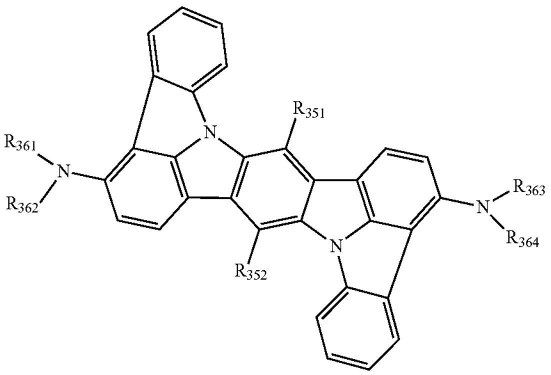

wherein in the formula (33), $R_{351}$, $R_{352}$, and $R_{361}$ to $R_{364}$ are as defined in the formula (32).

In one embodiment, the compound represented by the formula (31) is a compound represented by the formula (34) or (35):

(34)

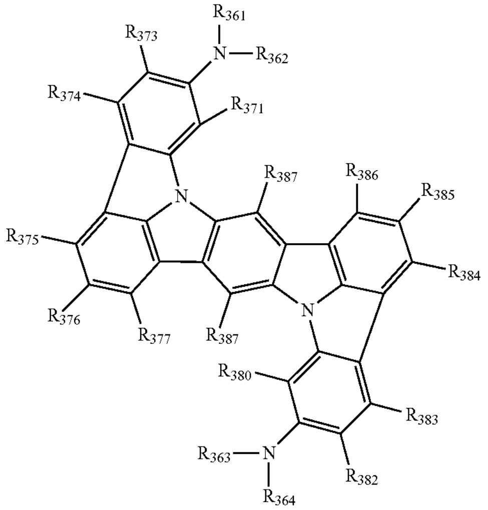

(35)

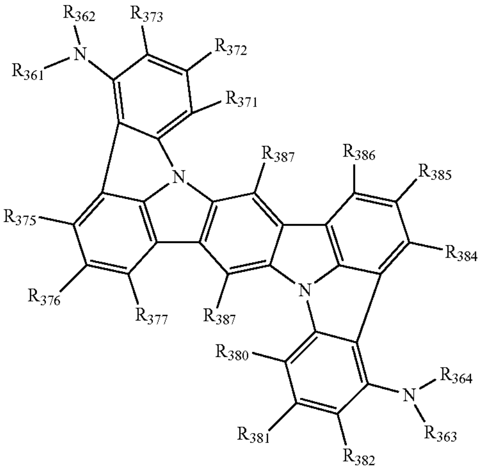

wherein in the formulas (34) and (35), $R_{361}$ to $R_{364}$ are as defined in the formula (32);

one or more pairs of two or more adjacent groups of $R_{371}$ to $R_{377}$ and $R_{380}$ to $R_{386}$ form a substituted or unsubstituted, saturated or unsaturated ring, or do not form a substituted or unsubstituted saturated or unsaturated ring; and $R_{371}$ to $R_{377}$ and $R_{380}$ to $R_{386}$ that do not form the substituted or unsubstituted, saturated or unsaturated ring and $R_{387}$ are independently a hydrogen atom, a substituted or unsubstituted aryl group having 6 to 50 ring carbon atoms, or a substituted or unsubstituted monovalent heterocyclic group having 5 to 50 ring atoms, and two $R_{387}$s may be the same with or different from each other.

In one embodiment, the compound represented by the formula (31) is a compound represented by the formula (34-2) or (35-2):

(34-2)

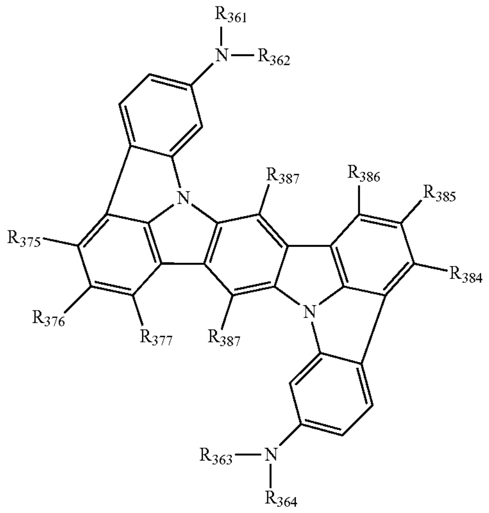

(35-2)

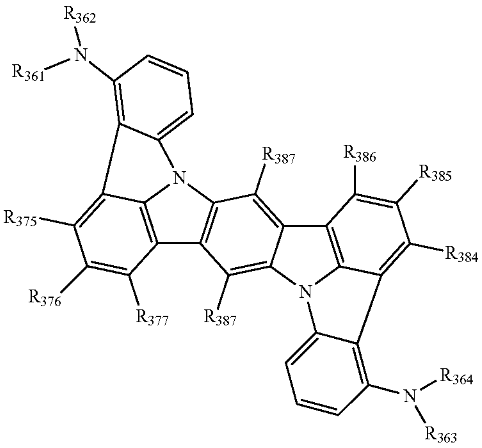

wherein in the formulas (34-2) and (35-2), $R_{361}$ to $R_{364}$, $R_{375}$ to $R_{377}$ and $R_{384}$ to $R_{387}$ are as defined in the formulas (34) and (35).

In one embodiment, $R_{361}$ to $R_{364}$ in the formulas (32), (33), (34), (35), (34-2) and (35-2) are independently a substituted or unsubstituted aryl group having 6 to 50 ring carbon atoms (preferably a substituted or unsubstituted phenyl group).

In one embodiment, $R_{321}$ and $R_{322}$ in the formula (31) and $R_{351}$, $R_{352}$ and $R_{387}$ in the formulas (32), (33), (34), (35), (34-2) and (35-2) are independently a hydrogen atom or a substituted or unsubstituted aryl group having 6 to 50 ring carbon atoms (preferably a substituted or unsubstituted phenyl group).

In one embodiment, the compound represented by the formula (31) is one or more compounds selected from the group consisting of the following formulas (32-11), (34-11) and (35-11):

(32-11)

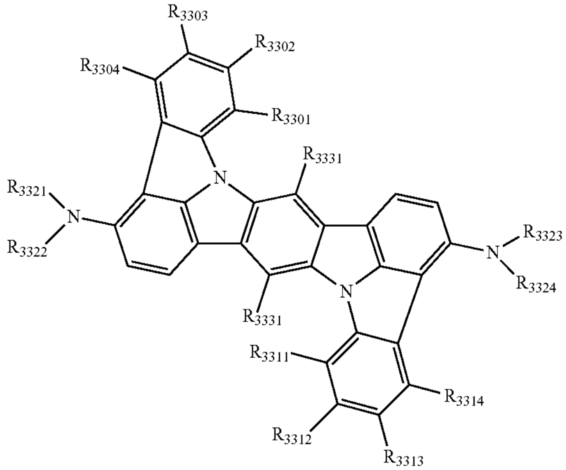

(34-11)

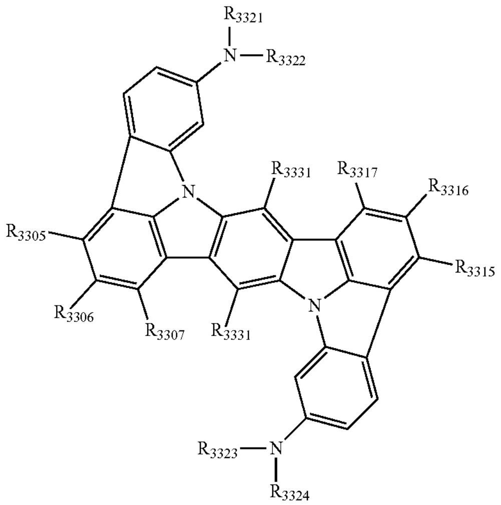

-continued (35-11)

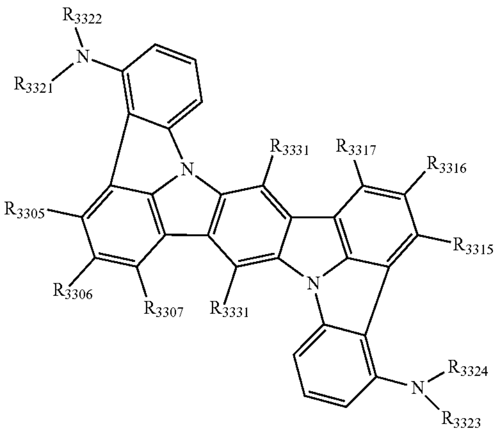

wherein in the formulas (32-11), (34-11) and (35-11), one or more pairs of two or more adjacent groups of $R_{3301}$ to $R_{3307}$ and $R_{3311}$, to $R_{3317}$ form a substituted or unsubstituted, saturated or unsaturated ring, or do not form a substituted or unsubstituted, saturated or unsaturated ring;

$R_{3301}$ to $R_{3307}$ and $R_{3311}$ to $R_{3317}$ that do not form the substituted or unsubstituted, saturated or unsaturated ring, and $R_{3331}$ are independently a hydrogen atom, a substituted or unsubstituted aryl group having 6 to 20 ring carbon atoms, or a substituted or unsubstituted monovalent heterocyclic group having 5 to 20 ring atoms;

two $R_{3331}$s may be the same with or different from each other; and $R_{3321}$ to $R_{3324}$ are independently a substituted or unsubstituted aryl group having 6 to 20 ring carbon atoms, or a substituted or unsubstituted monovalent heterocyclic group having 5 to 20 ring atoms.

In one embodiment, the one or more compounds selected from the group consisting of the formulas (32-11), (34-11) and (35-11) is one or more compounds selected from a group consisting of the following formulas (32-12), (34-12) and (35-12):

(32-12)

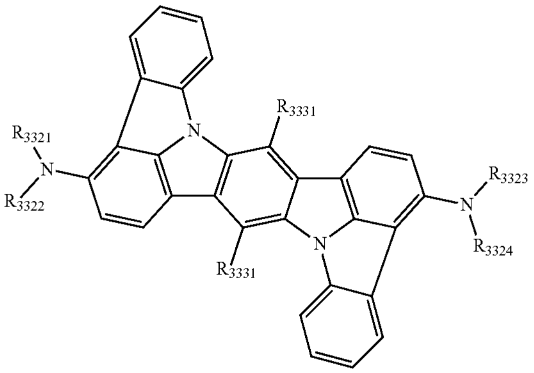

-continued (34-12)

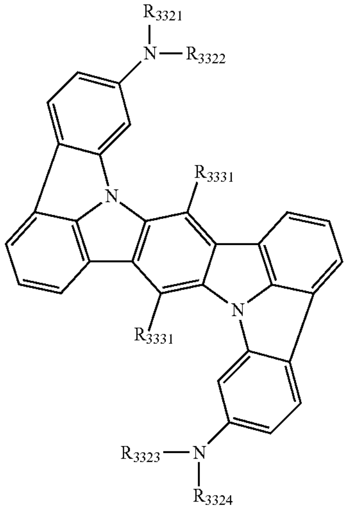

(35-12)

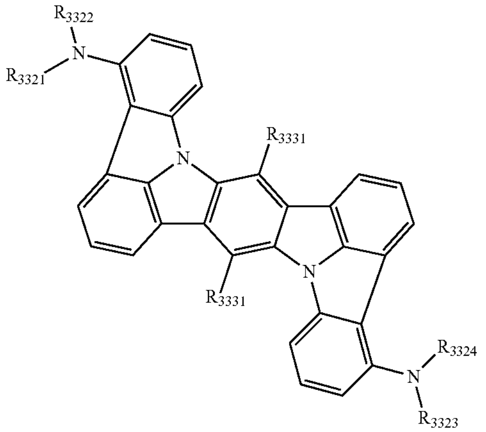

wherein in the formulas (32-12), (34-12) and (35-12), $R_{3321}$ to $R_{3324}$ and $R_{3331}$ are as defined in the formulas (32-11), (34-11) and (35-11).

In one embodiment, in the formulas (32-11), (34-11), (35-11), (32-12), (34-12) and (35-12), $R_{3321}$ to $R_{3324}$ are independently a substituted or unsubstituted phenyl group.

In one embodiment, in the formulas (32-11), (34-11), (35-11), (32-12), (34-12) and (35-12), two $R_{3331}$s are independently a hydrogen atom.

In one embodiment, in the formulas (32-11), (34-11), (35-11), (32-12), (34-12) and (35-12), the substituent in the case of "substituted or unsubstituted" is selected from the group consisting of an alkyl group having 1 to 20 carbon atoms, an aryl group having 6 to 20 ring carbon atoms, and a monovalent heterocyclic group having 5 to 20 ring atoms.

In one embodiment, in the formulas (32-11), (34-11), (35-11), (32-12), (34-12) and (35-12), the substituent in the case of "substituted or unsubstituted" is an alkyl group having 1 to 5 carbon atoms.

In one embodiment, in the formulas (32-11), (34-11), (35-11), (32-12), (34-12) and (35-12), $R_{3321}$ to $R_{3324}$ are independently a substituted or unsubstituted phenyl group, and two $R_{3331}$s are independently a hydrogen atom.

In one embodiment, in the formulas (32-11), (34-11), (35-11), (32-12), (34-12) and (35-12), $R_{3321}$ to $R_{3324}$ are independently a substituted or unsubstituted phenyl group, two $R_{3331}$s are independently a hydrogen atom, and the substituent in the case of "substituted or unsubstituted" is selected from the group consisting of an alkyl group having 1 to 20 carbon atoms, an aryl group having 6 to 20 ring carbon atoms, and a monovalent heterocyclic group having 5 to 20 ring atoms.

In one embodiment, in the formulas (32-11), (34-11), (35-11), (32-12), (34-12) and (35-12), $R_{3321}$ to $R_{3324}$ are independently a substituted or unsubstituted phenyl group, two $R_{3331}$s are independently a hydrogen atom, and the substituent in the case of "substituted or unsubstituted" is an alkyl group having 1 to 5 carbon atoms.

In one embodiment, in the compound represented by the formula (31), one or more pairs of two or more adjacent groups of $R_{301}$ to $R_{307}$ and $R_{311}$ to $R_{317}$ form a substituted or unsubstituted, saturated or unsaturated ring.

In one embodiment, the compound represented by the formula (31) is one or more compounds selected from the group consisting of the following formulas (36-1) to (36-6):

(36-1)

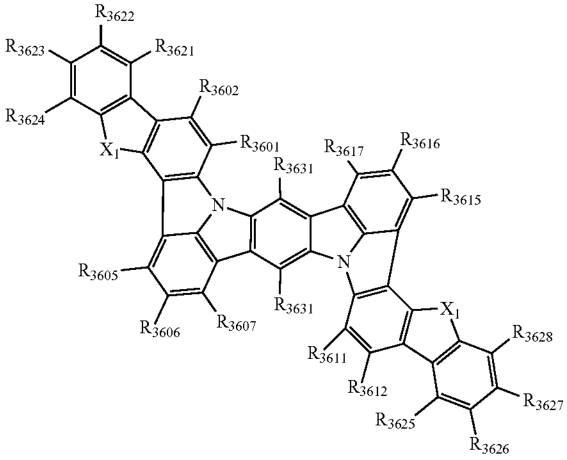

(36-2)

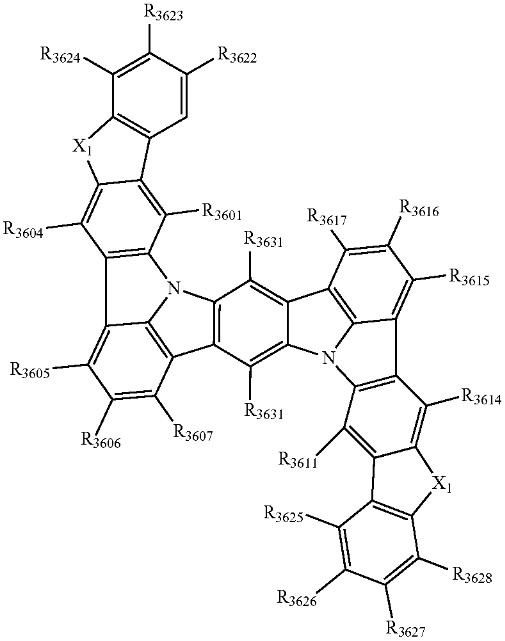

-continued (36-3)

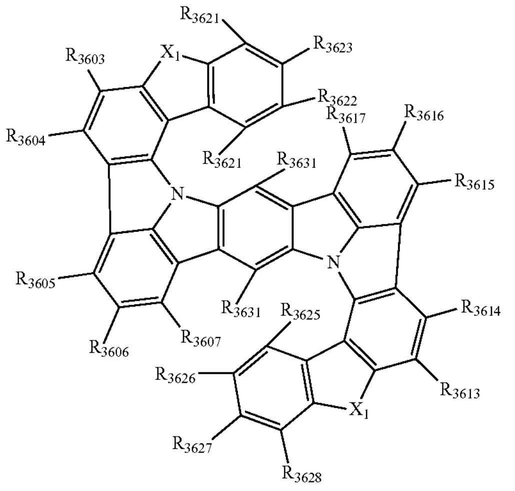

(36-4)

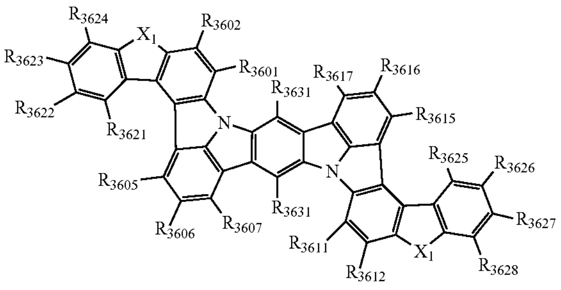

(36-5)

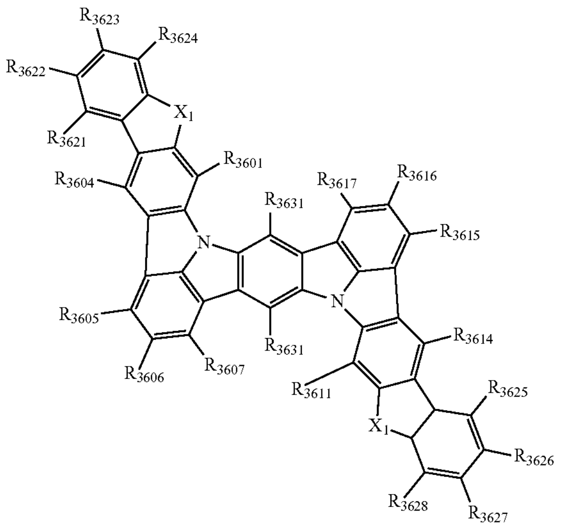

-continued (36-6)

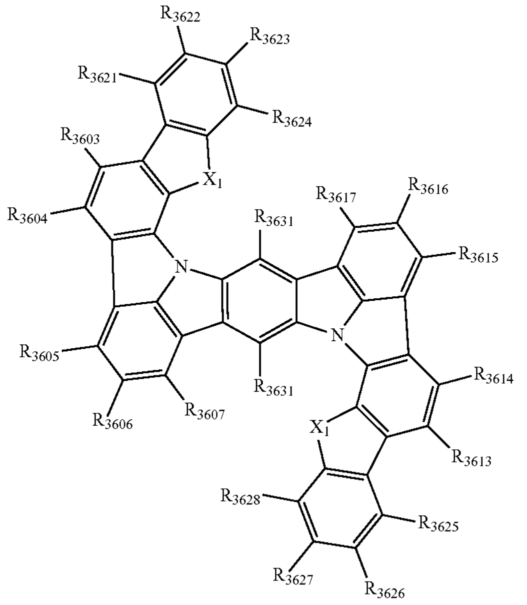

wherein in the formulas (36-1) to (36-6), one or more pairs of two or more adjacent groups of $R_{3605}$ to $R_{3607}$, $R_{3615}$ to $R_{3617}$ and $R_{3631}$ bond with each other to form a substituted or unsubstituted, saturated or unsaturated ring or do not form the ring;

one or more pairs of two or more adjacent groups of $R_{3601}$ to $R_{3604}$, $R_{3611}$ to $R_{3614}$ and $R_{3621}$ to $R_{3628}$ bond with each other to form a substituted or unsubstituted, saturated or unsaturated ring or do not form the ring;

$R_{3601}$ to $R_{3607}$, $R_{3611}$ to $R_{3617}$, $R_{3621}$ to $R_{3628}$ and $R_{3631}$, that do not form the ring are independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a substituted or unsubstituted aryl group having 6 to 50 ring carbon atoms, or a substituted or unsubstituted monovalent heterocyclic group having 5 to 50 ring atoms;

$R_{901}$ to $R_{907}$ are independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

when two or more of $R_{901}$ to $R_{907}$ exist, two or more of $R_{901}$ to $R_{907}$ may be the same with or different from each other;

$X_1$ is selected from O, S and $N(R_{3641})$, and two $X_1$s may be the same with or different from each other;

$R_{6641}$ and one or more groups selected from $R_{3601}$ to $R_{3604}$, $R_{3611}$ to $R_{3614}$, $R_{3624}$ and $R_{3628}$ bond with each other to form a substituted or unsubstituted, saturated or unsaturated ring or do not form the ring; and $R_{3641}$ that do not form the ring is a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

In one embodiment, the compound represented by the formula (31) is a compound represented by the formula (36-1) or (36-2), In one embodiment, the compound represented by the formula (31) is a compound represented by the formula (36-1).

In one embodiment, in the compound represented by the formulas (36-1) to (36-6), two $R_{3631}$s are phenyl groups.

In one embodiment, in the compound represented by the formulas (36-1) to (36-6), $X_1$ is $N(R_{3641})$.

In one embodiment, in the compound represented by the formulas (36-1) to (36-6), $R_{3641}$ is a substituted or unsubstituted aryl group having 6 to 50 ring carbon atoms.

In one embodiment, the compound represented by the formula (31) is a compound represented by the following formula (36-1-1):

(36-1-1)

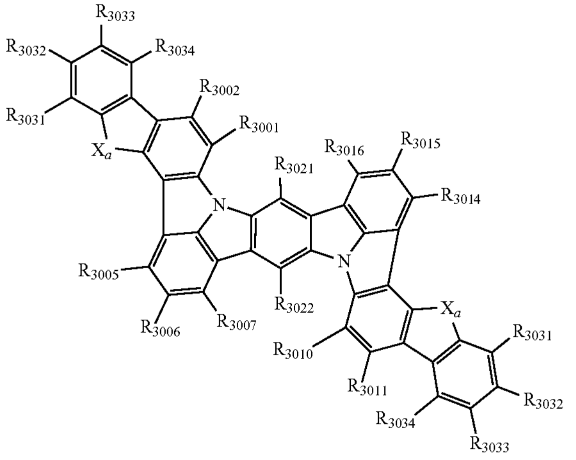

wherein in the formula (36-1-1), one or more pairs of two or more adjacent groups of $R_{3001}$, $R_{3002}$, $R_{3005}$ to $R_{3007}$, $R_{3010}$, $R_{3011}$, $R_{3014}$ to $R_{3016}$ and $R_{3031}$ to $R_{3034}$ bond with each other to form a substituted or unsubstituted, saturated or unsaturated ring or do not form the ring;

$X_a$s are independently selected from O, S and $N(R_{3035})$;

$R_{3035}$ and $R_{3031}$ bond with each other to form a substituted or unsubstituted, saturated or unsaturated ring or do not form the ring; and $R_{3001}$, $R_{3002}$, $R_{3005}$ to $R_{3007}$, $R_{3010}$, $R_{3011}$, $R_{3014}$ to $R_{3016}$ and $R_{3031}$ to $R_{3035}$ that do not form the ring and $R_{3021}$ and $R_{3022}$ are independently a hydrogen atom, a substituted or unsubstituted aryl group having 6 to 50 ring carbon atoms, or a substituted or unsubstituted monovalent heterocyclic group having 5 to 50 ring atoms.

In one embodiment, a substituent in the case of "substituted or unsubstituted" in the formulas (31) to (35), (34-2), (35-2), (32-11), (34-11), (35-11), (32-12), (34-12), (35-12), (36-1) to (36-6) and (36-1-1) is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

As the compound represented by the formula (31), the following compounds can be given for example. In the following example compounds, Me represents methyl group.

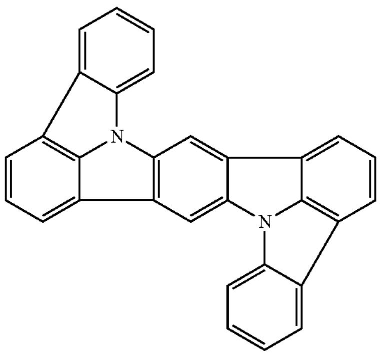
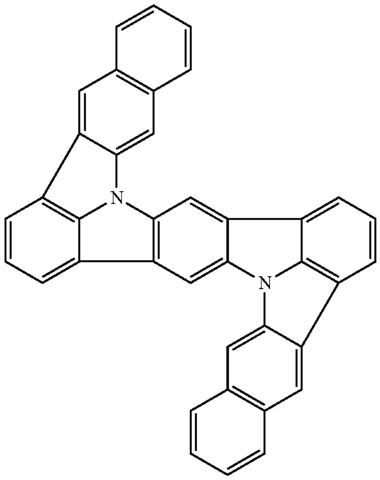
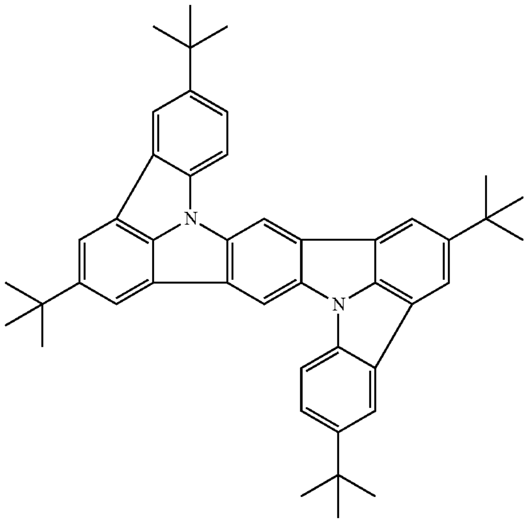
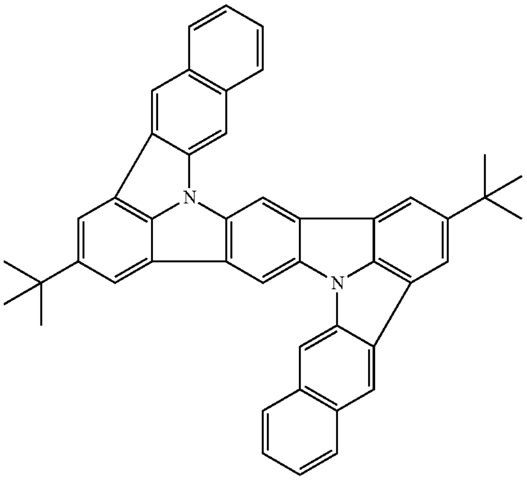
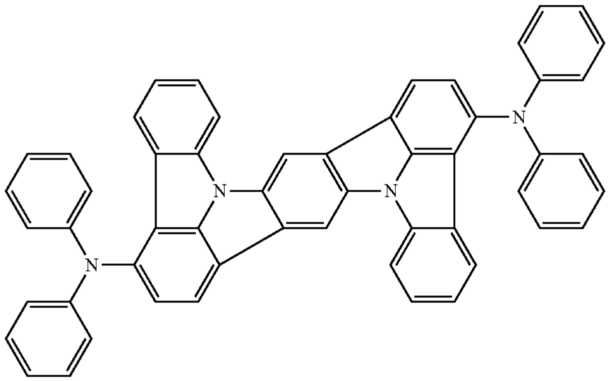

-continued
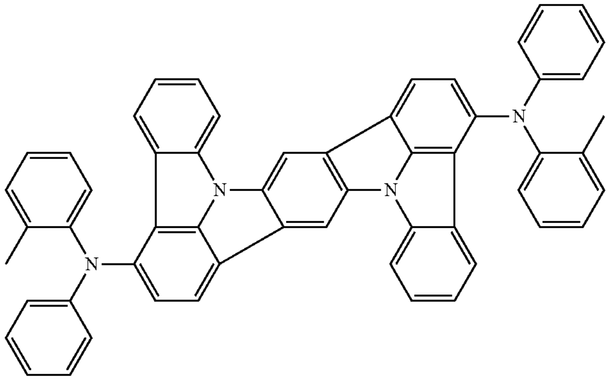
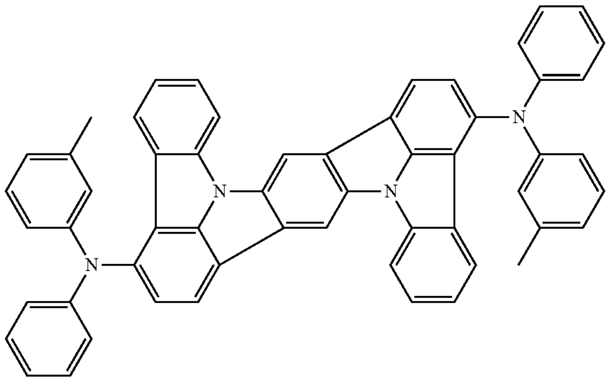
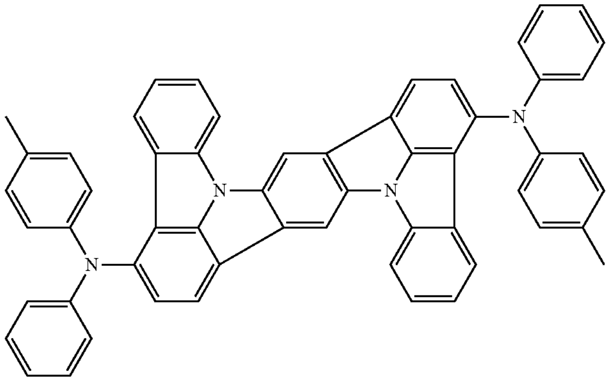
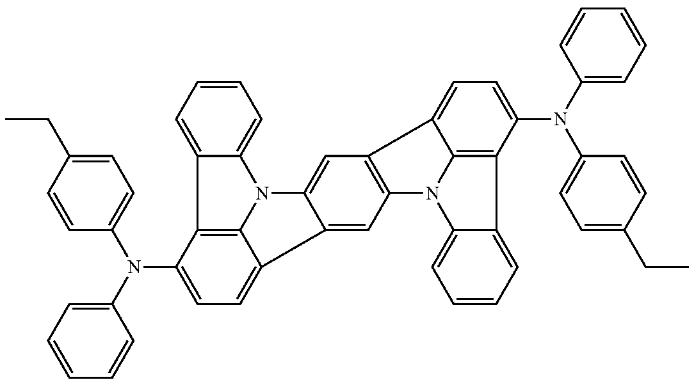

-continued
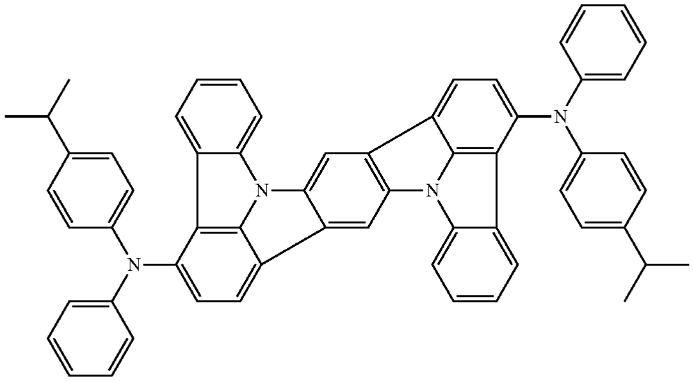
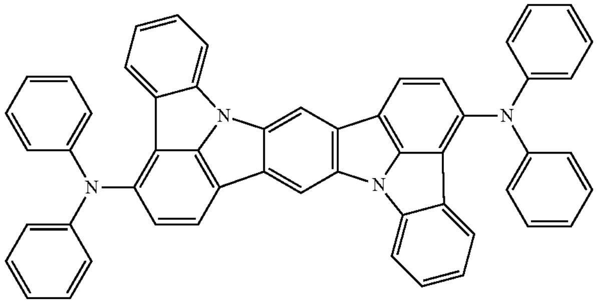
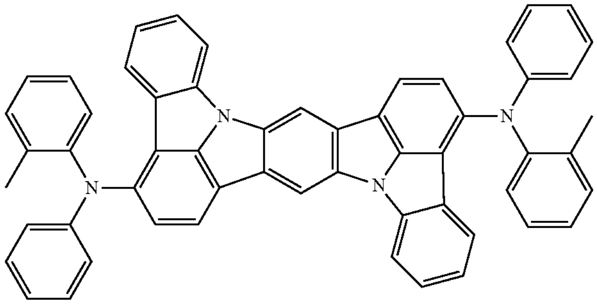
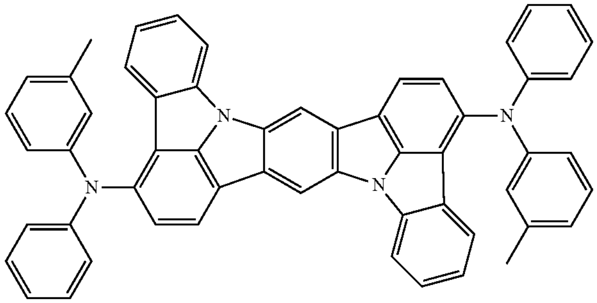
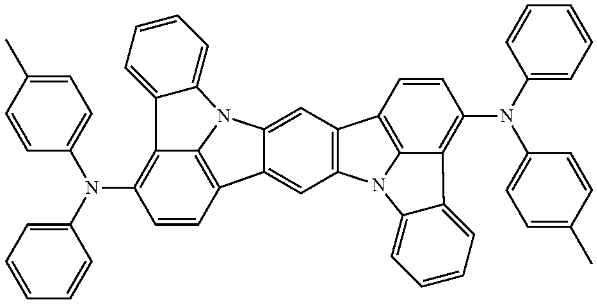

-continued
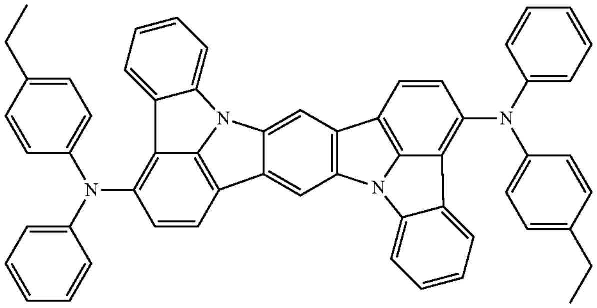
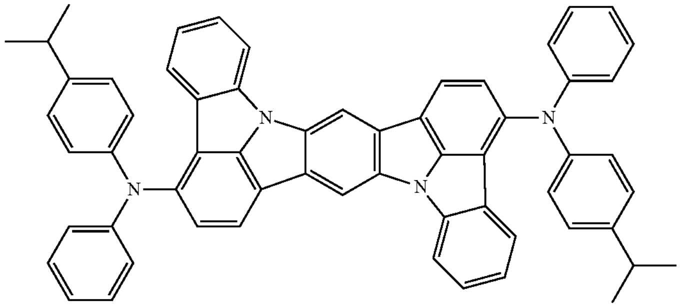
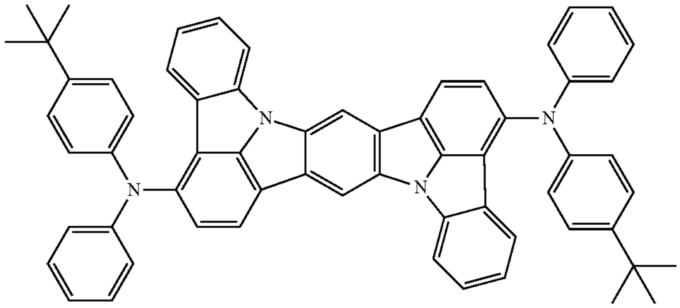
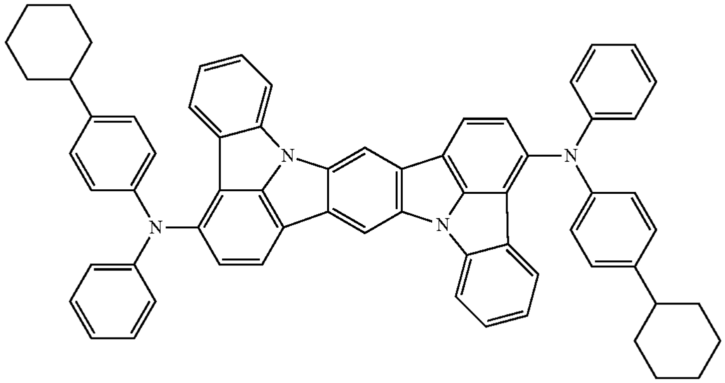
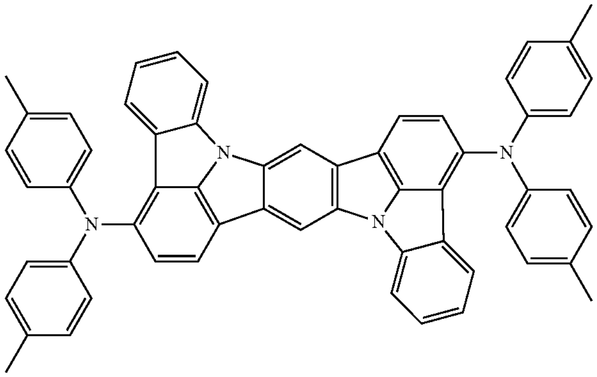

-continued
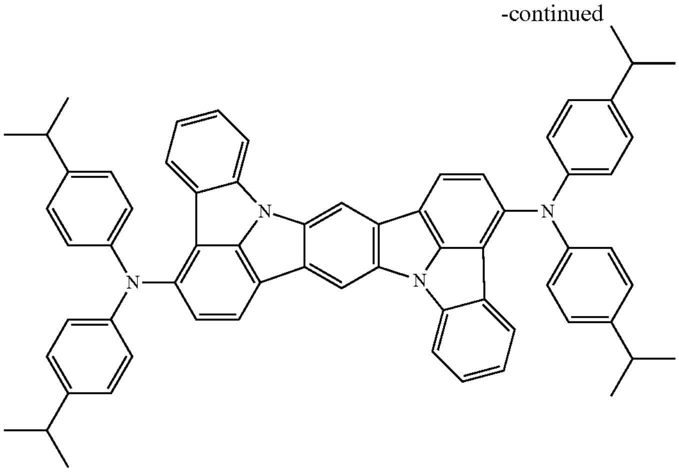
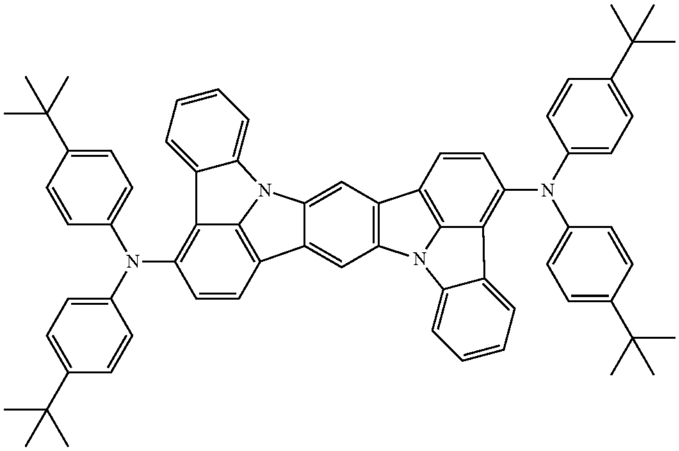
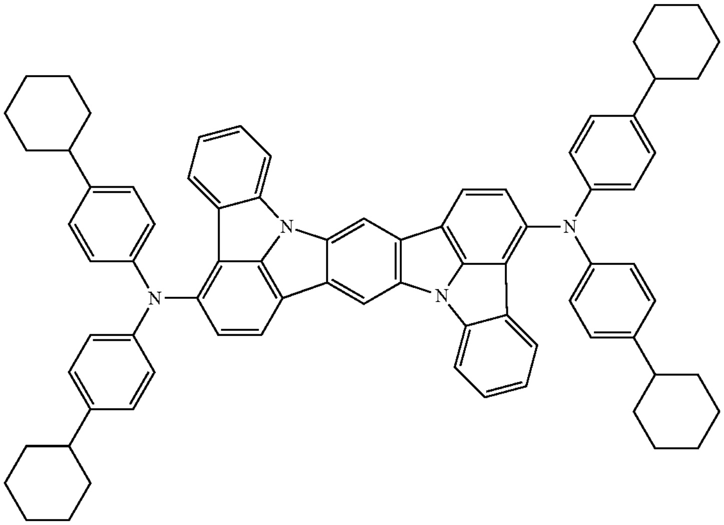
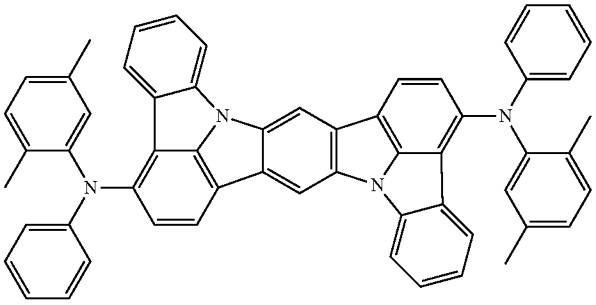

-continued
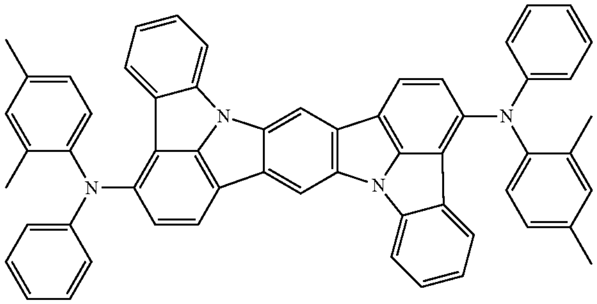
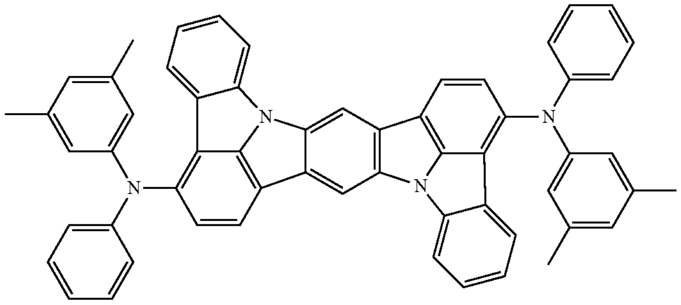
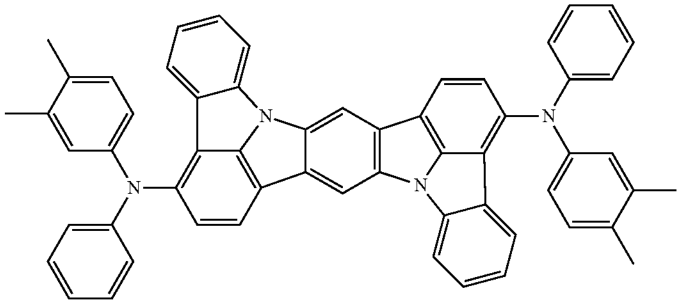
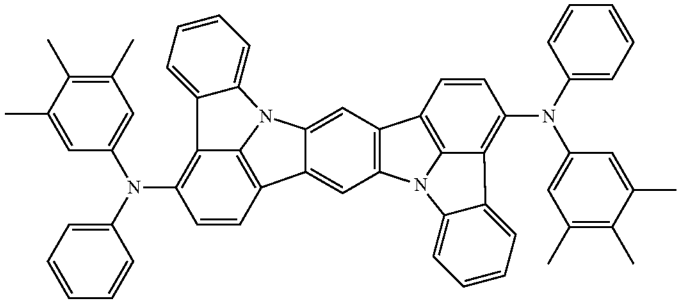
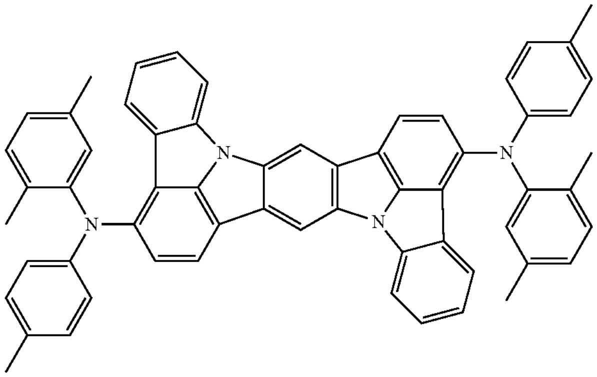

-continued
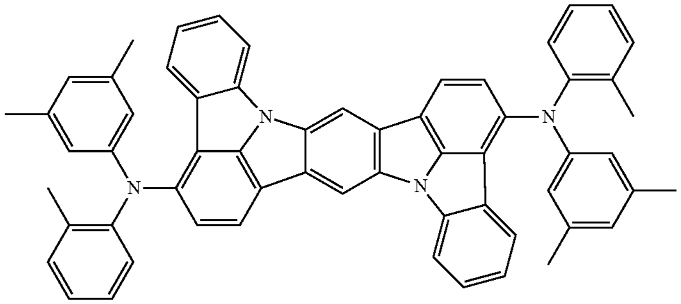
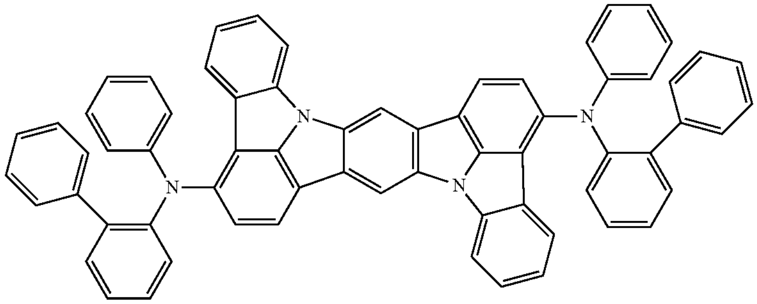
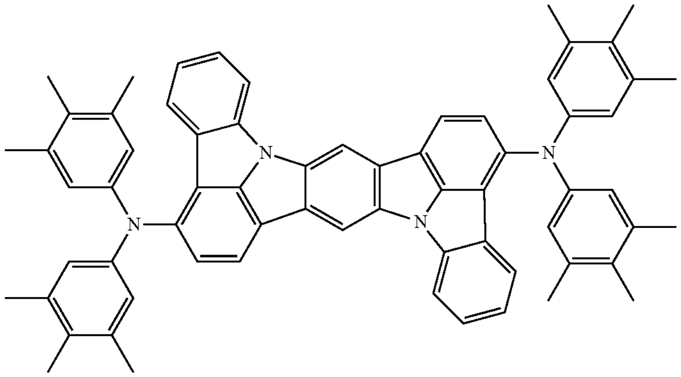
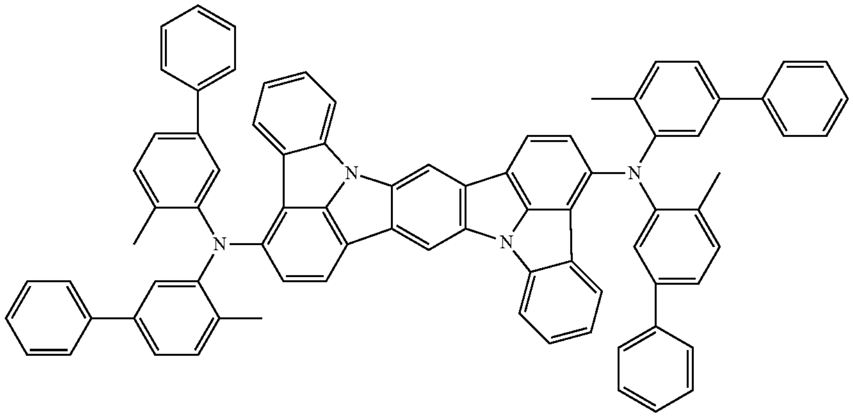

-continued
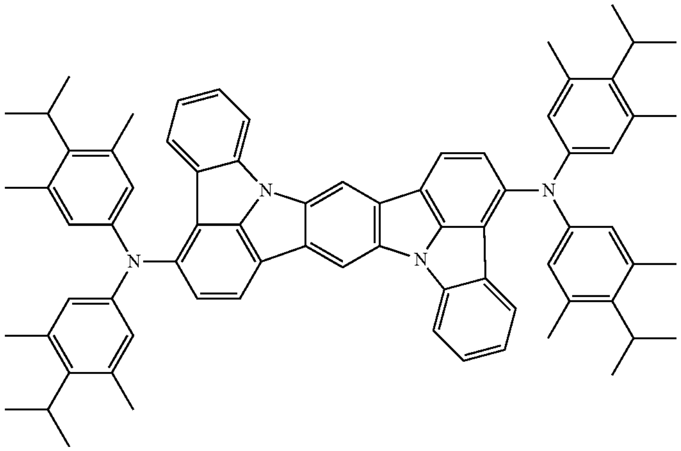
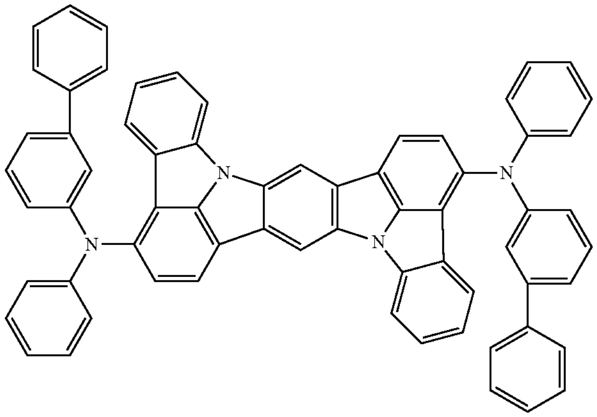
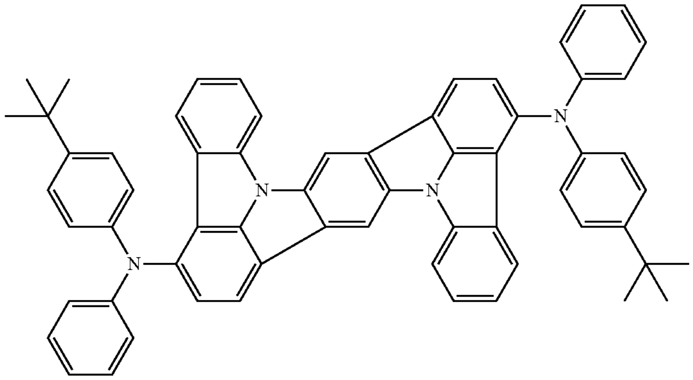
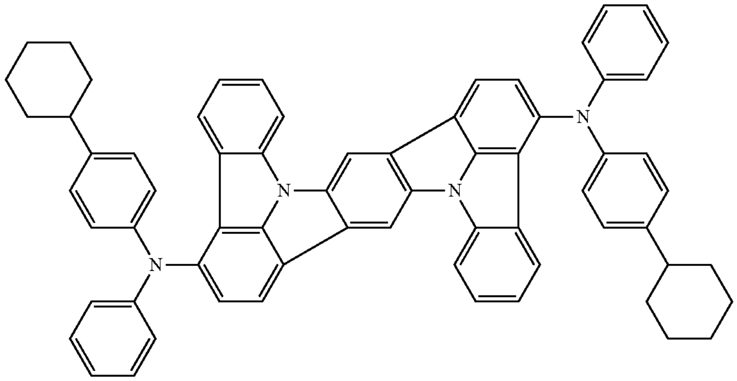

-continued
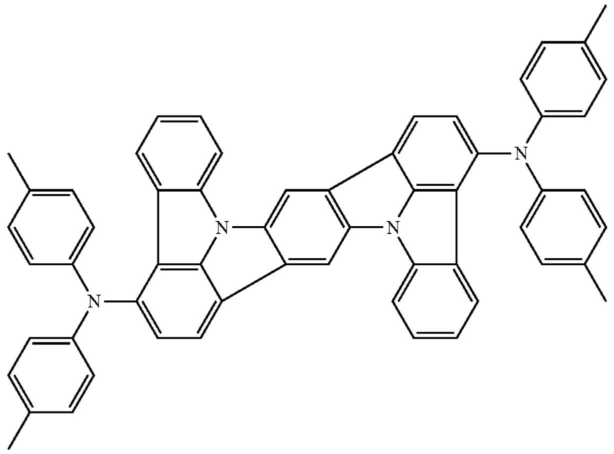
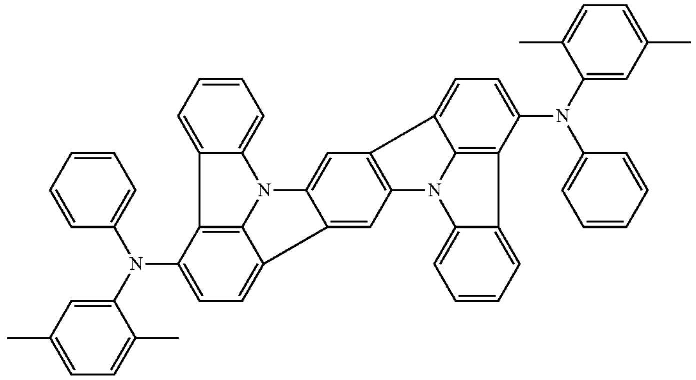
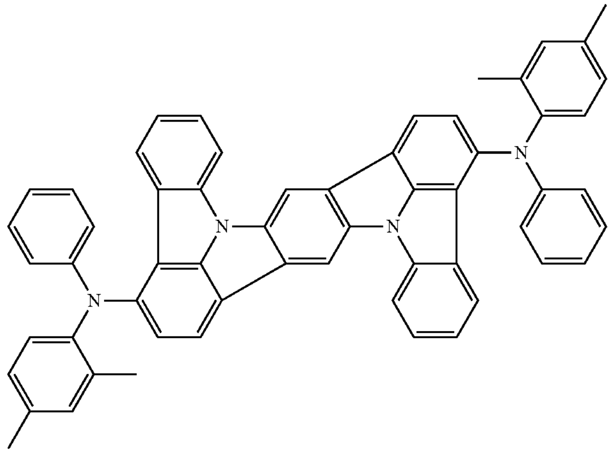

-continued
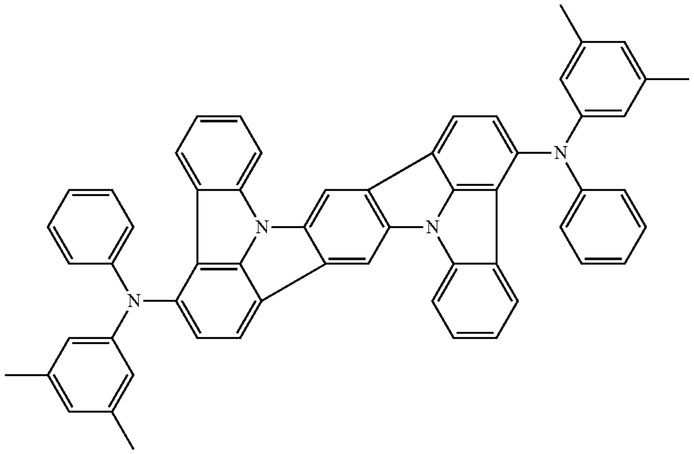
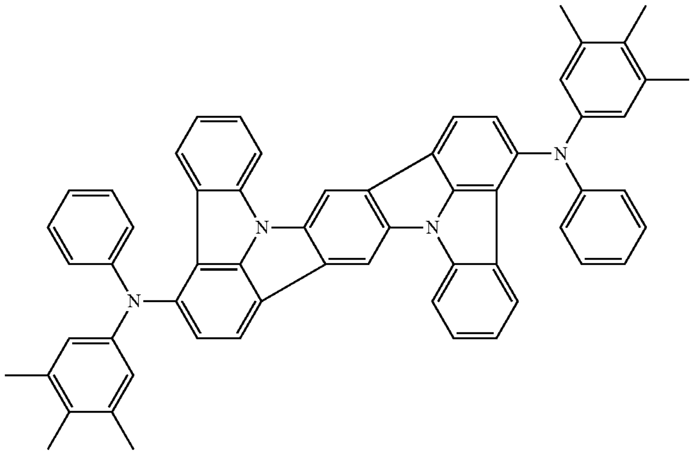
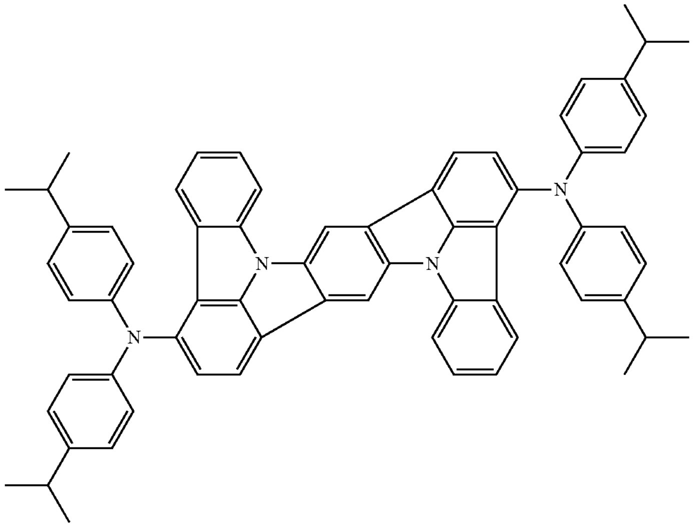

-continued
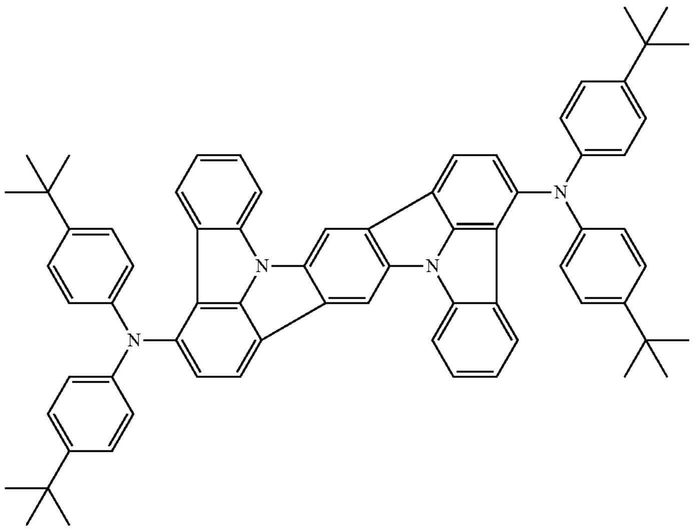
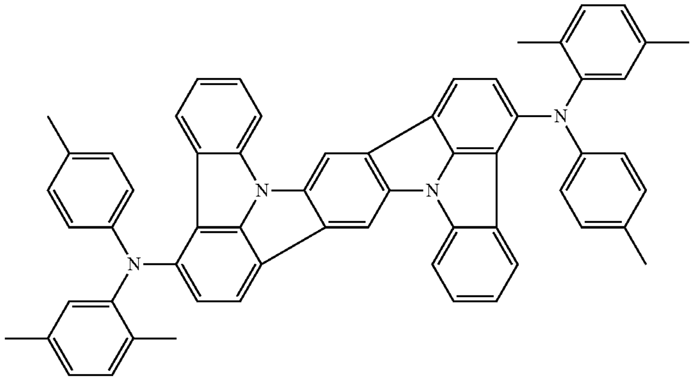
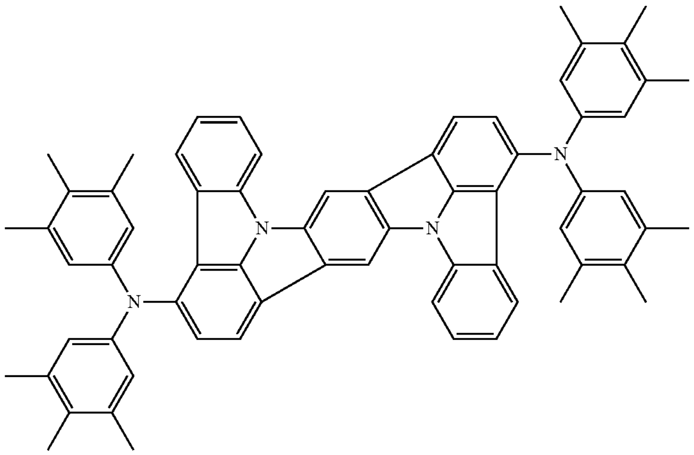
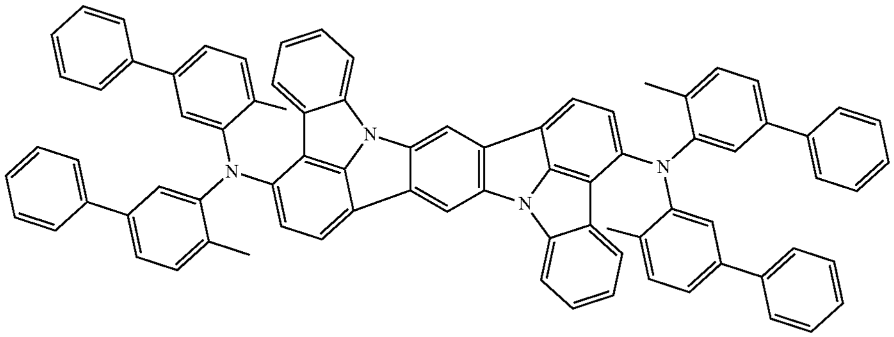

-continued
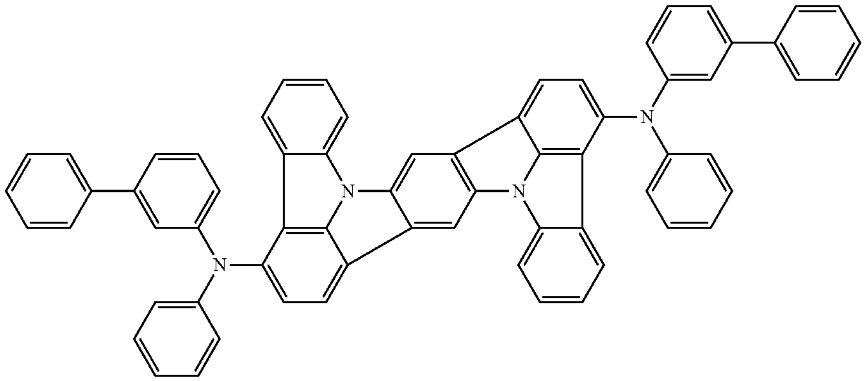
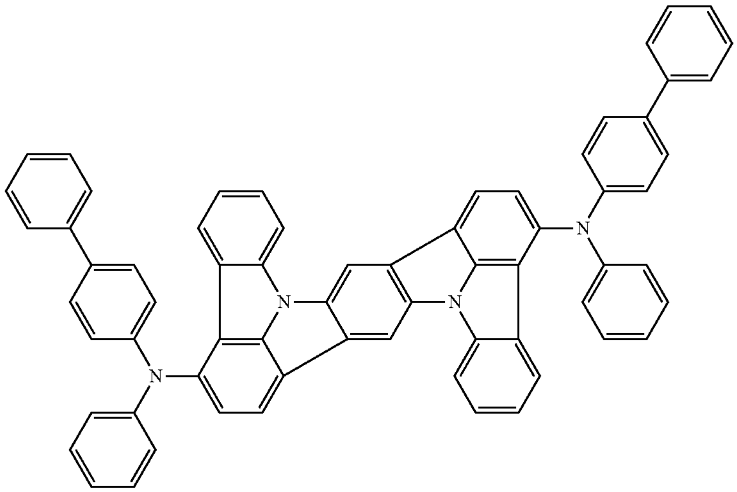
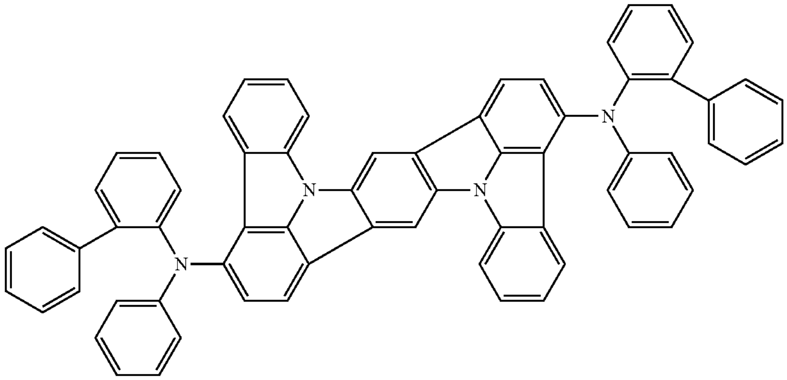
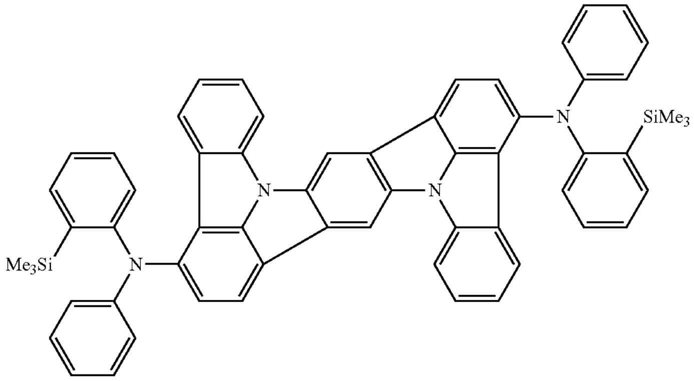

-continued
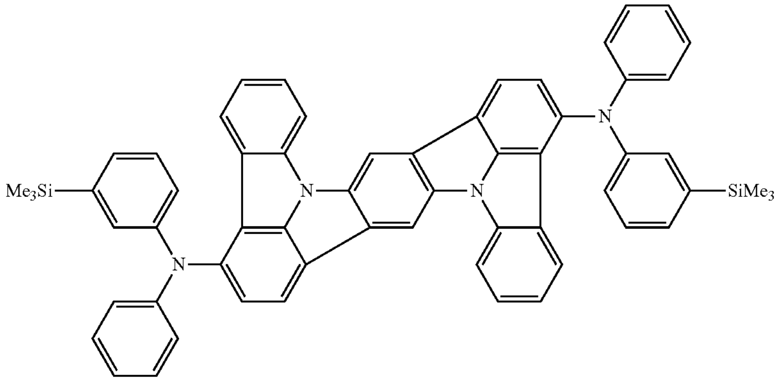
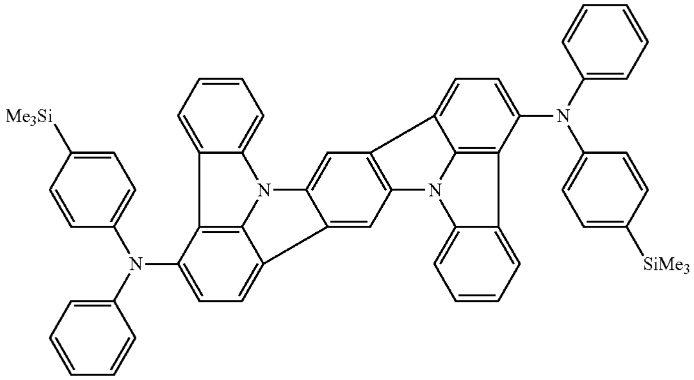
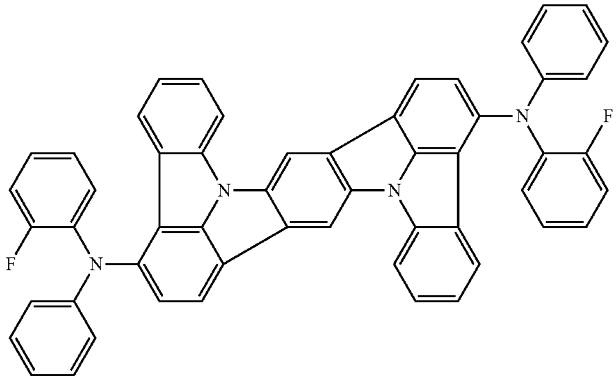
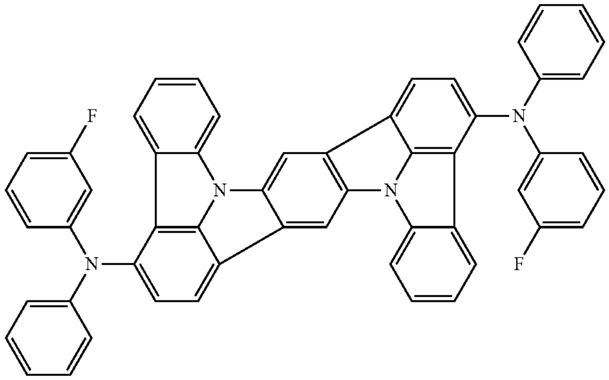

-continued
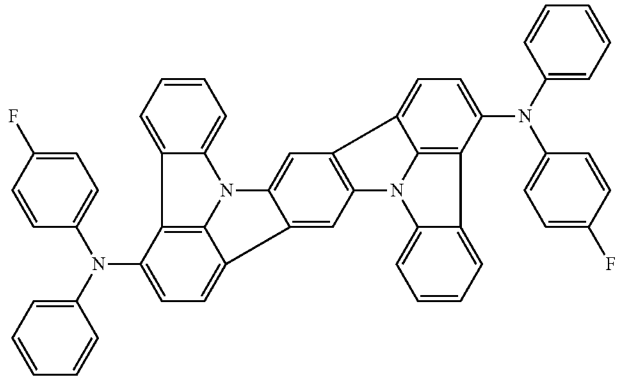
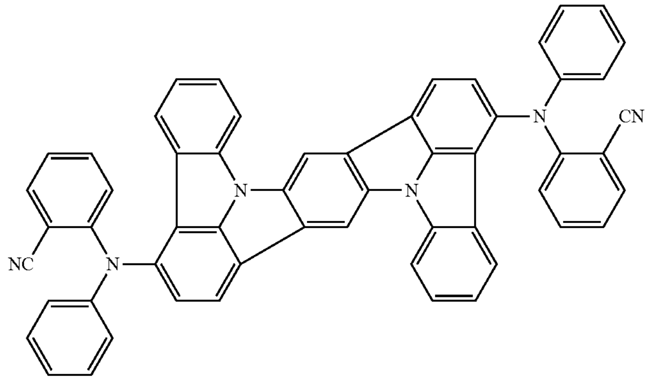
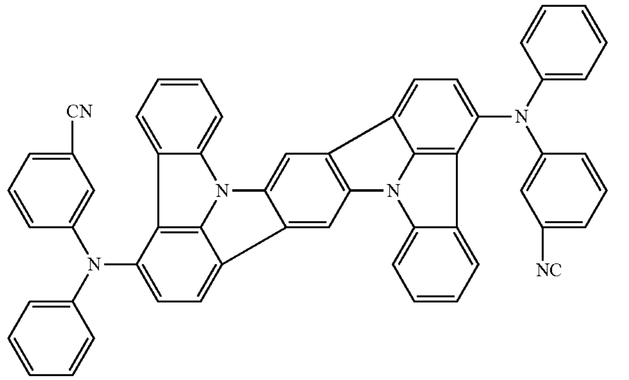
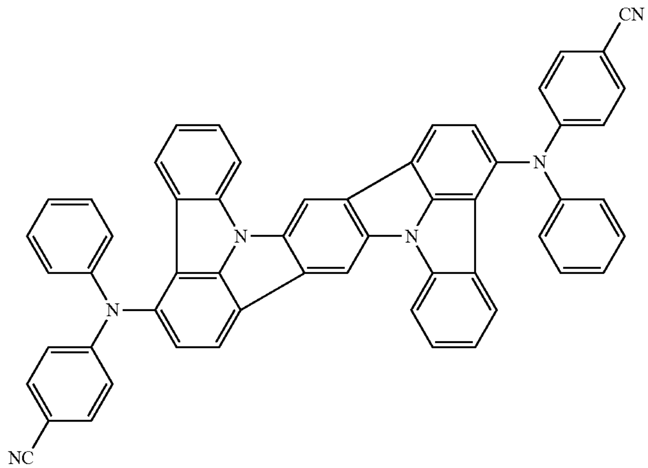

-continued
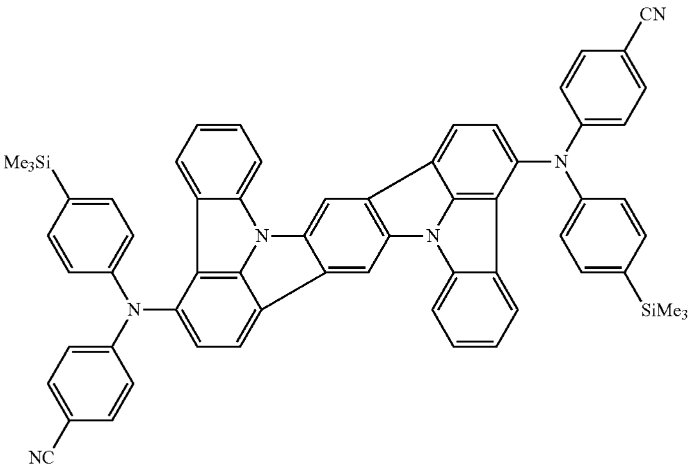
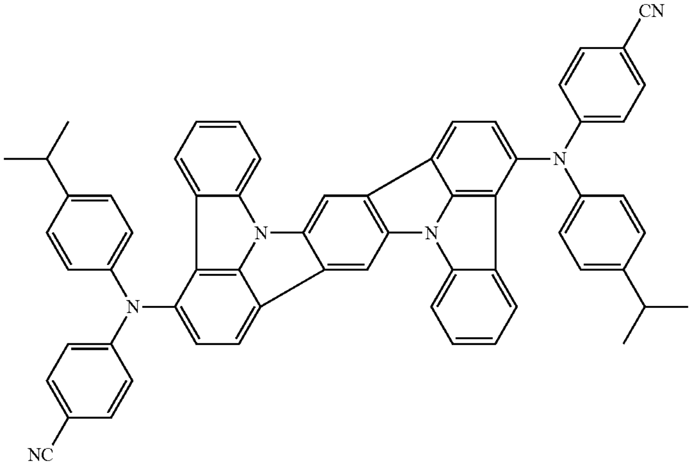
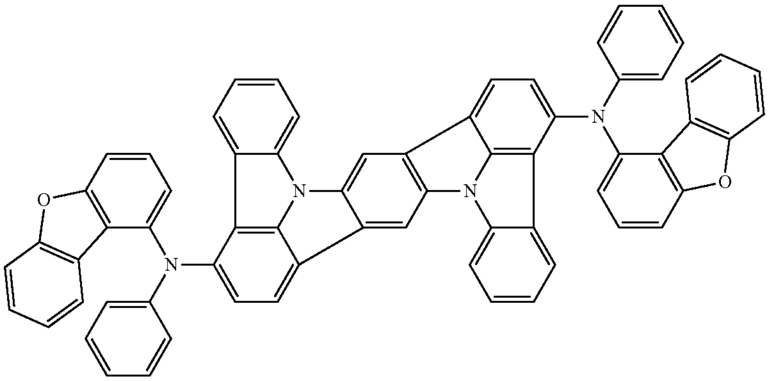
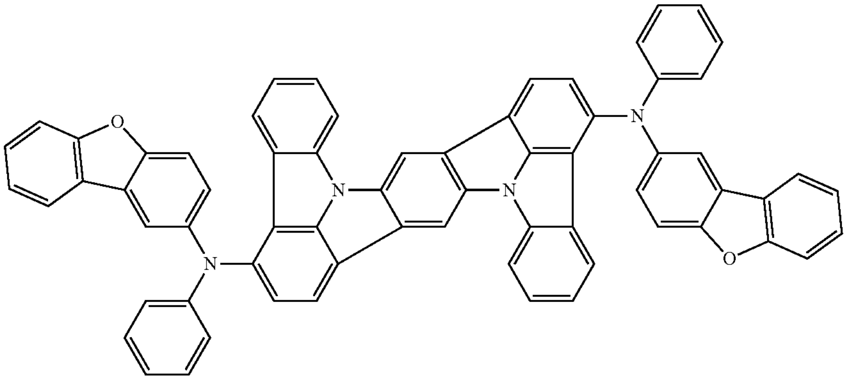

-continued
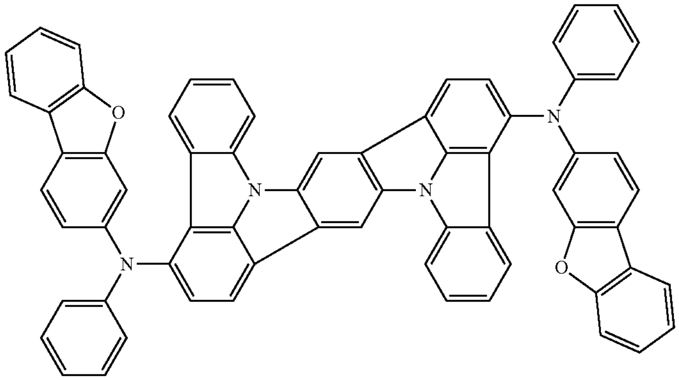
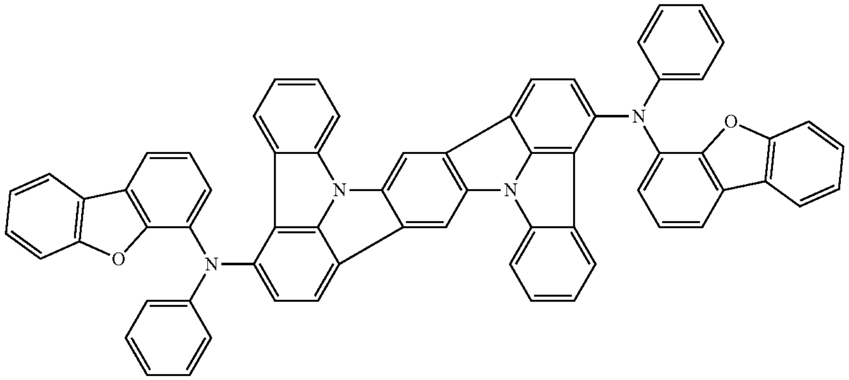
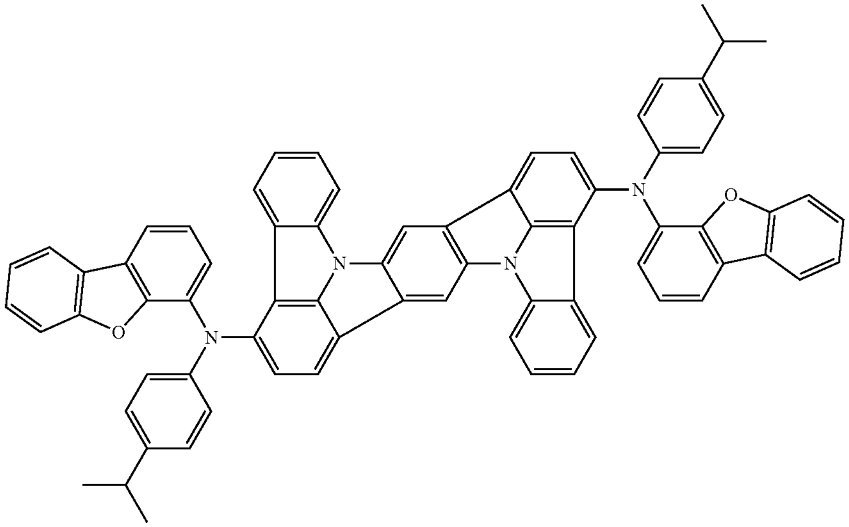
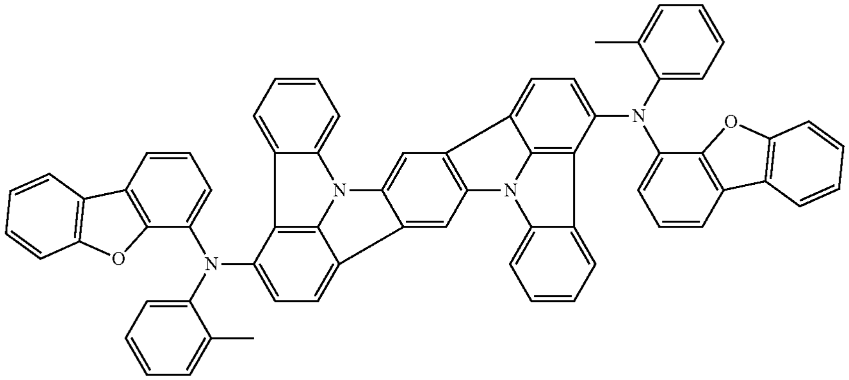

-continued
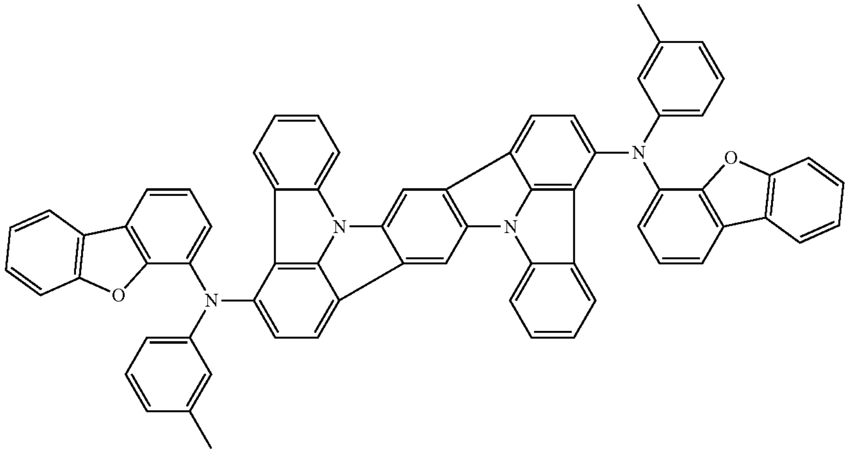
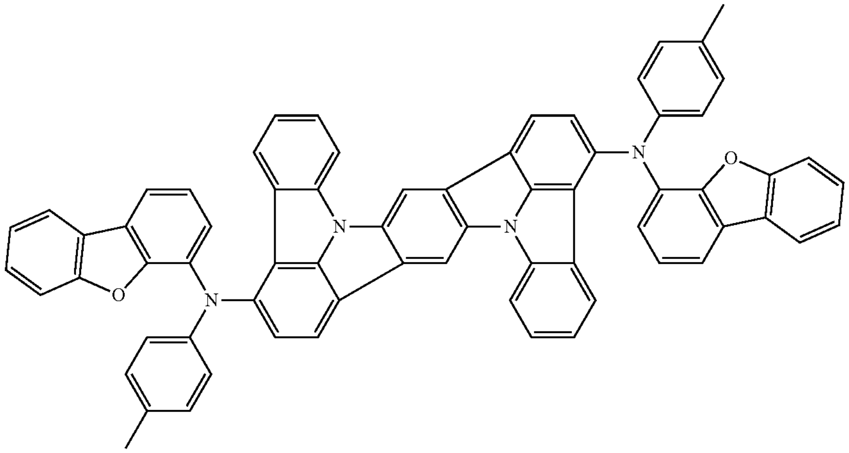
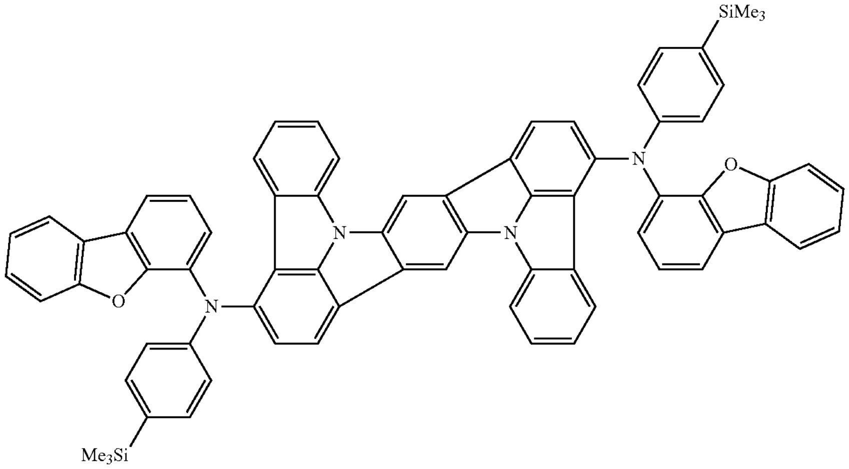

-continued
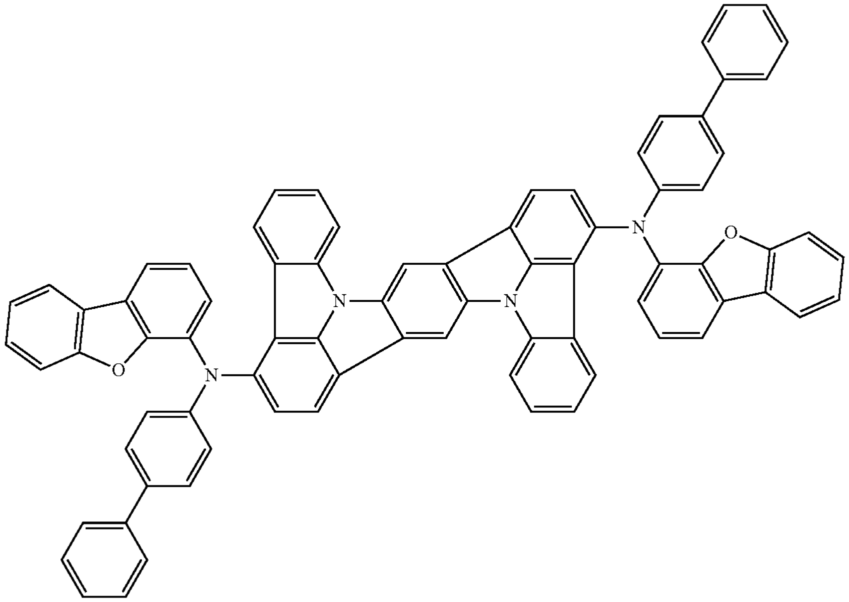
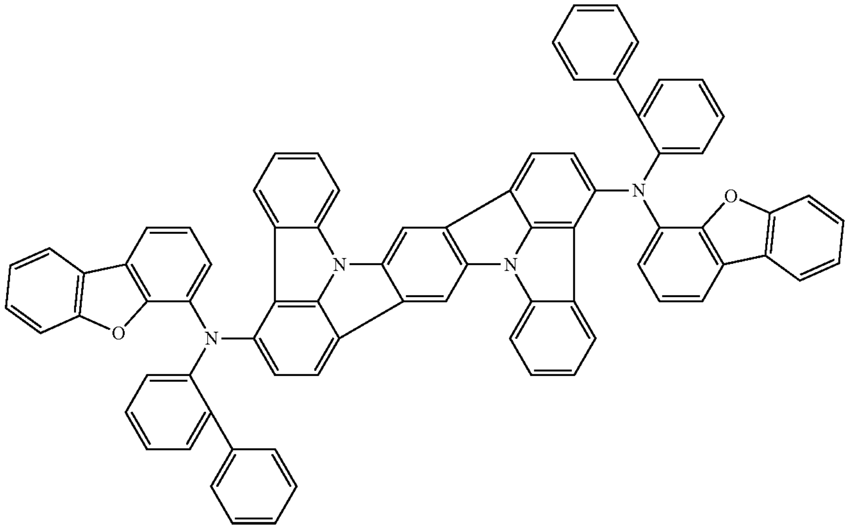
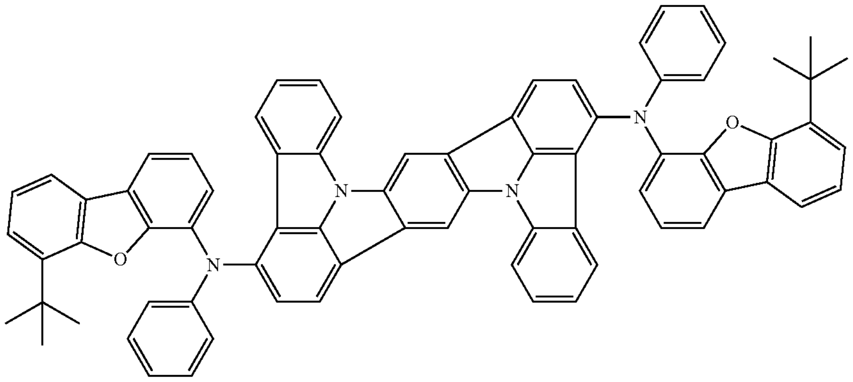

-continued
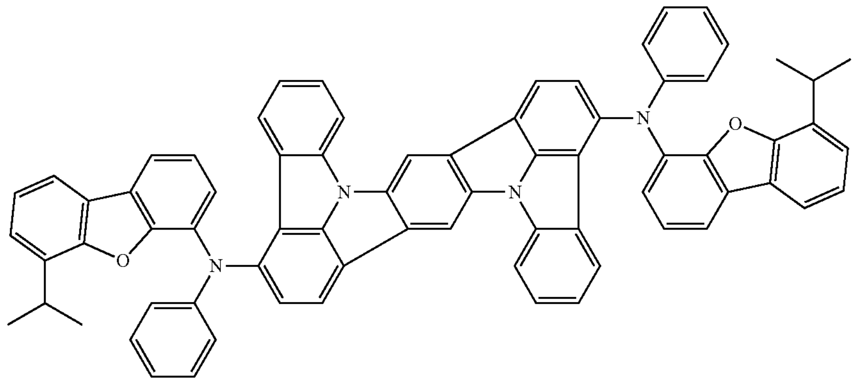
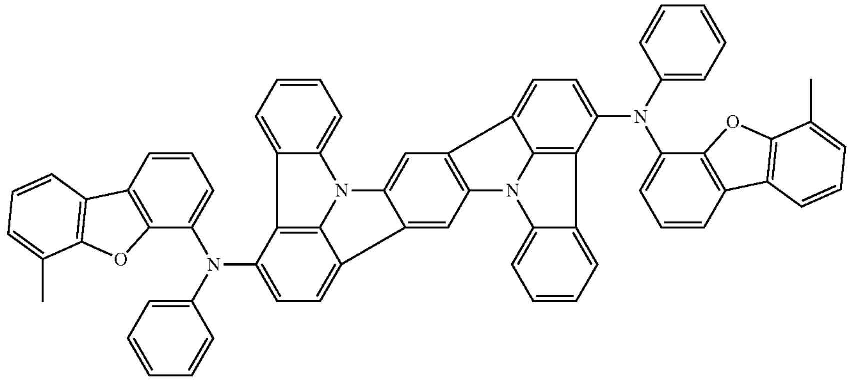
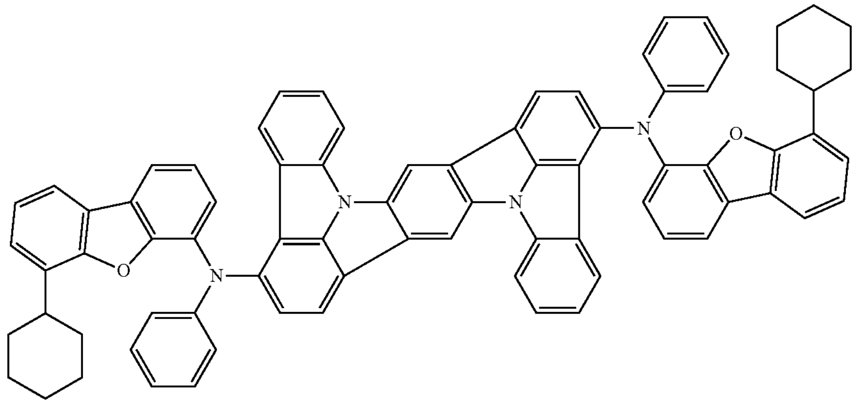
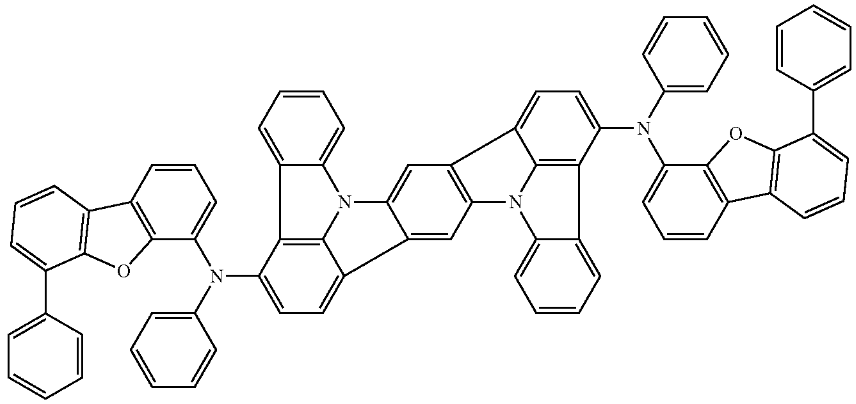

-continued
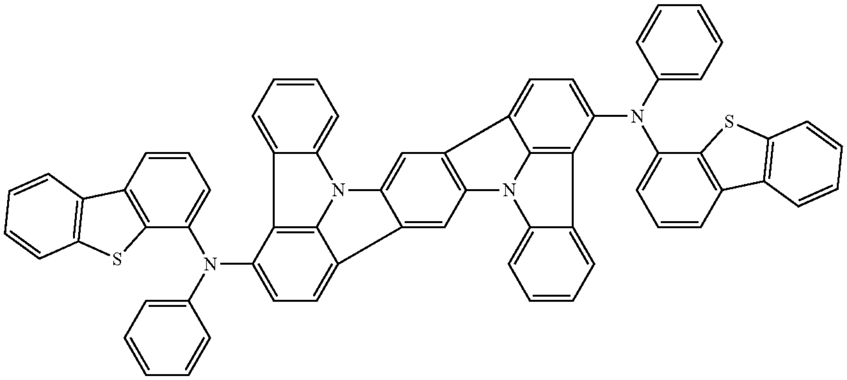
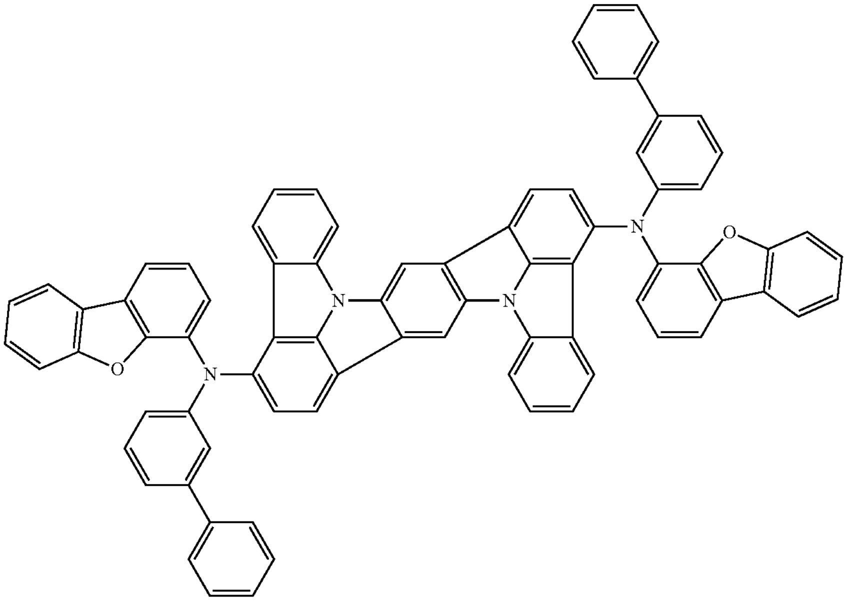
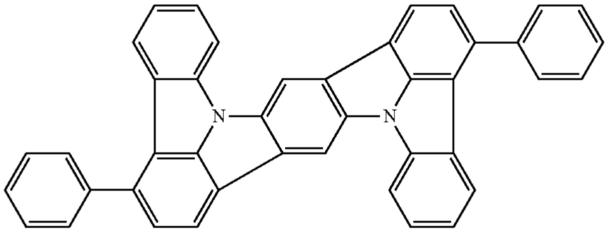
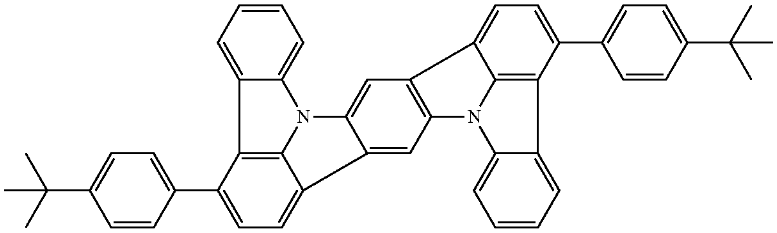
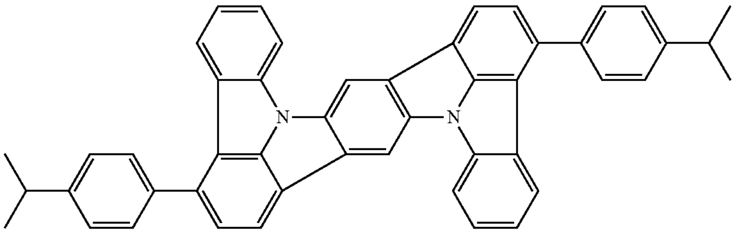

-continued
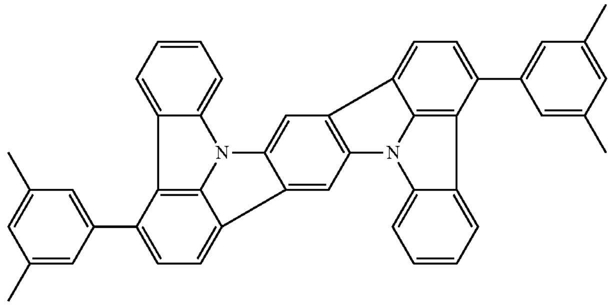
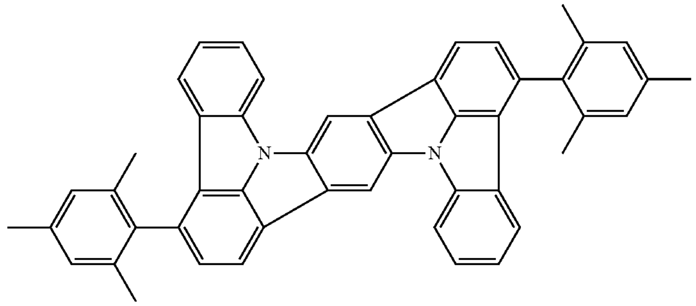
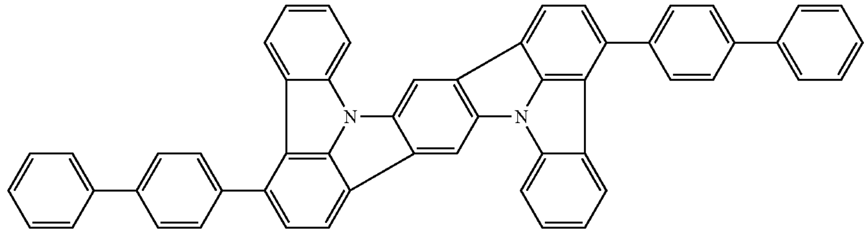
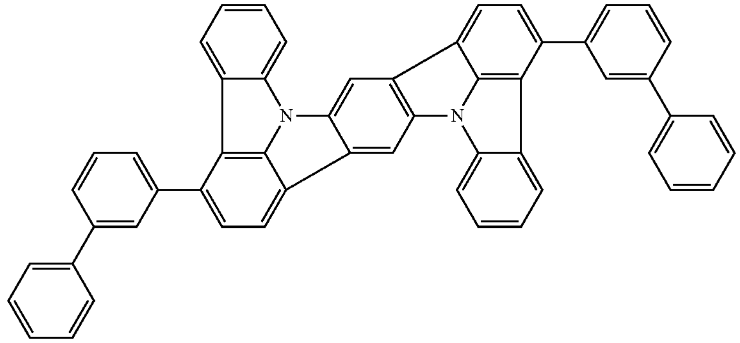
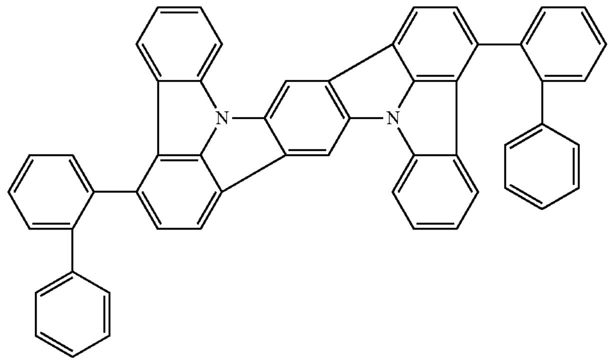

-continued
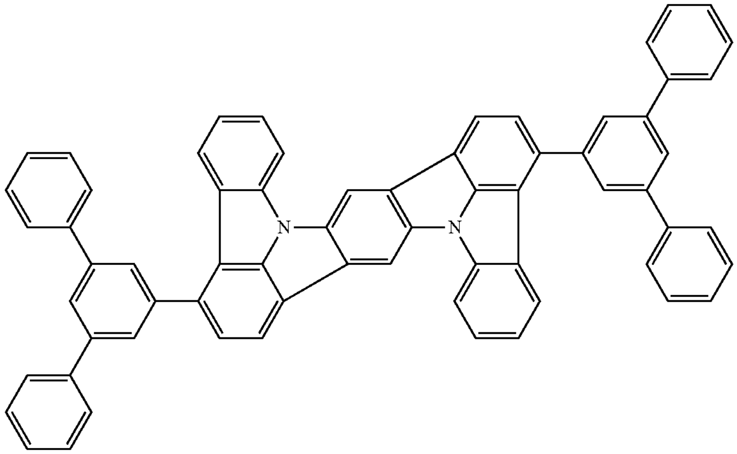
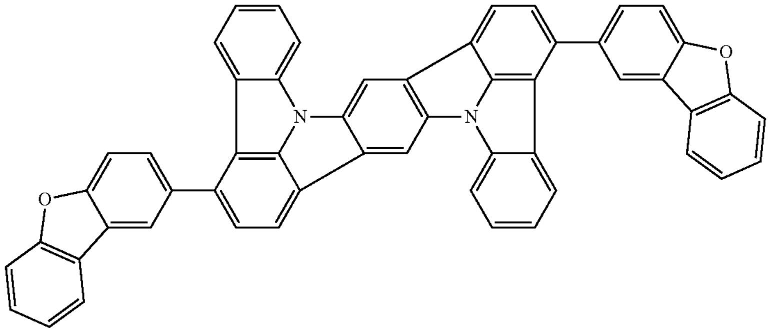
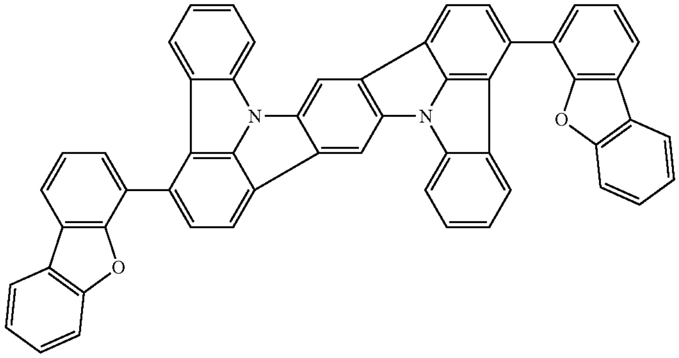
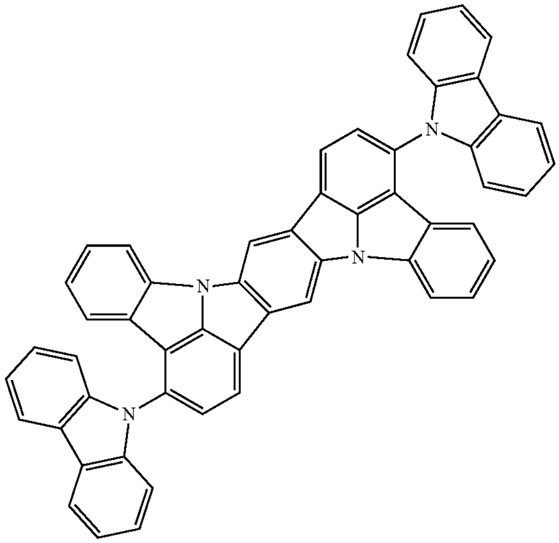

-continued
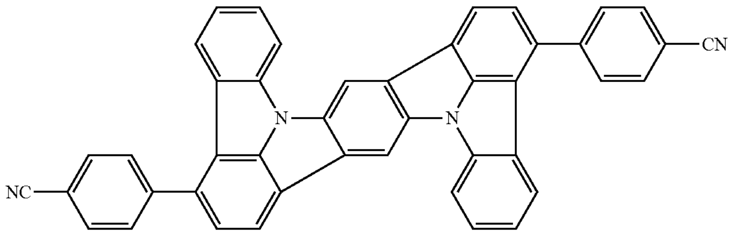
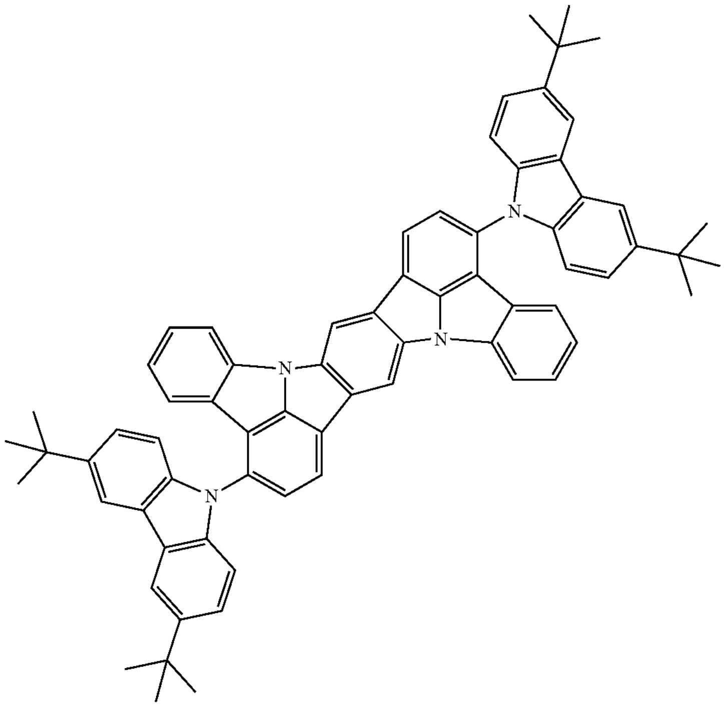
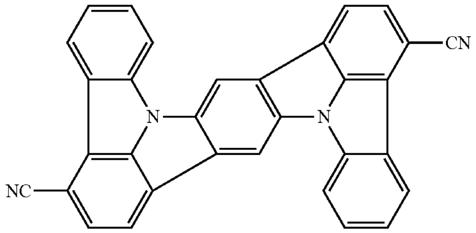
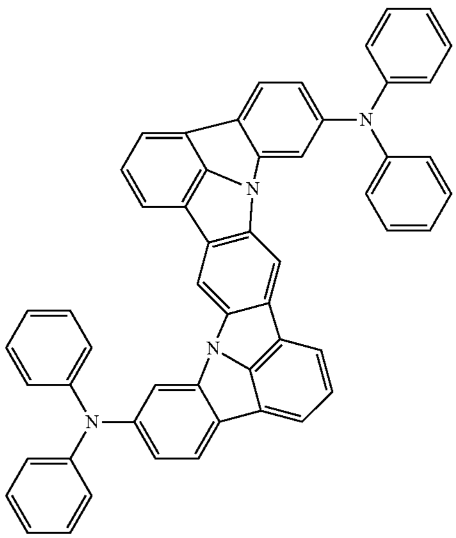

-continued
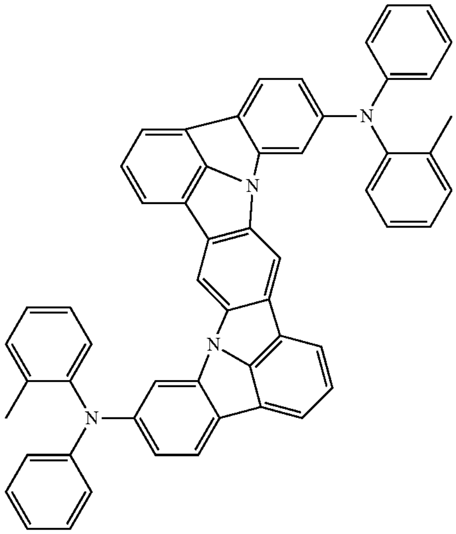
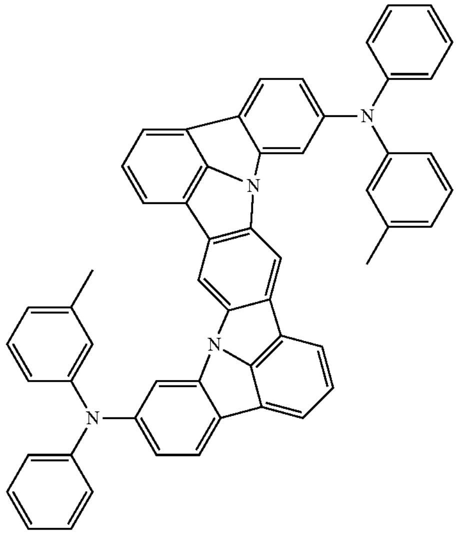
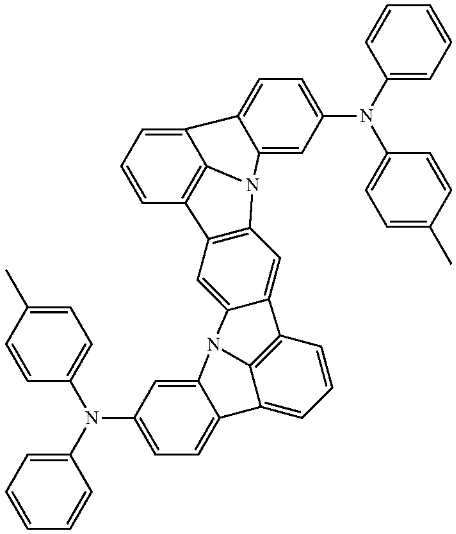
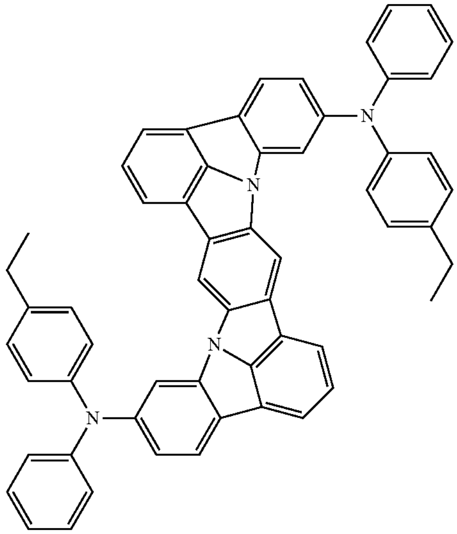
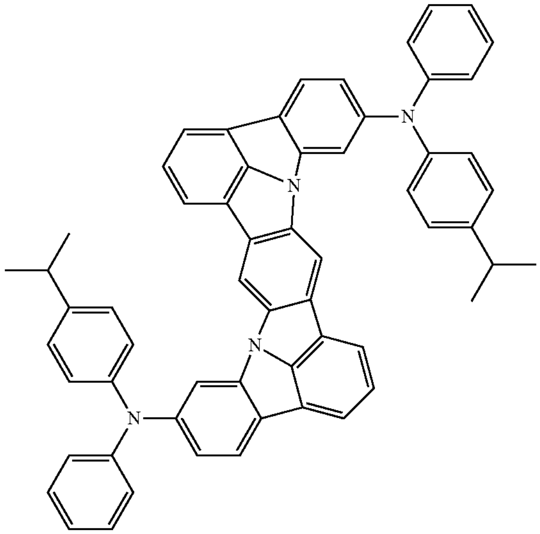
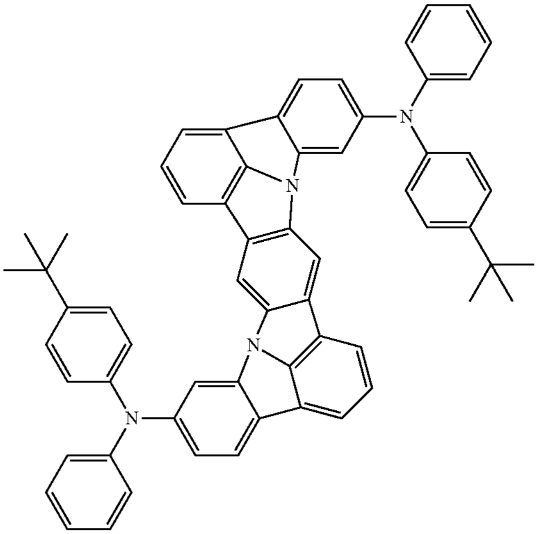

-continued
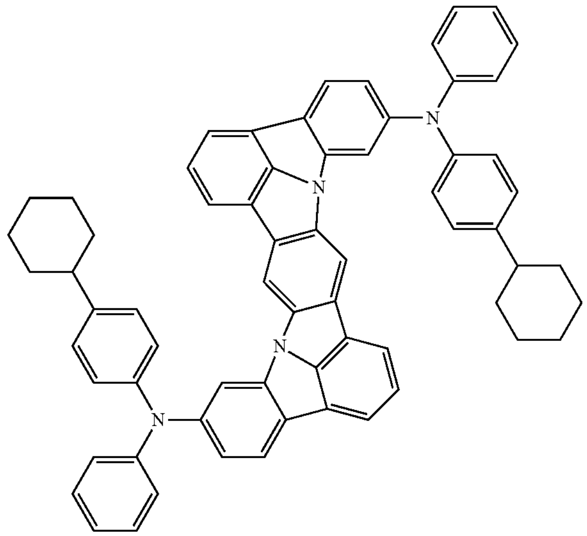
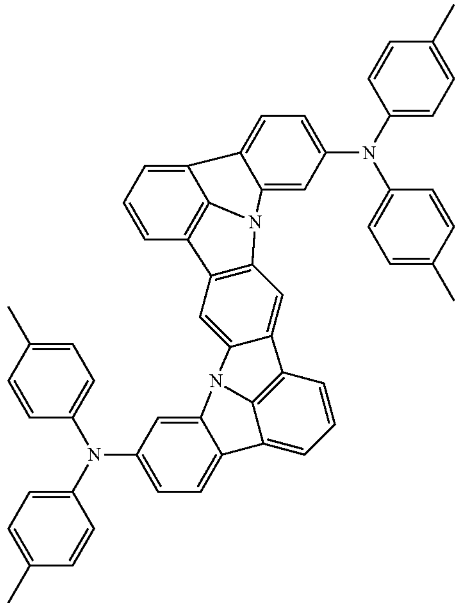
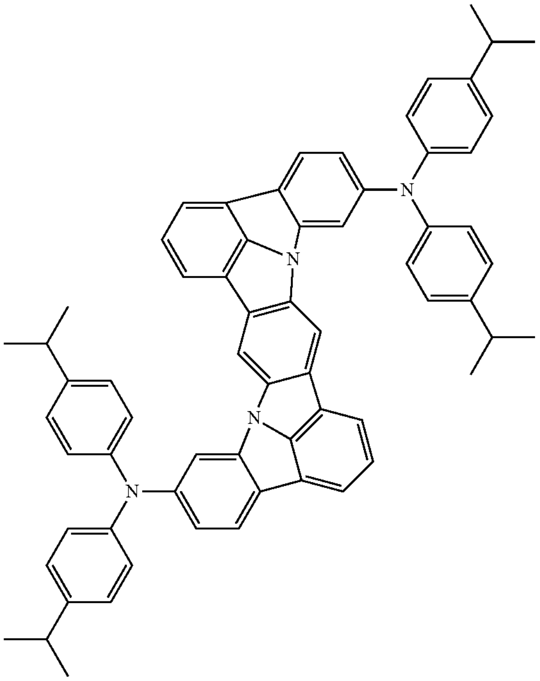

-continued
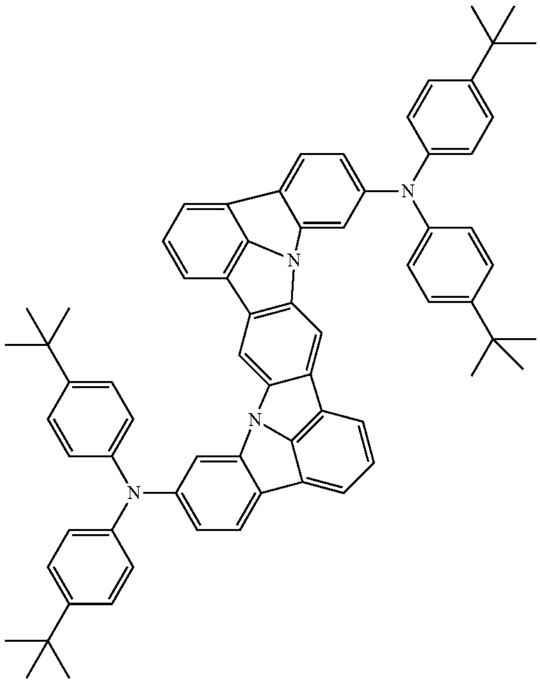
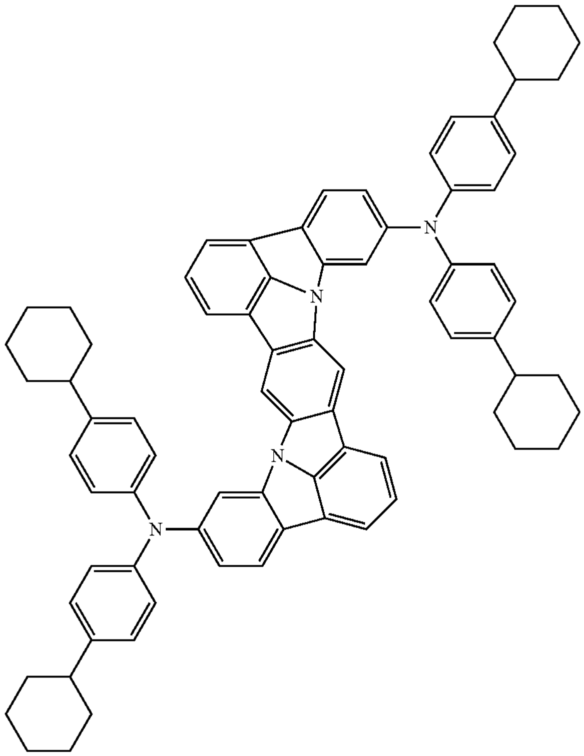

-continued
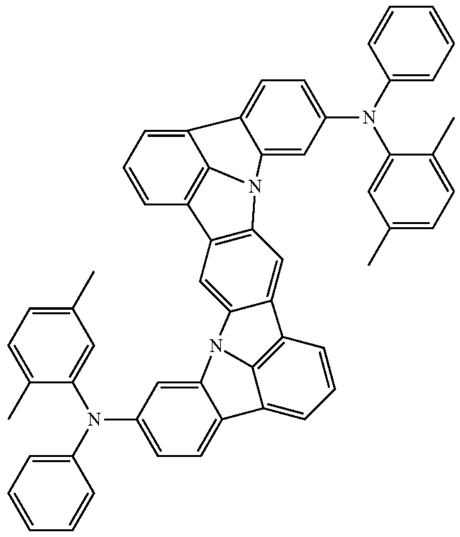
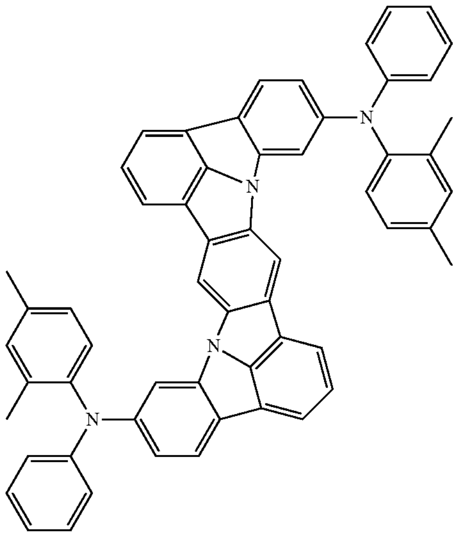
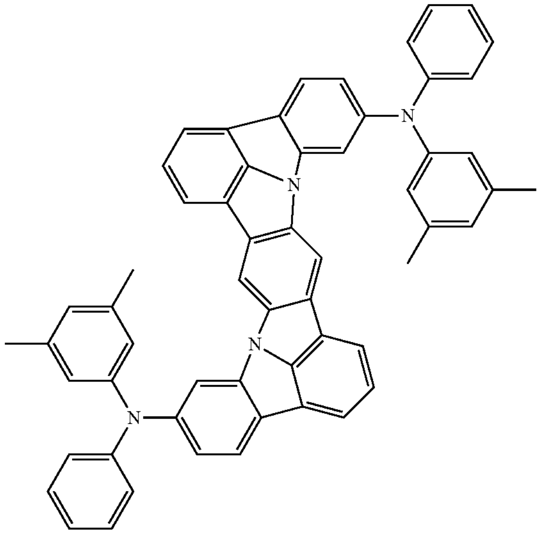
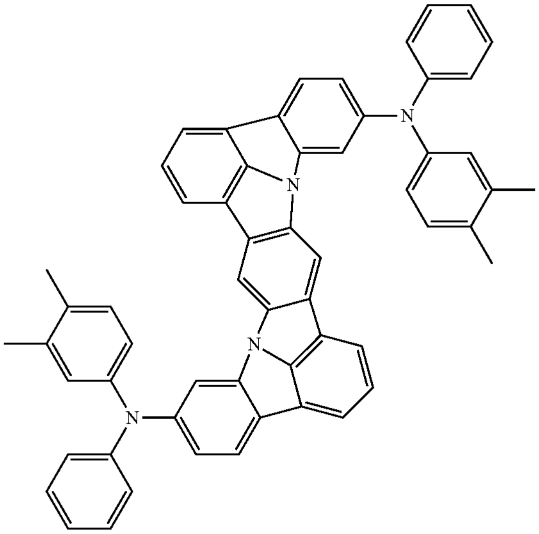
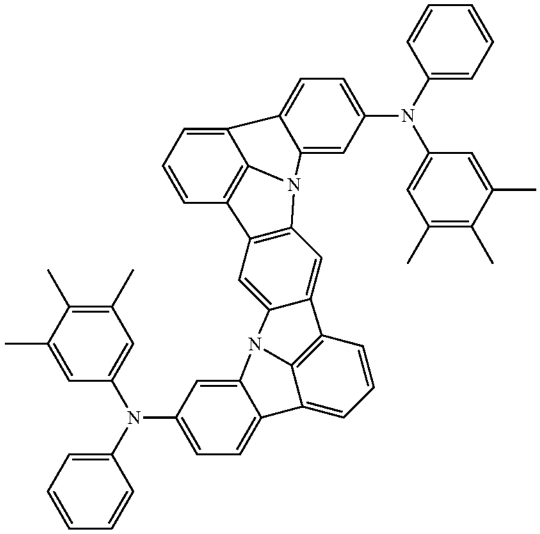
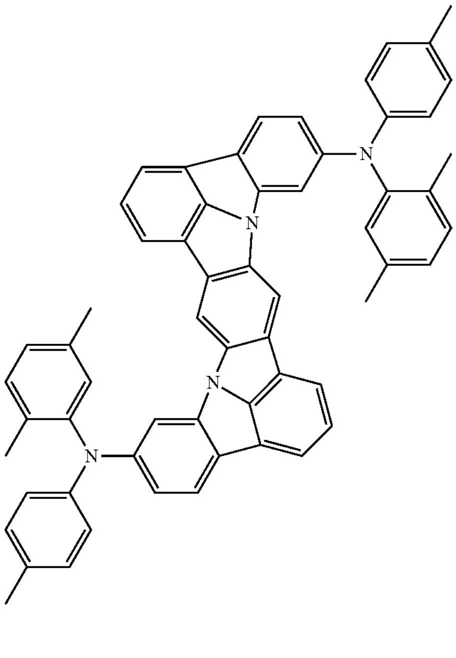

-continued
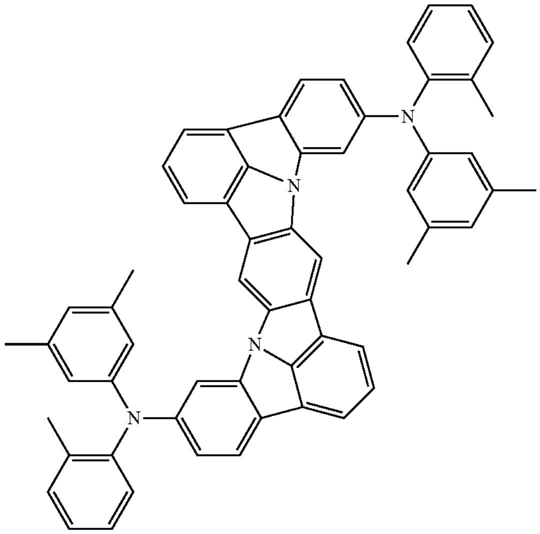
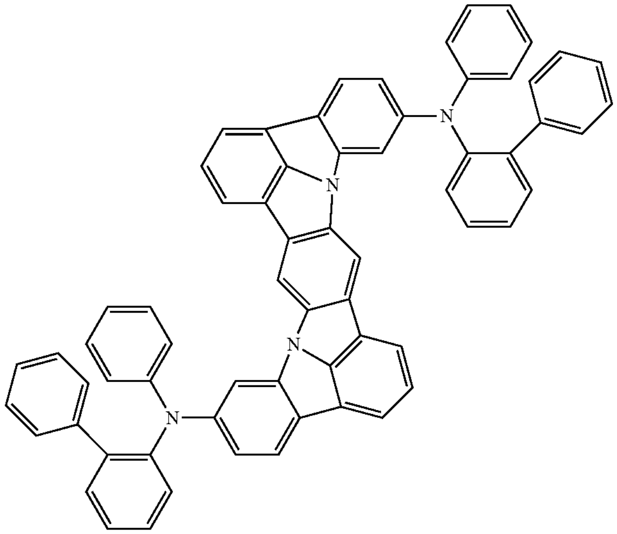
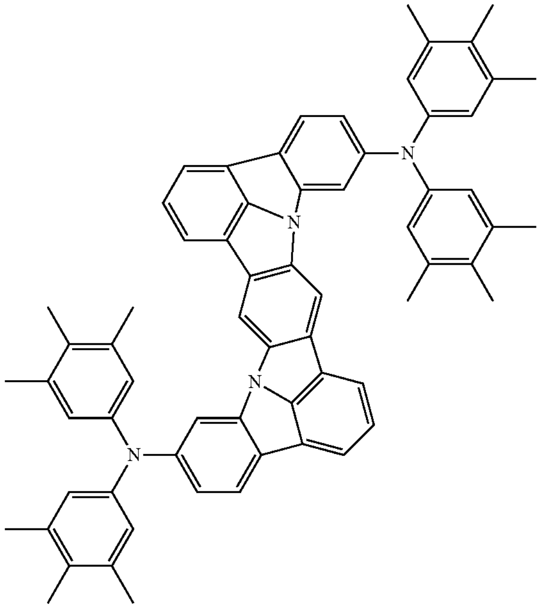

-continued
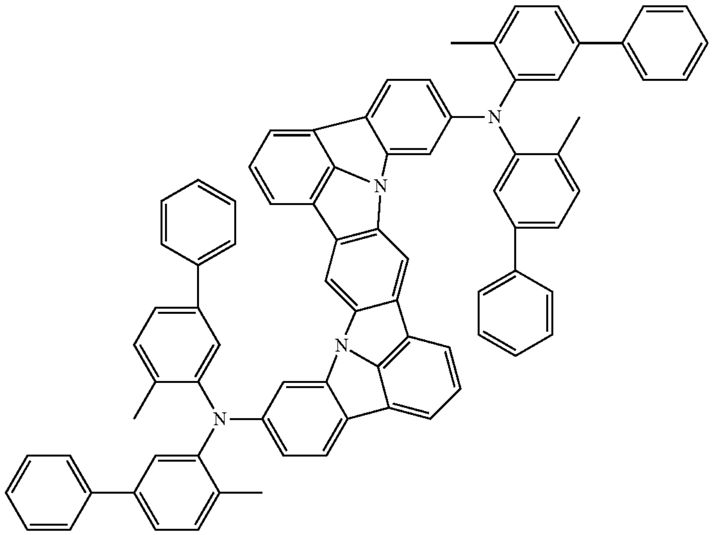
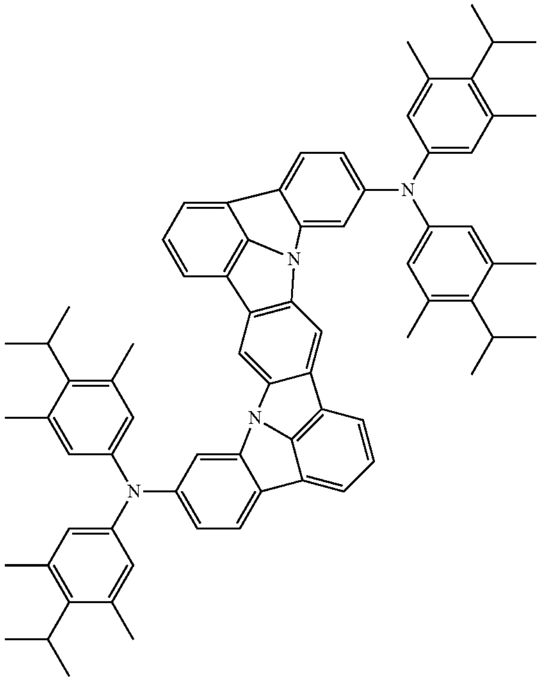
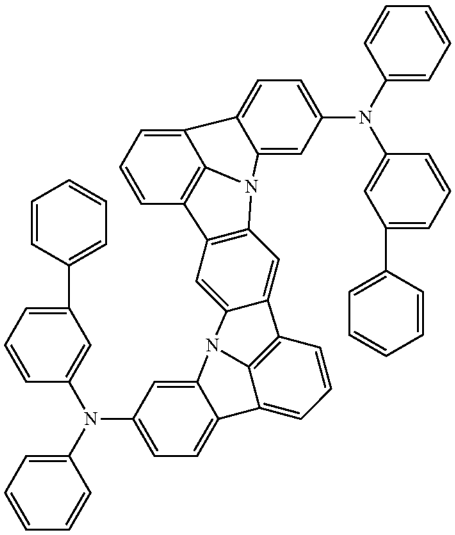

-continued
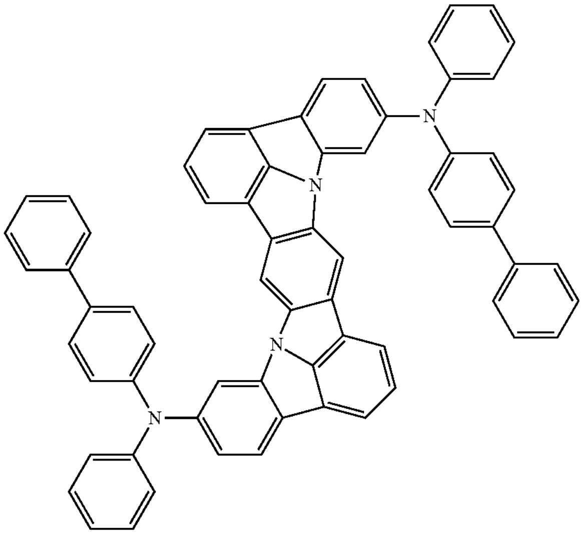
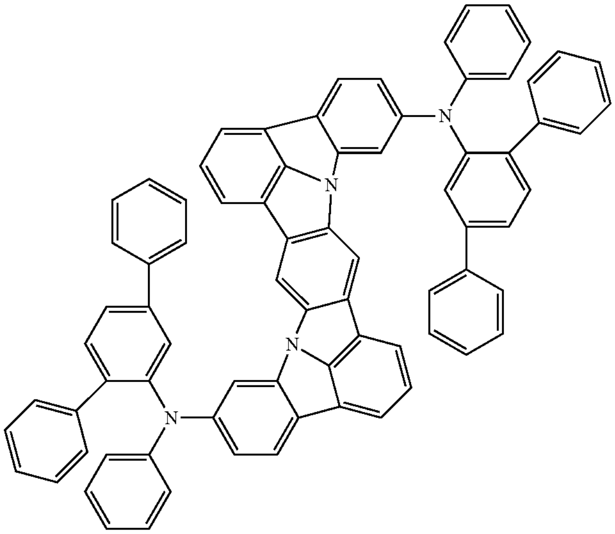
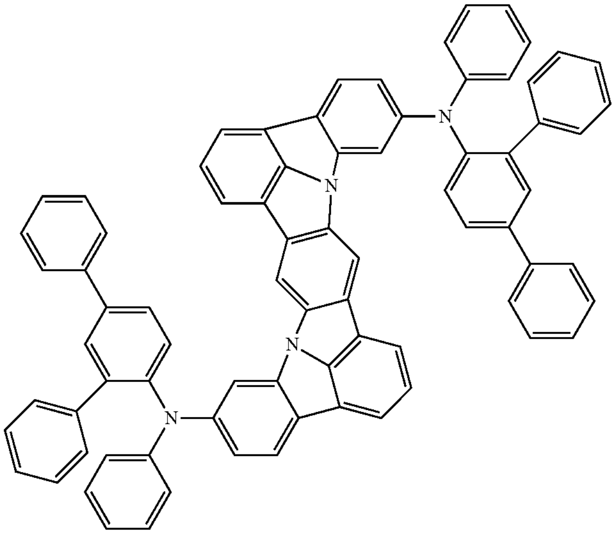

-continued
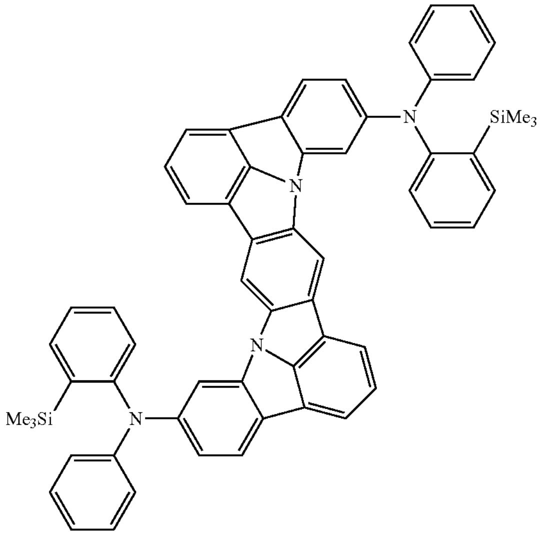
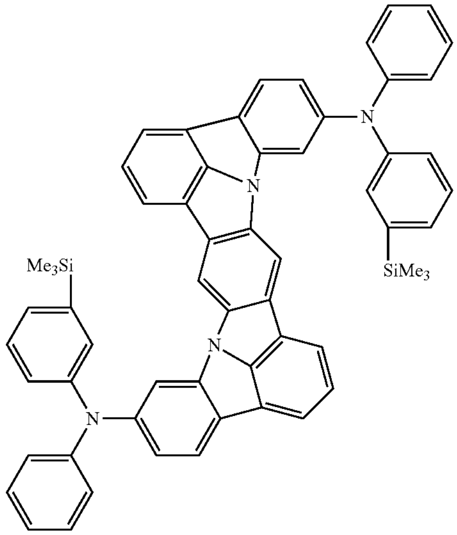
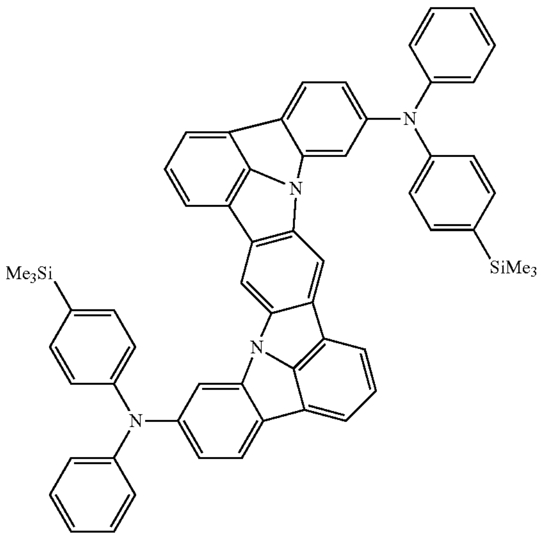
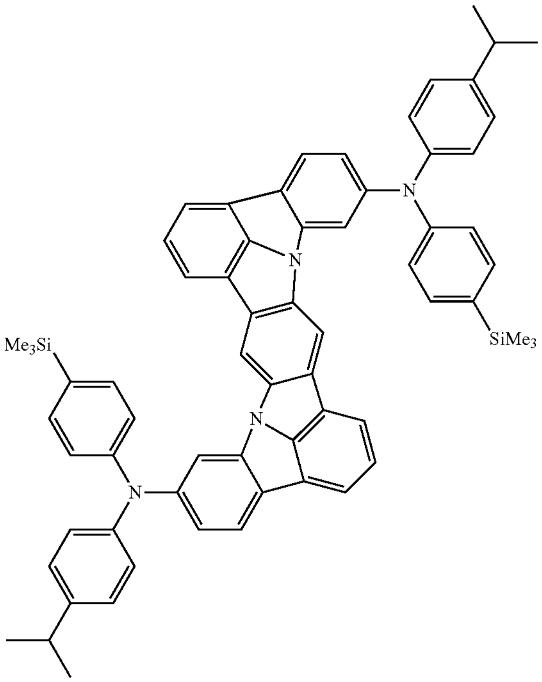

-continued
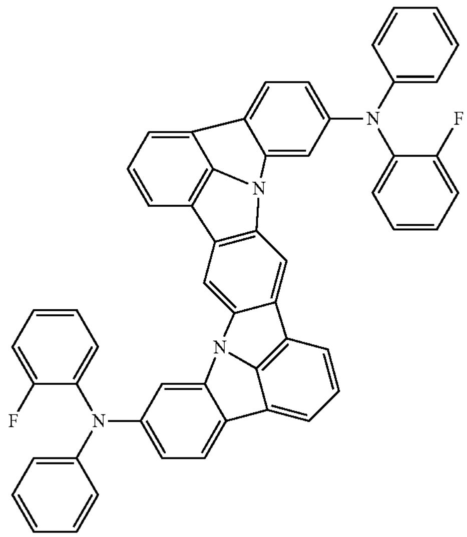
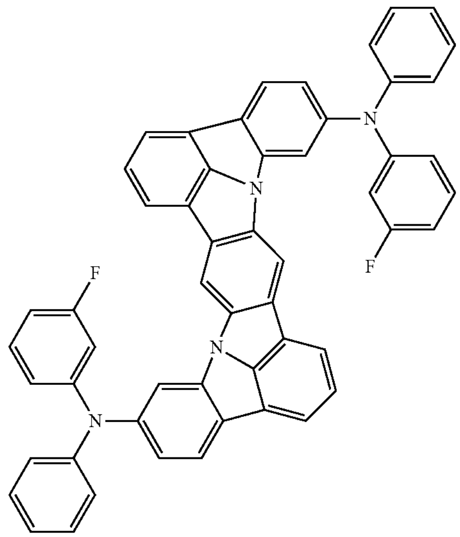
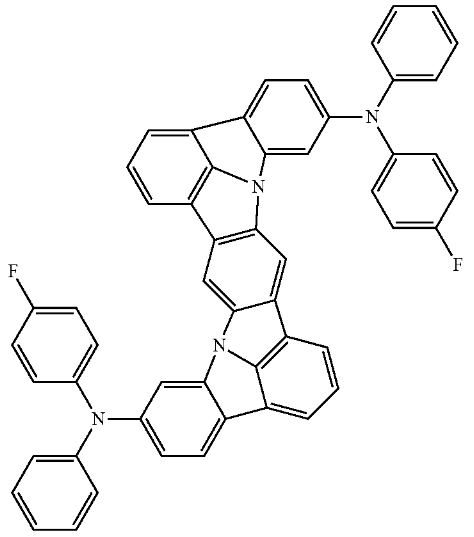
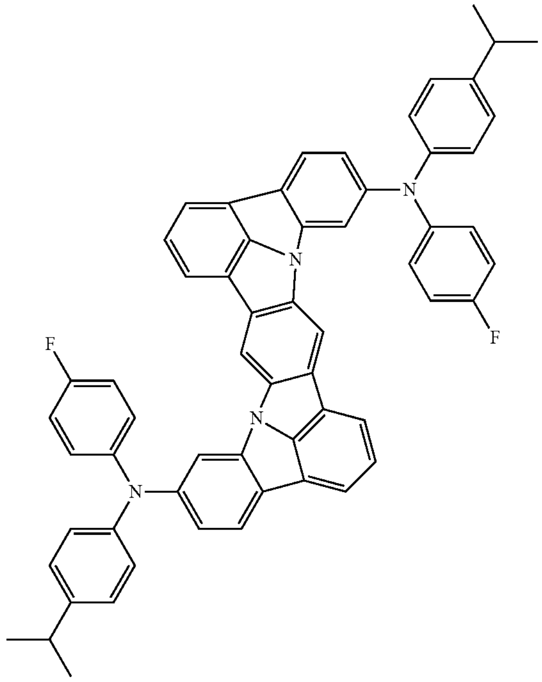

-continued
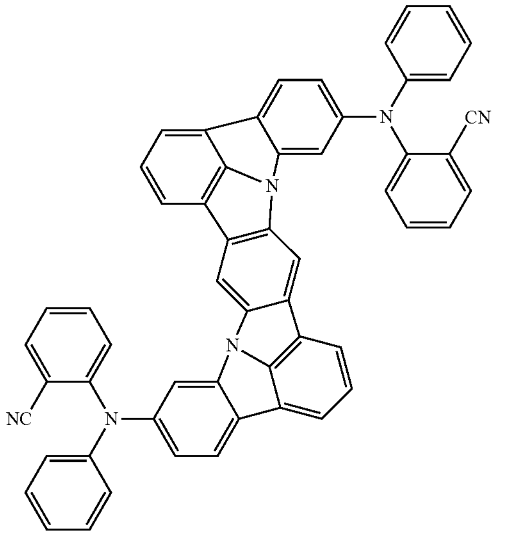
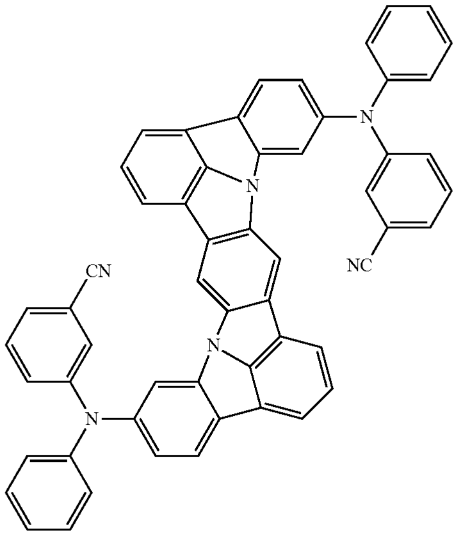
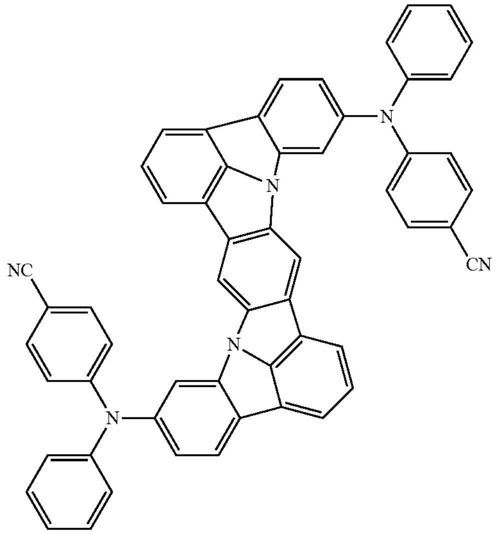
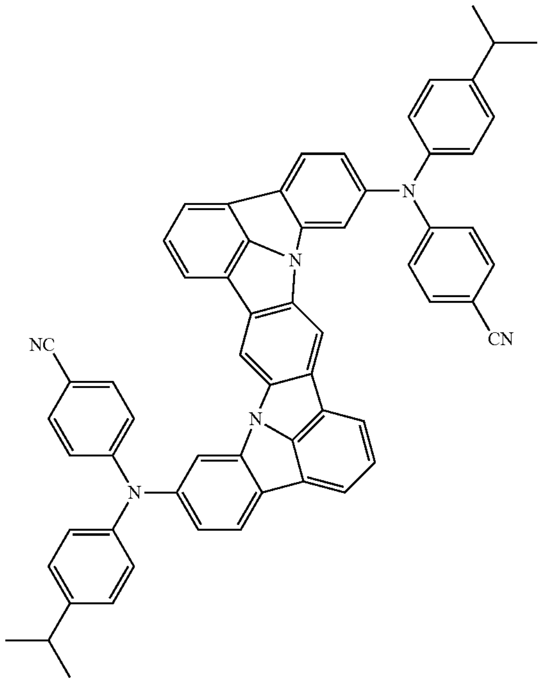

-continued
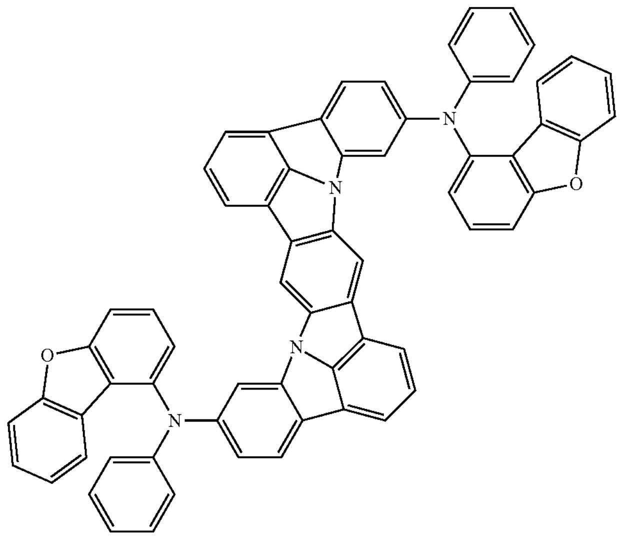
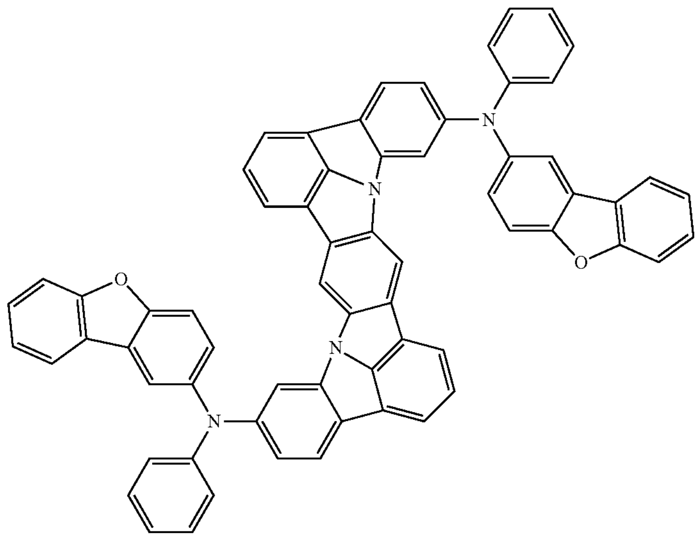
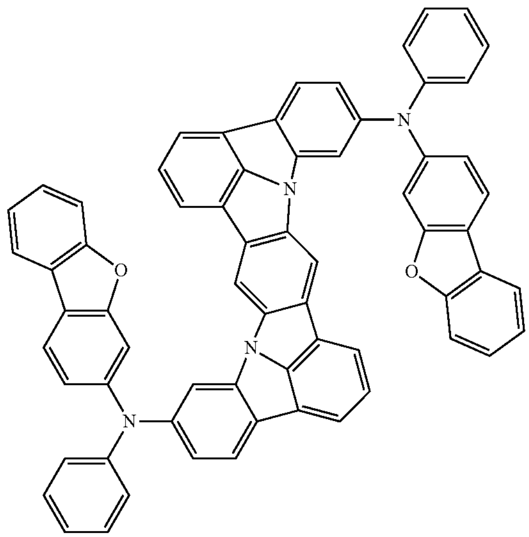

-continued
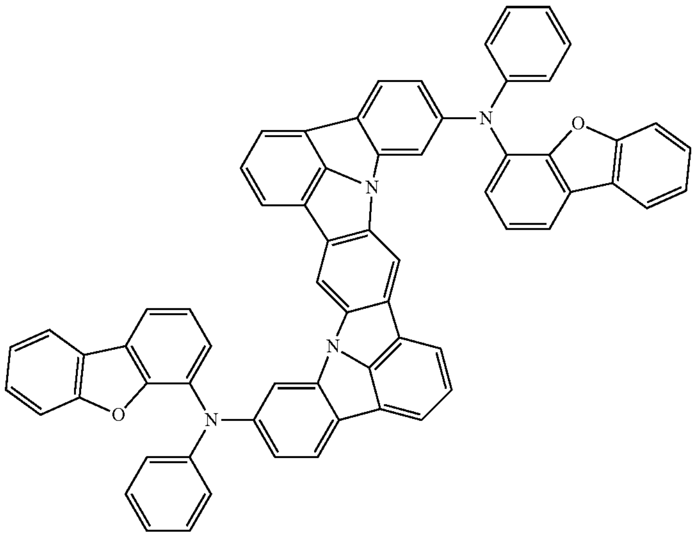
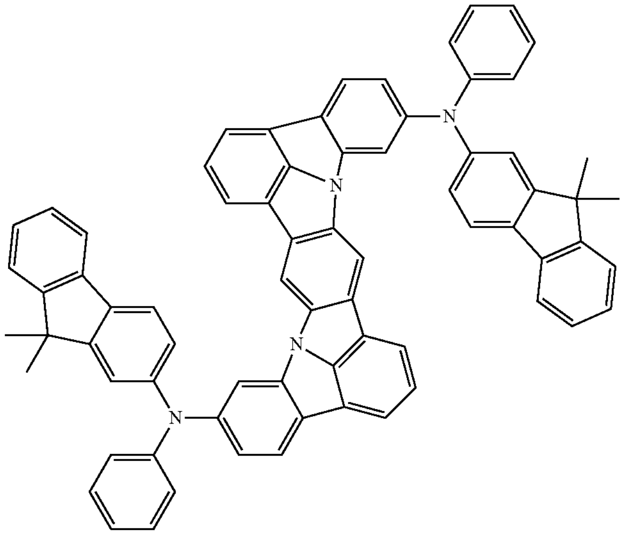
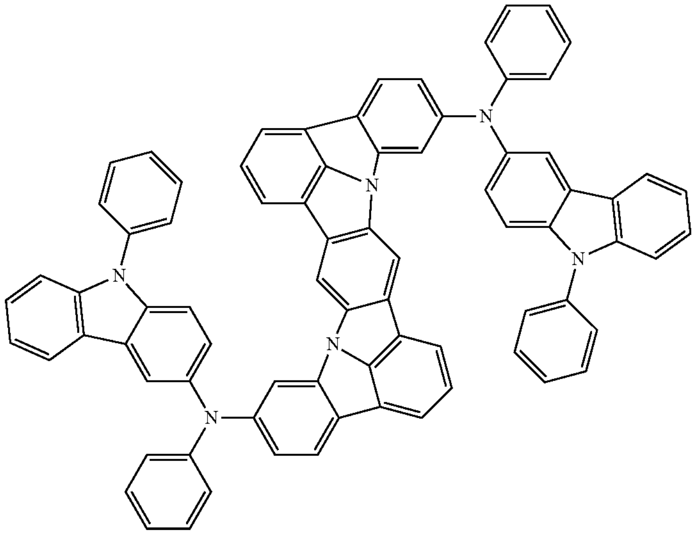

-continued
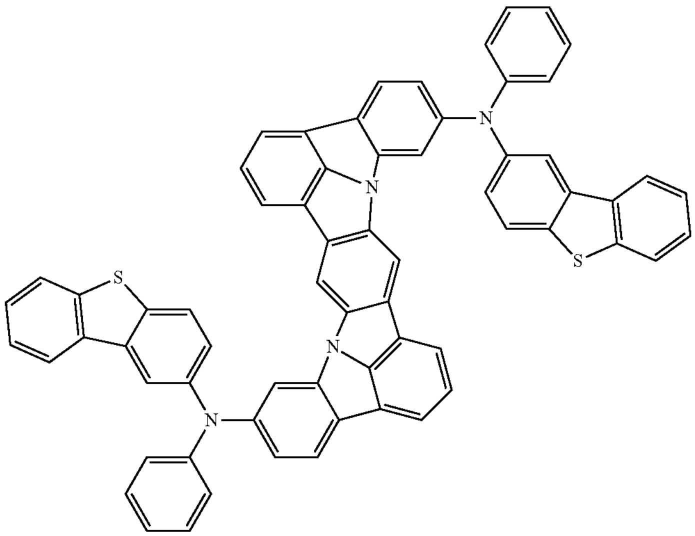
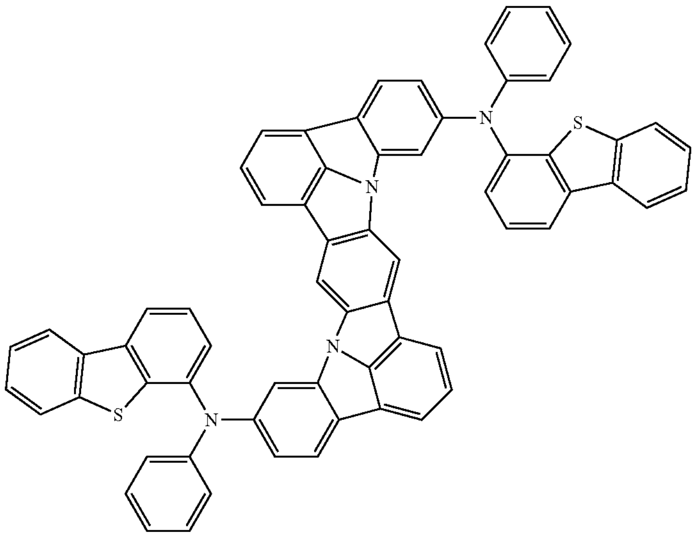
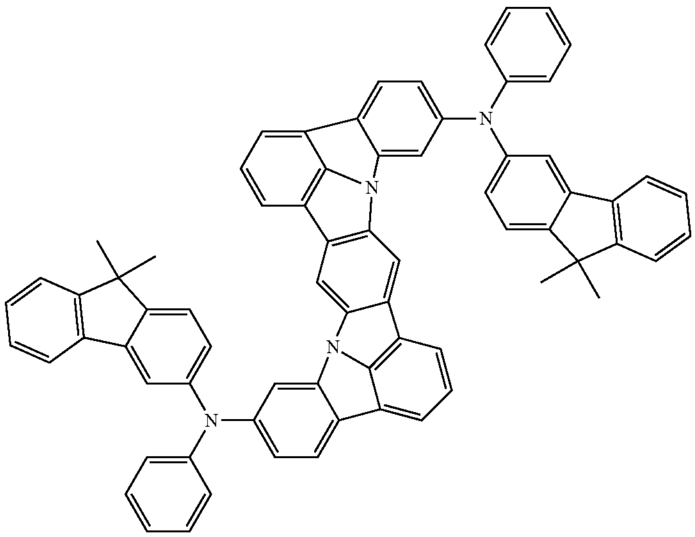

-continued
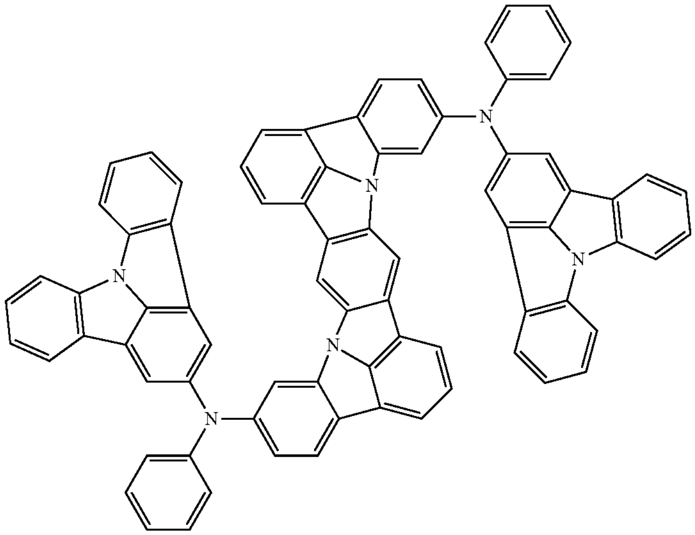
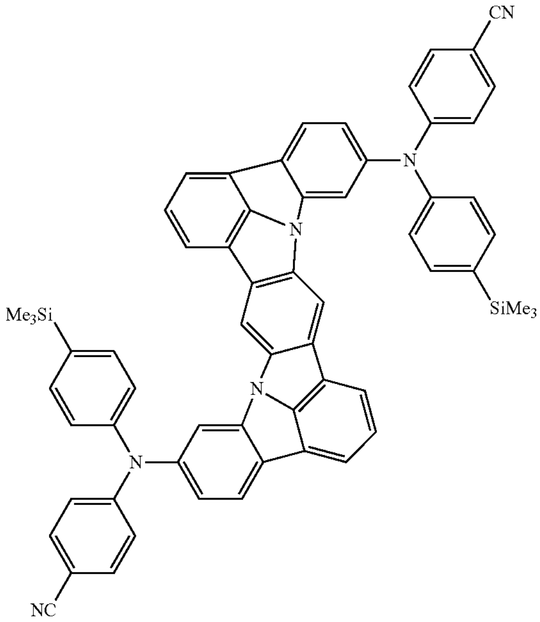
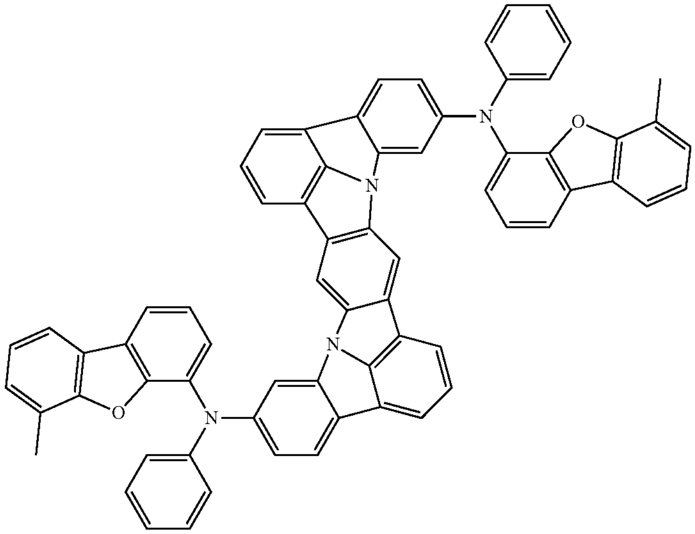

-continued
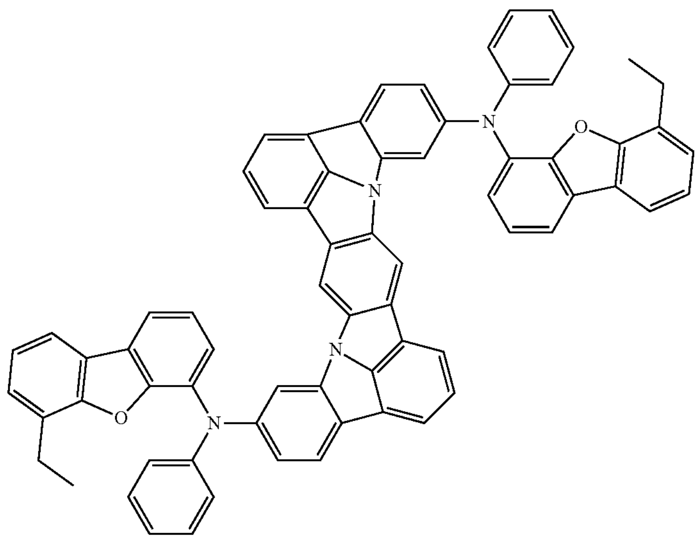
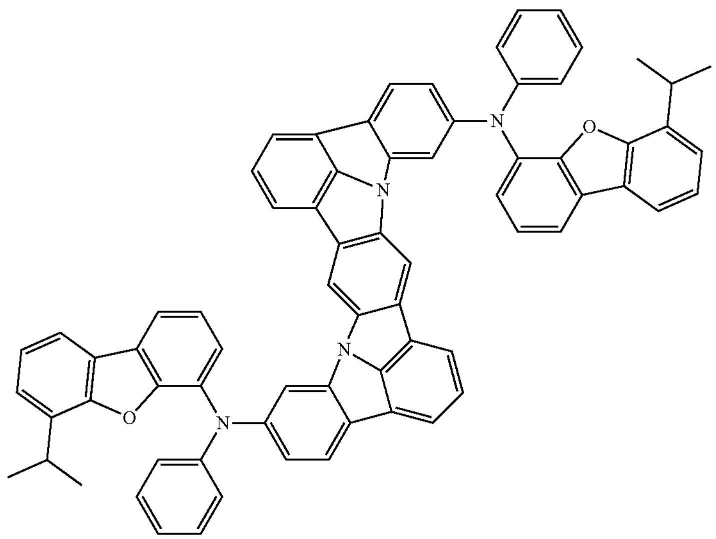
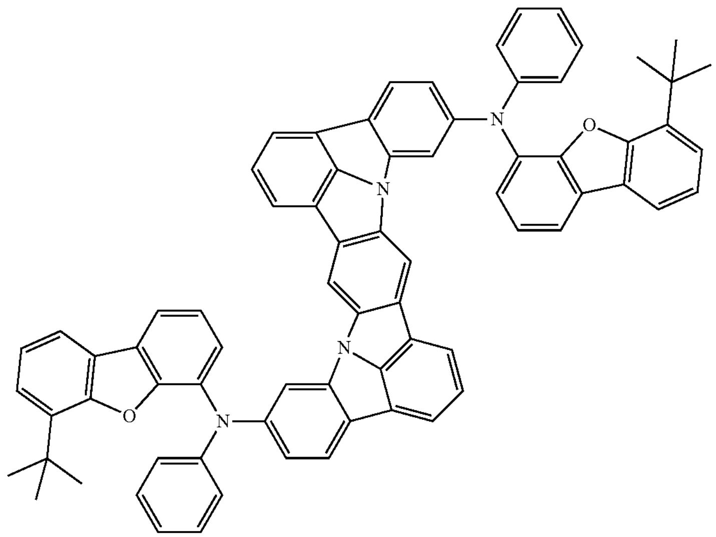

-continued
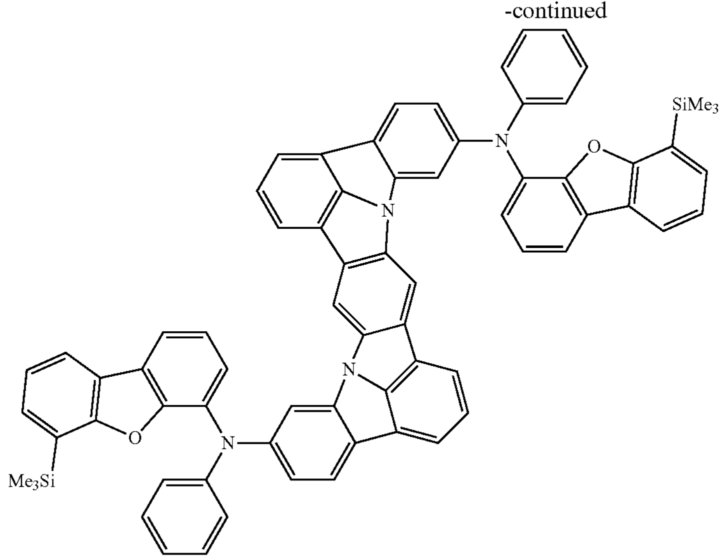
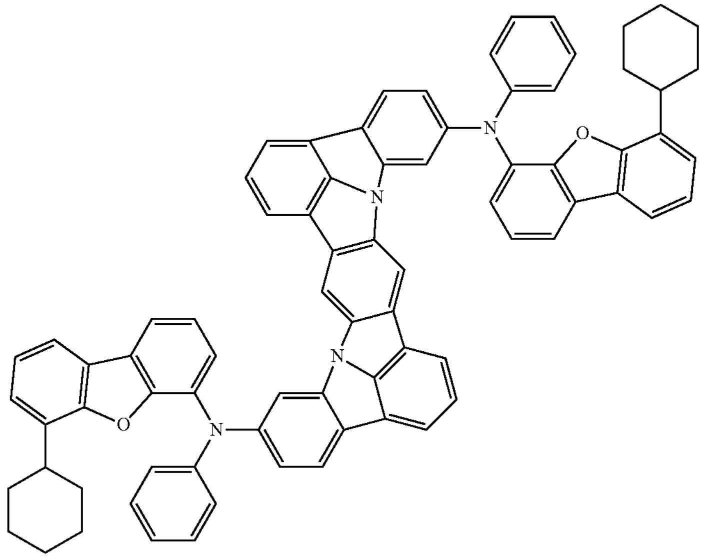
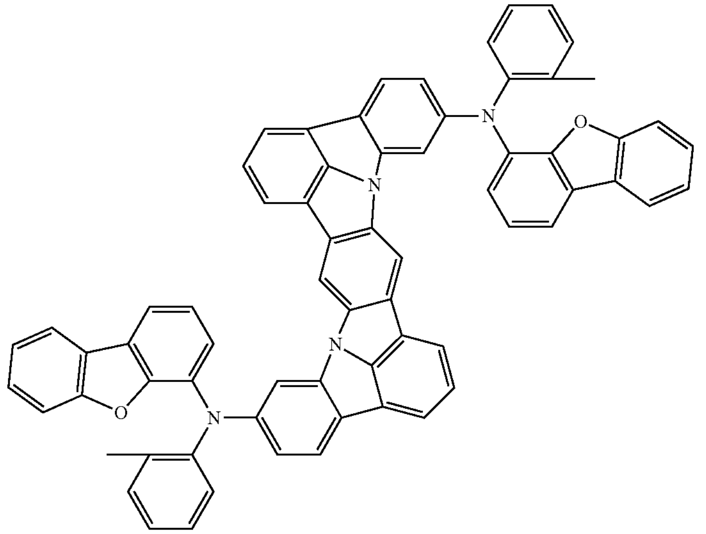

-continued
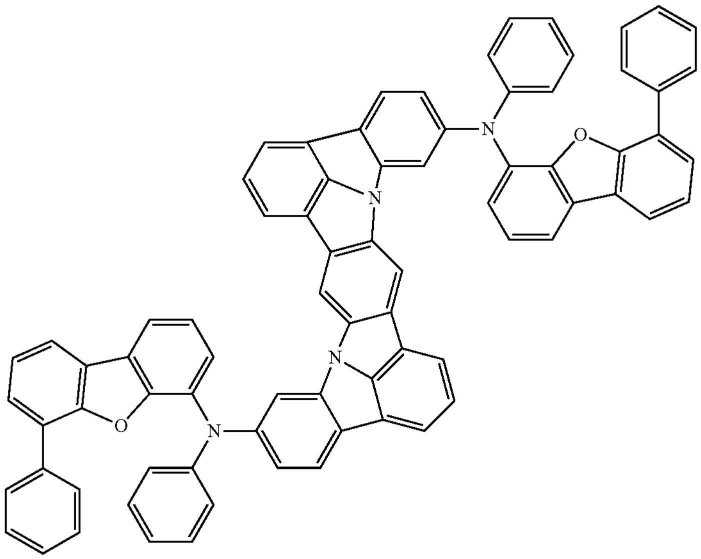
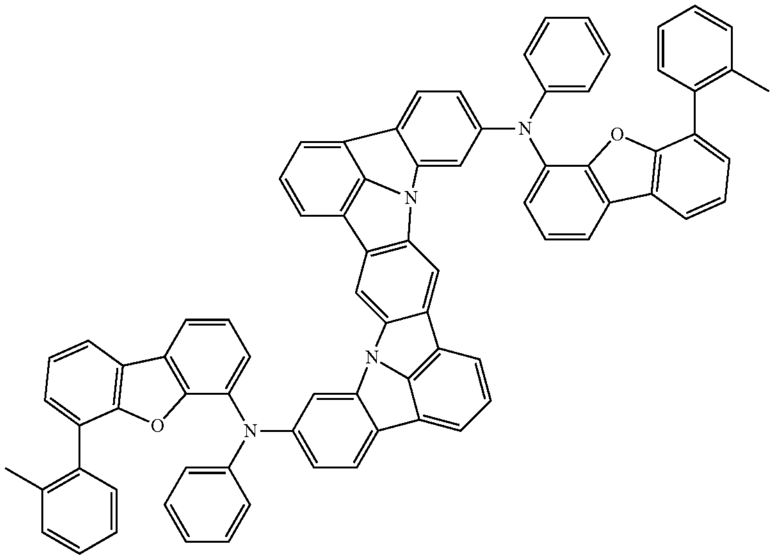
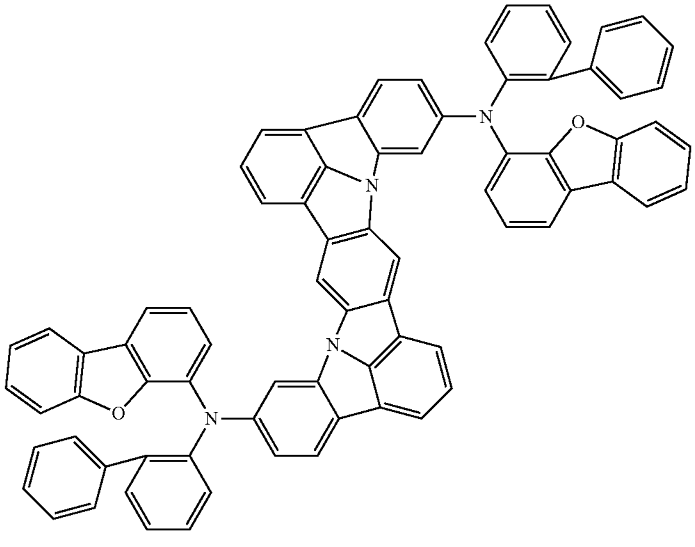

-continued
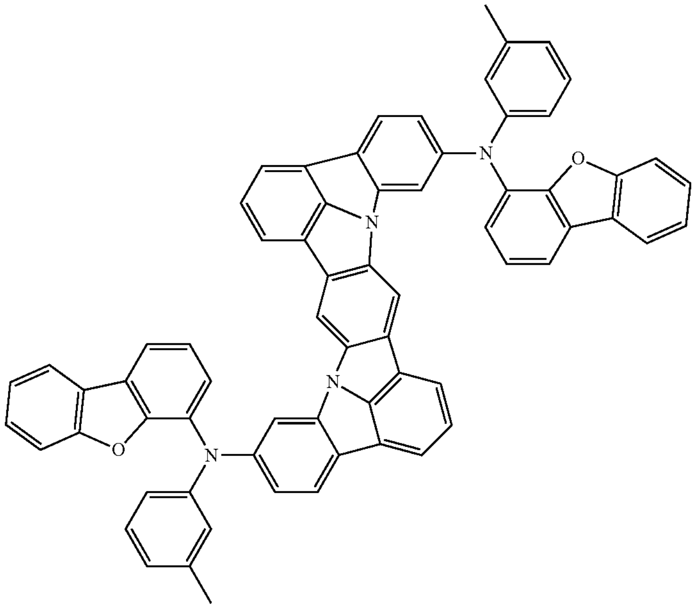
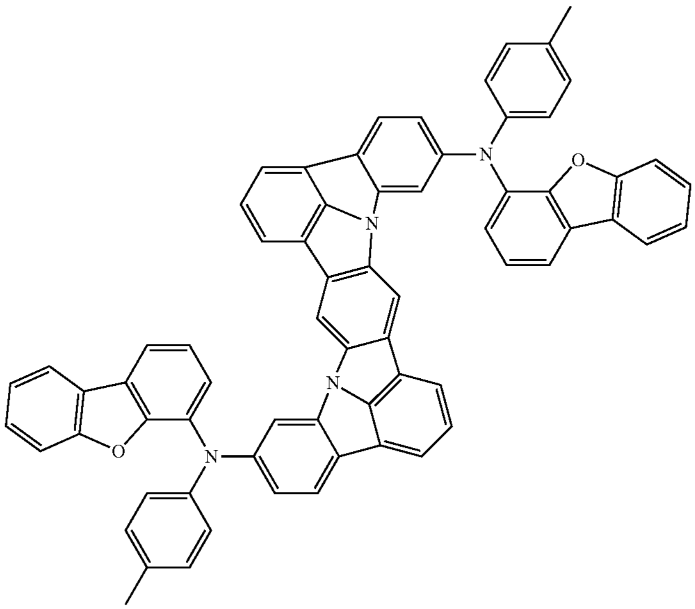

-continued
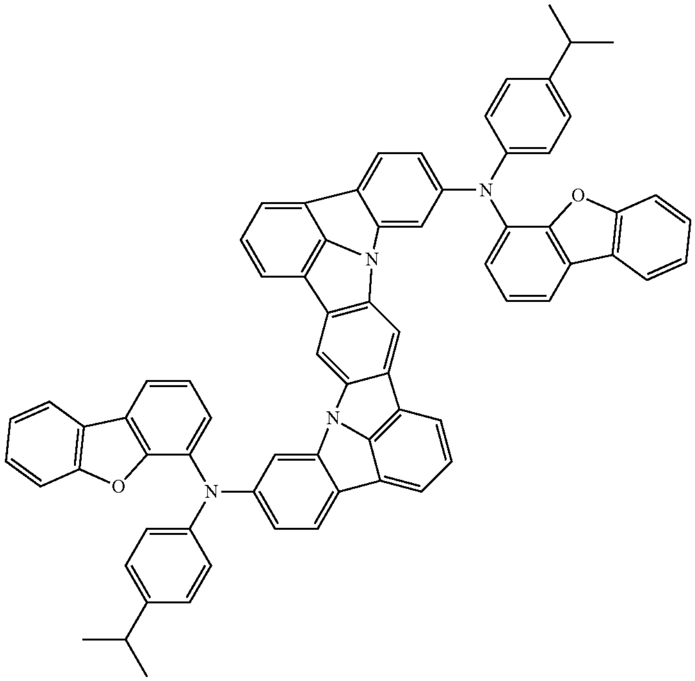
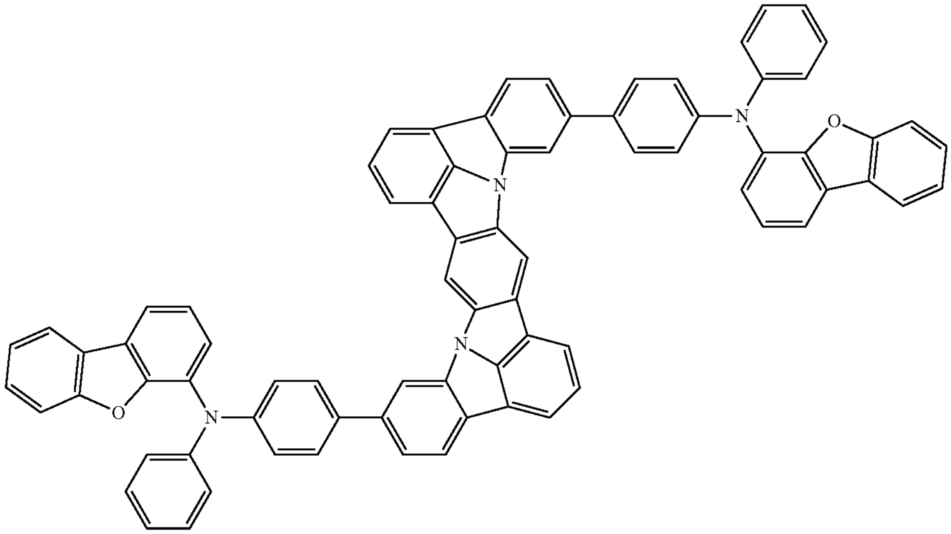

-continued
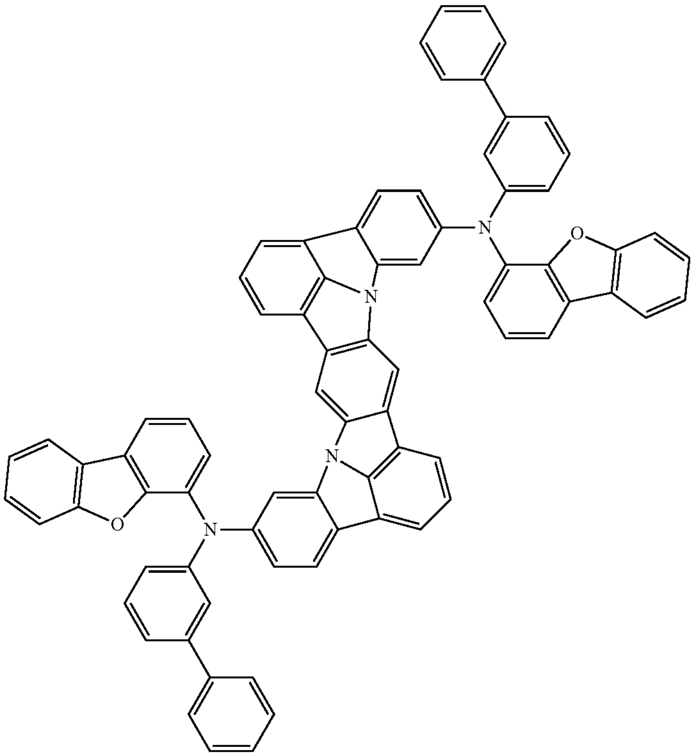
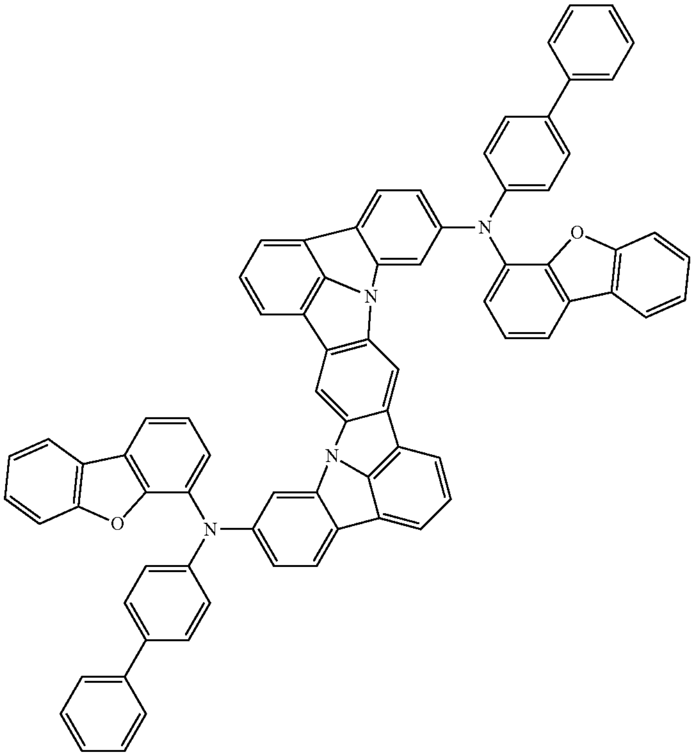

-continued
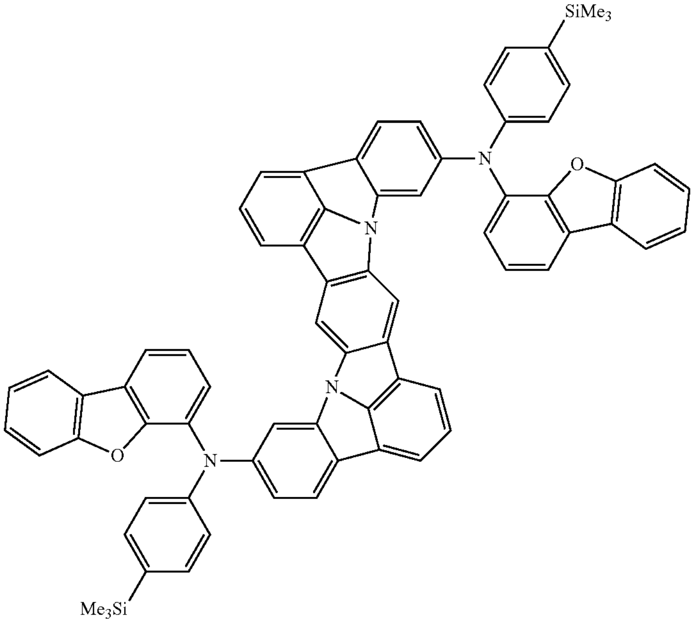
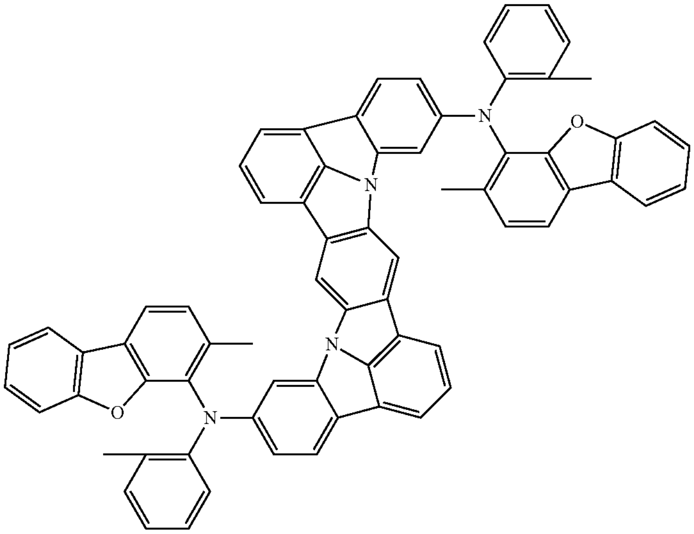
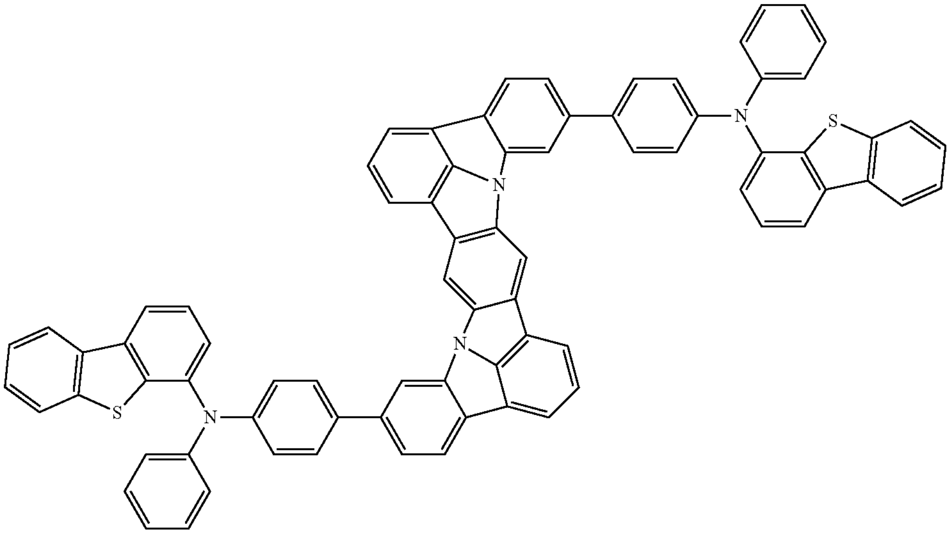

-continued
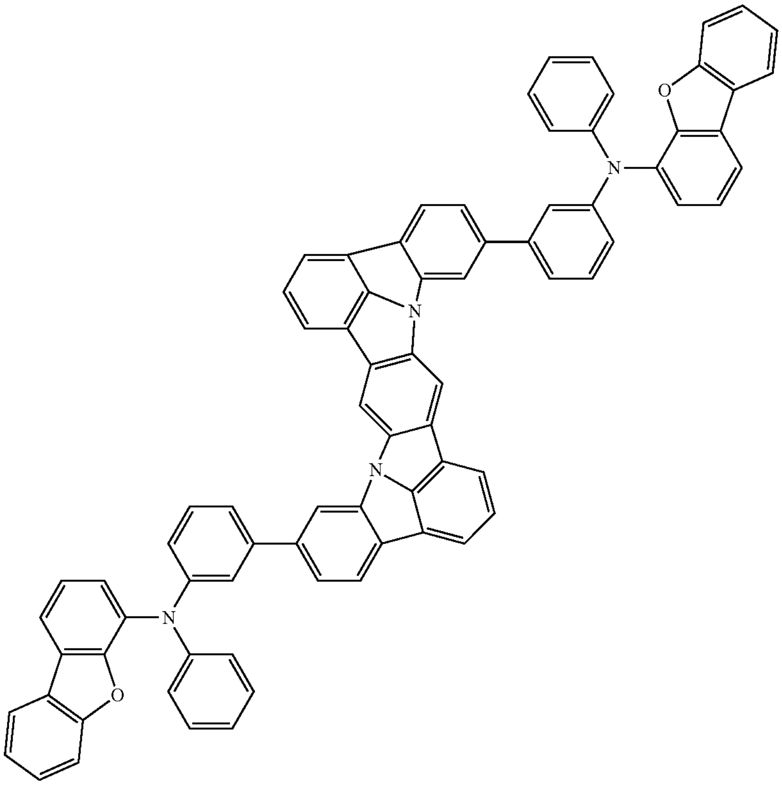
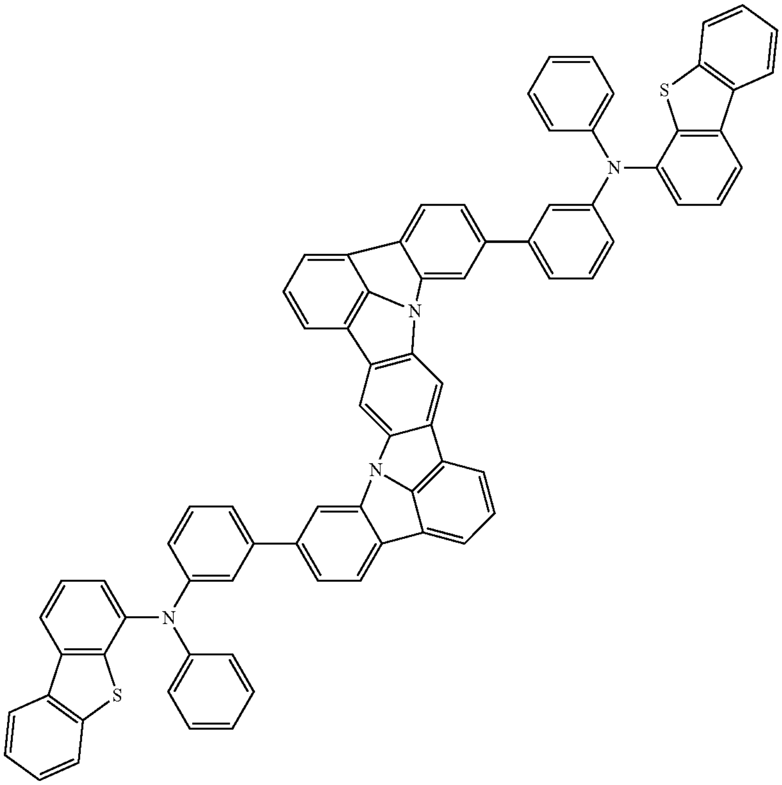

-continued
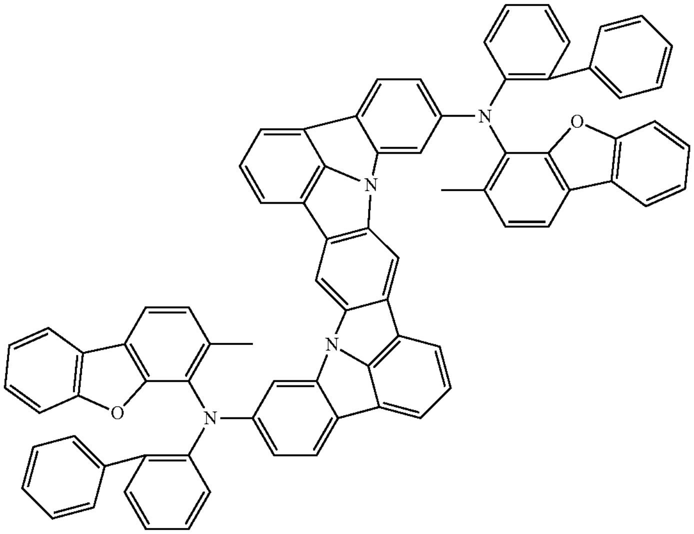
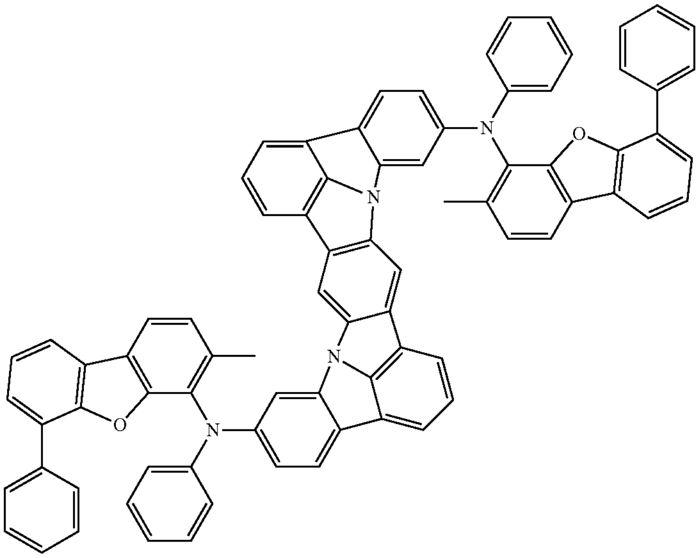
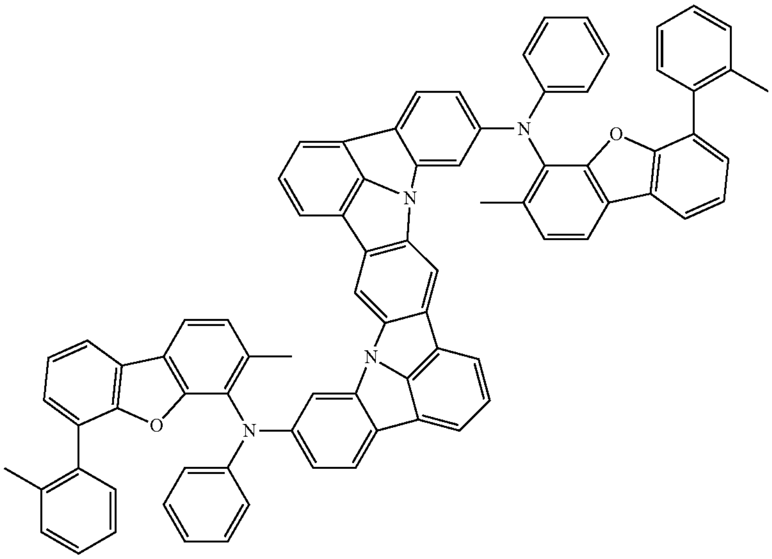

-continued
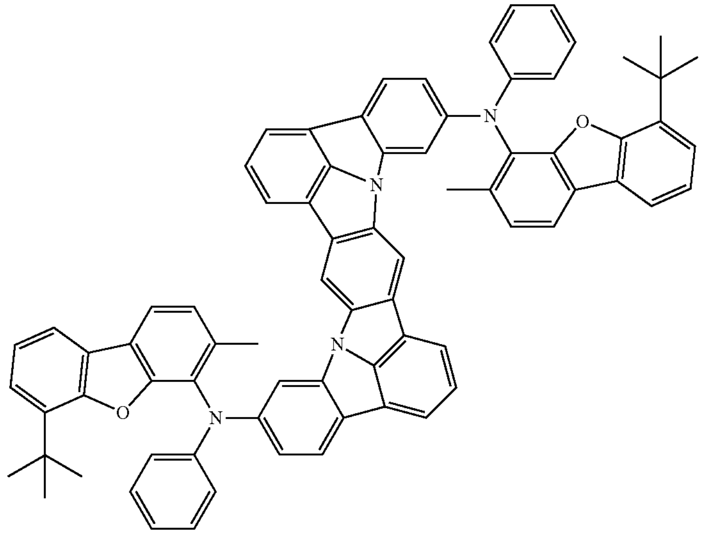
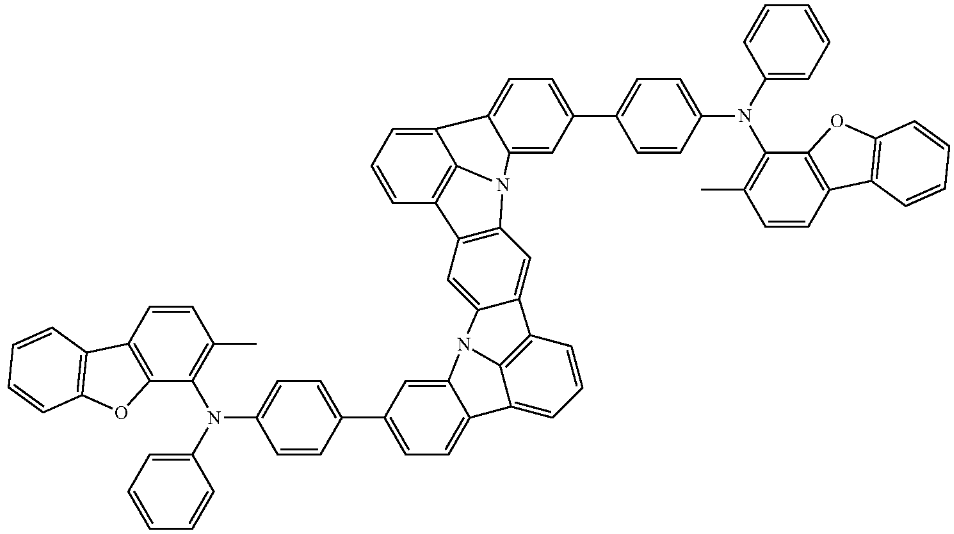

-continued
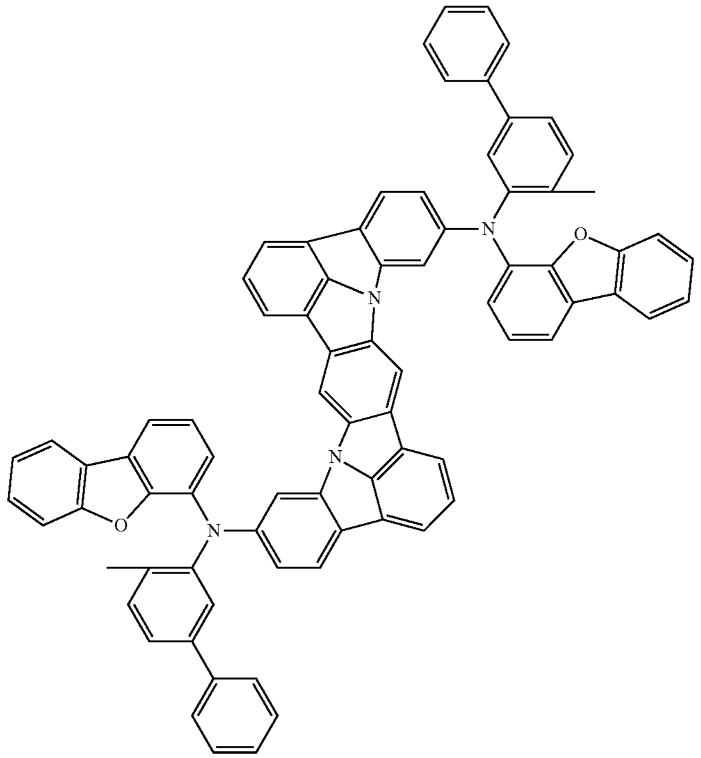
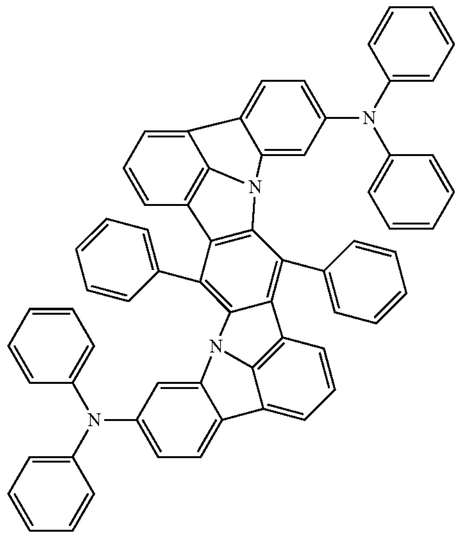
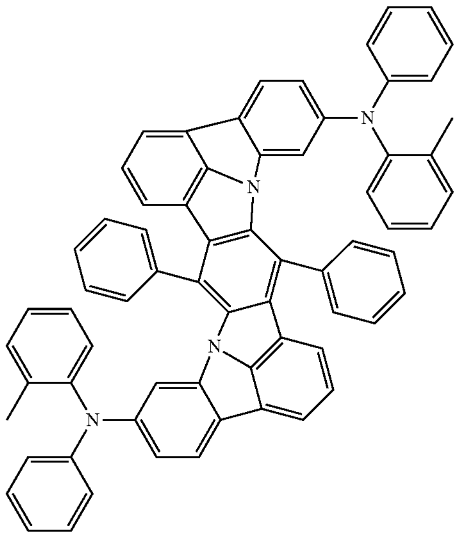

-continued
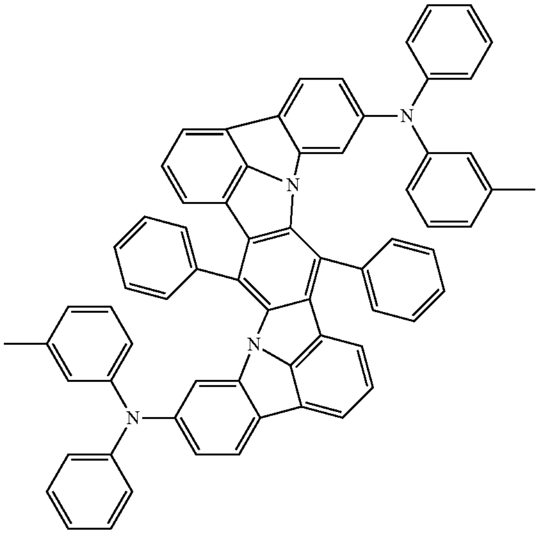
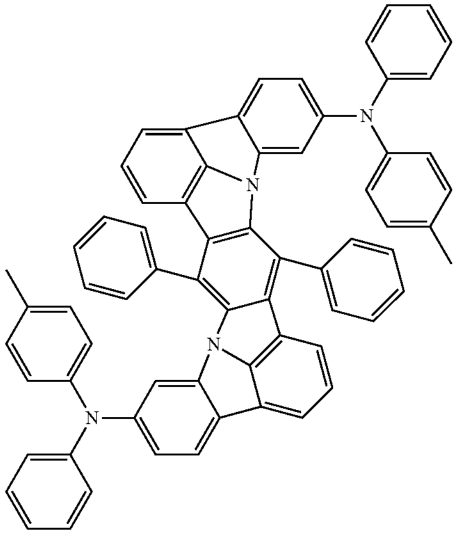
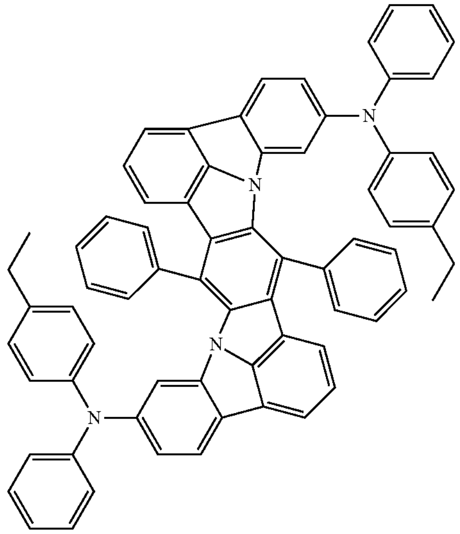
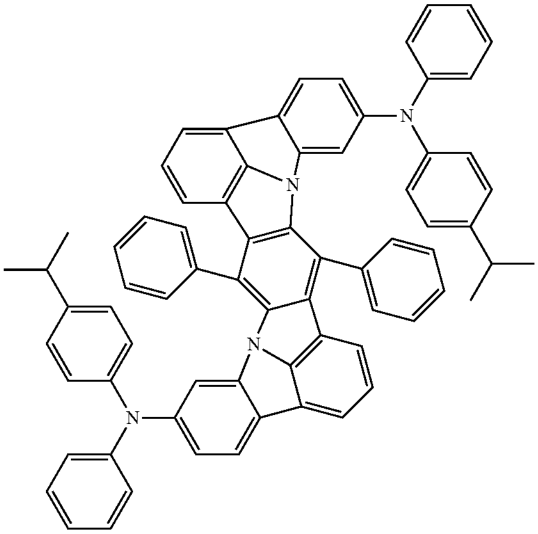
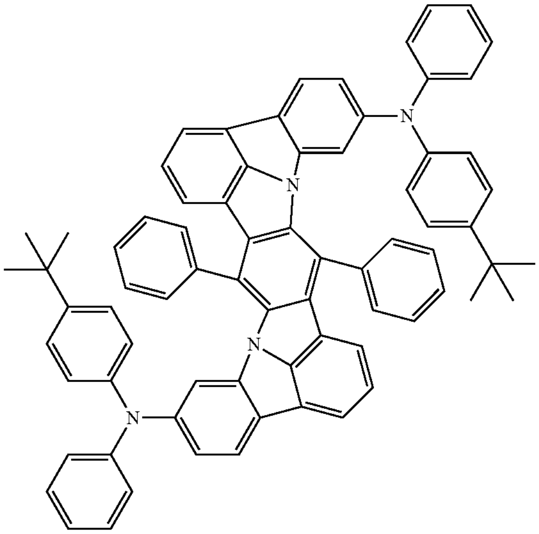
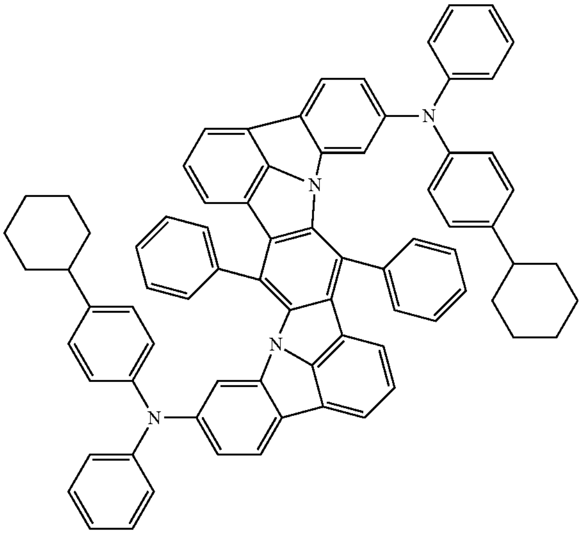

-continued
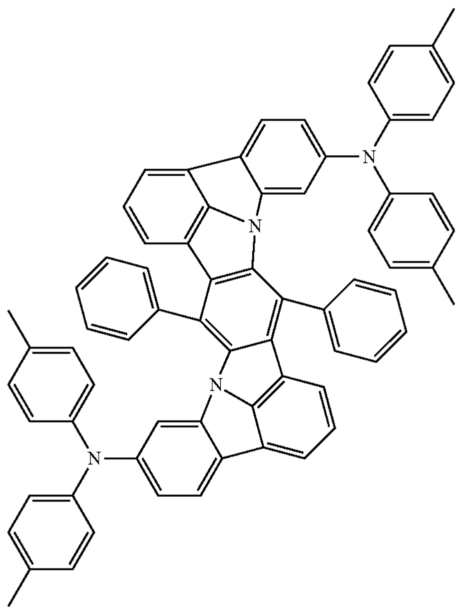
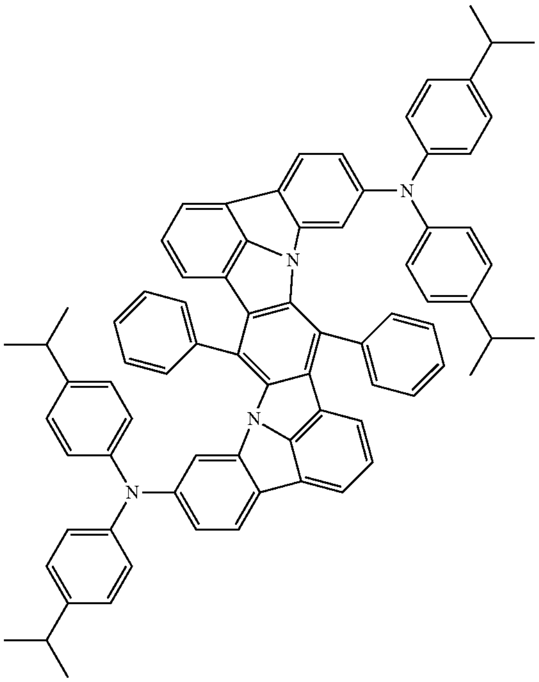
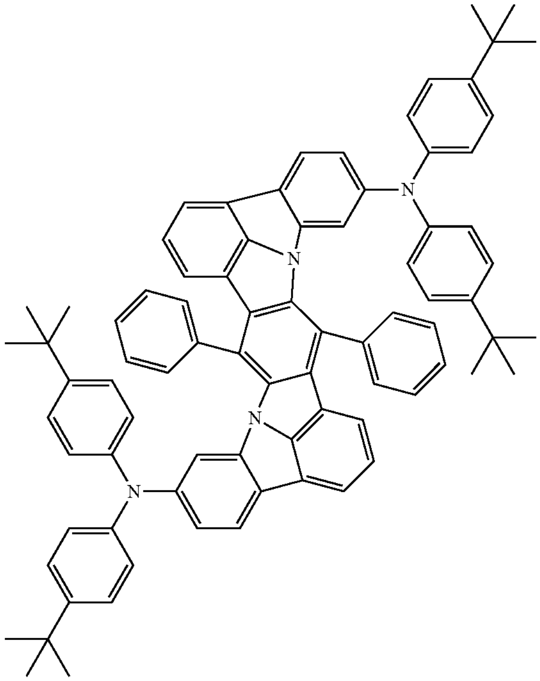

-continued
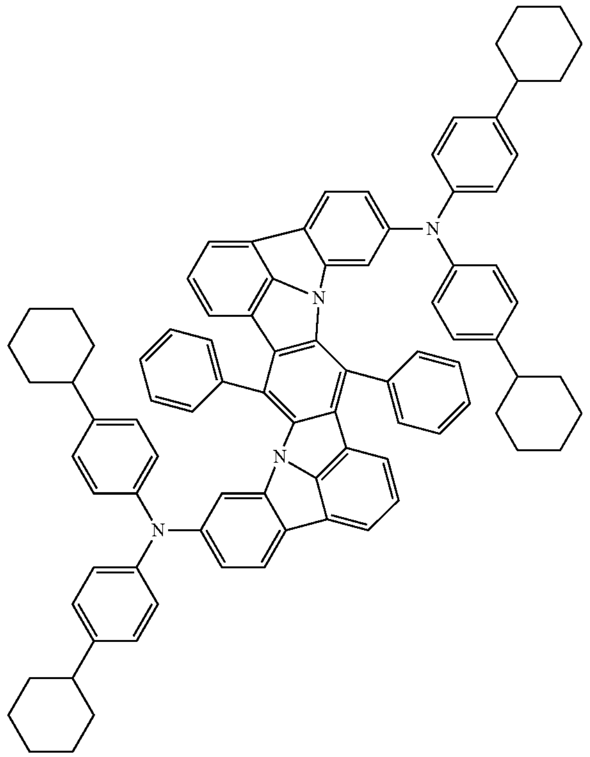
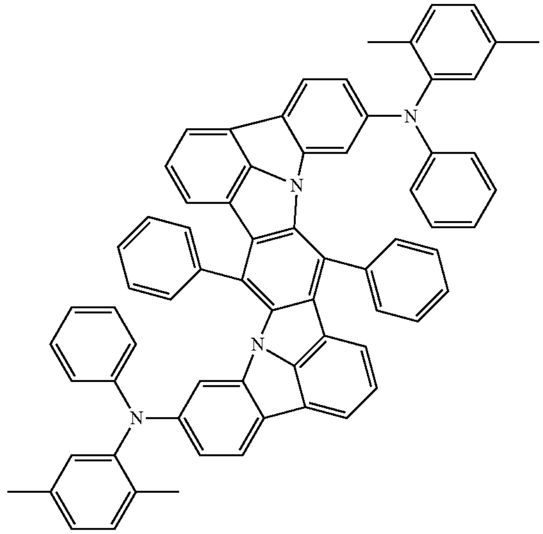
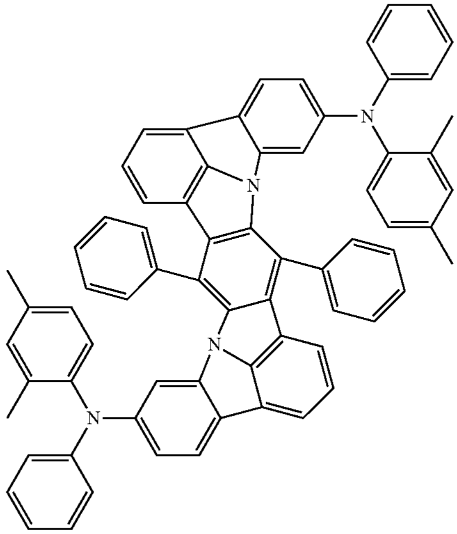

-continued
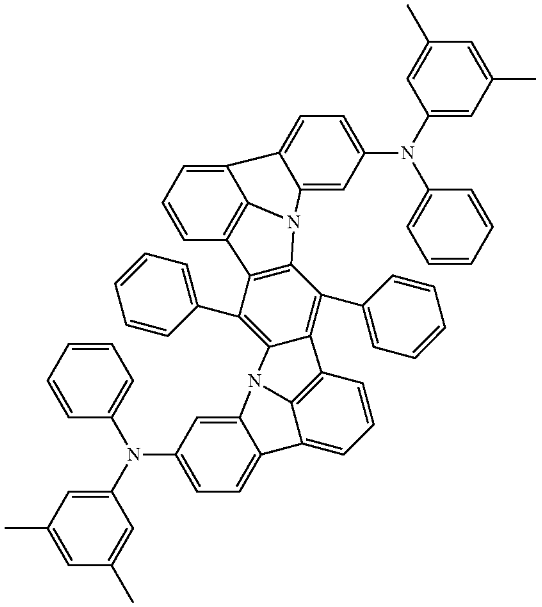
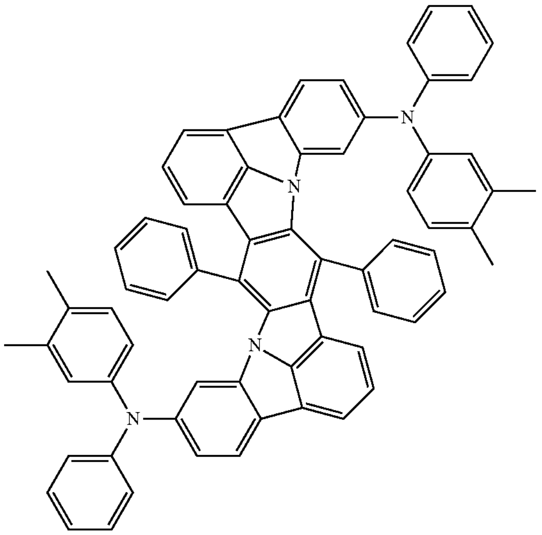
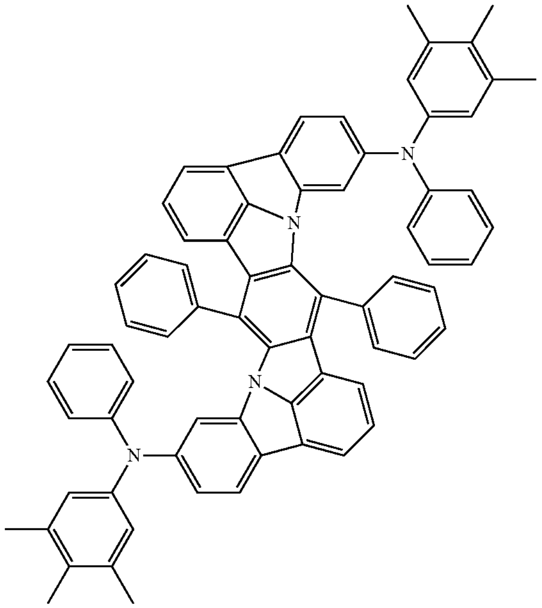
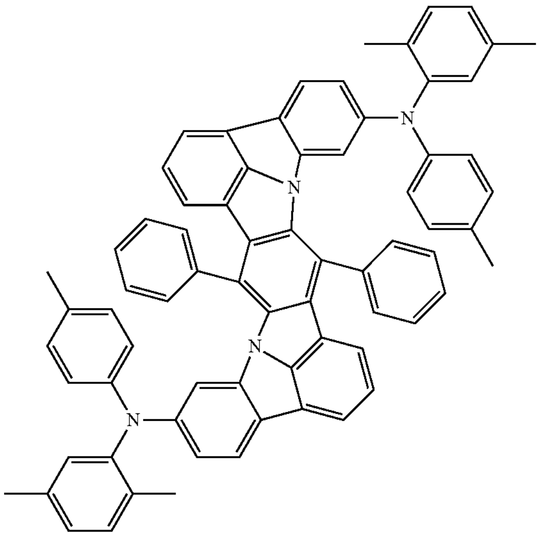

-continued
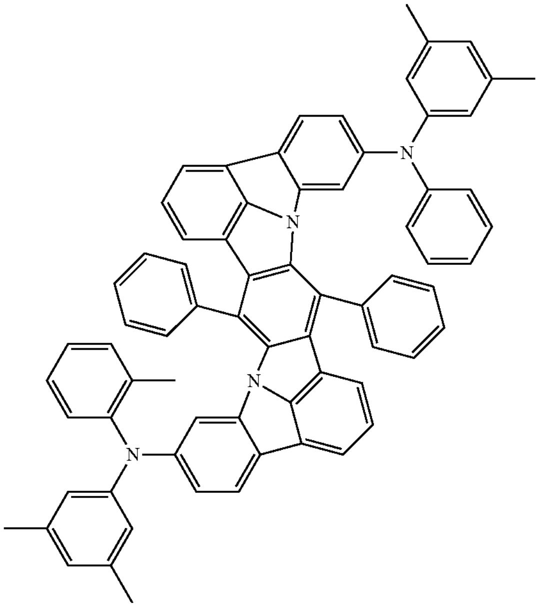
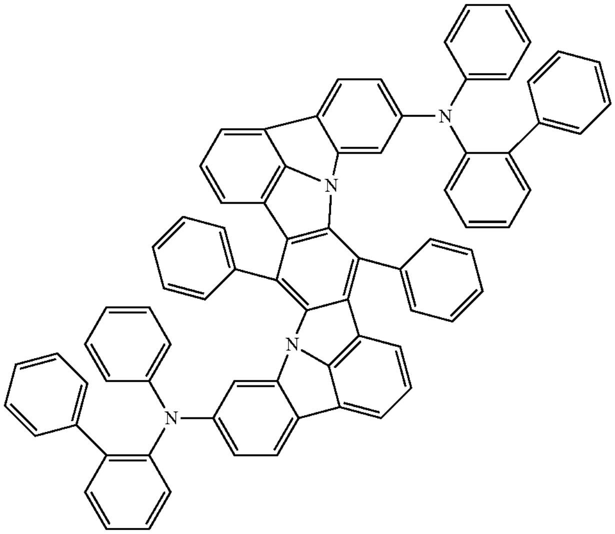
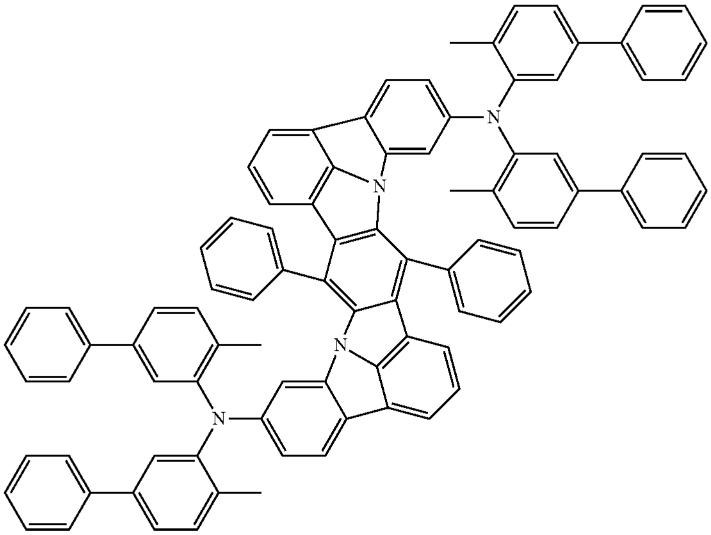

-continued
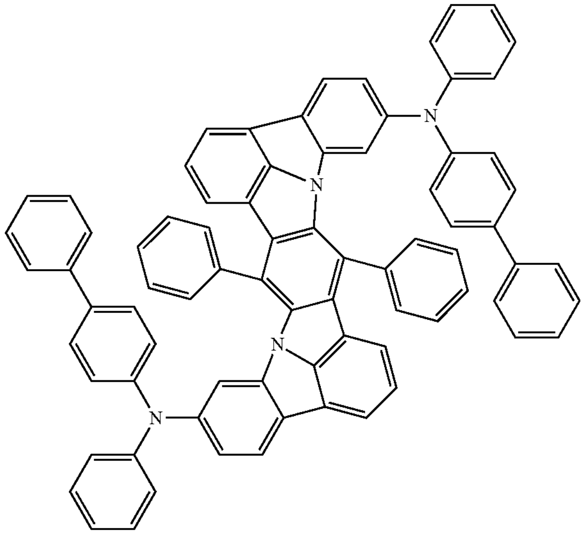
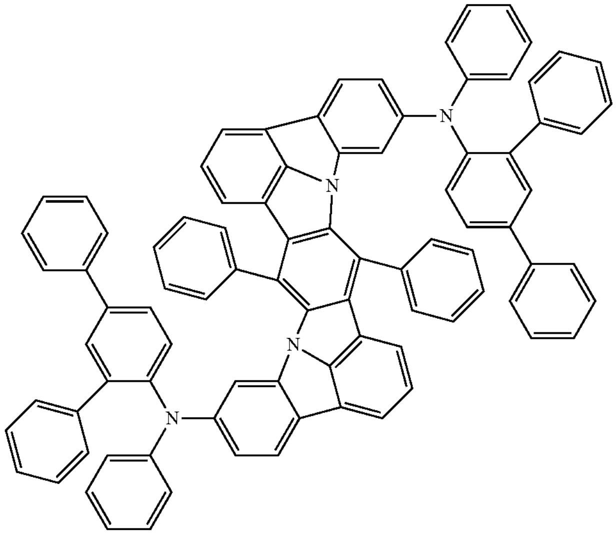
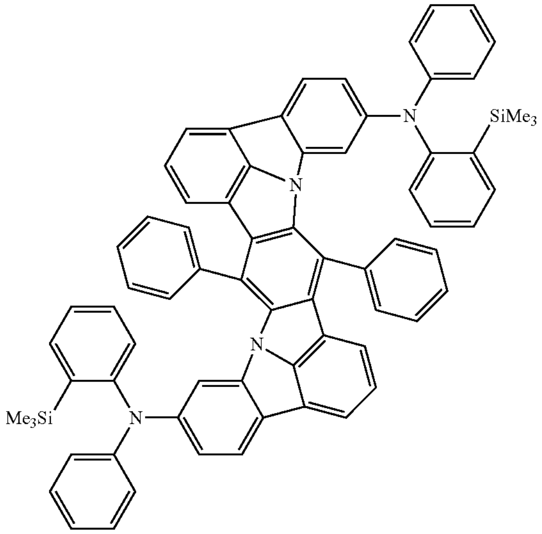

-continued
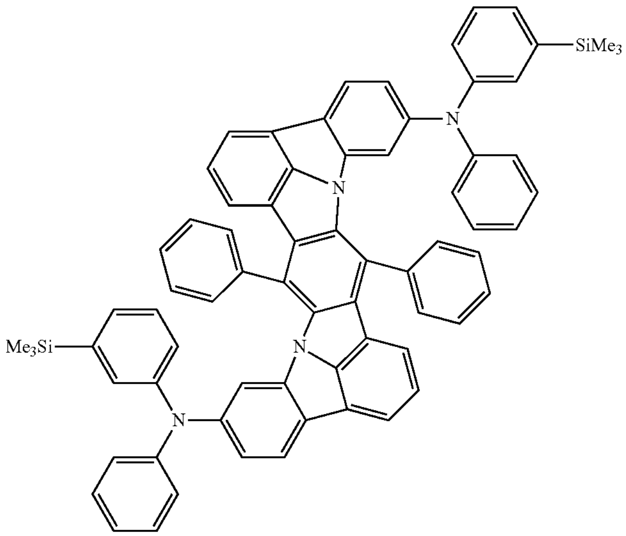
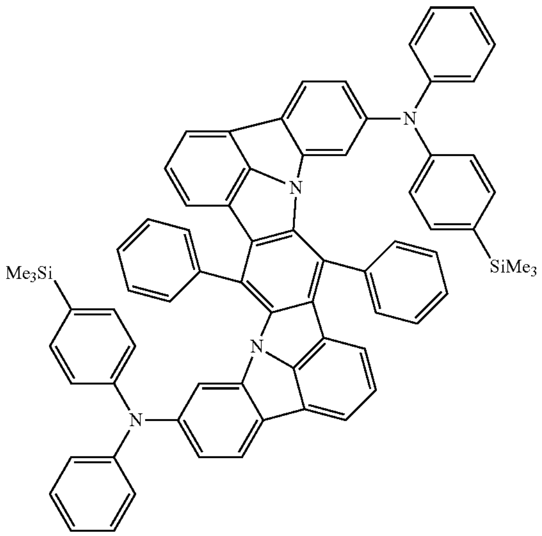
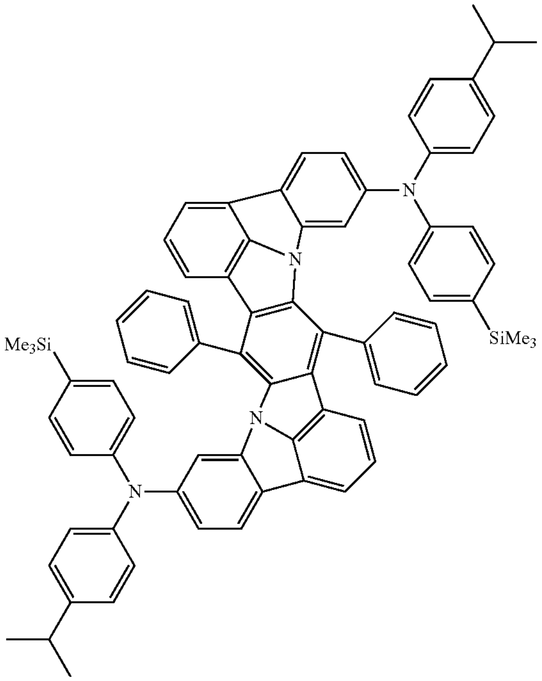

-continued
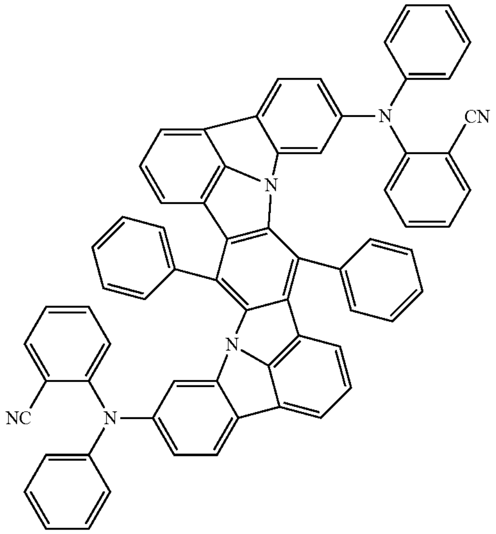
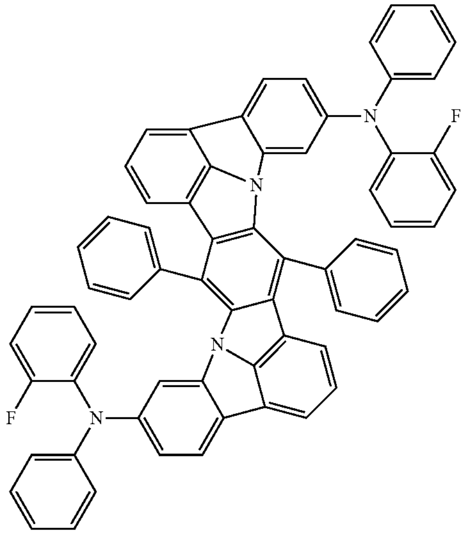
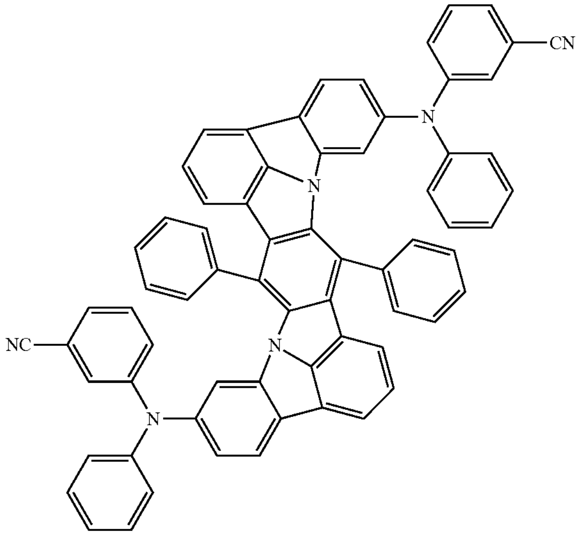
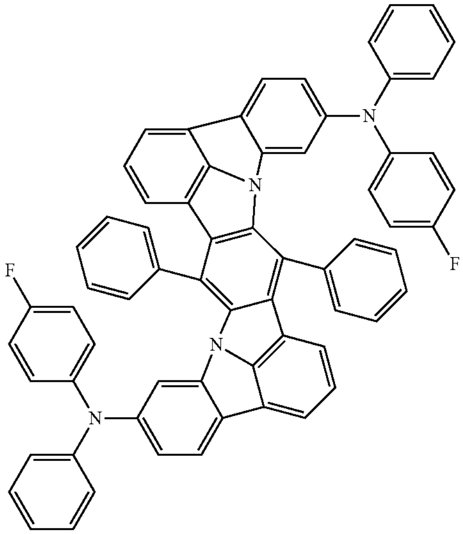
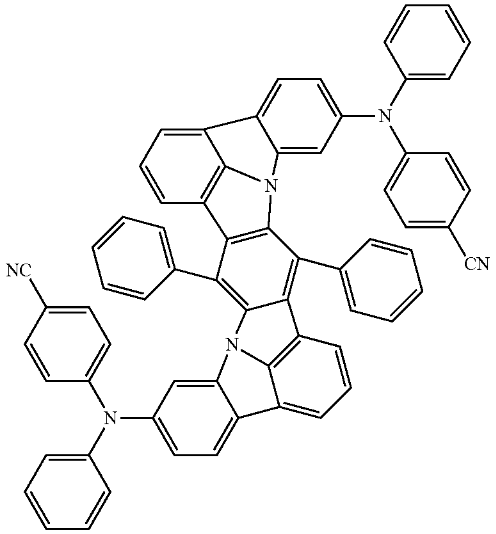

-continued
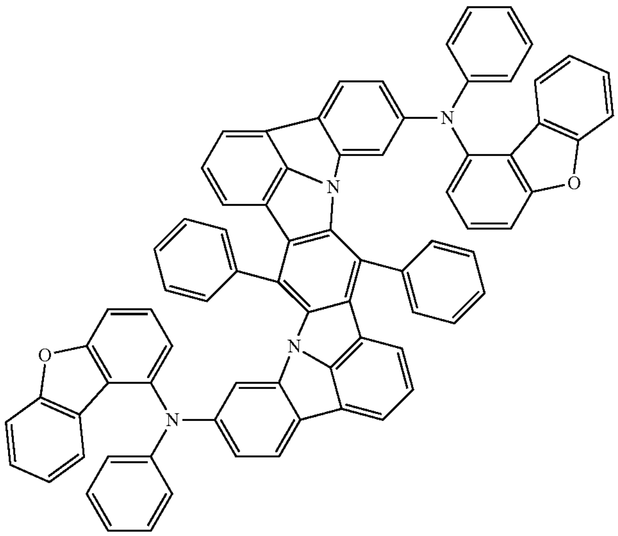
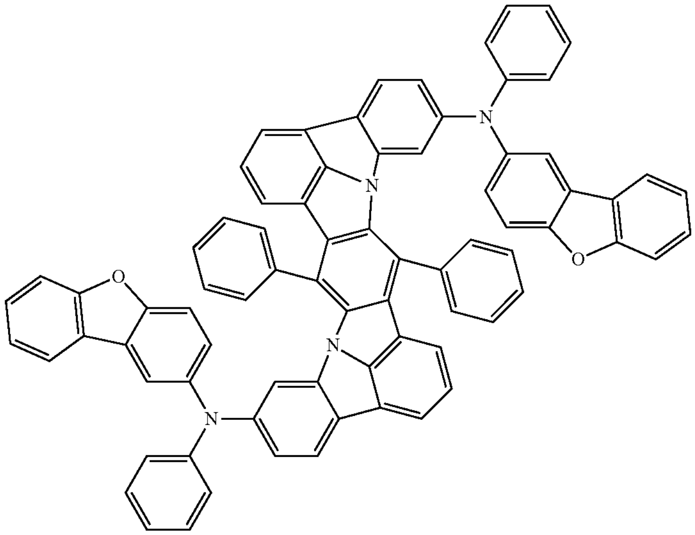
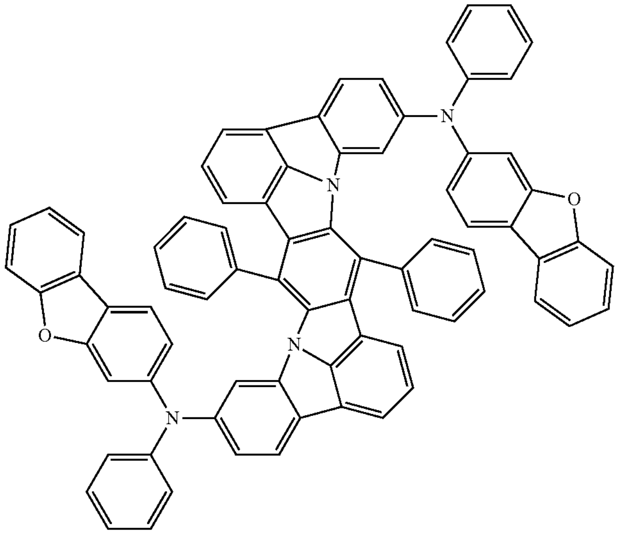

-continued
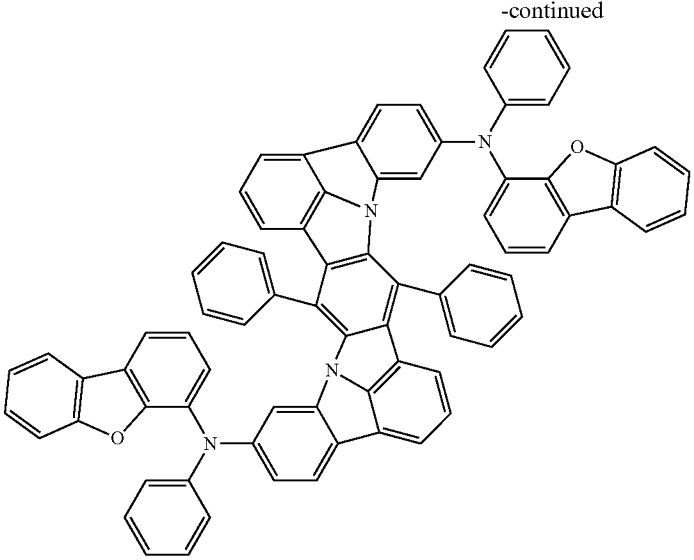
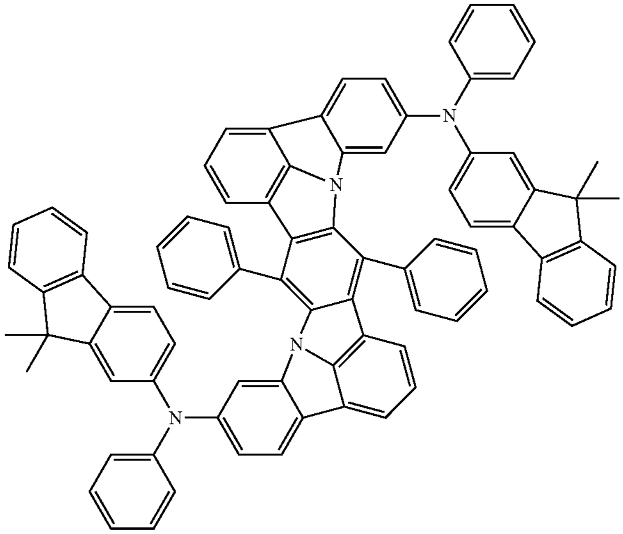
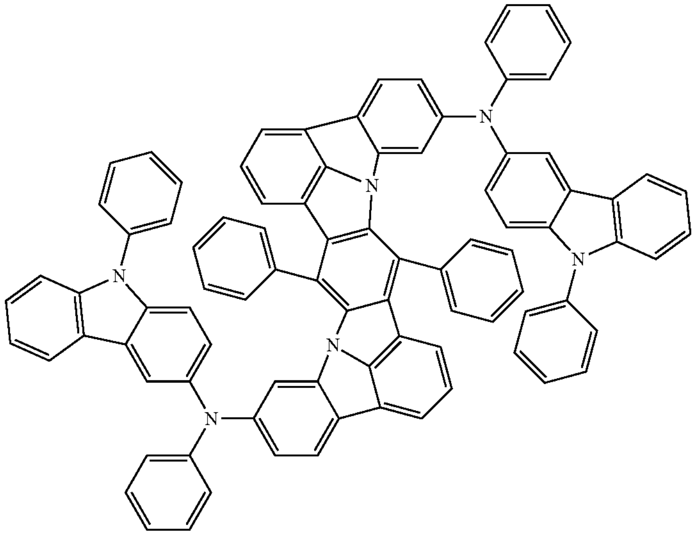

-continued
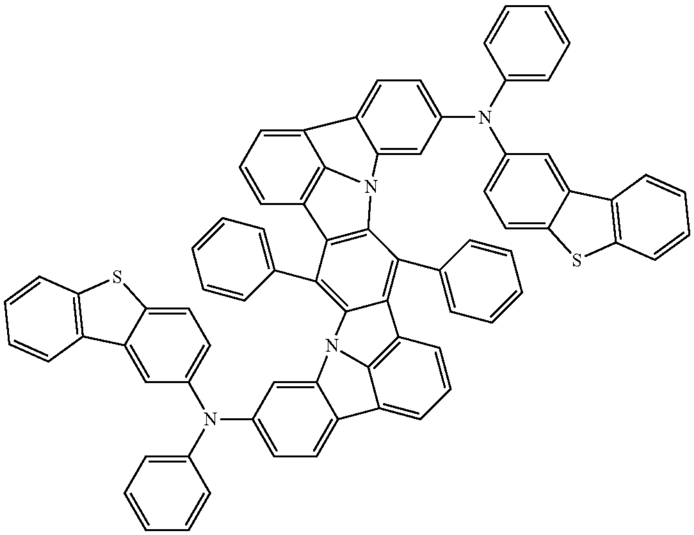
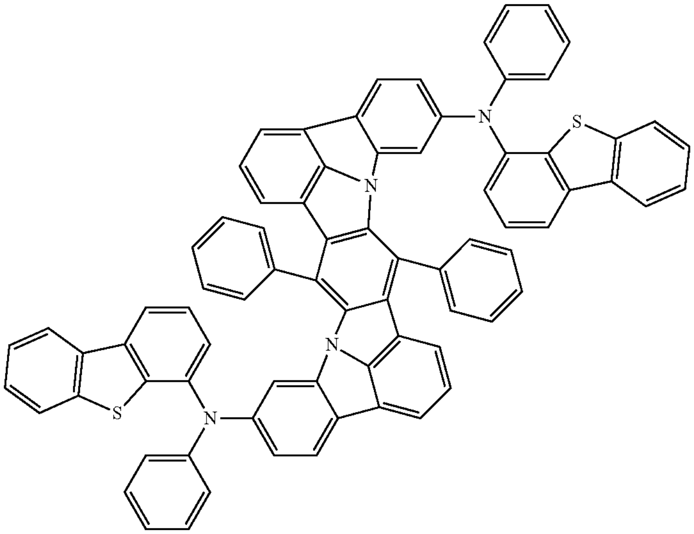
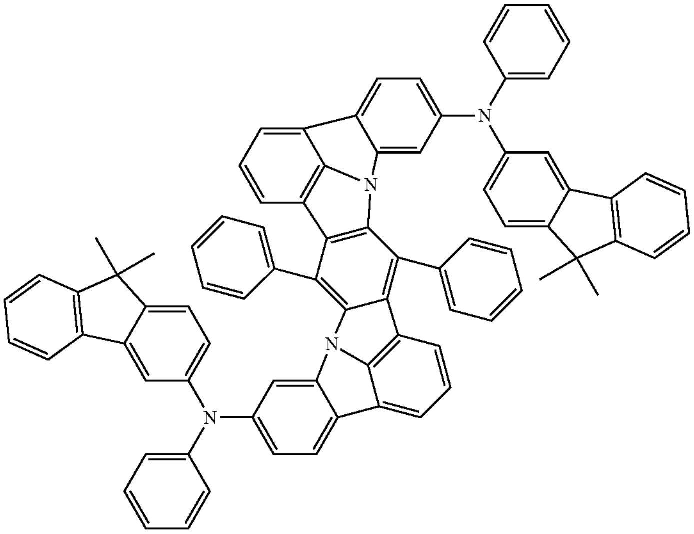

-continued
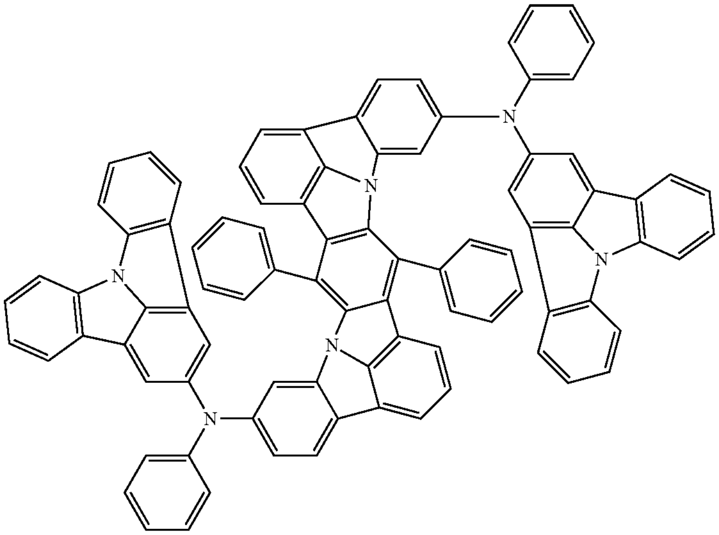
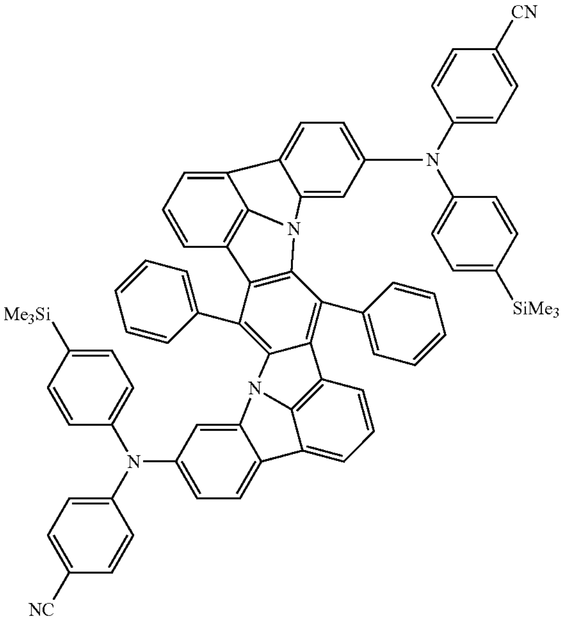
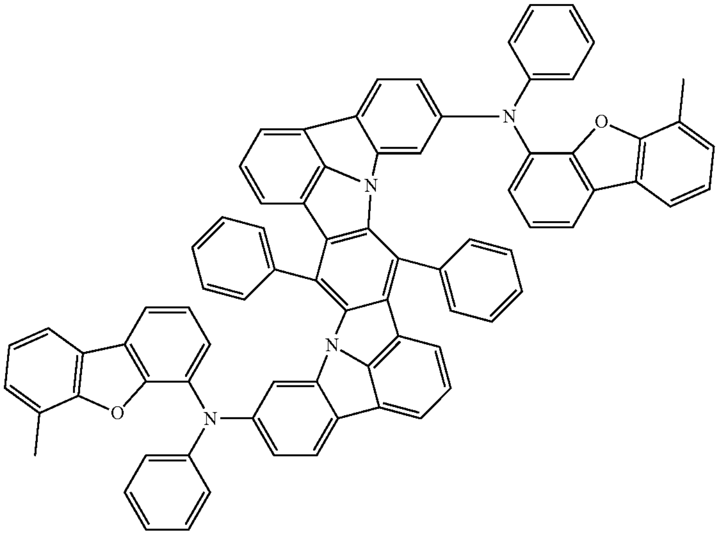

-continued
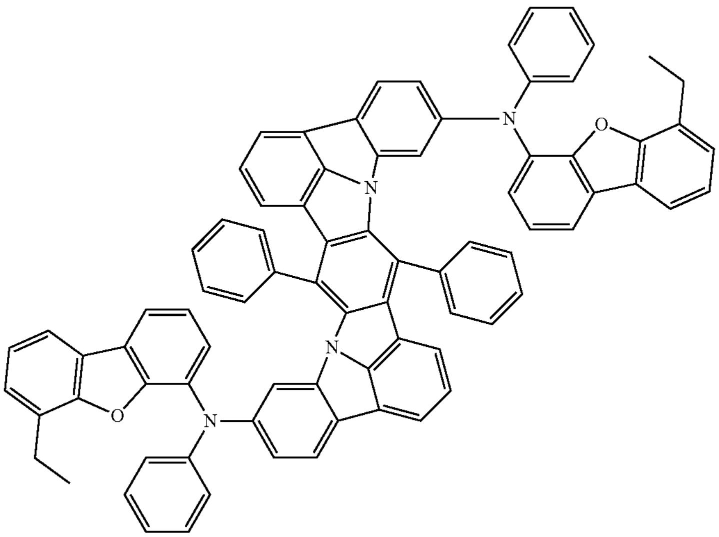
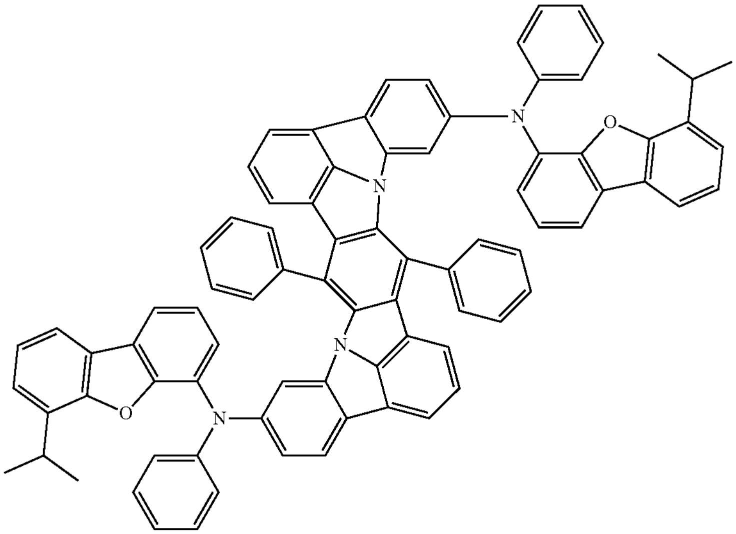
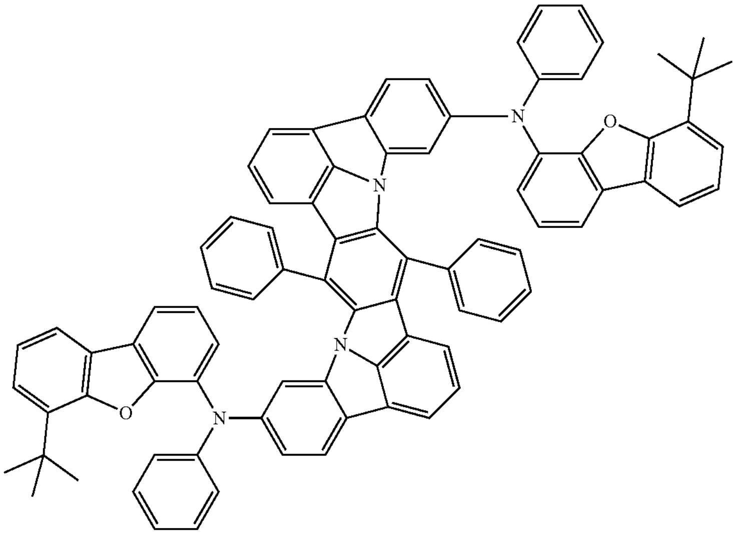

-continued
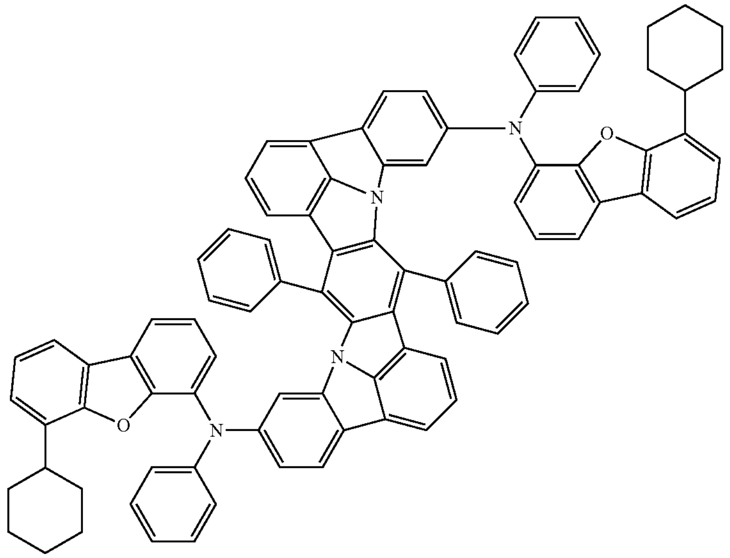
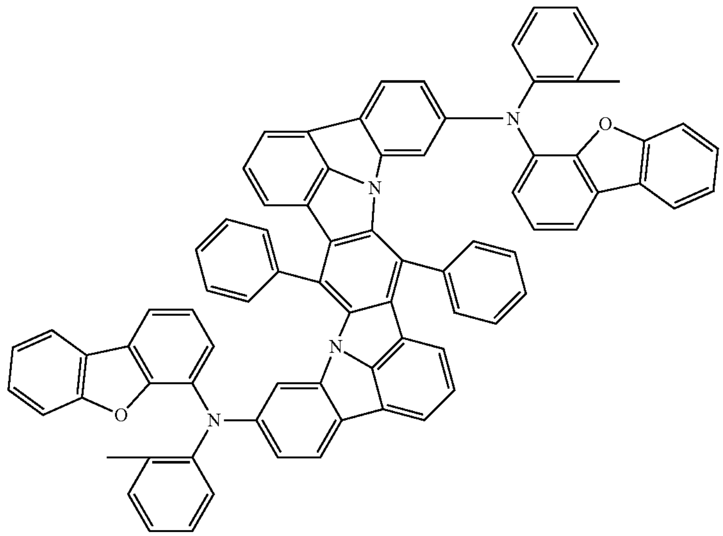
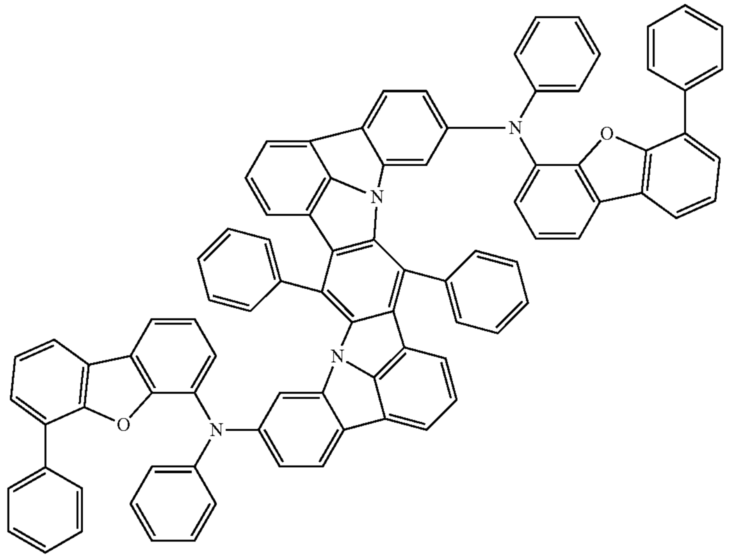

-continued
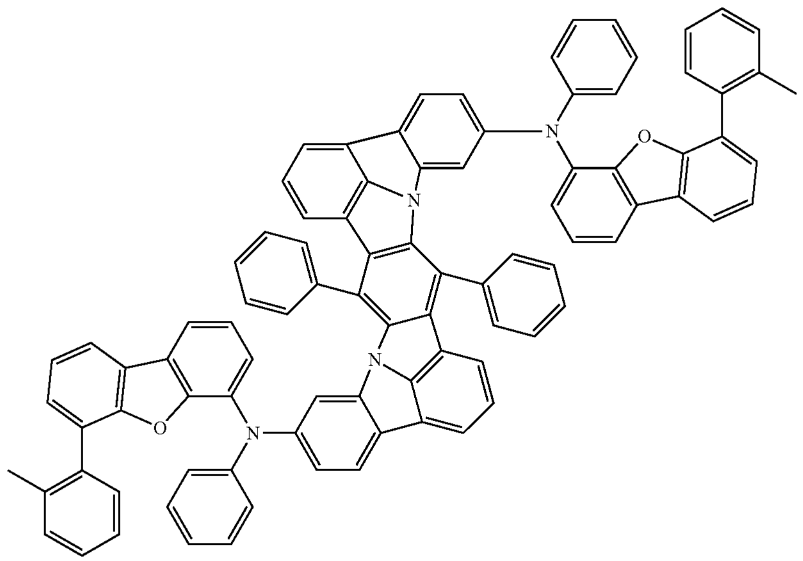
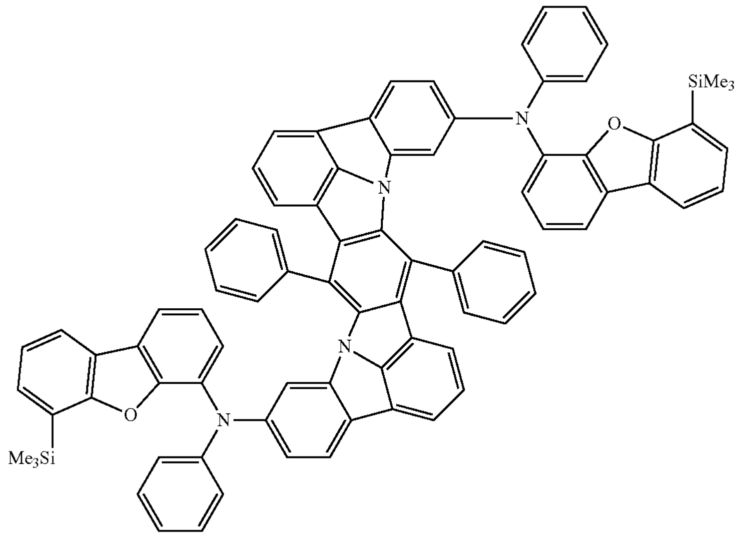
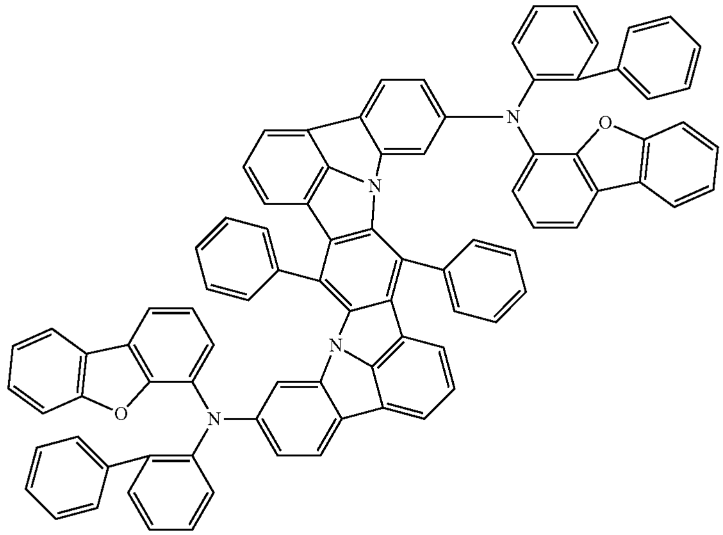

-continued
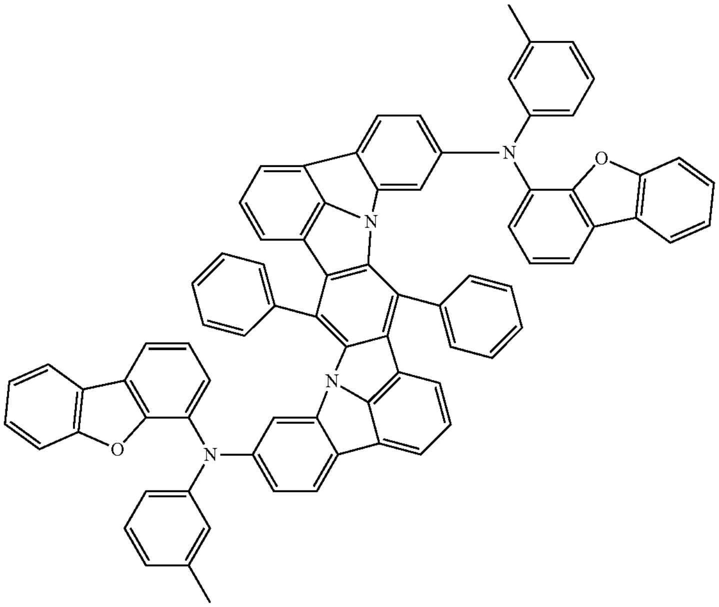
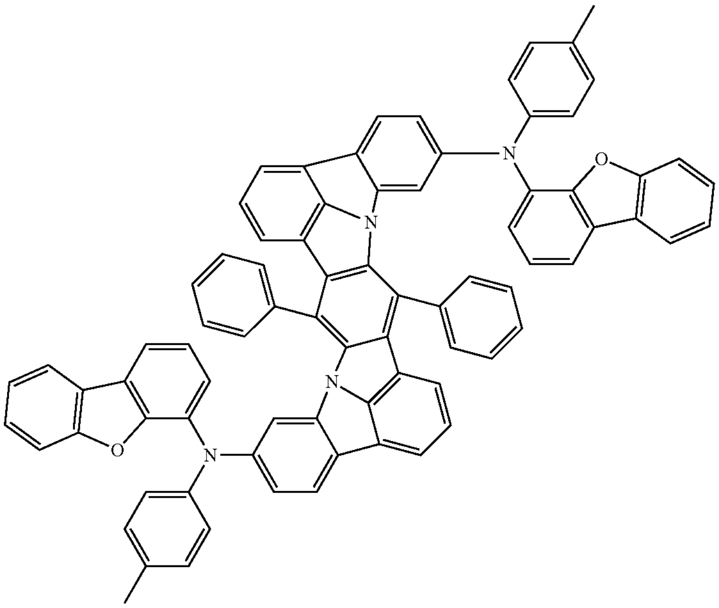

-continued
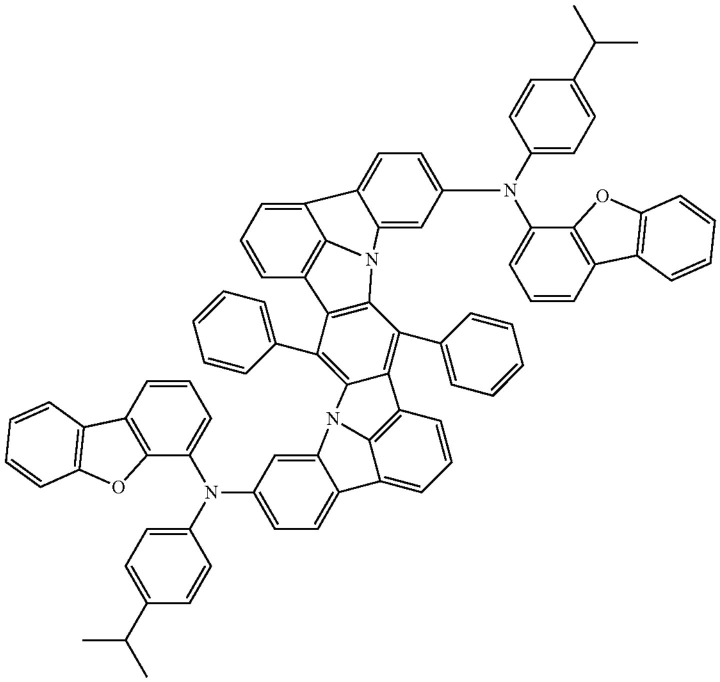
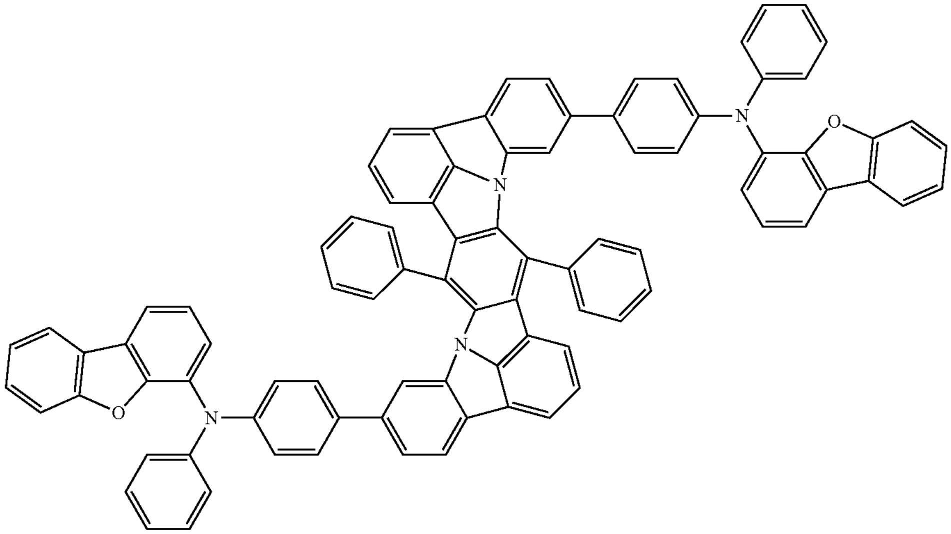

-continued
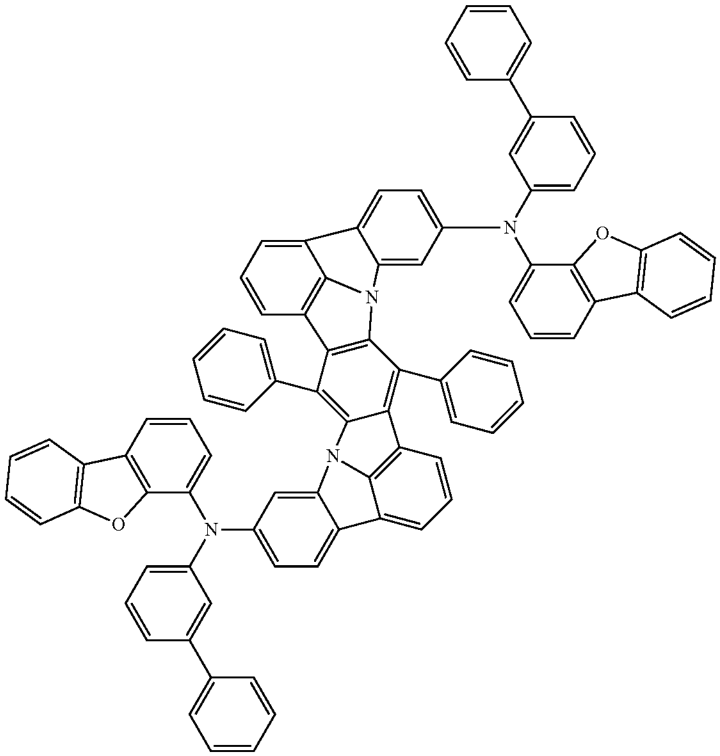
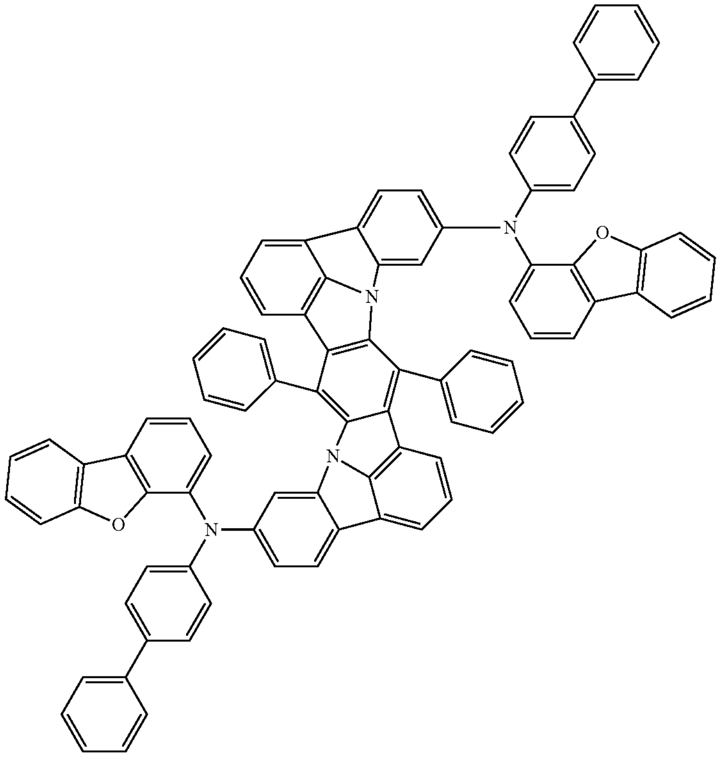

-continued
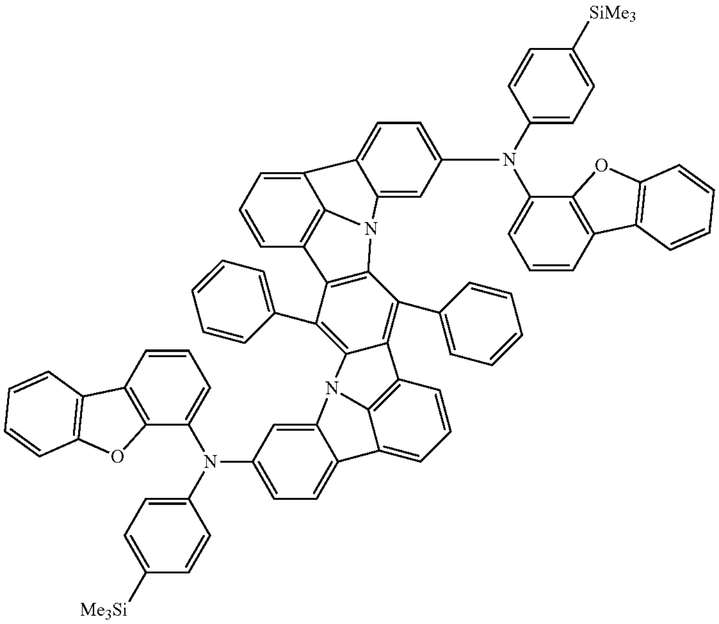
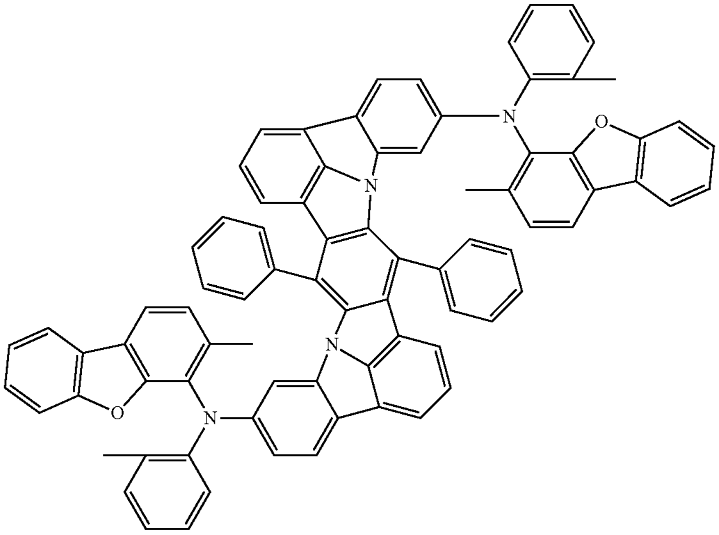
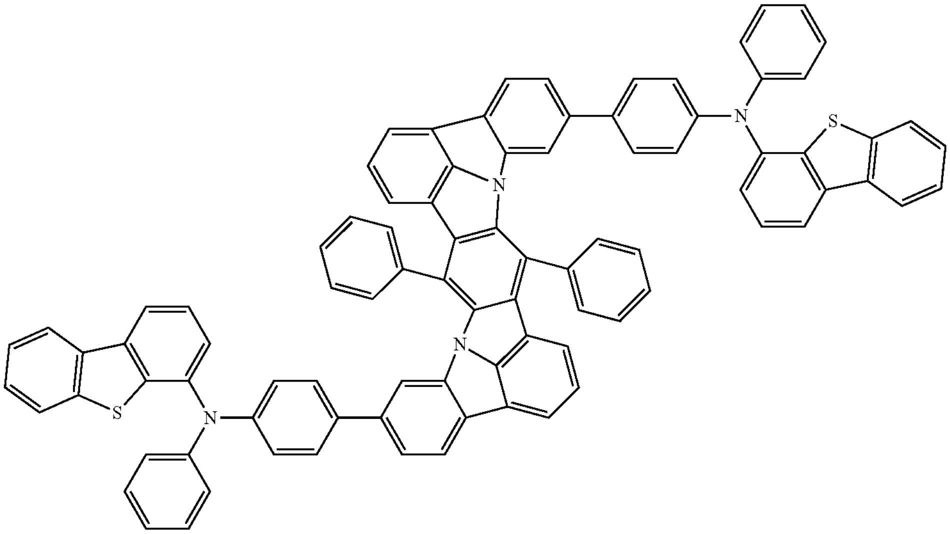

-continued
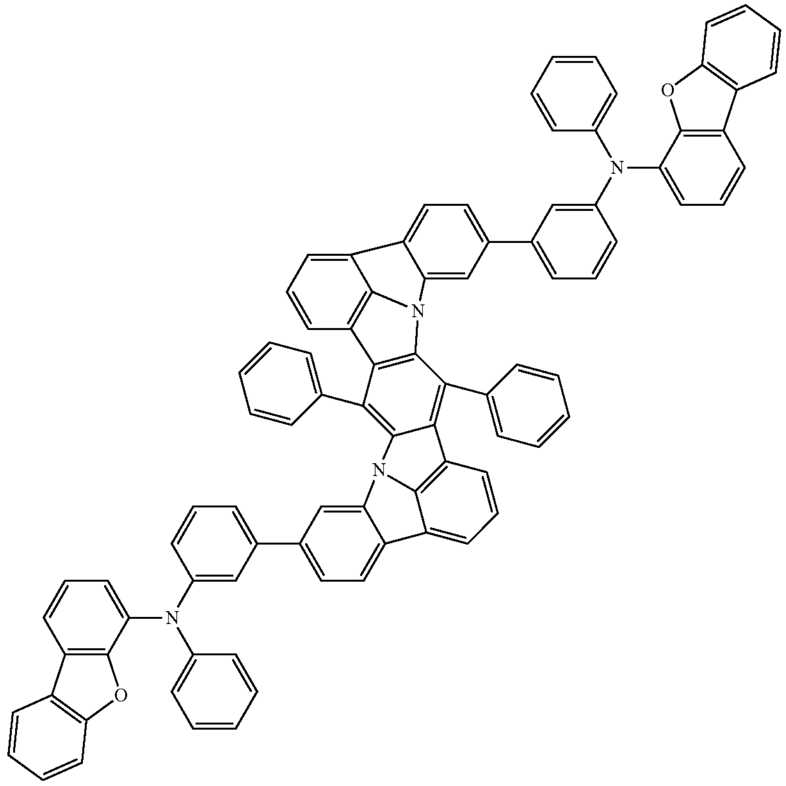
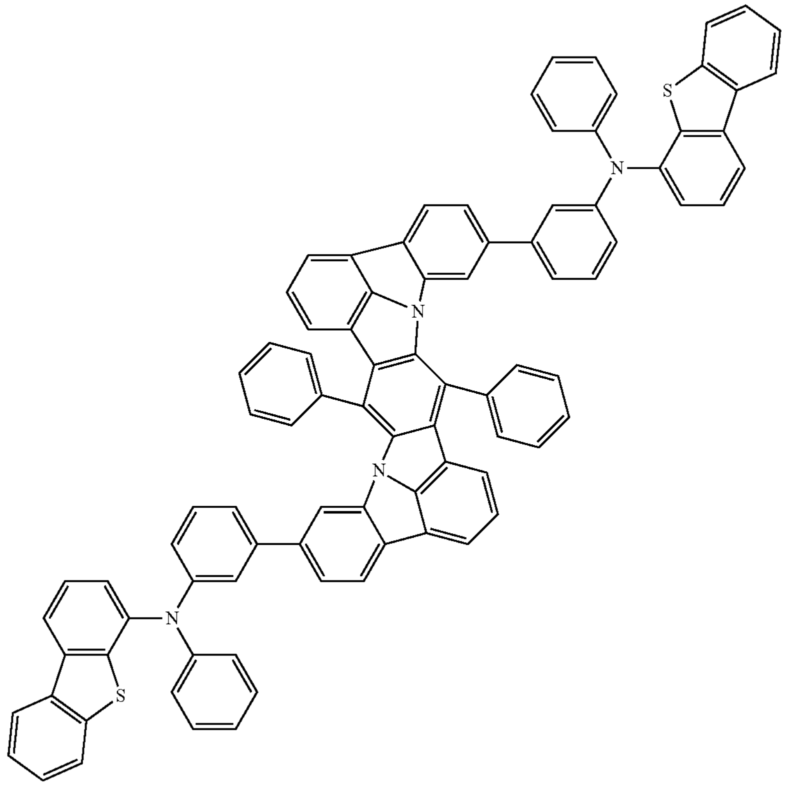

-continued
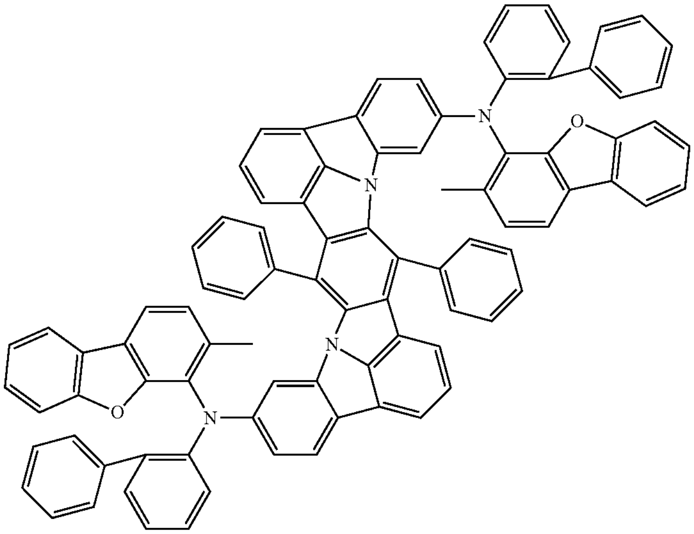
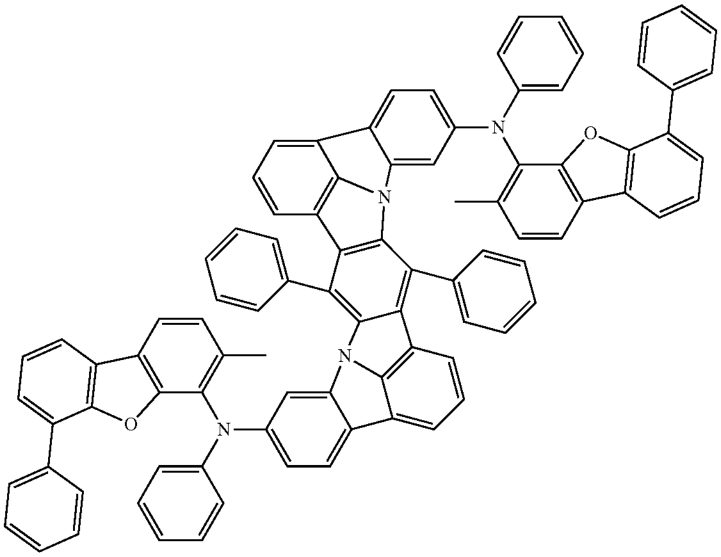
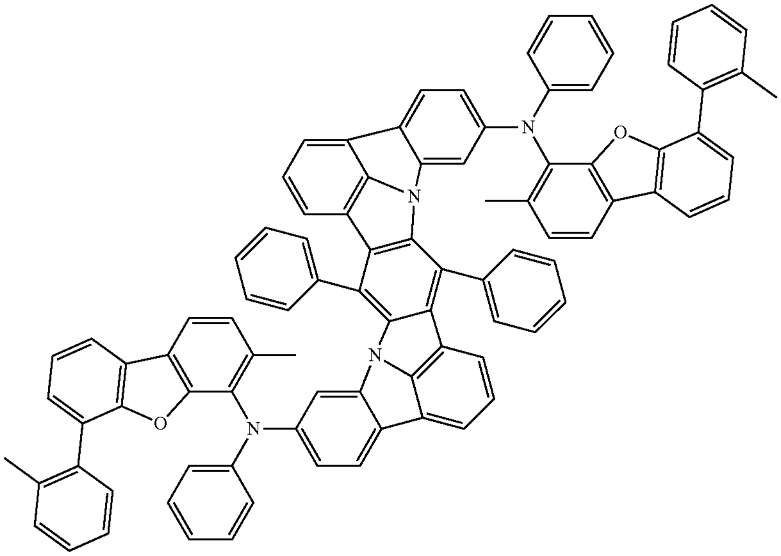

-continued
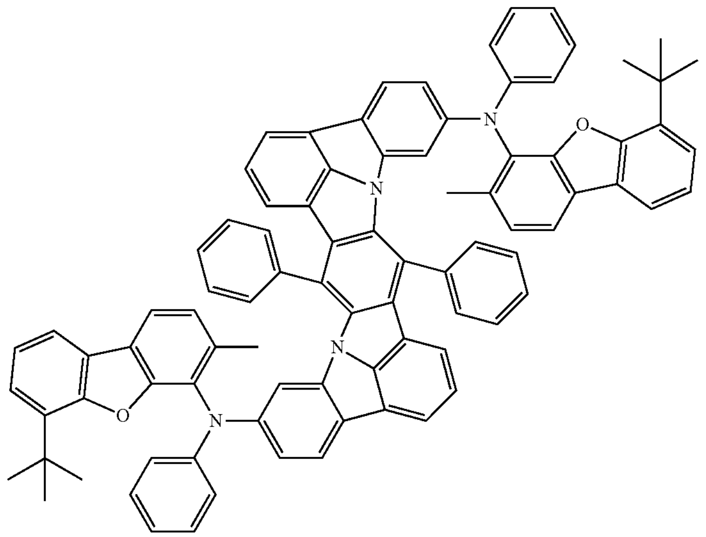
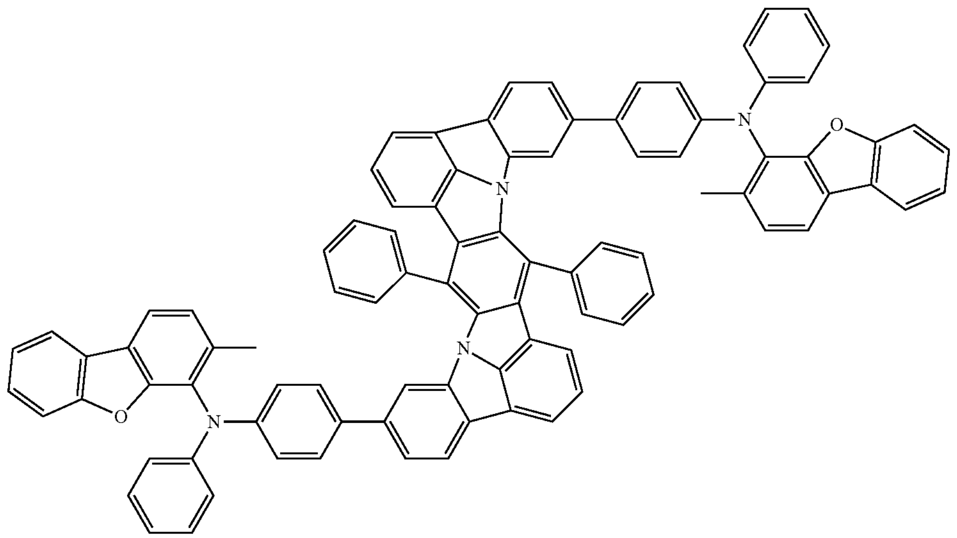

-continued
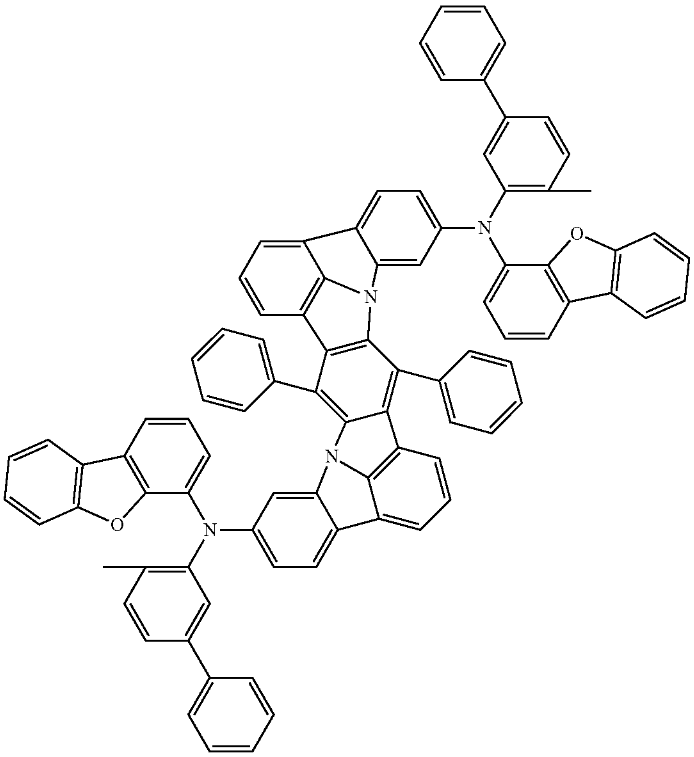
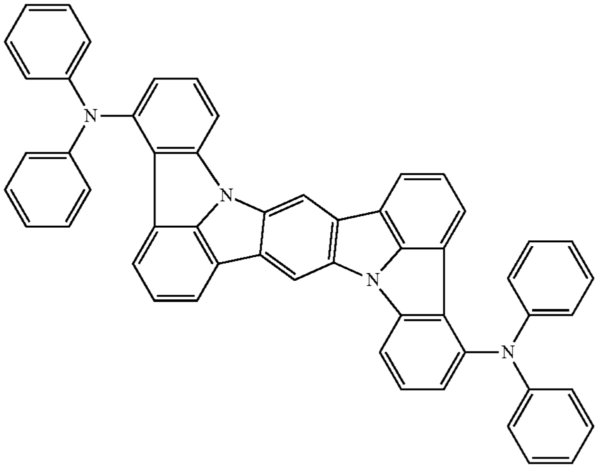
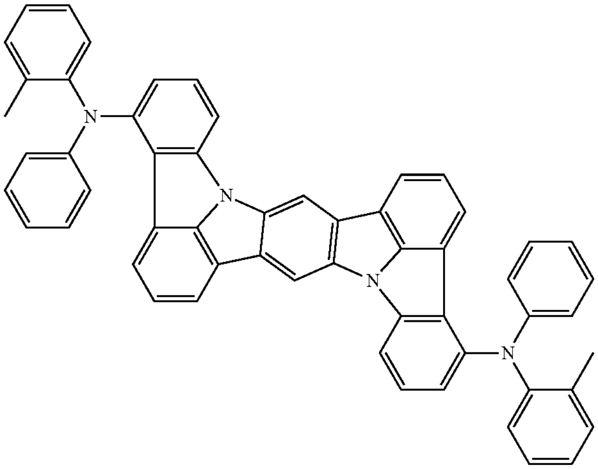

-continued
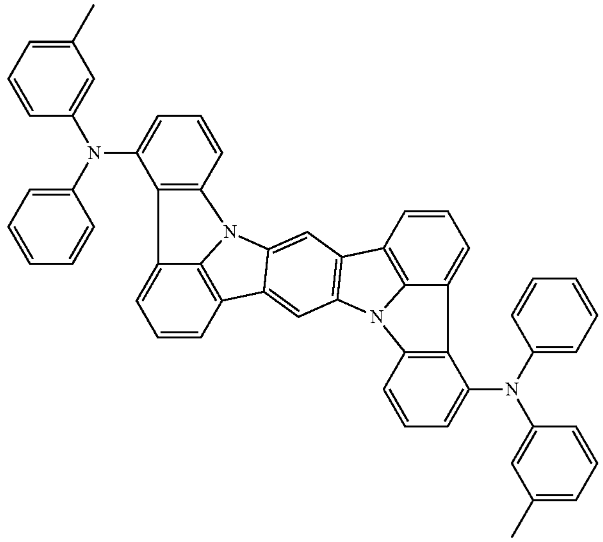
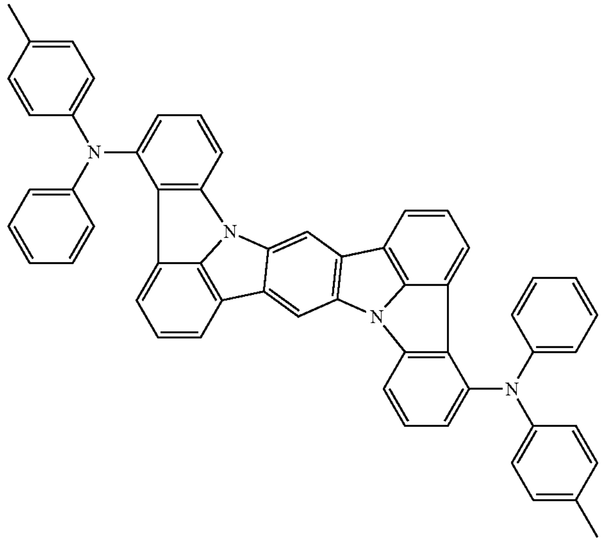
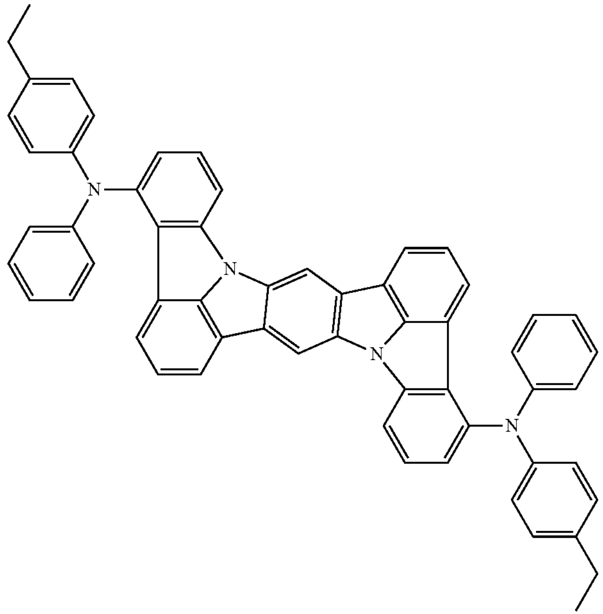

-continued
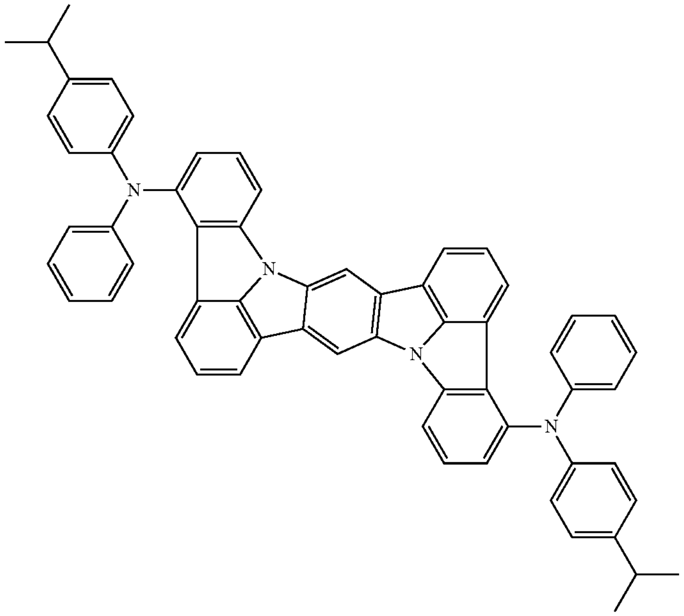
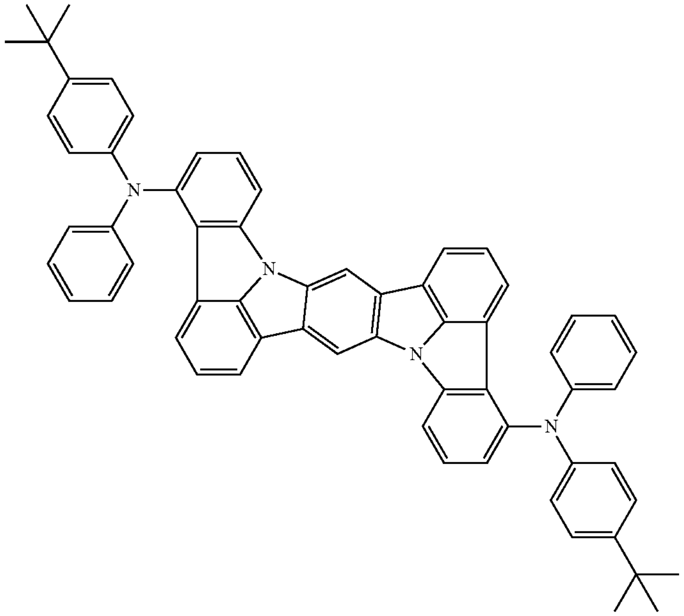

-continued
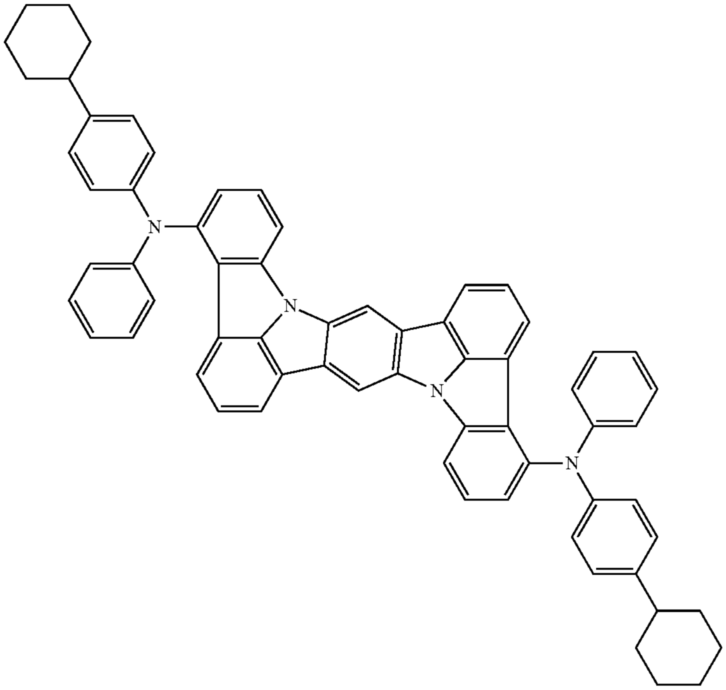
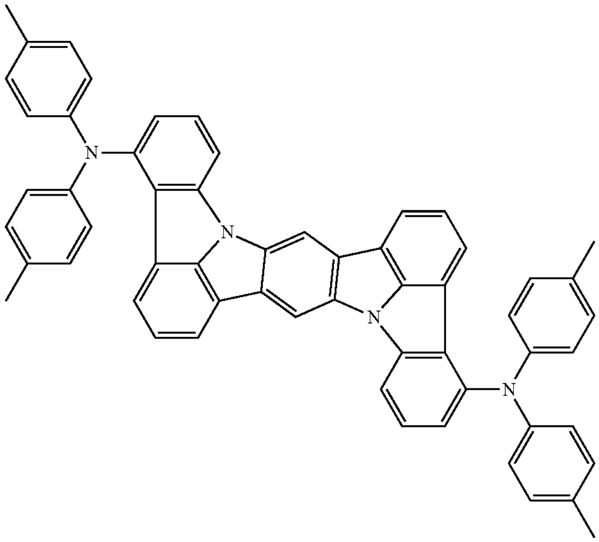

-continued
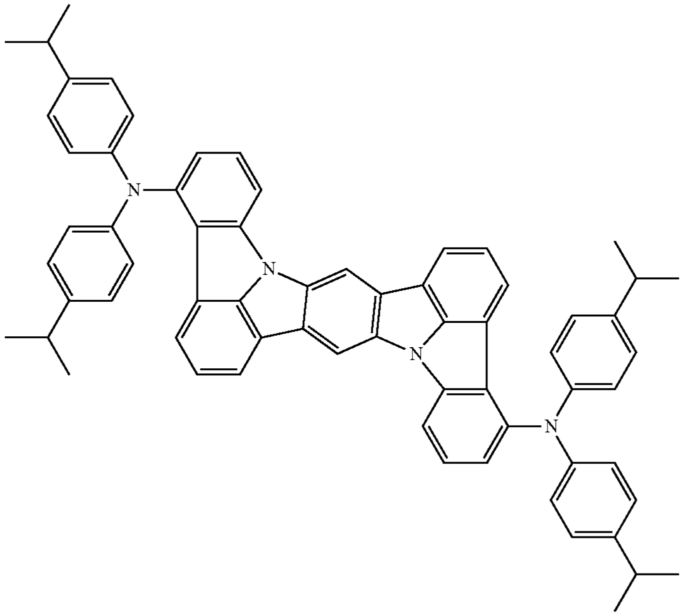
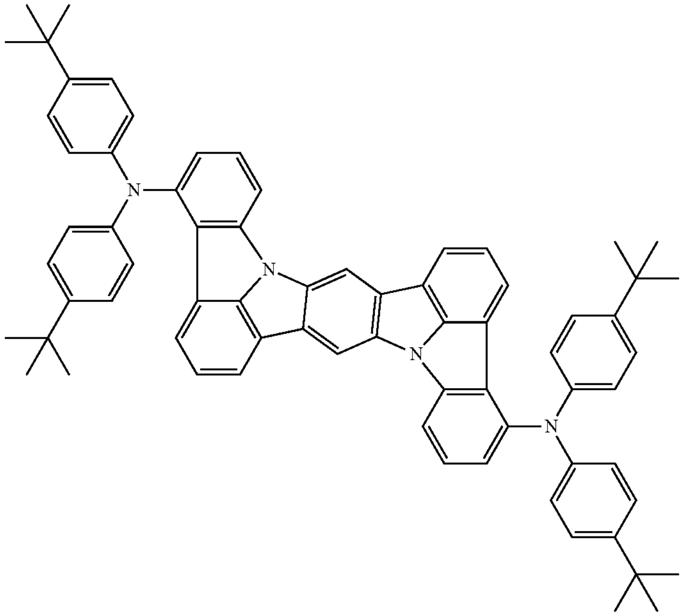

-continued
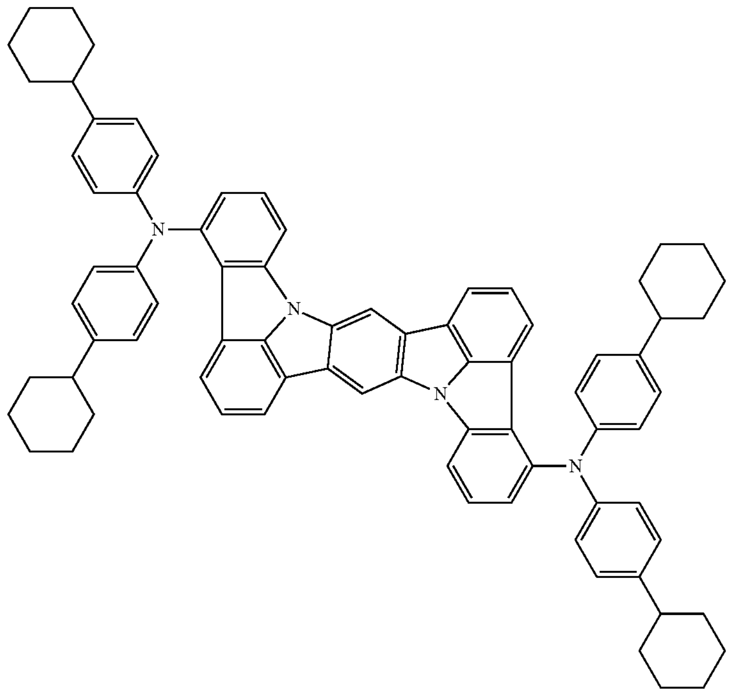
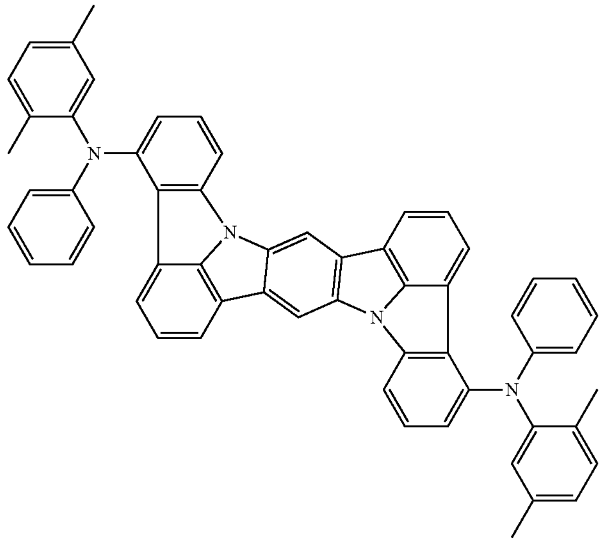

-continued
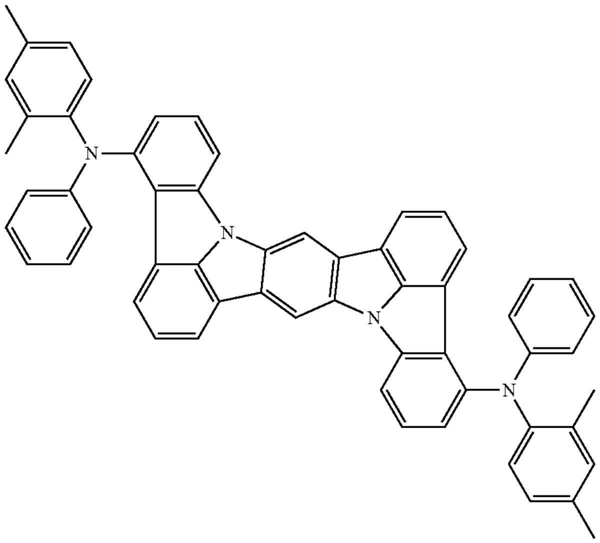
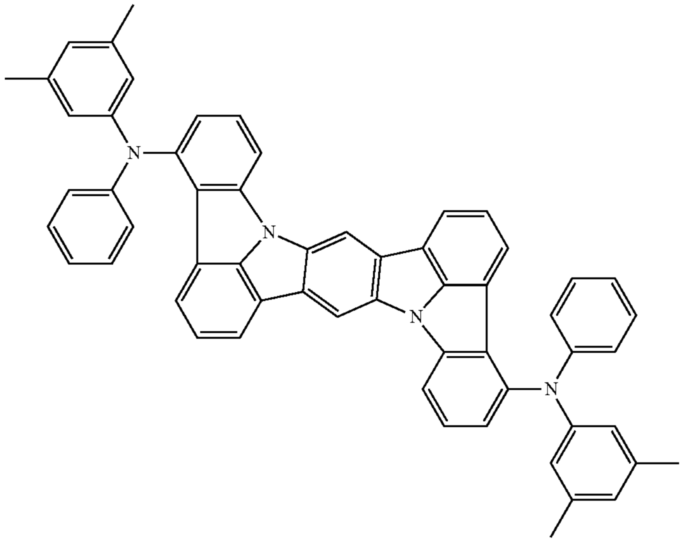
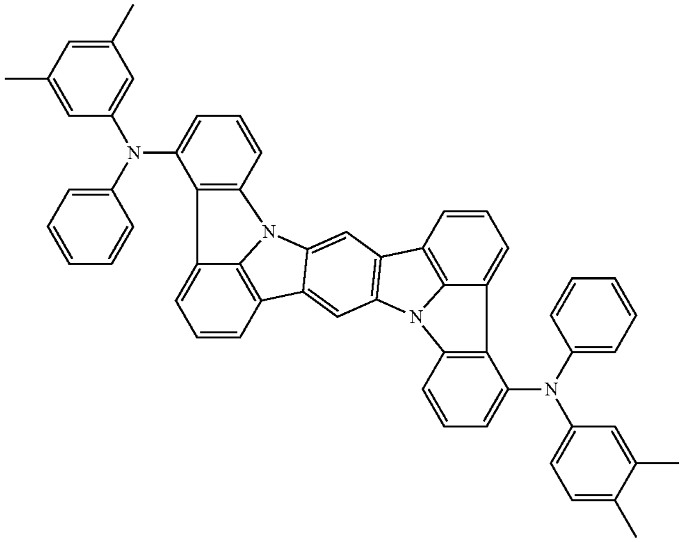

-continued
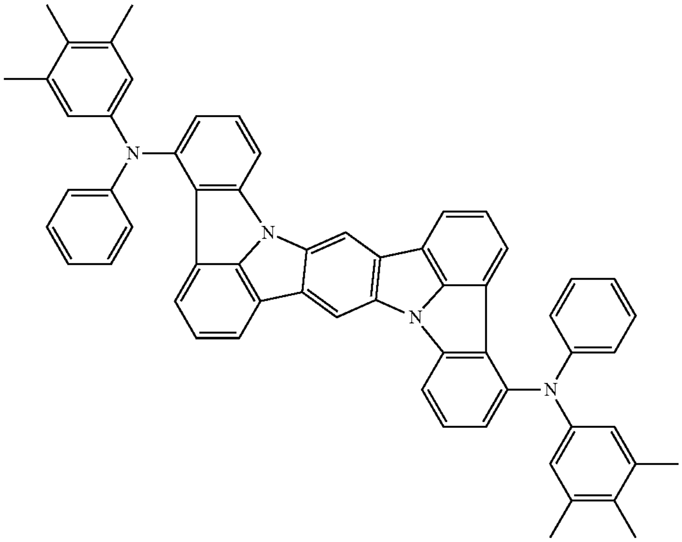
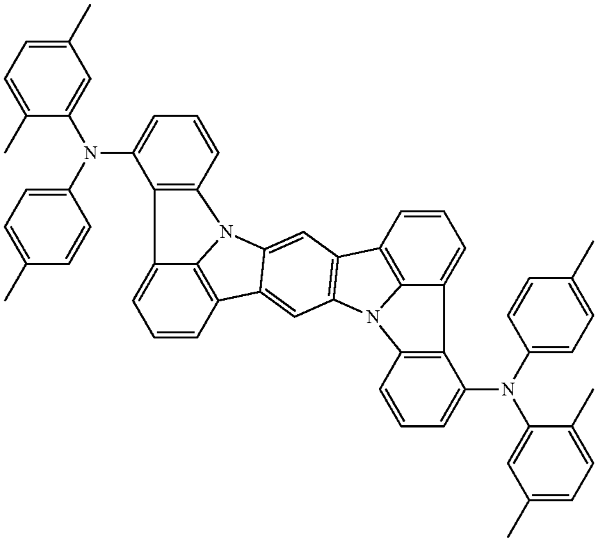
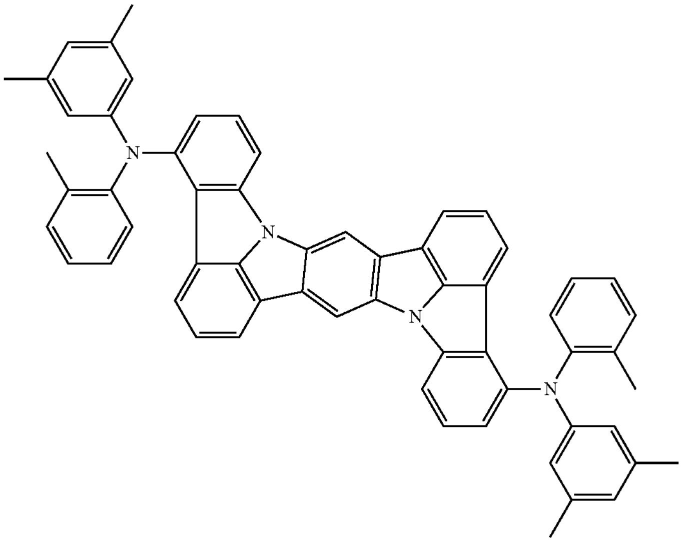

-continued
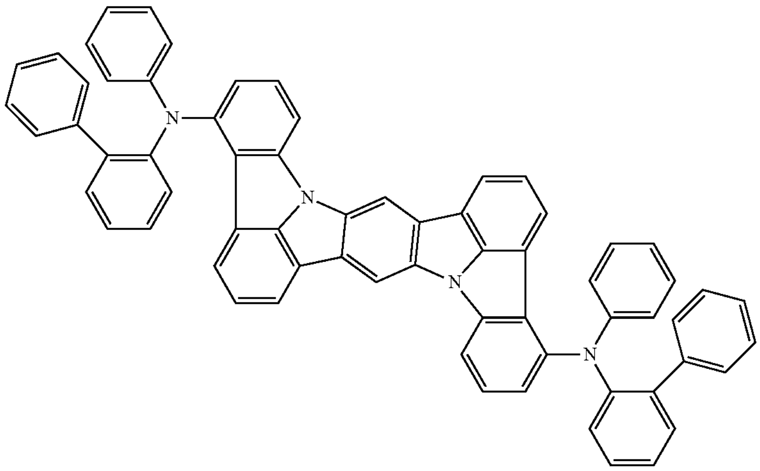
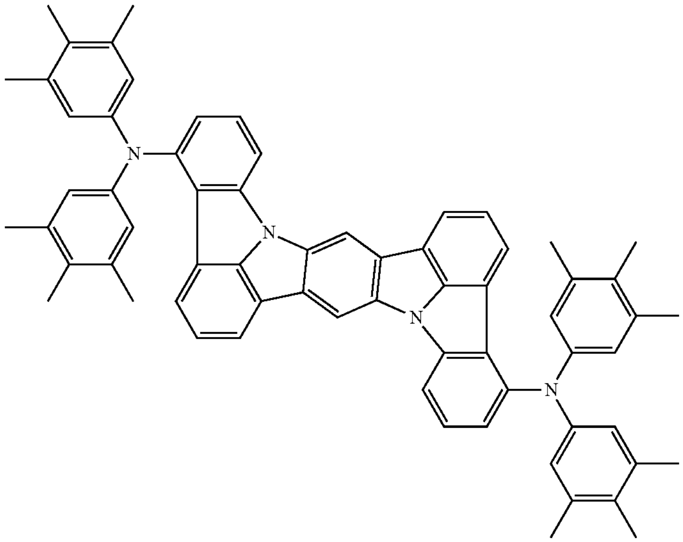
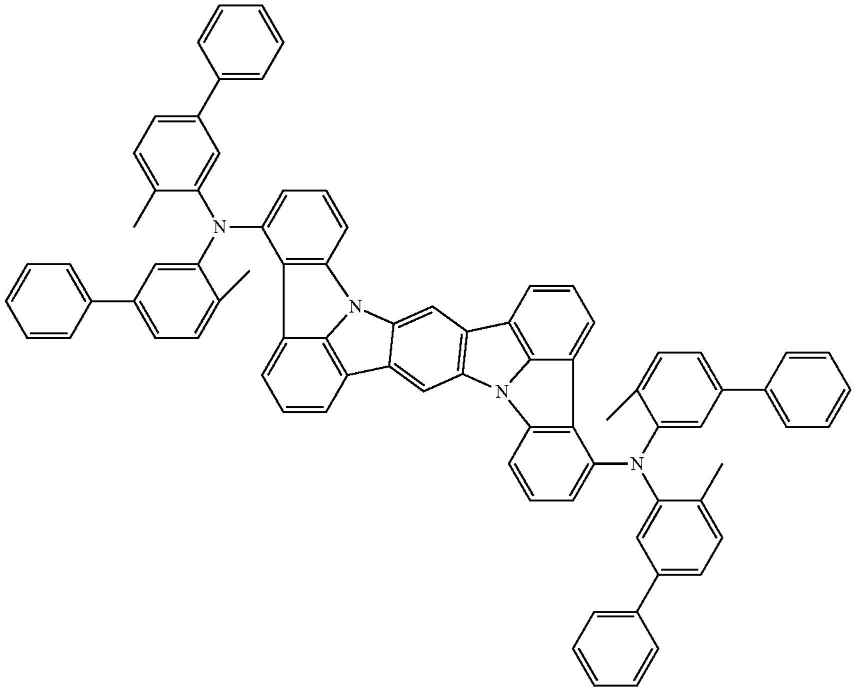

-continued
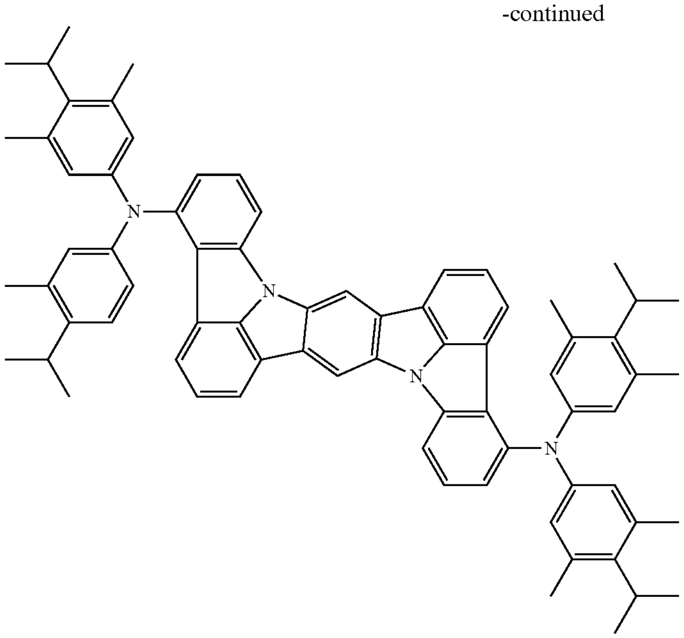
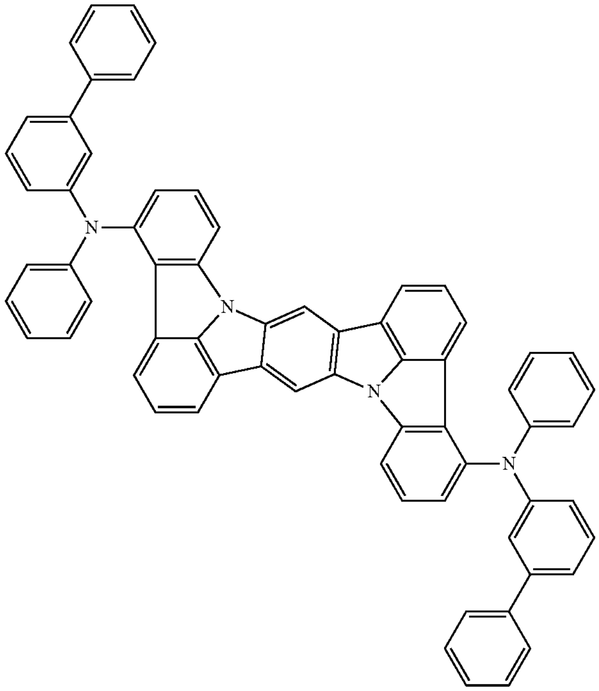

-continued
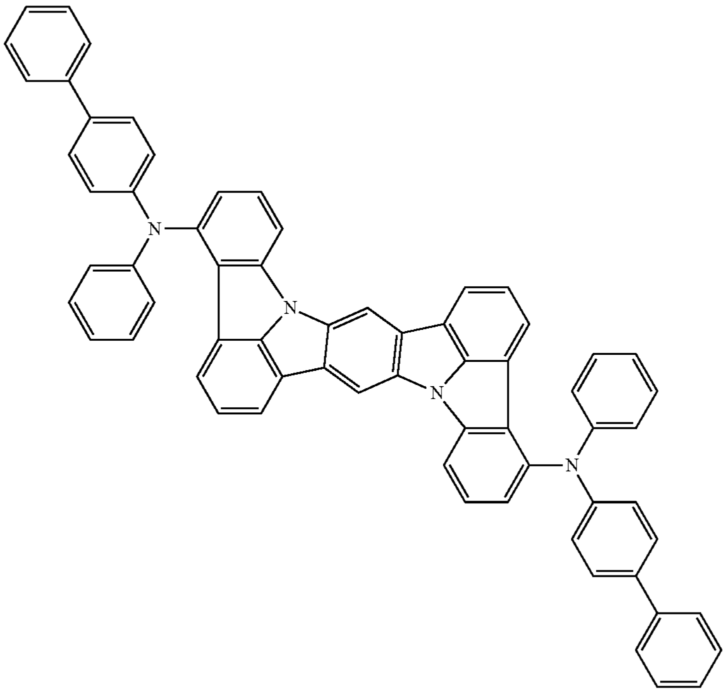
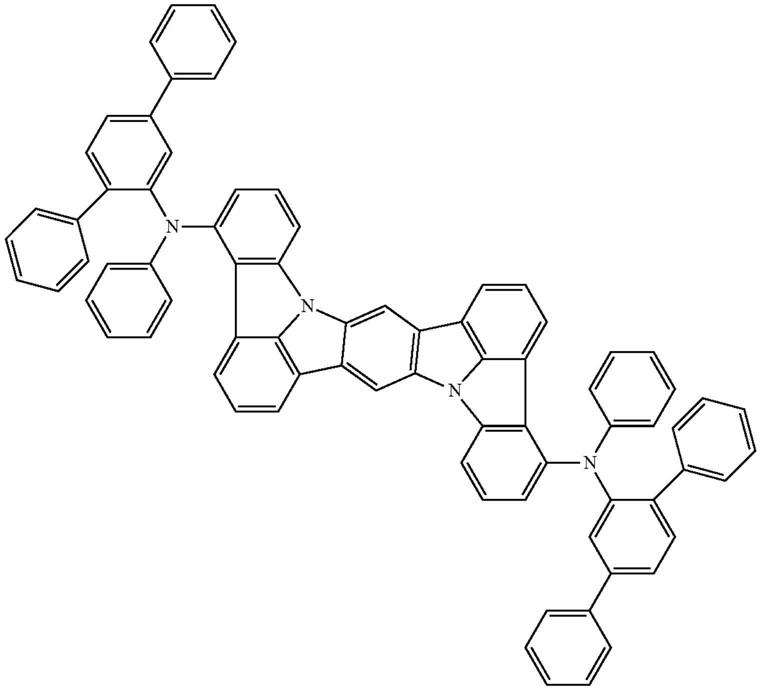

-continued
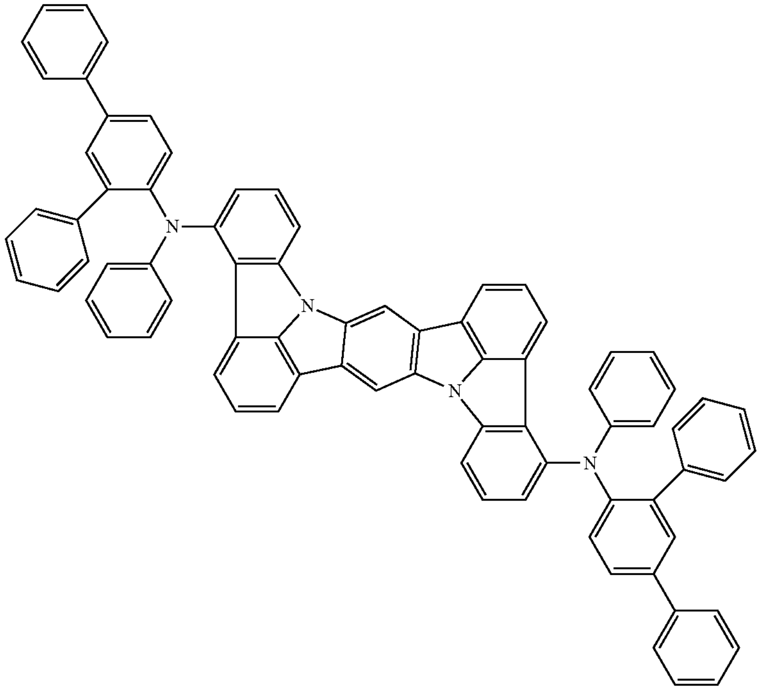
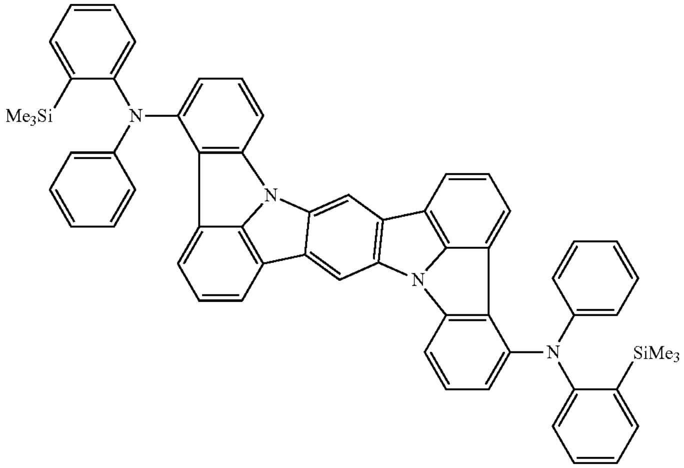
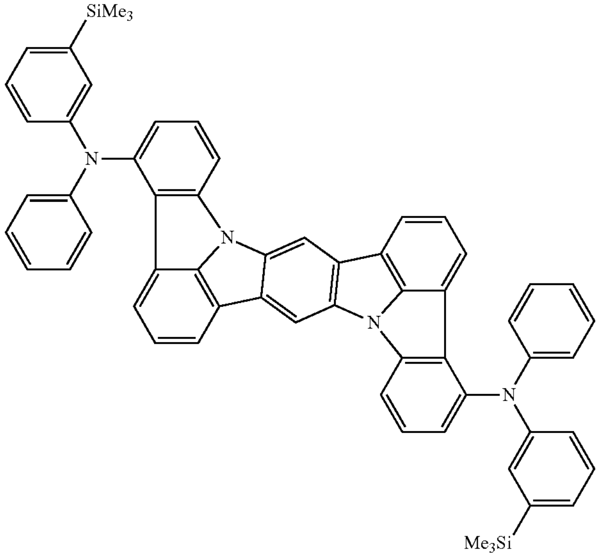

-continued
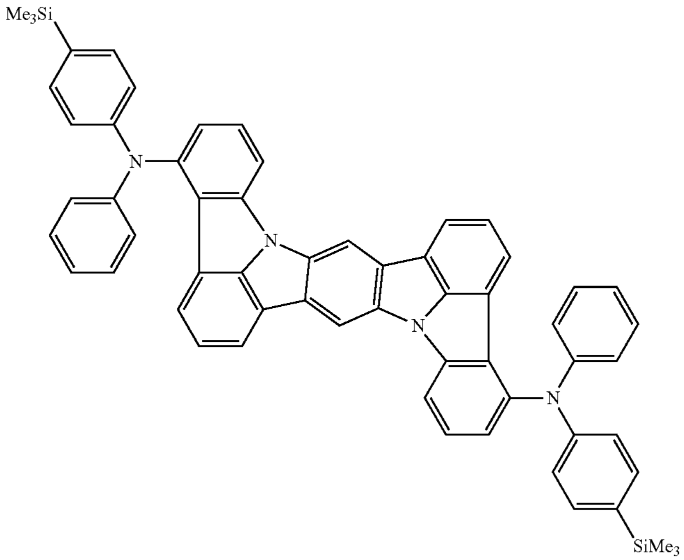
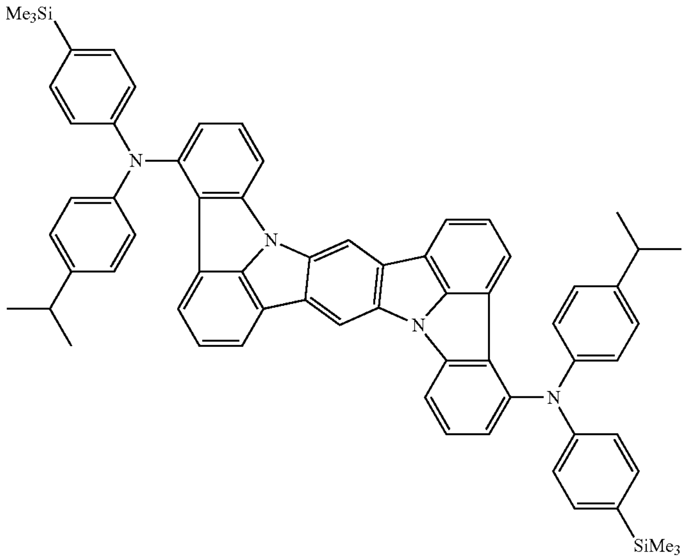
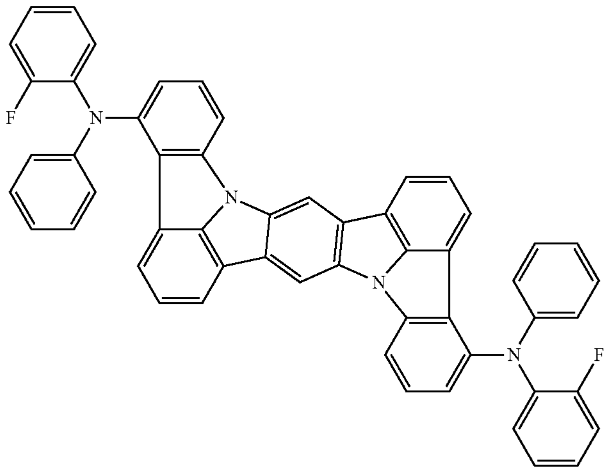

-continued
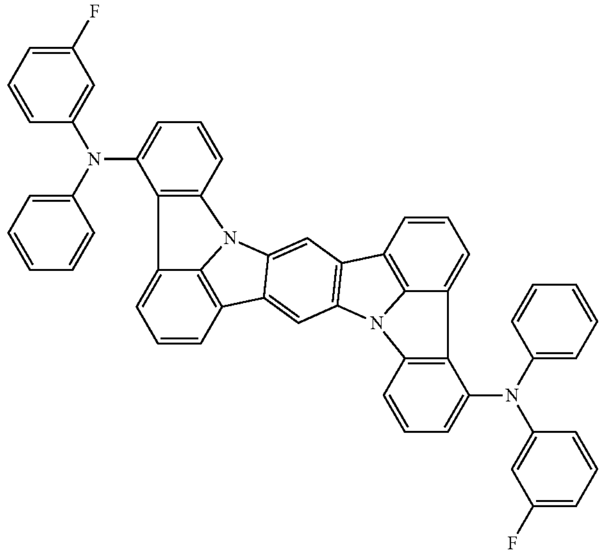
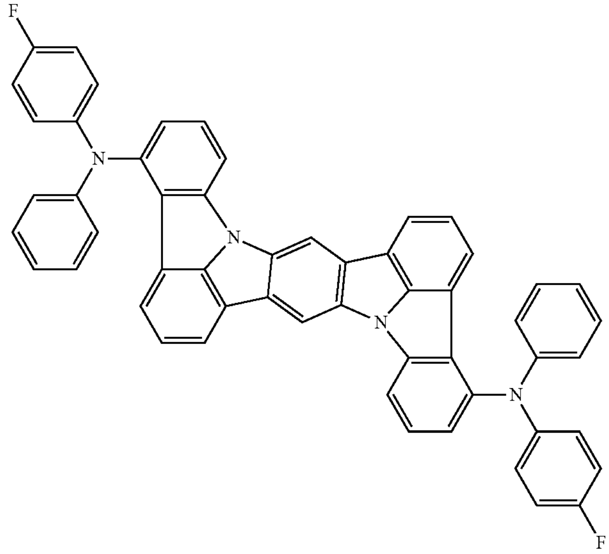
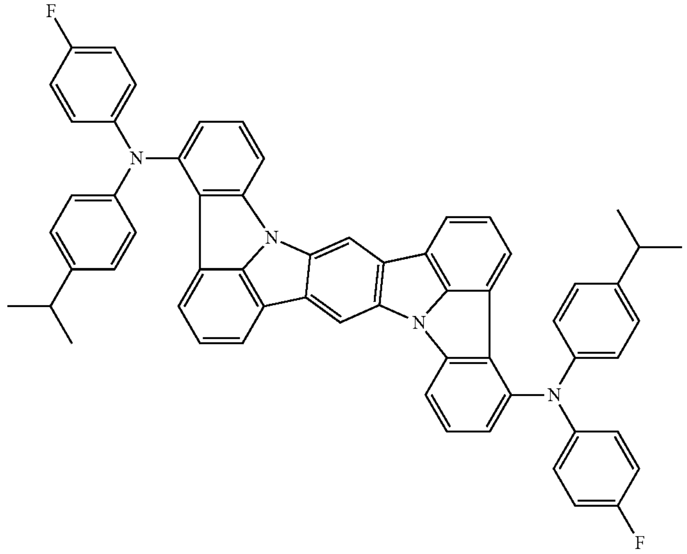

-continued
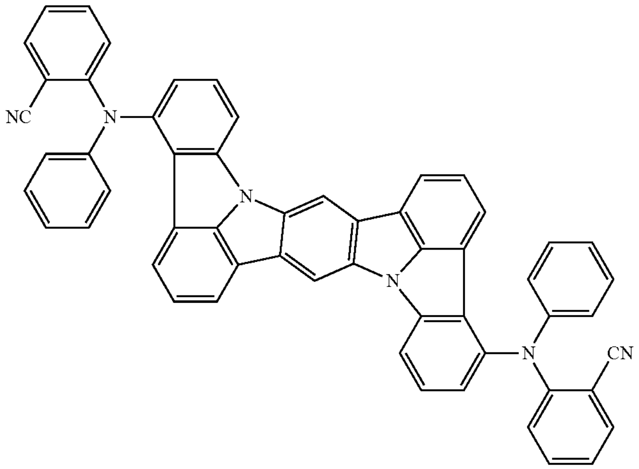
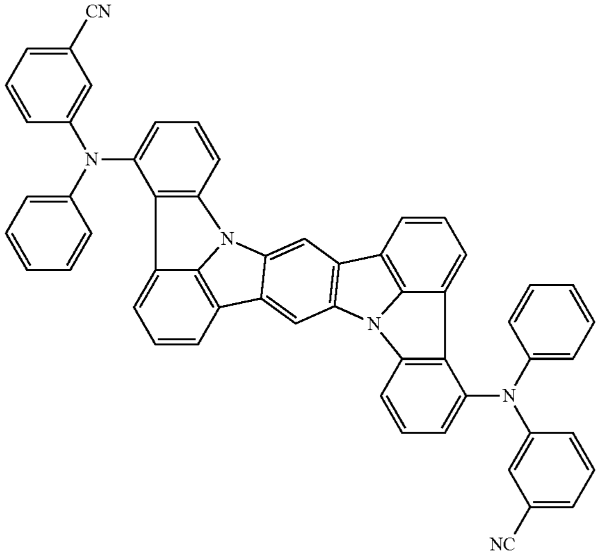
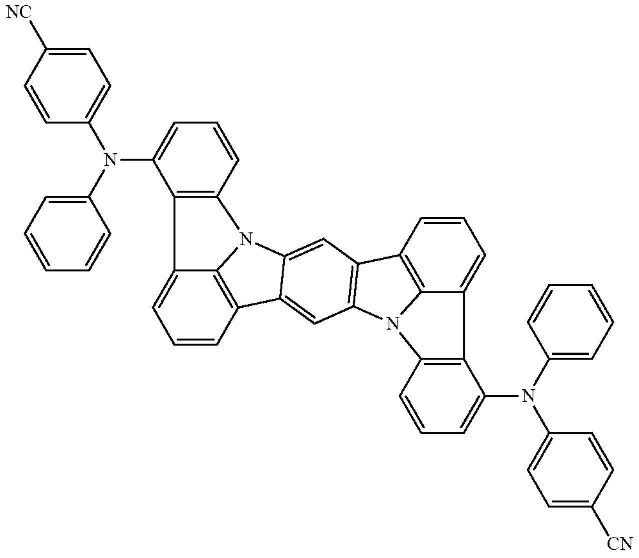

-continued
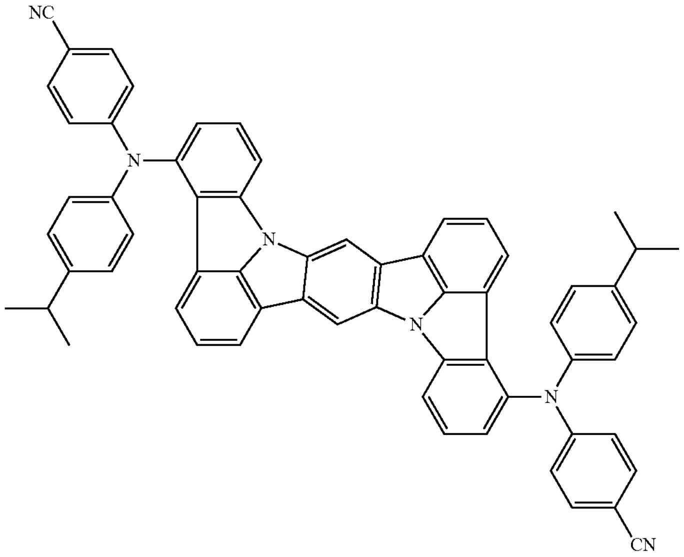
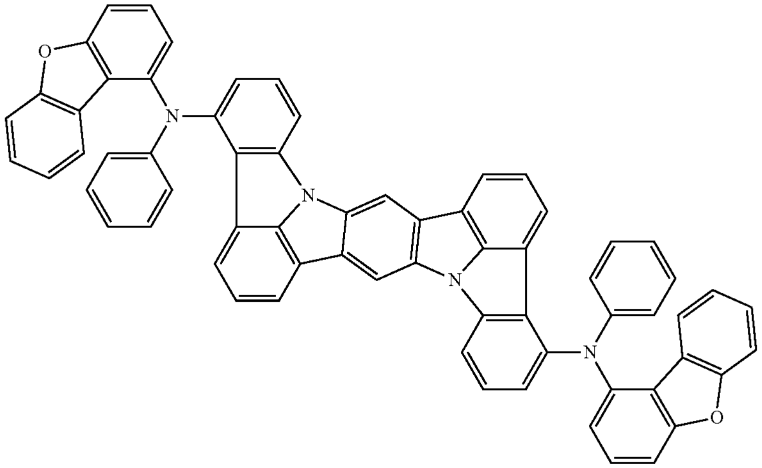
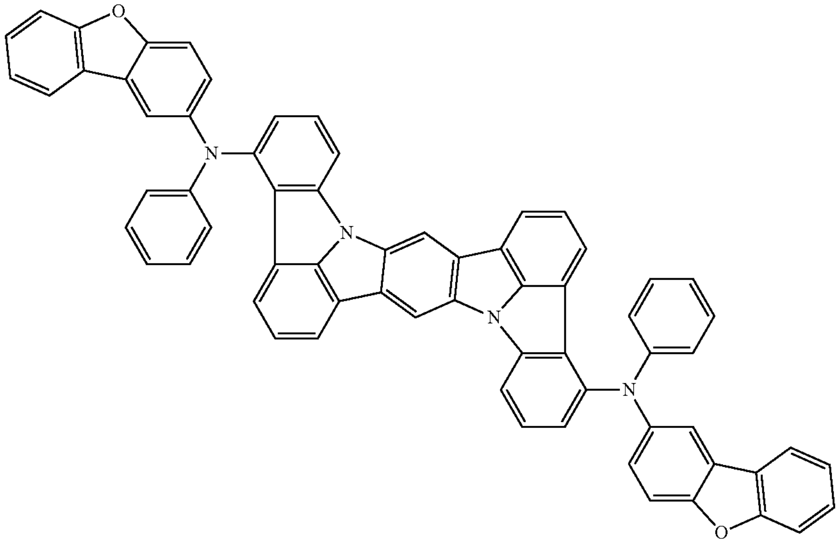

-continued
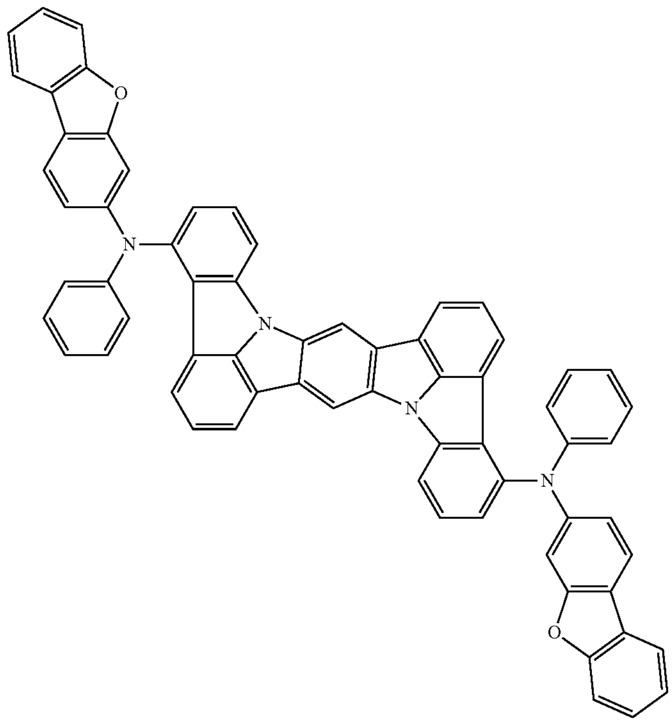
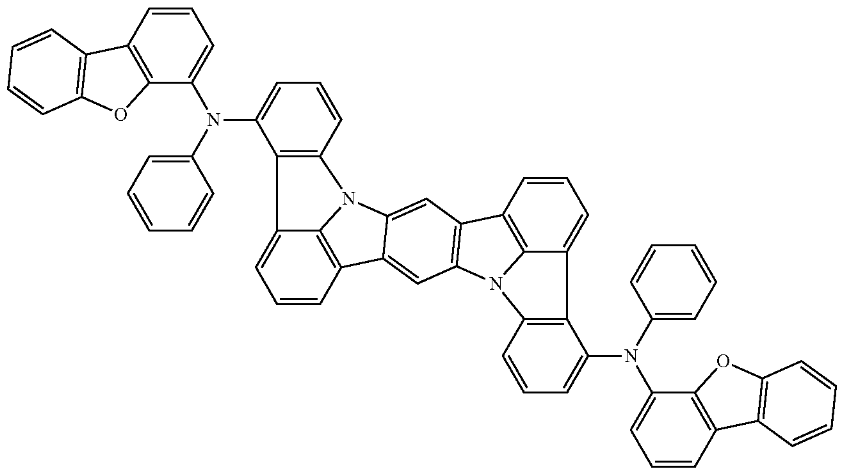

-continued
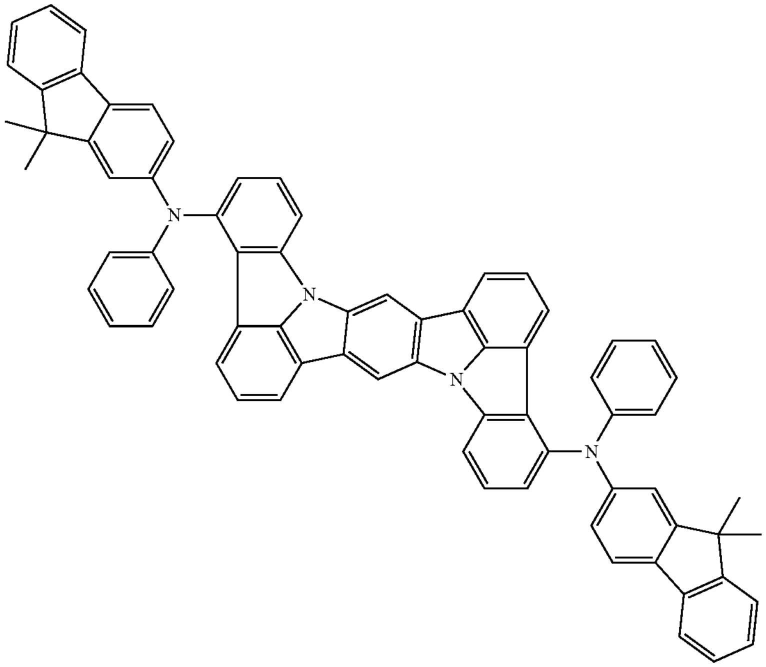
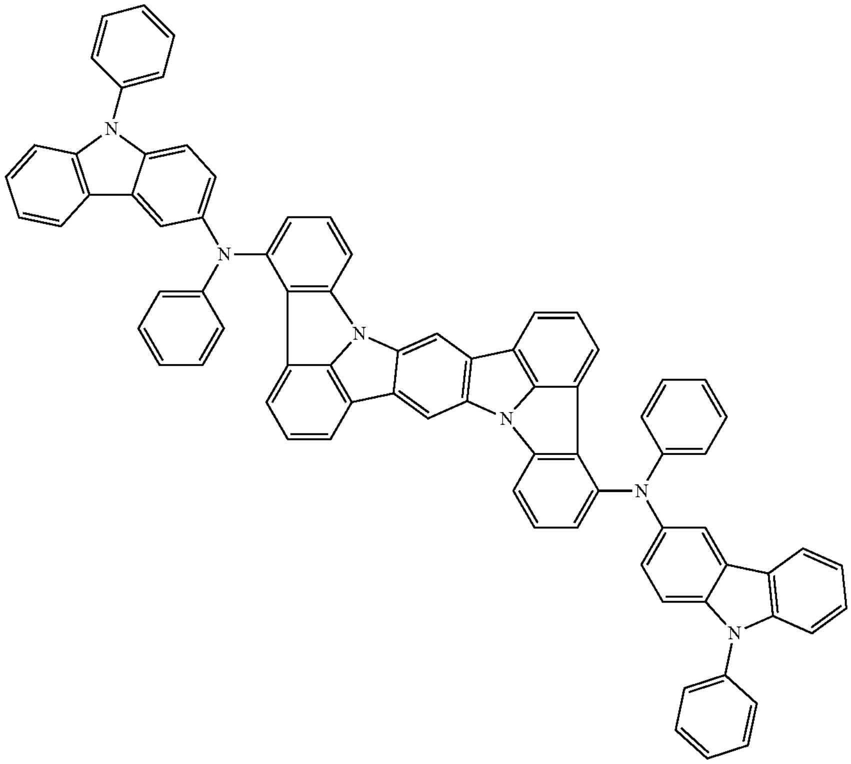

-continued
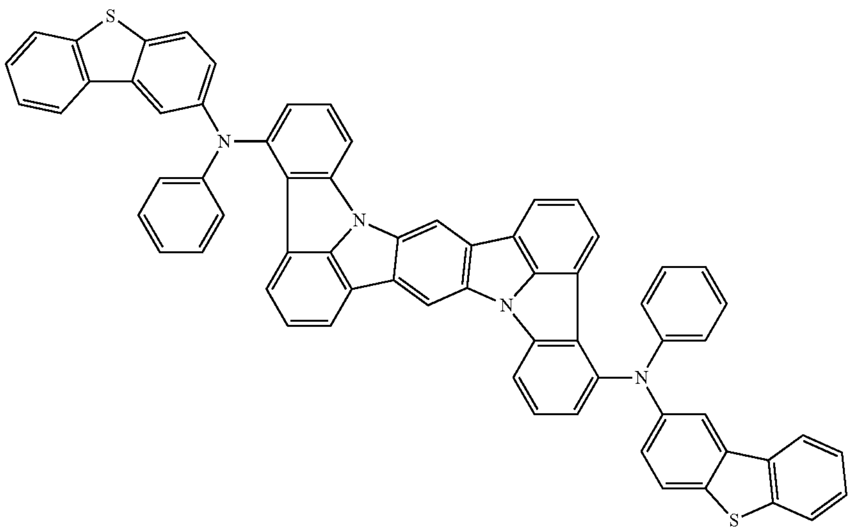
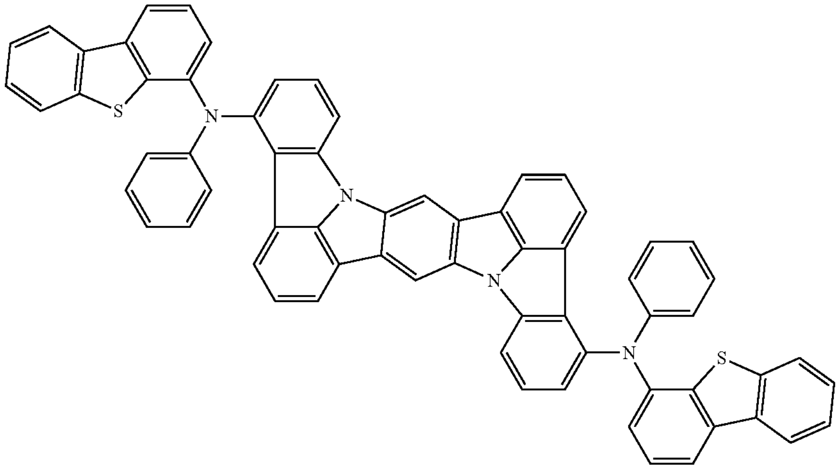
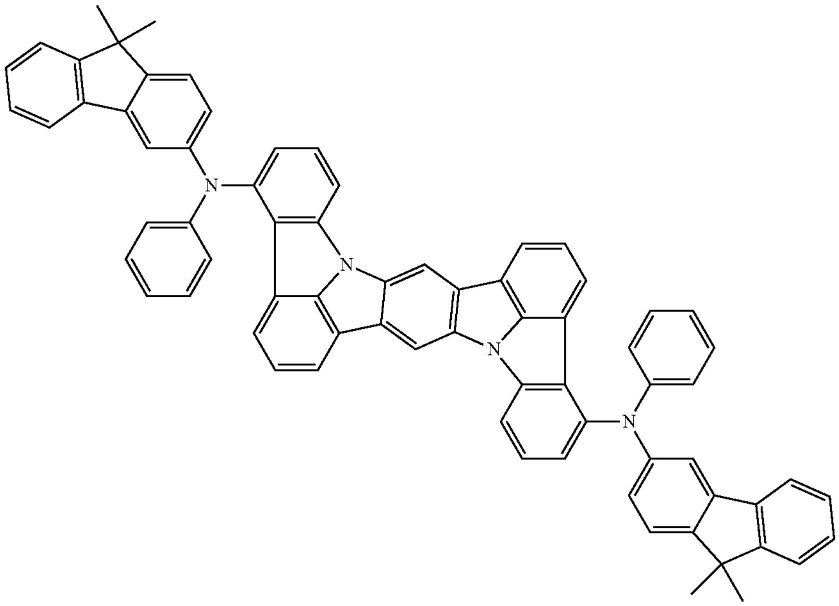

-continued
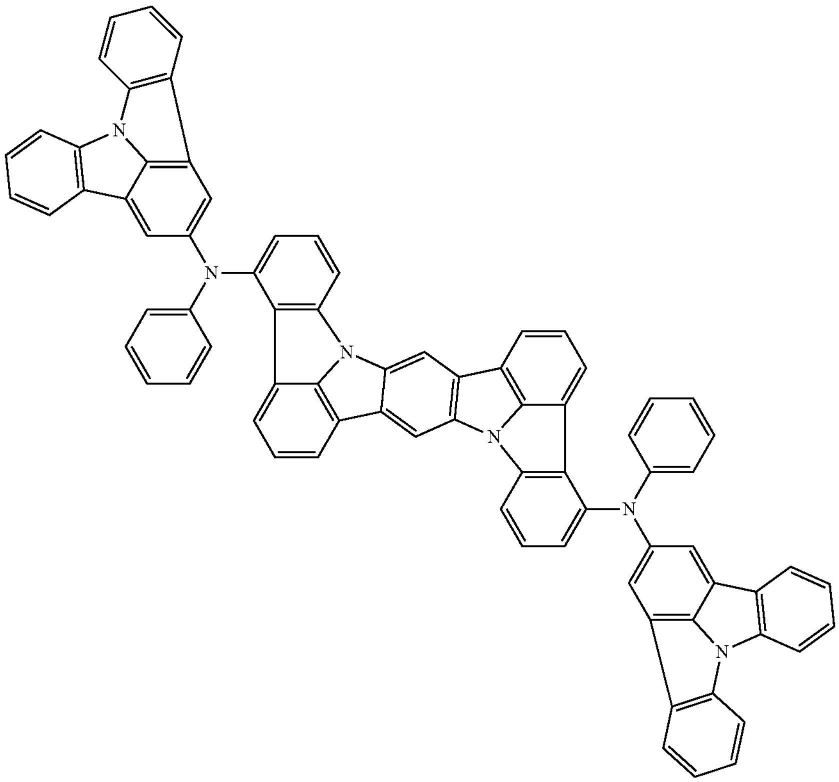
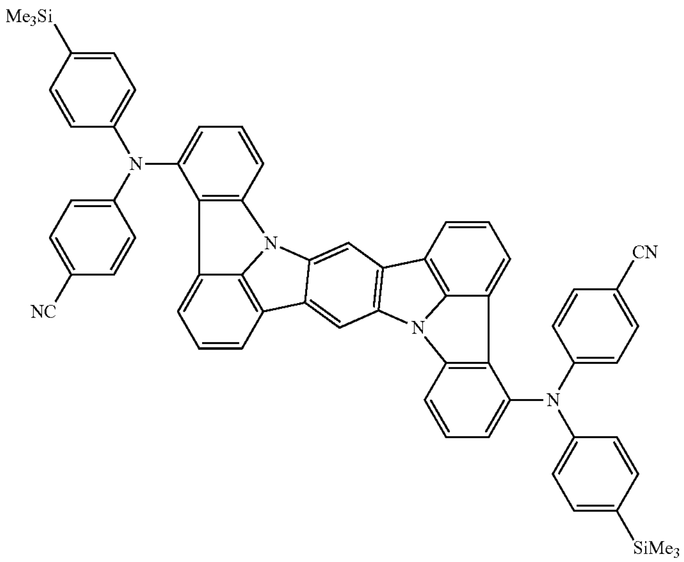

-continued
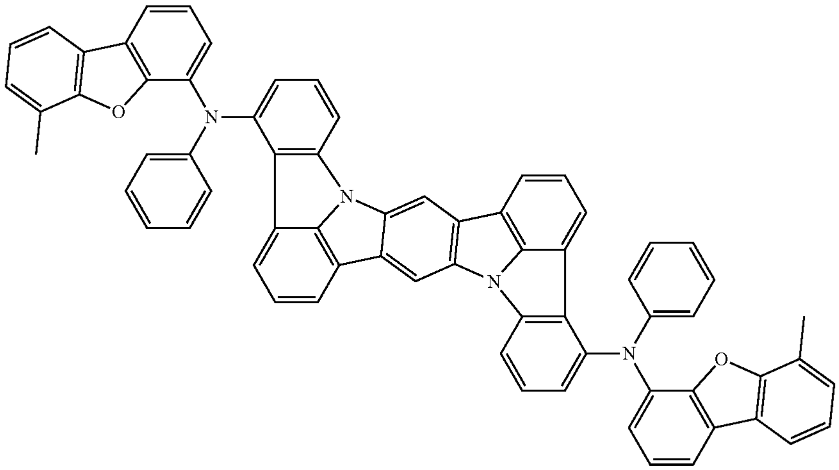
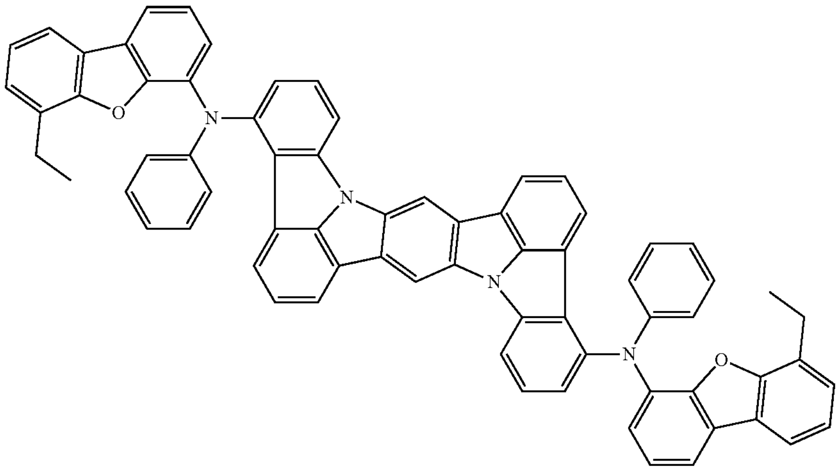
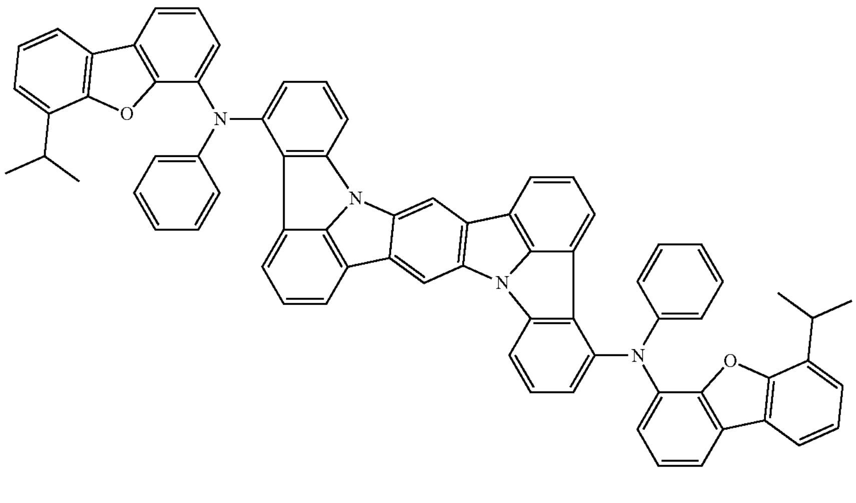 [SMILES: CC(C)(C)c1cccc2c1oc1c(N(c3ccccc3)c3cccc4c3c3cccc5c6cc7c(cc6n4c53)c3cccc4c5c(N(c6ccccc6)c6cccc8c6oc6c(C(C)(C)C)cccc68)cccc5n7c34)cccc12]

-continued
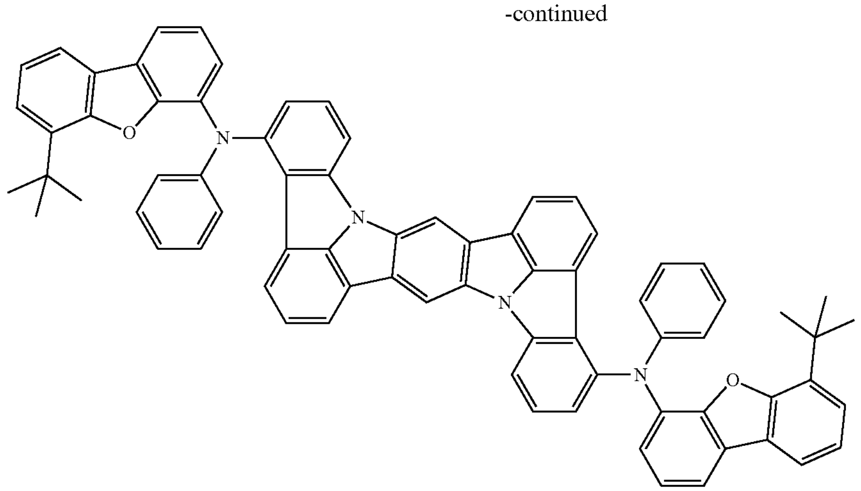
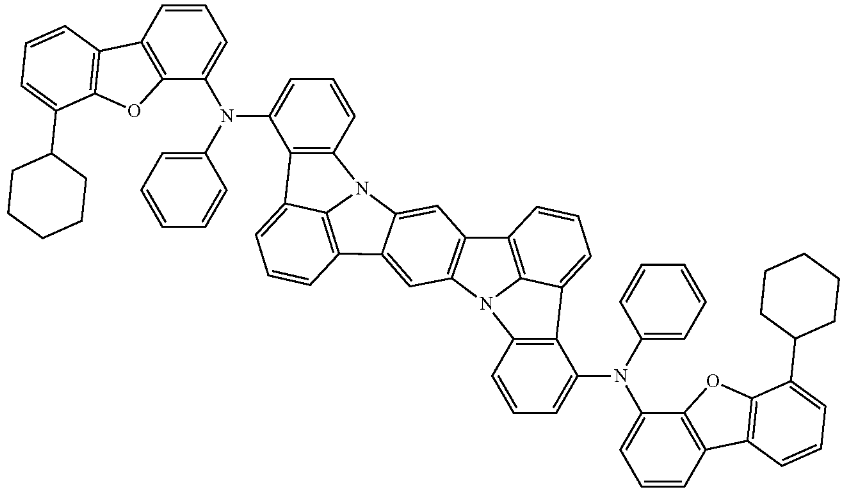
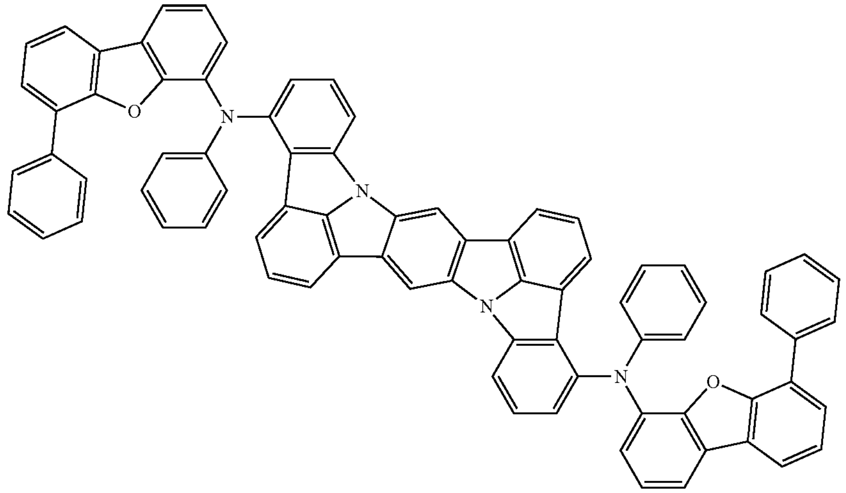

-continued
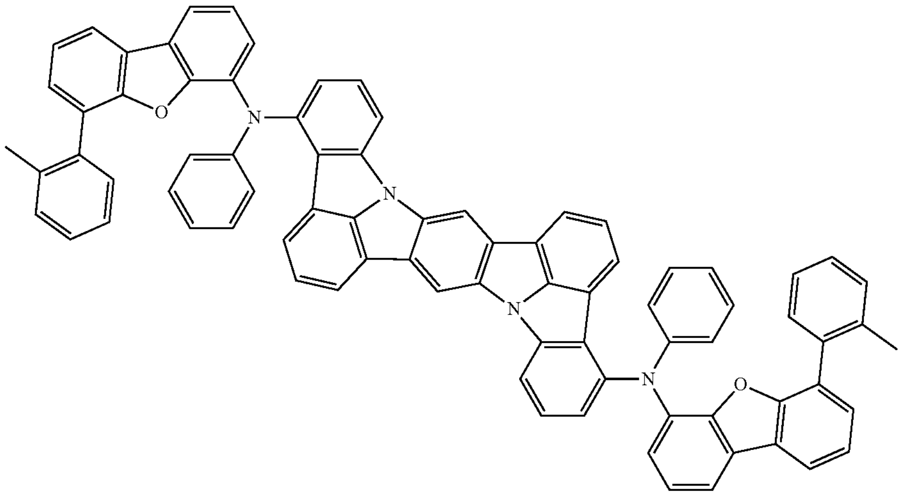
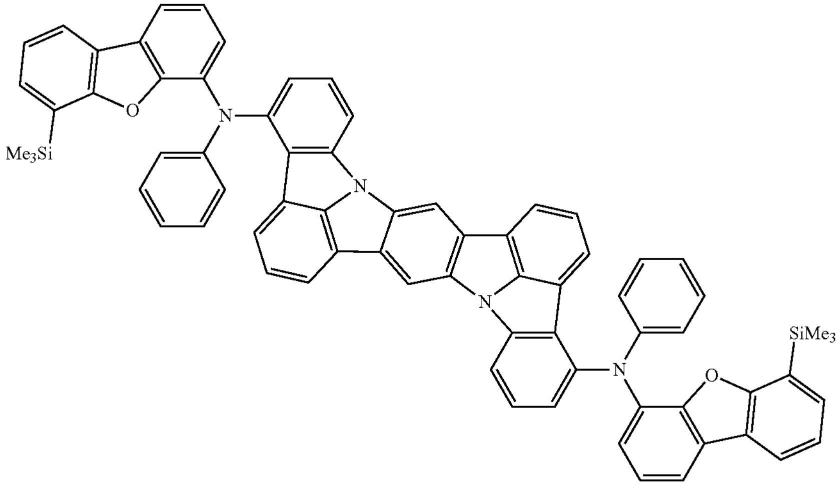
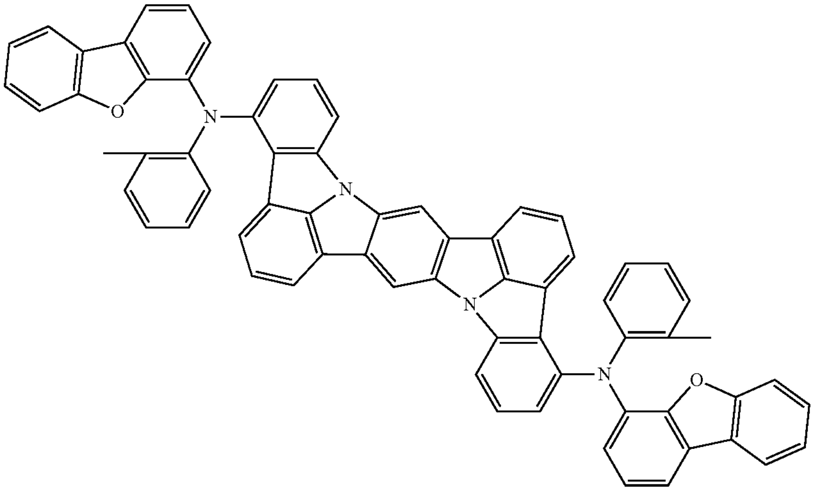

-continued
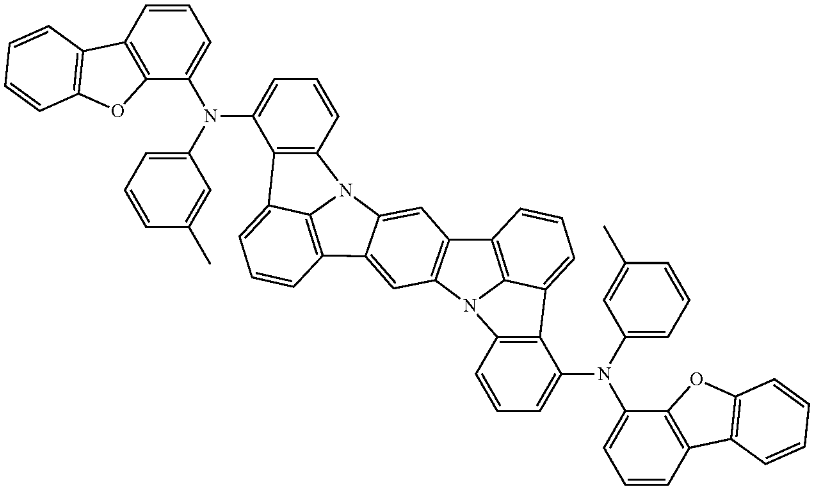
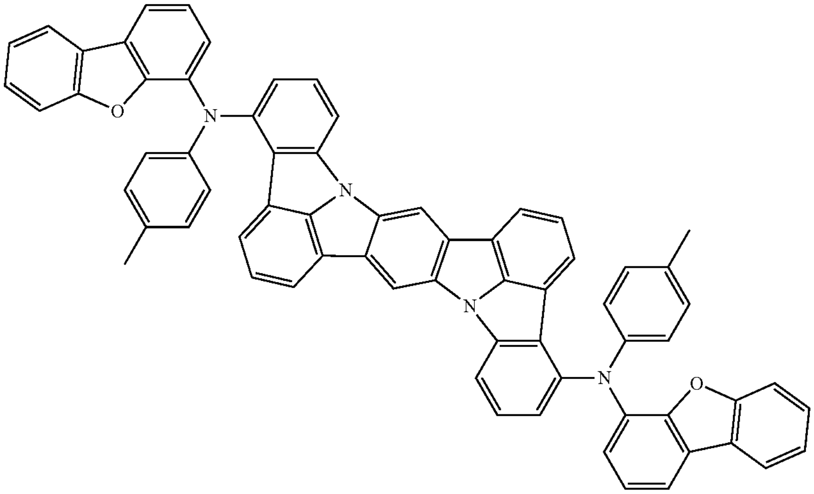
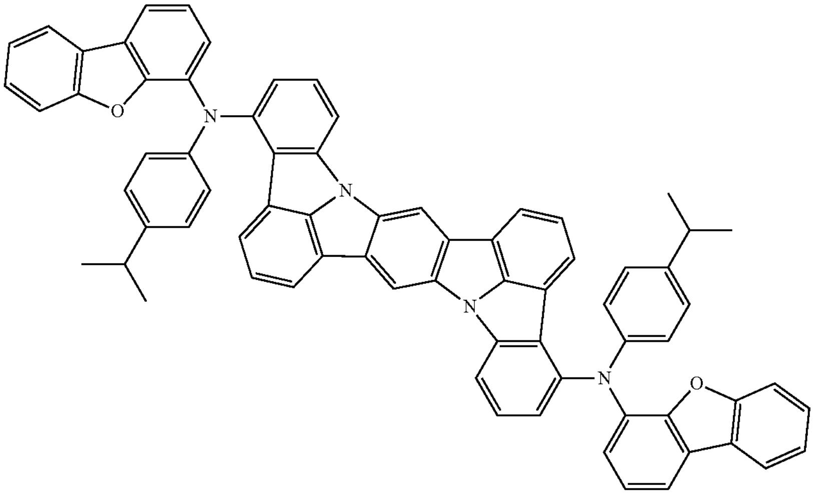

-continued
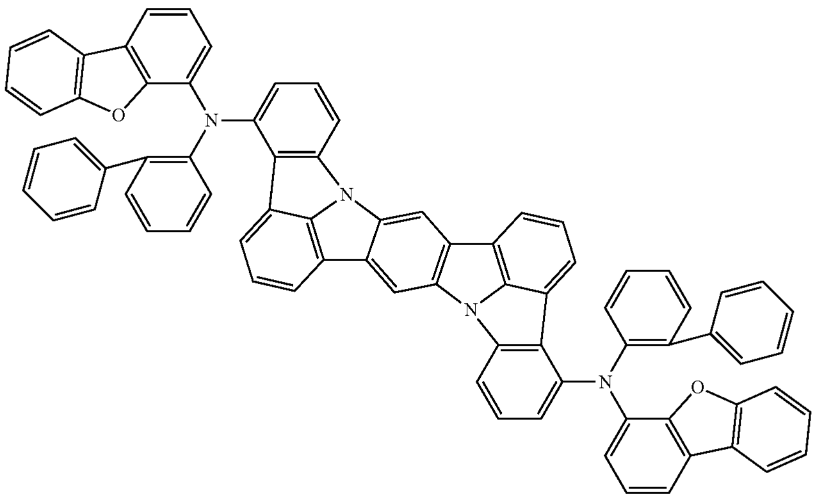
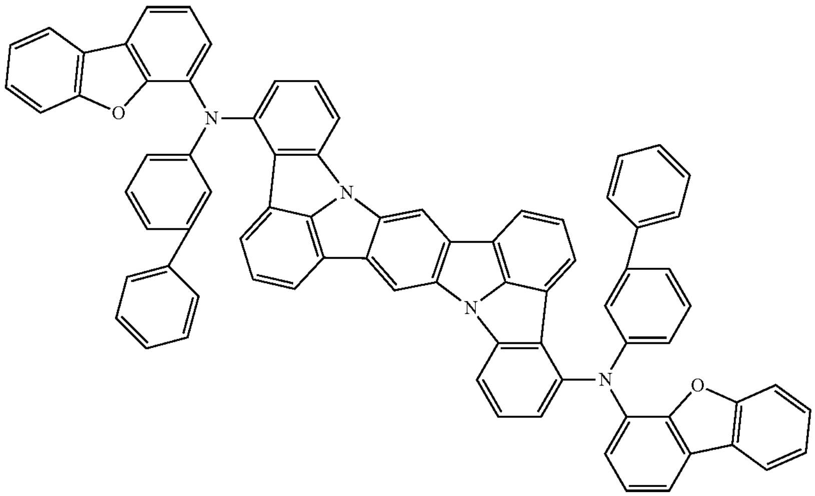
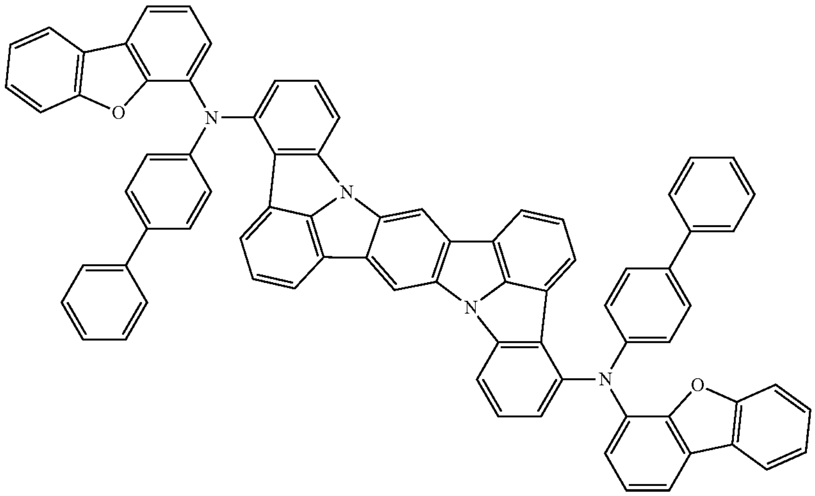

-continued
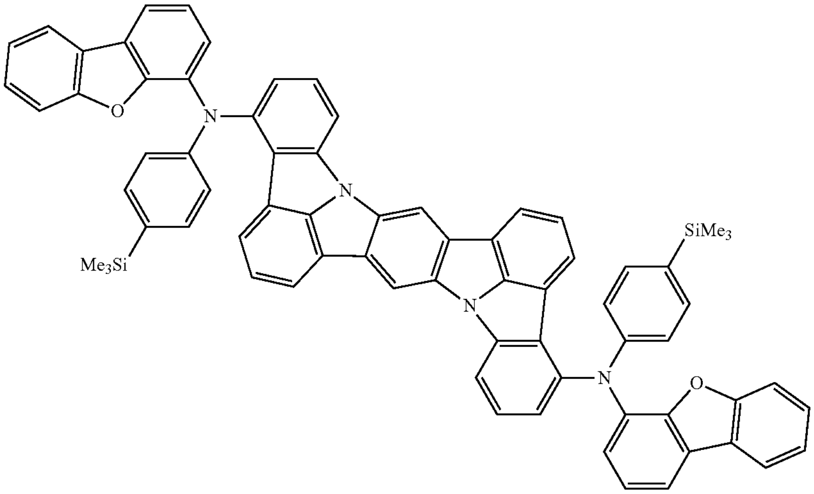
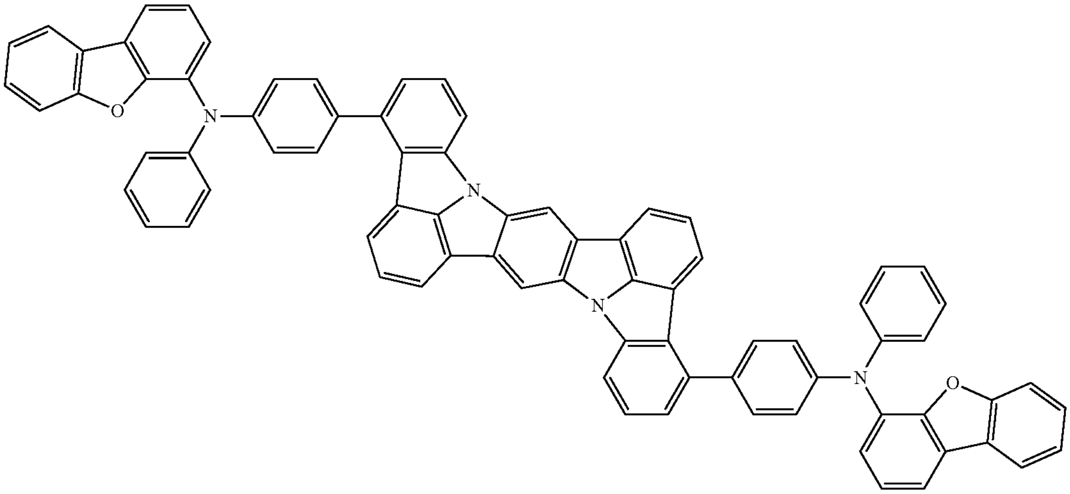
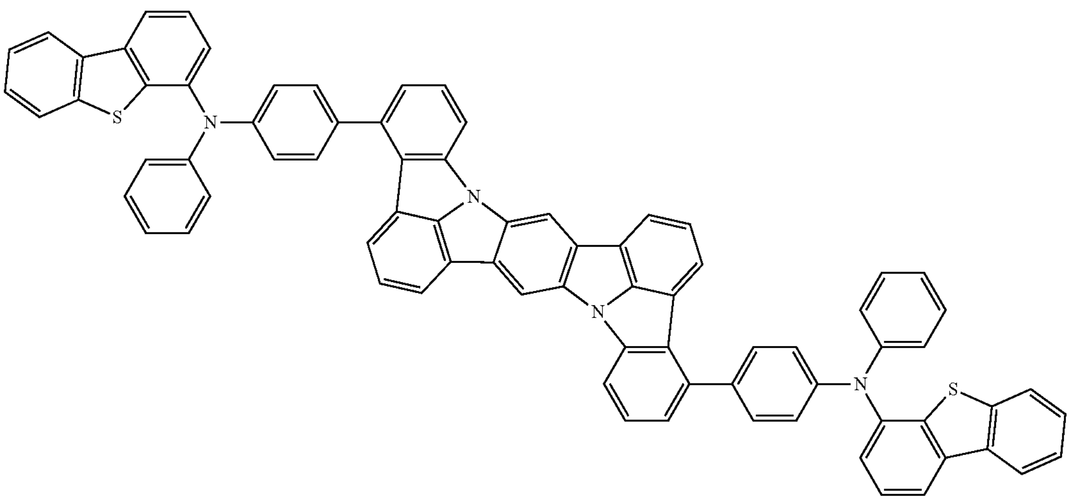

-continued
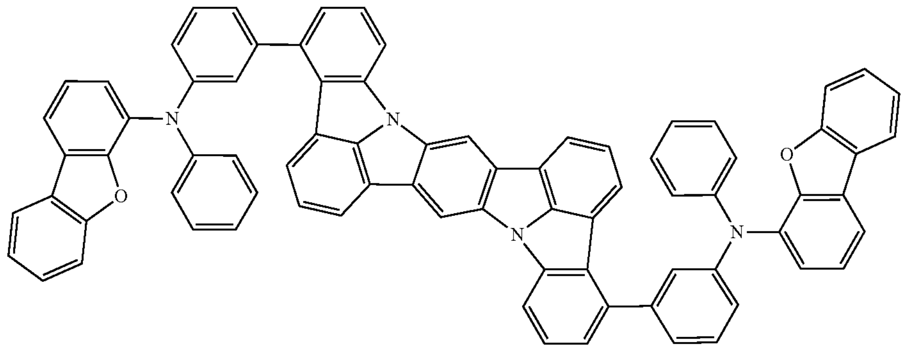
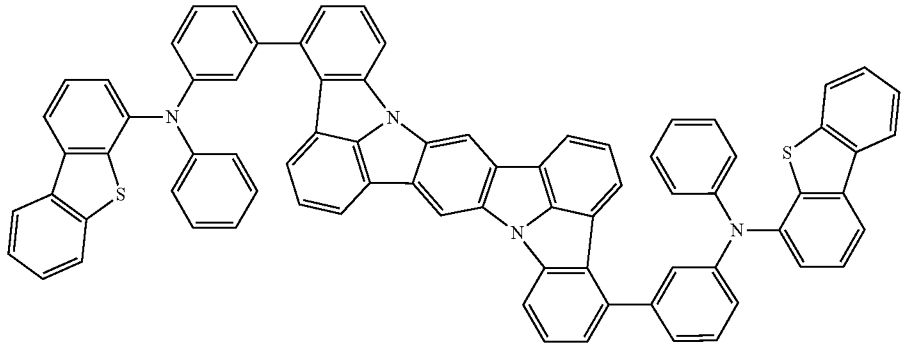
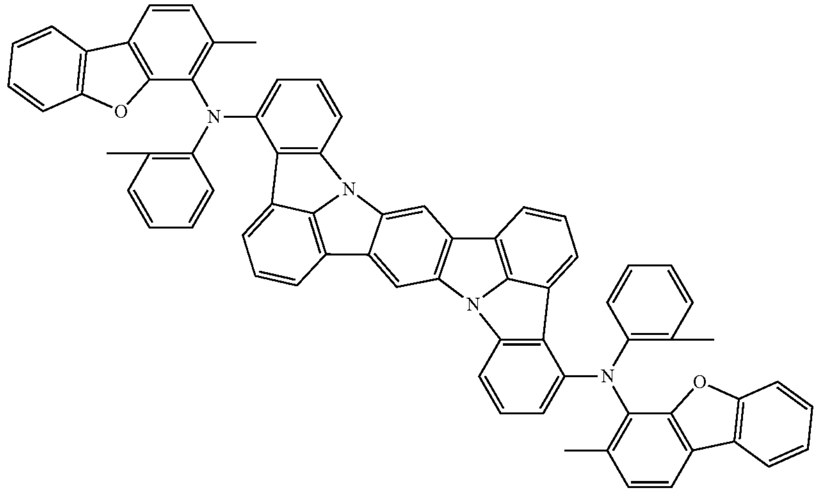
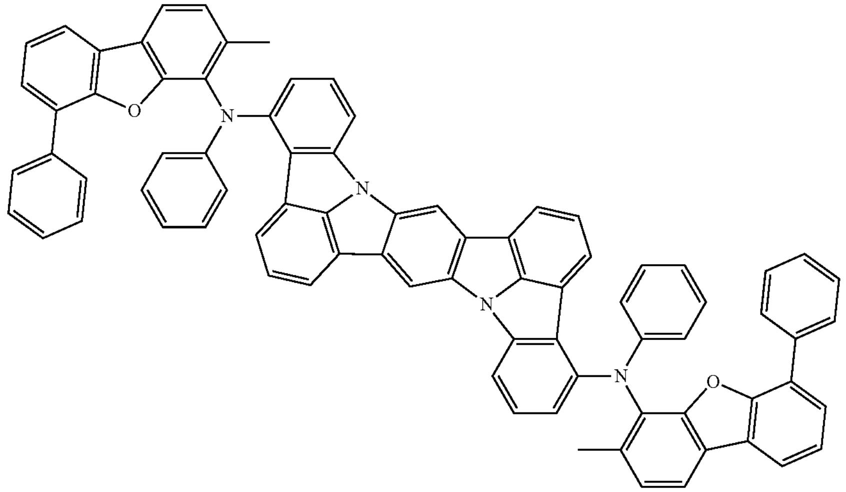

-continued
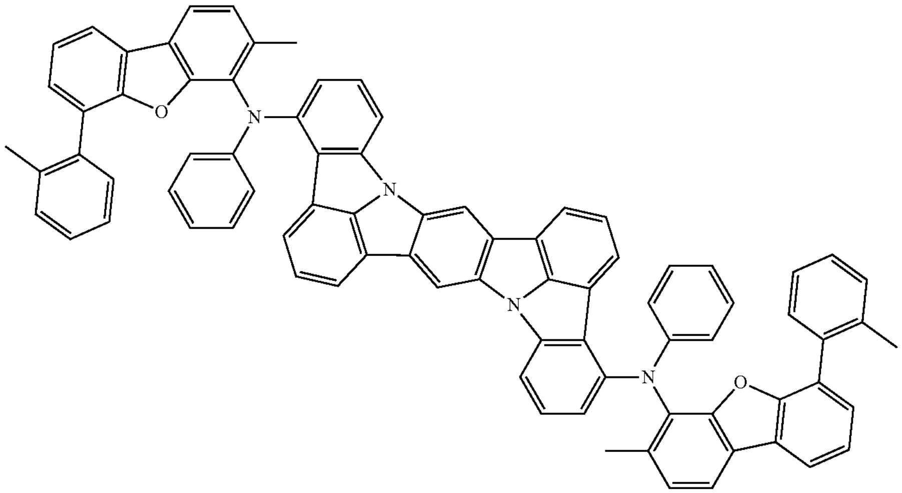
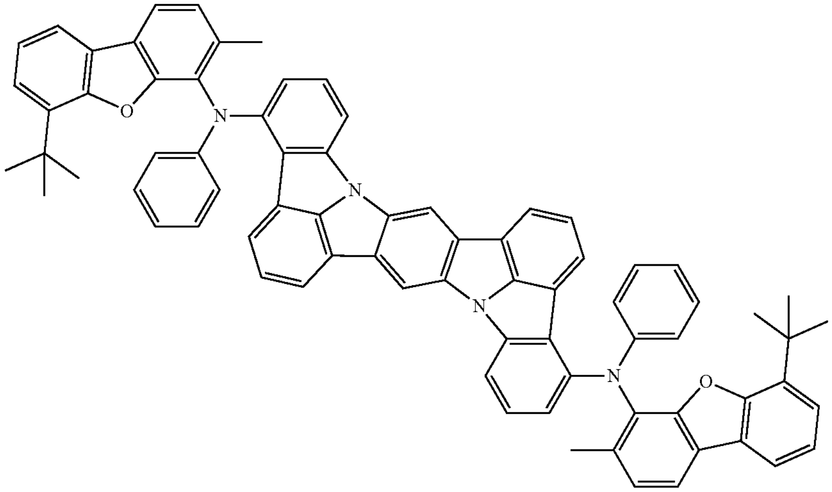
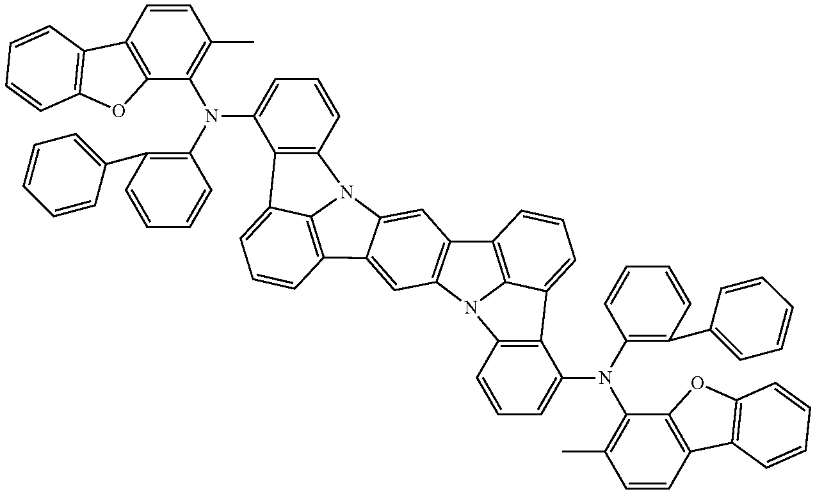

-continued
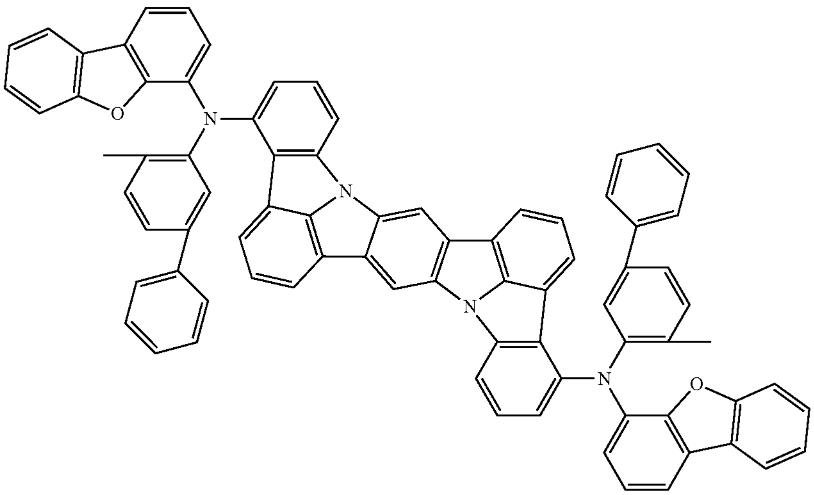
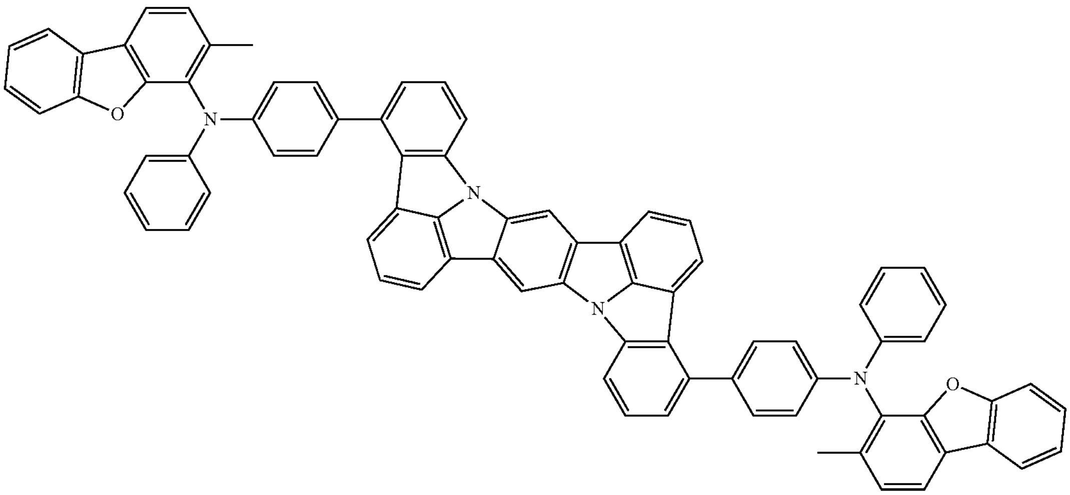
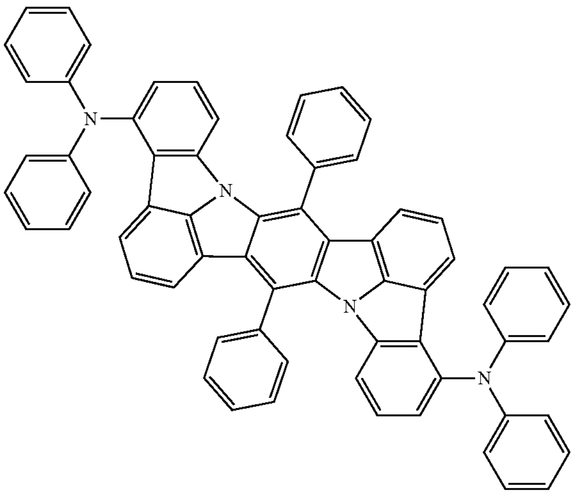

-continued
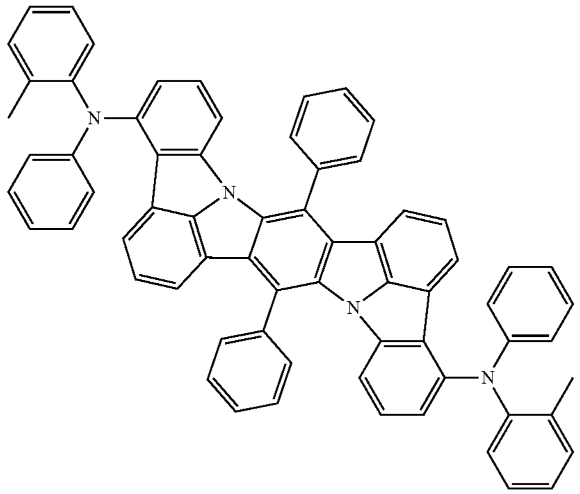
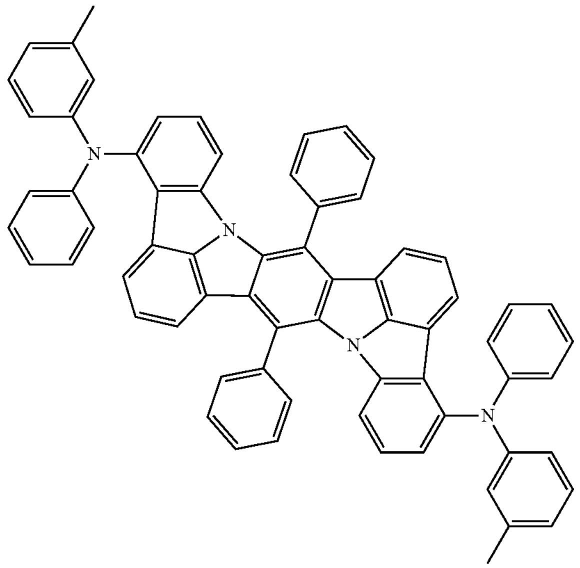
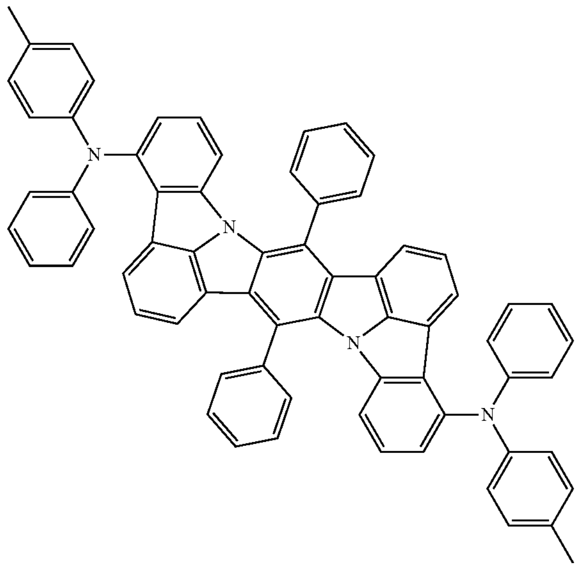

-continued
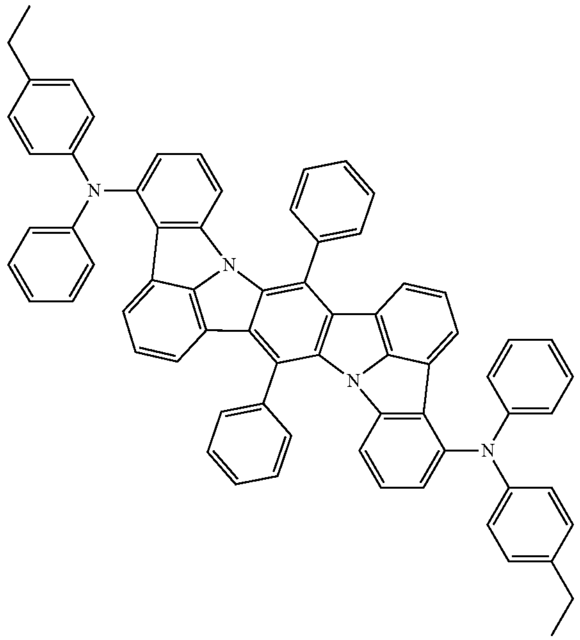
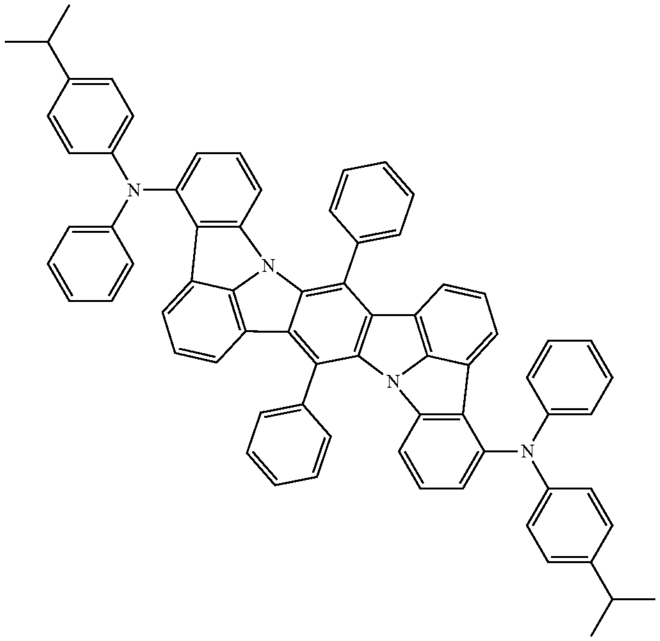

-continued
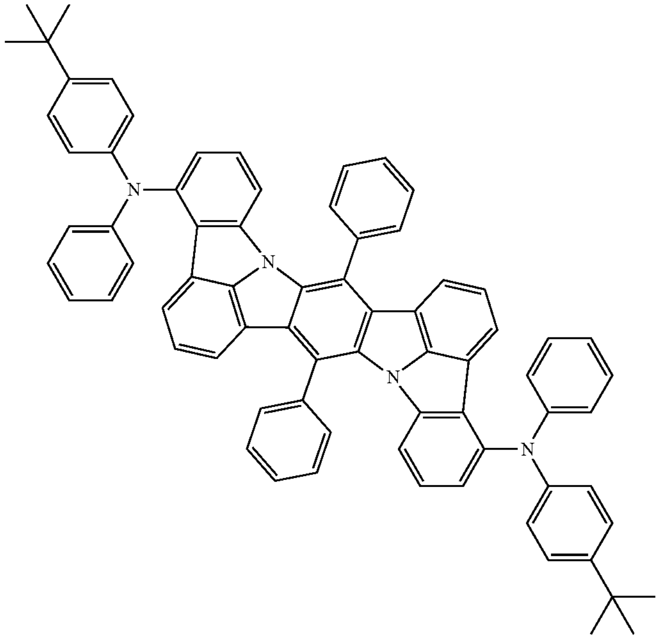
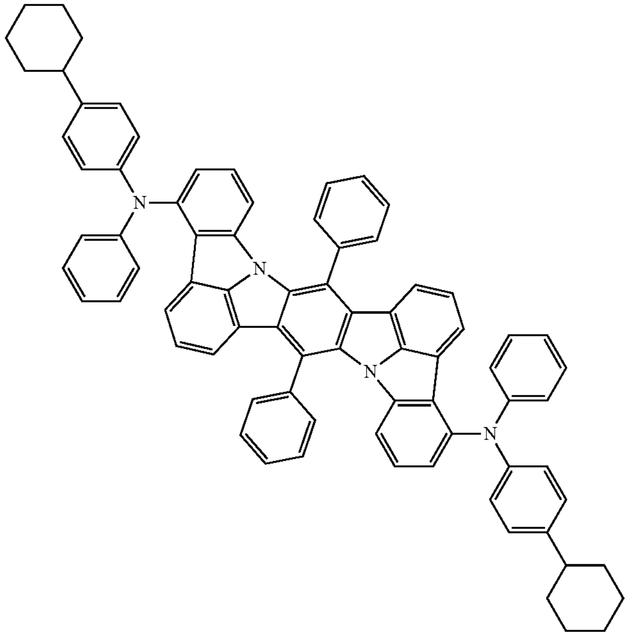

-continued
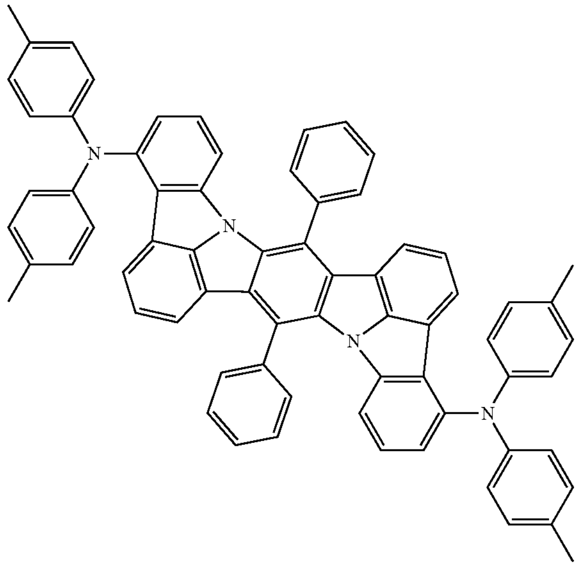
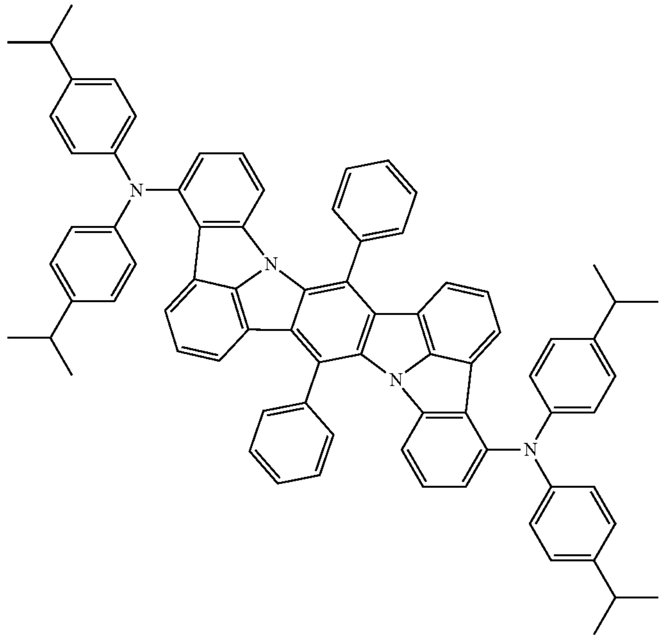

-continued
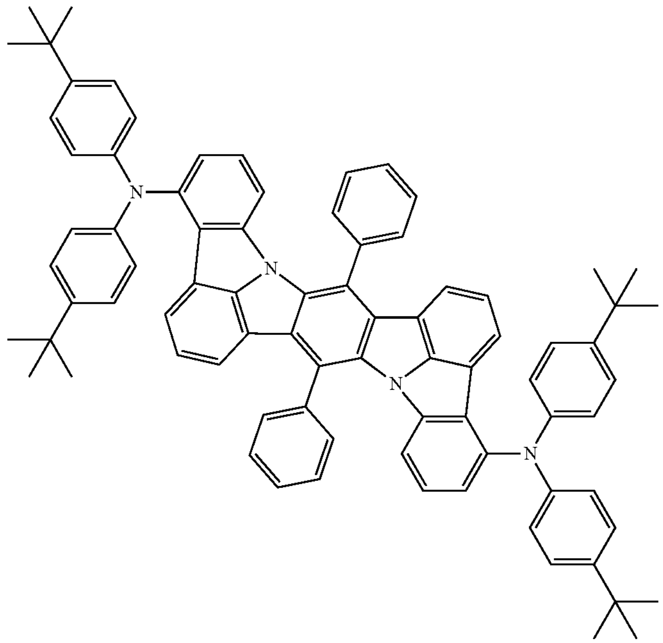
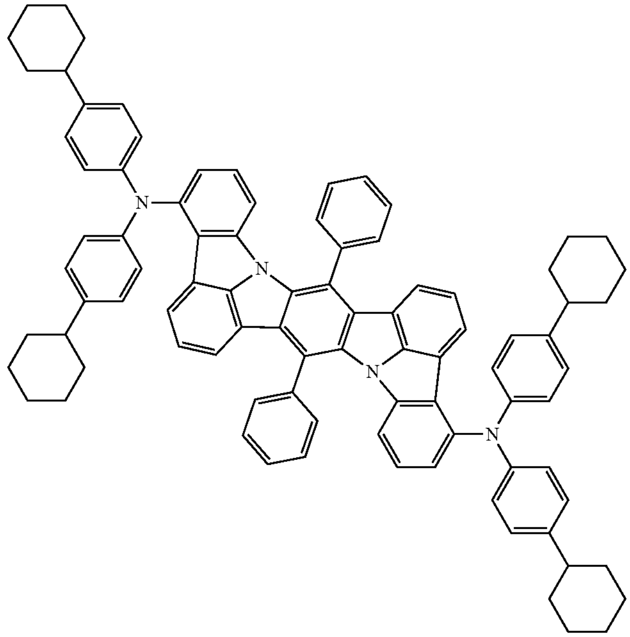

-continued
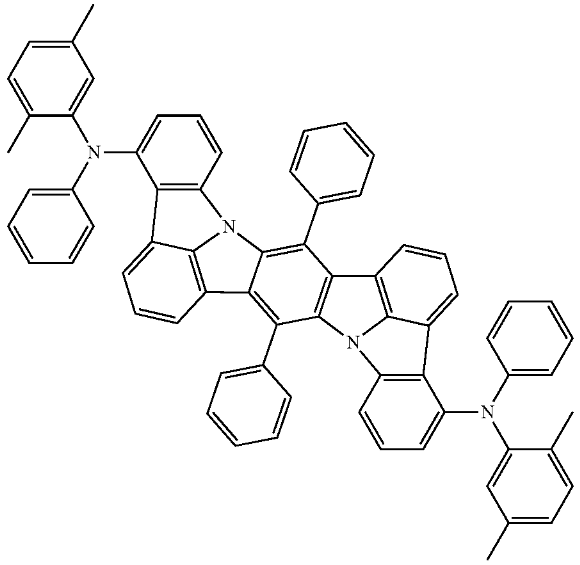
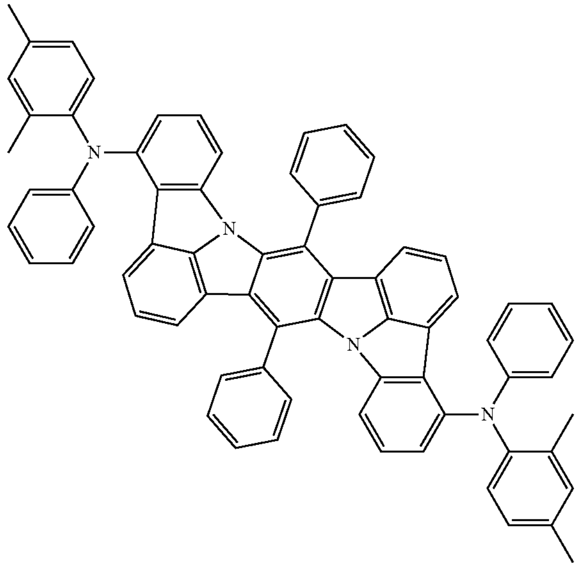
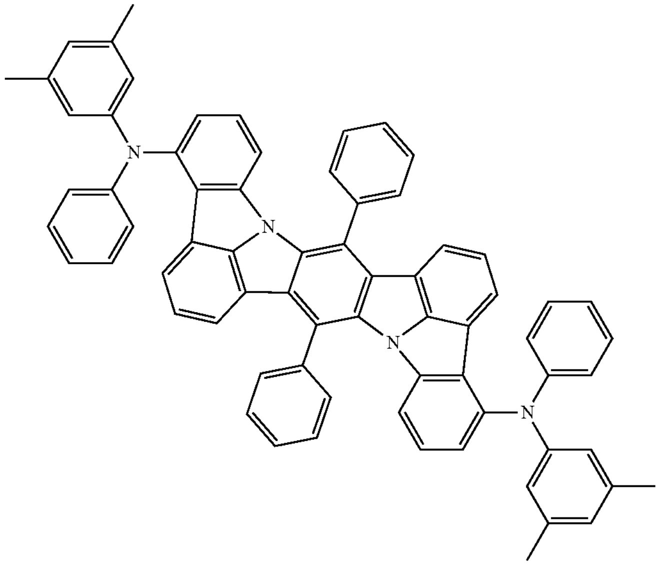

-continued
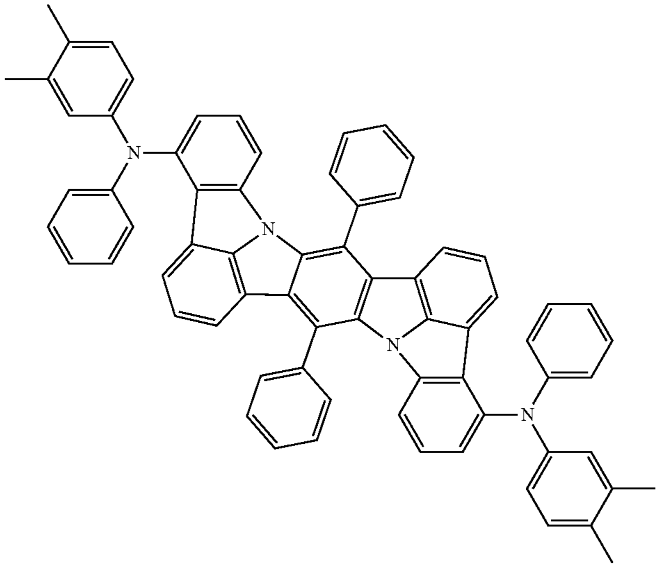
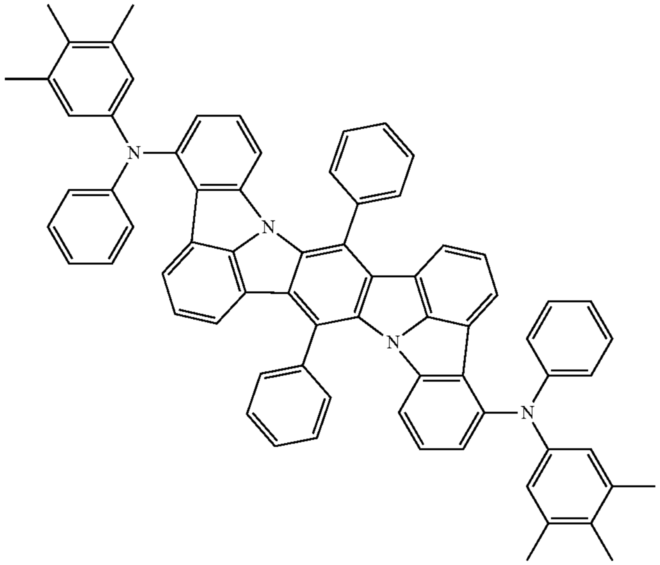
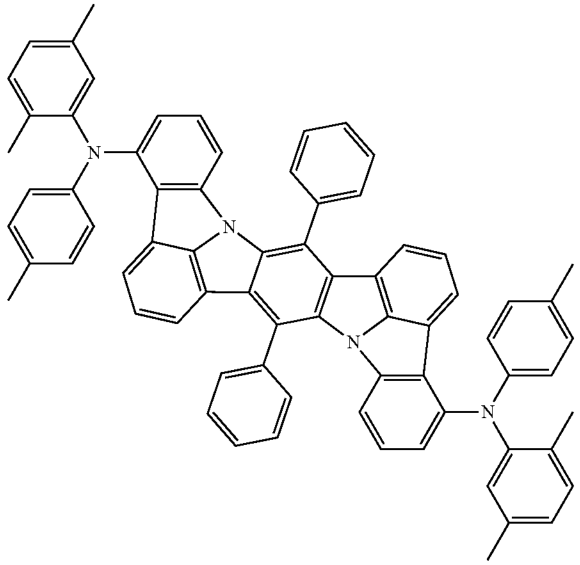 [SMILES: Cc1ccc(N(c2cc(C)ccc2C)c2cccc3c2c2cccc4c5c(-c6ccccc6)c6c(c(-c7ccccc7)c5n3c24)c2cccc3c4c(N(c5ccc(C)cc5)c5cc(C)ccc5C)cccc4n6c32)cc1]

-continued
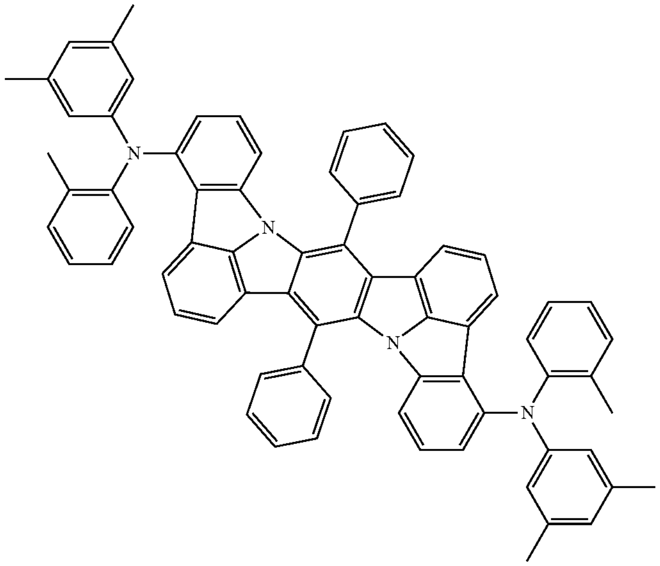
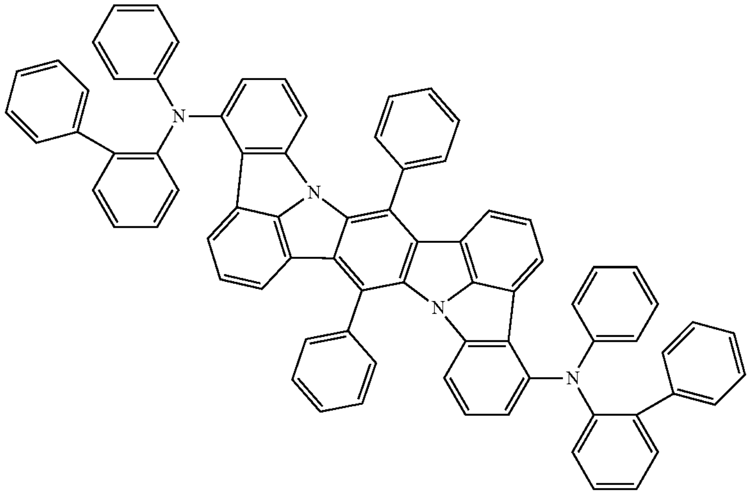
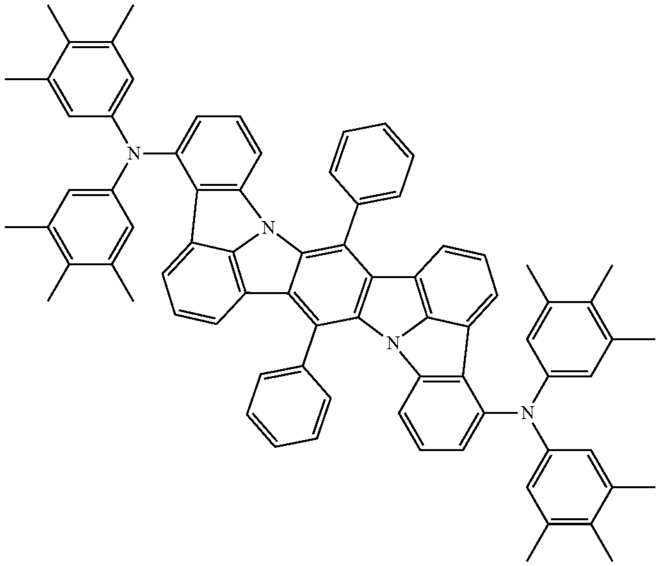

-continued
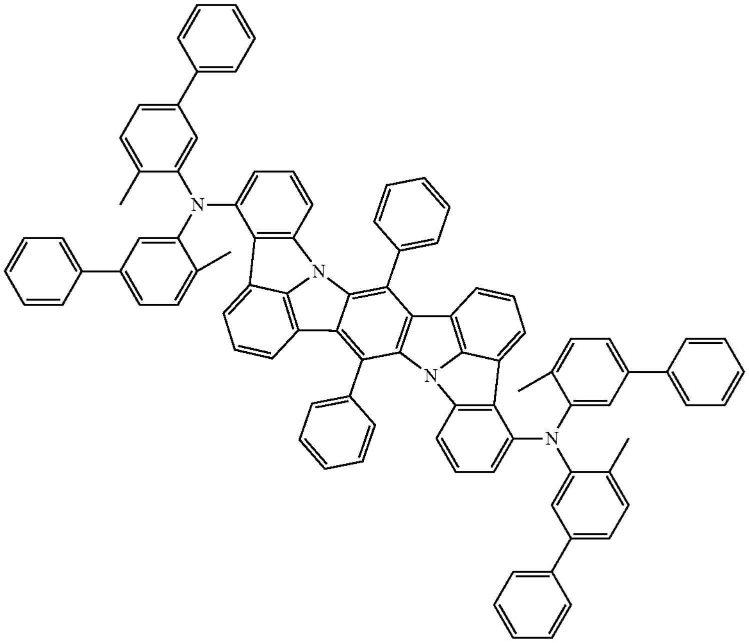
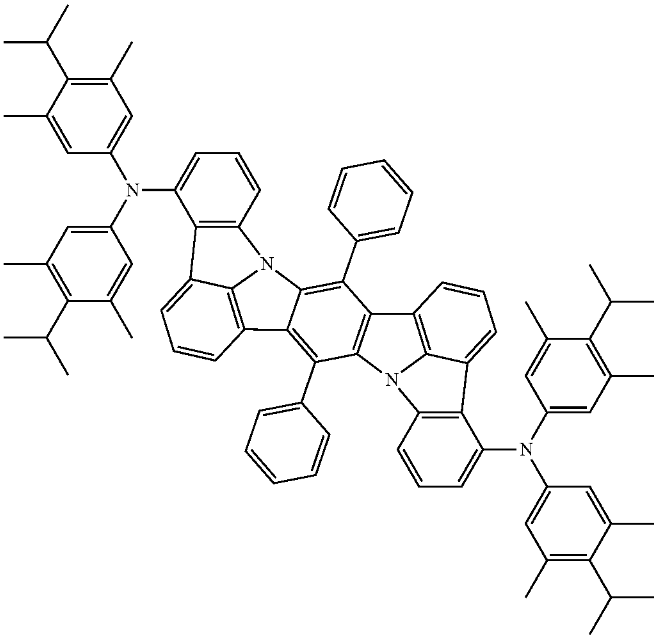

-continued
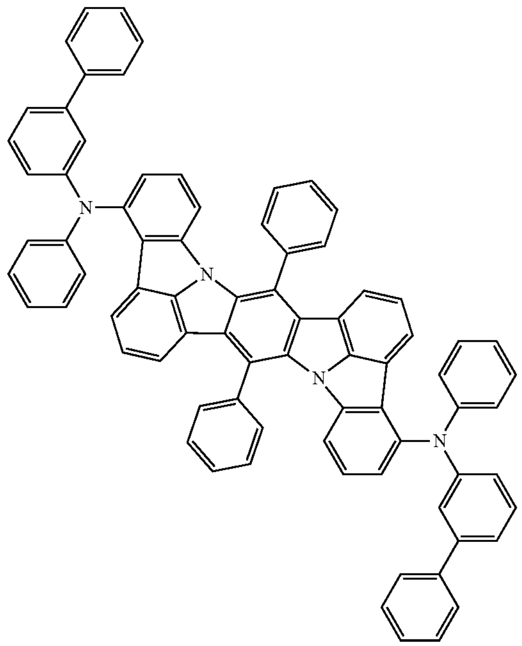
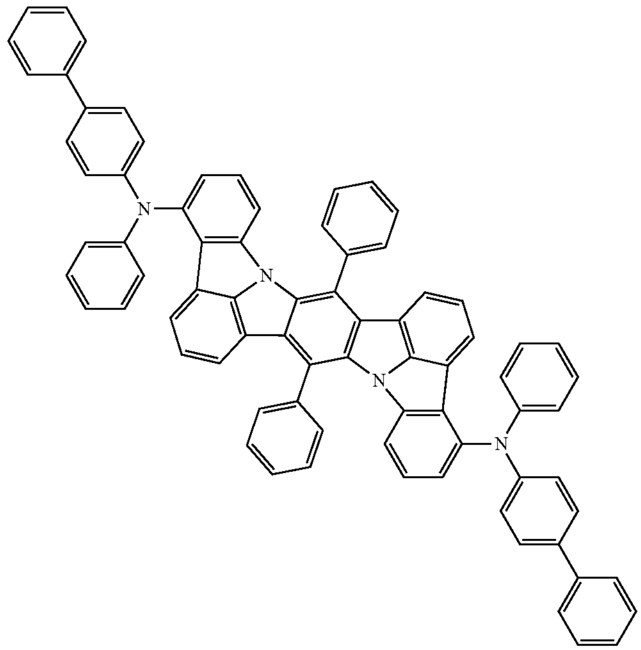

-continued
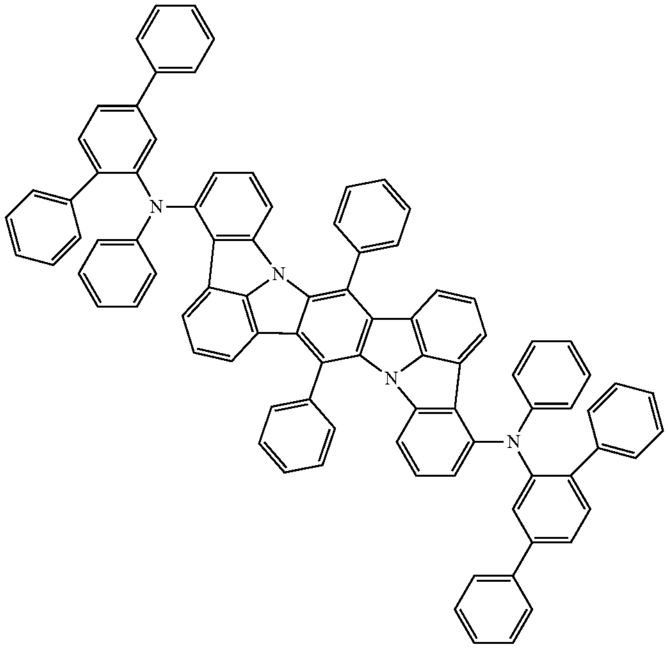
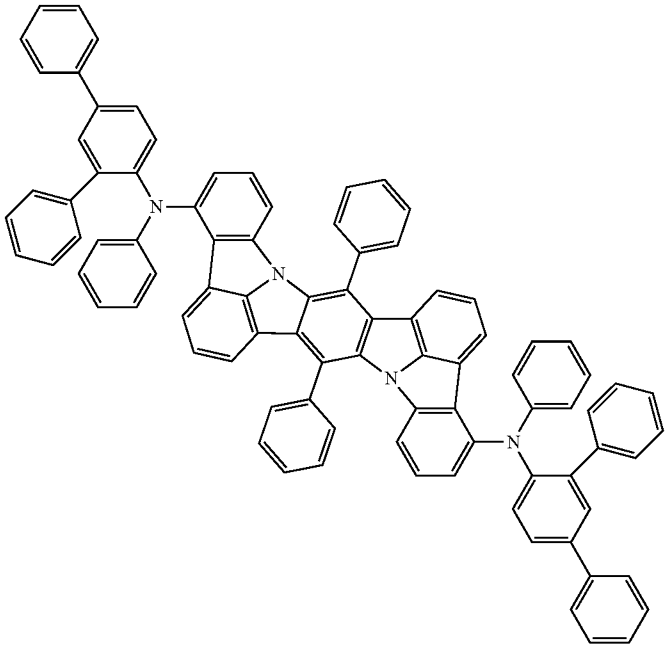

-continued
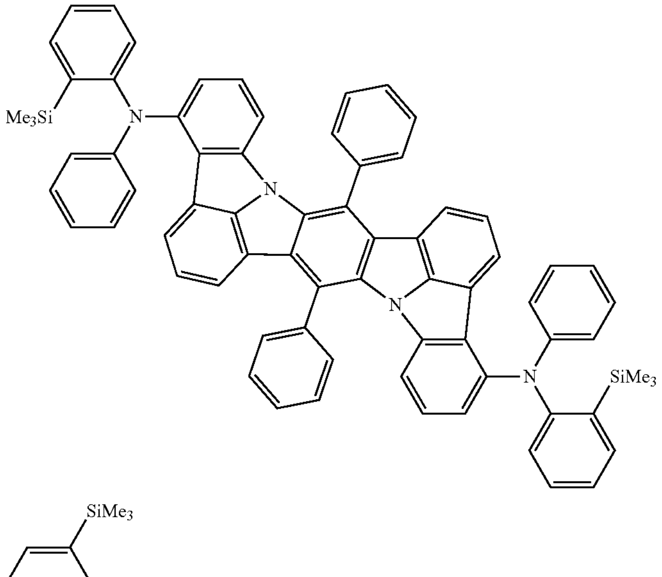
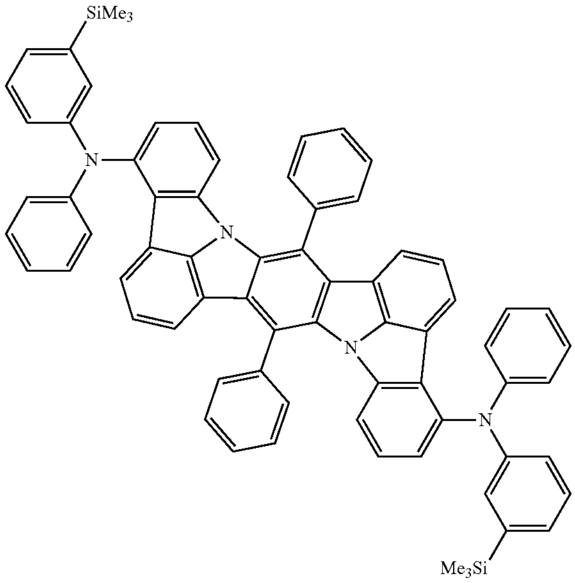
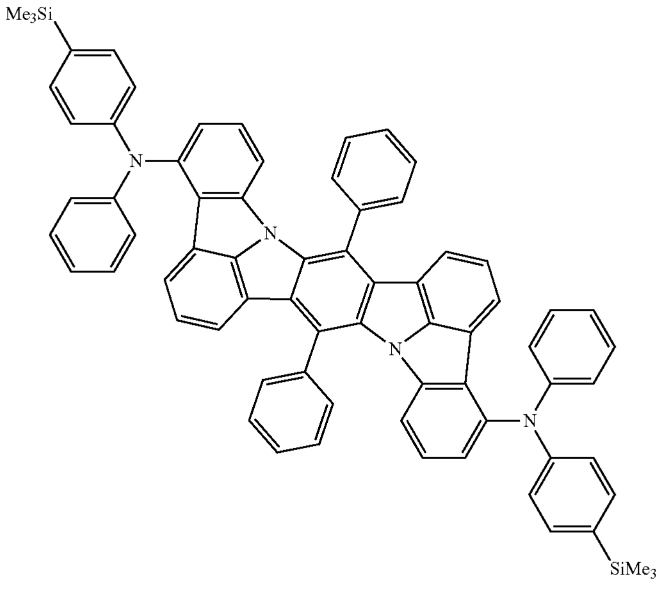

-continued
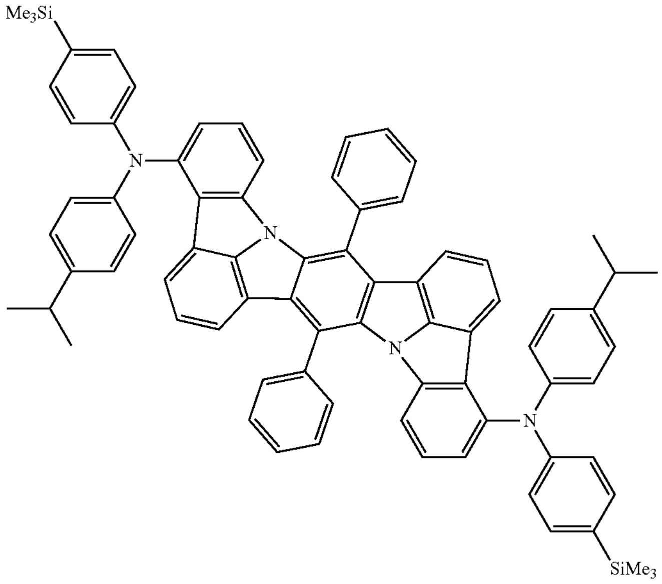
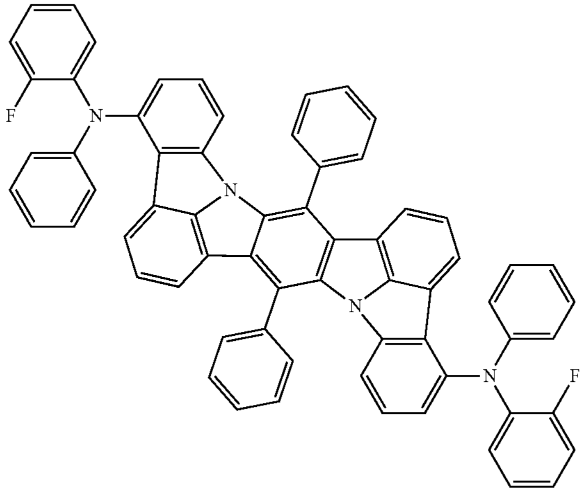
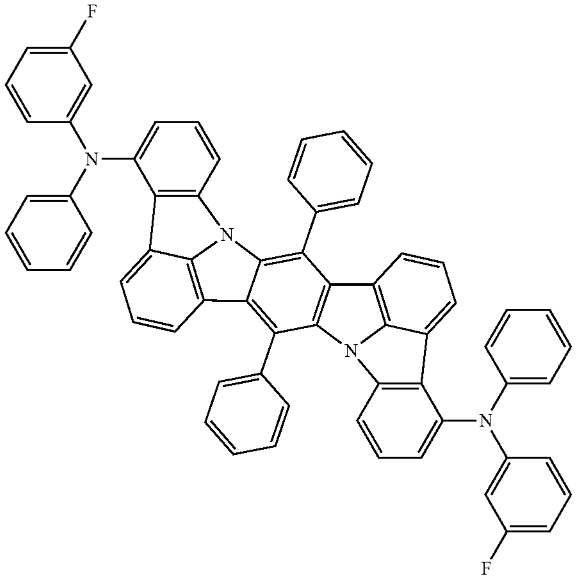

-continued
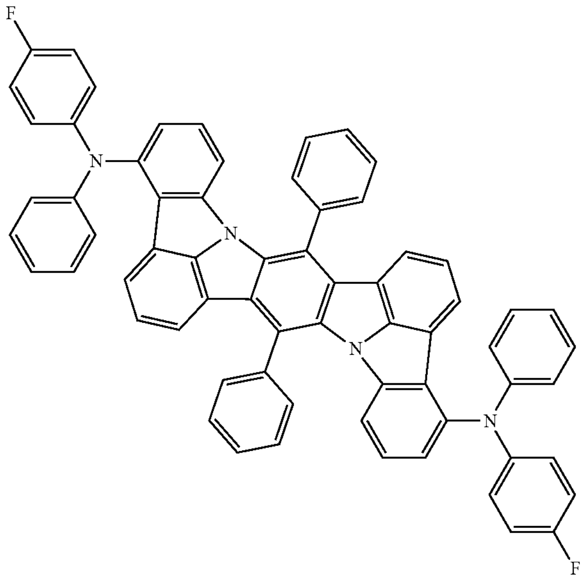
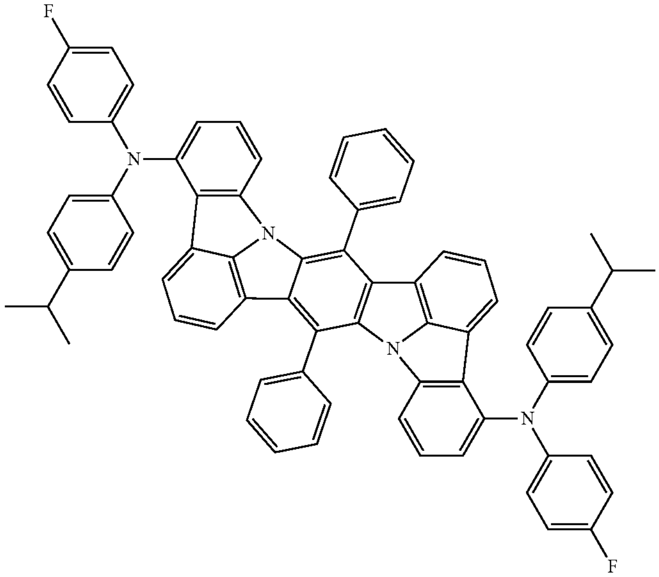
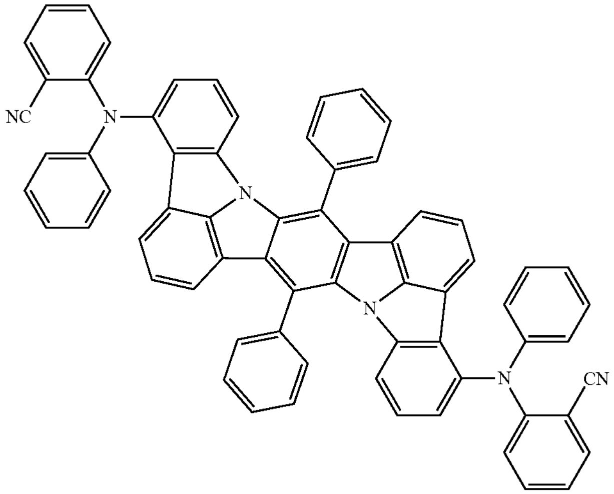

-continued
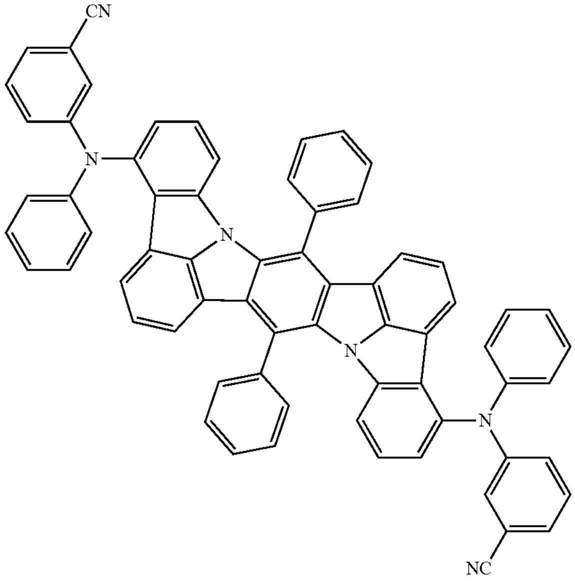 [SMILES: N#Cc1cccc(N(c2ccccc2)c2cccc3c2c2cccc4c5c(-c6ccccc6)c6c(c(-c7ccccc7)c5n3c24)c2cccc3c4c(N(c5ccccc5)c5cccc(C#N)c5)cccc4n6c32)c1]
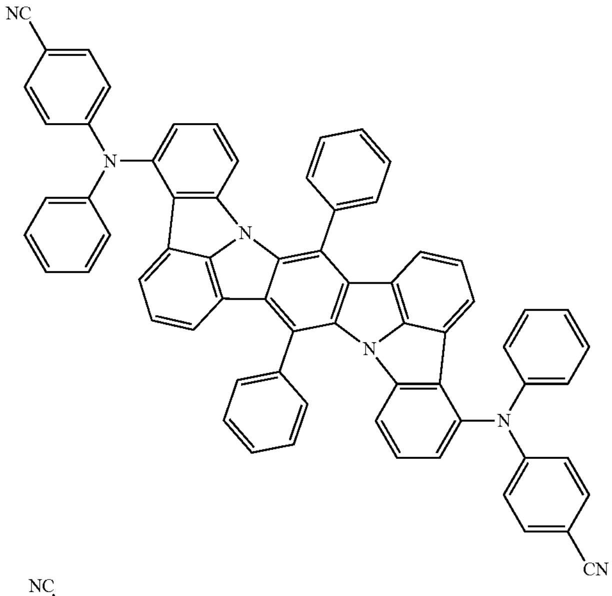
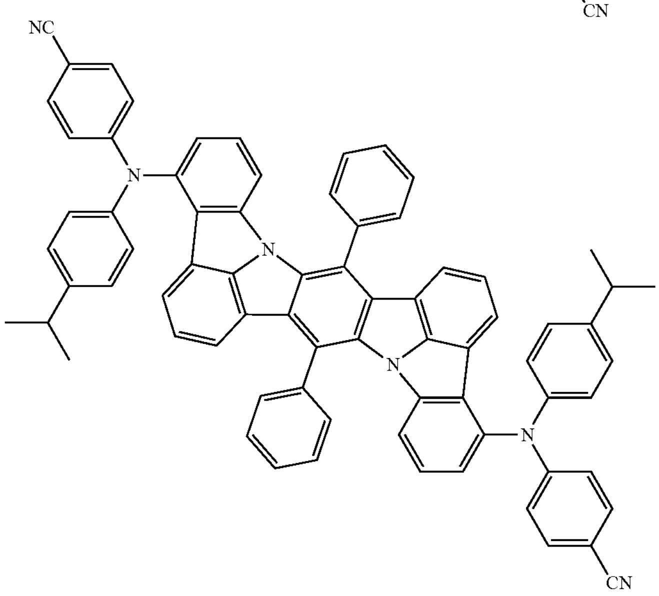

-continued
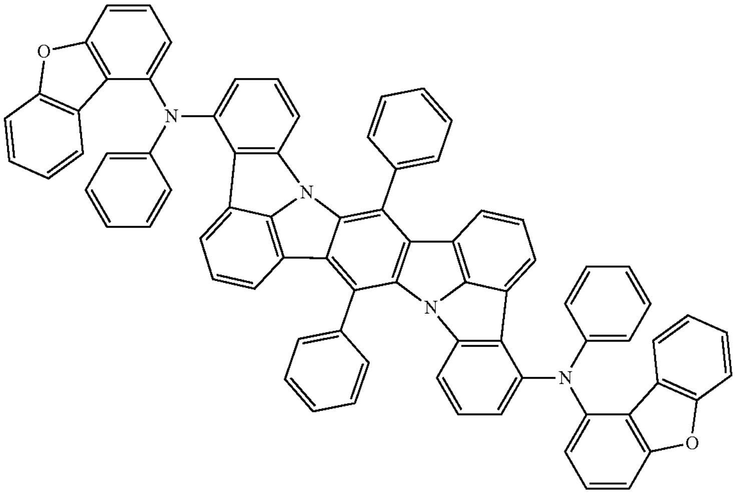
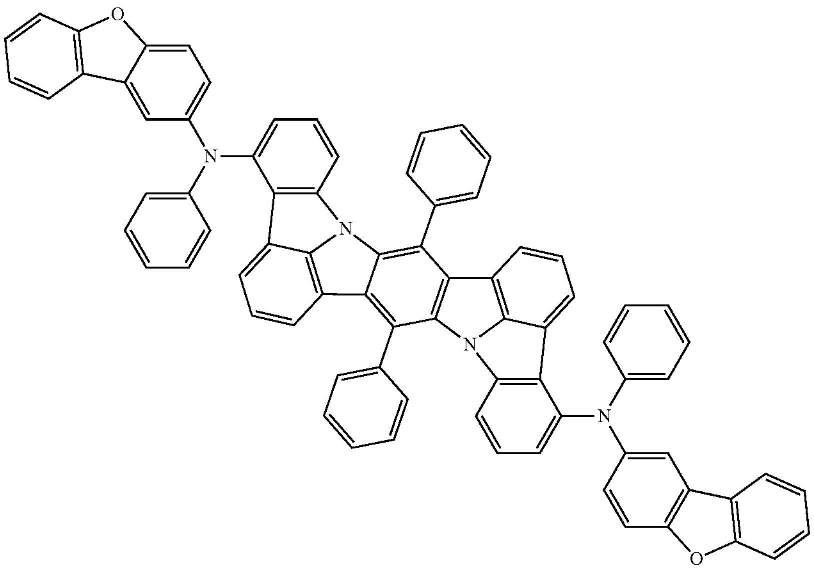

-continued
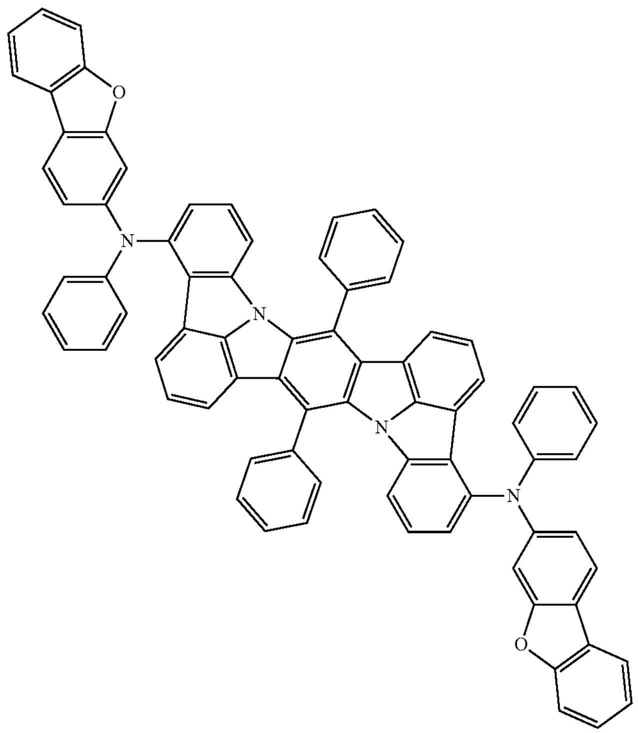
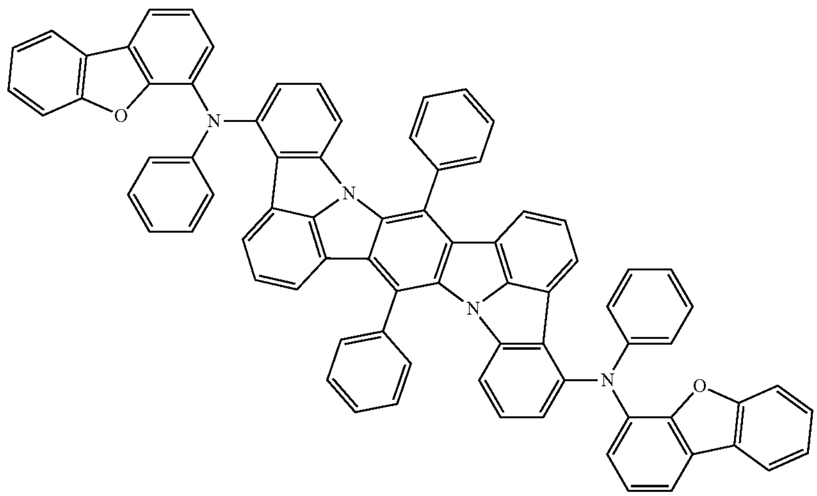

-continued
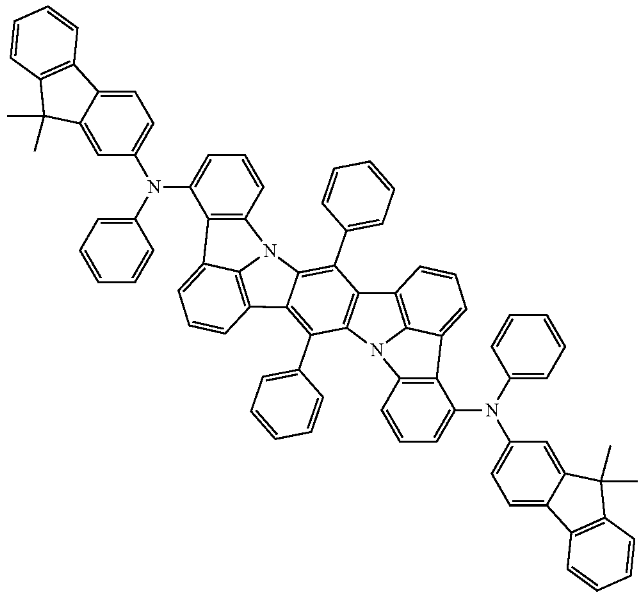
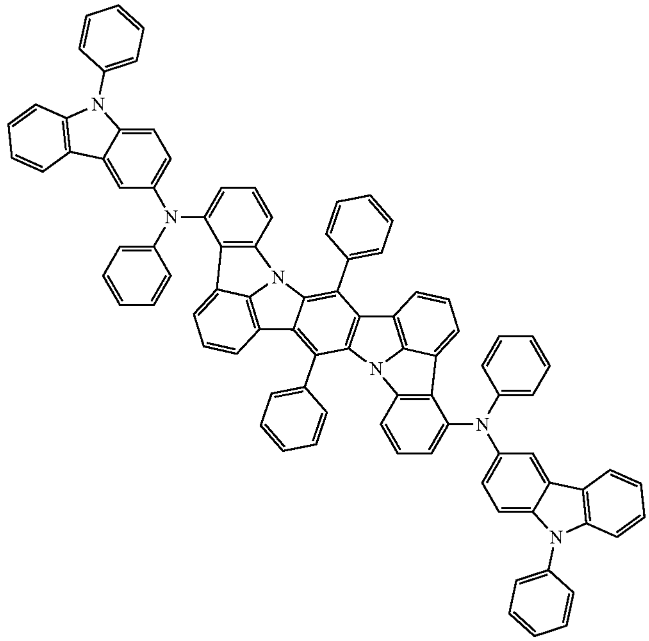

-continued
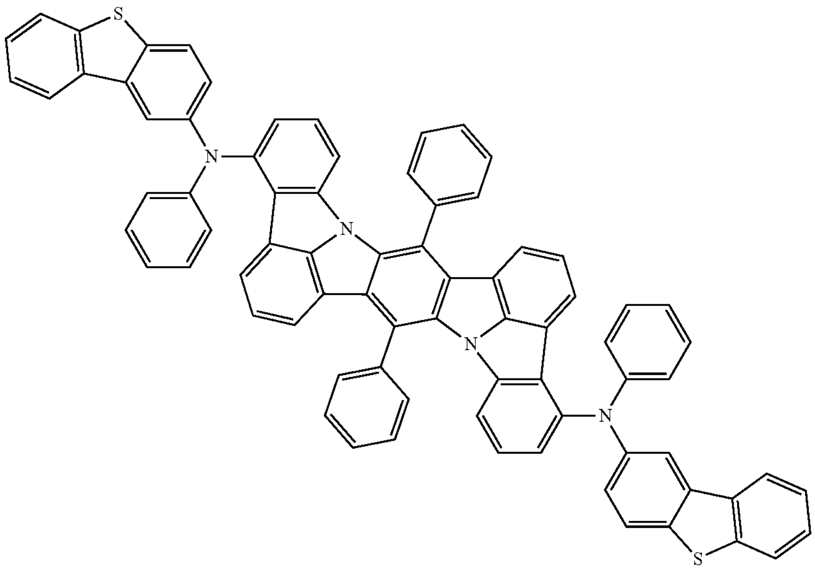
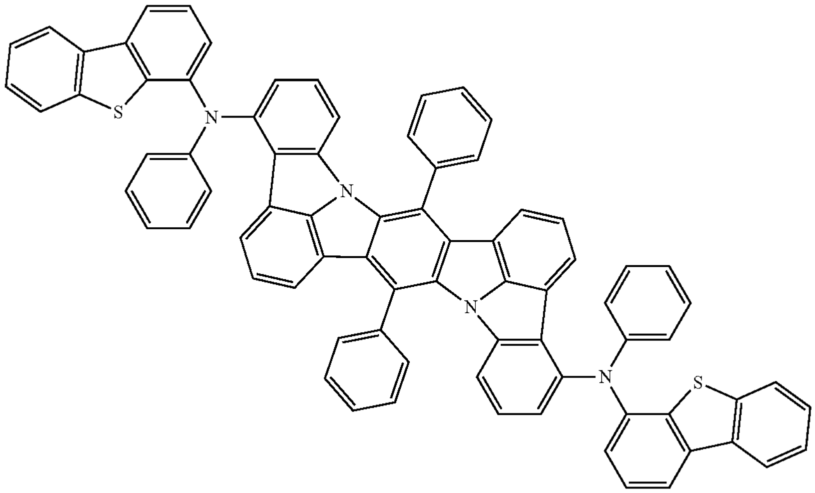
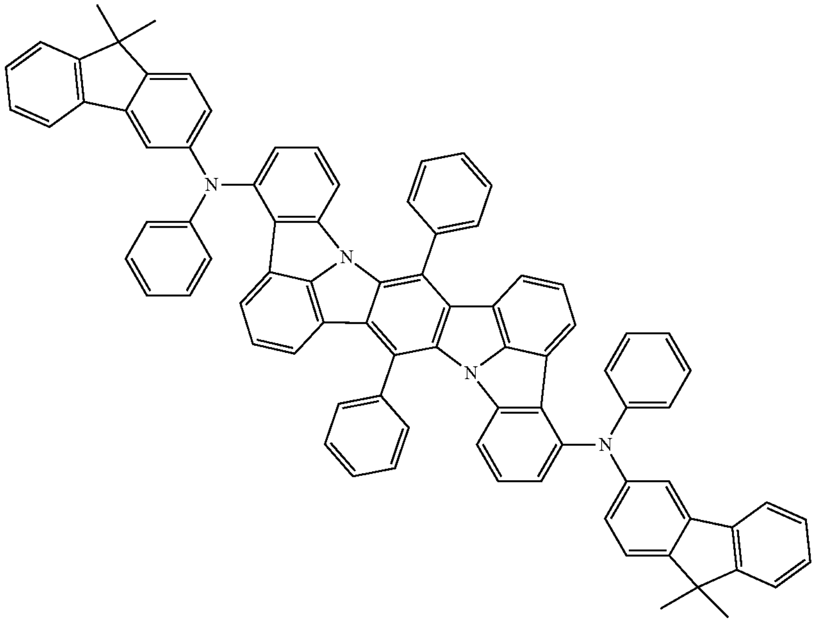

-continued
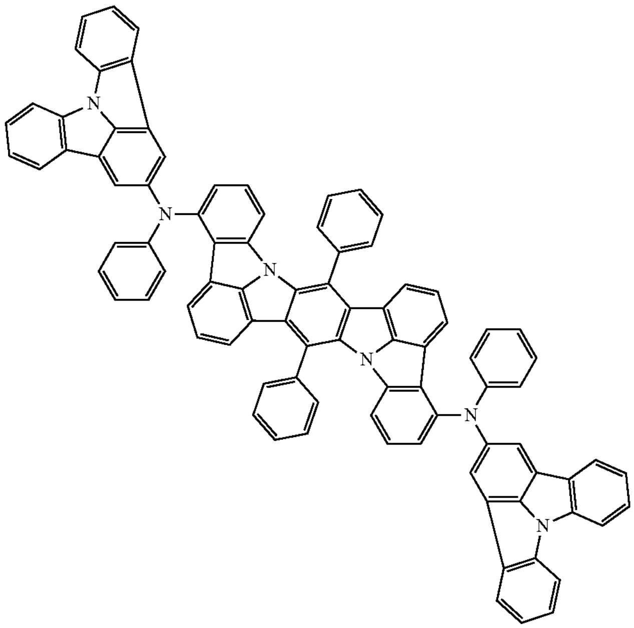
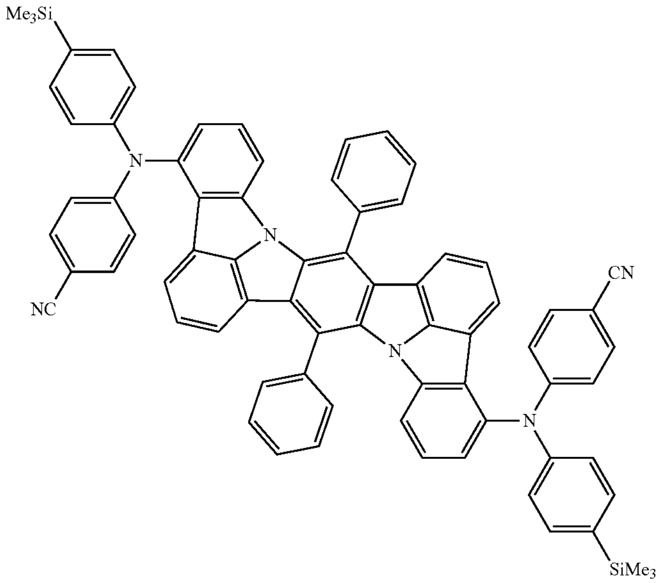
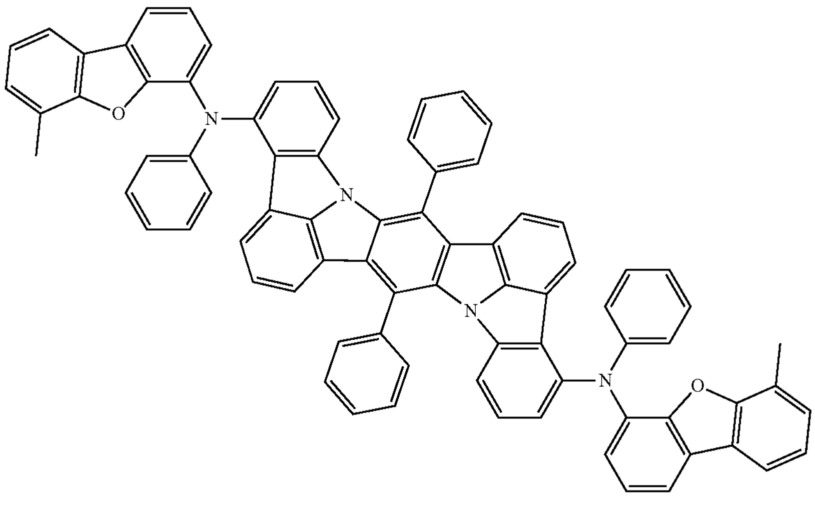

-continued
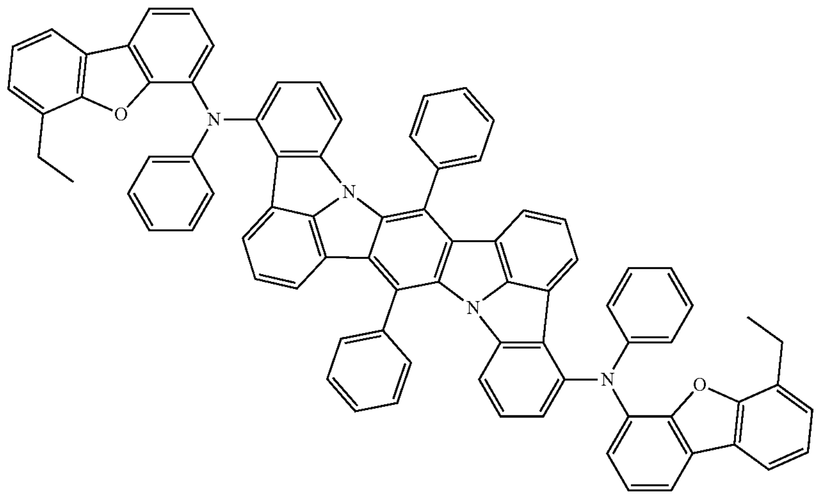
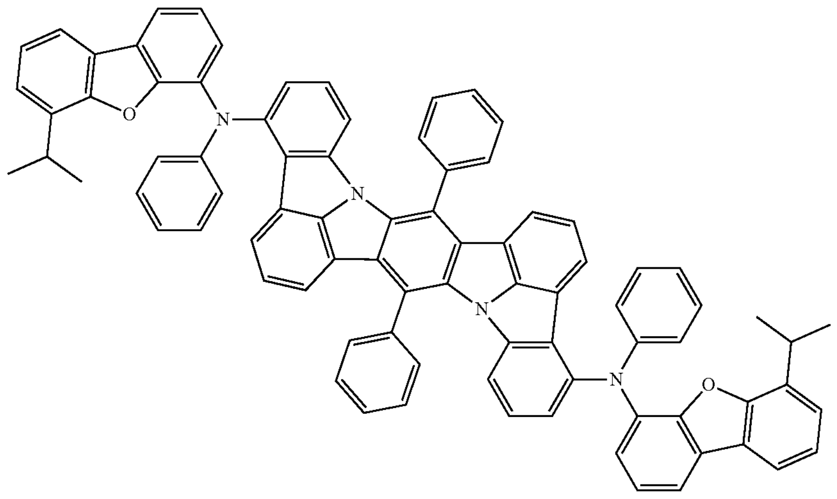
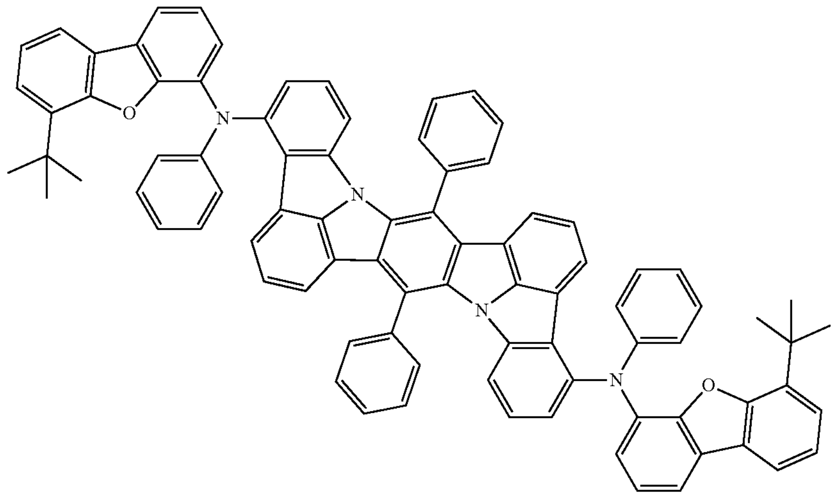

-continued
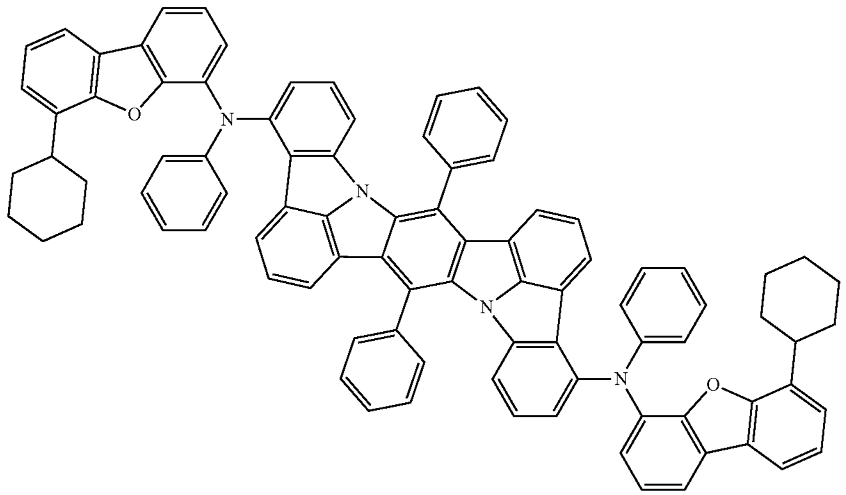
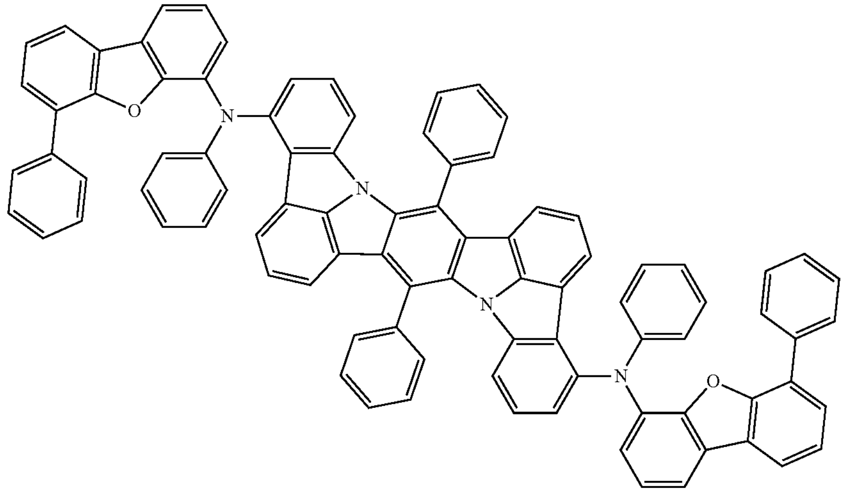
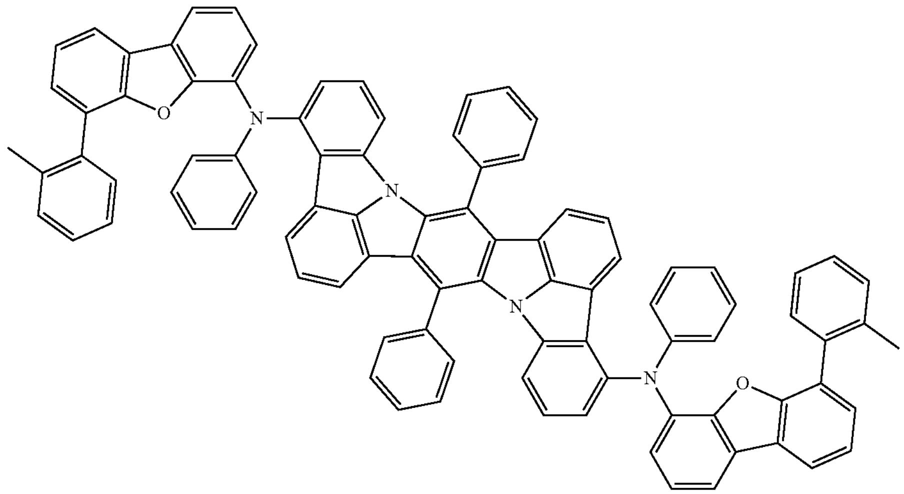

-continued
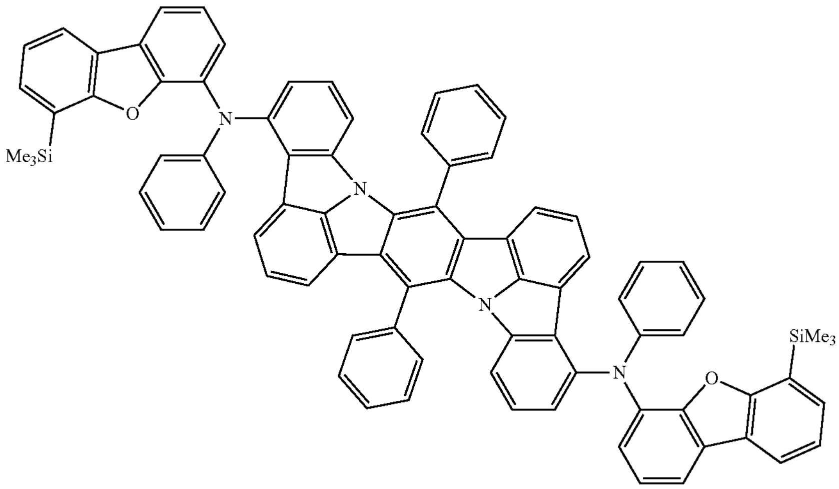
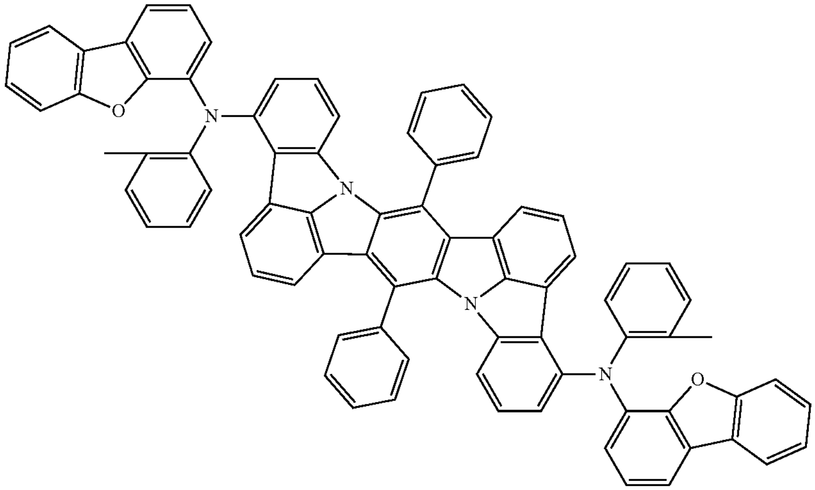
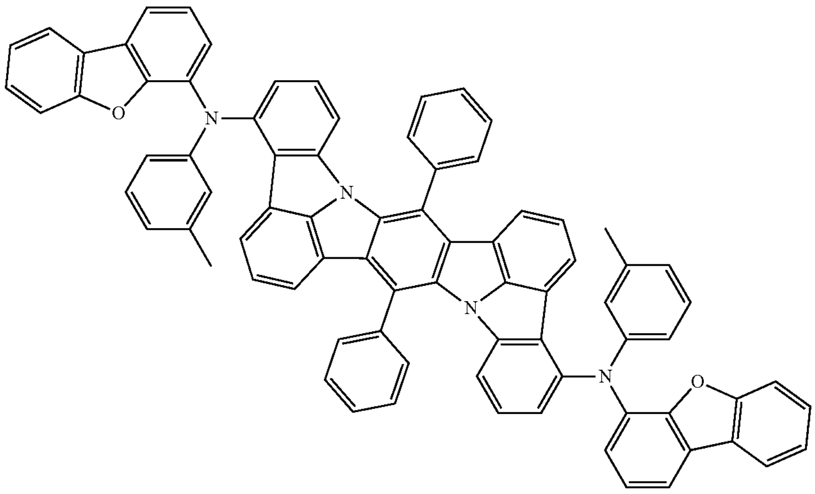

-continued
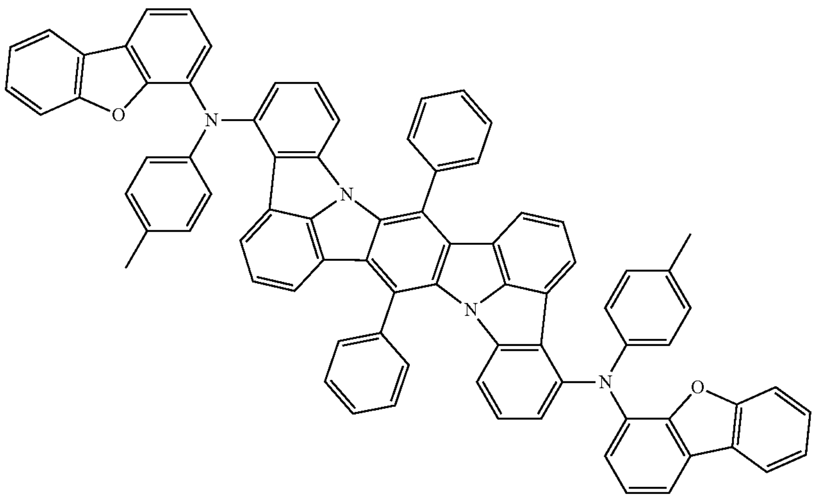
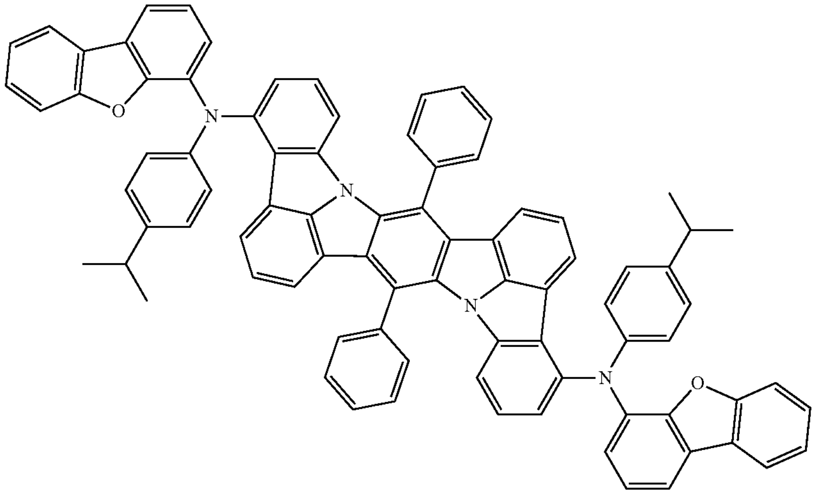
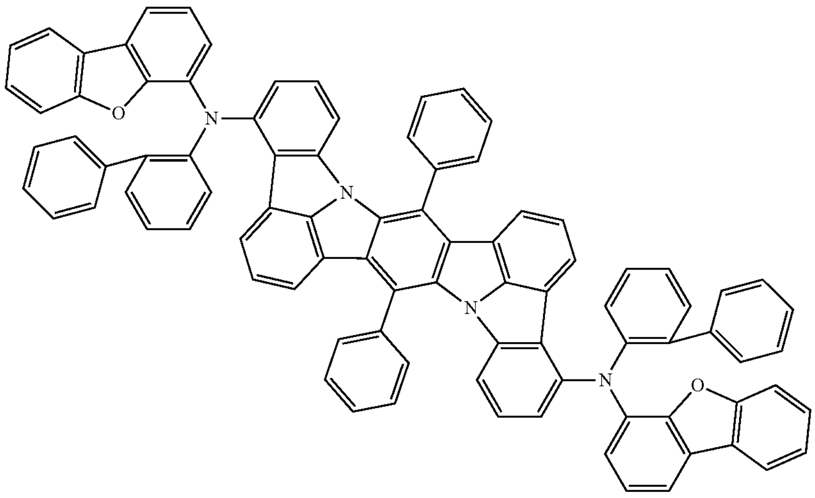

-continued
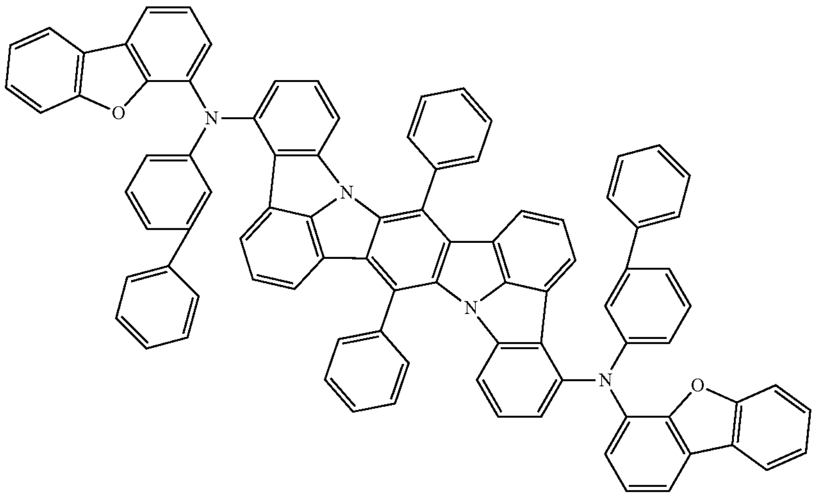
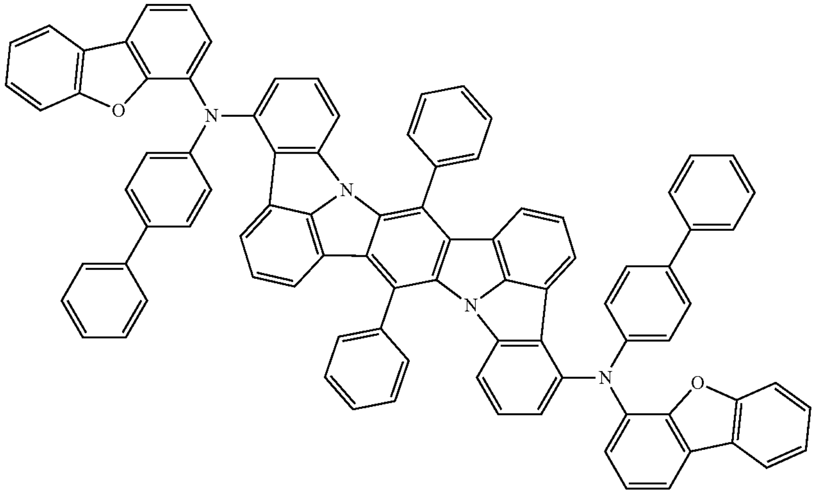
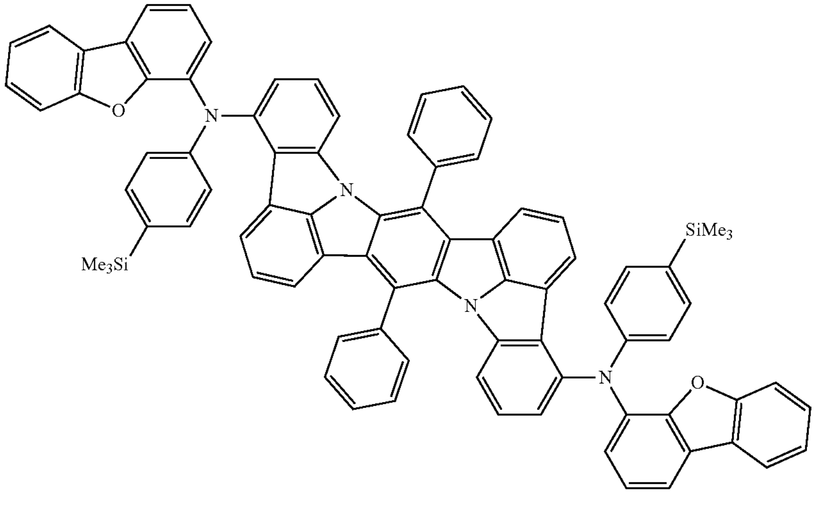

-continued
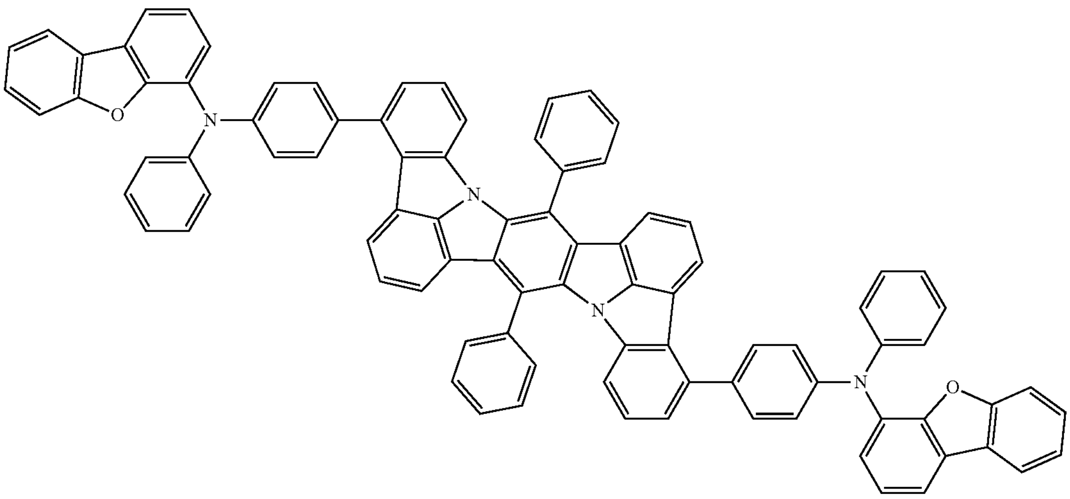
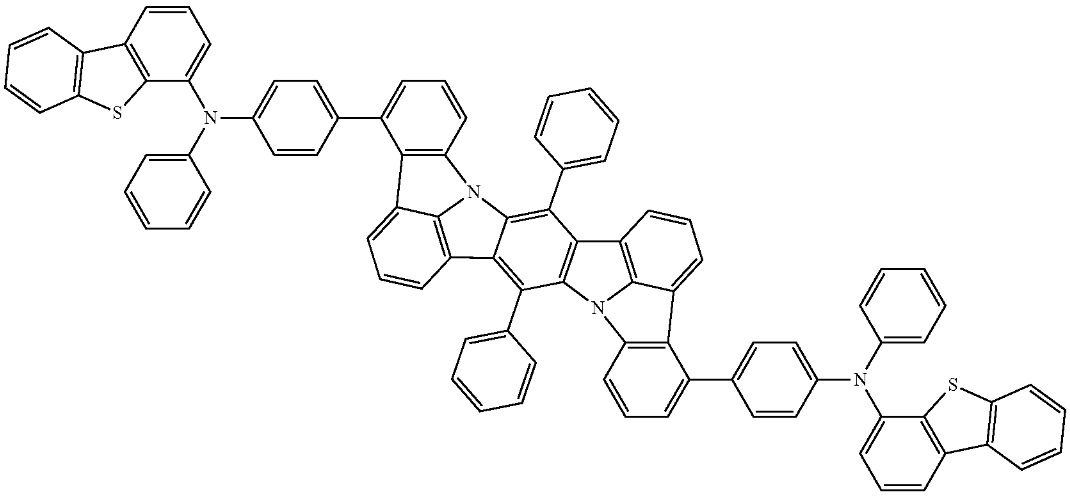
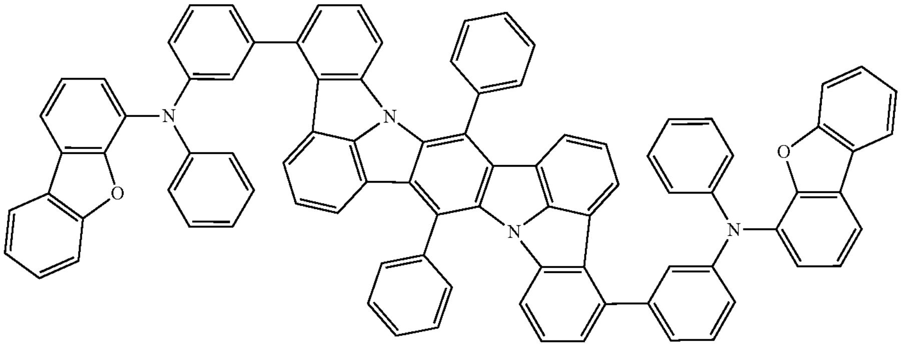
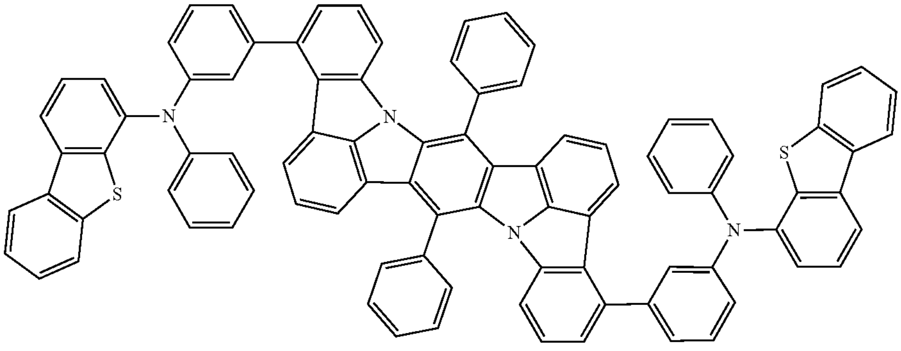

-continued
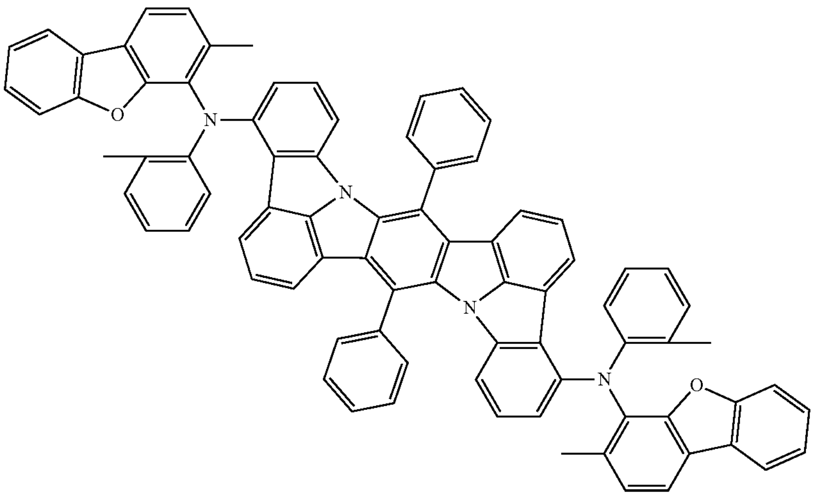
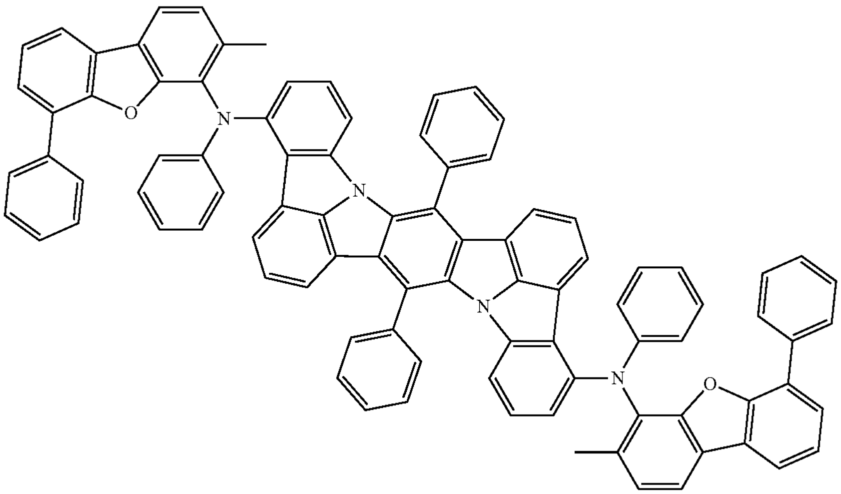
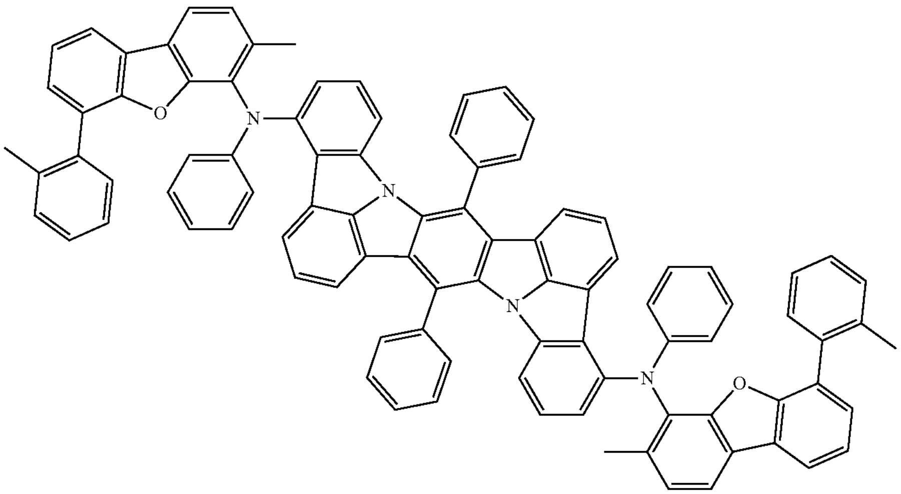

-continued
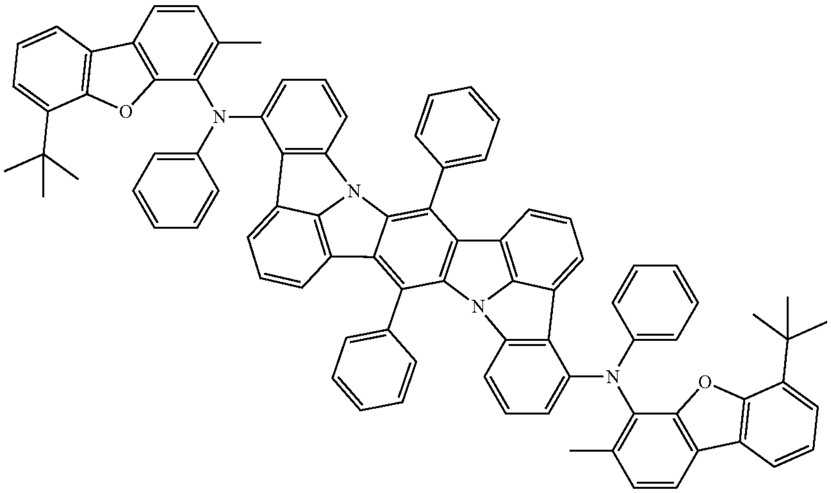
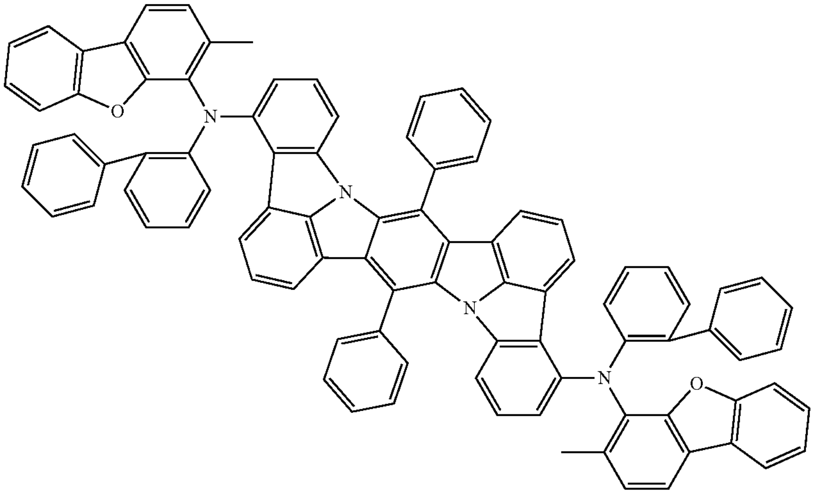
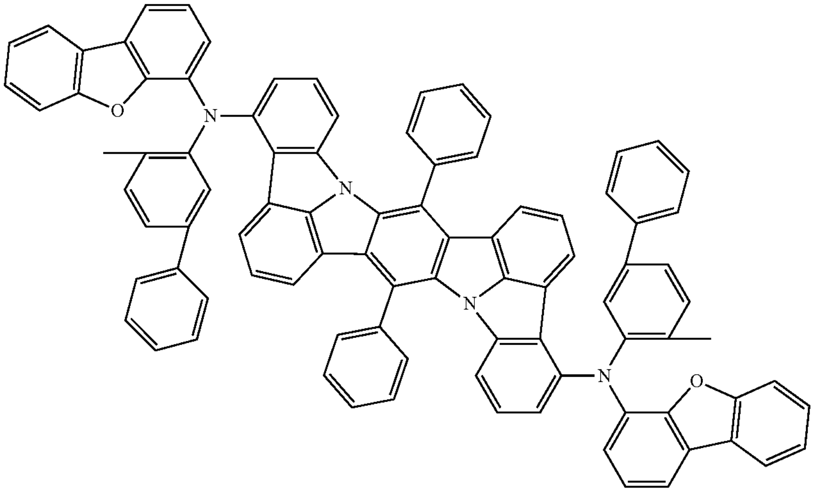

-continued
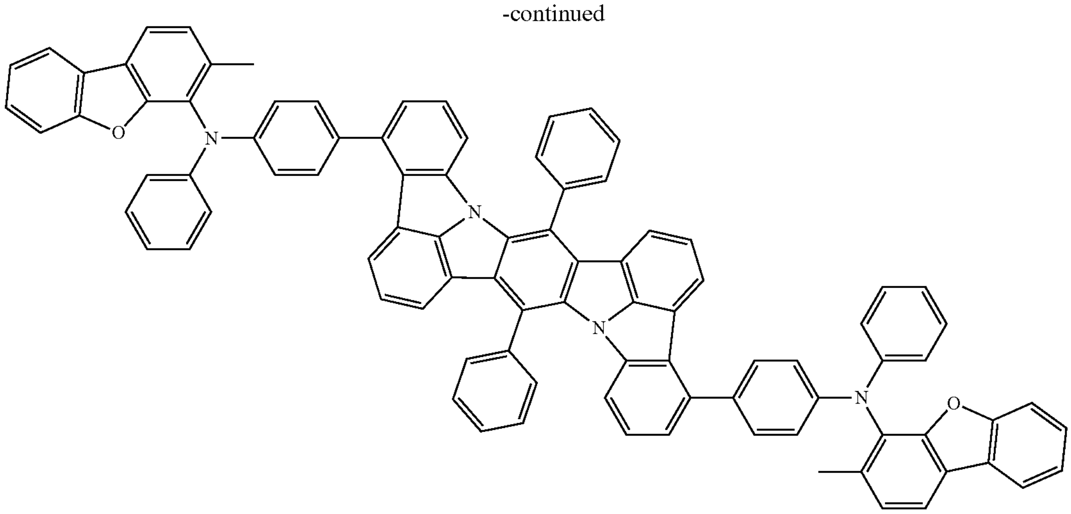
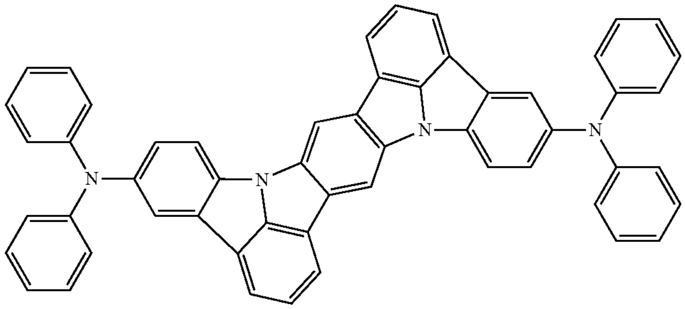
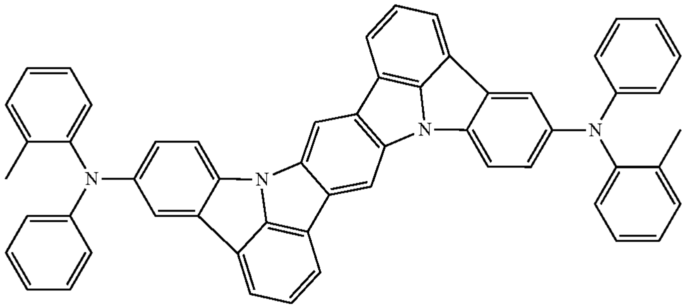
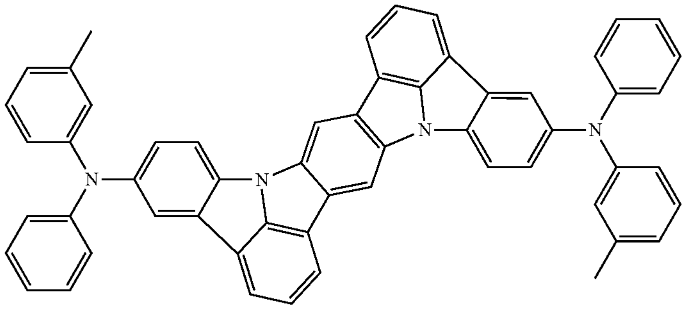
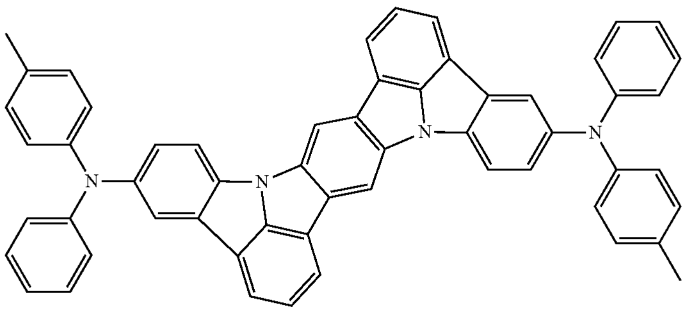

-continued
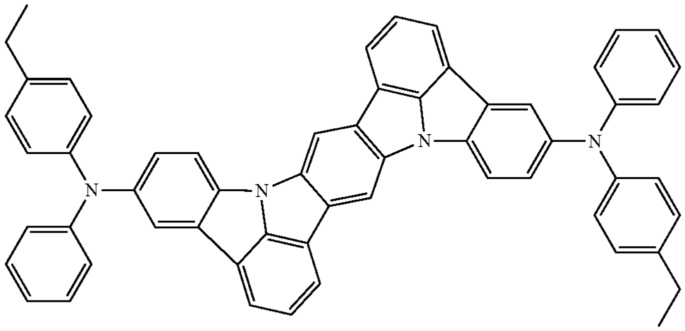
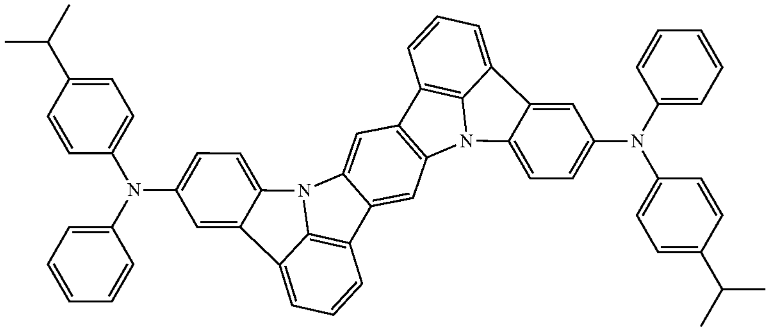
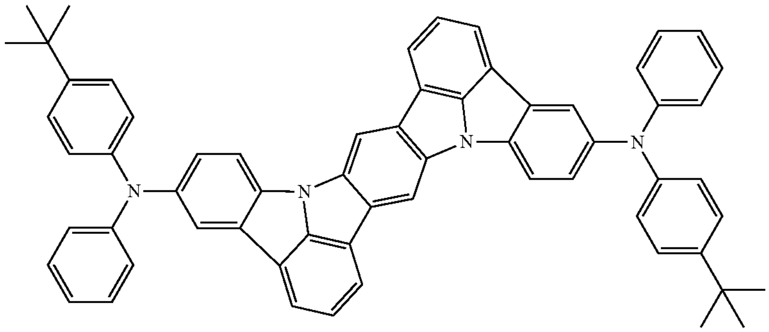
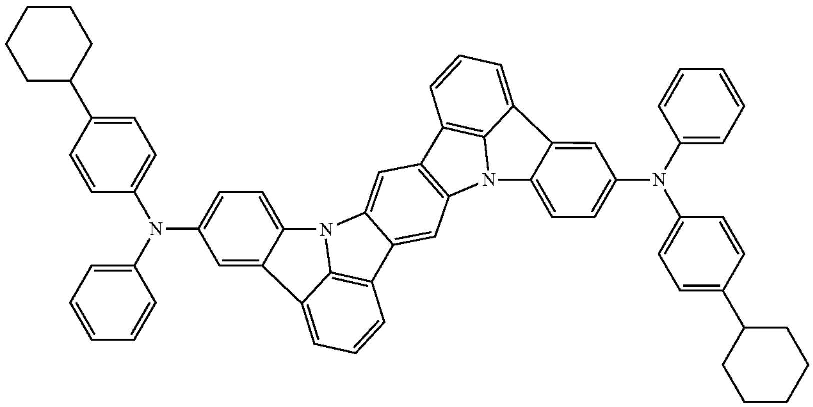

-continued
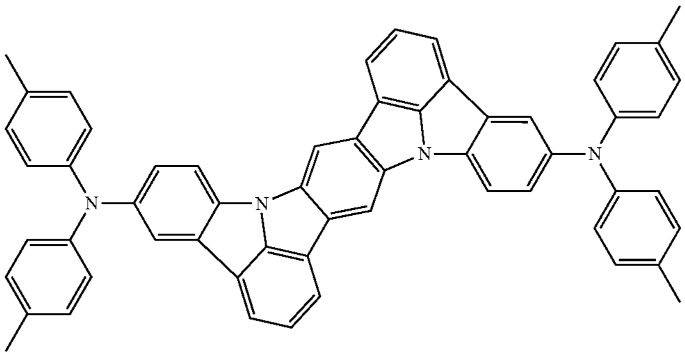
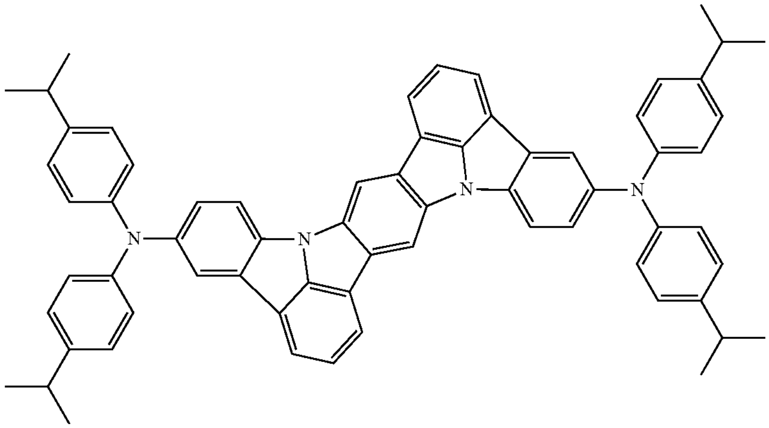
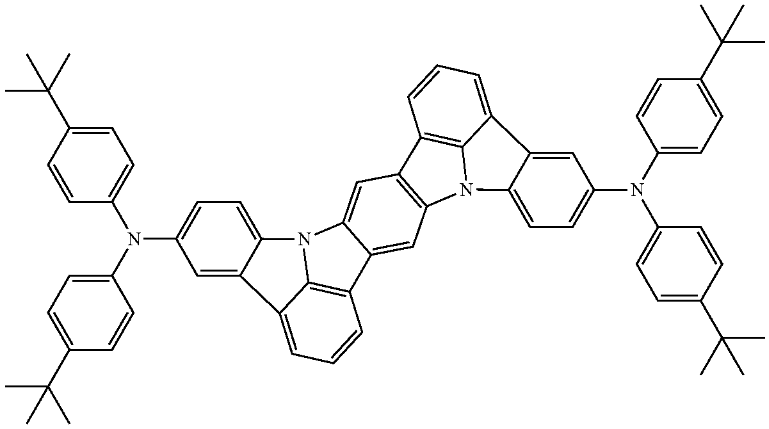
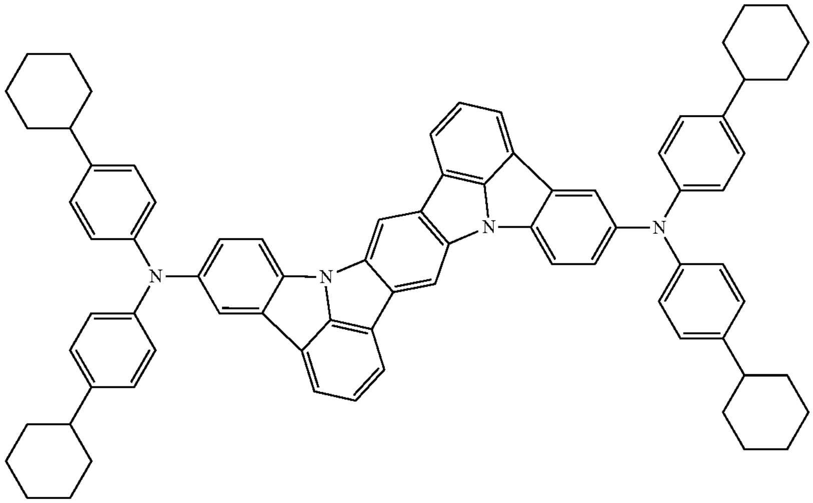

-continued
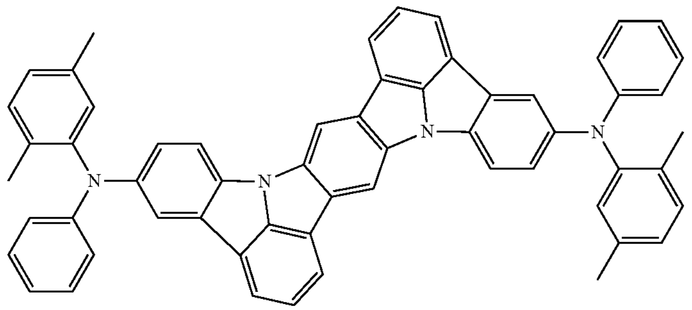
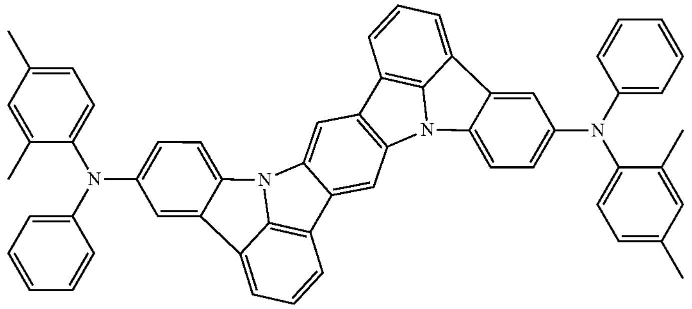
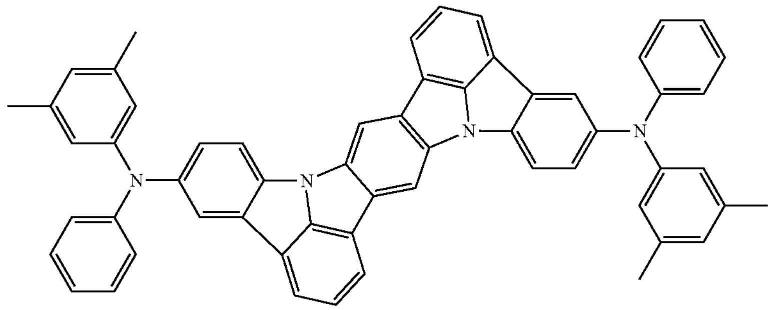
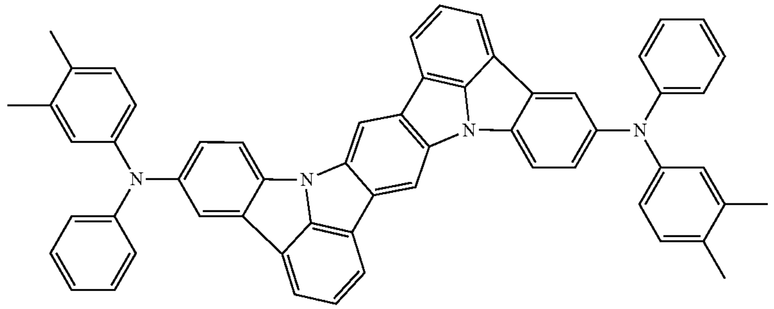
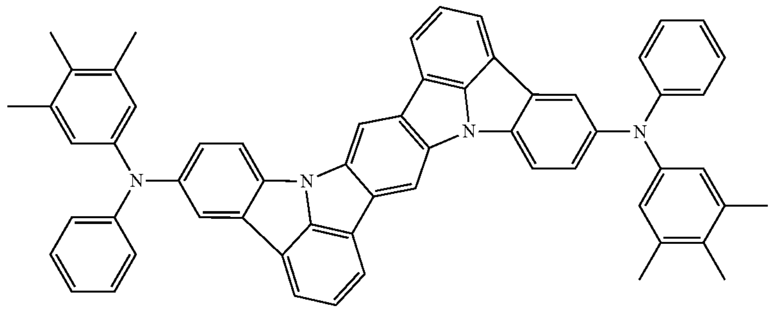

-continued
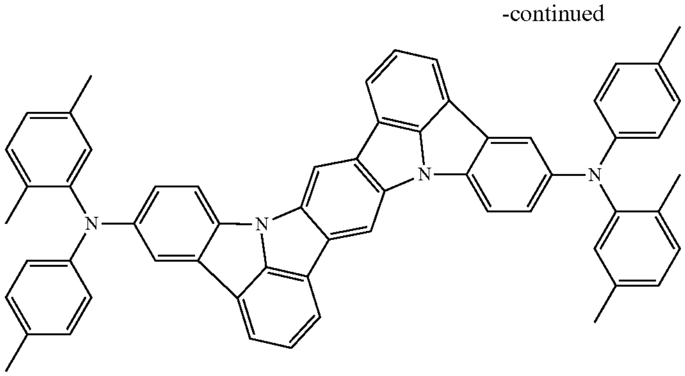
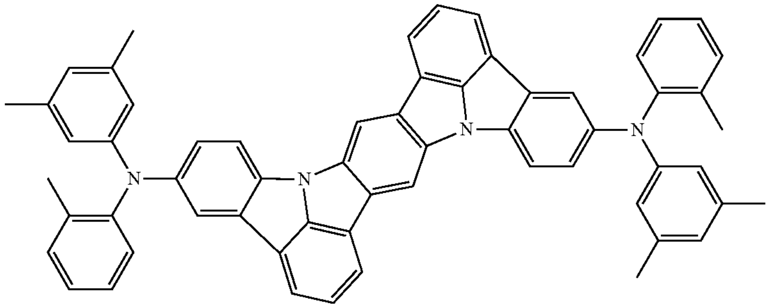
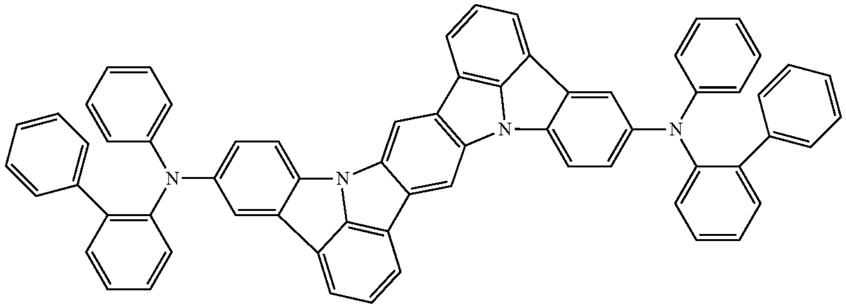
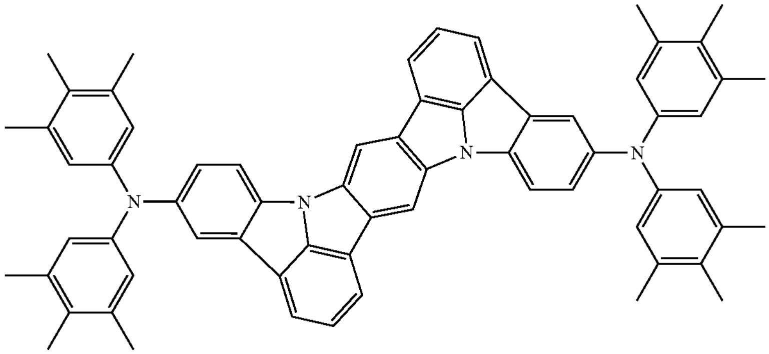
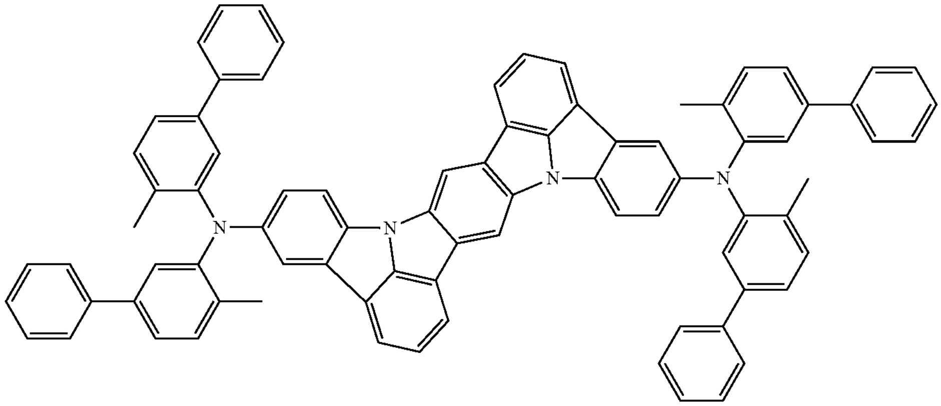

-continued
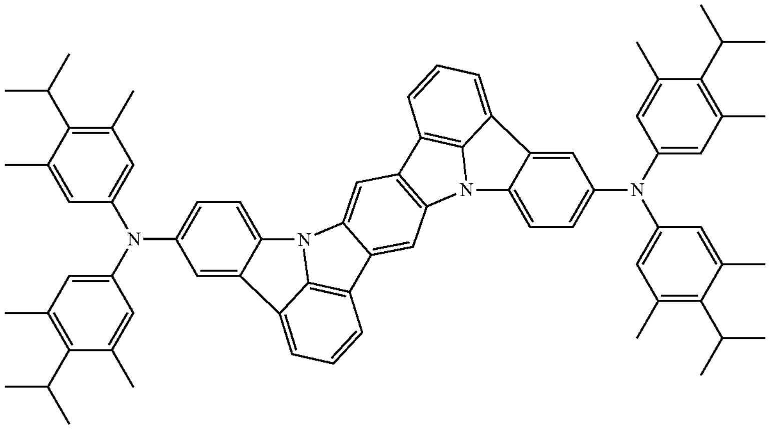
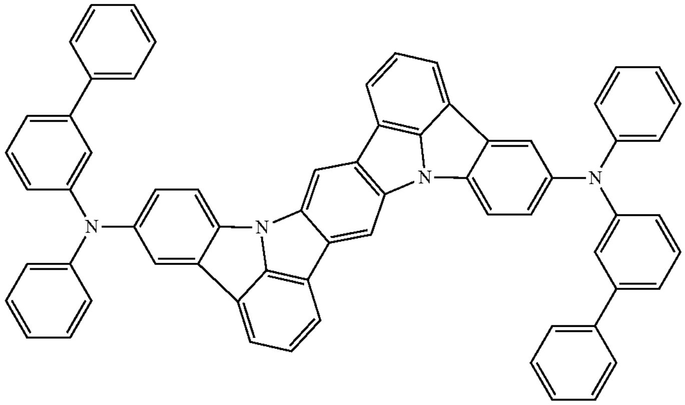
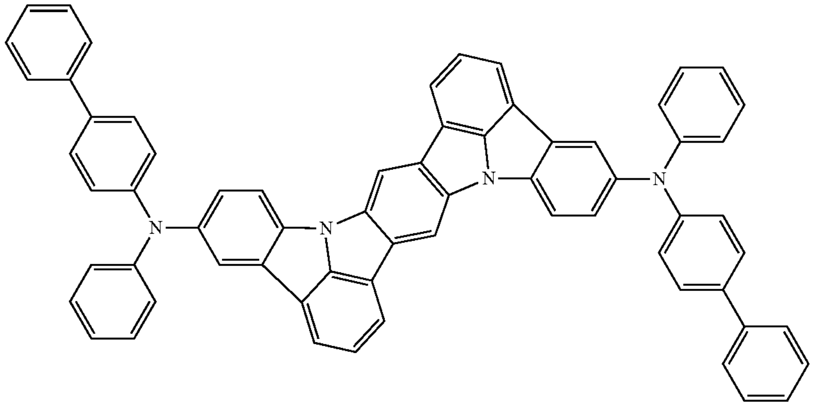
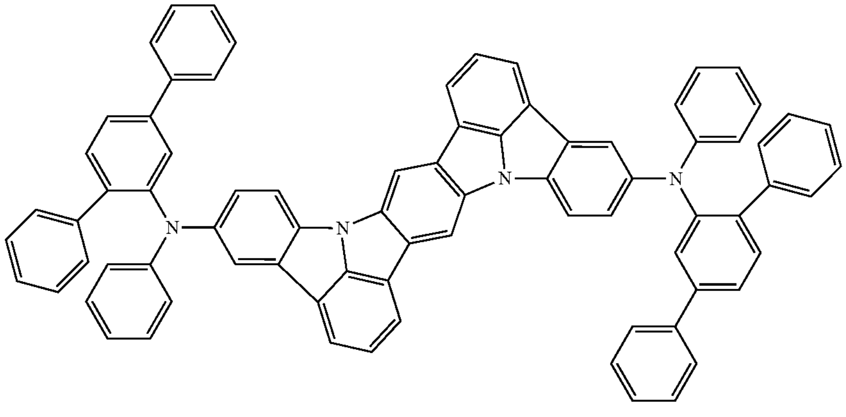

-continued
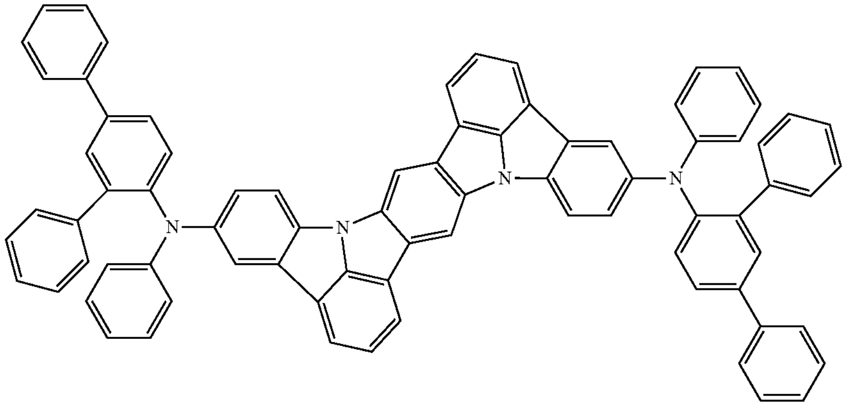
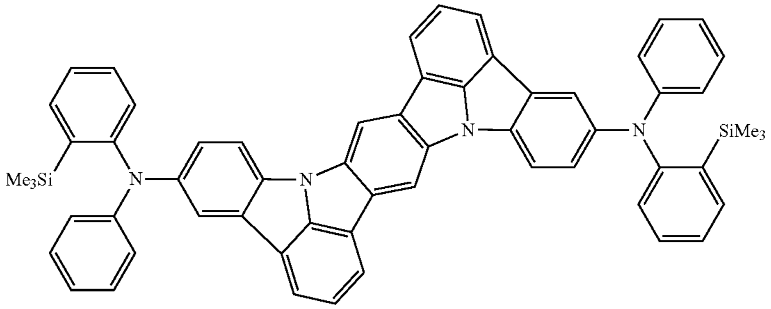
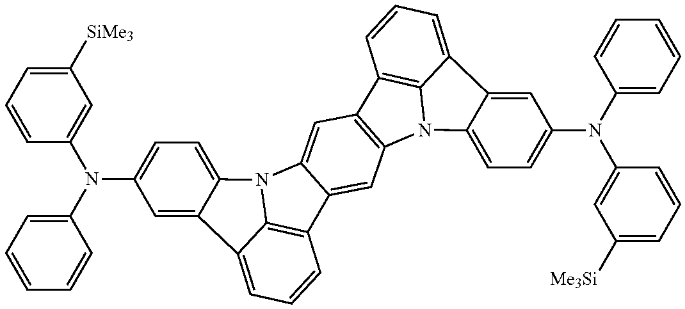
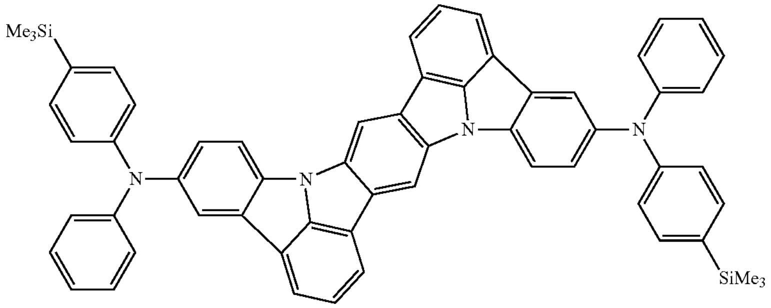

-continued
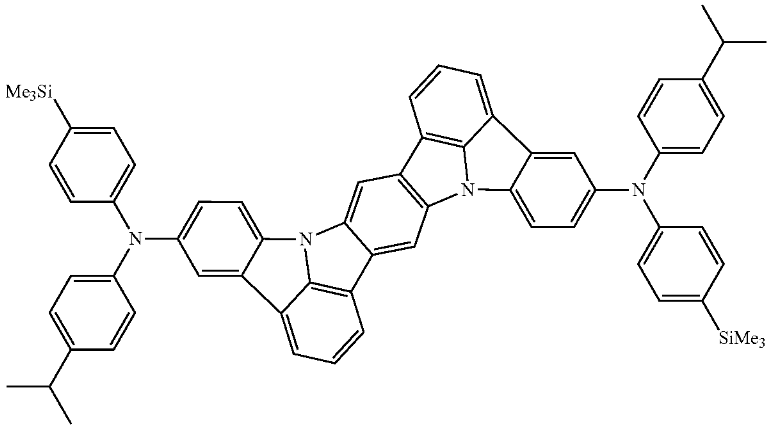
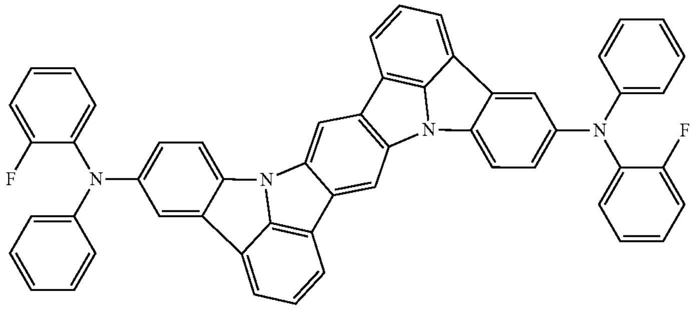
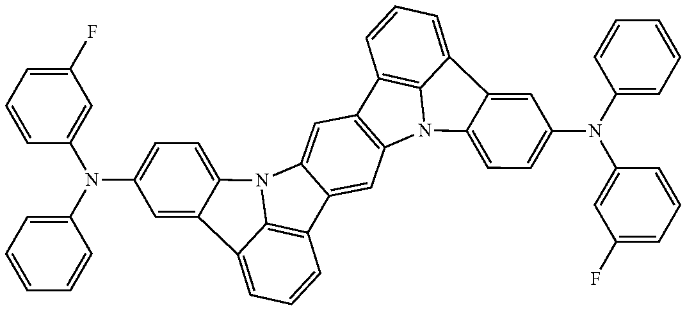
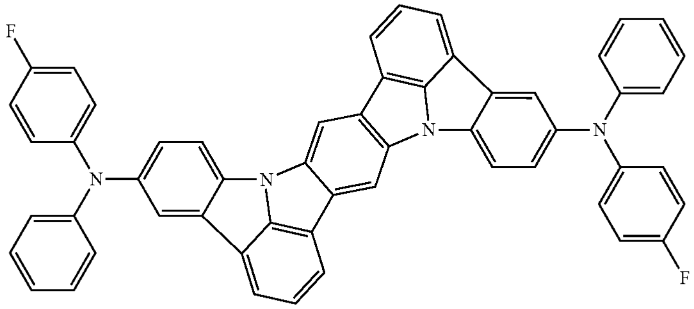

-continued
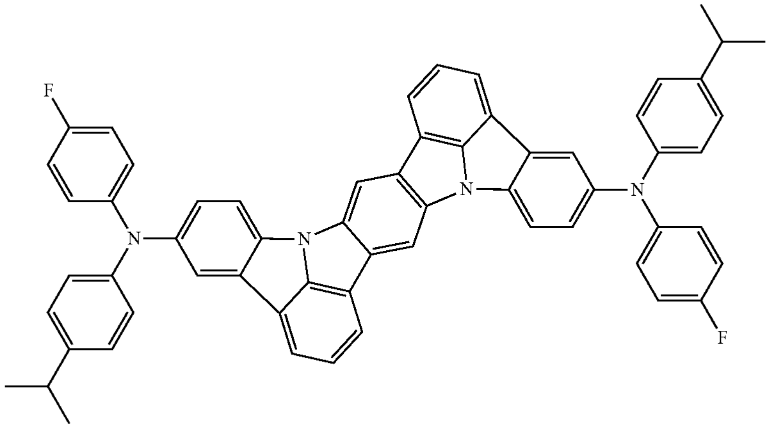
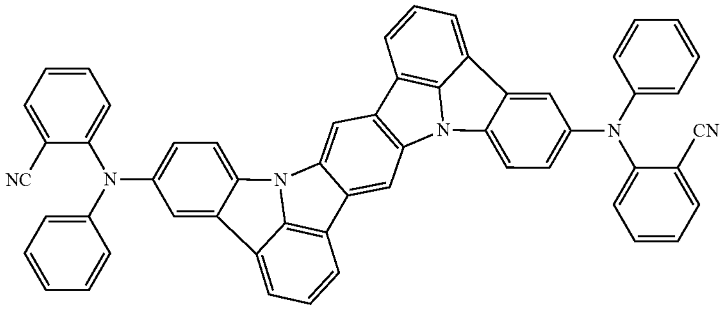
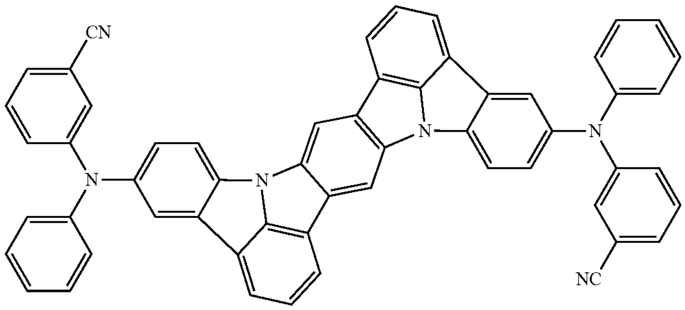
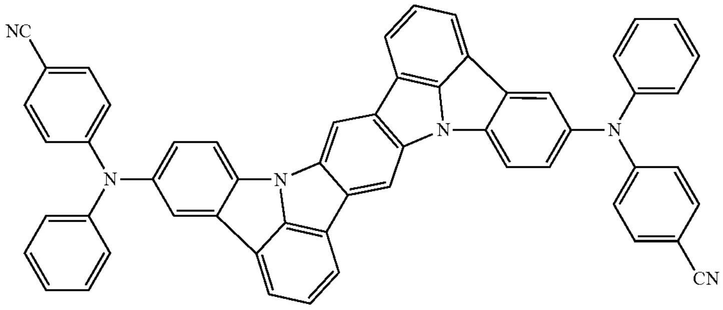

-continued
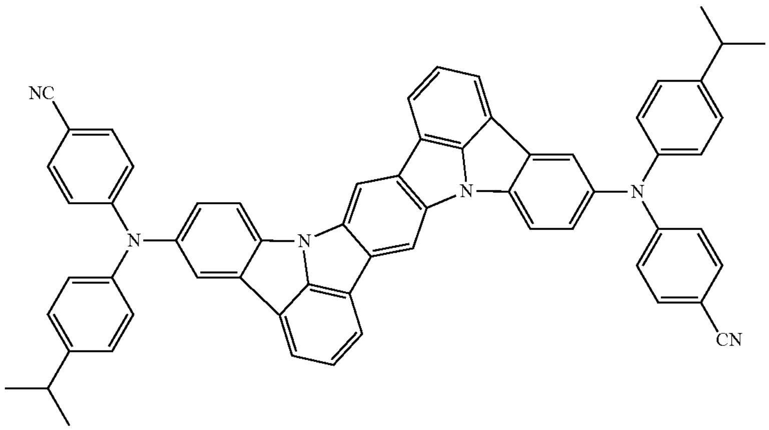
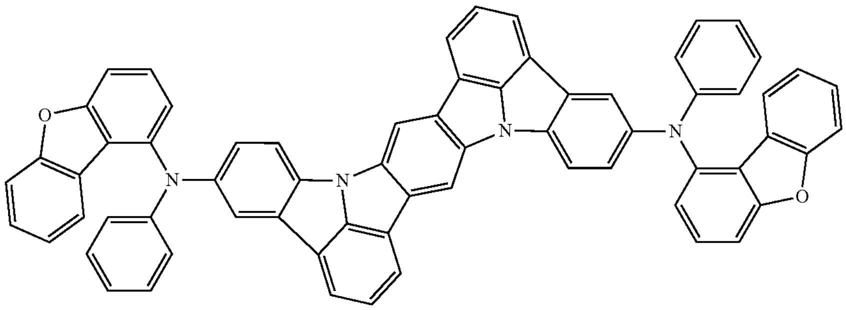
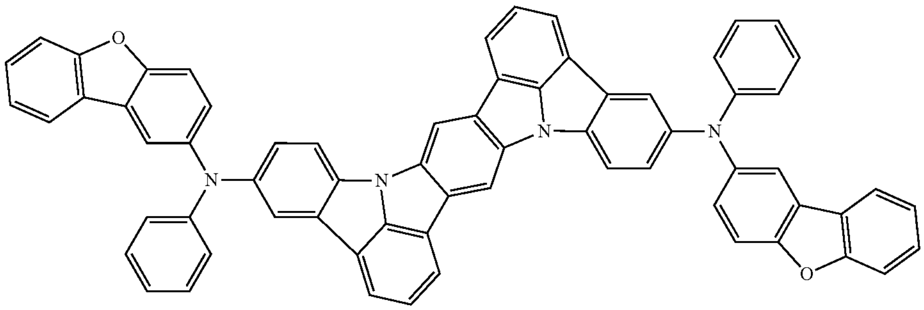
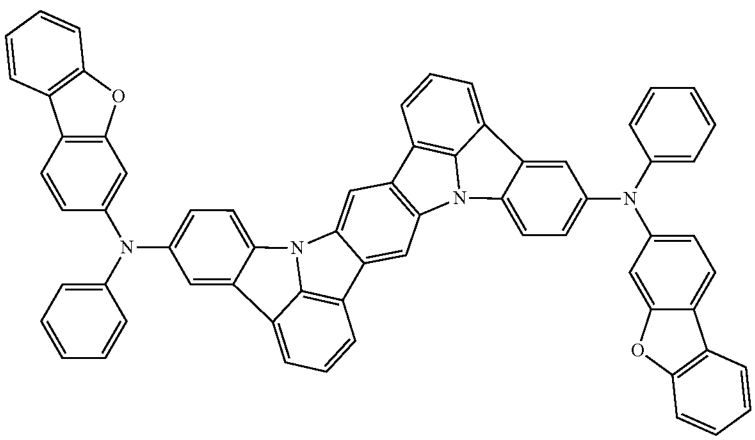

-continued
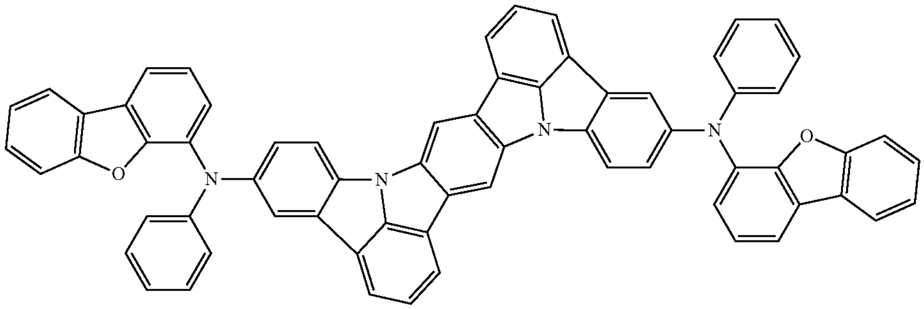
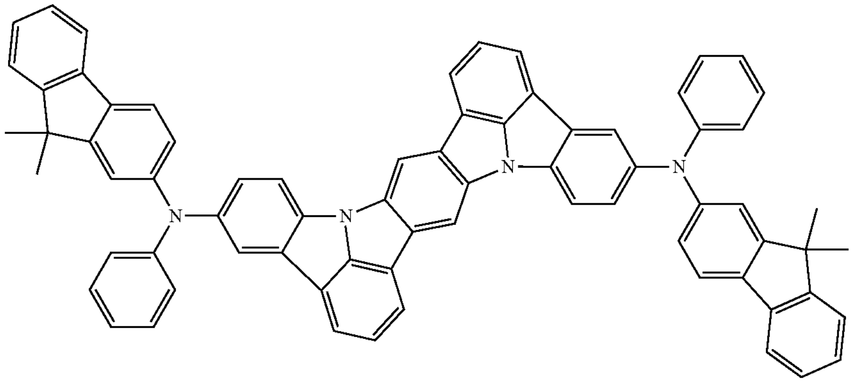
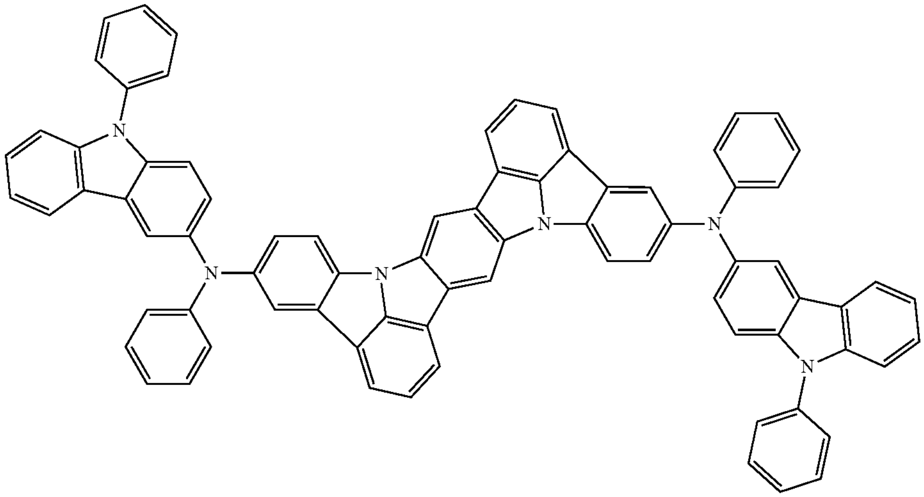
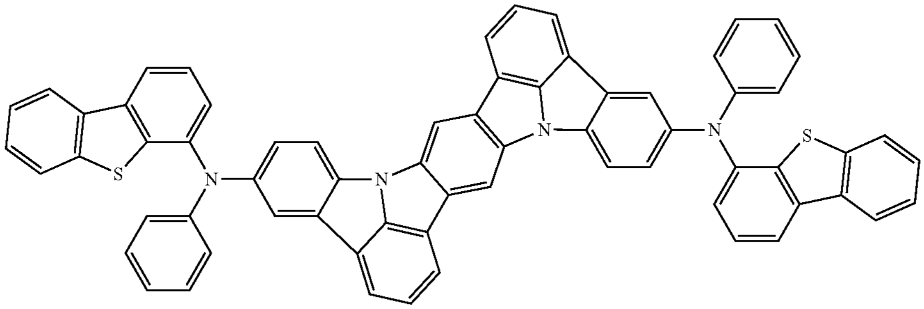

-continued
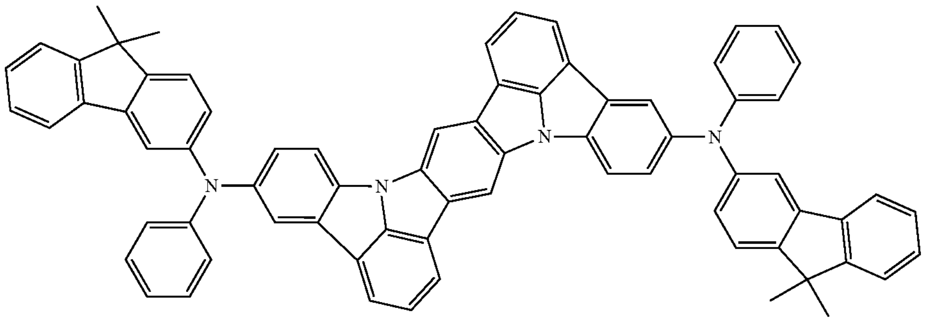
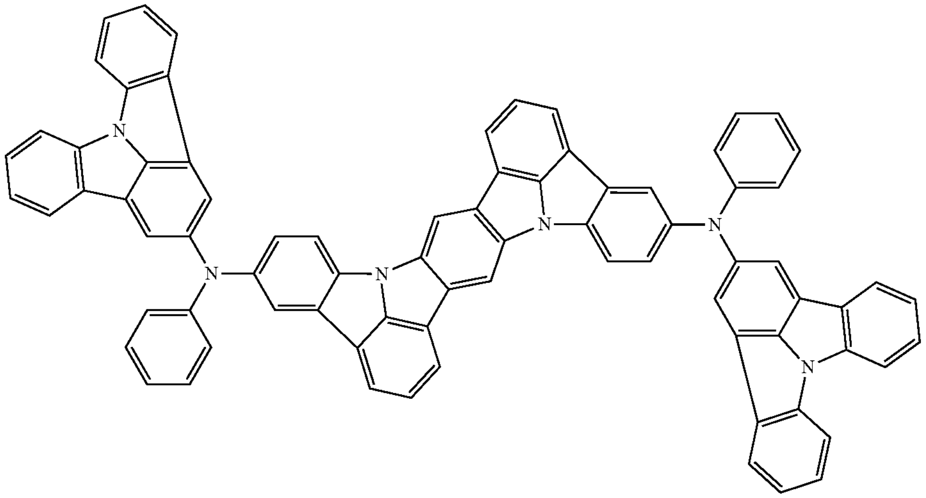
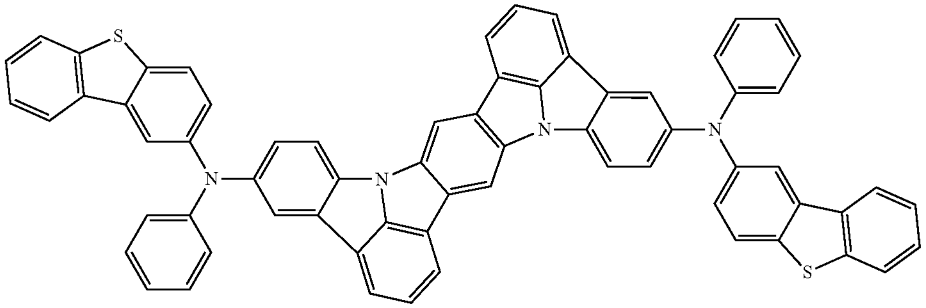
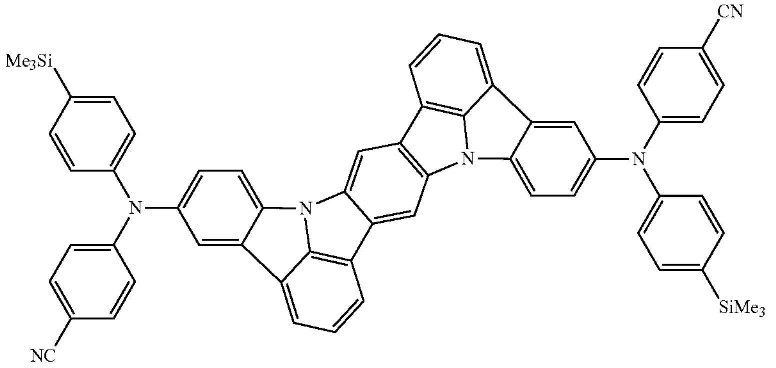

-continued
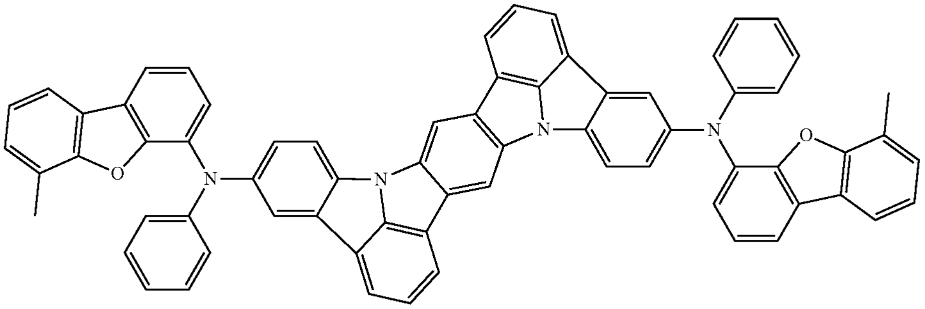
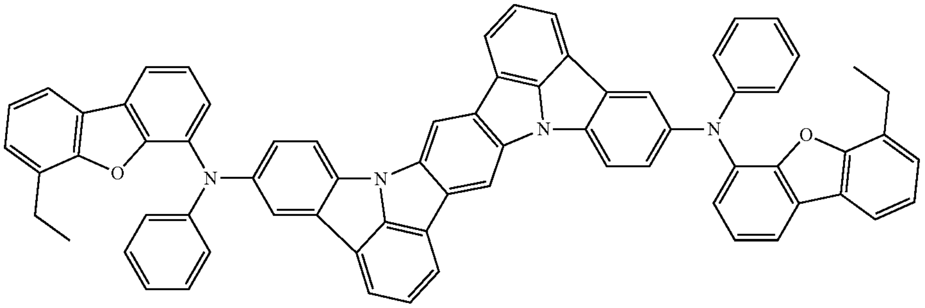
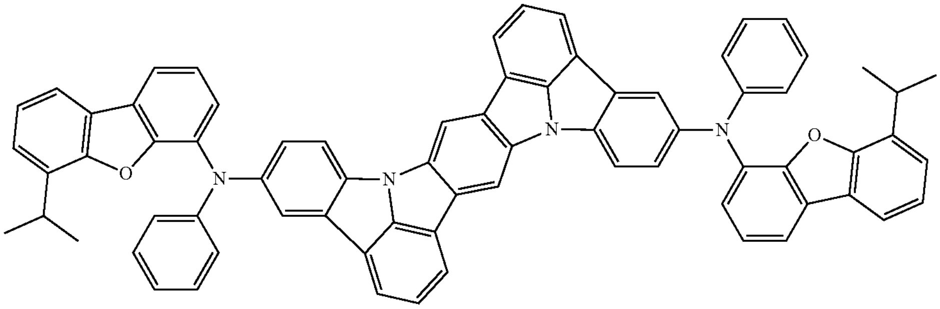
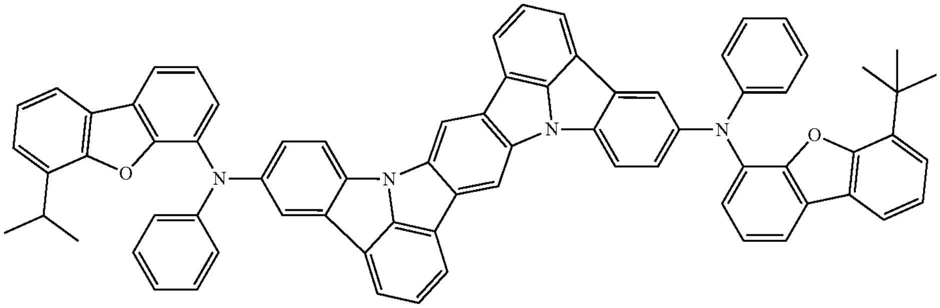
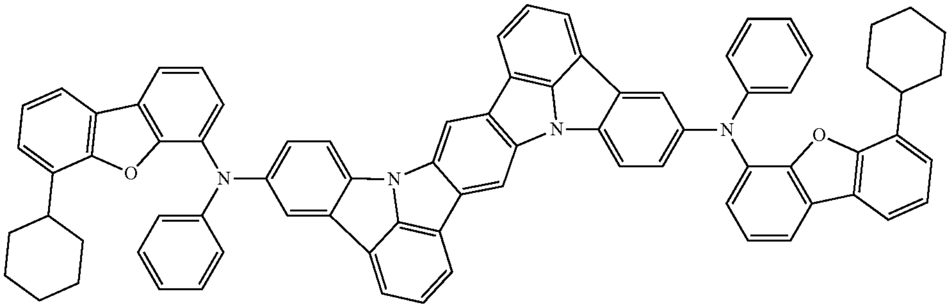

-continued
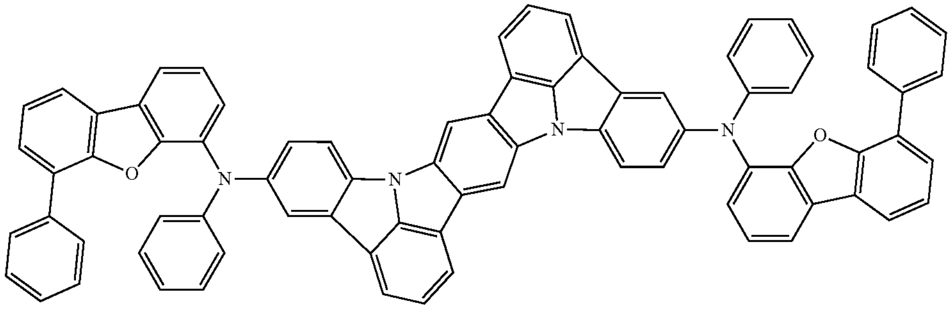
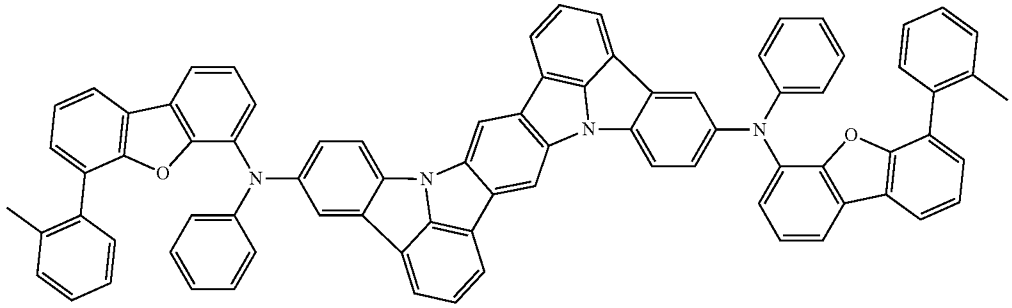
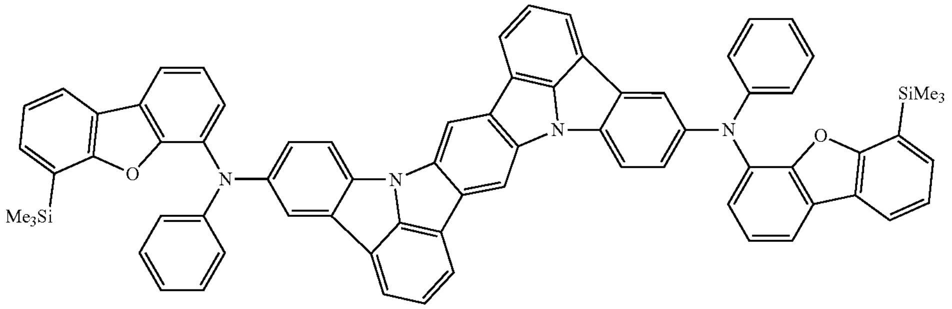
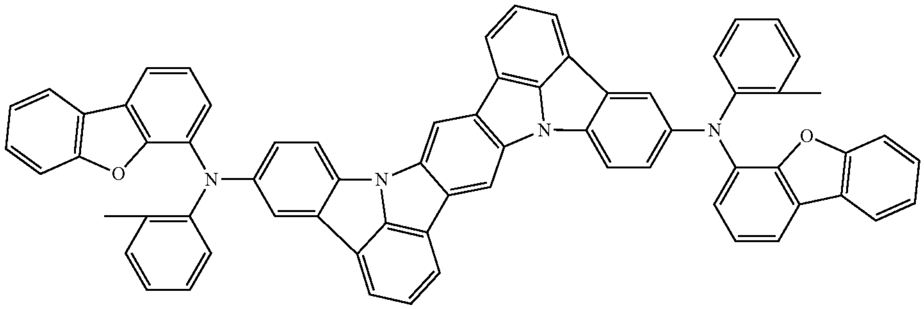
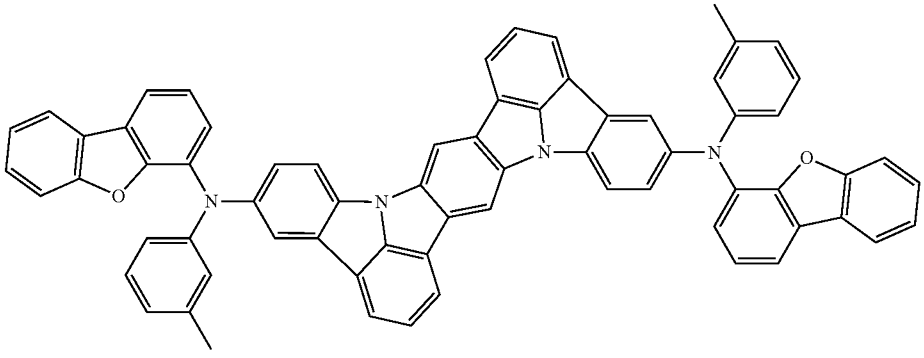

-continued
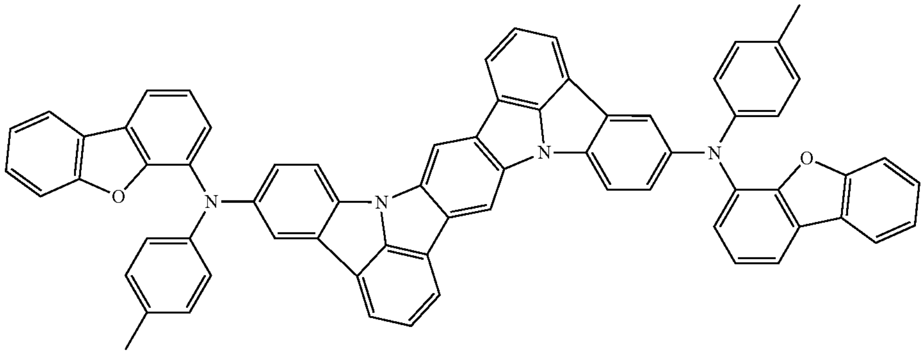
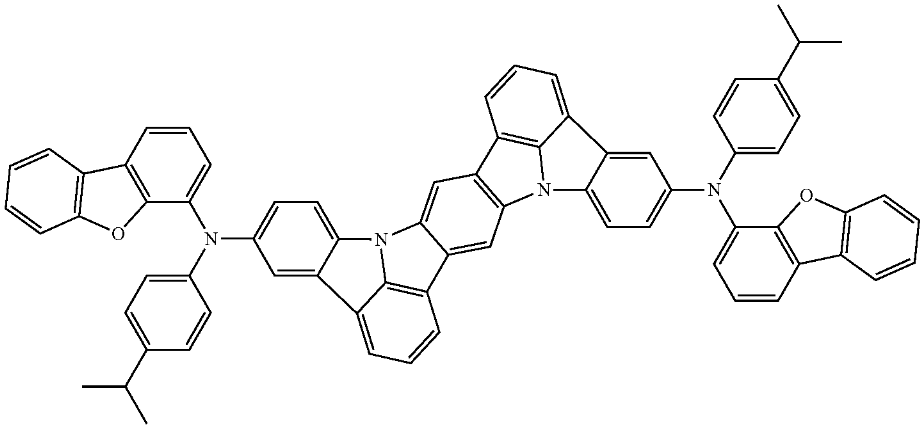
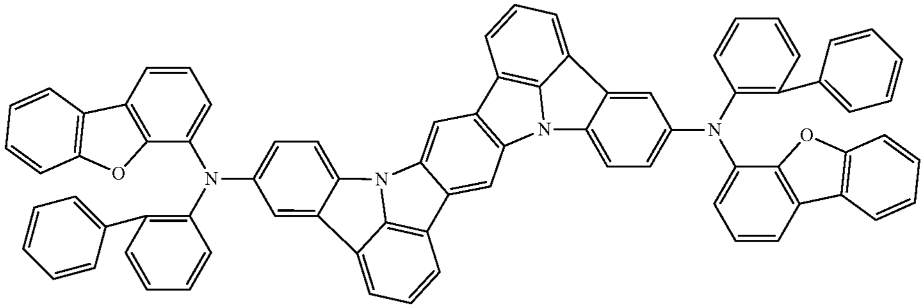
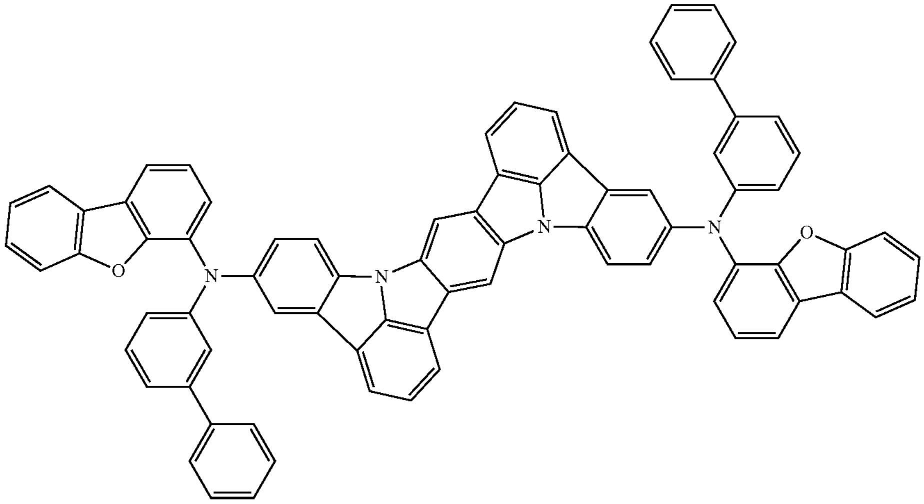

-continued
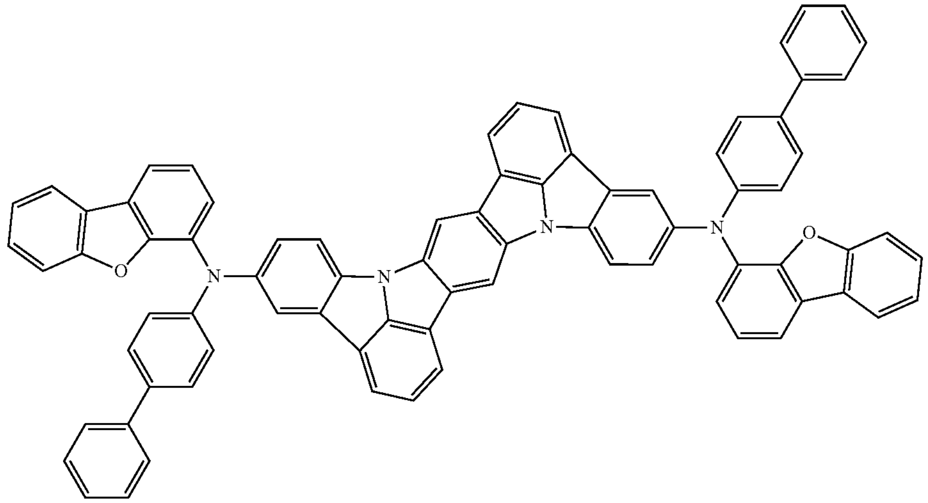
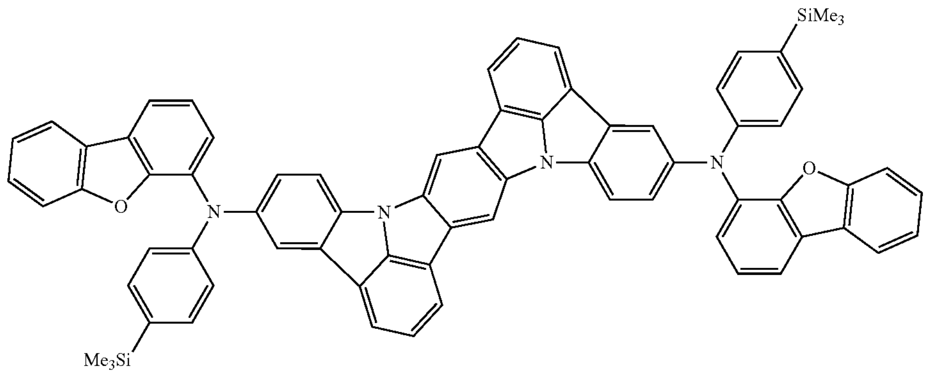
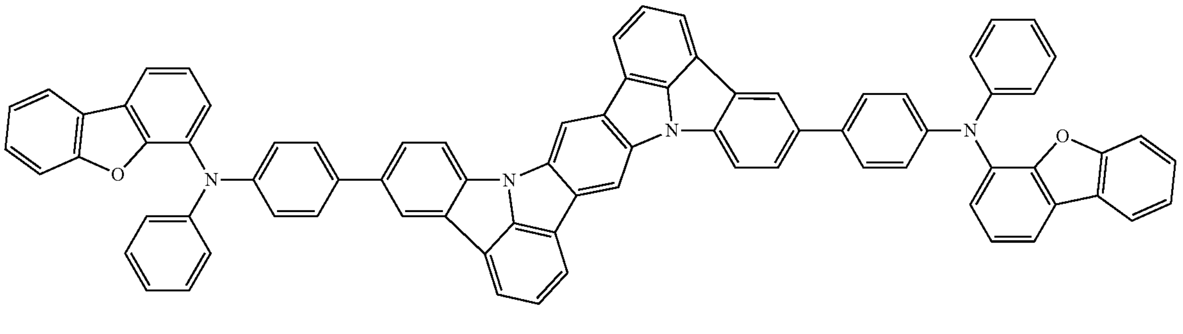
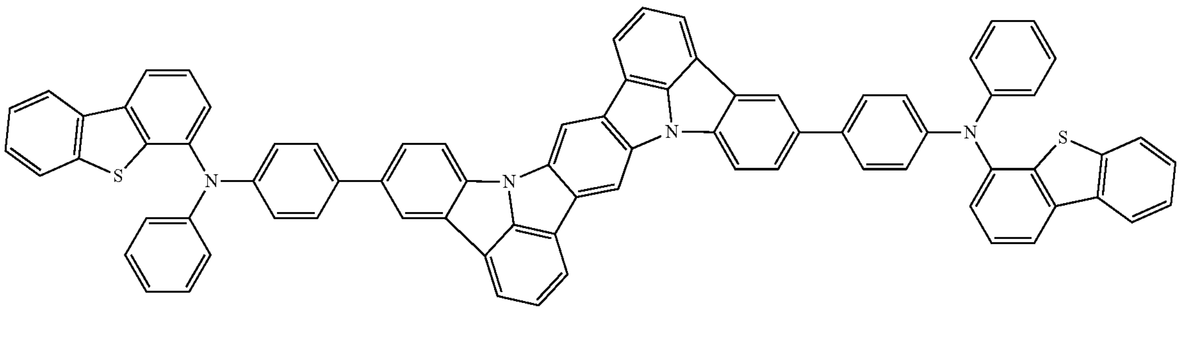

-continued
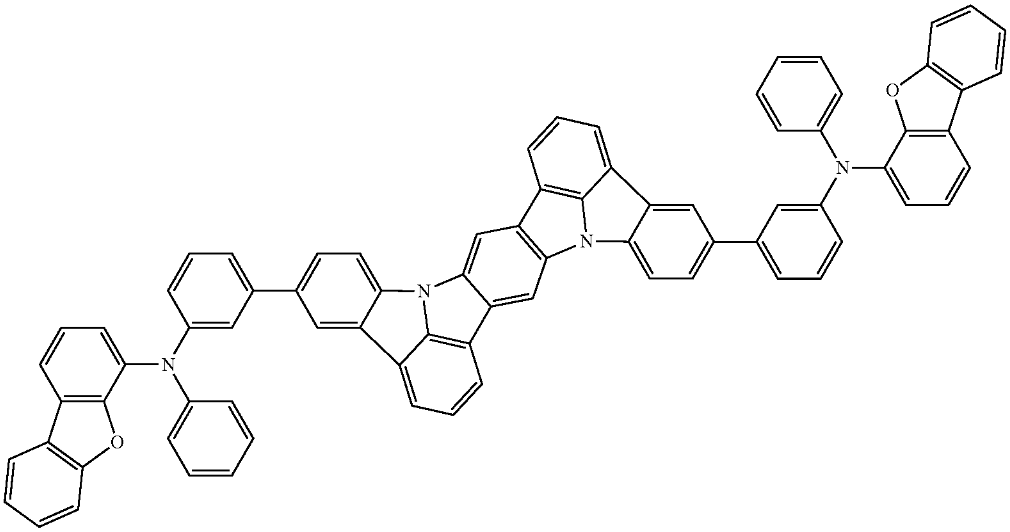
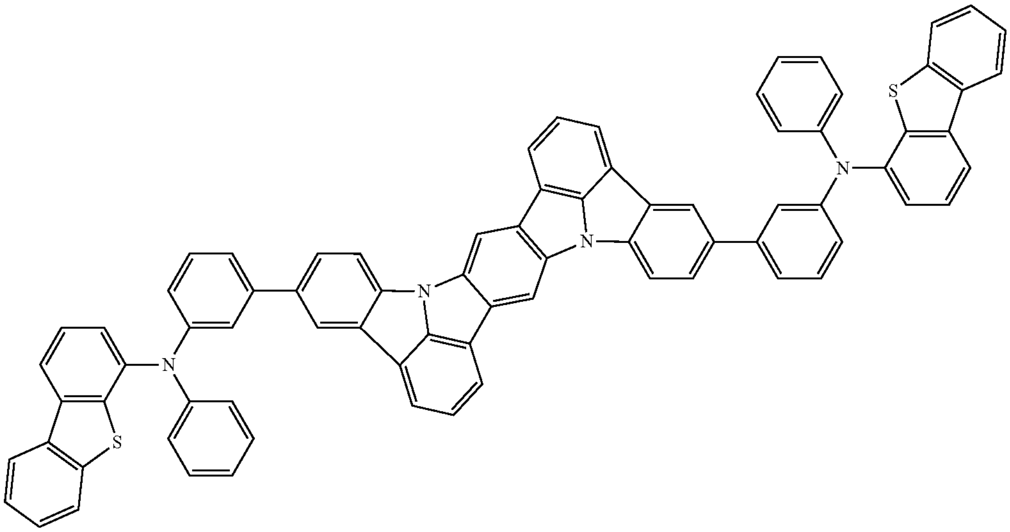
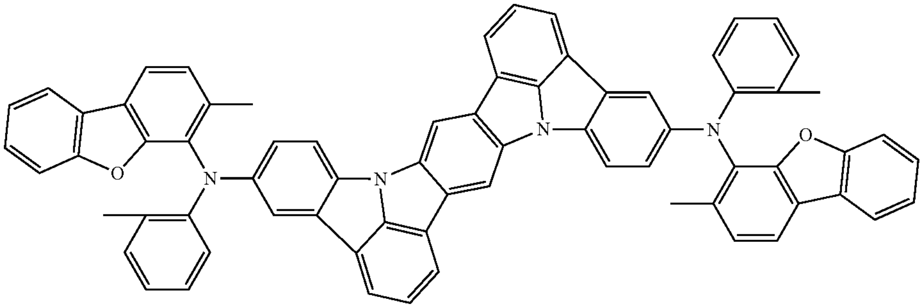
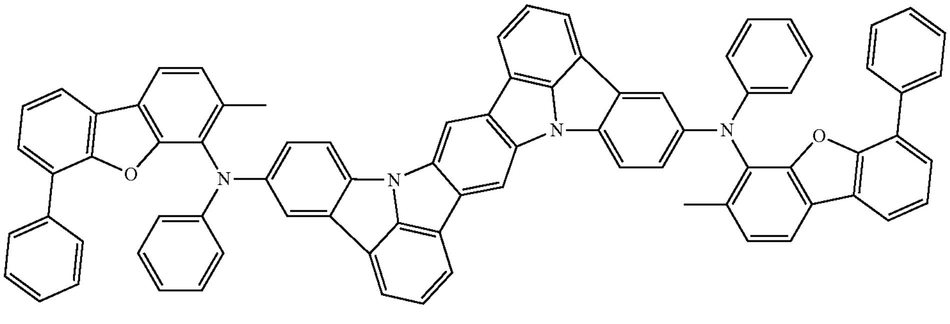

-continued
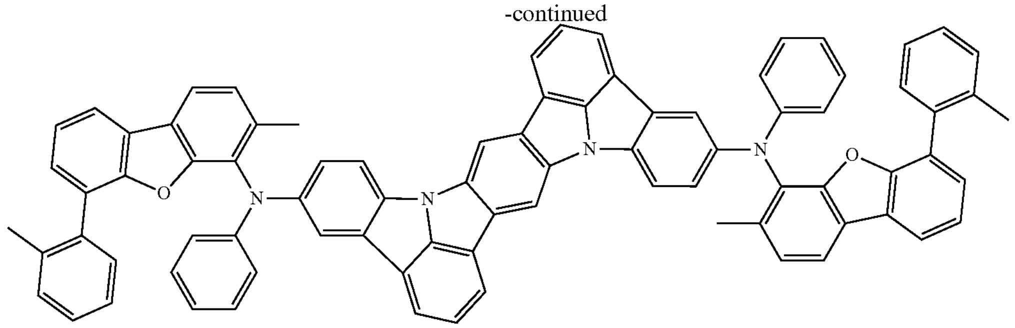
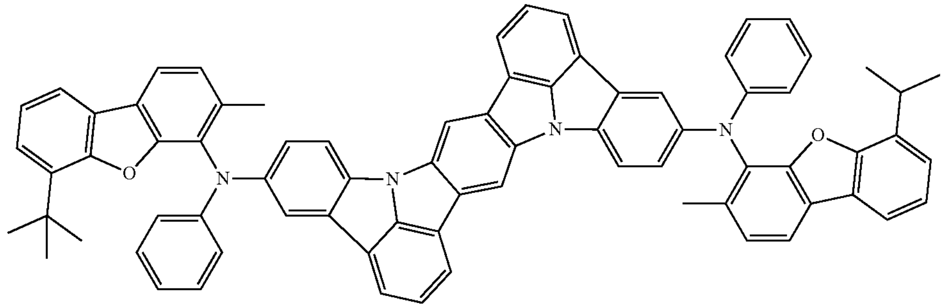
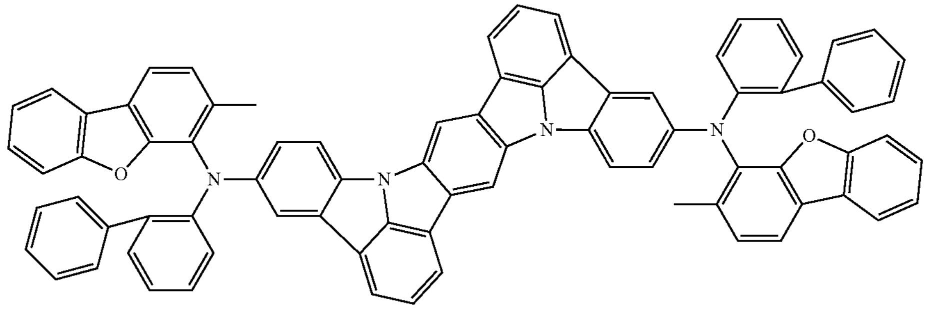
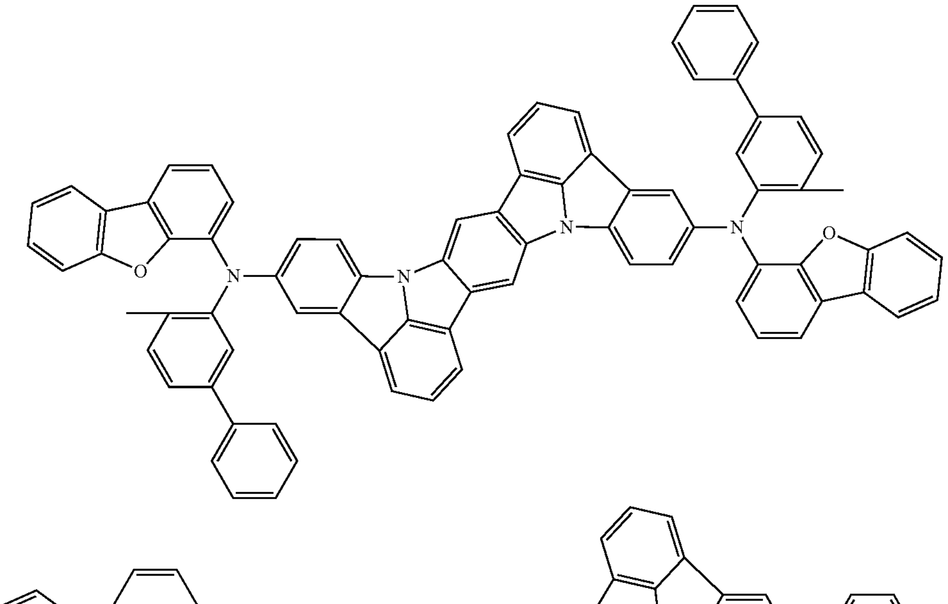
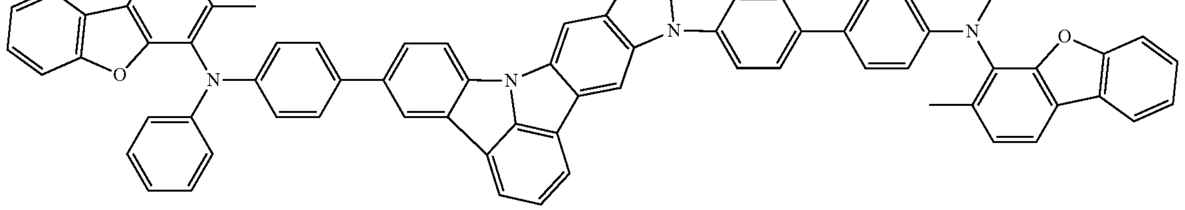

-continued
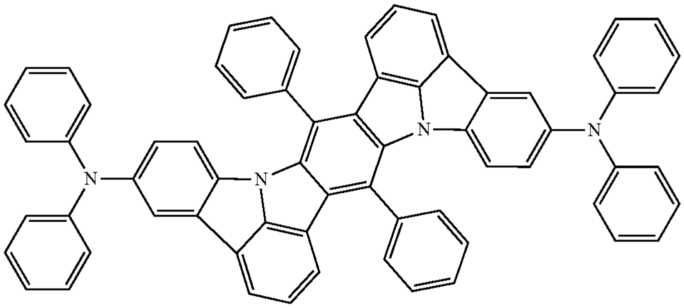
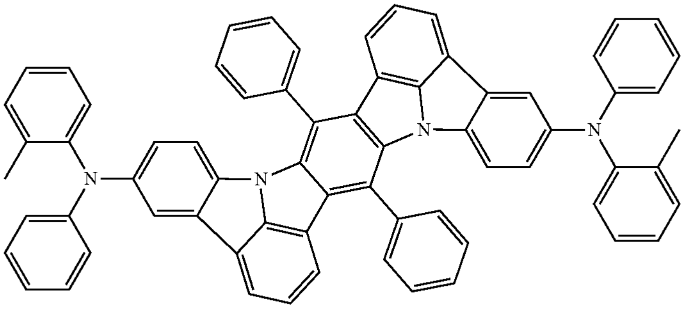
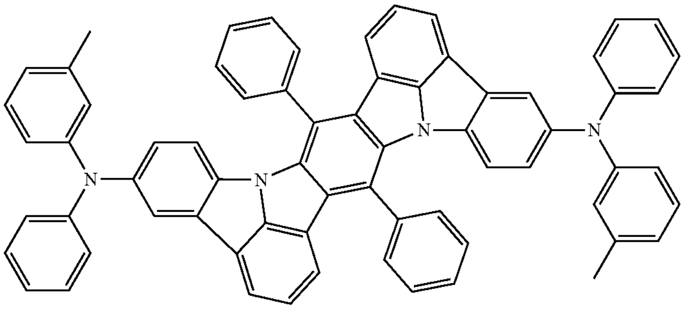
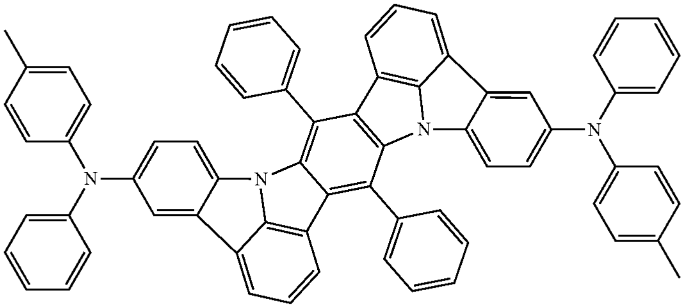
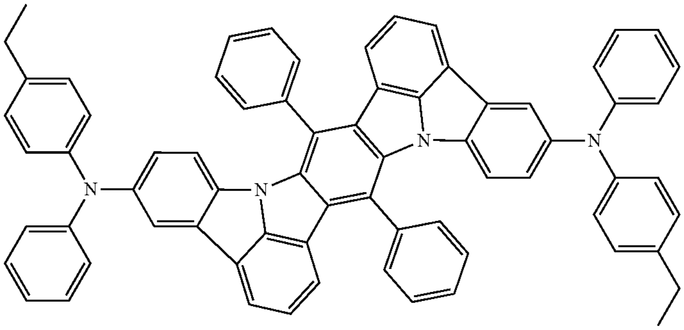

-continued
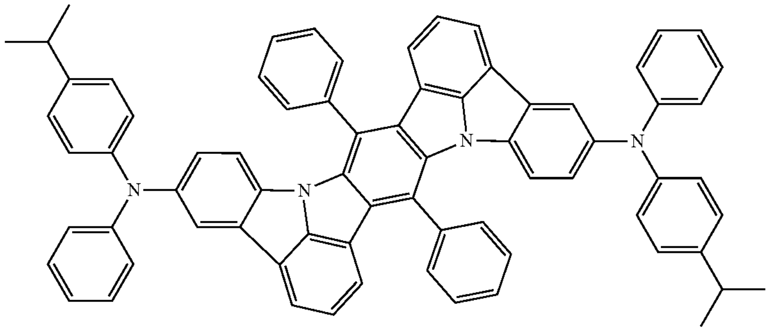
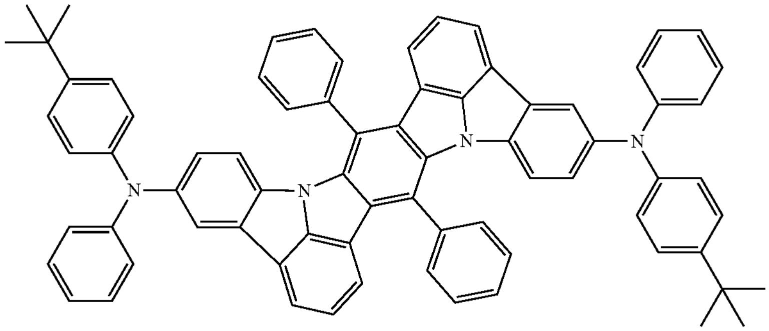
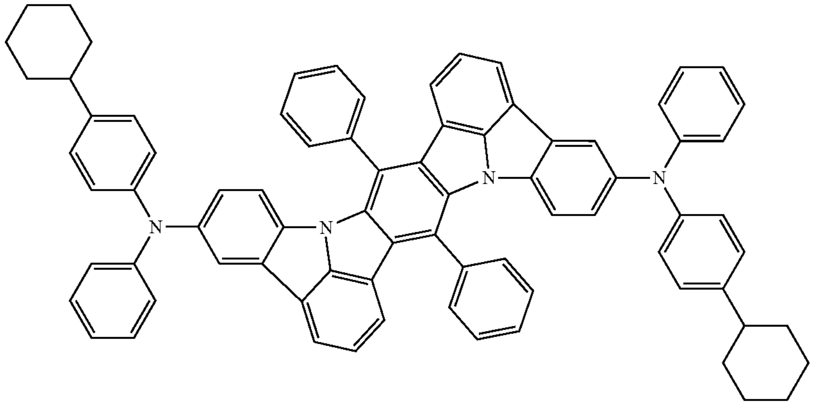
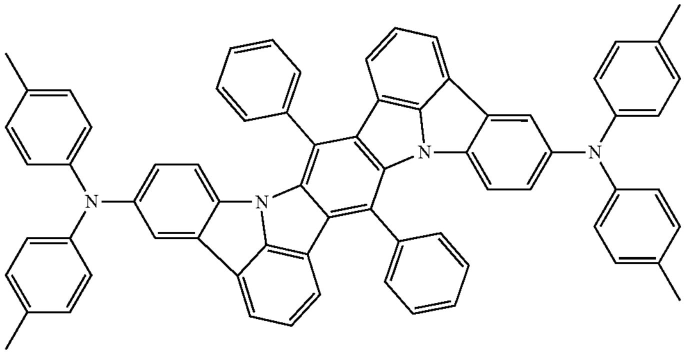

-continued
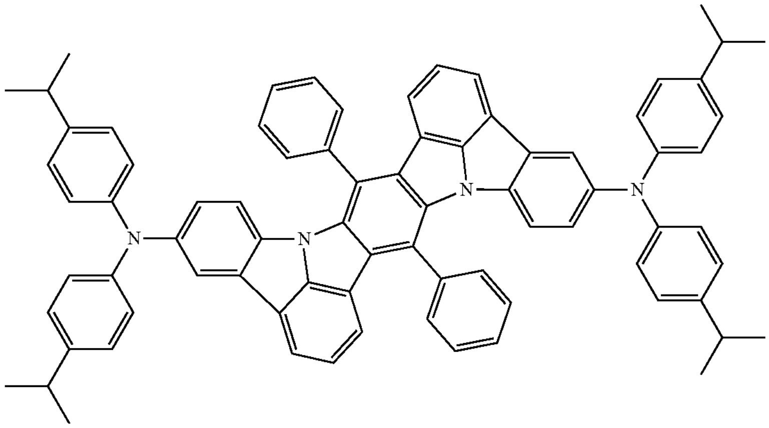
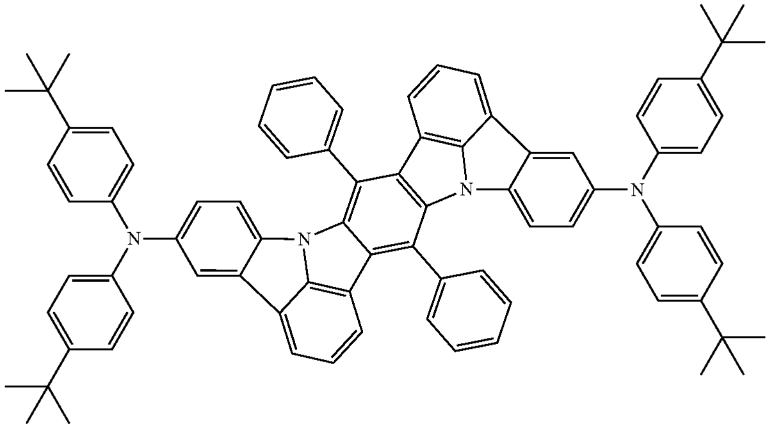
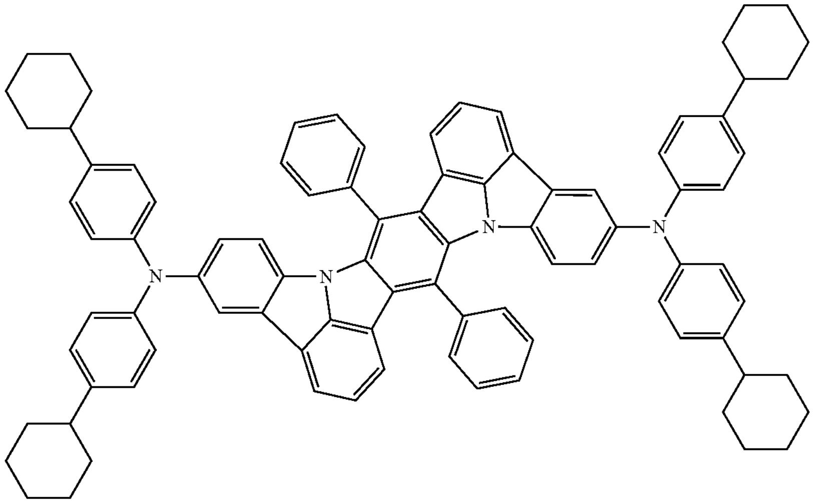
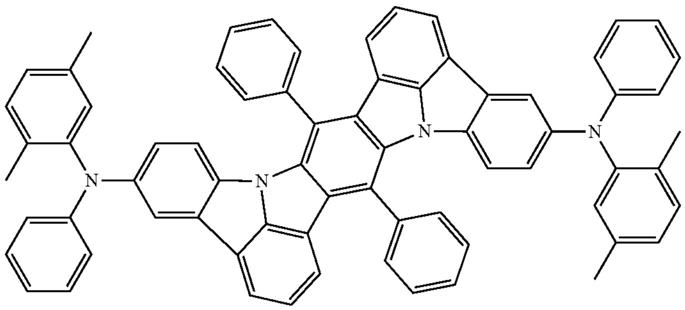

-continued
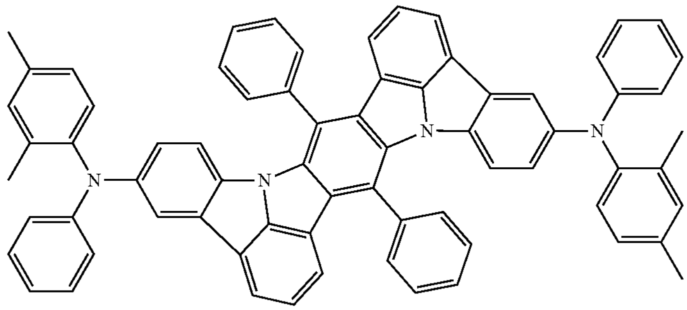
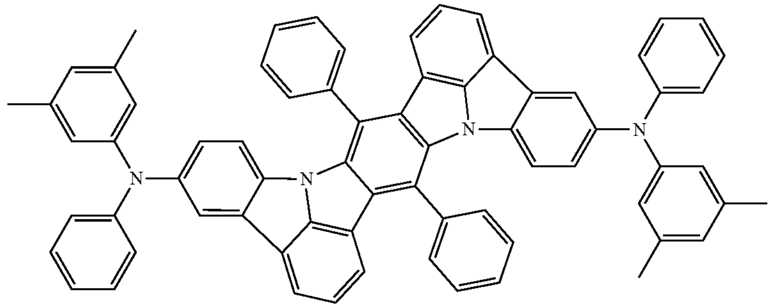
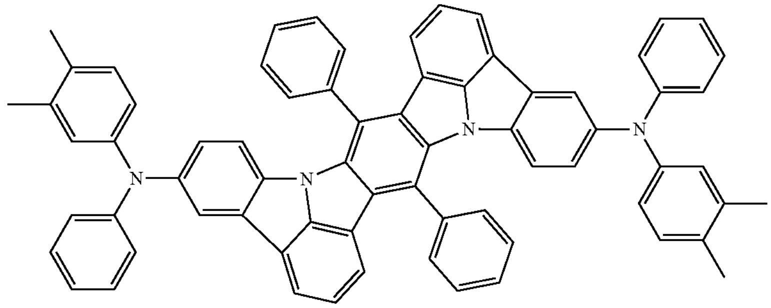
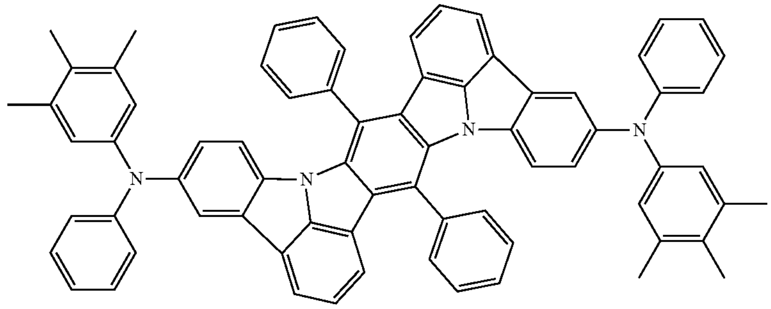
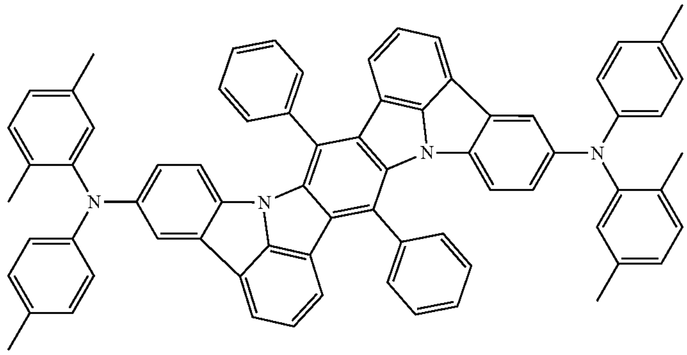

-continued
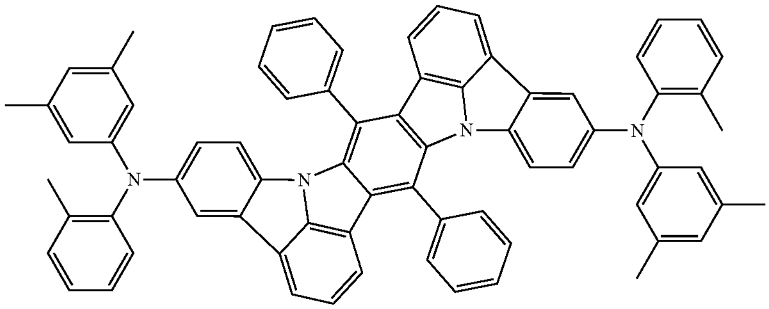
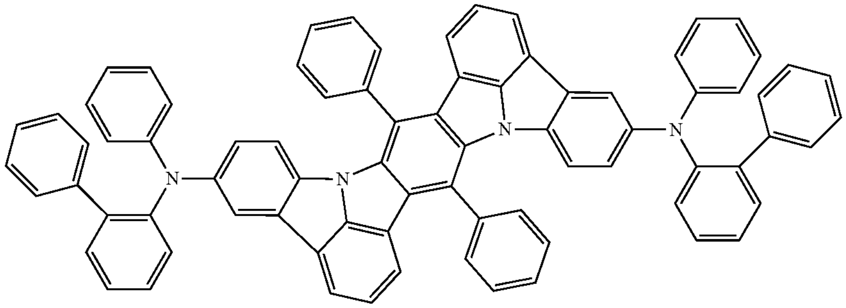
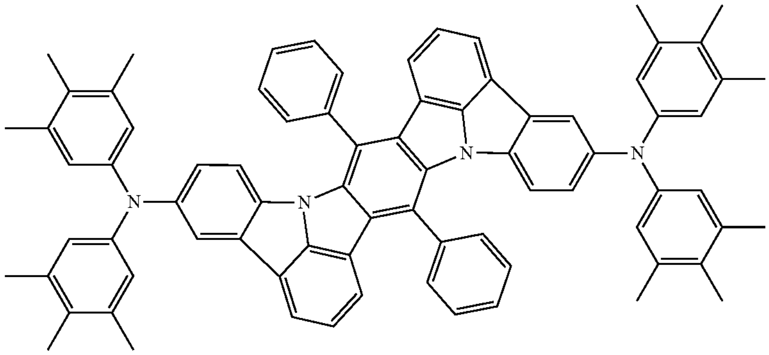
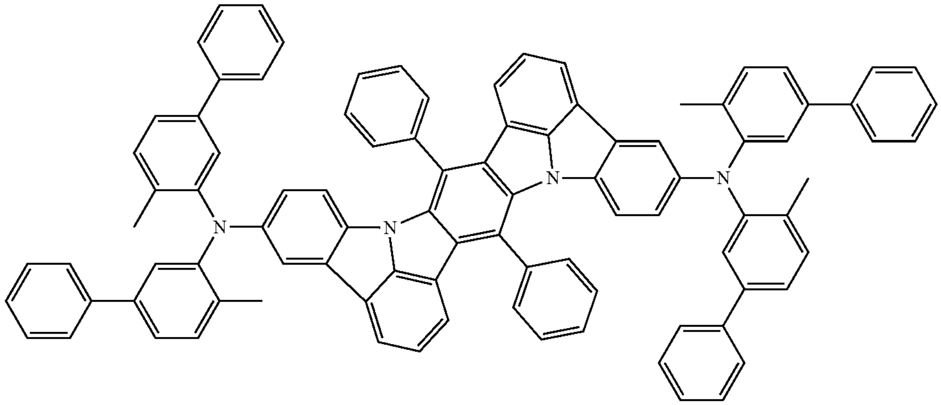

-continued
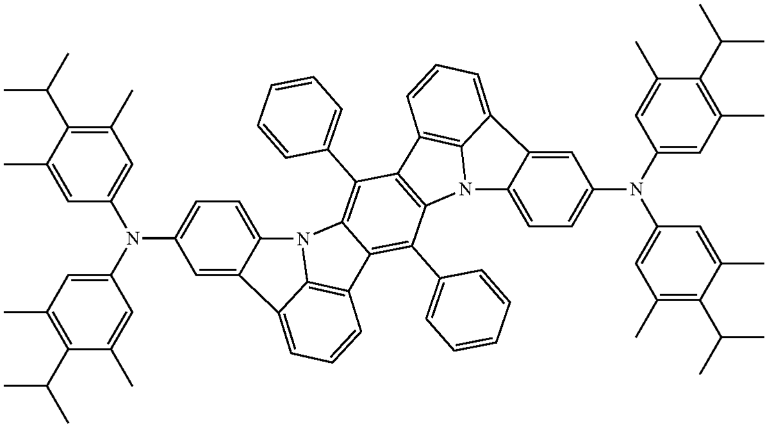
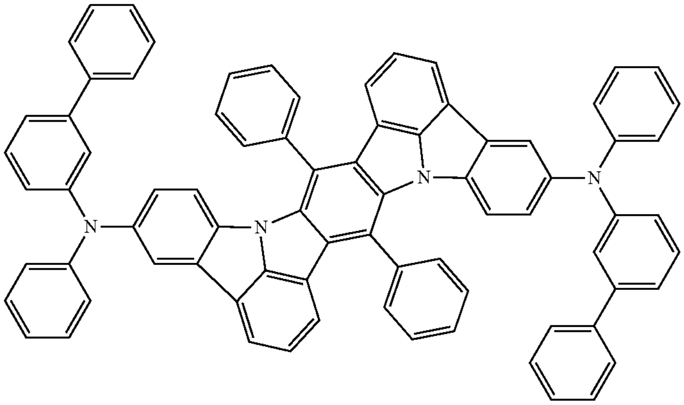
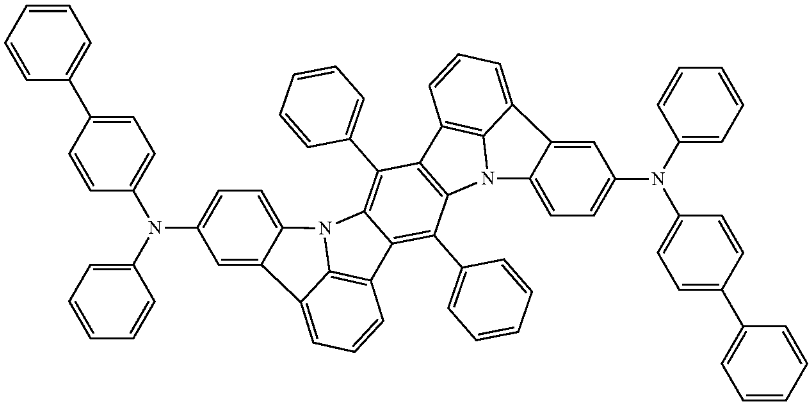
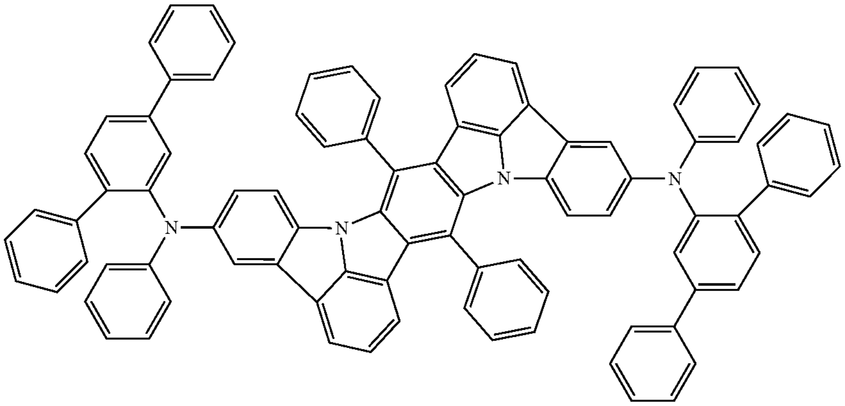

-continued
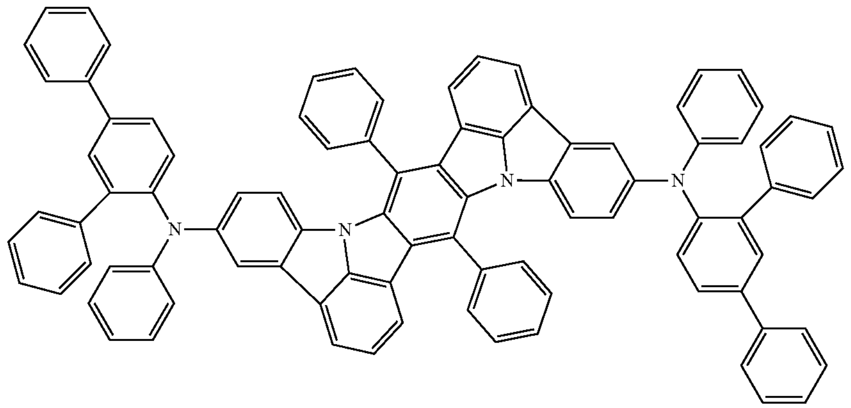
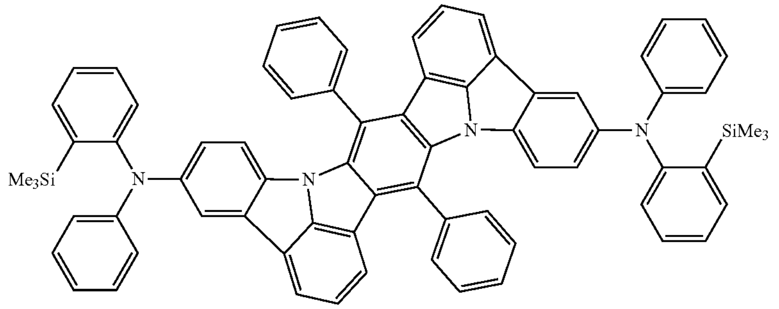
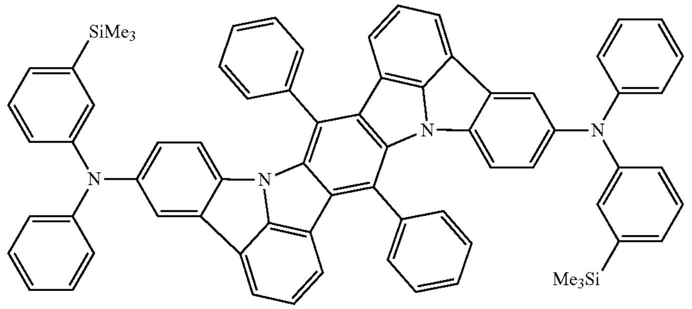
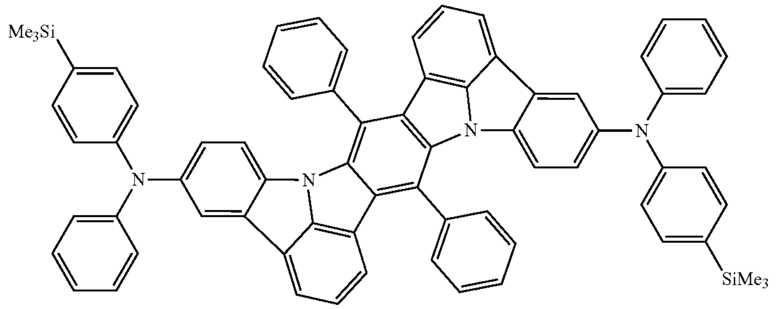

-continued
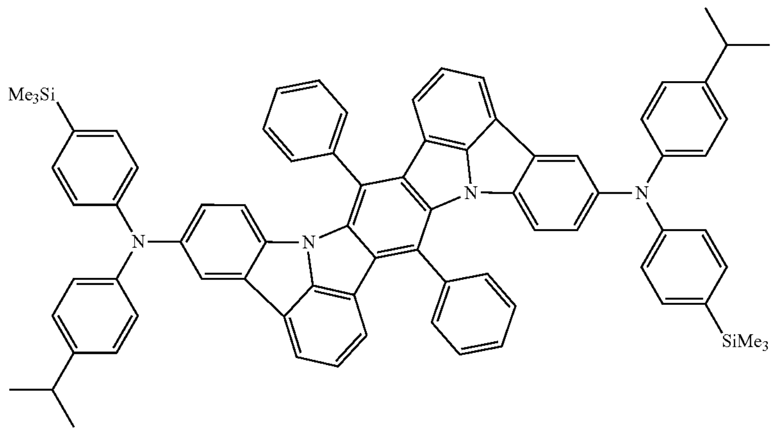
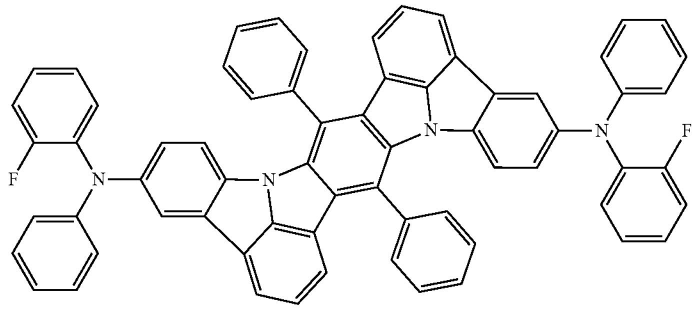
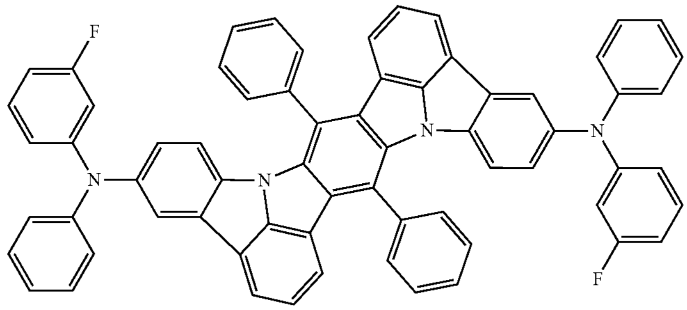
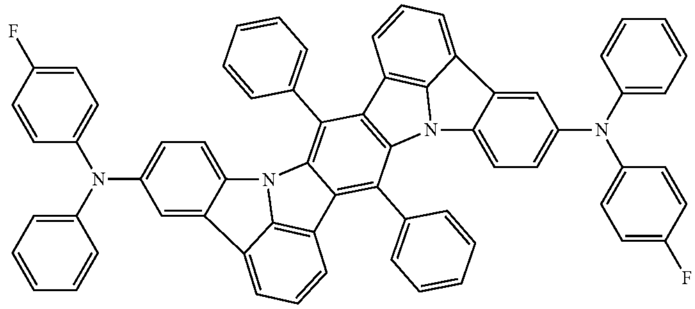

-continued
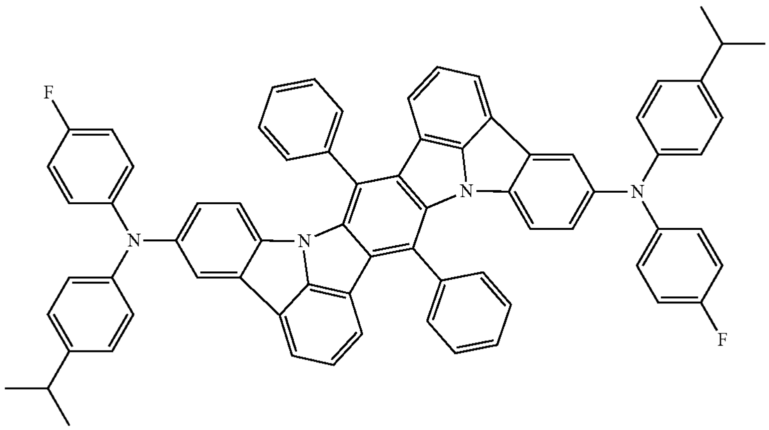
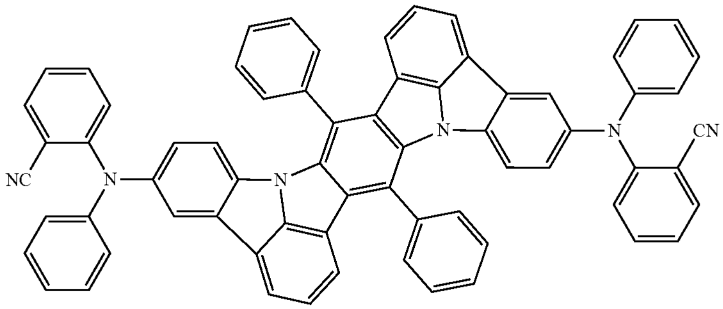
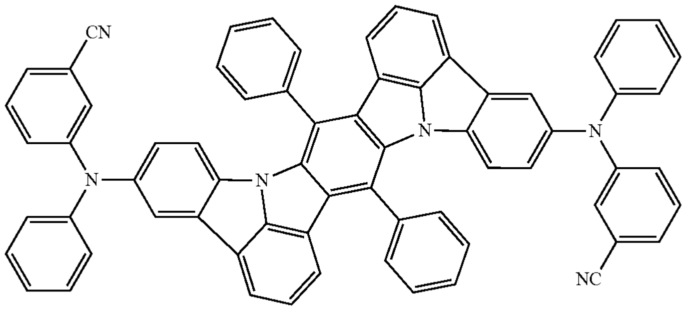
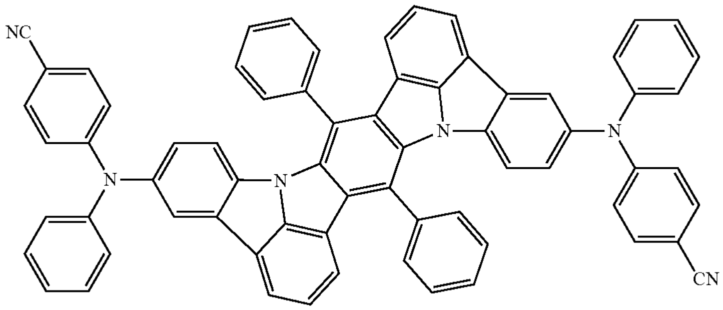

-continued
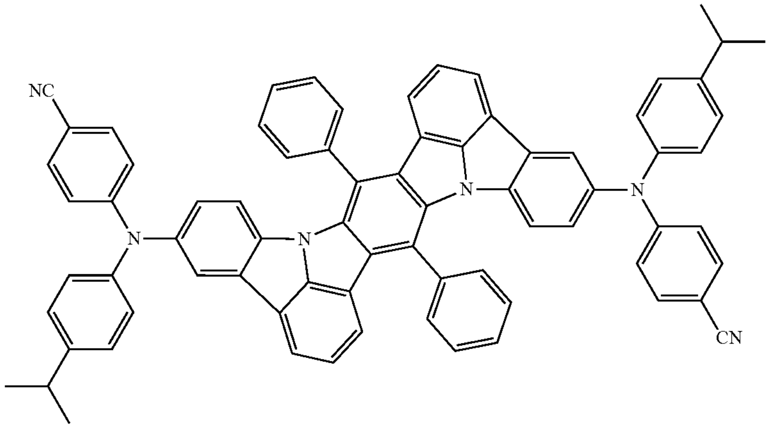
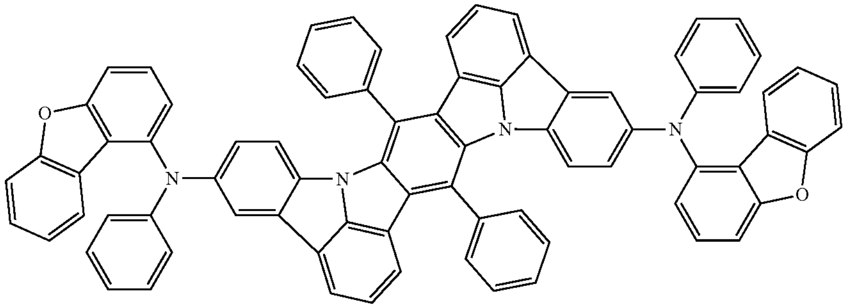
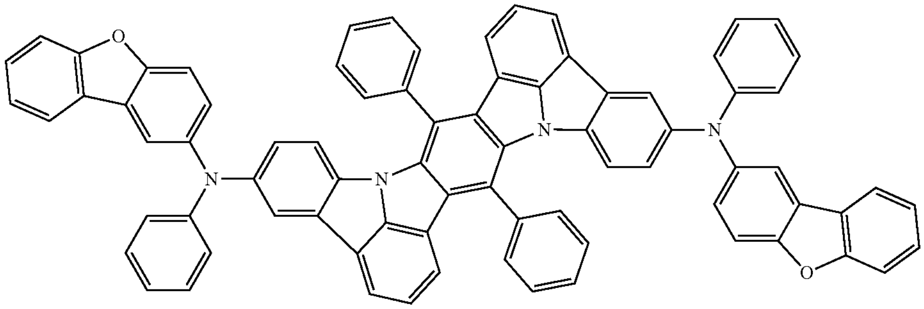
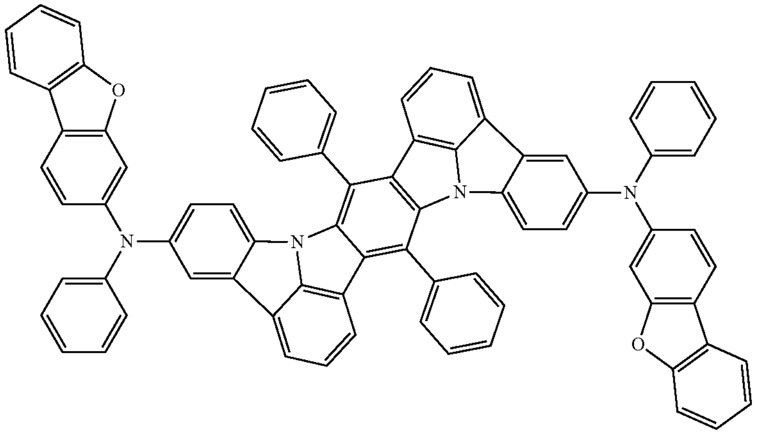

-continued
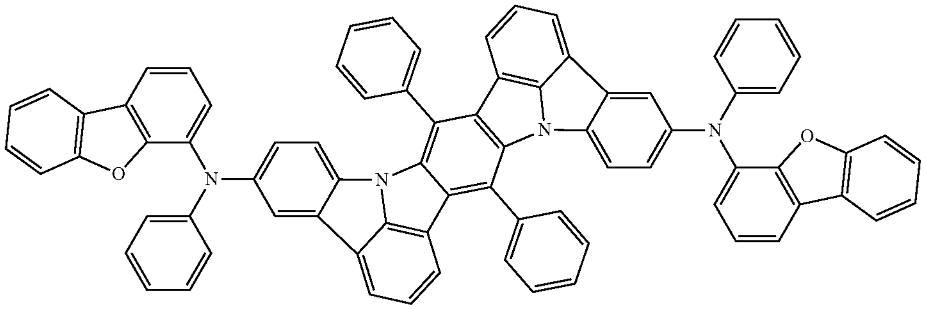
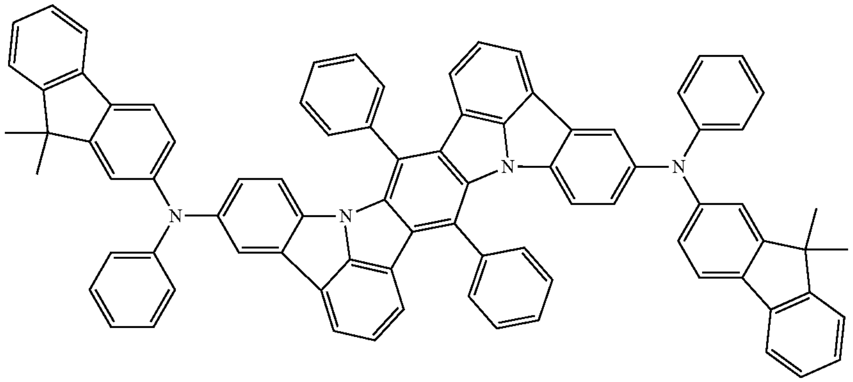
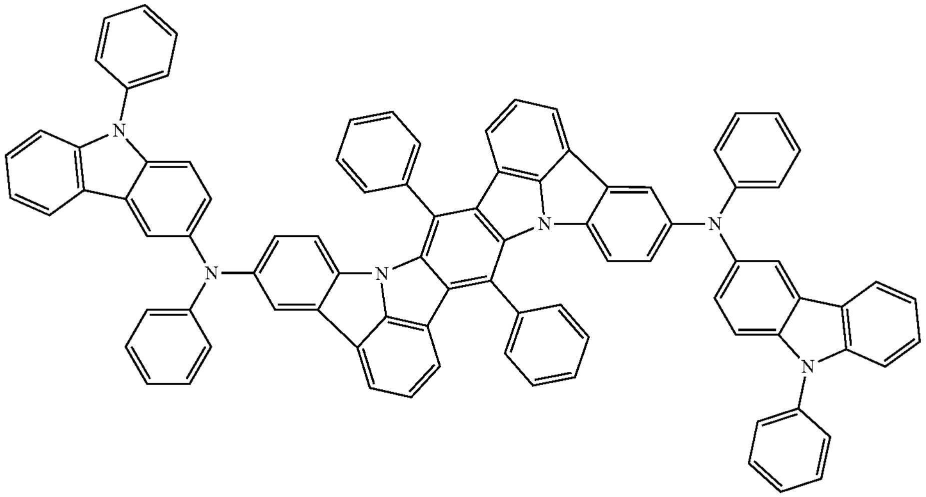
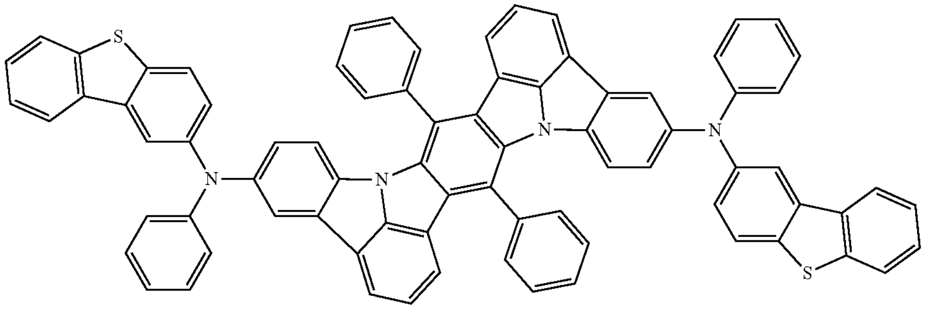

-continued
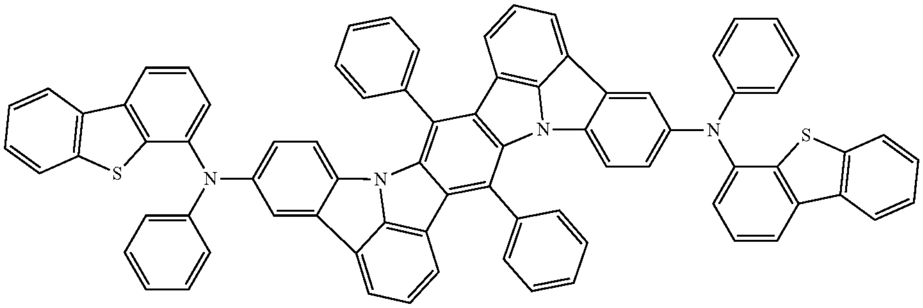
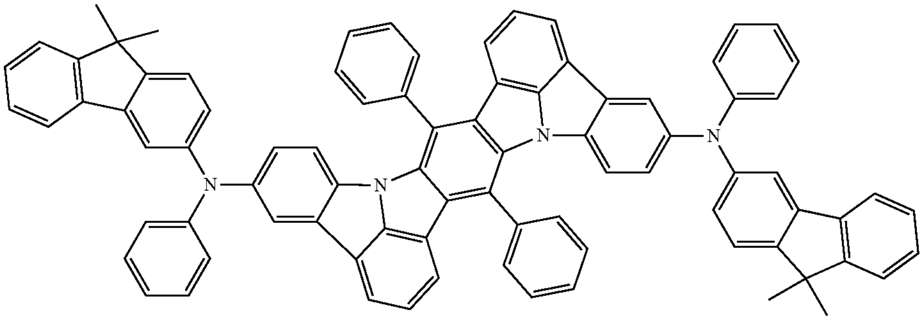
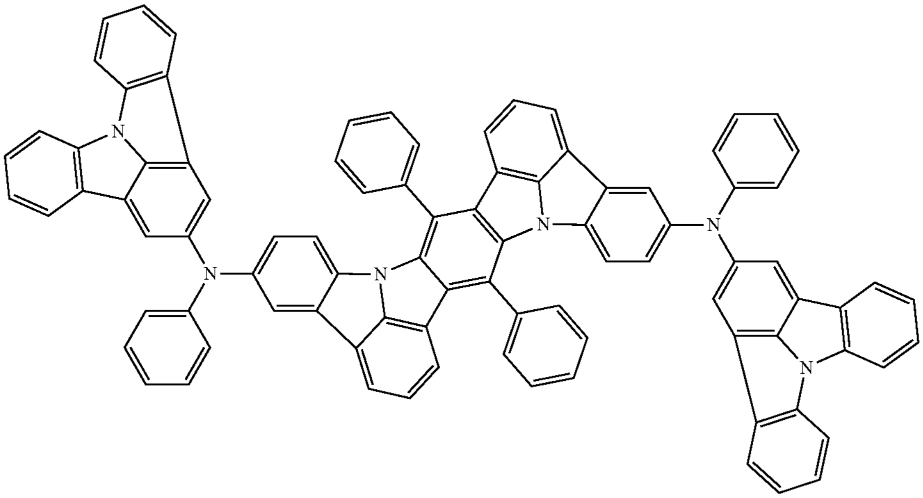
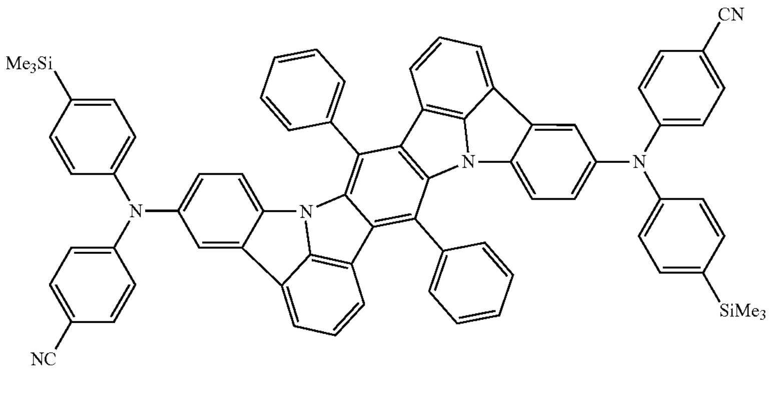

-continued
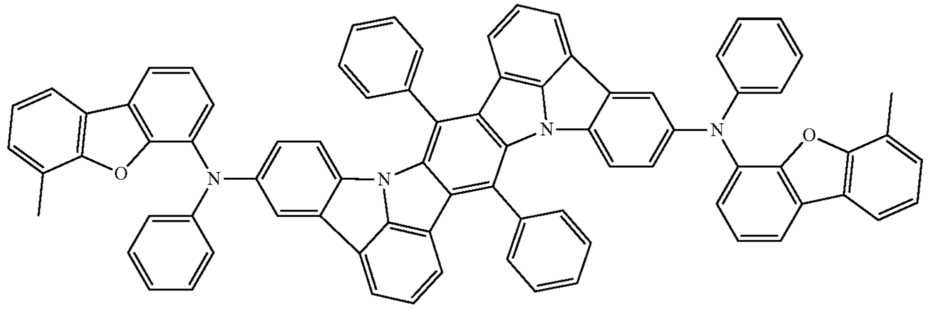
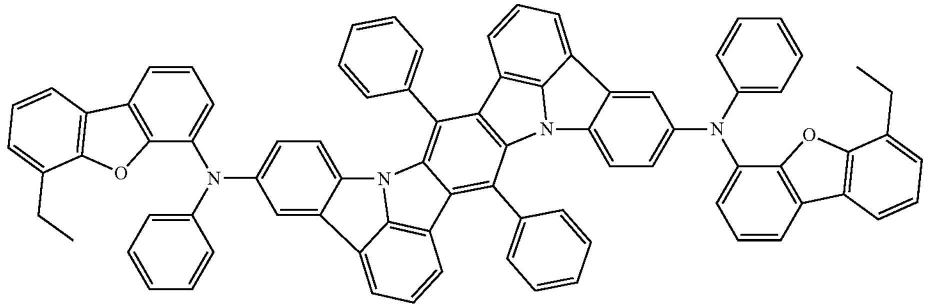
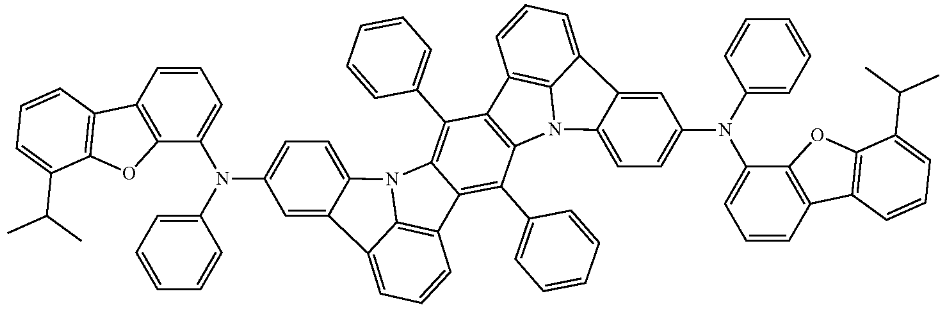
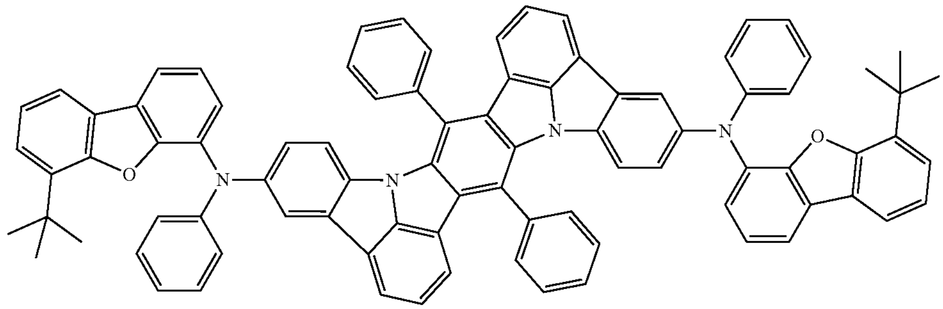
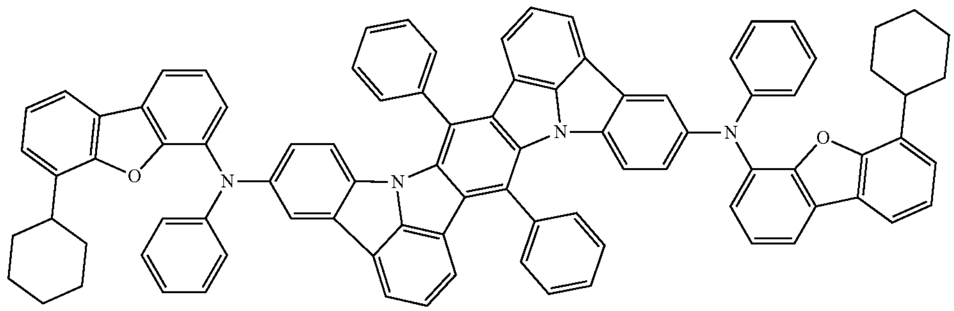

-continued
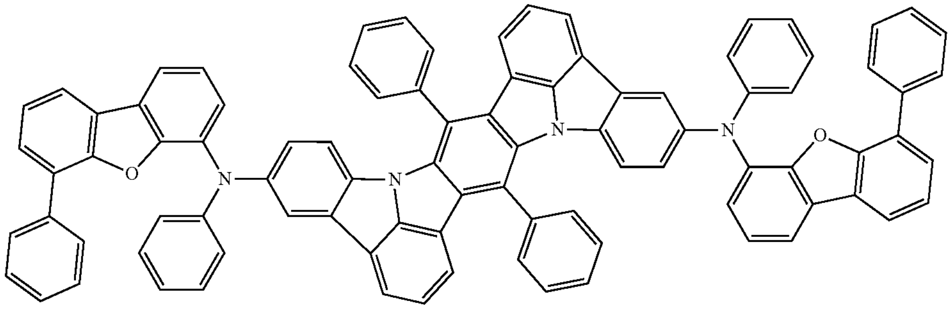
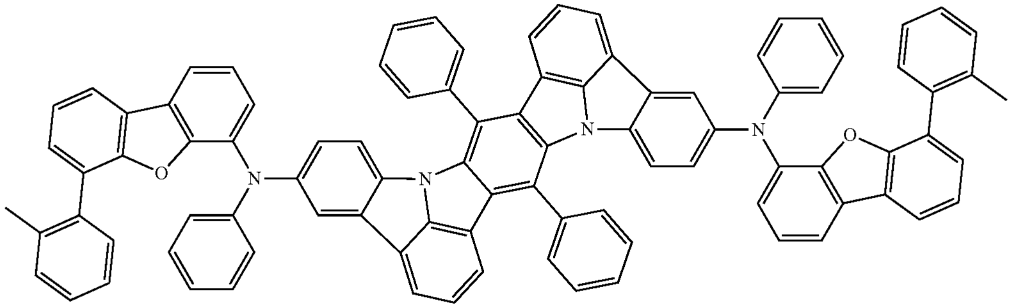
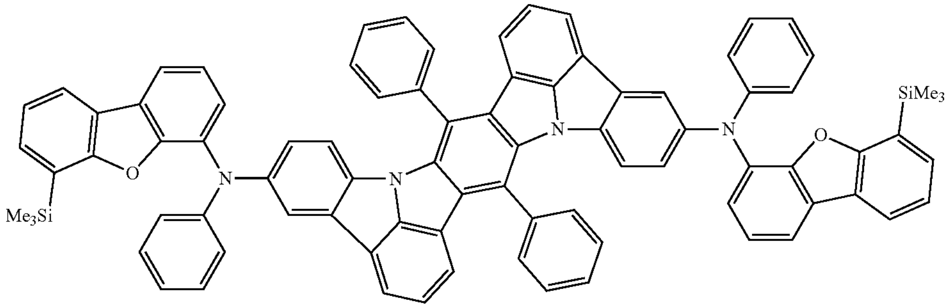
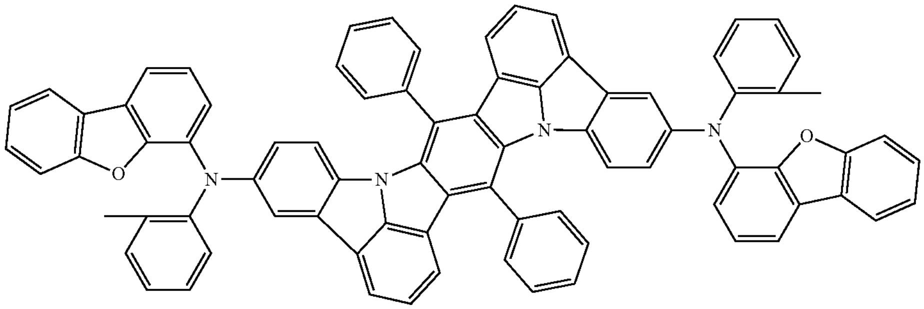
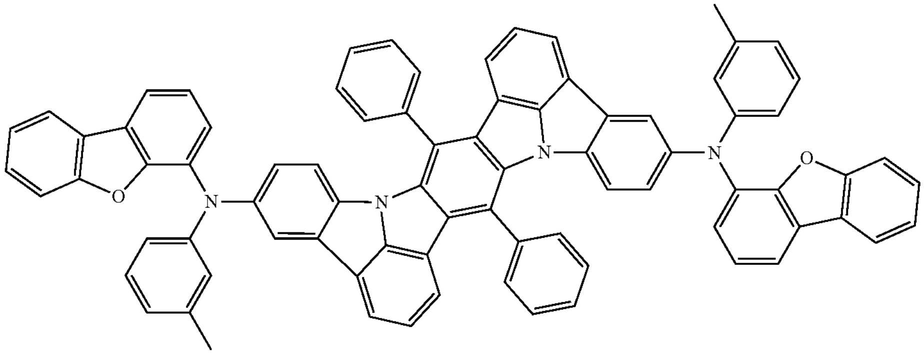

-continued
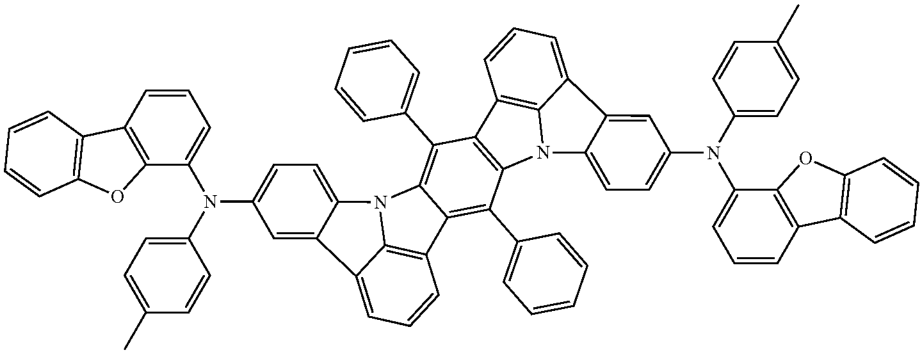
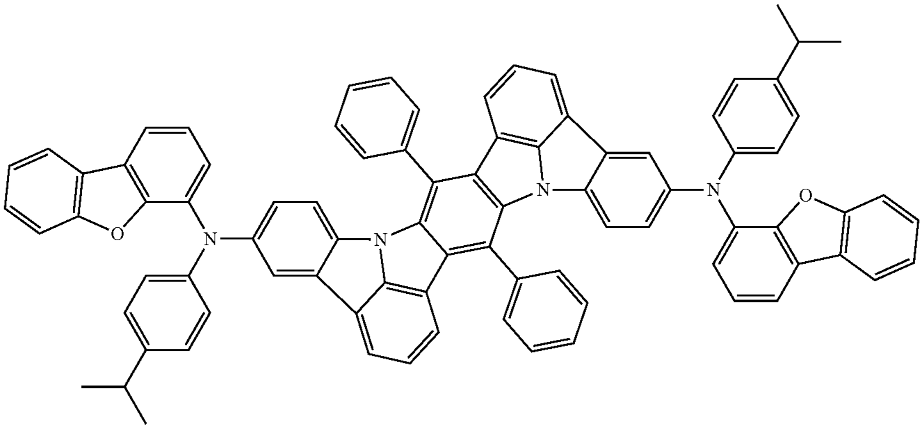
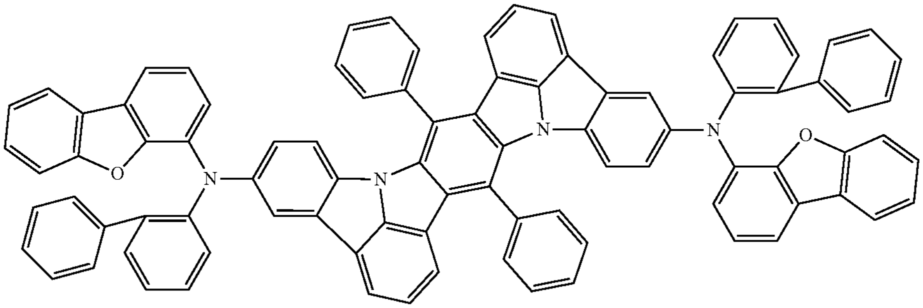
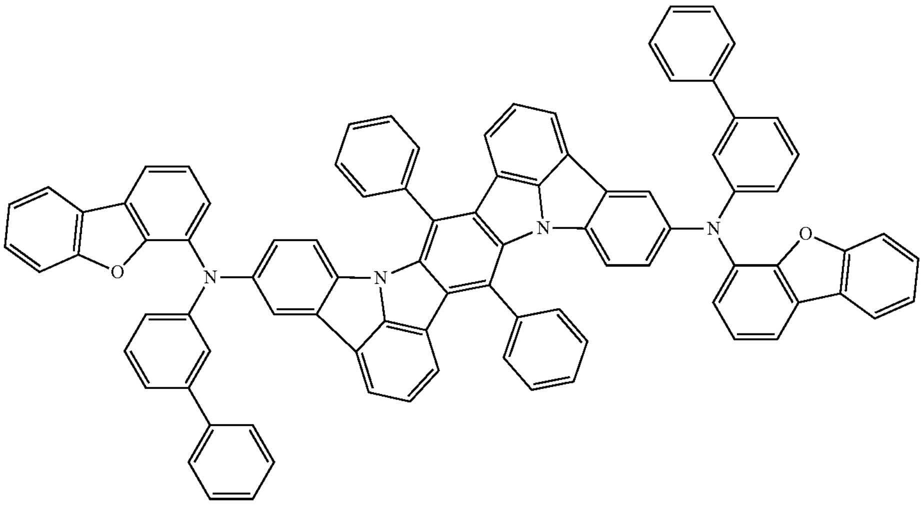

-continued
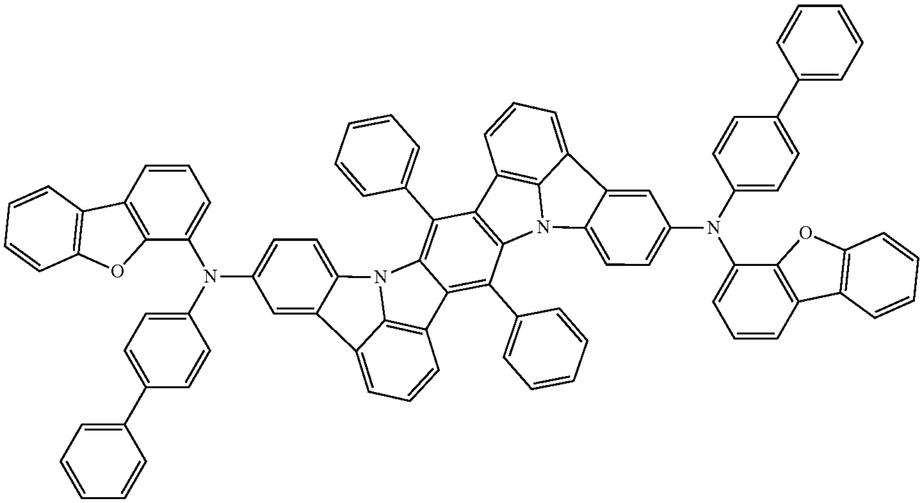
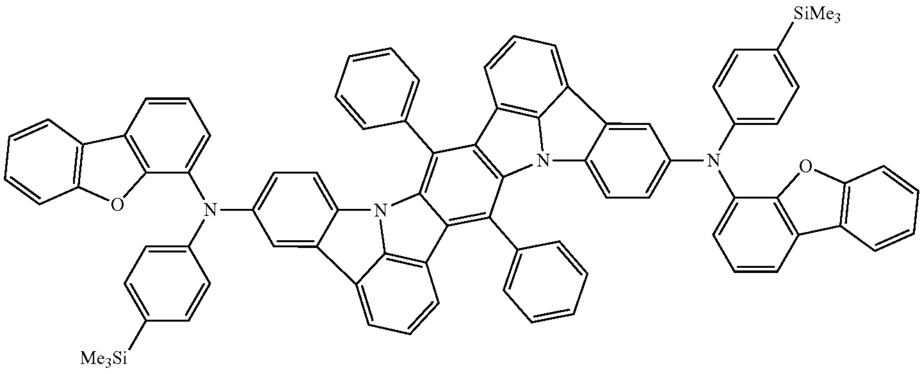
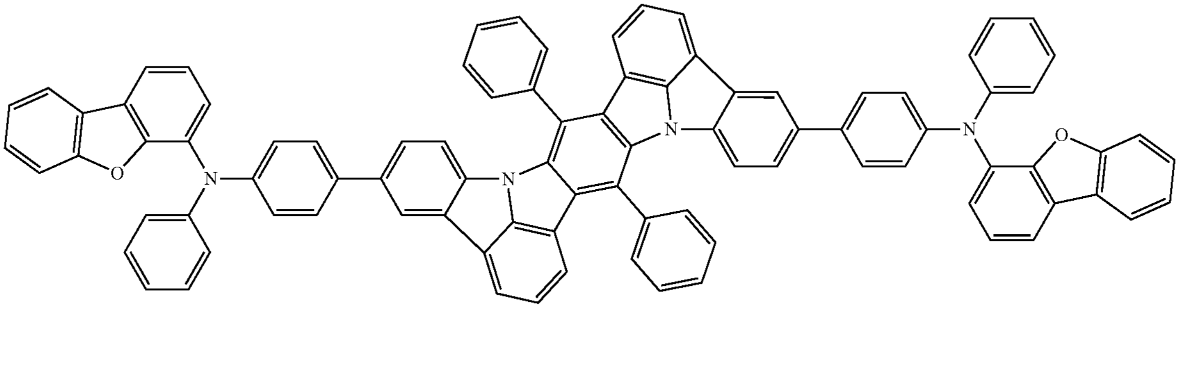
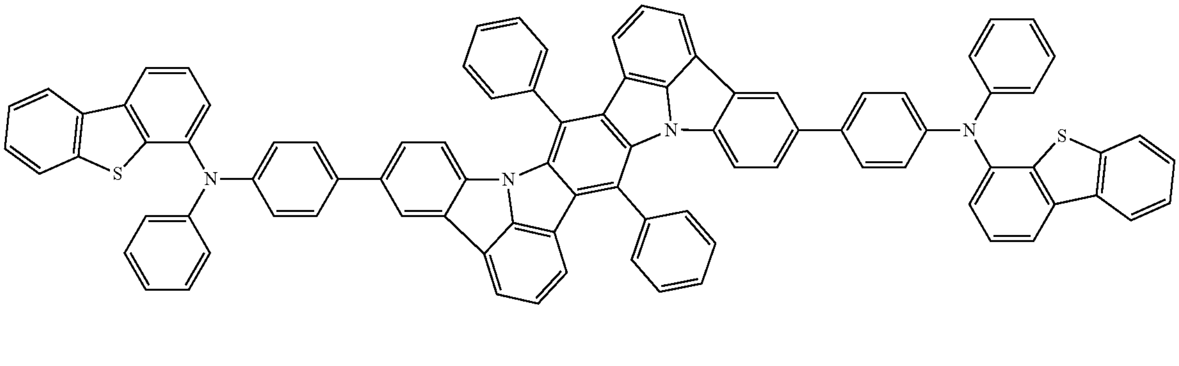

-continued
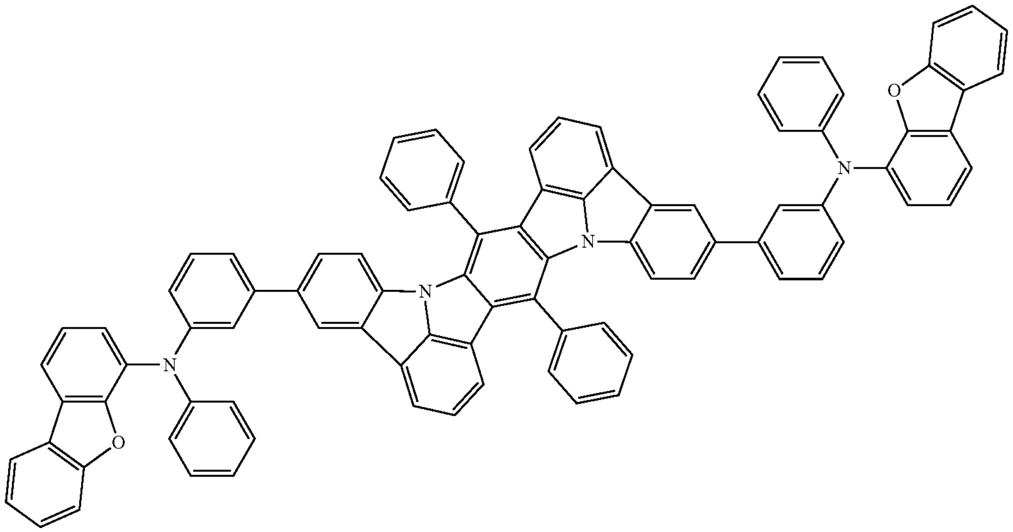
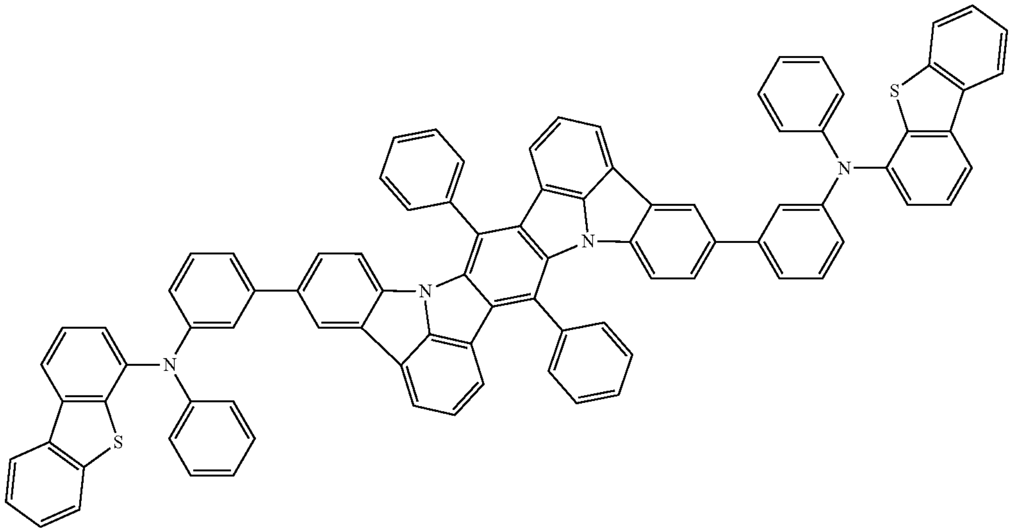
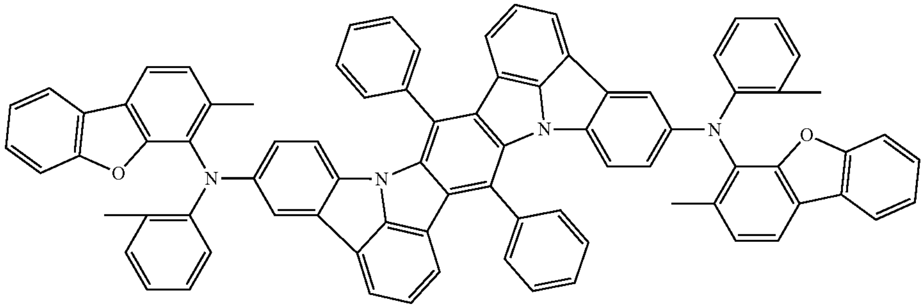
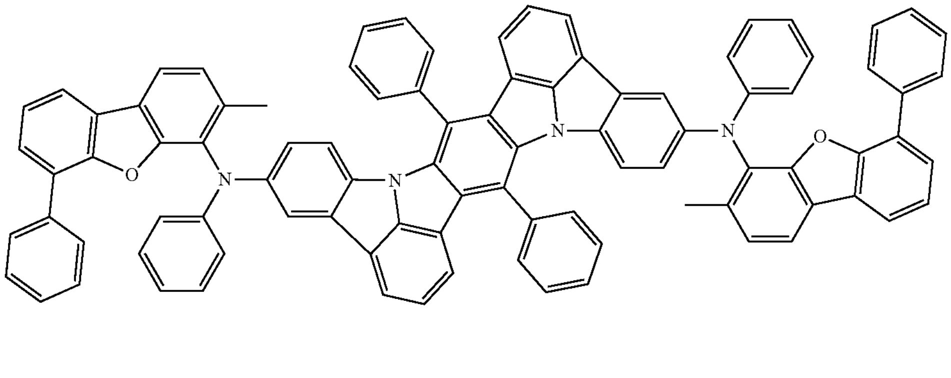

-continued
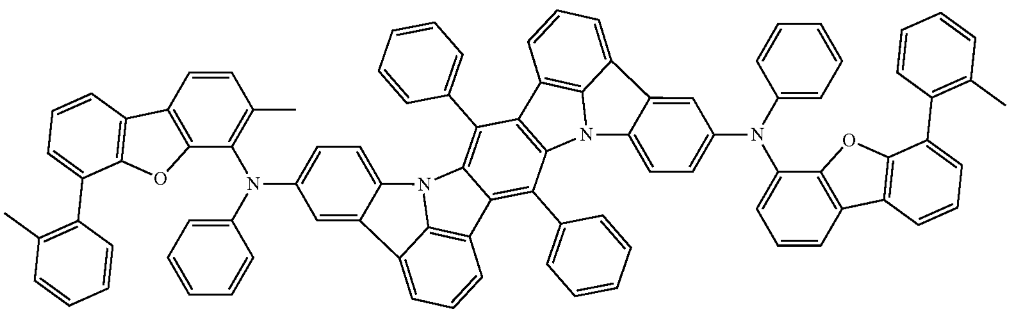
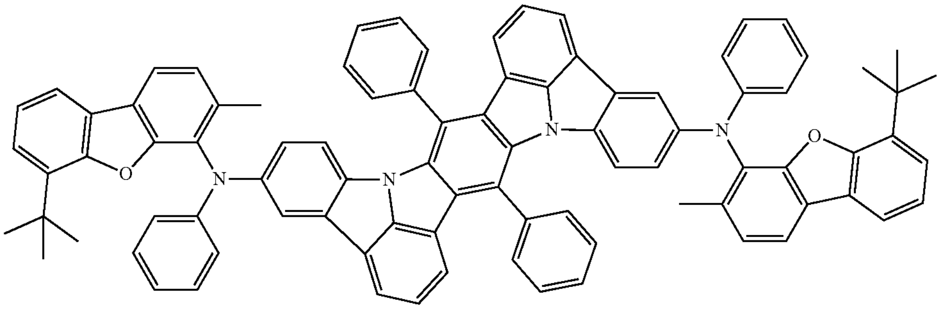
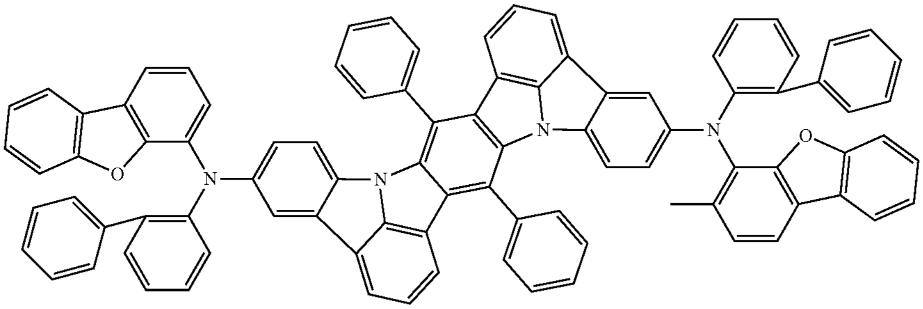
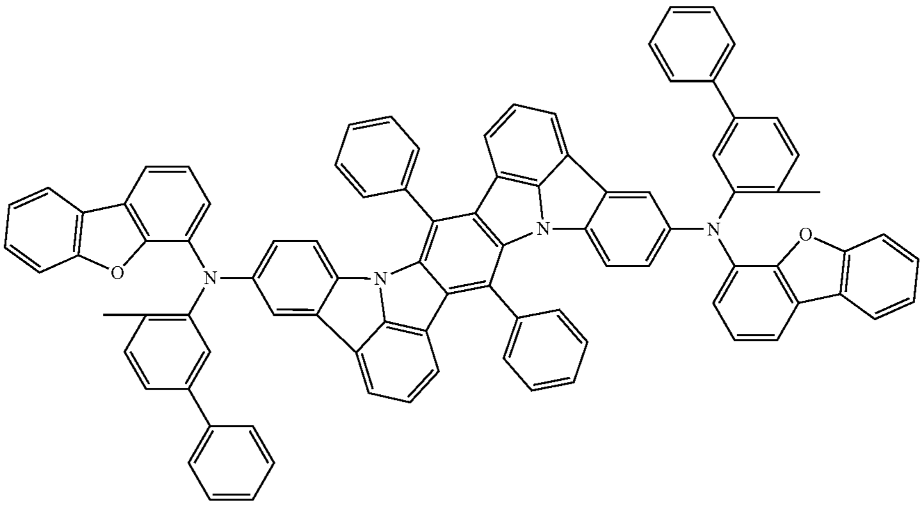

-continued
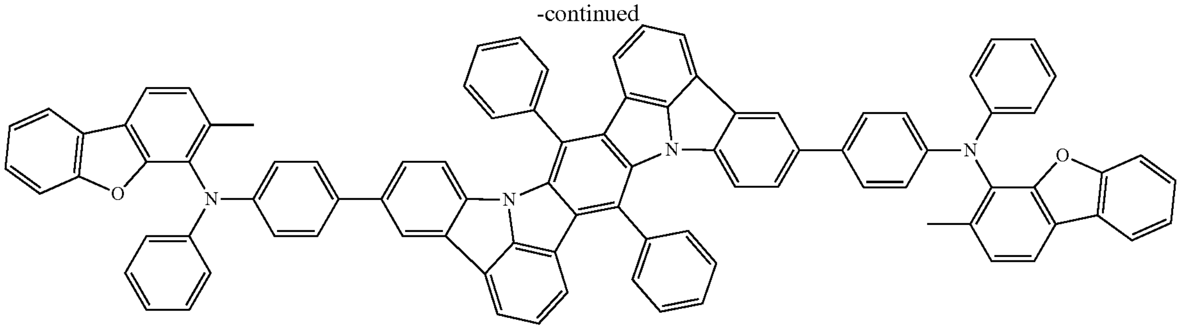
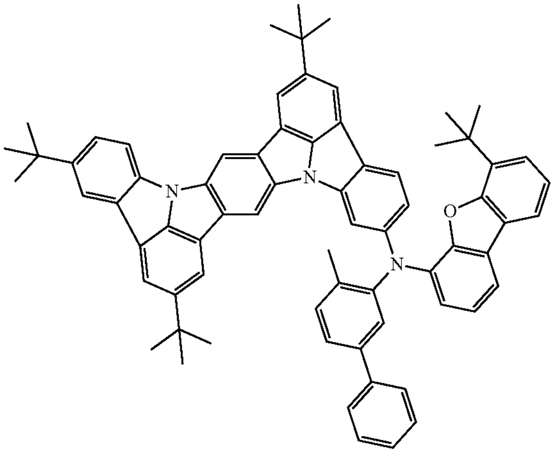
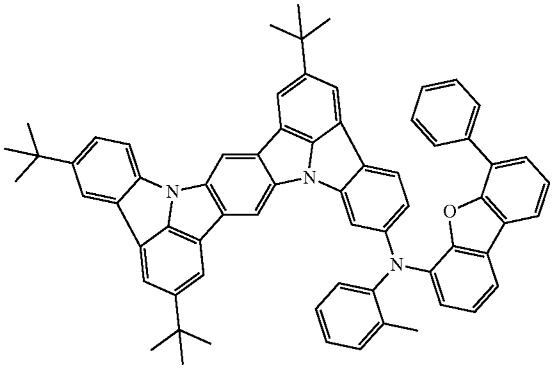
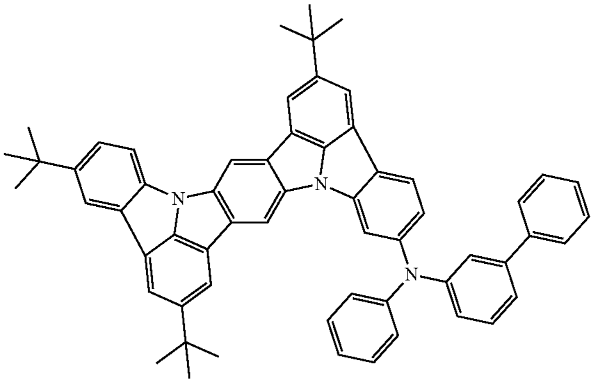
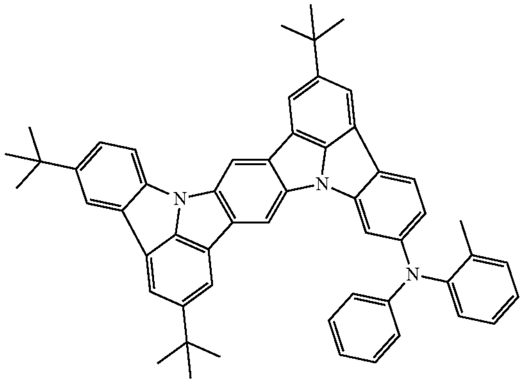
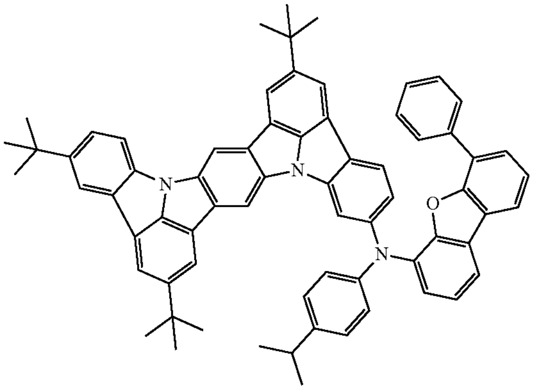
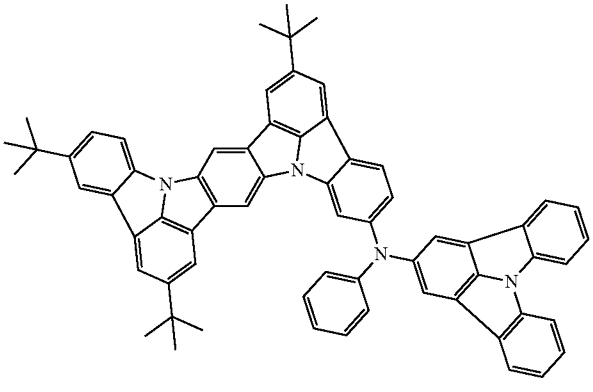

-continued
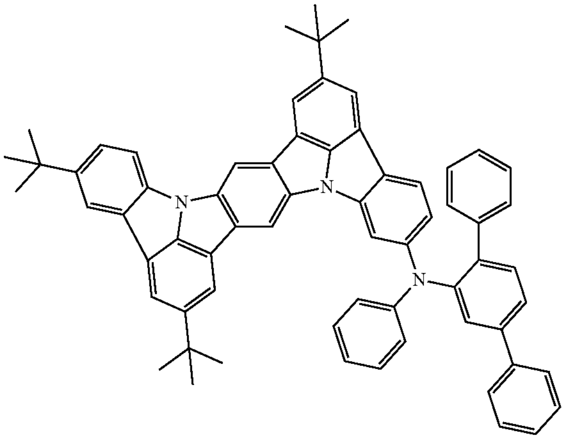
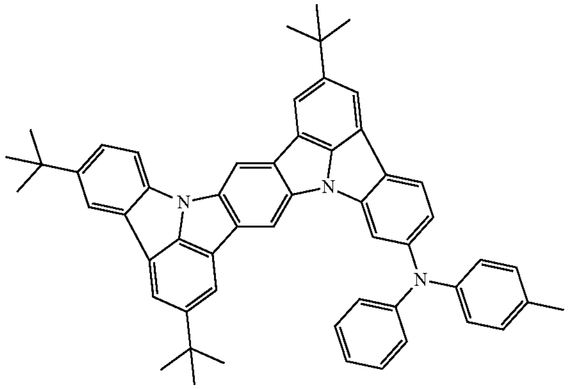
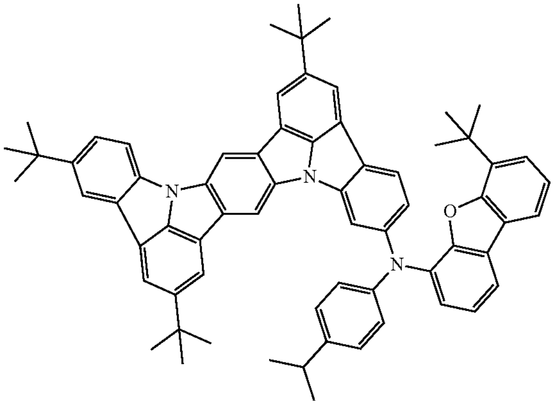
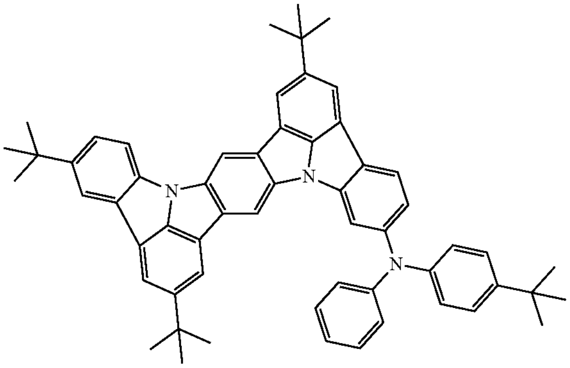
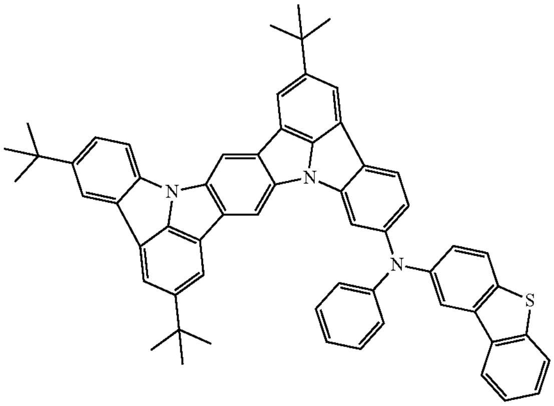
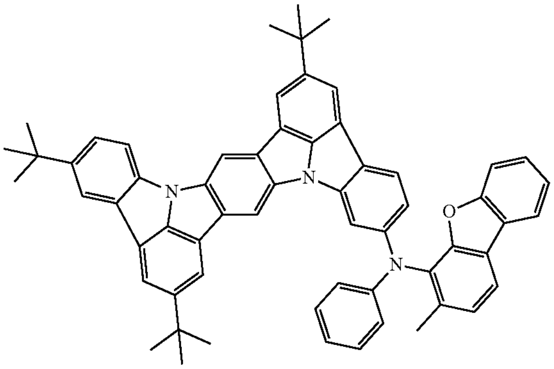
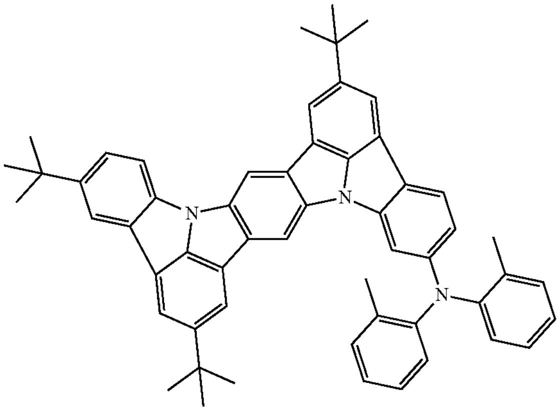
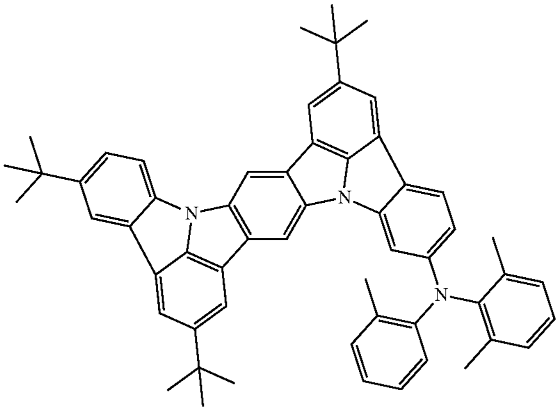

-continued
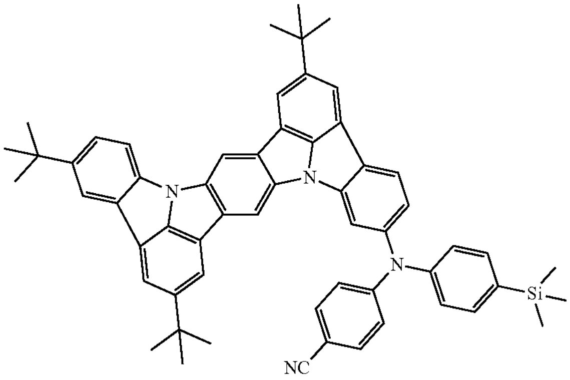
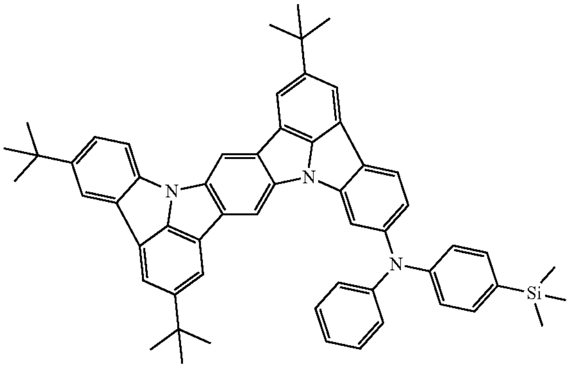
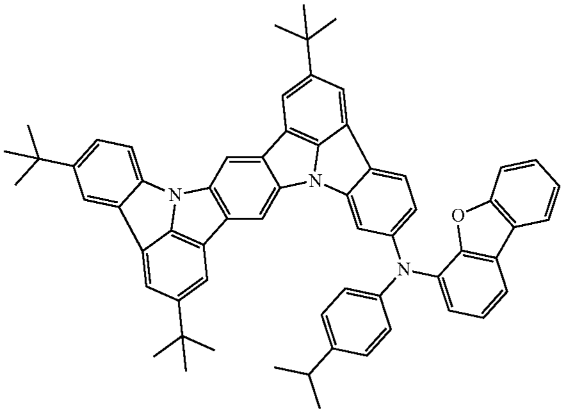
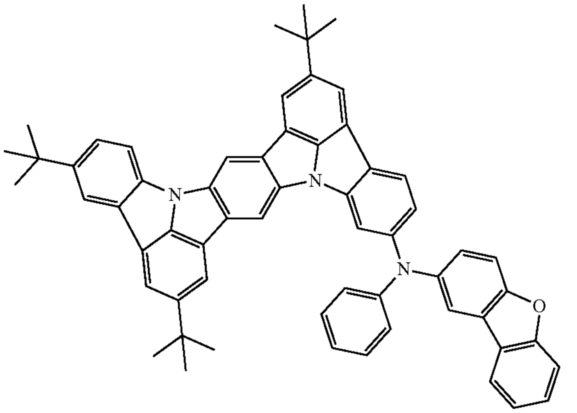
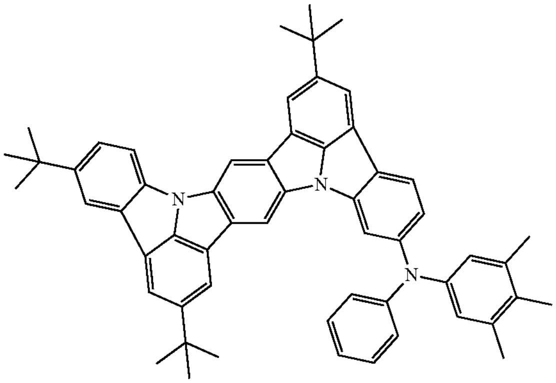
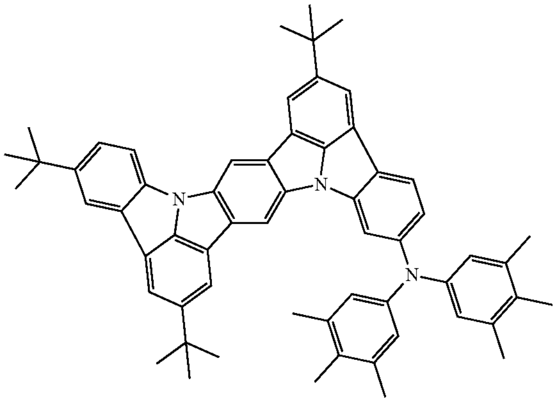
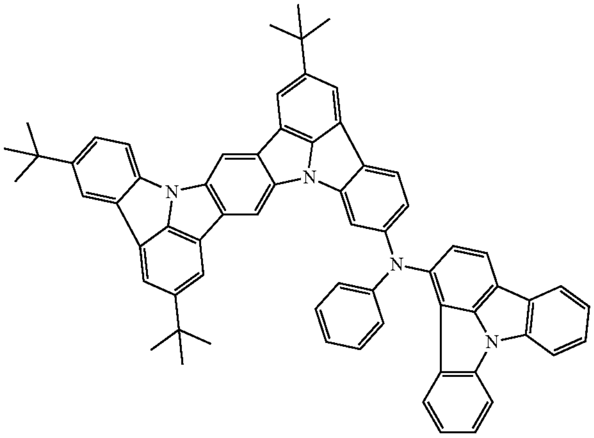
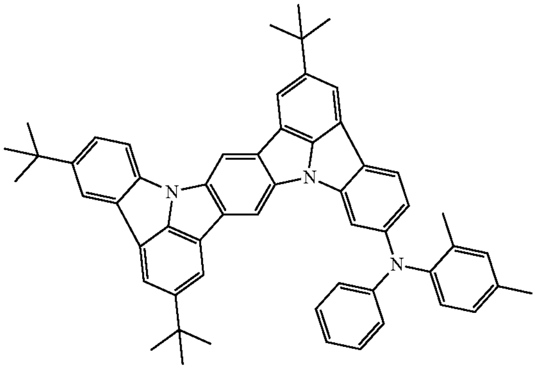

-continued
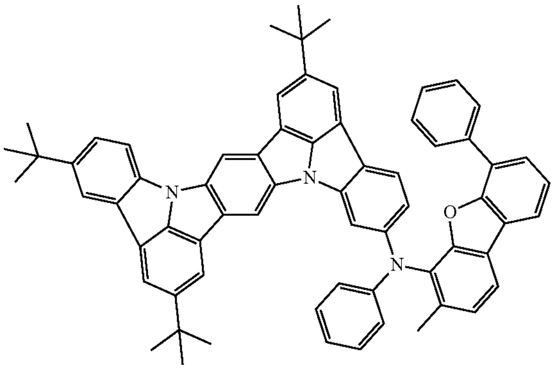
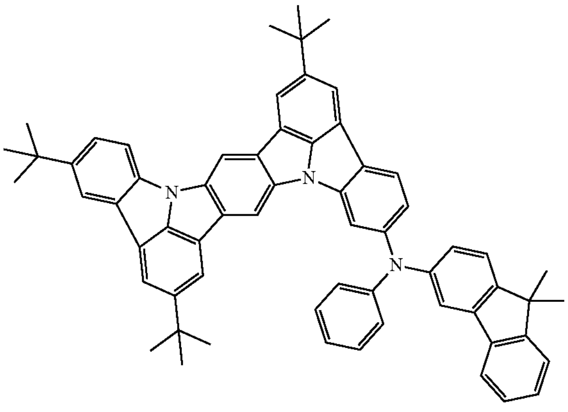
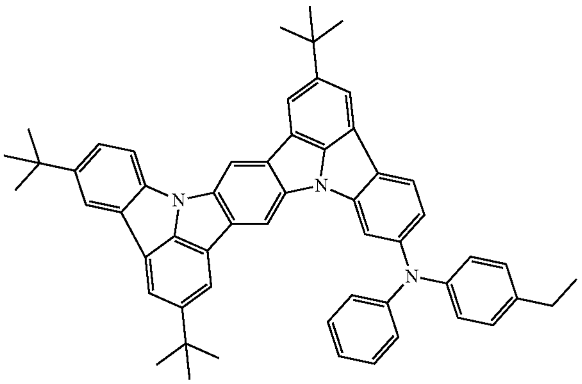
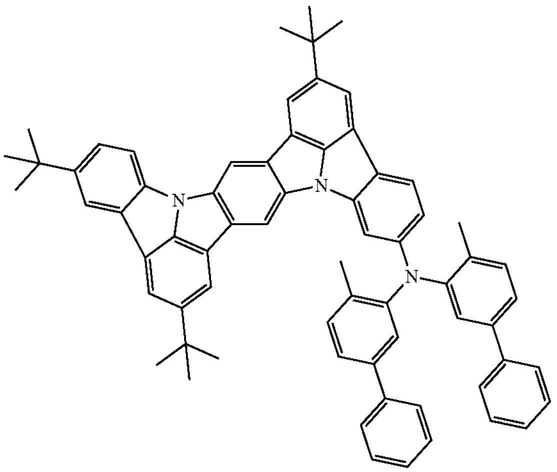
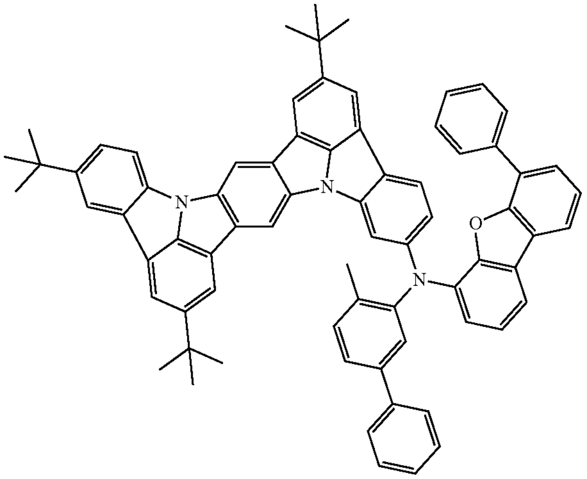
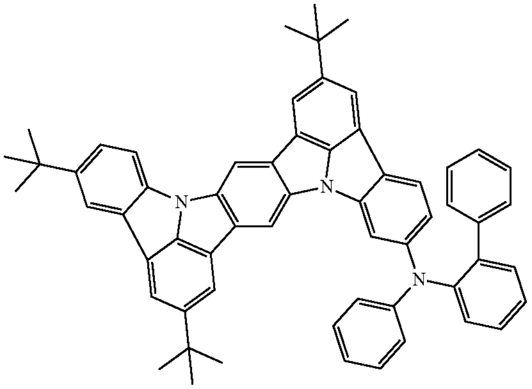

-continued
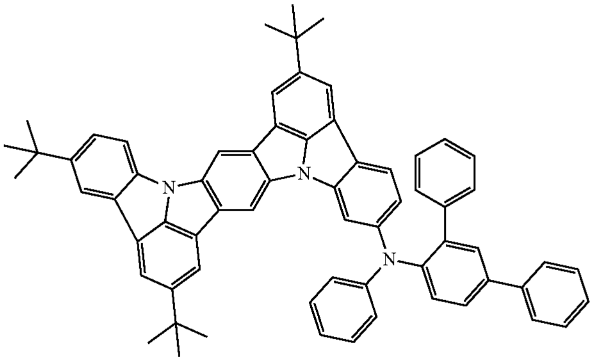
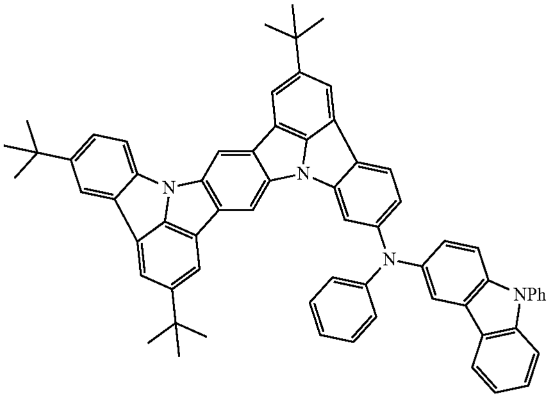
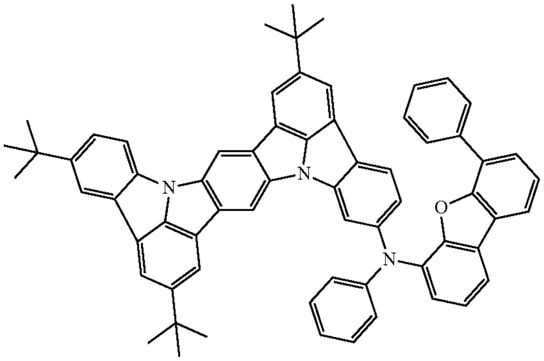
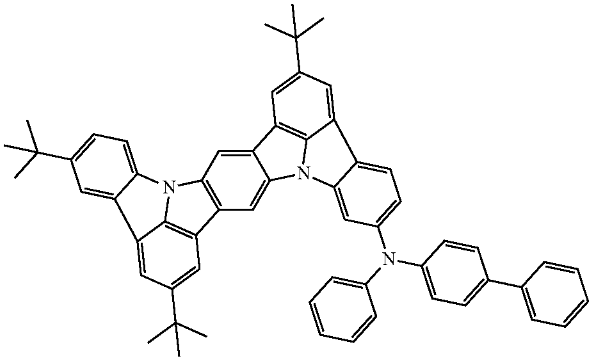
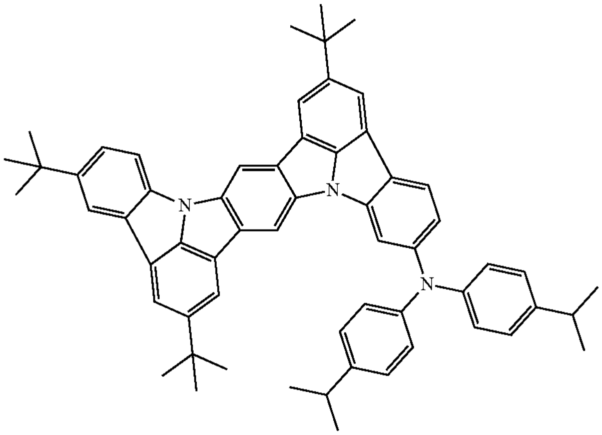
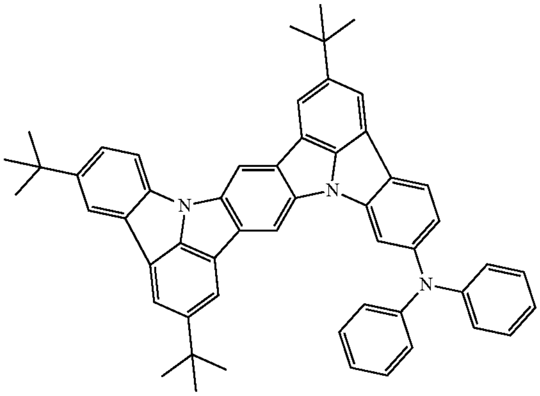
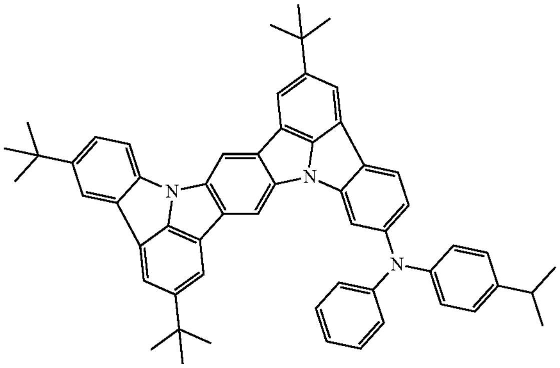
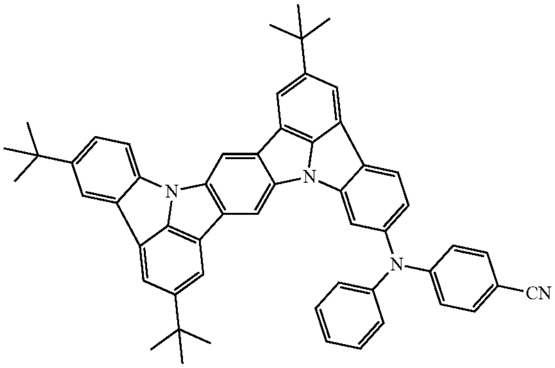

-continued
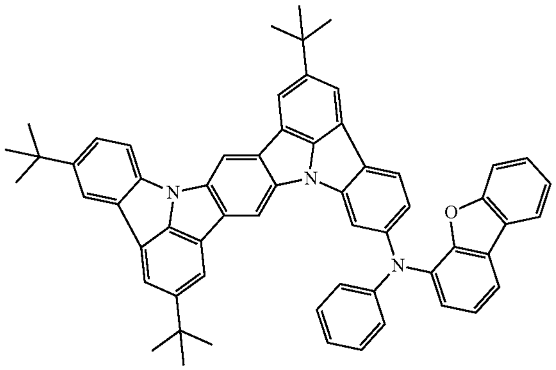
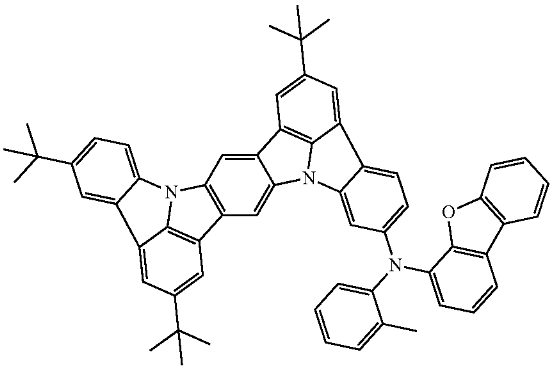
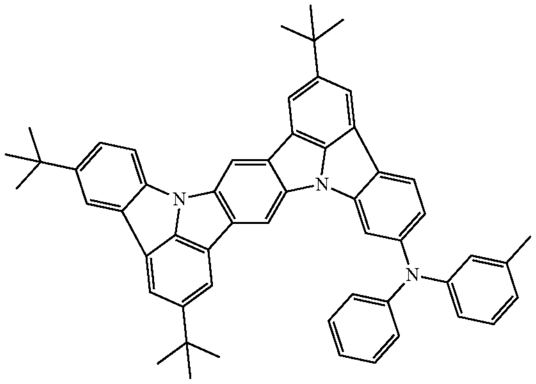
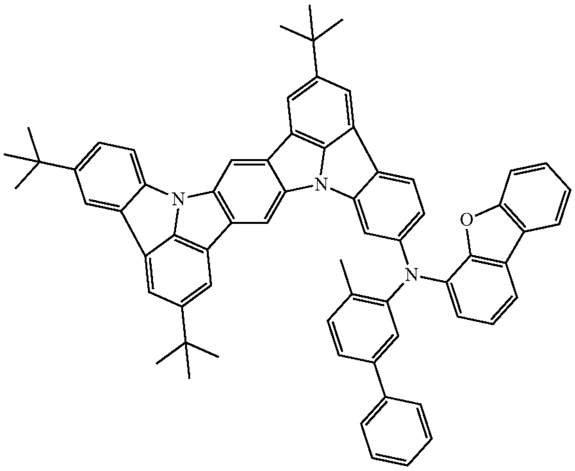
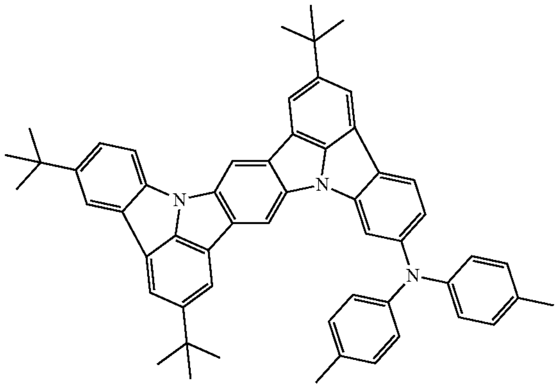
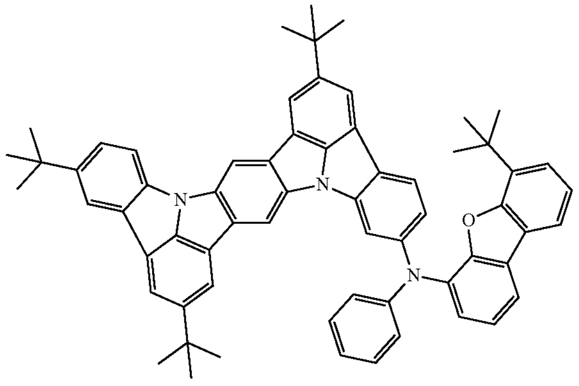
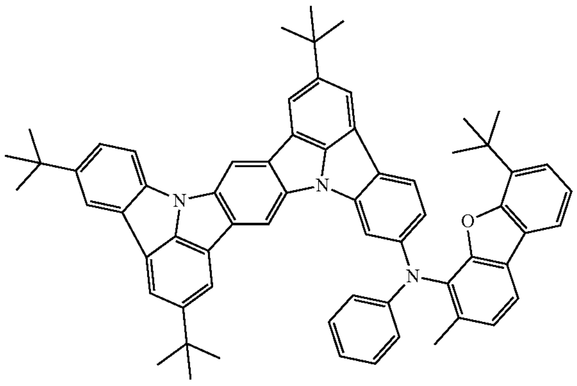
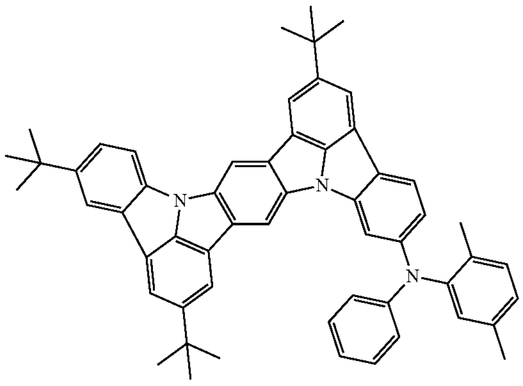

-continued
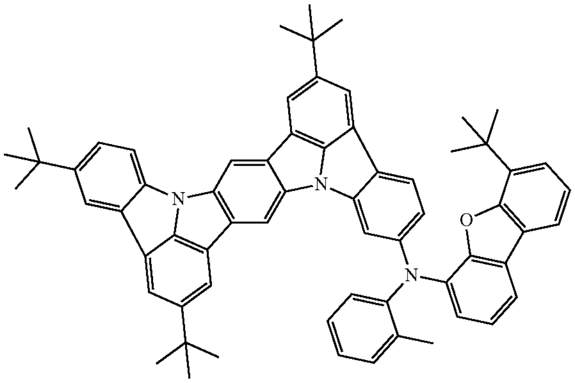
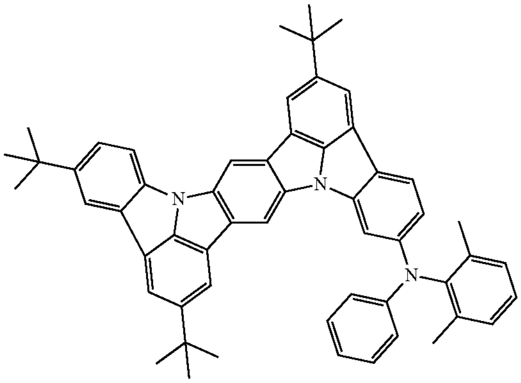
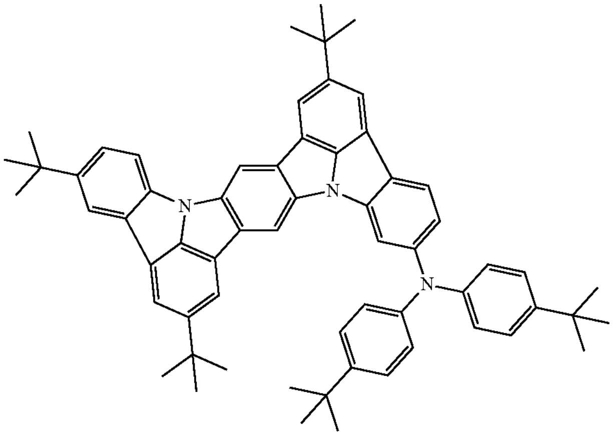
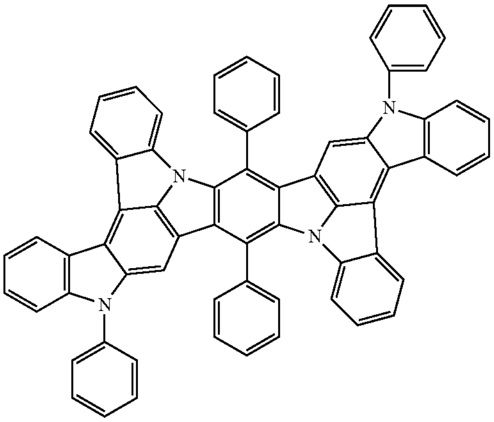
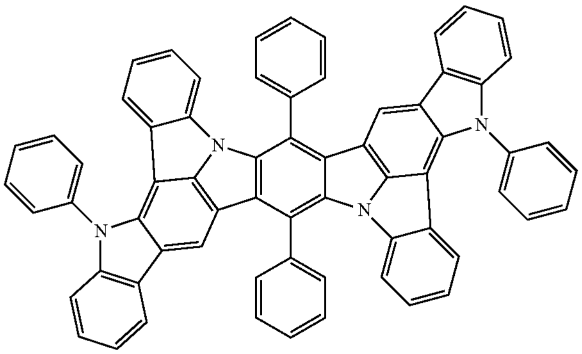
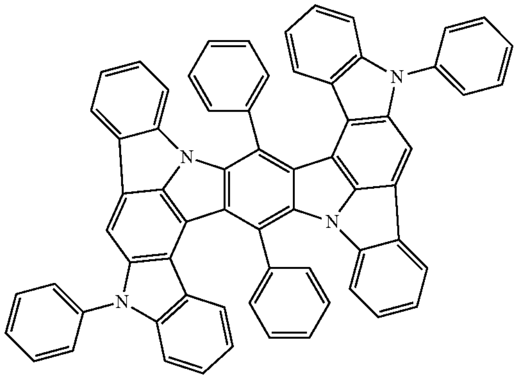

-continued
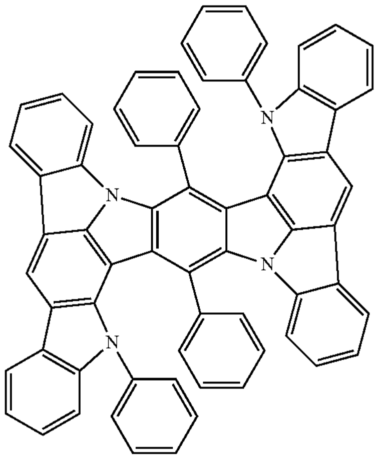
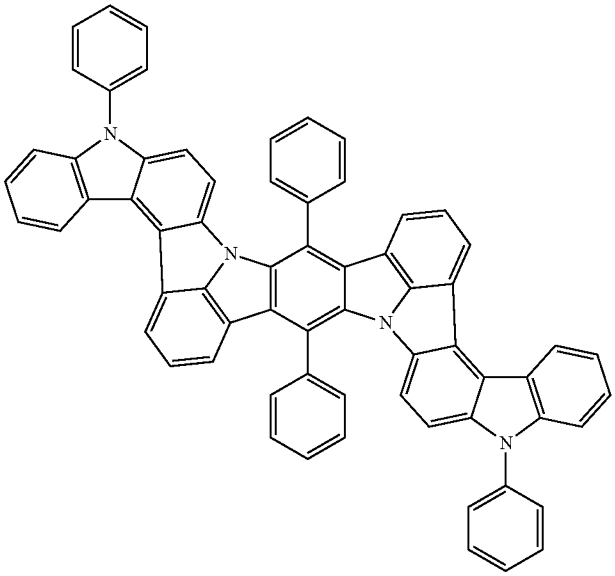
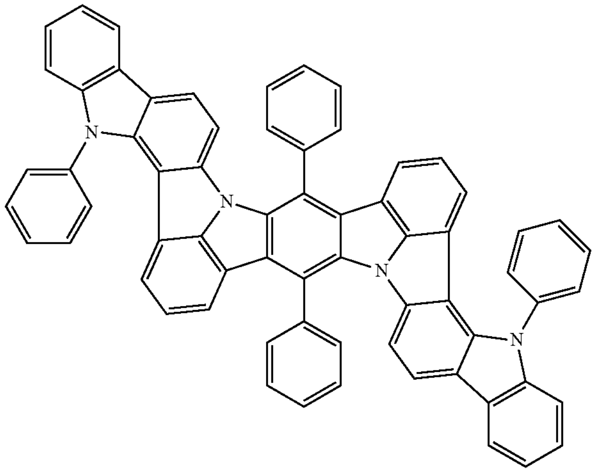
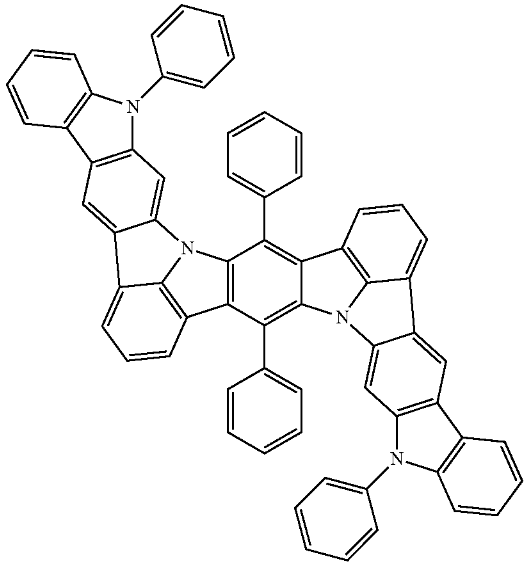
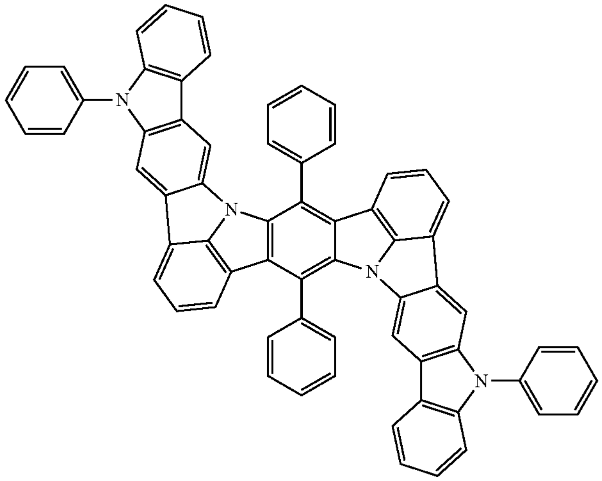
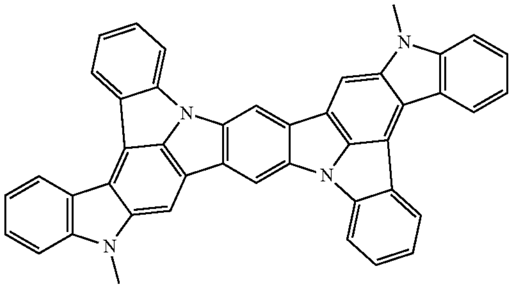

-continued
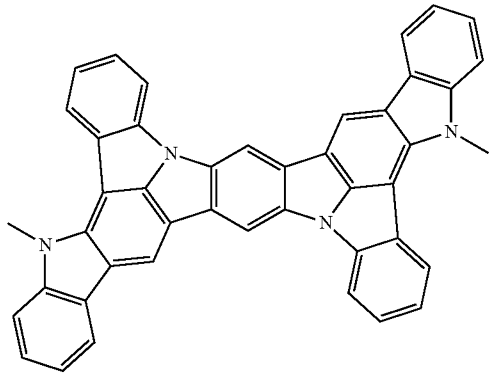
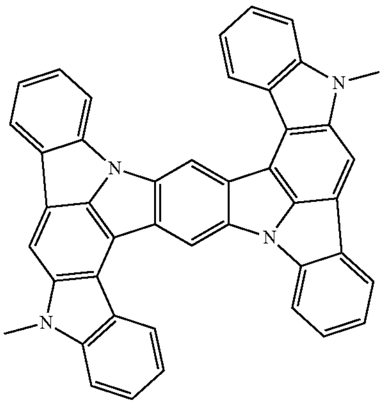
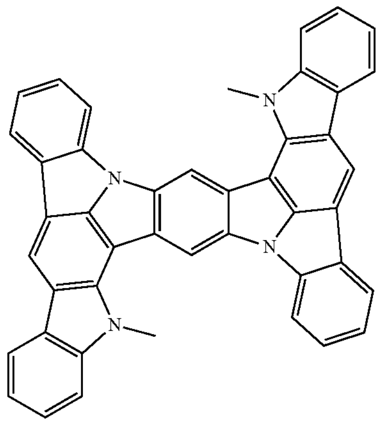
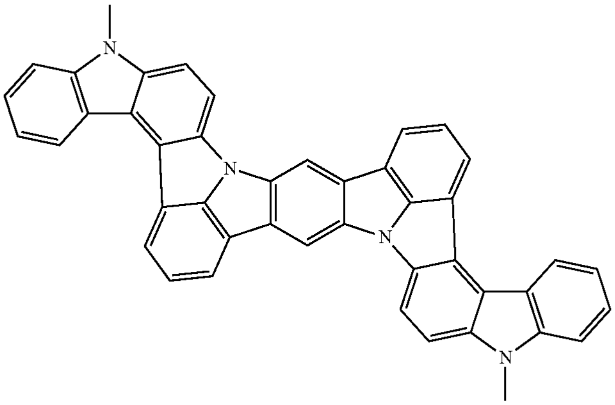
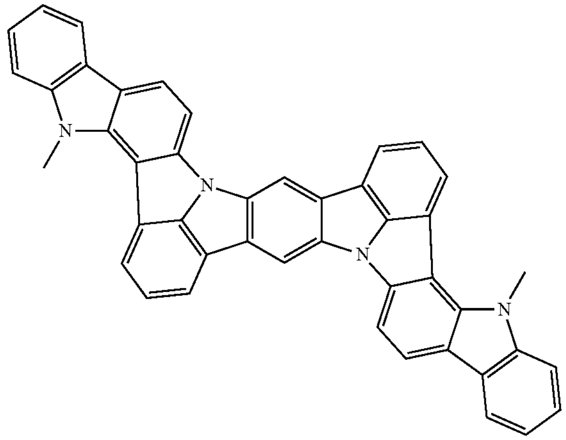
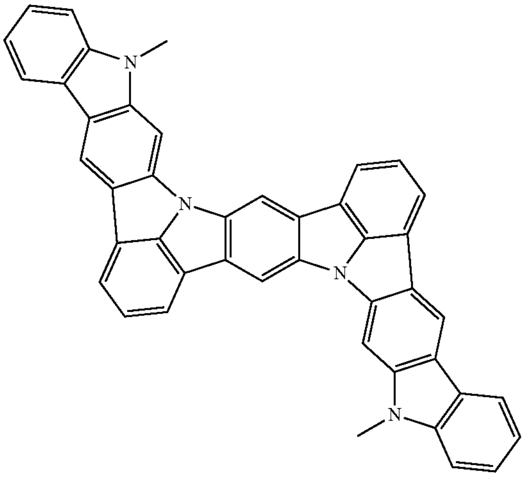

-continued
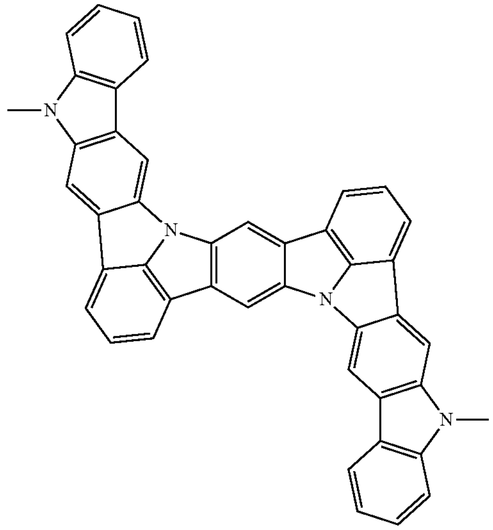
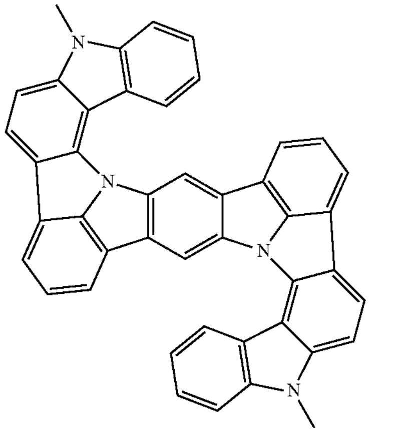
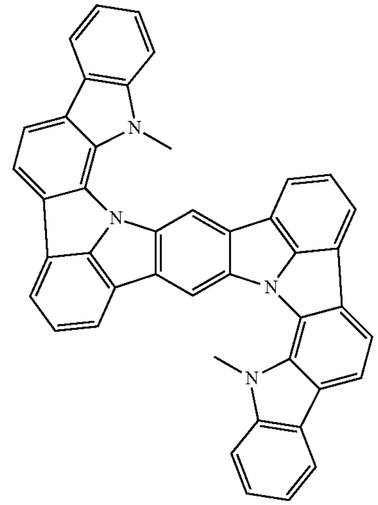
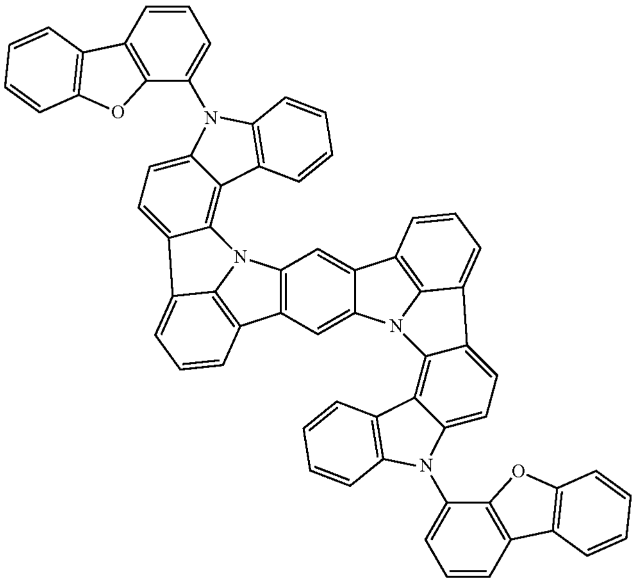
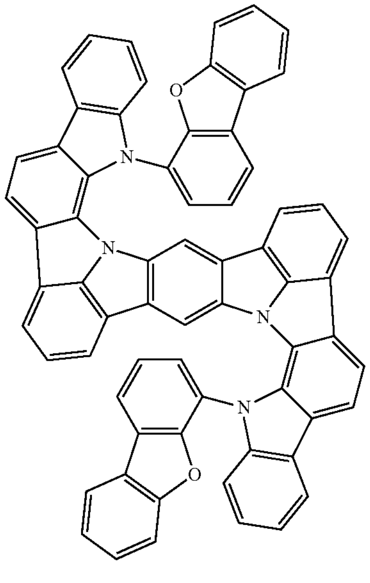
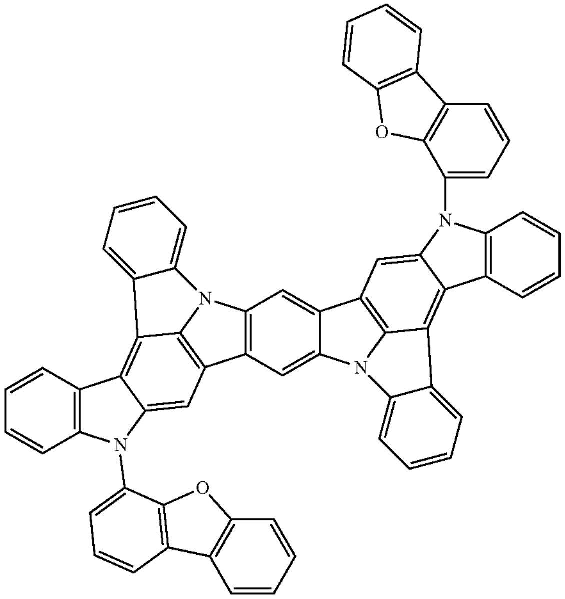

-continued
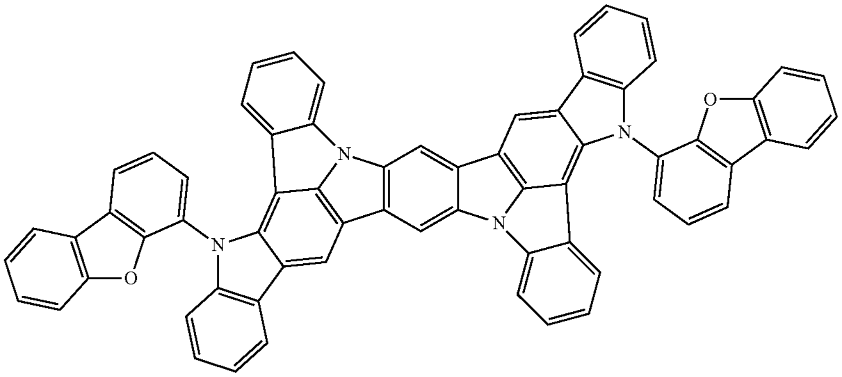
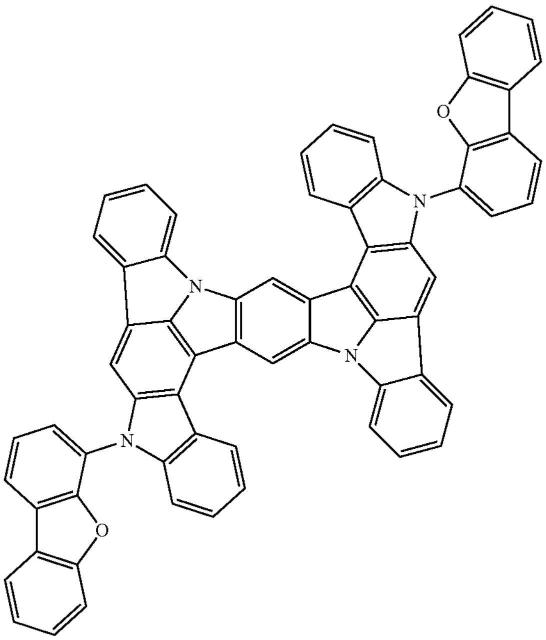
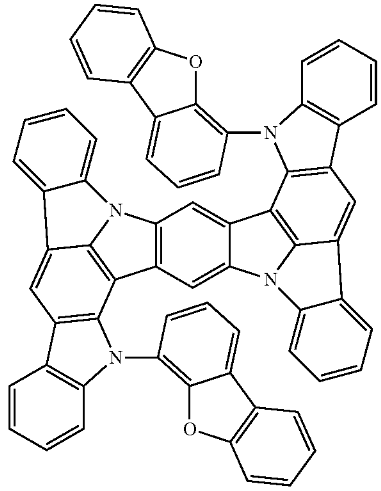
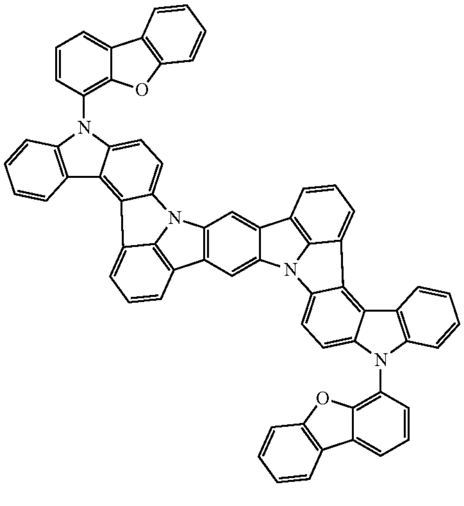
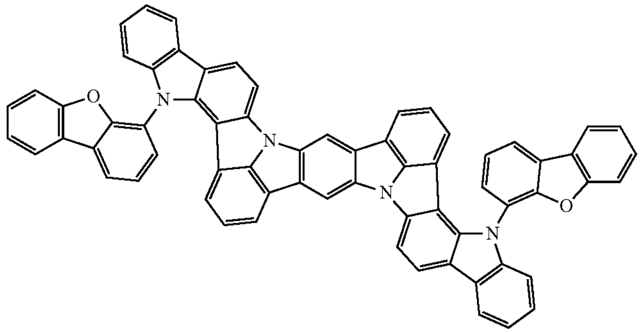

-continued
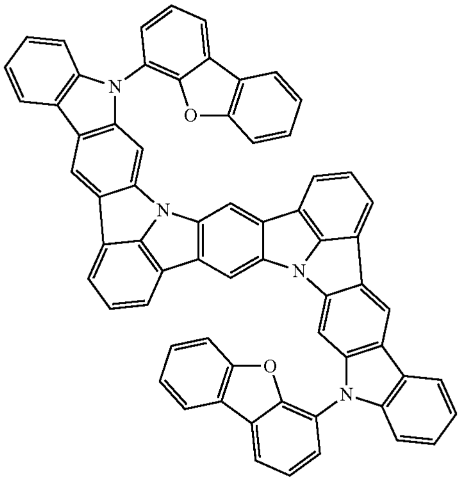
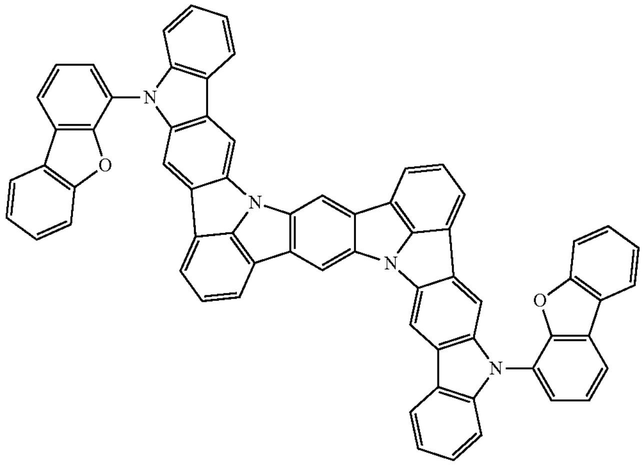
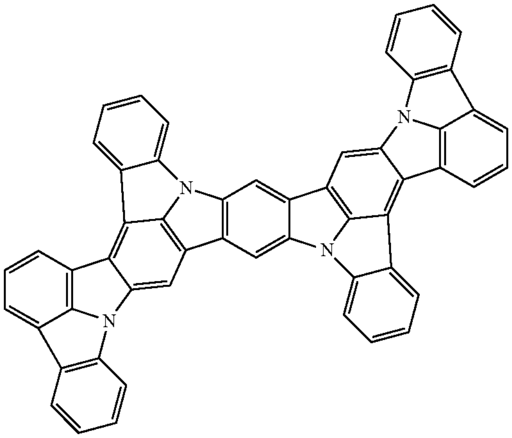
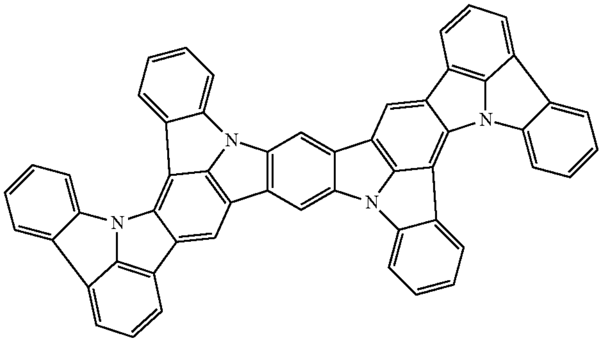
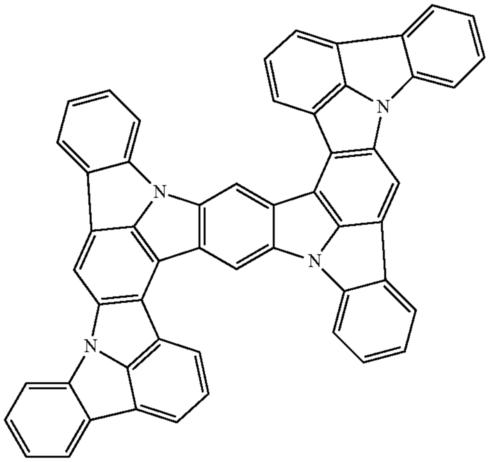
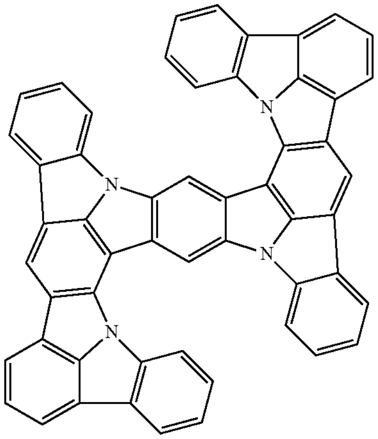

-continued
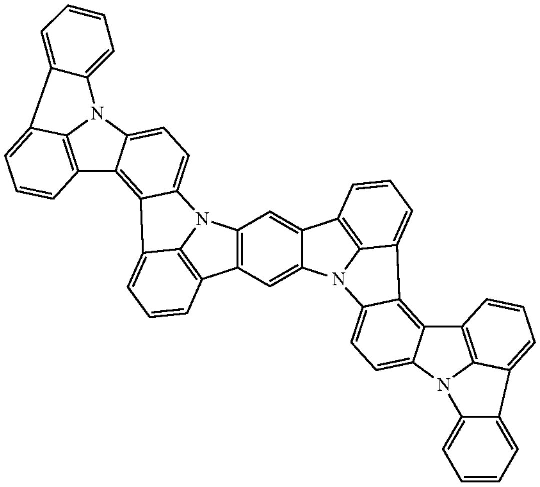
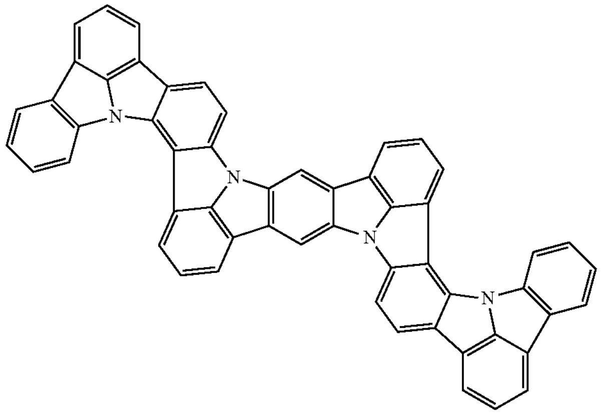
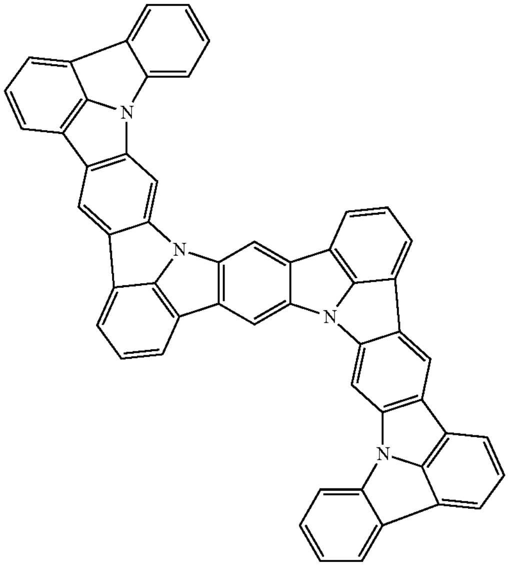
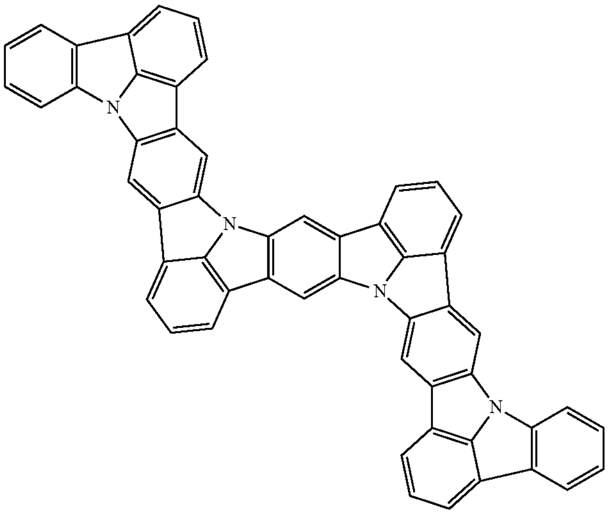
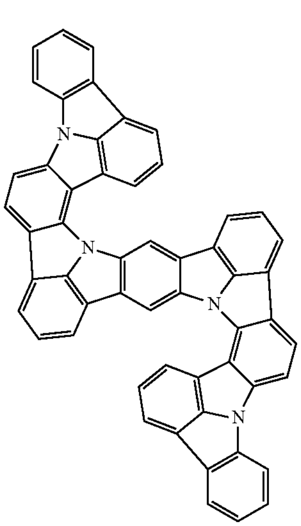
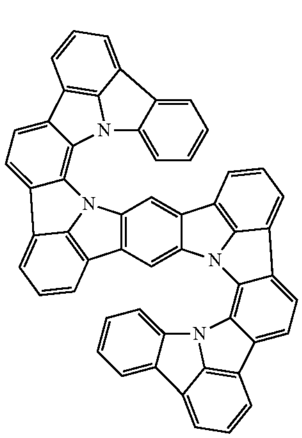
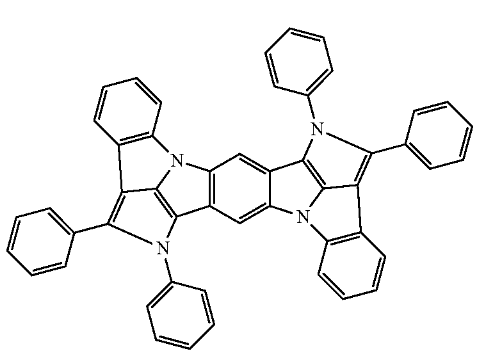

-continued
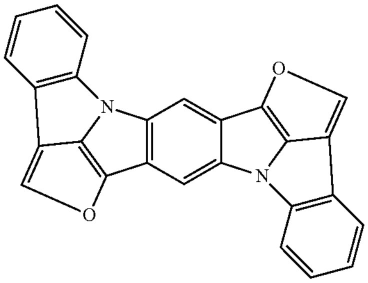
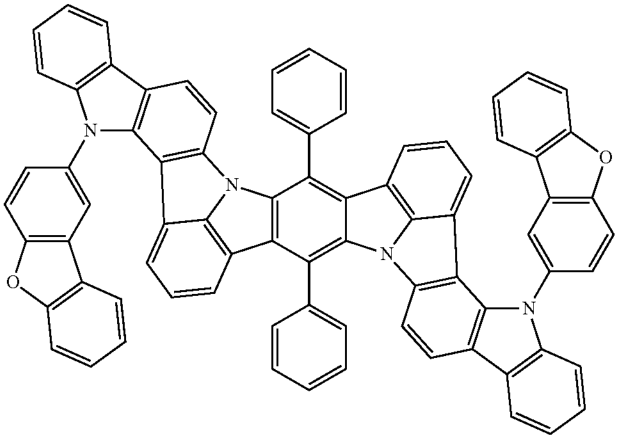
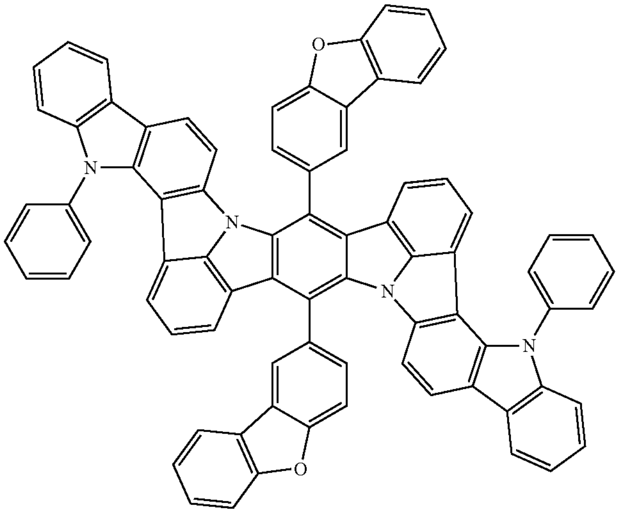
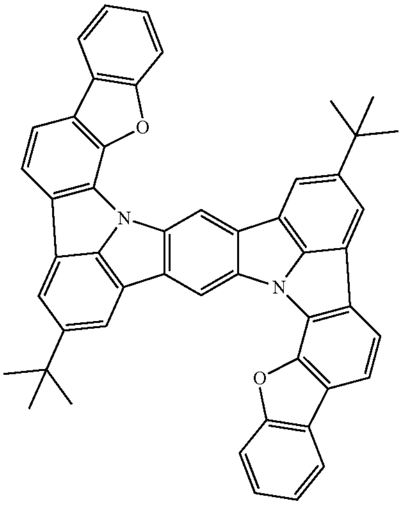
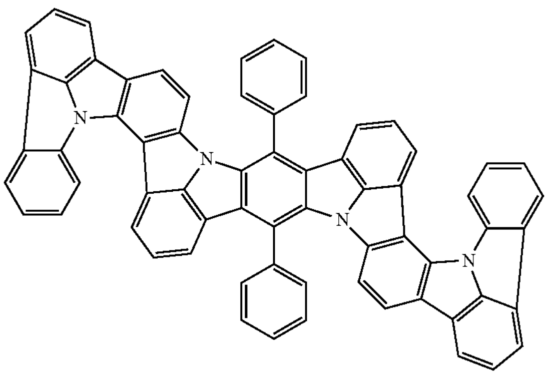
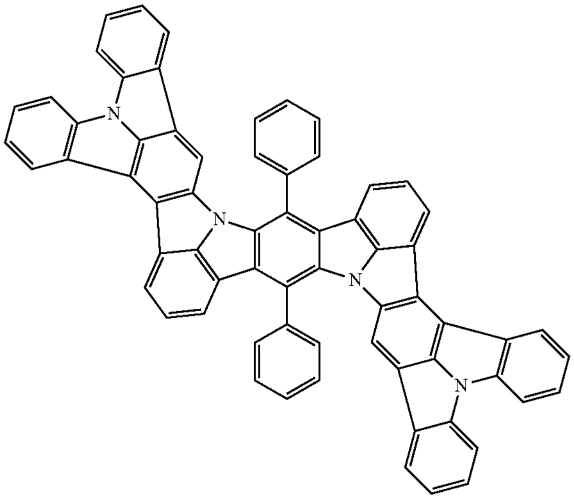

(Compound Represented by Formula (41))

The compound represented by the formula (41) is explained below.

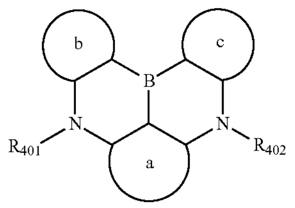

(41)

In the formula (41), a ring, b ring and c ring are independently a substituted or unsubstituted aromatic hydrocarbon ring having 6 to 50 ring carbon atoms, or a substituted or unsubstituted heterocyclic ring having 5 to 50 ring atoms;

$R_{401}$ and $R_{402}$ are independently bonded to the a ring, the b ring or the c ring to form a substituted or unsubstituted heterocyclic ring or do not form a substituted or unsubstituted heterocyclic ring;

$R_{401}$ and $R_{402}$ that do not form the substituted or unsubstituted heterocyclic ring are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

The a ring, b ring and c ring are rings (a substituted or unsubstituted aromatic hydrocarbon ring having 6 to 50 ring carbon atoms or a substituted or unsubstituted heterocyclic ring having 5 to 50 ring atoms) fuse to the fused bicyclic structure composed of B atom and two N atoms in the center of the formula (41).

The "aromatic hydrocarbon ring" of the a ring, the b ring and the c ring has the same structure as the compound obtained by introducing a hydrogen atom into the "aryl group" described above. The "aromatic hydrocarbon ring" of the a ring contains three carbon atoms in the fused bicyclic structure in the center of the formula (41) as ring atoms. The "aromatic hydrocarbon ring" of the b ring and the c ring contain two carbon atoms in the fused bicyclic structure in the center of the formula (41) as ring atoms. As examples of "substituted or unsubstituted aromatic hydrocarbon ring having 6 to 50 ring carbon atoms", compounds in which a hydrogen atom is introduced into the "aryl group" described in the group G1 and the like can be given.

The "heterocyclic ring" of the a ring, the b ring and the c ring has the same structure as the compound obtained by introducing a hydrogen atom into the "heterocyclic group" described above. The "heterocyclic ring" of the a ring contains three carbon atoms in the fused bicyclic structure in the center of the formula (41) as ring atoms. The "heterocyclic ring" of the b ring and the c ring contain two carbon atoms in the fused bicyclic structure in the center of the formula (41) as ring atoms. As examples of "substituted or unsubstituted heterocyclic ring having 5 to 50 ring atoms", compounds in which a hydrogen atom is introduced into the "heterocyclic group" described in the group G2.

$R_{401}$ and $R_{402}$ may be independently bonded to the a ring, the b ring or the c ring to form a substituted or unsubstituted heterocyclic ring. This heterocyclic ring contains the nitrogen atom in the fused bicyclic structure in the center of the formula (41). This heterocyclic ring may contain a heteroatom other than the nitrogen atom. "$R_{401}$ and $R_{402}$ are bonded to the a ring, the b ring or the c ring" means, specifically, an atom forming the a ring, the b ring or the c ring is bonded to an atom forming $R_{401}$ and $R_{402}$. For example, it is possible that $R_{401}$ is bonded to the a ring to form a nitrogen-containing heterocyclic ring having a two-ring fused structure (or three or more rings fused structure) in which a ring containing $R_{401}$ and the a ring are fused.

The same applies to the case where $R_{401}$ is bonded to the b ring, $R_{402}$ is bonded to the a ring, and $R_{402}$ is bonded to the c ring.

In one embodiment, the a ring, the b ring and the c ring in the formula (41) are independently a substituted or unsubstituted aromatic hydrocarbon ring having 6 to 50 ring carbon atoms.

In one embodiment, the a ring, the b ring and the c ring in the formula (41) are independently a substituted or unsubstituted benzene ring or a substituted or unsubstituted naphthalene ring.

In one embodiment, $R_{401}$ and $R_{402}$ in the formula (41) are independently a substituted or unsubstituted aryl group having 6 to 50 ring carbon atoms, or a substituted or unsubstituted monovalent heterocyclic group having 5 to 50 ring atoms, and preferably a substituted or unsubstituted aryl group having 6 to 50 ring carbon atoms.

In one embodiment, the compound represented by the formula (41) is a compound represented by the following formula (42):

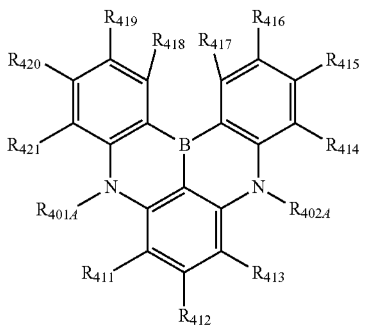

(42)

wherein in the formula (42), $R_{401A}$ is bonded with one or more groups selected from $R_{411}$ or $R_{421}$ to form a substituted or unsubstituted heterocyclic ring, or does not form a substituted or unsubstituted heterocyclic ring; $R_{402A}$ is bonded with one or more group selected from $R_{413}$ or $R_{414}$ to form a substituted or unsubstituted heterocyclic ring, or does not form a substituted or unsubstituted heterocyclic ring;

$R_{401A}$ and $R_{402A}$ that do not form a substituted or unsubstituted heterocyclic ring are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

One or more pairs of two or more adjacent groups of $R_{411}$ to $R_{421}$ are bonded with each other to form a substituted or unsubstituted, saturated or unsaturated ring, or do not form a substituted or unsubstituted, saturated or unsaturated ring;

$R_{411}$ to $R_{421}$ that do not form the substituted or unsubstituted heterocyclic ring or the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

$R_{401A}$ and $R_{402A}$ in the formula (42) correspond to $R_{401}$ and $R_{402}$ in the formula (41). $R_{401A}$ and $R_{411}$ may be bonded with each other to form a nitrogen-containing heterocyclic ring having two-ring fused structure (or three or more rings fused structure) which is a fused ring of a ring containing $R_{401A}$ and $R_{411}$ and the benzene ring of the a ring, for example. As examples of the nitrogen-containing heterocyclic ring, compounds correspond to nitrogen-containing heterocyclic group having two or more ring fused structure in the group G2 can be given. The same applies to the cases where $R_{401A}$ and $R_{412}$ are bonded, $R_{402A}$ and $R_{413}$ are bonded, and $R_{402A}$ and $R_{414}$ are bonded.

One or more pairs of two or more adjacent groups of $R_{411}$ to $R_{421}$ are bonded with each other to form a substituted or unsubstituted, saturated or unsaturated ring. For example, $R_{411}$ and $R_{412}$ are bonded to form a benzene ring, an indole ring, a pyrrole ring, a benzofuran ring, a benzothiophene ring or the like which fuses to the six-membered ring to which $R_{411}$ and $R_{412}$ bond, and the formed fused ring is a naphthalene ring, a carbazole ring, an indole ring, a dibenzofuran ring or a dibenzothiophene ring.

In one embodiment, $R_{411}$ to $R_{421}$ that do not contribute to form a ring are independently a hydrogen atom, a substituted or unsubstituted alkyl group having 1 to 50 carbon atoms, a substituted or unsubstituted aryl group having 6 to 50 ring carbon atoms, or a substituted or unsubstituted monovalent heterocyclic group having 5 to 50 ring atoms.

In one embodiment, $R_{411}$ to $R_{421}$ that do not contribute to form a ring are independently a hydrogen atom, a substituted or unsubstituted aryl group having 6 to 50 ring carbon atoms, or a substituted or unsubstituted monovalent heterocyclic group having 5 to 50 ring atoms.

In one embodiment, $R_{411}$ to $R_{421}$ that do not contribute to form a ring are independently a hydrogen atom or a substituted or unsubstituted alkyl group having 1 to 50 carbon atoms.

In one embodiment, $R_{411}$ to $R_{421}$ that do not contribute to form a ring are independently a hydrogen atom, a substituted or unsubstituted alkyl group having 1 to 50 carbon atoms, and at least one of $R_{411}$ to $R_{421}$ is a substituted or unsubstituted alkyl group having 1 to 50 carbon atoms.

In one embodiment, the compound represented by the formula (42) is a compound represented by the following formula (43):

(43)

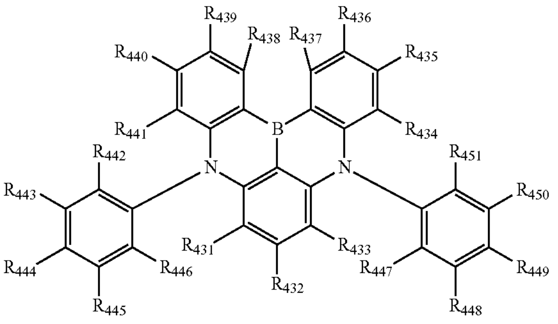

wherein in the formula (43), $R_{431}$ is bonded with $R_{446}$ to form a substituted or unsubstituted heterocyclic ring, or does not form a substituted or unsubstituted heterocyclic ring; $R_{433}$ is bonded with $R_{447}$ to form a substituted or unsubstituted heterocyclic ring, or does not form a substituted or unsubstituted heterocyclic ring; $R_{434}$ is bonded with $R_{451}$ to form a substituted or unsubstituted heterocyclic ring, or does not form a substituted or unsubstituted heterocyclic ring; $R_{441}$ is bonded with $R_{442}$ to form a substituted or unsubstituted heterocyclic ring, or does not form a substituted or unsubstituted heterocyclic ring;

One or more pairs of two or more adjacent groups of $R_{431}$ to $R_{451}$ are bonded with each other to form a substituted or unsubstituted, saturated or unsaturated ring, or do not form a substituted or unsubstituted, saturated or unsaturated ring;

$R_{431}$ to $R_{451}$ that do not form a substituted or unsubstituted heterocyclic ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

$R_{431}$ may bond to $R_{446}$ to form a substituted or unsubstituted heterocyclic ring. For example, $R_{431}$ may bonds with $R_{446}$ to form a nitrogen-containing heterocyclic ring with three or more fused rings of the benzene ring to which $R_{45}$ bond, a nitrogen-containing ring and the benzene ring of the a ring. As examples of the nitrogen-containing heterocyclic ring, compounds correspond to nitrogen-containing heterocyclic group having three or more ring fused structure in the group G2 can be given. The same applies to the cases where $R_{433}$ and $R_{447}$ are bonded, $R_{434}$ and $R_{451}$ are bonded, and $R_{441}$ and $R_{42}$ are bonded.

In one embodiment, $R_{431}$ to $R_{451}$ that do not contribute to form a ring are independently, a hydrogen atom, a substituted or unsubstituted alkyl group having 1 to 50 carbon atoms, a substituted or unsubstituted aryl group having 6 to 50 carbon atoms, or a substituted or unsubstituted monovalent heterocyclic group having 5 to 50 ring atoms.

In one embodiment, $R_{431}$ to $R_{451}$ that do not contribute to form a ring are independently, a hydrogen atom, a substituted or unsubstituted aryl group having 6 to 50 carbon atoms, or a substituted or unsubstituted monovalent heterocyclic group having 5 to 50 ring atoms.

In one embodiment, $R_{431}$ to $R_{451}$ that do not contribute to form a ring are independently a hydrogen atom or a substituted or unsubstituted alkyl group having 1 to 50 carbon atoms.

In one embodiment, $R_{431}$ to $R_{451}$ that do not contribute to form a ring are independently a hydrogen atom, a substituted or unsubstituted alkyl group having 1 to 50 carbon atoms, and at least one of $R_{431}$ to $R_{451}$ is a substituted or unsubstituted alkyl group having 1 to 50 carbon atoms.

In one embodiment, the compound represented by the formula (43) is a compound represented by the following formula (43A):

(43A)

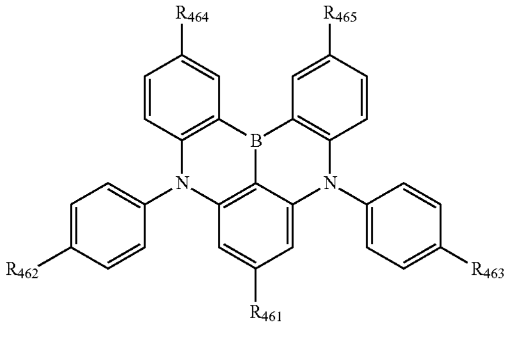

wherein in the formula (43A), $R_{461}$ is a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{462}$ to $R_{465}$ are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In one embodiment, $R_{461}$ to $R_{465}$ are independently a substituted or unsubstituted alkyl group having 1 to 50 carbon atoms or a substituted or unsubstituted aryl group having 6 to 50 ring carbon atoms.

In one embodiment, $R_{461}$ and $R_{465}$ are independently a substituted or unsubstituted alkyl group having 1 to 50 carbon atoms.

In one embodiment, the compound represented by the formula (43) is a compound represented by the following formula (43B):

(43B)

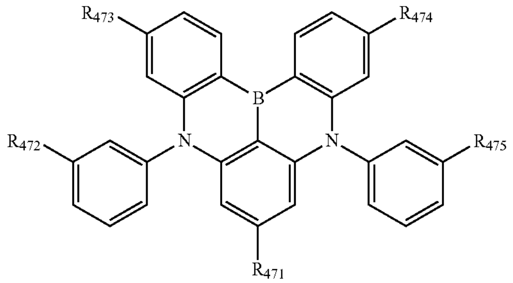

wherein in the formula (43B), $R_{471}$ and $R_{472}$ are independently, a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —N($R_{906}$) ($R_{907}$), or a substituted or unsubstituted aryl group having 6 to 50 ring carbon atoms;

$R_{473}$ to $R_{475}$ are independently, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —N($R_{906}$) ($R_{907}$), or a substituted or unsubstituted aryl group having 6 to 50 ring carbon atoms; and $R_{906}$ and $R_{907}$ are as defined in the formula (1).

In one embodiment, the compound represented by the formula (43) is the compound represented by the following formula (43B'):

(43B')

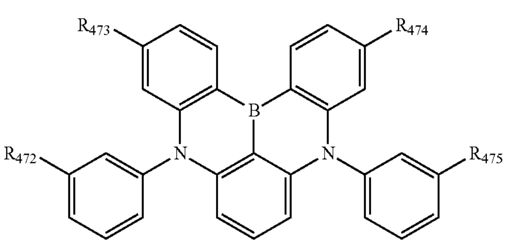

wherein in the formula (43B'), $R_{472}$ to $R_{475}$ are as defined in the formula (43B).

In one embodiment, at least one of $R_{471}$ to $R_{475}$ is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $-N(R_{906})(R_{907})$, or a substituted or unsubstituted aryl group having 6 to 50 ring carbon atoms.

In one embodiment, $R_{472}$ is a hydrogen atom, a substituted or unsubstituted alkyl group having 1 to 50 carbon atoms, $-N(R_{906})(R_{907})$, or a substituted or unsubstituted aryl group having 6 to 50 ring carbon atoms; and $R_{471}$ and $R_{473}$ to $R_{475}$ are independently a substituted or unsubstituted alkyl group having 1 to 50 carbon atoms, $-N(R_{906})(R_{907})$, or a substituted or unsubstituted aryl group having 6 to 50 ring carbon atoms.

In one embodiment, the compound represented by the formula (43) is a compound represented by the formula (43C):

(43C)

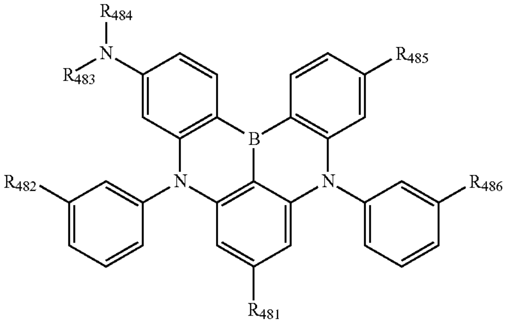

wherein in the formula (43C), $R_{481}$ and $R_{482}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{483}$ to $R_{486}$ are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In one embodiment, the compound represented by the formula (43) is the compound represented by the following formula (43C'):

(43C')

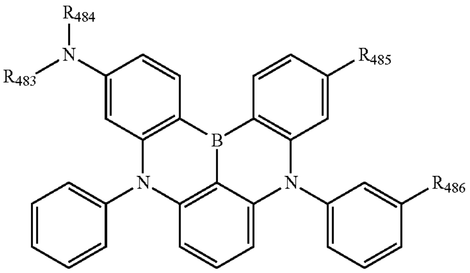

wherein in the formula (43C'), $R_{483}$ to $R_{486}$ are as defined in the formula (43C).

In one embodiment, $R_{481}$ to $R_{486}$ are independently a substituted or unsubstituted alkyl group having 1 to 50 carbon atoms or a substituted or unsubstituted aryl group having 6 to 50 ring carbon atoms.

In one embodiment, $R_{481}$ to $R_{486}$ are independently a substituted or unsubstituted aryl group having 6 to 50 ring carbon atoms.

In one embodiment, the compound represented by the formula (43) is the compound represented by the following formula (43D):

(43D)

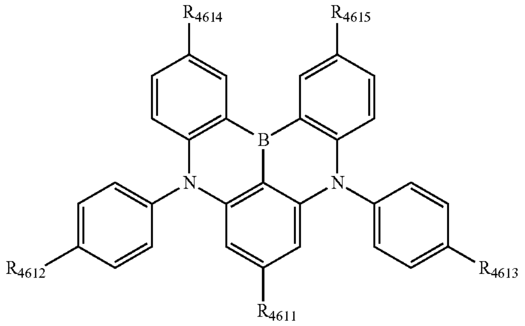

wherein in the formula (43D), $R_{4611}$ is a hydrogen atom, an unsubstituted alkyl group including 1 to 6 carbon atoms, an unsubstituted cycloalkyl group including 3 to 10 ring carbon atoms, —Si($R_{911}$)($R_{912}$)($R_{913}$), or —N($R_{914}$)($R_{915}$);

$R_{4612}$ to $R_{4615}$ are independently an unsubstituted alkyl group including 1 to 6 carbon atoms, an unsubstituted cycloalkyl group including 3 to 10 ring carbon atoms, or —Si($R_{911}$)($R_{912}$)($R_{913}$);

$R_{911}$ to $R_{913}$ are independently an unsubstituted alkyl group including 1 to 6 carbon atoms or an unsubstituted aryl group including 6 to 18 ring carbon atoms; and $R_{914}$ to $R_{915}$ are independently an unsubstituted aryl group having 6 to 18 ring carbon atoms.

In one embodiment, in the formula (43D), $R_{4611}$ is a hydrogen atom, an unsubstituted alkyl group including 1 to 6 carbon atoms, or —N($R_{914}$)($R_{915}$).

In one embodiment, in the formula (43D), $R_{4612}$ to $R_{4615}$ are independently an unsubstituted alkyl group including 1 to 6 carbon atoms or an unsubstituted cycloalkyl group including 3 to 10 ring carbon atoms.

In one embodiment, in the formula (43D), $R_{4611}$ is —N($R_{914}$)($R_{915}$), and $R_{4612}$ to $R_{4615}$ are independently an unsubstituted alkyl group including 1 to 6 carbon atoms.

In one embodiment, in the formula (43D), $R_{4611}$ is an unsubstituted alkyl group including 1 to 6 carbon atoms, and $R_{4612}$ to $R_{4615}$ are independently an unsubstituted alkyl group including 1 to 6 carbon atoms.

In one embodiment, in the formula (43D), $R_{4611}$ is a hydrogen atom, and $R_{4612}$ to $R_{4615}$ are independently an unsubstituted alkyl group including 1 to 6 carbon atoms or an unsubstituted cycloalkyl group including 3 to 10 ring carbon atoms.

In one embodiment, in the formula (43D), at least one hydrogen atom contained in one or more selected from the group consisting of $R_{914}$ and $R_{915}$ is a deuterium atom.

The compound represented by the formula (41) can be synthesized by the following method: An intermediate is obtained by bonding the a ring, the b ring and the c ring with linking groups (a group containing N—$R_1$ and a group containing N—$R_2$) (first reaction), and a final compound is obtained by bonding the a ring, the b ring and the c ring with a linking group (a group containing B) (second reaction). In the first reaction, an amination reaction such as Buchwald-Hartwig reaction can be applied. In the second reaction, tandem hetero-Friedel-Crafts reaction or the like can be applied.

Examples of the compound represented by the formula (41) are described below. They are just exemplified compounds and the compound represented by the formula (41) is not limited to the following examples. In the following example compounds, Me represents methyl group, and tBu represents tert-butyl group.

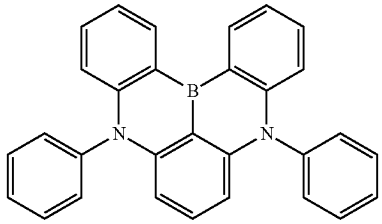

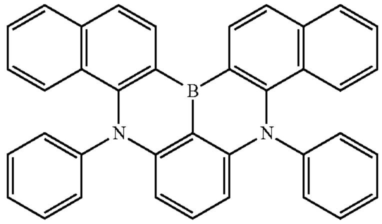

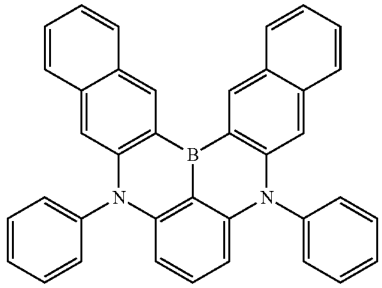

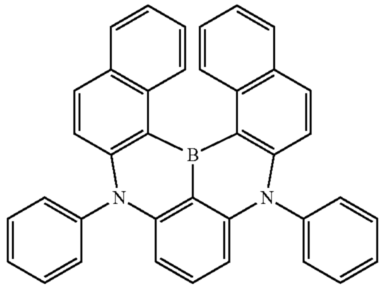

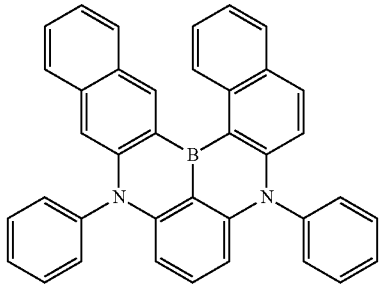

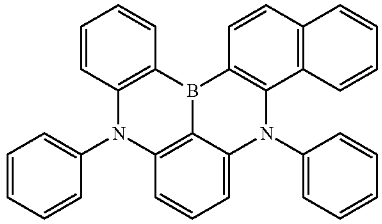

-continued
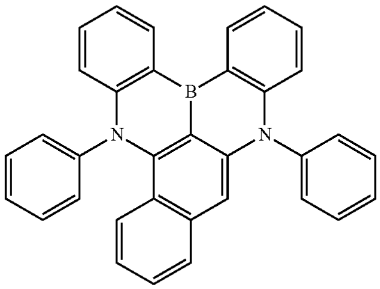
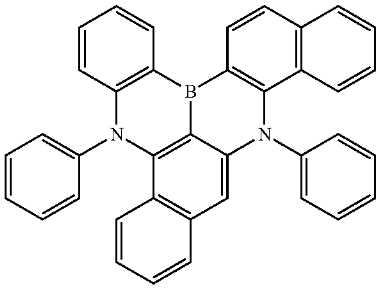
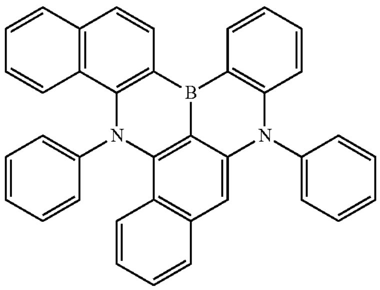
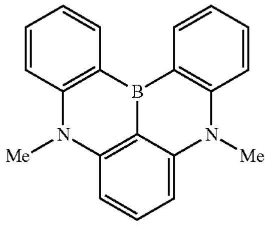
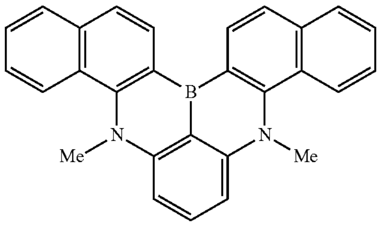
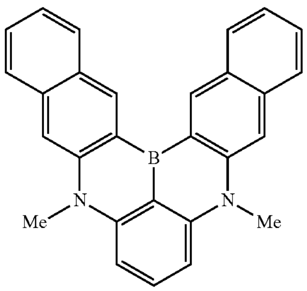
-continued
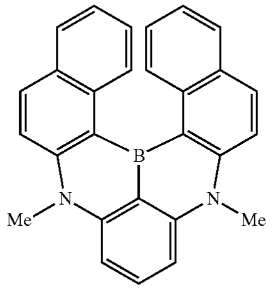
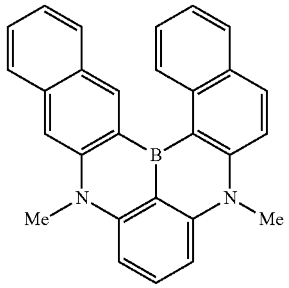
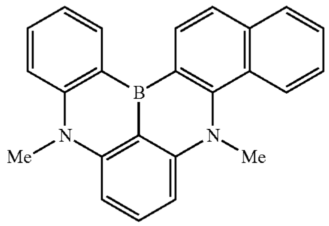
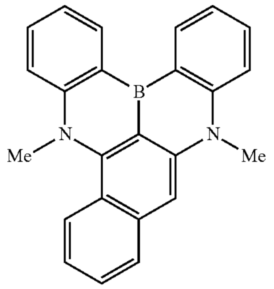
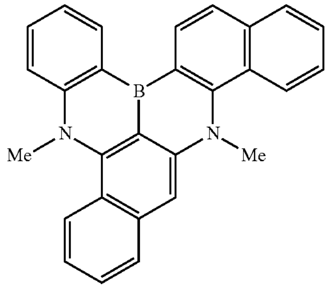
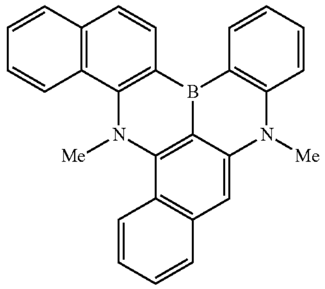

-continued
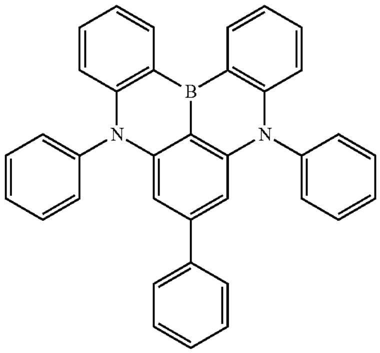
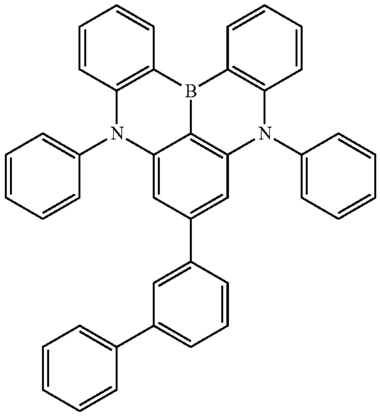
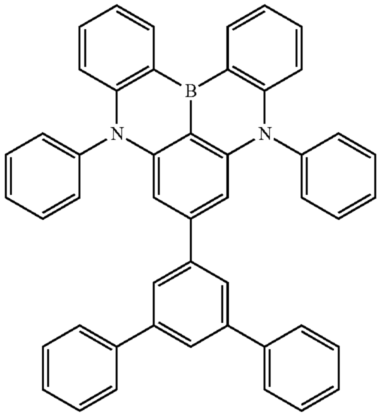
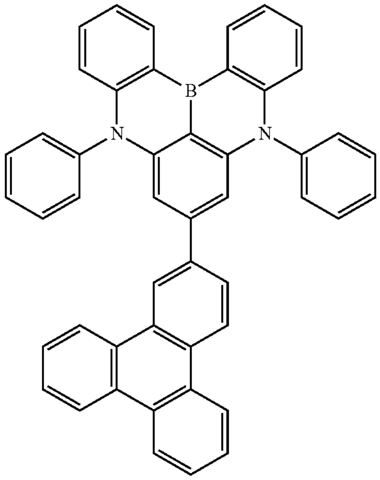
-continued
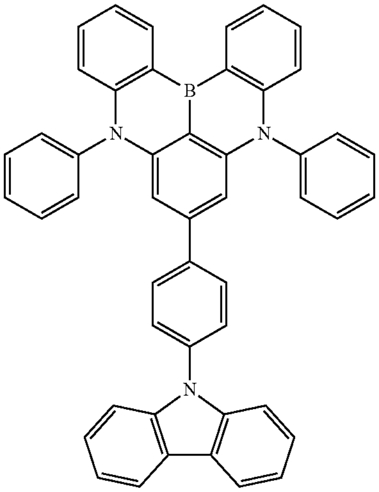
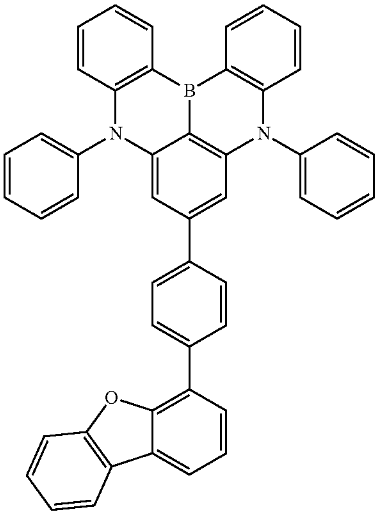
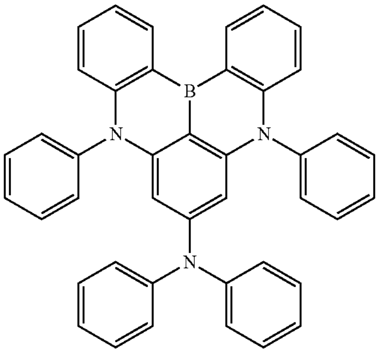
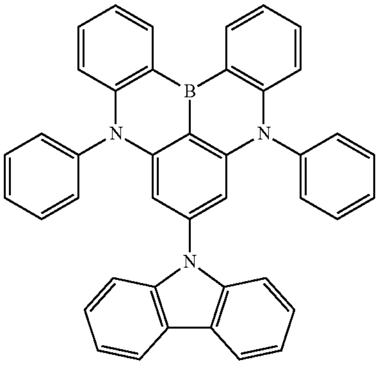

-continued
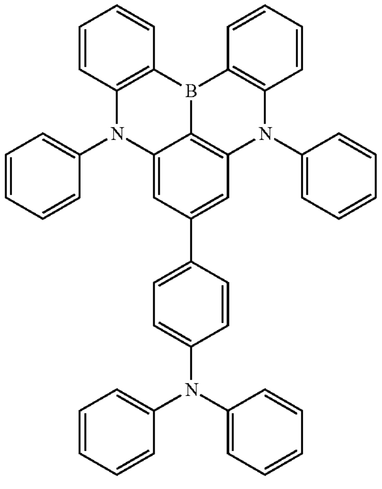
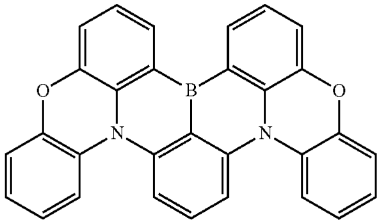
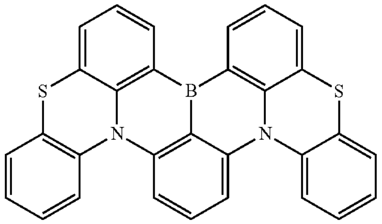
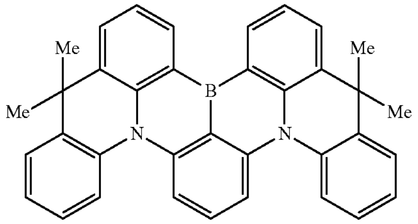
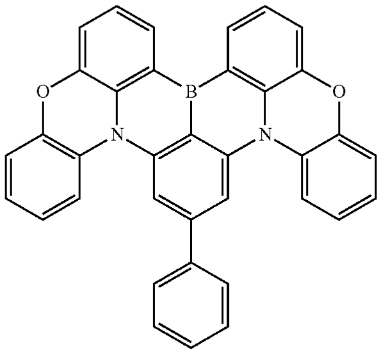
-continued
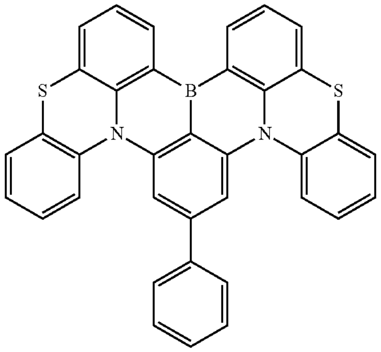
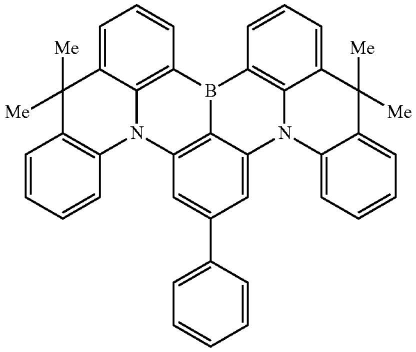
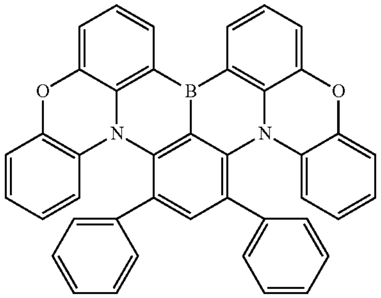
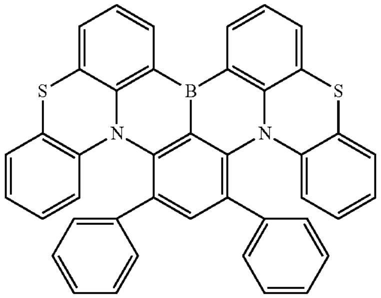
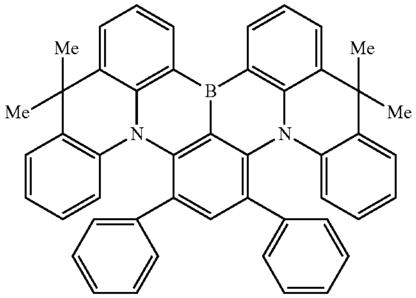

-continued
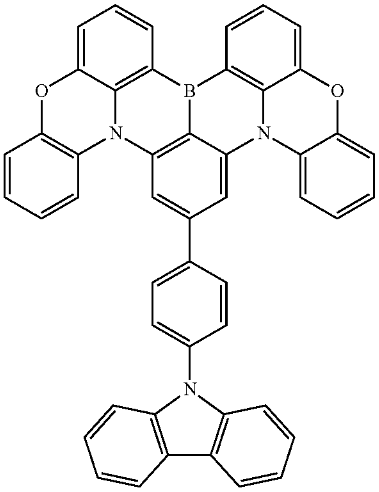
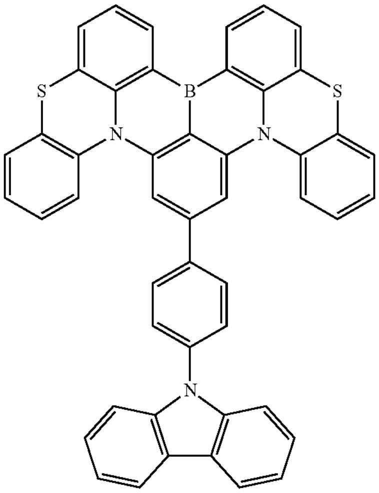
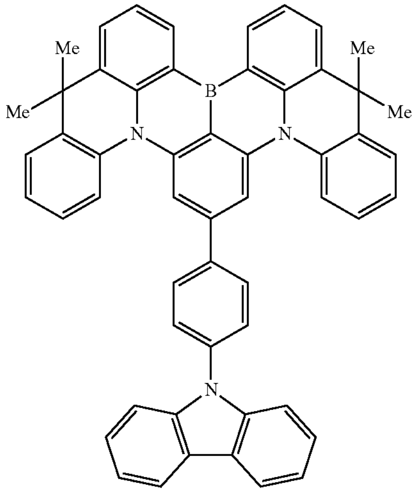
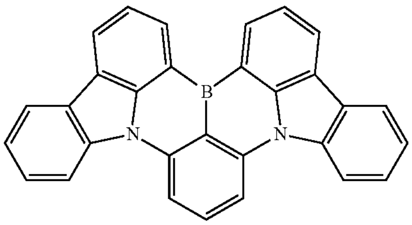
-continued
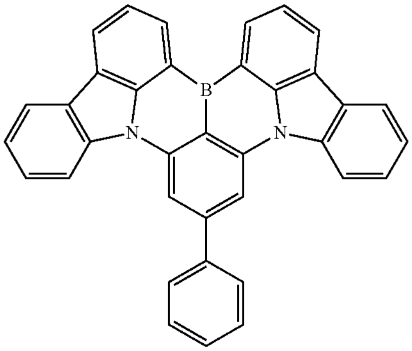
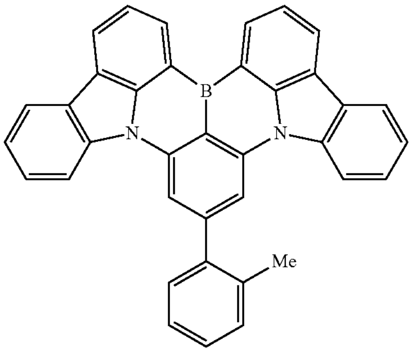
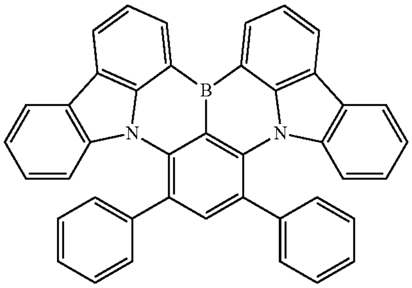
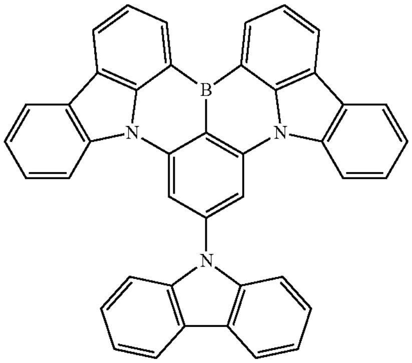
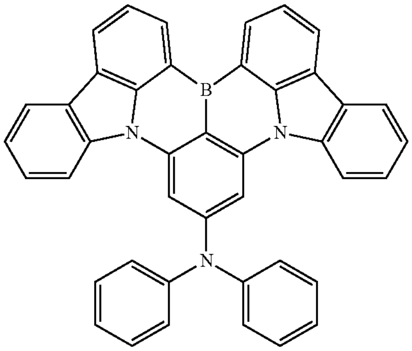

-continued
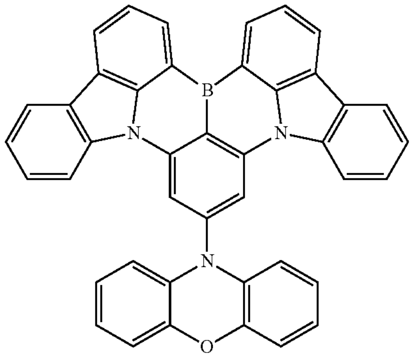
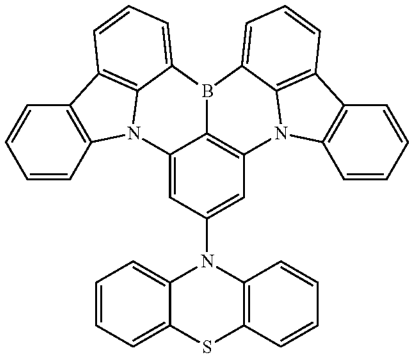
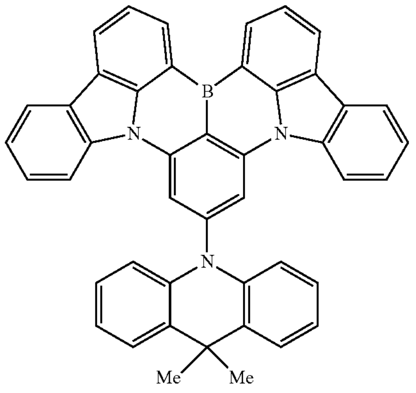
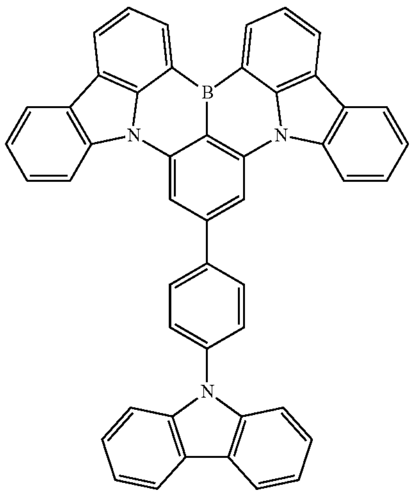
-continued
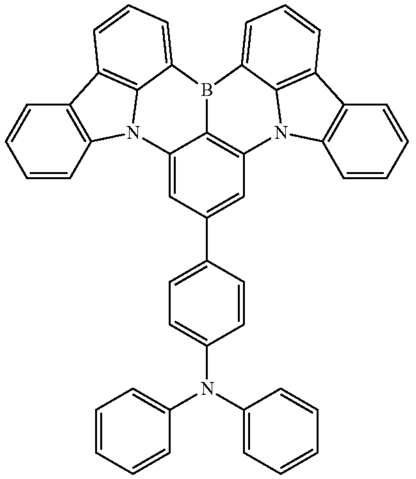
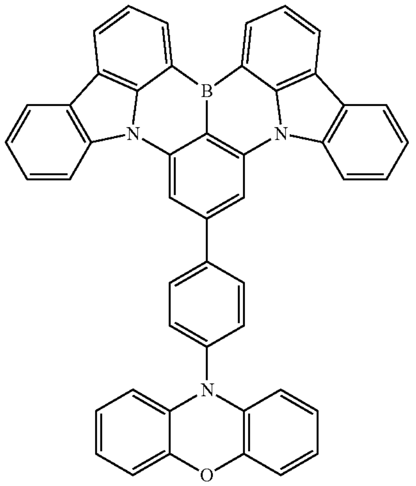
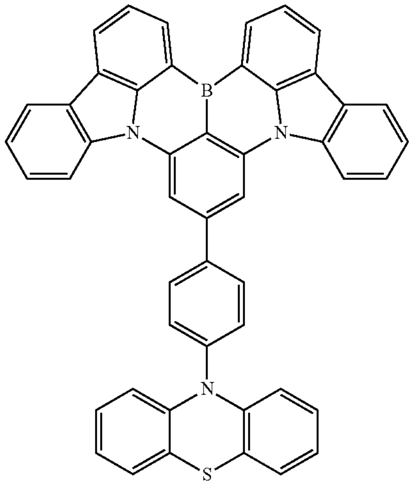

-continued
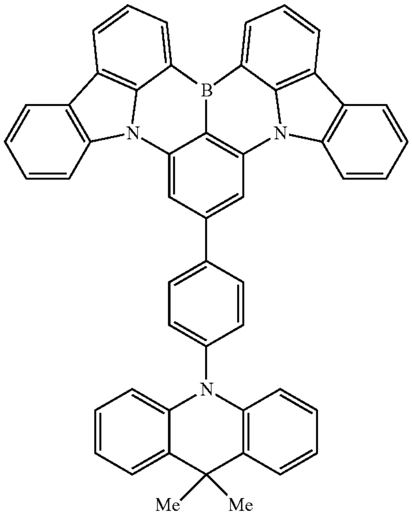
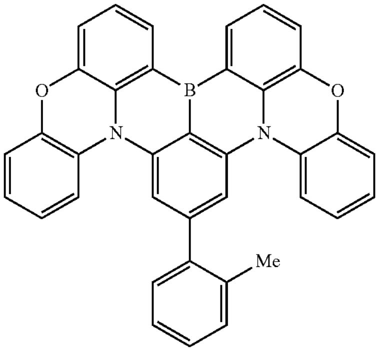
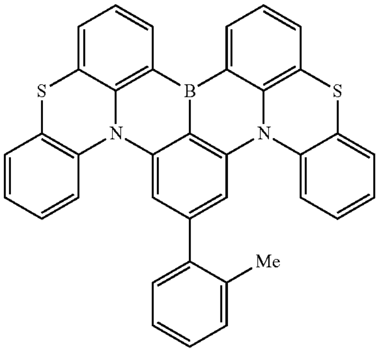
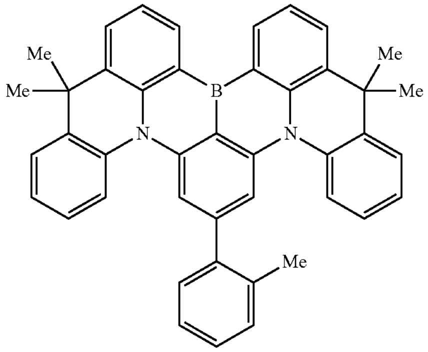
-continued
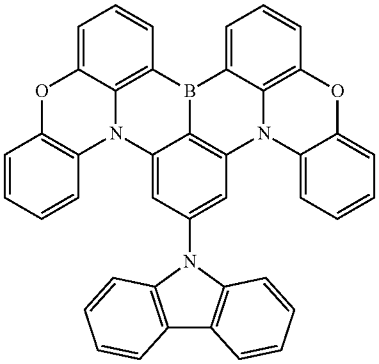
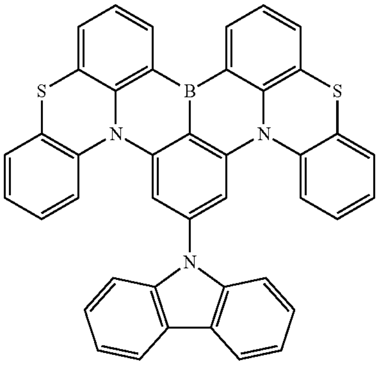
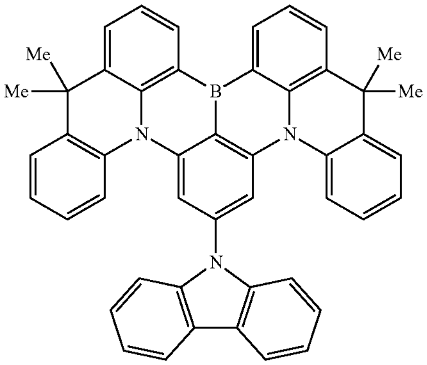
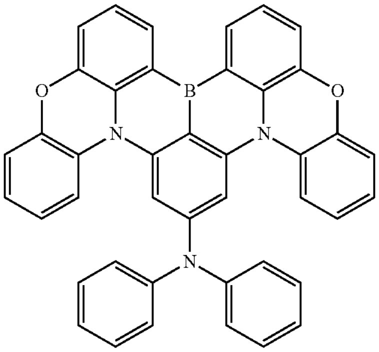

-continued
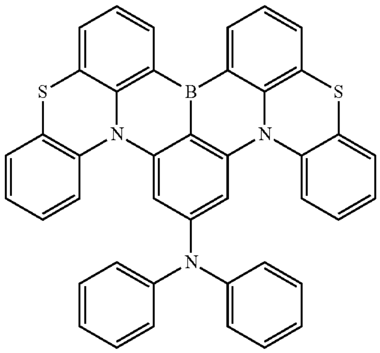
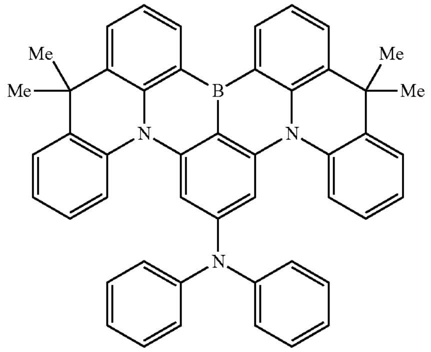
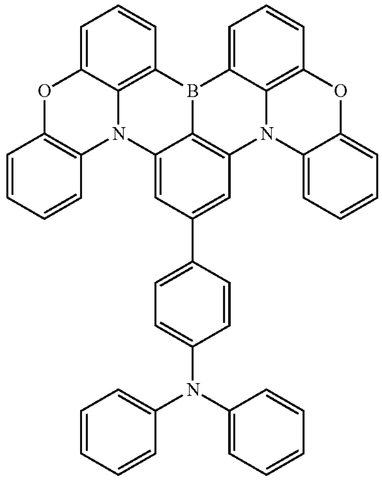
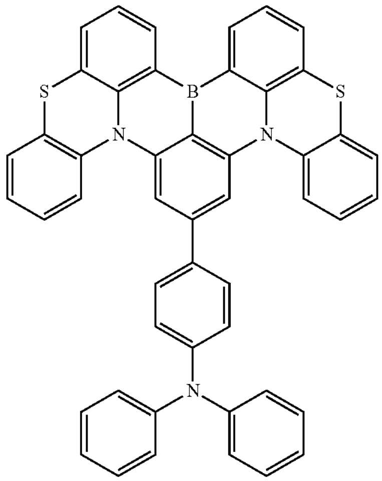
-continued
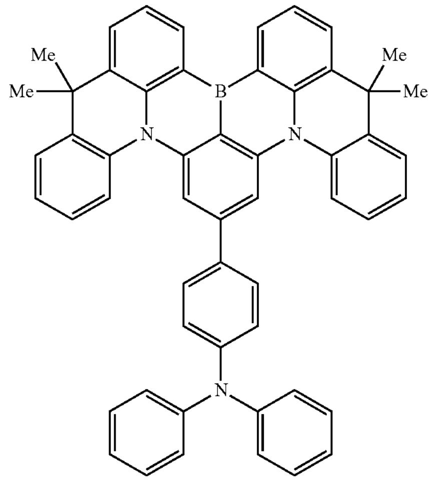
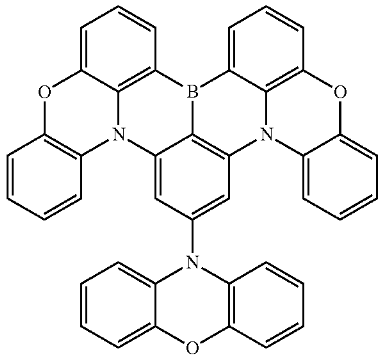
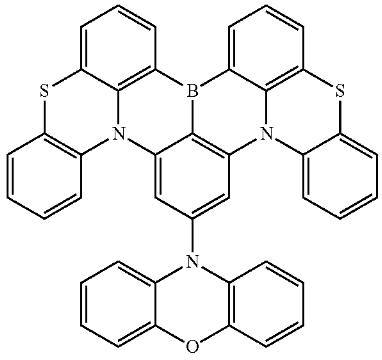
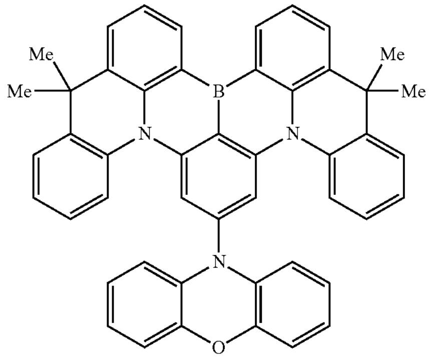

-continued
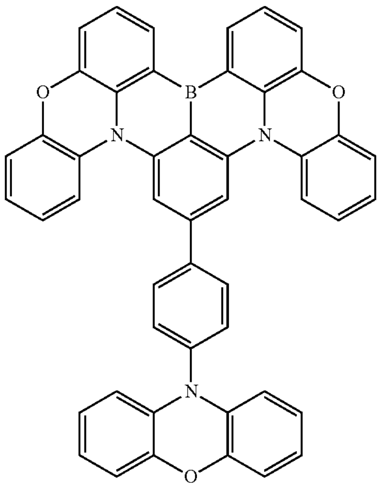
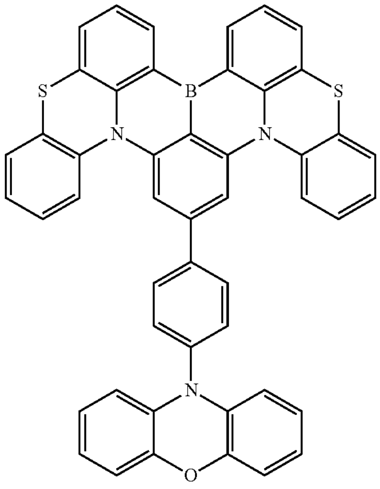
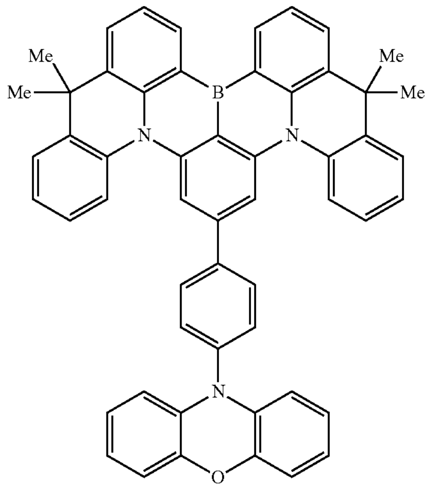
-continued
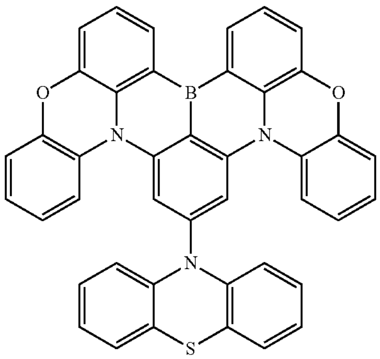
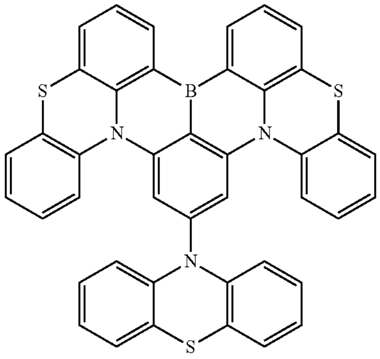
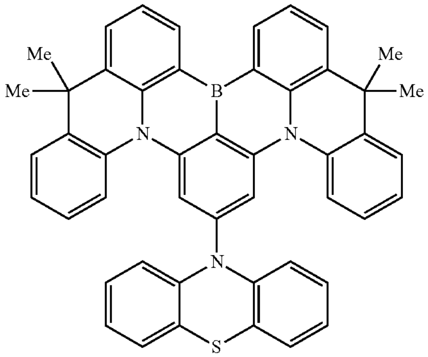
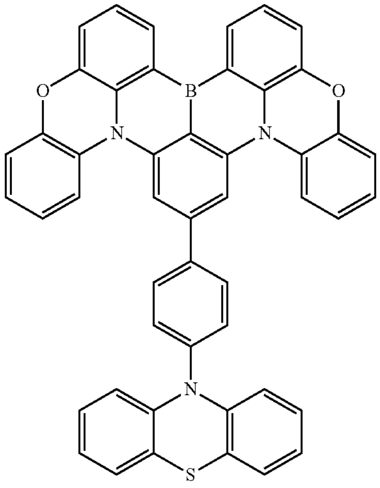

-continued
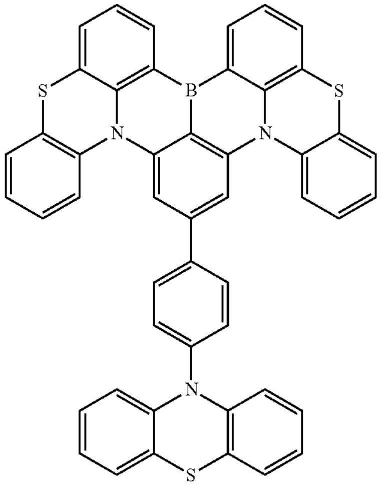
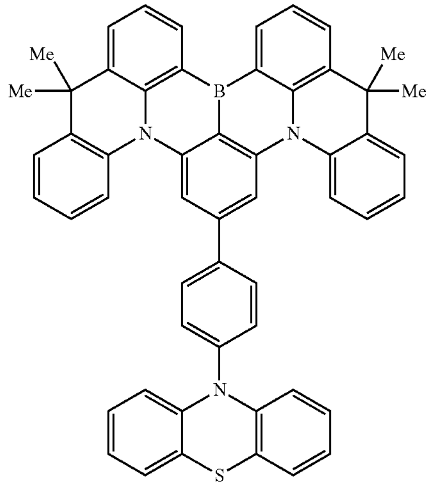
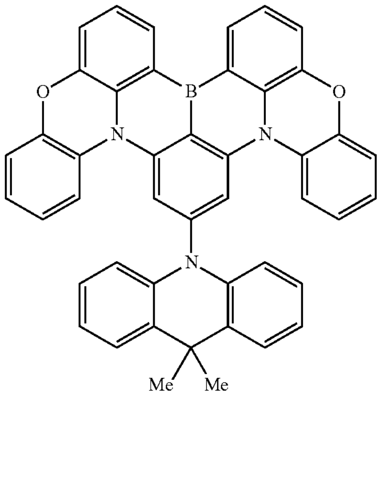
-continued
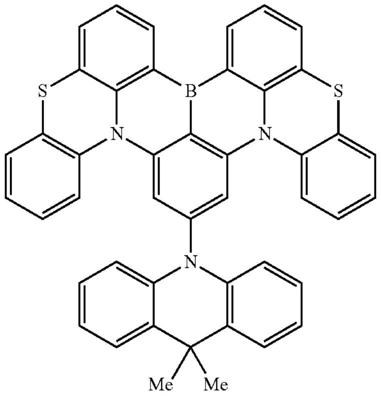
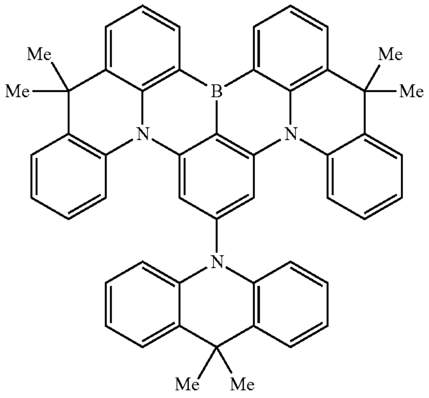
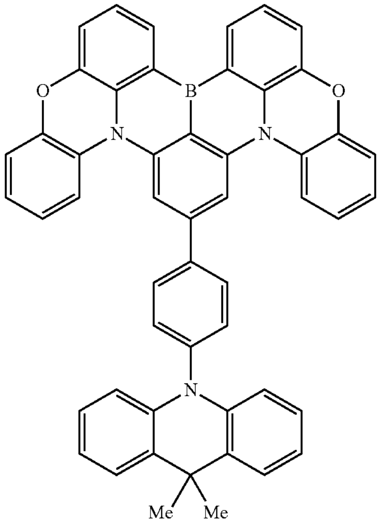

-continued
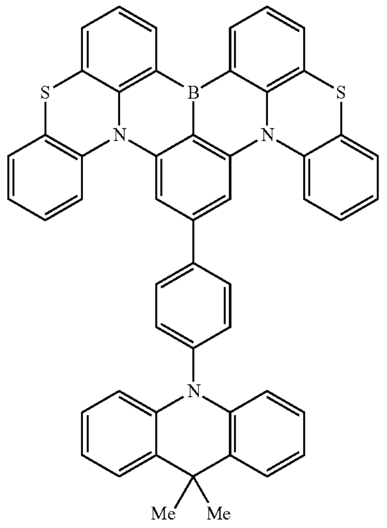
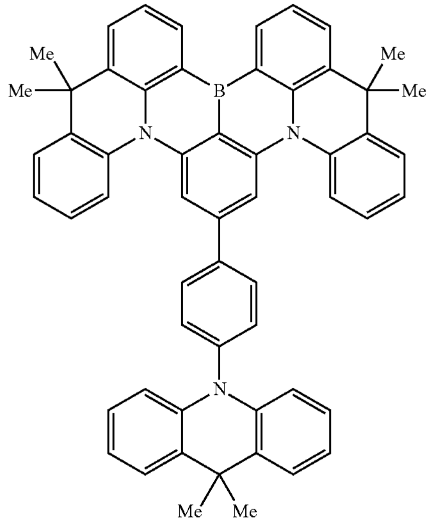
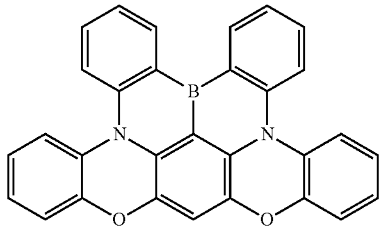
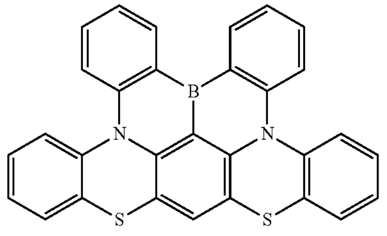
-continued
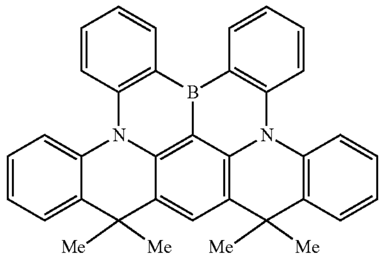
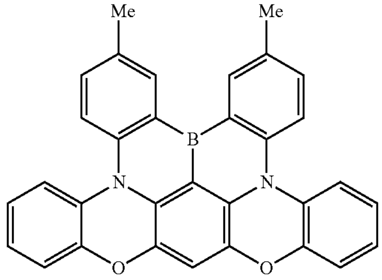
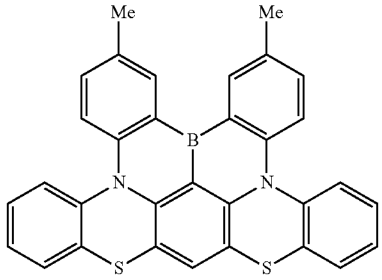
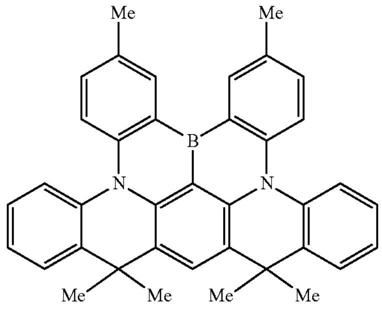
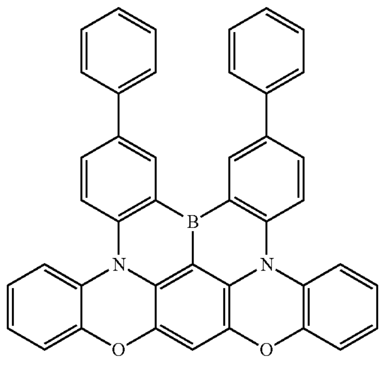

-continued
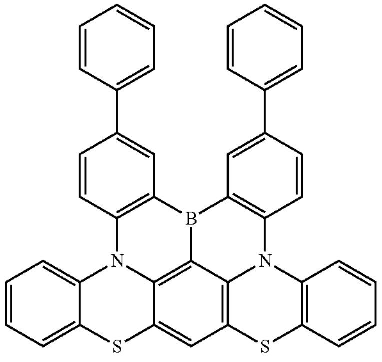
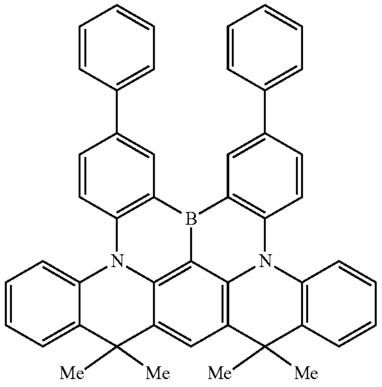
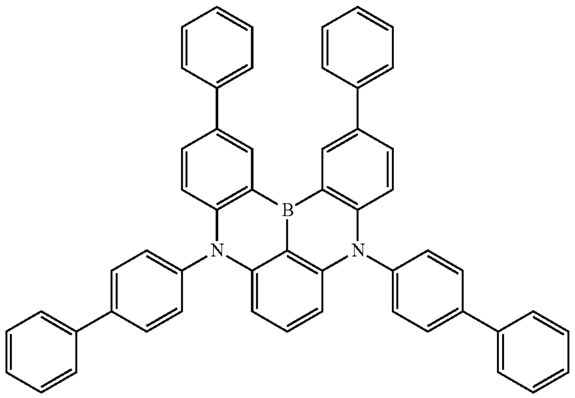
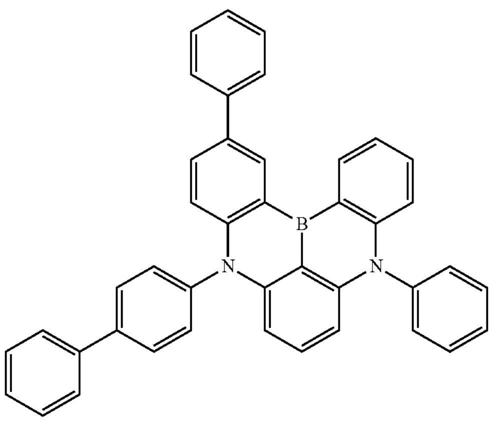
-continued
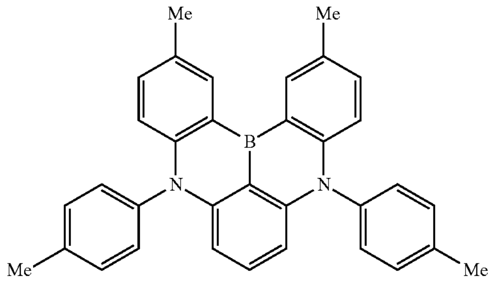
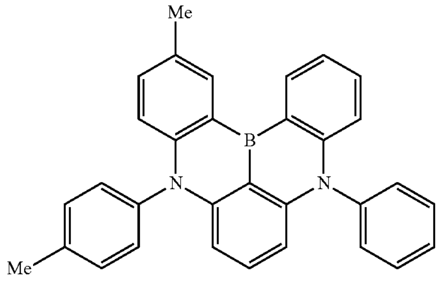
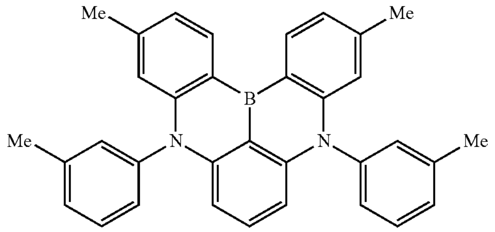
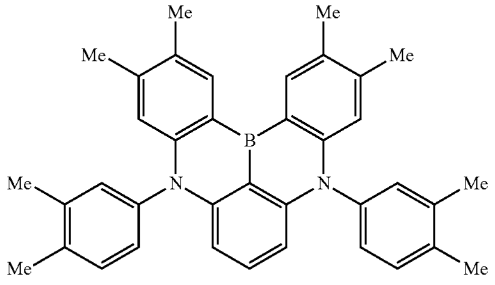
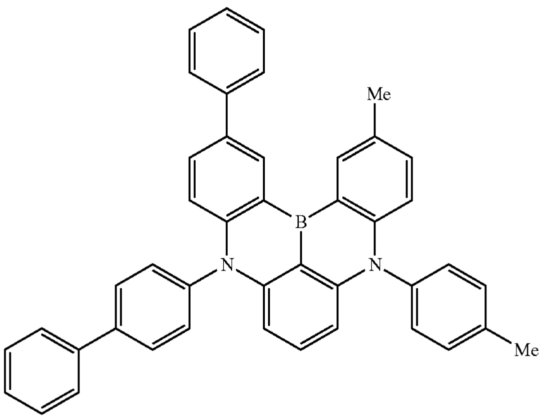

-continued
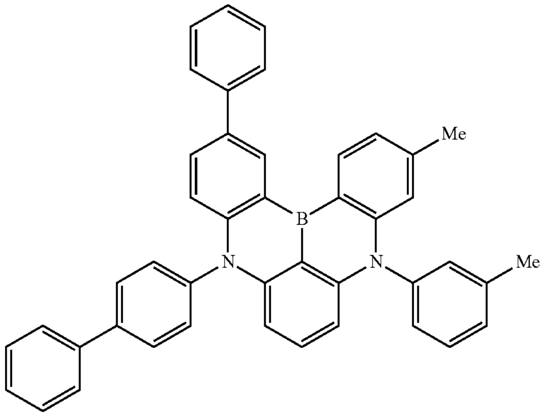
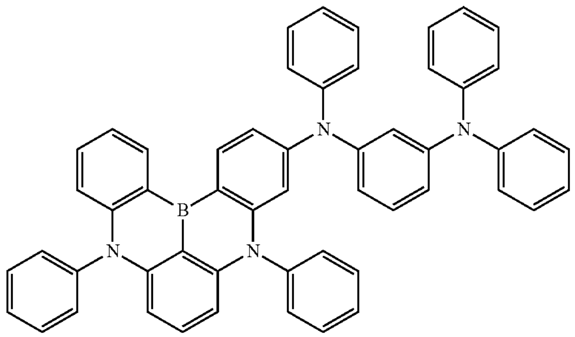
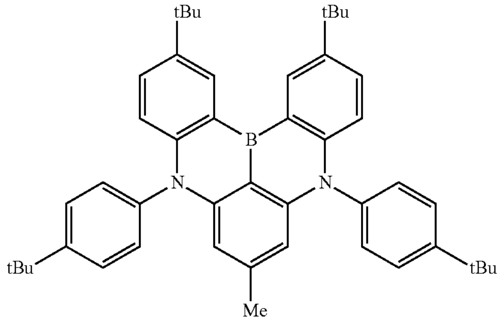
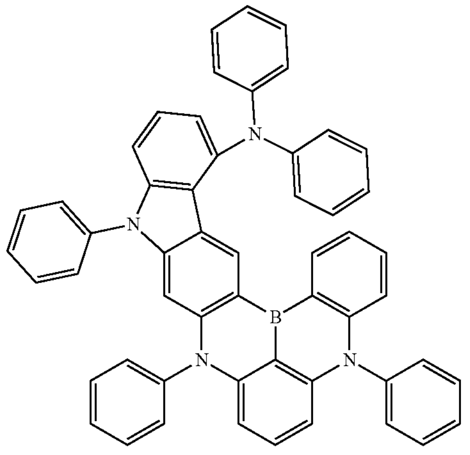
-continued
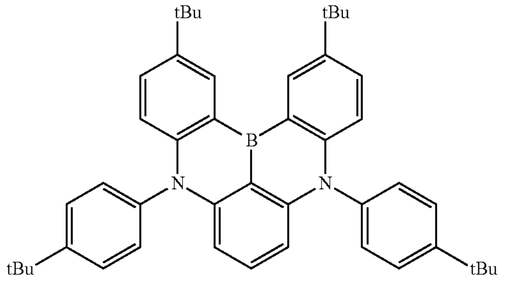
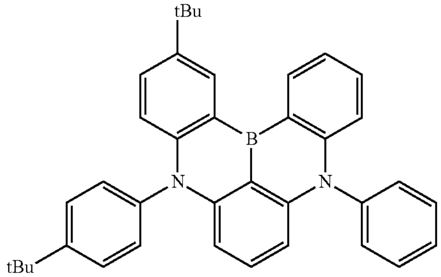
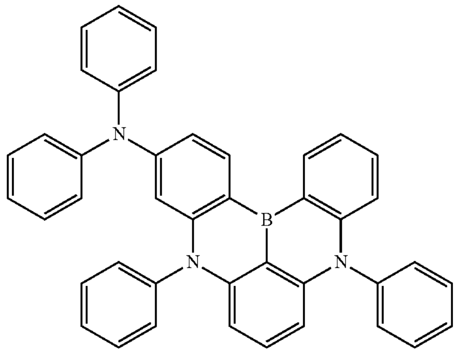
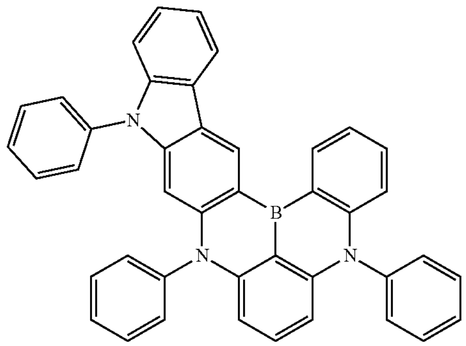
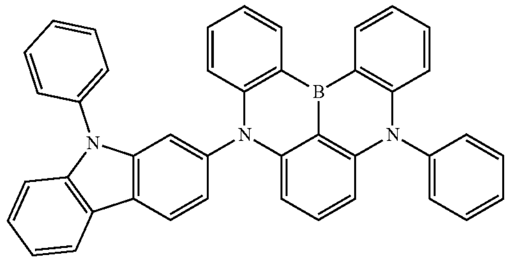

-continued
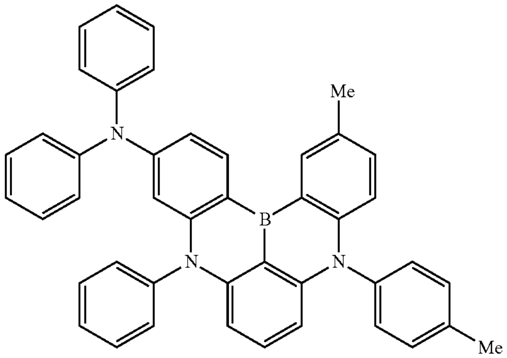
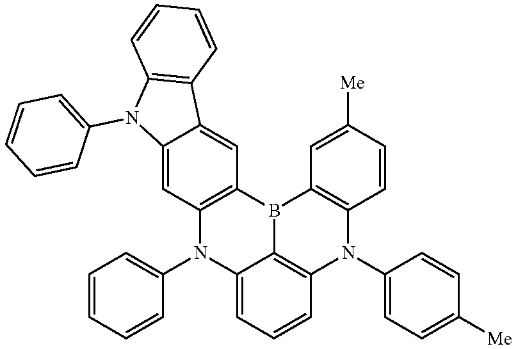
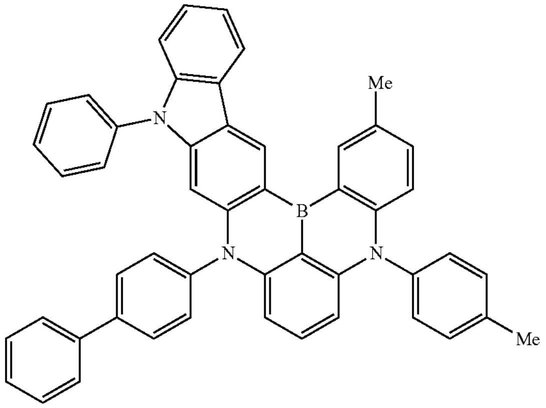
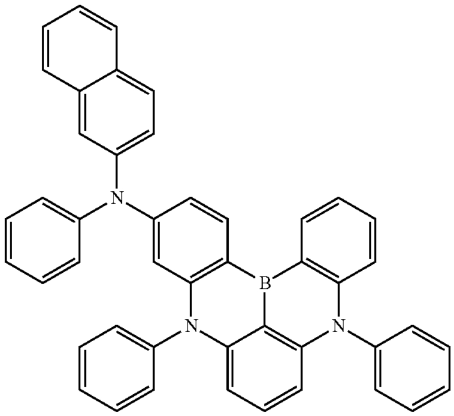
-continued
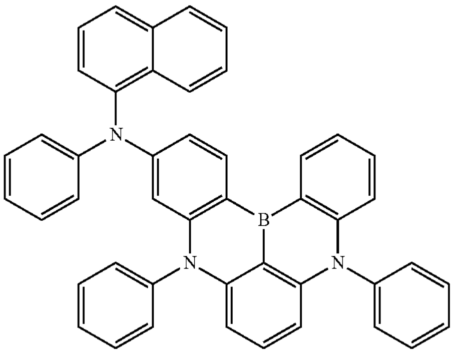
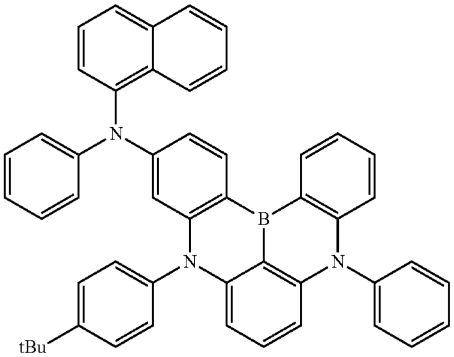
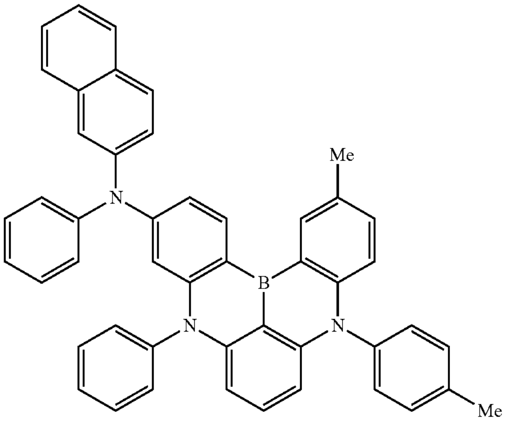
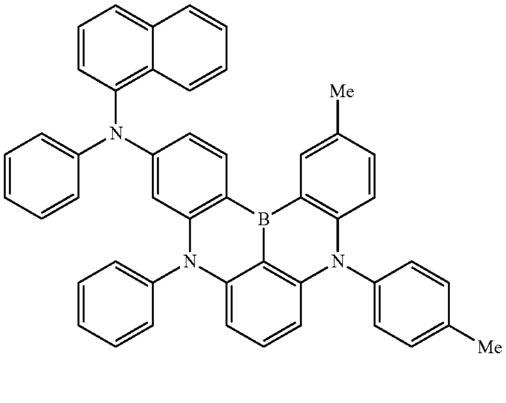

-continued
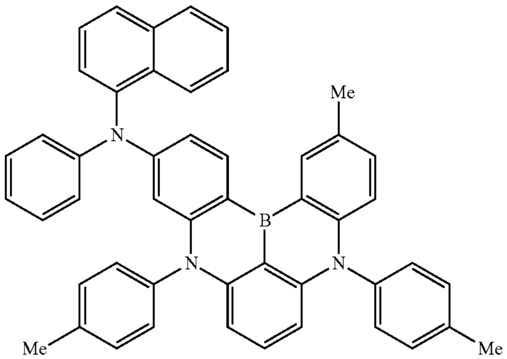 [SMILES: Cc1ccc(N2c3ccc(C)cc3B3c4ccc(N(c5ccccc5)c5cccc6ccccc56)cc4N(c4ccc(C)cc4)c4cccc2c43)cc1]
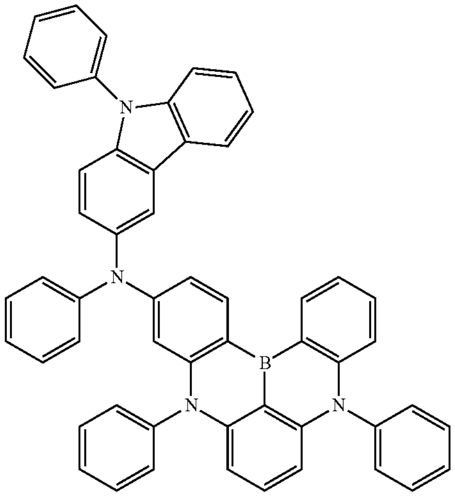
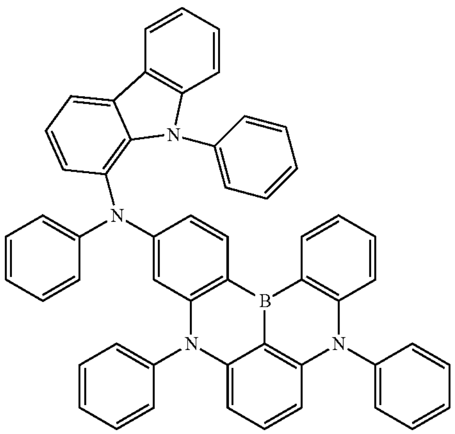
-continued
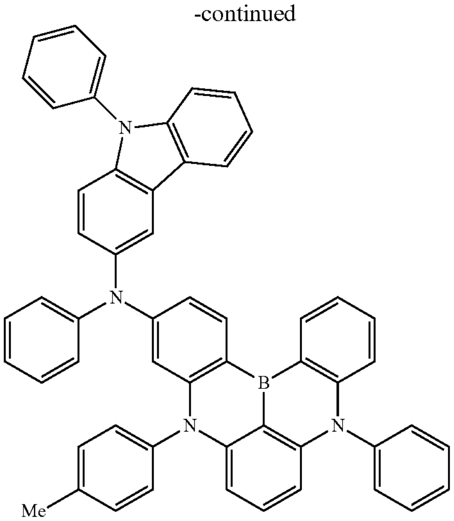
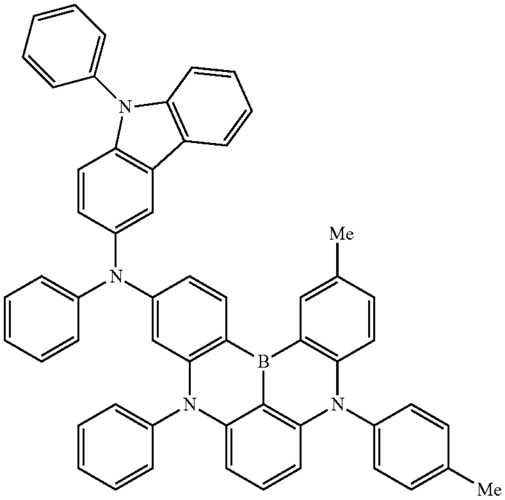
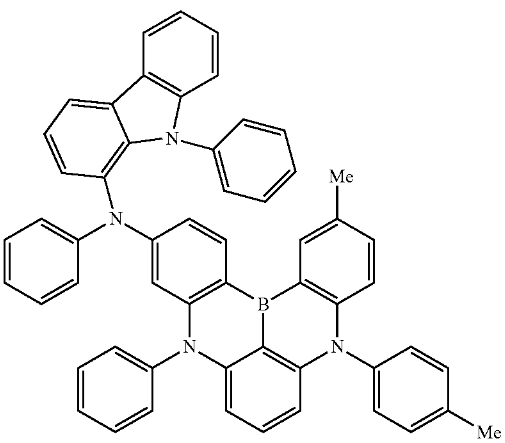

-continued
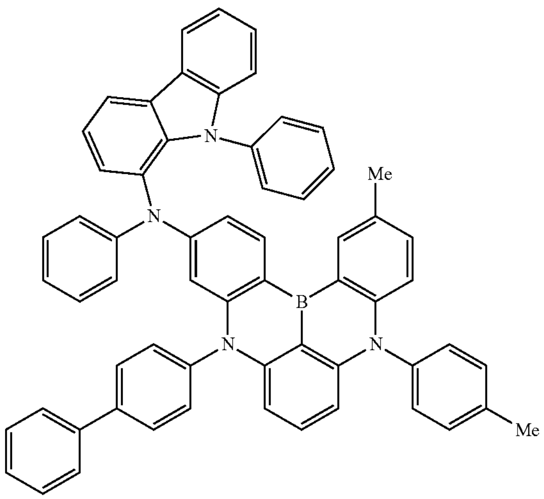
-continued
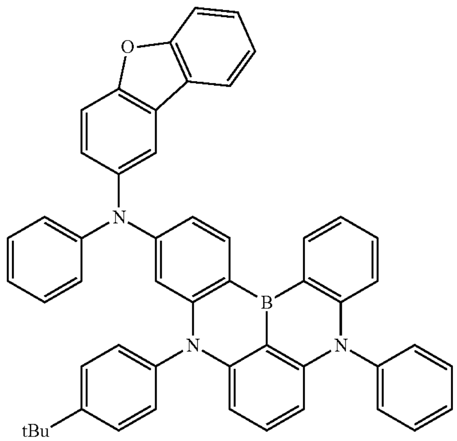
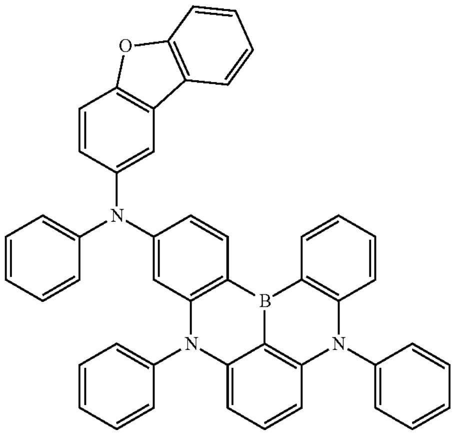
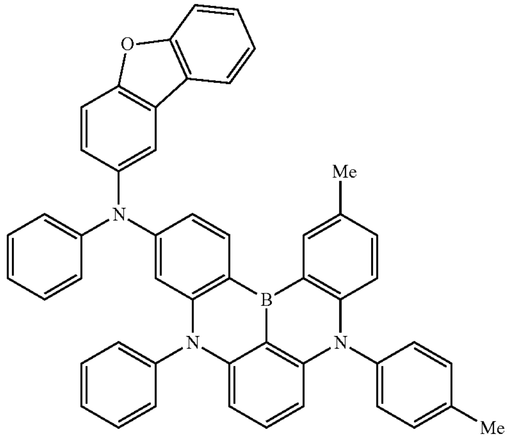
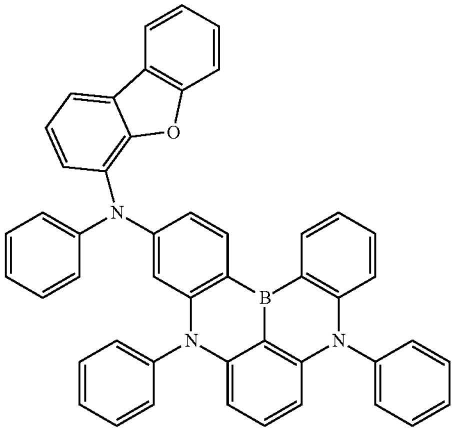
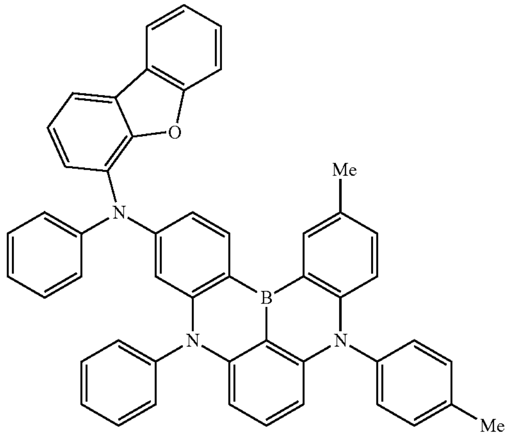

-continued
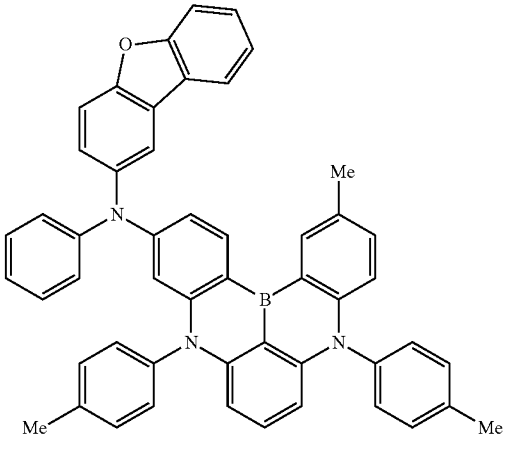
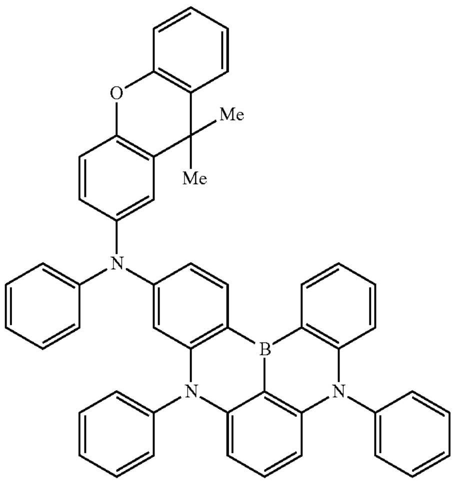
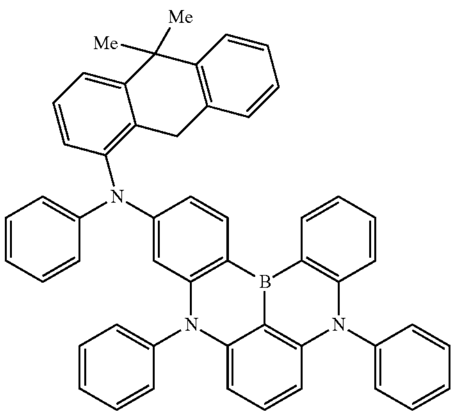
-continued
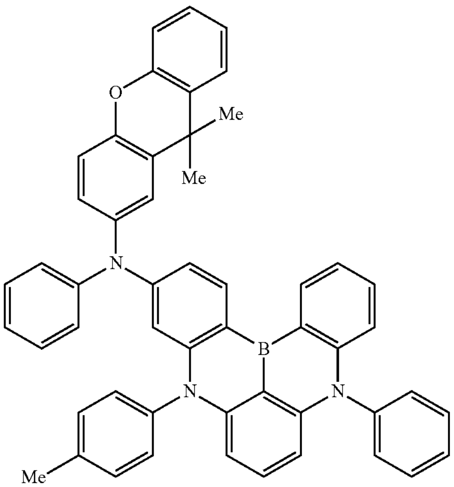
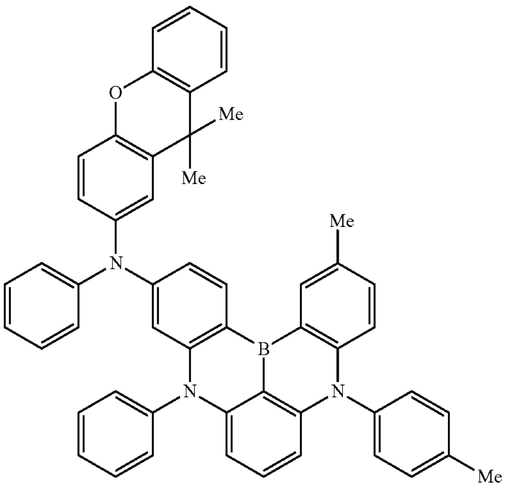
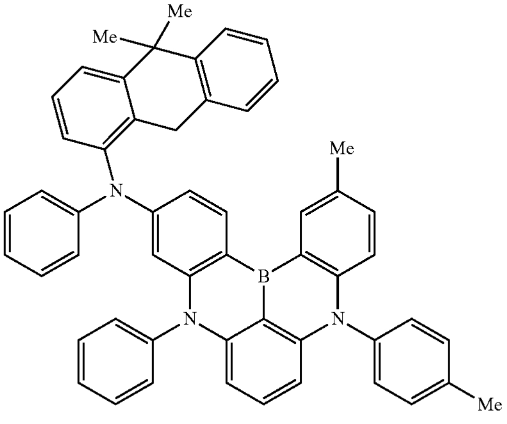

-continued
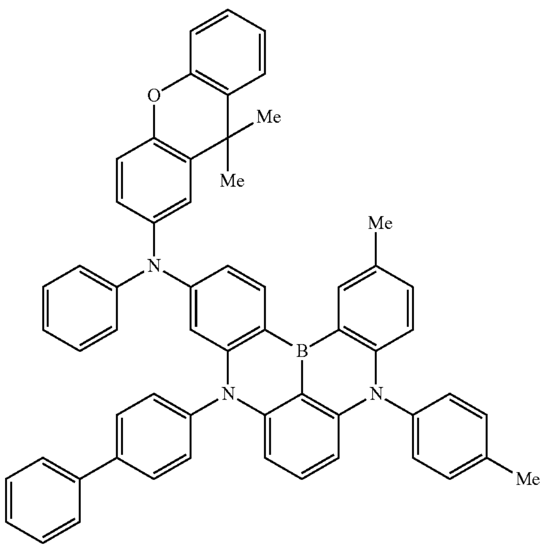
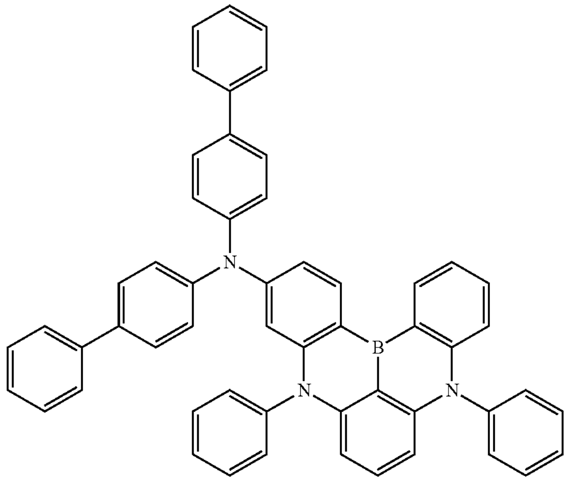
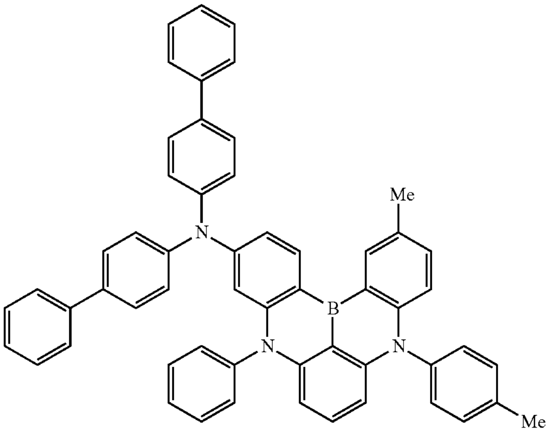
-continued
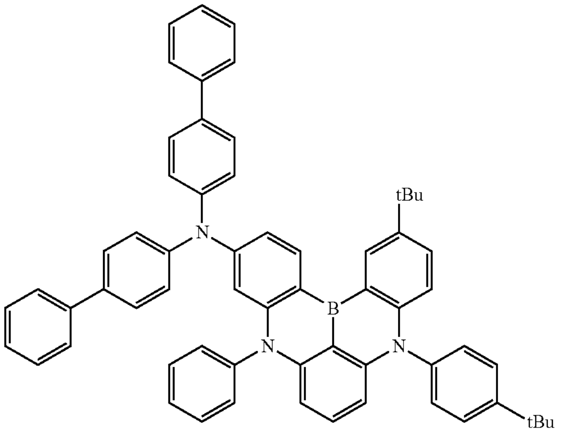
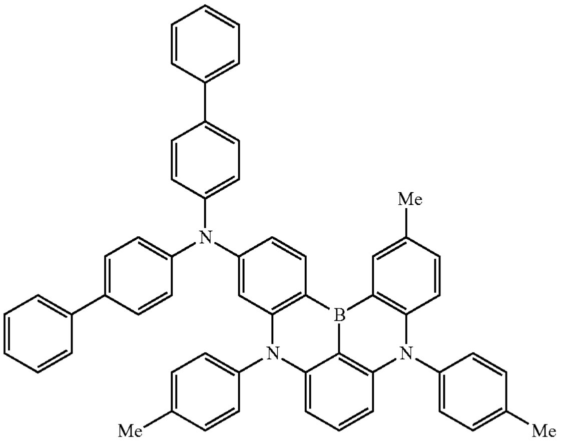
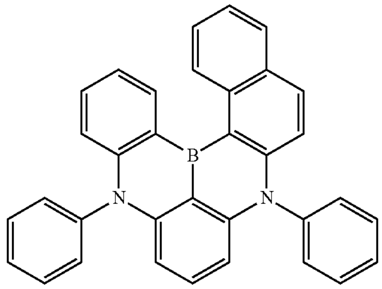
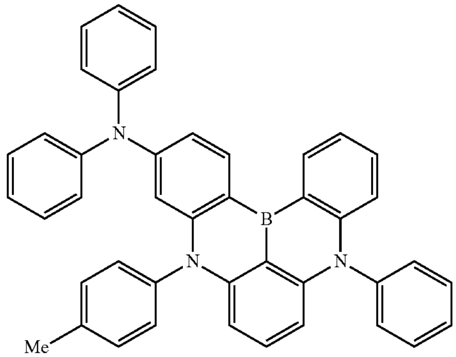

-continued
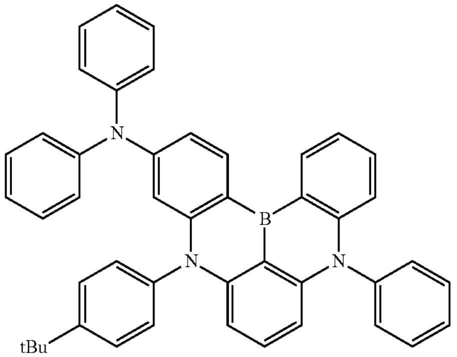
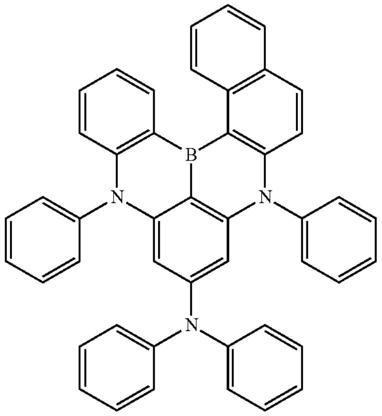
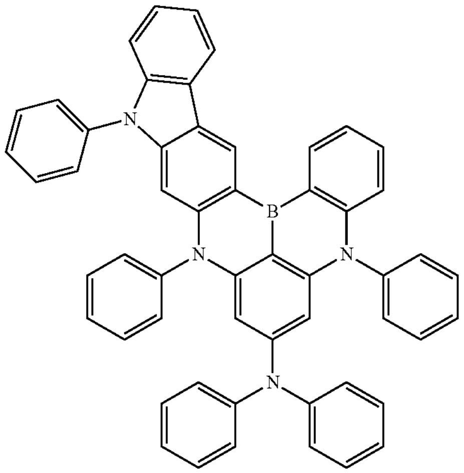
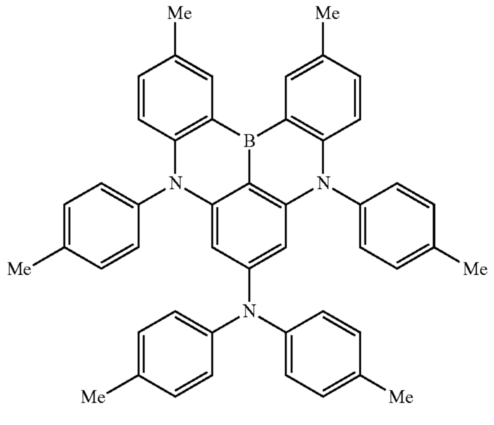
-continued
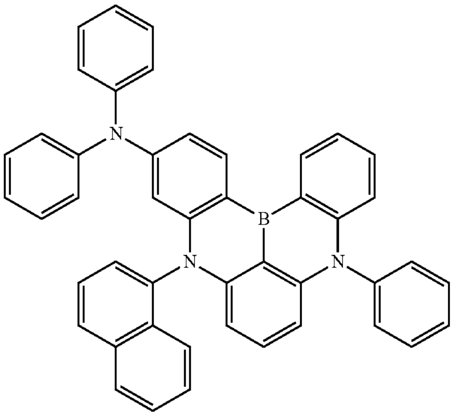
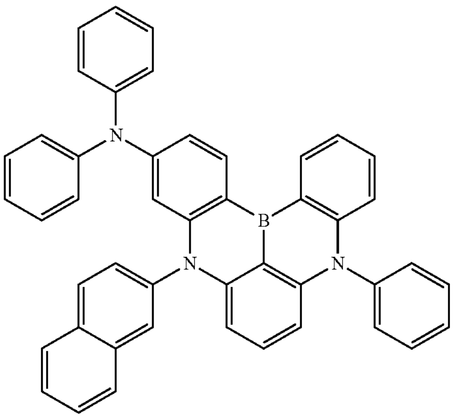
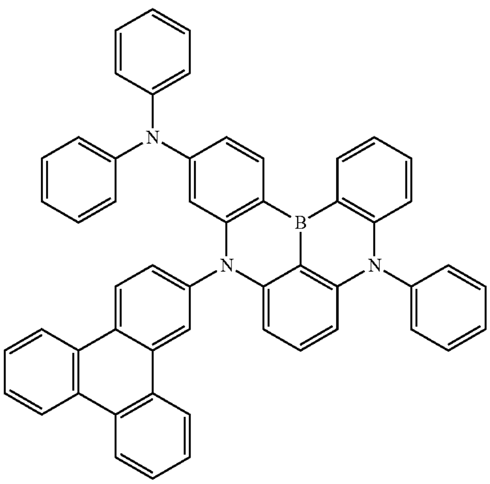

-continued
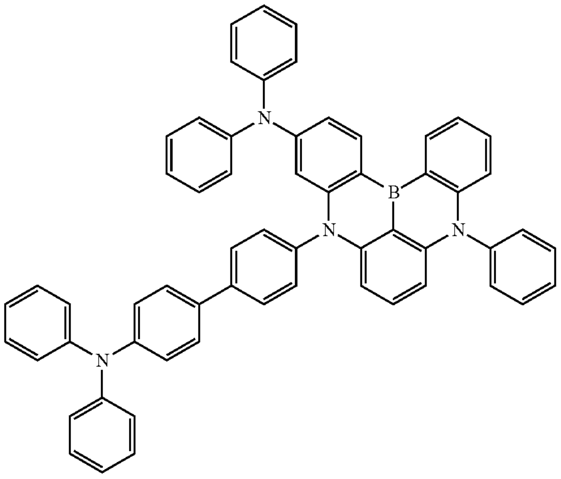
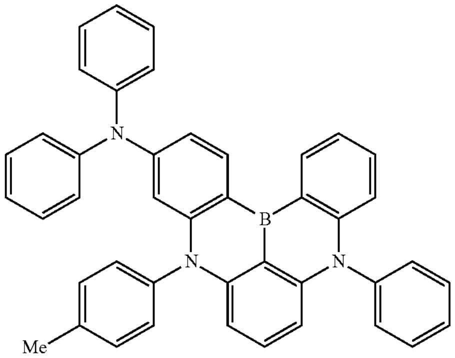
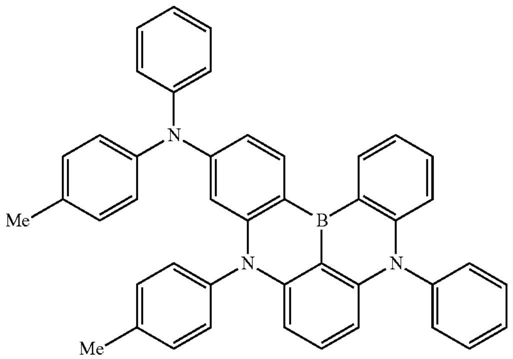
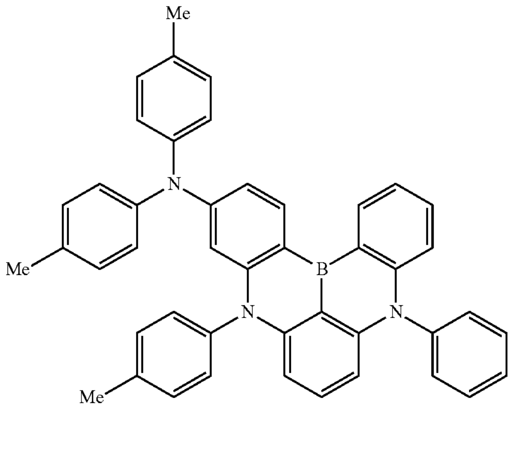
-continued
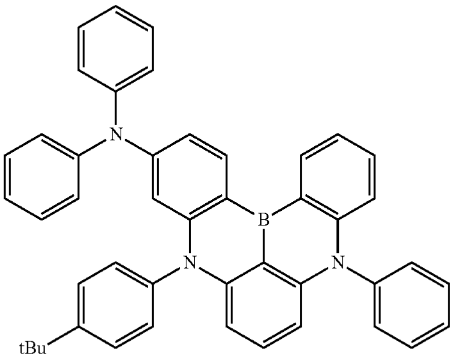
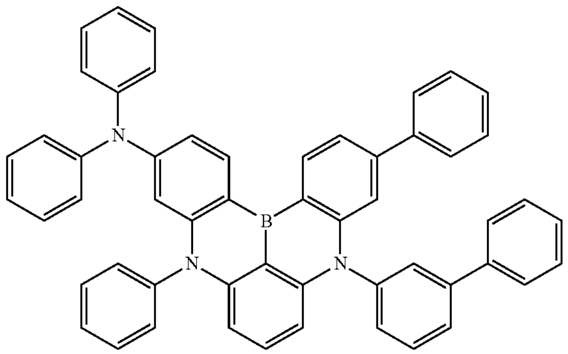
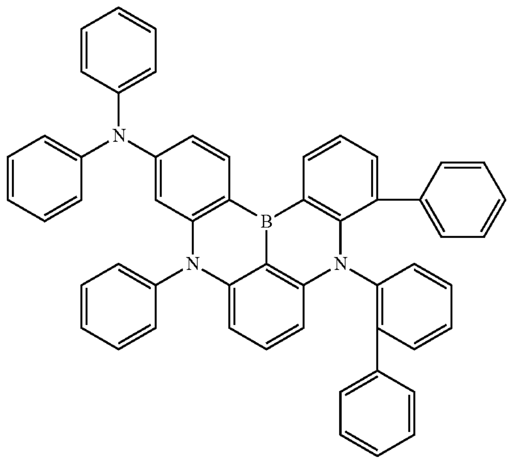
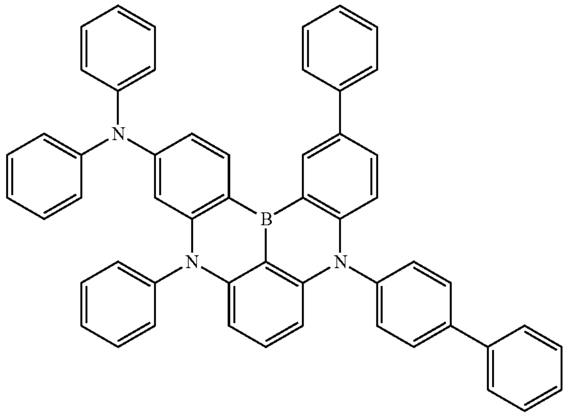

-continued
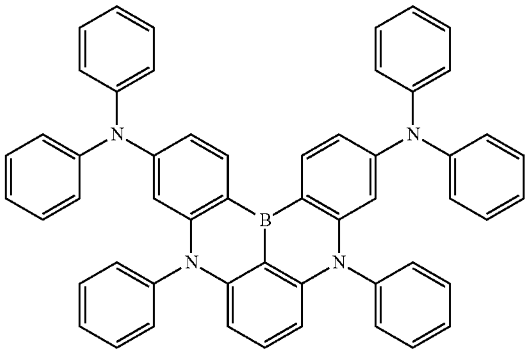
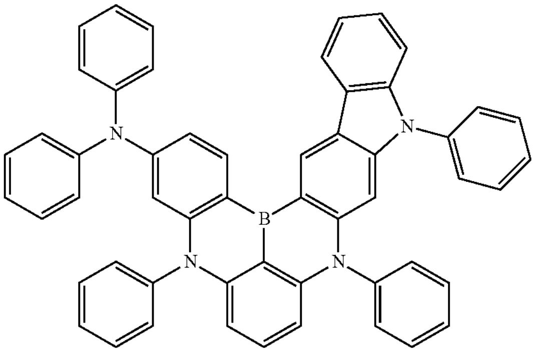
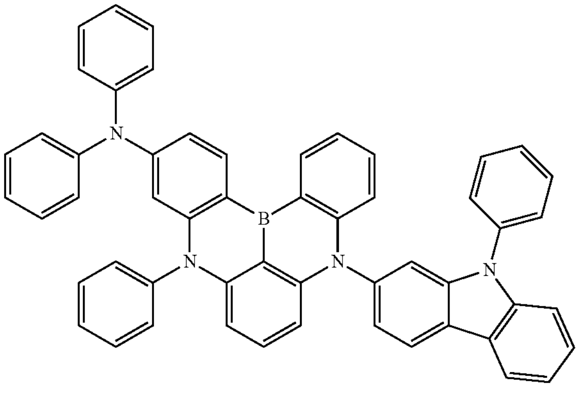
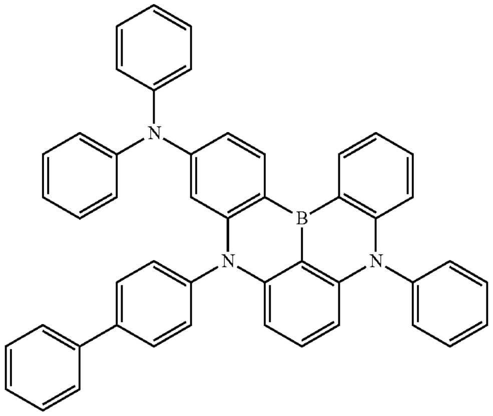
-continued
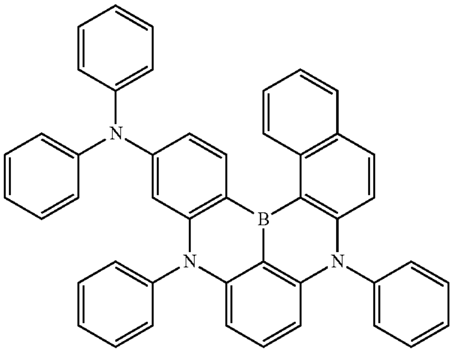
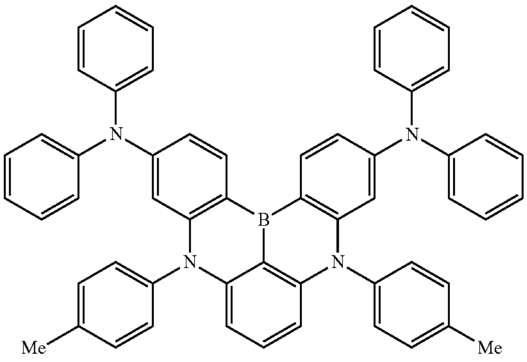
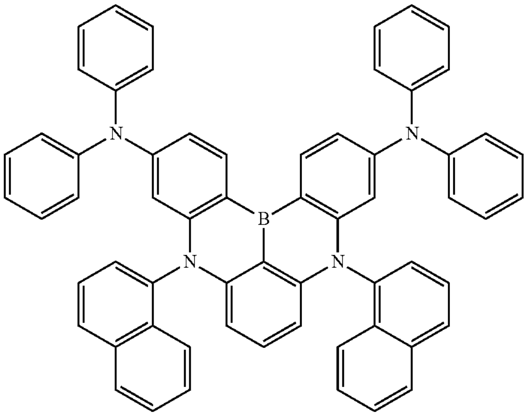
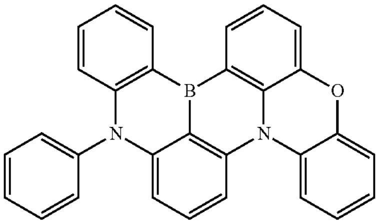
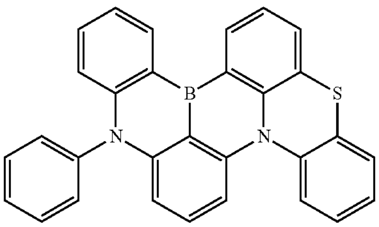

-continued
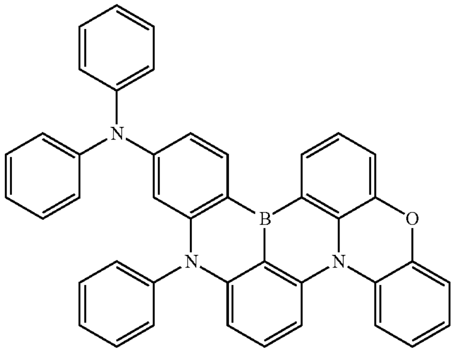
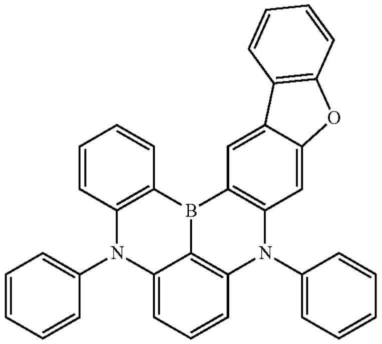
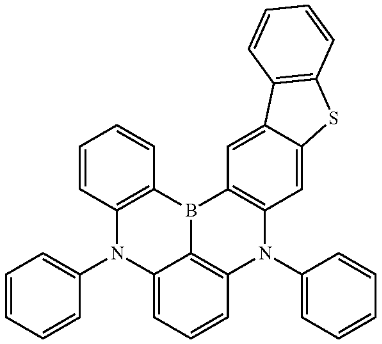
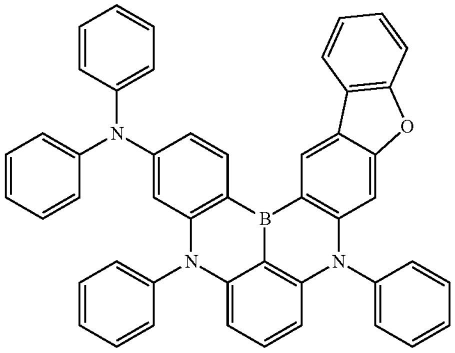
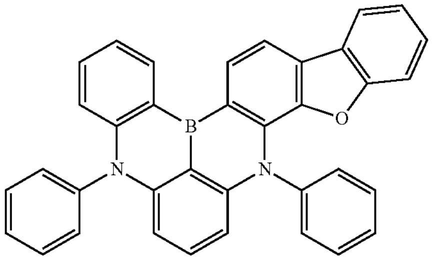
-continued
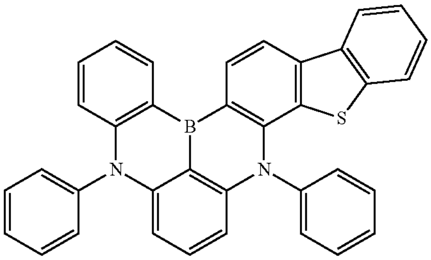
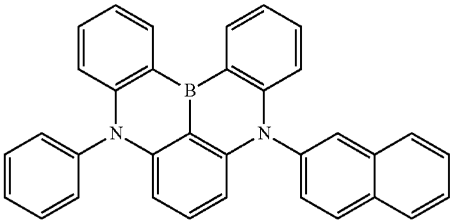
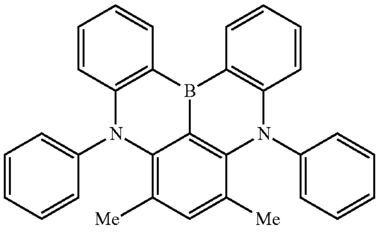
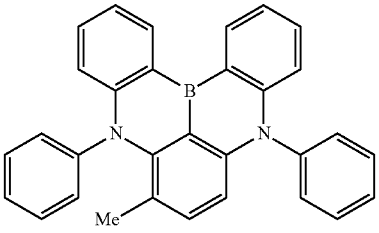
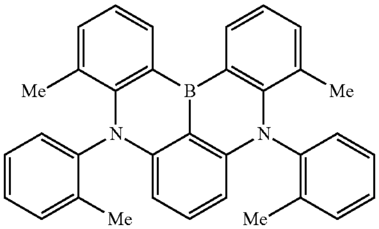
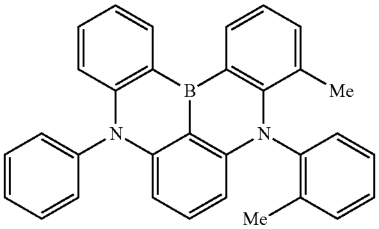
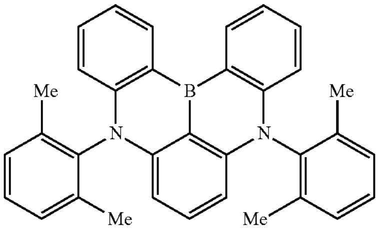

-continued
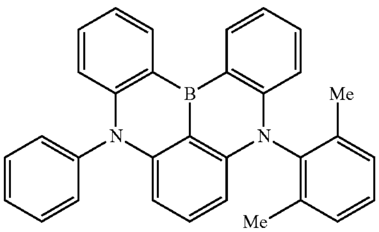
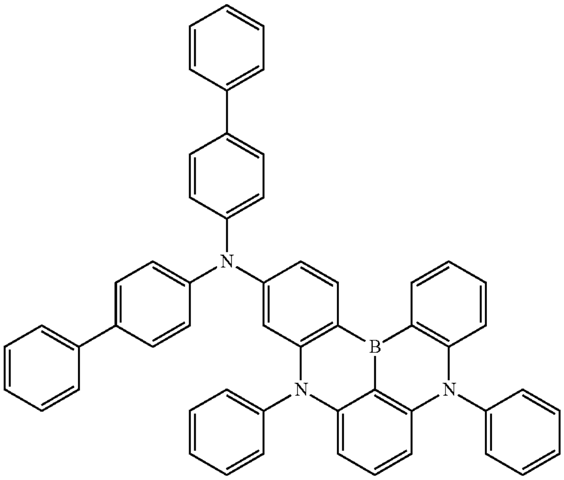
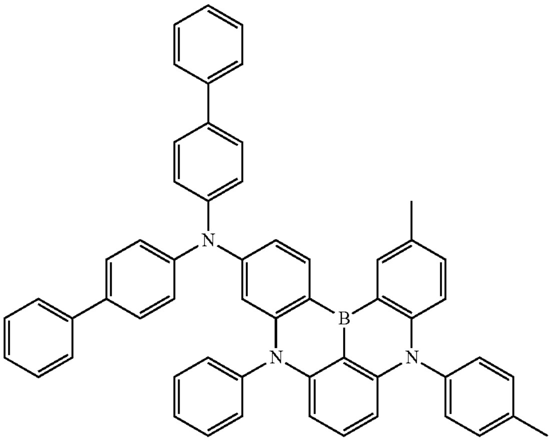
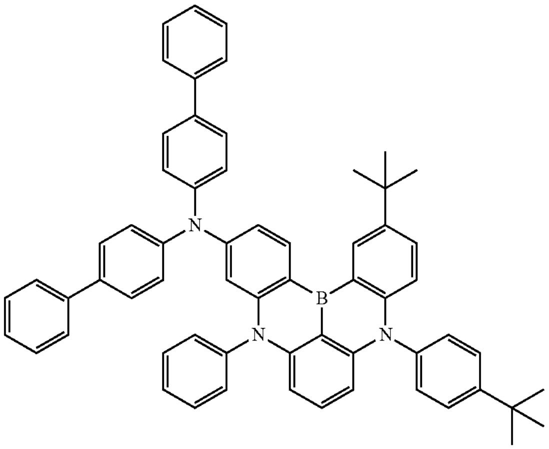
-continued
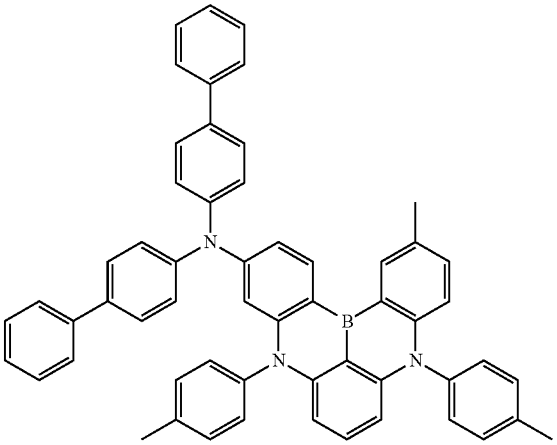
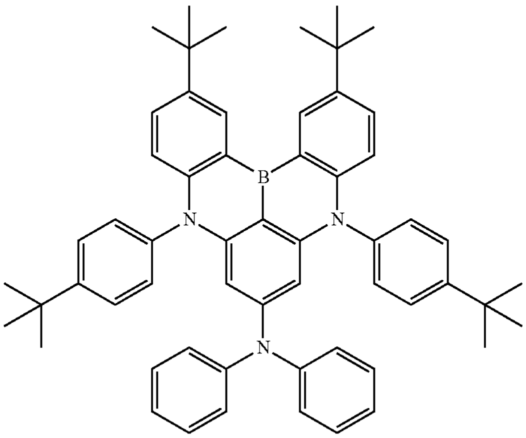
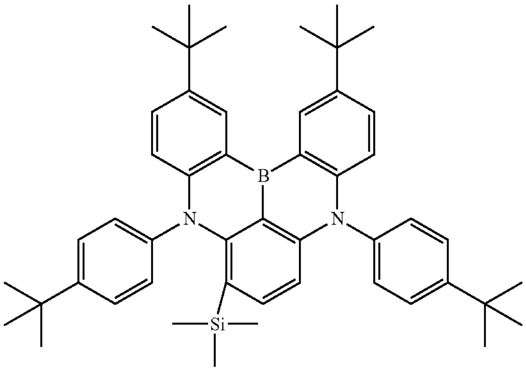
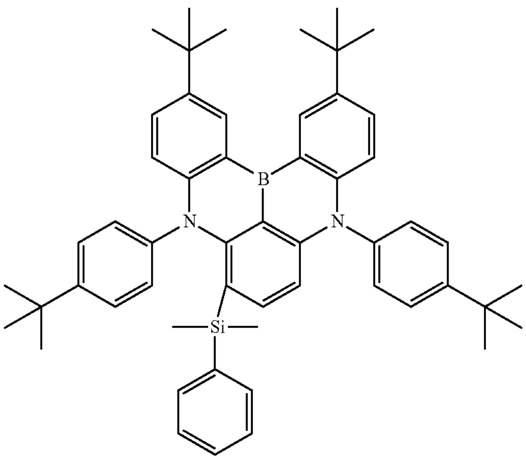

-continued
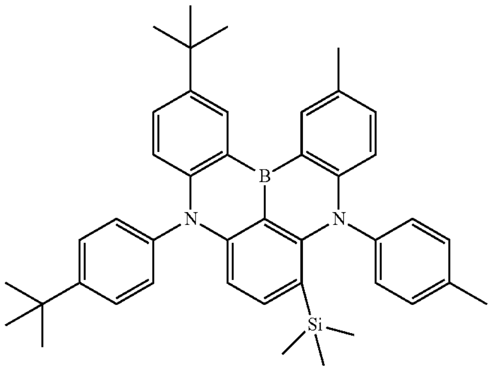
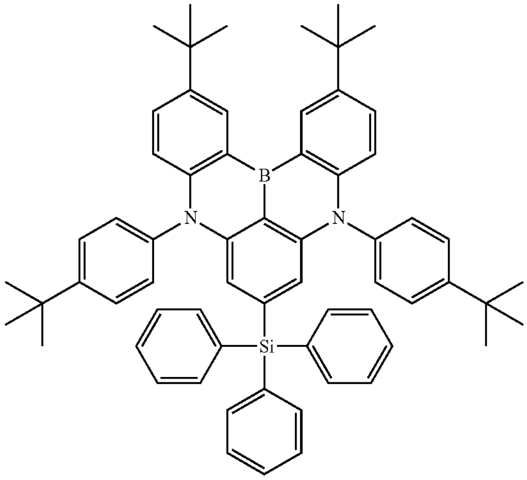
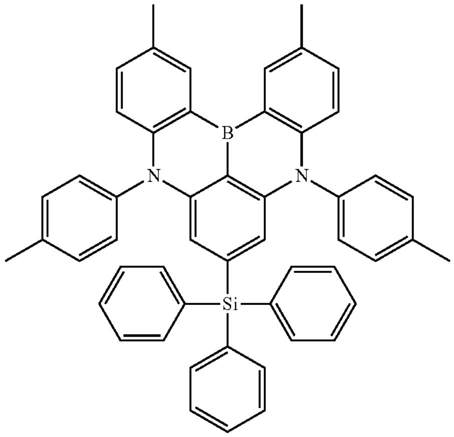
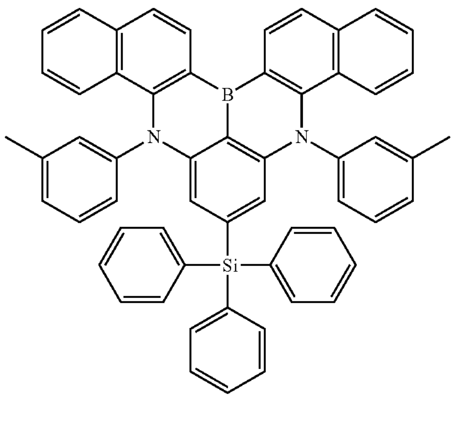
-continued
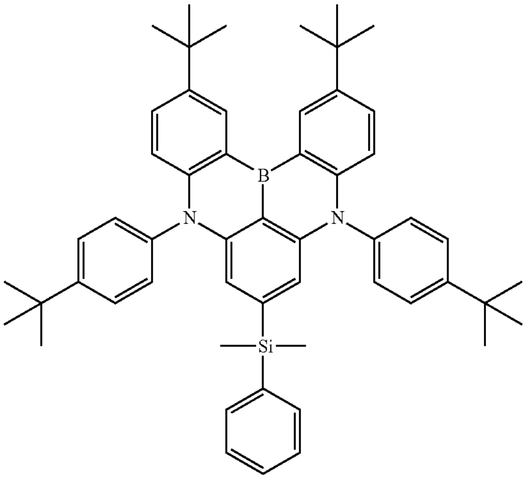
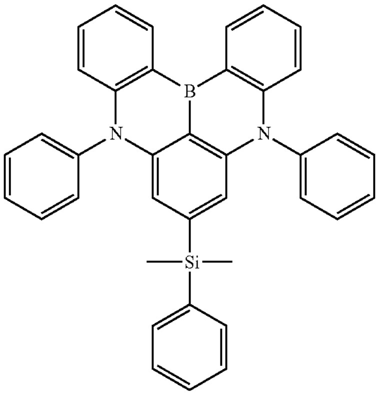
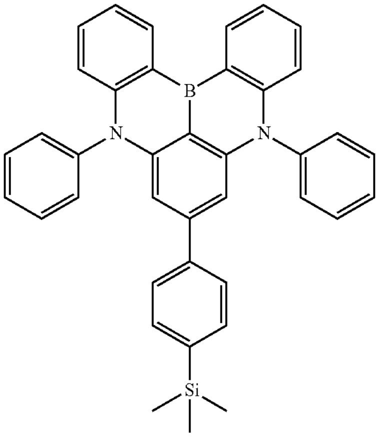
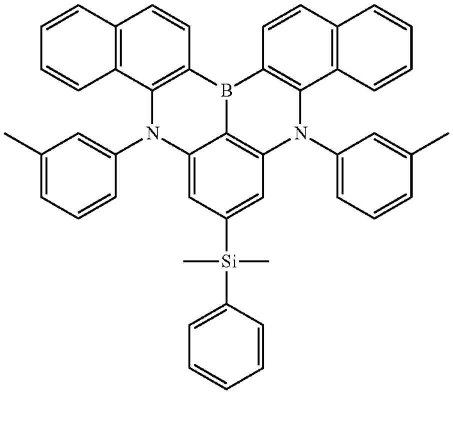

-continued
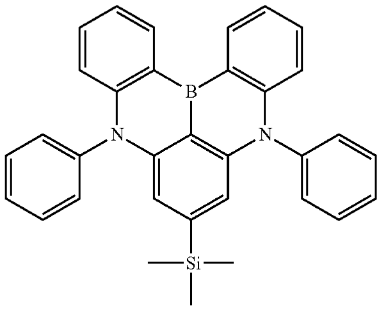
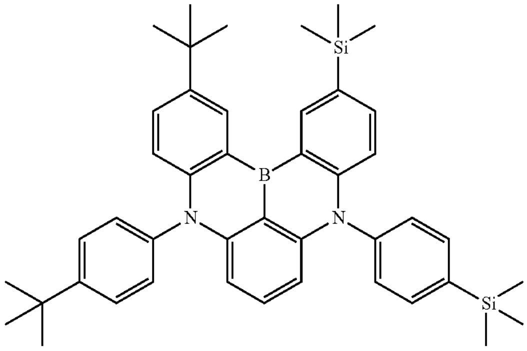
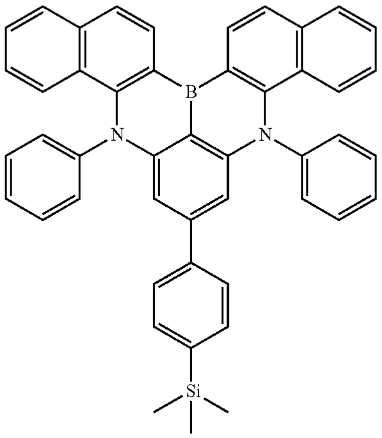
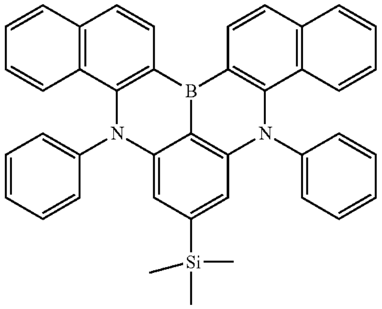
-continued
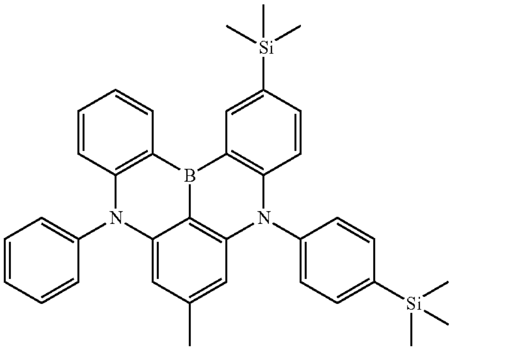
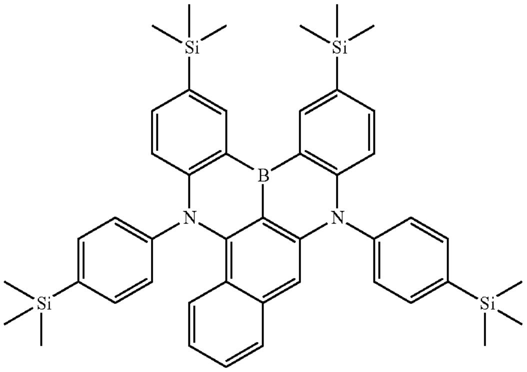
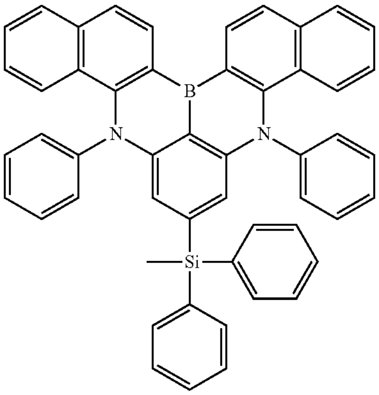
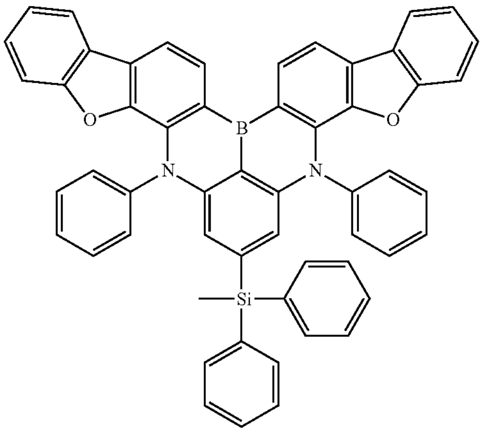

-continued
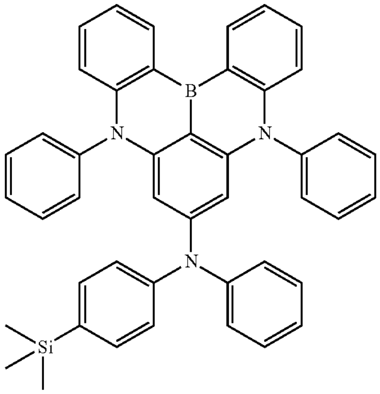
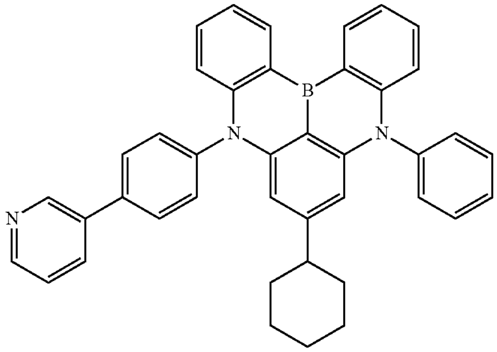
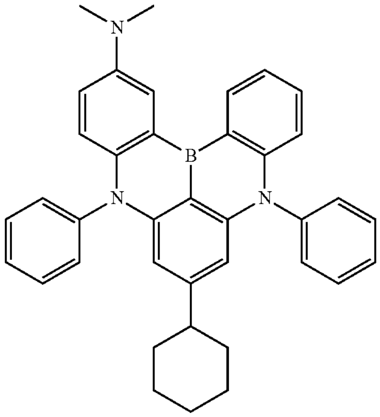
-continued
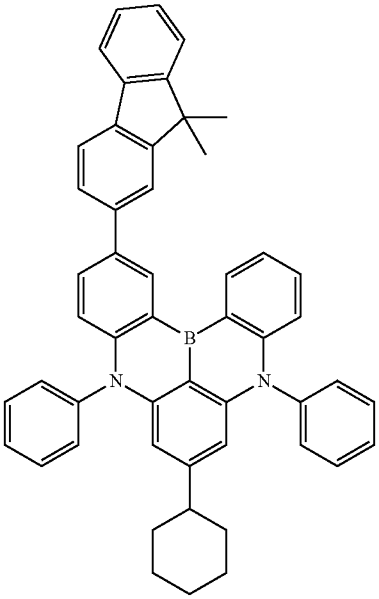
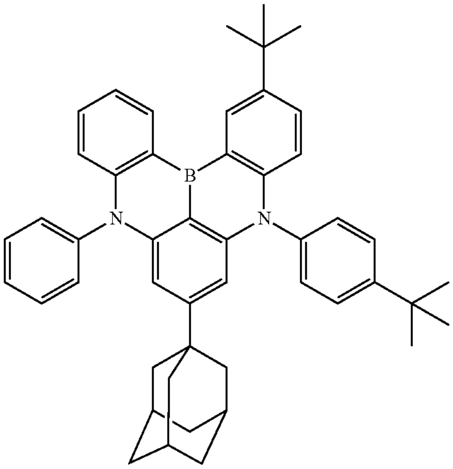
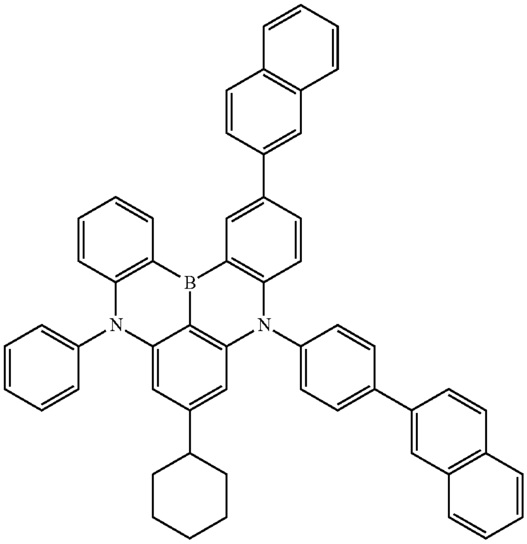

-continued
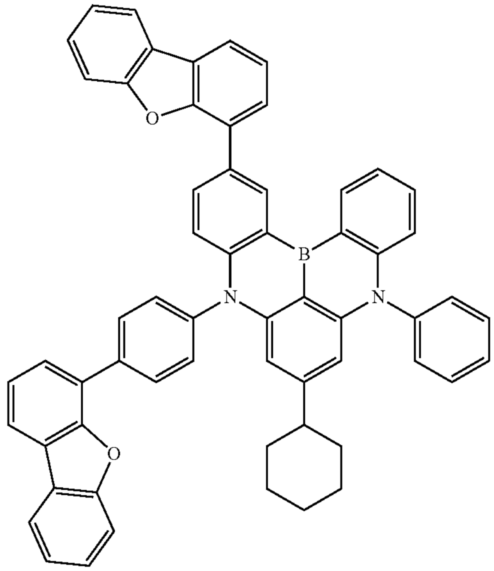
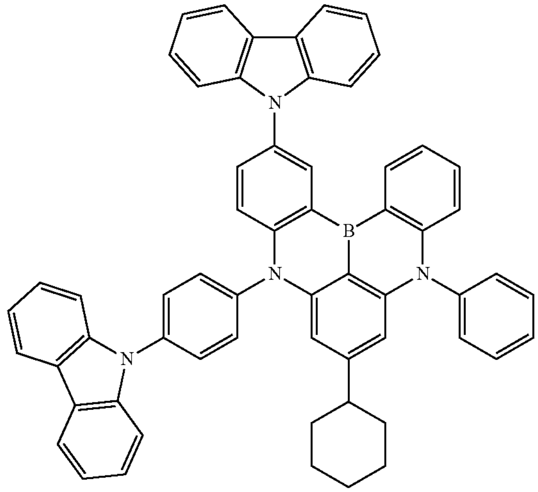
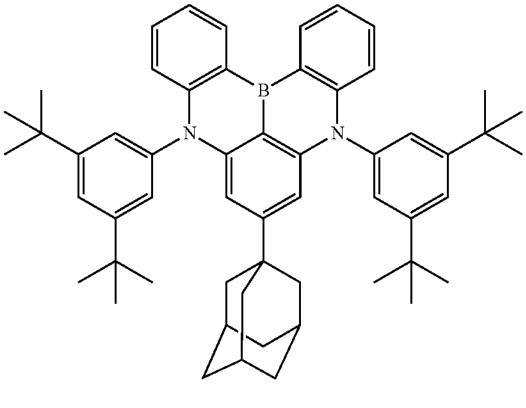
-continued
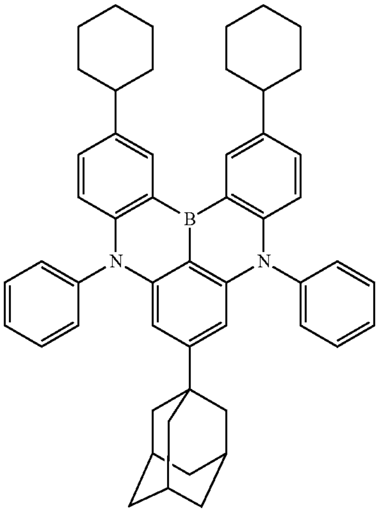
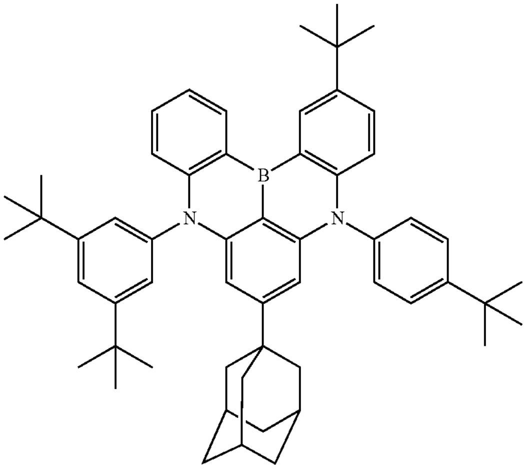
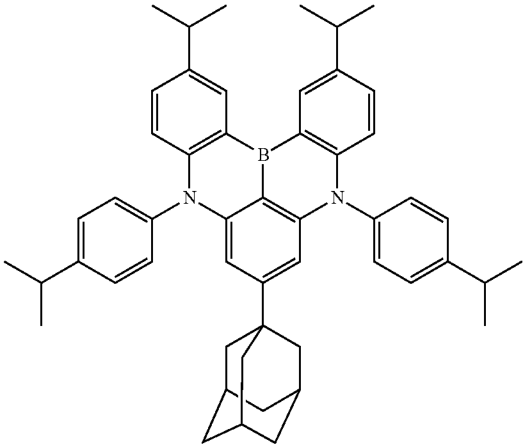

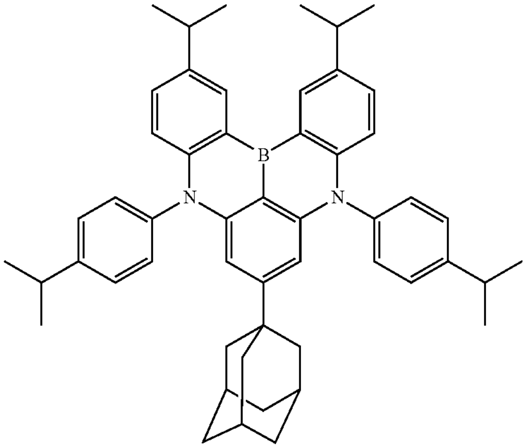
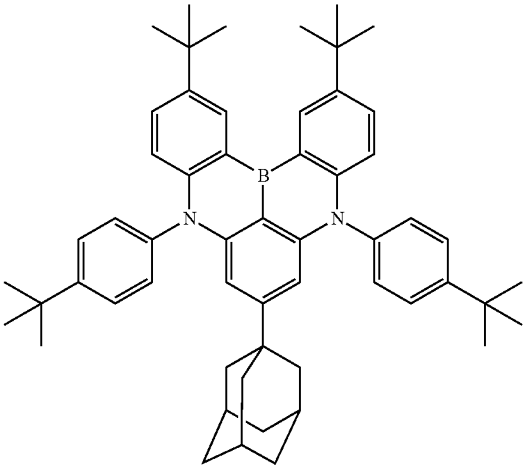
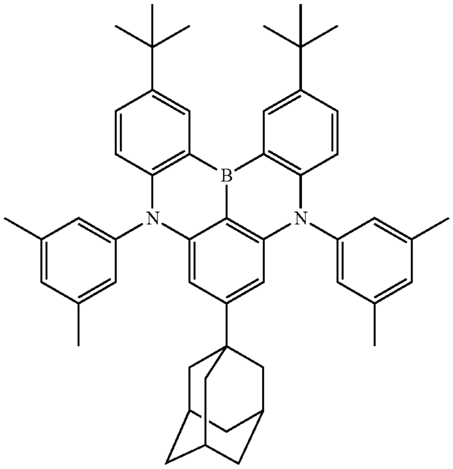
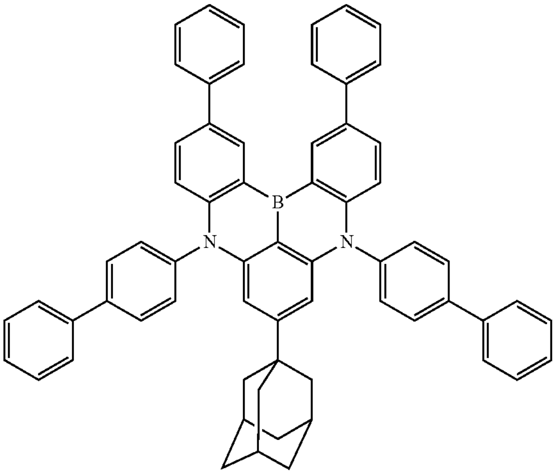
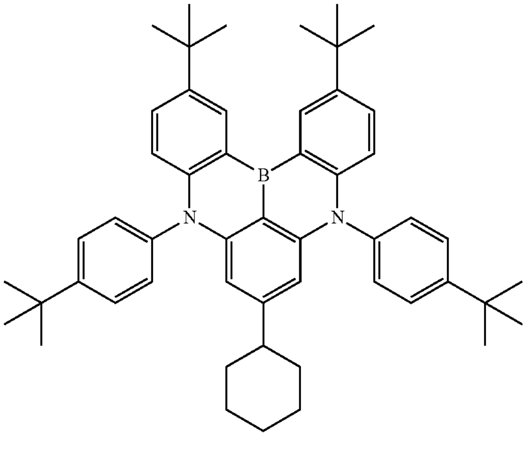
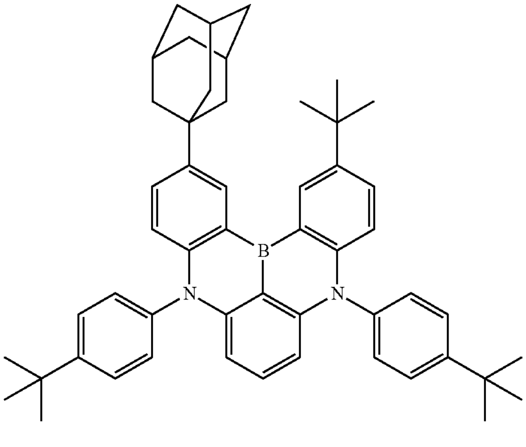

-continued
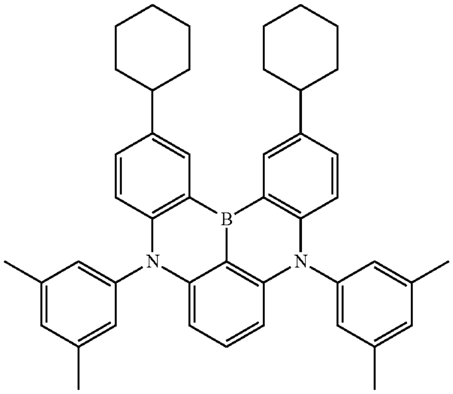
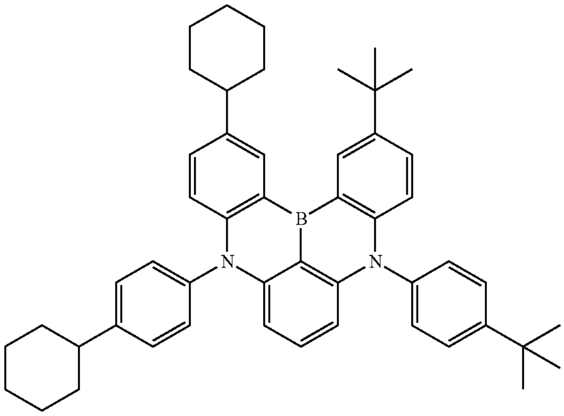
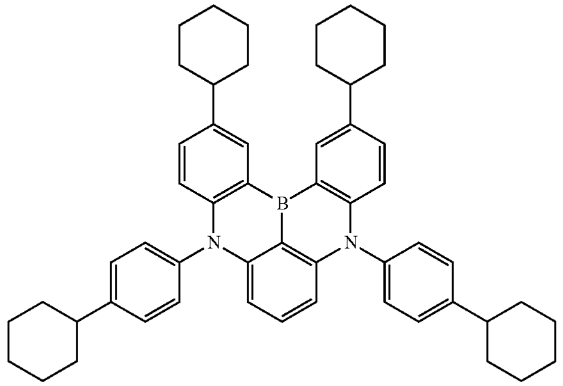
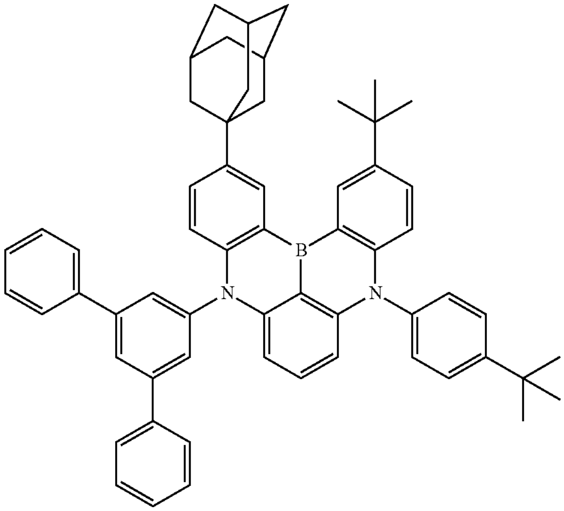
-continued
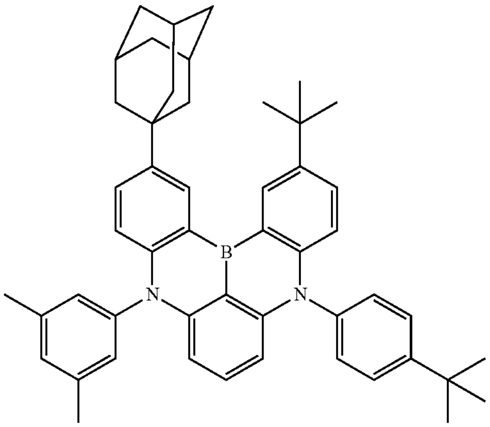
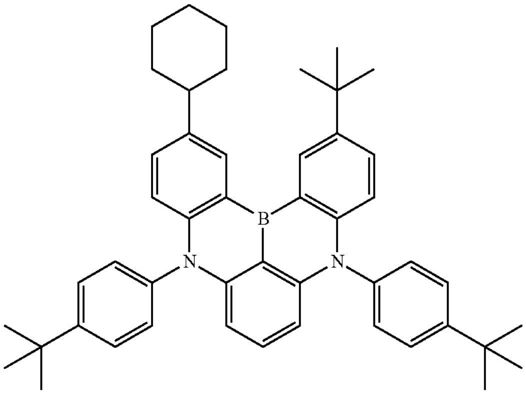
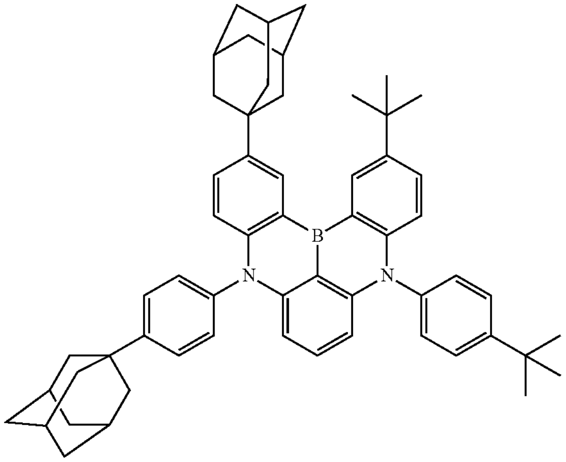
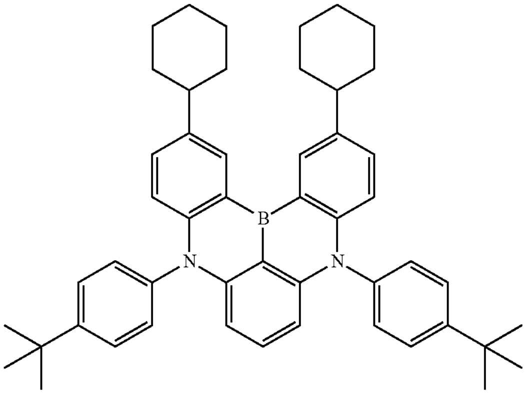

-continued
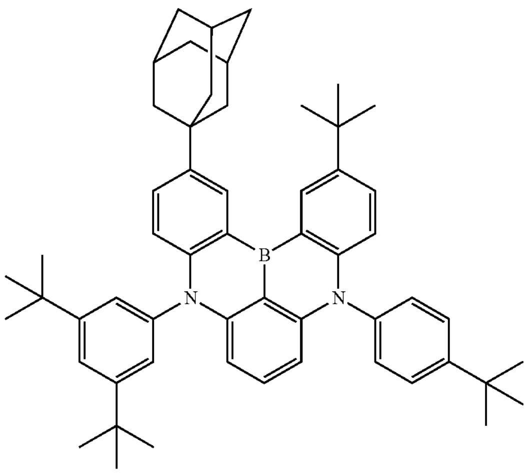
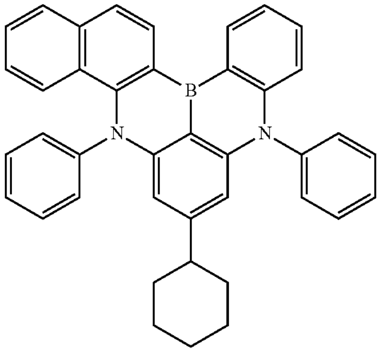
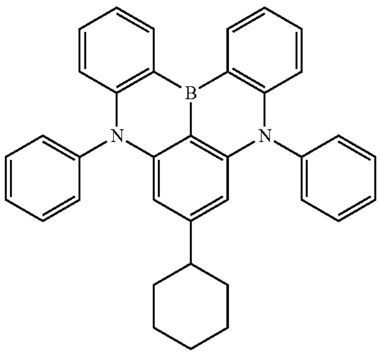
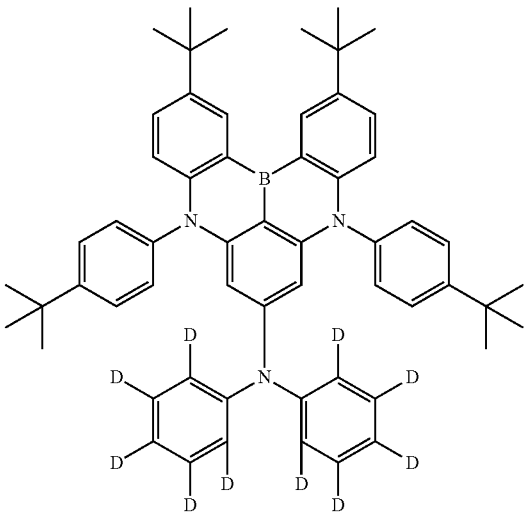
-continued
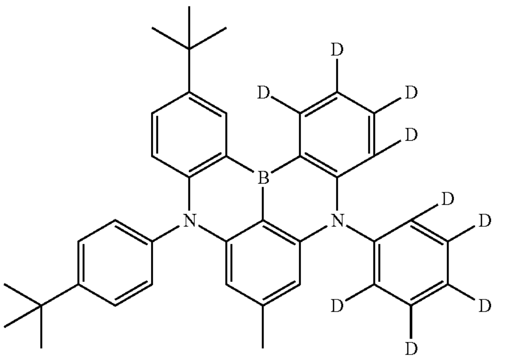
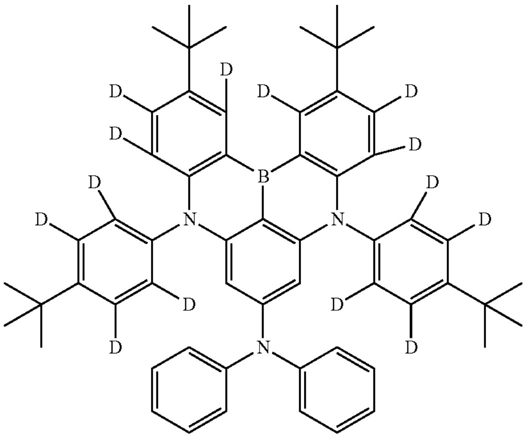
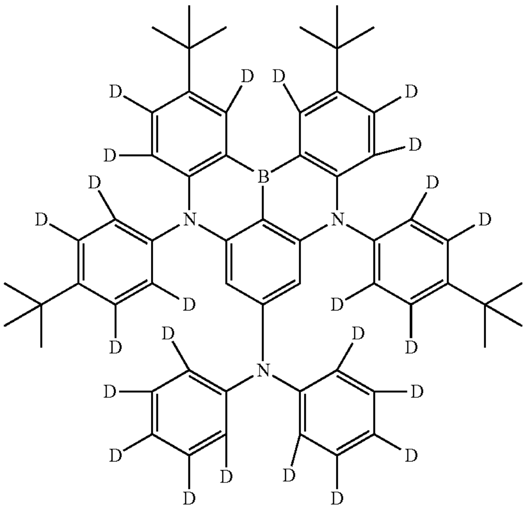
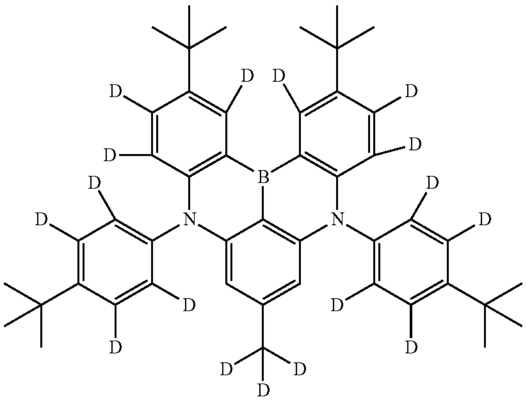

-continued
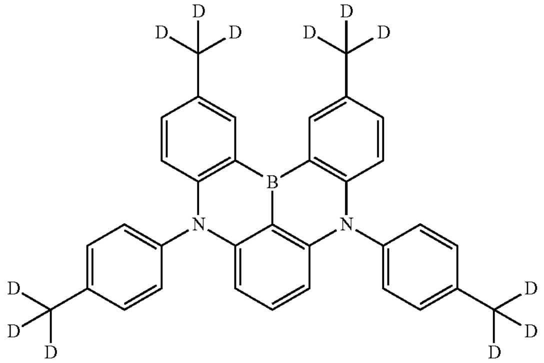
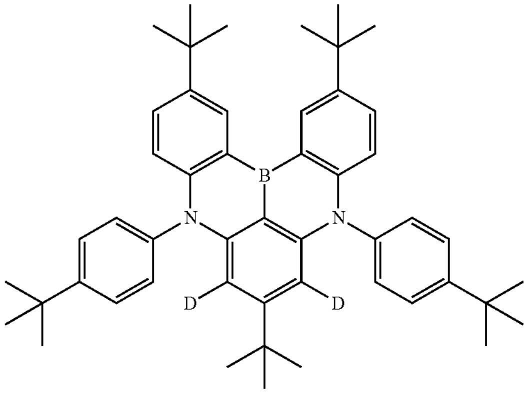
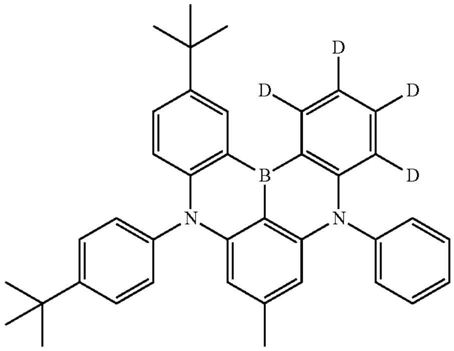
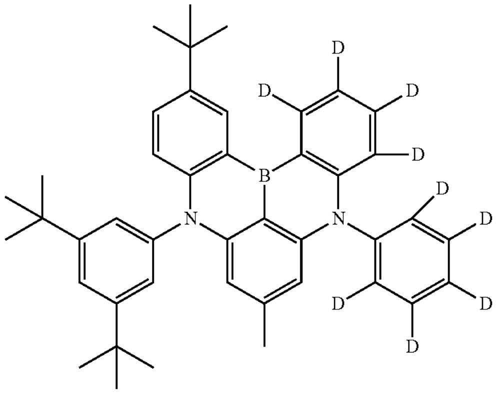
-continued
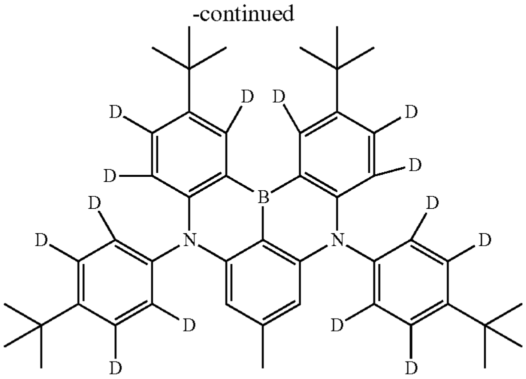
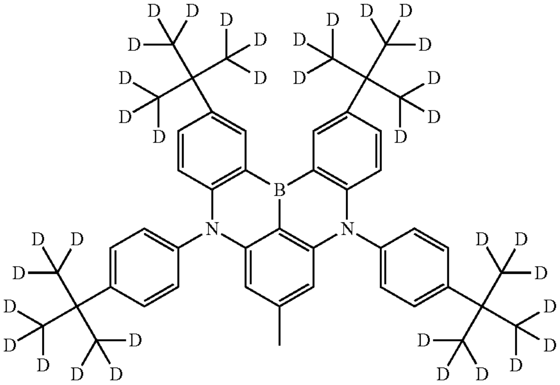
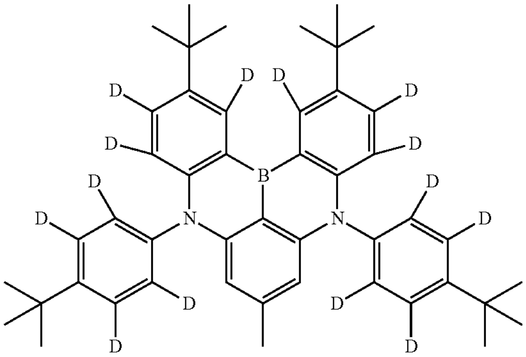 [SMILES: [2H]c1c([2H])c(C(C)(C)C)c([2H])c([2H])c1N1c2cc(C)cc3c2B(c2c([2H])c(C(C)(C)C)c([2H])c([2H])c21)c1c([2H])c(C(C)(C)C)c([2H])c([2H])c1N3c1c([2H])c([2H])c(C(C)(C)C)c([2H])c1[2H]]
(Compound Represented by Formula (51))
The compound represented by the formula (51) is explained below.
(51)
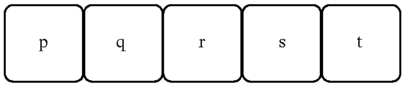
(52)
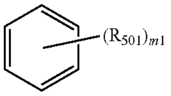
(53)
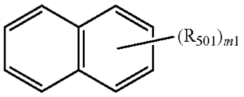
(54)
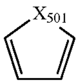

-continued (55)

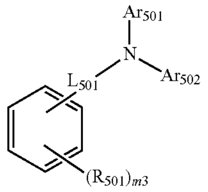

(56)

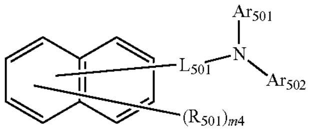

In the formula (51), r ring is a ring represented by the formula (52) or formula (53) which is fused to an adjacent ring at an arbitrary position;

q ring and s ring are independently a ring represented by the formula (54) which is fused to an adjacent ring at an arbitrary position;

p ring and t ring are independently a ring represented by the formula (55) or the formula (56) which is fused to an adjacent ring at an arbitrary position;

when a plurality of $R_{501}$s exist, adjacent $R_{501}$s are bonded with each other to form a substituted or unsubstituted, saturated or unsaturated ring, or do not form a substituted or unsubstituted, saturated or unsaturated ring;

$X_{501}$ is an oxygen atom, a sulfur atom, or $NR_{502}$;

$R_{501}$ and $R_{502}$ that do not form the substituted or unsubstituted saturated or unsaturated ring are a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

$Ar_{501}$ and $Ar_{502}$ are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

$L_{501}$ is a substituted or unsubstituted alkylene group having 1 to 50 carbon atoms, a substituted or unsubstituted alkenylene group having 2 to 50 carbon atoms, a substituted or unsubstituted alkynylene group having 2 to 50 carbon atoms, a substituted or unsubstituted cycloalkylene group having 3 to 50 ring carbon atoms, a substituted or unsubstituted arylene group having 6 to 50 ring carbon atoms, or a substituted or unsubstituted divalent heterocyclic group having 5 to 50 ring atoms;

m1 is independently an integer of 0 to 2, m2 is independently an integer of 0 to 4, m3s are independently an integer of 0 to 3, and m4s are independently an integer of 0 to 5; when a plurality of $R_{501}$s exist, $R_{501}$s may be the same or different.

In the formula (51), each of the p ring to the t ring is fused to an adjacent ring by sharing two carbon atoms. The position and direction of fusing are not limited, and condensation is possible at any position and direction.

In one embodiment, in the formula (52) or (53) of the r ring, $R_{501}$ is a hydrogen atom.

In one embodiment, the compound represented by the formula (51) is represented by any one of the following formulas (51-1) to (51-6):

(51-1)

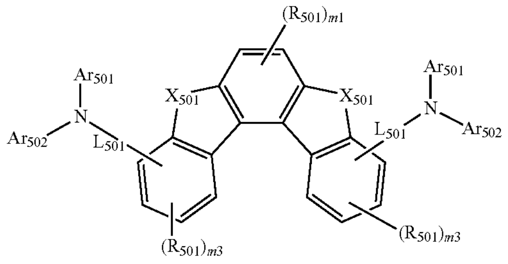

(51-2)

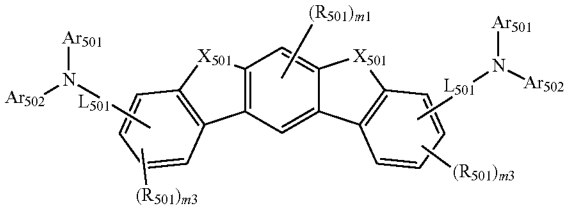

(51-3)

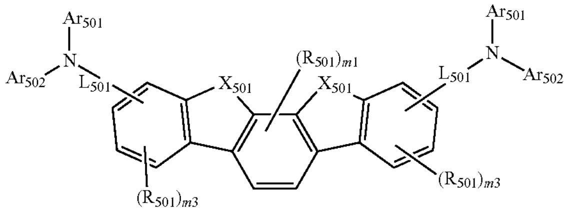

-continued (51-4)

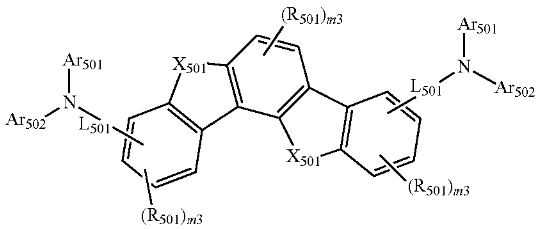

(51-5)

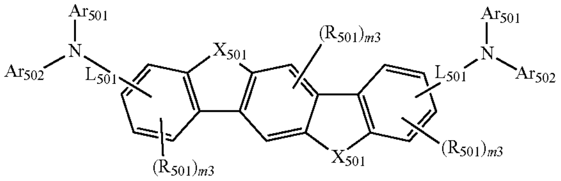

(51-6)

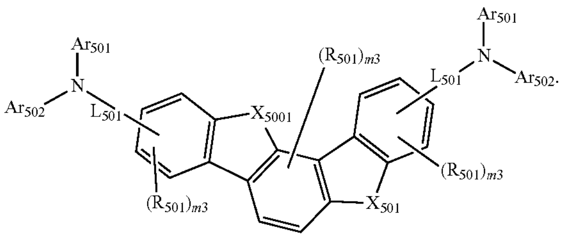

wherein in the formulas (51-1) to (51-6), $R_{501}$, $X_{501}$, $Ar_{501}$, $Ar_{502}$, $L_{501}$, m1 and m3 are as defined in the formula (51).

In one embodiment, the compound represented by the formula (51) is represented by any one of the following formulas (51-11) to (51-13):

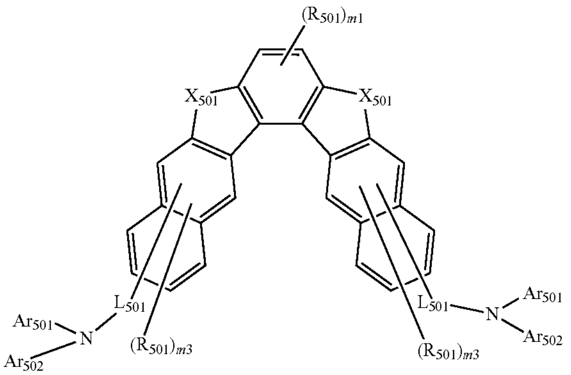

(51-11)

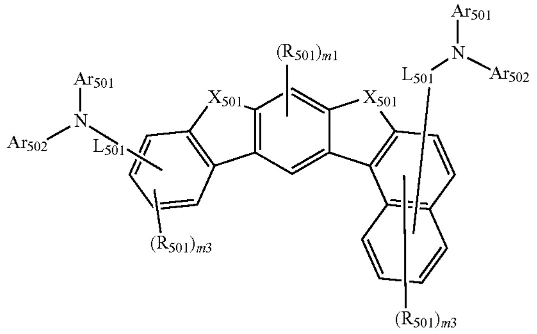

(51-12)

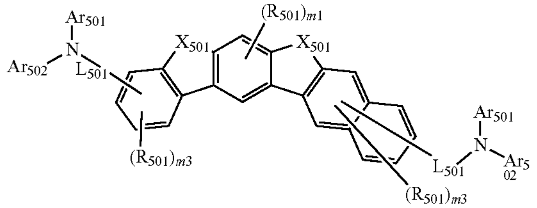

(51-13)

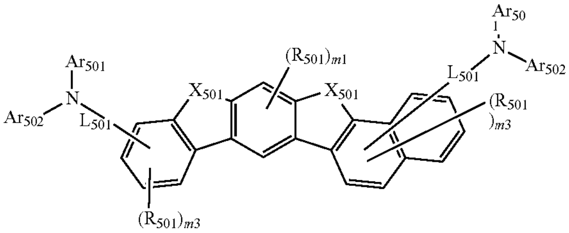

wherein in the formulas (51-11) to (51-13), $R_{501}$, $X_{501}$, $Ar_{501}$, $Ar_{502}$, $L_{501}$, m1, m3 and m4 are as defined in the formula (51).

In one embodiment, the compound represented by the formula (51) is represented by any one of the following formulas (51-21) to (51-25):

(51-21)

-continued
(51-22)
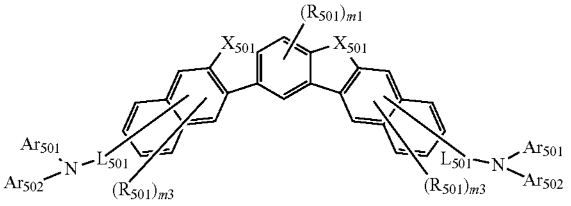
(51-23)
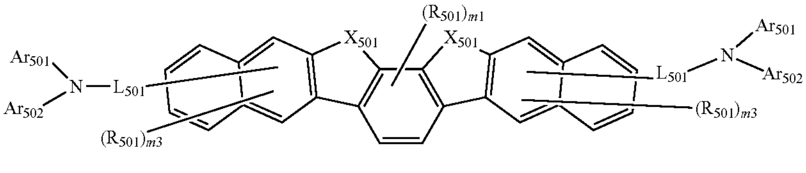
(51-24)
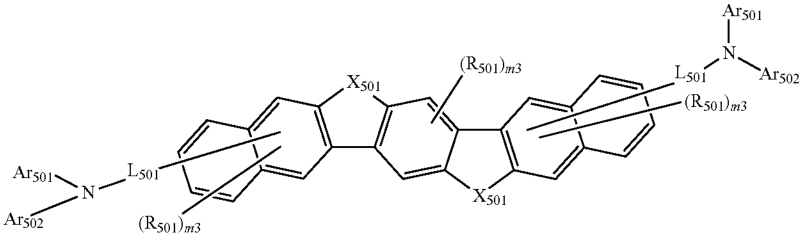
(51-25)
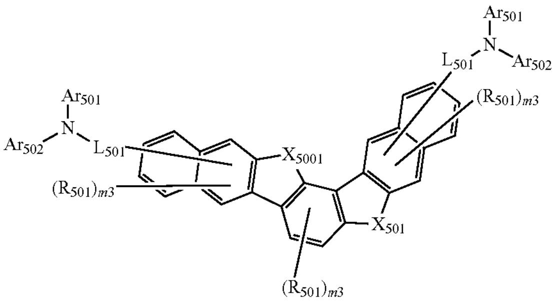
wherein in the formulas (51-21) to (51-25), $R_{501}$, $X_{501}$, $Ar_{502}$, $Ar_{502}$, $L_{501}$, m1 and m4 are as defined in the formula (51).
In one embodiment, the compound represented by the formula (51) is represented by any one of the following formulas (51-31) to (51-33):
(51-31)
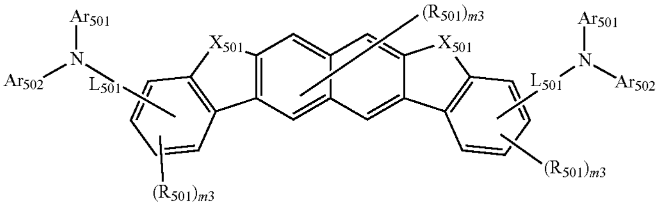
(51-32)
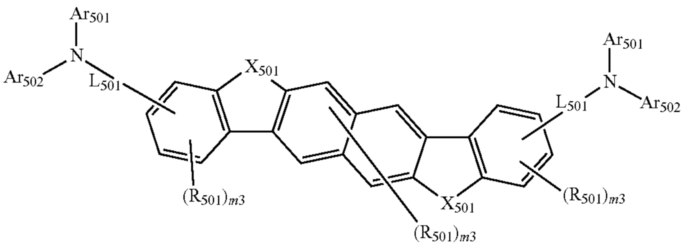

-continued (51-33)

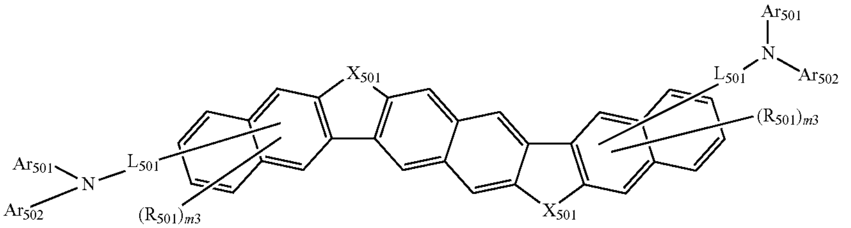

wherein in the formulas (51-31) to (51-33), $R_{501}$, $X_{501}$, $Ar_{501}$, $Ar_{502}$, $L_{501}$, m1 to m4 are as defined in the formula (51).

In one embodiment, $Ar_{501}$ and $Ar_{502}$ are independently a substituted or unsubstituted aryl group having 6 to 50 ring carbon atoms.

In one embodiment, one of $Ar_{501}$ and $Ar_{502}$ is a substituted or unsubstituted aryl group having 6 to 50 ring carbon atoms and the other is a substituted or unsubstituted monovalent heterocyclic ring having 5 to 50 ring atoms.

As examples of the compound represented by the formula (51), the following compounds can be given, for example. In the following example compounds, Me represents methyl group.

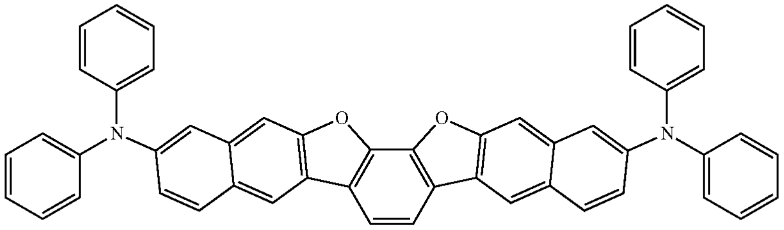

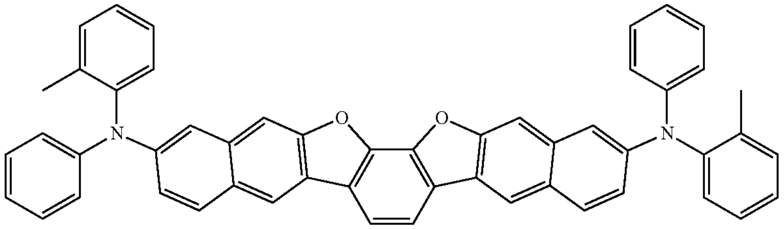

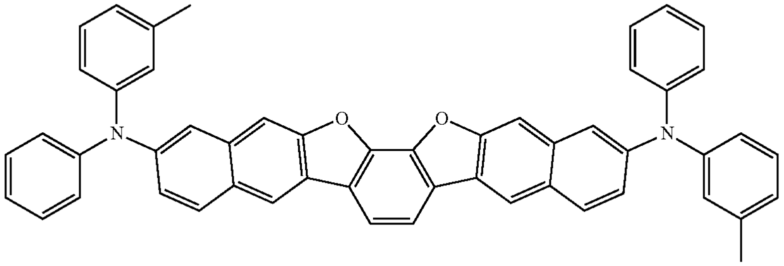

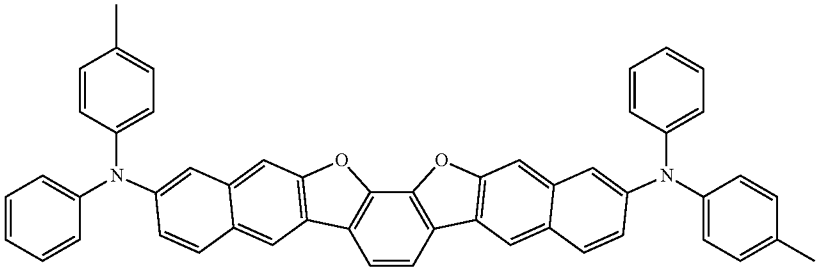

-continued
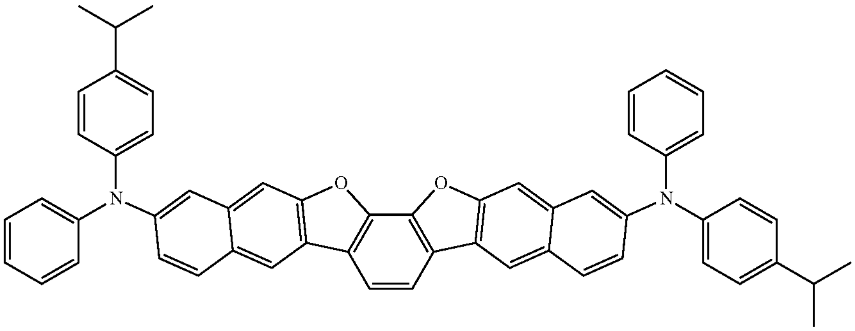
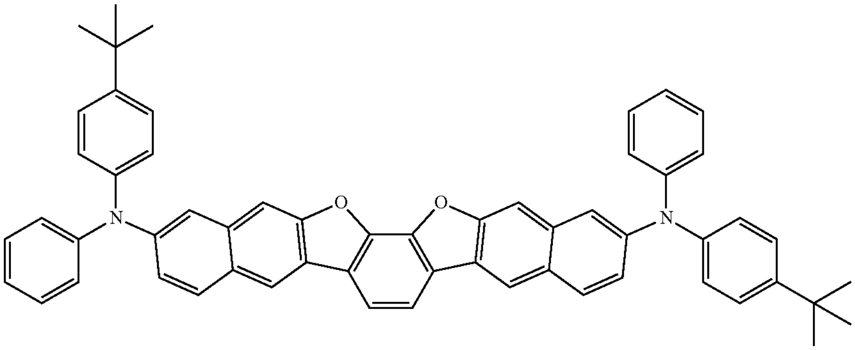
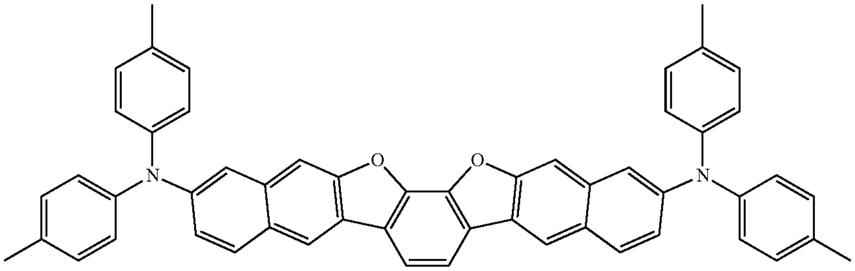
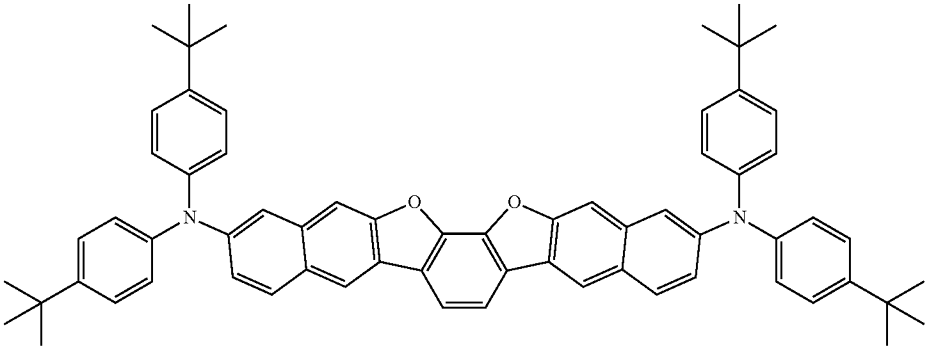
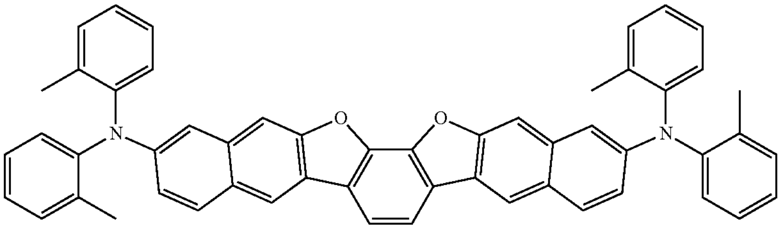

-continued
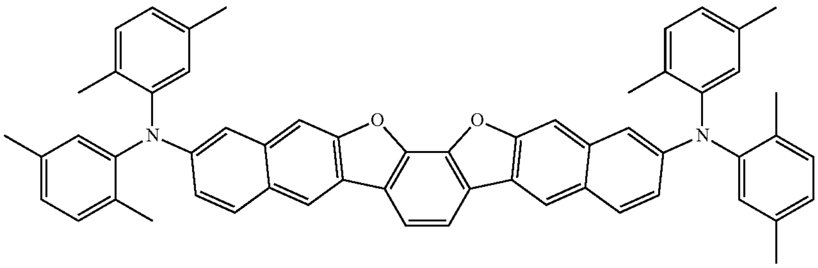
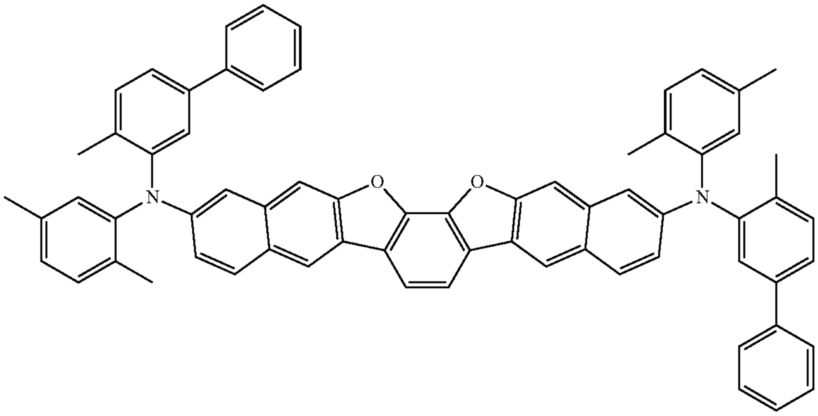
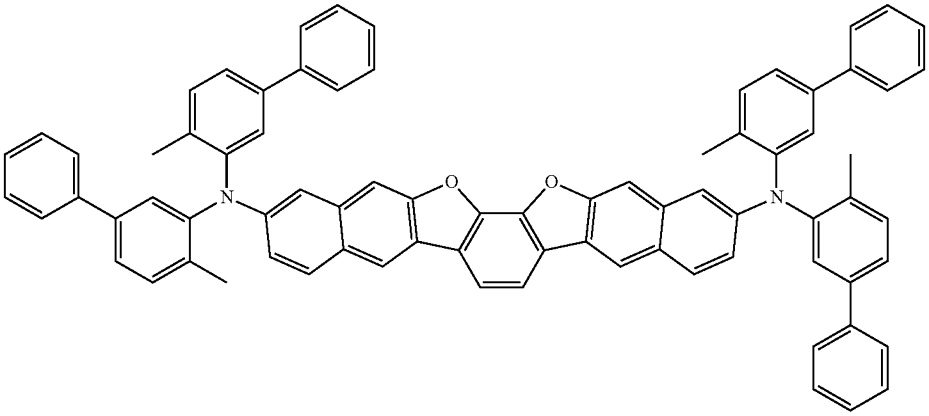
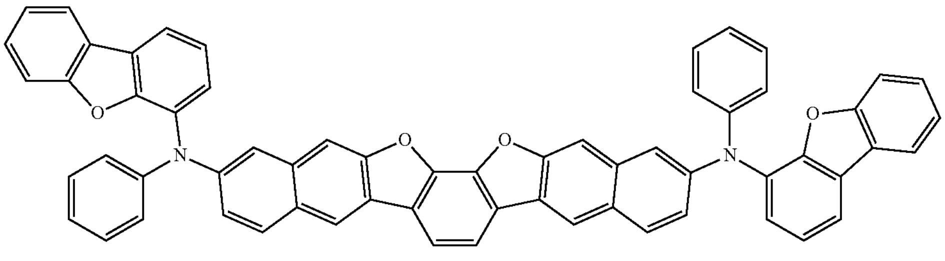
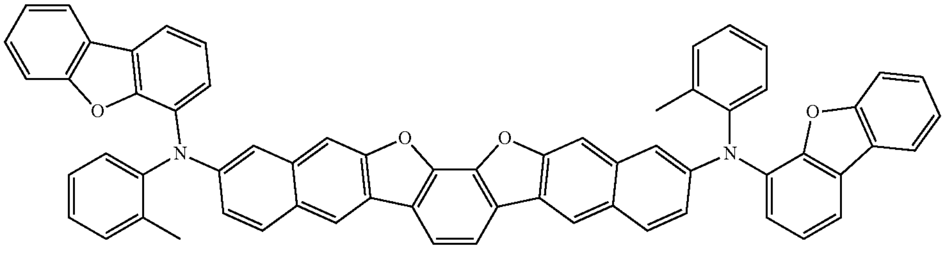

-continued
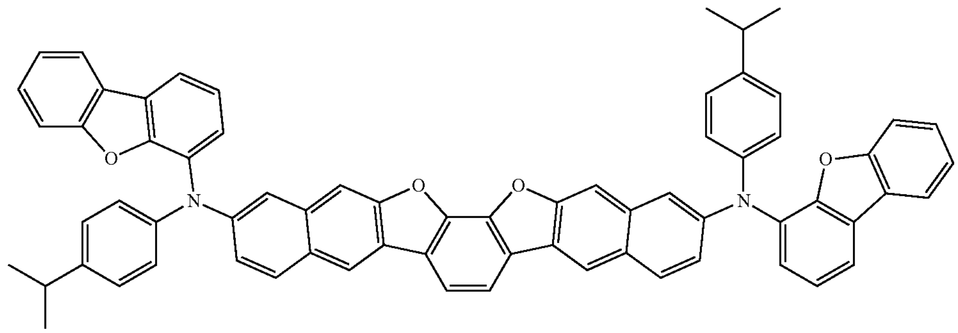
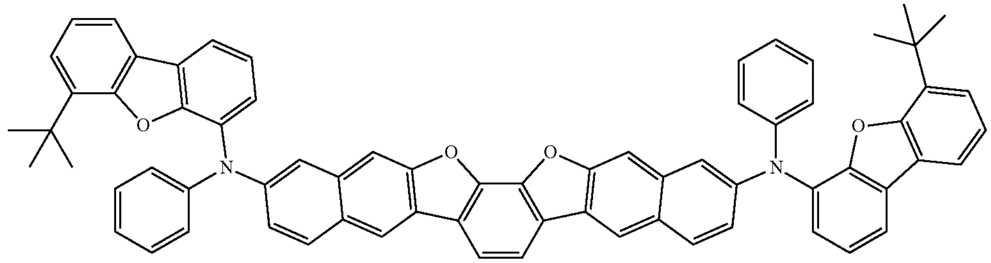
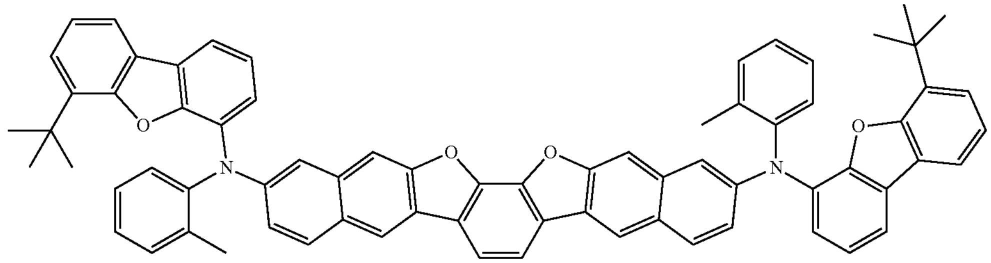
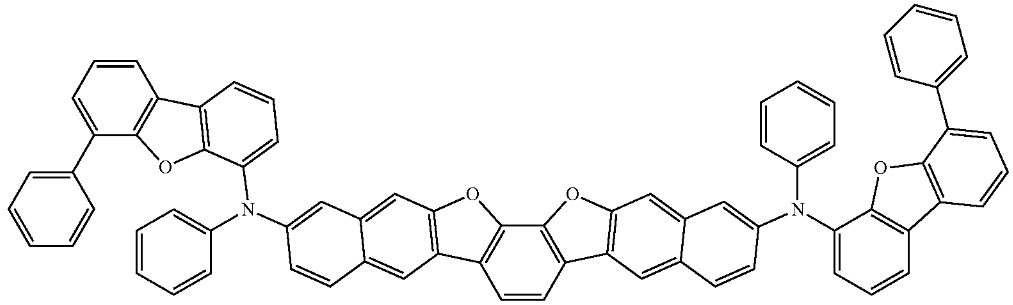
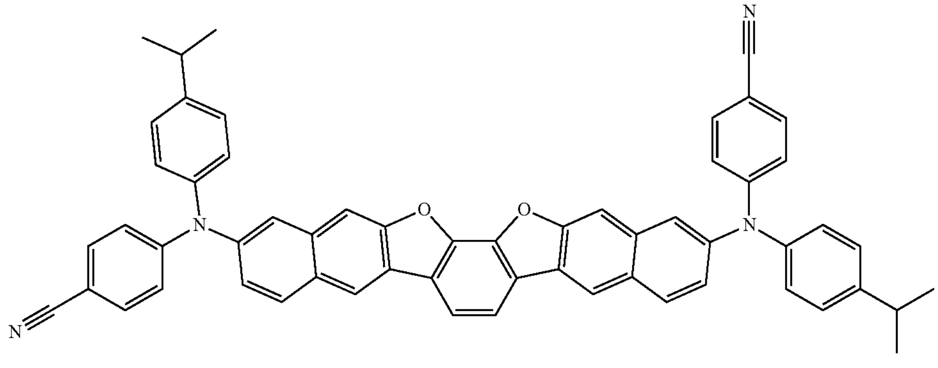

-continued
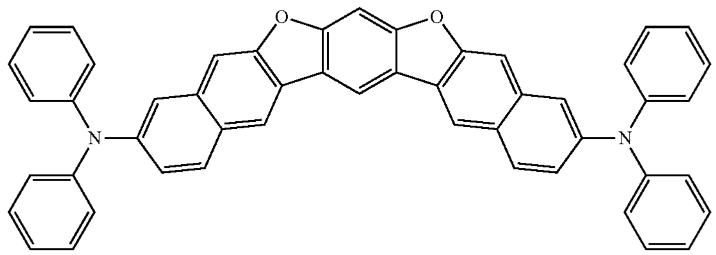
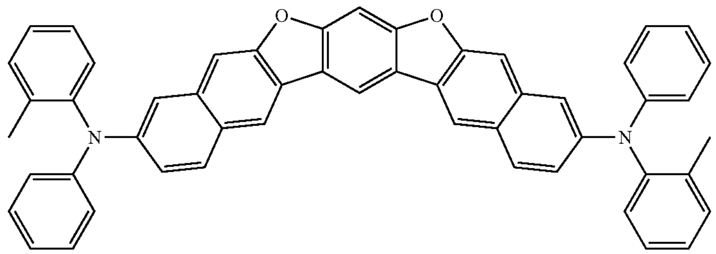
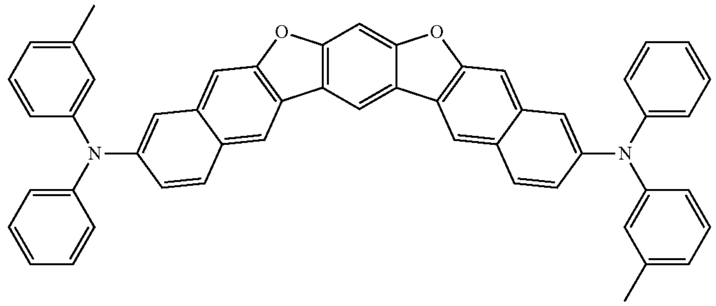
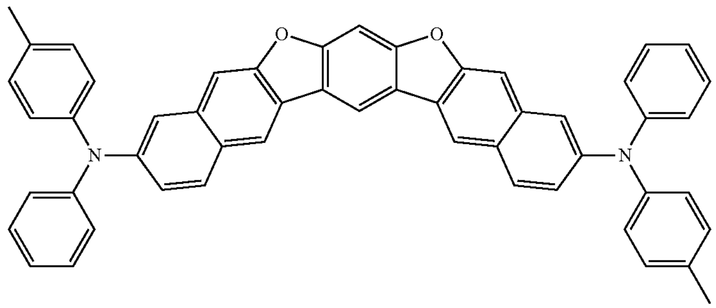
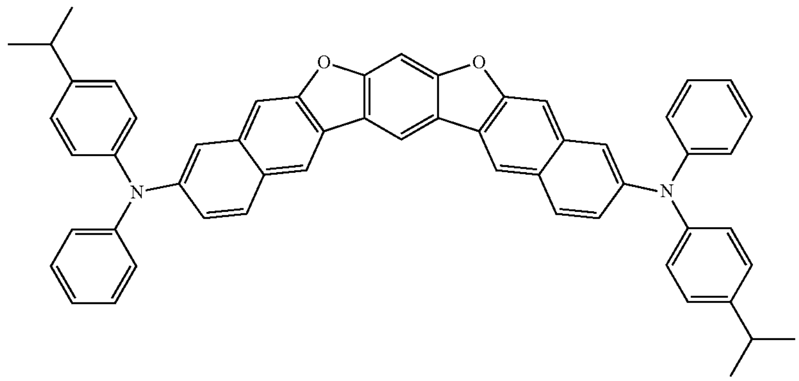

-continued
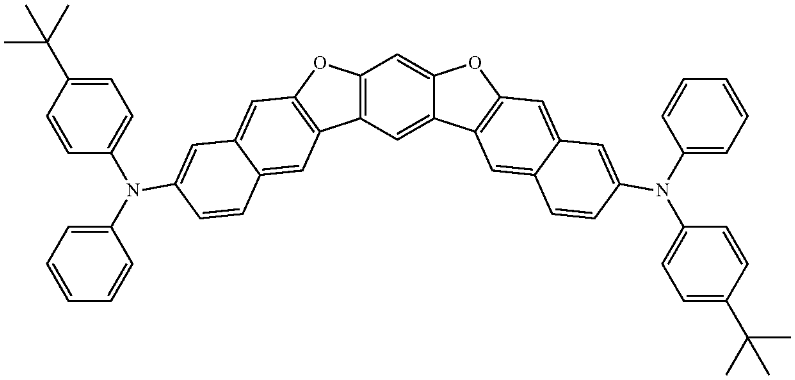
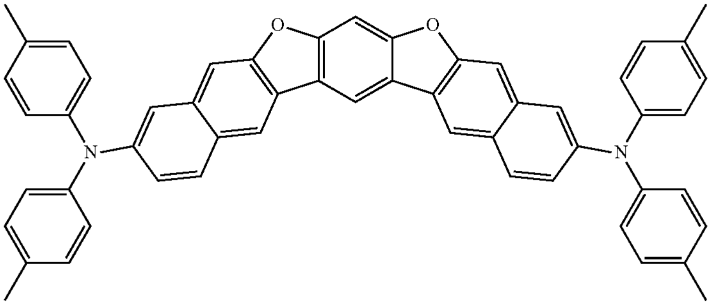
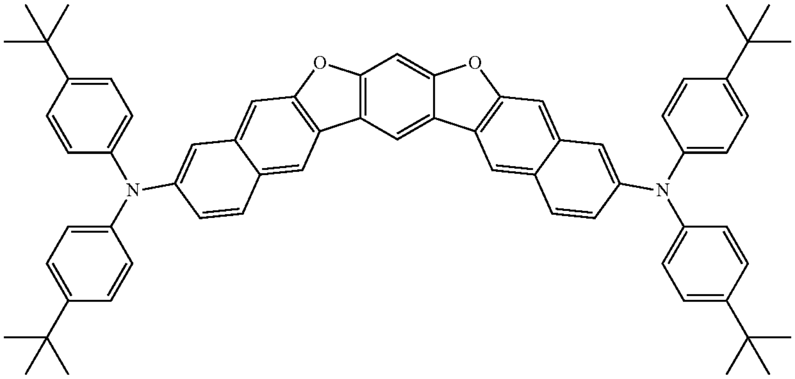
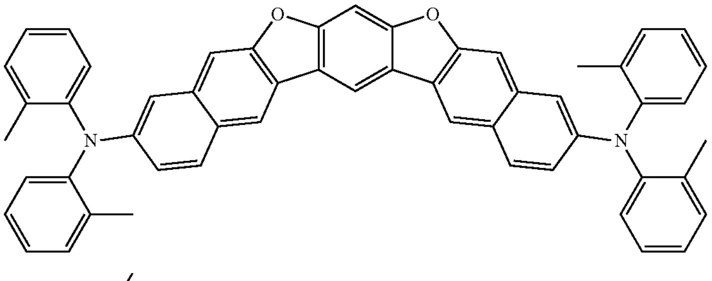
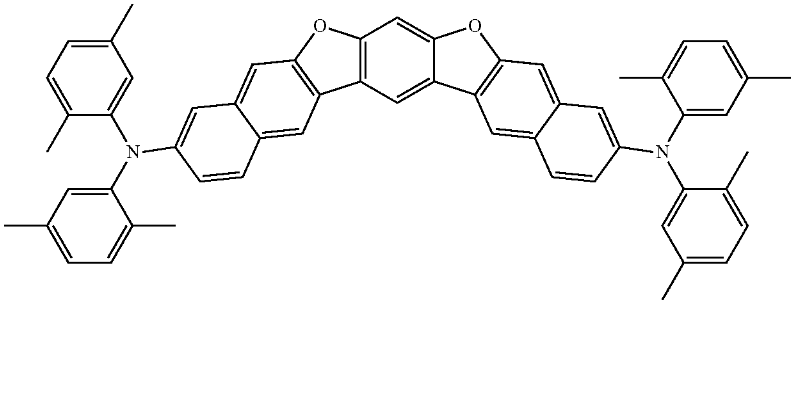

-continued
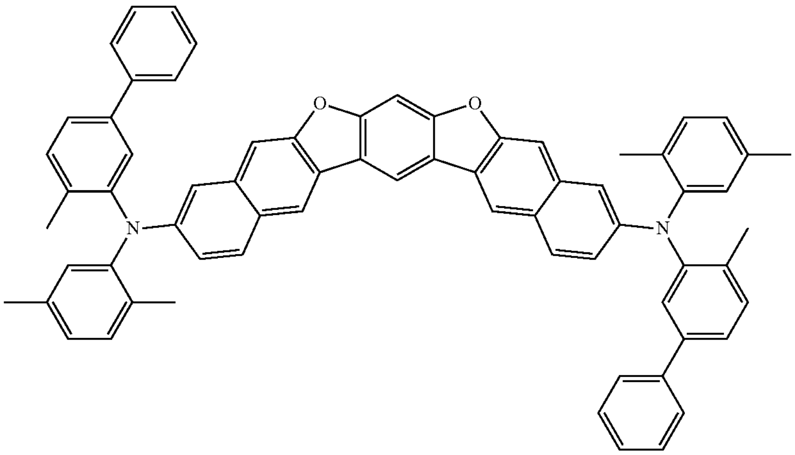
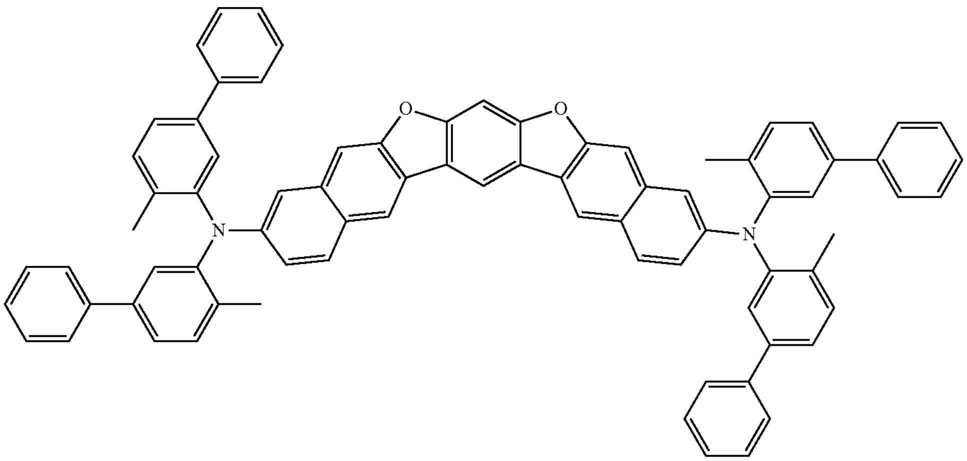
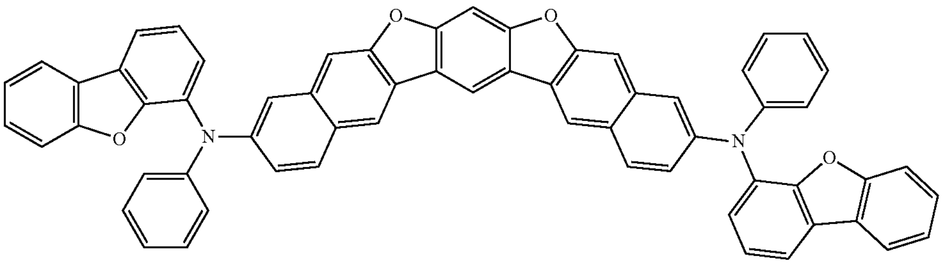
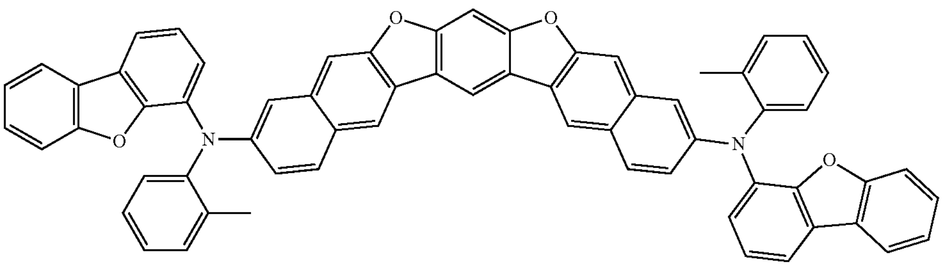

-continued
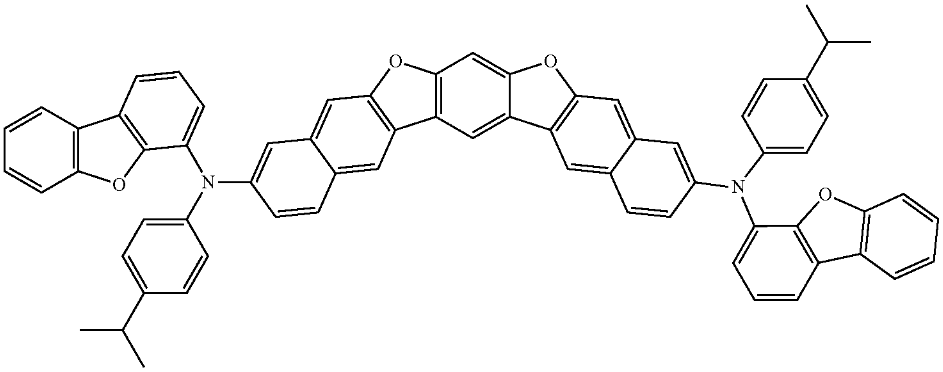
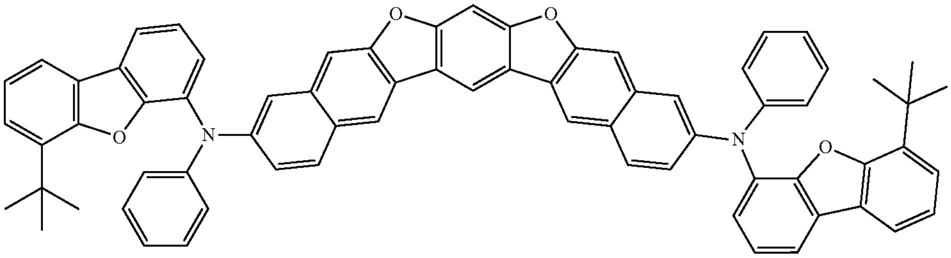
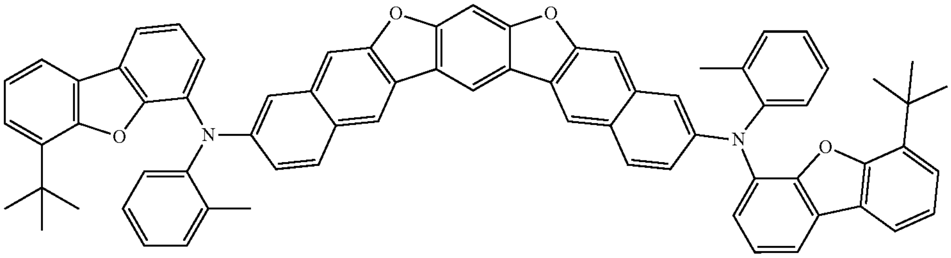
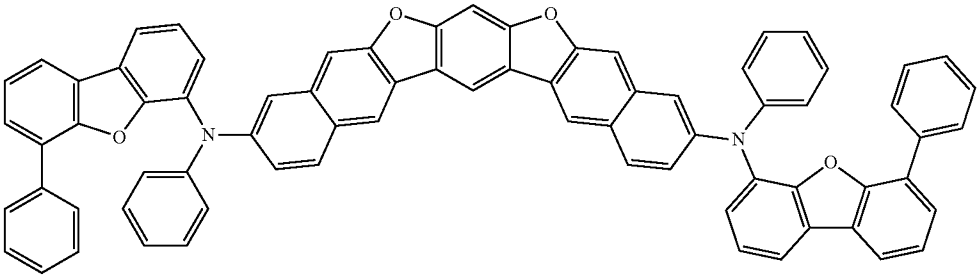
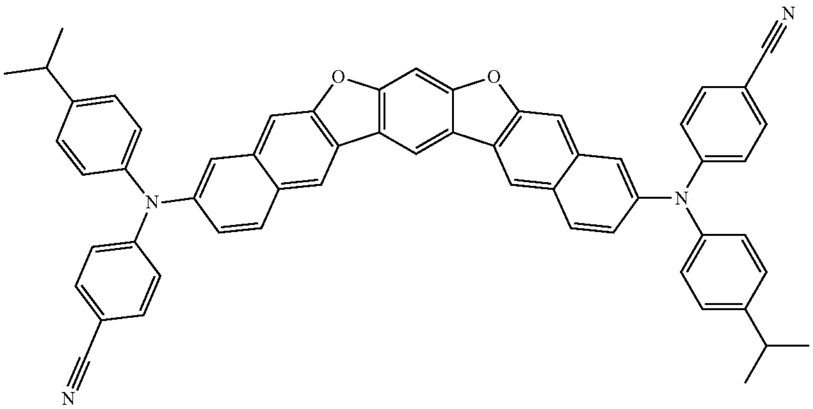

-continued
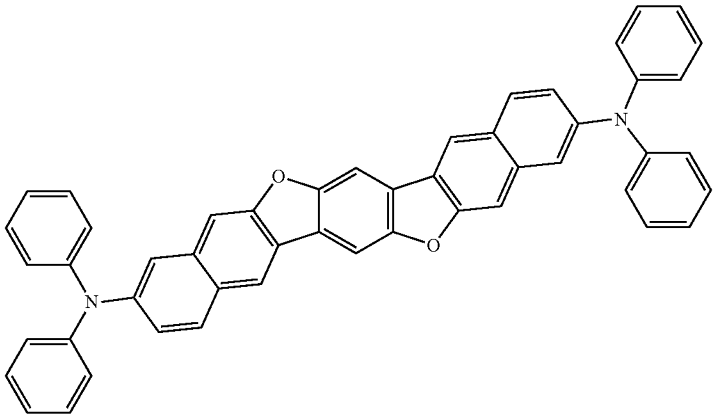
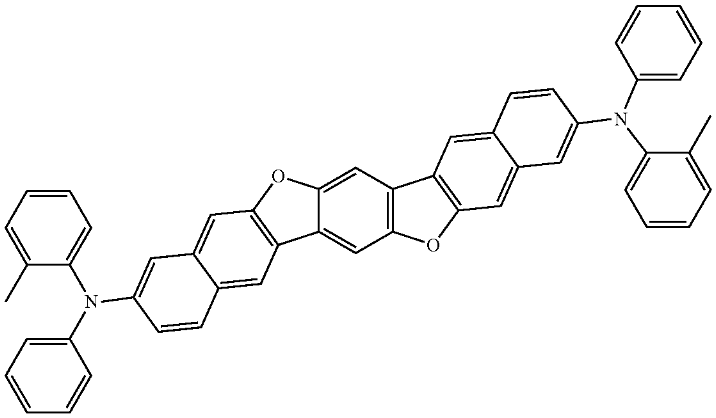
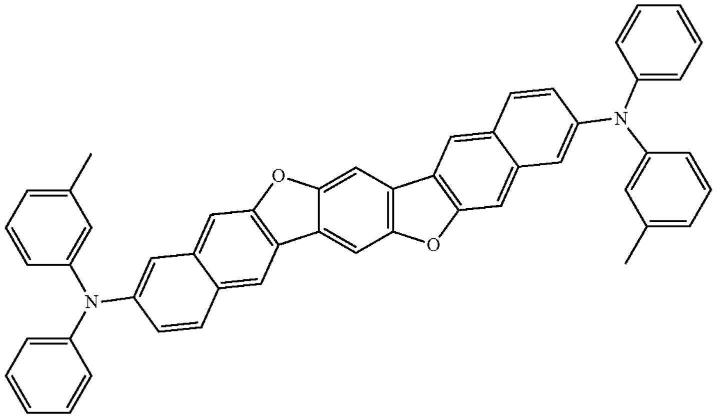
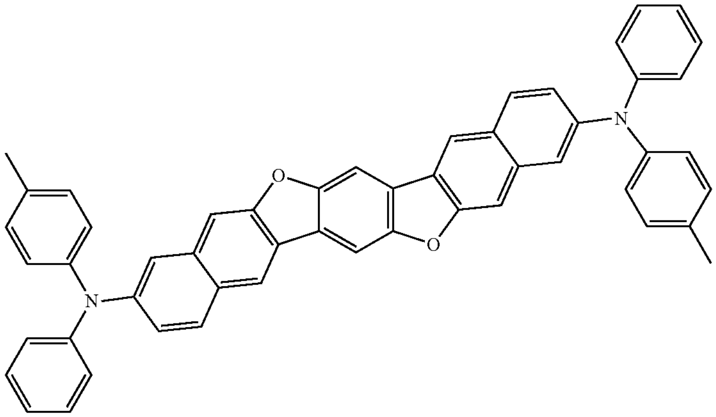

-continued
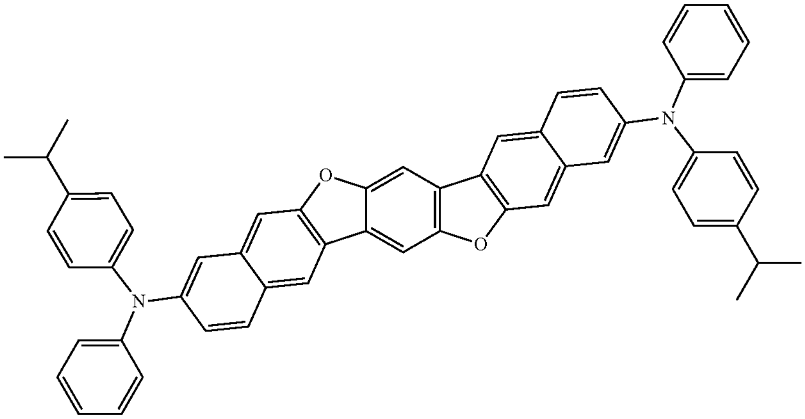
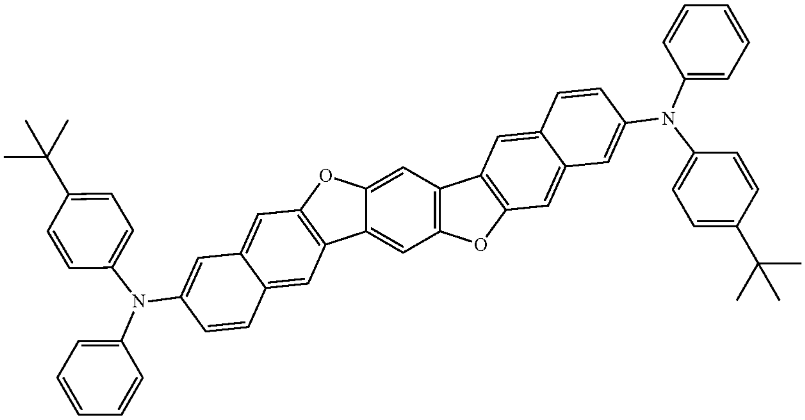
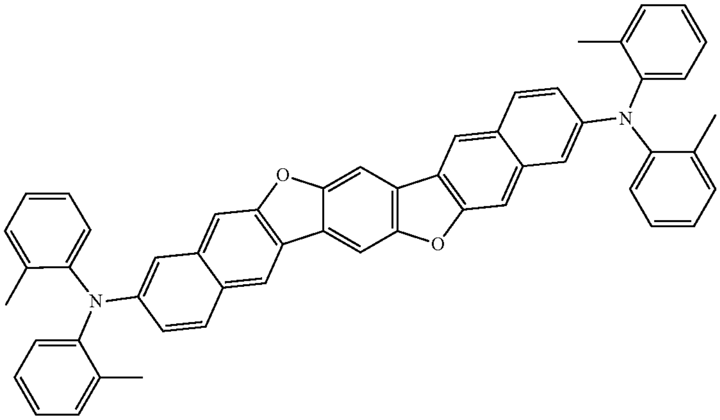
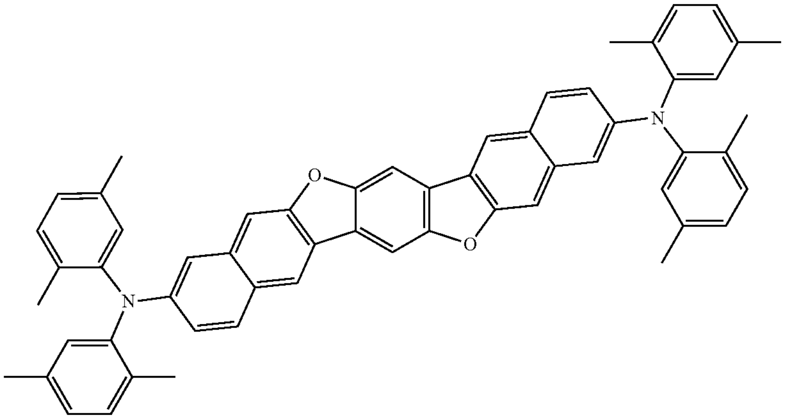

-continued
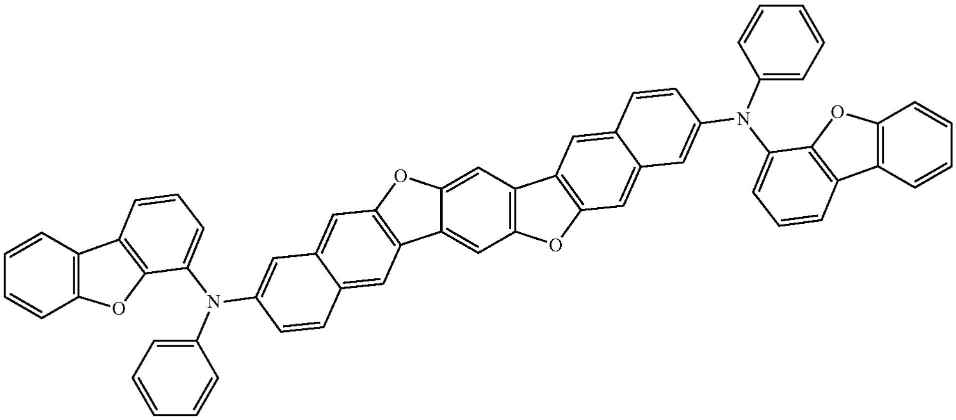
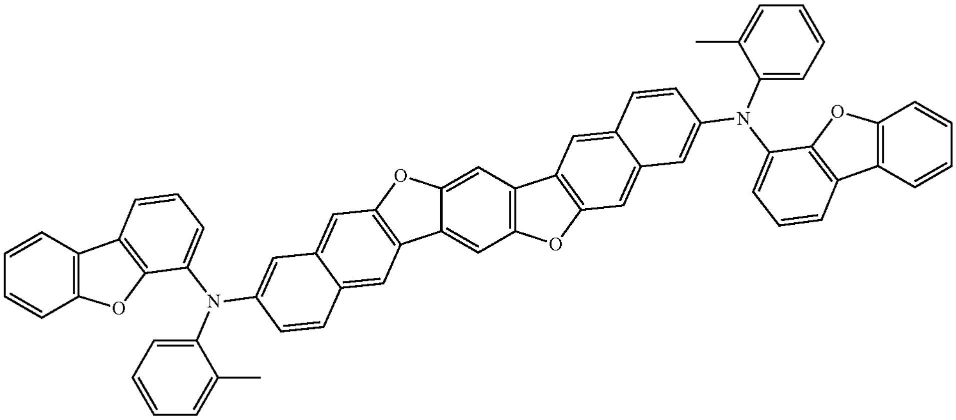
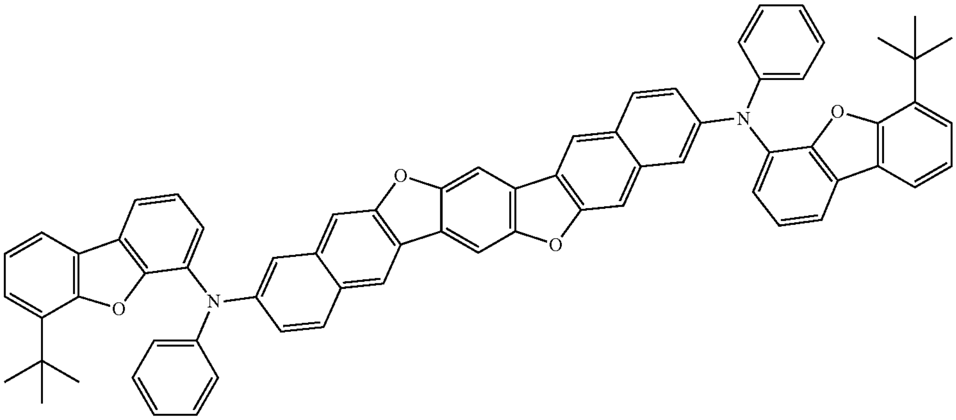

-continued
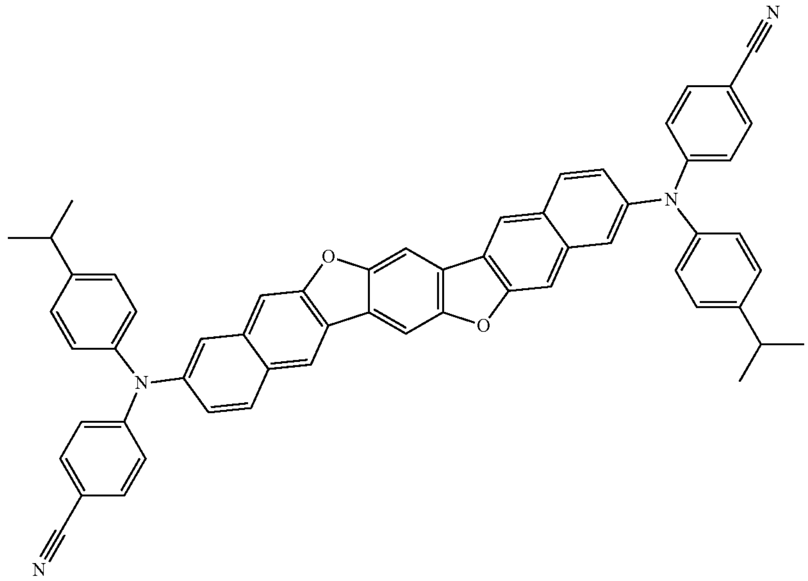
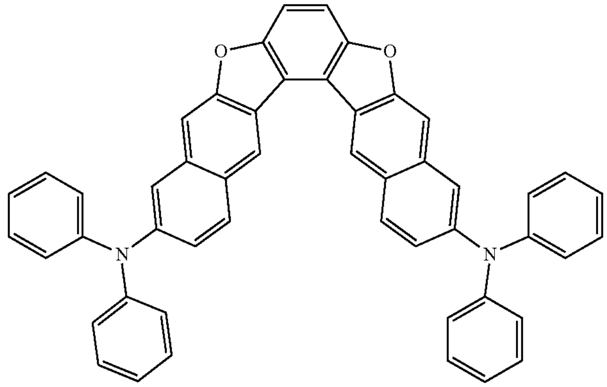
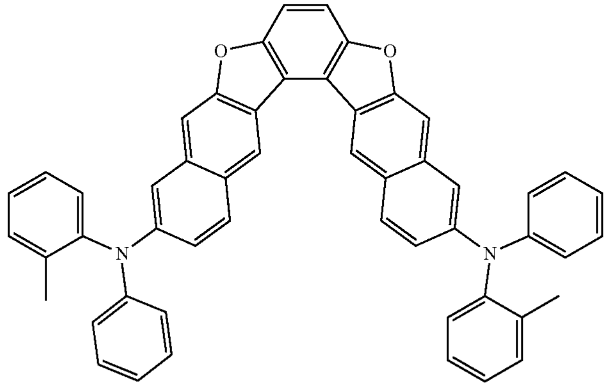

-continued
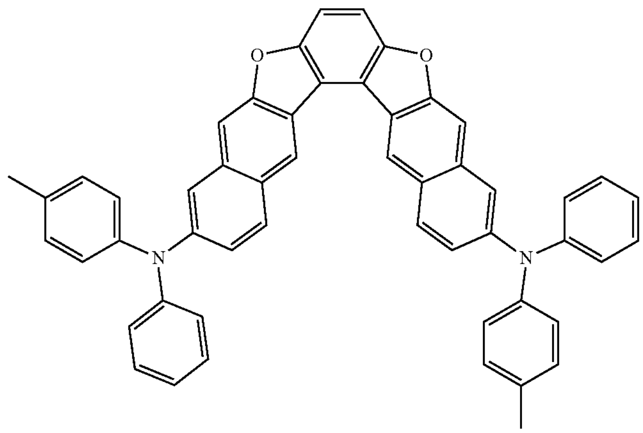
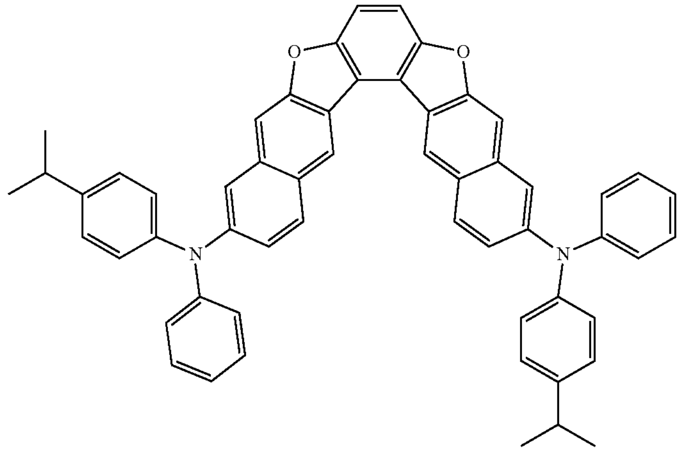
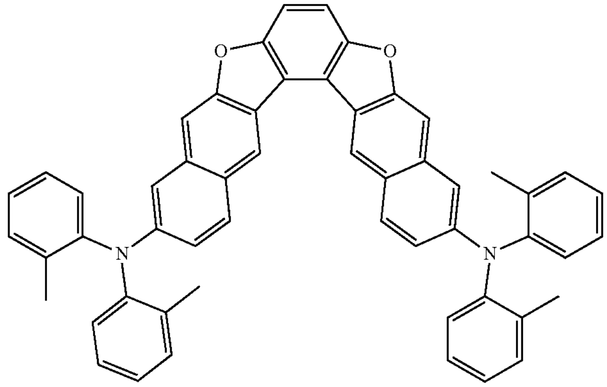
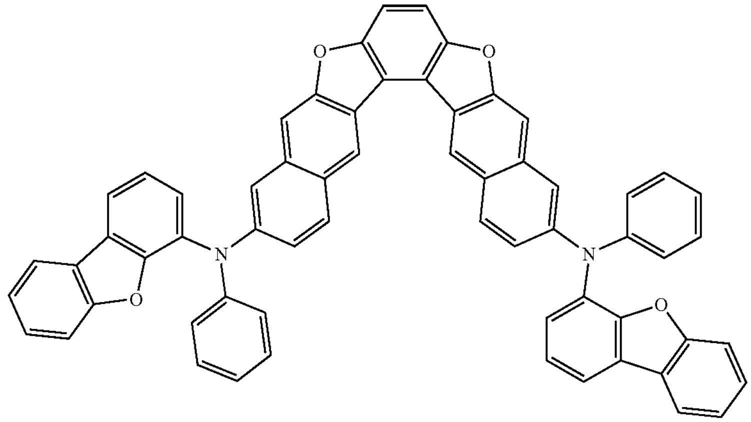

-continued
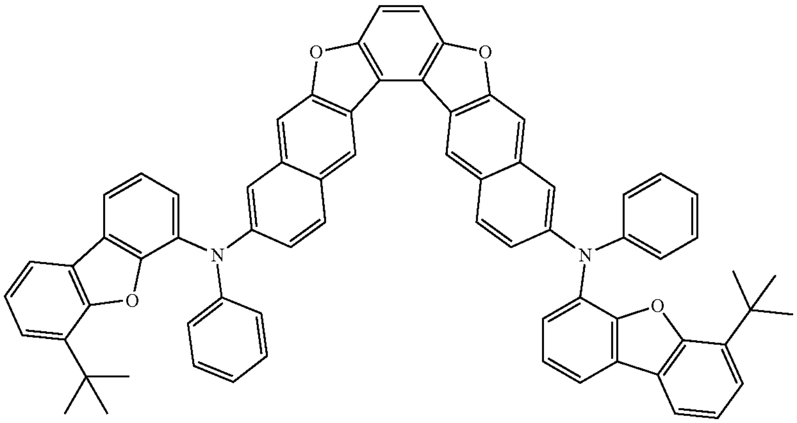
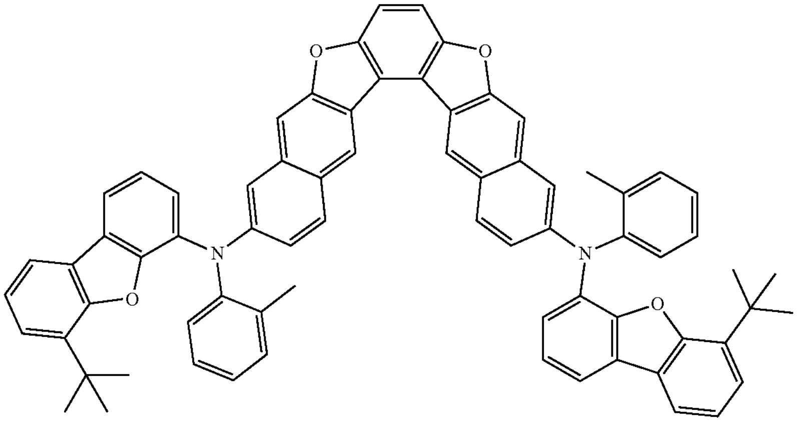
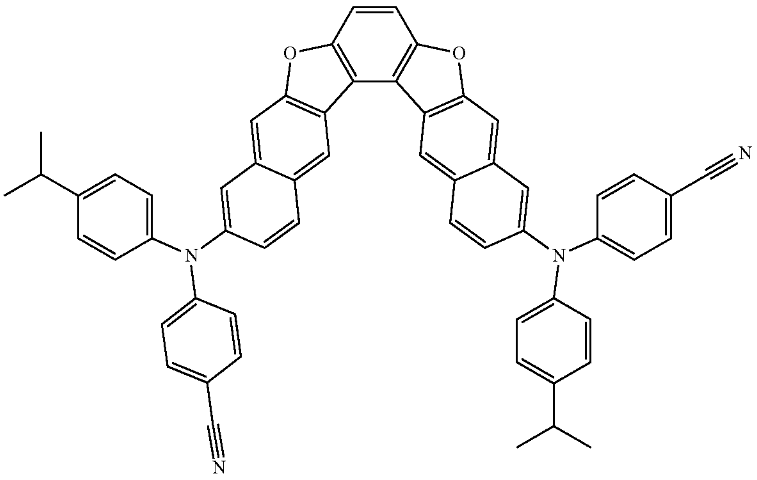
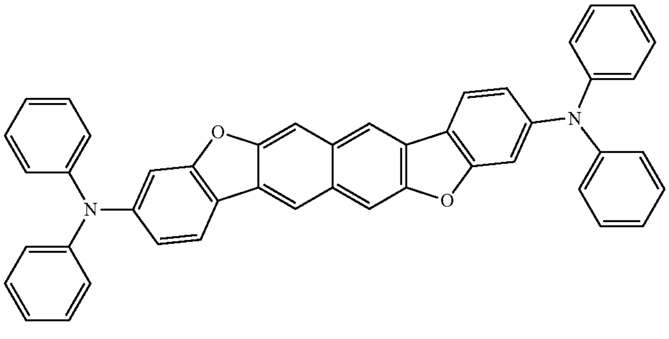

-continued
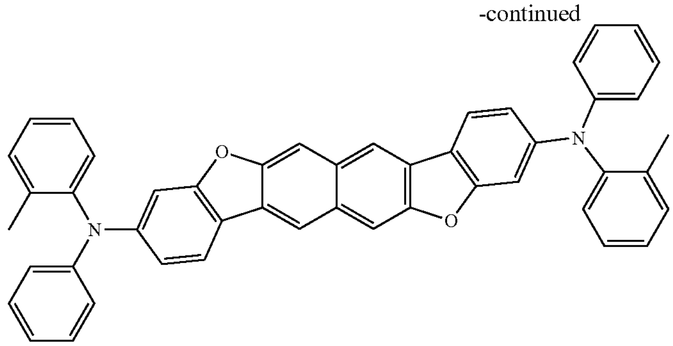
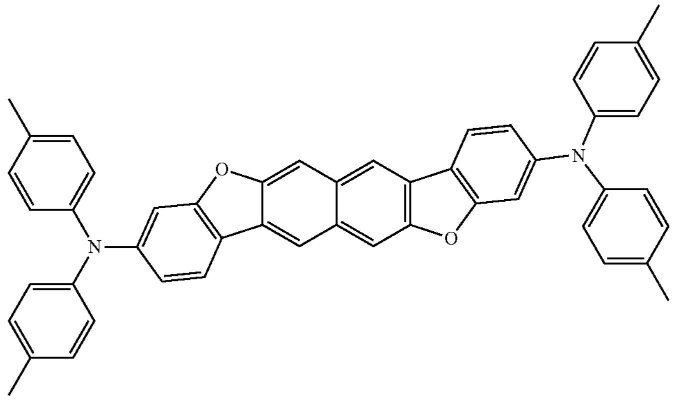
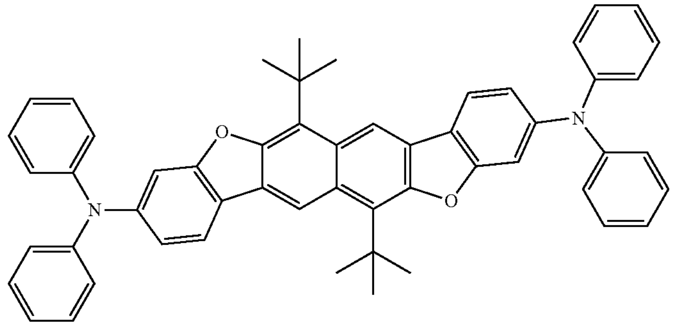
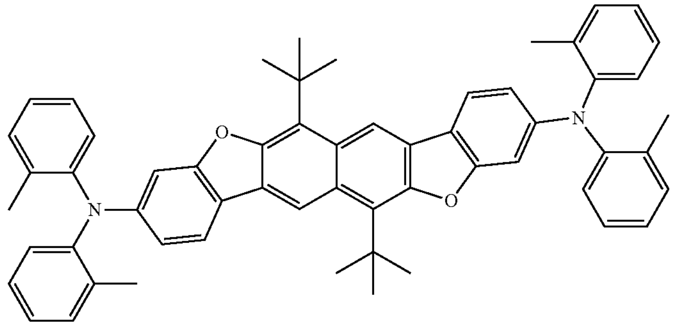
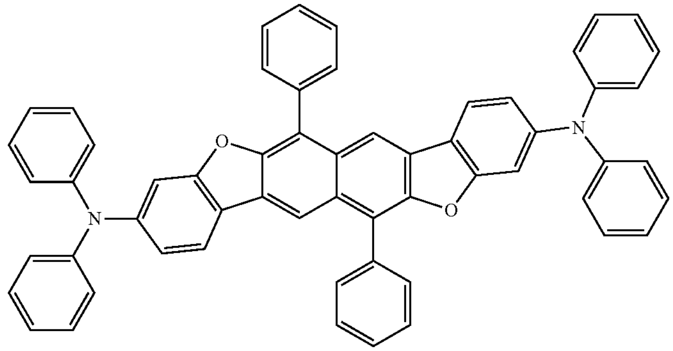

-continued
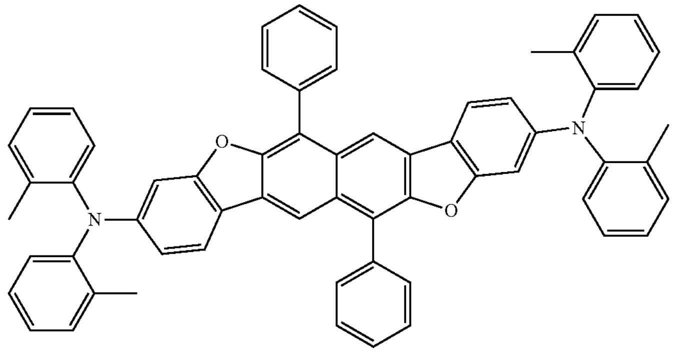
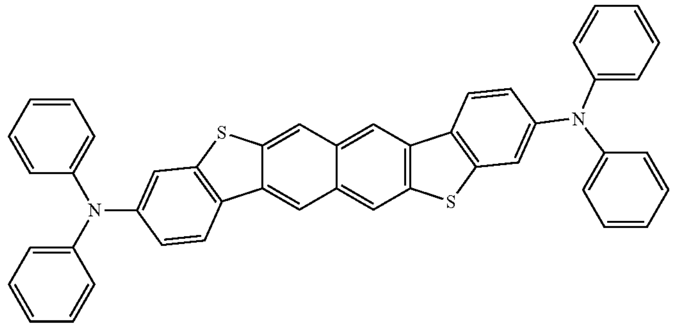
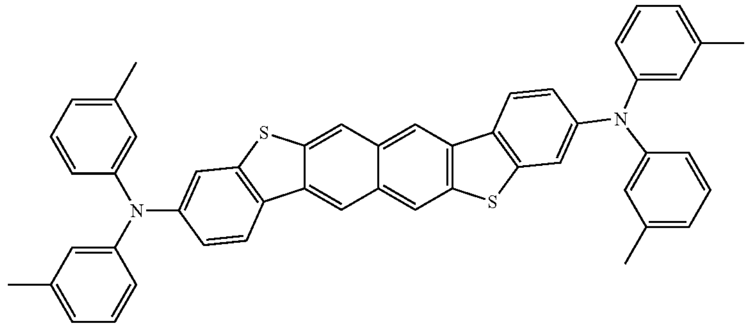
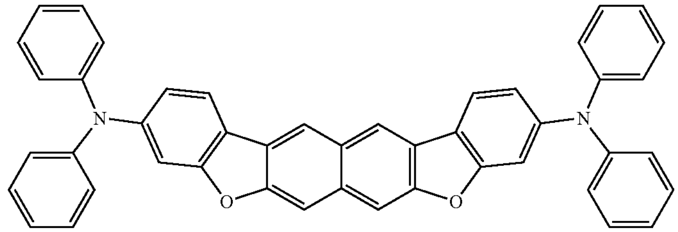
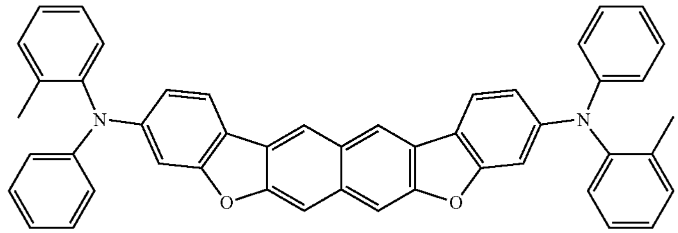

-continued
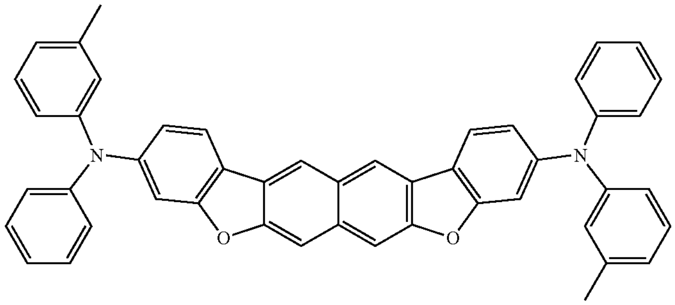
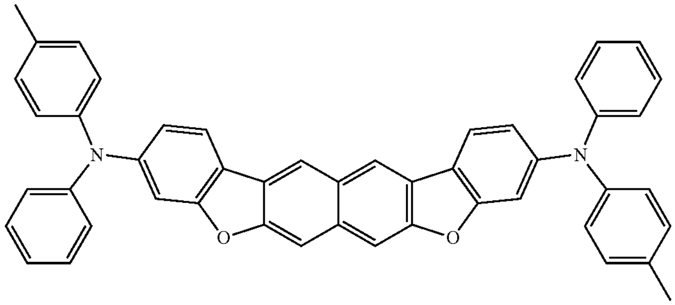
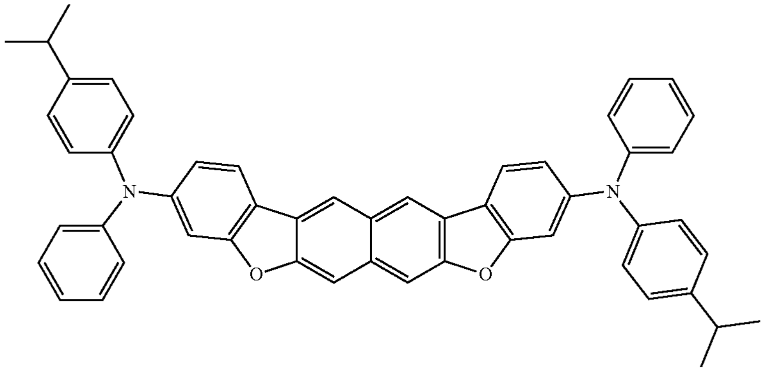
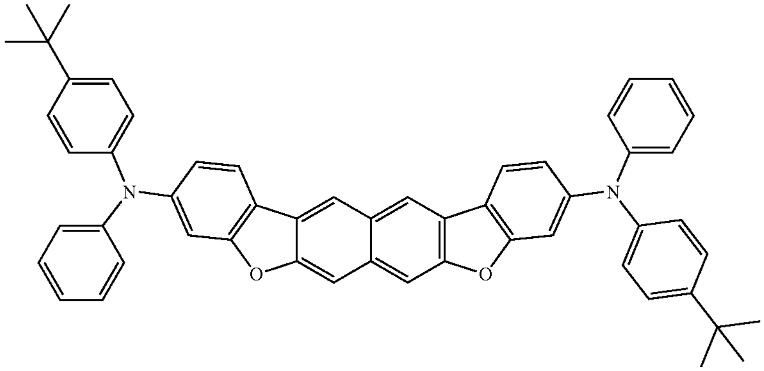
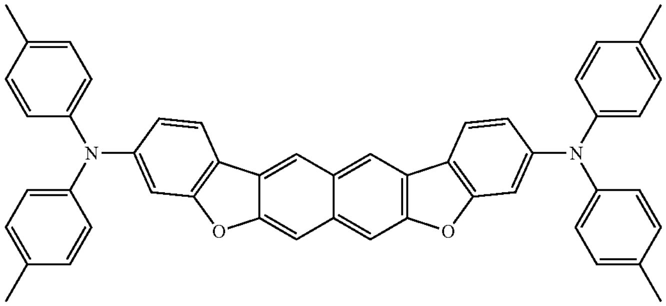

-continued
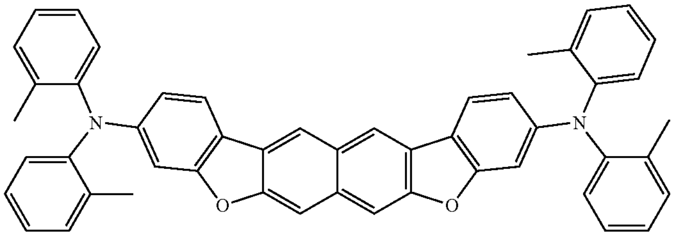
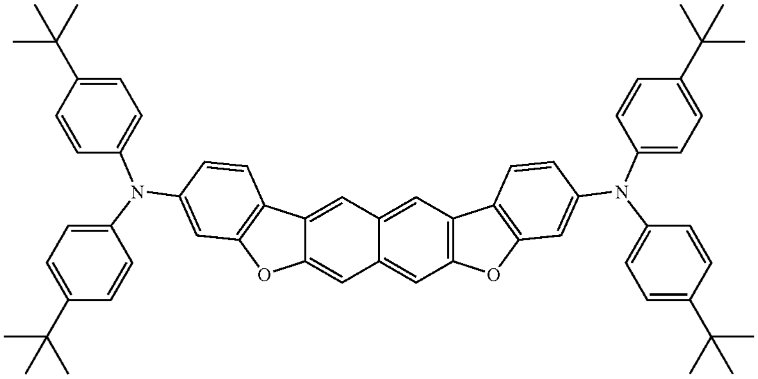
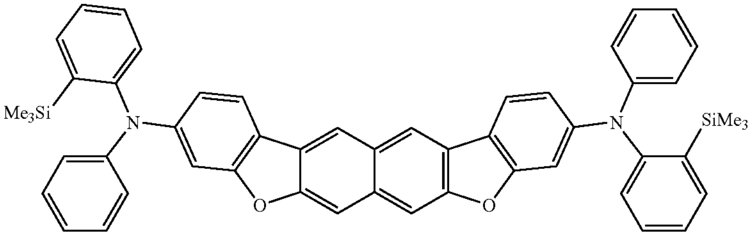
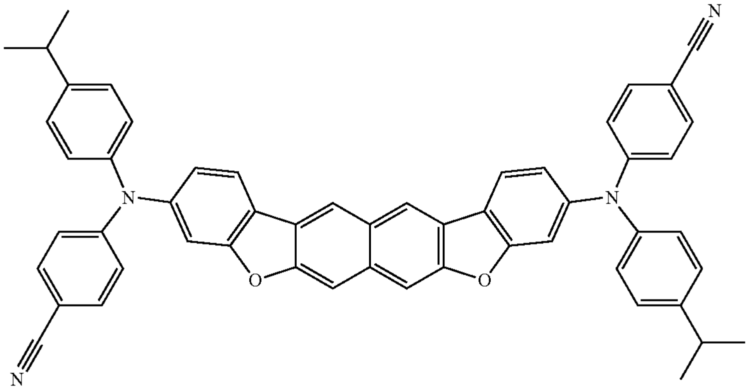
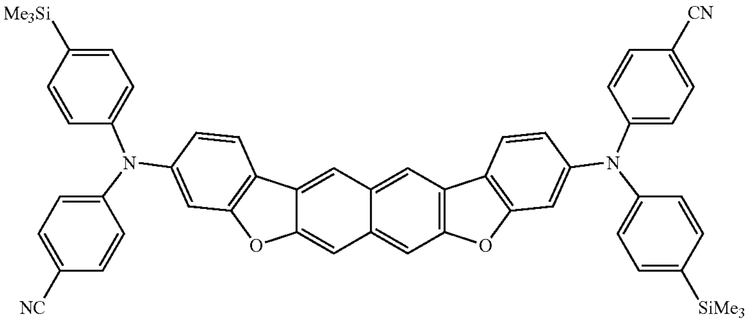

-continued
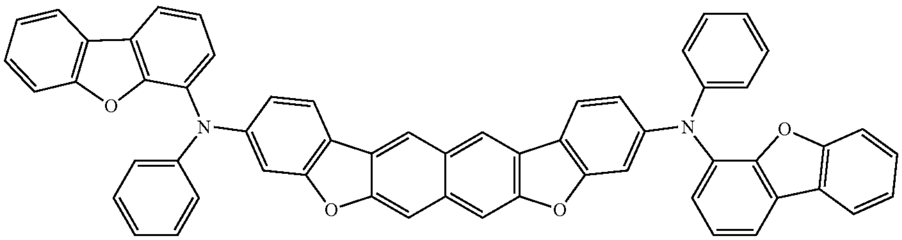
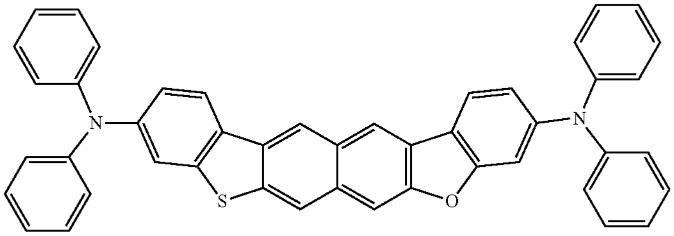
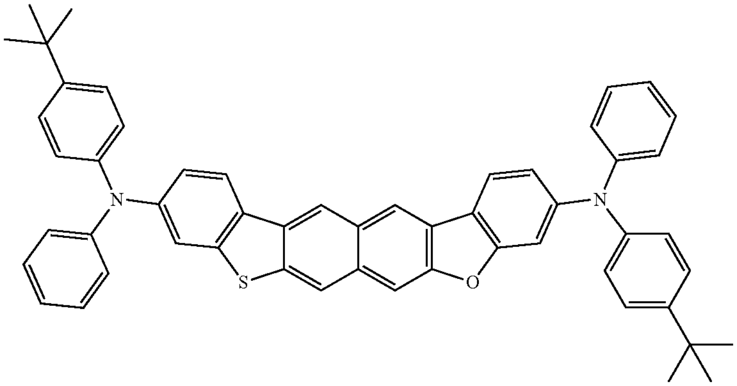
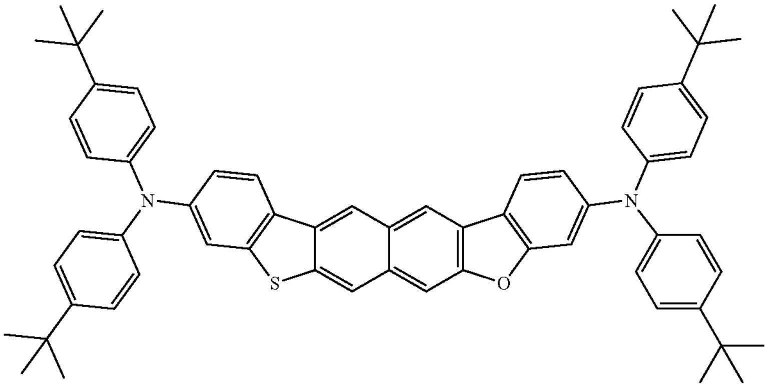
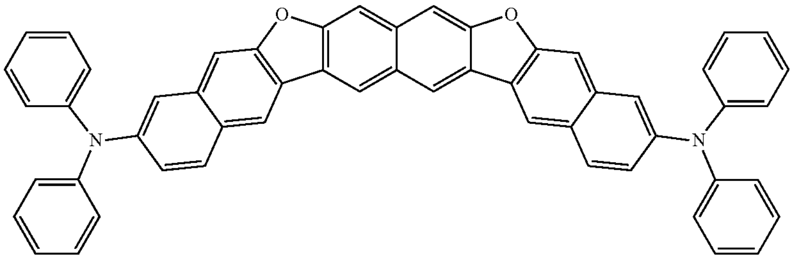

-continued
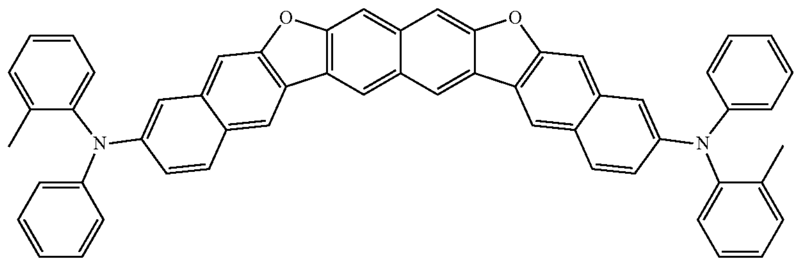
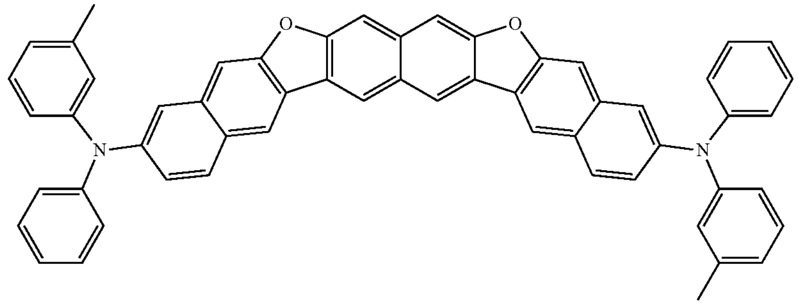
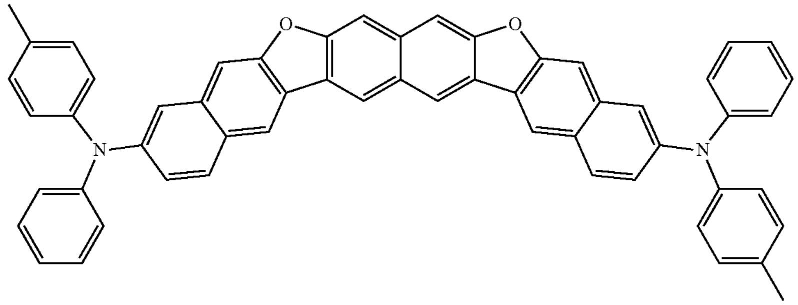
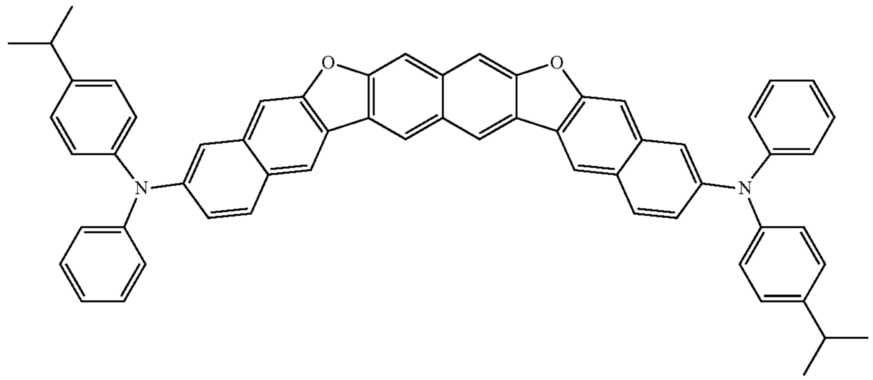
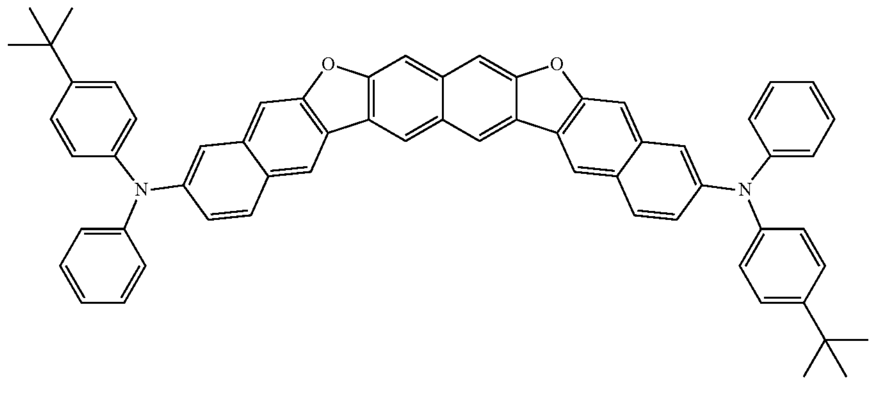

-continued
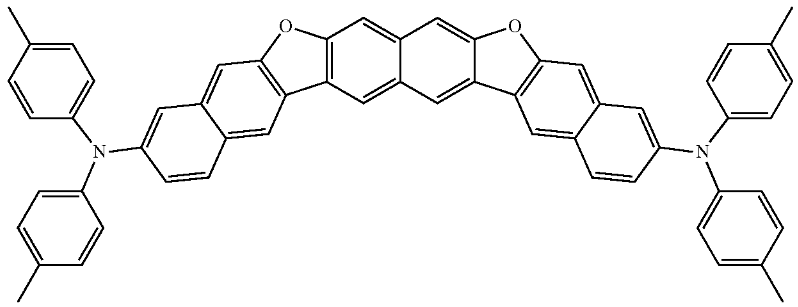
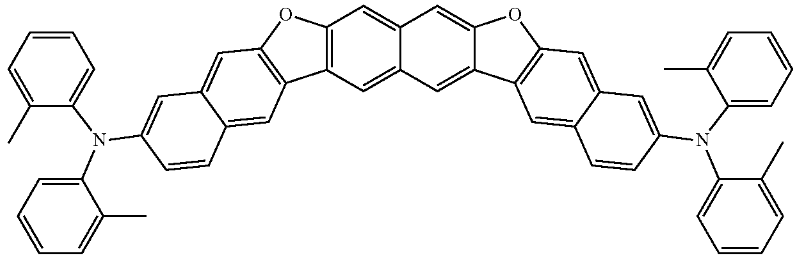
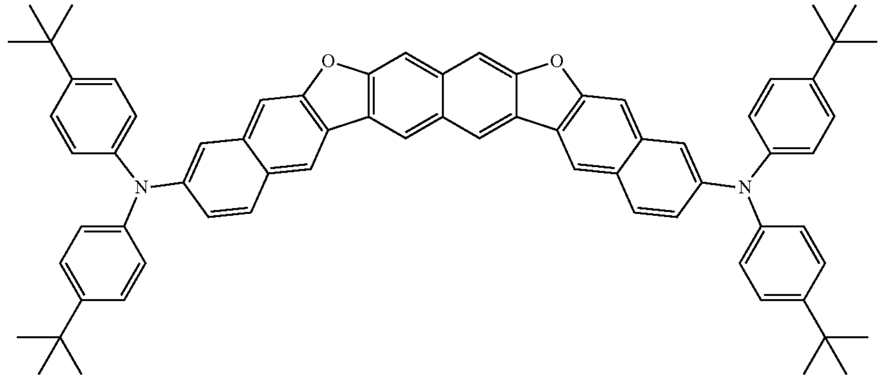
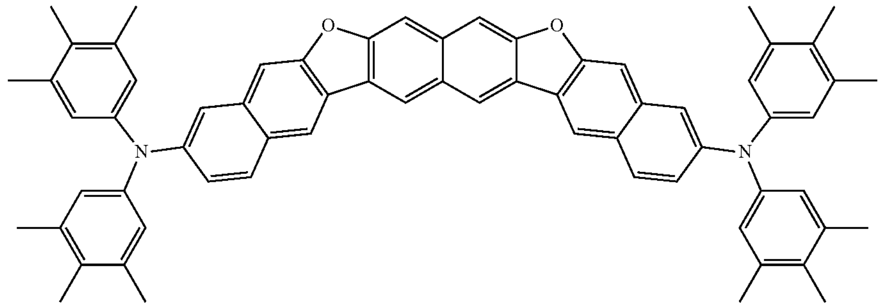
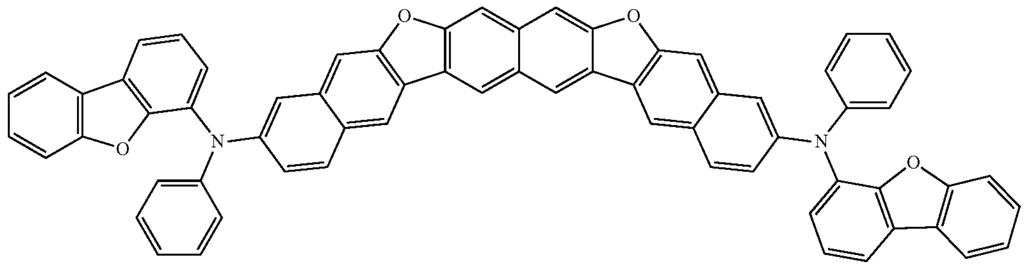

-continued

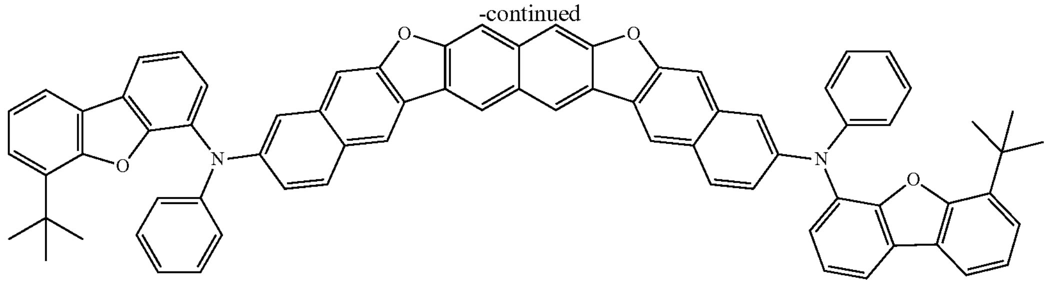

(Compound Represented by Formula (61))

The compound represented by the formula (61) is explained below (61)

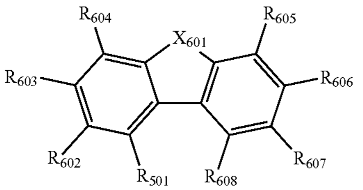

In the formula (61), at least one pair of $R_{601}$ and $R_{602}$, $R_{602}$ and $R_{603}$ and $R_{603}$ and $R_{604}$ are bonded with each other to form a divalent group represented by the formula (62);

at least one pair of $R_{605}$ and $R_6$, $R_{606}$ and $R_{607}$, and $R_{607}$ and $R_{608}$ are bonded with each other to form a divalent group represented by formula (63);

(62)

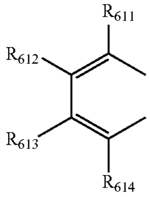

(63)

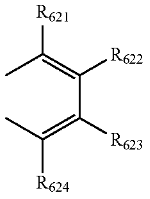

at least one of $R_{601}$ to $R_{604}$ that does not form the divalent group represented by the formula (62), and $R_{611}$ to $R_{614}$ is a monovalent group represented by the following formula (64);

at least one of $R_{605}$ to $R_{608}$ that do not form the divalent group represented by the formula (63), and $R_{621}$ to $R_{624}$ is a monovalent group represented by the following formula (64);

$X_{601}$ is an oxygen atom, a sulfur atom, or $NR_{609}$;

$R_{601}$ to $R_{608}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

(64)

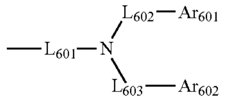

wherein, in the formula (64), $Ar_{601}$ and $Ar_{602}$ are independently a substituted or unsubstituted aryl group having 6 to 50 ring carbon atoms, or a substituted or unsubstituted monovalent heterocyclic group having 5 to 50 ring atoms;

$L_{601}$ to $L_{603}$ are independently a single bonded, a substituted or unsubstituted arylene group having 6 to 30 ring carbon atoms, a substituted or unsubstituted divalent heterocyclic group having 5 to 30 ring atoms, or a divalent linking group formed by bonding 2 to 4 of a substituted or unsubstituted arylene group having 6 to 30 ring carbon atoms, and a substituted or unsubstituted divalent heterocyclic group having 5 to 30 ring atoms.

In the formula (61), positions at which the divalent group represented by the formula (62) and the divalent group represented by the formula (63) are formed are not limited, and said groups can be formed at possible positions in $R_{601}$ to $R_{606}$.

In one embodiment, the compound represented by the formula (61) is represented by any one of the following formulas (61-1) to (61-6):

(61-1)

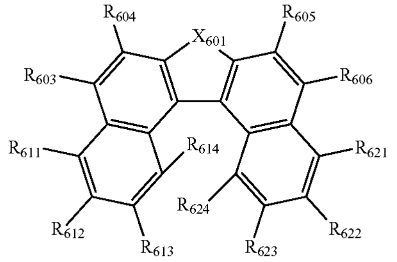

(61-2)

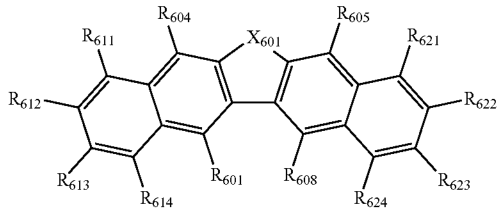

(61-3)

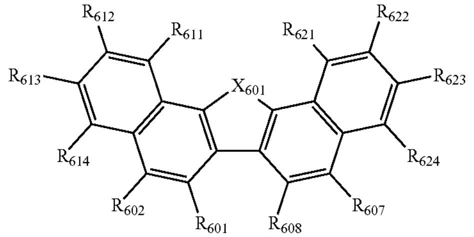

(61-4)

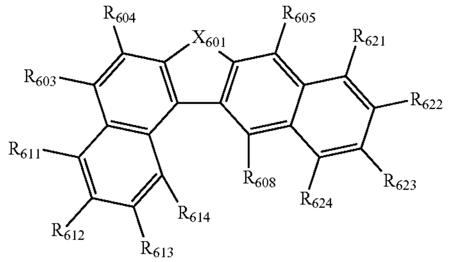

(61-5)

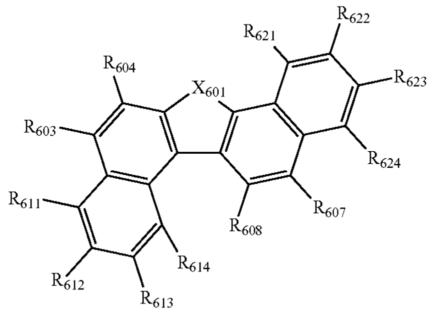

(61-6)

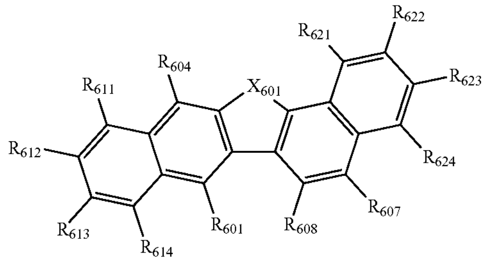

wherein in the formulas (61-1) to (61-6), $X_{601}$ is as defined in the formula (61);

at least two of $R_{601}$ to $R_{624}$ are monovalent groups represented by the formula (64);

$R_{601}$ to $R_{624}$ that are not monovalent groups represented by the formula (64) are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

In one embodiment, the compound represented by the formula (61) is represented by any one of the following formulas (61-7) to (61-18):

(61-7)

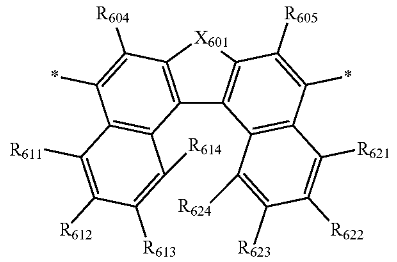

(61-8)

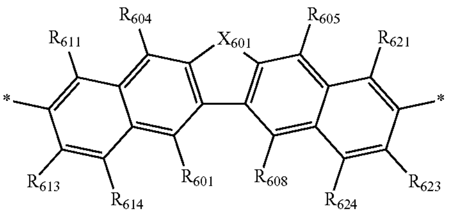

(61-9)

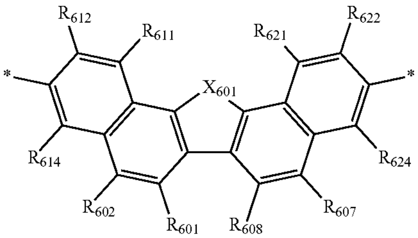

-continued (61-10)

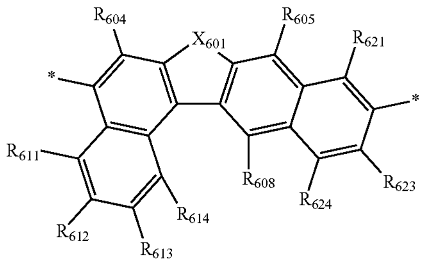

(61-11)

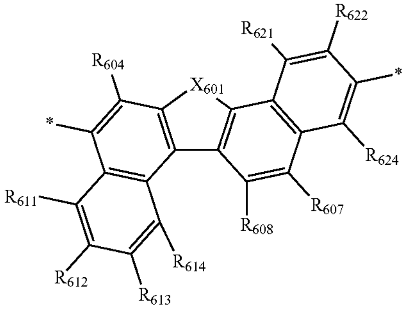

(61-12)

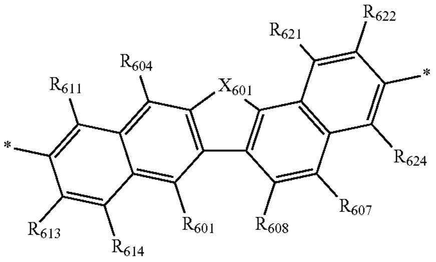

(61-13)

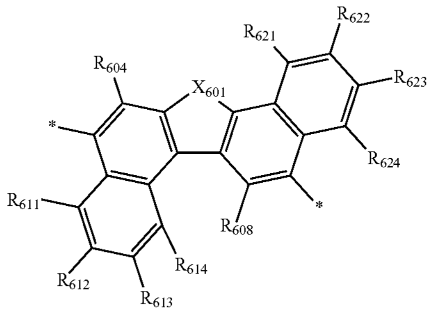

(61-14)

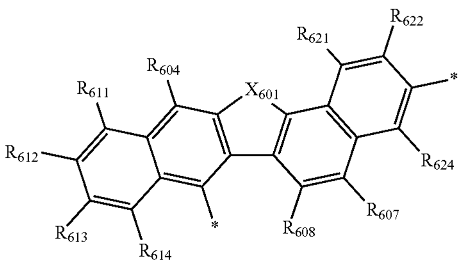

-continued (61-15)

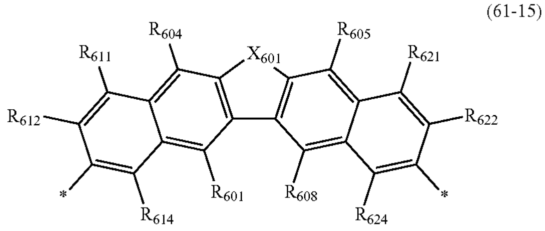

(61-16)

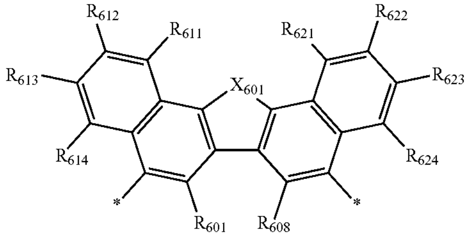

(61-17)

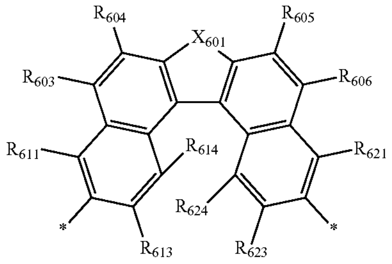

(61-18)

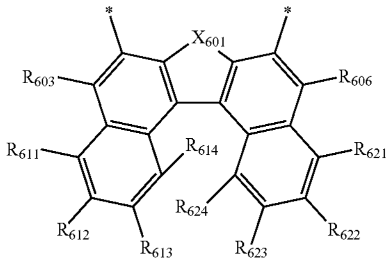

wherein in the formulas (61-7) to (61-18), $X_{601}$ is as defined in the formula (61); * is a single bond bonding to the monovalent group represented by the formula (64); and $R_{601}$ to $R_{624}$ are the same as $R_{601}$ to $R_{624}$ that are not monovalent groups represented by the formula (64).

$R_{601}$ to $R_{608}$ which do not form the divalent group represented by the formula (62) and (63) and are not monovalent groups represented by the formula (64), and $R_{611}$ to $R_{614}$ and $R_{621}$ to $R_{624}$ which are not monovalent groups represented by the formula (64) are preferably independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

The monovalent group represented by the formula (64) is preferably represented by the following formulas (65) or (66):

(65)

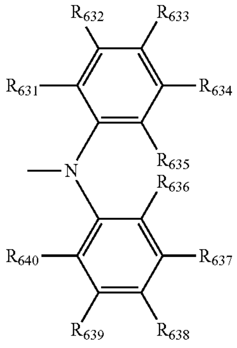

wherein in the formula (65), $R_{631}$ to $R_{640}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

(66)

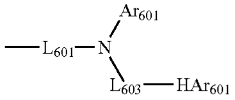

In the formula (66), $Ar_{601}$, $L_{601}$ and Leo are as defined in the formula (64); and $HAr_{601}$ is a structure represented by the following formula (67);

(67)

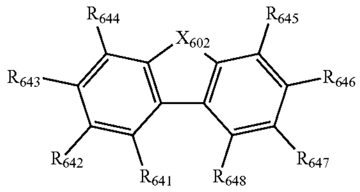

wherein in the formula (67) $X_{602}$ is an oxygen atom or a sulfur atom;

any one of $R_{641}$ to $R_{648}$ is a single bond bonding to $L_{603}$;

$R_{641}$ to $R_{646}$ which are not single bonds are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).)

As specific example of the compound represented by the formula (61), in addition to the compounds described in WO2014/104144, the following compounds can be given, for example. In the following example compounds, Me represents methyl group.

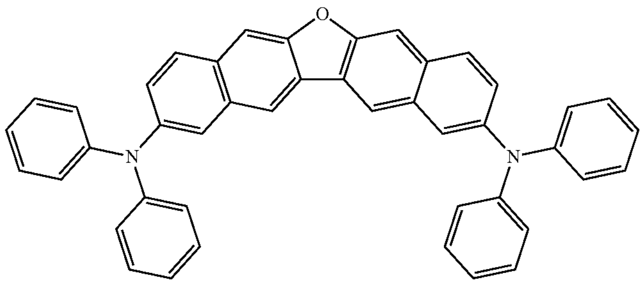

-continued
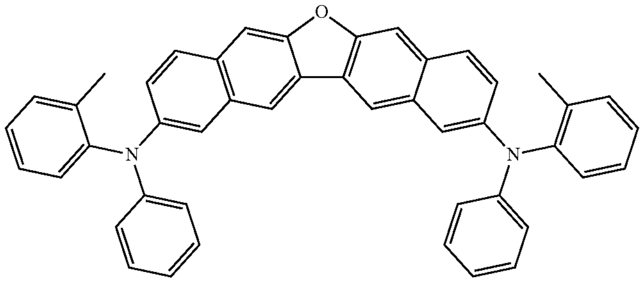
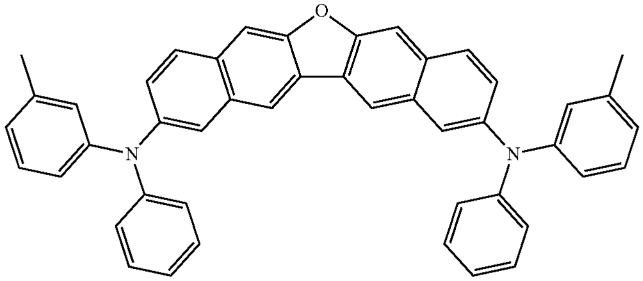
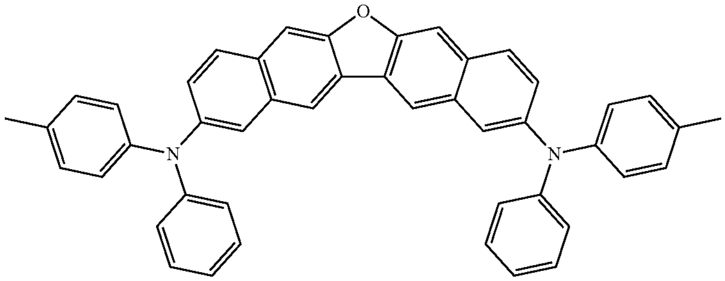
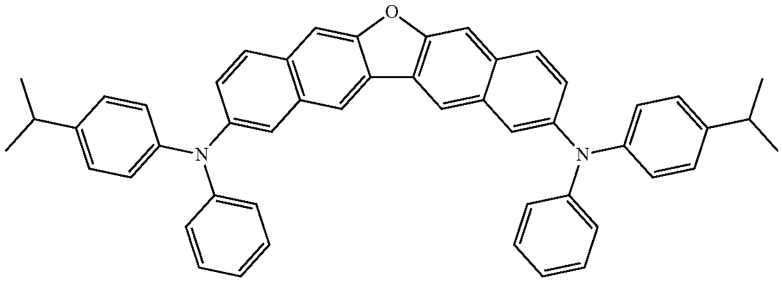
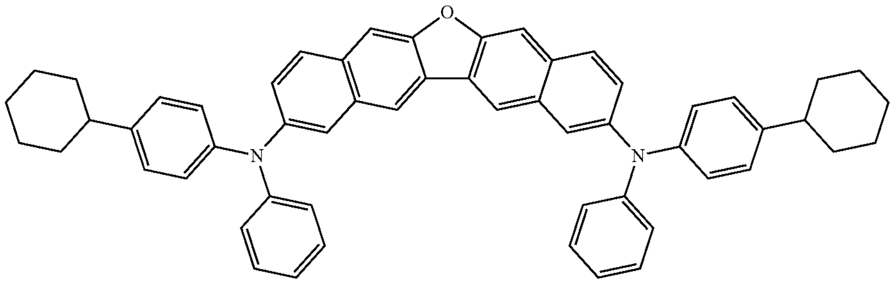
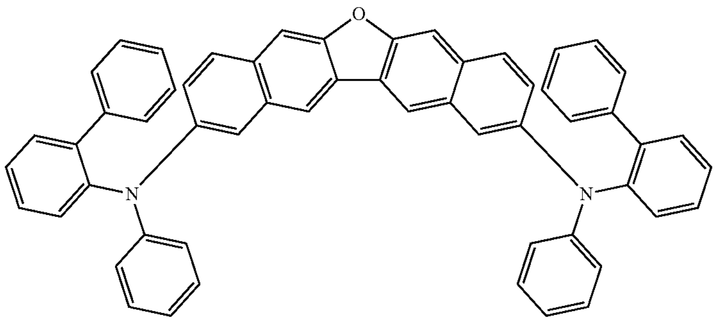

-continued
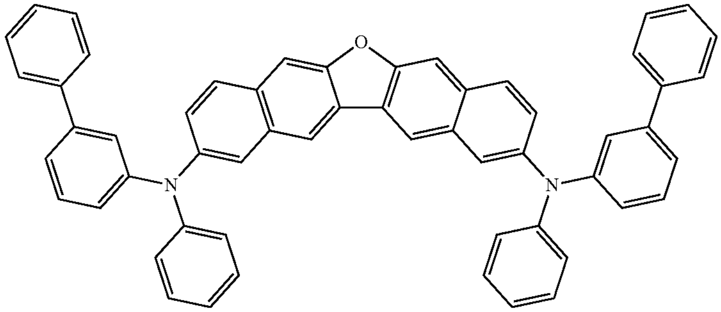
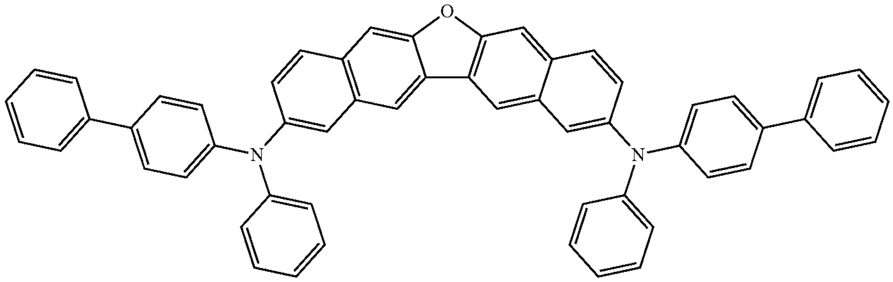
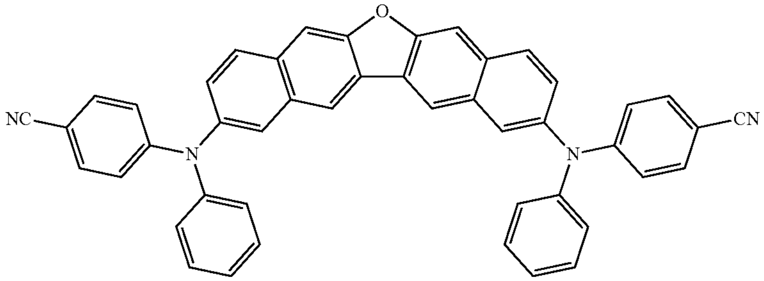
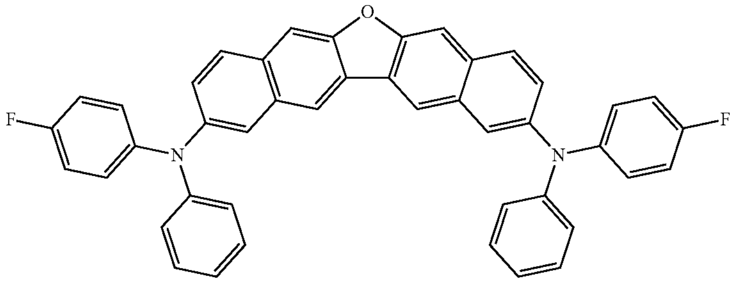
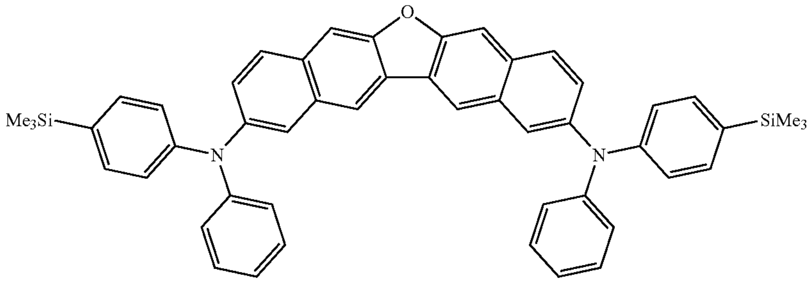
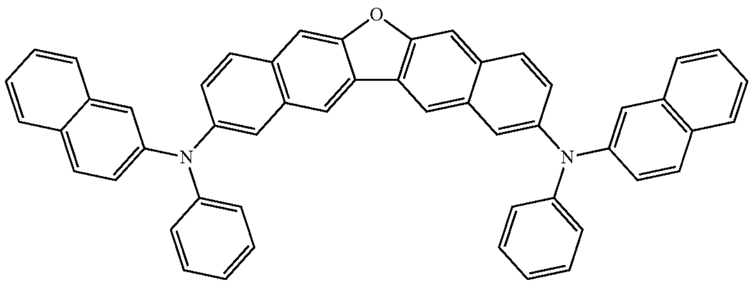

-continued
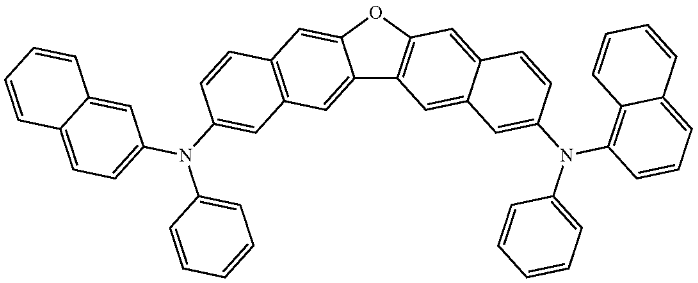
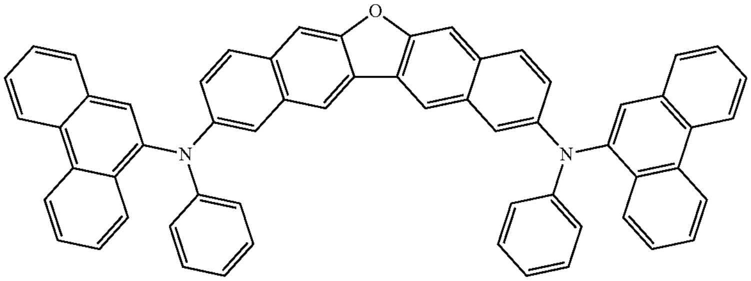
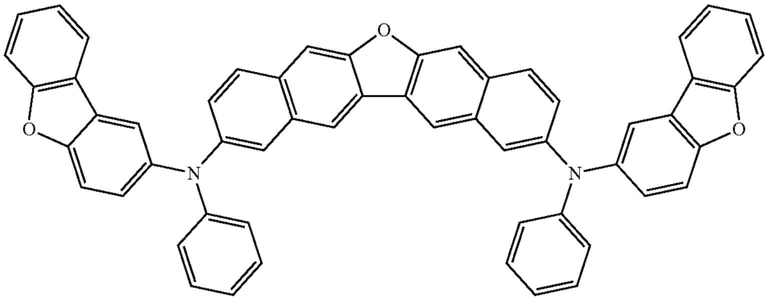
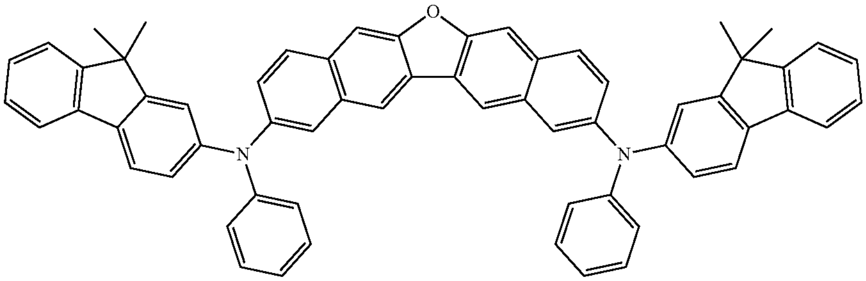
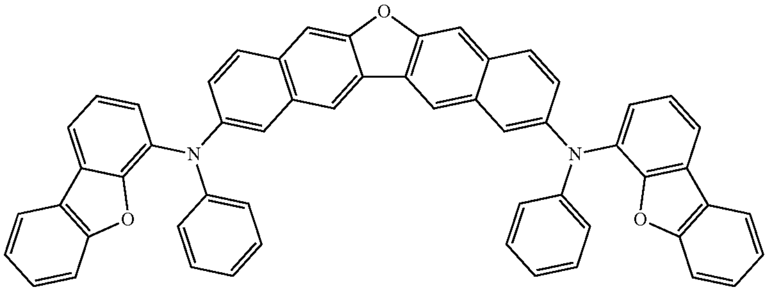
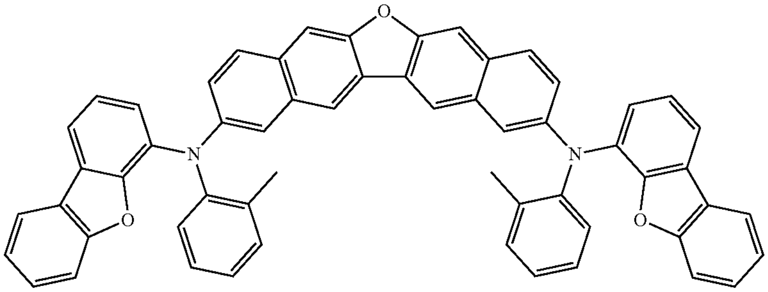

-continued
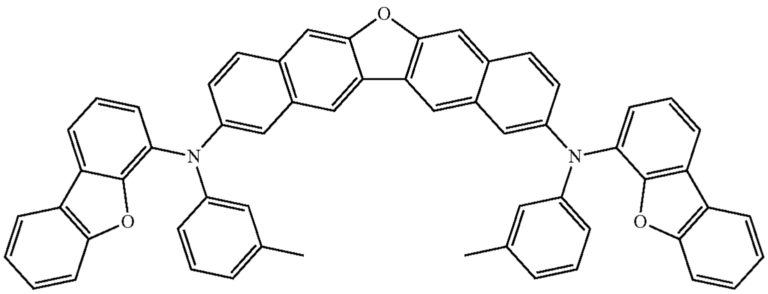
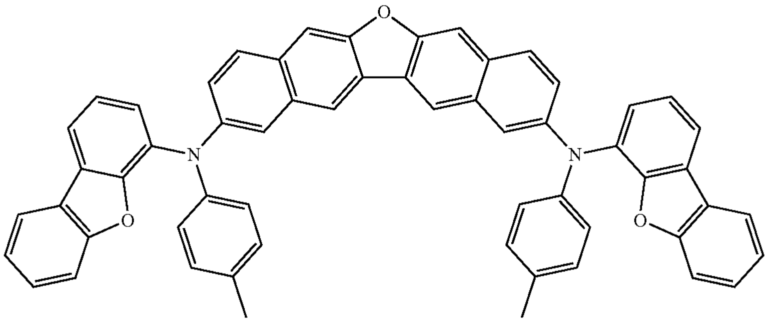
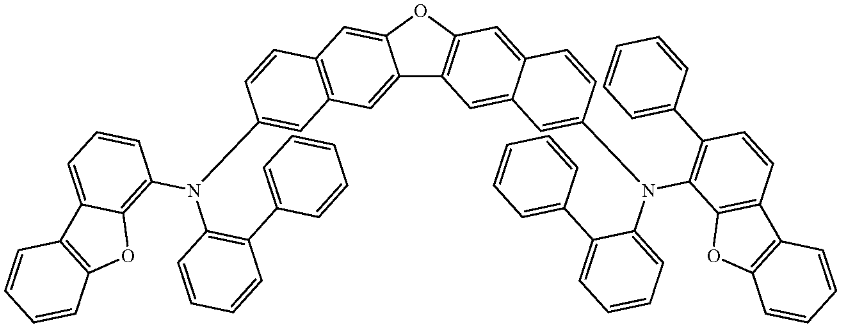
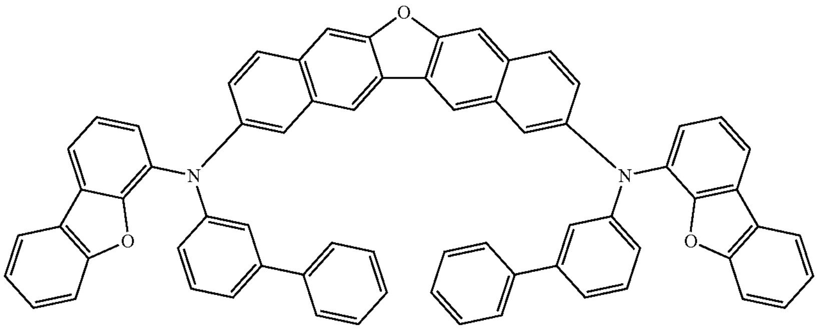
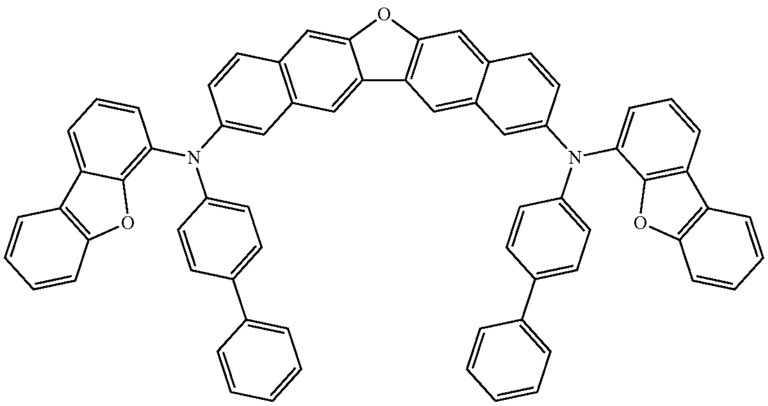

-continued
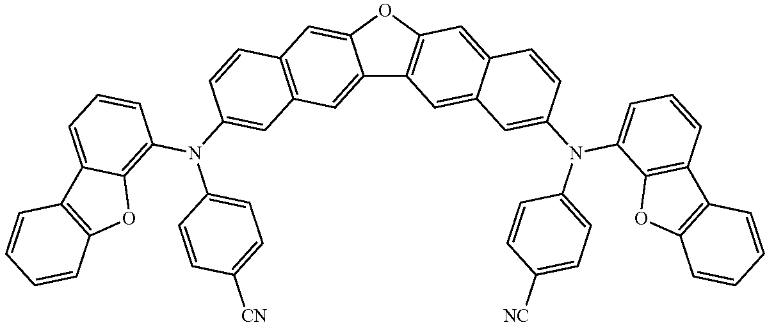
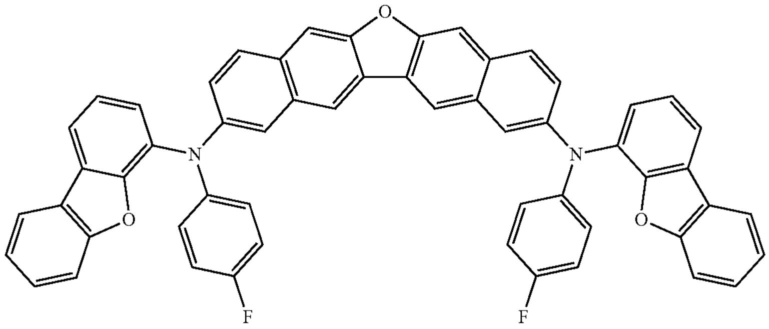
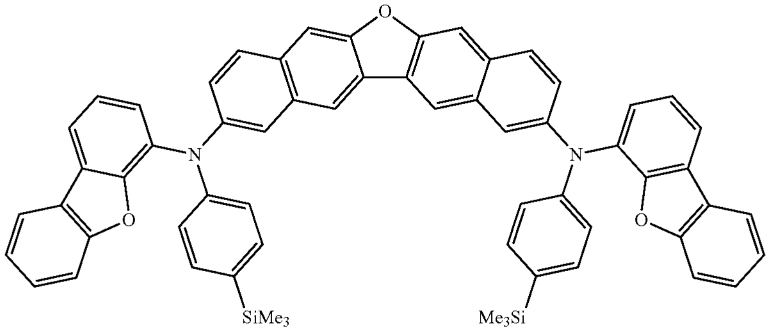
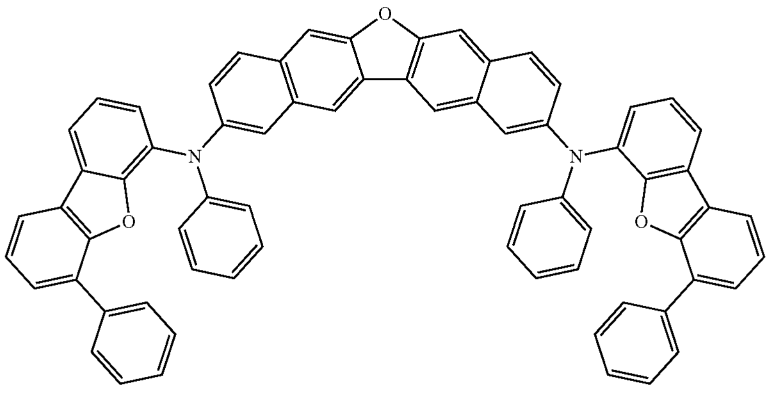

-continued
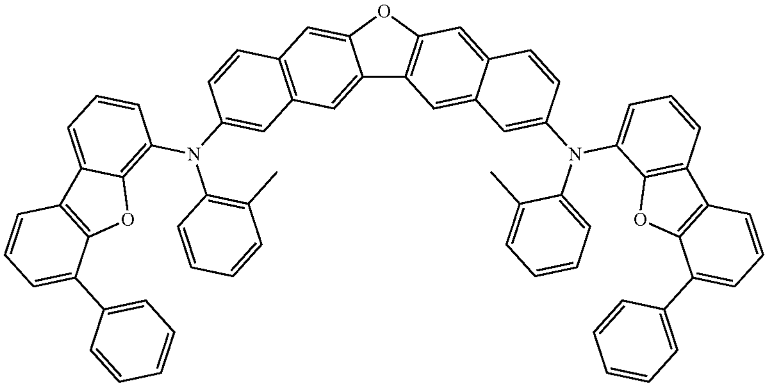
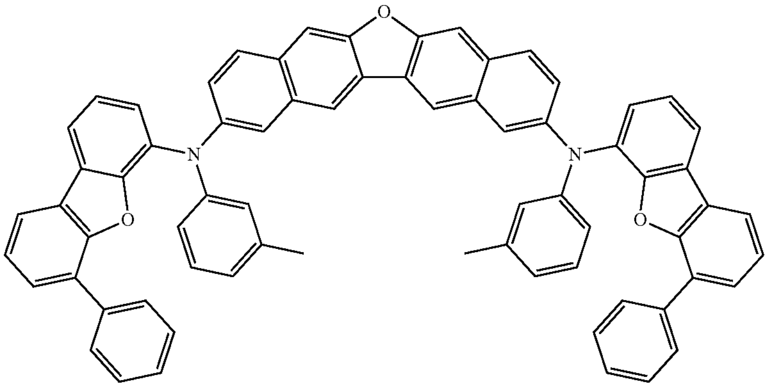
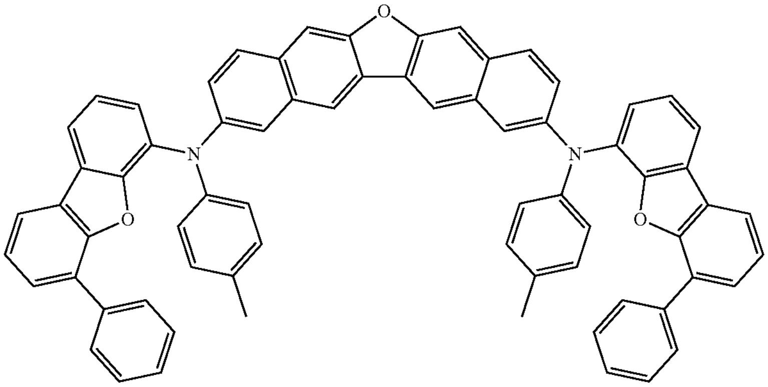
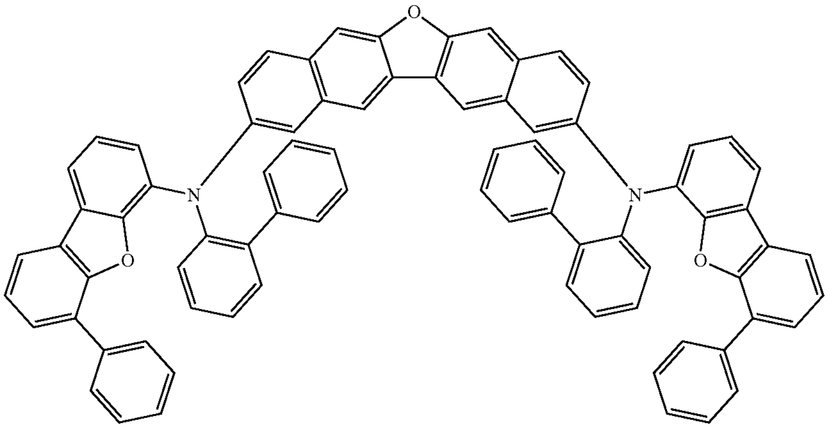

-continued
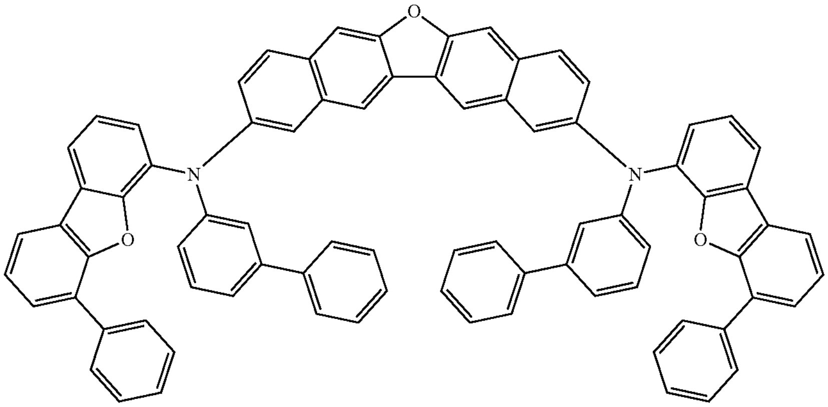
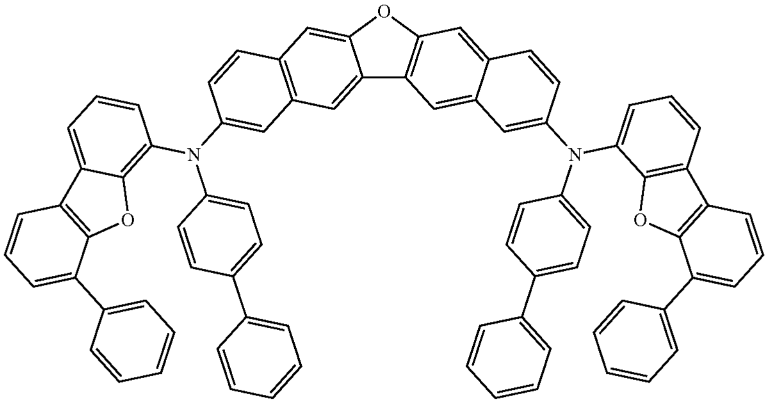
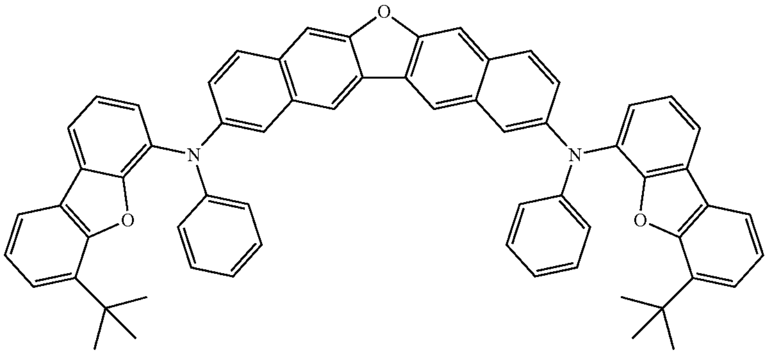
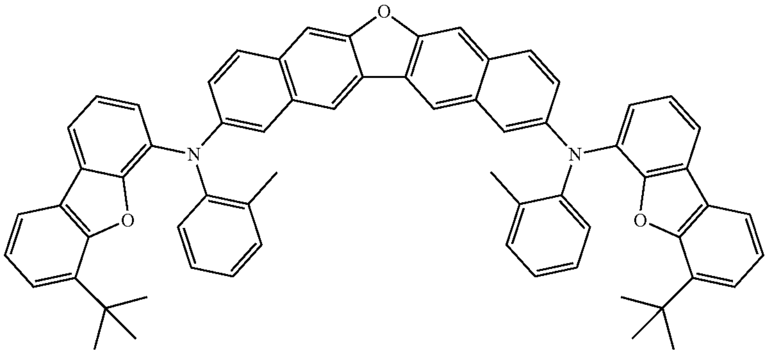

-continued
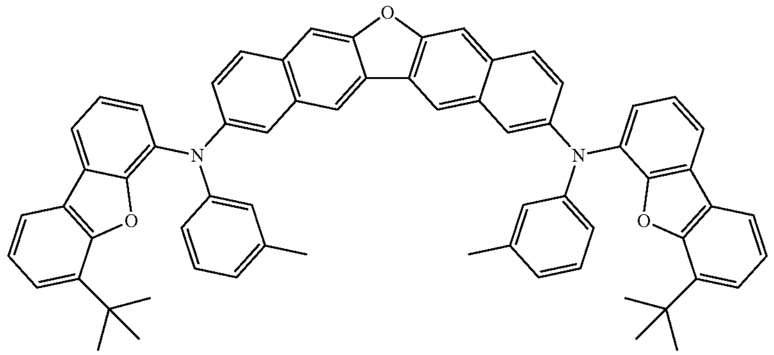
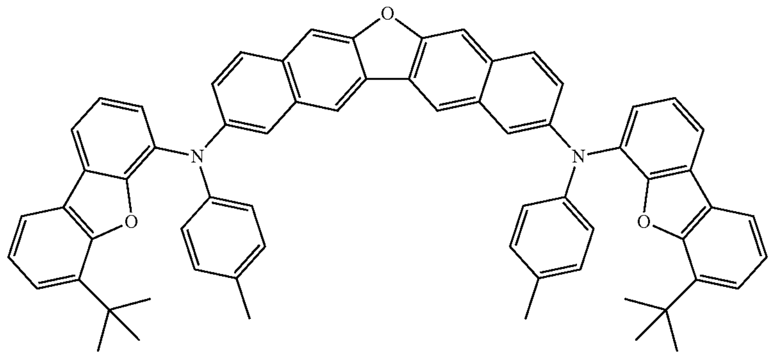
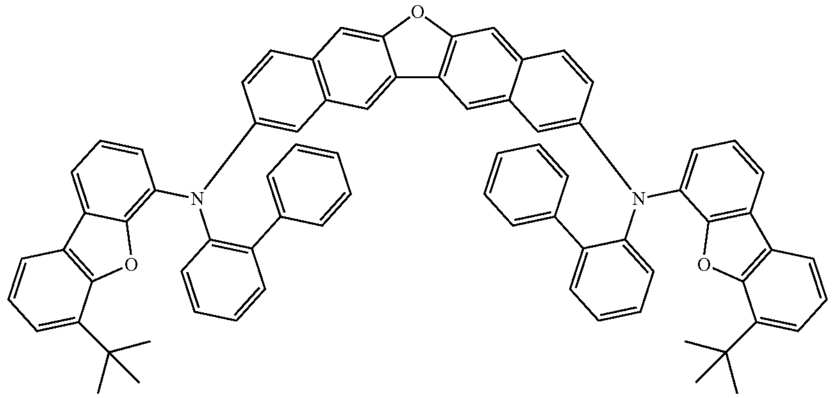
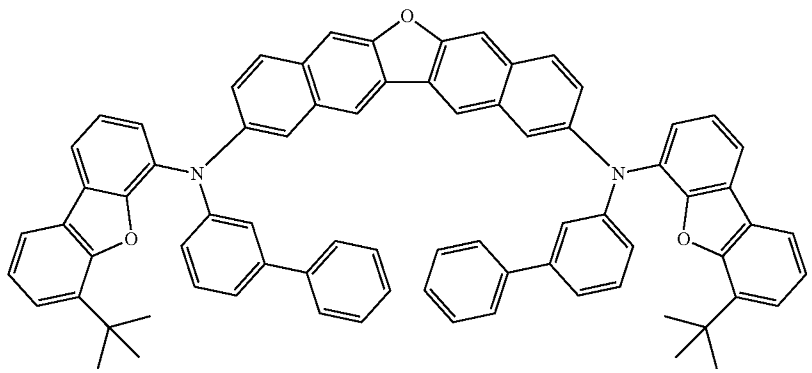

-continued
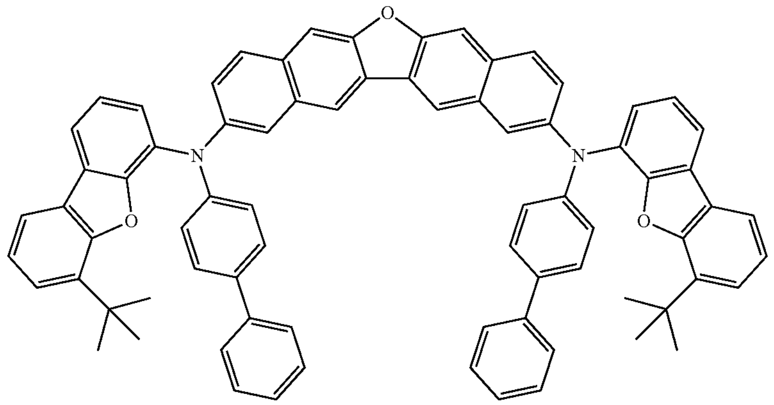
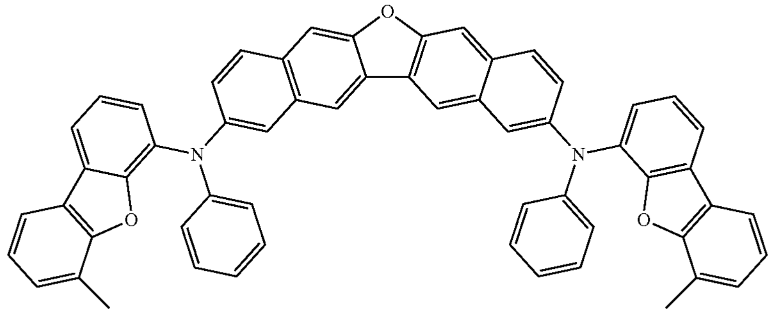
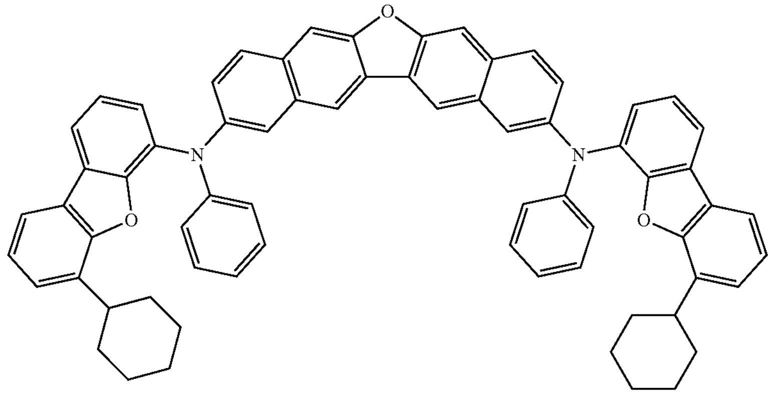
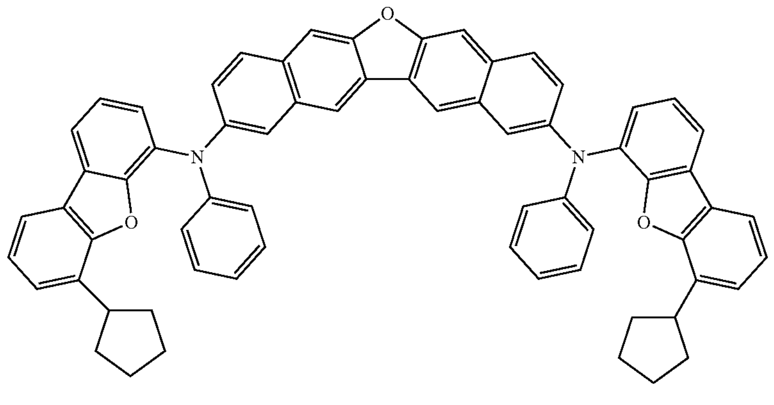

-continued
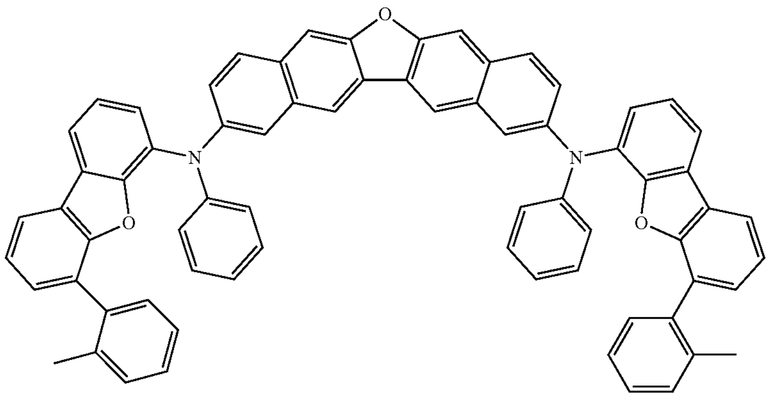
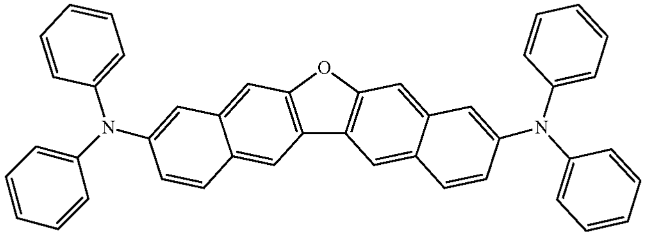
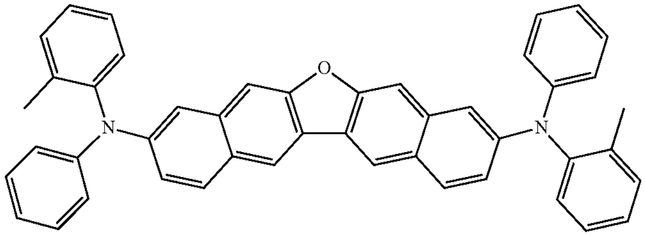
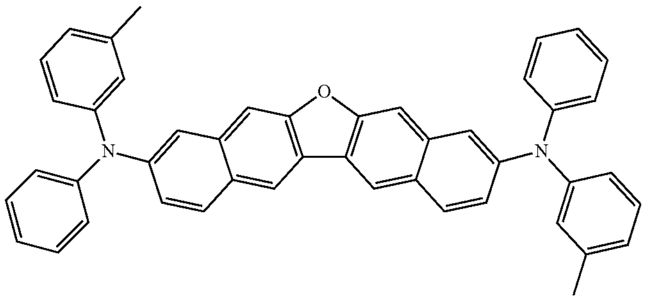
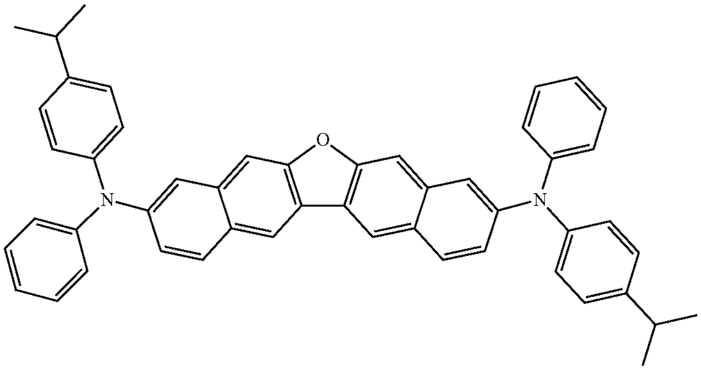

-continued
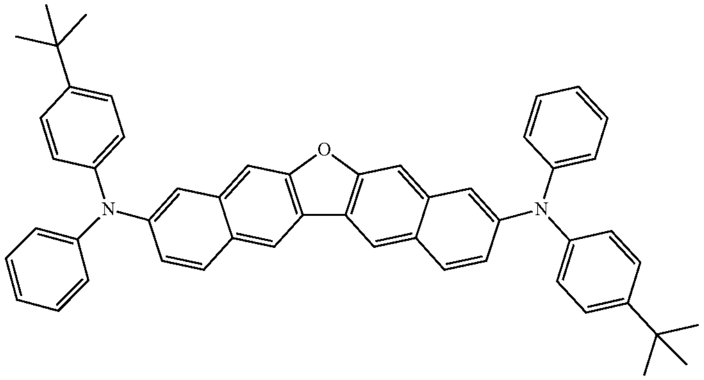
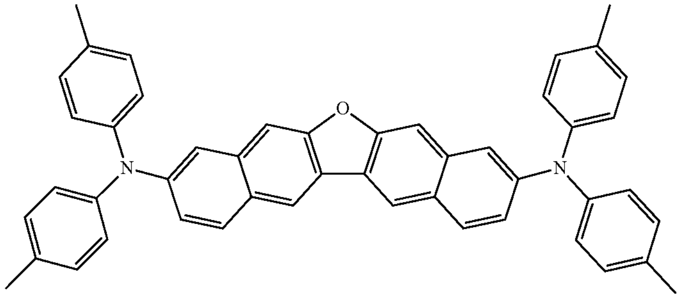
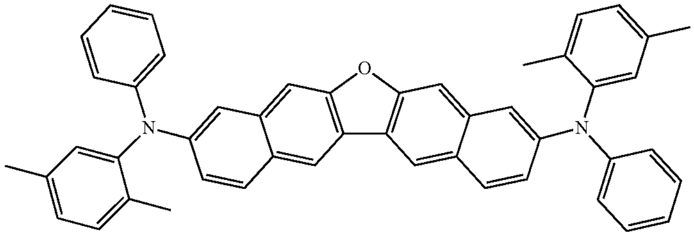
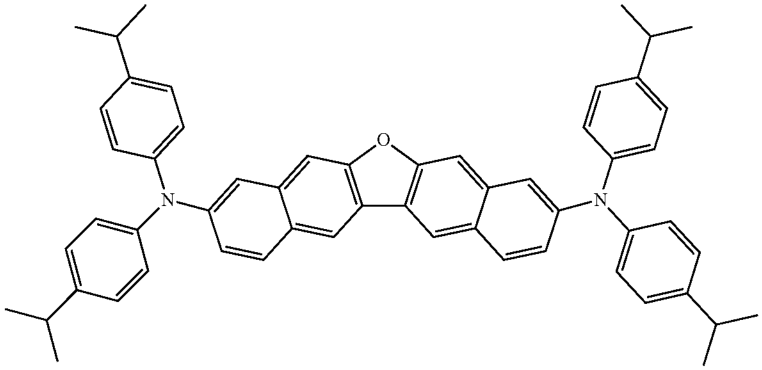
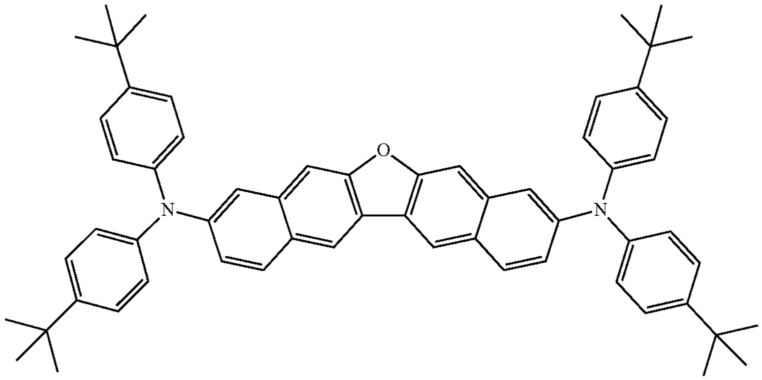

-continued
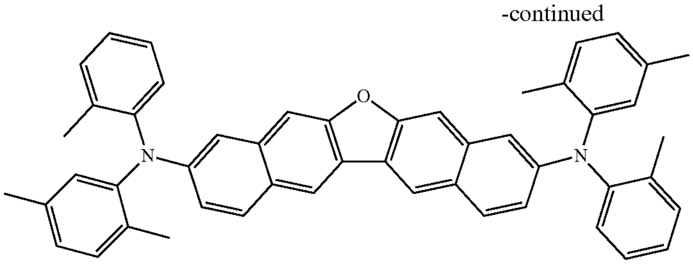
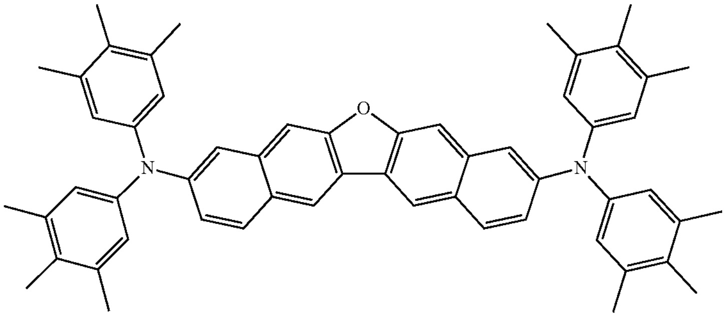
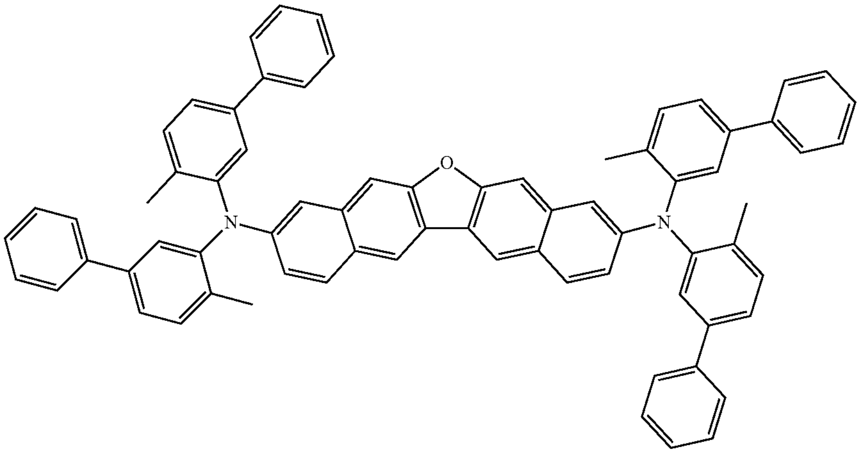
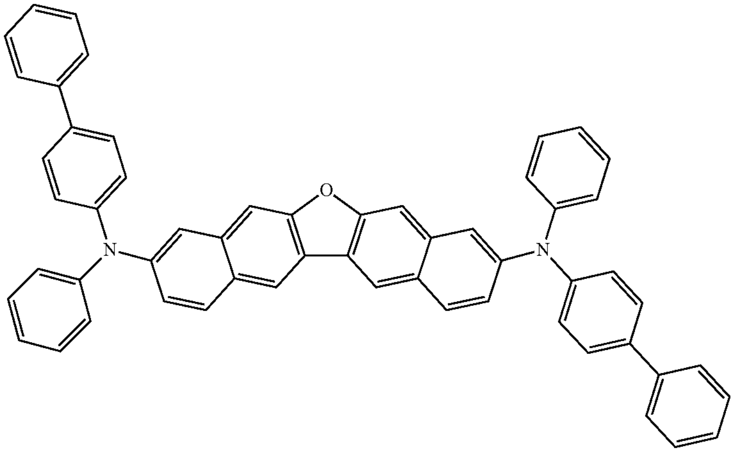
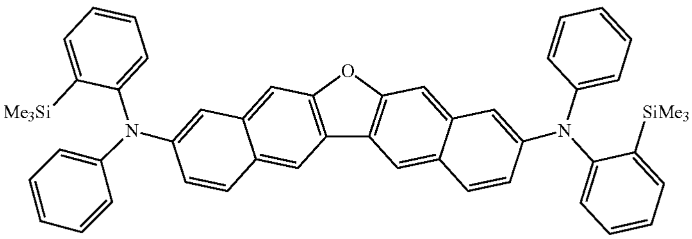

-continued
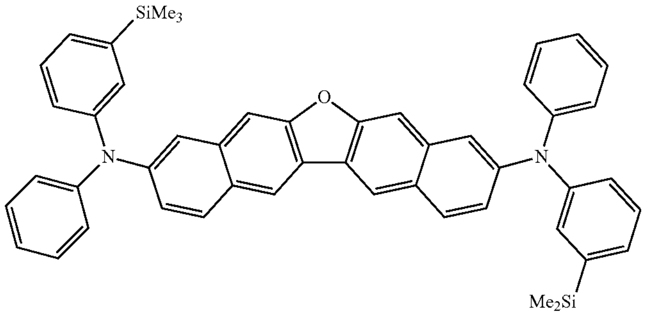
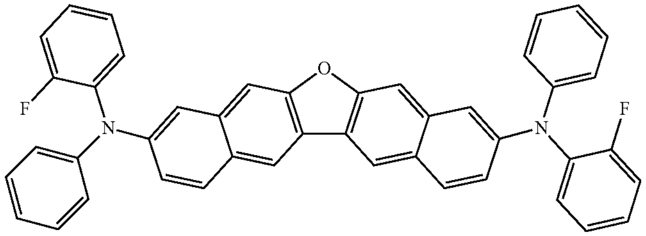
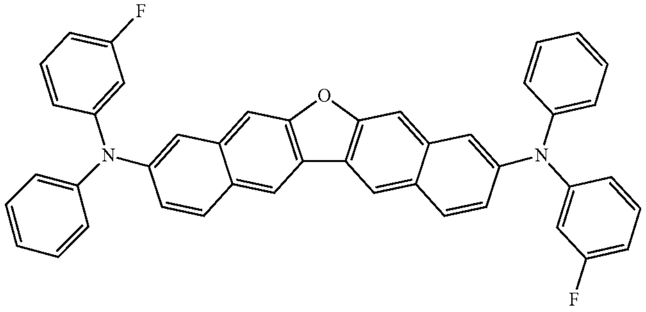
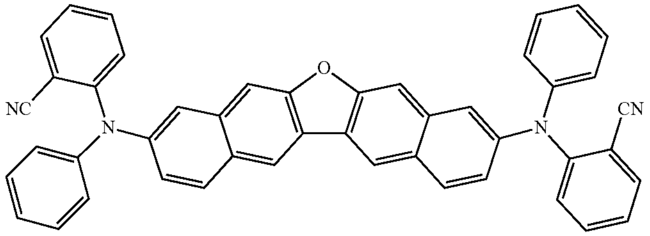
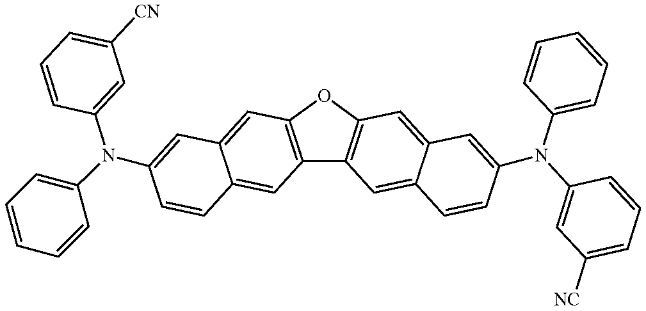
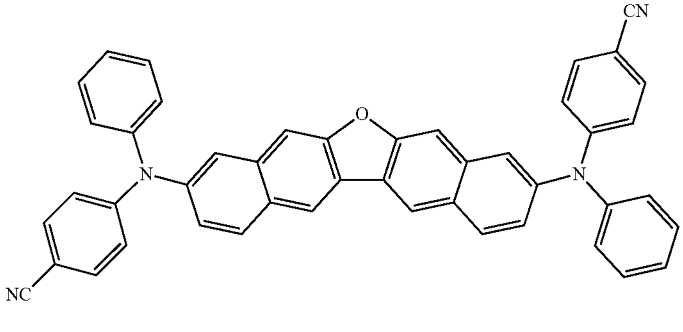

-continued
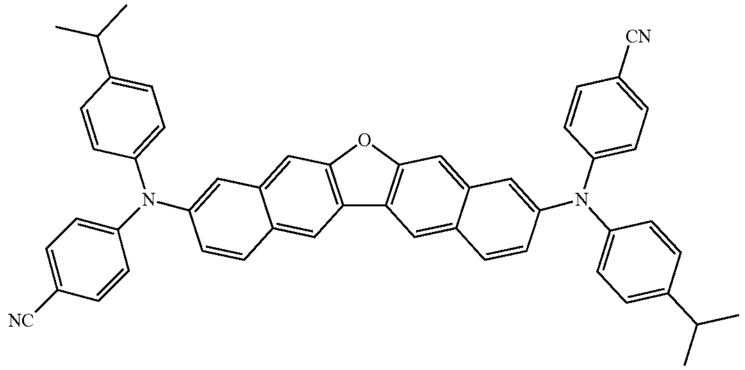
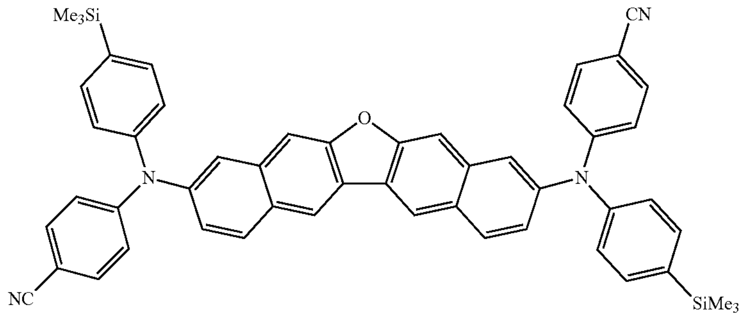
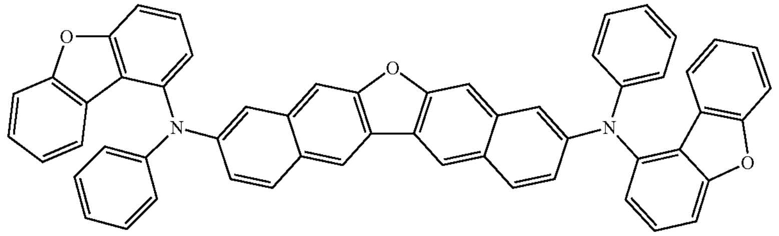
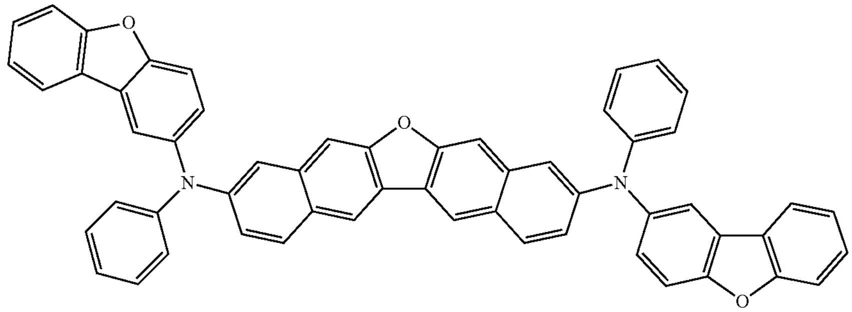
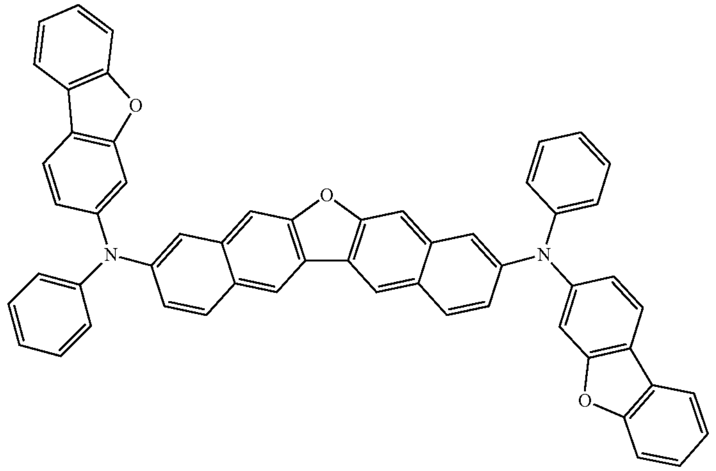

-continued
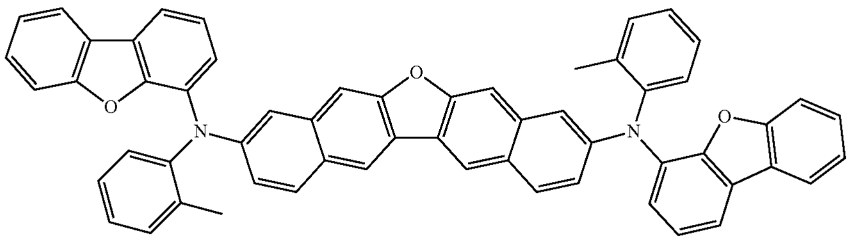
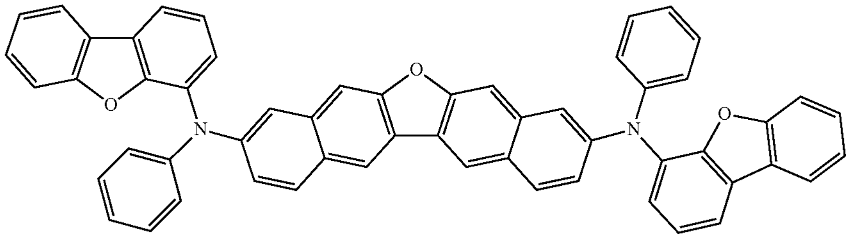
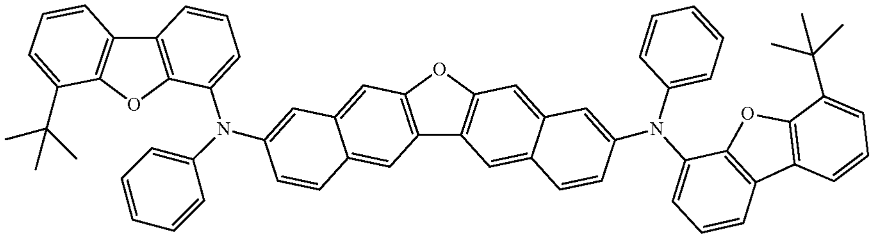
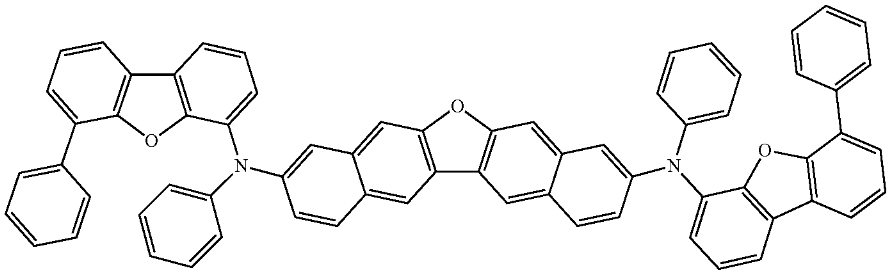
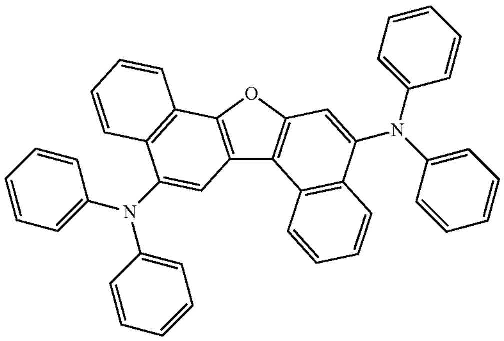
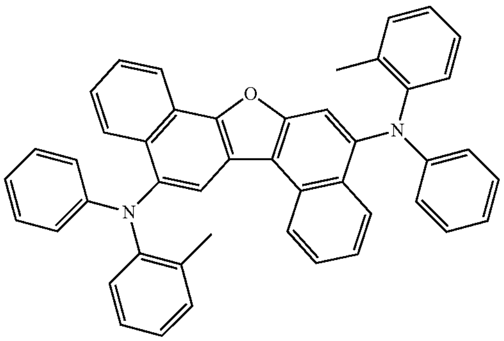

-continued
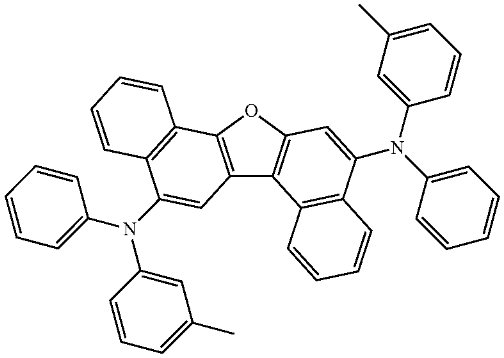
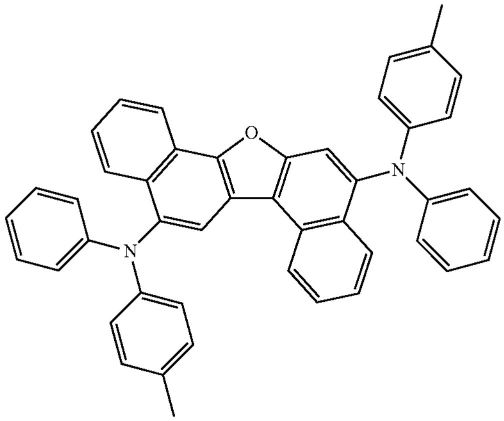
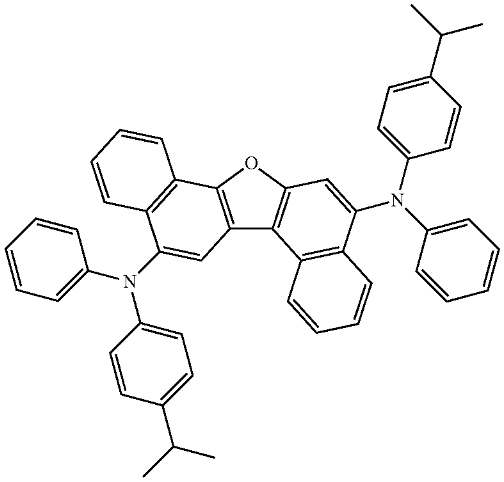
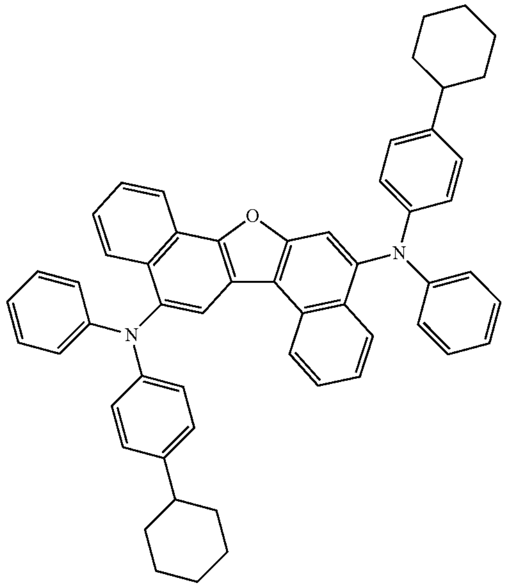
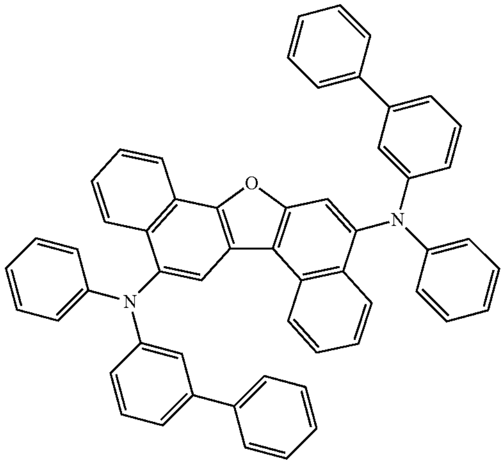
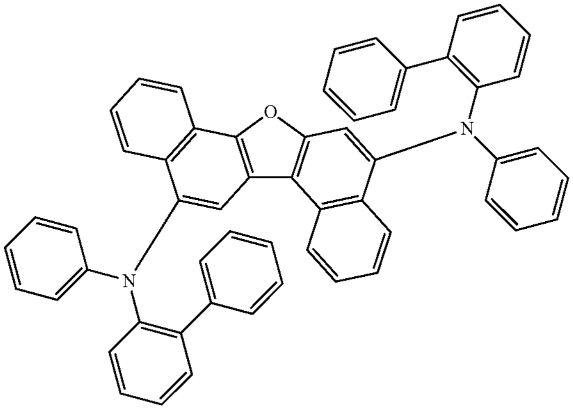

-continued
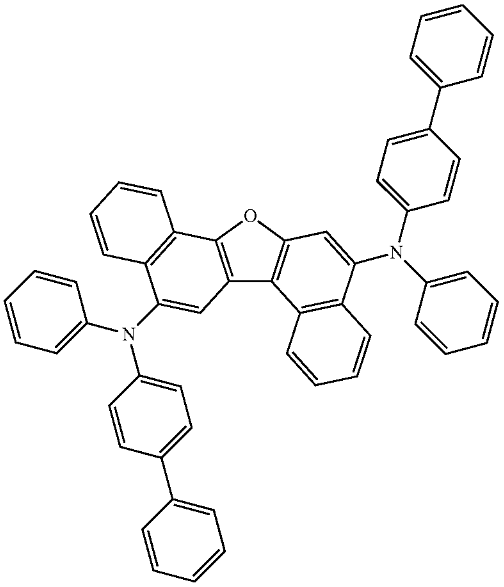
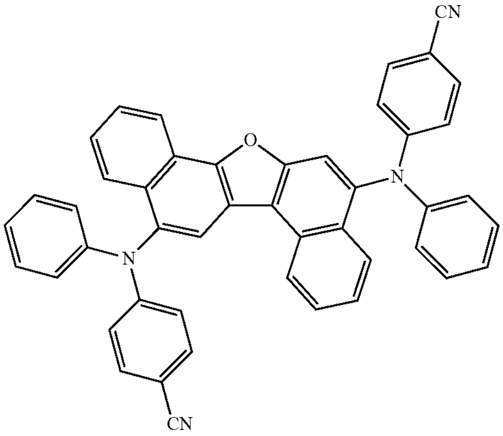
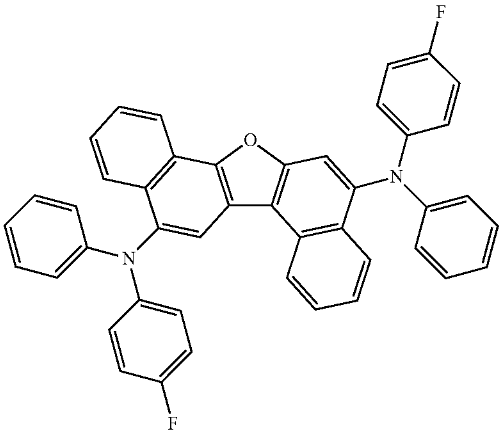
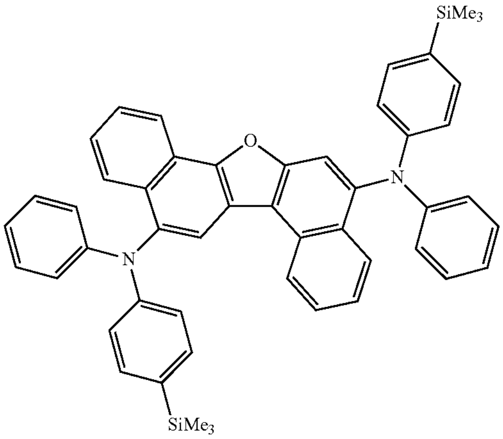
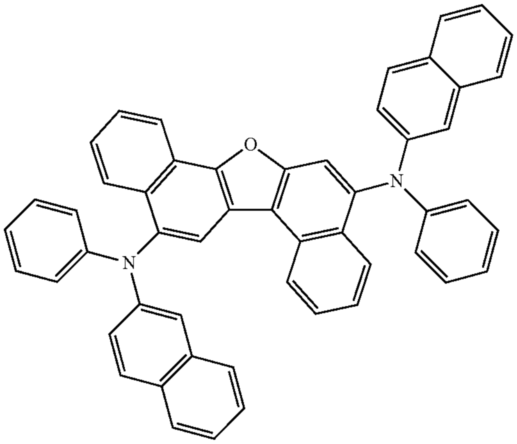
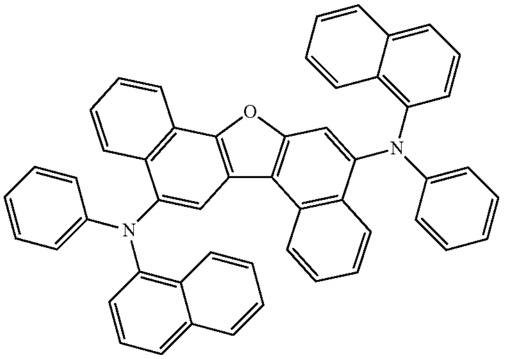

-continued
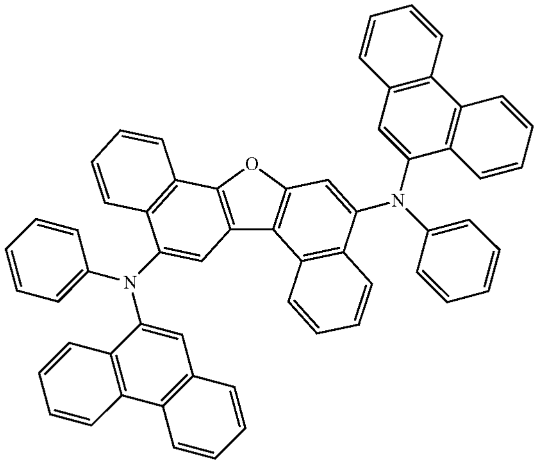
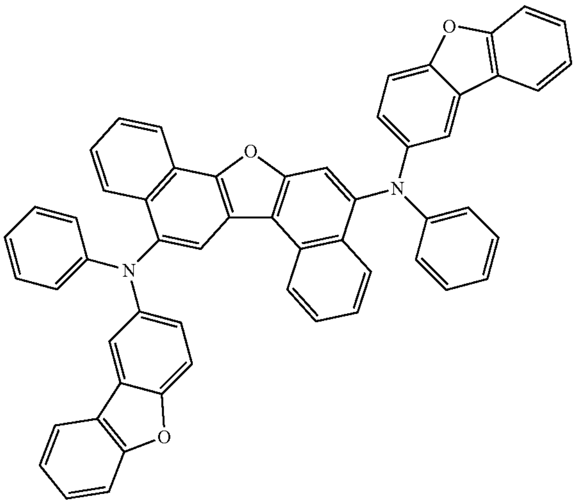
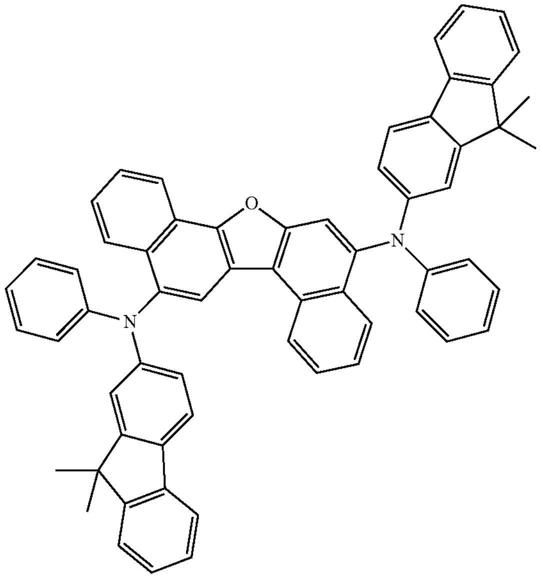
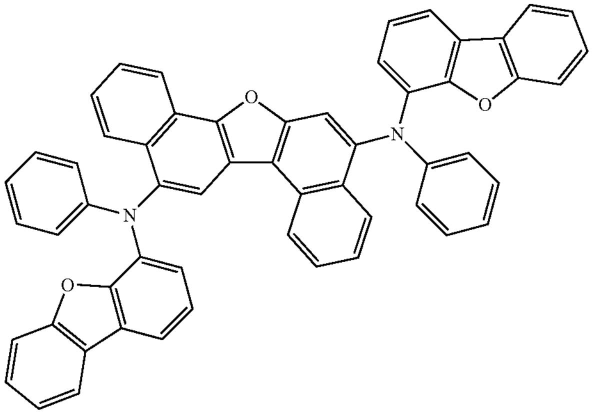
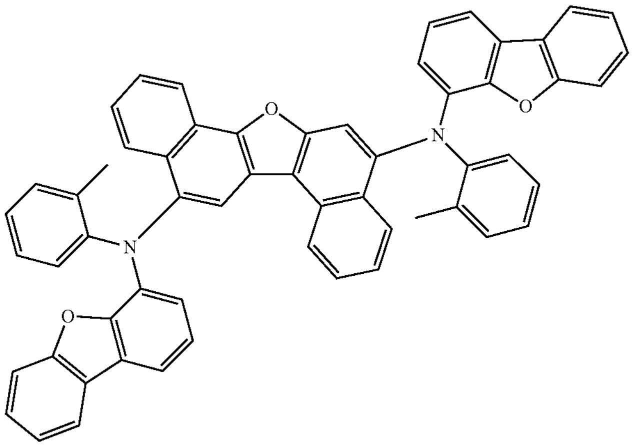

-continued
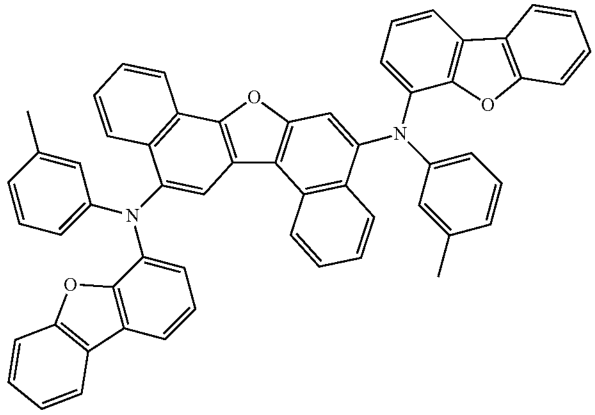
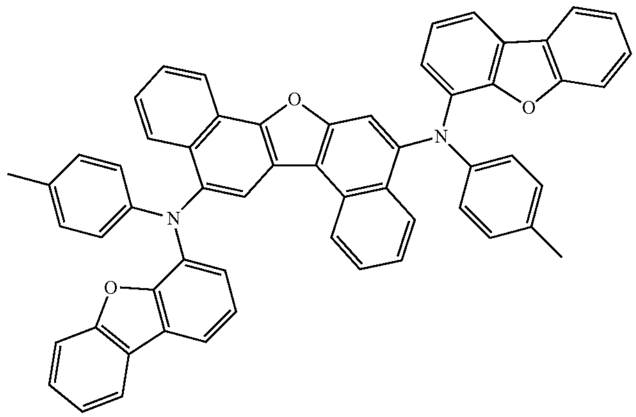
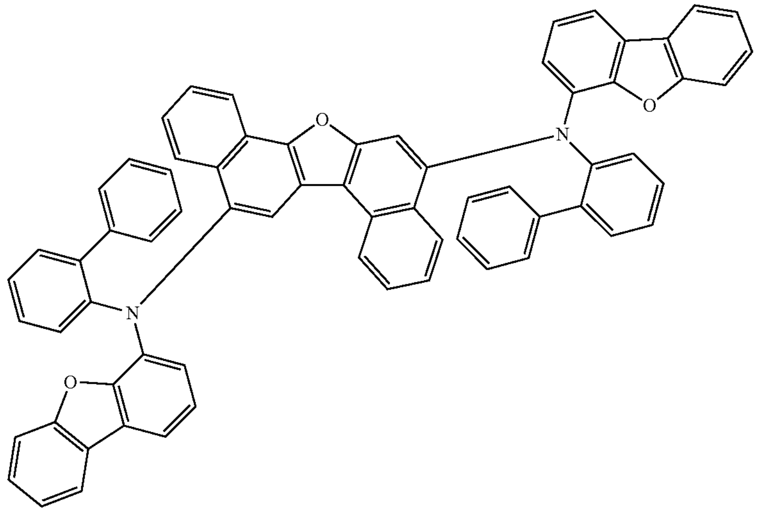

-continued
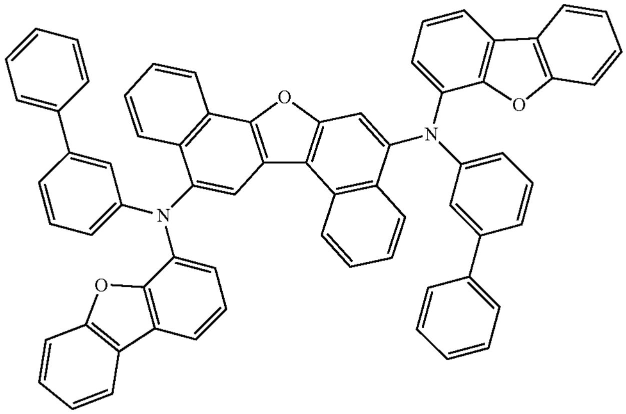
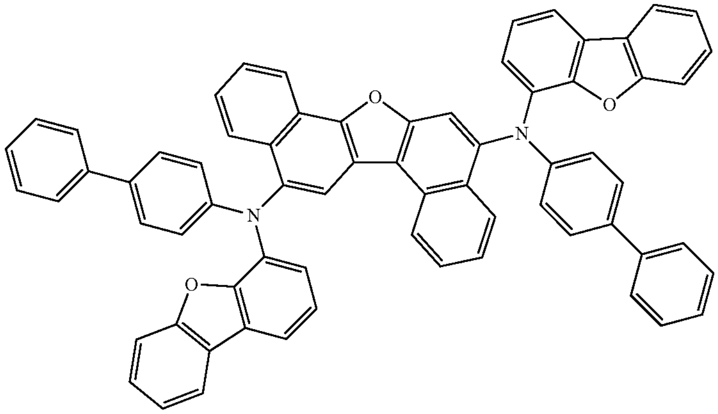
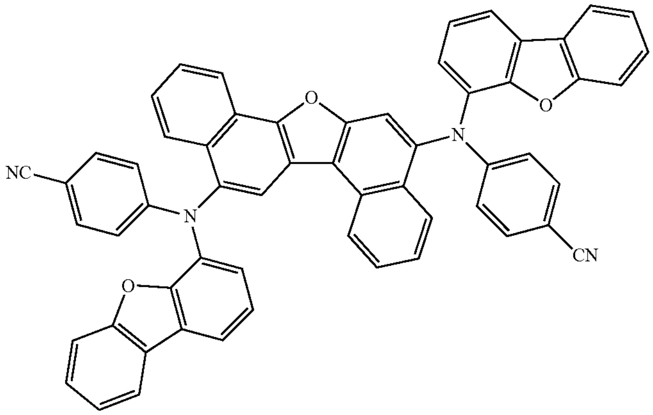
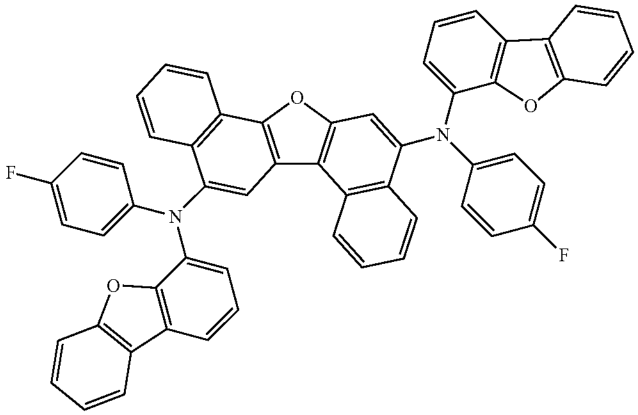

-continued
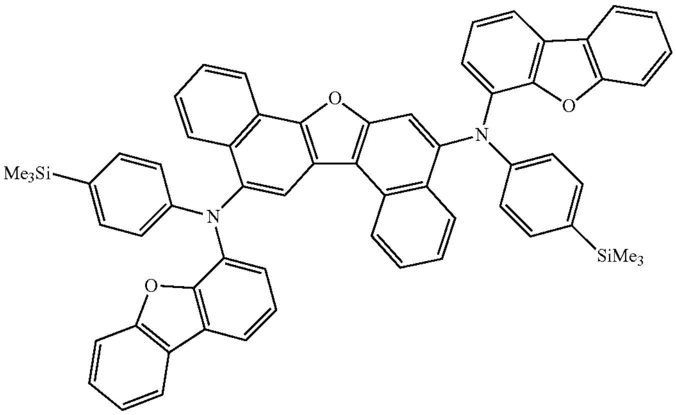
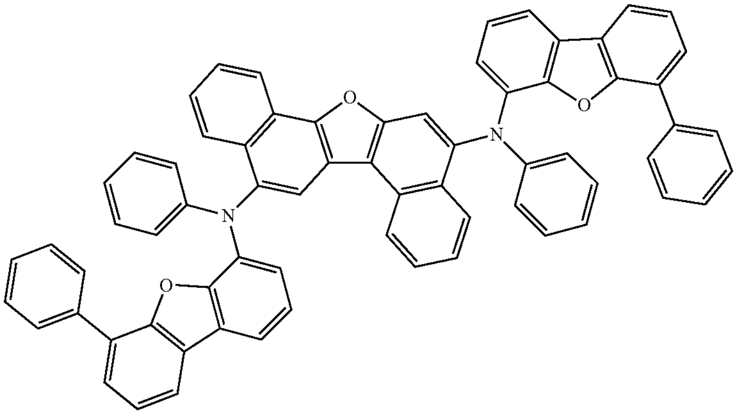
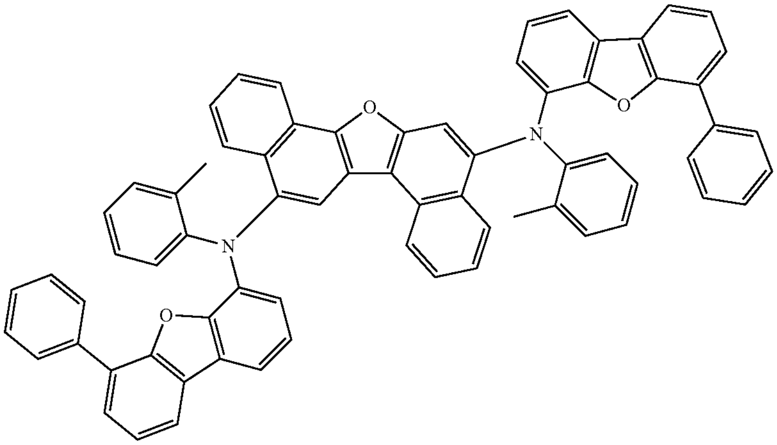
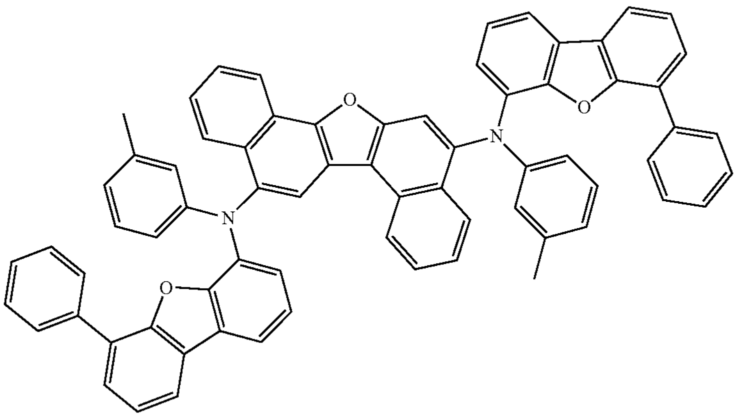

-continued
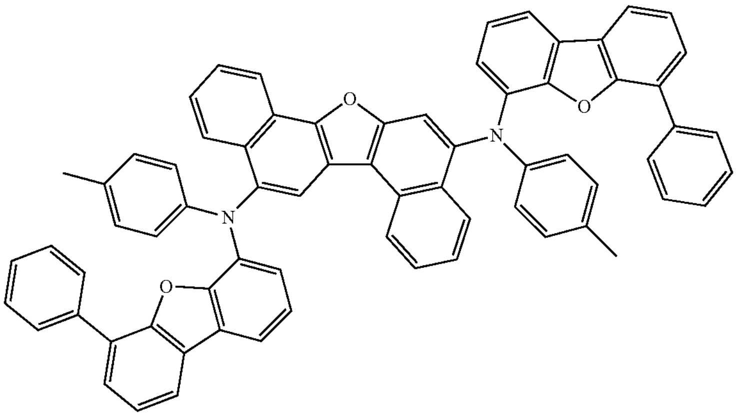
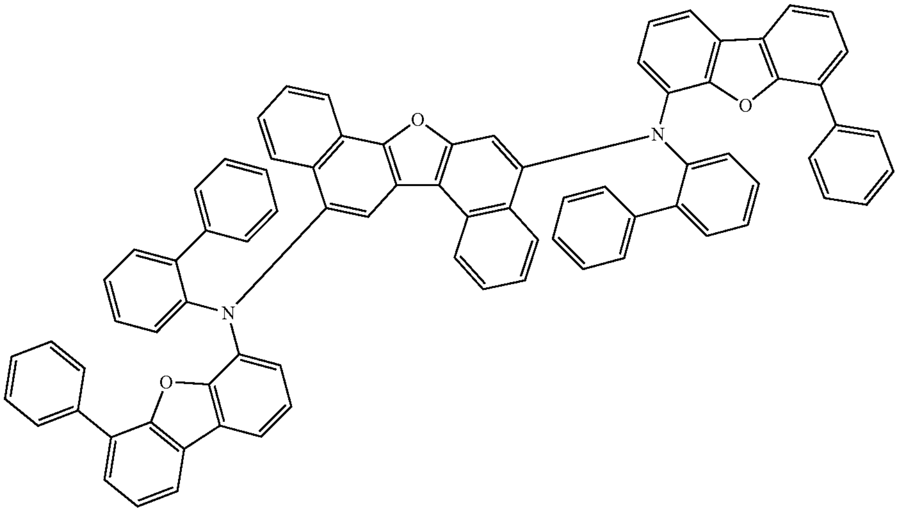
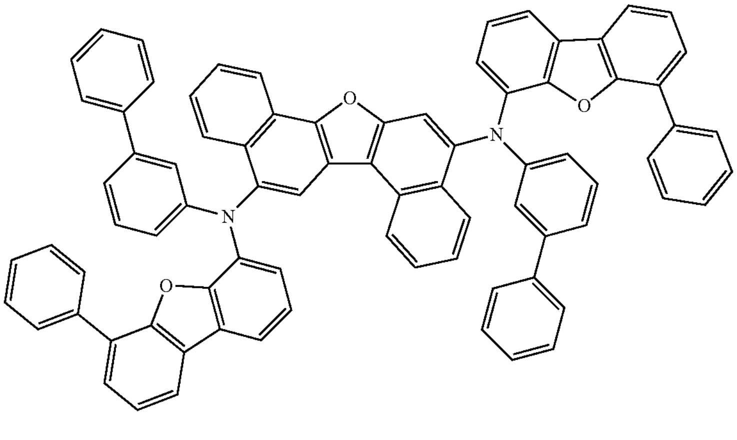

-continued
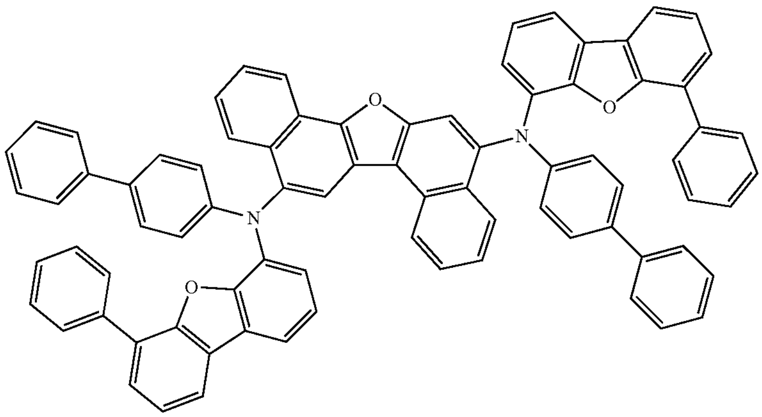
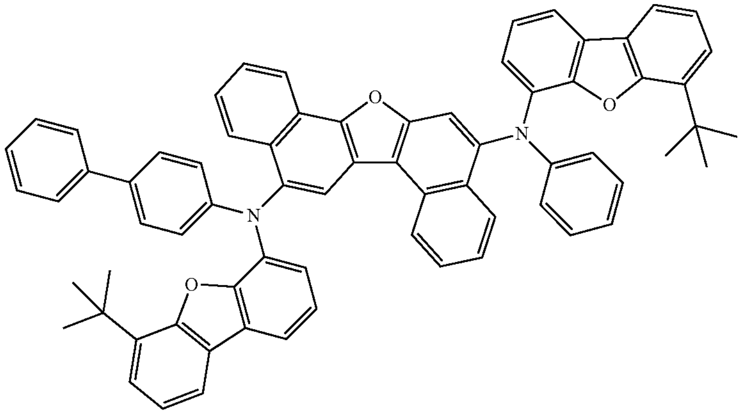
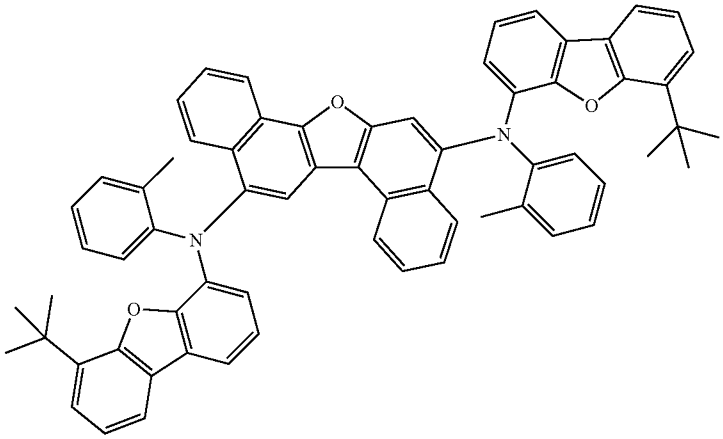
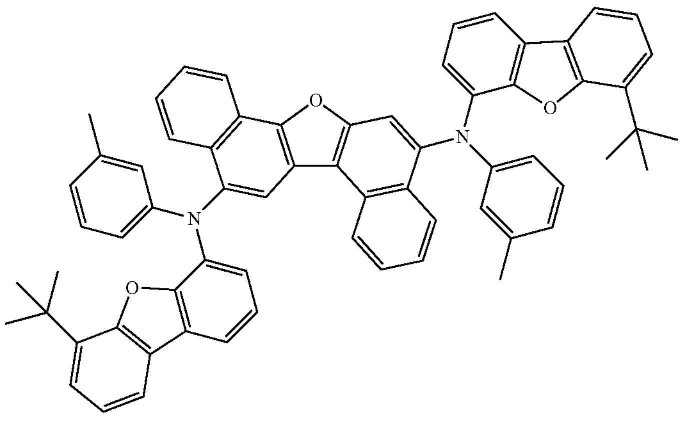

-continued
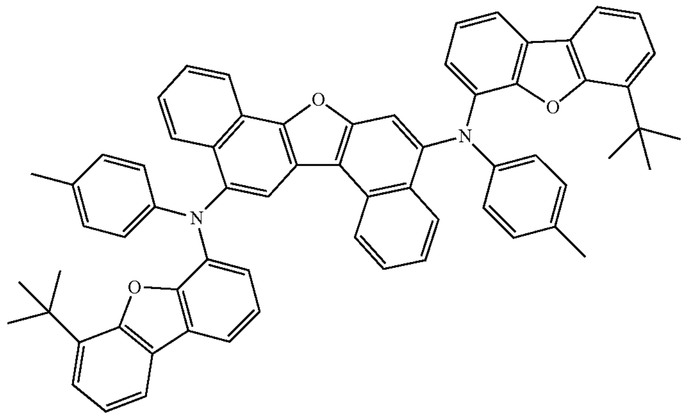
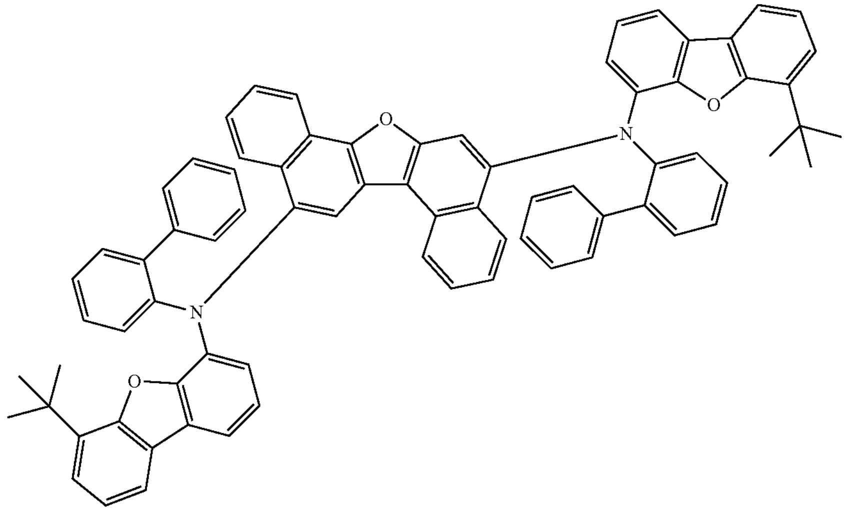
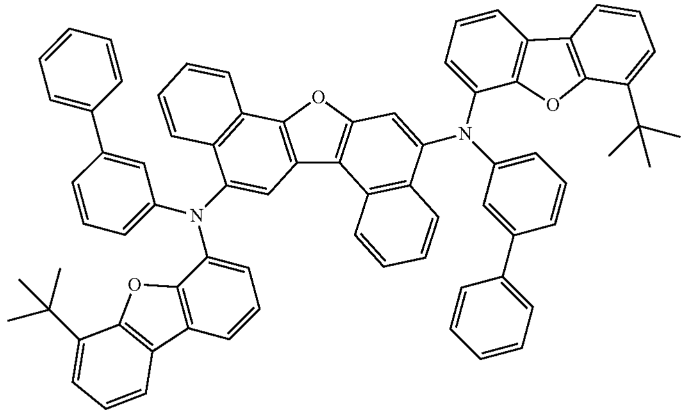

-continued
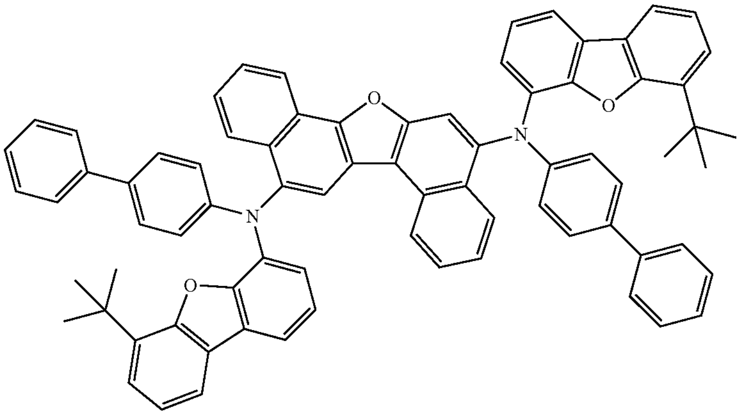
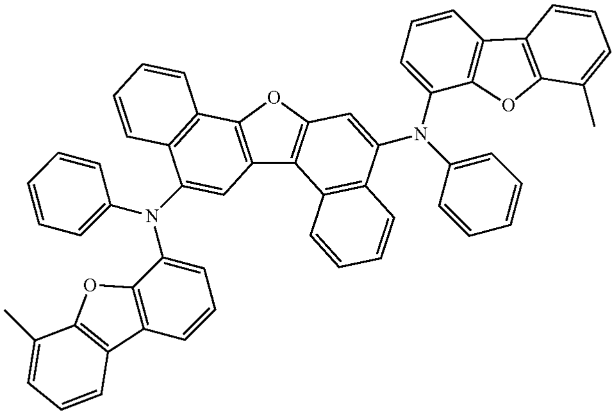
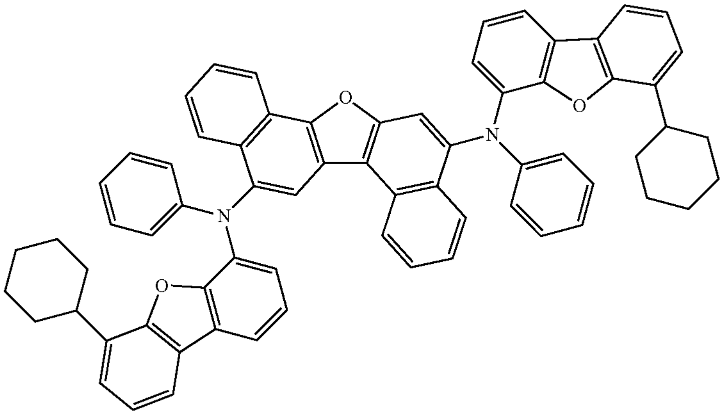
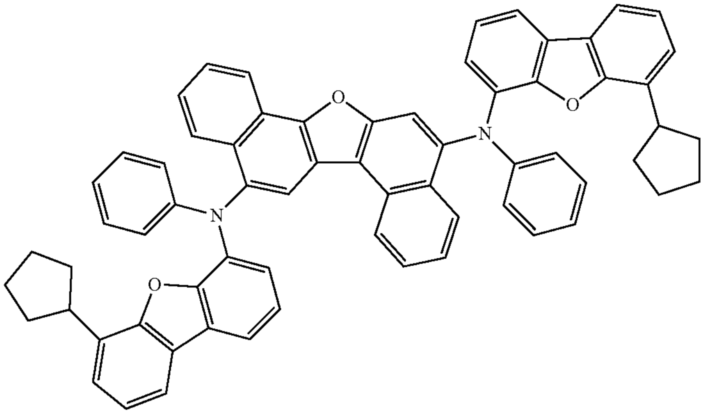

-continued
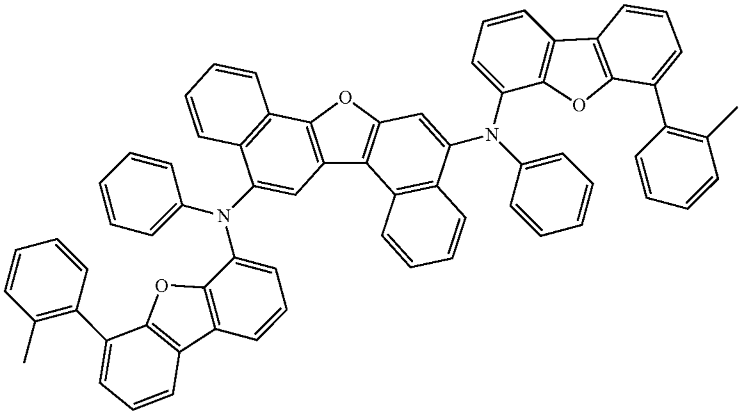
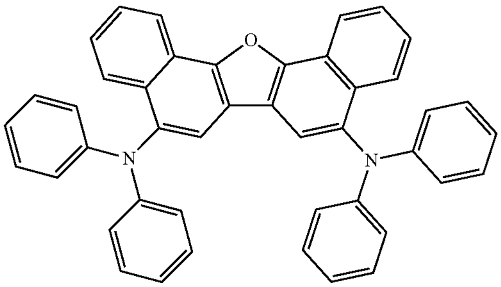
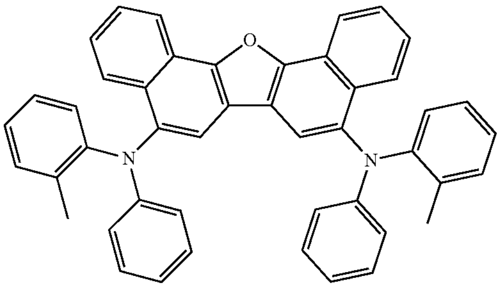
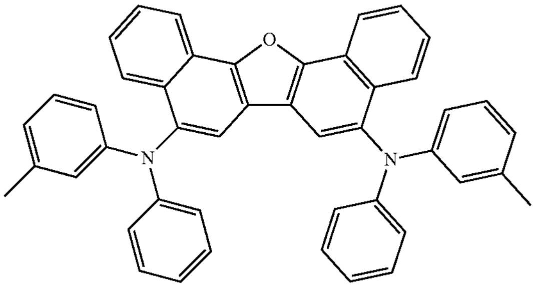
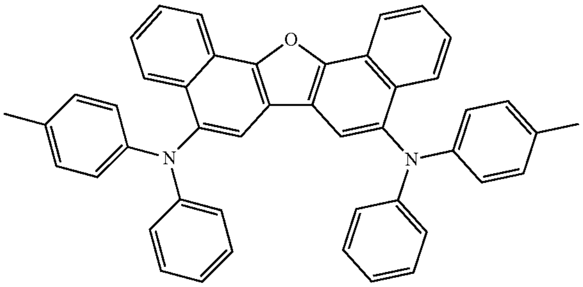
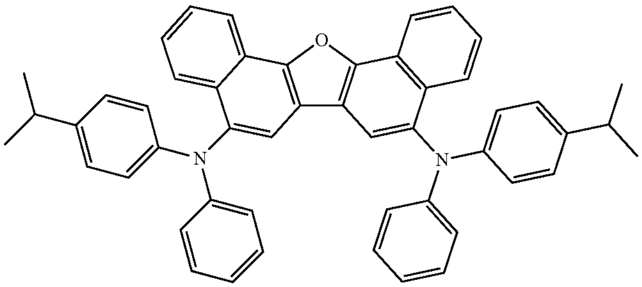
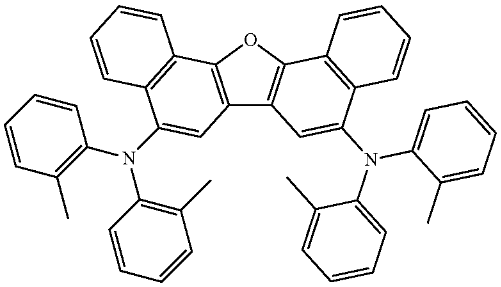
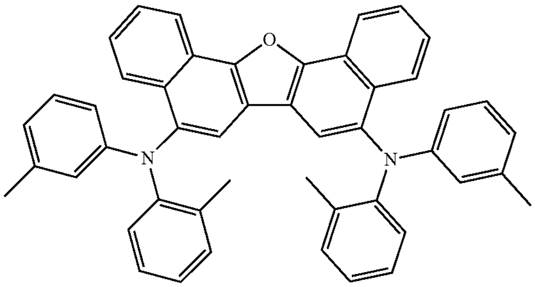
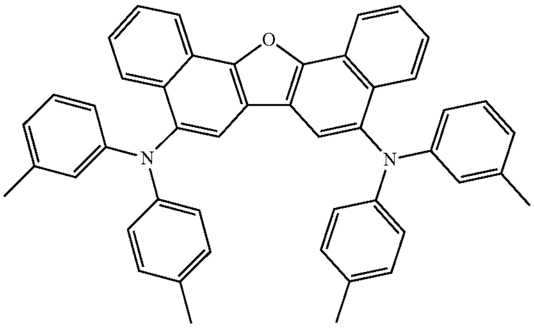

-continued
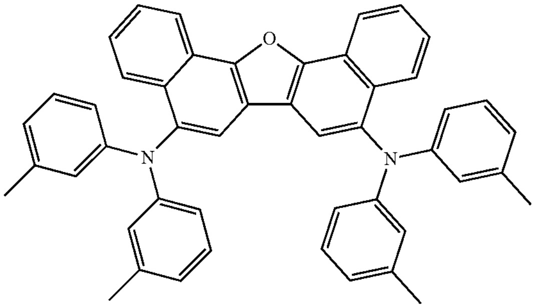
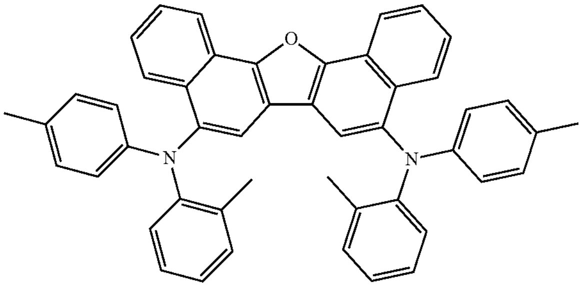
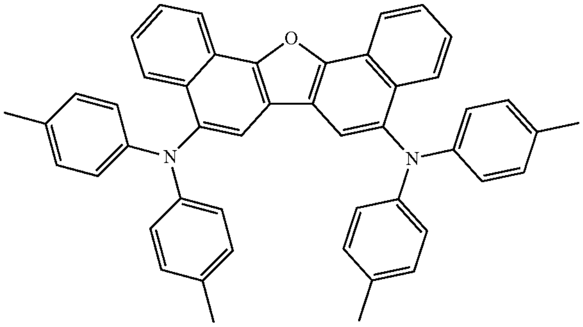
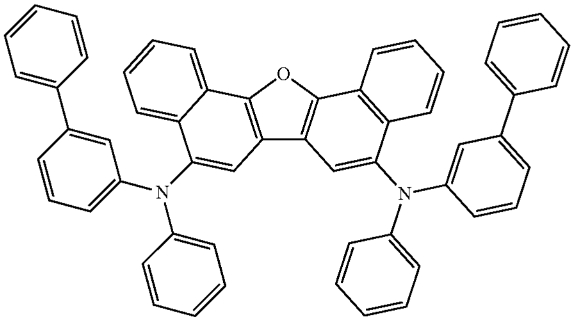
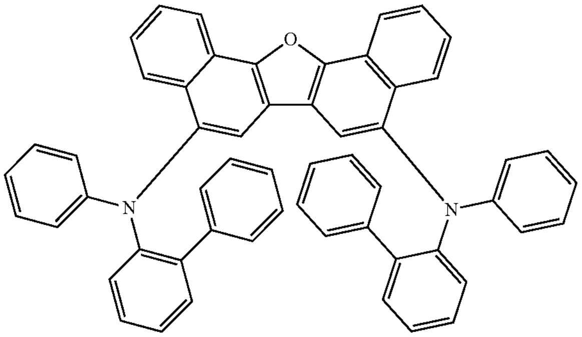
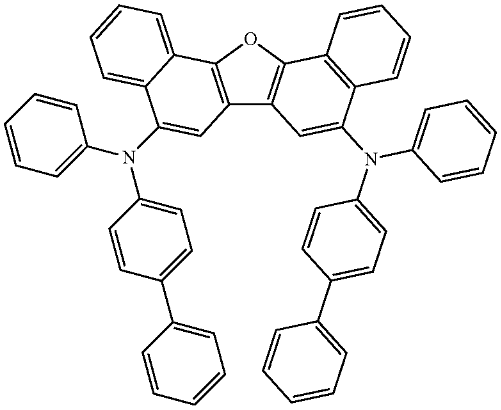
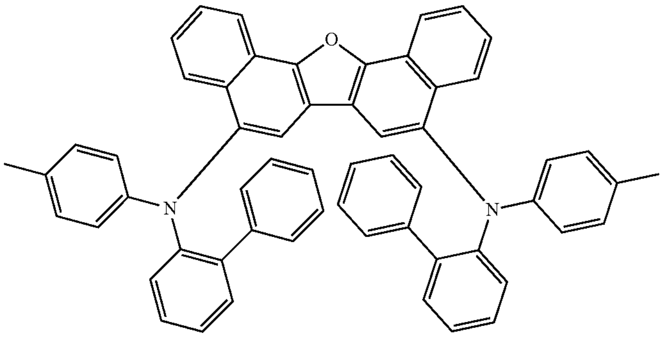

-continued
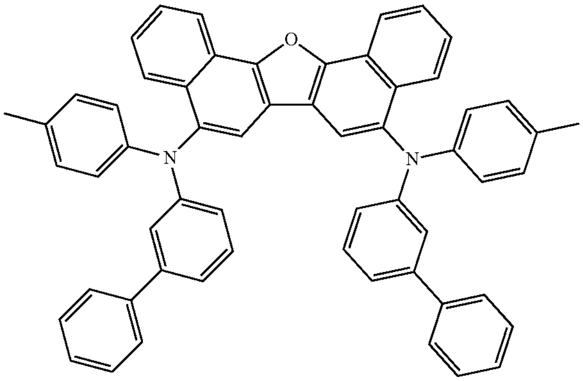
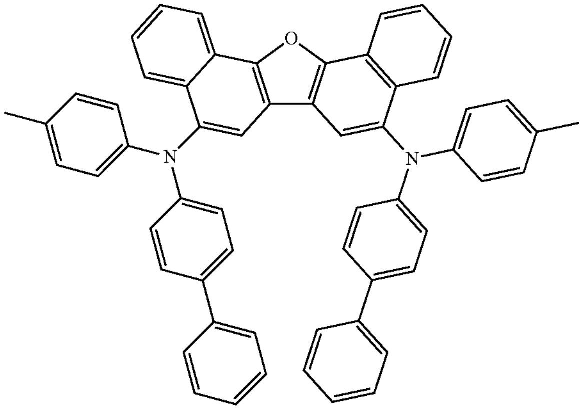
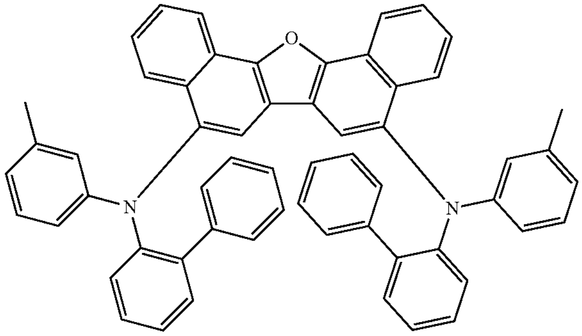
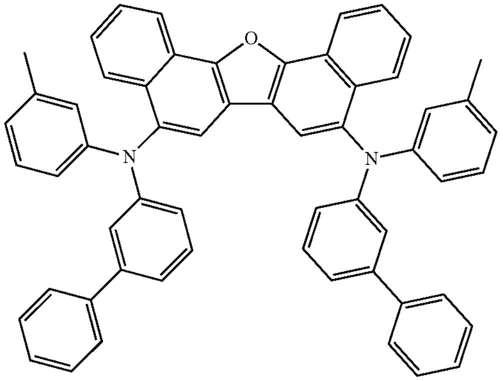
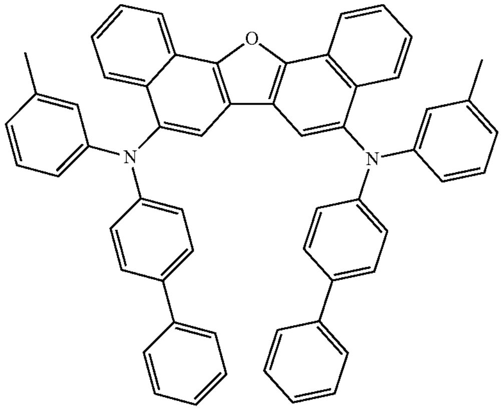
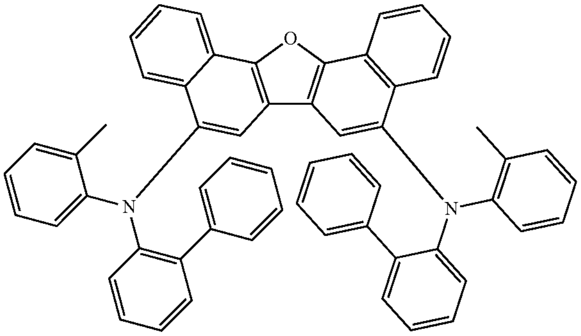

-continued
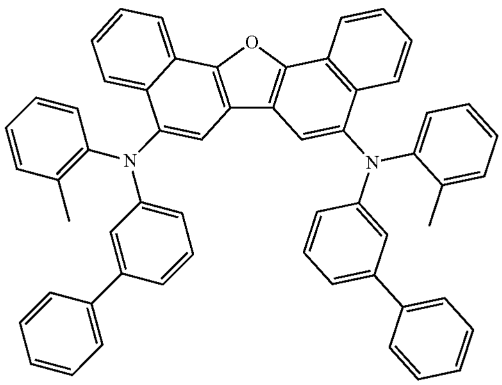
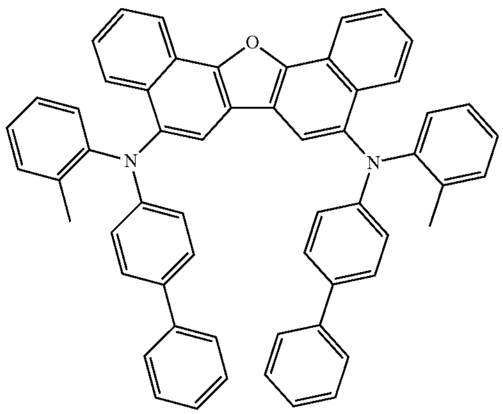
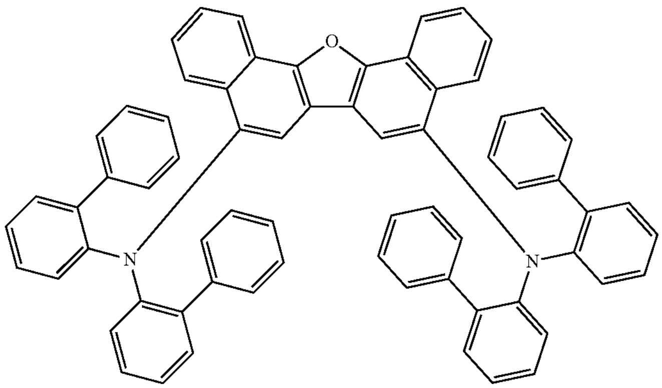
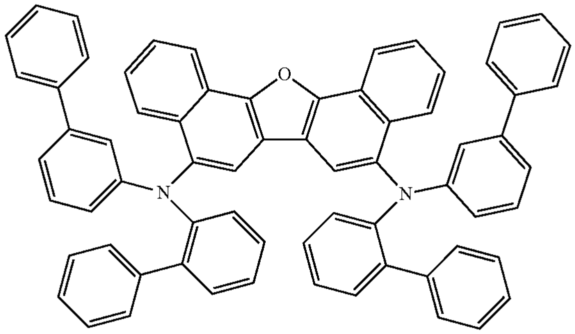
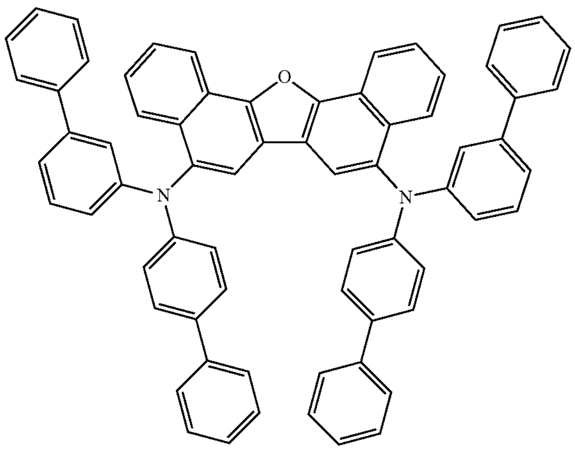

-continued
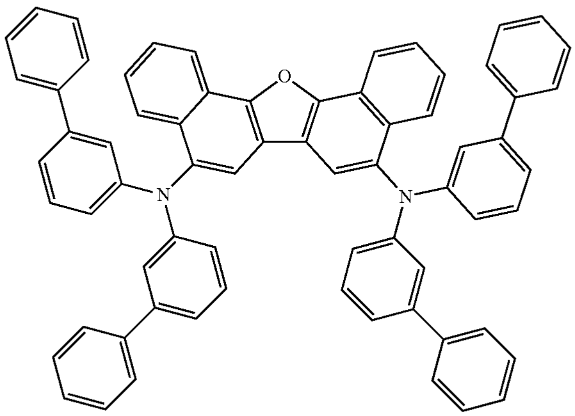
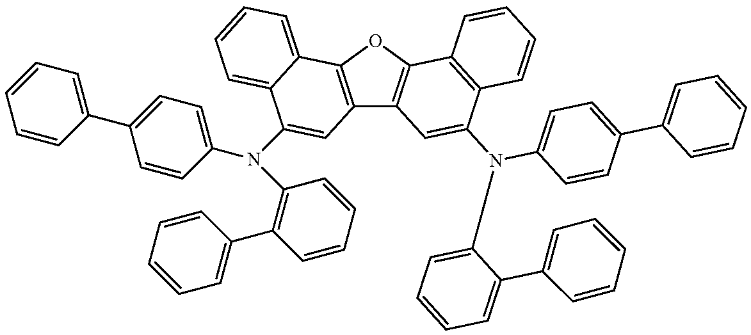
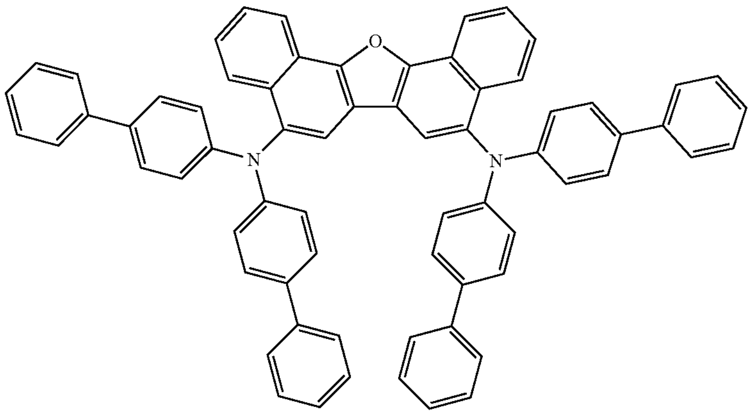
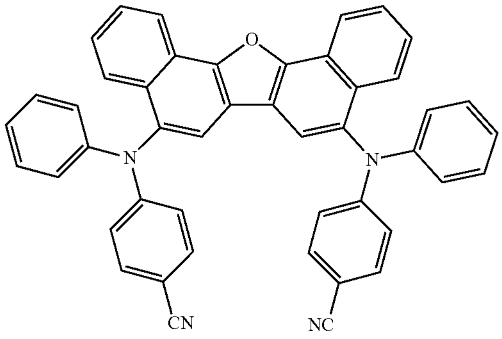
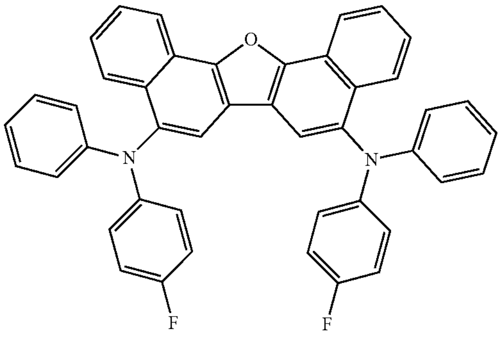

-continued
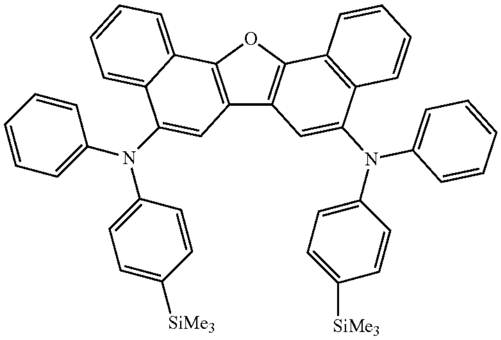
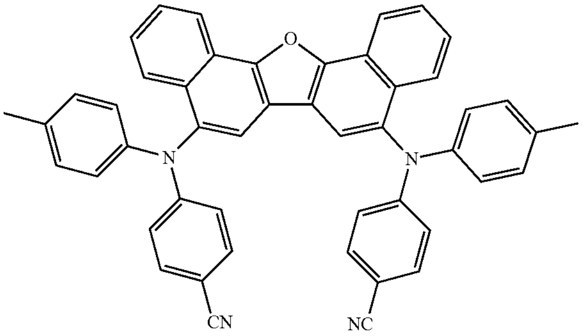
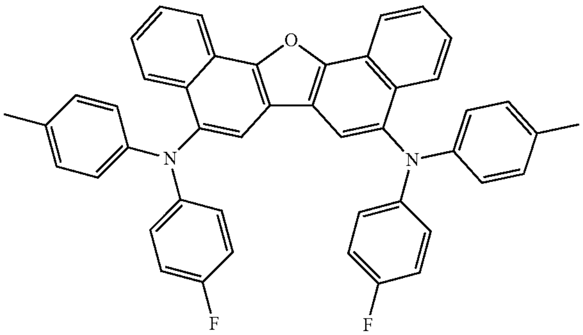
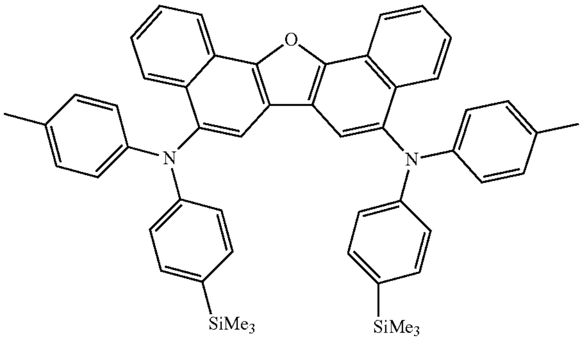
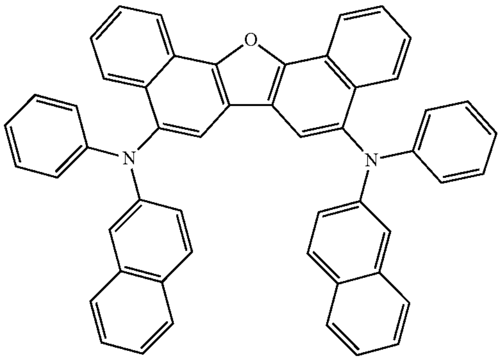
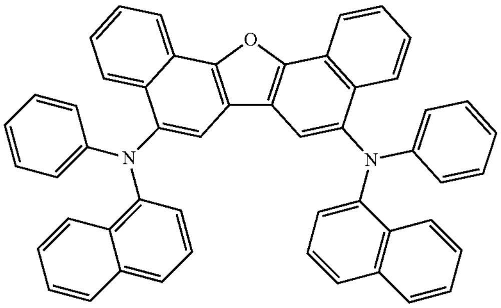
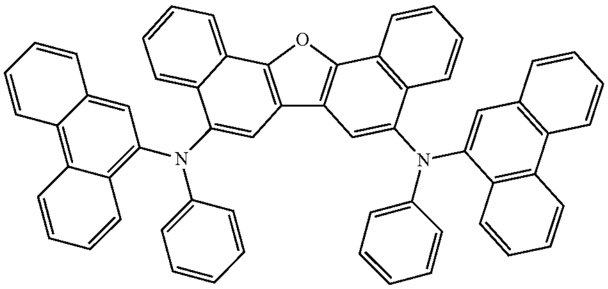
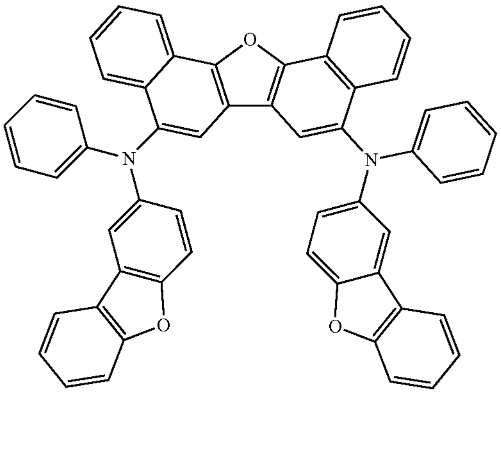

-continued
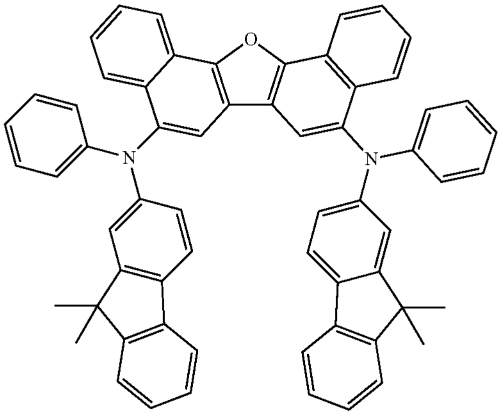
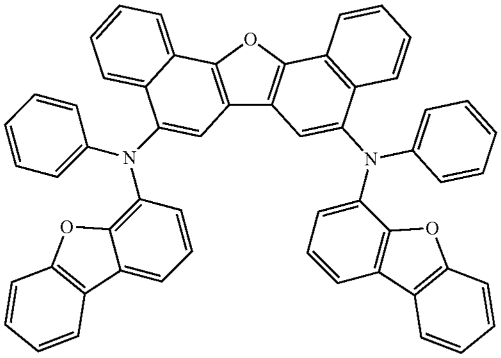
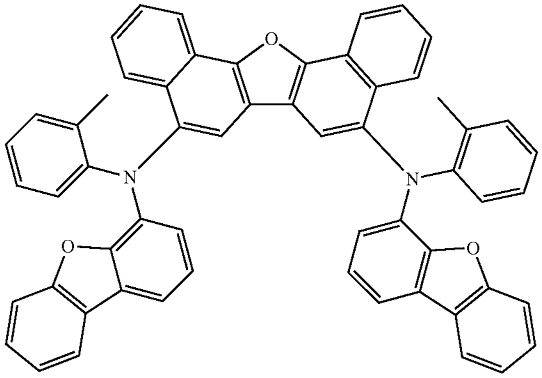
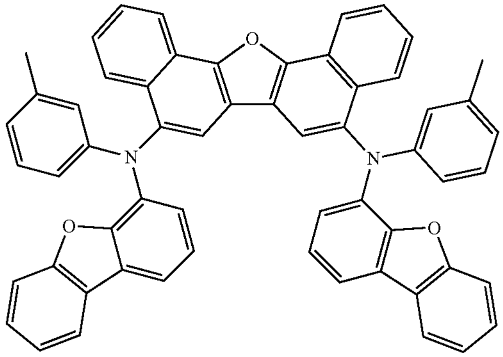
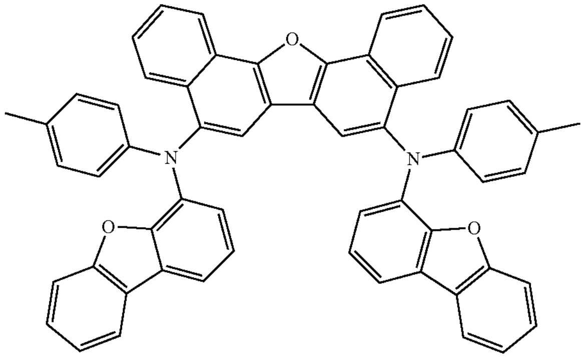
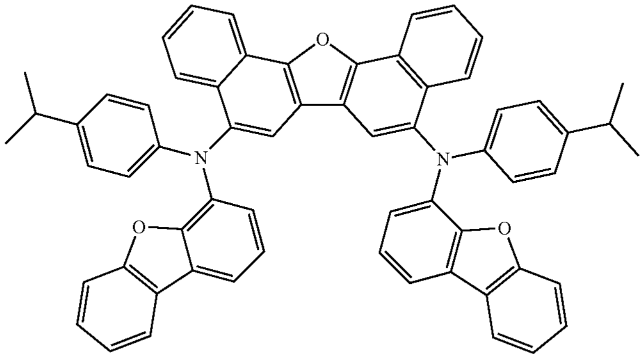

-continued
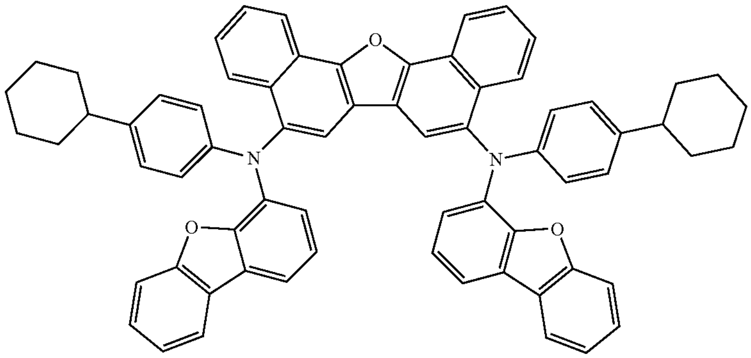
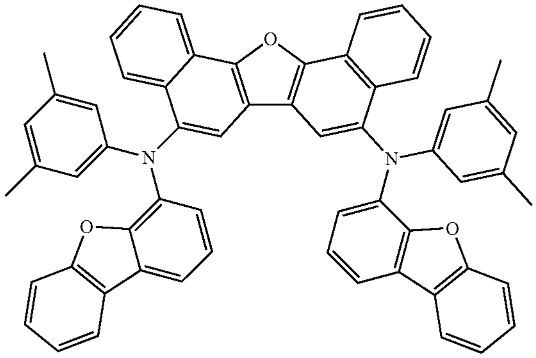
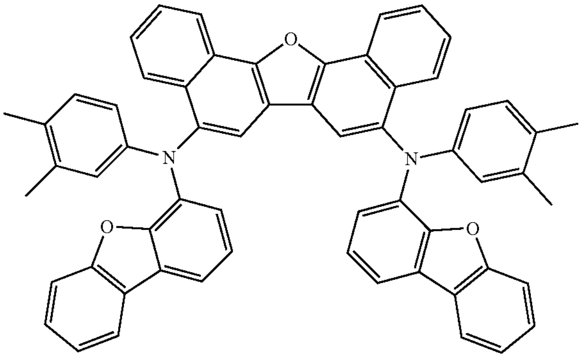
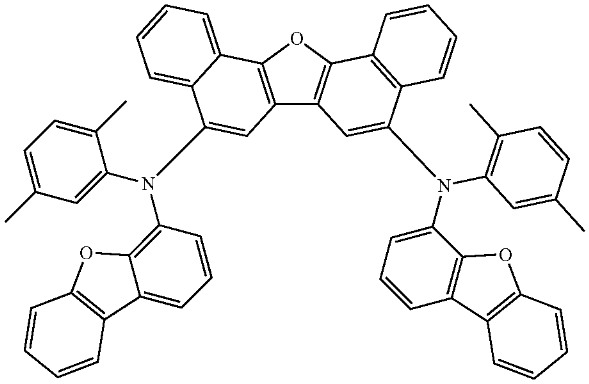
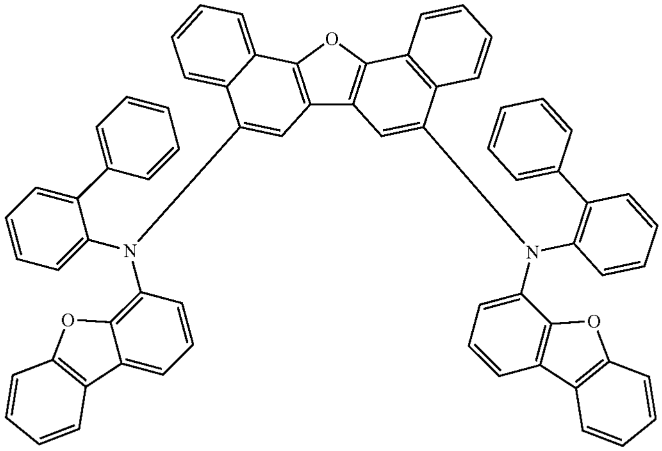

-continued
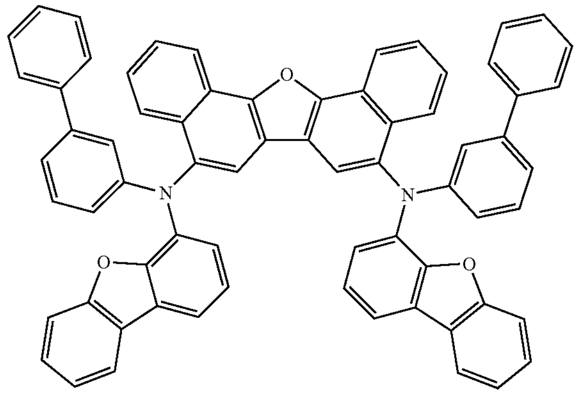
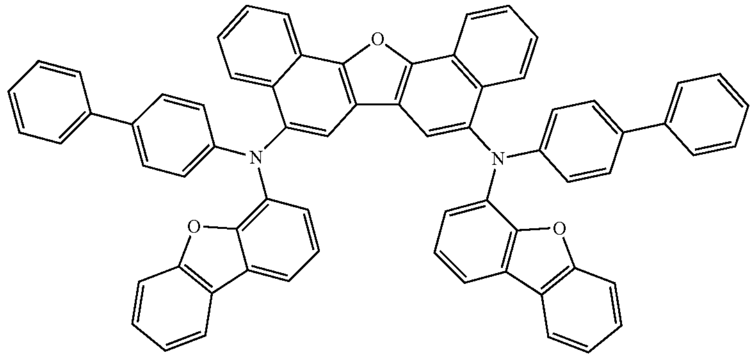
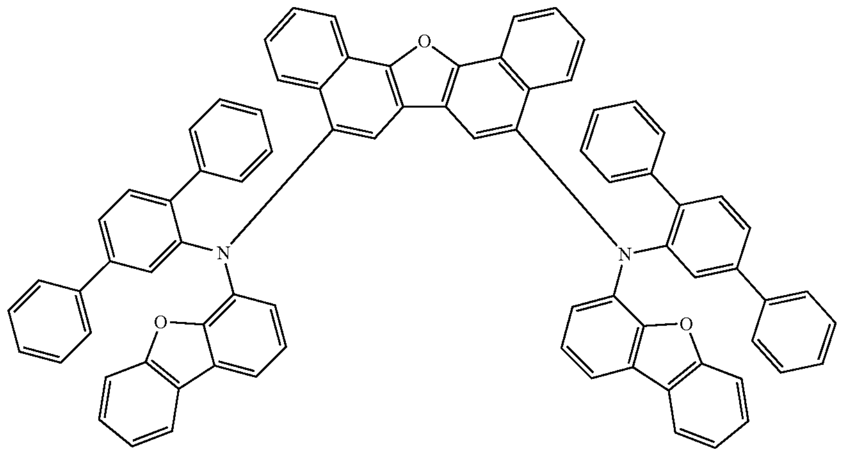
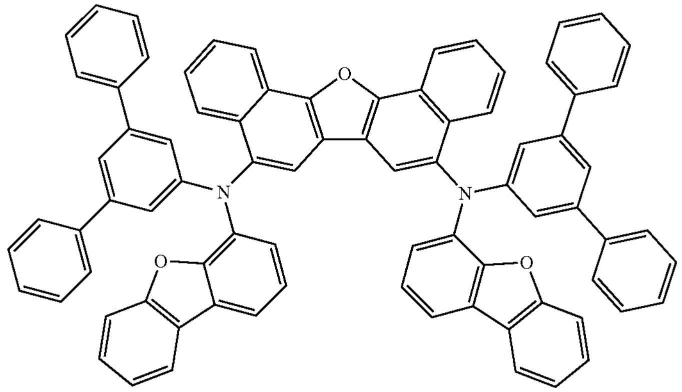

-continued
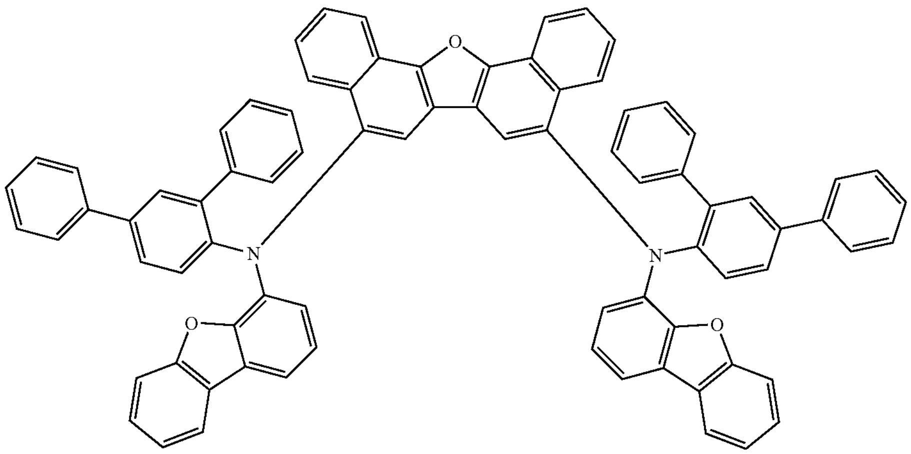
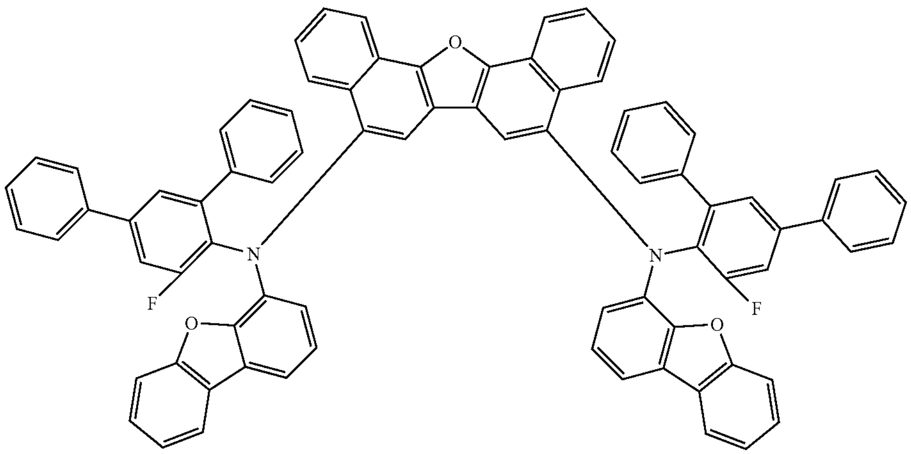
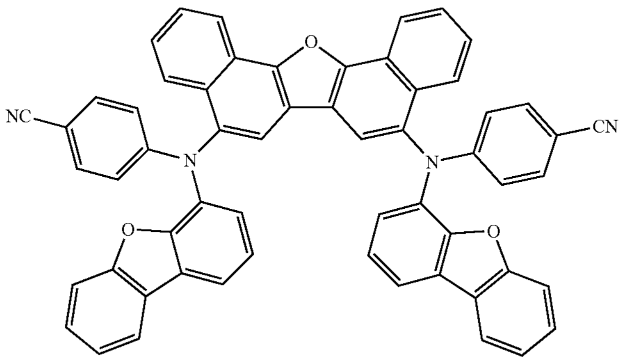
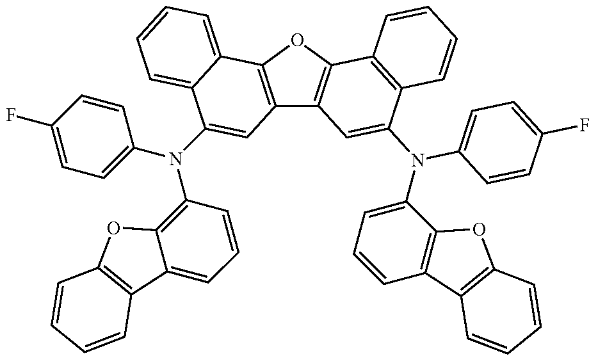

-continued
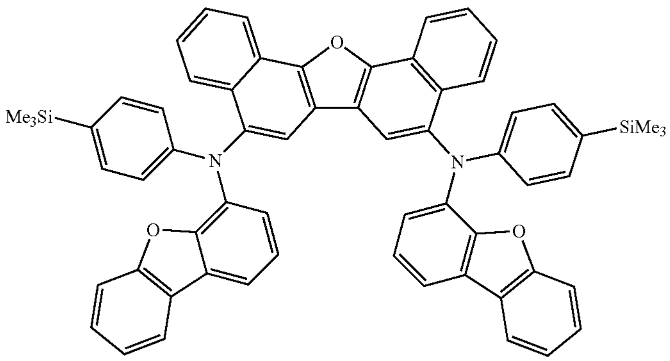
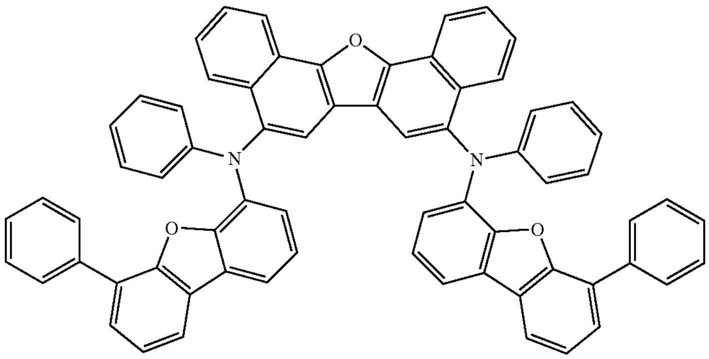
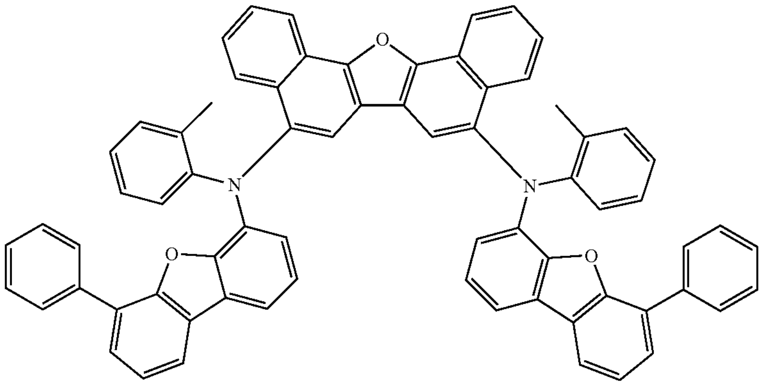
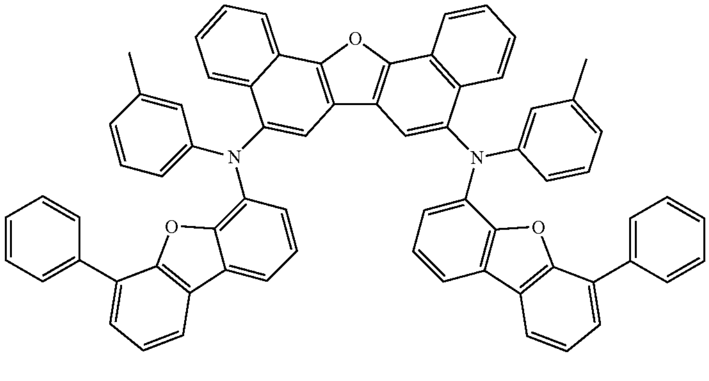

-continued
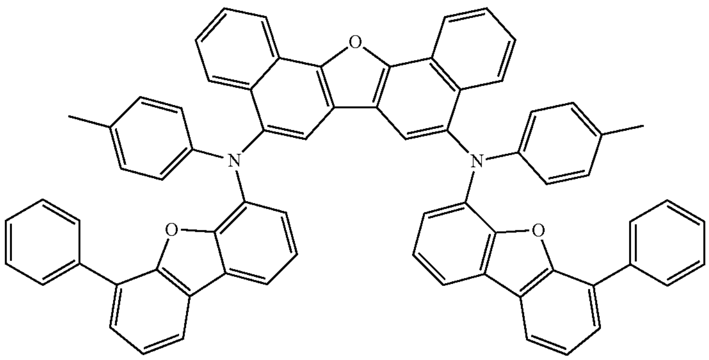
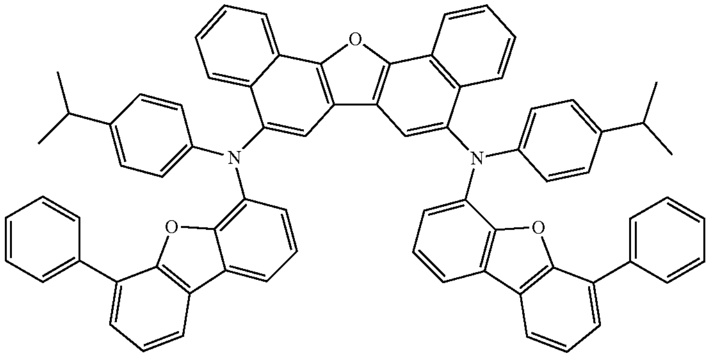
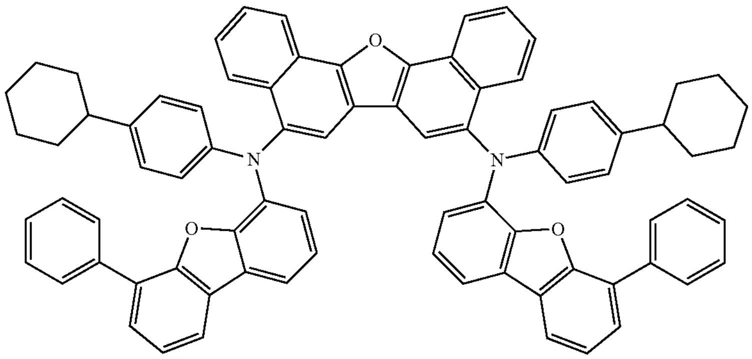
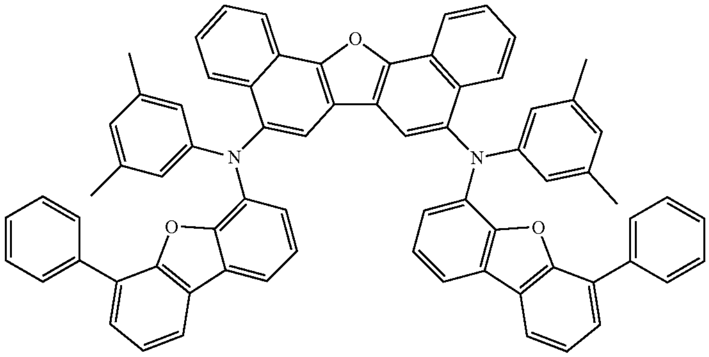

-continued
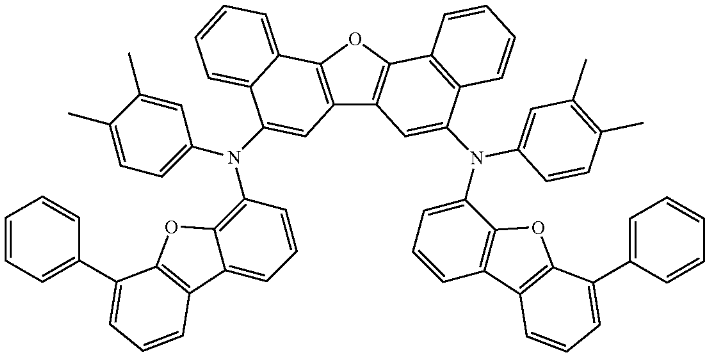
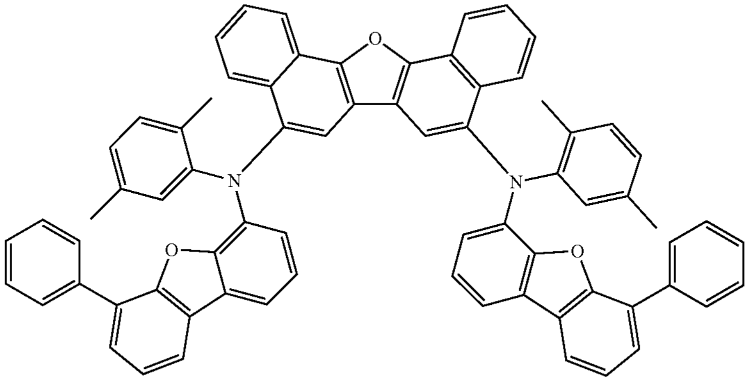
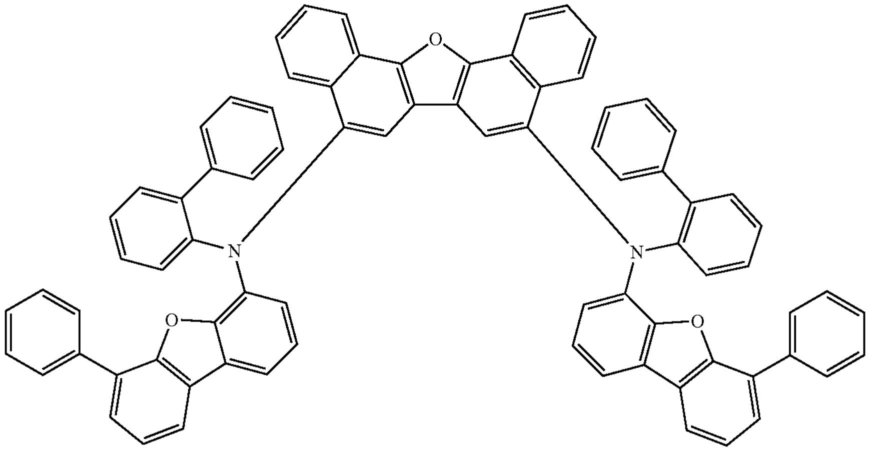
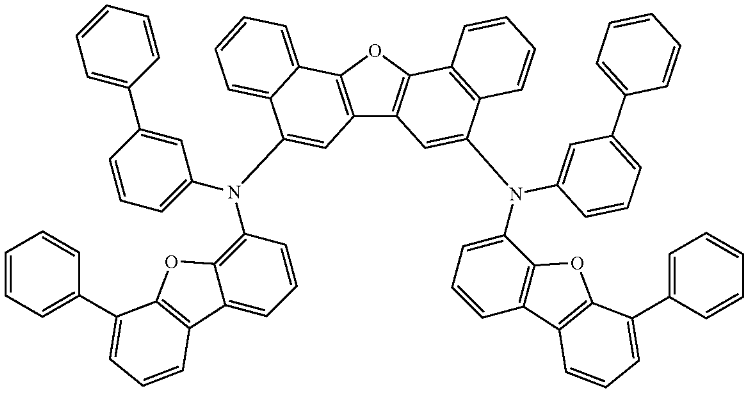

-continued
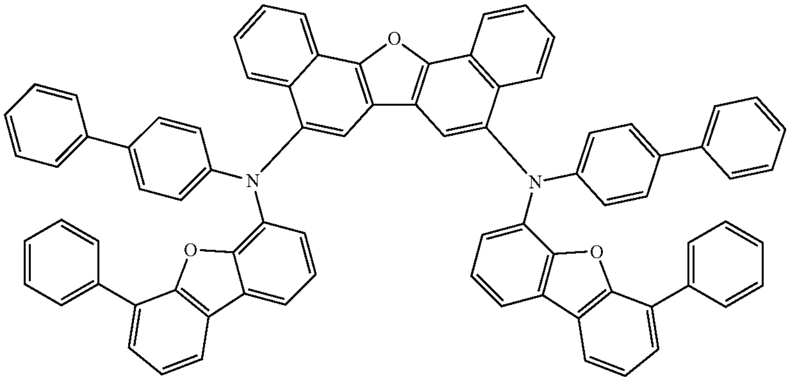
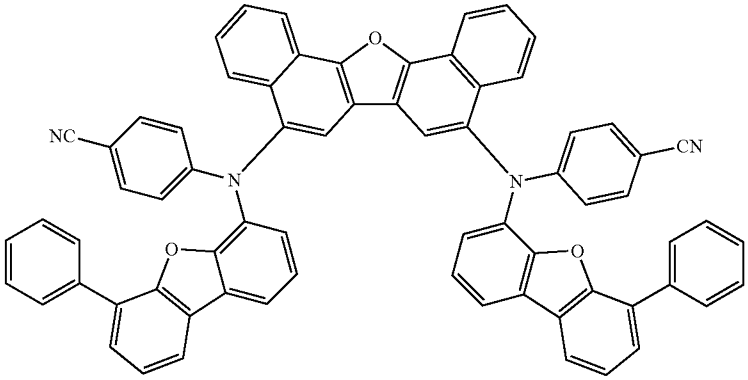
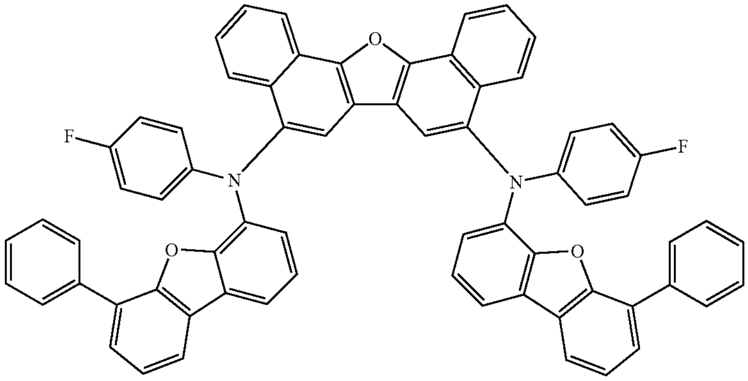
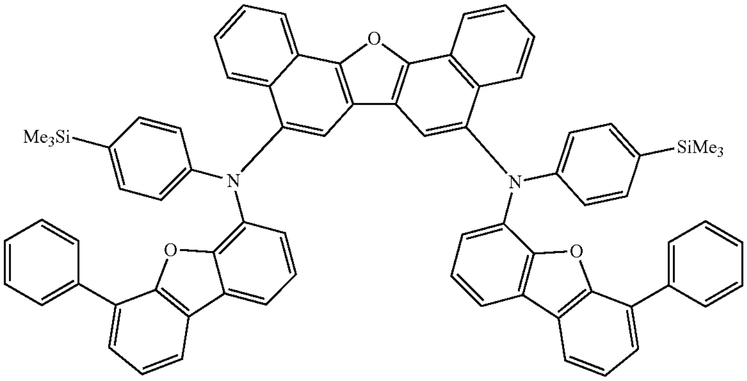

-continued
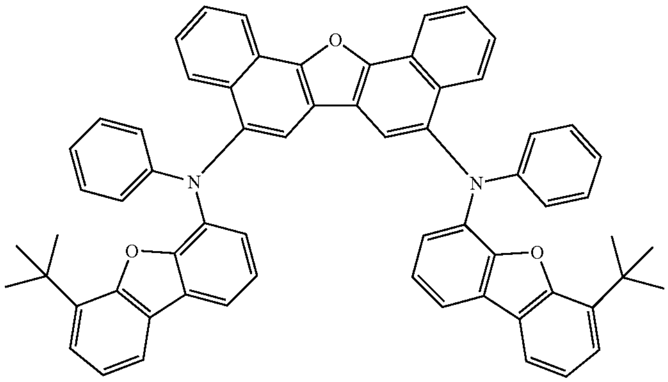
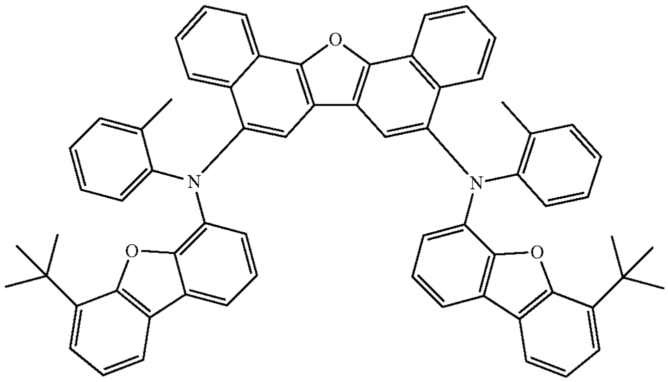
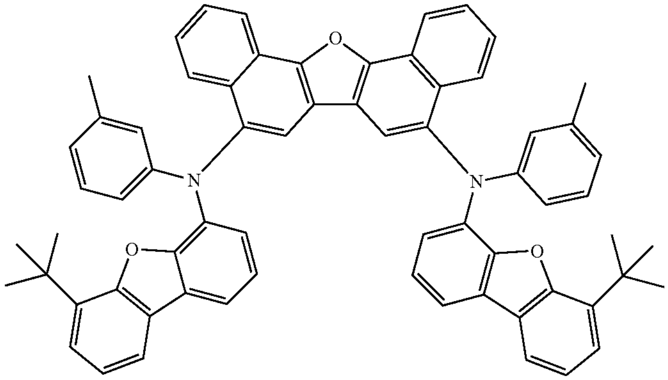
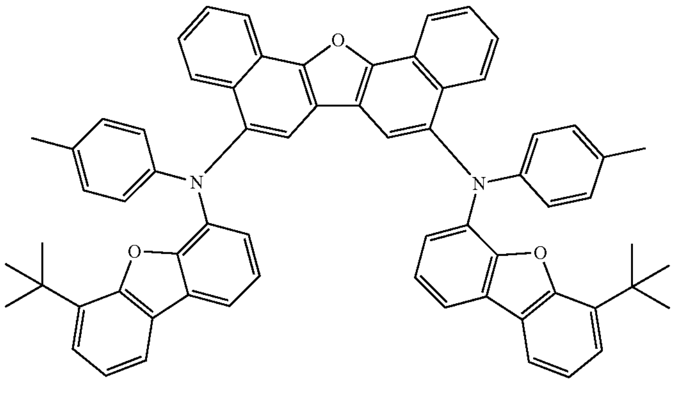

-continued
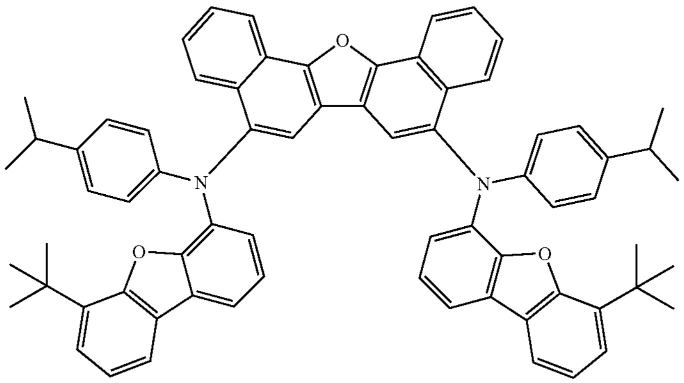
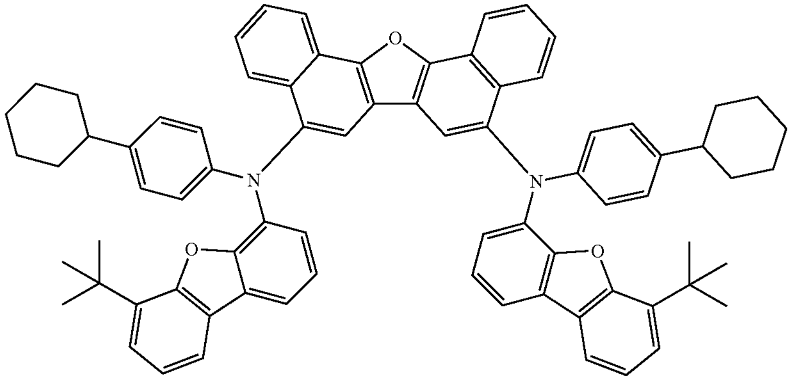
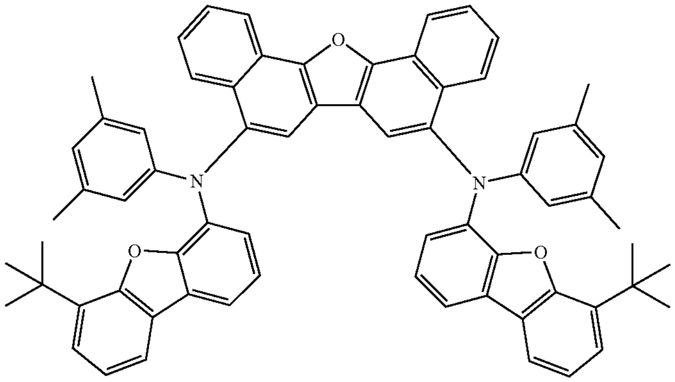
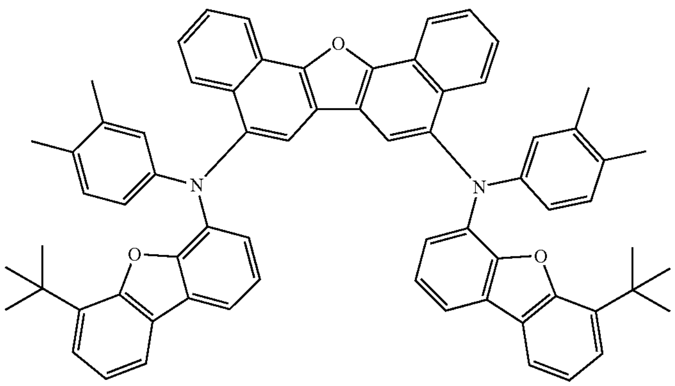

-continued
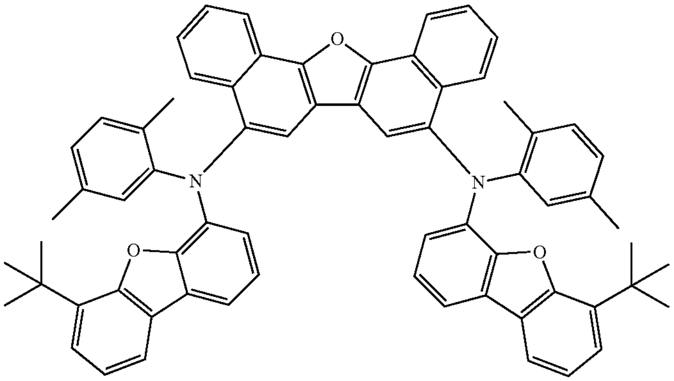
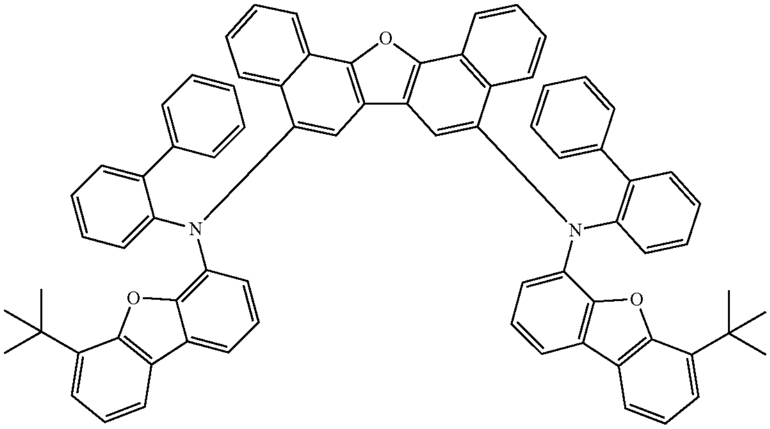
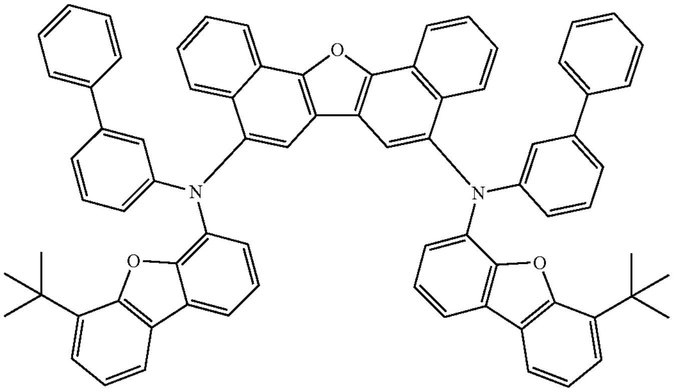
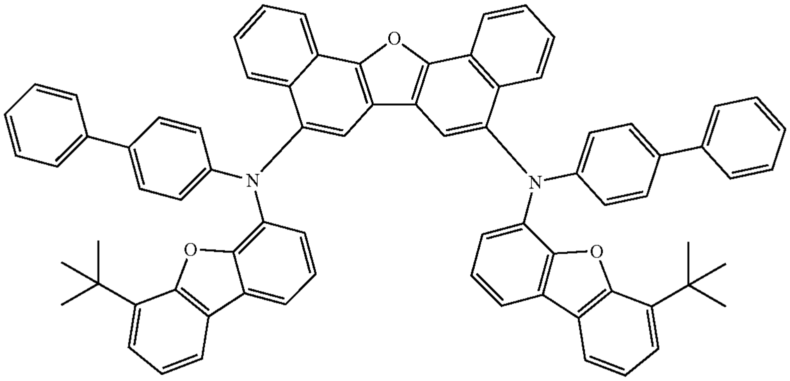

-continued
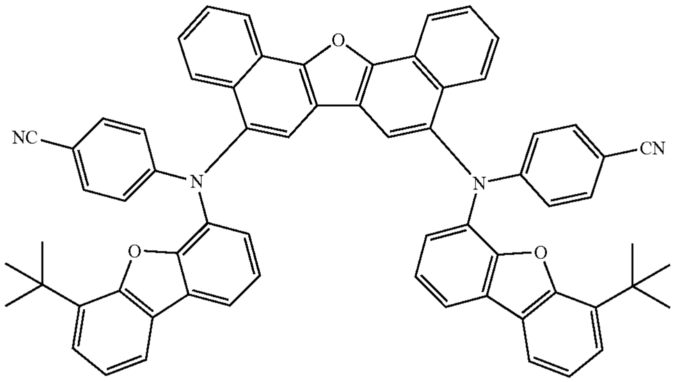
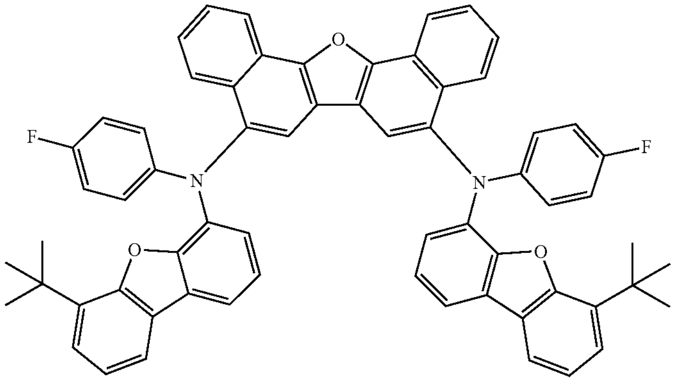
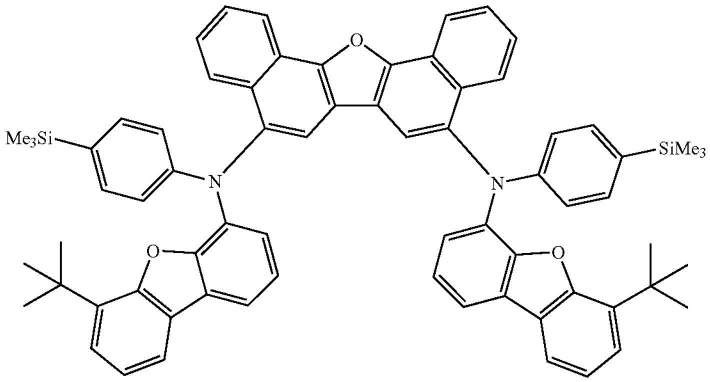
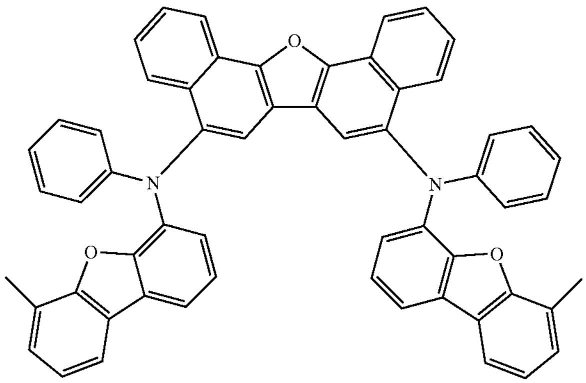

-continued
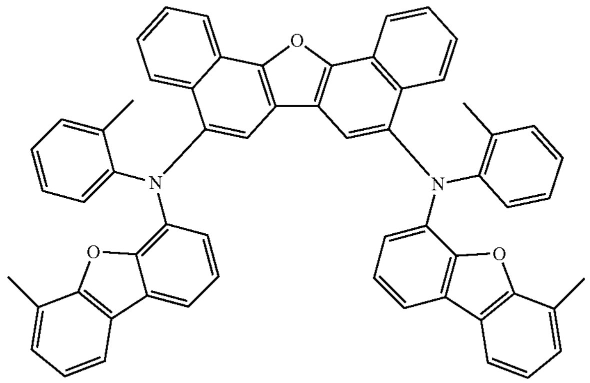
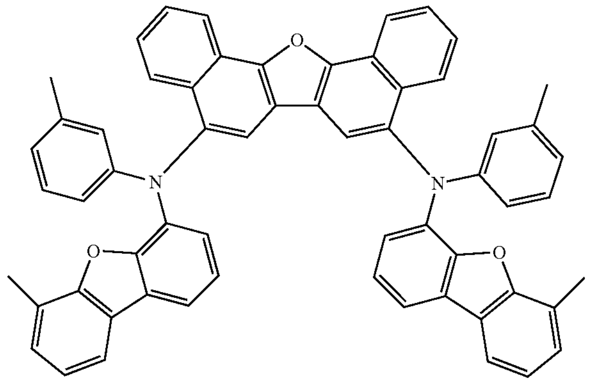
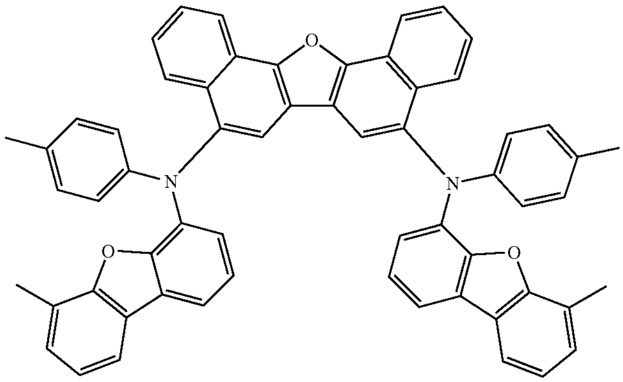
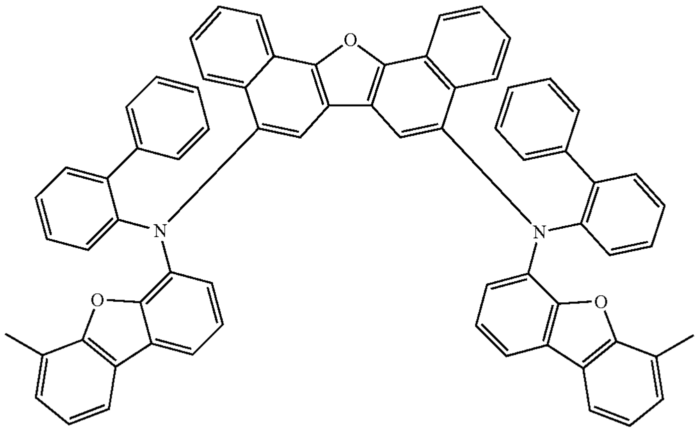

-continued
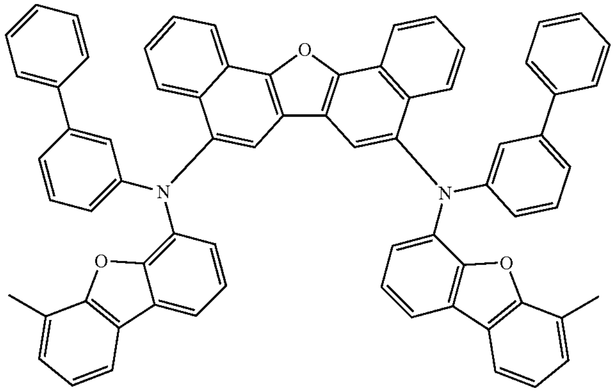
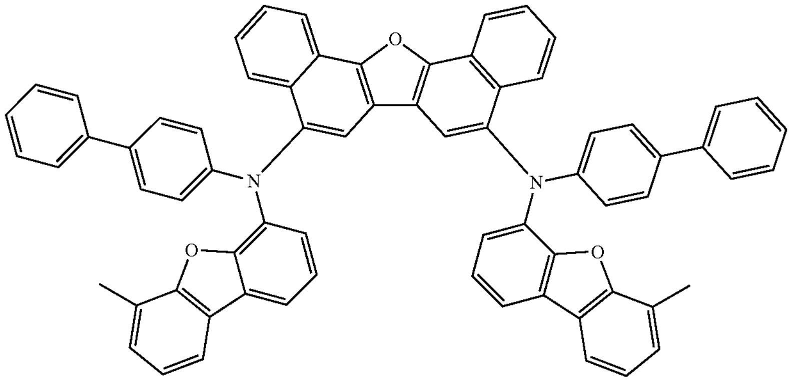
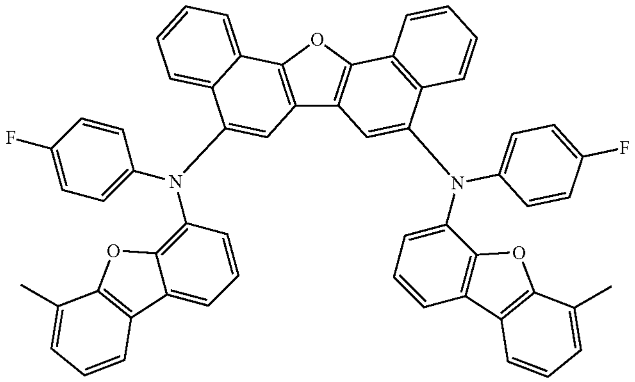
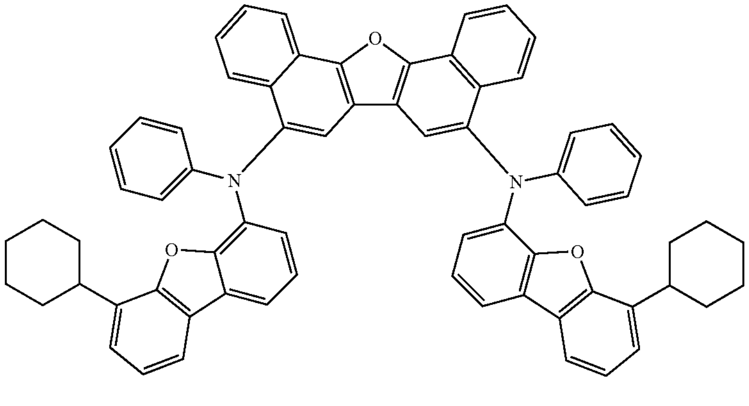

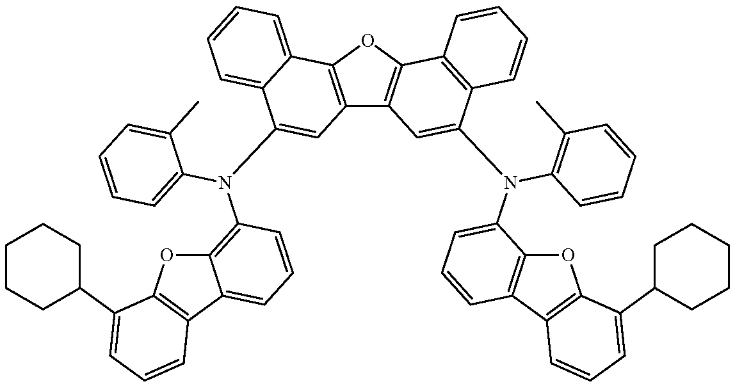
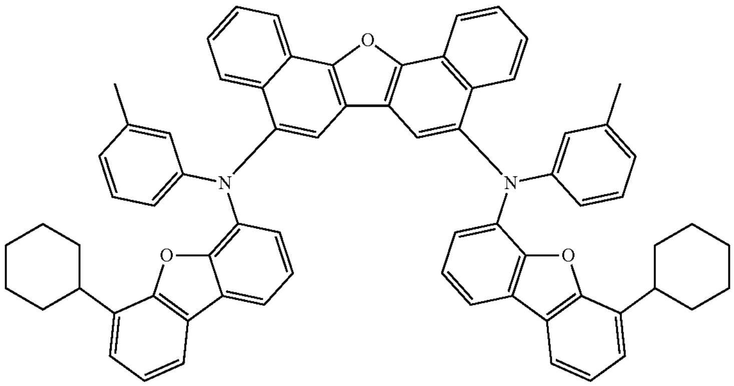
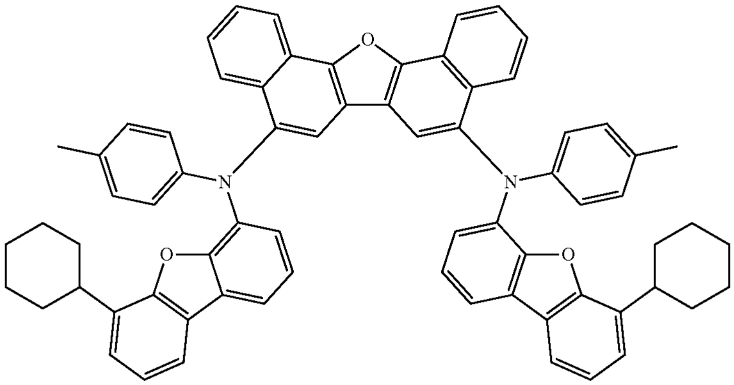
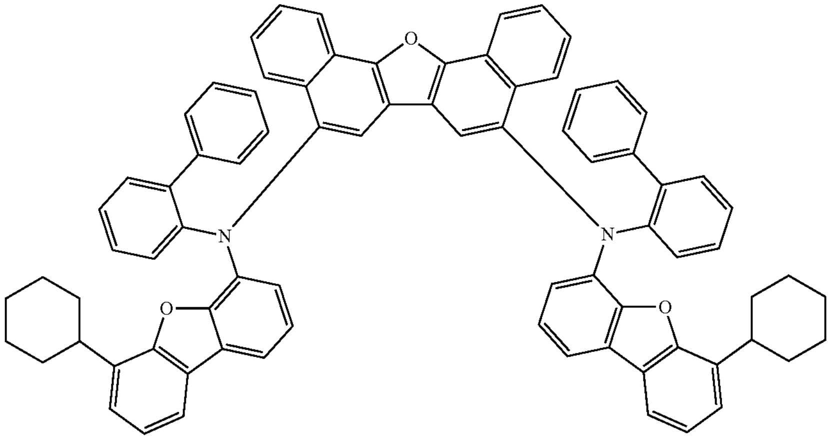

-continued
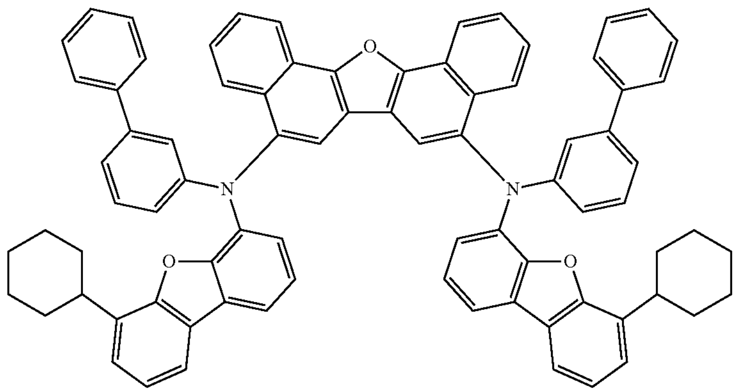
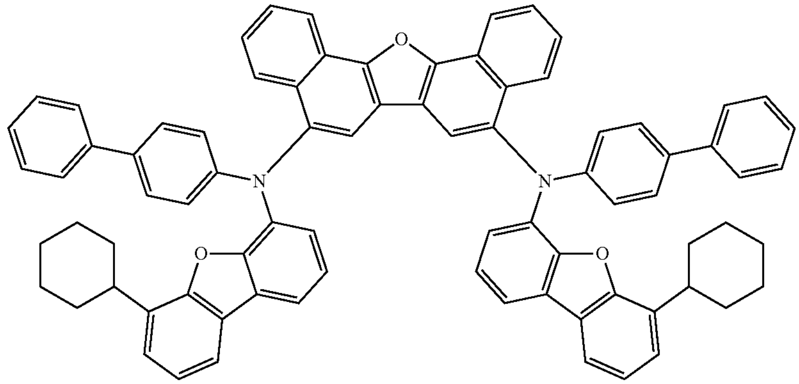
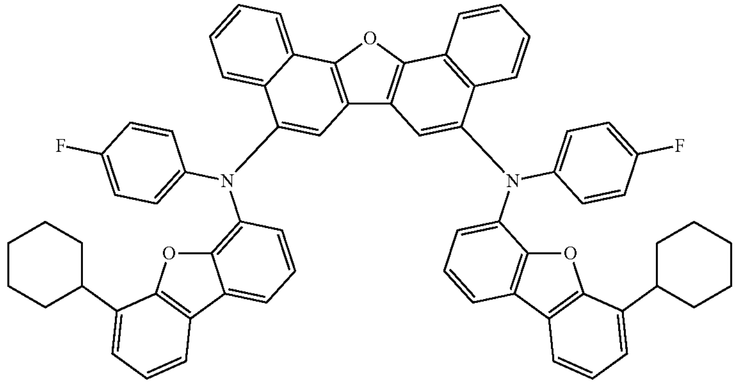
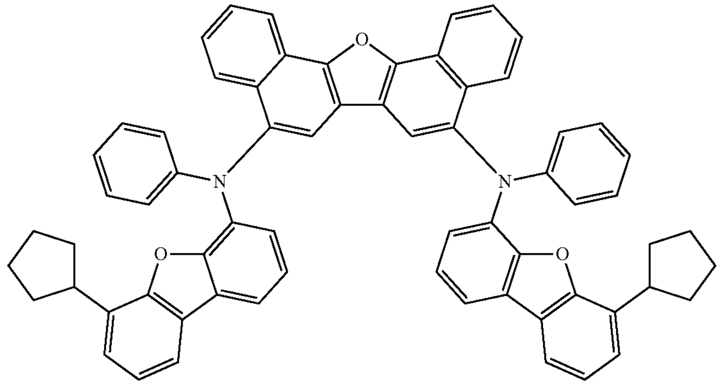

-continued
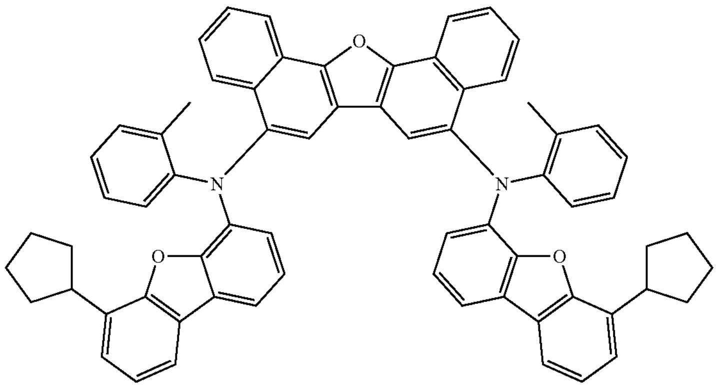
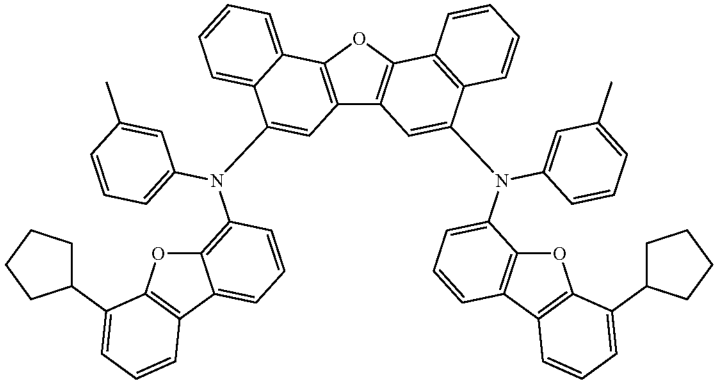
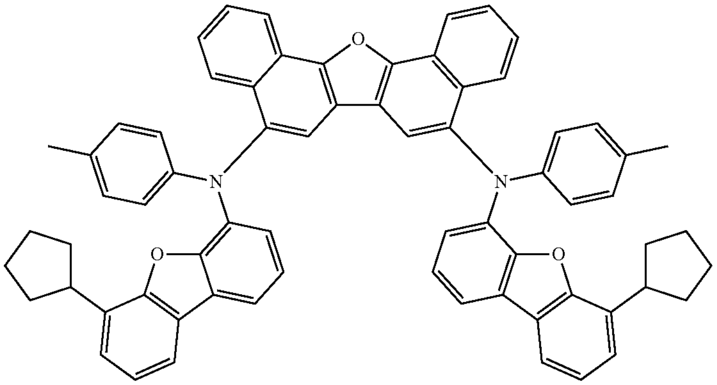
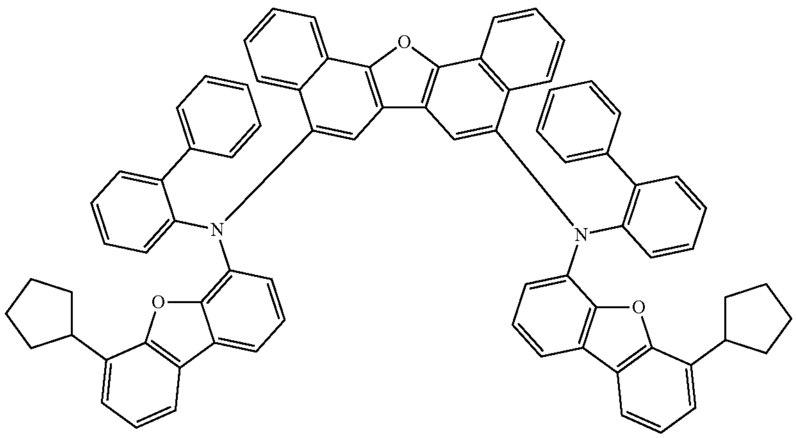

-continued
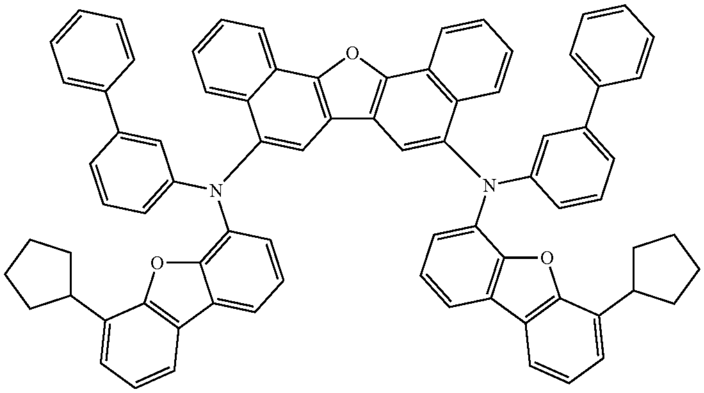
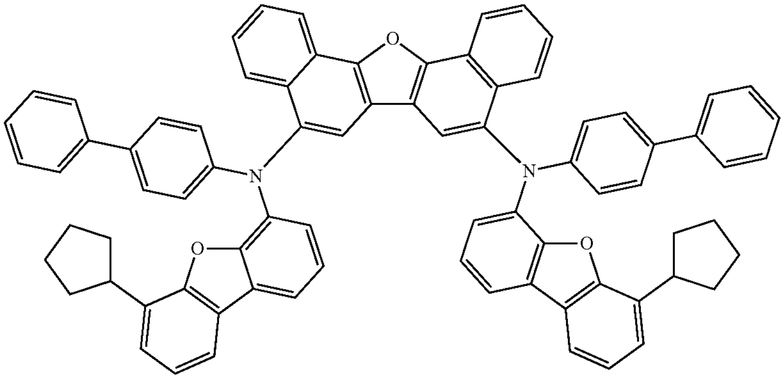
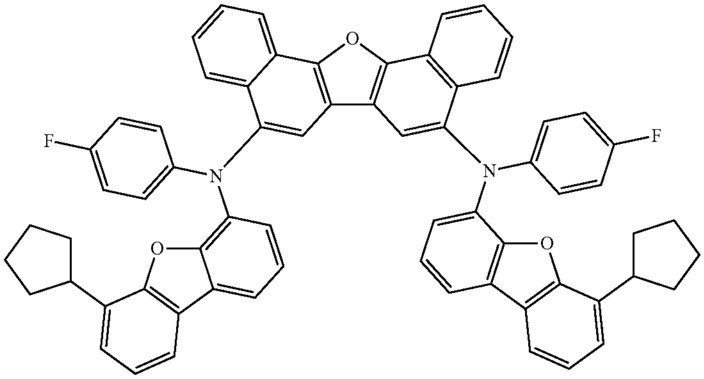
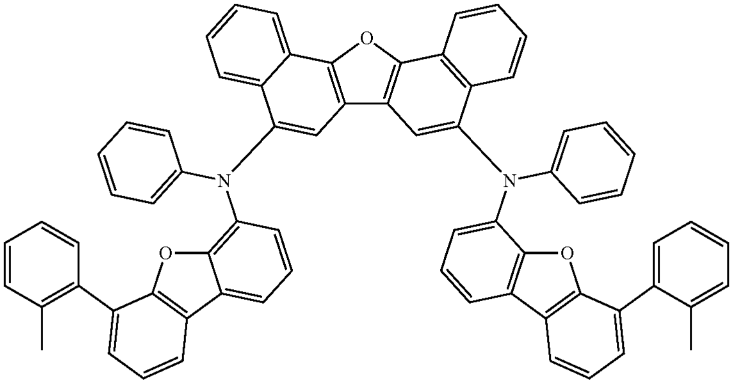

-continued
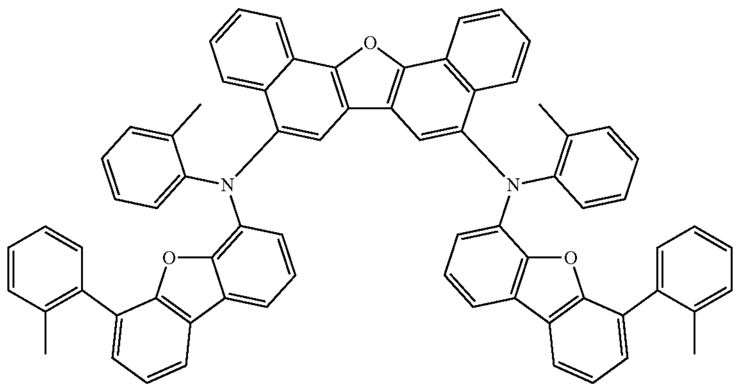
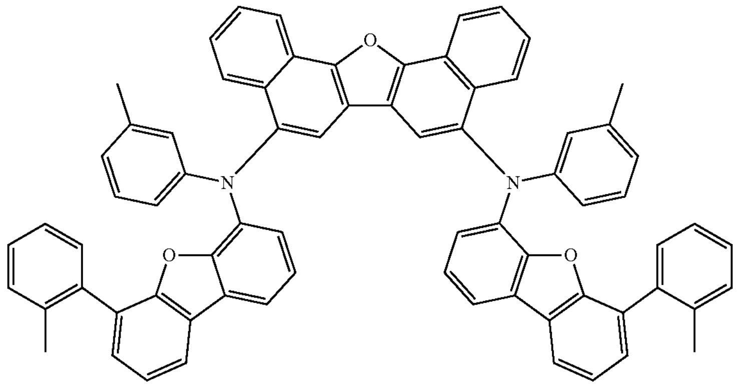
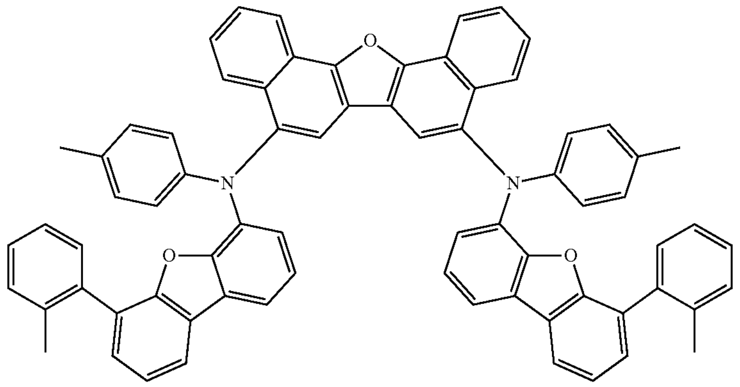
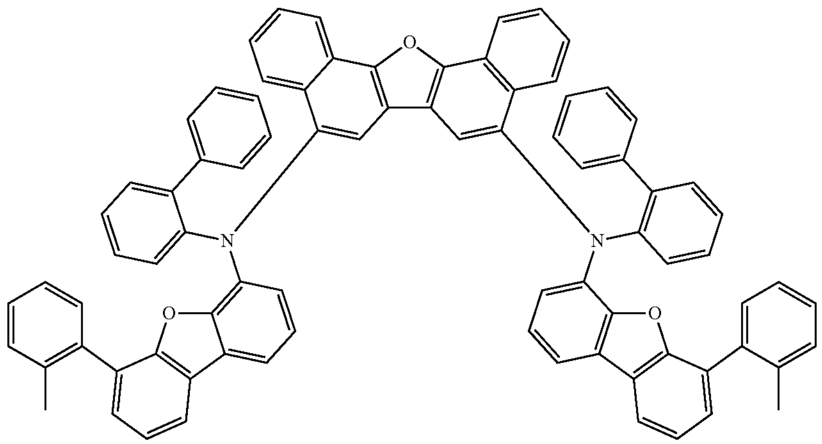

-continued
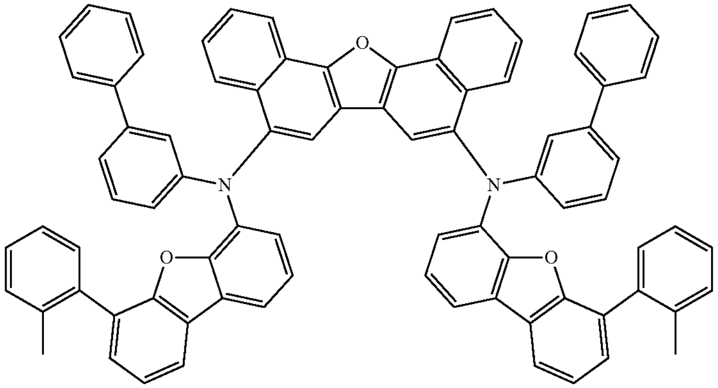
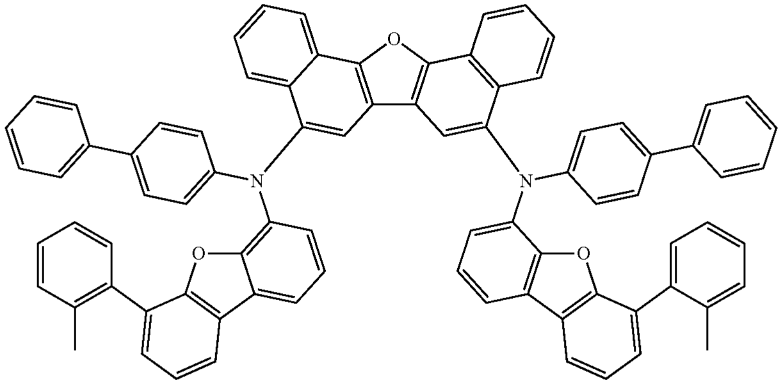
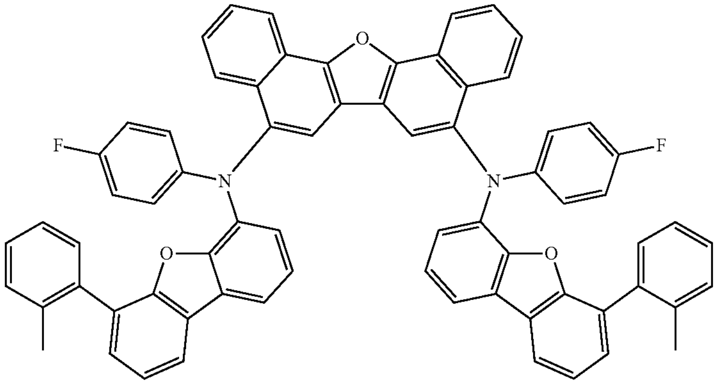
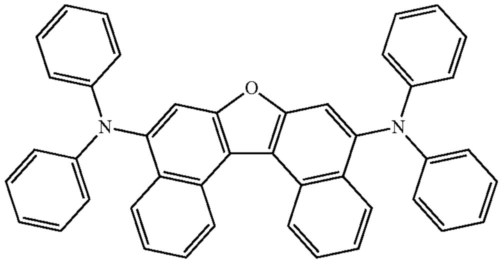
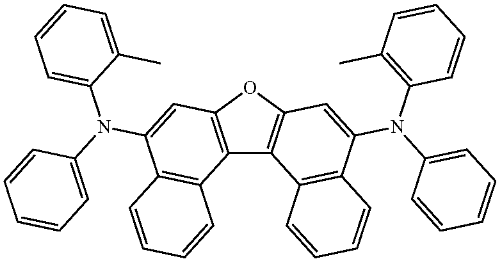

-continued
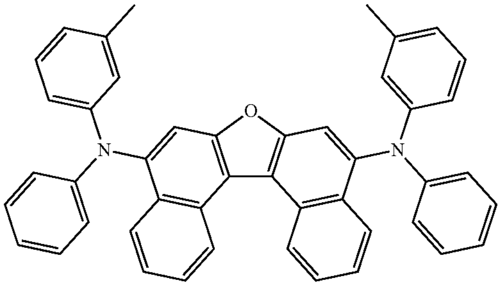
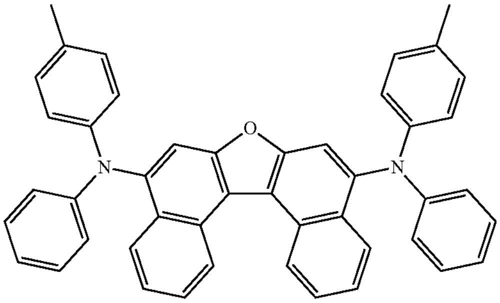
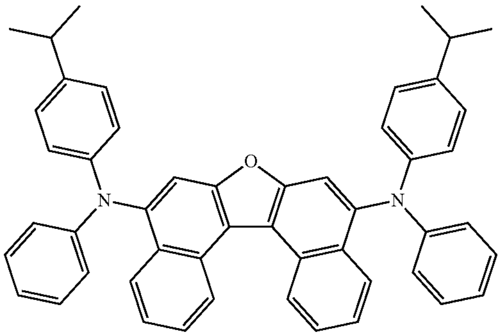
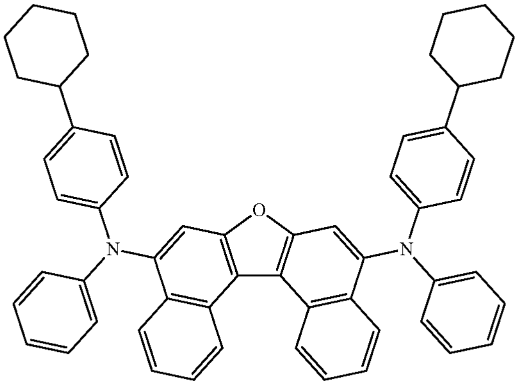
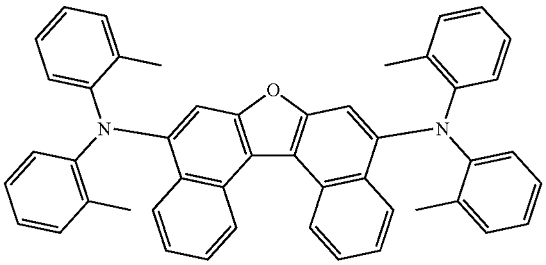
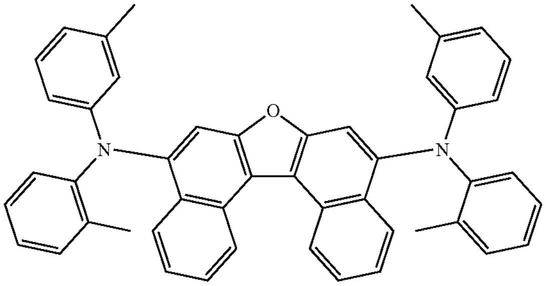
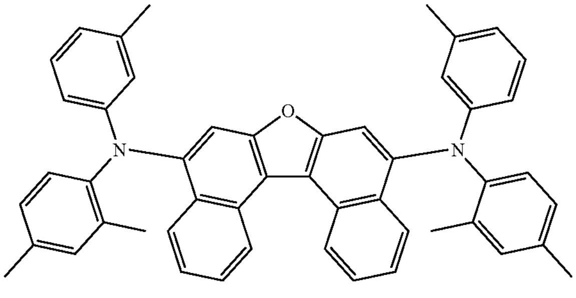
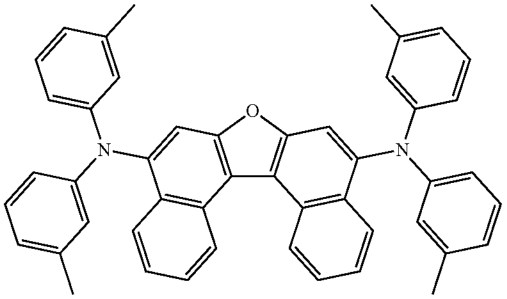
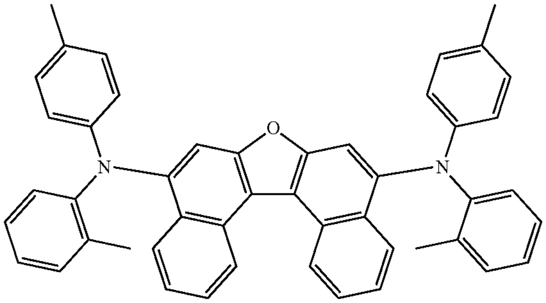
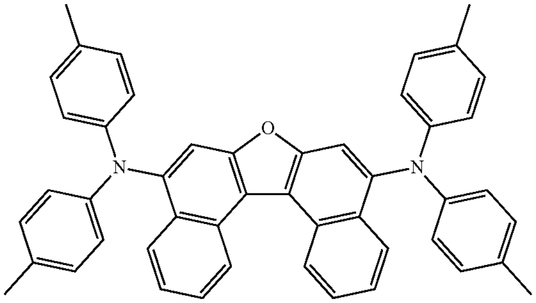

-continued
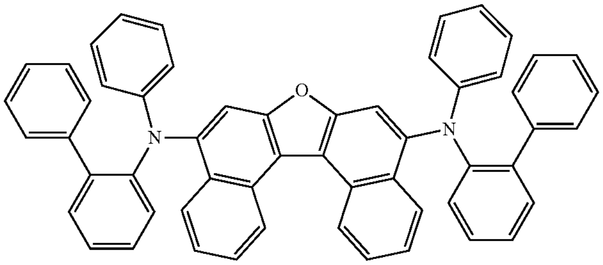
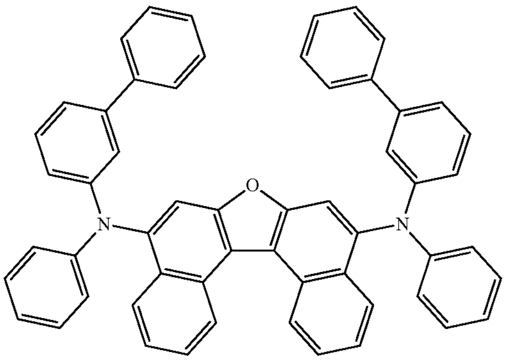
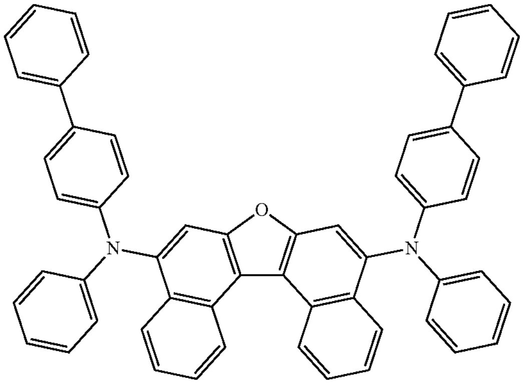
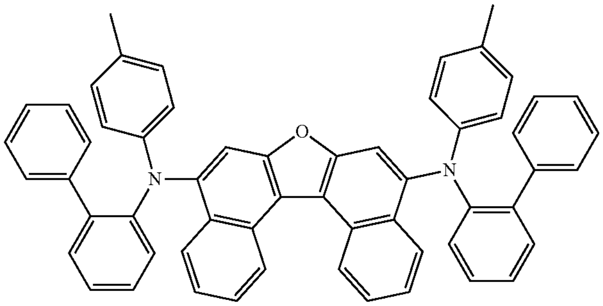
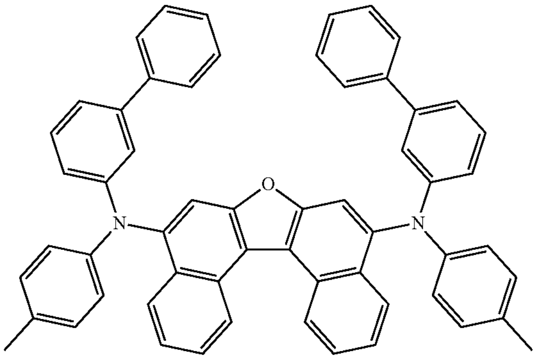
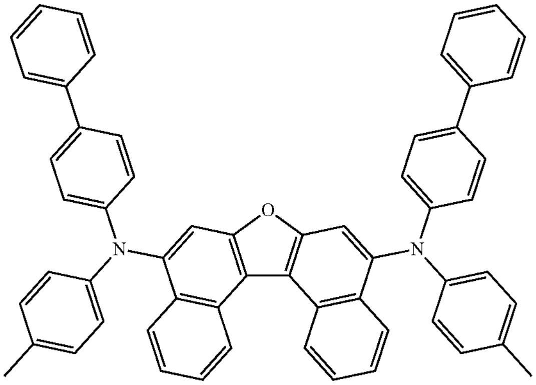
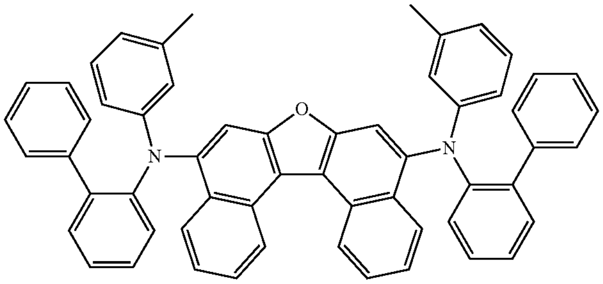
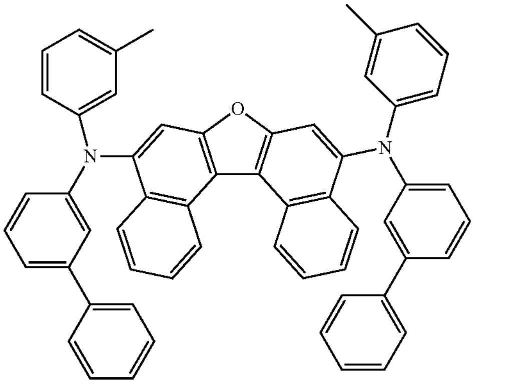

-continued
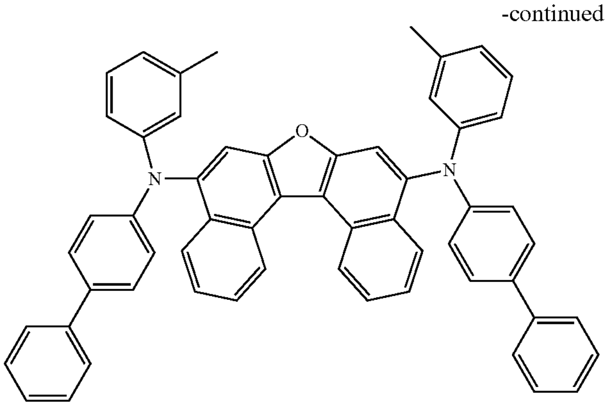
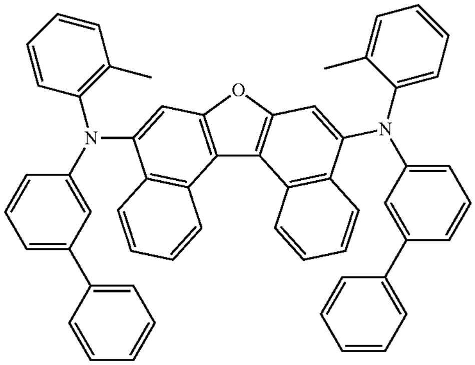
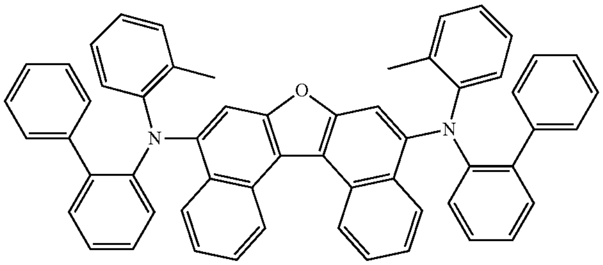
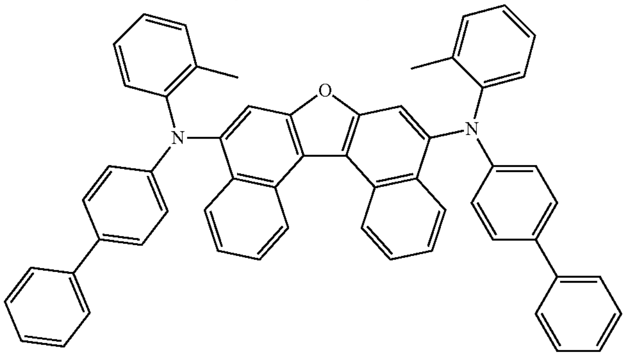
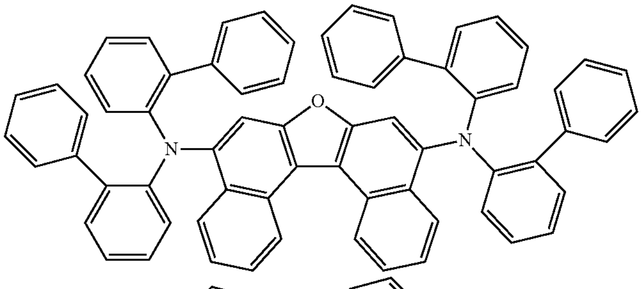
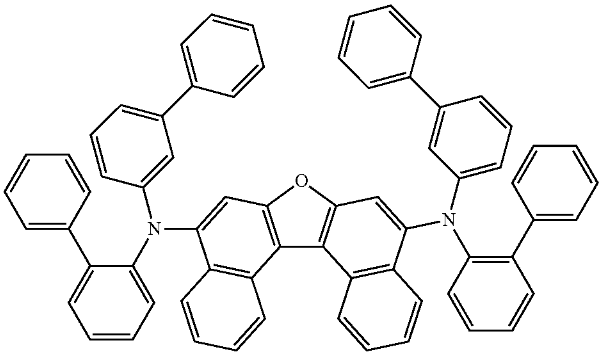

-continued
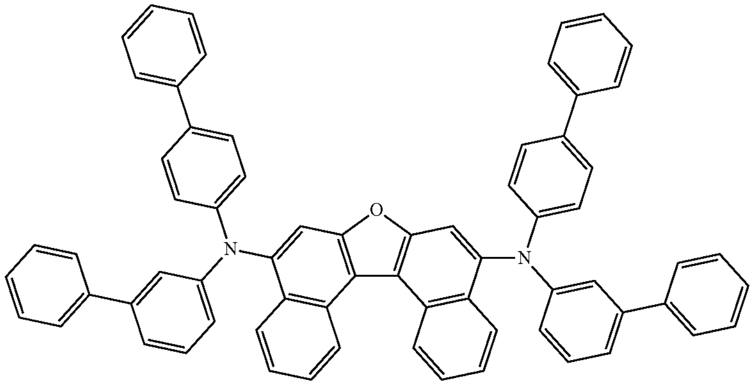
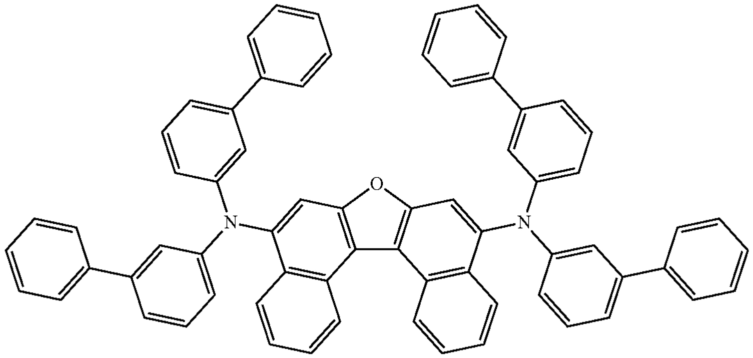
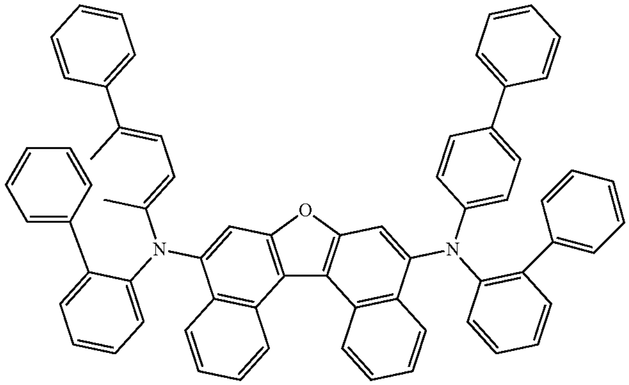
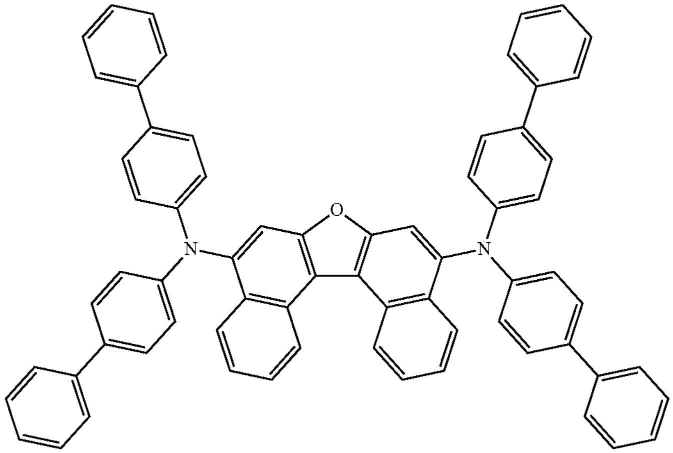

-continued
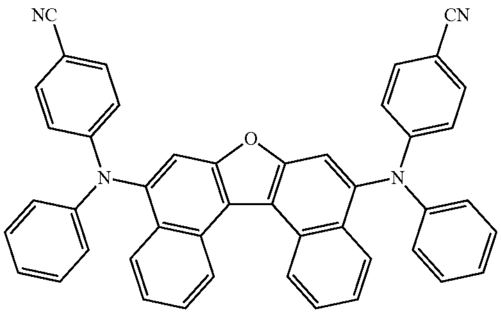
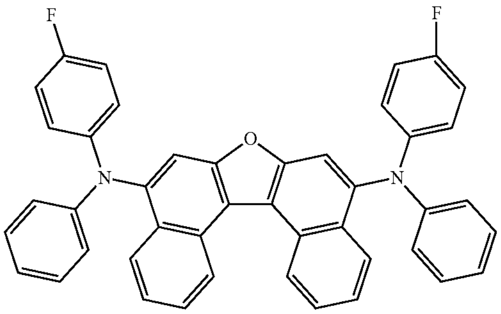
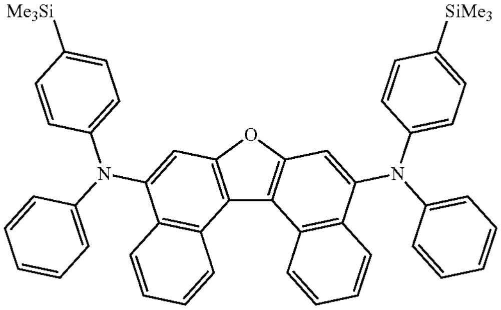
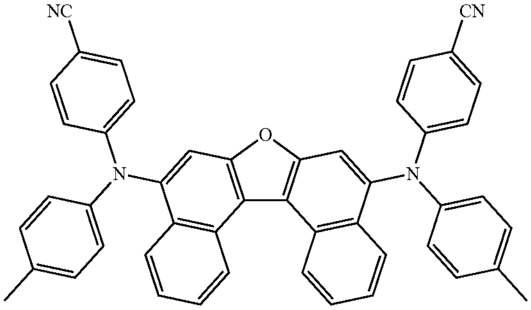
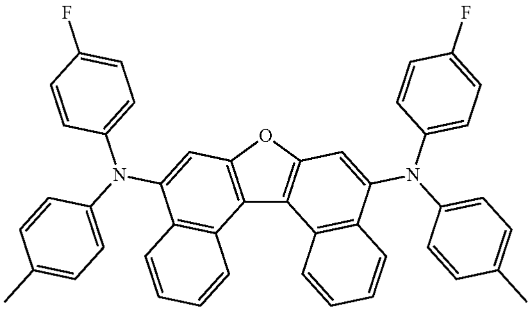
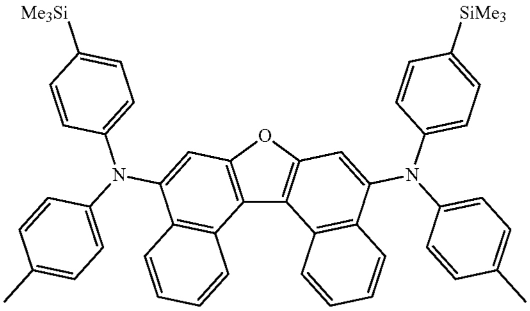
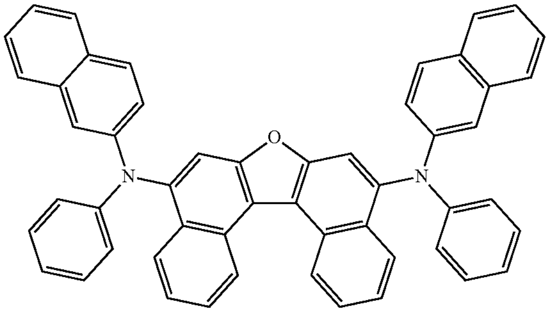
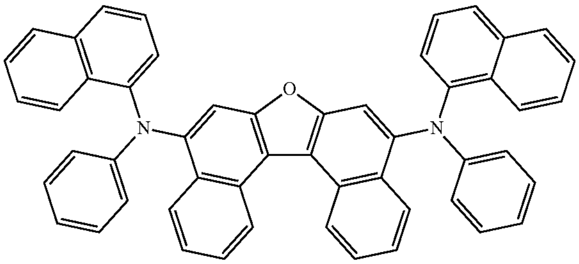
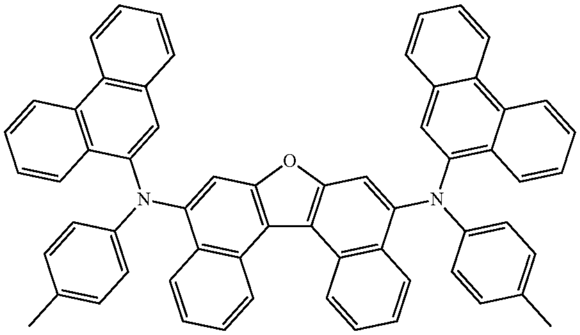

-continued
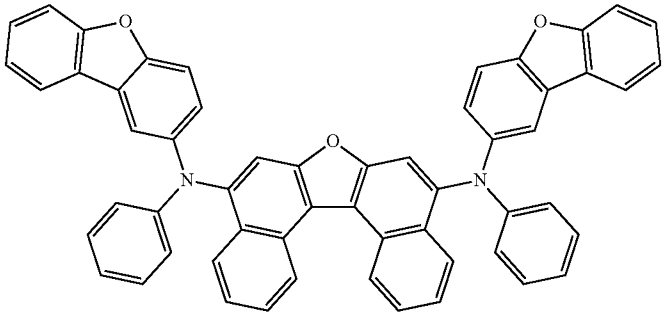
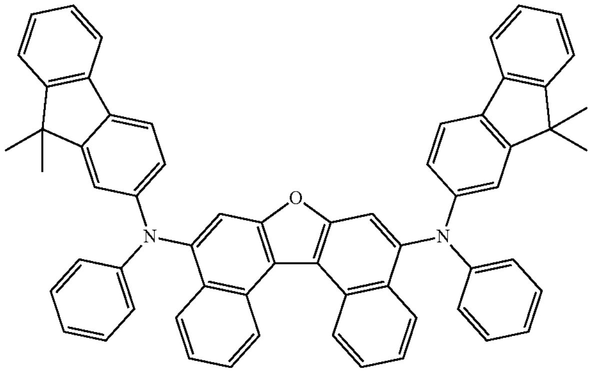
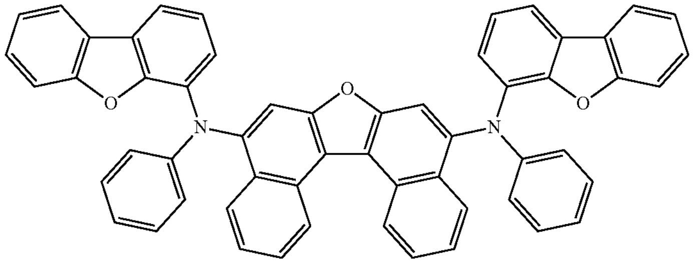
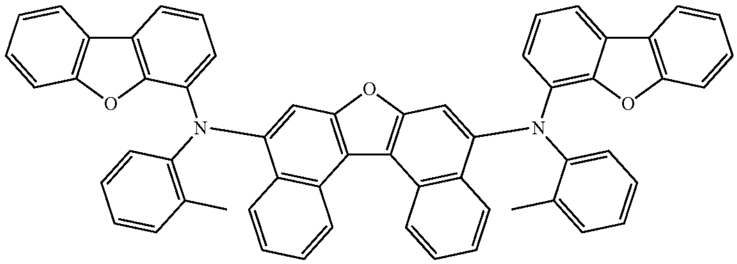
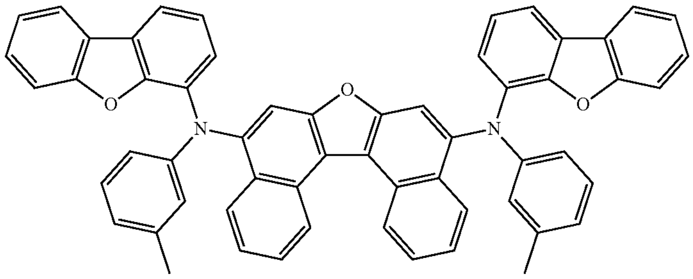

-continued
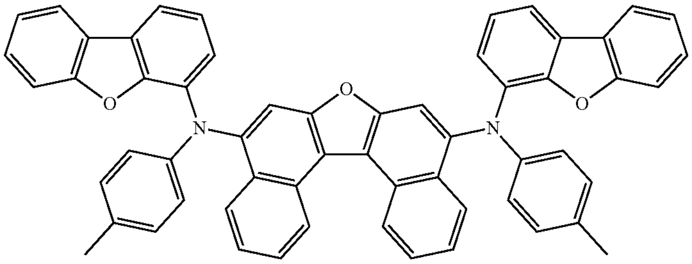
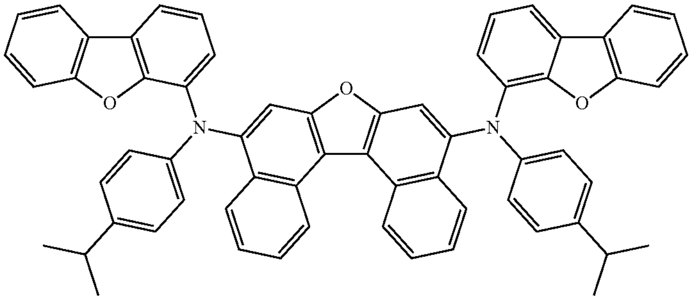
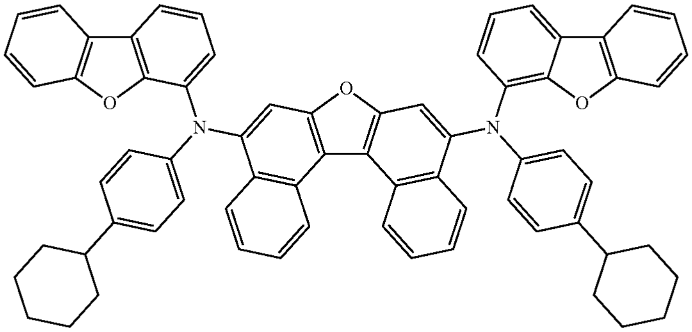
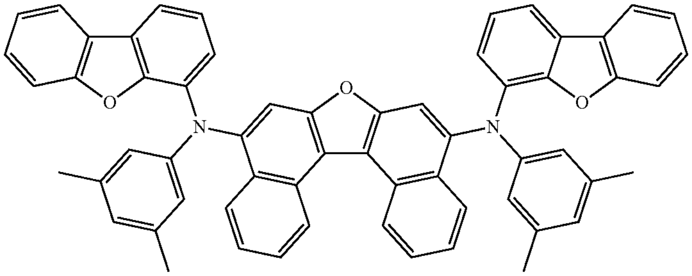
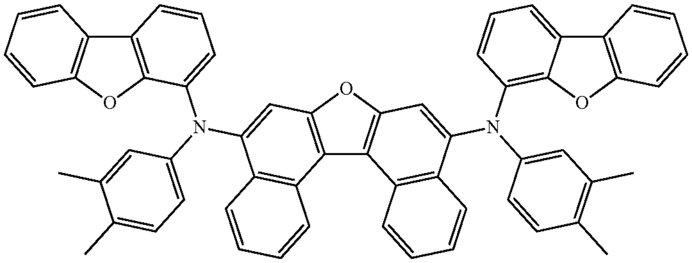
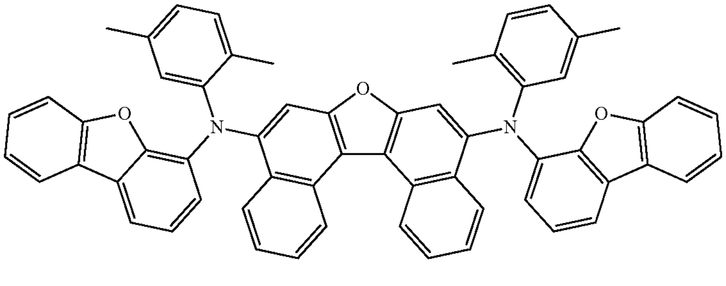

-continued
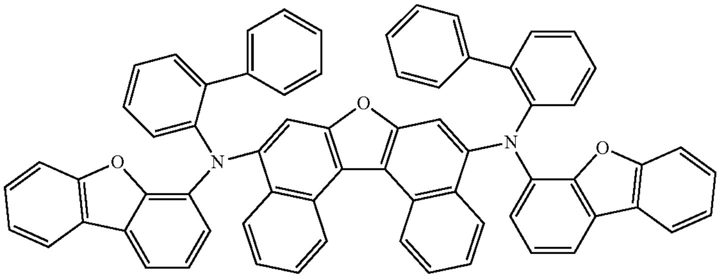
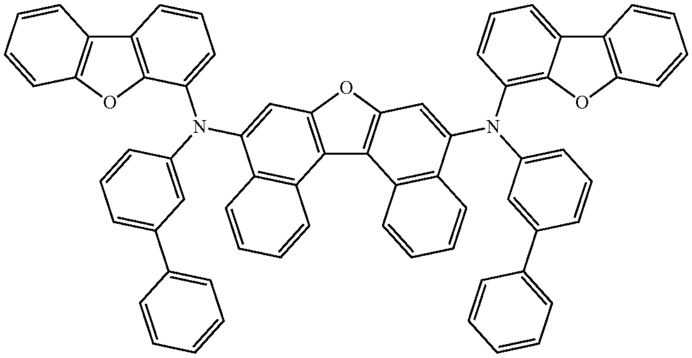
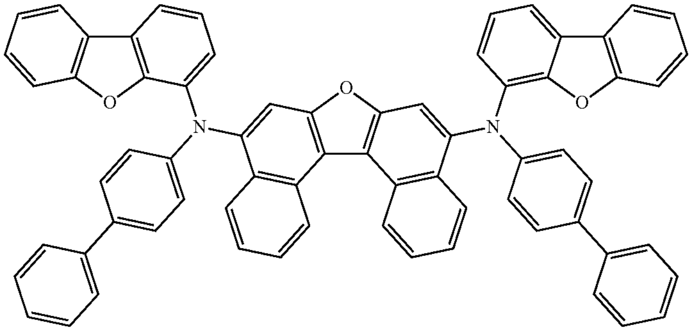
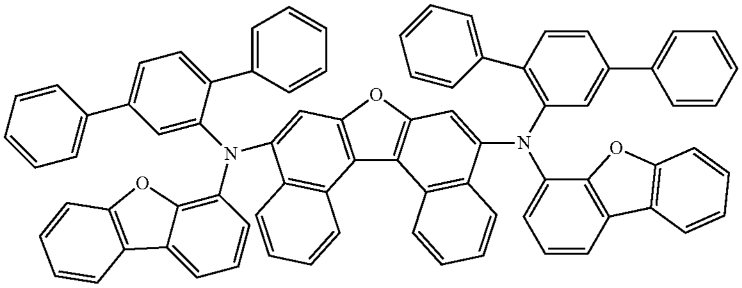
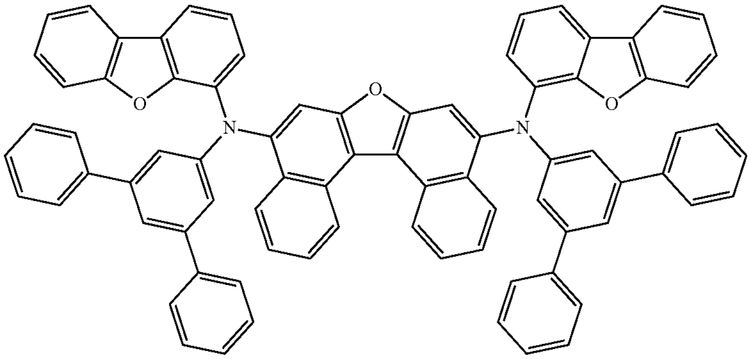

-continued
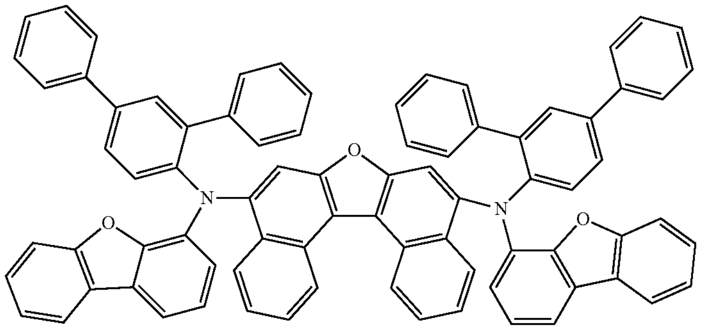
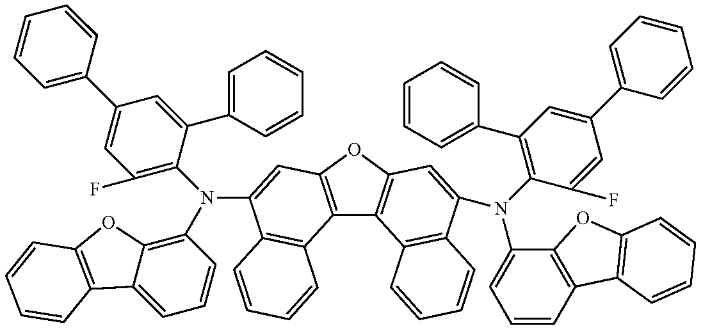
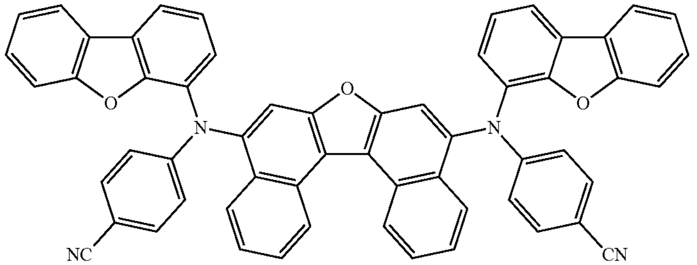
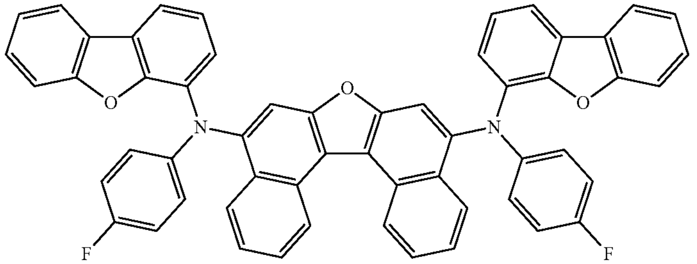
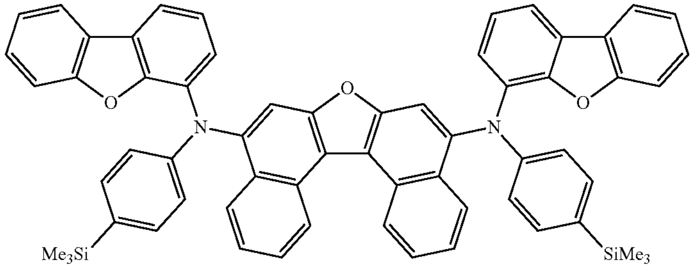
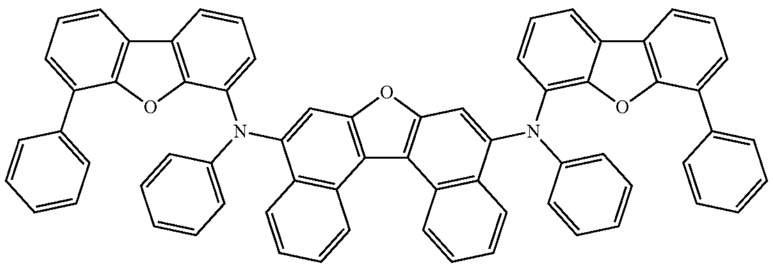

-continued
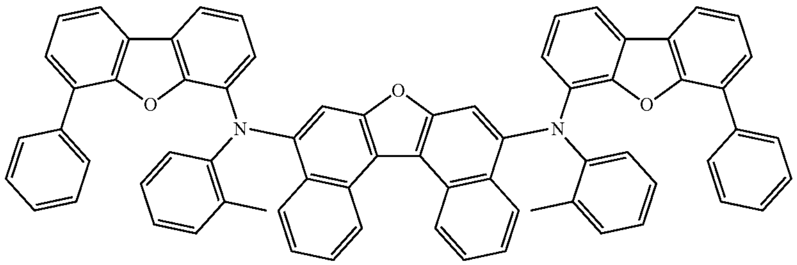
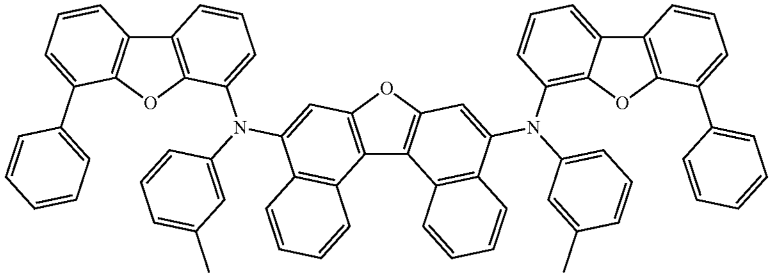
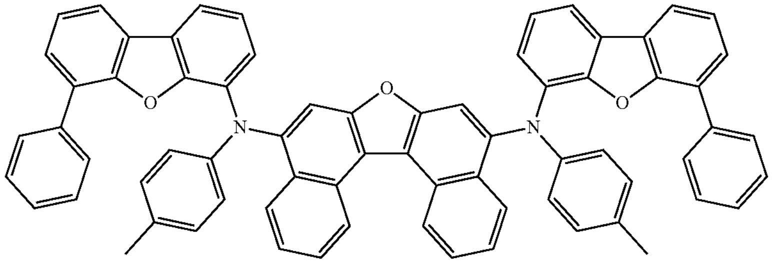
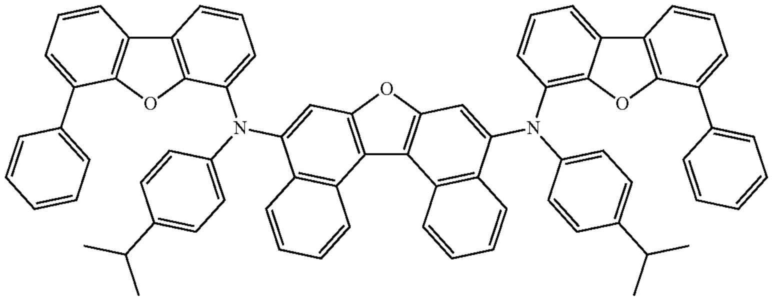
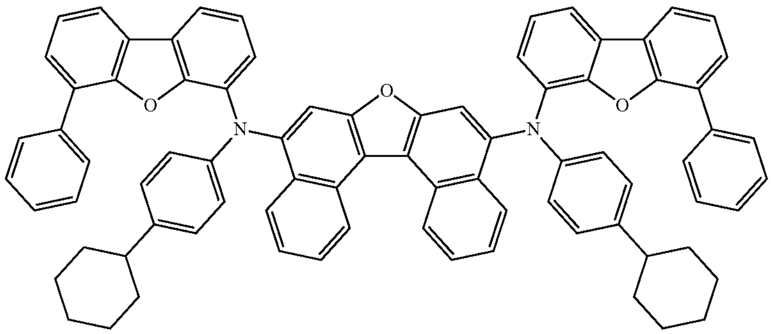
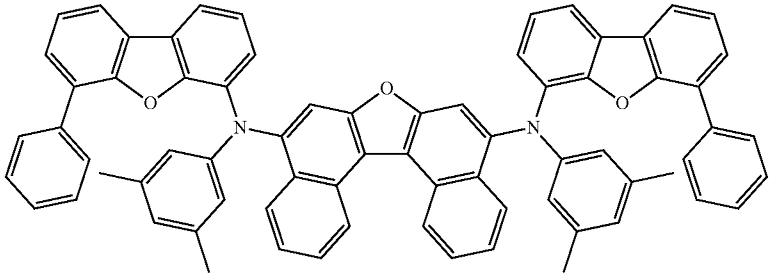

-continued
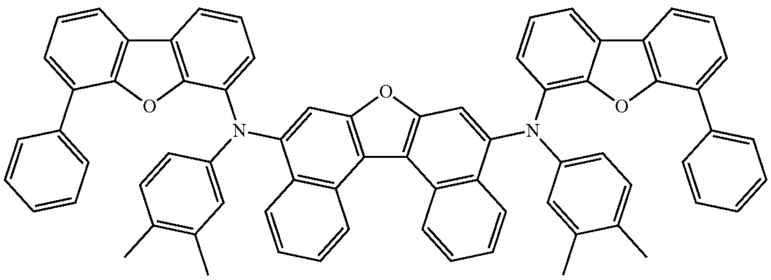
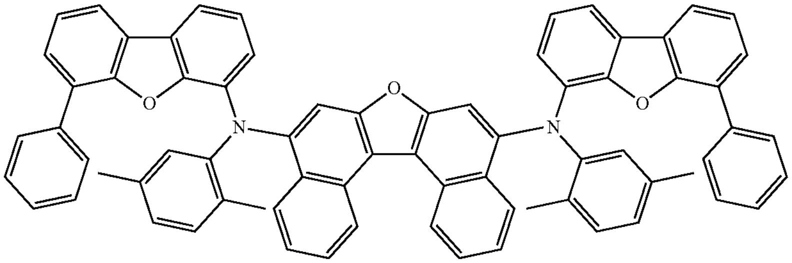
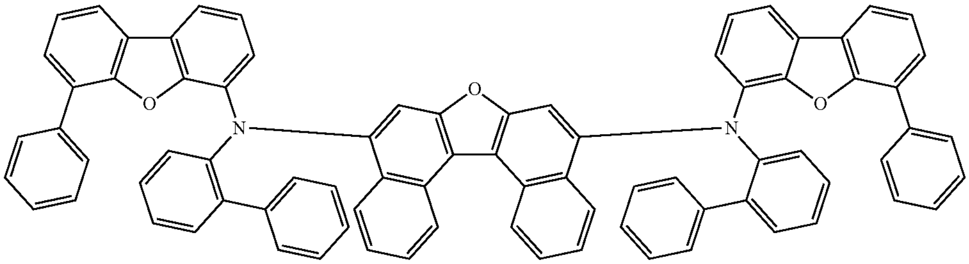
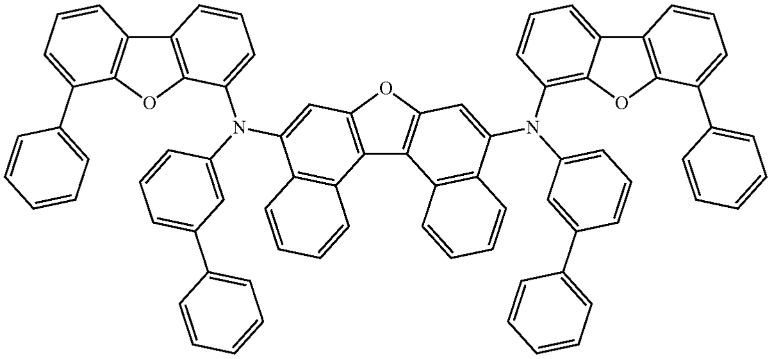
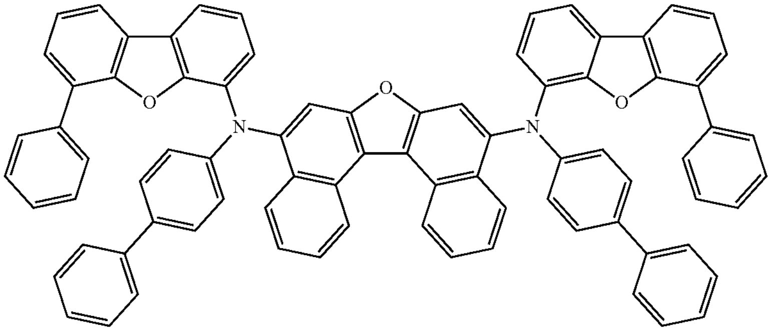

-continued
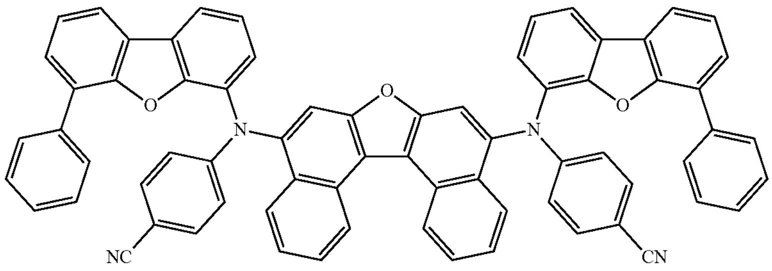
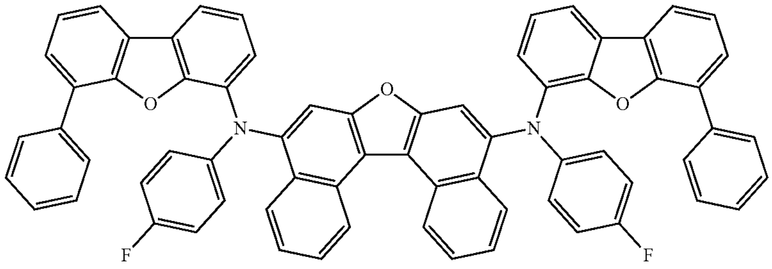
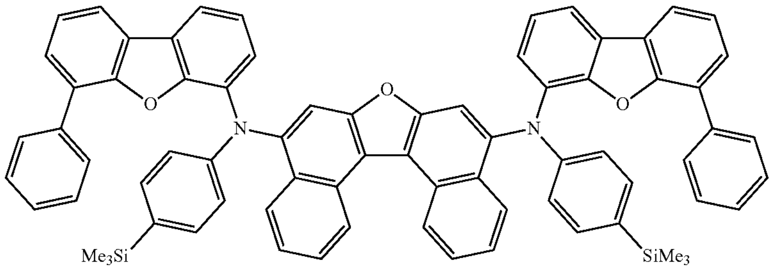
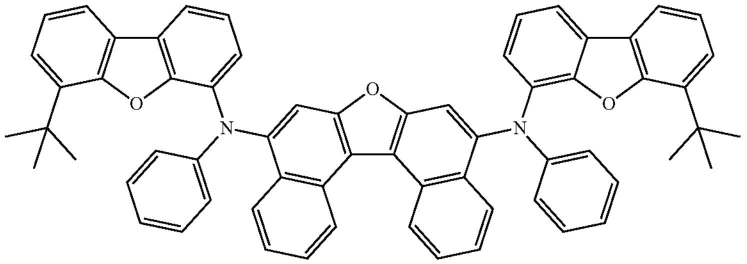
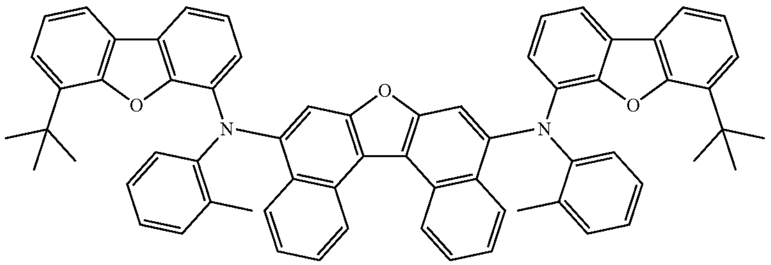
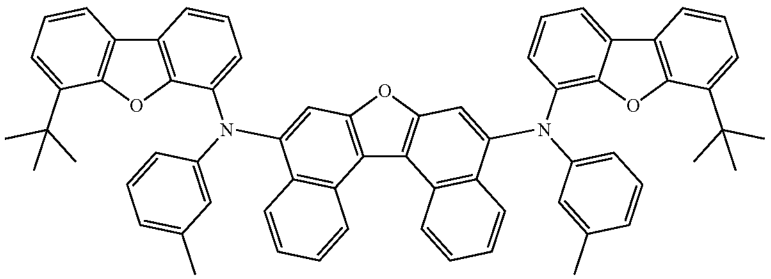

-continued
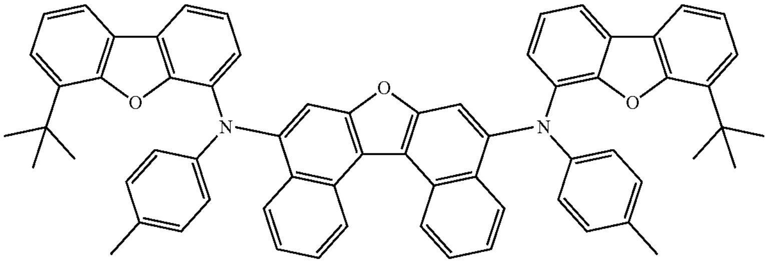
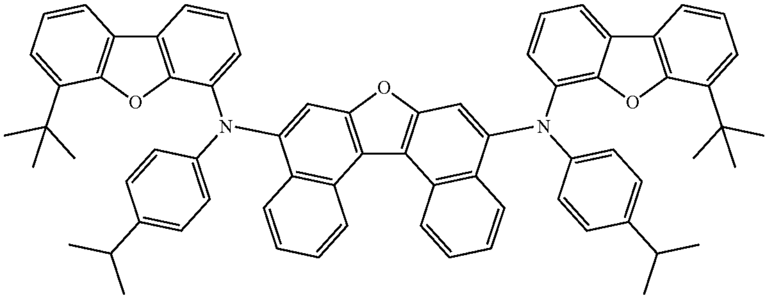
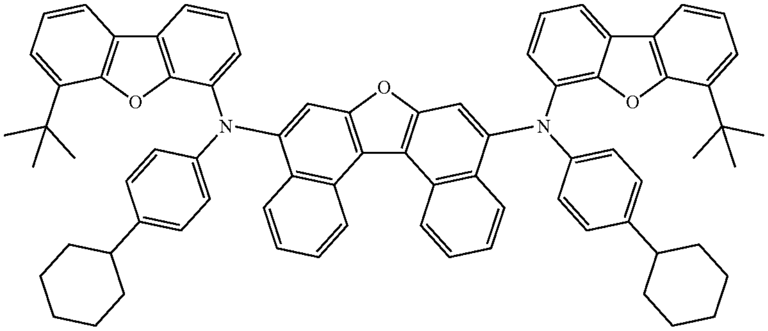
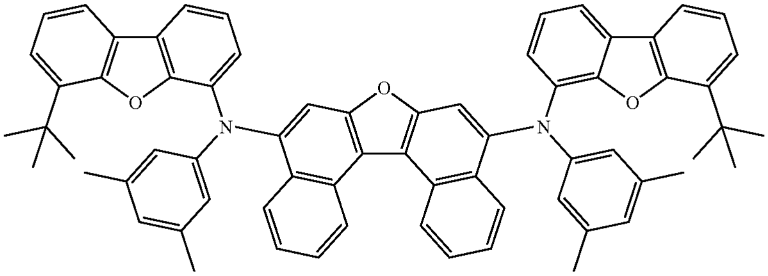
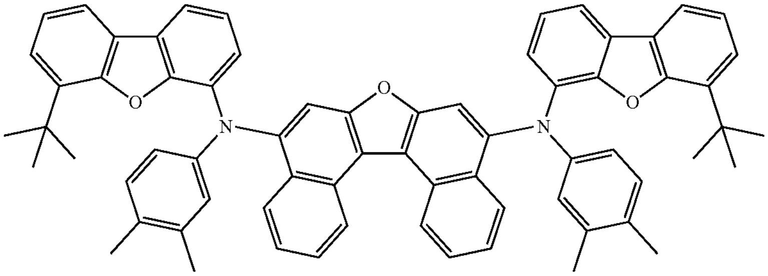
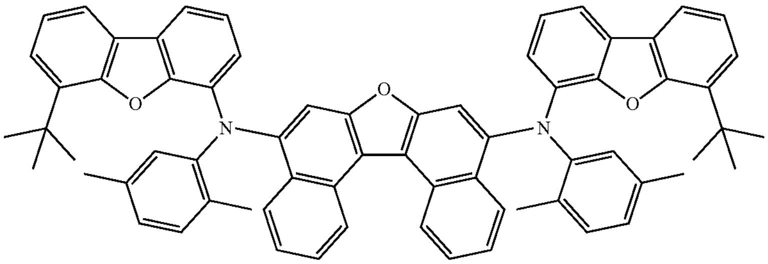

-continued
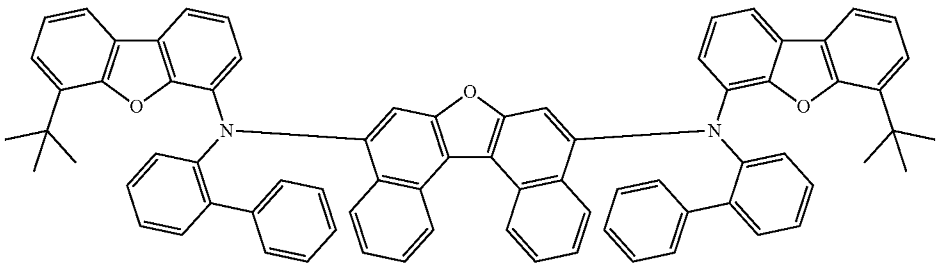
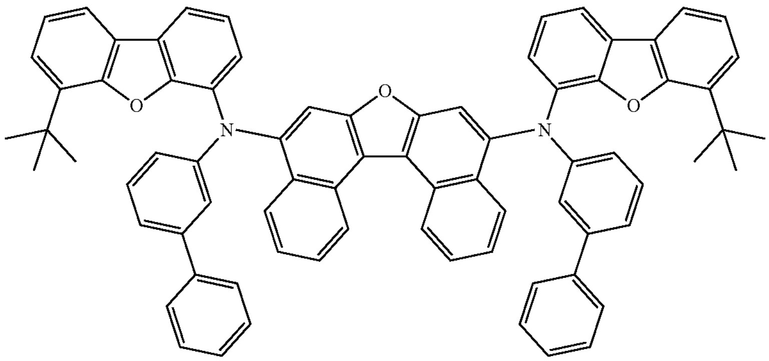
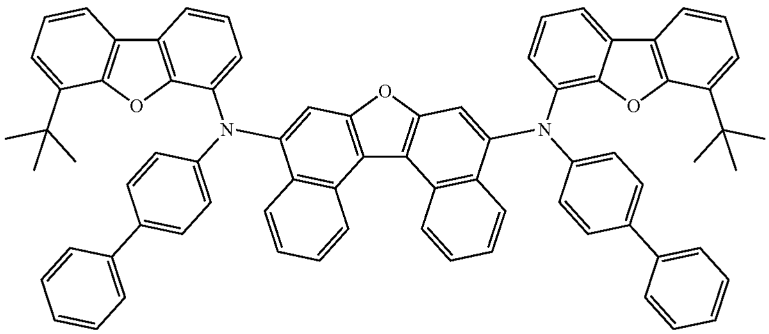
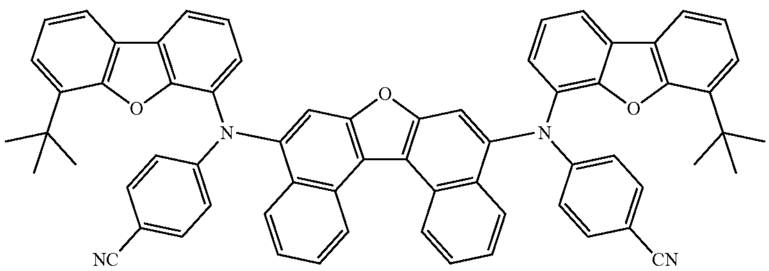
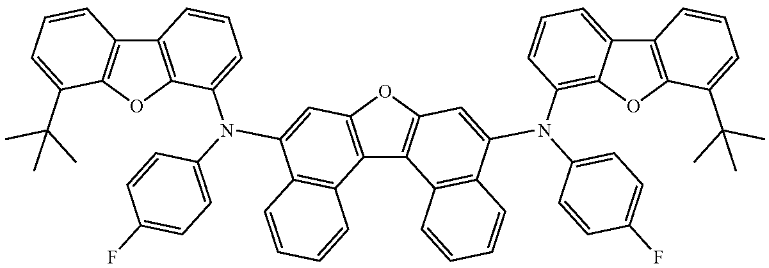

-continued
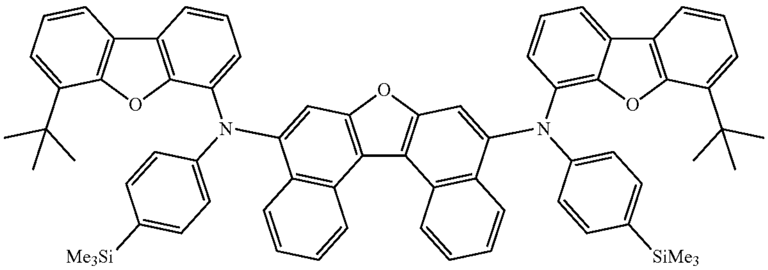
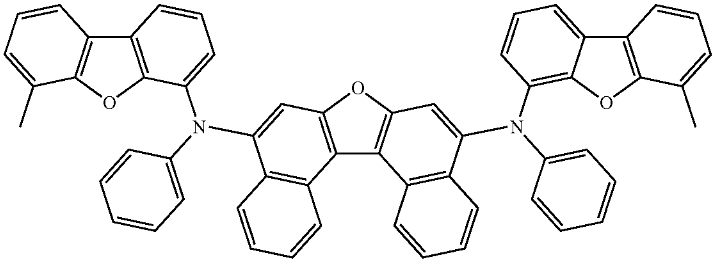
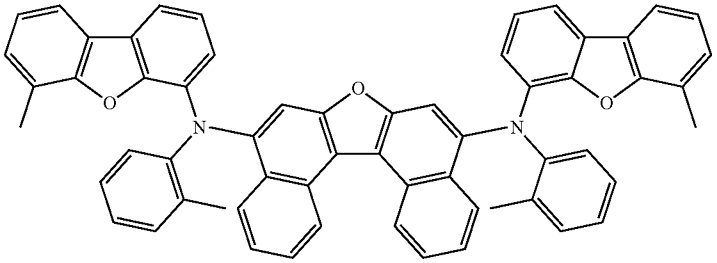
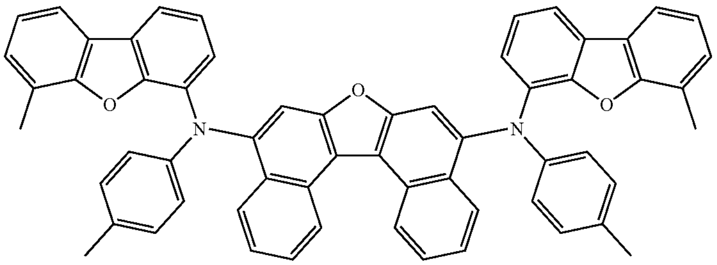
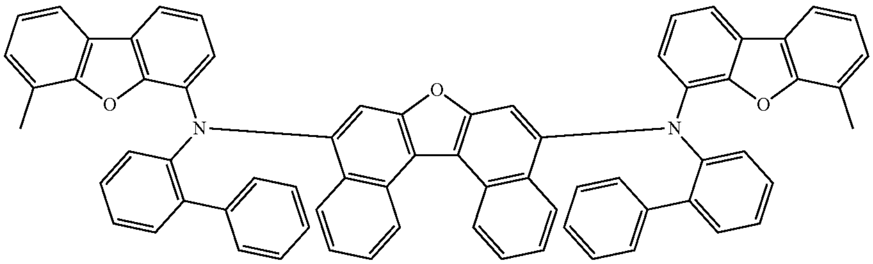
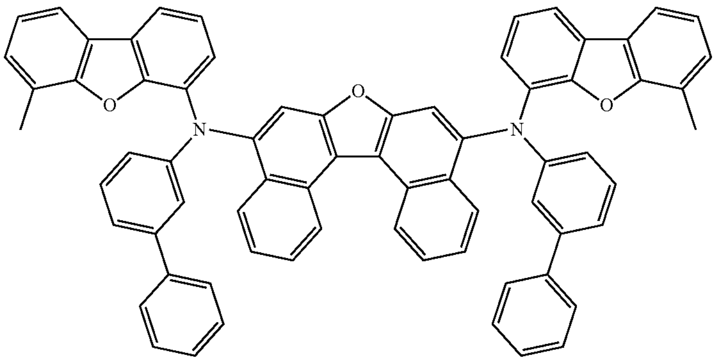

-continued
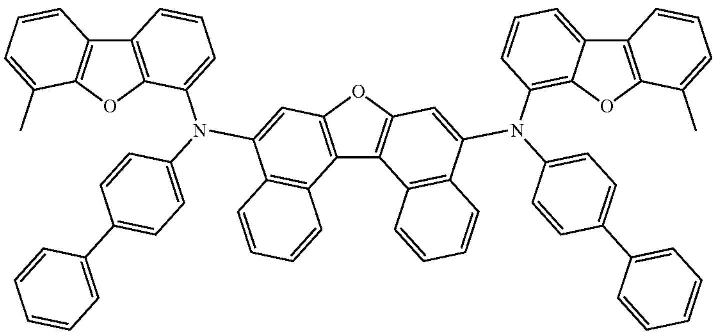
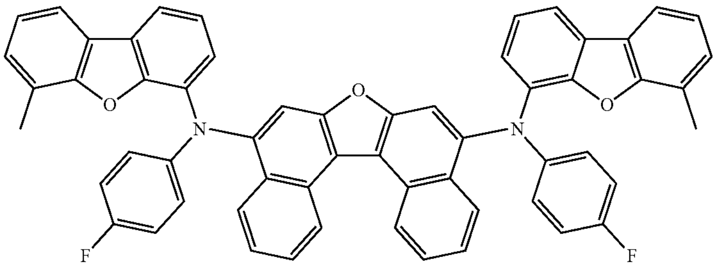
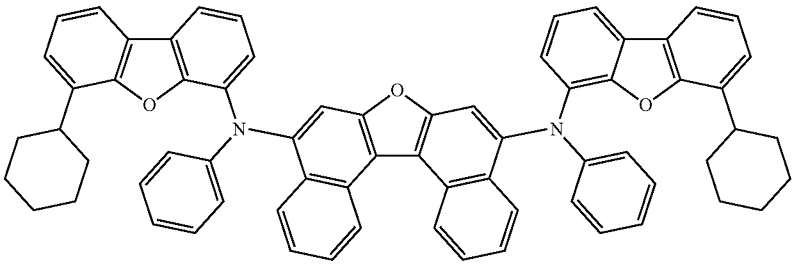
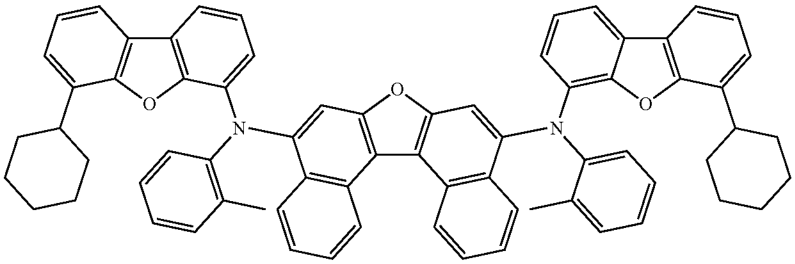
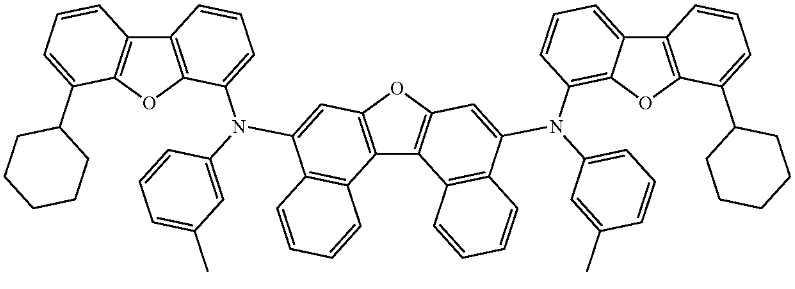
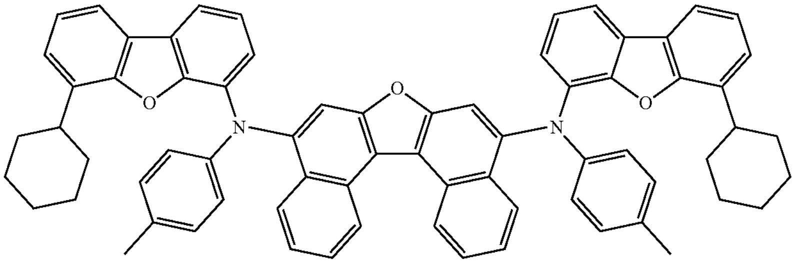

-continued
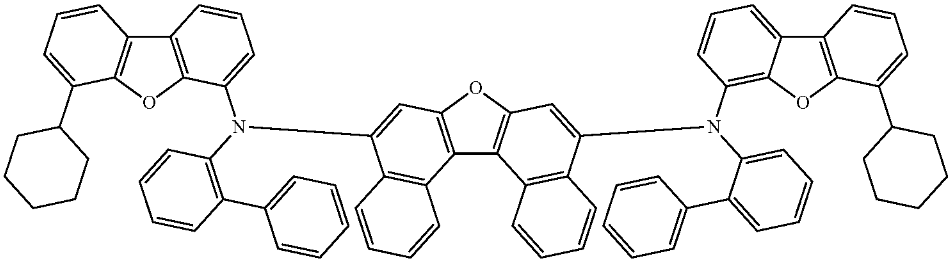
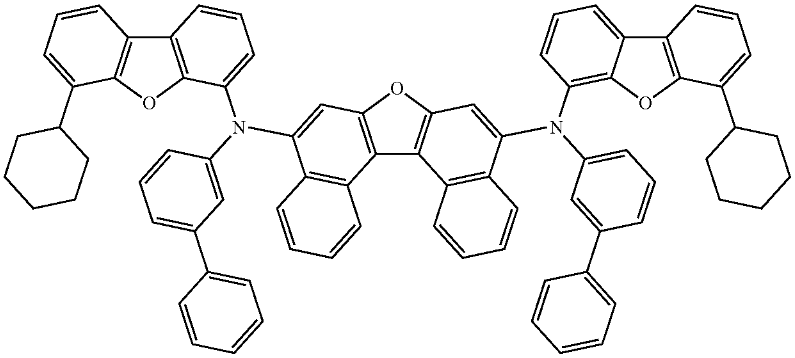
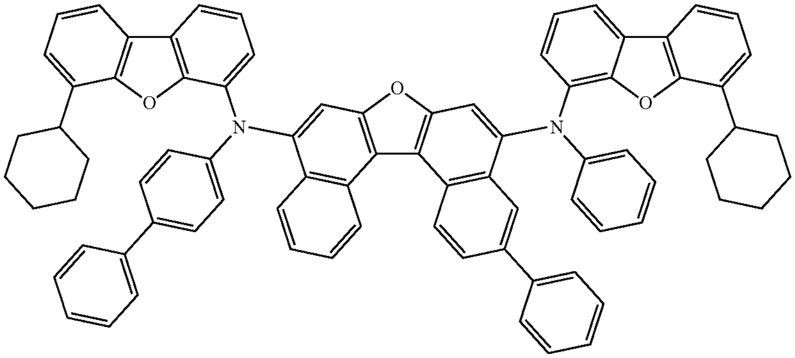
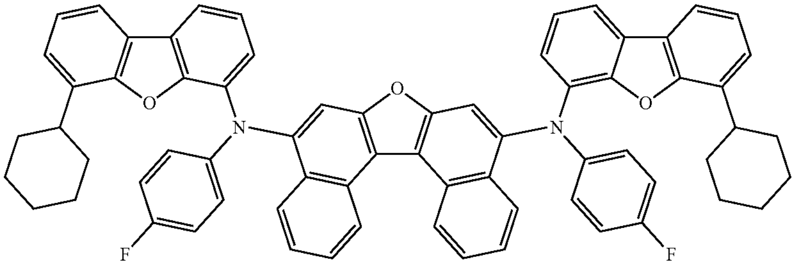
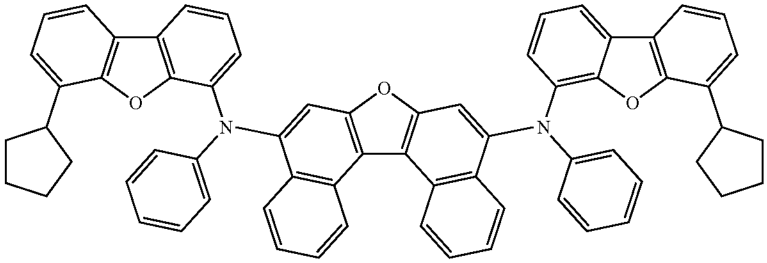

-continued
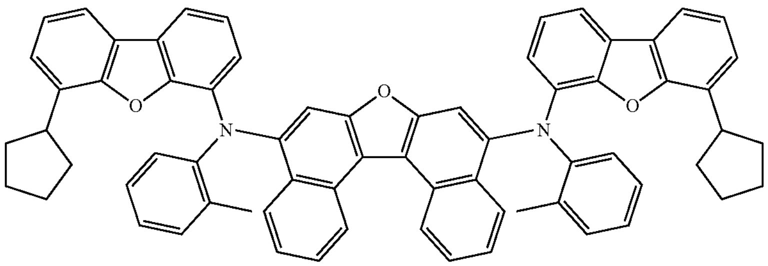
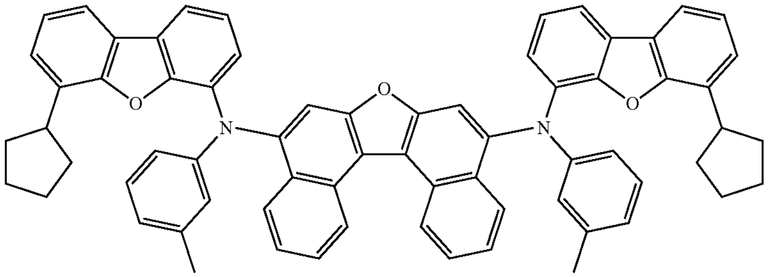
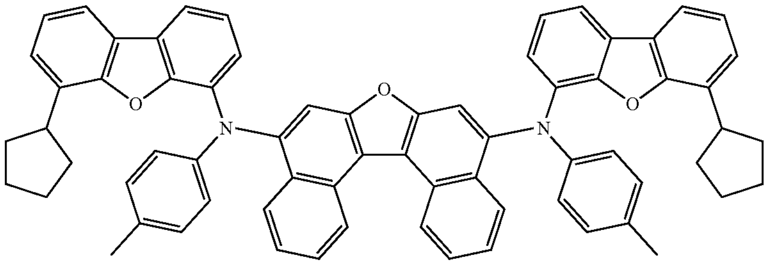
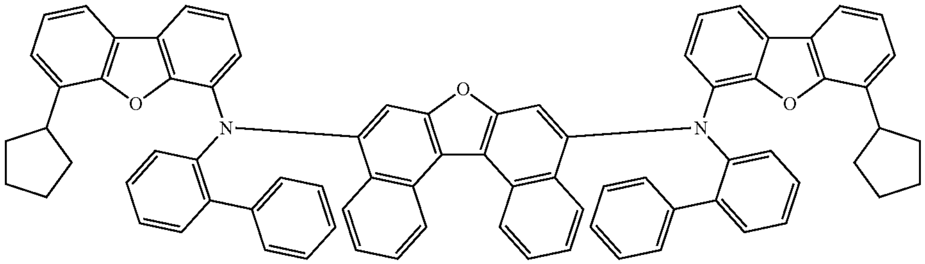
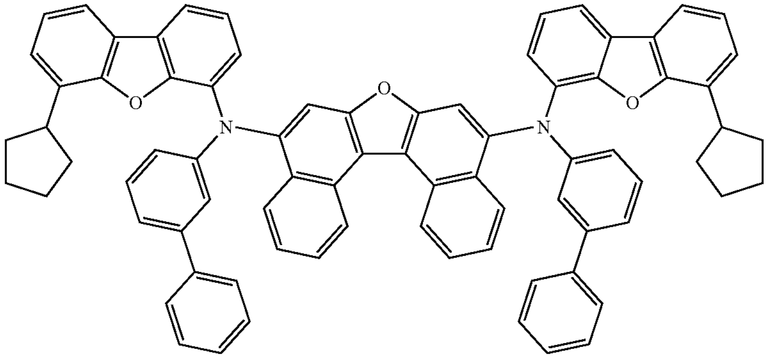

-continued
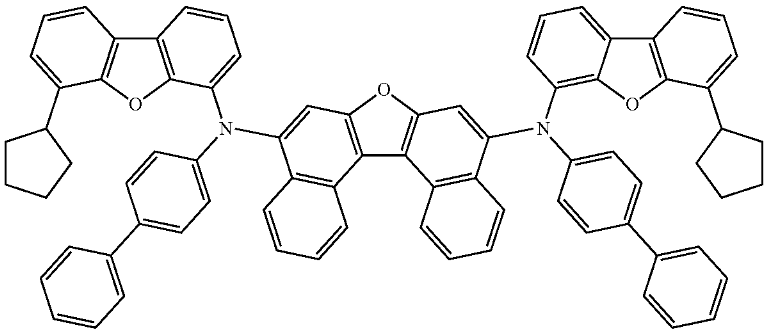
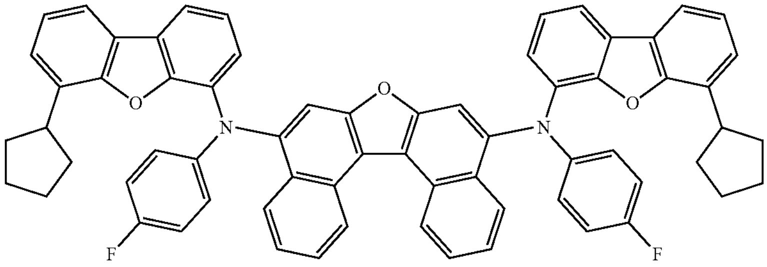
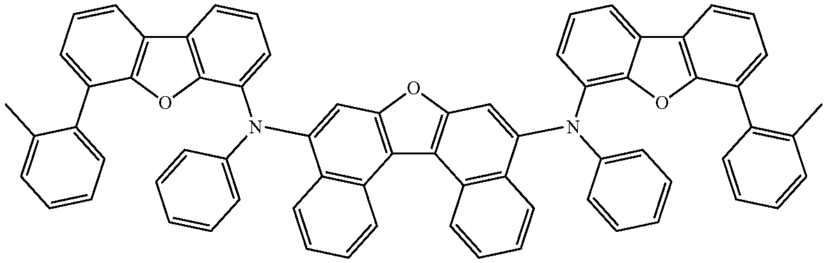
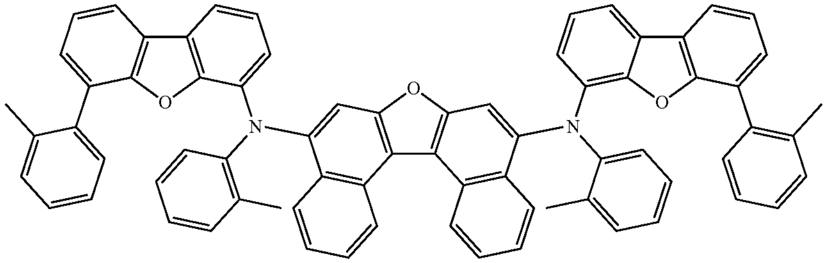
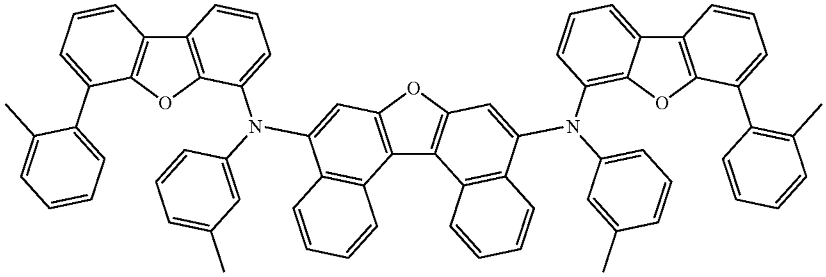
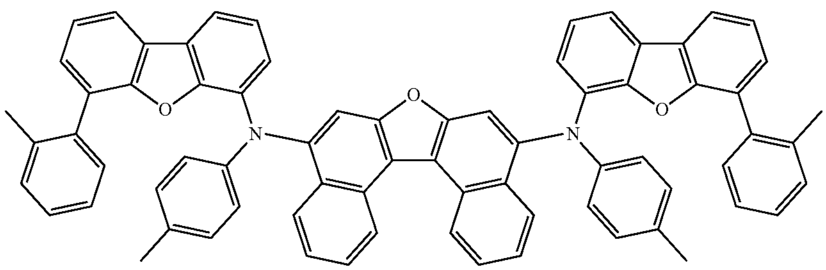

-continued
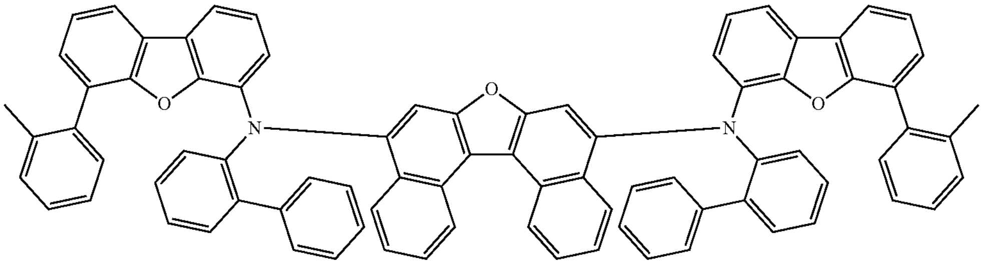
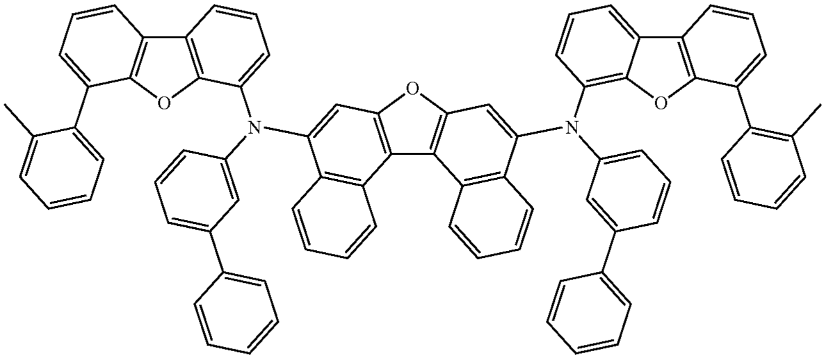
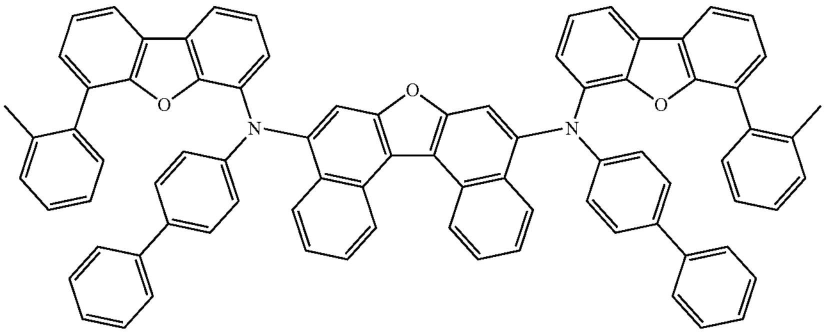
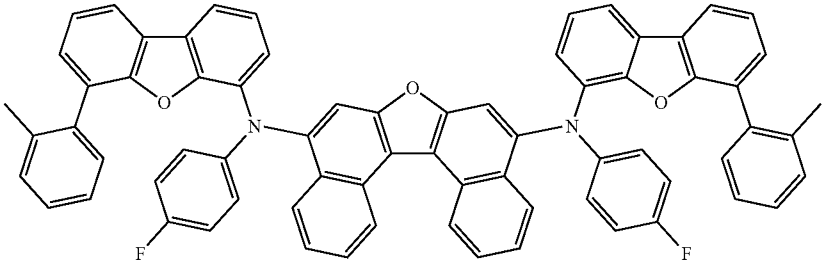
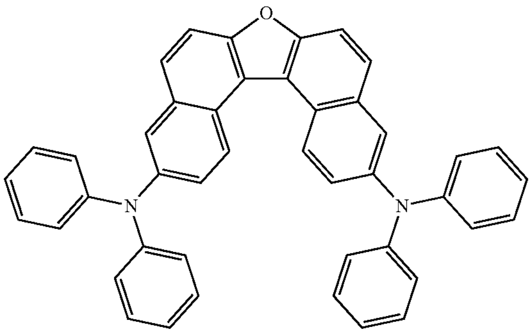
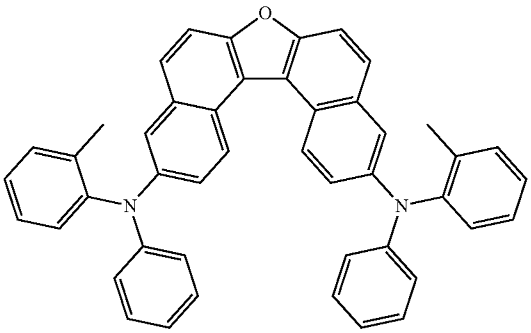

-continued
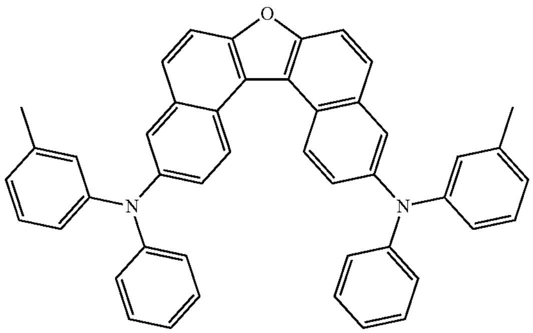
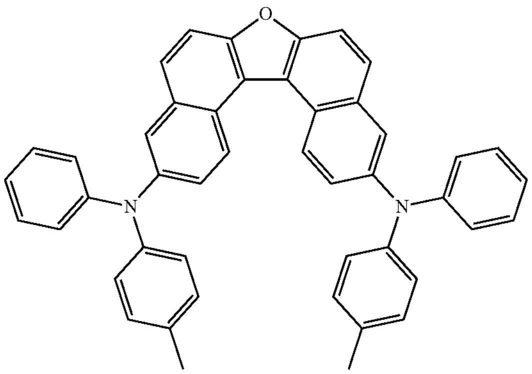
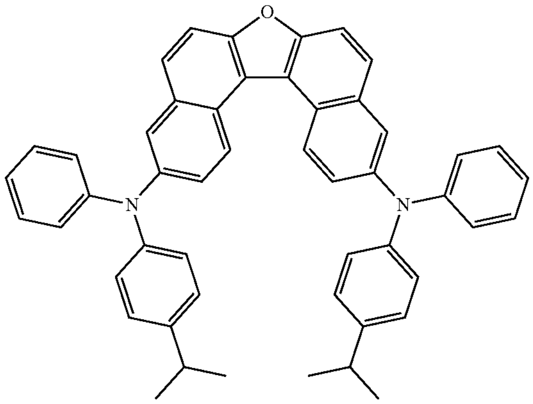
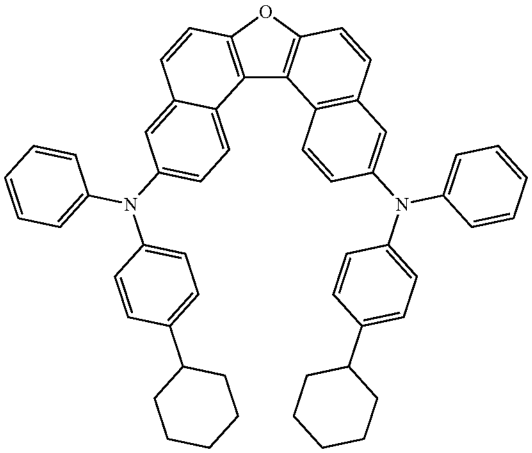
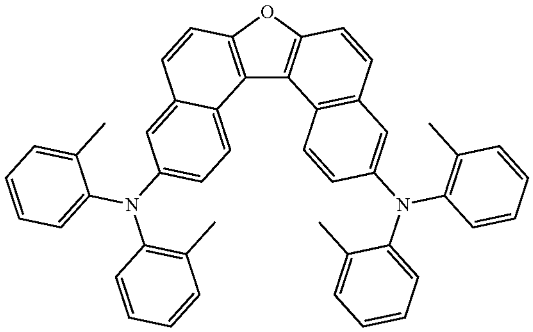
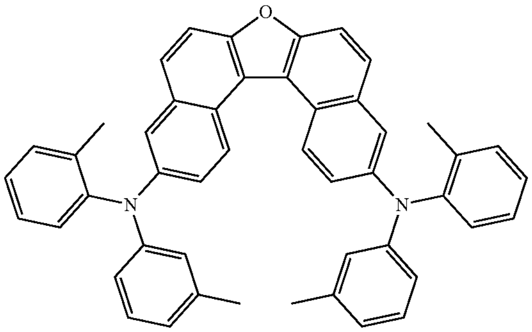
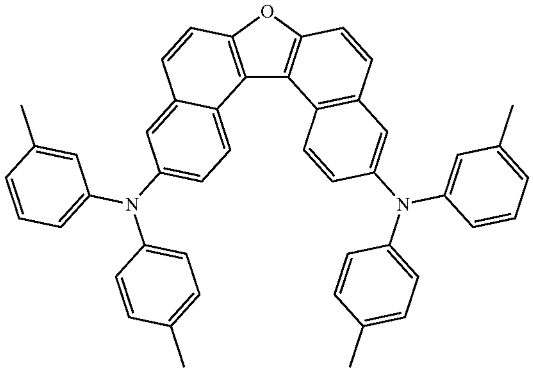
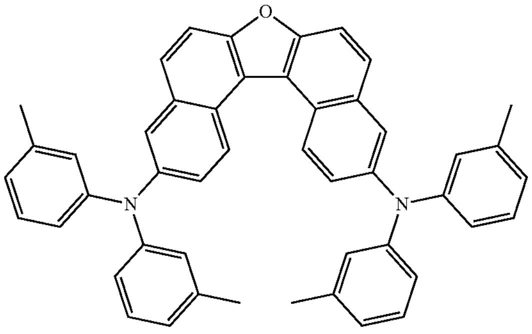

-continued
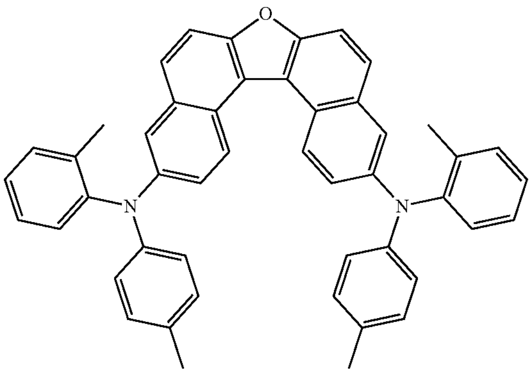
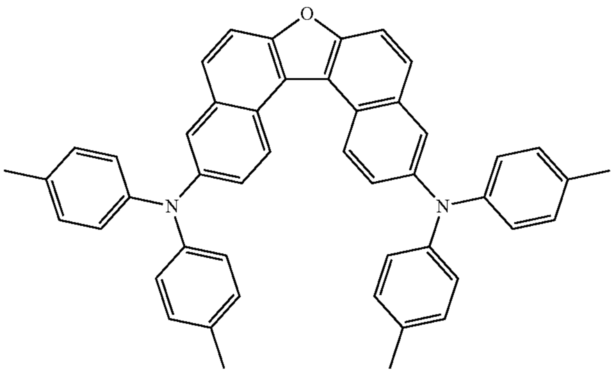
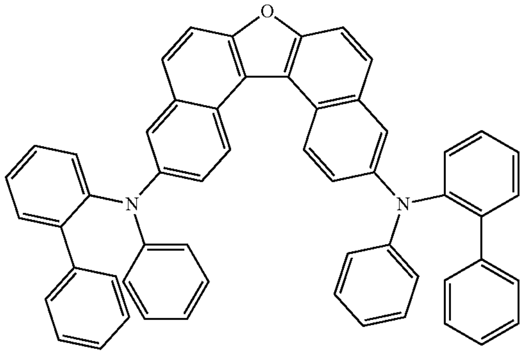
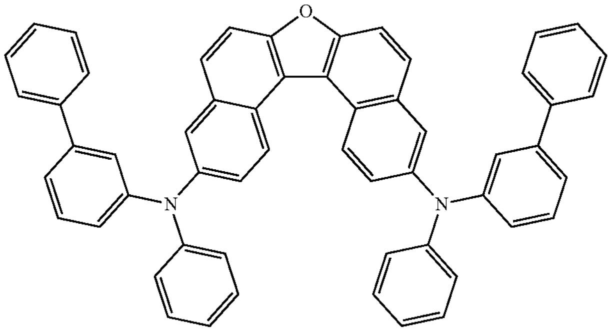
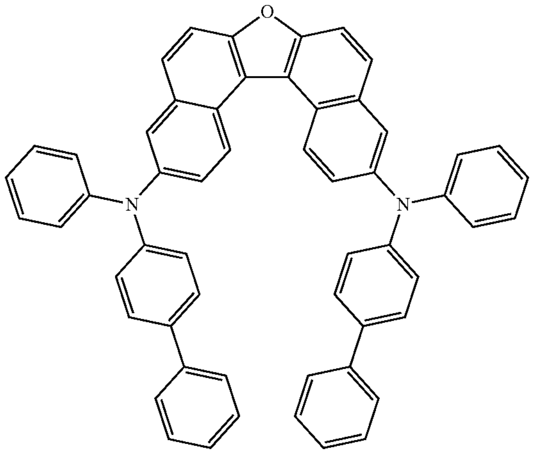
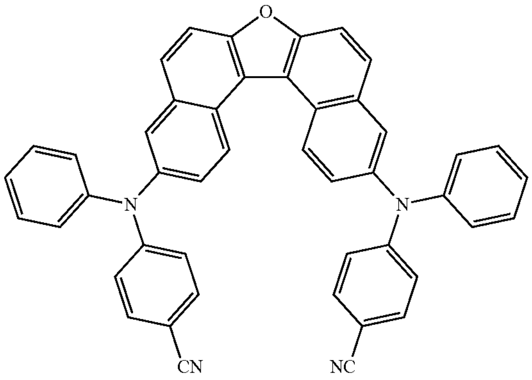
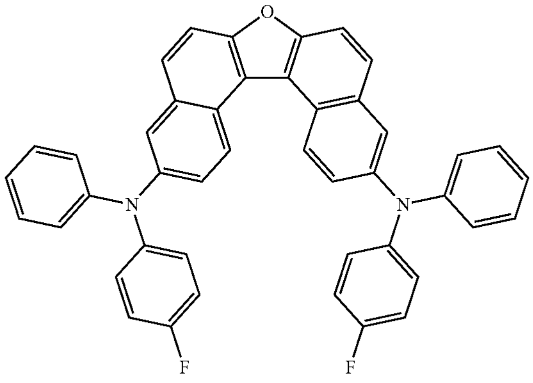
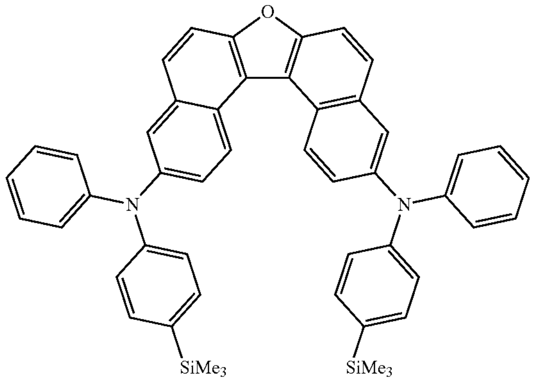

-continued
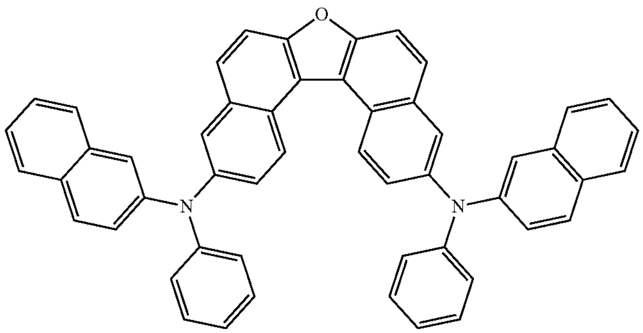
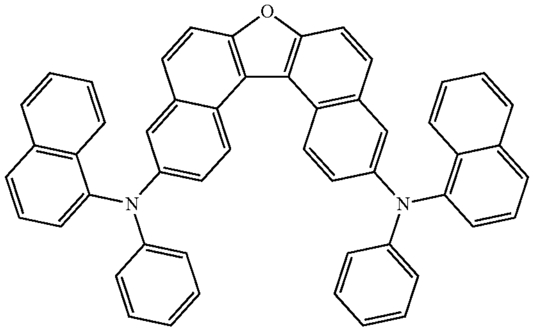
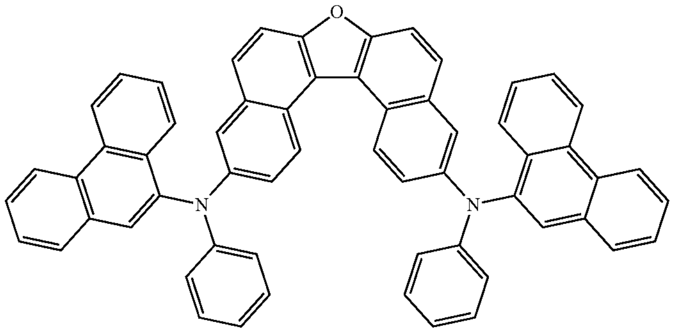
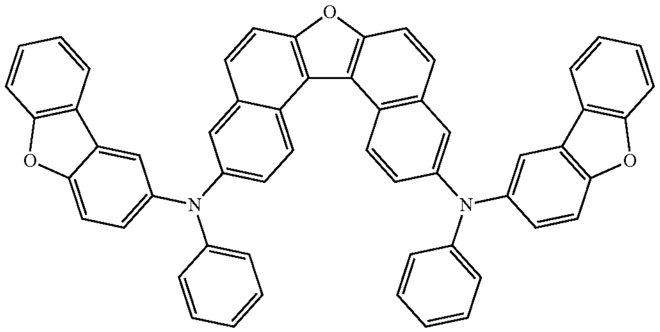
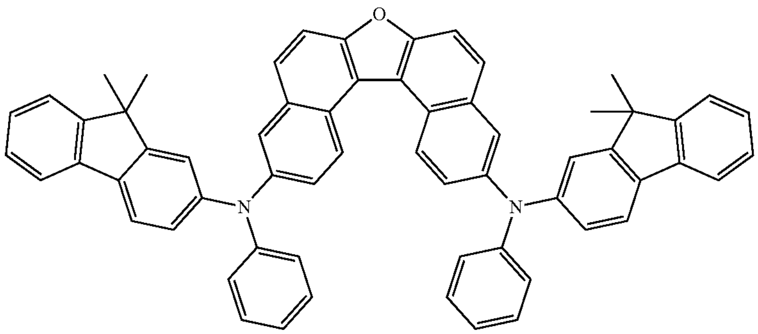

-continued
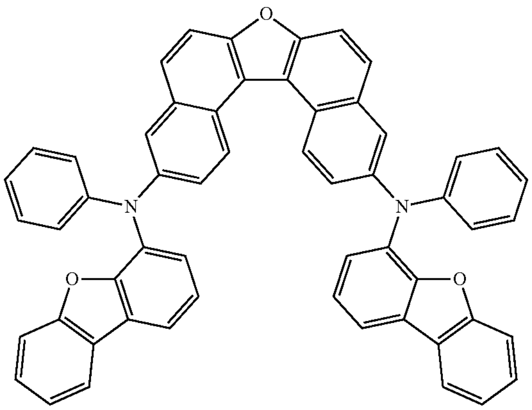
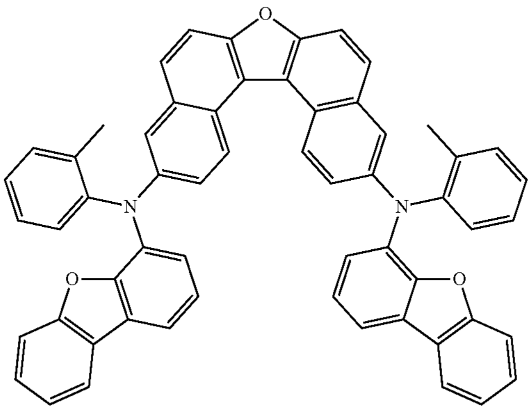
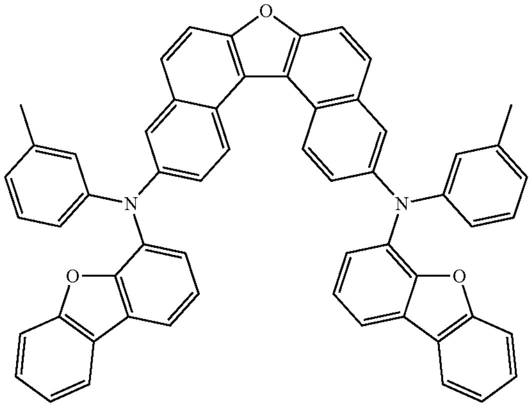
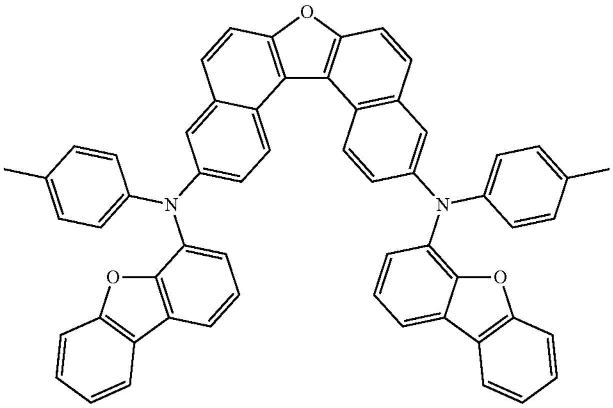
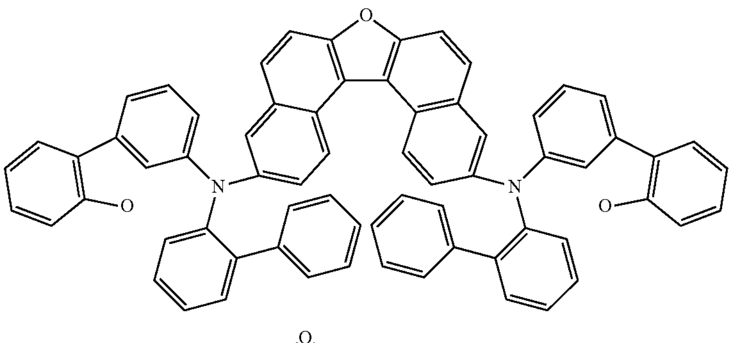
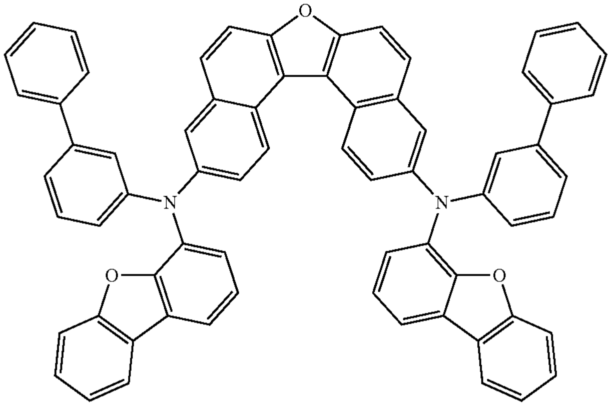

-continued
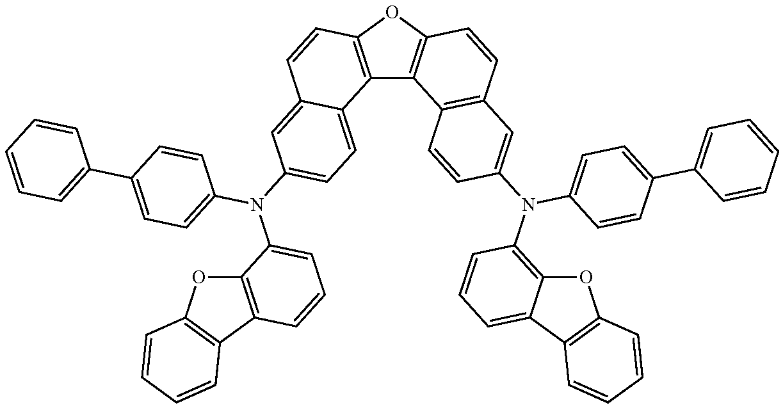
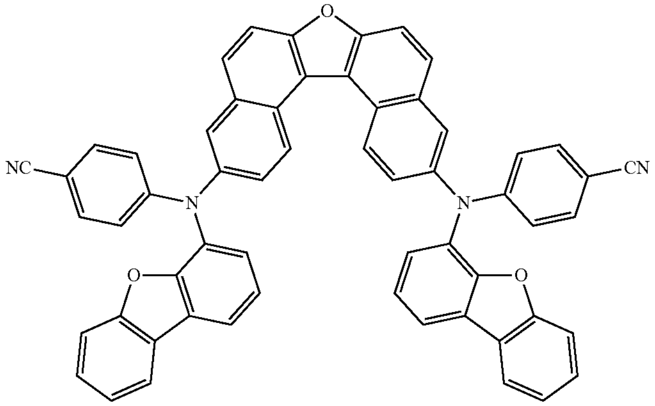
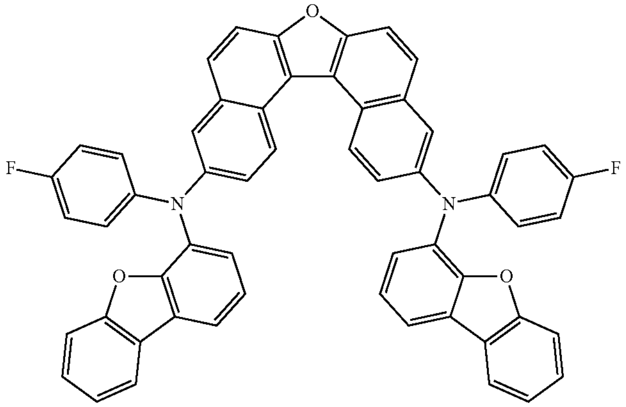
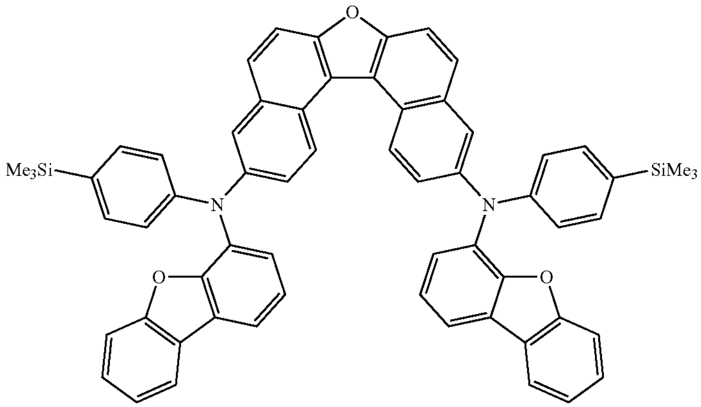

-continued
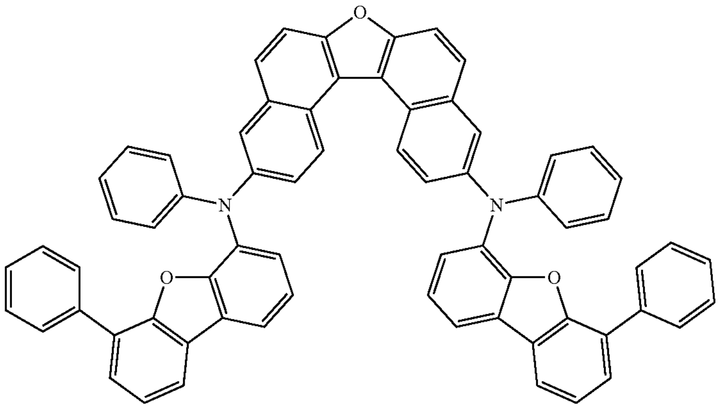
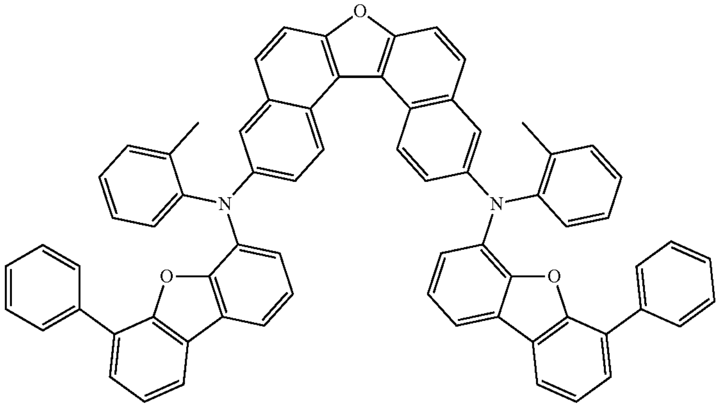
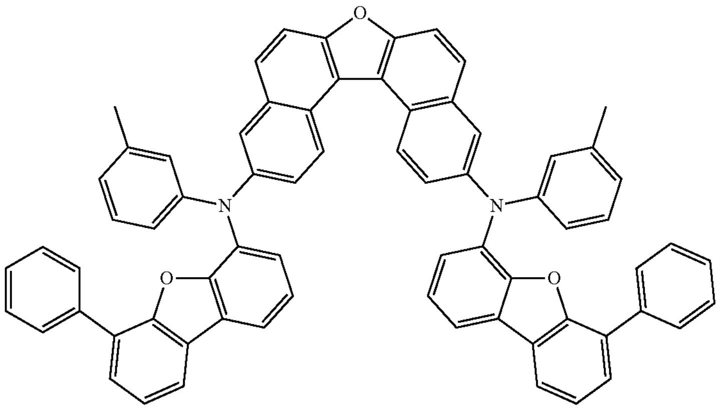
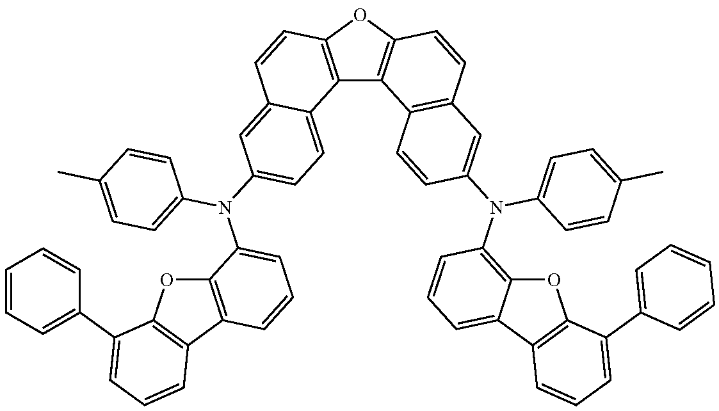

-continued
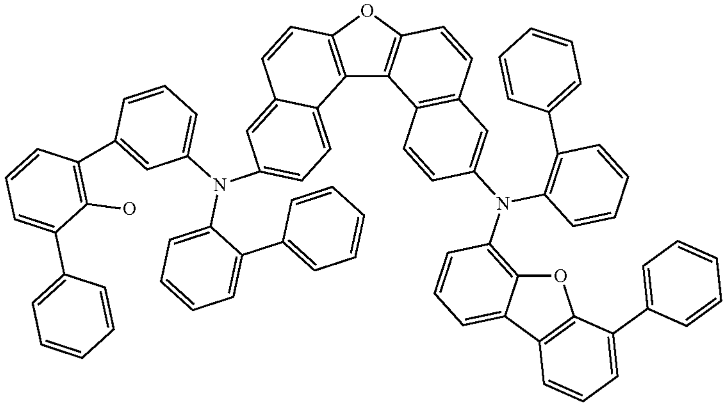
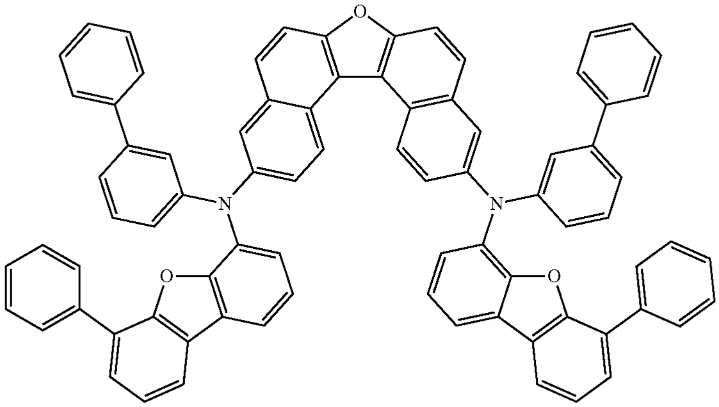
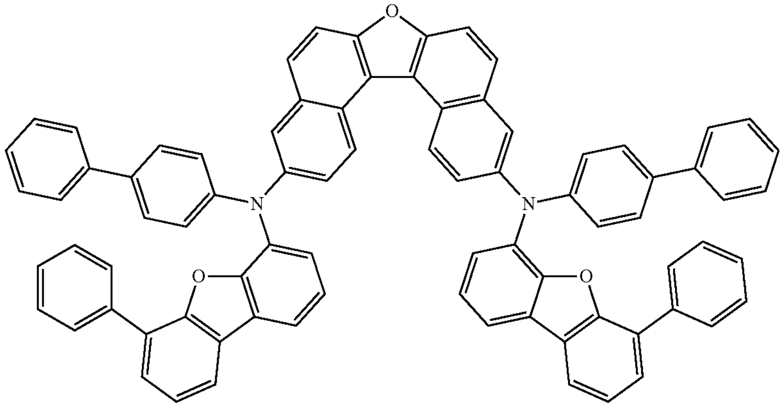
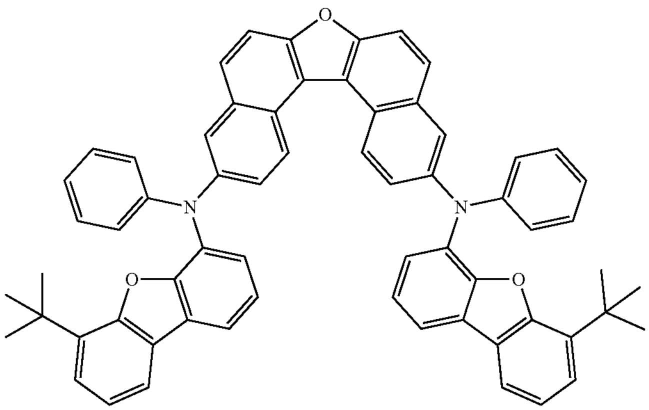

-continued
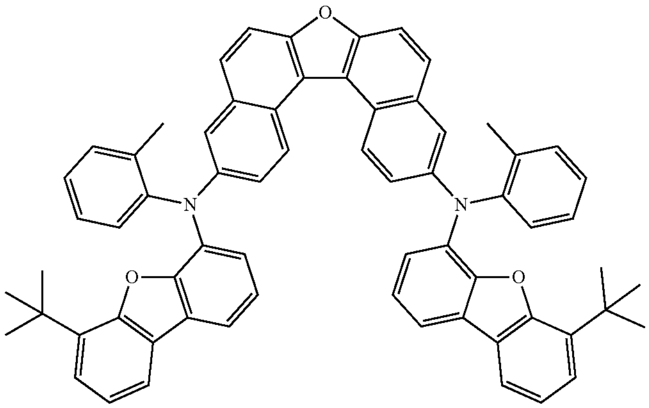
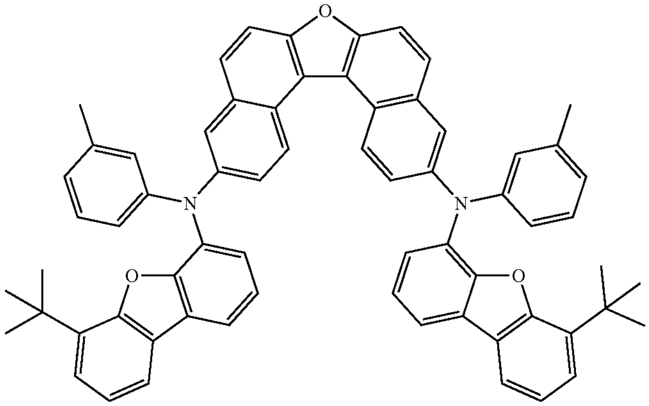
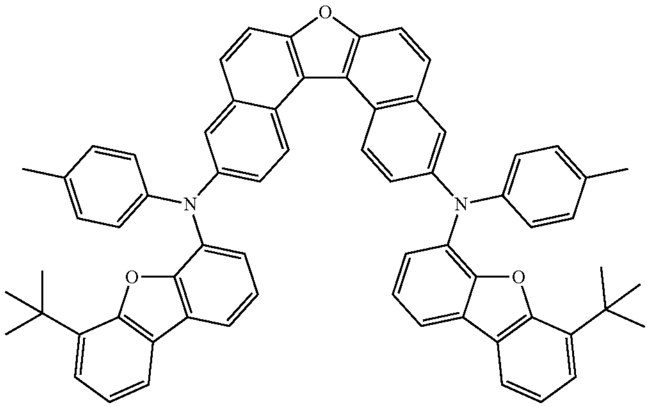
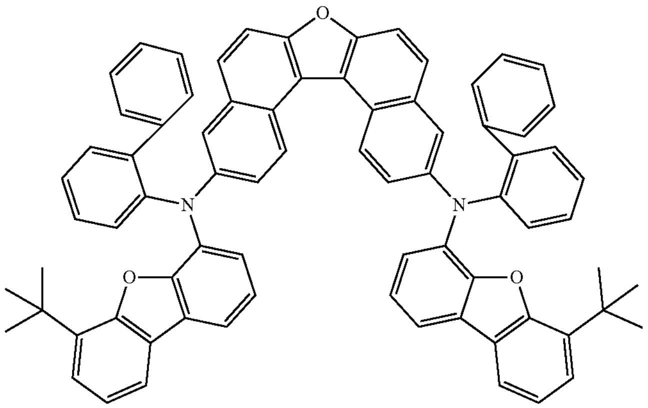

-continued
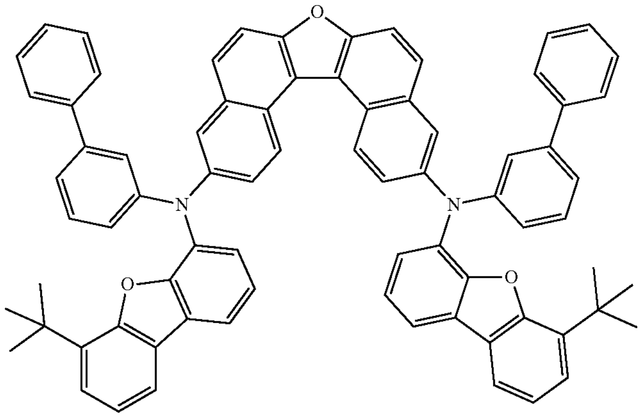
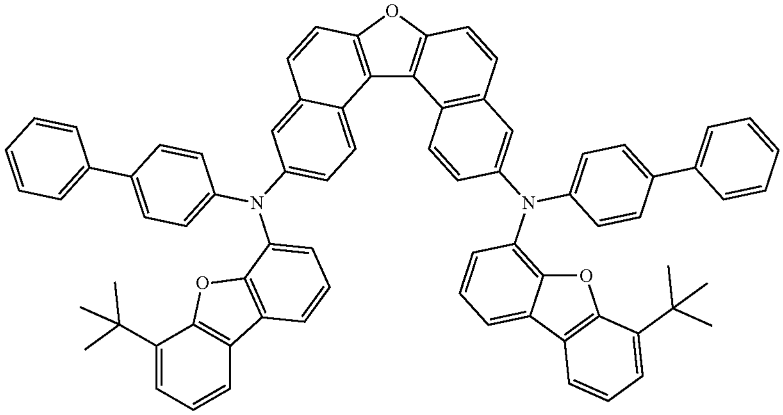
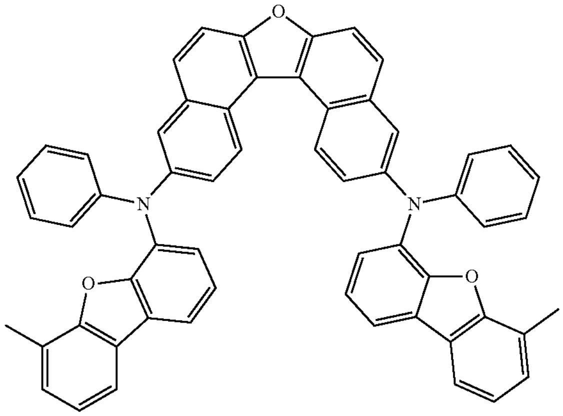
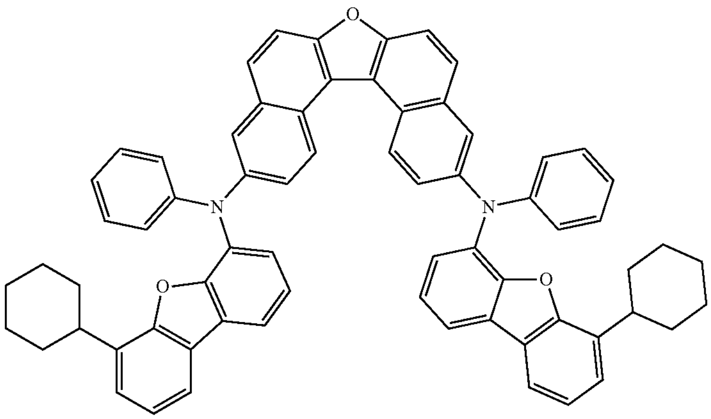

-continued
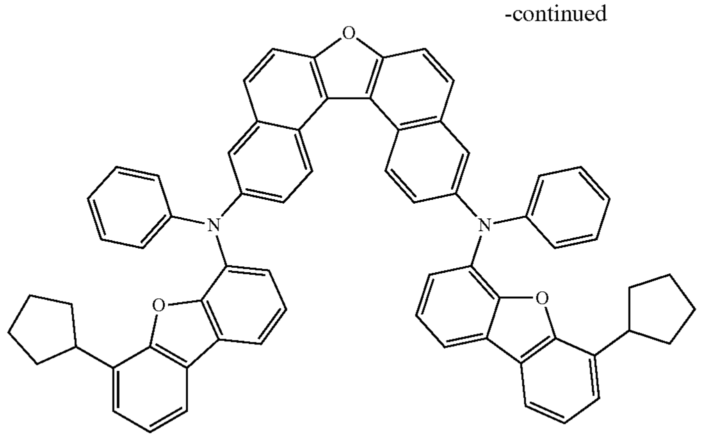
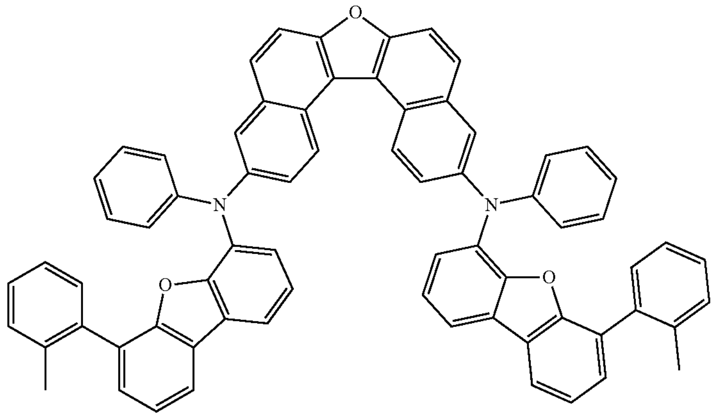
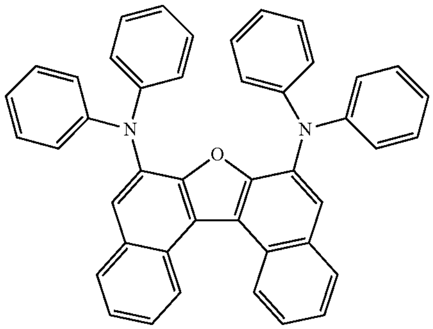
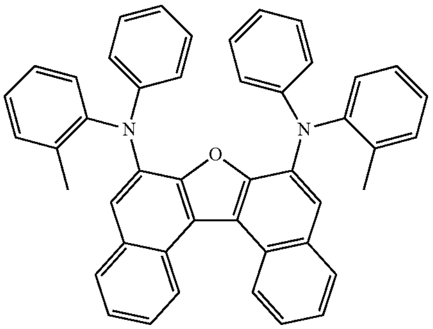
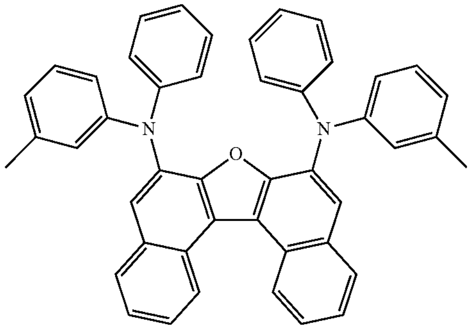
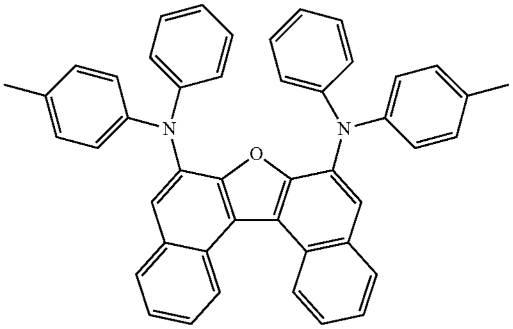

-continued
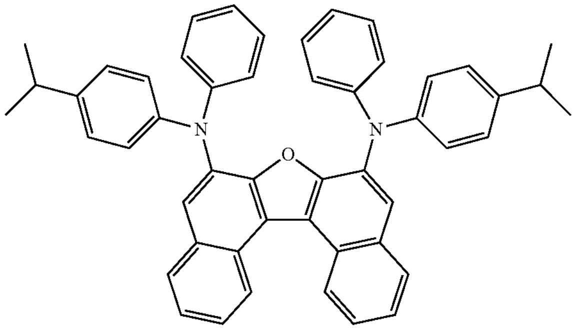
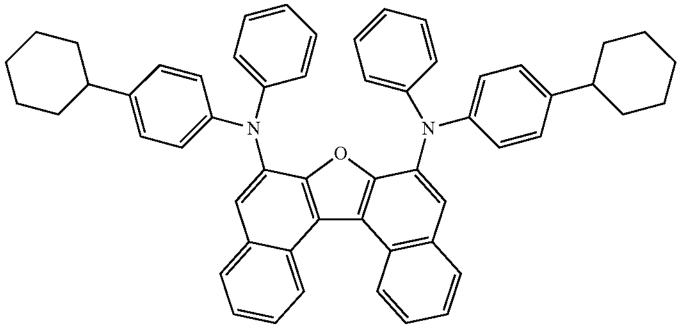
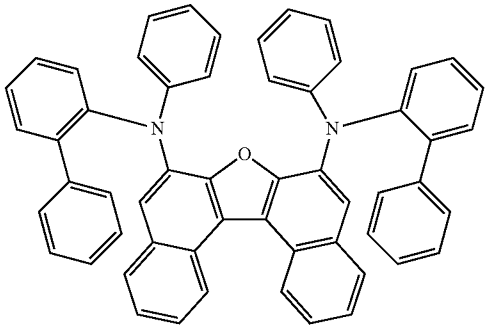
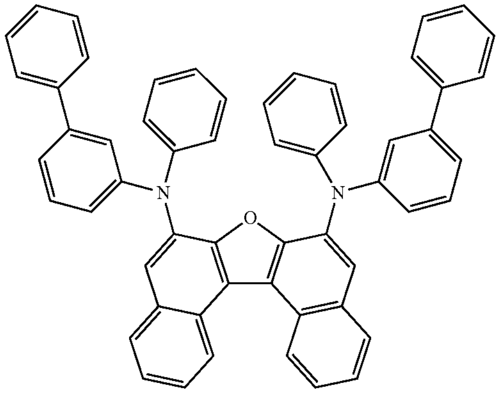
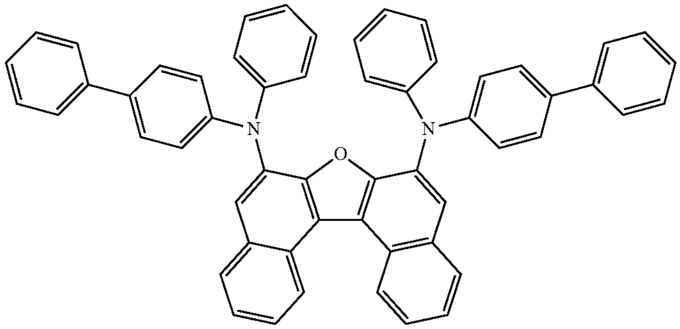

-continued
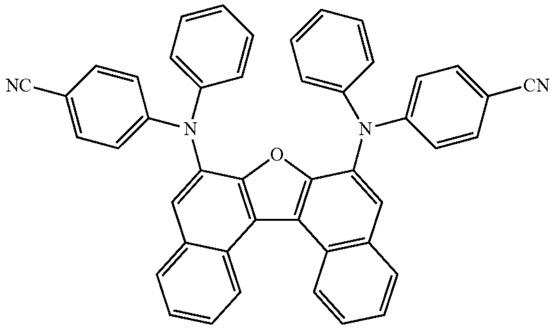
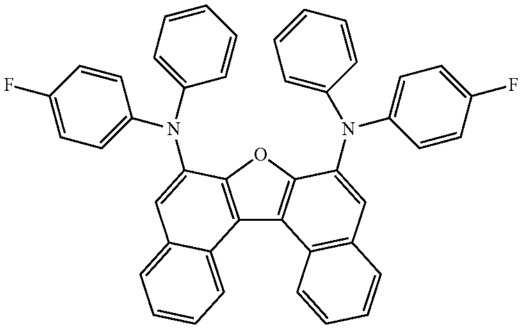
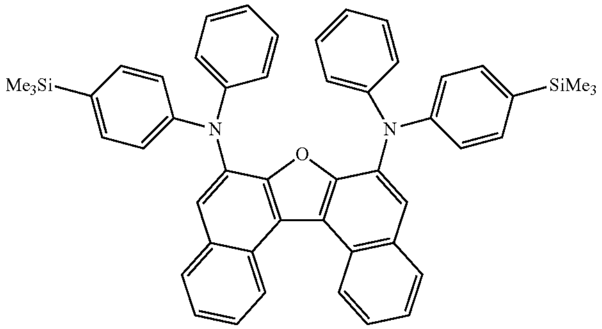
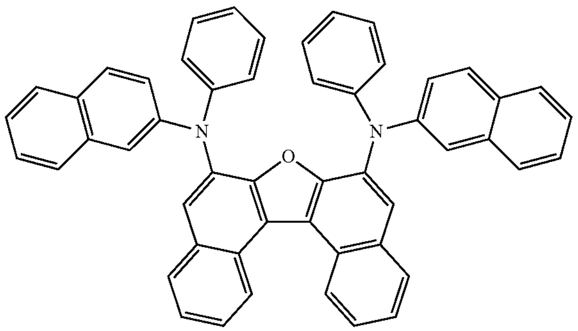
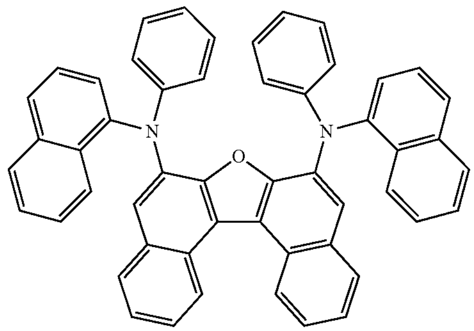
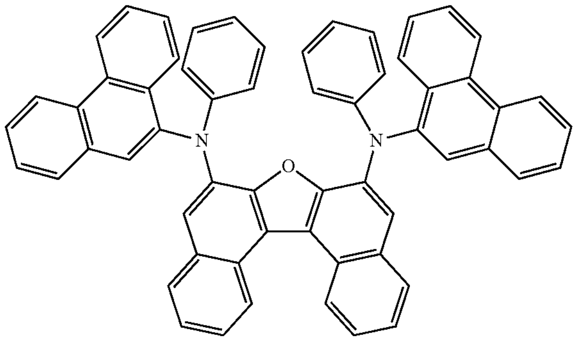
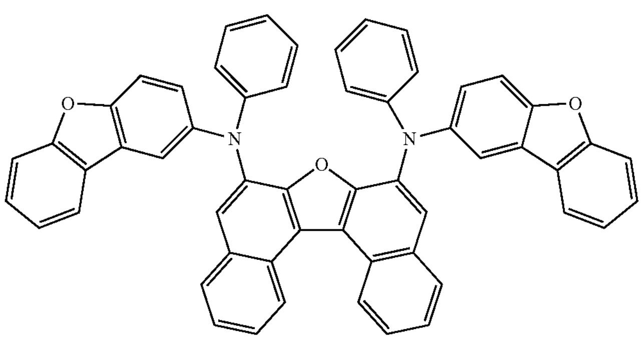

-continued
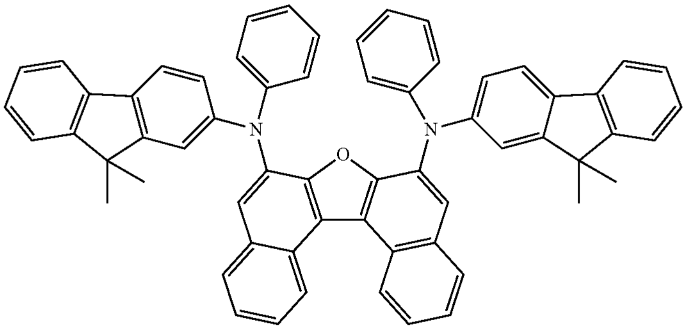
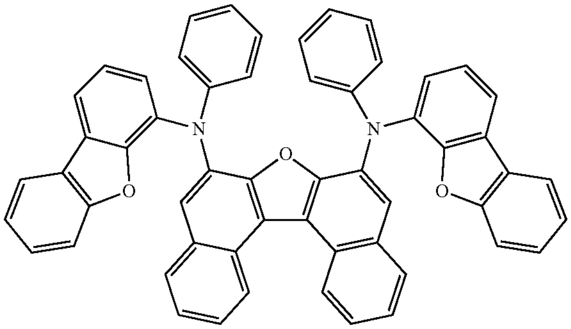
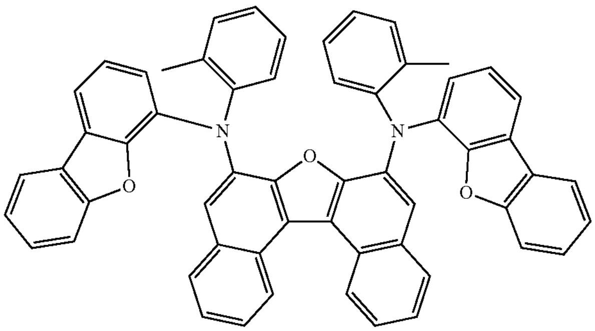
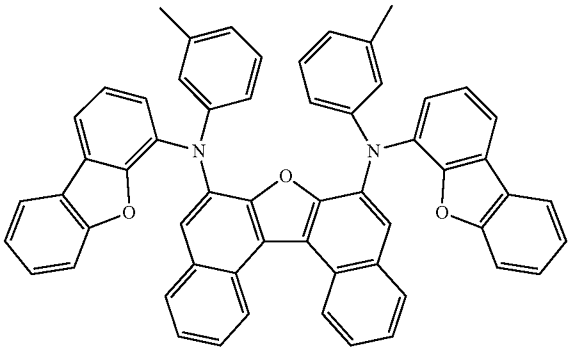

-continued
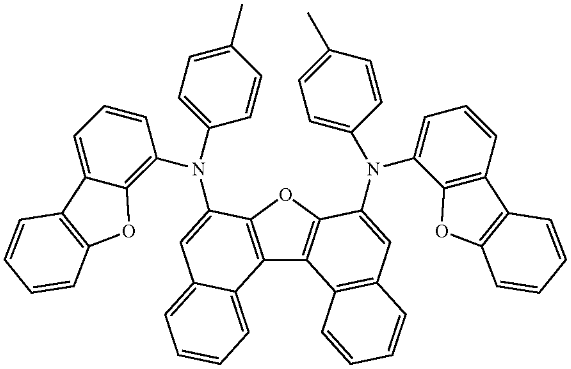
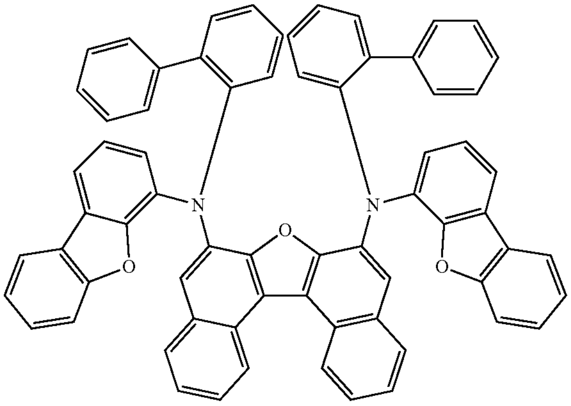
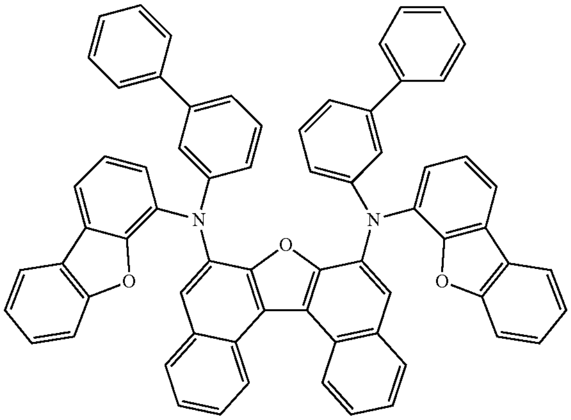
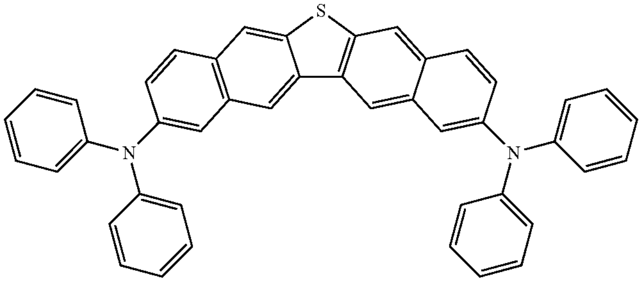
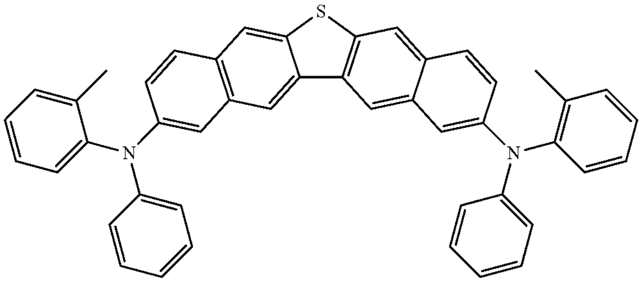
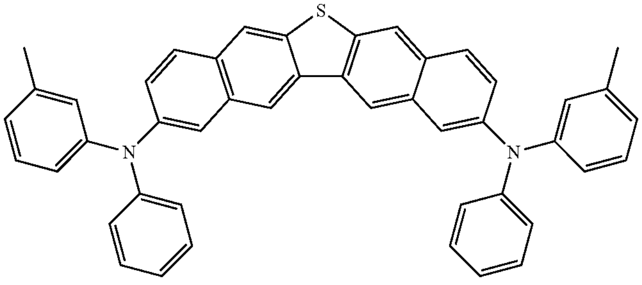

-continued
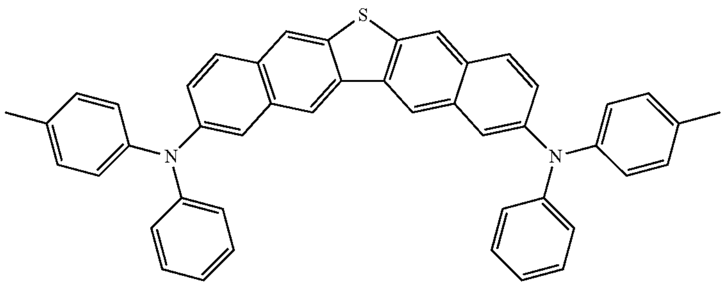
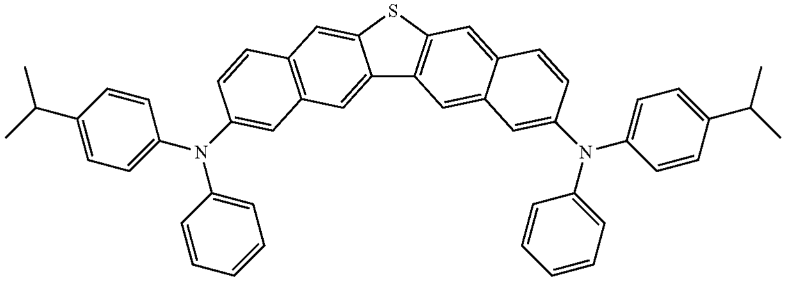
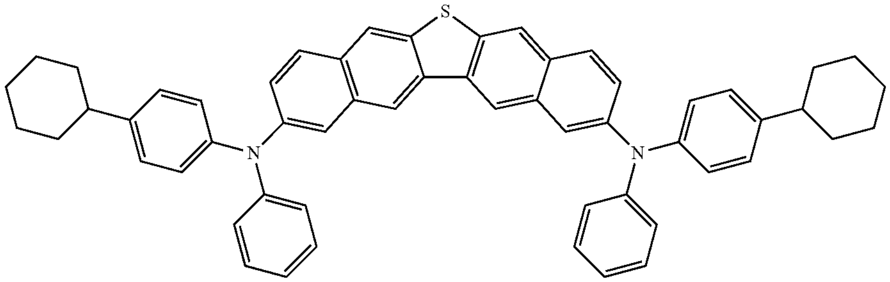
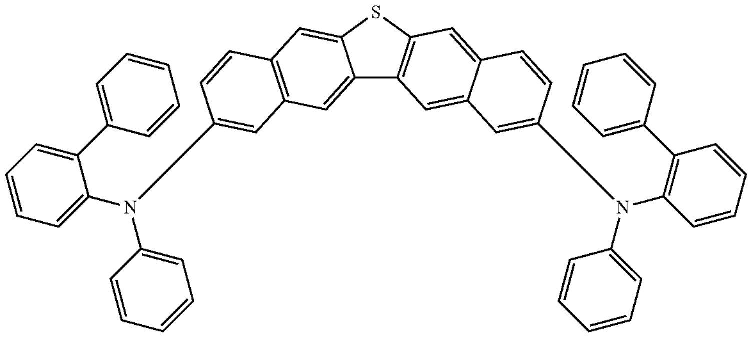
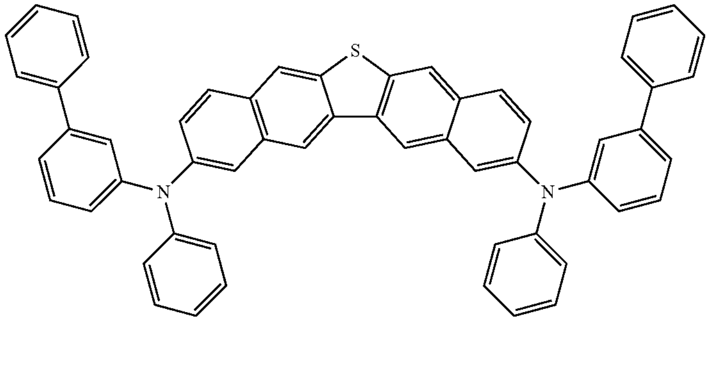

-continued
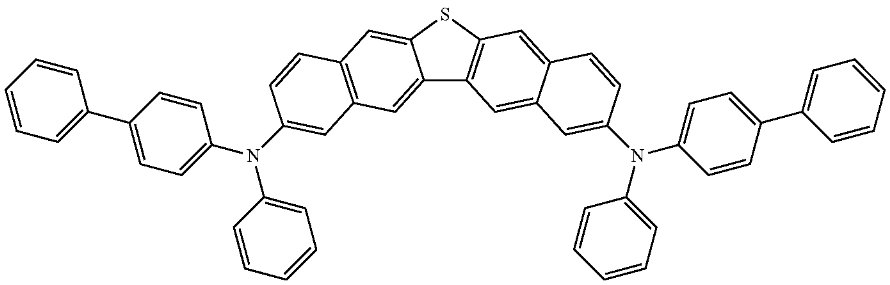
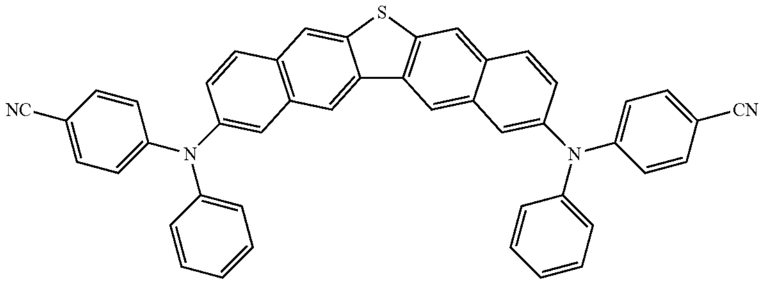
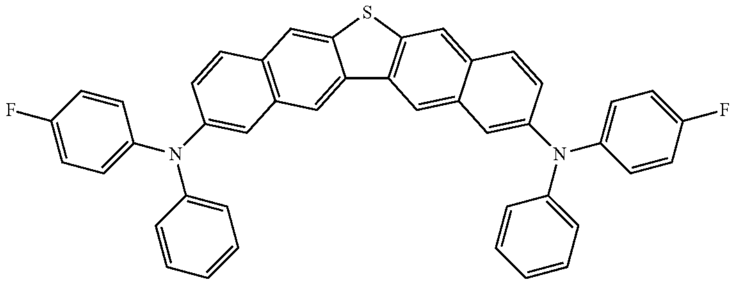
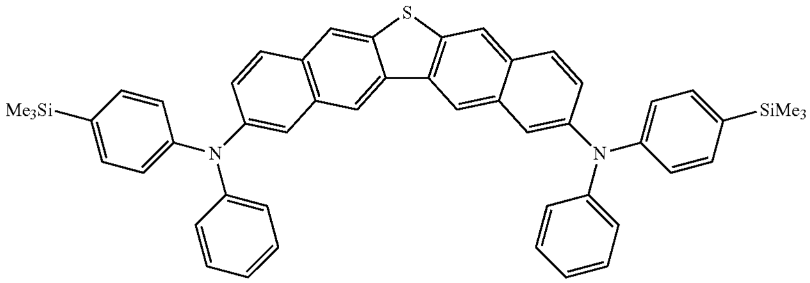
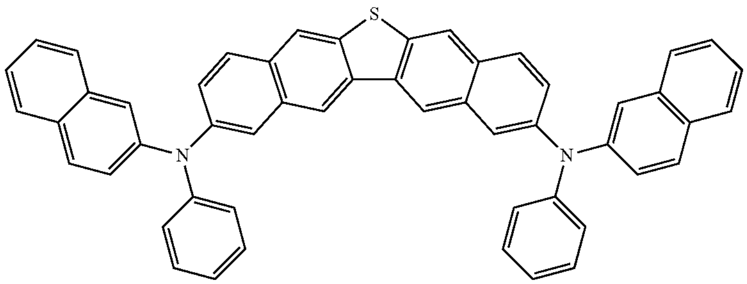
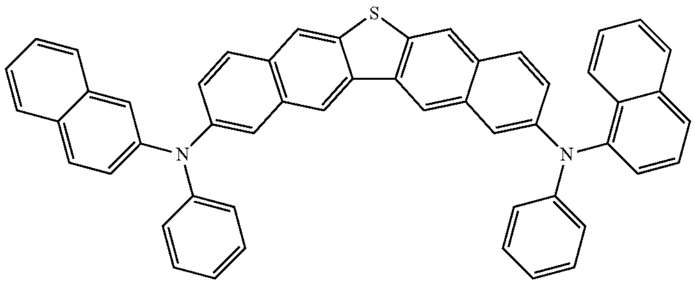

-continued
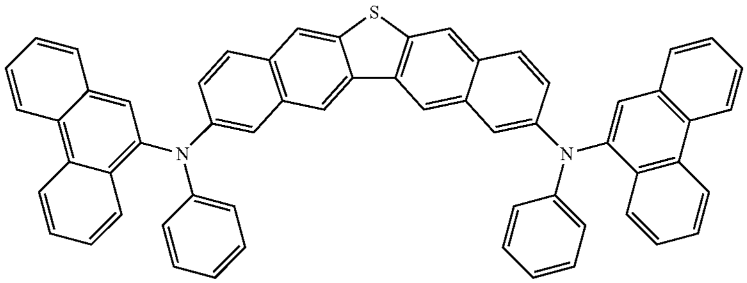
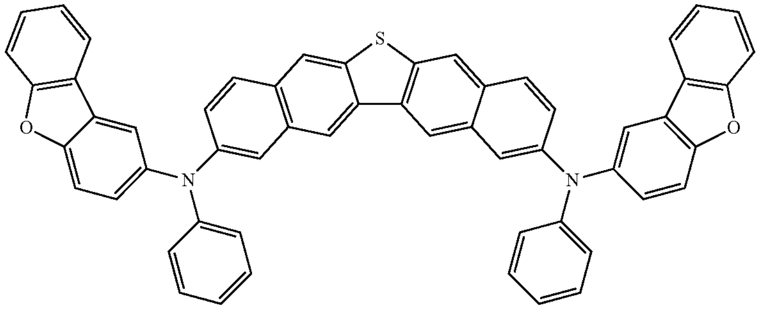
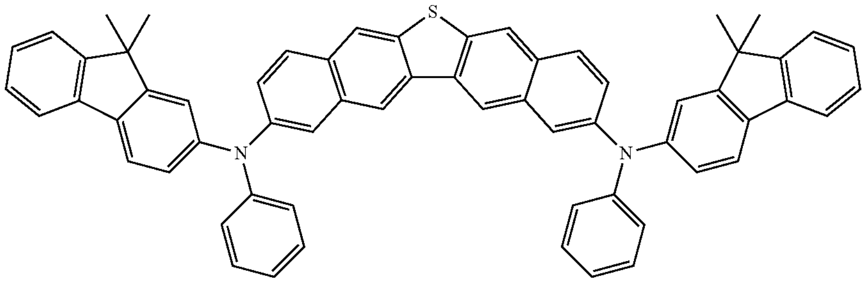
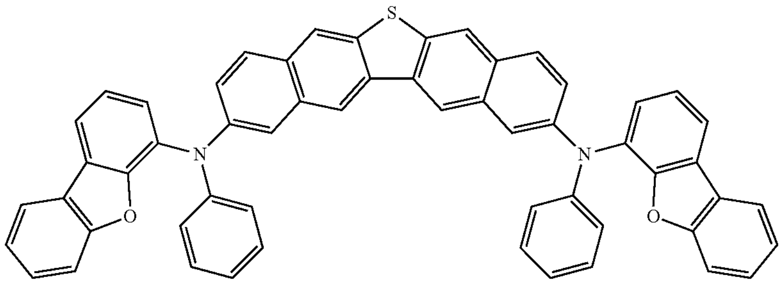
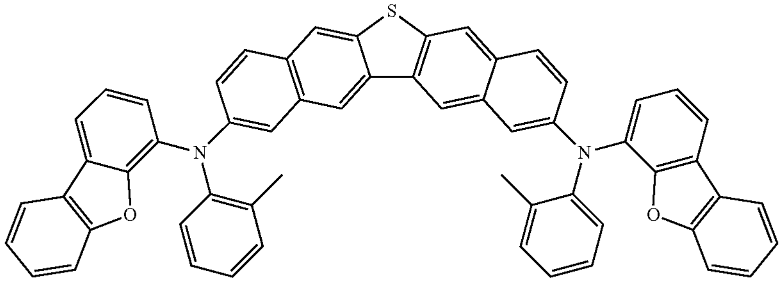
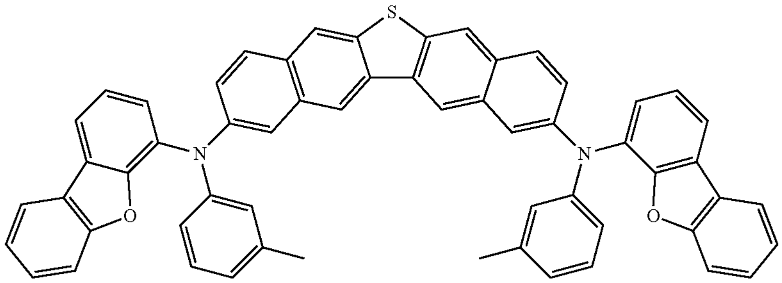

-continued
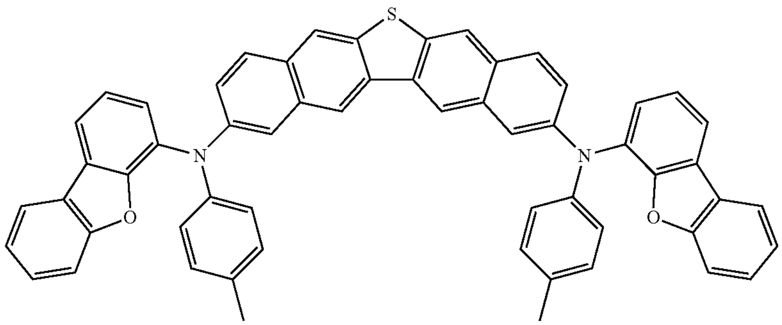
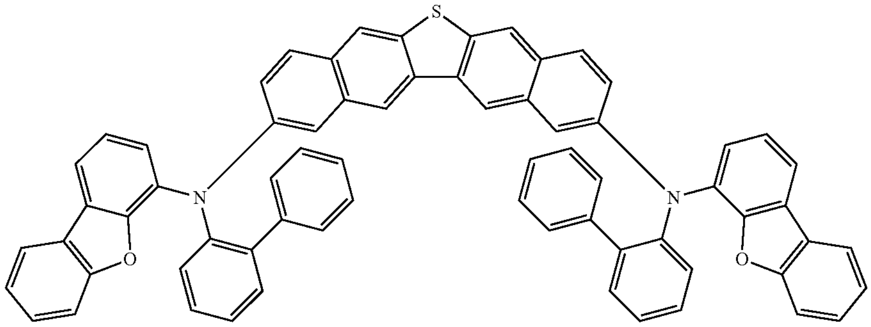
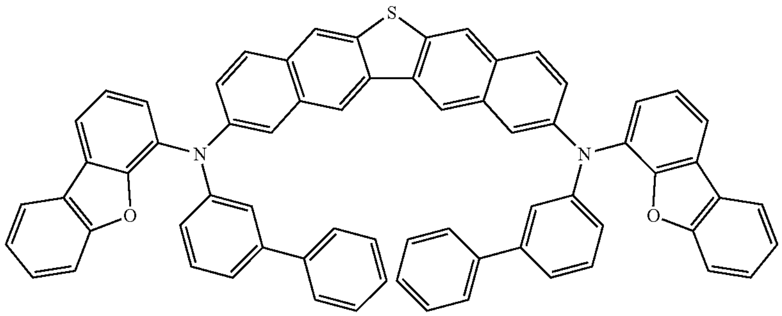
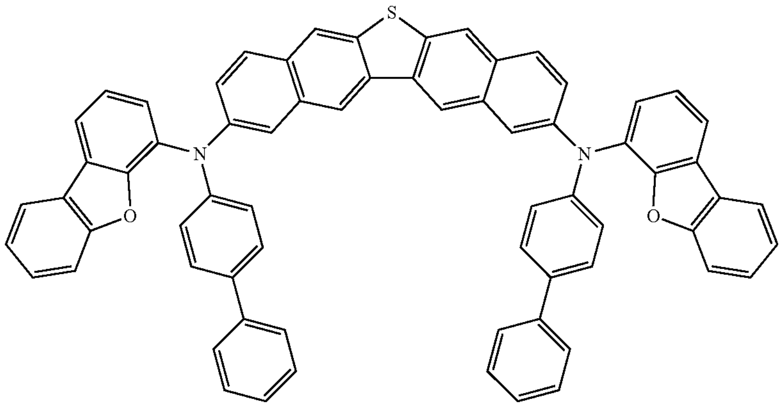
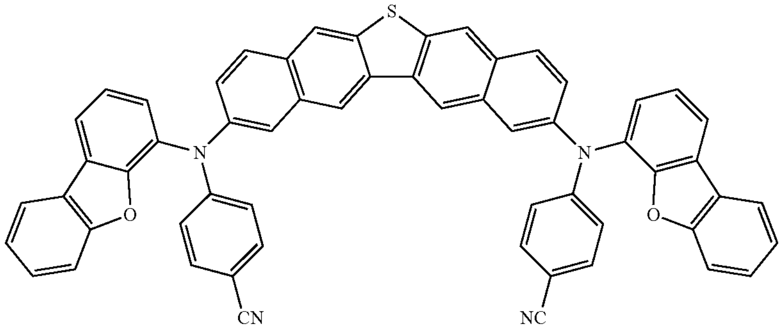

-continued
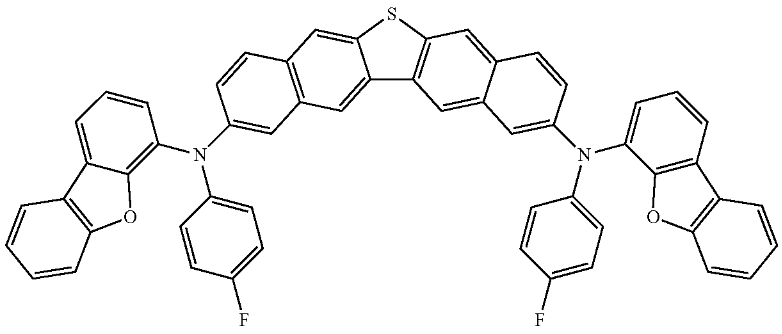
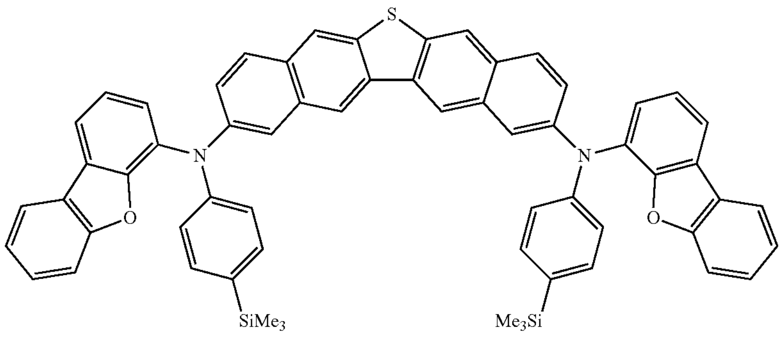
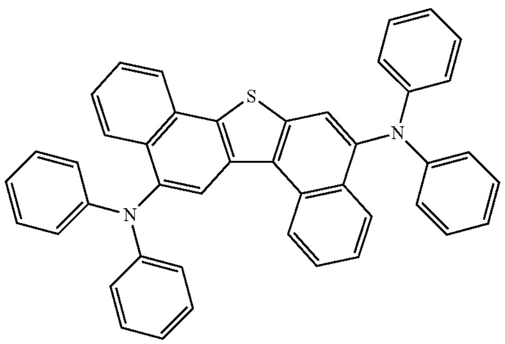
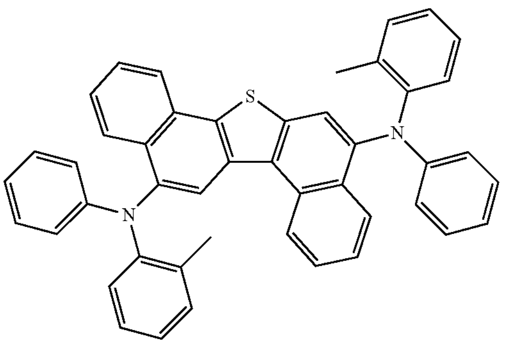
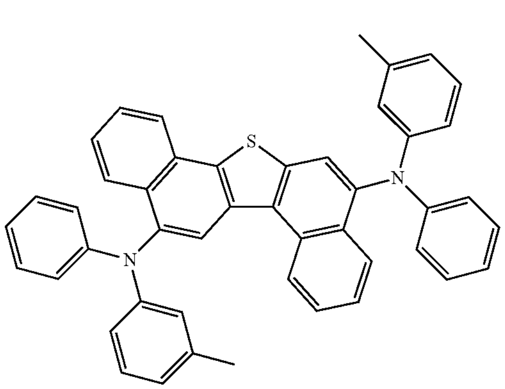
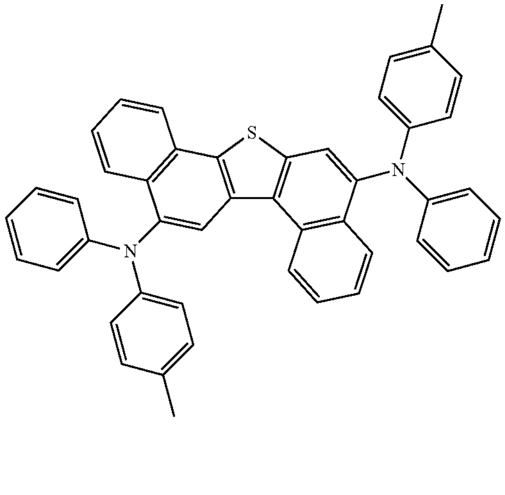

-continued
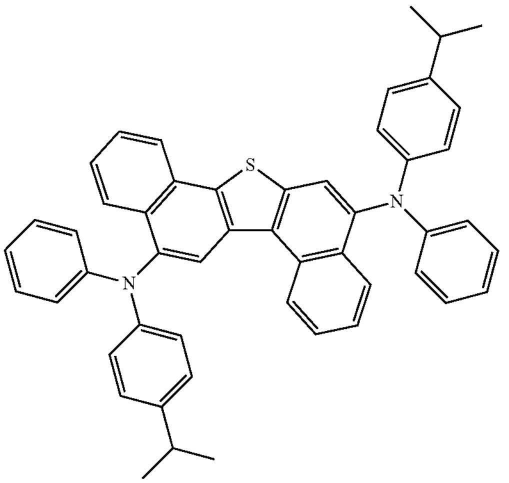
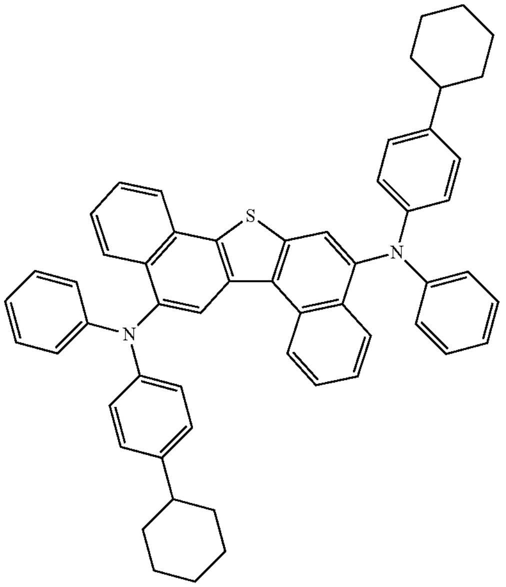
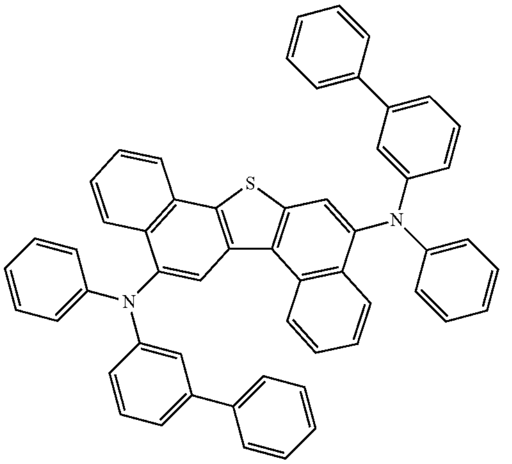
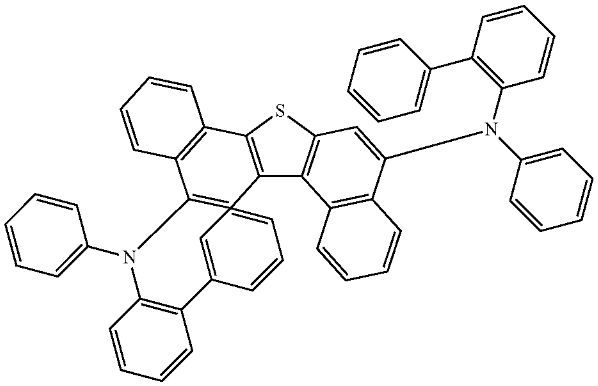
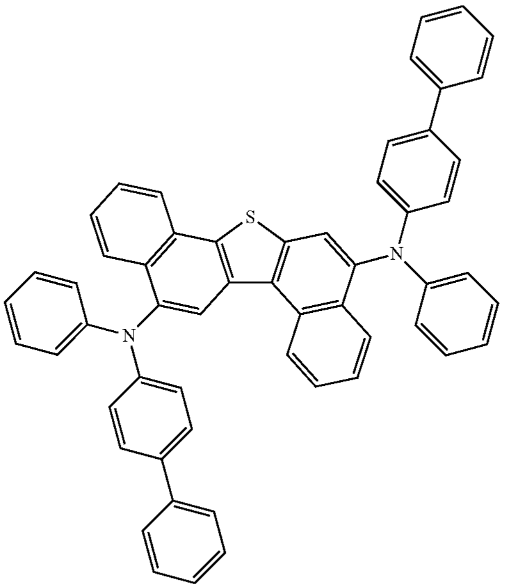
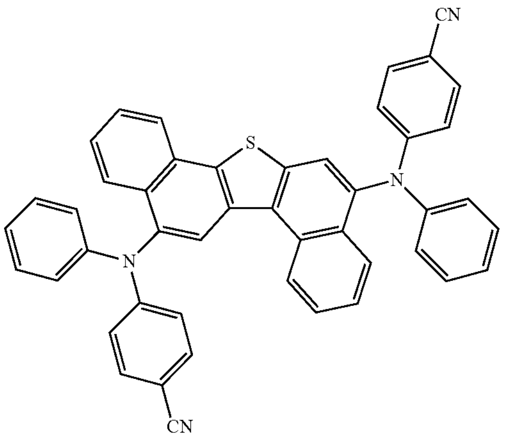

-continued
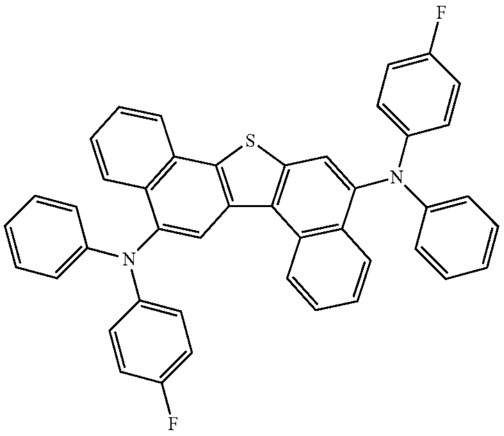
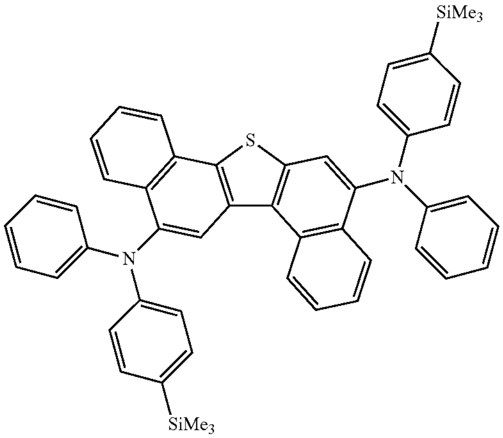
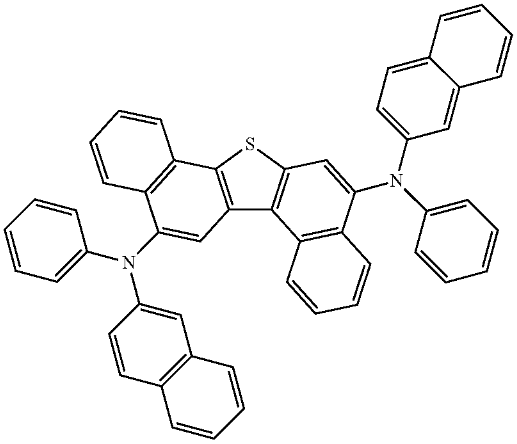
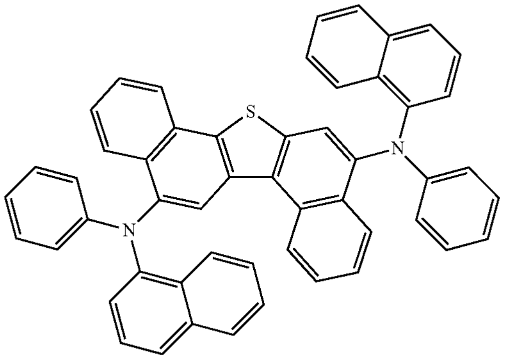
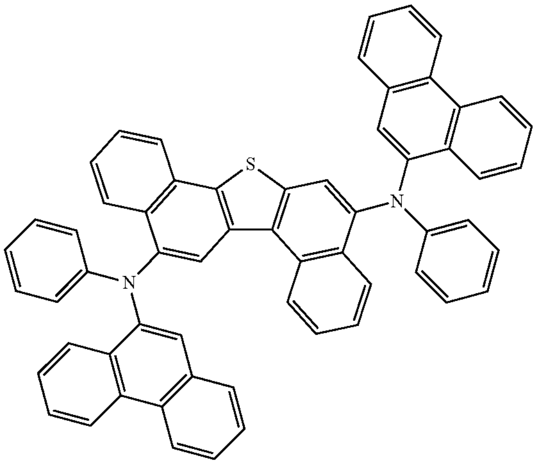

-continued
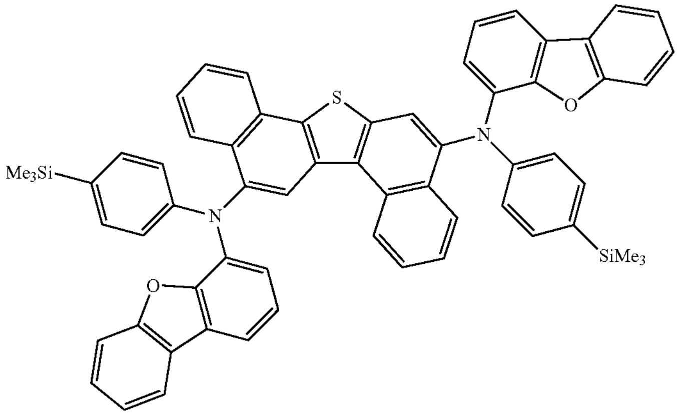
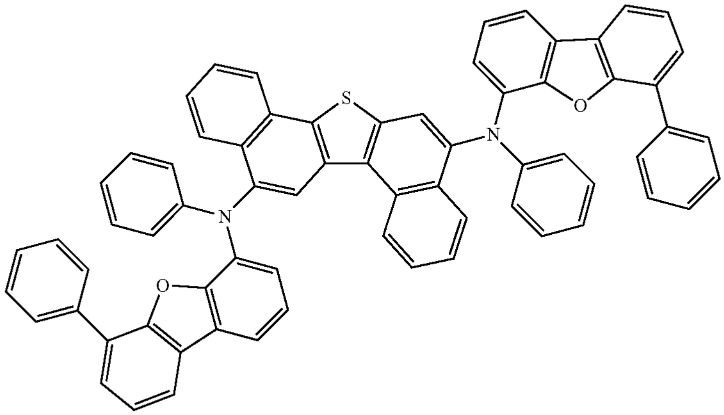
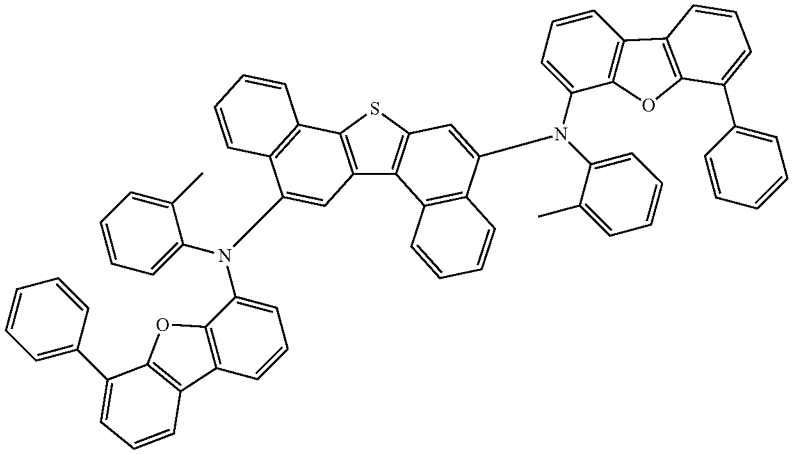
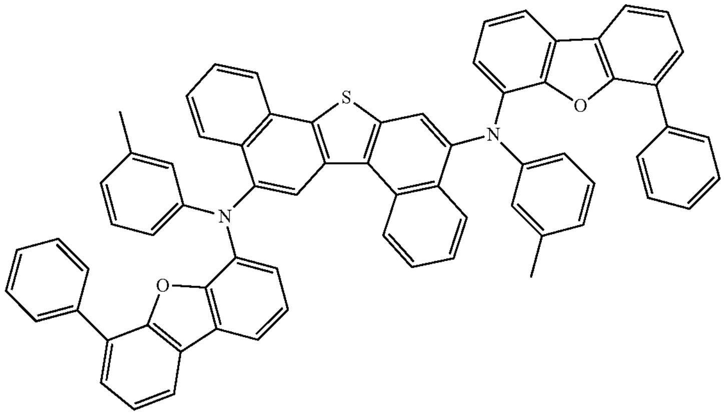

-continued
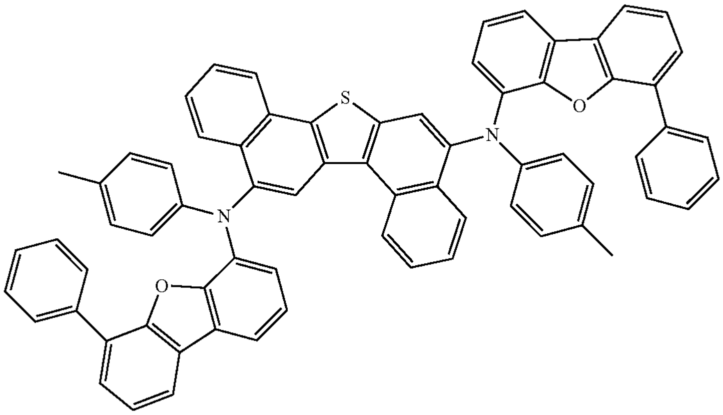
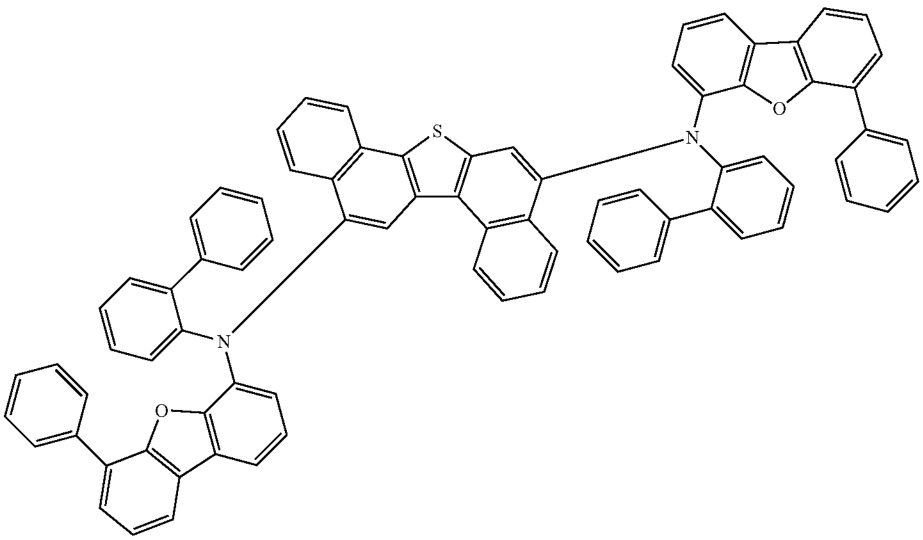
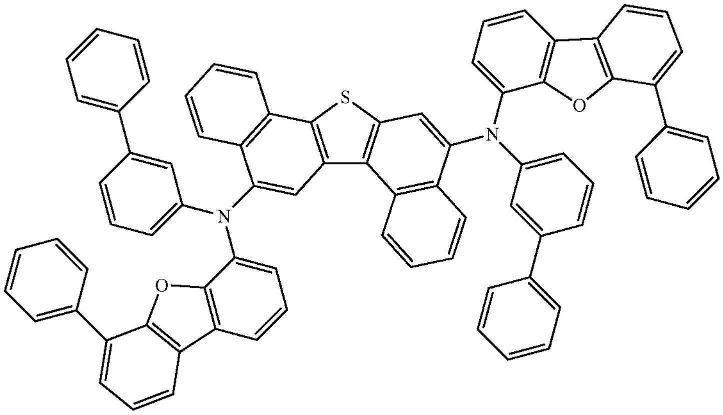

-continued
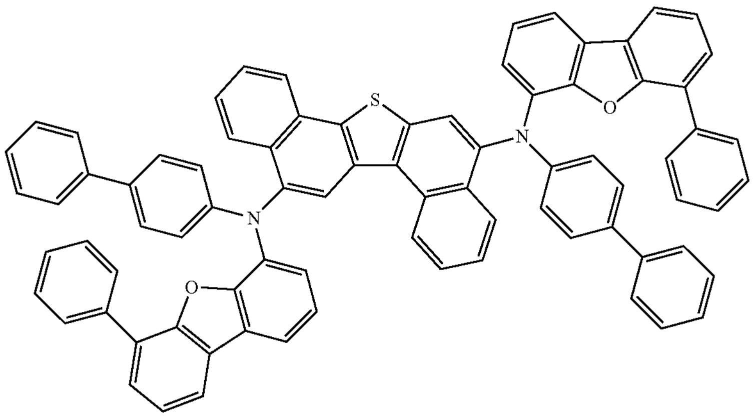
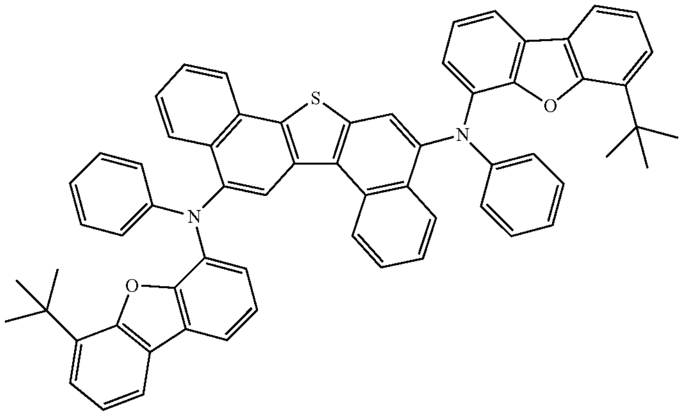
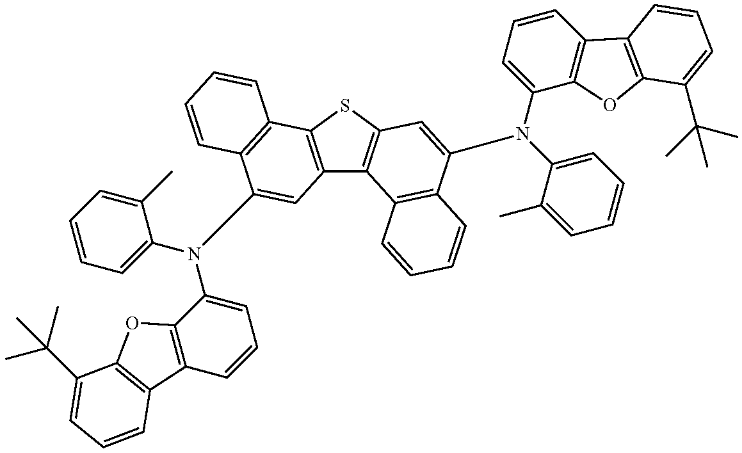
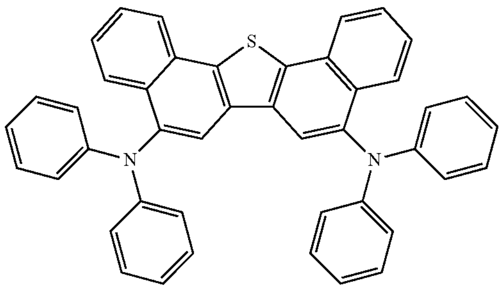
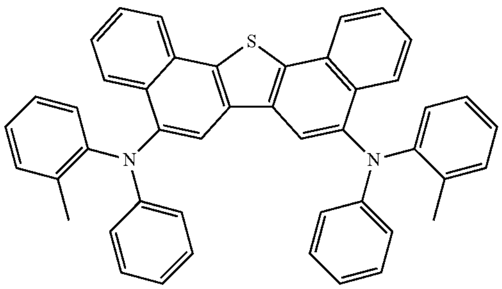

-continued
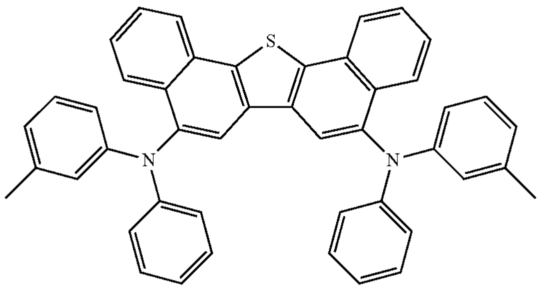
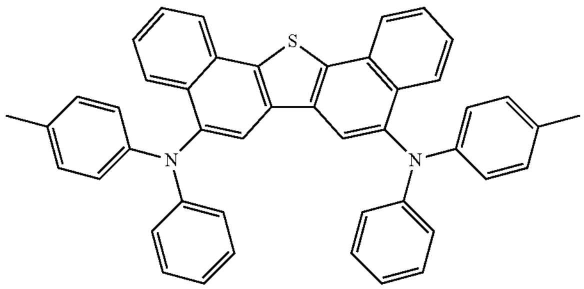
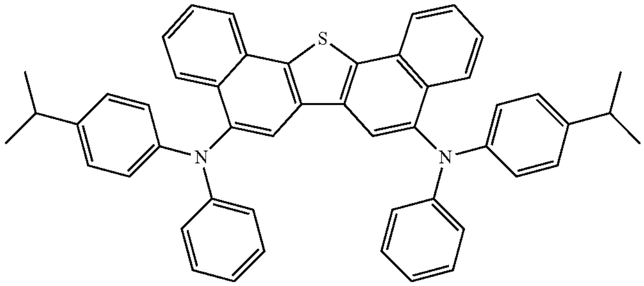
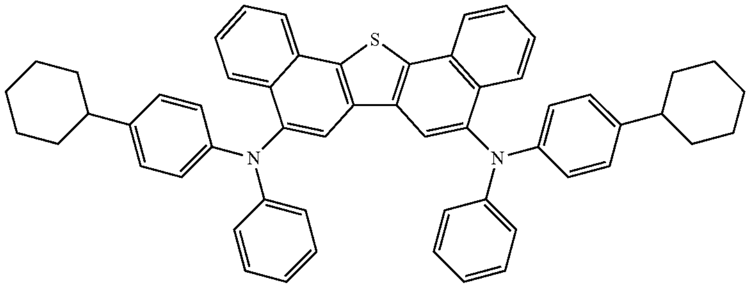
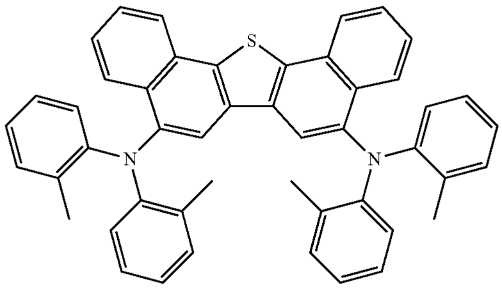
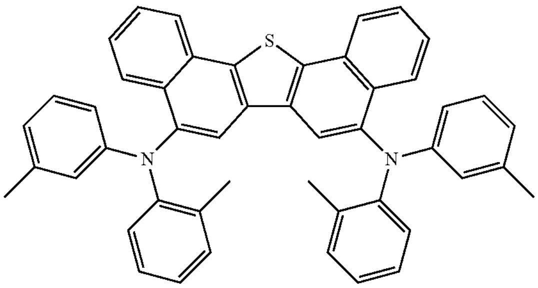
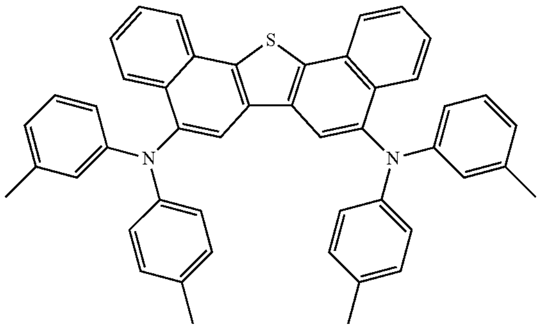
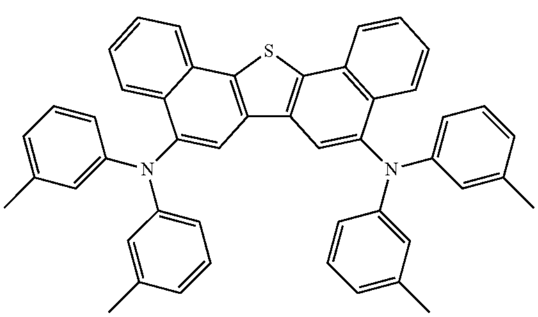

-continued
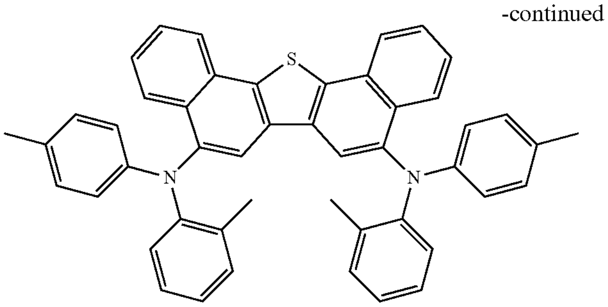
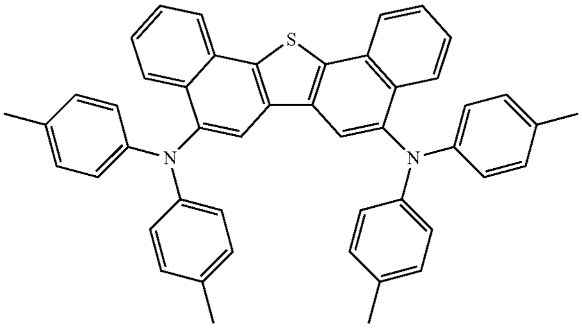
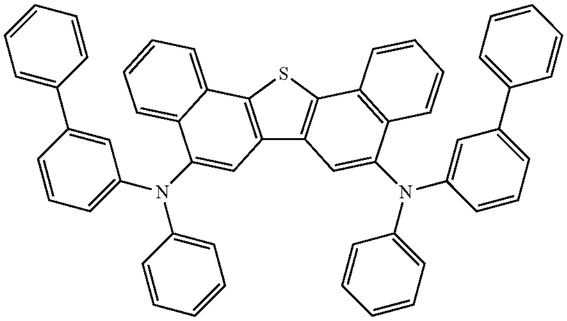
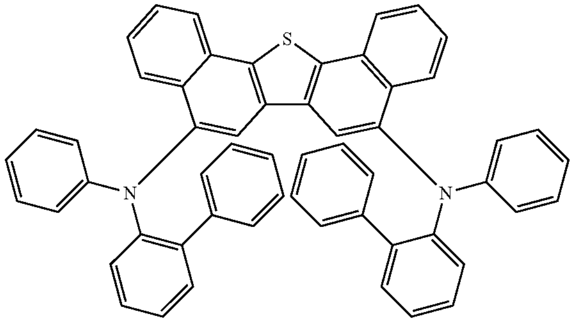
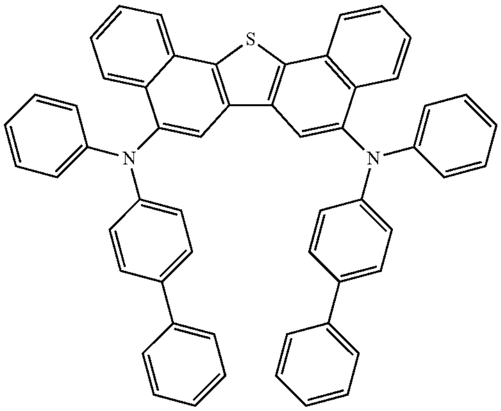
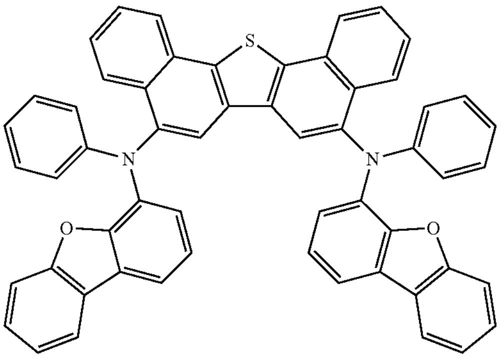
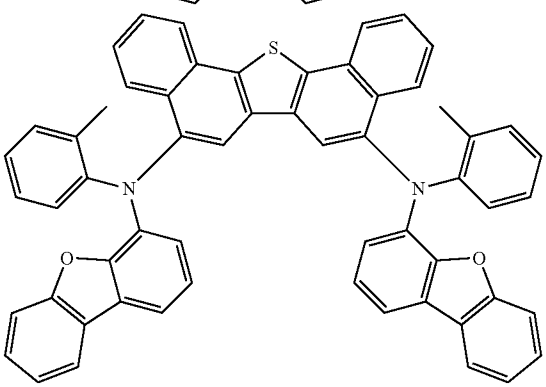
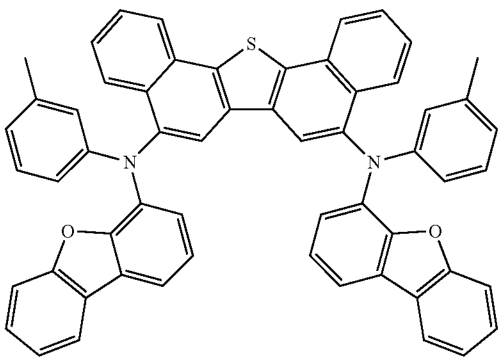

-continued
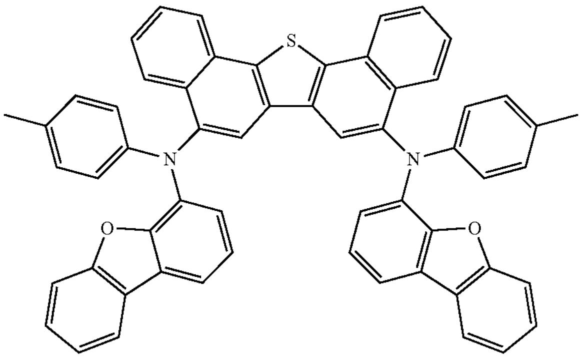
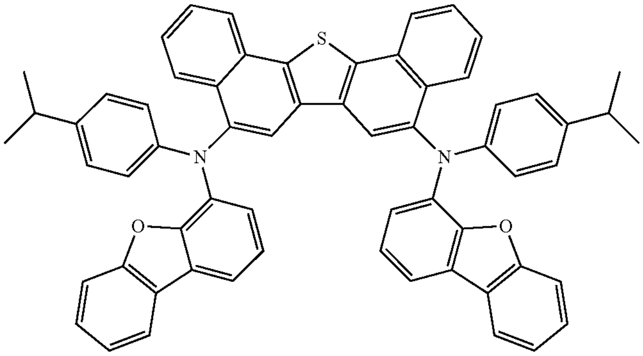
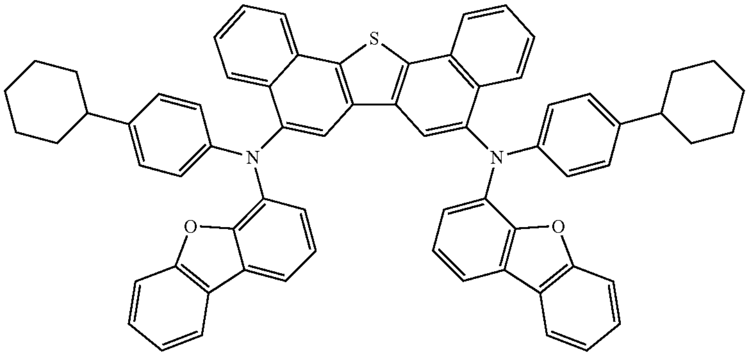
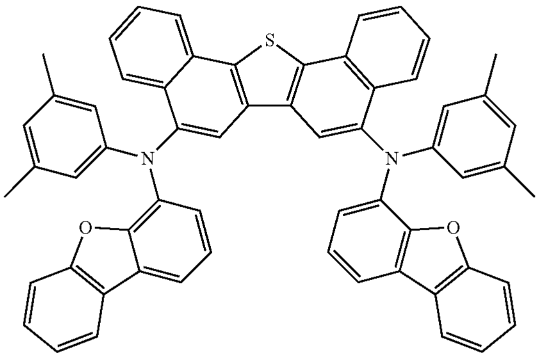

-continued
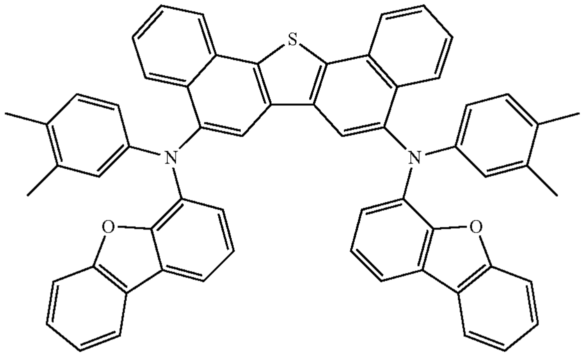
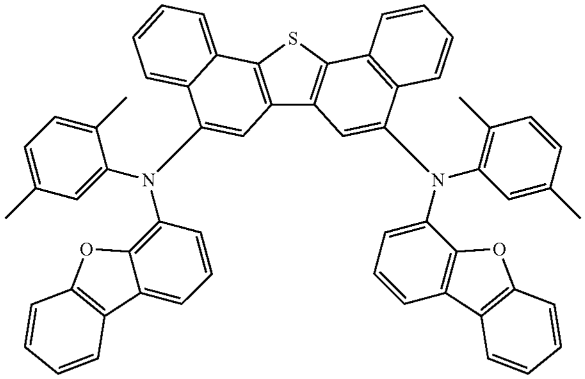
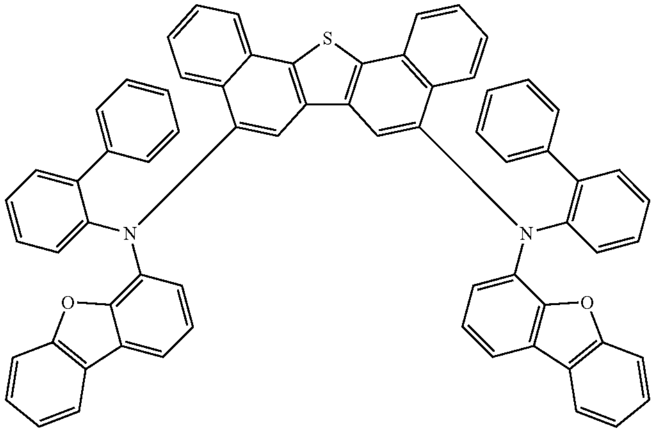
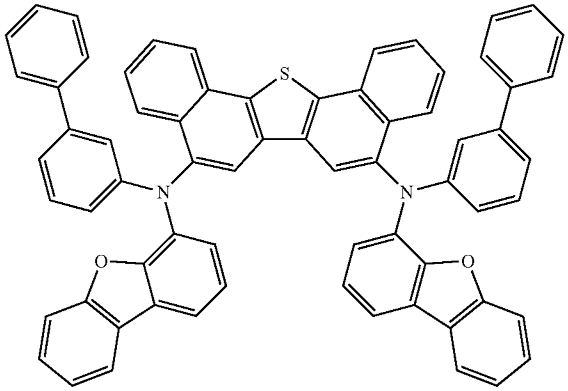
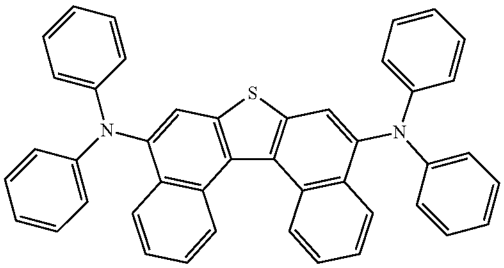

-continued
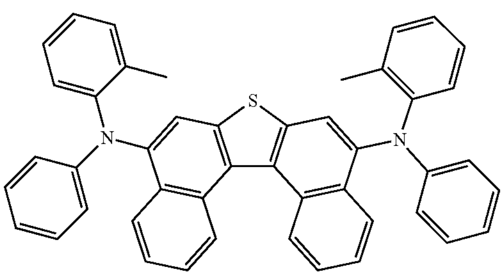
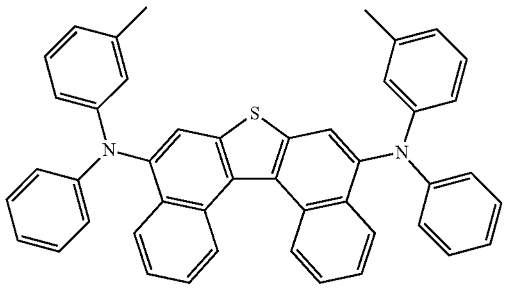
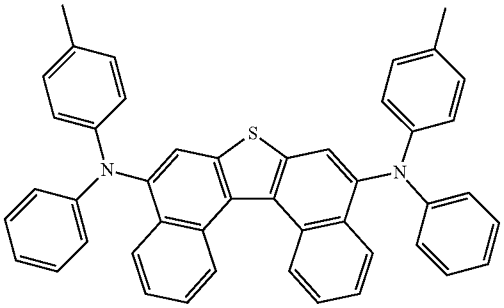
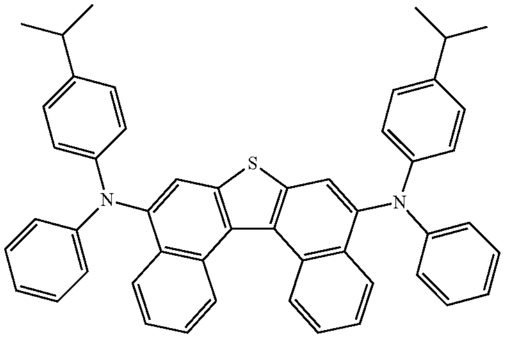
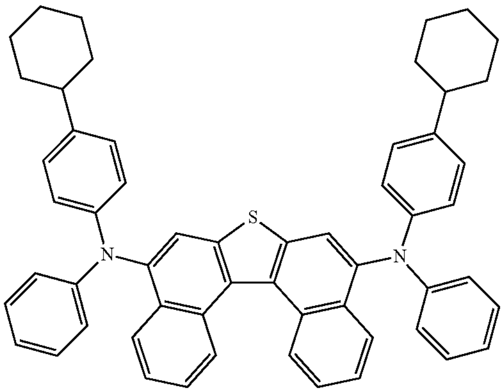
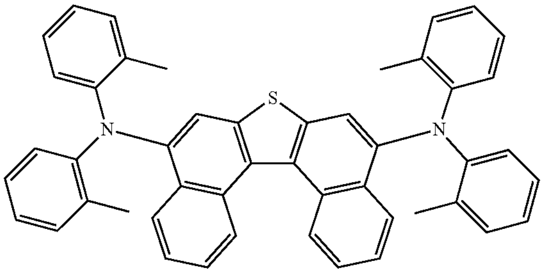
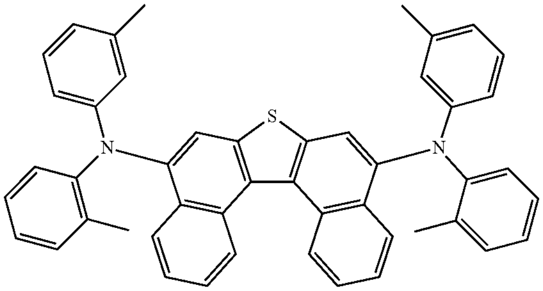
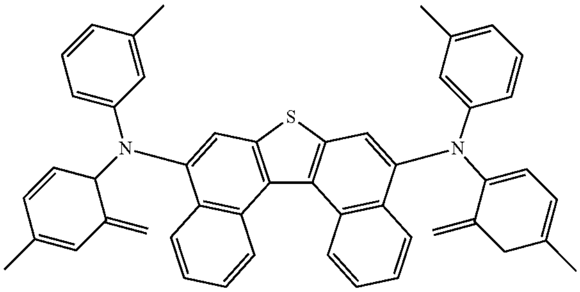
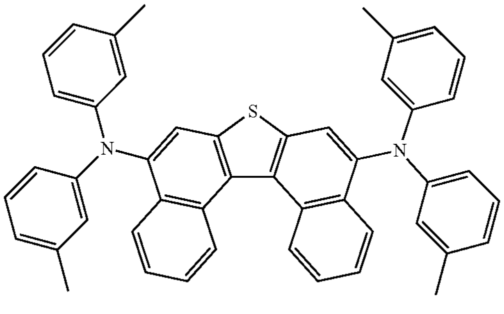
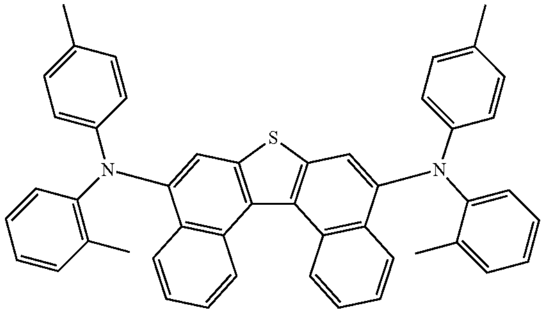

-continued
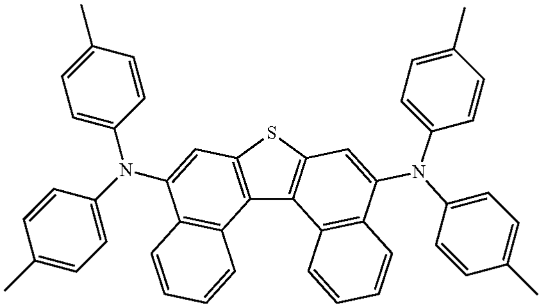
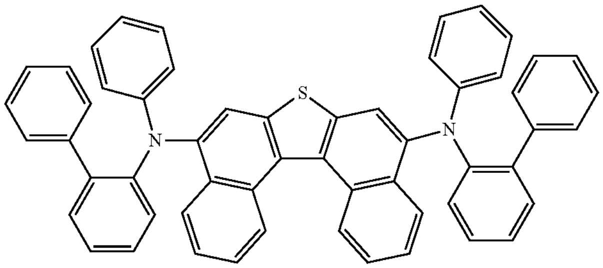
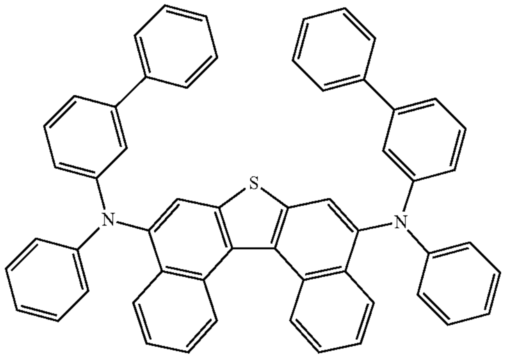
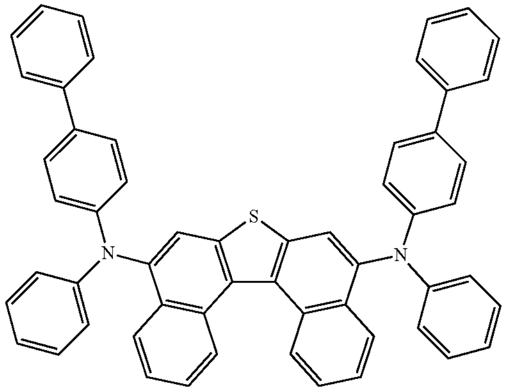
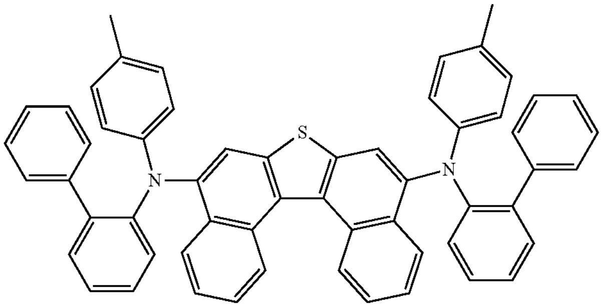
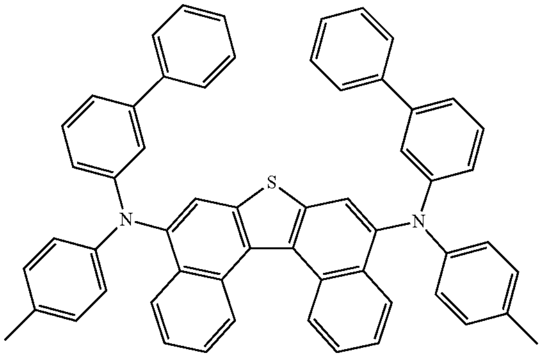
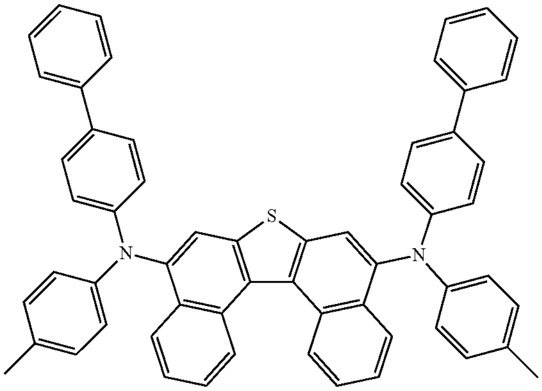

-continued
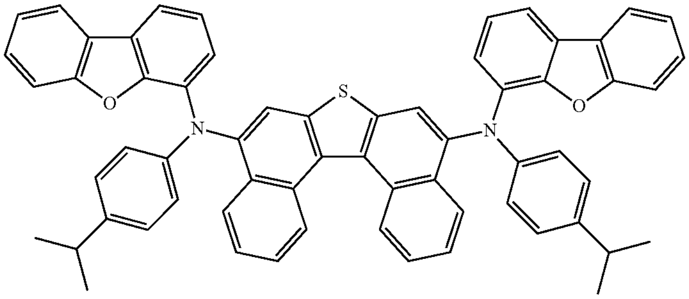
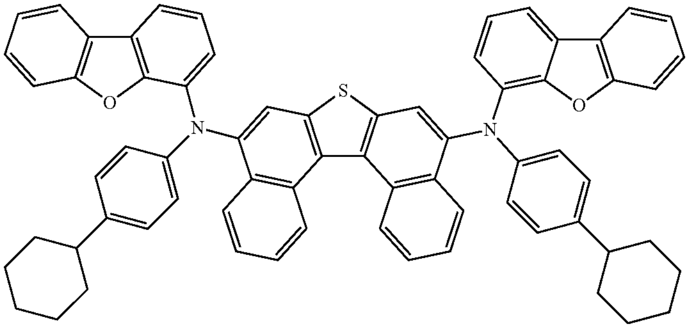
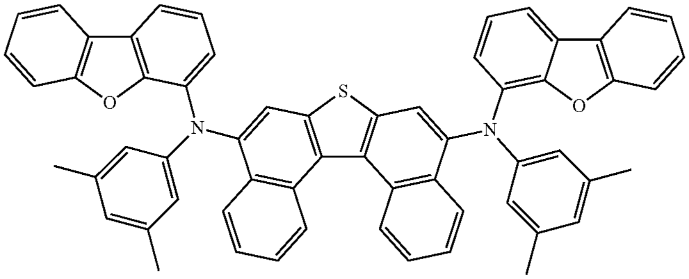
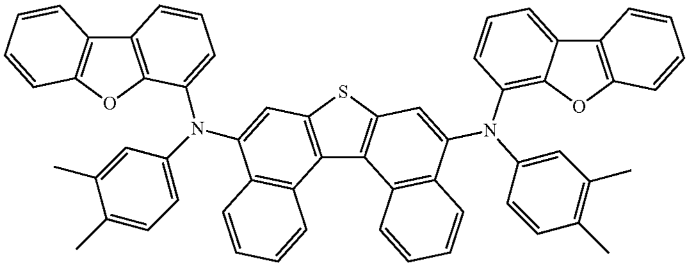
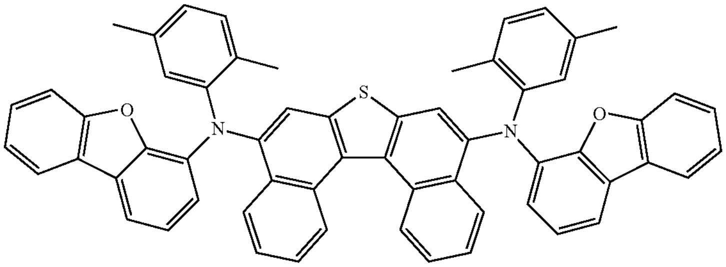
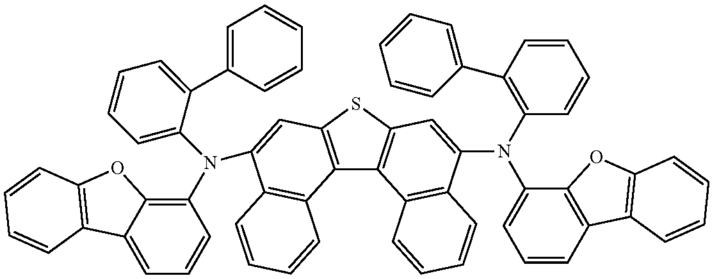

-continued
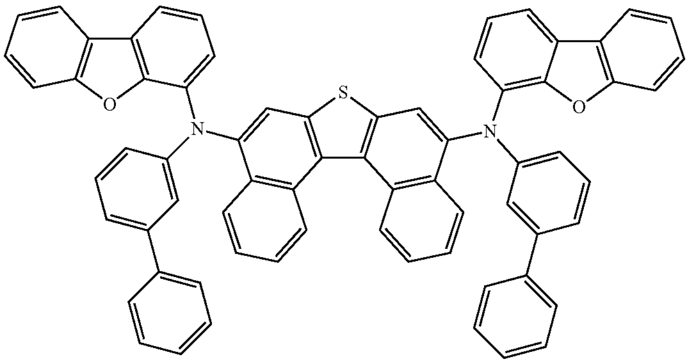
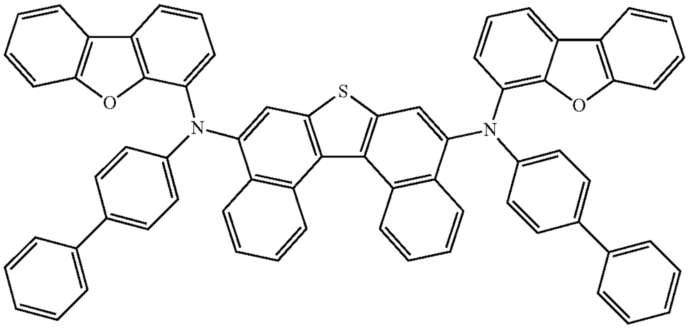
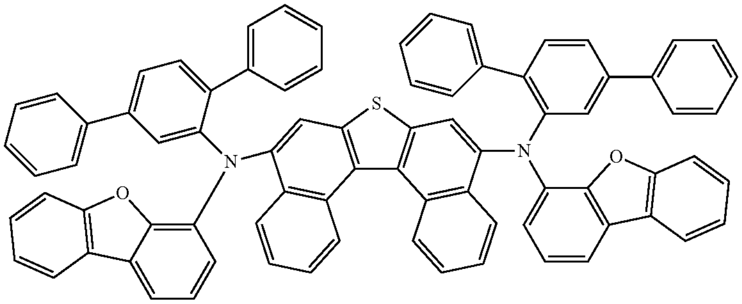
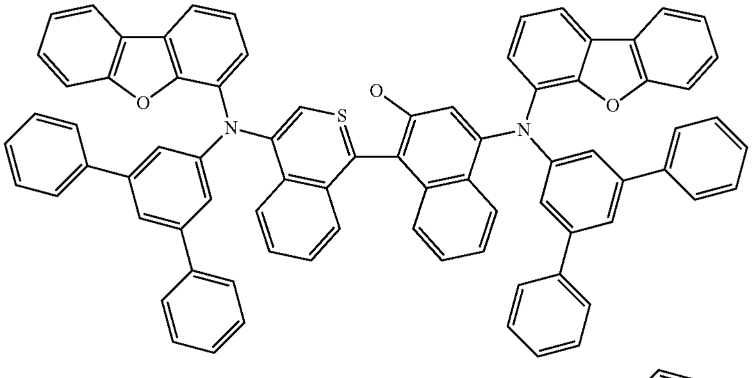
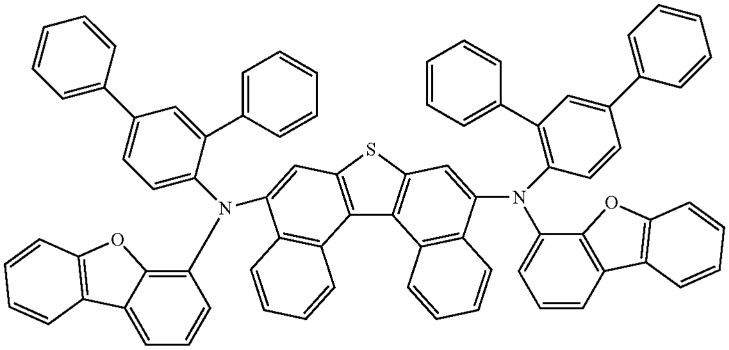

-continued
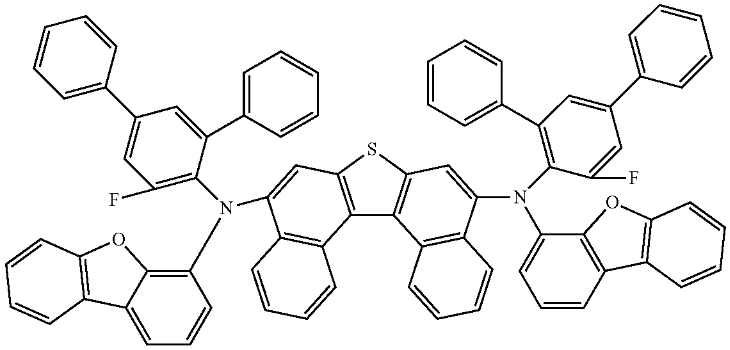
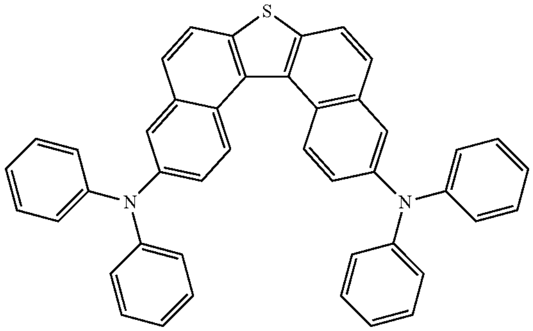
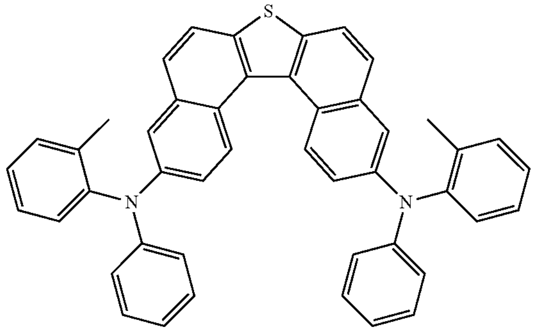
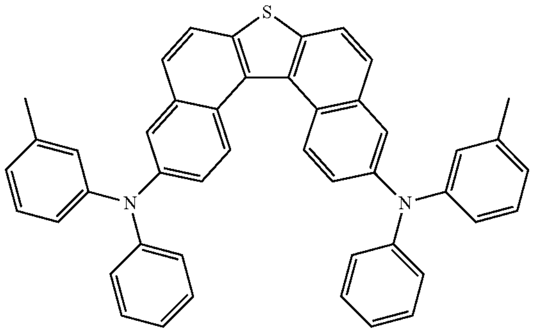
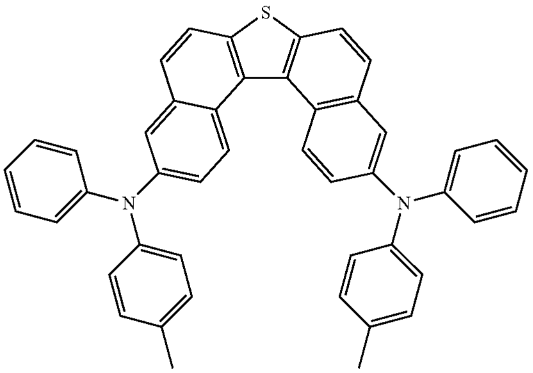
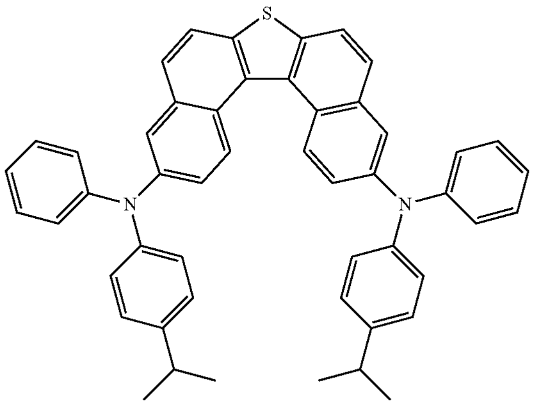
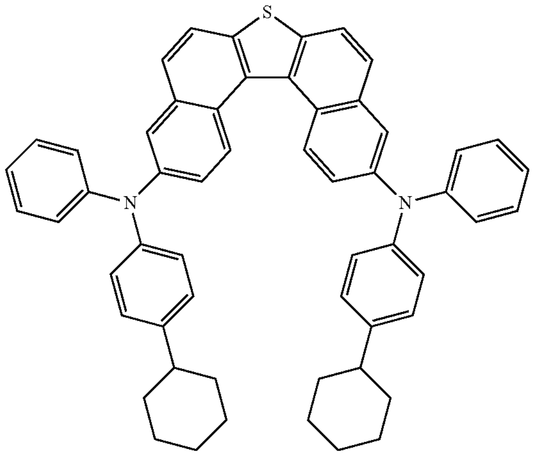

-continued
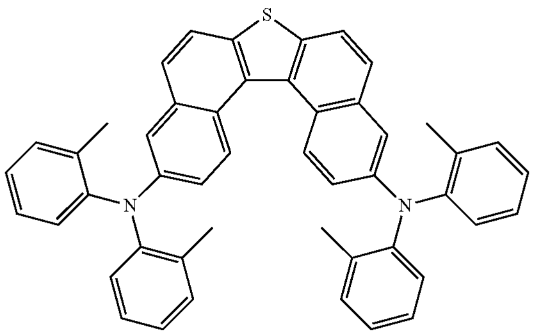
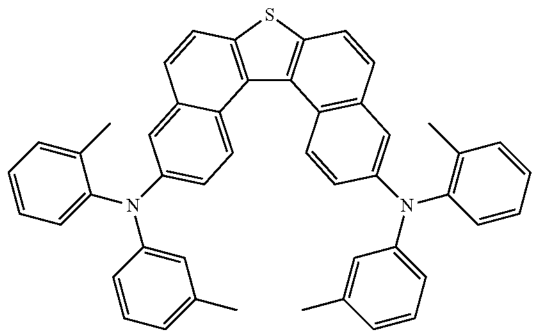
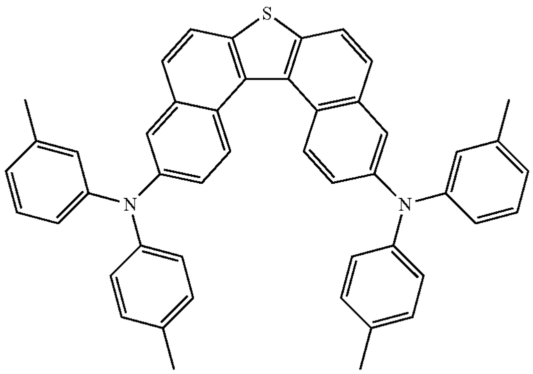
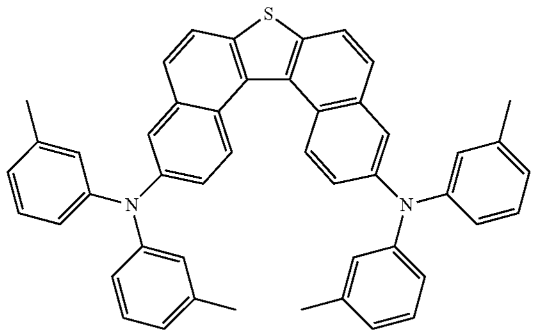
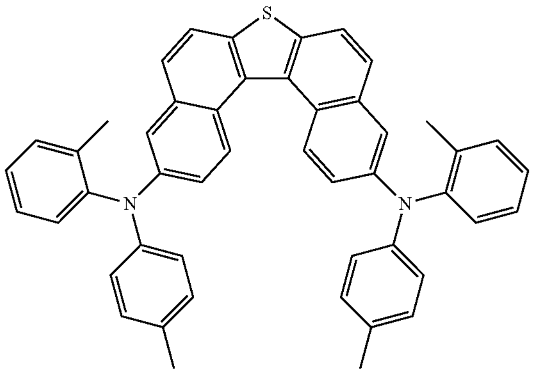
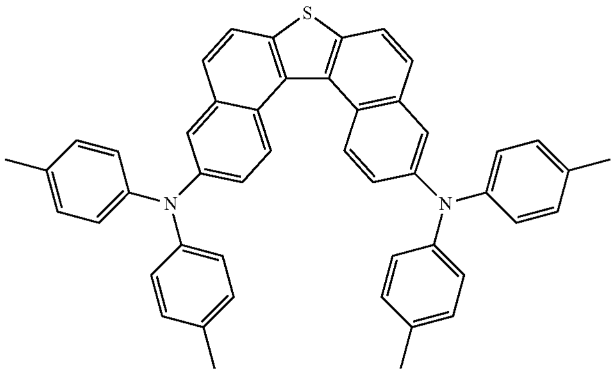
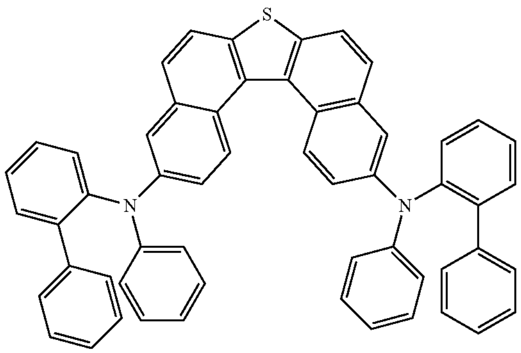
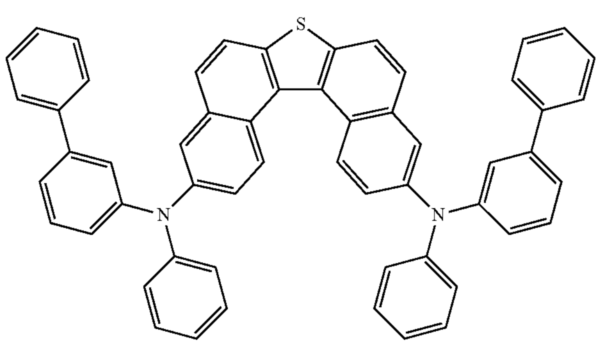

-continued
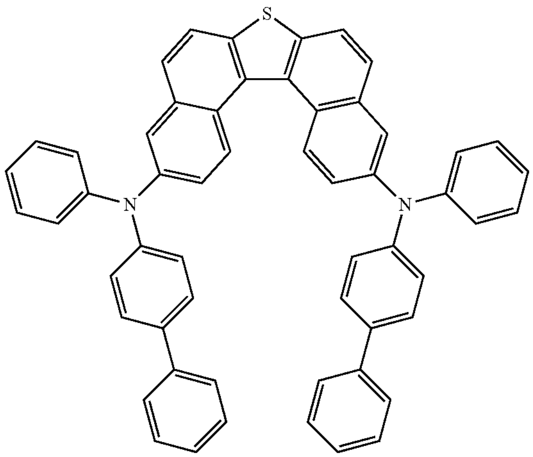
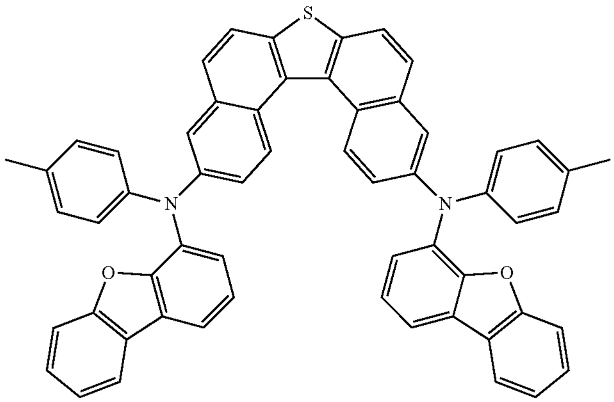
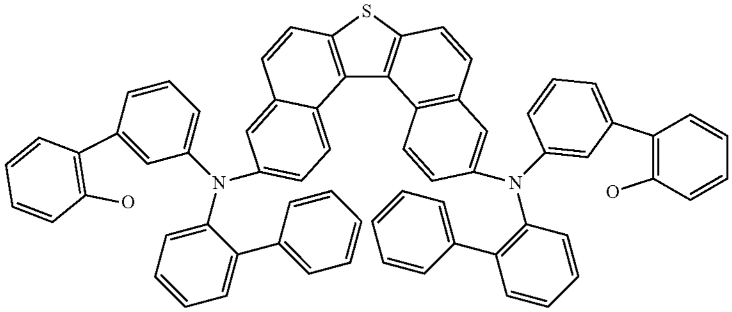
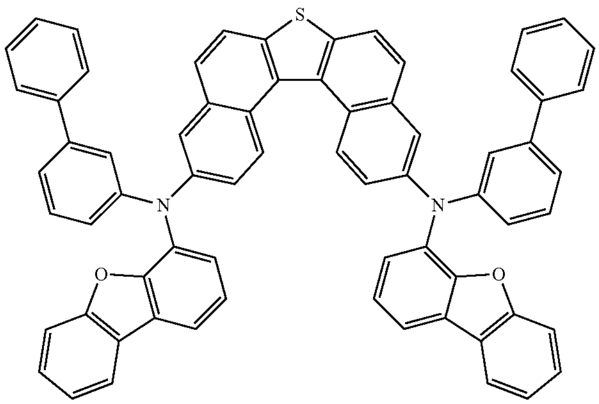

-continued
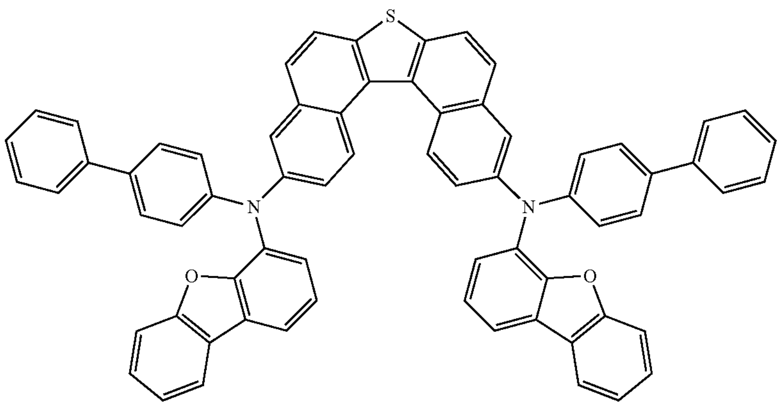
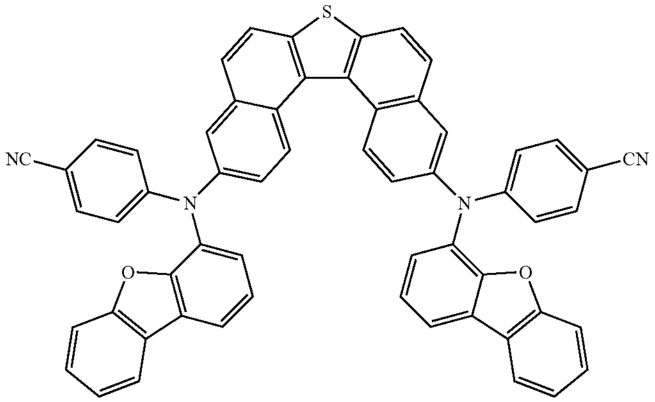
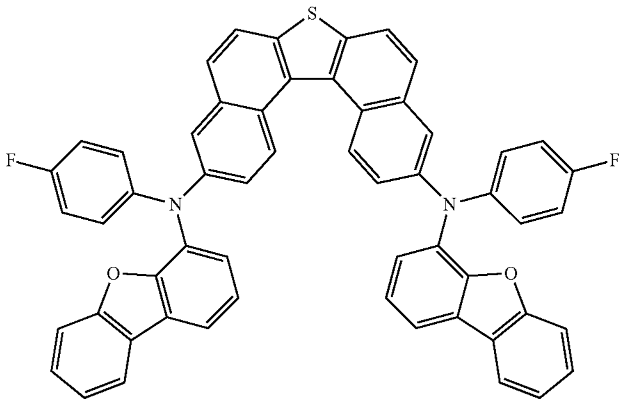
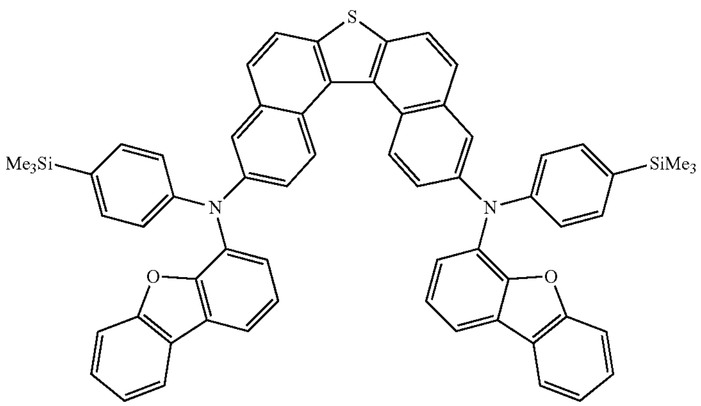

-continued
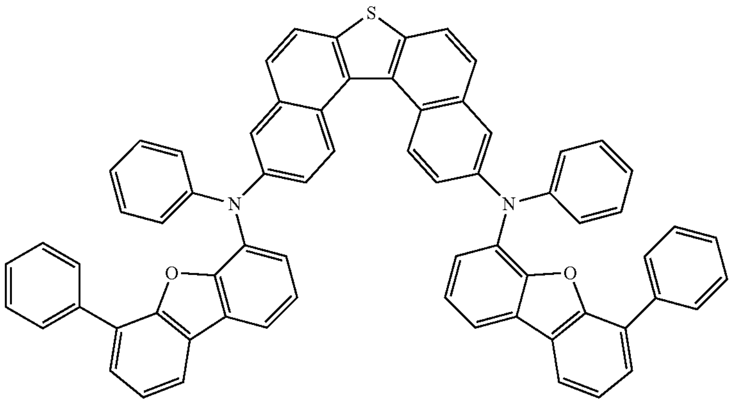
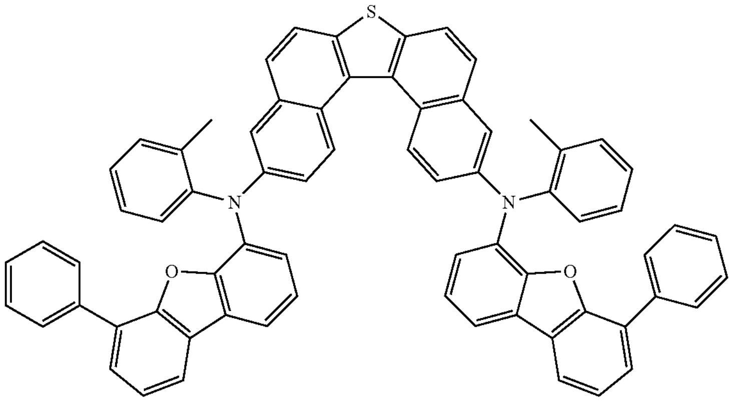
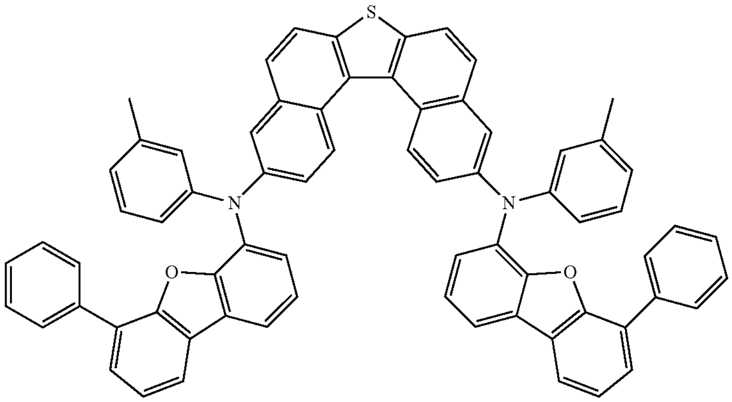
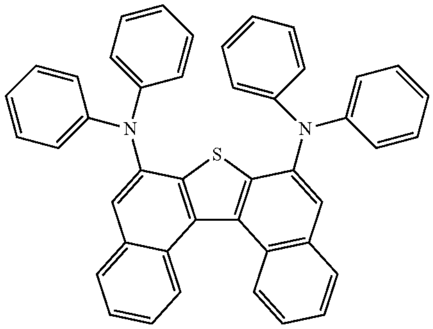
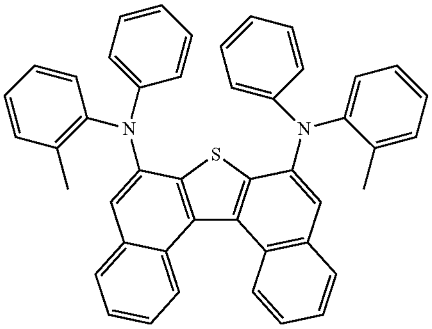

-continued
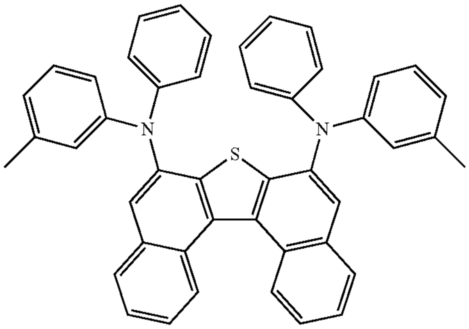
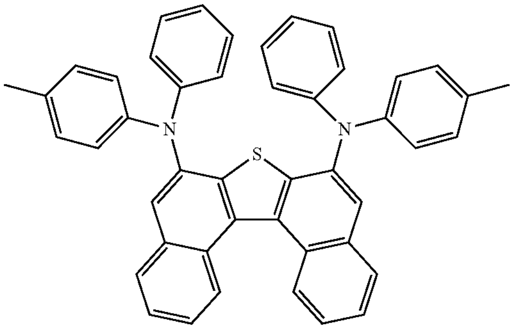
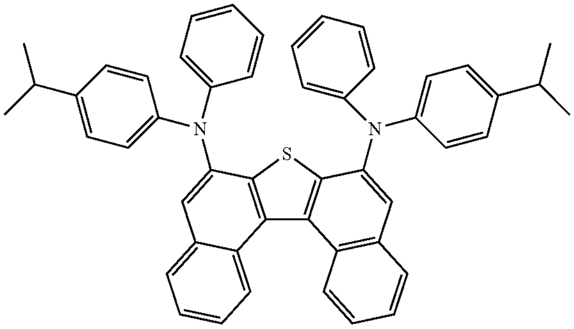
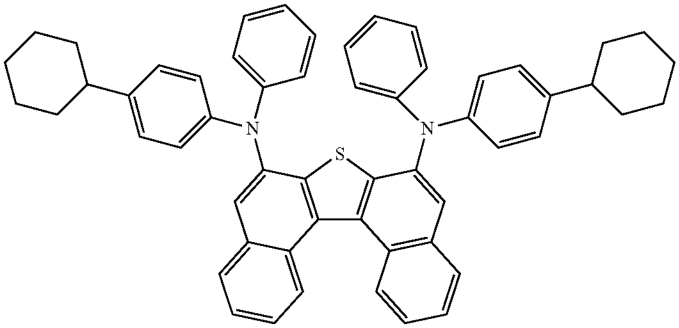
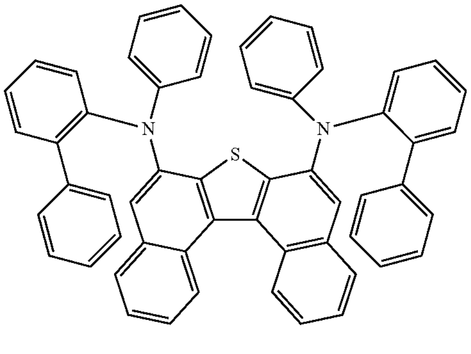
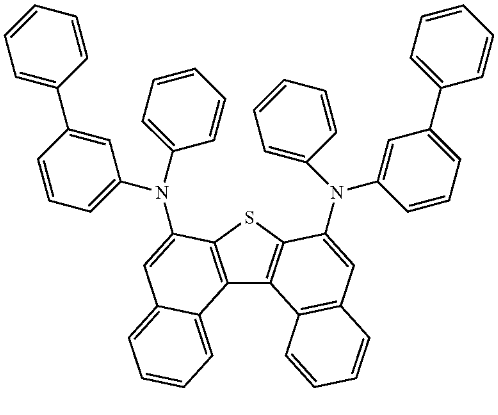
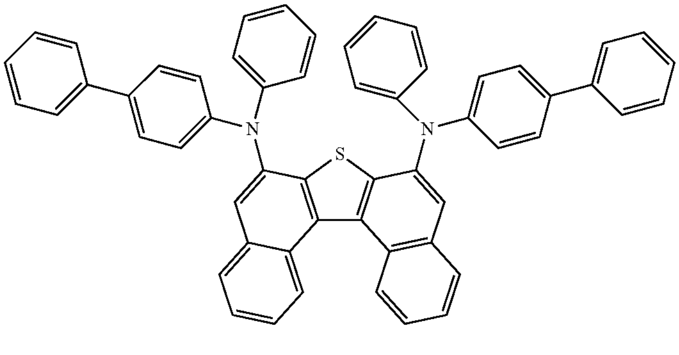

-continued
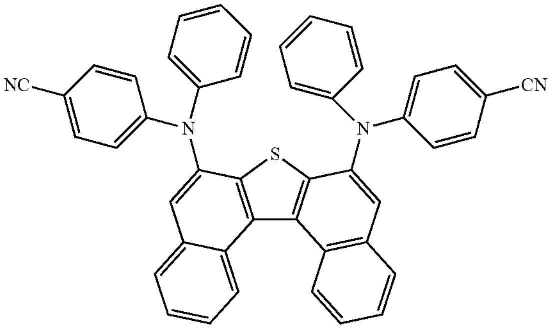
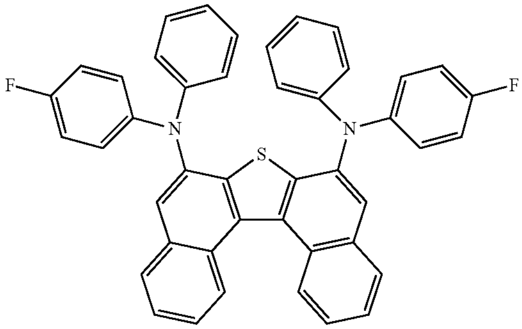
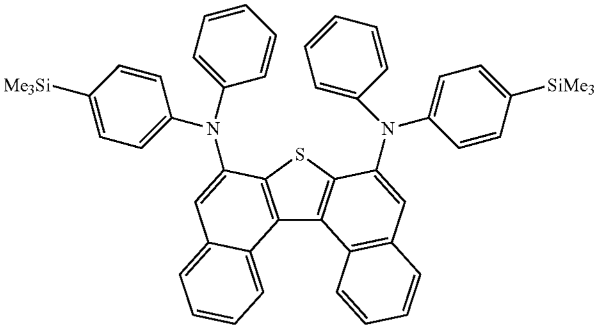
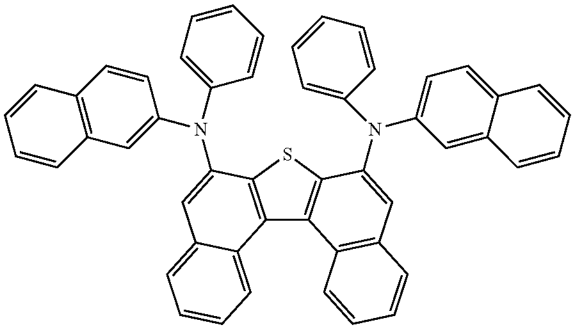
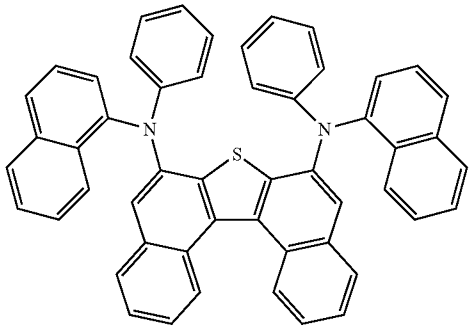
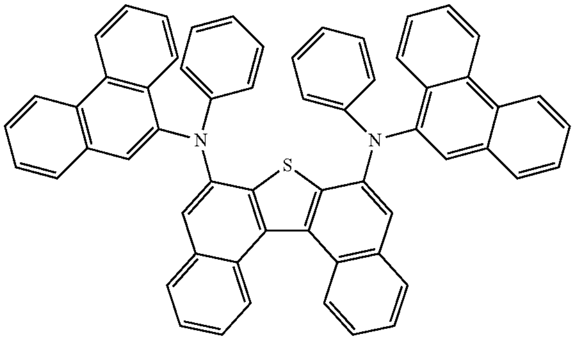
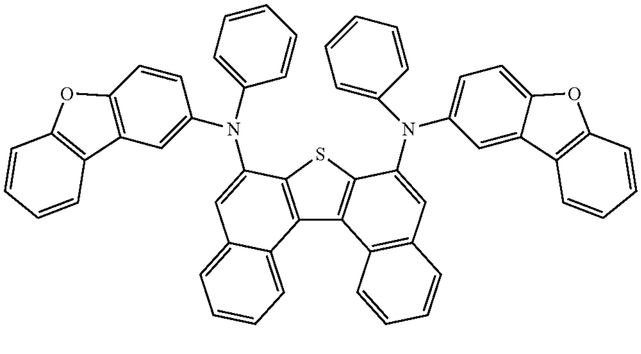

-continued
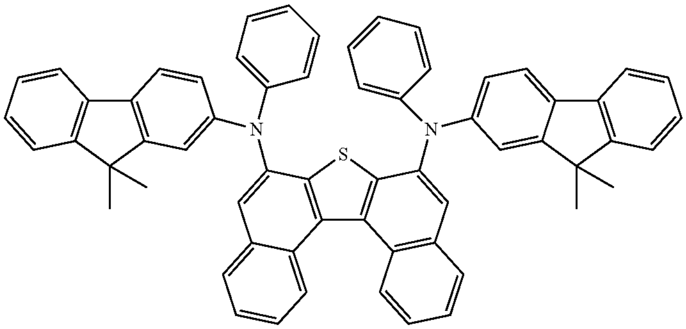
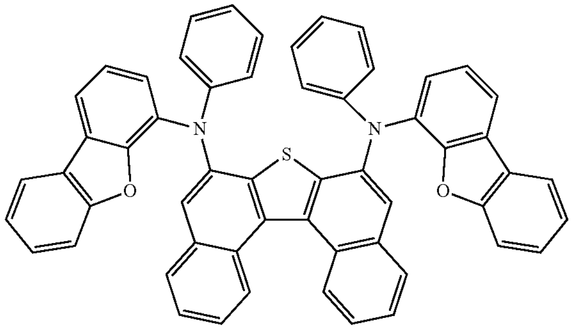
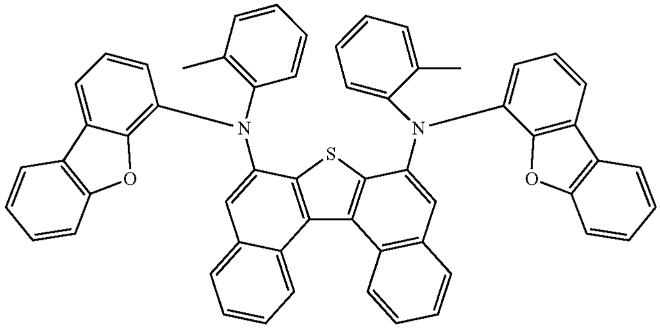
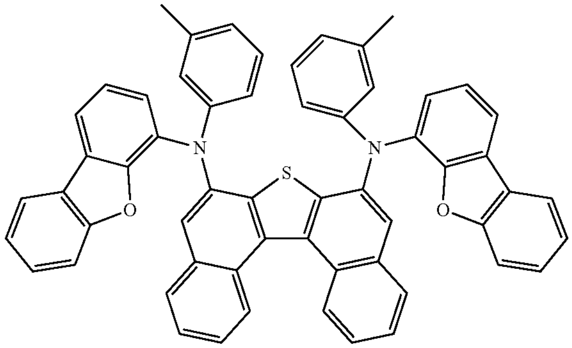
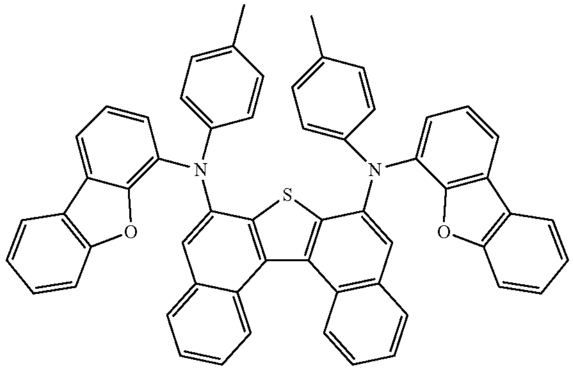

-continued

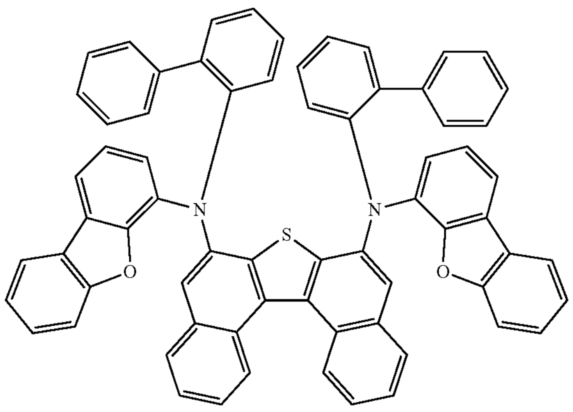

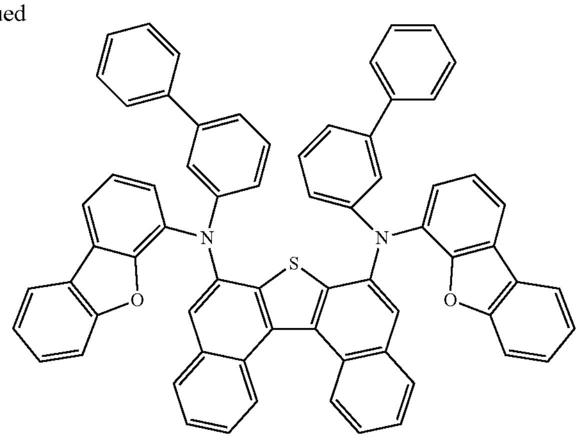

(Compound Represented by Formula (71))

The compound represented by the formula (71) is explained below

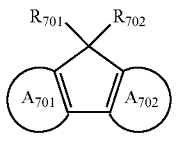

(71)

In the formula (71), $A_{701}$ ring and $A_{702}$ ring are independently a substituted or unsubstituted aromatic hydrocarbon ring having 6 to 50 ring carbon atoms, or a substituted or unsubstituted heterocyclic ring having 5 to 50 ring atoms;

one or more rings selected from the group consisting of $A_{701}$ ring and $A_{702}$ ring are bonded to the bond * of the structure represented by the following formula (72);

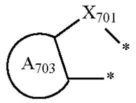

(72)

wherein, in the formula (72), $A_{703}$ rings are independently a substituted or unsubstituted aromatic hydrocarbon ring having 6 to 50 ring carbon atoms, or a substituted or unsubstituted heterocyclic ring having 5 to 50 ring atoms;

$X_{701}$ is $NR_{703}$, $C(R_{704})(R_{705})$, $Si(R_{706})$ $(R_{707})$, $Ge(R_{708})$ $(R_{709})$, O, S or Se;

$R_{701}$ and $R_{702}$ are bonded with each other to form a substituted or unsubstituted, saturated or unsaturated ring or do not form a substituted or unsubstituted saturated or unsaturated ring;

$R_{701}$ and $R_{702}$ that do not form the substituted or unsubstituted, saturated or unsaturated ring, and $R_{703}$ to $R_{709}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $-Si(R_{901})(R_{902})(R_{903})$, $-O-(R_{904})$, $-S-(R_{905})$, $-N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1).

One or more selected from the group consisting of $A_{701}$ ring and $A_{702}$ ring is bonded to * in the structure represented by the formula (72). That is, in one embodiment, the ring carbon atom of the aromatic hydrocarbon ring or the ring atom of the heterocyclic ring of $A_{701}$ ring is bonded to * in the structure represented by the formula (72). In one embodiment, the ring carbon atom of the aromatic hydrocarbon ring or the ring atom of the heterocyclic ring of $A_{702}$ ring is bonded to * in the structure represented by the formula (72).

In one embodiment, the group represented by the following formula (73) is bonded to one or both of $A_{701}$ ring and $A_{702}$ ring.

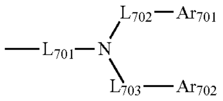

(73)

In the formula (73), $Ar_{701}$ and $Ar_{702}$ are independently a substituted or unsubstituted aryl group having 6 to 50 ring carbon atoms, or a substituted or unsubstituted monovalent heterocyclic group having 5 to 50 ring atoms; and $L_{701}$ to $L_{703}$ are independently a single bonded, a substituted or unsubstituted arylene group having 6 to 30 ring carbon atoms, a substituted or unsubstituted divalent heterocyclic group having 5 to 30 ring atoms, or a divalent linking group formed by bonding 2 to 4 above mentioned groups.

In one embodiment, in addition to $A_{701}$ ring, the ring carbon atom of the aromatic hydrocarbon ring or the ring atom of the heterocyclic ring of $A_{702}$ ring is bonded to * in the structure represented by the formula (72). In this case, the structures represented by formula (72) may be the same or different.

In one embodiment, $R_{701}$ and $R_{702}$ are independently a substituted or unsubstituted aryl group having 6 to 50 ring carbon atoms.

In one embodiment, $R_{701}$ and $R_{702}$ are bonded with each other to form a fluorene structure.

In one embodiment, $Ar_{701}$ ring and $Ar_{702}$ ring are substituted or unsubstituted aromatic hydrocarbon rings having 6 to 50 ring carbon atoms, and they are substituted or unsubstituted benzene rings, for example.

In one embodiment, $Ar_{703}$ ring is a substituted or unsubstituted aromatic hydrocarbon ring having 6 to 50 ring carbon atoms, and it is a substituted or unsubstituted benzene ring, for example.

In one embodiment, $X_{701}$ is O or S.

As specific example of the compound represented by the formula (71), the following compounds can be given, for example. In the following example compounds, Me represents methyl group.

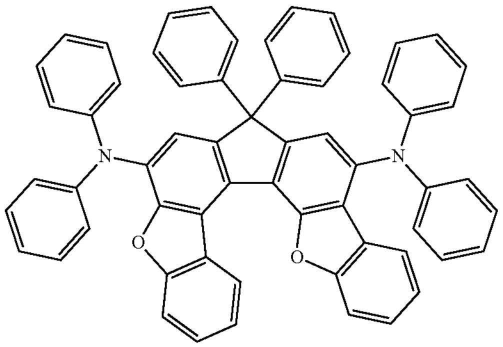

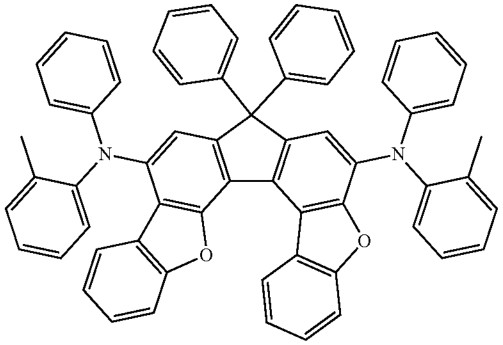

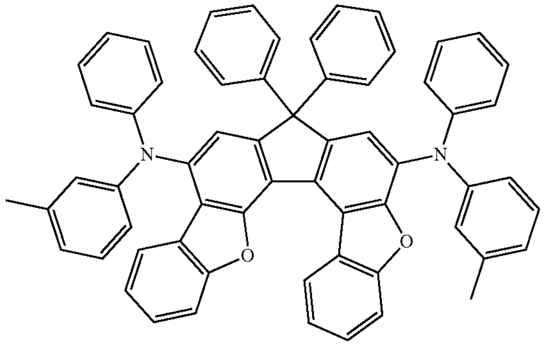

-continued

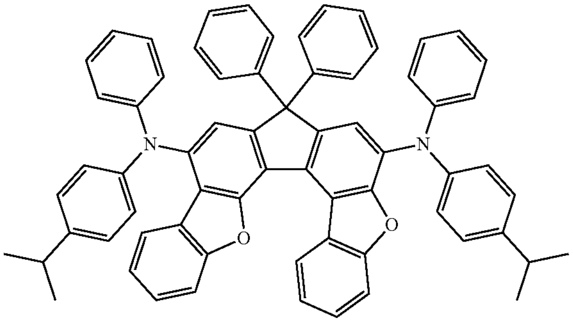

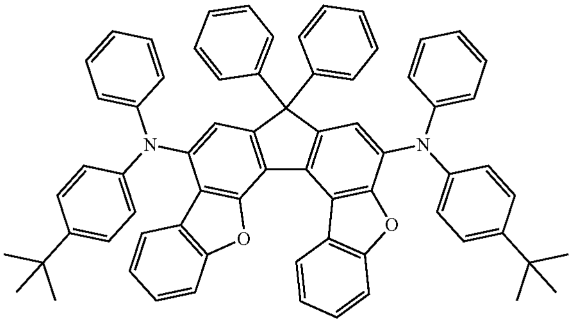

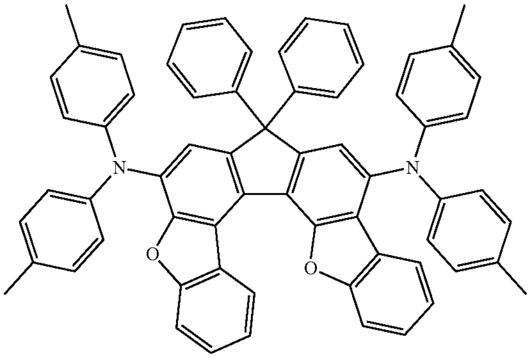

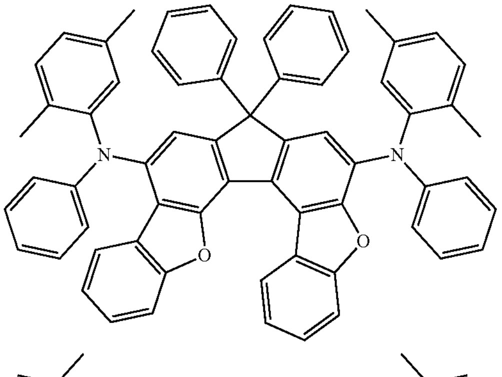

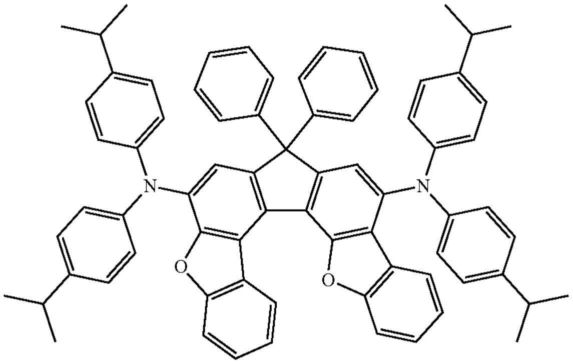

-continued
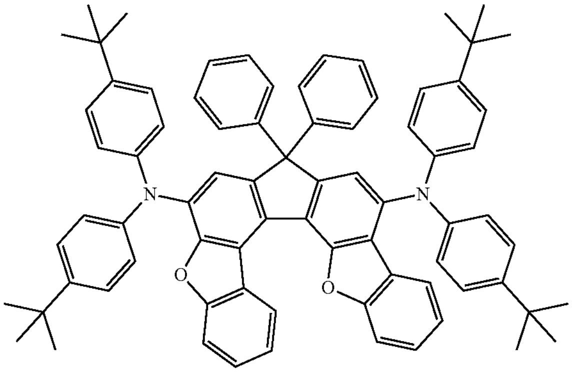
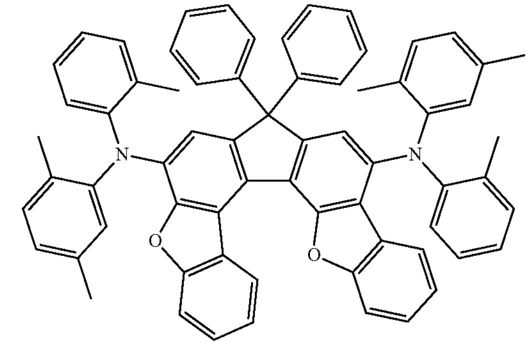
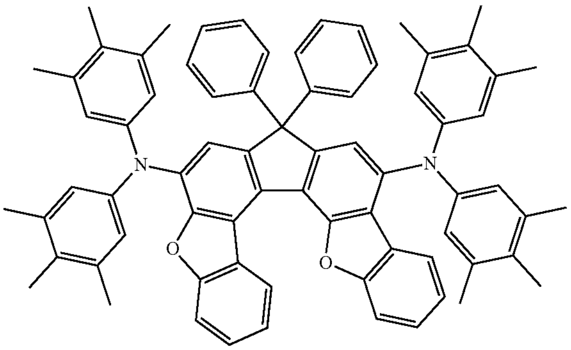
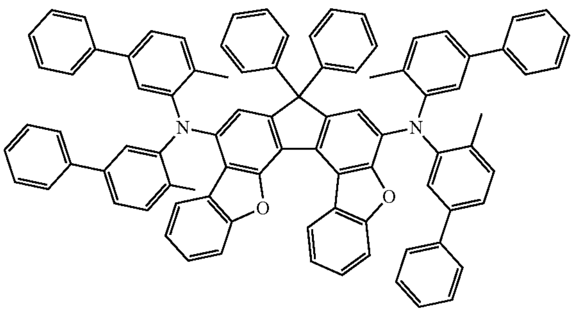
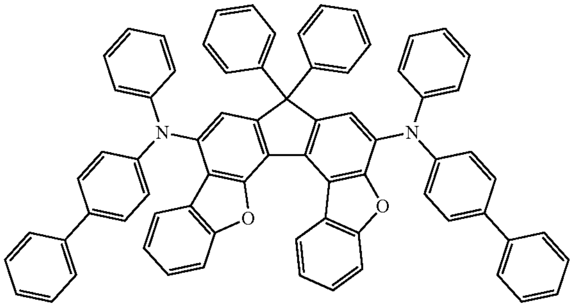
-continued
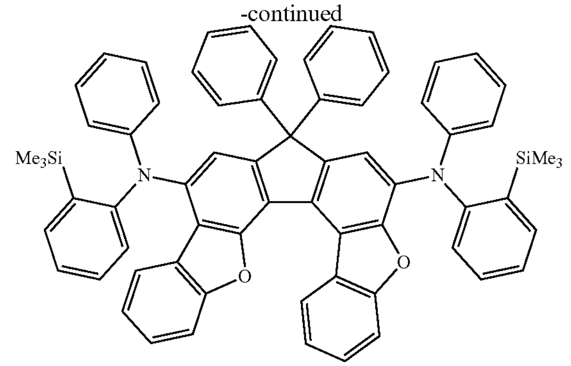
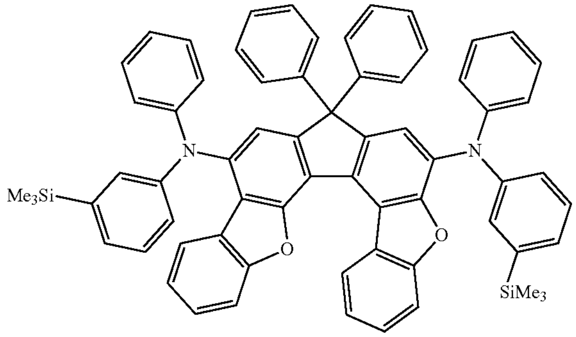
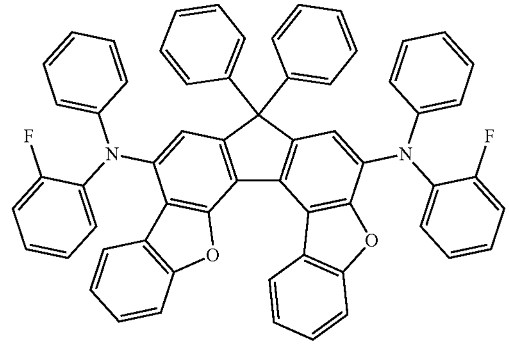
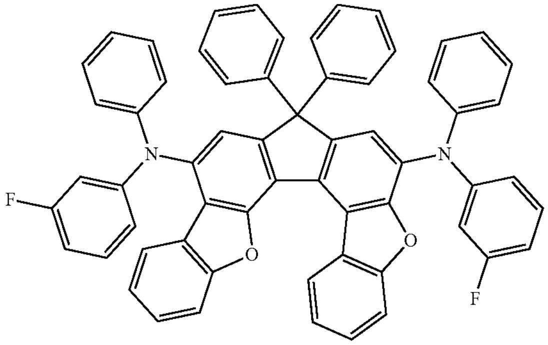
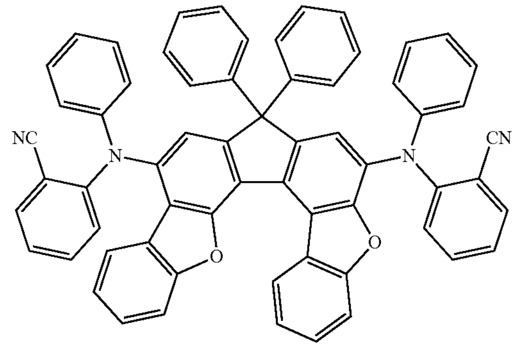

-continued
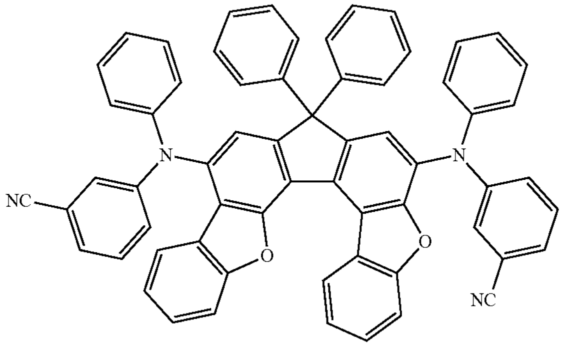
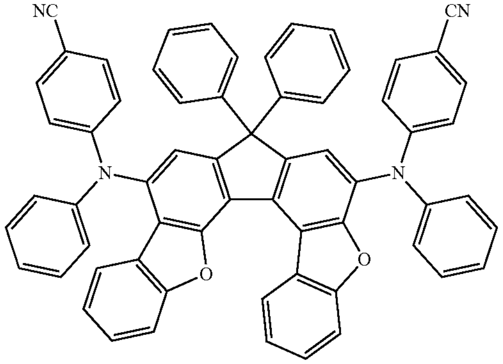
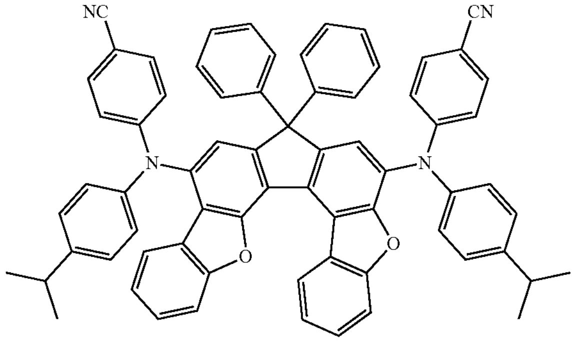
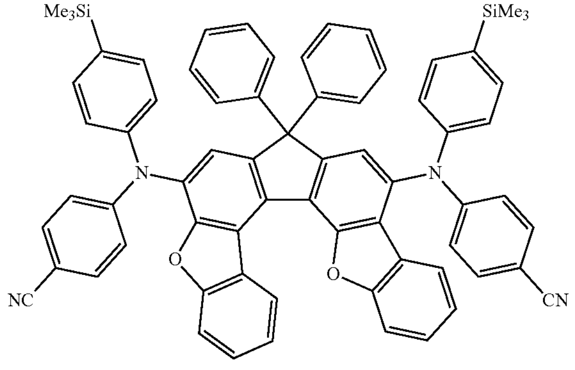
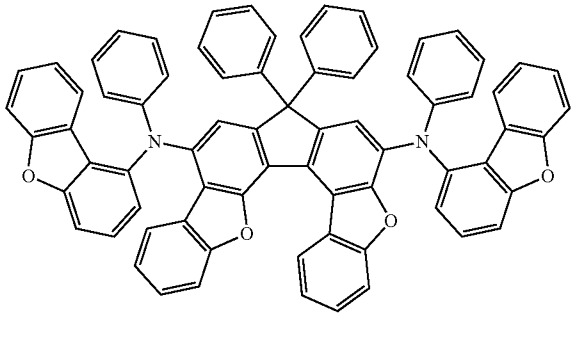
-continued
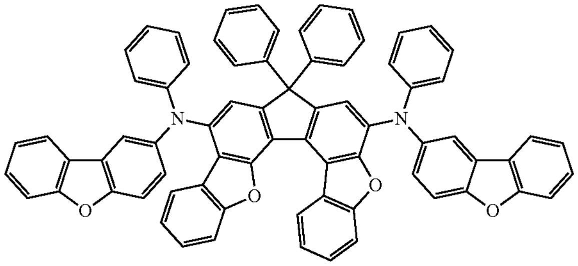
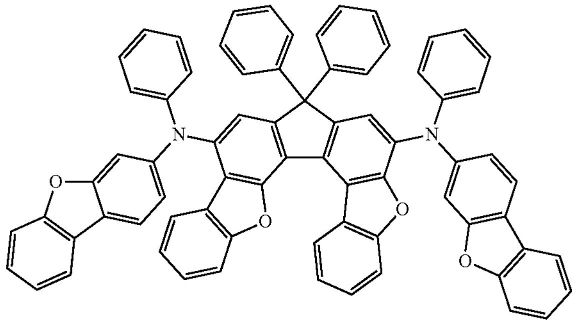
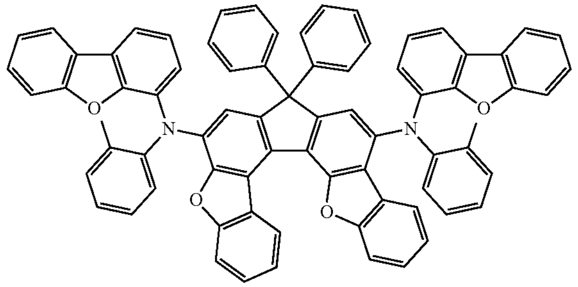
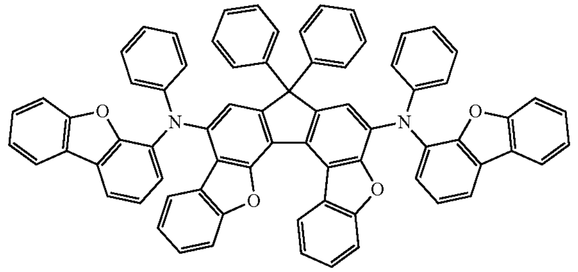
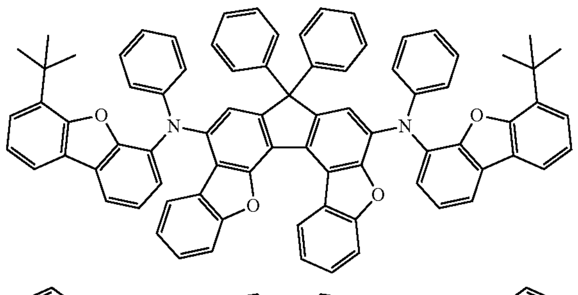
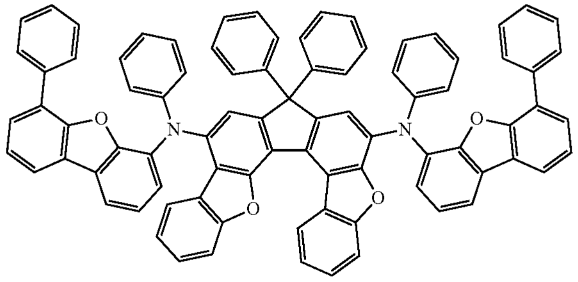

-continued
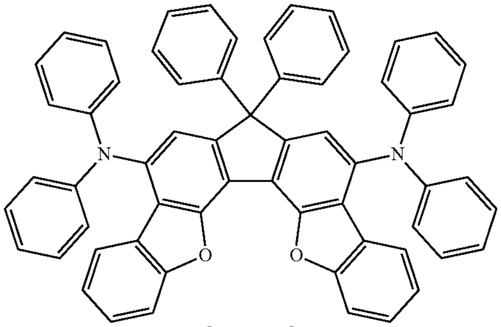
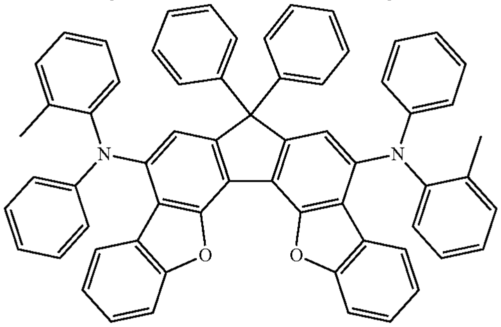
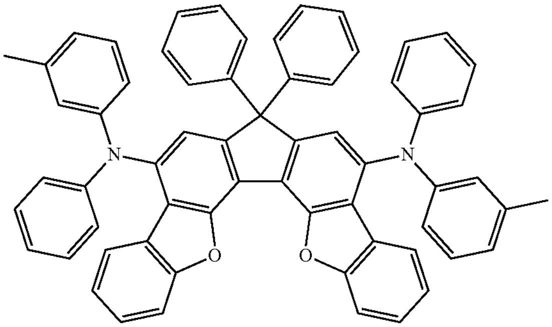
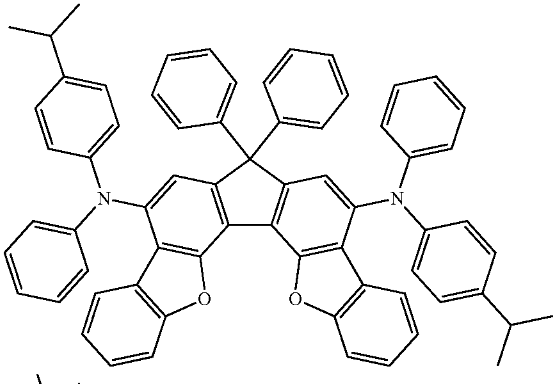
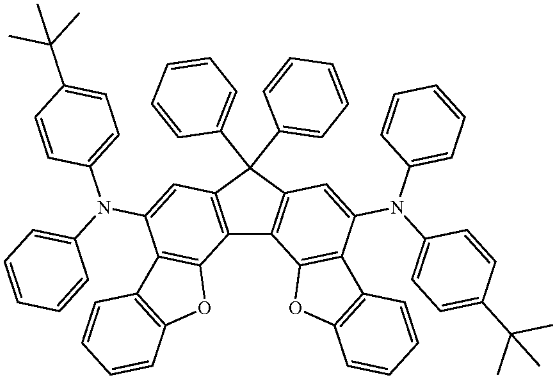
-continued
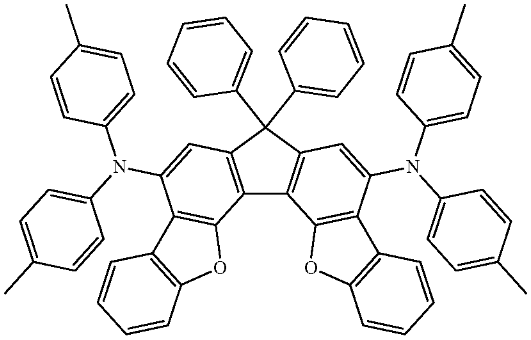
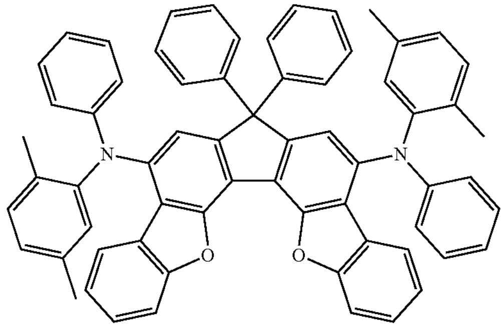
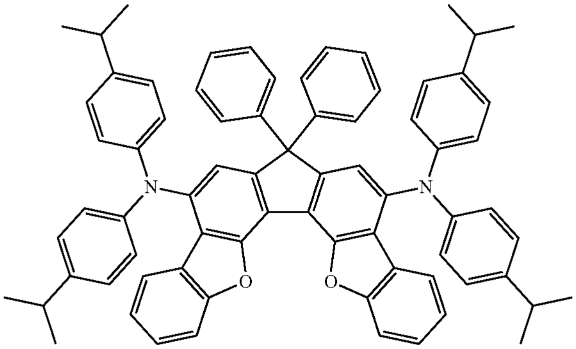
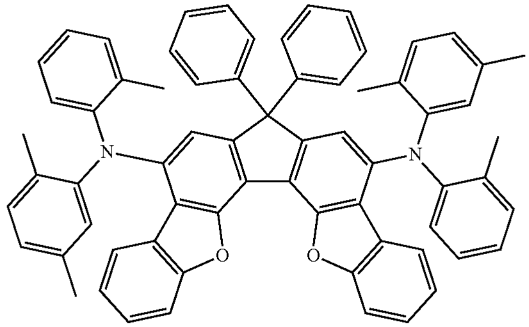
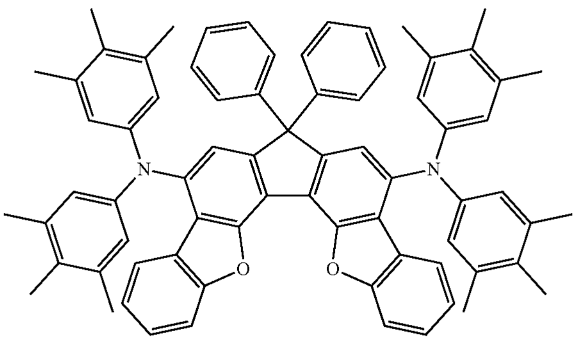

-continued
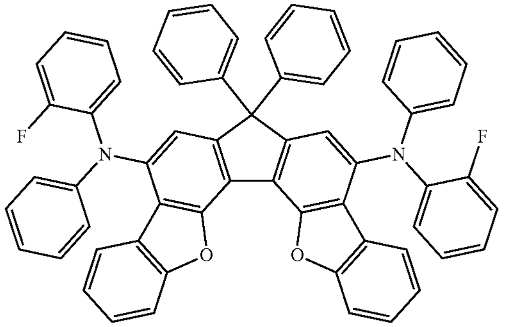
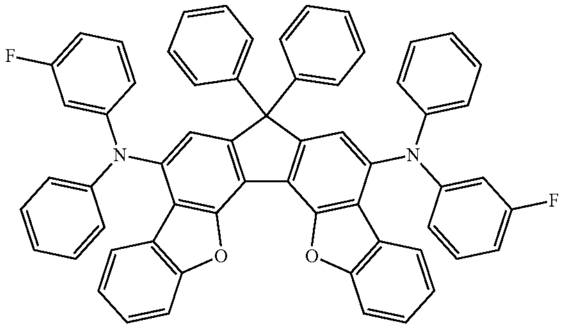
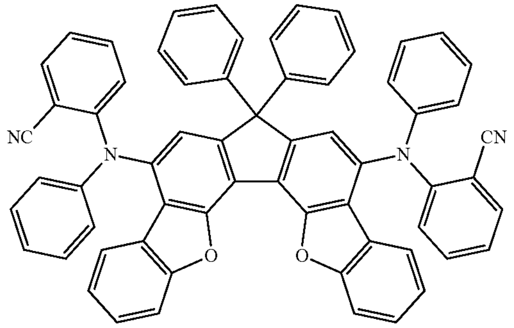
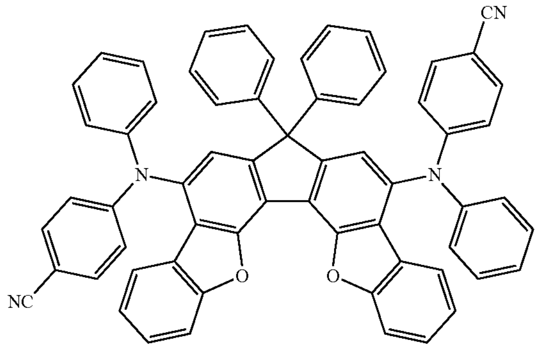
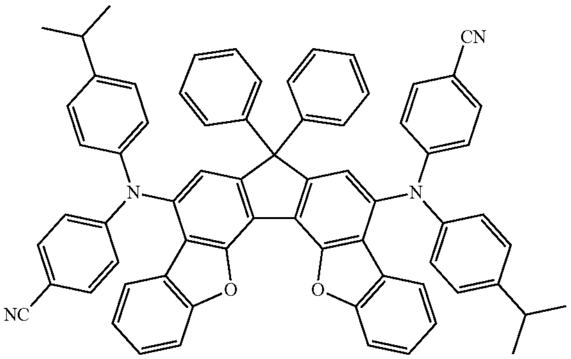
-continued
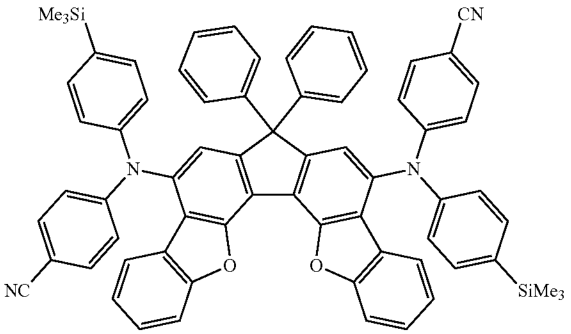
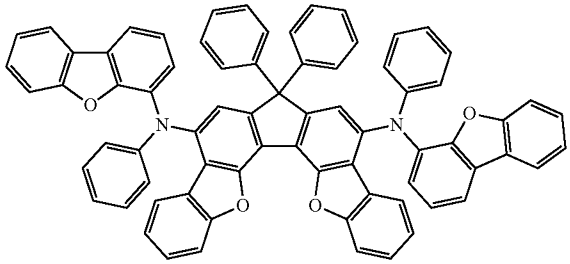
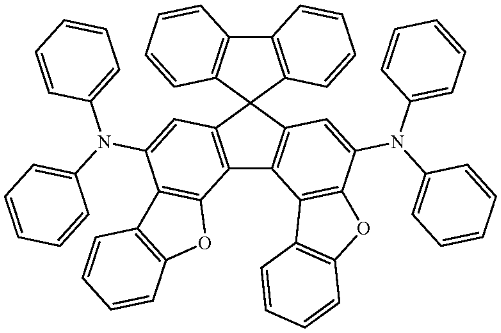
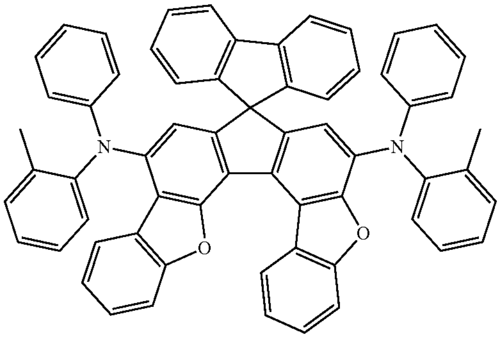
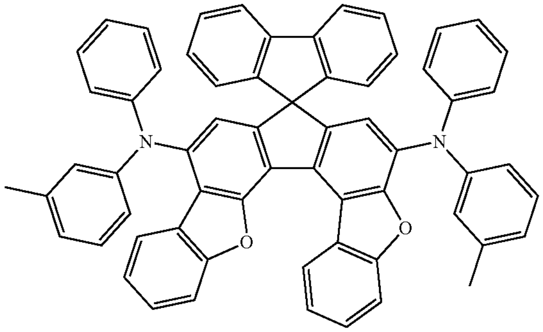

-continued
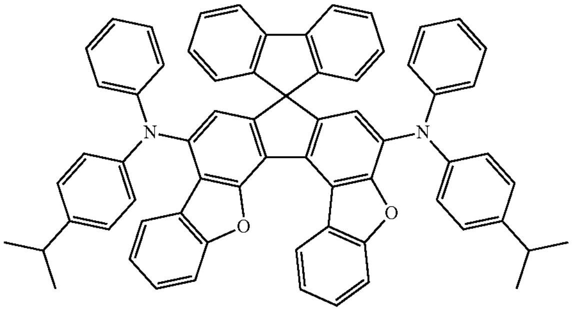
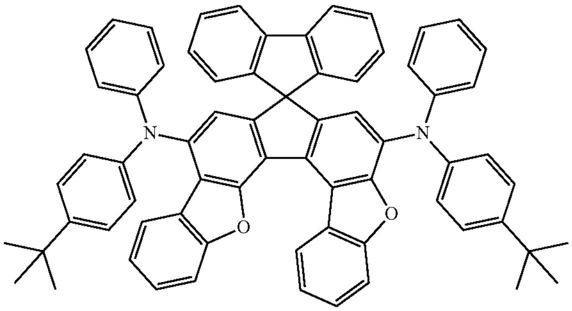
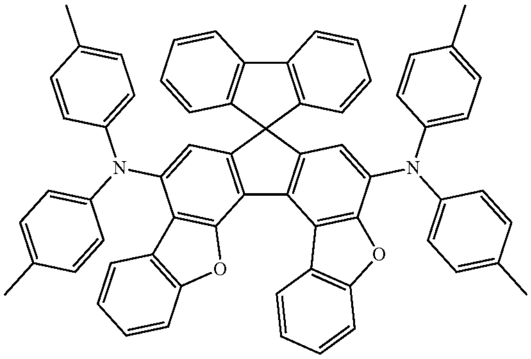
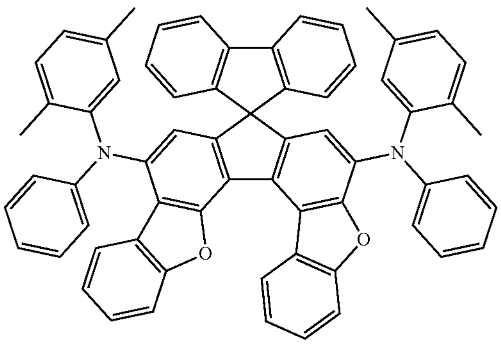
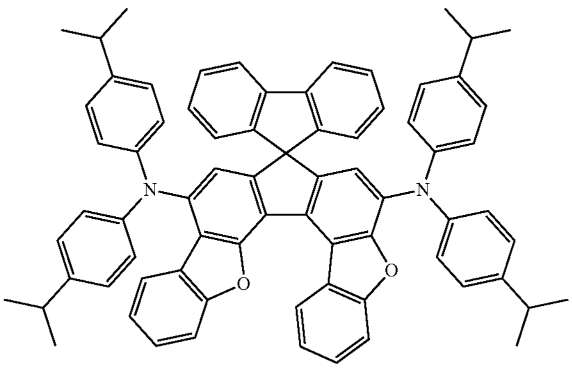
-continued
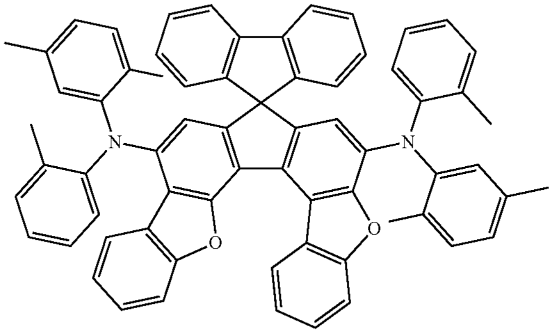
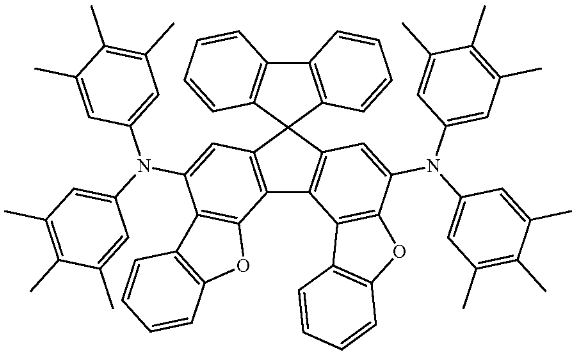
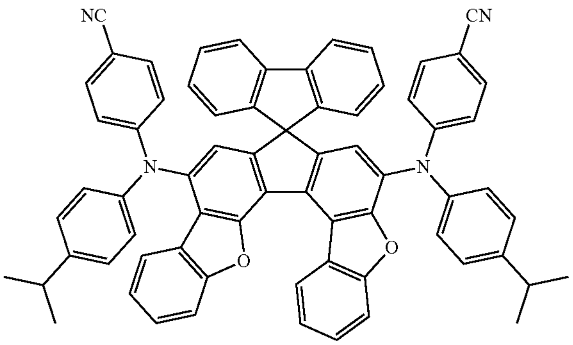
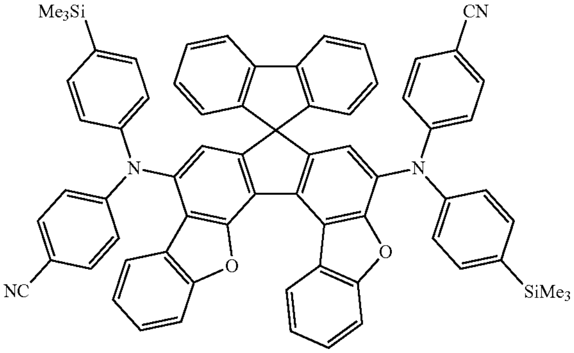
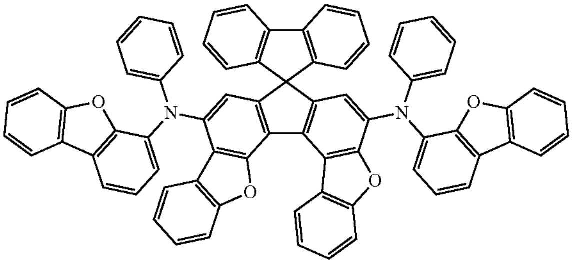

-continued

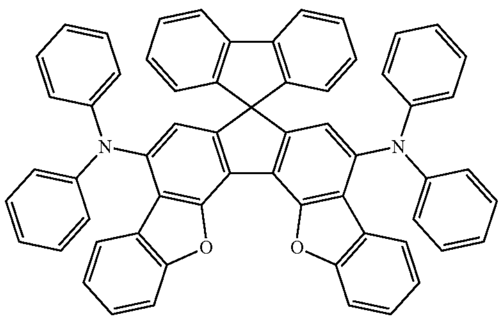

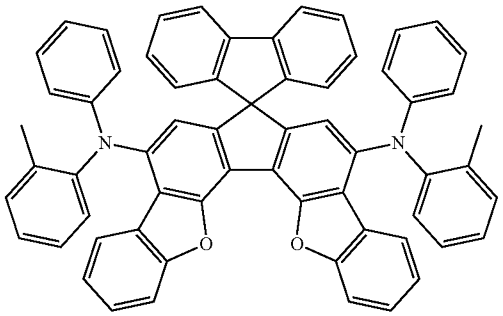

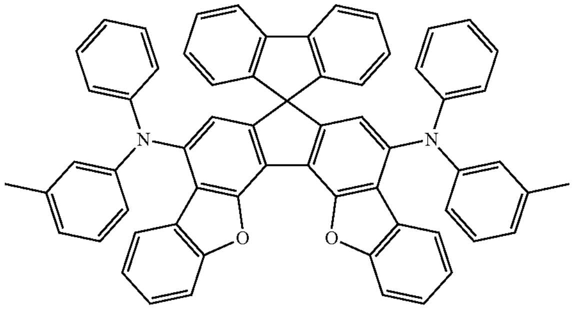

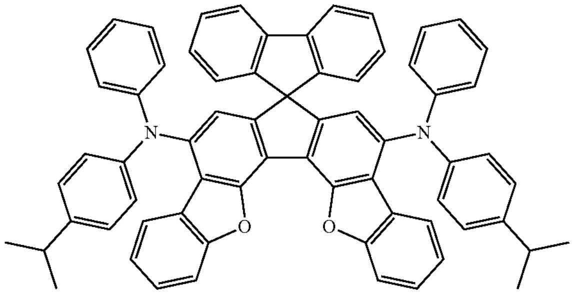

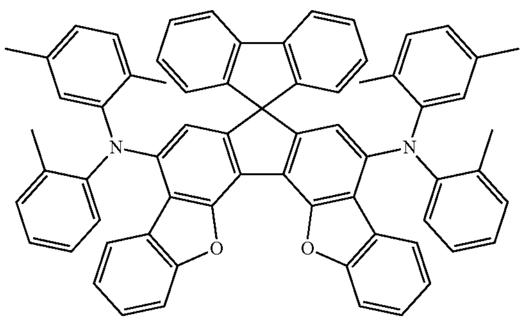

-continued

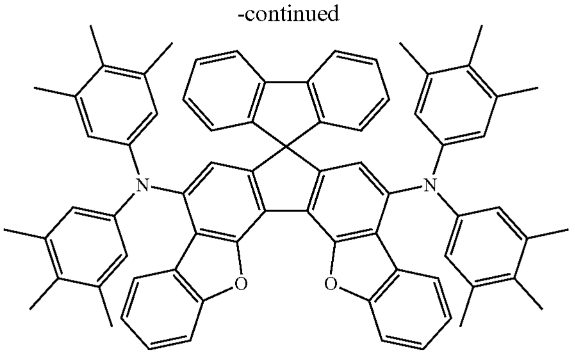

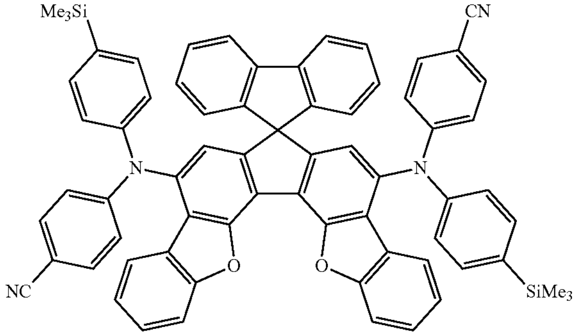

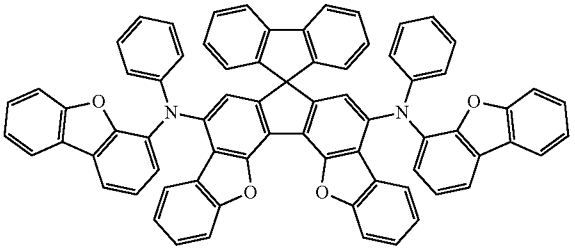

(Compound Represented by Formula (81))

The compound represented by the formula (81) is explained below (81)

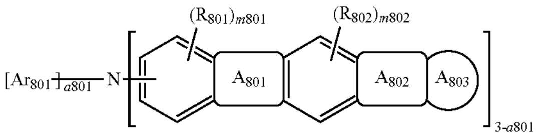

(82)

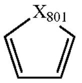

(83)

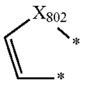

In the formula (81), $A_{801}$ ring is a ring represented by the formula (82) which is fused to an adjacent ring at an arbitrary position;

$A_{802}$ ring is a ring represented by the formula (83) which is fused to an adjacent ring at an arbitrary position;

two bonds * bond to $A_{803}$ ring at an arbitrary position;

$X_{801}$ and $X_{802}$ are independently $C(R_{803})(R_{804})$, $Si(R_{805})(R_{806})$, an oxygen atom, or a sulfur atom;

$A_{803}$ ring is a substituted or unsubstituted aromatic hydrocarbon ring having 6 to 50 ring carbon atoms, or a substituted or unsubstituted heterocyclic ring having 5 to 50 ring atoms;

$Ar_{801}$ is a substituted or unsubstituted aryl group having 6 to 50 ring carbon atoms, or a substituted or unsubstituted monovalent heterocyclic group having 5 to 50 ring atoms;

$R_{801}$ to $R_{806}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

m801 and m802 are independently an integer of 0 to 2; when m801 is 2, $R_{801}$'s may be the same as or different from each other, and when m802 is 2, $R_{802}$'s may be the same as or different from each other;

a801 is an integer of 0 to 2; when a801 is 0 or 1, the structure in the parentheses indicated by "3-a801" may be the same or different from each other; when a801 is 2, $Ar_{801}$s may be the same or different from each other.

In one embodiment, $Ar_{801}$ is a substituted or unsubstituted aryl group having 6 to 50 ring carbon atoms.

In one embodiment, $A_{803}$ ring is a substituted or unsubstituted aromatic hydrocarbon ring having 6 to 50 ring carbon atoms, and it is a substituted or unsubstituted benzene ring, a substituted or unsubstituted naphthalene ring, or a substituted or unsubstituted anthracene ring, for example.

In one embodiment, $R_{803}$ and $R_{804}$ are independently a substituted or unsubstituted alkyl group having 1 to 50 carbon atoms.

In one embodiment, a801 is 1.

As specific example of the compound represented by the formula (81), the following compounds can be given, for example.

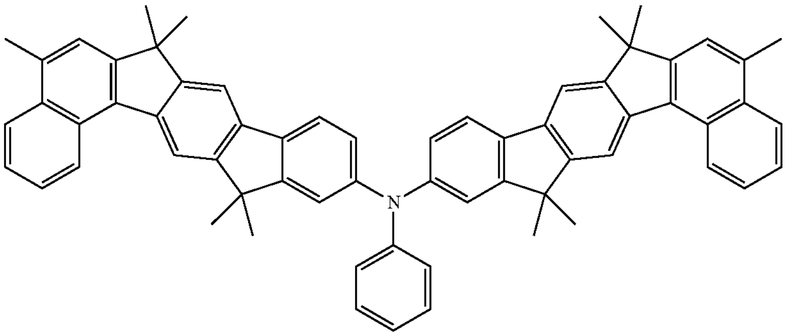

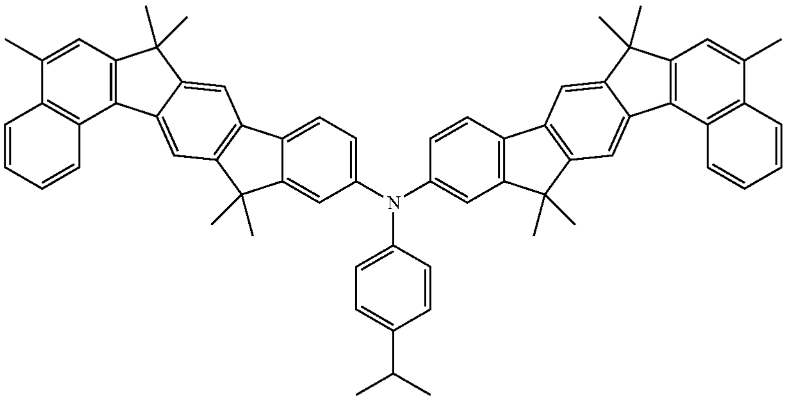

-continued
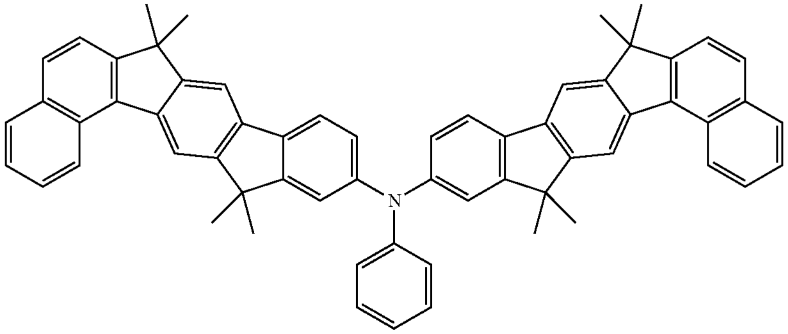
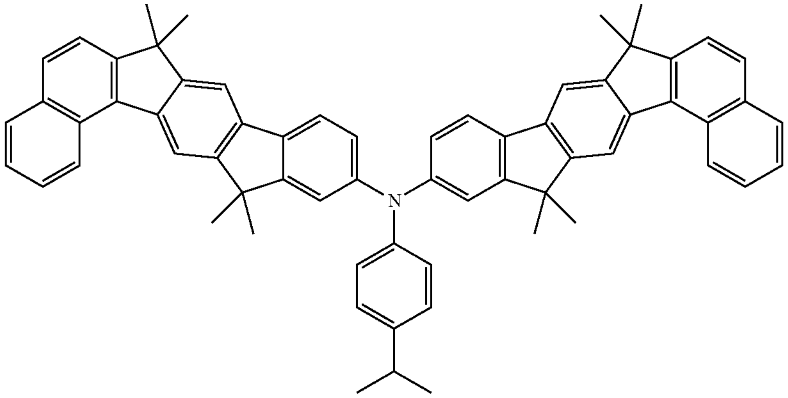
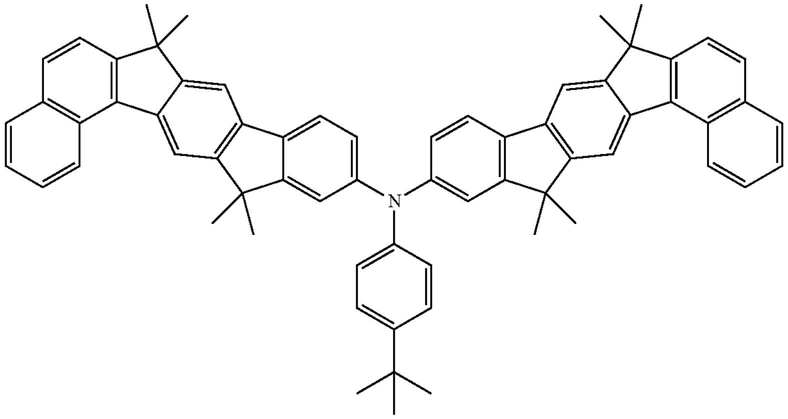
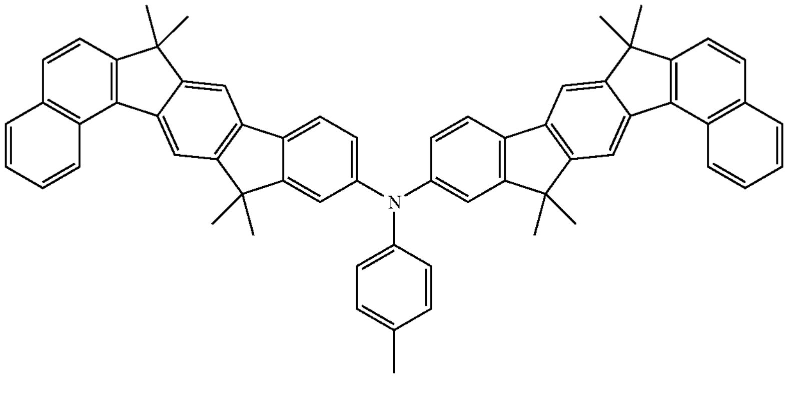

-continued
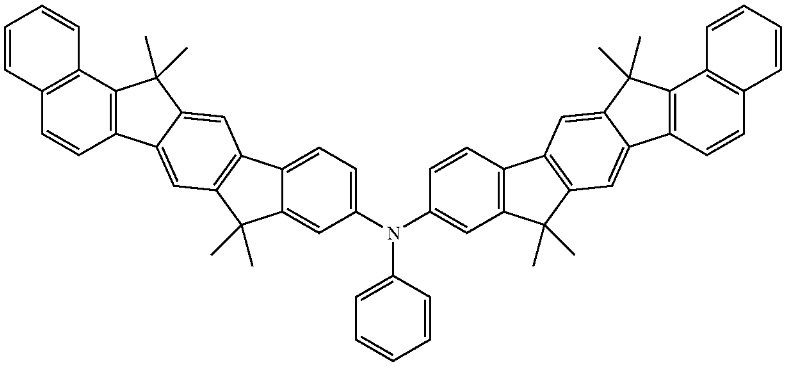
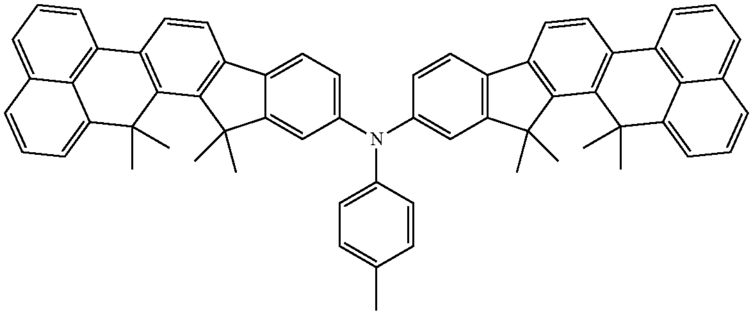
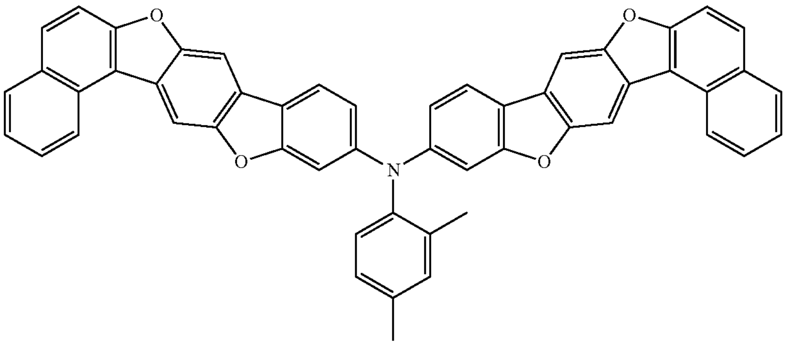
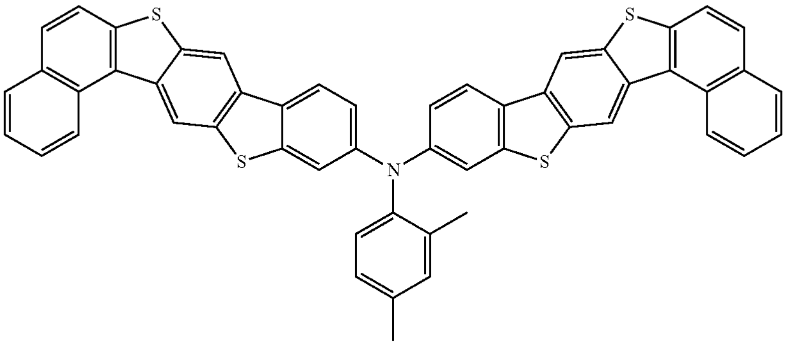

-continued

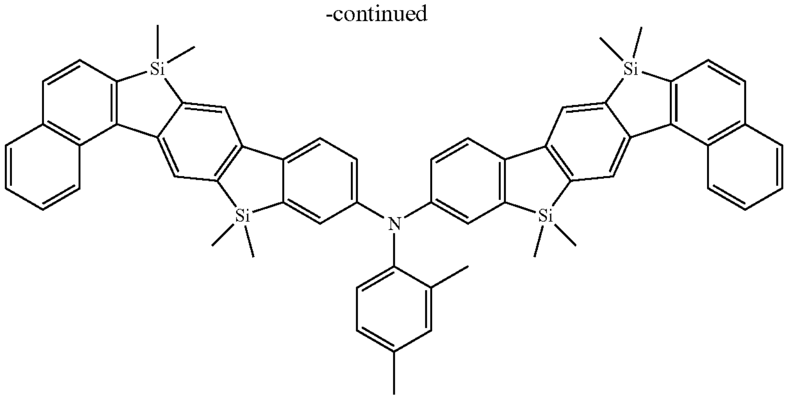

Specific examples of the above groups are as described in [Definition] of this specification.

In the organic EL device according to one aspect of the invention, known materials and device configurations may be applied as long as the device contains a cathode, an anode, and an emitting layer disposed between the cathode and the anode, and the emitting layer contains a compound represented by the following formula (1) and one or more compounds selected from the group consisting of a compound represented by formula (11), a compound represented by formula (21), a compound represented by formula (31), a compound represented by formula (41), a compound represented by formula (51), a compound represented by formula (61), a compound represented by formula (71) and a compound represented by formula (81) as described above, and as long as the effect of the invention is not impaired.

In one embodiment, the emitting layer contains the compound represented by the formula (1A) and the compound represented by the formula (43D).

In one embodiment, the compound represented by the formula (1A) is one or more selected from the group consisting of the compounds represented by the following formulas BH-1, BH-2, BH-4, BH-5 and BH-9; and the compound represented by the formula (43D) is one or more selected from the group consisting of the compounds represented by the following formulas BD-9, BD-10, BD-11, and BD-12.

BH-1

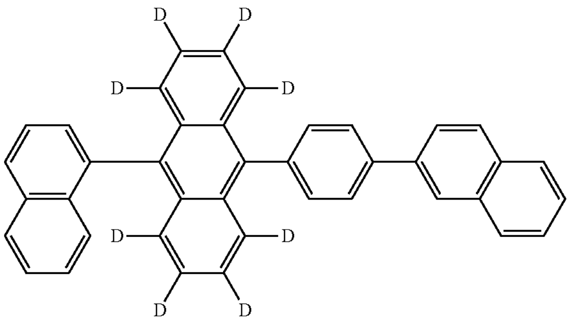

-continued

BH-2

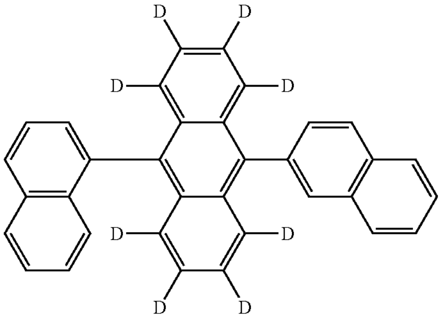

BH-4

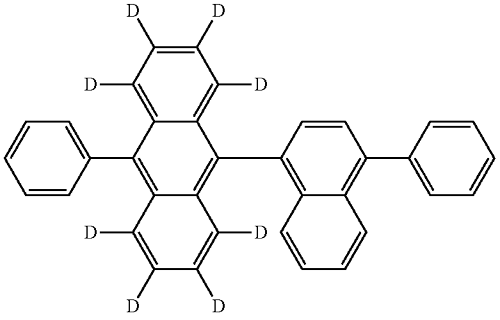

BH-5

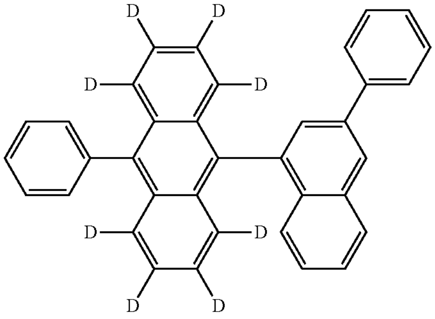

-continued

BH-9

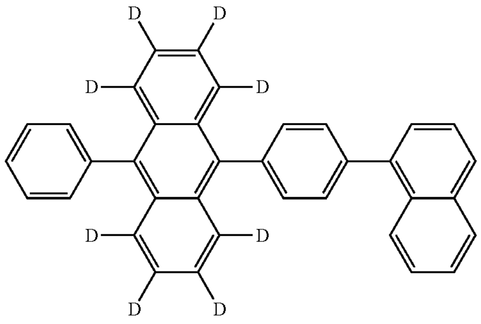

BH-9

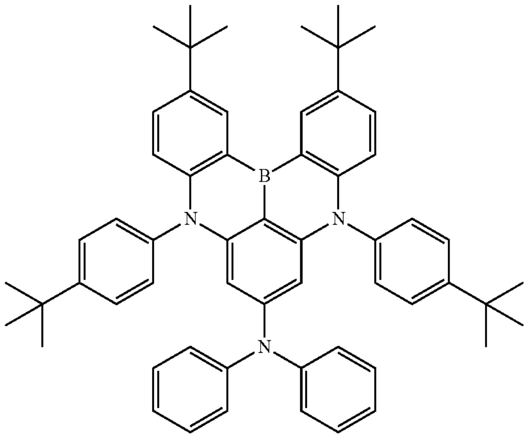

BH-10

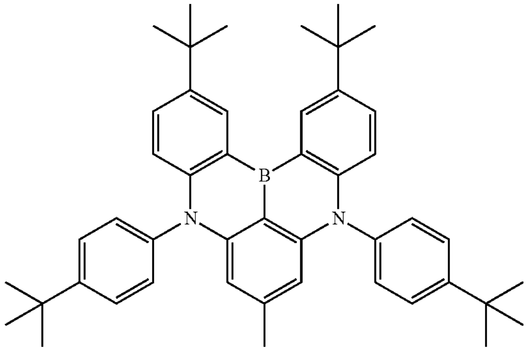

BD-11

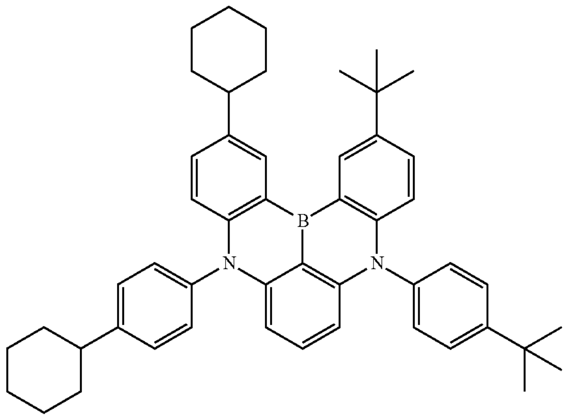

-continued

BD-12

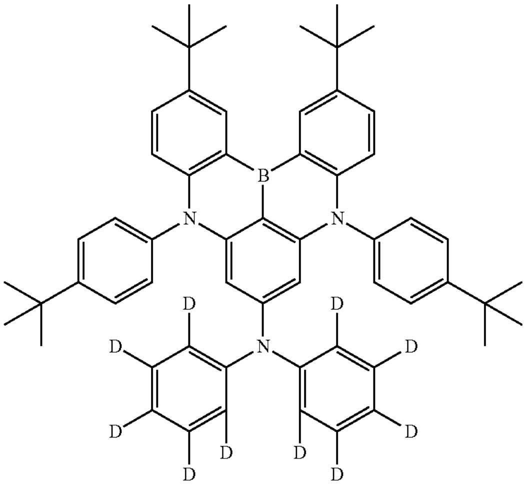

Hereinbelow, an explanation will be made on elements and materials other than the above-mentioned compound constituting each layer that can be used in the organic EL device according to one aspect of the invention.

(Substrate)

The substrate is used as a supporting body of the emitting device. As the substrate, glass, quarts, plastic or the like can be used. Further, a flexible substrate may be used. The flexible substrate means a substrate that can be bent. For example, a plastic substrate made of polycarbonate or vinyl polychloride or the like can be given.

(Anode)

In an anode formed on a substrate, it is preferable to use a metal having a large work function (specifically, 4.0 eV or more), an alloy, an electric conductive compound, a mixture of these or the like. Specifically, indium oxide-tin oxide (ITO: Indium Tin Oxide), indium oxide-tin oxide containing silicon or silicon oxide, indium oxide-zinc oxide, tungsten oxide, indium oxide containing zinc oxide, graphene, or the like can be given. In addition, gold (Au), platinum (Pt) or a nitride of a metal material (e.g. titanium nitride) or the like can be given.

(Hole-Injecting Layer)

The hole-injecting layer is a layer containing a substance having a high hole-injecting property. As a substance having a high hole-injecting property, a substance selected from molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, a polymer compound (oligomer, dendrimer, polymer, etc.) or the like can also be used (Hole-Transporting Layer)

The hole-transporting layer is a layer containing a substance having a high hole-transporting property. For the hole-transporting layer, aromatic amine compounds, carbazole derivatives, anthracene derivatives and the like can be used. Polymer compounds such as poly (N-vinylcarbazole) (abbreviation: PVK) and poly(4-vinyltriphenylamine) (abbreviation: PVTPA) can also be used. However, any substance other than these may be used as long as it is a substance having a higher transporting property for holes than electrons. Note that the layer containing a substance having a high hole-transporting property is not limited to a single layer, but may be a stacked body of two or more layers made of the above substances.

(Guest Material of the Emitting Layer)

The emitting layer is a layer that comprises a substance having high luminous property, and various materials can be used. For example, as the substance having high luminous property, a fluorescent compound that emits fluorescent light or a phosphorescent compound that emits phosphorescent light can be used. The fluorescent compound is a compound capable of emitting light from a singlet excited state and the phosphorescent compound is a compound capable of emitting light from a triplet excited state.

As a blue fluorescent material that can be used for the emitting layer, pyrene derivatives, styrylamine derivatives, chrysene derivatives, fluoranthene derivatives, fluorene derivatives, diamine derivatives, triarylamine derivatives and the like can be used. An aromatic amine derivative or the like can be used as a green fluorescent light-emitting material that can be used in the emitting layer. As a red fluorescent material which can be used in emitting layer, a tetracene derivative, a diamine derivative or the like can be used.

Metal complexes such as iridium complexes, osmium complexes, platinum complexes and the like are used as the blue phosphorescent material that can be used in the emitting layer. An iridium complex or the like is used as a green phosphorescent material that can be used in the emitting layer. Metal complexes such as iridium complexes, platinum complexes, terbium complexes, europium complexes and the like are used as red phosphorescent materials that can be used in the emitting layer.

(Host Material of Emitting Layer)

The emitting layer may have a structure in which the substance having high luminescent property (guest material) described above is dispersed in another substance (host material). In addition to the compound represented by the formula (1), various materials can be used as substances for dispersing substances with high luminescent properties, and it is preferable to use a material having a high lowest unoccupied molecular orbital level (LUMO level) and a low highest occupied molecular orbital level (HOMO level), rather than a material having a high luminous property.

As a substance (host material) for dispersing a substance having a high luminous property, 1) a metal complex such as an aluminum complex, a beryllium complex or a zinc complex, 2) a heterocyclic compound such as an oxadiazole derivative, a benzimidazole derivative, a phenanthroline derivative or the like, 3) a fused aromatic compound such as a carbazole derivative, an anthracene derivative, a phenanthrene derivative, a pyrene derivative or a chrysene derivative, and 4) an aromatic amine compound such as a triarylamine derivative or a fused polycyclic aromatic amine derivative are used.

(Electron-Transporting Layer)

The electron-transporting layer is a layer containing a substance having a high electron-transporting property. For the electron-transporting layer, 1) a metal complex such as an aluminum complex, a beryllium complex, or a zinc complex, 2) a heteroaromatic compound such as an imidazole derivative, a benzimidazole derivative, an azine derivative, a carbazole derivative or a phenanthroline derivative, and 3) a polymer compound can be used.

(Electron-Injecting Layer)

The electron-injection layer is a layer containing a substance having a high electron-injection property. For the electron-injection layer, alkali metals, alkaline earth metals or a compound thereof such as lithium (Li), lithium fluoride (LiF), cesium fluoride (CsF), calcium fluoride ($CaF_2$), lithium oxide ($LiO_x$) or the like can be used.

(Cathode)

It is preferable to use a metal, an alloy, an electrically conductive compound, a mixture thereof, or the like having a small work function (specifically, 3.8 eV or less) for the cathode. Specific examples of such cathode material include elements belonging to Group 1 or Group 2 of the periodic table of elements, that is, alkali metals such as lithium (Li) and cesium (Cs), alkaline earth metals such as magnesium (Mg), calcium (Ca), and strontium (Sr), an alloy containing these metals (for example, MgAg and AlLi), a rare earth metal such as europium (Eu) and ytterbium (Yb), and an alloy containing a rare earth metal.

In the organic EL device according to one aspect of the invention, the method for forming each layer is not particularly restricted. A conventionally known forming method such as a vacuum deposition method, a spin coating method or the like can be used. Each layer such as the emitting layer or the like can be formed by a vacuum deposition method, a molecular beam evaporation method (MBE method), or a known coating method such as a dipping method, a solution spin coating method, a casting method, a bar coating method, or the like, that uses a solution of a material forming each layer dissolved in a solvent.

In the organic EL device according to one aspect of the invention, the thickness of each layer is not particularly restricted. In general, in order to suppress occurrence of defects such as pinholes and to suppress the applied voltage and to improve luminous efficiency, the thickness is normally preferably in a range of several nm to 1 μm.

[Electronic Device]

The electronic device according to one aspect of the invention is characterized in that it is provided with the organic EL device according to one aspect of the invention.

Specific examples of the electronic device include a display element such as an organic EL panel module; a display such as a TV, a mobile phone or a PC; and emitting devices such as lightings and lights for automobiles or the like.

EXAMPLES

Now, the invention will be explained in detail with reference to Examples and Comparative Examples. However, it should be understood that the invention be not restricted at all by these Examples.

Synthesis Example 1 (Synthesis of BH-1)

Synthesis scheme of BH-1 is shown below. Hereinafter, TfO represents trifluoromethanesulfonate.

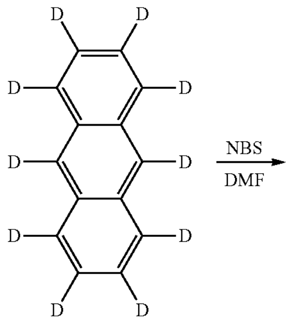

-continued

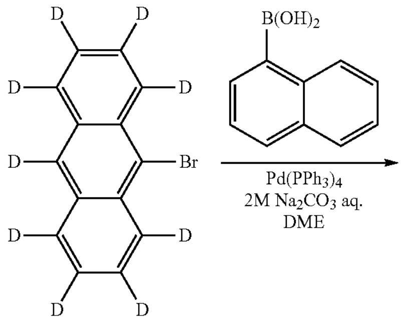

BH-1-1

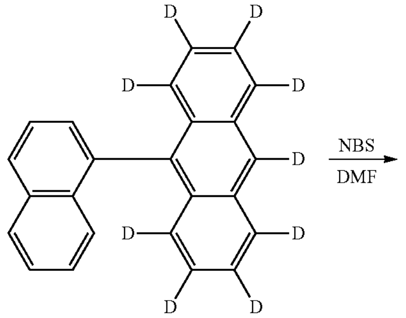

BH-1-2

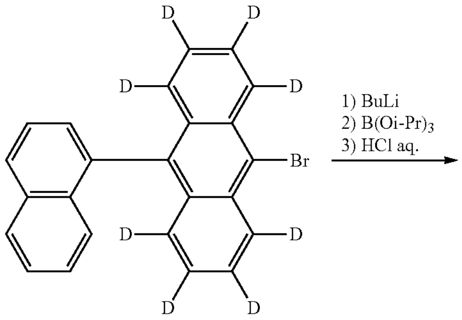

BH-1-3

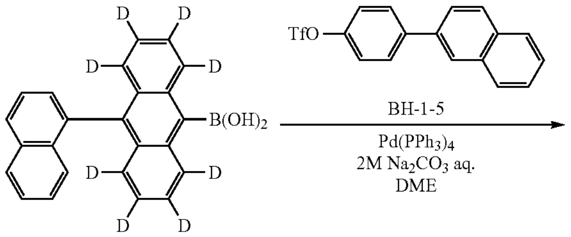

BH-1-4

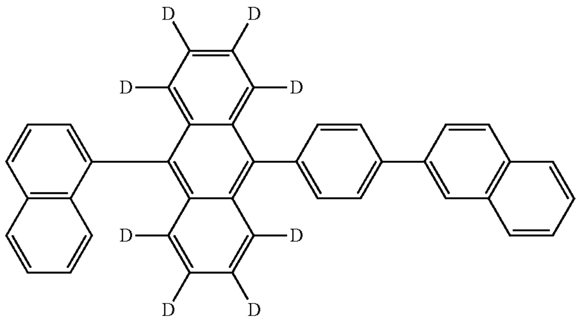

BH-1

(1-1) Synthesis of BH-1-1

Under an argon atmosphere, a mixture of 40.0 g of anthracene d-10, 38.0 g of NBS (N-bromosuccinimide), and 1200 mL of dimethyl formamide (DMF) was stirred at room temperature for 16 hours. The resultant reaction liquid was cooled to room temperature, followed by filtration. Then, the solvent of the obtained filtrate was distilled off under reduced pressure. The obtained residue was purified by column chromatography to give 42.0 g of BH-1-1 in an yield of 75%.

(1-2) Synthesis of BH-1-2

Under an argon atmosphere, a mixture of 42.0 g of BH-1-1, 30.0 g of 1-naphthaleneboronic acid, 3.70 g of tetrakistriphenylphosphine palladium, 160 mL of a 2M sodium carbonate aqueous solution, and 750 mL of dimethoxyethane (DME) was stirred at 80° C. for 8 hours. The resultant reaction liquid was cooled to room temperature, and extracted with ethyl acetate. Then, the organic phase was washed with water, dried over anhydrous magnesium sulfate, followed by distillation of the solvent under reduced pressure. The obtained residue was purified by silica gel chromatography to give 29.6 g of BH-1-2 in an yield of 65%.

(1-3) Synthesis of BH-1-3

Under an argon atmosphere, a mixture of 28.0 g of BH-1-2, 15.9 g of NBS, and 500 mL of DMF is stirred at 80° C. for 12 hours. The resultant reaction liquid was cooled to room temperature, followed by filtration. Then, the solvent of the obtained filtrate was distilled off under reduced pressure. The obtained residue was purified by column chromatography to give 16.4 g of BH-1-3 in an yield of 47%.

(1-4) Synthesis of BH-1-4

Under an argon atmosphere, a reactor was charged with 13.0 g of BH-1-3 and 130 mL of tetrahydrofuran (THF), and cooled to −78° C. To the reactor, 25 mL of a 1.6M n-butyllithium in hexane was added, and the reaction mixture was stirred for one hour. Subsequently, 19 g of triisopropoxyboron was added thereto, followed by stirring for more one hour. The reaction liquid was warmed to room temperature, stirred for one hour. Then, 480 mL of a 1N hydrochloric acid solution was added thereto, followed by stirring for 30 minutes. The organic phase of the resultant reaction liquid was extracted with dichloromethane, washed with water, dried over anhydrous magnesium sulfate, followed by distillation of the solvent under reduced pressure. The obtained residue was purified by silica gel column chromatography to give 8.4 g of BH-1-4 in an yield of 71%.

(1-5) Synthesis of BH-1

Under an argon atmosphere, a mixture of 3.1 g of BH-1-4, 2.5 g of BH-1-5, 0.200 g of tetrakistriphenylphosphine palladium, 10 mL of a 2M sodium carbonate aqueous solution, and 60 mL of DME was stirred at 80° C. for 8 hours. Then, the resultant reaction liquid was cooled to room temperature, extracted with ethyl acetate. The organic phase was washed with water, dried over anhydrous magnesium sulfate, followed by distillation of the solvent under reduced pressure. The obtained residue was purified by silica gel column chromatography and recrystallization to give 2.5 g of BH-1 in an yield of 56%.

The compound was identified by molecular weight determination with FD/MS (Field Desorption Mass Spectrometry). It was confirmed that m/e=514 for the molecular weight of 514.

Synthesis Example 2 (Synthesis of BH-2)

Synthesis scheme of BH-2 is shown below.

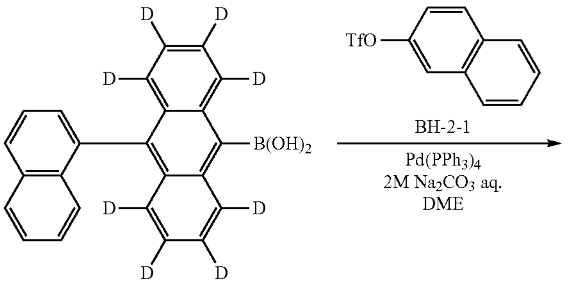

BH-1-4

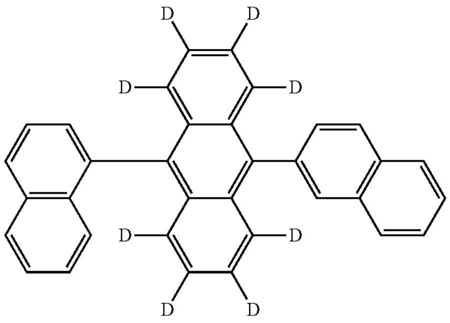

BH-2

(2-1) Synthesis of BH-2

Under an argon atmosphere, a mixture of 4.0 g of BH-1-4, 3.5 g of BH-2-1, 0.260 g of tetrakistriphenylphosphine palladium, 10 mL of a 2M sodium carbonate aqueous solution, and 70 mL of DME was stirred at 80° C. for 8 hours. The resultant reaction liquid was cooled to room temperature, and extracted with ethyl acetate. Then, the organic phase was washed with water, dried over anhydrous magnesium sulfate, followed by distillation of the solvent under reduced pressure. The obtained residue was purified by silica gel column chromatography and recyclization to give 2.9 g of BH-2 in an yield of 59%. The compound was identified by molecular weight determination with FD/MS. It was confirmed that m/e=438 for the molecular weight of 438.

Synthesis Example 3 (Synthesis of BH-3)

Synthesis scheme of BH-3 is shown below.

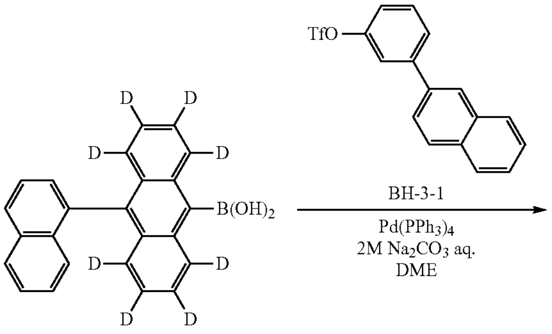

BH-1-4

-continued

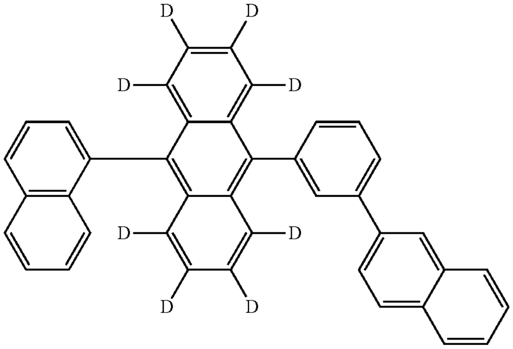

BH-3

(3-1) Synthesis of BH-3

Under an argon atmosphere, a mixture of 4.0 g of BH-1-4, 4.5 g of BH-3-1, 0.260 g of tetrakistriphenylphosphine palladium, 10 mL of a 2M sodium carbonate aqueous solution, and 70 mL of DME was stirred at 80° C. for 8 hours. The resultant reaction liquid was cooled to room temperature, and extracted with ethyl acetate. Then, the organic phase was washed with water, dried over anhydrous magnesium sulfate, followed by distillation of the solvent under reduced pressure. The obtained residue was purified by silica gel column chromatography and recrystallization to give 3.2 g of BH-3 in an yield of 55%. The compound was identified by molecular weight determination with FD/MS. It was confirmed that m/e=514 for the molecular weight of 514.

Synthesis Example 4 (Synthesis of BH-4)

Synthesis scheme of BH-4 is shown below.

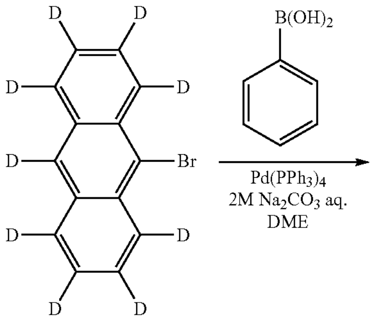

BH-1-1

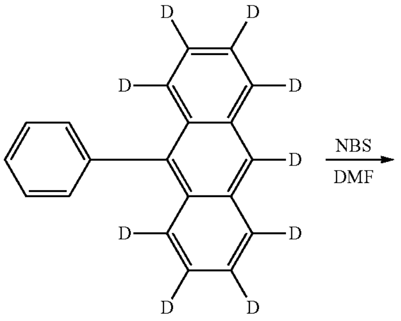

BH-4-1

-continued

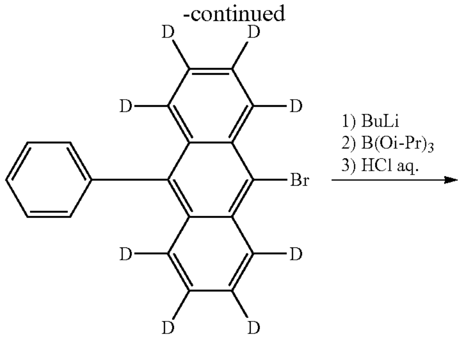

BH-4-2

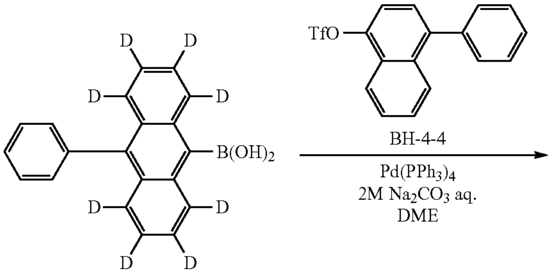

BH-4-3

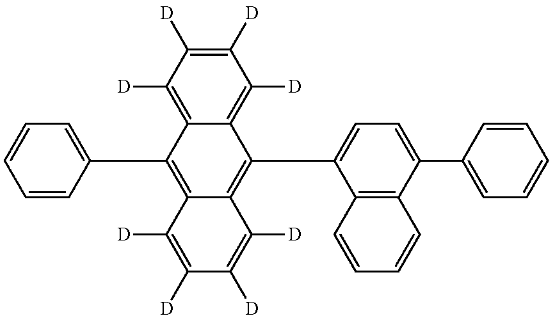

BH-4

(4-1) Synthesis of BH-4-1

Under an argon atmosphere, a mixture of 42.0 g of BH-1-1, 21.3 g of phenylboronic acid, 3.70 g of tetrakistriphenylphosphine palladium, 160 mL of a 2M sodium carbonate aqueous solution, and 750 mL of dimethoxyethane (DME) was stirred at 80° C. for 8 hours. The resultant reaction liquid was cooled to room temperature, and extracted with ethyl acetate. Then, the organic phase was washed with water, dried over anhydrous magnesium sulfate, followed by distillation of the solvent under reduced pressure. The obtained residue was purified by silica gel column chromatography to give 29.9 g of BH-4-1 in an yield of 72%.

(4-2) Synthesis of BH-4-2

Under an argon atmosphere, a mixture of 23.5 g of BH-4-1, 15.9 g of NBS, and 500 mL of DMF was stirred at 80° C. for 12 hours. The resultant reaction liquid was cooled to room temperature, and filtered. Subsequently, the solvent of the obtained filtrate was distilled off under reduced pressure. The obtained residue was purified by column chromatography to give 15.2 g of BH-4-2 in an yield of 50%.

(4-3) Synthesis of BH-4-3

Under an argon atmosphere, a reactor was charged with 11.0 g of BH-4-2, and 130 mL of tetrahydrofuran (THF), and cooled to −78° C. To the reactor, 25 mL of a 1.6M n-butyllithium in hexane was added, and the reaction mixture was stirred for one hour. Then, 19 g of triisopropoxy boron was added thereto, and stirred for one hour. The reaction liquid was warmed to room temperature, stirred for one hour. Subsequently, 480 mL of a 1N hydrochloric acid solution was added thereto and stirred for 30 minutes. The organic phase of the resultant reaction liquid was extracted with dichloromethane, washed with water, dried over anhydrous magnesium sulfate, followed by distillation of the solvent under reduced pressure. The obtained residue was purified by silica gel column chromatography to give 7.4 g of BH-4-3 in an yield of 75%.

(4-4) Synthesis of BH-4

Under an argon atmosphere, a mixture of 2.7 g of BH-4-3, 2.5 g of BH-4-4, 0.200 g of tetrakistriphenylphosphine palladium, 10 mL of a 2M sodium carbonate aqueous solution, and 60 mL of DME was stirred at 80° C. for 8 hours. The resultant reaction liquid was cooled to room temperature, and extracted with ethyl acetate. Then, the organic phase was washed with water, dried over anhydrous magnesium sulfate, followed by distillation of the solvent under reduced pressure. The.obtained residue was purified by silica gel column chromatography and recrystallization to give 1.8 g of BH-4 in an yield of 45%.

The compound was identified by molecular weight determination with FD/MS (Field Desorption Mass Spectrometry). It was confirmed that m/e=464 for the molecular weight of 464.

Synthesis Example 5 (Synthesis of BH-5)

Synthesis scheme of BH-5 is shown below.

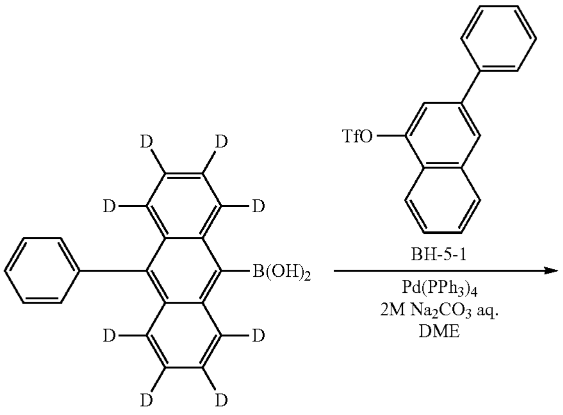

BH-4-3

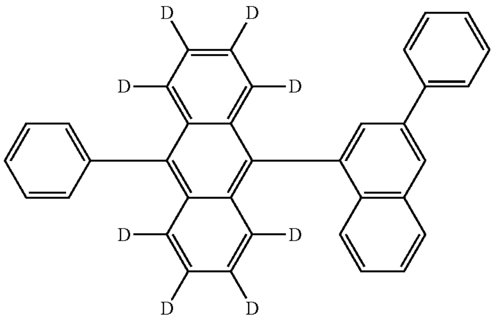

BH-5

(5-1) Synthesis of BH-5

Under an argon atmosphere, a mixture of 3.4 g of BH-4-3, 4.5 g of BH-5-1, 0.260 g of tetrakistriphenylphosphine palladium, 10 mL of a 2M sodium carbonate aqueous solution, and 70 mL of DME was stirred at 80° C. for 8 hours. The resultant reaction liquid was cooled to room temperature, and extracted with ethyl acetate. Subsequently, the organic phase was washed with water, dried over anhydrous magnesium sulfate, followed by distillation of the solvent under reduced pressure. The obtained residue was purified by silica gel column chromatography and recrystallization to give 2.2 g of BH-5 in an yield of 43%. The compound was identified by molecular weight determination with FD/MS. It was confirmed that m/e=464 for the molecular weight of 464.

Synthesis Example 6 (Synthesis of BH-6)

Synthesis scheme of BH-6 is shown below.

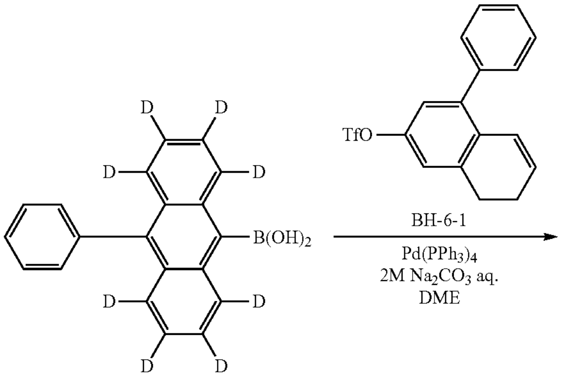

BH-4-3

-continued

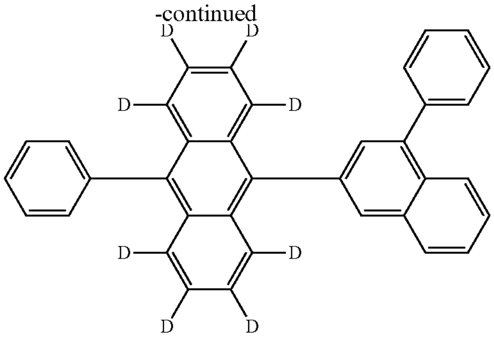

BH-6

(6-1) Synthesis of BH-6

Under an argon atmosphere, a mixture of 3.4 g of BH-4-3, 4.5 g of BH-6-1, 0.260 g of tetrakistriphenylphosphine palladium, 10 mL of a 2M sodium carbonate aqueous solution, and 70 mL of DME was stirred at 80° C. for 8 hours. The resultant reaction liquid was cooled to room temperature, and extracted with ethyl acetate. Then, the organic phase was washed with water, dried over anhydrous magnesium sulfate, followed by distillation of the solvent under reduced pressure. The obtained residue was purified by silica gel column chromatography and recrystallization to give 2.5 g of BH-6 in an yield of 47%. The compound was identified by molecular weight determination with FD/MS. It was confirmed that m/e=464 for the molecular weight of 464.

Synthesis Example 7 (Synthesis of BH-7)

Synthesis scheme of BH-7 is shown below.

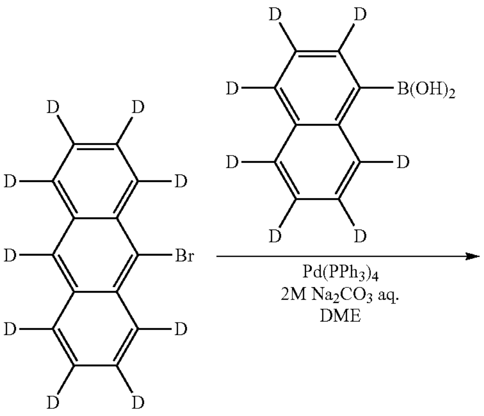

BH-1-1

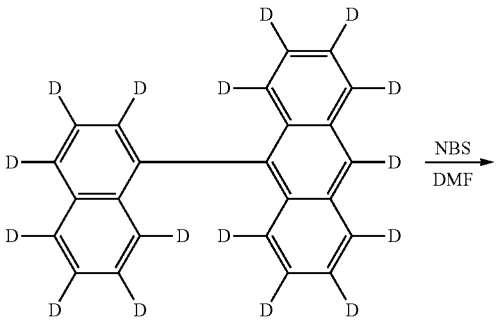

BH-7-1

-continued

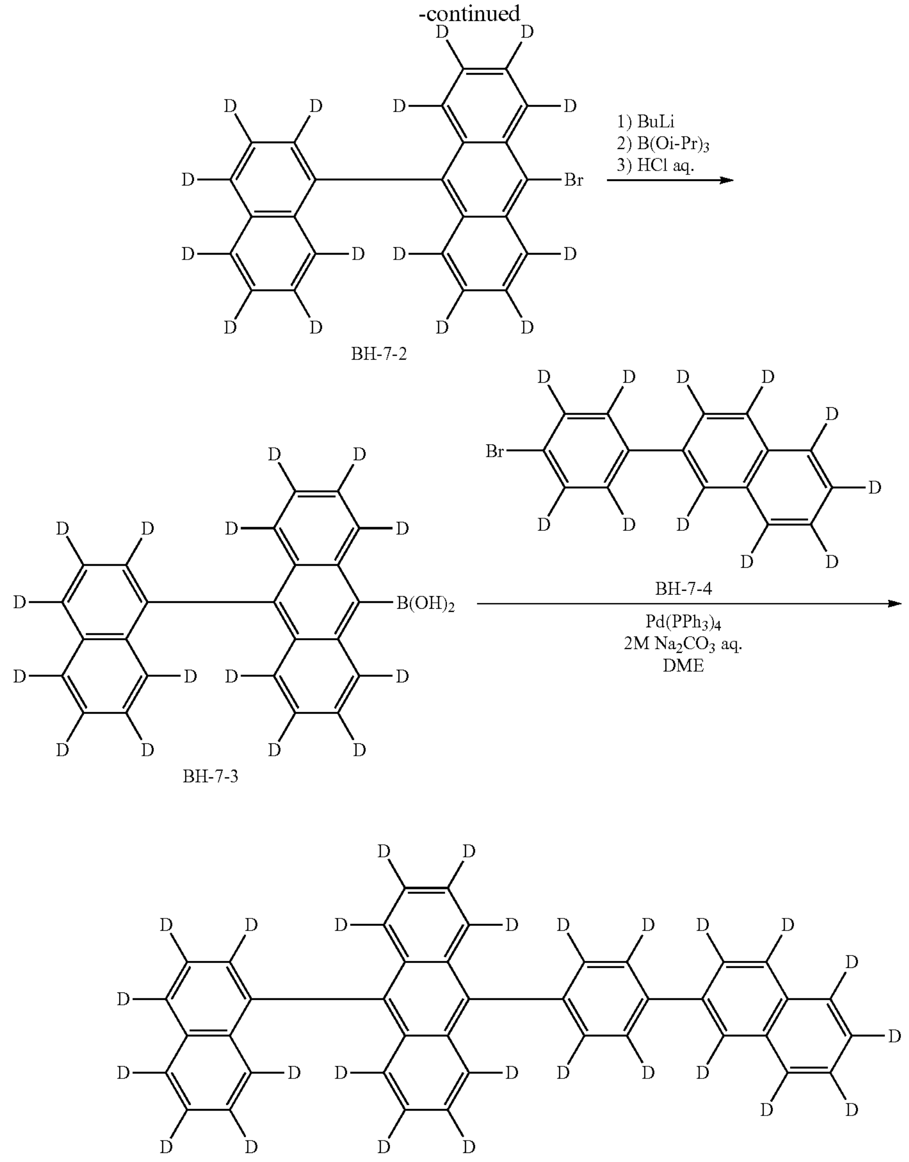

BH-7-2

BH-7-4

BH-7-3

BH-7

(7-1) Synthesis of BH-7-1

Under an argon atmosphere, a mixture of 39.9 g of BH-1-1, 29.7 g of 1-naphthalene boronic acid d-7, 3.51 g of tetrakistriphenylphosphine palladium, 160 mL of a 2M sodium carbonate aqueous solution, and 750 mL of dimethoxyethane (DME) was stirred at 80° C. for 8 hours. The resultant reaction liquid was cooled to room temperature, and extracted with ethyl acetate. Then, the organic phase was washed with water, dried over anhydrous magnesium sulfate, followed by distillation of the solvent under reduced pressure. The obtained residue was purified by silica gel column chromatography to give 32.2 g of BH-7-1 in an yield of 67%.

(7-2) Synthesis of BH-7-2

Under an argon atmosphere, a mixture of 32.0 g of BH-7-1, 17.8 g of NBS, and 560 mL of DMF was stirred at 80° C. for 12 hours. The resultant reaction liquid was cooled to room temperature, and filtered. Then, the solvent of the obtained filtrate was distilled off under reduced pressure. The obtained residue was purified by column chromatography to give 17.9 g of BH-7-2 in an yield of 45%.

(7-3) Synthesis of BH-7-3

Under an argon atmosphere, a reactor was charged with 12.0 g of BH-7-2, and 120 mL of tetrahydrofuran (THF), and cooled to −78° C. To the reactor, 23.2 mL of a solution of 1.6M n-butyllithium in hexane was added, and stirred for one hour. Then, 18 g of triisopropoxyboron was added to the reaction liquid, and stirred for more one hour. The reaction liquid was warmed to room temperature, and stirred for one hour. Subsequently, 450 mL of a 1N hydrochloric acid solution was added thereto, and the reaction liquid was stirred for 30 minutes. The organic phase of the resultant reaction liquid was extracted with dichloromethane, washed with water, dried over anhydrous magnesium sulfate, followed by distillation of the solvent under reduced pressure. The obtained residue was purified by silica gel column chromatography to give 7.2 g of BH-7-3 in an yield of 66%.

(7-4) Synthesis of BH-7

Under an argon atmosphere, a mixture of 3.6 g of BH-7-3, 2.9 g of BH-7-4, 0.230 g of tetrakistriphenylphosphine palladium, 11.5 mL of a 2M sodium carbonate aqueous solution, and 70 mL of DME was stirred at 80° C. for 8 hours. The resultant reaction liquid was cooled to room temperature, and extracted with ethyl acetate. Then, the organic phase was washed with water, dried over anhydrous magnesium sulfate, followed by distillation of the solvent under reduced pressure. The obtained residue was purified by silica gel column chromatography and recrystallization to give 2.1 g of BH-7 in an yield of 40%.

The compound was identified by molecular weight determination with FD/MS (Field Desorption Mass Spectrometry). It was confirmed that m/e=532 for the molecular weight of 532.

Synthesis Example 8 (Synthesis of BH-8)

Synthesis scheme of BH-8 is shown below.

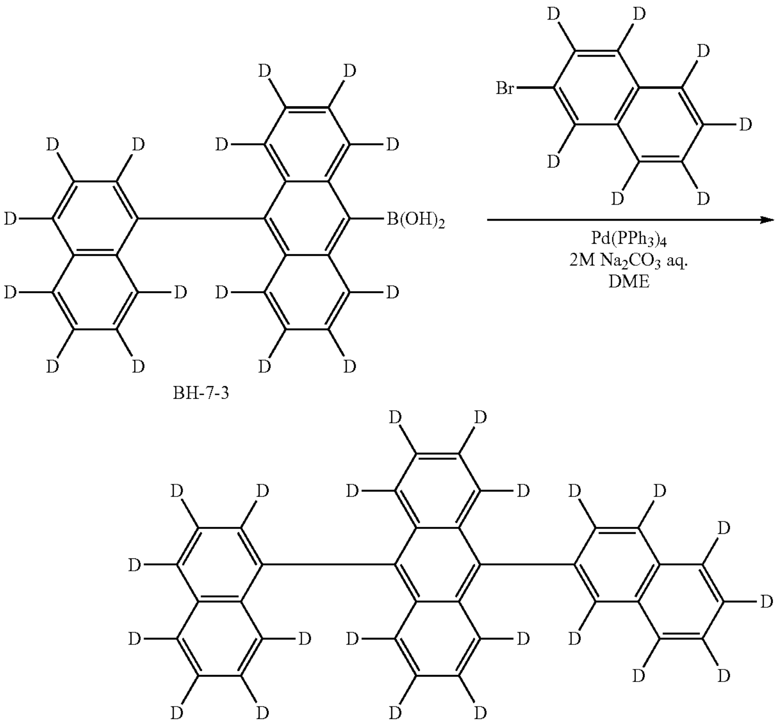

BH-7-3

BH-8

(8-1) Synthesis of BH-8

Under an argon atmosphere, a mixture of 3.6 g of BH-7-3, 2.6 g of 2-bromonaphthalene d-7, 0.260 g of tetrakistriphenylphosphine palladium, 10 mL of a 2M sodium carbonate aqueous solution, and 70 mL of DME was stirred at 80° C. for 8 hours. The resultant reaction liquid was cooled to room temperature, and extracted with ethyl acetate. Then, the organic phase was washed with water, dried over anhydrous magnesium sulfate, followed by distillation of the solvent under reduced pressure. The obtained residue was purified by silica gel column chromatography and recrystallization to give 2.1 g of BH-8 in an yield of 47%. The compound was identified by molecular weight determination with FD/MS. It was confirmed that m/e=452 for the molecular weight of 452.

Synthesis Example 9 (Synthesis of BH-9)

Synthesis scheme of BH-9 is shown below

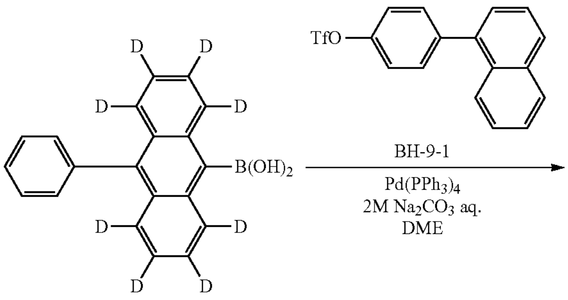

BH-4-3

-continued

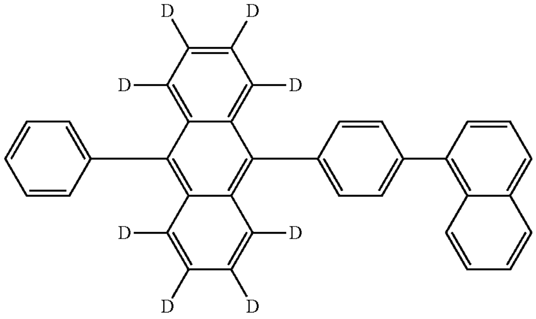

BH-9

(9-1) Synthesis of BH-9

Under an argon atmosphere, a mixture of 3.1 g of BH-4-3, 4.1 g of BH-9-1, 0.234 g of tetrakistriphenylphosphine palladium, 10 mL of a 2M sodium carbonate aqueous solution, and 60 mL of DME was stirred at 80° C. for 9 hours. The resultant reaction liquid was cooled to room temperature, and extracted with ethyl acetate. Then, the organic phase was washed with water, and dried over anhydrous magnesium sulfate, followed by distillation of the solvent under reduced pressure. The obtained residue was purified by silica gel column chromatography and recrystallization to give 2.8 g of BH-9 in an yield of 54%. The compound was identified by molecular weight determination with FD/MS. It was confirmed that m/e=464 for the molecular weight of 464.

Compounds used in the following Examples and Comparative Examples are shown below.

HI-1

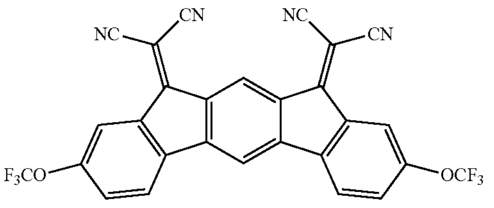

HT-1

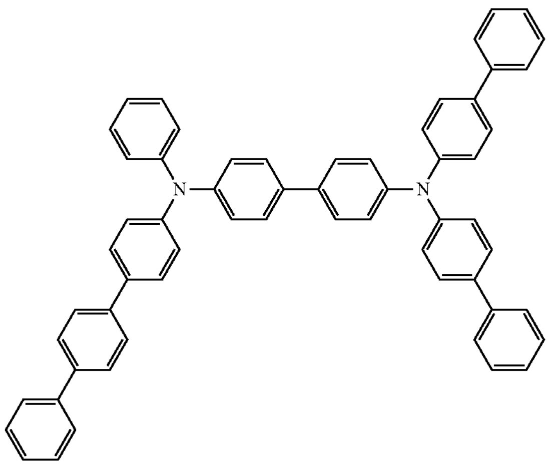

HT-2

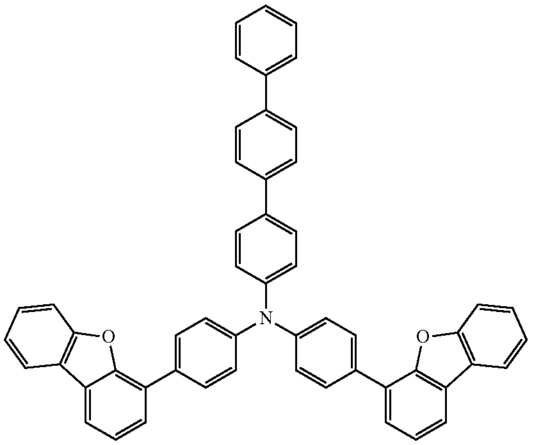

ET-1

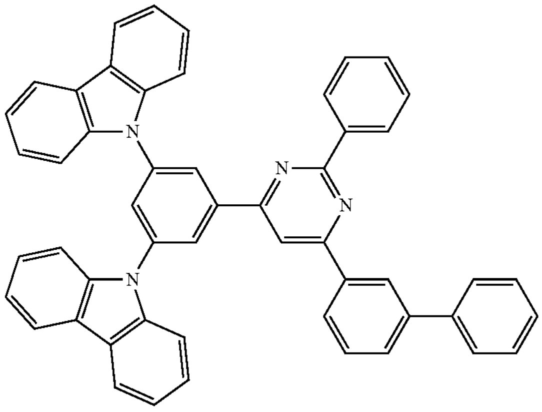

ET-2

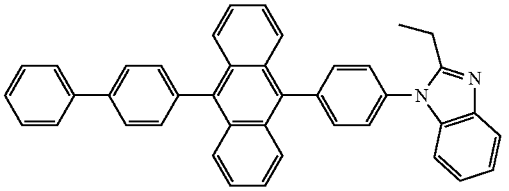

BH-1

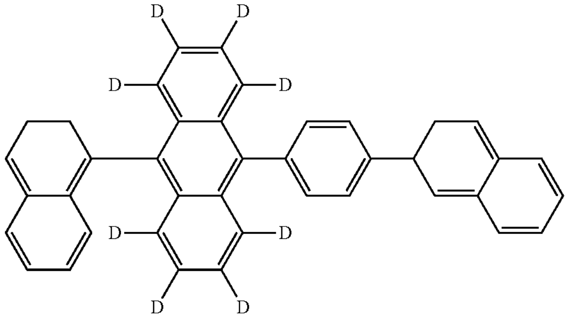

-continued
BH-2
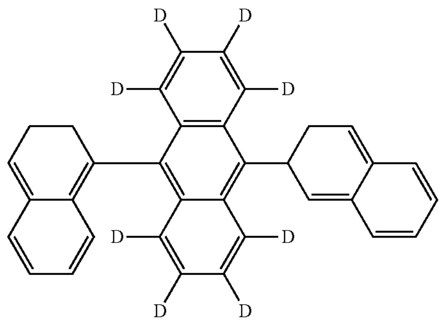
BH-3
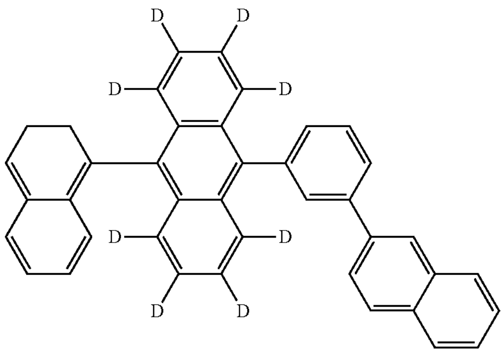
BH-4
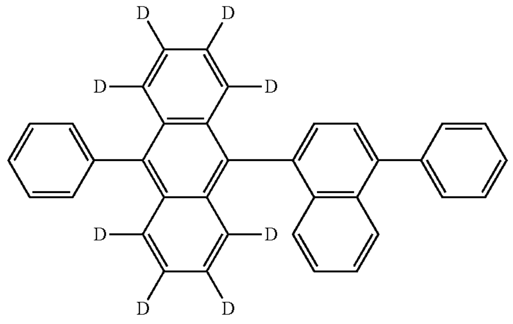
BH-5
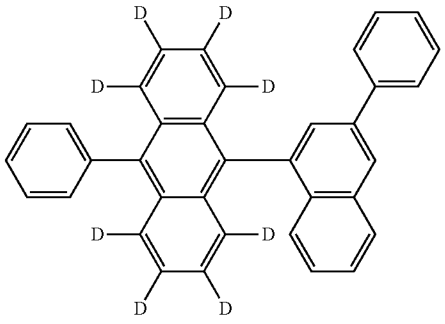
BH-6
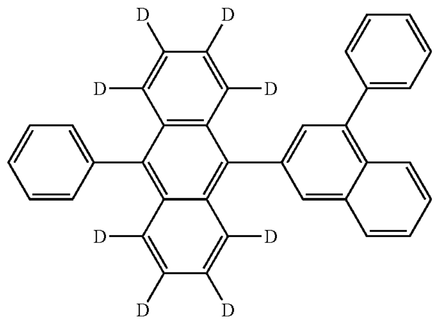
BH-7
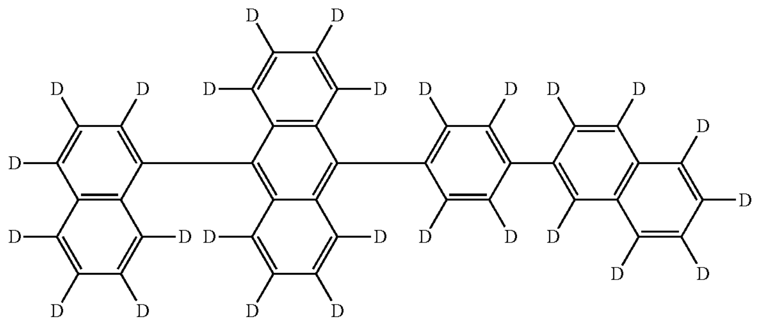

-continued
BH-8
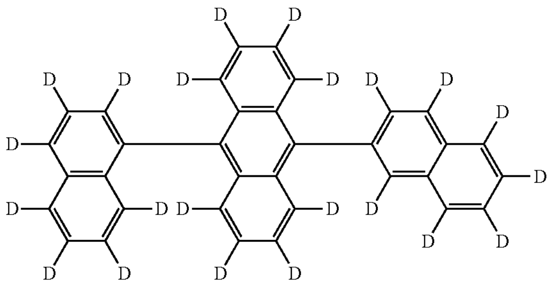
BH-9
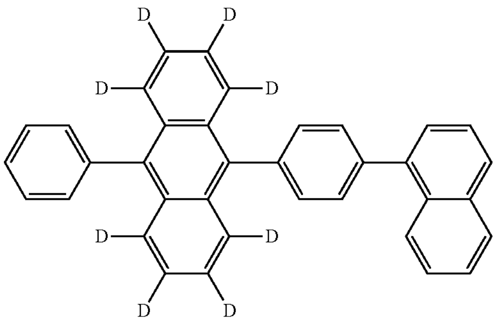
BH-A
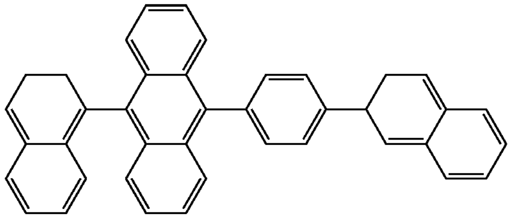
BH-B
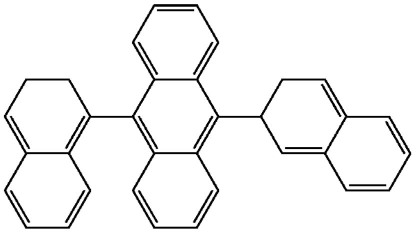
BH-C
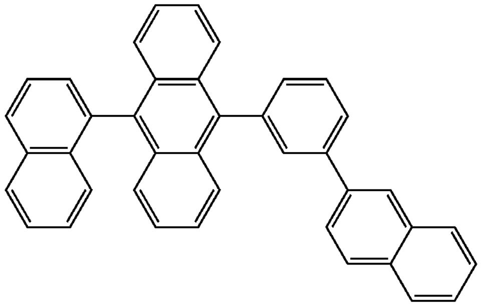
BH-D
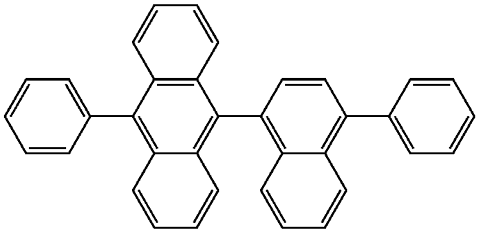
BH-E
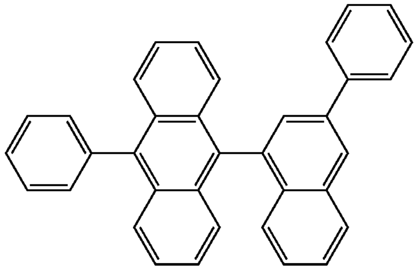
BH-F
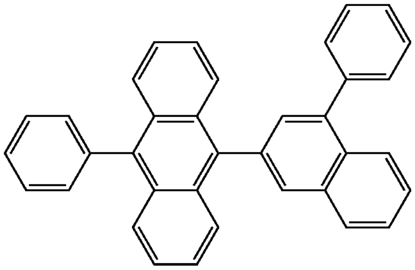
BH-G
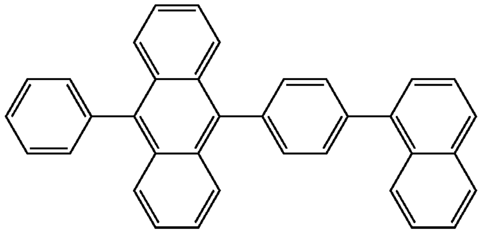
BD-1
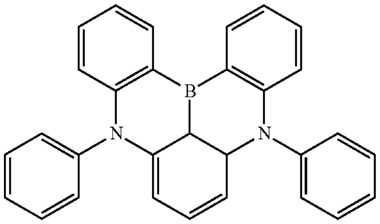

-continued
BD-2
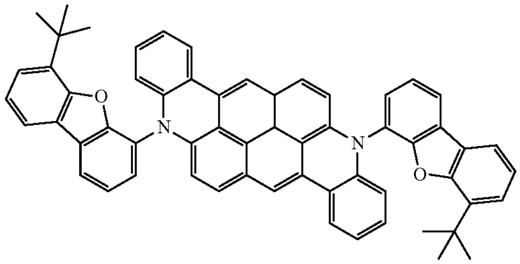
BD-3
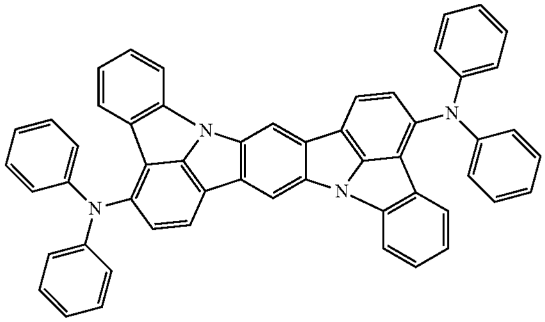
BD-4
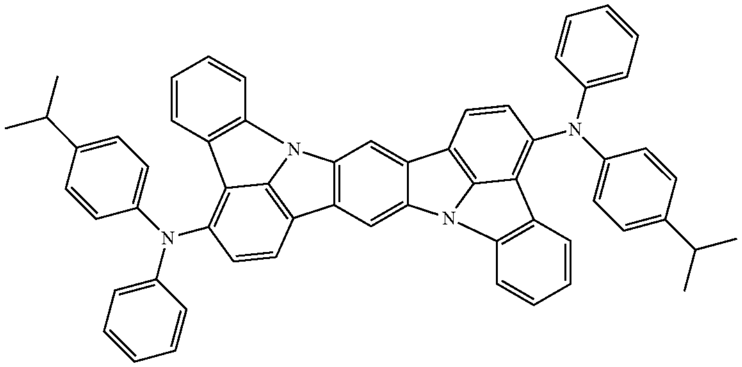
BD-5
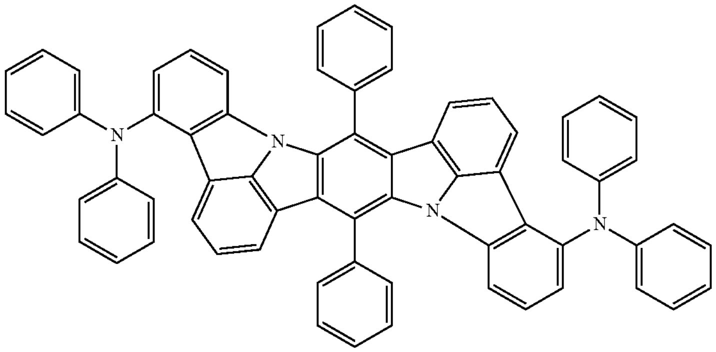

-continued
BD-6
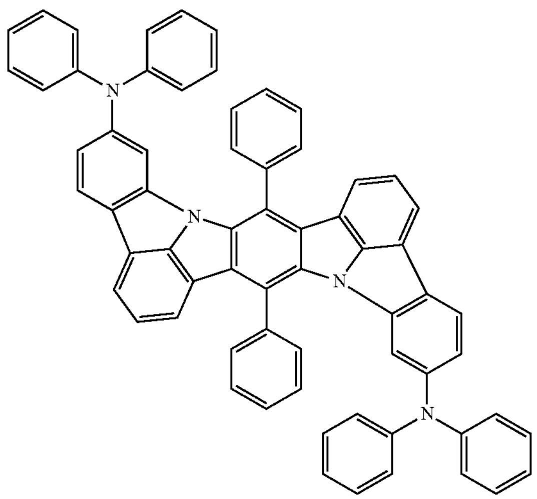
BD-7
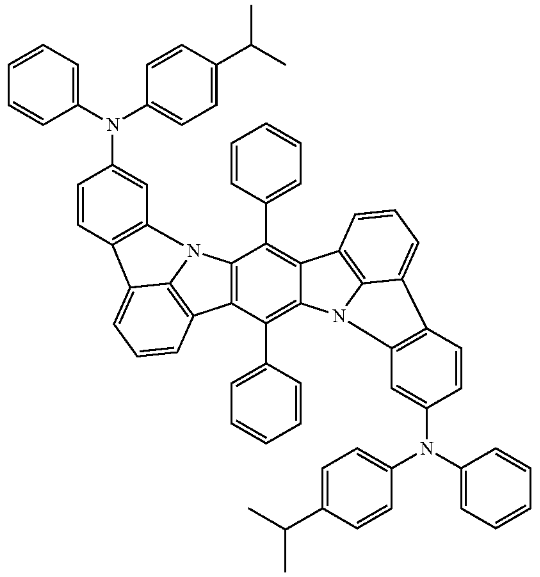
BD-8
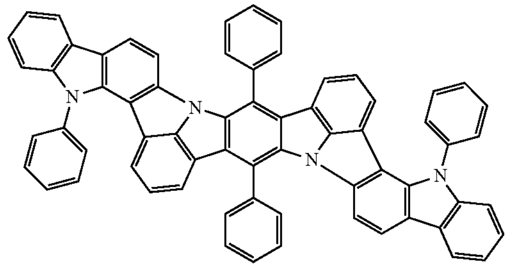
BD-9
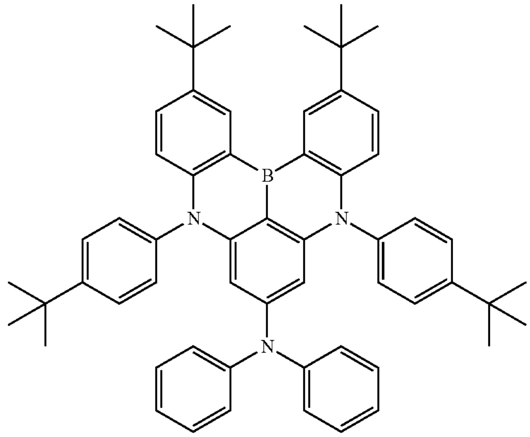
BD-10
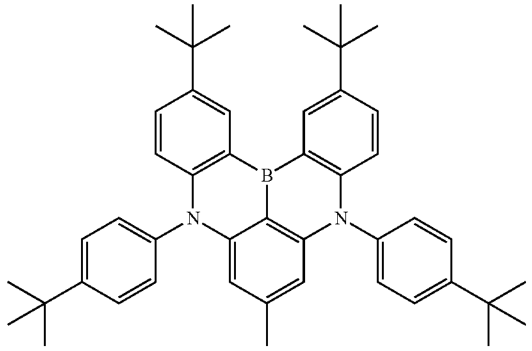
BD-11
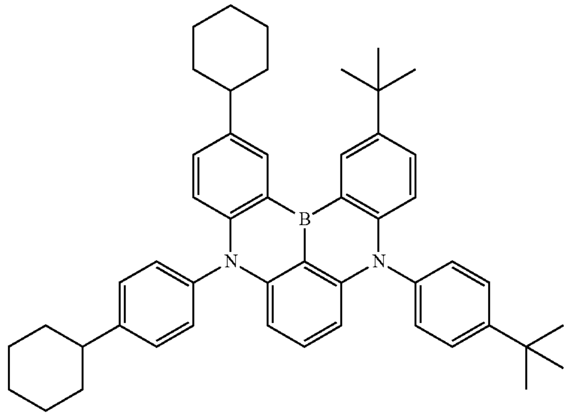

-continued
BD-12
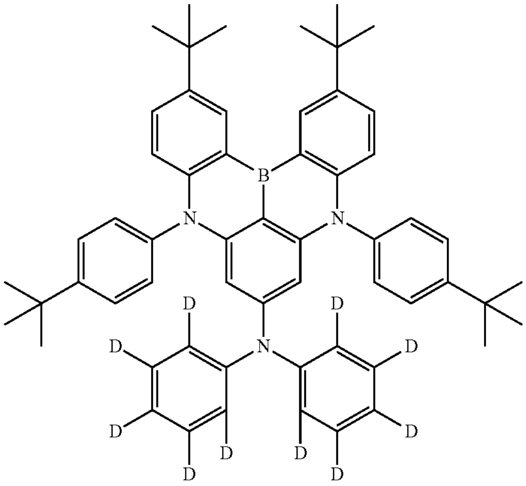
BD-13
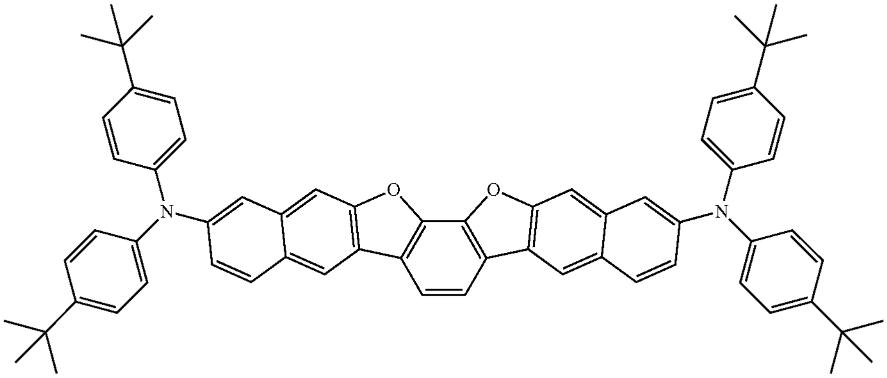
BD-14
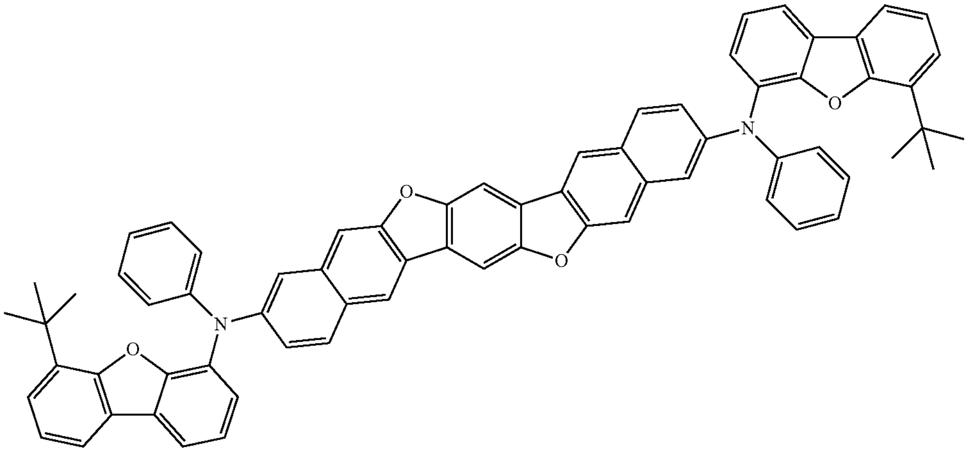
BD-15
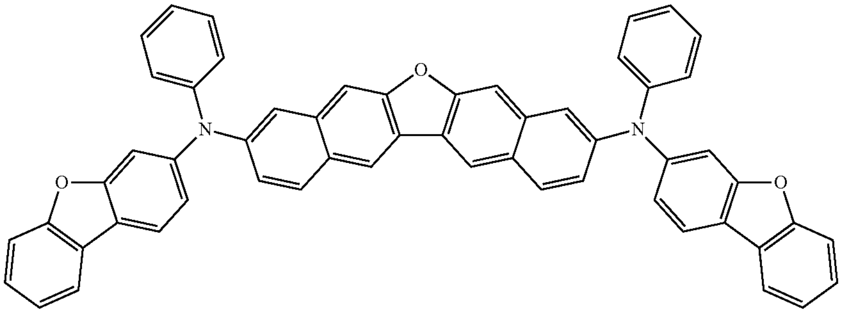

-continued

BD-16

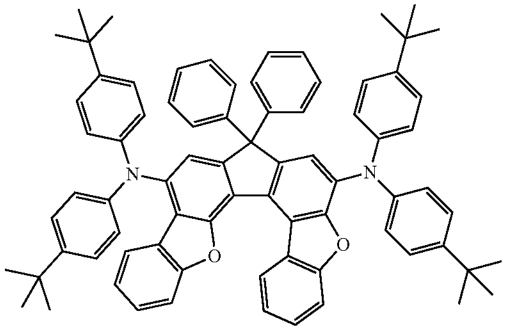

BD-17

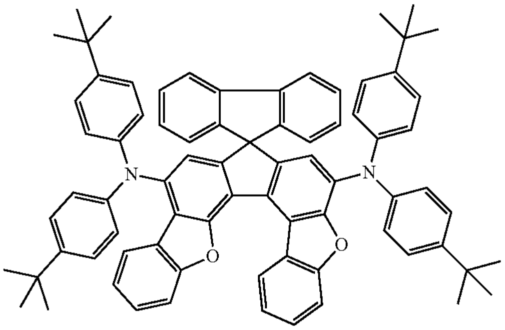

BD-18

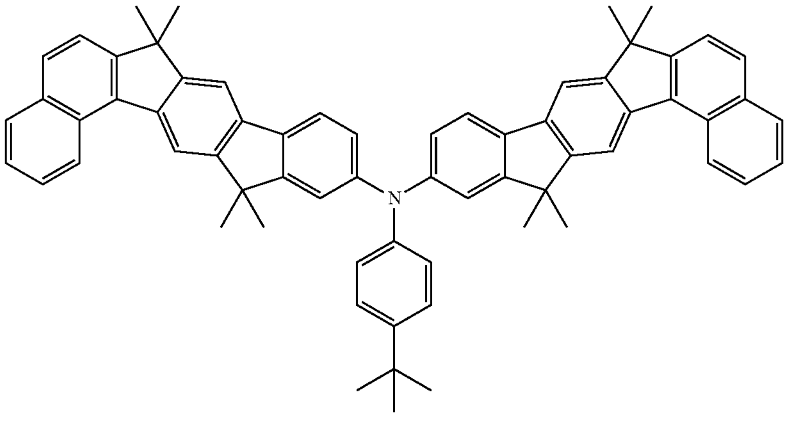

Example 1

(Fabrication of organic EL device)

A glass substrate of 25 mm by 75 mm by 1.1 mm thick with an ITO transparent electrode (anode) (manufactured by GEOMATEC Co., Ltd.) was subjected to ultrasonic cleaning with isopropyl alcohol for 5 minutes, and then subjected to UV-ozone cleaning for 30 minutes. The thickness of the ITO was 130 nm.

The cleaned glass substrate with a transparent electrode was mounted in a substrate holder of a vacuum vapor deposition apparatus. First, the compound HI-1 was deposited on the surface where the transparent electrode was formed so as to cover the transparent electrode, thereby a 5 nm-thick HI-1 film was formed. This HI-1 film serves as a hole-injecting layer.

Subsequent to the formation of the HI-1 film, the compound HT-1 was deposited, whereby a 80 nm-thick HT-1 film was formed on the HI-1 film. This HT-1 film serves as a hole-transporting layer (first hole-transporting layer).

Subsequent to the formation of the HT-1 film, the compound HT-2 was deposited, whereby a 10 nm-thick HT-2 film was formed on the HT-1 film. This HT-2 film serves as an electron blocking layer (second hole-transporting layer).

On the HT-2 film, compound BH-1 (host material) and compound BD-1 (dopant material) were co-deposited such that the amount ratio of compound BD-1 became 2mass %, whereby a 25 nm-thick BH-1:BD-1 film was formed. The BH-1:BD-1 film serves as an emitting layer.

On the emitting layer, compound ET-1 was deposited, whereby a 10 nm-thick ET-1 film was formed. This ET-1 film serves as a hole barrier layer.

On the ET-1 film, compound ET-2 was deposited, whereby a 15 nm-thick ET-2 film was formed. This ET-2 film serves as an electron transporting layer. On this ET-2 film, LiF was deposited, whereby a 1 nm-thick LiF film was formed. On this LiF film, metal Al was deposited, whereby a 80 nm-thick metal cathode was formed. By the above-mentioned procedures, an organic EL device was fabricated.

The resultant organic EL device has the following layer structure: ITO(130)/HI-1(5)/HT-1(80)/HT-2(10)/BH-1:BD-1(25:2mass %)/ET-1(10)/ET-2(15)/LiF(1)/Al(80).

The numerical value in the parenthesis indicates the film thickness (unit: nm).

(Evaluation of Organic EL Device)

A voltage was applied to the resulting organic EL device such that the current density became 50 mA/cm$^2$, and the time taken until the luminance became 95% of the initial luminance (LT95 (unit: hour)) were measured. The results are shown in Table 1.

Further, the CIE1931 chromaticity coordinates (CIEx and CIEy) of the resulting organic EL device at the time when a voltage was applied thereto such that the current density became 10 mA/cm$^2$, were determined from a spectral radiance spectrum measured by means of a spectral radiance meter CS-1000 (manufactured by Konica Minolta, Inc.). The results are shown in Table 1.

Example 2 and Comparative Examples 1 and 2

Organic EL devices were fabricated in the same manner as in Example 1 except that compounds indicated in Table 1 were used as the materials for the emitting layer, and evaluated. The results are shown in Table 1.

TABLE 1

| | Emitting layer | | LT95 | Chromaticity | |
|---|---|---|---|---|---|
| | BH | BD | (hr) | CIEx | CIEy |
| Example 1 | BH-1 | BD-1 | 54 | 0.136 | 0.069 |
| Example 2 | BH-2 | BD-1 | 95 | 0.137 | 0.065 |
| Com. Ex. 1 | BH-A | BD-1 | 29 | 0.137 | 0.067 |
| Com. Ex. 2 | BH-B | BD-1 | 48 | 0.137 | 0.066 |

Examples 3 and 4, and Comparative Examples 3 and 4

Organic EL devices were fabricated in the same manner as in Example 1 except that compounds indicated in Table 2 were used as the materials for the emitting layer, and evaluated. The results are shown in Table 2.

TABLE 2

| | Emitting layer | | LT95 | Chromaticity | |
|---|---|---|---|---|---|
| | BH | BD | (hr) | CIEx | CIEy |
| Example 3 | BH-1 | BD-2 | 209 | 0.139 | 0.090 |
| Example 4 | BH-2 | BD-2 | 282 | 0.139 | 0.090 |
| Com. Ex. 3 | BH-A | BD-2 | 101 | 0.139 | 0.091 |
| Com. Ex. 4 | BH-B | BD-2 | 181 | 0.139 | 0.090 |

Examples 5 to 12, and Comparative Examples 5 to 10

Organic EL devices were fabricated in the same manner in Example 1 except that compounds indicated in Table 3 were used as the materials for the emitting layer, and evaluated. The results are shown in Table 3.

TABLE 3

| | Emitting layer | | LT95 | Chromaticity | |
|---|---|---|---|---|---|
| | BH | BD | (hr) | CIEx | CIEy |
| Example 5 | BH-1 | BD-3 | 130 | 0.140 | 0.080 |
| Example 6 | BH-2 | BD-3 | 217 | 0.140 | 0.080 |
| Example 7 | BH-3 | BD-3 | 178 | 0.140 | 0.080 |
| Example 8 | BH-4 | BD-3 | 175 | 0.140 | 0.080 |
| Example 9 | BH-5 | BD-3 | 132 | 0.140 | 0.080 |
| Example 10 | BH-6 | BD-3 | 124 | 0.140 | 0.080 |
| Example 11 | BH-7 | BD-3 | 135 | 0.140 | 0.081 |
| Example 12 | BH-8 | BD-3 | 231 | 0.140 | 0.080 |
| Com. Ex. 5 | BH-A | BD-3 | 77 | 0.140 | 0.080 |
| Com. Ex. 6 | BH-B | BD-3 | 120 | 0.140 | 0.080 |
| Com. Ex. 7 | BH-C | BD-3 | 100 | 0.140 | 0.080 |
| Com. Ex. 8 | BH-D | BD-3 | 101 | 0.140 | 0.080 |
| Com. Ex. 9 | BH-E | BD-3 | 73 | 0.140 | 0.080 |
| Com. Ex. 10 | BH-F | BD-3 | 70 | 0.140 | 0.080 |

Examples 13 to 20, and Comparative Examples 11 to 15

Organic EL devices were fabricated in the same manners in Example 1 except that compounds indicated in Table 4 were used as the materials for the emitting layer, and evaluated. The results are shown in Table 4.

TABLE 4

| | Emitting layer | | LT95 | Chromaticity | |
|---|---|---|---|---|---|
| | BH | BD | (hr) | CIEx | CIEy |
| Example 13 | BH-1 | BD-4 | 155 | 0.135 | 0.098 |
| Example 14 | BH-2 | BD-4 | 270 | 0.135 | 0.098 |
| Example 15 | BH-3 | BD-4 | 214 | 0.135 | 0.098 |
| Example 16 | BH-4 | BD-4 | 208 | 0.135 | 0.098 |
| Example 17 | BH-5 | BD-4 | 142 | 0.135 | 0.098 |
| Example 18 | BH-6 | BD-4 | 127 | 0.135 | 0.098 |
| Example 19 | BH-7 | BD-4 | 155 | 0.135 | 0.098 |
| Example 20 | BH-8 | BD-4 | 268 | 0.135 | 0.098 |
| Com. Ex. 11 | BH-A | BD-4 | 88 | 0.135 | 0.098 |
| Com. Ex. 12 | BH-C | BD-4 | 120 | 0.135 | 0.098 |
| Com. Ex. 13 | BH-D | BD-4 | 123 | 0.135 | 0.098 |
| Com. Ex. 14 | BH-E | BD-4 | 80 | 0.135 | 0.099 |
| Com. Ex. 15 | BH-F | BD-4 | 75 | 0.135 | 0.098 |

Examples 21 to 28, and Comparative Examples 16 to 20

Organic EL devices were fabricated in the same manner as in Example 1 except that compounds indicated in Table 5 were used as the materials for the emitting layer, and evaluated. The results are shown in Table 5.

TABLE 5

| | Emitting layer | | LT95 | Chromaticity | |
|---|---|---|---|---|---|
| | BH | BD | (hr) | CIEx | CIEy |
| Example 21 | BH-1 | BD-5 | 162 | 0.135 | 0.086 |
| Example 22 | BH-2 | BD-5 | 270 | 0.135 | 0.086 |
| Example 23 | BH-3 | BD-5 | 227 | 0.135 | 0.086 |
| Example 24 | BH-4 | BD-5 | 217 | 0.135 | 0.086 |
| Example 25 | BH-5 | BD-5 | 153 | 0.135 | 0.087 |
| Example 25 | BH-6 | BD-5 | 137 | 0.135 | 0.086 |
| Example 27 | BH-7 | BD-5 | 165 | 0.135 | 0.086 |
| Example 28 | BH-8 | BD-5 | 278 | 0.135 | 0.086 |
| Com. Ex. 16 | BH-A | BD-5 | 90 | 0.135 | 0.086 |
| Com. Ex. 17 | BH-C | BD-5 | 128 | 0.135 | 0.086 |
| Com. Ex. 18 | BH-D | BD-5 | 123 | 0.135 | 0.086 |
| Com. Ex. 19 | BH-E | BD-5 | 87 | 0.135 | 0.086 |
| Com. Ex. 20 | BH-F | BD-5 | 80 | 0.135 | 0.086 |

Examples 29 to 36, and Comparative Examples 21 to 25

Organic EL devices were fabricated in the same manner as in Example 1 except that compounds indicated in Table 6 were used as the materials for the emitting layer, and evaluated. The results are shown in Table 6.

TABLE 6

| | Emitting layer | | LT95 | Chromaticity | |
|---|---|---|---|---|---|
| | BH | BD | (hr) | CIEx | CIEy |
| Example 29 | BH-1 | BD-6 | 192 | 0.135 | 0.080 |
| Example 30 | BH-2 | BD-6 | 338 | 0.135 | 0.081 |
| Example 31 | BH-3 | BD-6 | 268 | 0.135 | 0.080 |
| Example 32 | BH-4 | BD-6 | 268 | 0.135 | 0.080 |
| Example 33 | BH-5 | BD-6 | 181 | 0.135 | 0.080 |
| Example 34 | BH-6 | BD-6 | 178 | 0.135 | 0.080 |
| Example 35 | BH-7 | BD-6 | 202 | 0.135 | 0.080 |
| Example 36 | BH-8 | BD-6 | 332 | 0.135 | 0.080 |
| Com. Ex. 21 | BH-A | BD-6 | 111 | 0.135 | 0.080 |
| Com. Ex. 22 | BH-C | BD-6 | 155 | 0.135 | 0.080 |
| Com. Ex. 23 | BH-D | BD-6 | 150 | 0.135 | 0.080 |

TABLE 6-continued

| | Emitting layer | | LT95 | Chromaticity | |
|---|---|---|---|---|---|
| | BH | BD | (hr) | CIEx | CIEy |
| Com. Ex. 24 | BH-E | BD-6 | 104 | 0.135 | 0.080 |
| Com. Ex. 25 | BH-F | BD-6 | 100 | 0.135 | 0.080 |

Examples 37 to 44, and Comparative Examples 26 to 30

Organic EL devices were fabricated in the same manner as in Example 1 except that compounds indicated in Table 7 were used as the materials for the emitting layer, and evaluated. The results are shown in Table 7.

TABLE 7

| | Emitting layer | | LT95 | Chromaticity | |
|---|---|---|---|---|---|
| | BH | BD | (hr) | CIEx | CIEy |
| Example 37 | BH-1 | BD-7 | 228 | 0.136 | 0.090 |
| Example 38 | BH-2 | BD-7 | 405 | 0.136 | 0.090 |
| Example 39 | BH-3 | BD-7 | 317 | 0.136 | 0.090 |
| Example 40 | BH-4 | BD-7 | 320 | 0.136 | 0.090 |
| Example 41 | BH-5 | BD-7 | 222 | 0.136 | 0.090 |
| Example 42 | BH-6 | BD-7 | 197 | 0.136 | 0.090 |
| Example 43 | BH-7 | BD-7 | 228 | 0.136 | 0.090 |
| Example 44 | BH-8 | BD-7 | 401 | 0.136 | 0.090 |
| Com. Ex. 26 | BH-A | BD-7 | 129 | 0.136 | 0.090 |
| Com. Ex. 27 | BH-C | BD-7 | 178 | 0.136 | 0.090 |
| Com. Ex, 28 | BH-D | BD-7 | 185 | 0.136 | 0.091 |
| Com. Ex. 29 | BH-E | BD-7 | 130 | 0.136 | 0.090 |
| Com. Ex. 30 | BH-F | BD-7 | 105 | 0.136 | 0.090 |

Examples 45 to 52, and Comparative Examples 31 to 34

Organic EL devices were fabricated in the same manner as in Example 1 except that compounds indicated in Table 8 were used as the materials for the emitting layer. The results are shown in Table 8.

TABLE 8

| | Emitting layer | | LT95 | Chromaticity | |
|---|---|---|---|---|---|
| | BH | BD | (hr) | CIEx | CIEy |
| Example 45 | BH-1 | BD-8 | 120 | 0.144 | 0.061 |
| Example 46 | BH-2 | BD-8 | 226 | 0.144 | 0.061 |
| Example 47 | BH-3 | BD-8 | 172 | 0.144 | 0.061 |
| Example 48 | BH-4 | BD-8 | 174 | 0.144 | 0.061 |
| Example 49 | BH-5 | BD-8 | 112 | 0.144 | 0.061 |
| Example 50 | BH-6 | BD-8 | 108 | 0.144 | 0.061 |
| Example 51 | BH-7 | BD-8 | 127 | 0.144 | 0.061 |
| Example 52 | BH-8 | BD-8 | 226 | 0.144 | 0.061 |
| Com. Ex. 31 | BH-A | BD-8 | 70 | 0.144 | 0.061 |
| Com. Ex. 32 | BH-D | BD-8 | 98 | 0.144 | 0.061 |
| Com. Ex. 33 | BH-E | BD-8 | 63 | 0.144 | 0.061 |
| Com. Ex. 34 | BH-F | BD-8 | 63 | 0.144 | 0.061 |

Example 53 and Comparative Example 35

Organic EL devices were fabricated in the same manner as in Example 1 except that compounds indicated in Table 9 were used as the materials for the emitting layer. The results are shown in Table 9.

TABLE 9

| | Emitting layer | | LT95 | Chromaticity | |
|---|---|---|---|---|---|
| | BH | BD | (h) | CIEx | CIEy |
| Example 53 | BH-1 | BD-9 | 100 | 0.141 | 0.057 |
| Com. Ex. 35 | BH-A | BD-9 | 83 | 0.141 | 0.057 |

Example 54 and Comparative Example 36

Organic EL devices were fabricated in the same manner as in Example 1 except that compounds indicated in Table 10 were used as the materials for the emitting layer. The results are shown in Table 10.

TABLE 10

| | Emitting layer | | LT95 | Chromaticity | |
|---|---|---|---|---|---|
| | BH | BD | (h) | CIEx | CIEy |
| Example 54 | BH-2 | BD-9 | 131 | 0.141 | 0.056 |
| Com. Ex. 36 | BH-B | BD-9 | 103 | 0.141 | 0.056 |

Example 55 and Comparative Example 37

Organic EL devices were fabricated in the same manner as in Example 1 except that compounds indicated in Table 11 were used as the materials for the emitting layer. The results are shown in Table 11.

TABLE 11

| | Emitting layer | | LT95 | Chromaticity | |
|---|---|---|---|---|---|
| | BH | BD | (h) | CIEx | CIEy |
| Example 55 | BH-4 | BD-9 | 92 | 0.141 | 0.057 |
| Com. Ex. 37 | BH-D | BD-9 | 76 | 0.141 | 0.057 |

Example 56 and Comparative Example 38

Organic EL devices were fabricated in the same manner as in Example 1 except that compounds indicated in Table 12 were used as the materials for the emitting layer. The results are shown in Table 12.

TABLE 12

| | Emitting layer | | LT95 | Chromaticity | |
|---|---|---|---|---|---|
| | BH | BD | (h) | CIEx | CIEy |
| Example 56 | BH-5 | BD-9 | 78 | 0.141 | 0.057 |
| Com. Ex. 38 | BH-E | BD-9 | 62 | 0.141 | 0.057 |

Example 57 and Comparative Example 39

Organic EL devices were fabricated in the same manner as in Example 1 except that compounds indicated in Table 13 were used as the materials for the emitting layer. The results are shown in Table 13.

TABLE 13

| | Emitting layer | | LT95 | Chromaticity | |
|---|---|---|---|---|---|
| | BH | BD | (h) | CIEx | CIEy |
| Example 57 | BH-9 | BD-9 | 70 | 0.141 | 0.057 |
| Com. Ex. 39 | BH-G | BD-9 | 56 | 0.141 | 0.057 |

Example 58 and Comparative Example 40

Organic EL devices were fabricated in the same manner as in Example 1 except that compounds indicated in Table 14 were used as the materials for the emitting layer. The results are shown in Table 14.

TABLE 14

| | Emitting layer | | LT95 | Chromaticity | |
|---|---|---|---|---|---|
| | BH | BD | (h) | CIEx | CIEy |
| Example 58 | BH-1 | BD-10 | 167 | 0.133 | 0.078 |
| Com. Ex. 40 | BH-A | BD-10 | 139 | 0.133 | 0.078 |

Example 59 and Comparative Example 41

Organic EL devices were fabricated in the same manner as in Example 1 except that compounds indicated in Table 15 were used as the materials for the emitting layer. The results are shown in Table 15.

TABLE 15

| | Emitting layer | | LT95 | Chromaticity | |
|---|---|---|---|---|---|
| | BH | BD | (h) | CIEx | CIEy |
| Example 59 | BH-2 | BD-10 | 212 | 0.133 | 0.078 |
| Com. Ex. 41 | BH-B | BD-10 | 165 | 0.133 | 0.078 |

Example 60 and Comparative Example 42

Organic EL devices were fabricated in the same manner as in Example 1 except that compounds indicated in Table 16 were used as the materials for the emitting layer. The results are shown in Table 16.

TABLE 16

| | Emitting layer | | LT95 | Chromaticity | |
|---|---|---|---|---|---|
| | BH | BD | (h) | CIEx | CIEy |
| Example 60 | BH-4 | BD-10 | 161 | 0.133 | 0.078 |
| Com. Ex. 42 | BH-D | BD-10 | 131 | 0.133 | 0.078 |

Example 61 and Comparative Example 43

Organic EL devices were fabricated in the same manner as in Example 1 except that compounds indicated in Table 17 were used as the materials for the emitting layer. The results are shown in Table 17.

TABLE 17

| | Emitting layer | | LT95 | Chromaticity | |
|---|---|---|---|---|---|
| | BH | BD | (h) | CIEx | CIEy |
| Example 61 | BH-5 | BD-10 | 131 | 0.133 | 0.078 |
| Com. Ex. 43 | BH-E | BD-10 | 104 | 0.133 | 0.078 |

Example 62 and Comparative Example 44

Organic EL devices were fabricated in the same manner as in Example 1 except that compounds indicated in Table 18 were used as the materials for the emitting layer. The results are shown in Table 18.

TABLE 18

| | Emitting layer | | LT95 | Chromaticity | |
|---|---|---|---|---|---|
| | BH | BD | (h) | CIEx | CIEy |
| Example 62 | BH-9 | BD-10 | 124 | 0.133 | 0.078 |
| Com. Ex. 44 | BH-G | BD-10 | 103 | 0.133 | 0.078 |

Example 63 and Comparative Example 45

Organic EL devices were fabricated in the same manner as in Example 1 except that compounds indicated in Table 19 were used as the materials for the emitting layer. The results are shown in Table 19.

TABLE 19

| | Emitting layer | | LT95 | Chromaticity | |
|---|---|---|---|---|---|
| | BH | BD | (h) | CIEx | CIEy |
| Example 63 | BH-1 | BD-11 | 165 | 0.133 | 0.077 |
| Com. Ex. 45 | BH-A | BD-11 | 131 | 0.133 | 0.077 |

Example 64 and Comparative Example 46

Organic EL devices were fabricated in the same manner as in Example 1 except that compounds indicated in Table 20 were used as the materials for the emitting layer. The results are shown in Table 20.

TABLE 20

| | Emitting layer | | LT95 | Chromaticity | |
|---|---|---|---|---|---|
| | BH | BD | (h) | CIEx | CIEy |
| Example 64 | BH-2 | BD-11 | 214 | 0.133 | 0.076 |
| Com. Ex. 46 | BH-B | BD-11 | 158 | 0.133 | 0.076 |

Example 65 and Comparative Example 47

Organic EL devices were fabricated in the same manner as in Example 1 except that compounds indicated in Table 21 were used as the materials for the emitting layer. The results are shown in Table 21.

TABLE 21

| | Emitting layer | | LT95 | Chromaticity | |
|---|---|---|---|---|---|
| | BH | BD | (h) | CIEx | CIEy |
| Example 65 | BH-4 | BD-11 | 163 | 0.133 | 0.076 |
| Com. Ex. 47 | BH-D | BD-11 | 135 | 0.133 | 0.076 |

Example 66 and Comparative Example 48

Organic EL devices were fabricated in the same manner as in Example 1 except that compounds indicated in Table 22 were used as the materials for the emitting layer. The results are shown in Table 22.

TABLE 22

| | Emitting layer | | LT95 | Chromaticity | |
|---|---|---|---|---|---|
| | BH | BD | (h) | CIEx | CIEy |
| Example 66 | BH-5 | BD-11 | 132 | 0.133 | 0.076 |
| Com. Ex. 48 | BH-E | BD-11 | 104 | 0.133 | 0.076 |

Example 67 and Comparative Example 49

Organic EL devices were fabricated in the same manner as in Example 1 except that compounds indicated in Table 23 were used as the materials for the emitting layer. The results are shown in Table 23.

TABLE 23

| | Emitting layer | | LT95 | Chromaticity | |
|---|---|---|---|---|---|
| | BH | BD | (h) | CIEx | CIEy |
| Example 67 | BH-9 | BD-11 | 123 | 0.133 | 0.076 |
| Com. Ex. 49 | BH-G | BD-11 | 103 | 0.133 | 0.076 |

Example 68 and Comparative Example 50

Organic EL devices were fabricated in the same manner as in Example 1 except that compounds indicated in Table 24 were used as the materials for the emitting layer. The results are shown in Table 24.

TABLE 24

| | Emitting layer | | LT95 | Chromaticity | |
|---|---|---|---|---|---|
| | BH | BD | (h) | CIEx | CIEy |
| Example 68 | BH-1 | BD-12 | 115 | 0.141 | 0.059 |
| Com. Ex. 50 | BH-A | BD-12 | 90 | 0.141 | 0.059 |

Example 69 and Comparative Example 51

Organic EL devices were fabricated in the same manner as in Example 1 except that compounds indicated in Table 25 were used as the materials for the emitting layer. The results are shown in Table 25.

TABLE 25

| | Emitting layer | | LT95 | Chromaticity | |
|---|---|---|---|---|---|
| | BH | BD | (h) | CIEx | CIEy |
| Example 69 | BH-2 | BD-12 | 152 | 0.141 | 0.059 |
| Com. Ex. 51 | BH-B | BD-12 | 120 | 0.141 | 0.059 |

Example 70 and Comparative Example 52

Organic EL devices were fabricated in the same manner as in Example 1 except that compounds indicated in Table 26 were used as the materials for the emitting layer. The results are shown in Table 26.

TABLE 26

| | Emitting layer | | LT95 | Chromaticity | |
|---|---|---|---|---|---|
| | BH | BD | (h) | CIEx | CIEy |
| Example 70 | BH-4 | BD-12 | 110 | 0.141 | 0.058 |
| Com. Ex. 52 | BH-D | BD-12 | 91 | 0.141 | 0.058 |

Example 71 and Comparative Example 53

Organic EL devices were fabricated in the same manner as in Example 1 except that compounds indicated in Table 27 were used as the materials for the emitting layer. The results are shown in Table 27.

TABLE 27

| | Emitting layer | | LT95 | Chromaticity | |
|---|---|---|---|---|---|
| | BH | BD | (h) | CIEx | CIEy |
| Example 71 | BH-5 | BD-12 | 94 | 0.141 | 0.059 |
| Com. Ex. 53 | BH-E | BD-12 | 73 | 0.141 | 0.059 |

Example 72 and Comparative Example 54

Organic EL devices were fabricated in the same manner as in Example 1 except that compounds indicated in Table 28 were used as the materials for the emitting layer. The results are shown in Table 28.

TABLE 28

| | Emitting layer | | LT95 | Chromaticity | |
|---|---|---|---|---|---|
| | BH | BD | (h) | CIEx | CIEy |
| Example 72 | BH-9 | BD-12 | 84 | 0.141 | 0.058 |
| Com. Ex. 54 | BH-G | BD-12 | 66 | 0.141 | 0.058 |

Example 73 and Comparative Example 55

Organic EL devices were fabricated in the same manner as in Example 1 except that compounds indicated in Table 29 were used as the materials for the emitting layer. The results are shown in Table 29.

TABLE 29

| | Emitting layer | | LT95 | Chromaticity | |
|---|---|---|---|---|---|
| | BH | BD | (h) | CIEx | CIEy |
| Example 73 | BH-1 | BD-13 | 187 | 0.138 | 0.117 |
| Com. Ex. 55 | BH-A | BD-13 | 160 | 0.138 | 0.117 |

Example 74 and Comparative Example 56

Organic EL devices were fabricated in the same manner as in Example 1 except that compounds indicated in Table 30 were used as the materials for the emitting layer. The results are shown in Table 30.

TABLE 30

| | Emitting layer | | LT95 | Chromaticity | |
|---|---|---|---|---|---|
| | BH | BD | (h) | CIEx | CIEy |
| Example 74 | BH-2 | BD-13 | 257 | 0.138 | 0.116 |
| Com. Ex. 56 | BH-B | BD-13 | 198 | 0.138 | 0.116 |

Example 75 and Comparative Example 57

Organic EL devices were fabricated in the same manner as in Example 1 except that compounds indicated in Table 31 were used as the materials for the emitting layer. The results are shown in Table 31.

TABLE 31

| | Emitting layer | | LT95 | Chromaticity | |
|---|---|---|---|---|---|
| | BH | BD | (h) | CIEx | CIEy |
| Example 75 | BH-4 | BD-13 | 173 | 0.138 | 0.116 |
| Com. Ex. 57 | BH-D | BD-13 | 144 | 0.138 | 0.116 |

Example 76 and Comparative Example 58

Organic EL devices were fabricated in the same manner as in Example 1 except that compounds indicated in Table 32 were used as the materials for the emitting layer. The results are shown in Table 32.

TABLE 32

| | Emitting layer | | LT95 | Chromaticity | |
|---|---|---|---|---|---|
| | BH | BD | (h) | CIEx | CIEy |
| Example 76 | BH-5 | BD-13 | 146 | 0.138 | 0.116 |
| Com. Ex. 58 | BH-E | BD-13 | 117 | 0.138 | 0.116 |

Example 77 and Comparative Example 59

Organic EL devices were fabricated in the same manner as in Example 1 except that compounds indicated in Table 33 were used as the materials for the emitting layer. The results are shown in Table 33.

TABLE 33

| | Emitting layer | | LT95 | Chromaticity | |
|---|---|---|---|---|---|
| | BH | BD | (h) | CIEx | CIEy |
| Example 77 | BH-9 | BD-13 | 116 | 0.138 | 0.116 |
| Com. Ex. 59 | BH-G | BD-13 | 96 | 0.138 | 0.116 |

Example 78 and Comparative Example 60

Organic EL devices were fabricated in the same manner as in Example 1 except that compounds indicated in Table 34 were used as the materials for the emitting layer. The results are shown in Table 34.

TABLE 34

| | Emitting layer | | LT95 | Chromaticity | |
|---|---|---|---|---|---|
| | BH | BD | (h) | CIEx | CIEy |
| Example 78 | BH-1 | BD-14 | 158 | 0.139 | 0.122 |
| Com. Ex. 60 | BH-A | BD-14 | 136 | 0.139 | 0.122 |

Example 79 and Comparative Example 61

Organic EL devices were fabricated in the same manner as in Example 1 except that compounds indicated in Table 35 were used as the materials for the emitting layer. The results are shown in Table 35.

TABLE 35

| | Emitting layer | | LT95 | Chromaticity | |
|---|---|---|---|---|---|
| | BH | BD | (h) | CIEx | CIEy |
| Example 79 | BH-2 | BD-14 | 207 | 0.139 | 0.120 |
| Com. Ex. 61 | BH-B | BD-14 | 166 | 0.139 | 0.120 |

Example 80 and Comparative Example 62

Organic EL devices were fabricated in the same manner as in Example 1 except that compounds indicated in Table 36 were used as the materials for the emitting layer. The results are shown in Table 36.

TABLE 36

| | Emitting layer | | LT95 | Chromaticity | |
|---|---|---|---|---|---|
| | BH | BD | (h) | CIEx | CIEy |
| Example 80 | BH-4 | BD-14 | 144 | 0.139 | 0.121 |
| Com. Ex. 62 | BH-D | BD-14 | 120 | 0.139 | 0.121 |

Example 81 and Comparative Example 63

Organic EL devices were fabricated in the same manner as in Example 1 except that compounds indicated in Table 37 were used as the materials for the emitting layer. The results are shown in Table 37.

TABLE 37

| | Emitting layer | | LT95 | Chromaticity | |
|---|---|---|---|---|---|
| | BH | BD | (h) | CIEx | CIEy |
| Example 81 | BH-5 | BD-14 | 135 | 0.139 | 0.121 |
| Com. Ex. 63 | BH-E | BD-14 | 109 | 0.139 | 0.121 |

Example 82 and Comparative Example 64

Organic EL devices were fabricated in the same manner as in Example 1 except that compounds indicated in Table 38 were used as the materials for the emitting layer. The results are shown in Table 38.

TABLE 38

| | Emitting layer | | LT95 | Chromaticity | |
|---|---|---|---|---|---|
| | BH | BD | (h) | CIEx | CIEy |
| Example 82 | BH-9 | BD-14 | 107 | 0.139 | 0.121 |
| Com. Ex. 64 | BH-G | BD-14 | 88 | 0.139 | 0.121 |

Example 83 and Comparative Example 65

Organic EL devices were fabricated in the same manner as in Example 1 except that compounds indicated in Table 39 were used as the materials for the emitting layer. The results are shown in Table 39.

TABLE 39

| | Emitting layer | | LT95 | Chromaticity | |
|---|---|---|---|---|---|
| | BH | BD | (h) | CIEx | CIEy |
| Example 83 | BH-1 | BD-15 | 92 | 0.140 | 0.095 |
| Com. Ex. 65 | BH-A | BD-15 | 77 | 0.140 | 0.095 |

Example 84 and Comparative Example 66

Organic EL devices were fabricated in the same manner as in Example 1 except that compounds indicated in Table 40 were used as the materials for the emitting layer. The results are shown in Table 40.

TABLE 40

| | Emitting layer | | LT95 | Chromaticity | |
|---|---|---|---|---|---|
| | BH | BD | (h) | CIEx | CIEy |
| Example 84 | BH-2 | BD-15 | 125 | 0.140 | 0.095 |
| Com. Ex. 66 | BH-B | BD-15 | 95 | 0.140 | 0.095 |

Example 85 and Comparative Example 67

Organic EL devices were fabricated in the same manner as in Example 1 except that compounds indicated in Table 41 were used as the materials for the emitting layer. The results are shown in Table 41.

TABLE 41

| | Emitting layer | | LT95 | Chromaticity | |
|---|---|---|---|---|---|
| | BH | BD | (h) | CIEx | CIEy |
| Example 85 | BH-4 | BD-15 | 85 | 0.140 | 0.094 |
| Com. Ex. 67 | BH-D | BD-15 | 70 | 0.140 | 0.094 |

Example 86 and Comparative Example 68

Organic EL devices were fabricated in the same manner as in Example 1 except that compounds indicated in Table 42 were used as the materials for the emitting layer. The results are shown in Table 42.

TABLE 42

| | Emitting layer | | LT95 | Chromaticity | |
|---|---|---|---|---|---|
| | BH | BD | (h) | CIEx | CIEy |
| Example 86 | BH-5 | BD-15 | 71 | 0.140 | 0.094 |
| Com. Ex. 68 | BH-E | BD-15 | 60 | 0.140 | 0.094 |

Example 87 and Comparative Example 69

Organic EL devices were fabricated in the same manner as in Example 1 except that compounds indicated in Table 43 were used as the materials for the emitting layer. The results are shown in Table 43.

TABLE 43

| | Emitting layer | | LT95 | Chromaticity | |
|---|---|---|---|---|---|
| | BH | BD | (h) | CIEx | CIEy |
| Example 87 | BH-9 | BD-15 | 55 | 0.140 | 0.094 |
| Com. Ex. 69 | BH-G | BD-15 | 46 | 0.140 | 0.094 |

Example 88 and Comparative Example 70

Organic EL devices were fabricated in the same manner as in Example 1 except that compounds indicated in Table 44 were used as the materials for the emitting layer. The results are shown in Table 44.

TABLE 44

| | Emitting layer | | LT95 | Chromaticity | |
|---|---|---|---|---|---|
| | BH | BD | (h) | CIEx | CIEy |
| Example 88 | BH-1 | BD-16 | 147 | 0.141 | 0.098 |
| Com. Ex. 70 | BH-A | BD-16 | 128 | 0.141 | 0.098 |

Example 89 and Comparative Example 71

Organic EL devices were fabricated in the same manner as in Example 1 except that compounds indicated in Table 45 were used as the materials for the emitting layer. The results are shown in Table 45.

TABLE 45

| | Emitting layer | | LT95 | Chromaticity | |
|---|---|---|---|---|---|
| | BH | BD | (h) | CIEx | CIEy |
| Example 89 | BH-2 | BD-16 | 188 | 0.141 | 0.098 |
| Com. Ex. 71 | BH-8 | BD-16 | 147 | 0.141 | 0.098 |

Example 90 and Comparative Example 72

Organic EL devices were fabricated in the same manner as in Example 1 except that compounds indicated in Table 46 were used as the materials for the emitting layer. The results are shown in Table 46.

TABLE 46

| | Emitting layer | | LT95 | Chromaticity | |
|---|---|---|---|---|---|
| | BH | BD | (h) | CIEx | CIEy |
| Example 90 | BH-4 | BD-16 | 144 | 0.141 | 0.098 |
| Com. Ex. 72 | BH-D | BD-16 | 115 | 0.141 | 0.098 |

Example 91 and Comparative Example 73

Organic EL devices were fabricated in the same manner as in Example 1 except that compounds indicated in Table 47 were used as the materials for the emitting layer. The results are shown in Table 47.

TABLE 47

| | Emitting layer | | LT95 | Chromaticity | |
|---|---|---|---|---|---|
| | BH | BD | (h) | CIEx | CIEy |
| Example 91 | BH-5 | BD-16 | 120 | 0.141 | 0.098 |
| Com. Ex. 73 | BH-E | BD-16 | 96 | 0.141 | 0.098 |

Example 92 and Comparative Example 74

Organic EL devices were fabricated in the same manner as in Example 1 except that compounds indicated in Table 48 were used as the materials for the emitting layer. The results are shown in Table 48.

TABLE 48

| | Emitting layer | | LT95 | Chromaticity | |
|---|---|---|---|---|---|
| | BH | BD | (h) | CIEx | CIEy |
| Example 92 | BH-9 | BD-16 | 95 | 0.141 | 0.098 |
| Com. Ex. 74 | BH-G | BD-16 | 77 | 0.141 | 0.098 |

Example 93 and Comparative Example 75

Organic EL devices were fabricated in the same manner as in Example 1 except that compounds indicated in Table 49 were used as the materials for the emitting layer. The results are shown in Table 49.

TABLE 49

| | Emitting layer | | LT95 | Chromaticity | |
|---|---|---|---|---|---|
| | BH | BD | (h) | CIEx | CIEy |
| Example 93 | BH-1 | BD-17 | 144 | 0.140 | 0.096 |
| Com. Ex. 75 | BH-A | BD-17 | 123 | 0.140 | 0.096 |

Example 94 and Comparative Example 76

Organic EL devices were fabricated in the same manner as in Example 1 except that compounds indicated in Table 50 were used as the materials for the emitting layer. The results are shown in Table 50.

TABLE 50

| | Emitting layer | | LT95 | Chromaticity | |
|---|---|---|---|---|---|
| | BH | BD | (h) | CIEx | CIEy |
| Example 94 | BH-2 | BD-17 | 186 | 0.140 | 0.096 |
| Com. Ex. 76 | BH-B | BD-17 | 147 | 0.140 | 0.096 |

Example 95 and Comparative Example 77

Organic EL devices were fabricated in the same manner as in Example 1 except that compounds indicated in Table 51 were used as the materials for the emitting layer. The results are shown in Table 51.

TABLE 51

| | Emitting layer | | LT95 | Chromaticity | |
|---|---|---|---|---|---|
| | BH | BD | (h) | CIEx | CIEy |
| Example 95 | BH-4 | BD-17 | 141 | 0.140 | 0.096 |
| Com. Ex. 77 | BH-D | BD-17 | 114 | 0.140 | 0.096 |

Example 96 and Comparative Example 78

Organic EL devices were fabricated in the same manner as in Example 1 except that compounds indicated in Table 52 were used as the materials for the emitting layer. The results are shown in Table 52.

TABLE 52

| | Emitting layer | | LT95 | Chromaticity | |
|---|---|---|---|---|---|
| | BH | BD | (h) | CIEx | CIEy |
| Example 96 | BH-5 | BD-17 | 120 | 0.140 | 0.096 |
| Com. Ex. 78 | BH-E | BD-17 | 94 | 0.140 | 0.096 |

Example 97 and Comparative Example 79

Organic EL devices were fabricated in the same manner as in Example 1 except that compounds indicated in Table 53 were used as the materials for the emitting layer. The results are shown in Table 53.

TABLE 53

| | Emitting layer | | LT95 | Chromaticity | |
|---|---|---|---|---|---|
| | BH | BD | (h) | CIEx | CIEy |
| Example 97 | BH-9 | BD-17 | 92 | 0.140 | 0.096 |
| Com. Ex. 79 | BH-G | BD-17 | 75 | 0.140 | 0.096 |

Example 98 and Comparative Example 80

Organic EL devices were fabricated in the same manner as in Example 1 except that compounds indicated in Table 54 were used as the materials for the emitting layer. The results are shown in Table 54.

TABLE 54

| | Emitting layer | | LT95 | Chromaticity | |
|---|---|---|---|---|---|
| | BH | BD | (h) | CIEx | CIEy |
| Example 98 | BH-1 | BD-18 | 114 | 0.143 | 0.110 |
| Com. Ex. 80 | BH-A | BD-18 | 93 | 0.143 | 0.110 |

Example 99 and Comparative Example 81

Organic EL devices were fabricated in the same manner as in Example 1 except that compounds indicated in Table 55 were used as the materials for the emitting layer. The results are shown in Table 55.

TABLE 55

| | Emitting layer | | LT95 | Chromaticity | |
|---|---|---|---|---|---|
| | BH | BD | (h) | CIEx | CIEy |
| Example 99 | BH-2 | BD-18 | 147 | 0.143 | 0.109 |
| Com. Ex. 81 | BH-B | BD-18 | 112 | 0.143 | 0.109 |

Example 100 and Comparative Example 82

Organic EL devices were fabricated in the same manner as in Example 1 except that compounds indicated in Table 56 were used as the materials for the emitting layer. The results are shown in Table 56.

TABLE 56

| | Emitting layer | | LT95 | Chromaticity | |
|---|---|---|---|---|---|
| | BH | BD | (h) | CIEx | CIEy |
| Example 100 | BH-4 | BD-18 | 100 | 0.143 | 0.109 |
| Com. Ex. 82 | BH-D | BD-18 | 84 | 0.143 | 0.109 |

Example 101 and Comparative Example 83

Organic EL devices were fabricated in the same manner as in Example 1 except that compounds indicated in Table 57 were used as the materials for the emitting layer. The results are shown in Table 57.

TABLE 57

| | Emitting layer | | LT95 | Chromaticity | |
|---|---|---|---|---|---|
| | BH | BD | (h) | CIEx | CIEy |
| Example 101 | BH-5 | BD-18 | 85 | 0.143 | 0.109 |
| Com. Ex. 83 | BH-E | BD-18 | 68 | 0.143 | 0.109 |

Example 102 and Comparative Example 84

Organic EL devices were fabricated in the same manner as in Example 1 except that compounds indicated in Table 58 were used as the materials for the emitting layer. The results are shown in Table 58.

TABLE 58

| | Emitting layer | | LT95 | Chromaticity | |
|---|---|---|---|---|---|
| | BH | BD | (h) | CIEx | CIEy |
| Example 102 | BH-9 | BD-18 | 68 | 0.143 | 0.109 |
| Com. Ex. 84 | BH-G | BD-18 | 56 | 0.143 | 0.109 |

From the results shown in Tables 1 to 58, it is understood that the organic EL devices of Examples 1 to 102 in which a particular host material and a particular dopant material were used in combination have a low CIEy value and long lifetime, and simultaneously satisfied both these properties.

Several embodiments and/or examples of the present invention have been described in detail above. However, without substantially departing from novel teachings and effects of the present invention, the person skilled in the art can readily make a number of modifications to the embodiments and/or examples which are exemplifications of these teachings and effects. Thus, these modifications are included in the scope of the present invention.

The invention claimed is:

1. An organic electroluminescence device comprising:

a cathode, an anode, and an emitting layer disposed between the cathode and the anode, wherein the emitting layer comprises a compound represented by the following formula (1) and one or more compounds selected from the group consisting of a compound represented by formula (11), a compound represented by formula (21), a compound represented by formula (31), a compound represented by formula (41), a compound represented by formula (51), a compound represented by formula (61), a compound represented by formula (71) and a compound represented by formula (81):

(1)

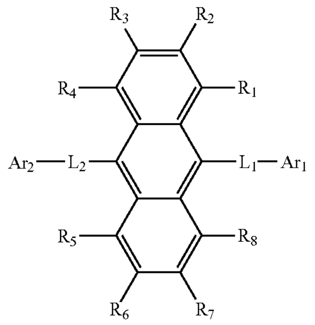

wherein in the formula (1), each of $R_1$ to $R_8$ is a deuterium atom, $L_1$ and $L_2$ are independently
a single bond,
a substituted or unsubstituted phenylene group,
a substituted or unsubstituted naphthylene group,
a substituted or unsubstituted biphenylene group,
a substituted or unsubstituted terphenylene group,
a substituted or unsubstituted anthrylene group, or
a substituted or unsubstituted phenanthrylene group;

$Ar_1$ and $Ar_2$ are independently
a substituted or unsubstituted phenyl group,
a substituted or unsubstituted naphthyl group,
a substituted or unsubstituted biphenyl group,
a substituted or unsubstituted terphenyl group,
a substituted or unsubstituted anthryl group, or
a substituted or unsubstituted phenanthryl group;

when $L_1$, $L_2$, $Ar_1$ and $Ar_2$ have a substituent, the substituent is an alkyl group having 1 to 50 carbon atoms,
an alkenyl group having 2 to 50 carbon atoms,
an alkynyl group having 2 to 50 carbon atoms,
a cycloalkyl group having 3 to 50 ring carbon atoms,
an alkylsilyl group having 1 to 50 carbon atoms,
a halogen atom, or
a cyano group;

(11)

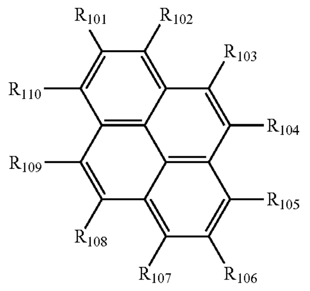

wherein, in the formula (11), one or more pairs of two or more adjacent groups of $R_{101}$ to $R_{110}$ are bonded with each other to form a substituted or unsubstituted, saturated or unsaturated ring, or do not form a substituted or unsubstituted, saturated or unsaturated ring;

at least one of $R_{101}$ to $R_{110}$ is a monovalent group represented by the formula (12);

$R_{101}$ to $R_{110}$ that do not form the substituted or unsubstituted, saturated or unsaturated ring and that are not a monovalent group represented by the following formula (12) are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
—$Si(R_{901})(R_{902})(R_{903})$,
—O—$(R_{904})$,
—S—$(R_{905})$,
$N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms;

$R_{901}$ to $R_{907}$ are as defined in the formula (1);

(12)

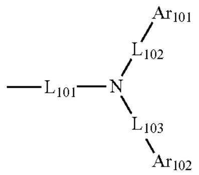

wherein, in the formula (12), $Ar_{101}$ and $Ar_{102}$ are independently
a substituted or unsubstituted aryl group having 6 to 50 ring carbon atoms, or
a substituted or unsubstituted monovalent heterocyclic group having 5 to 50 ring atoms;

$L_{101}$ to $L_{103}$ are independently
a single bonded,
a substituted or unsubstituted arylene group having 6 to 30 ring carbon atoms, or
a substituted or unsubstituted divalent heterocyclic group having 5 to 30 ring atoms;

(21)

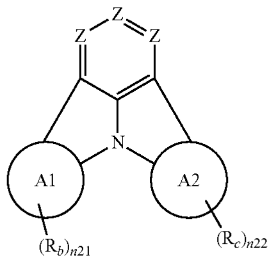

wherein, in the formula (21),

Zs are independently $CR_a$ or N;

A1 ring and A2 ring are independently a substituted or unsubstituted aromatic hydrocarbon ring having 6 to 50 ring carbon atoms, or a substituted or unsubstituted heterocyclic ring having 5 to 50 ring atoms;

when a plurality of $R_a$s exist, two or more adjacent groups of $R_a$ are bonded with each other to form a substituted or unsubstituted, saturated or unsaturated ring, or do not form a substituted or unsubstituted, saturated or unsaturated ring;

when a plurality of $R_b$s exist, two or more adjacent groups of $R_b$ are bonded with each other to form a substituted or unsubstituted, saturated or unsaturated ring, or do not form a substituted or unsubstituted, saturated or unsaturated ring;

when a plurality of $R_c$s exist, one or more pairs of two or more adjacent groups of $R_c$ are bonded with each other to form a substituted or unsubstituted, saturated or unsaturated ring, or do not form a substituted or unsubstituted, saturated or unsaturated ring;

n21 and n22 are independently an integer of 0 to 4;

$R_a$ to $R_c$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

(31)

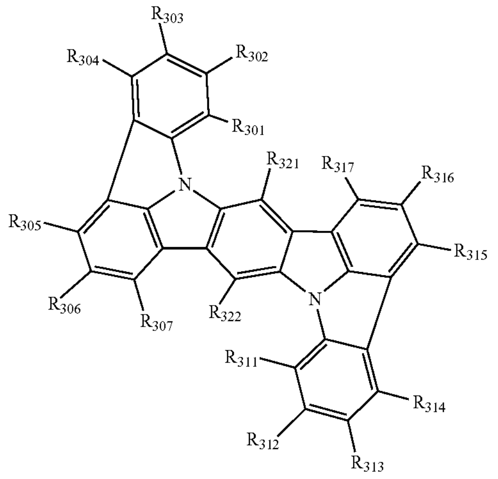

wherein, in the formula (31), one or more pairs of two or more adjacent groups of $R_{301}$ to $R_{307}$ and $R_{311}$ to $R_{317}$ form a substituted or unsubstituted, saturated or unsaturated ring, or do not form a substituted or unsubstituted saturated or unsaturated ring;

$R_{301}$ to $R_{307}$ and $R_{311}$ to $R_{317}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{321}$ and $R_{322}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

(41)

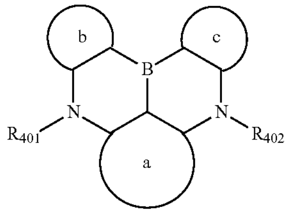

wherein, in the formula (41), a ring, b ring and c ring are independently a substituted or unsubstituted aromatic hydrocarbon ring having 6 to 50 ring carbon atoms, or a substituted or unsubstituted heterocyclic ring having 5 to 50 ring atoms;

$R_{401}$ and $R_{402}$ are independently bonded to the a ring, the b ring or the c ring to form a substituted or unsubstituted heterocyclic ring or do not form a substituted or unsubstituted heterocyclic ring;

$R_{401}$ and $R_{402}$ that do not form the substituted or unsubstituted heterocyclic ring are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

(51)

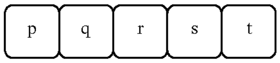

(52)

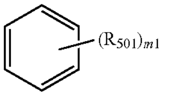

(53)

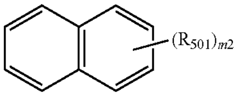

(54)

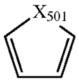

(55)

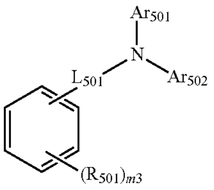

(56)

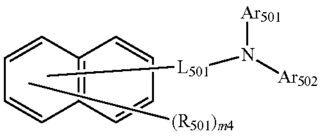

wherein, in the formula (51), r ring is a ring represented by the formula (52) or formula (53) which is fused to an adjacent ring at an arbitrary position;

q ring and s ring are independently a ring represented by the formula (54) which is fused to an adjacent ring at an arbitrary position;

p ring and t ring are independently a ring represented by the formula (55) or the formula (56) which is fused to an adjacent ring at an arbitrary position;

when a plurality of $R_{501}$s exist, adjacent $R_{501}$s are bonded with each other to form a substituted or unsubstituted, saturated or unsaturated ring, or do not form a substituted or unsubstituted, saturated or unsaturated ring;

$X_{501}$ is an oxygen atom, a sulfur atom, or $NR_{502}$;

$R_{501}$ and $R_{502}$ that do not form the substituted or unsubstituted saturated or unsaturated ring are a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

$Ar_{501}$ and $Ar_{502}$ are independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

$L_{501}$ is a substituted or unsubstituted alkylene group having 1 to 50 carbon atoms, a substituted or unsubstituted alkenylene group having 2 to 50 carbon atoms, a substituted or unsubstituted alkynylene group having 2 to 50 carbon atoms, a substituted or unsubstituted cycloalkylene group having 3 to 50 ring carbon atoms, a substituted or unsubstituted arylene group having 6 to 50 ring carbon atoms, or a substituted or unsubstituted divalent heterocyclic group having 5 to 50 ring atoms;

m1 is an integer of 0 to 2, m2 is an integer of 0 to 4, m3s are independently an integer of 0 to 3, and m4s are independently an integer of 0 to 5; when a plurality of $R_{501}$ s exist, $R_{501}$s may be the same or different;

(61)

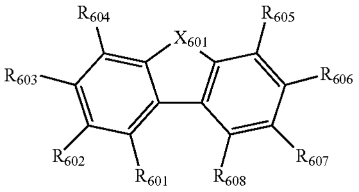

wherein, in the formula (61), at least one pair of $R_{601}$ and $R_{602}$, $R_{602}$ and $R_{603}$, and $R_{603}$ and $R_{604}$ are bonded with each other to form a divalent group represented by the formula (62);

at least one pair of $R_{605}$ and $R_{606}$, $R_{606}$ and $R_{607}$, and $R_{607}$ and $R_{608}$ are bonded with each other to form a divalent group represented by formula (63);

(62)

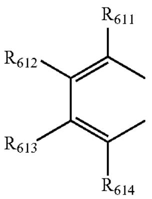

-continued (63)

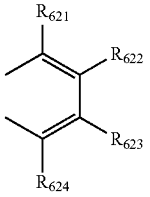

at least one of $R_{601}$ to $R_{604}$ that does not form the divalent group represented by the formula (62), and $R_{611}$ to $R_{614}$ is a monovalent group represented by the following formula (64);

at least one of $R_{605}$ to $R_{608}$ that do not form the divalent group represented by the formula (63), and $R_{621}$ to $R_{624}$ is a monovalent group represented by the following formula (64);

$X_{601}$ is an oxygen atom, a sulfur atom, or $NR_{609}$;

$R_{601}$ to $R_{608}$ that do not form the divalent group represented by the formulas (62) and (63) and that is not the monovalent group represented by the formula (64), $R_{611}$ to $R_{614}$ and $R_{621}$ to $R_{624}$ that are not the monovalent group represented by the formula (64), and $R_{609}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

(64)

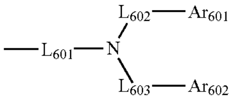

wherein, in the formula (64), $Ar_{601}$ and $Ar_{602}$ are independently a substituted or unsubstituted aryl group having 6 to 50 ring carbon atoms, or a substituted or unsubstituted monovalent heterocyclic group having 5 to 50 ring atoms;

$L_{601}$ to $L_{603}$ are independently a single bonded, a substituted or unsubstituted arylene group having 6 to 30 ring carbon atoms, a substituted or unsubstituted divalent heterocyclic group having 5 to 30 ring atoms, or a divalent linking group formed by bonding 2 to 4 of a substituted or unsubstituted arylene group having 6 to 30 ring carbon atoms, and a substituted or unsubstituted divalent heterocyclic group having 5 to 30 ring atoms;

(71)

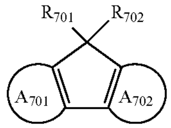

wherein, in the formula (71), $A_{701}$ ring and $A_{702}$ ring are independently a substituted or unsubstituted aromatic hydrocarbon ring having 6 to 50 ring carbon atoms, or a substituted or unsubstituted heterocyclic ring having 5 to 50 ring atoms;

One or more rings selected from the group consisting of $A_{701}$ ring and $A_{702}$ ring are bonded to the bond * of the structure represented by the following formula (72);

(72)

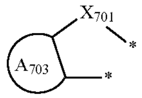

wherein, in the formula (72), $A_{703}$ rings are independently a substituted or unsubstituted aromatic hydrocarbon ring having 6 to 50 ring carbon atoms, or a substituted or unsubstituted heterocyclic ring having 5 to 50 ring atoms;

$X_{701}$ is $NR_{703}$, $C(R_{704})(R_{705})$, $Si(R_{706})(R_{707})$, $Ge(R_{708})(R_{709})$, O, S or Se;

$R_{701}$ and $R_{702}$ are bonded with each other to form a substituted or unsubstituted, saturated or unsaturated ring or do not form a substituted or unsubstituted saturated or unsaturated ring;

$R_{701}$ and $R_{702}$ that do not form the substituted or unsubstituted, saturated or unsaturated ring, and $R_{703}$ to $R_{709}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

(81)

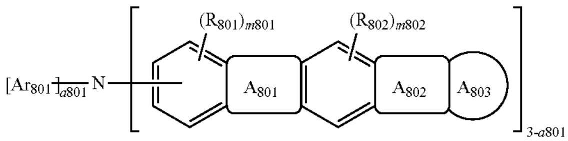

(82)

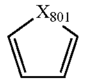

(83)

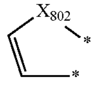

wherein, in the formula (81), $A_{801}$ ring is a ring represented by the formula (82) which is fused to an adjacent ring at an arbitrary position;

$A_{802}$ ring is a ring represented by the formula (83) which is fused to an adjacent ring at an arbitrary position;

two bonds * bond to $A_{803}$ ring at an arbitrary position;

$X_{801}$ and $X_{802}$ are independently $C(R_{803})(R_{804})$, $Si(R_{85})(R_{806})$, an oxygen atom, or a sulfur atom;

$A_{803}$ ring is a substituted or unsubstituted aromatic hydrocarbon ring having 6 to 50 ring carbon atoms, or a substituted or unsubstituted heterocyclic ring having 5 to 50 ring atoms;

$Ar_{801}$ is a substituted or unsubstituted aryl group having 6 to 50 ring carbon atoms, or a substituted or unsubstituted monovalent heterocyclic group having 5 to 50 ring atoms;

$R_{801}$ to $R_{806}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

m801 and m802 are independently an integer of 0 to 2; when m801 is 2, $R_{801}$'s may be the same as or different from each other, and when m802 is 2, $R_{802}$'s may be the same as or different from each other;

a801 is an integer of 0 to 2; when a801 is 0 or 1, the structure in the parentheses indicated by "3-a801" may be the same or different from each other; when a801 is 2, $Ar_{801}$s may be the same or different from each other, wherein the emitting layer comprises the compound represented by the formula (1), and a non-deuterated compound having the structure same as the compound represented by the formula (1) except for containing only protium atoms as hydrogen atoms, and a content of the compound represented by the formula (1) is from 30 mass % to 99 mass % based on a combined amount of the compound represented by the formula (1) and the non-deuterated compound.

2. The organic electroluminescence device according to claim 1, wherein in the formula (1), at least one hydrogen atom possessed in one or more selected from the group consisting of $L_1$ and $L_2$ is a deuterium atom.

3. The organic electroluminescence device according to claim 1, wherein in the formula (1), $L_1$ and $L_2$ are independently a single bond, a substituted or unsubstituted phenylene group, or a substituted or unsubstituted naphthylene group.

4. The organic electroluminescence device according to claim 1, wherein in the formula (1), at least one hydrogen atom possessed in one or more selected from the group consisting of $Ar_1$ and $Ar_2$ is a deuterium atom.

5. The organic electroluminescence device according to claim 1, wherein in the formula (1), $Ar_1$ and $Ar_2$ are independently a substituted or unsubstituted phenyl group, a substituted or unsubstituted naphthyl group, or a substituted or unsubstituted phenanthryl group.

6. The organic electroluminescence device according to claim 1, wherein in the formula (11), two of $R_{101}$ to $R_{110}$ are the groups represented by the formula (12).

7. The organic electroluminescence device according to claim 1, wherein the compound represented by the formula (11) is a compound represented by the following formula (13):

(13)

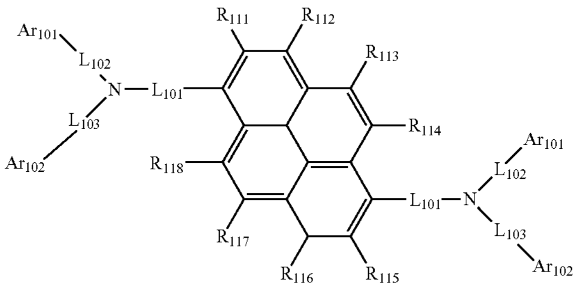

wherein in the formula (13), $R_{111}$ to $R_{118}$ are the same as $R_{101}$ to $R_{110}$ in the formula (11) that are not a monovalent group represented by the formula (12); and $Ar_{101}$, $Ar_{102}$, $L_{101}$, $L_{102}$ and $L_{103}$ are as defined in the formula (12).

8. The organic electroluminescence device according to claim 7, wherein the compound represented by the formula (13) is a compound represented by the following formula (14):

(14)

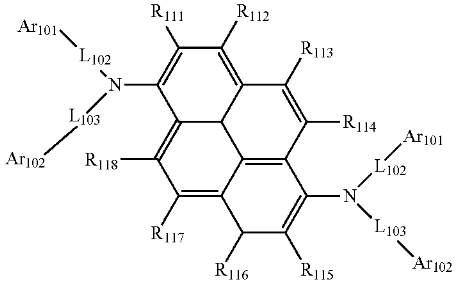

wherein in the formula (14), $R_{111}$ to $R_{118}$ are as defined in the formula (13), and $Ar_{101}$, $Ar_{102}$, $L_{102}$ and $L_{103}$ are as defined in the formula (12).

9. The organic electroluminescence device according to claim 7, wherein the compound represented by the formula (13) is a compound represented by the following formula (15):

(15)

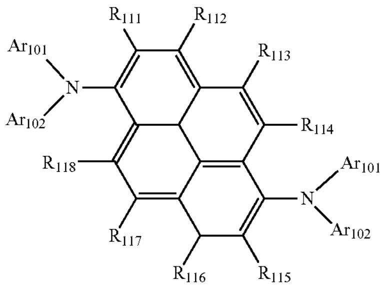

wherein in the formula (15), $R_{111}$ to $R_{118}$ are as defined in the formula (13), and $Ar_{101}$ and $Ar_{102}$ are as defined in the formula (12).

10. The organic electroluminescence device according to claim 7, wherein the compound represented by the formula (13) is a compound represented by the following formula (17):

wherein in the formula (17), $R_{111}$ to $R_{118}$ are as defined in the formula (13);

one or more sets of adjacent two or more of $R_{121}$ to $R_{127}$ are form a substituted or unsubstituted, saturated or unsaturated ring by bonding with each other, or do not form a substituted or unsubstituted, saturated or unsaturated ring;

$R_{121}$ to $R_{127}$ that do not form the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are as defined in the formula (1);

$R_{131}$ to $R_{135}$ are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, (17)

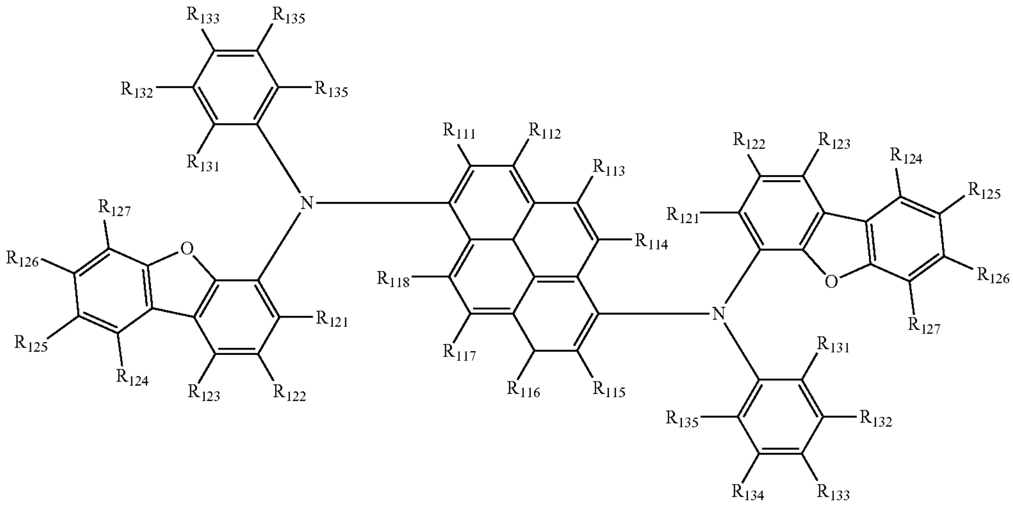

a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1).

11. The organic electroluminescence device according to claim 1, wherein in the formula (41), the a ring, the b ring and the c ring are independently a substituted or unsubstituted aromatic hydrocarbon ring having 6 to 50 ring carbon atoms.

12. The organic electroluminescence device according to claim 1, wherein in the formula (41), $R_{401}$ and $R_{402}$ are independently a substituted or unsubstituted aryl group having 6 to 50 ring carbon atoms, or a substituted or unsubstituted monovalent heterocyclic group having 5 to 50 ring atoms.

13. The organic electroluminescence device according to claim 1, wherein in the formula (41), $R_{401}$ and $R_{402}$ are independently a substituted or unsubstituted aryl group having 6 to 50 ring carbon atoms.

14. The organic electroluminescence device according to claim 1, wherein the compound represented by the formula (41) is a compound represented by the following formula (42):

(42)

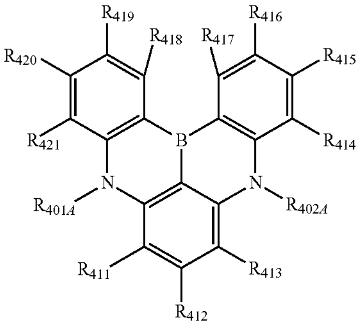

wherein in the formula (42),
$R_{401A}$ forms a substituted or unsubstituted heterocyclic ring by bonding with one or more selected from the group consisting of $R_{411}$ and $R_{421}$, or does not form a substituted or unsubstituted heterocyclic ring, and $R_{402A}$ forms a substituted or unsubstituted heterocyclic ring by bonding with one or more selected from the group consisting of $R_{413}$ and $R_{414}$, or does not form a substituted or unsubstituted heterocyclic ring;
$R_{401A}$ and $R_{402A}$ that do not form the substituted or unsubstituted heterocyclic ring are independently
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms;
at least one pair of adjacent two or more of $R_{411}$ to $R_{421}$ forms a substituted or unsubstituted, saturated or unsaturated ring by bonding with each other, or do not form a substituted or unsubstituted, saturated or unsaturated ring;
$R_{411}$ to $R_{421}$ that do not form the substituted or unsubstituted heterocyclic ring or the substituted or unsubstituted, saturated or unsaturated ring are independently
a hydrogen atom,
a substituted or unsubstituted alkyl group having 1 to 50 carbon atoms,
a substituted or unsubstituted alkenyl group having 2 to 50 carbon atoms,
a substituted or unsubstituted alkynyl group having 2 to 50 carbon atoms,
a substituted or unsubstituted cycloalkyl group having 3 to 50 ring carbon atoms,
$-Si(R_{901})(R_{902})(R_{903})$,
$-O-(R_{904})$,
$-S-(R_{905})$,
$-N(R_{906})(R_{907})$,
a halogen atom, a cyano group, a nitro group,
a substituted or unsubstituted aryl group having 6 to 50 ring carbon atoms, or
a substituted or unsubstituted monovalent heterocyclic group having 5 to 50 ring atoms; and
$R_{901}$ to $R_{907}$ are as defined in the formula (1).

15. The organic electroluminescence device according to claim 1, wherein the compound represented by the formula (41) is a compound represented by the following formula (43):

(43)

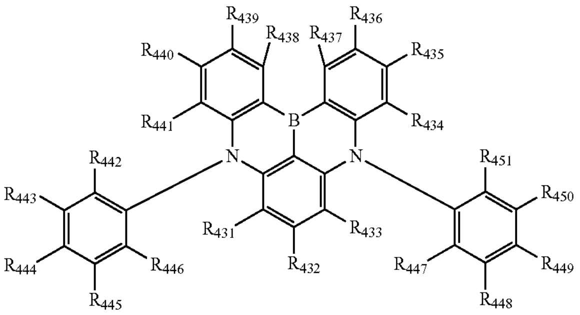

wherein in the formula (43),
$R_{431}$ forms a substituted or unsubstituted heterocyclic ring by bonding with $R_{446}$, or does not form a substituted or unsubstituted heterocyclic ring, $R_{433}$ forms a substituted or unsubstituted heterocyclic ring by bonding with $R_{447}$, or does not form a substituted or unsubstituted heterocyclic ring, $R_{434}$ forms a substituted or unsubstituted heterocyclic ring by bonding with $R_{451}$, or does not form a substituted or unsubstituted heterocyclic ring, and $R_{441}$ forms a substituted or unsubstituted heterocyclic ring by bonding with $R_{442}$, or does not form a substituted or unsubstituted heterocyclic ring;
at least one pair of adjacent two or more of $R_{431}$ to $R_{451}$ forms a substituted or unsubstituted, saturated or unsaturated ring by bonding with each other, or does not form a substituted or unsubstituted, saturated or unsaturated ring;
$R_{431}$ to $R_{451}$ that do not form the substituted or unsubstituted heterocyclic ring, or the substituted or unsubstituted, saturated or unsaturated ring are independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $-Si(R_{901})(R_{902})(R_{903})$, $-O-(R_{904})$, $-S-(R_{905})$, $-N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ are as defined in the formula (1).

16. The organic electroluminescence device according to claim 1, which further comprises a hole-transporting layer between the anode and the emitting layer.

17. The organic electroluminescence device according to claim 1, which further comprises an electron-transporting layer between the cathode and the emitting layer.

18. An electronic appliance wherein the organic electroluminescence device according to claim 1 is provided.

* * * * *